US010947252B2

(12) United States Patent
Barbay et al.

(10) Patent No.: US 10,947,252 B2
(45) Date of Patent: Mar. 16, 2021

(54) INHIBITORS OF KEAP1-NRF2 PROTEIN-PROTEIN INTERACTION

(71) Applicant: Janssen Pharmaceutica NV, Beerse (BE)

(72) Inventors: J. Kent Barbay, Flourtown, PA (US); Wenying Chai, San Diego, CA (US); Gavin C. Hirst, San Diego, CA (US); Kevin D. Kreutter, Arlington, MA (US); David A. Kummer, San Diego, CA (US); Kelly J. McClure, Ramona, CA (US); Rachel T. Nishimura, San Diego, CA (US); Amy Y. Shih, San Diego, CA (US); Jennifer D. Venable, Solana Beach, CA (US); Hariharan Venkatesan, San Diego, CA (US); Jianmei Wei, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/544,462

(22) Filed: Aug. 19, 2019

(65) Prior Publication Data

US 2020/0055874 A1 Feb. 20, 2020

Related U.S. Application Data

(60) Provisional application No. 62/881,639, filed on Aug. 1, 2019, provisional application No. 62/875,737, filed on Jul. 18, 2019, provisional application No. 62/823,450, filed on Mar. 25, 2019, provisional application No. 62/801,433, filed on Feb. 5, 2019, provisional application No. 62/719,978, filed on Aug. 20, 2018.

(51) Int. Cl.
*C07D 513/14* (2006.01)
*C07D 519/00* (2006.01)
*C07D 515/20* (2006.01)
*C07D 513/10* (2006.01)
*C07D 515/04* (2006.01)
*C07D 513/04* (2006.01)
*C07D 471/04* (2006.01)
*C07D 419/10* (2006.01)
*C07D 515/10* (2006.01)

(52) U.S. Cl.
CPC ......... *C07D 513/14* (2013.01); *C07D 419/10* (2013.01); *C07D 471/04* (2013.01); *C07D 513/04* (2013.01); *C07D 513/10* (2013.01); *C07D 515/04* (2013.01); *C07D 515/10* (2013.01); *C07D 515/20* (2013.01); *C07D 519/00* (2013.01)

(58) Field of Classification Search
CPC .................................................. C07D 513/14
See application file for complete search history.

(56) References Cited

FOREIGN PATENT DOCUMENTS

| WO | WO2007/005879 A2 | 1/2007 |
|---|---|---|
| WO | WO2012/116362 A2 | 8/2012 |
| WO | WO2013/067036 A1 | 5/2013 |
| WO | WO2015/092713 A1 | 6/2015 |
| WO | WO2016/202253 A1 | 12/2016 |
| WO | WO2016/203400 A1 | 12/2016 |
| WO | WO2017/060855 A1 | 4/2017 |
| WO | WO2017/161172 A1 | 9/2017 |
| WO | WO2017/214709 A1 | 12/2017 |
| WO | WO2018/104766 A1 | 6/2018 |
| WO | WO2018/109641 A1 | 6/2018 |
| WO | WO2018/109642 A1 | 6/2018 |
| WO | WO2018/109643 A1 | 6/2018 |
| WO | WO2018/109646 A1 | 6/2018 |
| WO | WO2018/109647 A1 | 6/2018 |
| WO | WO2018/109648 A1 | 6/2018 |
| WO | WO2018/109649 A1 | 6/2018 |
| WO | WO2018/140876 A1 | 8/2018 |
| WO | WO2020/041169 | 2/2020 |

OTHER PUBLICATIONS

Abed, D. A. et al., Discovery of direct inhibitors of Keap1-Nrf2 protein-protein interaction as potential therapeutic and preventive agents, Acta Pharmaceutica Sinica B, 2015, 5 (4), 285-299.
Adenuga, D. et al., Nrf2 deficiency influences susceptibility to steroid resistance via HDAC2 reduction, Biochem. Biophys. Res. Commun., 2010, 403, (3-4), 452-456.
Aleksunes, L.M. et al., Nuclear Factor Erythroid 2-Related Factor 2 Deletion Impairs Glucose Tolerance and Exacerbates Hyperglycemia in Type 1 Diabetic Mice, J. Pharmacol. Exp. Ther., 2010, 333 (1), 140-151.
Aleksunes, L.M., et al., Transcriptional Regulation of Renal Cytoprotective Genes by Nrf2 and Its Potential Use as a Therapeutic Target to Mitigate Cisplatin-Induced Nephrotoxicity, J. Pharmacol. Exp. Ther., 2010, 335, 2-12.
Almenier, H. A. et al., Oxidative stress and inflammatory bowel disease, Fronteirs in Bioscience E4, 2012, 1335-1344.
Arisawa, T. et al., Nrf2 Gene Promoter Polymorphism is Associated with Ulcerative Colitis in a Japanese Population, Hepato-Gastroenterology, 2008, 55, 394-397.
Berge, S.M. et al., Pharmaceutical Salts, J. Pharm. Sci., 1977, 66(1), 1-19.
Bhakkiyalakshmi, E. et al., The emerging role of redox-sensitive Nrf2-Keap1 pathway in diabetes, Pharmacol. Research, 2015, 91, 104-114.
Bitar, M. S. et al., A defect in Nrf2 signaling constitutes a mechanism for cellular stress hypersensitivity in a genetic rat model of type 2 diabetes, Am. J. Phsiol. Endocrinol. Metab., 2011, 301 (6), E1119-1129.
Bitar, M. S. et al., Decline in DJ-1 and Decreased Nuclear Translocation of Nrf2 in Fuchs Endothelial Corneal Dystrophy, Invest. Ophthalmol. Visual Sci, 2012, 53 (9), 5806-5813.

(Continued)

*Primary Examiner* — Paul V Ward

(57) ABSTRACT

Sultam compounds, pharmaceutical compositions containing them, methods of making them, and methods of using them including methods for treating disease states, disorders, and conditions associated with the KEAP1-Nrf2 interaction, such as inflammatory bowel disease, including Crohn's disease and ulcerative colitis.

1 Claim, No Drawings

(56) References Cited

OTHER PUBLICATIONS

Boutten, A., et al., NRF2 targeting: a promising therapeutic strategy in chronic obstructive pulmonary disease, Trends Mol. Med., 2011, 17, 363-371.
Catarzi, S., et al., Oxidative State and IL-6 Production in Intestinal Myofibroblasts of Crohn's Disease Patients, Inflamm. Bowel Dis., 2011, 17, 1674-84.
Chin, M.P., et al., Mechanisms Contributing to Adverse Cardiovascular Events in Patients with Type 2 Diabetes Mellitus and Stage 4 Chronic Kidney Disease Treated with Bardoxolone Methyl, Am. J. Nephrol., 2014, 39, 499-508.
Cho, H.-Y., et al., Nrf2 protects against airway disorders, Toxicol. Appl. Pharmacol., 2010, 244, 43-56.
Chowdry, S. et al., Loss of Nrf2 markedly exacerbates nonalcoholic steatohepatitis, Free Radical Biology and Medicine, 2010, 48, 357-371.
ClinicalTrials.gov, NCT02036970, Bardoxolone Methyl Evaluation in Patients With Pulmonary Hypertension (PH)—LARIAT, <https://clinicaltrials.gov/ct2/show/NCT02036970>, accessed Nov. 20, 2017.
Cope, G. F., et al., Cigarette Smoking and Inflammatory Bowel Disease: A Review, Human Toxicol., 1987, 6, 189-193.
Cracowski, J-L., et al., Increased Urinary F2-Isoprostanes in Patients With Crohn's Disease, Am. J. Gastroenterol., 2002, 97, 99-103.
Davies, T.G. et al., Monoacidic Inhibitors of the Kelch-like ECH-Associated Protein 1: Nuclear Factor Erythroid 2-Related Factor 2 (KEAP1:NRF2) Protein-Protein Interaction with High Cell Potency Identified by Fragment-Based Discovery, J. Med. Chem., 2016, 59, 3991-4006.
Deshmukh, P., et al., The Keap1-Nrf2 pathway: promising therapeutic target to counteract ROS-mediated damage in cancers and neurodegenerative diseases, Biophys Rev, 2017, 9, 41-56.
Eitas, T.K. et al., Differential regulation of innate immune cytokine production through pharmacological activation of Nuclear Factor-Erythroid-2-Related Factor 2 (NRF2) in burn patient immune cells and monocytes, PLoS/One 12(9): e0184164, 2017, https://doi.org/10.1371/journal.pone.0184164.
Gonzalez-Donquiles, C., et al., The NRF2 transcription factor plays a dual role in colorectal cancer: A systematic review, PLoS/One 12(5): e0177549, 2017, https://doi.org/10.1371/journal.pone.0177549.
Hatsugai, M., et al., Protein profiles of peripheral blood mononuclear cells are useful for differential diagnosis of ulcerative colitis and Crohn's disease, J. Gastroenterol., 2010, 45, 488-500.
Houstis, N. et al., Reactive oxygen species have a causal role in multiple forms of insulin resistance, Nature, 2006, 440 (7086) 944-948.
Howden, R., et al., The Influence of Nrf2 on Cardiac Responses to Environmental Stressors, Oxidative Medicine and Cellular Longevity, 2013, 1-10.
Iizuka, T. et al., Nrf2-deficient mice are highly susceptible to cigarette smoke-induced emphysema, Genes to Cells, 2005, 10 (12) 1113-1125.
Jiang, S. et al., An overview of the mechanisms and novel roles of Nrf2 in cardiovascular diseases, Expert Opinion on Therapeutic Targets, 2016, 20, 1413-1424.
Jiang, Z-Y., et al., Structure-Activity and Structure-Property Relationship and Exploratory in Vivo Evaluation of the Nanomolar Keap1-Nrf2 Protein-Protein Interaction Inhibitor, J. Med. Chem., 2015, 58(16), 6410-6421.
Kadam, D. P., et al., Role of Oxidative Stress in Various Stages of Psoriasis, Ind. J. Clin. Biochem., 2010, 25(4), 388-392.
Kerr, F., et al., Direct Keap1-Nrf2 disruption as a potential therapeutic target for Alzheimer's disease, PLoS/Genetics, 2017, 13(3): e1006593. doi:10.1371/journal. pgen.1006593.
Khor, B., et al., Genetics and pathogenesis of inflammatory bowel disease, Nature, 2011, 474(7351), 307-317.
Khor, T. O., et al., Increased Susceptibility of Nrf2 Knockout Mice to Colitis-Associated Colorectal Cancer, Cancer Prev Res, 2008, 1(3) 187-191.
Khor, T. O., et al., Nrf2-Deficient Mice Have an Increased Susceptibility to Dextran Sulfate Sodium-Induced Colitis, Cancer Res., 2006, 66(24), 11580-11584.
Kim, J.-H. et al., NRF2-mediated Notch pathway activation enhances hematopoietic reconstitution following myelosuppressive radiation, J. Clin. Investigation, 2014, 124, 730-741.
Kruidenier, L., et al., Review article: oxidative stress as a pathogenic factor in inflammatory bowel disease—radicals or ridiculous?, Aliment Pharmacol. Ther., 2002, 16, 1997-2015.
Kweider, N. et al., A possible protective role of Nrf2 in preeclampsia, Annals of Anatomy, 2014, 196, 268-277.
Lisk, C. et al., Nrf2 activation: A potential strategy for the prevention of acute mountain sickness, Free Radical Biology and Medicine, 2013, 63, 264-273.
Lu, M. C., et al., An inhibitor of the Keap1-Nrf2 protein-protein interaction protects NCM460 colonic cells and alleviates experimental colitis, Nature, 2016, Scientific Reports, 6:26585, DOI: 10.1038/srep26585.
Lu, M. C., et al., The Keap1-Nrf2-ARE Pathway As a Potential Preventive and Therapeutic Target: An Update, Medicinal Research Reviews, 2016, 36(5), 924-963.
Matulis, D. et al., Thermodynamic Stability of Carbonic Anhydrase: Measurements of Binding Affinity and Stoichiometry Using ThermoFluor, Biochemistry, 2005, 44, 5258-66.
Mimoto, T. et al., Impaired antioxydative Keap1/Nrf2 system and the downstream stress protein responses in the motor neuron of ALS model mice, Brain Research, 2012, 1446, 109-118.
Niture, S. K., et al., Regulation ofNrf2—an update, Free Radical Biology and Medicine, 2014, 66, 36-44.
Onyiah, J. C. et al., Heme oxygenase-1 and carbon monoxide regulate intestinal homeostasis and mucosal immune responses to the enteric microbiota, Gut Microbes, 2014, 5(2), 220-224.
Onyiah, J. C., et al., Carbon Monoxide and Heme Oxygenase-1 Prevent Intestinal Inflammation in Mice by Promoting Bacterial Clearance, Gastroenterology, 2013, 144, 789-798.
Pantoliano, M. W., et al., High-Density Miniaturized Thermal Shift Assays as a General Strategy for Drug Discovery*, J. Biomol. Screen, 2001, 6, 429-40.
Rezaie, A., et al., Oxidative Stress and Pathogenesis of Inflammatory Bowel Disease: An Epiphenomenon or the Cause?, Dig. Dis. Sci., 2007, 52, 2015-2021.
Rochette, L. et al., Diabetes, oxidative stress and therapeutic strategies, Biochimica et Biophysica Acta, 2014, 1840, 2709-2729.
Schäfer, M. et al., Nrf2 establishes a glutathione-mediated gradient of UVB cytoprotection in the epidermis, Genes and Development, 2010, 24(10), 1045-1058.
Schimel, A. M. et al., N-Acetylcysteine Amide (NACA) Prevents Retinal Degeneration by Up-Regulating Reduced Glutathione Production and Reversing Lipid Peroxidation, Am. J. Pathol., 2011, 178, 2032-2043.
Shelton, L. M., et al., Role of Nrf2 in protection against acute kidney injury, Kidney International, 2013, 84, 1090-1095.
Shimozono, R. et al., Nrf2 Activators Attenuate the Progression of Nonalcoholic Steatohepatitis-Related Fibrosis in a Dietary Rat Model, Mol. Pharmacol., 2013, 84, 62-70.
Yamada, K., et al., Impaired nuclear factor erythroid 2-related factor 2 expression increases apoptosis of airway epithelial cells in patients with chronic obstructive pulmonary disease due to cigarette smoking, BMC Pulmonary Medicine, 2016, 16:27, DOI 10.1186/s12890-016-0189-1.
Yasuda, D., et al., Discovery of benzo[g]indoles as a novel class of non-covalent Keap1-Nrf2 protein-protein interaction inhibitor, Bioorganic & Medicinal Chemistry Letters, 2017, 27, 5006-5009.
Zhuang, C., et al., Rapid Identification of Keap1-Nrf2 Small-Molecule Inhibitors through Structure-Based Virtual Screening and Hit-Based Substructure Search, J. Med. Chem., 2014, 57, 1121-1126.
International Search Report and Written Opinion for PCT Application No. PCT/US2019/047015 dated Feb. 19, 2020.

INHIBITORS OF KEAP1-NRF2 PROTEIN-PROTEIN INTERACTION

This application claims the benefit of U.S. Provisional Application No. 62/881,639 filed on Aug. 1, 2019; U.S. Provisional Application No. 62/875,737 filed on Jul. 18, 2019; U.S. Provisional Application No. 62/823,450 filed on Mar. 25, 2019; U.S. Provisional Application No. 62/801,433 filed on Feb. 5, 2019 and U.S. Provisional Application No. 62/719,978 filed on Aug. 20, 2018.

FIELD OF THE INVENTION

The present invention relates to certain sultam compounds, pharmaceutical compositions containing them, methods of making them, and methods of using them including methods for treating disease states, disorders, and conditions associated with the KEAP1-Nrf2 interaction.

BACKGROUND OF THE INVENTION

KEAP1 has been shown to interact with Nrf2, a regulator of the antioxidant response, which is important for the amelioration of oxidative stress. Nrf2 activation is desirable because it leads to coordinated antioxidant and anti-inflammatory responses. However, KEAP1 represses Nrf2 activation. So, there is interest in inhibiting the interaction that KEAP1 has with Nrf2.

In more detail, nuclear factor erythroid 2-related factor 2 (Nrf2) is a basic leucine zipper transcription factor that comprises seven functional domains, Neh1 (Nrf2-ECH homology) to Neh7. Neh1 is a CNC-bZIP domain that allows Nrf2 to interact with small musculoaponeurotic fibrosarcoma (Maf) protein, other transcription partners, and DNA, while Neh3, Neh4, and Neh5 bind to other co-activators to enhance Nrf2 targeted gene expression. Neh2 contains two important motifs known as DLG and ETGE, which are essential for the interaction between Nrf2 and its negative regulator KEAP1 (Kelch-like ECH associated protein 1).

KEAP1 is a substrate adaptor for cullin-based E3 ubiquitin ligase, which binds to Nrf2 under basal conditions and inhibits the transcriptional activity of Nrf2 via ubiquitination and proteasomal degradation of Nrf2. The KELCH domains of the KEAP1 homodimer bind with the ETGE and DLG motifs of the Nrf2-Neh2 domain in the cytosol. Under oxidative stress, thiol modification of KEAP1 cysteine residues leads to conformational change in KEAP1 and dissociation of Nrf2 from KEAP1, which prevents Nrf2 ubiquitination and proteasomal degradation. Nrf2 then translocates into the nucleus and induces anti-oxidative responses by binding to ARE (antioxidant response element) in the promoter of antioxidant genes. More recently, Nrf2 has been shown to bind to promoter regions of pro-inflammatory cytokine genes (with or without ARE) and inhibit RNA Pol II recruitment, leading to inhibition of cytokine gene expression. In addition, Nrf2 negatively regulates the NF-kB signaling, a pathway that is involved in inflammation and apoptosis. Oxidative stress and inflammation are common features in many diseases. Nrf2 signaling pathway plays a critical role in antioxidant and anti-inflammatory responses by regulating >600 genes, many of which are associated with immune diseases. Preclinical and clinical data has demonstrated therapeutic potential of targeting the pathway in neuronal, kidney, cardiovascular, respiratory, eye, skin, and inflammatory bowel diseases. Nrf2 activators could also be useful for treatment of other neuronal diseases including Parkinson's disease (PD), Alzheimer's disease (AD), amyotrophic lateral sclerosis (ALS) (Mimoto, T. et al., Brain Research. 2012, 1446, 109-118) and Friedreich's Ataxia.

In the clinic, dimethyl fumarate, a covalent small molecule that can activate Nrf2 (among other targets) via robust modification of cysteine residues on KEAP1, and is approved in the U.S. to treat multiple sclerosis (MS). Another small molecule targeting the Nrf2 pathway by covalently modifying KEAP1, bardoxolone methyl, has shown clinical efficacy in chronic kidney disease (CKD) (Aleksunes, L. M., et al., J. Pharmacol. Exp. Ther. 2010, 335, 2-12), although the phase III trials were terminated due to adverse events. (Chin, M. P., et al., Am. J. Nephrol. 2014, 39, 499-508). There is an increasing body of evidence supporting a role for the KEAP1-Nrf2 ARE pathway in the regulation of physiological processes that serve to inhibit the development and progression of multiple diseases affecting the kidney (Shelton, L. M., et al., Kidney International 2013, 84, 1090-1095).

Despite the termination of bardoxolone methyl for CKD phase III trials, this drug has ongoing clinical trials in patients with pulmonary arterial hypertension≤https://clinicaltrials.gov/ct2/show/NCT2036970>, accessed Nov. 20, 2017. Nrf2 activation may be involved in myocardial repair and cardiac remodeling and useful for treatment of cardiovascular diseases including but not limited to atherosclerosis (Niture, S. K., et al., Free Radic. Biol. Med. 2014, 66, 36-44), hypertension, and heart failure (Howden, R. Oxidative Medicine and Cellular Longevity 2013, 1-10), acute coronary syndrome, myocardial infarction, cardiac arrhythmias, heart failure with preserved ejection fraction, heart failure with reduced ejection fraction and diabetic cardiomyopathy. (Jiang, S. et al., Expert Opinion on Therapeutic Targets 2016, 20, 1413-1424).

The modulation of the KEAP1-Nrf2 interaction is an attractive approach for intervention and prevention strategies in chronic obstructive pulmonary disease (COPD) (Davies, T. G. et al., J. Med. Chem. 2016, 59, 3991-4006). Evidence suggests that low Nrf2 activity in the lung contributes to the pathophysiology of COPD (Yamada, K., et al., BMC Pulmonary Medicine, 2016, 16, 27), probably due to an altered equilibrium between positive and negative Nrf2 regulators. Compared to wild-type littermates, Nrf2 knockout mice show more pronounced inflammation and neutrophilic elastase activity in the bronchoalveolar lavage and exhibit a higher susceptibility to cigarette smoke—or elastase-induced pulmonary emphysema. Conversely, KEAP1 deletion in the lungs activates Nrf2 signaling and attenuates acute cigarette smoke-induced oxidative stress and inflammation in mice (Boutten, A., et al., Trends Mol. Med. 2011, 17, 363-371). Molecules targeting the KEAP1-Nrf2 protein-protein interaction may treat COPD and other respiratory diseases such as asthma, pulmonary fibrosis (Cho, H-Y., et al., Toxicol. Appl. Pharmacol. 2010, 244, 43-56, Adenuga, D. et al., Biochem. Biophys. Res. Commun. 2010, 403, (3-4), 452-456), and cigarette smoke-induced emphysema (Iizuka, T. et al., Genes to Cells, 2005, 10 (12) 1113-1125.

Inflammatory bowel disease (IBD), including Crohn's disease (CD) and ulcerative colitis (UC), is an inappropriate immune response to environmental changes and the intestinal microbiota in a genetically susceptible background. Accumulating data from both experimental models and clinical studies indicate that oxidative stress and Nrf2 signaling dysfunction contributes to the development of IBD.

Increased reactive oxygen species (ROS) and oxidative injury have been demonstrated in intestinal mucosa of patients with either UC or CD (Cracowski, J-L., et al., Am. J. Gastroenterol. 2002, 97, 99-103; Hatsugai, M., et al., J. Gastroenterol. 2010, 45, 488-500). On the other hand, the levels of intestinal mucosal antioxidants are reduced in IBD patients as compared with control subjects (Rezaie, A., et al., Dig. Dis. Sci. 2007, 52, 2015-2021; Kruidenier, L., et al., Aliment Pharmacol. Ther. 2002, 16, 1997-2015; Catarzi, S., et al., Inflamm. Bowel Dis. 2011, 17, 1674-84). The antioxidant levels and the oxidative stress biomarkers are usually correlated with the disease severity and the extent of intestinal inflammation in the IBD patients. Many of the reduced antioxidants in IBD, including glutathione, glutathione S-transferase (GST), superoxide dismutase, catalase, paraoxonase-1 and metallothionein, are regulated by Nrf2.

Genome-wide association studies have linked IBD-associated single nucleotide polymorphisms (SNPs) to the genes involved in oxidative stress response (e.g. GPX1, GPX4, PARK7, BACH2, PRDX5, ADO, SLC22A4, LRRK2, NOD2, CARD9, HSPA6, DLD, UTS2, and PEX13) (Khor, B., et a. Nature 2011, 474(7351), 307-317), many of which are Nrf2 targeted genes or regulators of Nrf2 signaling.

In line with these findings, a mutation in Nrf2 gene promoter decreases Nrf2 expression and predisposes to UC in a Japanese population (Arisawa, T. et al. Hepato-Gastroenterology 2008, 55, 394-397). In addition, one of the strongest epidemiologic observations in the IBD field is that cigarette smoking is protective against the development of UC (Cope, G. F., et al., Human Toxicol. 1987, 6, 189-193) and the effect is linked to Nrf2 activation by a prominent component of cigarette smoke, carbon monoxide (CO) (Onyiah, J. C. et al., Gut Microbes 2014, 5(2), 220-224).

Preclinical data indicates that Nrf2 plays an important role in protecting intestinal integrity and preserving tolerance to the enteric microbiota. Nrf2 knockout mice were found to be more susceptible to DSS-induced colitis, with a substantial loss of crypts compared with those of wild-type. The increased severity of colitis in Nrf2 knockout mice was found to be associated with decreased expression of antioxidant/phase II detoxifying enzymes including heme-oxygenase-1 (HO-1), NAD(P)H-quinone reductase-1 (NQO1), UDP-glucurosyltransferase 1A1 (UGT1A1), and glutathione S-transferase Mu-1 (GSTM1), and increased expression of proinflammatory genes, including IL-1β, IL-6, IL-8, iNOS, and COX-2 (Khor, T. O., et al., Cancer Res. 2006, 66(24), 11580-11584). In addition, it was demonstrated that enteric microbiota activates Nrf2, leading to induction of Nrf2 targeted genes such as HO-1. Nrf2 activation/HO-1 induction prevents enteric microbiota induced colitis in IL-10 knockout mice, with augmented bacterial clearance (Onyiah, J. C., et al., Gastroenterology 2013, 144, 789-798). More recently, a non-covalent KEAP1-Nrf2 small molecule protein-protein-interaction (PPI) inhibitor was shown to protect human colonic cells against stress-induced cell damage in vitro and ameliorate DSS-induced colitis in mice (Lu, M. C., et al., Nature, Sci Rep. 2016, 6, 26585). The same molecule was also shown to dampen LPS-induced serum cytokines in mice (TNFα, IFNγ, IL-6, IL-12, IL-17) (Jiang, Z-Y., et al., J. Med. Chem. 2015, 58(16), 6410-6421).

Oxidative stress leads to damages of the mucosal layer in the GI tract and bacterial invasion, which in turn stimulates the immune response and initiates IBD. Nrf2 can maintain mucosa homeostasis by protecting against oxidative injury and proinflammatory response in IBD. Thus, pharmacological activation of Nrf2 signaling may represent an effective strategy for the intervention of human IBD (Almenier, H. A. et al., Fronteirs in Bioscience E4, 2012, 1335-1344).

The KEAP1-Nrf2 interaction has also been implicated in skin diseases such as psoriasis (Kadam, D. P., et al., Ind. J. Clin. Biochem. 2010, 25(4), 388-392) and inflammatory eye diseases such as age-related macular degeneration (Schimel, A. M. et al., Am. J. Pathol. 2011, 178, 2032-2043), Fuchs Endothelial Corneal Dystrophy (FECD) (Bitar, M. S. et al., 2012, Invest. Ophthalmol. Visual Sci, 2012, 53 (9), 5806-5813), uveitis and other inflammatory eye conditions. Nrf2 activation may have potential in treating oxidative stress-related inflammatory diseases in general. In addition, KEAP1-Nrf2 interaction inhibitors-shortly also referred to herein as "KEAP1-Nrf2 inhibitors" are envisaged as treatment candidates for other diseases (Abed, D. A. et al., Acta Pharmaceutica Sinica B, 2015, 5 (4), 285-299). They are envisaged for use in the treatment of type-1 diabetes (Aleksunes, L. M. et al., J. Pharmacol. Exp. Ther. 2010, 333 (1), 140-151), type-2 diabetes (Bitar, M. S. et al., Am. J. Phsiol. Endocrinol. Metab. 2011, 301 (6), E1119-1129; Rochette, L. et al., Biochimica et Biophysica Acta 2014, 1840 (9), 2709-2729, Bhakkiyalakshmi, E. et al., Pharmacol. Research 2015, 91, 104-114), and insulin resistance (Houstis, N. et al., Nature, 2006, 440 (7086) 944-948), sepsis-induced acute kidney injury and acute kidney injury (see Shelton, 2013, cited above), preeclampsia (Kweider, N. et al., Annals of Anatomy, 2014, 196, 268-277), acute mountain sickness (Lisk, C. et al., Free Radical Biology and Medicine, 2013, 63, 264-273), dermatitis and topical effects of radiation (Schafer, M. et al., Genes and Development 2010, 24(10), 1045), immunosuppression due to radiation exposure (Kim, J.-H. et al., J. Clin. Investigation 2014, 124, 730-741), non-alcoholic steatohepatitis (Shimozono, R. et al., Mol. Pharmacol. 2013, 84, 62-70; Chowdry, S. et al., Free Radical Biology and Medicine, 2010, 48, 357-371), viral hepatitis, cirrhosis, and toxin-induced liver disease such as acetaminophen-induced hepatic disease (see Howden, 2013, cited above).

BRIEF SUMMARY OF THE INVENTION

Embodiments of the present invention relate to compounds, pharmaceutical compositions containing them, methods of making and purifying them, methods of using them as KEAP1-Nrf2 inhibitors and methods for using them the treatment of disease states, disorders, and conditions associated with the KEAP1-Nrf2 interaction. An additional embodiment of the invention is a method of treating a subject suffering from or diagnosed with a disease, disorder, or medical condition associated with the KEAP1-Nrf2 interaction using compounds of the invention or active agents of the invention.

Additional embodiments, features, and advantages of the invention will be apparent from the following detailed description and through practice of the invention.

Embodiments of this invention are compounds of Formula (I), and pharmaceutically acceptable salts thereof wherein X is CH or N;

Q is CH or N;

M is CH or N;
  wherein
    when X is N, each of Q and M is CH;
    when Q is N, each of X and M is CH; and
    when M is N, each of X and Q are CH;

$R^{15}$ is $CH_3$ or Cl;

$R^{13}$ is H, F or $C_1$-$C_4$alkyl;

$R^{14}$ is H, F or $C_1$-$C_4$alkyl;

HetA is selected from the group consisting of wherein $R^1$ is selected from the group consisting of $C_3$-$C_4$cycloalkyl, $C_1$-$C_4$alkyl and $C_1$-$C_4$alkyl monosubstituted with cyclopropyl or cyclobutyl;

$R^2$ is selected from the group consisting of H, $C_1$-$C_4$alkyl and $C_1$-$C_4$perhaloalkyl;

$R^3$ is H or $C_1$-$C_4$alkyl;

$R^4$ is selected from the group consisting of $C_1$-$C_4$alkyl, $C_1$-$C_4$perhaloalkyl and $C_3$-$C_4$cycloalkyl;

$R^7$ is H or $C_1$-$C_4$alkyl;

$R^8$ is $C_1$-$C_4$alkyl;

$R^9$ is $C_1$-$C_4$alkyl;

$R^{10}$ is selected from the group consisting of H, —$OC_3$-$C_4$cycloalkyl and —$OC_1$-$C_4$perhaloalkyl;

HetB is selected from the group consisting of wherein

Z is selected from the group consisting of O, $CH_2$, NH and $N(CH_3)$;

T is CH or N;

Y is CH or N;

W is CH or N;

V is O or $N(CH_3)$;

$R^{16}$ is H or F;

$R^{17}$ is H or F;

n is 0, 1 or 2;

$R^{18}$ is selected from the group consisting of H, —CN, halo, $C(O)NH_2$, $C_1$-$C_4$alkyl and $C_1$-$C_4$perhaloalkyl;

$R^{19}$ is selected from the group consisting of H; CN; halo; $C(O)NH_2$; $N(R^{38})C_1$-$C_6$alkyl; $C_1$-$C_4$alkyl; $C_1$-$C_4$perhaloalkyl;

$OC_1$-$C_6$alkyl;

$OC_1$-$C_6$alkyl substituted with one or two substituents selected from the group consisting of —OH, —$OCH_3$, —$O(CH_2)_3OH$, —$N(R^{36})R^{37}$, $C_1$-$C_4$alkyl,

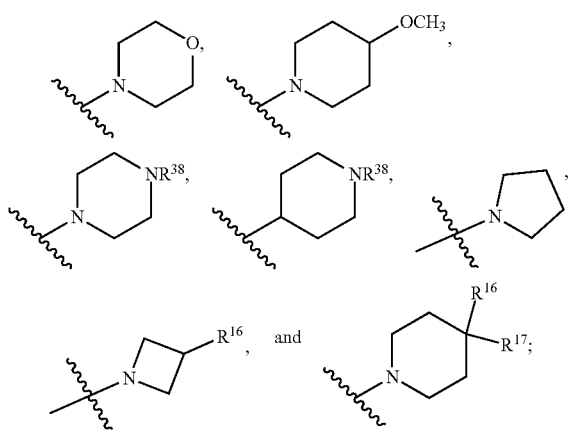

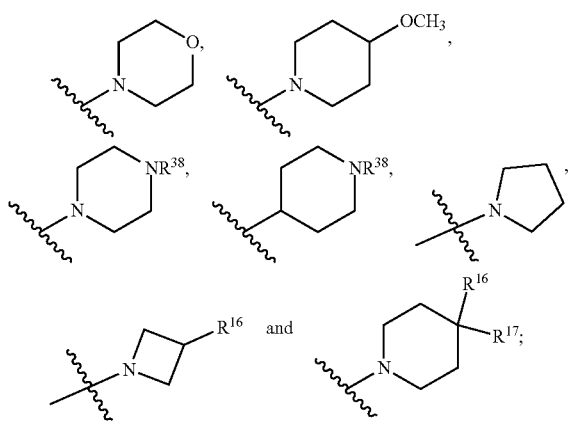

—N(R$^{38}$)C$_1$-C$_6$alkyl substituted with one or two substituents selected from the group consisting of OH, —OCH$_3$, —N(R$^{36}$)R$^{37}$, C$_1$-C$_4$alkyl, and C$_1$-C$_4$alkyl monosubstituted with a substituent selected from the group consisting of —C(O)NHCH$_2$CH$_2$OH, —C(O)NHCH$_2$CH$_2$OCH$_2$CH$_2$NH$_2$, C(O)NH$_2$ and OH;

R$^{20}$ is H or C$_1$-C$_4$alkyl;

R$^{21}$ is selected from the group consisting of H, —CN, halo, C$_1$-C$_4$alkyl and C$_1$-C$_4$perhaloalkyl;

R$^{22}$ and R$^{23}$ are taken together with the carbon to which they are attached to form (a) the moiety

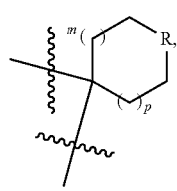

wherein R is selected from the group consisting of CH$_2$, NR$^{38}$ and O, m is 0 or 1, and p is 0 or 1; or (b) the moiety

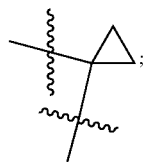 [SMILES: *C1(*)CC1]

R$^{22'}$ is selected from the group consisting of H, C$_1$-C$_4$alkyl and C$_3$-C$_4$cycloalkyl, and R$^{23'}$ is selected from the group consisting of H, C$_1$-C$_4$alkyl and C$_3$-C$_4$cycloalkyl;

R$^{24}$ is selected from the group consisting of H; CN; halo; C(O)NH$_2$;

C(O)(NH)C$_3$-C$_4$cycloalkyl   N(R$^{38}$)C$_1$-C$_6$alkyl; C$_1$-C$_4$alkyl; C$_1$-C$_4$perhaloalkyl;

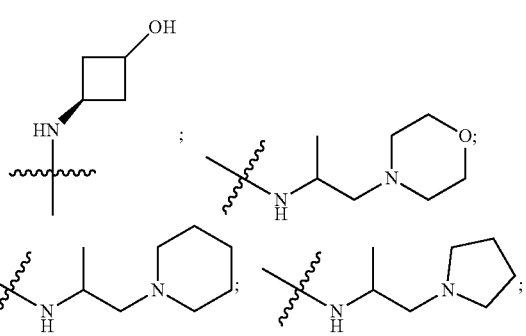

OC$_1$-C$_6$alkyl;

OC$_1$-C$_6$alkyl substituted with one or two substituents selected from the group consisting of —OH, —OCH$_3$, —O(CH$_2$)$_3$OH, —N(R$^{36}$)R$^{37}$, C$_1$-C$_4$alkyl;

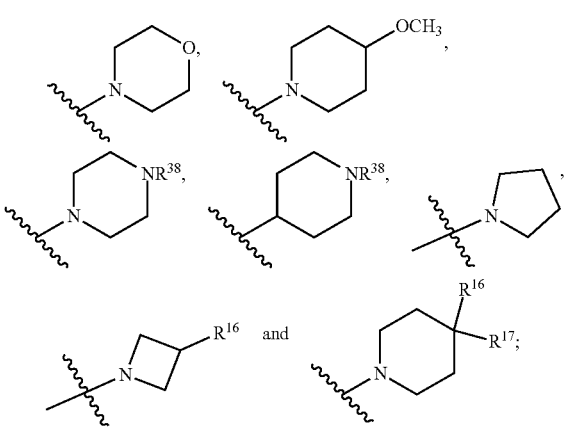

—N(R$^{38}$)C$_1$-C$_6$alkyl substituted with one or two substituents selected from the group consisting of OH, —OCH$_3$, —N(R$^{36}$)R$^{37}$, C$_1$-C$_4$alkyl,

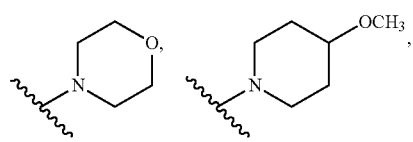

-continued

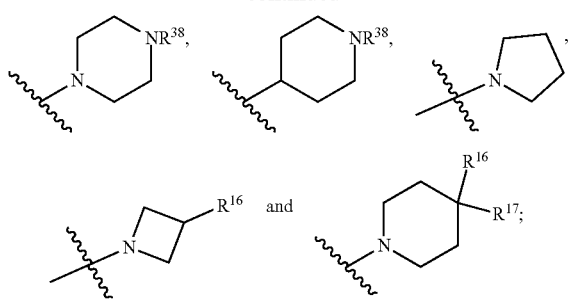

and

C₁-C₄alkyl monosubstituted with a substituent selected from the group consisting of —C(O)NHCH₂CH₂OH, —C(O)NHCH₂CH₂OCH₂CH₂NH₂, C(O)NH₂ and OH;

$R^{25}$ is selected from the group consisting of H; CN; halo; C(O)NH₂; $N(R^{38})C_1-C_6$alkyl; $C_1-C_4$alkyl; $C_1-C_4$perhaloalkyl;

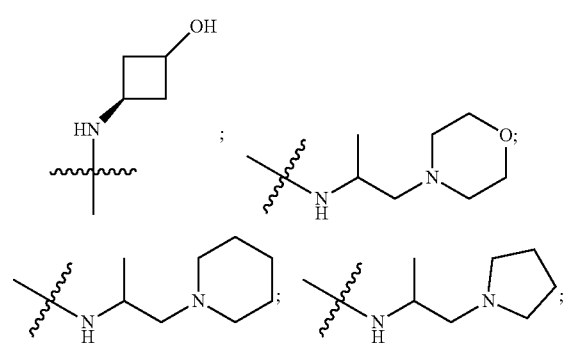

OC₁-C₆alkyl;

OC₁-C₆alkyl substituted with one or two substituents selected from the group consisting of —OH, —OCH₃, —O(CH₂)₃OH, —N(R³⁶)R³⁷, C₁-C₄alkyl,

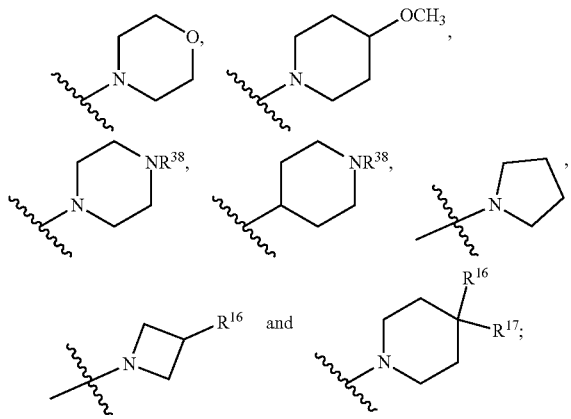

—N(R³⁸)C₁-C₆alkyl substituted with one or two substituents selected from the group consisting of OH, —OCH₃, —N(R³⁶)R³⁷, C₁-C₄alkyl,

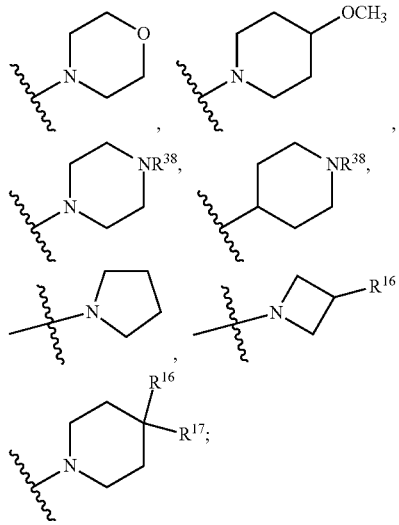

and

C₁-C₄alkyl monosubstituted with a substituent selected from the group consisting of —C(O)NHCH₂CH₂OH, —C(O)NHCH₂CH₂OCH₂CH₂NH₂, C(O)NH₂ and OH;

$R^{26}$ is selected from the group consisting of H, —CN, halo, $C_1-C_4$alkyl and $C_1-C_4$perhaloalkyl;

$R^{27}$ is H or $C_1-C_4$alkyl;

$R^{36}$ and $R^{37}$ are independently selected from the group consisting of H and $C_1-C_4$alkyl;

$R^{38}$ is H or $C_1-C_4$alkyl;

provided that when HetA is

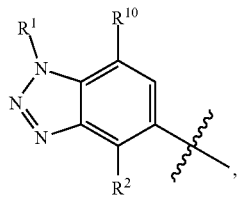

then HetB is not

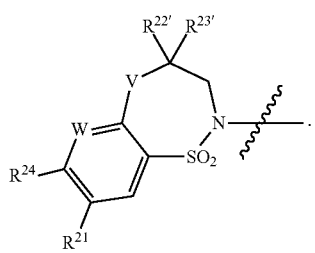

Illustrative embodiments of Formula (I) are compounds selected from the group consisting of
3-(7-(Difluoromethoxy)-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;
(*S)-3-(7-(Difluoromethoxy)-1-methyl-1H-benzo[d][1,2,3]triazol-5-yl)-3-(3-((((*R)-5,5-dioxido-7,7a,8,9,10,11- hexahydro-6H-dipyrido[2,1-d:2',3'-f][1,2,5]thiadiazepin-6-yl)methyl)-4-methylphenyl)propanoic acid;
(*R)-3-(7-(Difluoromethoxy)-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;
3-(7-Cyclopropoxy-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid
(*S)-3-(7-Cyclopropoxy-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;
(*R)-3-(7-Cyclopropoxy-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;
(*S)-3-(3-((1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;
(*R)-3-(3-((1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;
(*S)-3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;
(*S)-3-(3-(((*S)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;
3-(1-(Cyclopropylmethyl)-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;
(*S)-3-(1-(cyclopropylmethyl)-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;
(*R)-3-(1-(cyclopropylmethyl)-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;
3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic acid;
(*S)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic acid;
(R)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic acid;
2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;
(*S)-2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;
(*R)-2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;
3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;
(*S)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;
(*R)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;
3-(1-Cyclopropyl-4-methyl-1H-benzo[d][1,2,3]triazol-5-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid;
(*S)-3-(1-Cyclopropyl-4-methyl-1H-benzo[d][1,2,3]triazol-5-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid;
(*R)-3-(1-Cyclopropyl-4-methyl-1H-benzo[d][1,2,3]triazol-5-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid;
(*S)-3-(3-((1,1-Dioxidospiro[benzo[b][1,4,5]oxathiazepine-4,3'-oxetan]-2(3H)-yl)methyl)-4-methylphenyl)-3-(8-methyl-3-(trifluoromethyl)-[1,2,4]triazolo[4,3-a]pyridin-7-yl)propanoic acid;
(*S)-3-(4-Methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;
3-(3-((3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid;
(*S)-3-(3-(((*S)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid;
(*R)-3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid;
(*S)-3-(3-(((*S)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid;
(*S)-3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid;
3-(6-((3-cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;
(*S)-3-(6-(((*S)-3-cyano-5,5-dioxido-7,7a,8,9,10,11-hexahydro-6H-dipyrido[2,1-d:2',3'-f][1,2,5]thiadiazepin-6-yl)

methyl)-5-methylpyridin-2-yl)-3-(8-methyl-3-(trifluoromethyl)-[1,2,4]triazolo[4,3-a]pyridin-7-yl)propanoic acid;

(*S)-3-(6-(((*R)-3-cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

(*R)-3-(6-(((*R)-3-cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

(*R)-3-(6-(((*S)-3-cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

(*S)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid;

(*R)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid;

(R/S)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*S)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*R)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(R/S)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid;

(*S)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid;

(*R)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid;

2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

(*S)-2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

(*R)-2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methyl-3-trifluoromethyl)-[1,2,4]triazolo[4,3-a]pyridine-7-yl)propanoic acid;

(*S)-3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methy-3-trifluoromethyl)-[1,2,4]triazolo[4,3-a]pyridine-7-yl)propanoic acid;

(*R) 3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methyl-3-trifluoromethyl)-[1,2,4]triazolo[4,3-a]pyridine-7-yl)propanoic acid;

(R/S)-3-(3-(Difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*S)-3-(3-(Difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*R)-3-(3-(Difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(R/S)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid;

(*S)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid;

(*R)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid;

(R/S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic acid;

(*S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic acid;

(*R)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic acid;

(R/S)-3-(1-Ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*S)-3-(1-Ethyl-4-methyl-1H-benzo[d][1,2,3]triazol-5-yl)-2,2-dimethyl-3-(6-methyl-5-((8'-methyl-1',1'-dioxido-2, 3,5,6-tetrahydrospiro[pyran-4,4'-pyrido[2,3-b][1,4,5]ox-athiazepin]-2'(3'H)-yl)methyl)pyridin-3-yl)propanoic acid;

(*R)-3-(1-Ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]ox-athiazepin]-2'(3'H)-yl)methyl)pyridin-3-yl)propanoic acid;

(*R)-3-(4-methyl-3-((8'-methyl-1',1'-dioxidospiro[cyclo-propane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

3-(1-(Cyclopropylmethyl)-4-(difluoromethyl-1H-benzo[d][1,2,3]triazol-5-yl)-3-(3-((R-5,5-dioxido-7a,8,9,10-tetra-hydropyridi[2,3-f]pyrrolo[2,1-d][1,2,5]thiadiazepin-6(7H)-yl)methyl)-4-methylphenyl)propanoic acid;

(*S)-3-(1-(Cyclopropylmethyl)-4-(difluoromethyl-1H-benzo[d][1,2,3]triazol-5-yl)-3-(3-((R-5,5-dioxido-7a,8,9,10-tetrahydropyridi[2,3-f]pyrrolo[2, 1-d][1,2,5]thiadiaz-epin-6(7H)-yl)methyl)-4-methylphenyl)propanoic acid;

3-(1-(Cyclopropylmethyl)-4-methyl-1H-benzo[d][1,2,3]tri-azol-5-yl)-3-(3-((1',1'-dioxidospiro[oxetane-3,3'-pyrido[2,3-b][1,4,5]oxathiazepin]-2'(3'H)-yl)methyl)-4-meth-ylphenyl)propanoic acid;

(*R)-3-(1-(Cyclopropylmethyl)-4-(difluoromethyl-1H-benzo[d][1,2,3]triazol-5-yl)-3-(3-((R-5,5-dioxido-7a,8,9,10-tetrahydropyridi[2,3-f]pyrrolo[2,1-d][1,2,5]thiadiaz-epin-6(7H)-yl)methyl)-4-methylphenyl)propanoic acid;

(*S)-3-(1-(Cyclopropylmethyl)-4-methyl-1H-benzo[d][1,2,3]triazol-5-yl)-3-(3-((1',1'-dioxidospiro[oxetane-3,4'-pyrido[2,3-b][1,4,5]oxathiazepin]-2'(3'H)-yl)methyl)-4-methylphenyl)propanoic acid;

(*R)-3-(1-(Cyclopropylmethyl)-4-methyl-1H-benzo[d][1,2,3]triazol-5-yl)-3-(3-((1',1'-dioxidospiro[oxetane-3,4'-pyrido[2,3-b][1,4,5]oxathiazepin]-2'(3'H)-yl)methyl)-4-methylphenyl)propanoic acid;

3-(4-(Difluoromethyl-1-methyl-1H-benzo[d][1,2,3]triazol-5-yl)-3-(3-(((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid;

(*S)-3-(4-(Difluoromethyl-1-methyl-1H-benzo[d][1,2,3]tri-azol-5-yl)-3-(3-(((R-5,5-dioxido-7a,8,9,10-tetrahydro-pyridi[2,3-f]pyrrolo[2,1-d][1,2,5]thiadiazepin-6(7H)-yl)methyl)-4-methylphenyl)propanoic acid;

(*R) 3-(4-(Difluoromethyl-1-methyl-1H-benzo[d][1,2,3]tri-azol-5-yl)-3-(3-(((R-5,5-dioxido-7a,8,9,10-tetrahydro-pyridi[2,3-f]pyrrolo[2,1-d][1,2,5]thiadiazepin(6(7H)-yl)methyl)-4-methylphenyl)propanoic acid;

3-(1-(Cyclopropylmethyl)-4-methyl-1H-benzo[d][1,2,3]tri-azol-5-yl)-3-(3-((1',1'-dioxidospiro[benzo[b][1,4,5]ox-athiazepine-4,3'-oxetan]-2, (3H)-yl)methyl)-4-methylphe-nyl)propanoic acid;

3-(1-(Cyclopropylmethyl)-4-methyl-1H-benzo[d][1,2,3]tri-azol-5-yl)-3-(4-methyl-3-((5'-methyl-1',1'-dioxido-5'H-spiro[cyclopropane-1,4'-pyrido[2,3-f][1,2,5]thiadiaz-epin]-2'(3'H)-yl)methyl)phenyl)propanoic acid;

(*R)-3-(1-(cyclopropylmethyl)-4-methyl-1H-benzo[d][1,2,3]triazol-5-yl)-3-(3-((1',1'-dioxidospiro[benzo[b][1,4,5]oxathiazepin-4,3'-oxetan]-2, (3H)-yl)methyl)-4-meth-ylphenyl)propanoic acid;

(*S)-3-(1-(Cyclopropylmethyl)-4-methyl-1H-benzo[d][1,2,3]triazol-5-yl)-3-(3-((1',1'-dioxidospiro[benzo[b][1,4,5]oxathiazepin-4,3'-oxetan]-2, (3H)-yl)methyl)-4-meth-ylphenyl)propanoic acid;

(*S)-3-(1-(Cyclopropylmethyl)-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiaz-epin]-2'(3'H)-yl)methyl)phenyl)propanoic acid;

(*R)-3-(1-(Cyclopropylmethyl)-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiaz-epin]-2'(3'H)-yl)methyl)phenyl)propanoic acid;

3-(1-(Cyclopropylmethyl)-4-methyl-1H-benzo[d][1,2,3]tri-azol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(*R)-3-(1-(Cyclopropylmethyl)-4-methyl-1H-benzo[d][1,2,3]triazol-5-yl)-3-(4-methyl-3-(((*R)-7a-methyl-5,5-di-oxido-7a,8,9,10-tetrahydropyrido[2,3-f]pyrrolo[2,1-d][1,2,5]thiadiazepin-6(7H)-yl)methyl)phenyl)propanoic acid;

(*S)-3-(1-(Cyclopropylmethyl)-4-methyl-1H-benzo[d][1,2,3]triazol-5-yl)-3-(4-methyl-3-(((*R)-7a-methyl-5,5-di-oxido-7a,8,9,10-tetrahydropyrido[2,3-f]pyrrolo[2,1-d][1,2,5]thiadiazepin-6(7H)-yl)methyl)phenyl)propanoic acid;

3-(4-Chloro-3-(((*S)-5,5-dioxido-7,7a,8,9,10,11-hexa-hydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid;

(*S)-3-(4-Chloro-3-(((*S)-5,5-dioxido-7,7a,8,9,10,11-hexa-hydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid;

(*R)-3-(4-Chloro-3-(((*S)-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid;

3-(4-Chloro-3-((1',1'-dioxoidospiro[oxetane-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyri-dine-7-yl)propanoic acid;

(*R)-3-(4-Chloro-3-((1',1'-dioxoidospiro[oxetane-3,4'-pyrido[2,3-b][1,4,5]oxathiazepin]-2'(3'H)-yl)methyl)phe-nyl)-3-(8-methyl-3-(trifluoromethyl)-[1,2,4]triazolo[4,3-a]pyridine-7-yl)propanoic acid;

(*S)-3-(4-Chloro-3-((1',1'-dioxoidospiro[oxetane-3,4'-pyrido[2,3-b][1,4,5]oxathiazepin]-2'(3'H)-yl)methyl)phe-nyl)-3-(8-methyl-3-(trifluoromethyl)-[1,2,4]triazolo[4,3-a]pyridine-7-yl)propanoic acid;

3-(4-Chloro-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid;

(*R)-3-(4-Chloro-3-(((*S)-3-methyl-5,5-dioxido-7,7a,8,9,10,11-hexahydro-6H-dipyrido[2,1-d:2',3'-f][1,2,5]thiadi-azepin-6-yl)methyl)phenyl)-3-(8-methyl-3-(trifluorom-ethyl)-[1,2,4]triazolo[4,3-a]pyridine-7-yl)propanoic acid;

(*S)-3-(4-Chloro-3-(((*S)-3-methyl-5,5-dioxido-7,7a,8,9,10,11-hexahydro-6H-dipyrido[2,1-d:2',3'-][1,2,5]thiadi-azepin-6-yl)methyl)phenyl)-3-(8-methyl-3-(trifluorom-ethyl)-[1,2,4]triazolo[4,3-a]pyridine-7-yl)propanoic acid;

3-(4-Chloro-3-(((*S)-3-fluoro-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid;

(*R)-3-(4-Chloro-3-(((*S)-3-fluoro-5,5-dioxido-7,7a,8,9,10,11-hexahydro-6H-dipyrido[2,1-d:2',3'-f][1,2,5]thiadi-azepin-6-yl)methyl)phenyl)-3-(8-methyl-3-(trifluorom-ethyl)-[1,2,4]triazolo[4,3-a]pyridine-7-yl)propanoic acid;

(*S)-3-(4-Chloro-3-(((*S)-3-fluoro-5,5-dioxido-7,7a,8,9,10,11-hexahydro-6H-dipyrido[2,1-d:2',3'-f][1,2,5]thiadi-azepin-6-yl)methyl)phenyl)-3-(8-methyl-3-(trifluorom-ethyl)-[1,2,4]triazolo[4,3-a]pyridine-7-yl)propanoic acid;

3-(4-Chloro-3-((1',1'-dioxoidospiro[benzo[b]]oxethiazepine-4,3'-oxetan]-2(3H)-yl)methyl)phenyl)-3-(8-methyl-3-(trifluoromethyl)-[1,2,4]triazolo[4,3-a]pyridine-7-yl)propanoic acid;

(*R)-3-(4-Chloro-3-((1',1'-dioxoidospiro[benzo[b]]oxethiazepine-4,3'-oxetan]-2(3H)-yl)methyl)phenyl)-3-(8-methyl-3-(trifluoromethyl)-[1,2,4]triazolo[4,3-a]pyridine-7-yl)propanoic acid;

(*S)-3-(4-Chloro-3-((1',1'-dioxoidospiro[benzo[b]]oxethiazepine-4,3'-oxetan]-2(3H)-yl)methyl)phenyl)-3-(8-methyl-3-(trifluoromethyl)-[1,2,4]triazolo[4,3-a]pyridine-7-yl)propanoic acid;

(*S)-3-(3-((8-Fluoro-1,1-dioxidospiro[benzo[b][1,4,5]oxathiazepin]-4,1'-cyclopropan]-2(3H)-yl)methyl)-4-methylphenyl)-3-(8-methyl-3-(trifluoromethyl)-[1,2,4]triazolo[4,3-a]pyridin-7-yl)propanoic acid;

(*S)-3-(3-((8-Fluoro-1,1-dioxidospiro[benzo[b][1,4,5]oxathiazepine-4,3'-oxetan]-2(3H)-yl)methyl]-4-methylphenyl)-3-(8-methyl-3-(trifluoromethyl)-[1,2,4]triazolo[4,3-a]pyridin-7-yl)propanoic acid;

(*S)-3-(3-((7'-Chloro-1',1'-dioxidospiro(cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-((7'-((2-Hydroxyethyl)amino-1',1'-dioxidospiro[cyclopropane-1.4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridinn-7-yl)propanoic acid;

(*S)-3-(3-((7'-((2-Hydroxypropyl)amino-1',1'-dioxidospiro[cyclopropane-1.4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridinn-7-yl)propanoic acid;

(*S)-3-(3-((7'-Hydroxy-1',1'-dioxidospiro[cyclopropane-1,4'-pyrido[2,3,-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

3-(4-Cyano-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]trizolo[4,3-a]pyridine-7-yl)propanoic acid;

(*S)-3-(4-Cyano-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]trizolo[4,3-a]pyridine-7-yl)propanoic acid;

(*R)-3-(4-Cyano-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]trizolo[4,3-a]pyridine-7-yl)propanoic acid;

(*S)-3-(3-((7'-((3-Methoxypropyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

(*S)-3-(-3-((7'-((3-Hydroxypropyl)(methyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

(*S)-3-(-3-((7'-((3-Methoxypropoxy)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

(*S)-3-(-3-((7'-((3-Hydroxyethyl)(methyl)amino)-1',1'-dioxidospiro[cyclopropane-1,4'-pyrido[2,3-b][1,4,5]oxathiazepin]-2'(3'H)-yl)methyl-4-methylphenyl)-3-(8-methyl-3-(trifluoromethyl)-[1,2,4]triazolo[4,3-a]pyridine-7-yl)propanoic acid;

(*S)-3-(4-Methyl-((7'-((2-morpholinoethyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

(*S)-3-(3-((1',1'-Dioxido-7'-((2-(piperidin-1-yl)ethyl)amino)spiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

(*S)-3-(3-((7'-(Butylamino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

3-(3-((7'-((3-Hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-3-(3-((7'-((3-Hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*R)-3-(3-((7'-((3-Hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

3-(3-((7'-(((R)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

3-(3-((7'-(((S)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-3-(3-((7'-(((R)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4][triazolo[4,3-a]pyridine-7-yl)propanoic acid;

(*R)-3-(3-((7'-(((R)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4][triazolo[4,3-a]pyridine-7-yl)propanoic acid;

(*S)-3-(3-((7'-(((S)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4][triazolo[4,3-a]pyridine-7-yl)propanoic acid;

(*R)-3-(3-((7'-(((S)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4][triazolo[4,3-a]pyridine-7-yl)propanoic acid;

(*S)-3-(3-((7'-(((S)-4-Hydroxybutan-2-yl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4- methylphenyl)-2,2-dimethyl-3-(8-methyl-3-(trifluoromethyl)-[1,2,4]triazolo[4,3-a]pyridine-7-yl) propanoic acid;
(*S)-3-(3-((7'-(((R)-3-Hydroxy-3-methylbutan-2-yl) amino)-8'-methyl-1',1'-dioxido-2,3,5,6-tetrahydrospiro [pyran-4,4'-pyrido[2,3-b][1,4,5]oxathiazepin]-2'(3'H)-yl) methyl)-4-methylphenyl)-2,2-dimethyl-3-(8-methyl-3-(trifluoromethyl)-[1,2,4]triazolo[4,3-a]pyridin-7-yl) propanoic acid;
(*R)-3-(3-((7'-(((1s,3S)-3-Hydroxycyclobutyl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl) propanoic acid;
2,2-Dimethyl-3-(4-methyl-3-((8'-methyl-1',1'-dioxido3-(3-((7'-(((R*)-4-hydroxybutan-2-yl)amino)-8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl) propanoic acid;
2,2-Dimethyl-3-(4-methyl-3-((8'-methyl-1',1'-dioxido-3-(3-((7'-(((*S)-4-hydroxybutan-2-yl)amino)-8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl) propanoic acid;
(*R)-3-(3-((7'-(3-((2-Hydroxyethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;
3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoic acid;
(3*R)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl) propanoic acid;
(3*S)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl) propanoic acid;
3-(5,8-Dimethyl-3)-(trifluoromethyl)-[1,2,4-triazolo[4,3-a] pyridine-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methylpropanoic acid;
(3*R)-3-(5,8-Dimethyl-3)-(trifluoromethyl)-[1,2,4-triazolo [4,3-a]pyridine-7-yl)-3-(3-(((*S)-5,5-dioxido-7,7a,8,9, 10,11-hexahydro-6H-dipyrido[2,1-d:2',3'-f][1,2,5]thiadiazepin-6-yl)methyl)-4-methylphenyl)-2-methylpropanoic acid;
(3*S)-3-(5,8-Dimethyl-3)-(trifluoromethyl)-[1,2,4-triazolo [4,3-a]pyridine-7-yl)-3-(3-(((*S)-5,5-dioxido-7,7a,8,9, 10,11-hexahydro-6H-dipyrido[2,1-d:2',3'-f][1,2,5]thiadiazepin-6-yl)methyl)-4-methylphenyl)-2-methylpropanoic acid;
(R/S)-3-(3-(((*S)-5,5-Dioxido-7a,8,10,11-tetrahydro-[1,4] oxazino[3,4-d]pyrido[2,3-f][1,2,5]thiadiazepin-6(7H)-yl) methyl)-4-methylphenyl)-3-(1-ethyl-4-methyl-1H-benzo [d][1,2,3]triazol-5-yl)propanoic acid;

(*S)-3-(3-(((*S)-5,5-Dioxido-7a,8,10,11-tetrahydro-[1,4] oxazino[3,4-d]pyrido[2,3-f][1,2,5]thiadiazepin-6(7H)-yl) methyl)-4-methylphenyl)-3-(1-ethyl-4-methyl-1H-benzo [d][1,2,3]triazol-5-yl)propanoic acid;
(*R)-3-(3-(((*S)-5,5-Dioxido-7a,8,10,11-tetrahydro-[1,4] oxazino[3,4-d]pyrido[2,3-f][1,2,5]thiadiazepin-6(7H)-yl) methyl)-4-methylphenyl)-3-(1-ethyl-4-methyl-1H-benzo [d][1,2,3]triazol-5-yl)propanoic acid;
(R/S)-3-(3-(((*R)-5,5-Dioxido-7a,8,10,11-tetrahydro-[1,4] oxazino[3,4-d]pyrido[2,3-f][1,2,5]thiadiazepin-6(7H)-yl) methyl)-4-methylphenyl)-3-(1-ethyl-4-methyl-1H-benzo [d][1,2,3]triazol-5-yl)propanoic acid;
(*S)-3-(3-(((*R)-5,5-Dioxido-7a,8,10,11-tetrahydro-[1,4] oxazino[3,4-d]pyrido[2,3-f][1,2,5]thiadiazepin-6(7H)-yl) methyl)-4-methylphenyl)-3-(1-ethyl-4-methyl-1H-benzo [d][1,2,3]triazol-5-yl)propanoic acid;
(*R)-3-(3-(((*R)-5,5-Dioxido-7a,8,10,11-tetrahydro-[1,4] oxazino[3,4-d]pyrido[2,3-f][1,2,5]thiadiazepin-6(7H)-yl) methyl)-4-methylphenyl)-3-(1-ethyl-4-methyl-1H-benzo [d][1,2,3]triazol-5-yl)propanoic acid;
(R/S)-3-(3-(((*S)-5,5-Dioxido-7,7a,8,9,10,11-hexahydro-6H-dipyrido[2,1-d:2',3'-f][1,2,5]thiadiazepin-6-yl) methyl)-4-methylphenyl)-3-(1-ethyl-4-methyl-1H-benzo [d][1,2,3]triazol-5-yl)propanoic acid;
(*S)-3-(3-(((*S)-5,5-Dioxido-7,7a,8,9,10,11-hexahydro-6H-dipyrido[2,1-d:2',3'-f][1,2,5]thiadiazepin-6-yl) methyl)-4-methylphenyl)-3-(1-ethyl-4-methyl-1H-benzo [d][1,2,3]triazol-5-yl)propanoic acid;
(*R)-3-(3-(((*S)-5,5-Dioxido-7,7a,8,9,10,11-hexahydro-6H-dipyrido[2,1-d:2',3'-f][1,2,5]thiadiazepin-6-yl) methyl)-4-methylphenyl)-3-(1-ethyl-4-methyl-1H-benzo [d][1,2,3]triazol-5-yl)propanoic acid;
(R/S)-3-(3-(((*R)-5,5-Dioxido-7,7a,8,9,10,11-hexahydro-6H-dipyrido[2,1-d:2',3'-f][1,2,5]thiadiazepin-6-yl) methyl)-4-methylphenyl)-3-(1-ethyl-4-methyl-1H-benzo [d][1,2,3]triazol-5-yl)propanoic acid;
(*S)-3-(3-(((*R)-5,5-Dioxido-7,7a,8,9,10,11-hexahydro-6H-dipyrido[2,1-d:2',3'-f][1,2,5]thiadiazepin-6-yl) methyl)-4-methylphenyl)-3-(1-ethyl-4-methyl-1H-benzo [d][1,2,3]triazol-5-yl)propanoic acid;
(*R)-3-(3-(((*R)-5,5-Dioxido-7,7a,8,9,10,11-hexahydro-6H-dipyrido[2,1-d:2',3'-f][1,2,5]thiadiazepin-6-yl) methyl)-4-methylphenyl)-3-(1-ethyl-4-methyl-1H-benzo [d][1,2,3]triazol-5-yl)propanoic acid;
(R/S)-3-(3-(((S)-5,5-Dioxido-7a,8,9,10-tetrahydrobenzo[f] pyrrolo[2,1-d][1,2,5]thiadiazepin-6(7H)-yl)methyl)-4-methylphenyl)-3-(1-ethyl-4-methyl-1H-benzo[d][1,2,3] triazol-5-yl)propanoic acid;
(*S)-3-[3-[(5,5-Dioxo-7a,8,9,10-tetrahydro-7H-pyrrolo[2, 1-d][1,2,5]benzothiadiazepin-6-yl)methyl]-4-methyl-phenyl]-3-(1-ethyl-4-methyl-benzotriazol-5-yl)propanoic acid;
(*R)-3-[3-[(5,5-Dioxo-7a,8,9,10-tetrahydro-7H-pyrrolo[2, 1-d][1,2,5]benzothiadiazepin-6-yl)methyl]-4-methyl-phenyl]-3-(1-ethyl-4-methyl-benzotriazol-5-yl)propanoic acid;
(R/S)-3-[3-[(4,4-Dimethyl-1,1-dioxo-3H-pyrido[2,3-b][1,4, 5]oxathiazepin-2-yl)methyl]-4-methyl-phenyl]-3-(1-ethyl-4-methyl-benzotriazol-5-yl)propanoic acid;
(R/S)-3-(3-((4,4-Dimethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl) propanoic acid;
(R/S)-3-(3-(((R)-5,5-Dioxido-7a,8,9,10-tetrahydrobenzo[f] pyrrolo[2,1-d][1,2,5]thiadiazepin-6(7H)-yl)methyl)-4-methylphenyl)-3-(1-ethyl-4-methyl-1H-benzo[d][1,2,3] triazol-5-yl)propanoic acid;

(*S)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;

(*R)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;

(R/S)-3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;

(*S)-3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;

(*R)-3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;

(*S)-3-(3-((4,4-Dimethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic acid;

(*R)-3-(3-((4,4-Dimethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic acid;

(R/S)-3-(3-((4,4-Dimethyl-1,1-dioxido-3,4-dihydro-2H-pyrido[2,3-b][1,4,5]oxathiazepin-2-yl)methyl)-4-methylphenyl)-3-(3-methyl-[1,2,4]triazolo[4,3-a]pyridin-7-yl)propanoic acid;

(R/S)-3-(3-((4,4-Dimethyl-1,1-dioxido-3,4-dihydro-2H-benzo[b][1,4,5]oxathiazepin-2-yl)methyl)-4-methylphenyl)-3-(3-methyl-[1,2,4]triazolo[4,3-a]pyridin-7-yl)propanoic acid;

(R/S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(3-methyl-[1,2,4]triazolo[4,3-a]pyridin-7-yl)propanoic acid;

(*S)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(3-methyl-[1,2,4]triazolo[4,3-a]pyridin-7-yl)propanoic acid;

(*R)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(3-methyl-[1,2,4]triazolo[4,3-a]pyridin-7-yl)propanoic acid;

(*S)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(3-methyl-[1,2,4]triazolo[4,3-a]pyridin-7-yl)propanoic acid;

(*R)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(3-methyl-[1,2,4]triazolo[4,3-a]pyridin-7-yl)propanoic acid;

(R/S)-3-(3-Cyclopropyl-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*S)-3-(3-Cyclopropyl-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*R)-3-(3-Cyclopropyl-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*S)-3-(1-(Cyclopropylmethyl)-4-(difluoromethyl)-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(1-(Cyclopropylmethyl)-4-(difluoromethyl)-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*S)-3-(1-(Cyclopropylmethyl)-4-(difluoromethyl)-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(1-(Cyclopropylmethyl)-4-(difluoromethyl)-1H-benzo[d][1,2,3]triazol-5-yl)-3-(3-(((R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(R/S)-3-(1-Cyclopropyl-4-methyl-1H-benzo[d][1,2,3]triazol-5-yl)-3-(6-(((R)-4-ethyl-1,1-dioxido-3,4-dihydro-2H-pyrido[2,3-b][1,4,5]oxathiazepin-2-yl)methyl)-5-methylpyridin-2-yl)propanoic acid;

(*S)-3-(1-Cyclopropyl-4-methyl-1H-benzo[d][1,2,3]triazol-5-yl)-3-(6-(((R)-4-ethyl-1,1-dioxido-3,4-dihydro-2H-pyrido[2,3-b][1,4,5]oxathiazepin-2-yl)methyl)-5-methylpyridin-2-yl)propanoic acid;

(*R)-3-(1-Cyclopropyl-4-methyl-1H-benzo[d][1,2,3]triazol-5-yl)-3-(6-(((R)-4-ethyl-1,1-dioxido-3,4-dihydro-2H-pyrido[2,3-b][1,4,5]oxathiazepin-2-yl)methyl)-5-methylpyridin-2-yl)propanoic acid;

(R/S)-3-(4-Methyl-3-(((*S)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(*S)-3-(4-Methyl-3-(((S)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(*R)-3-(4-Methyl-3-(((*S)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(R/S)-3-(4-Methyl-3-(((*R)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(*S)-3-(4-Methyl-3-(((*R)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(*R)-3-(4-Methyl-3-(((*R)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(R/S)-3-(4-Methyl-3-((5'-methyl-1',1'-dioxido-5'H-spiro[cyclopropane-1,4'-pyrido[2,3-f][1,2,5]thiadiazepin]-2'

(3'H)-yl)methyl)phenyl)-3-(8-methyl-3-(trifluoromethyl)-[1,2,4]triazolo[4,3-a]pyridin-7-yl)propanoic acid;

(*S)-3-(4-Methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)-3-(8-methyl-3-(t*rifluoromethyl)-[1,2,4]triazolo[4,3-a]pyridin-7-yl)propanoic acid;

(*R)-3-(4-Methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-3-(4-Methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)-3-(8-methyl-3-(trifluoromethyl)-[1,2,4]triazolo[4,3-a]pyridin-7-yl)propanoic acid;

(*R)-3-(4-Methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)-3-(8-methyl-3-(trifluoromethyl)-[1,2,4]triazolo[4,3-a]pyridin-7-yl)propanoic acid;

(R/S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid;

(*S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid;

(*R)-3-(3-(((R)-4-Ethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid;

(3*S)-3-(3-((3-Chloro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-3-Chloro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-3-Chloro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-4-Ethyl-8-methyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid;

(*S)-3-(3-((8'-Chloro-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-3-Cyano-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-3-Chloro-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-5,5-Dioxido-3-(trifluoromethyl)-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-5,5-Dioxido-3-(trifluoromethyl)-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-((8'-Cyano-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-((8'-Carbamoyl-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-2-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-2-Carbamoyl-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-2-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-2-Carbamoyl-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((S)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*S)-3-(3-(((R)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*S)-3-(4-Methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(R/S)-3-(1-Cyclopropyl-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*S)-3-(1-Cyclopropyl-4-methyl-1H-benzo[d][1,2,3]triazol-5-yl)-3-(3-(((R)-5,5-dioxido-7a, 8,9,10-tetrahydropyrido[2,3-f]pyrrolo[2,1-d][1,2,5]thiadiazepin-6(7H)-yl)methyl)-4-methylphenyl)propanoic acid;

(*R)-3-(1-Cyclopropyl-4-methyl-1H-benzo[d][1,2,3]triazol-5-yl)-3-(3-(((R)-5,5-dioxido-7a, 8,9,10-tetrahydropyrido[2,3-f]pyrrolo[2,1-d][1,2,5]thiadiazepin-6(7H)-yl)methyl)-4-methylphenyl)propanoic acid;

(*S)-3-(1-Cyclopropyl-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(1-Cyclopropyl-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(R/S)-3-(1-Cyclopropyl-4-methyl-1H-benzo[d][1,2,3]triazol-5-yl)-3-(3-((1,1-dioxidospiro[benzo[b][1,4,5]oxathiazepine-4,3'-oxetan]-2(3H)-yl)methyl)-4-methylphenyl)propanoic acid;

(*S)-3-(1-Cyclopropyl-4-methyl-1H-benzo[d][1,2,3]triazol-5-yl)-3-(3-((1,1-dioxidospiro[benzo[b][1,4,5]oxathiazepine-4,3'-oxetan]-2(3H)-yl)methyl)-4-methylphenyl)propanoic acid;

(*R)-3-(1-Cyclopropyl-4-methyl-1H-benzo[d][1,2,3]triazol-5-yl)-3-(3-((1,1-dioxidospiro[benzo[b][1,4,5]oxathiazepine-4,3'-oxetan]-2(3H)-yl)methyl)-4-methylphenyl)propanoic acid;

(R/S)-3-(1-Cyclopropyl-4-methyl-1H-benzo[d][1,2,3]triazol-5-yl)-3-(3-(((*S)-5,5-dioxido-7,7a,8,9,10,11-hexahydro-6H-benzo[f]pyrido[2,1-d][1,2,5]thiadiazepin-6-yl)methyl)-4-methylphenyl)propanoic acid;

(R/S)-3-(1-Cyclopropyl-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(*S)-3-(1-Cyclopropyl-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(*R)-3-(1-Cyclopropyl-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(R/S)-3-(1-Cyclopropyl-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(*S)-3-(1-Cyclopropyl-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(*R)-3-(1-Cyclopropyl-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(R/S)-3-(1-Cyclopropyl-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid;

(*S)-3-(1-Cyclopropyl-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid;

(*R)-3-(1-Cyclopropyl-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid;

(R/S)-3-(1-Cyclopropyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*S)-3-(1-Cyclopropyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*R)-3-(1-Cyclopropyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*S)-3-(3-Cyclopropyl-8-methyl-[1,2,4]triazolo[4,3-a]pyridin-7-yl)-3-(3-((8'-fluoro-1',1'-dioxidospiro[cyclopropane-1,4'-pyrido[2,3-b][1,4,5]oxathiazepin]-2'(3'H)-yl)methyl)-4-methylphenyl)propanoic acid;

(R/S)-3-(1-(Cyclopropylmethyl)-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*S)-3-(1-(Cyclopropylmethyl)-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(1-(Cyclopropylmethyl)-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(R/S)-3-(1-(Cyclopropylmethyl)-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(1-(Cyclopropylmethyl)-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*S)-3-(1-(Cyclopropylmethyl)-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(R/S)-3-(6-((1,1-Dioxidospiro[benzo[b][1,4,5]oxathiazepine-4,3'-oxetan]-2(3H)-yl)methyl)-5-methylpyridin-2-yl)-3-(1-ethyl-4-methyl-1H-benzo[d][1,2,3]triazol-5-yl)propanoic acid;

(*S)-3-(6-((1,1-Dioxidospiro[benzo[b][1,4,5]oxathiazepine-4,3'-oxetan]-2(3H)-yl)methyl)-5-methylpyridin-2-yl)-3-(1-ethyl-4-methyl-1H-benzo[d][1,2,3]triazol-5-yl)propanoic acid;

(*R)-3-(6-((1,1-Dioxidospiro[benzo[b][1,4,5]oxathiazepine-4,3'-oxetan]-2(3H)-yl)methyl)-5-methylpyridin-2-yl)-3-(1-ethyl-4-methyl-1H-benzo[d][1,2,3]triazol-5-yl)propanoic acid;

(R/S)-3-(6-((1',1'-Dioxidospiro[oxetane-3,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic acid;

(*S)-3-(6-((1',1'-Dioxidospiro[oxetane-3,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic acid;

(*R)-3-(6-((1',1'-Dioxidospiro[oxetane-3,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic acid;

(R/S)-3-(6-((1',1'-Dioxidospiro[cyclopropane-1,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic acid;

(*S)-3-(6-((1',1'-Dioxidospiro[cyclopropane-1,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3] triazol-5-yl)propanoic acid; and (*R)-3-(6-((1',1'-Dioxidospiro[cyclopropane-1,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3] triazol-5-yl)propanoic acid;

3-(7-(Difluoromethoxy)-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)
methyl)-4-methylphenyl)propanoic acid;
(*S)-3-(7-(Difluoromethoxy)-1-methyl-1H-benzo[d][1,2,3]
triazol-5-yl)-3-(3-(((R)-5,5-dioxido-7a,8,9,10-tetrahydro-
pyrido[2,3-f]pyrrolo[2,1-d][1,2,5]thiadiazepin-6(7H)-yl)
methyl)-4-methylphenyl)propanoic acid;
(*R)-3-(7-(Difluoromethoxy)-1-methyl-1H-benzo[d][1,2,3]
triazol-5-yl)-3-(3-(((R)-5,5-dioxido-7a,8,9,10-tetrahydro-
pyrido[2,3-f]pyrrolo[2,1-d][1,2,5]thiadiazepin-6(7H)-yl)
methyl)-4-methylphenyl)propanoic acid;
3-(7-(Difluoromethoxy)-1-methyl-1H-benzo[d][1,2,3]tri-
azol-5-yl)-3-(3-(((R)-4-ethyl-1,1-dioxido-3,4-dihydro-
2H-pyrido[2,3-b][1,4,5]oxathiazepin-2-yl)methyl)-4-
methylphenyl)propanoic acid;
(*S)-3-(7-(Difluoromethoxy)-1-methyl-1H-benzo[d][1,2,3]
triazol-5-yl)-3-(3-(((R)-4-ethyl-1,1-dioxido-3,4-dihydro-
2H-pyrido[2,3-b][1,4,5]oxathiazepin-2-yl)methyl)-4-
methylphenyl)propanoic acid;
(*R)-3-(7-(Difluoromethoxy)-1-methyl-1H-benzo[d][1,2,3]
triazol-5-yl)-3-(3-(((R)-4-ethyl-1,1-dioxido-3,4-dihydro-
2H-pyrido[2,3-b][1,4,5]oxathiazepin-2-yl)methyl)-4-
methylphenyl)propanoic acid;
3-(3-((1',1'-Dioxidospiro[oxetane-3,4'-pyrido[2,3-b][1,4,5]
oxathiazepin]-2'(3'H)-yl)methyl)-4-methylphenyl)-3-(1-
ethyl-4-methyl-1H-benzo[d][1,2,3]triazol-5-yl)propanoic
acid;
3-(3-(((S)-5,5-Dioxido-7a,8,9,10-tetrahydropyrido[2,3-f]
pyrrolo[2,1-d][1,2,5]thiadiazepin-6(7H)-yl)methyl)-4-
methylphenyl)-3-(3-(trifluoromethyl)-[1,2,4]triazolo[4,3-
a]pyridin-7-yl)propanoic acid;
(*S)-3-(3-(((S)-5,5-Dioxido-7a,8,9,10-tetrahydropyrido[2,
3-f]pyrrolo[2,1-d][1,2,5]thiadiazepin-6(7H)-yl)methyl)-
4-methylphenyl)-3-(3-(trifluoromethyl)-[1,2,4]triazolo[4,
3-a]pyridin-7-yl)propanoic acid;
(*R)-3-(3-(((S)-5,5-Dioxido-7a,8,9,10-tetrahydropyrido[2,
3-f]pyrrolo[2,1-d][1,2,5]thiadiazepin-6(7H)-yl)methyl)-
4-methylphenyl)-3-(3-(trifluoromethyl)-[1,2,4]triazolo[4,
3-a]pyridin-7-yl)propanoic acid;
3-(3-(((R)-4-Ethyl-1,1-dioxido-3,4-dihydro-2H-pyrido[2,3-
b][1,4,5]oxathiazepin-2-yl)methyl)-4-methylphenyl)-3-
(3-(trifluoromethyl)-[1,2,4]triazolo[4,3-a]pyridin-7-yl)
propanoic acid;
(*S)-3-(3-(((R)-4-Ethyl-1,1-dioxido-3,4-dihydro-2H-pyrido
[2,3-b][1,4,5]oxathiazepin-2-yl)methyl)-4-methylphe-
nyl)-3-(3-(trifluoromethyl)-[1,2,4]triazolo[4,3-a]pyridin-
7-yl)propanoic acid;
(*R)-3-(3-(((R)-4-Ethyl-1,1-dioxido-3,4-dihydro-2H-pyrido
[2,3-b][1,4,5]oxathiazepin-2-yl)methyl)-4-methylphe-
nyl)-3-(3-(trifluoromethyl)-[1,2,4]triazolo[4,3-a]pyridin-
7-yl)propanoic acid;
3-(3-((1',1'-Dioxidospiro[oxetane-3,4'-pyrido[2,3-b][1,4,5]
oxathiazepin]-2'(3'H)-yl)methyl)-4-methylphenyl)-3-(8-
methyl-3-(trifluoromethyl)-[1,2,4]triazolo[4,3-a]pyridin-
7-yl)propanoic acid;
(*S)-3-(3-((1',1'-Dioxidospiro[oxetane-3,4'-pyrido[2,3-b][1,
4,5]oxathiazepin]-2'(3'H)-yl)methyl)-4-methylphenyl)-3-
(8-methyl-3-(trifluoromethyl)-[1,2,4]triazolo[4,3-a]pyri-
din-7-yl)propanoic acid;
(*R)-3-(3-((1' 1'-Dioxidospiro[oxetane-3,4'-pyrido[2,3-b][1,
4,5]oxathiazepin]-2'(3'H)-yl)methyl)-4-methylphenyl)-3-
(8-methyl-3-(trifluoromethyl)-[1,2,4]triazolo[4,3-a]pyri-
din-7-yl)propanoic acid;
(*S)-3-(3-((((*S)-5,5-Dioxido-7a,8,10,11-tetrahydro-[1,4]
oxazino[3,4-d]pyrido[2,3-f][1,2,5]thiadiazepin-6(7H)-yl)
methyl)-4-methylphenyl)-3-(8-methyl-3-(trifluorom-
ethyl)-[1,2,4]triazolo[4,3-a]pyridin-7-yl)propanoic acid;
(*R)-3-(3-((((*S)-5,5-Dioxido-7a,8,10,11-tetrahydro-[1,4]
oxazino[3,4-d]pyrido[2,3-f][1,2,5]thiadiazepin-6(7H)-yl)
methyl)-4-methylphenyl)-3-(8-methyl-3-(trifluorom-
ethyl)-[1,2,4]triazolo[4,3-a]pyridin-7-yl)propanoic acid;
3-(3-(((R)-5,5-Dioxido-7a,8,9,10-tetrahydropyrido[2,3-f]
pyrrolo[2,1-d][1,2,5]thiadiazepin-6(7H)-yl)methyl)-4-
methylphenyl)-3-(8-methyl-3-(trifluoromethyl)-[1,2,4]
triazolo[4,3-a]pyridin-7-yl)propanoic acid;
3-(3-(((R)-5,5-Dioxido-7a,8,9,10-tetrahydrobenzo[f]pyrrolo
[2,1-d][1,2,5]thiadiazepin-6(7H)-yl)methyl)-4-meth-
ylphenyl)-3-(8-methyl-3-(trifluoromethyl)-[1,2,4]triazolo
[4,3-a]pyridin-7-yl)propanoic acid;
(*S)-3-(3-(((R)-5,5-Dioxido-7a,8,9,10-tetrahydrobenzo[f]
pyrrolo[2,1-d][1,2,5]thiadiazepin-6(7H)-yl)methyl)-4-
methylphenyl)-3-(8-methyl-3-(trifluoromethyl)-[1,2,4]
triazolo[4,3-a]pyridin-7-yl)propanoic acid;
(*R)-3-(3-(((R)-5,5-Dioxido-7a,8,9,10-tetrahydrobenzo[f]
pyrrolo[2,1-d][1,2,5]thiadiazepin-6(7H)-yl)methyl)-4-
methylphenyl)-3-(8-methyl-3-(trifluoromethyl)-[1,2,4]
triazolo[4,3-a]pyridin-7-yl)propanoic acid;
3-(3-((4,4-Dimethyl-1,1-dioxido-3,4-dihydro-2H-pyrido[2,
3-b][1,4,5]oxathiazepin-2-yl)methyl)-4-methylphenyl)-3-
(8-methyl-3-(trifluoromethyl)-[1,2,4]triazolo[4,3-a]pyri-
din-7-yl)propanoic acid;
(*S)-3-(3-((4,4-Dimethyl-1,1-dioxido-3,4-dihydro-2H-
pyrido[2,3-b][1,4,5]oxathiazepin-2-yl)methyl)-4-meth-
ylphenyl)-3-(8-methyl-3-(trifluoromethyl)-[1,2,4]triazolo
[4,3-a]pyridin-7-yl)propanoic acid;
(*R)-3-(3-((4,4-Dimethyl-1,1-dioxido-3,4-dihydro-2H-
pyrido[2,3-b][1,4,5]oxathiazepin-2-yl)methyl)-4-meth-
ylphenyl)-3-(8-methyl-3-(trifluoromethyl)-[1,2,4]triazolo
[4,3-a]pyridin-7-yl)propanoic acid;
3-(3-(((*R)-5,5-Dioxido-7,7a,8,9,10,11-hexahydro-6H-
dipyrido[2,1-d:2',3'-f][1,2,5]thiadiazepin-6-yl)methyl)-4-
methylphenyl)-3-(8-methyl-3-(trifluoromethyl)-[1,2,4]
triazolo[4,3-a]pyridin-7-yl)propanoic acid;
(*S)-3-(3-(((*R)-5,5-Dioxido-7,7a,8,9,10,11-hexahydro-
6H-dipyrido[2,1-d:2',3'-f][1,2,5]thiadiazepin-6-yl)
methyl)-4-methylphenyl)-3-(8-methyl-3-(trifluorom-
ethyl)-[1,2,4]triazolo[4,3-a]pyridin-7-yl)propanoic acid;
(*R)-3-(3-(((*R)-5,5-Dioxido-7,7a,8,9,10,11-hexahydro-
6H-dipyrido[2,1-d:2',3'-f][1,2,5]thiadiazepin-6-yl)
methyl)-4-methylphenyl)-3-(8-methyl-3-(trifluorom-
ethyl)-[1,2,4]triazolo[4,3-a]pyridin-7-yl)propanoic acid;
(*S)-3-(3-(((S)-5,5-Dioxido-7a,8,9,10-tetrahydrobenzo[f]
pyrrolo[2,1-d][1,2,5]thiadiazepin-6(7H)-yl)methyl)-4-
methylphenyl)-3-(8-methyl-3-(trifluoromethyl)-[1,2,4]
triazolo[4,3-a]pyridin-7-yl)propanoic acid;
(*R)-3-(3-(((S)-5,5-Dioxido-7a,8,9,10-tetrahydrobenzo[f]
pyrrolo[2,1-d][1,2,5]thiadiazepin-6(7H)-yl)methyl)-4-
methylphenyl)-3-(8-methyl-3-(trifluoromethyl)-[1,2,4]
triazolo[4,3-a]pyridin-7-yl)propanoic acid;
(*S)-3-(3-(((*R)-5,5-Dioxido-7a,8,10,11-tetrahydro-[1,4]
oxazino[3,4-d]pyrido[2,3-f][1,2,5]thiadiazepin-6(7H)-yl)
methyl)-4-methylphenyl)-3-(8-methyl-3-(trifluorom-
ethyl)-[1,2,4]triazolo[4,3-a]pyridin-7-yl)propanoic acid;
(*R)-3-(3-(((*R)-5,5-Dioxido-7a,8,10,11-tetrahydro-[1,4]
oxazino[3,4-d]pyrido[2,3-f][1,2,5]thiadiazepin-6(7H)-yl)
methyl)-4-methylphenyl)-3-(8-methyl-3-(trifluorom-
ethyl)-[1,2,4]triazolo[4,3-a]pyridin-7-yl)propanoic acid;
3-(3-(((R)-5,5-Dioxido-7a,8,9,10-tetrahydrobenzo[f]pyrrolo
[2,1-d][1,2,5]thiadiazepin-6(7H)-yl)methyl)-4-meth-
ylphenyl)-3-(3-ethyl-8-methyl-[1,2,4]triazolo[4,3-a]pyri-
din-7-yl)propanoic acid;

(*S)-3-(3-(((R)-5,5-Dioxido-7a,8,9,10-tetrahydrobenzo[f]
pyrrolo[2,1-d][1,2,5]thiadiazepin-6(7H)-yl)methyl)-4-
methylphenyl)-3-(3-ethyl-8-methyl-[1,2,4]triazolo[4,3-a]
pyridin-7-yl)propanoic acid;

(*R)-3-(3-(((R)-5,5-Dioxido-7a,8,9,10-tetrahydrobenzo[f]
pyrrolo[2,1-d][1,2,5]thiadiazepin-6(7H)-yl)methyl)-4-
methylphenyl)-3-(3-ethyl-8-methyl-[1,2,4]triazolo[4,3-a]
pyridin-7-yl)propanoic acid;

3-(3-(((R)-5,5-Dioxido-7a,8,9,10-tetrahydropyrido[2,3-f]
pyrrolo[2,1-d][1,2,5]thiadiazepin-6(7H)-yl)methyl)-4-
methylphenyl)-3-(3-ethyl-8-methyl-[1,2,4]triazolo[4,3-a]
pyridin-7-yl)propanoic acid;

(*S)-3-(3-(((R)-5,5-dioxido-7a,8,9,10-tetrahydropyrido[2,
3-f]pyrrolo[2,1-d][1,2,5]thiadiazepin-6(7H)-yl)methyl)-
4-methylphenyl)-3-(3-ethyl-8-methyl-[1,2,4]triazolo[4,3-
a]pyridin-7-yl)propanoic acid;

(*R)-3-(3-(((R)-5,5-dioxido-7a,8,9,10-tetrahydropyrido[2,
3-f]pyrrolo[2,1-d][1,2,5]thiadiazepin-6(7H)-yl)methyl)-
4-methylphenyl)-3-(3-ethyl-8-methyl-[1,2,4]triazolo[4,3-
a]pyridin-7-yl)propanoic acid;

3-(3-((4,4-Dimethyl-1,1-dioxido-3,4-dihydro-2H-benzo[b]
[1,4,5]oxathiazepin-2-yl)methyl)-4-methylphenyl)-3-(8-
methyl-3-(trifluoromethyl)-[1,2,4]triazolo[4,3-a]pyridin-
7-yl)propanoic acid;

(*S)-3-(3-((4,4-Dimethyl-1,1-dioxido-3,4-dihydro-2H-
benzo[b][1,4,5]oxathiazepin-2-yl)methyl)-4-methylphe-
nyl)-3-(8-methyl-3-(trifluoromethyl)-[1,2,4]triazolo[4,3-
a]pyridin-7-yl)propanoic acid;

(*R)-3-(3-((4,4-Dimethyl-1,1-dioxido-3,4-dihydro-2H-
benzo[b][1,4,5]oxathiazepin-2-yl)methyl)-4-methylphe-
nyl)-3-(8-methyl-3-(trifluoromethyl)-[1,2,4]triazolo[4,3-
a]pyridin-7-yl)propanoic acid;

3-(3-((1,1-Dioxidospiro[benzo[b][1,4,5]oxathiazepine-4,3'-
oxetan]-2(3H)-yl)methyl)-4-methylphenyl)-3-(8-methyl-
3-(trifluoromethyl)-[1,2,4]triazolo[4,3-a]pyridin-7-yl)
propanoic acid;

(*R)-3-(3-((1,1-dioxidospiro[benzo[b][1,4,5]oxathiazepine-
4,3'-oxetan]-2(3H)-yl)methyl)-4-methylphenyl)-3-(8-
methyl-3-(trifluoromethyl)-[1,2,4]triazolo[4,3-a]pyridin-
7-yl)propanoic acid;

3-(3-(((*S)-5,5-Dioxido-7,7a,8,9,10,11-hexahydro-6H-
dipyrido[2,1-d:2',3'-f][1,2,5]thiadiazepin-6-yl)methyl)-4-
methylphenyl)-3-(8-methyl-3-(trifluoromethyl)-[1,2,4]
triazolo[4,3-a]pyridin-7-yl)propanoic acid;

(*S)-3-(3-(((*S)-5,5-Dioxido-7,7a,8,9,10,11-hexahydro-
6H-dipyrido[2,1-d:2',3'-f][1,2,5]thiadiazepin-6-yl)
methyl)-4-methylphenyl)-3-(8-methyl-3-(trifluorom-
ethyl)-[1,2,4]triazolo[4,3-a]pyridin-7-yl)propanoic acid;

(*R)-3-(3-(((*S)-5,5-Dioxido-7,7a,8,9,10,11-hexahydro-
6H-dipyrido[2,1-d:2',3'-f][1,2,5]thiadiazepin-6-yl)
methyl)-4-methylphenyl)-3-(8-methyl-3-(trifluorom-
ethyl)-[1,2,4]triazolo[4,3-a]pyridin-7-yl)propanoic acid;

(*S)-3-(3-(((*S)-5,5-Dioxido-7,7a,8,9-tetrahydro-6H-azeto
[2,1-d]pyrido[2,3-f][1,2,5]thiadiazepin-6-yl)methyl)-4-
methylphenyl)-3-(8-methyl-3-(trifluoromethyl)-[1,2,4]
triazolo[4,3-a]pyridin-7-yl)propanoic acid;

(*R)-3-(3-(((*S)-5,5-Dioxido-7,7a,8,9-tetrahydro-6H-azeto
[2,1-d]pyrido[2,3-f][1,2,5]thiadiazepin-6-yl)methyl)-4-
methylphenyl)-3-(8-methyl-3-(trifluoromethyl)-[1,2,4]
triazolo[4,3-a]pyridin-7-yl)propanoic acid;

(*S)-3-(3-(((*R)-5,5-Dioxido-7,7a,8,9-tetrahydro-6H-azeto
[2,1-d]pyrido[2,3-f][1,2,5]thiadiazepin-6-yl)methyl)-4-
methylphenyl)-3-(8-methyl-3-(trifluoromethyl)-[1,2,4]
triazolo[4,3-a]pyridin-7-yl)propanoic acid;

(*R)-3-(3-(((*R)-5,5-Dioxido-7,7a,8,9-tetrahydro-6H-azeto
[2,1-d]pyrido[2,3-f][1,2,5]thiadiazepin-6-yl)methyl)-4-
methylphenyl)-3-(8-methyl-3-(trifluoromethyl)-[1,2,4]
triazolo[4,3-a]pyridin-7-yl)propanoic acid;

3-(6-(((R)-5,5-Dioxido-7a,8,9,10-tetrahydropyrido[2,3-f]
pyrrolo[2,1-d][1,2,5]thiadiazepin-6(7H)-yl)methyl)-5-
methylpyridin-2-yl)-3-(1-ethyl-4-methyl-1H-benzo[d][1,
2,3]triazol-5-yl)propanoic acid;

(*S)-3-(6-(((R)-5,5-Dioxido-7a,8,9,10-tetrahydropyrido[2,
3-f]pyrrolo[2,1-d][1,2,5]thiadiazepin-6(7H)-yl)methyl)-
5-methylpyridin-2-yl)-3-(1-ethyl-4-methyl-1H-benzo[d]
[1,2,3]triazol-5-yl)propanoic acid;

(*R)-3-(6-(((R)-5,5-Dioxido-7a,8,9,10-tetrahydropyrido[2,
3-f]pyrrolo[2,1-d][1,2,5]thiadiazepin-6(7H)-yl)methyl)-
5-methylpyridin-2-yl)-3-(1-ethyl-4-methyl-1H-benzo[d]
[1,2,3]triazol-5-yl)propanoic acid;

(*S)-3-(3-(((*S)-5,5-Dioxido-7,7a,8,9,10,11-hexahydro-
6H-benzo[f]pyrido[2,1-d][1,2,5]thiadiazepin-6-yl)
methyl)-4-methylphenyl)-3-(8-methyl-3-(trifluorom-
ethyl)-[1,2,4]triazolo[4,3-a]pyridin-7-yl)propanoic acid;

(*S)-3-(3-(((*R)-5,5-Dioxido-7,7a,8,9,10,11-hexahydro-
6H-benzo[f]pyrido[2,1-d][1,2,5]thiadiazepin-6-yl)
methyl)-4-methylphenyl)-3-(8-methyl-3-(trifluorom-
ethyl)-[1,2,4]triazolo[4,3-a]pyridin-7-yl)propanoic acid;

3-(6-(((*S)-5,5-Dioxido-7,7a,8,9,10,11-hexahydro-6H-
dipyrido[2,1-d:2',3'-f][1,2,5]thiadiazepin-6-yl)methyl)-5-
methylpyridin-2-yl)-3-(1-ethyl-4-methyl-1H-benzo[d][1,
2,3]triazol-5-yl)propanoic acid;

(*S)-3-(6-(((*S)-5,5-Dioxido-7,7a,8,9,10,11-hexahydro-
6H-dipyrido[2,1-d:2',3'-f][1,2,5]thiadiazepin-6-yl)
methyl)-5-methylpyridin-2-yl)-3-(1-ethyl-4-methyl-1H-
benzo[d][1,2,3]triazol-5-yl)propanoic acid;

(*R)-3-(6-(((*S)-5,5-Dioxido-7,7a,8,9,10,11-hexahydro-
6H-dipyrido[2,1-d:2',3'-f][1,2,5]thiadiazepin-6-yl)
methyl)-5-methylpyridin-2-yl)-3-(1-ethyl-4-methyl-1H-
benzo[d][1,2,3]triazol-5-yl)propanoic acid;

3-(6-(((*R)-5,5-Dioxido-7,7a,8,9,10,11-hexahydro-6H-
dipyrido[2,1-d:2',3'-f][1,2,5]thiadiazepin-6-yl)methyl)-5-
methylpyridin-2-yl)-3-(1-ethyl-4-methyl-1H-benzo[d][1,
2,3]triazol-5-yl)propanoic acid;

(*S)-3-(6-(((*R)-5,5-Dioxido-7,7a,8,9,10,11-hexahydro-
6H-dipyrido[2,1-d:2',3'-f][1,2,5]thiadiazepin-6-yl)
methyl)-5-methylpyridin-2-yl)-3-(1-ethyl-4-methyl-1H-
benzo[d][1,2,3]triazol-5-yl)propanoic acid;

(*R)-3-(6-(((*R)-5,5-Dioxido-7,7a,8,9,10,11-hexahydro-
6H-dipyrido[2,1-d:2',3'-f][1,2,5]thiadiazepin-6-yl)
methyl)-5-methylpyridin-2-yl)-3-(1-ethyl-4-methyl-1H-
benzo[d][1,2,3]triazol-5-yl)propanoic acid;

(*S)-3-(4-methyl-3-(((*S)-3-methyl-5,5-dioxido-7,7a,8,9,
10,11-hexahydro-6H-dipyrido[2,1-d:2',3'-f][1,2,5]thiadi-
azepin-6-yl)methyl)phenyl)-3-(8-methyl-3-(trifluorom-
ethyl)-[1,2,4]triazolo[4,3-a]pyridin-7-yl)propanoic acid;

(*S)-3-(4-methyl-3-(((*R)-3-methyl-5,5-dioxido-7,7a,8,9,
10,11-hexahydro-6H-dipyrido[2,1-d:2',3'-f][1,2,5]thiadi-
azepin-6-yl)methyl)phenyl)-3-(8-methyl-3-(trifluorom-
ethyl)-[1,2,4]triazolo[4,3-a]pyridin-7-yl)propanoic acid;

(*S)-3-(3-(((*S)-3-fluoro-5,5-dioxido-7,7a,8,9,10,11-hexa-
hydro-6H-dipyrido[2,1-d:2',3'-f][1,2,5]thiadiazepin-6-yl)
methyl)-4-methylphenyl)-3-(8-methyl-3-(trifluorom-
ethyl)-[1,2,4]triazolo[4,3-a]pyridin-7-yl)propanoic acid;

(*S)-3-(3-(((*R)-3-fluoro-5,5-dioxido-7,7a,8,9,10,11-hexa-
hydro-6H-dipyrido[2,1-d:2',3'-f][1,2,5]thiadiazepin-6-yl)
methyl)-4-methylphenyl)-3-(8-methyl-3-(trifluorom-
ethyl)-[1,2,4]triazolo[4,3-a]pyridin-7-yl)propanoic acid;

(*S)-3-(3-((8'-Fluoro-1',1'-dioxidospiro[cyclopropane-1,4'-
pyrido[2,3-b][1,4,5]oxathiazepin]-2'(3'H)-yl)methyl)-4-
methylphenyl)-3-(8-methyl-3-(trifluoromethyl)-[1,2,4]
triazolo[4,3-a]pyridin-7-yl)propanoic acid;

(*S)-3-(3-((3-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*R)-2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

3-(3-((1',1'-Dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*S)-3-(3-((1',1'-Dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*R)-3-(3-((1',1'-Dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(3-(trifluoromethyl)-[1,2,4]triazolo[4,3-a]pyridin-7-yl)propanoic acid;

(*S)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(3-(trifluoromethyl)-[1,2,4]triazolo[4,3-a]pyridin-7-yl)propanoic acid;

(*R)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(3-(trifluoromethyl)-[1,2,4]triazolo[4,3-a]pyridin-7-yl)propanoic acid;

2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(3-(trifluoromethyl)-[1,2,4]triazolo[4,3-a]pyridin-7-yl)propanoic acid;

(*S)-2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(3-(trifluoromethyl)-[1,2,4]triazolo[4,3-a]pyridin-7-yl)propanoic acid;

(*R)-2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(3-(trifluoromethyl)-[1,2,4]triazolo[4,3-a]pyridin-7-yl)propanoic acid;

(*S)-2,2-Dimethyl-3-(8-methyl-3-(trifluoromethyl)-[1,2,4]triazolo[4,3-a]pyridin-7-yl)-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid;

(*R)-2,2-Dimethyl-3-(8-methyl-3-(trifluoromethyl)-[1,2,4]triazolo[4,3-a]pyridin-7-yl)-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid;

3-(1-(Cyclopropylmethyl)-4-methyl-1H-benzo[d][1,2,3]triazol-5-yl)-2,2-dimethyl-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid;

(*S)-3-(1-(Cyclopropylmethyl)-4-methyl-1H-benzo[d][1,2,3]triazol-5-yl)-2,2-dimethyl-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid;

(*R)-3-(1-(Cyclopropylmethyl)-4-methyl-1H-benzo[d][1,2,3]triazol-5-yl)-2,2-dimethyl-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid;

(*S)-3-(3,7-Dimethyl-7H-pyrrolo[2,3-c]pyridazin-6-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;

(*R)-3-(3,7-Dimethyl-7H-pyrrolo[2,3-c]pyridazin-6-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;

(*S)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid;

(*R)-3-(3-(difluoromethyl)-8-methyl-[1,2,4]triazolo[4,3-a]pyridin-7-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid;

(*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid;

(*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid;

(*S)-3-(3-((1',1'-Dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*R)-3-(3-((1',1'-Dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*S)-3-(3-((1',1'-Dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*R)-3-(3-((1',1'-Dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*S)-2,2-Dimethyl-3-(4-methyl-3-((8'-methyl-1',1'-dioxidospiro[piperidine-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*R)-2,2-Dimethyl-3-(4-methyl-3-((8'-methyl-1',1'-dioxidospiro[piperidine-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-2,2-Dimethyl-3-(4-methyl-3-((8'-methyl-1',1'-dioxidospiro[azetidine-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*R)-2,2-Dimethyl-3-(4-methyl-3-((8'-methyl-1',1'-dioxidospiro[azetidine-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*R)-3-(3-((7'-(3-((2-(2-Aminoethoxy)ethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*S)-3-(3-((7'-(3-((2-(2-aminoethoxy)ethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*S)-3-(3,7-Dimethyl-7H-pyrrolo[2,3-c]pyridazin-6-yl)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoic acid;

(*R)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(pyrrolidine-1-yl)-ethoxy)2,3,5,6-tetrahydrospiro[pyran-4,4'-pyrido[2,3-b][1,4,5]oxathiazepin]-2'(3'H)-yl)methyl)phenyl)propanoic acid;

(*S)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)2,3,5,6-tetrahydrospiro[pyran-4,4'-pyrido[2,3-b][1,4,5]oxathiazepin]-2'(3'H)-yl)methyl)phenyl)propanoic acid;

(*R)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)2,3,5,6-tetrahydrospiro[pyran-4,4'-pyrido[2,3-b][1,4,5]oxathiazepin]-2'(3'H)-yl)methyl)phenyl)propanoic acid;

(*S)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)spiro[cyclopropane-1,4'-pyrido[2,3-b][1,4,5]oxathiazepin]-2',(3'H)-yl)methyl)phenyl)propanoic acid;

(*R)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)spiro[cyclopropane-1,4'-pyrido[2,3-b][1,4,5]oxathiazepin]-2',(3'H)-yl)methyl)phenyl)propanoic acid;

(*S)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(pyrrolidin-1-yl)-ethoxy)spiro[cyclopropane-1,4'-pyrido[2,3-b][1,4,5]oxathiazepin]-2',(3'H)-yl)methyl)phenyl)propanoic acid;

(*R)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(pyrrolidin-1-yl)-ethoxy)spiro[cyclopropane-1,4'-pyrido[2,3-b][1,4,5]oxathiazepin]-2'-(3'H)-yl)methyl)phenyl)propanoic acid;

(*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid;

(*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid;

(*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*R)-3-(3-(difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*R)-3-(3-((7'-(2-(4,4-Difluoropiperidin-1-yl)ethoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic acid;

(*R)-3-(3-((7'-(((1R,3R)-3-Hydroxycyclobutyl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*R)-2,2-Dimethyl-3-(4-methyl-3-((8'-methyl-7'-(((R-1-morpholinopropan-2-yl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-2,2-Dimethyl-3-(4-methyl-3-((8'-methyl-7'-(((S-1-morpholinopropan-2-yl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-2,2-Dimethyl-3-(4-methyl-3-((8'-methyl-7'-(((1-morpholinopropan-2-yl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-2,2-Dimethyl-3-(4-methyl-3-((8'-methyl-7'-((2-morpholinoethyl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-2,2-Dimethyl-3-(4-methyl-3-((8'-methyl-7'-((2-morpholinoethyl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-2,2-Dimethyl-3-(4-methyl-3-((8'-methyl-1',1'-dioxido-7'-(((S)-1-(pyrrolidine-1-yl)propan-2-yl)amino)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-3-(3-((1',1'-Dioxido-7'-(2-(piperazin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic acid;

(*R)-2,2-Dimethyl-3-(4-methyl-3-(8'-methyl-1',1'-dioxido-7'-(2-(piperidin-4-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic acid;

(*S)-2,2-Dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic acid;

(*S)-3-(3-1',1'-Dioxido-7'-(2-(piperidin-1-yl)ethoxy)spiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic acid;

(*S)-2,2-Dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*S)-2,2-Dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl)propanoic acid;

(*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoic acid;

3-(*R)-2,2-Dimethyl-3-(4-methyl-3-((8'-methyl-1',1'-dioxido-7'-((1-piperidin-1-yl)propan-2-yl)amino)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoic acid;

(*S)-3-(3-((7'-(2-(4-Methoxypiperidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoic acid;

(*R)-2,2-Dimethyl-3-(4-methyl-3-((8'-methyl-1',1'-dioxido-7'-(((S)-1-piperidin-1-yl)propan-2-yl)amino)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*S)-3-(3-(((*S)-1',1'-Dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*S)-3-(3-(((*R)-1',1'-Dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*S)-2,2-Dimethyl-3-(4-methyl-3-(((*S)-8'-methyl-1',1'-dioxido-4,5-dihydro-2H-spiro[furan-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-2,2-Dimethyl-3-(4-methyl-3-(((*R)-8'-methyl-1',1'-dioxido-4,5-dihydro-2H-spiro[furan-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*R)-3-(3-(((*S)-1',1'-Dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*R)-3-(3-(((*R)-1',1'-Dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*R)-2,2-Dimethyl-3-(4-methyl-3-(((*S)-8'-methyl-1',1'-dioxido-4,5-dihydro-2H-spiro[furan-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*R)-2,2-Dimethyl-3-(4-methyl-3-(((*R)-8'-methyl-1',1'-dioxido-4,5-dihydro-2H-spiro[furan-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*R)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(R/S)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;

(*S)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;

(*R)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;

(R/S)-3-(1-Cyclopropyl-4-methyl-1H-benzo[d][1,2,3]triazol-5-yl)-2,2-dimethyl-3-(6-methyl-5-((8'-methyl-1',1'- dioxidospiro[cyclopropane-1,4'-pyrido[2,3-b][1,4,5]oxathiazepin]-2'(3'H)-yl)methyl)pyridin-3-yl)propanoic acid;

(*S)-3-(1-Cyclopropyl-4-methyl-1H-benzo[d][1,2,3]triazol-5-yl)-2,2-dimethyl-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic acid;

(*R)-3-(1-Cyclopropyl-4-methyl-1H-benzo[d][1,2,3]triazol-5-yl)-2,2-dimethyl-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic acid;

(R/S)-3-(1-Cyclopropyl-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*S)-3-(1-Cyclopropyl-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(1-Cyclopropyl-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

3-(1-(cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*R)-3-(1-(Cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*S)-3-(1-(Cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

3-(7-Cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(7-Cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*S)-3-(7-Cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*R)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*R)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*S)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)-3-(8-methyl-3-(trifluoromethyl)-[1,2,4]triazolo[4,3-a]pyridin-7-yl)propanoic acid;

(3S*)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)-2-methyl-3-(8-methyl-3-(trifluoromethyl)-[1,2,4]triazolo[4,3-a]pyridin-7-yl) propanoic acid;

3-(1-Ethyl-4-methyl-1H-benzo[d][1,2,3]triazol-5-yl)-3-(6-((8-fluoro-1,1-dioxido-2',3',5',6'-tetrahydrospiro[benzo[b][1,4,5]oxathiazepine-4,4'-pyran]-2(3H)-yl)methyl)-5-methylpyridin-2-yl)propanoic acid;

(*S)-3-(1-ethyl-4-methyl-1H-benzo[d][1,2,3]triazol-5-yl)-3-(6-((8-fluoro-1,1-dioxido-2',3',5',6'-tetrahydrospiro[benzo[b][1,4,5]oxathiazepine-4,4'-pyran]-2(3H)-yl)methyl)-5-methylpyridin-2-yl)propanoic acid;

(*R)-3-(1-ethyl-4-methyl-1H-benzo[d][1,2,3]triazol-5-yl)-3-(6-((8-fluoro-1,1-dioxido-2',3',5',6'-tetrahydrospiro[benzo[b][1,4,5]oxathiazepine-4,4'-pyran]-2(3H)-yl)methyl)-5-methylpyridin-2-yl)propanoic acid;

(*S)-3-(1-ethyl-4-methyl-1H-benzo[d][1,2,3]triazol-5-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoic acid;

(*R)-3-(1-ethyl-4-methyl-1H-benzo[d][1,2,3]triazol-5-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoic acid;

(*S)-3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-2,2-dimethyl-3-(8-methyl-3-(trifluoromethyl)-[1,2,4]triazolo[4,3-a]pyridin-7-yl) propanoic acid;

(*R)-3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-2,2-dimethyl-3-(8-methyl-3-(trifluoromethyl)-[1,2,4]triazolo[4,3-a]pyridin-7-yl) propanoic acid;

(*S)-3-(3-(((*S)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-2,2-dimethyl-3-(8-methyl-3-(trifluoromethyl)-[1,2,4]triazolo[4,3-a]pyridin-7-yl) propanoic acid;

(*R)-3-(3-(((*S)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-2,2-dimethyl-3-(8-methyl-3-(trifluoromethyl)-[1,2,4]triazolo[4,3-a]pyridin-7-yl) propanoic acid;

(S)-3-(7-(difluoromethoxy)-1-methyl-1H-benzo[d][1,2,3]triazol-5-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(R*)-3-(7-(difluoromethoxy)-1-methyl-1H-benzo[d][1,2,3]triazol-5-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(S*)-3-(1-(cyclopropylmethyl)-4-methyl-1H-benzo[d][1,2,3]triazol-5-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(R*)-3-(1-(cyclopropylmethyl)-4-methyl-1H-benzo[d][1,2,3]triazol-5-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*S)-3-(3-((4,4-dimethyl-1,1-dioxido-3,4-dihydro-2H-pyrido[2,3-b][1,4,5]oxathiazepin-2-yl)methyl)-4-methylphenyl)-2,2-dimethyl-3-(8-methyl-3-(trifluoromethyl)-[1,2,4]triazolo[4,3-a]pyridin-7-yl)propanoic acid;

(*R)-3-(3-((4,4-dimethyl-1,1-dioxido-3,4-dihydro-2H-pyrido[2,3-b][1,4,5]oxathiazepin-2-yl)methyl)-4-methylphenyl)-2,2-dimethyl-3-(8-methyl-3-(trifluoromethyl)-[1,2,4]triazolo[4,3-a]pyridin-7-yl)propanoic acid;

(*S)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-2,2-difluoro-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)-3-(8-methyl-3-(trifluoromethyl)-[1,2,4]triazolo[4,3-a]pyridin-7-yl)propanoic acid;

3-(3,7-Dimethyl-7H-pyrrolo[2,3-c]pyridazin-6-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*S)-3-(3,7-Dimethyl-7H-pyrrolo[2,3-c]pyridazin-6-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*R)-3-(3,7-Dimethyl-7H-pyrrolo[2,3-c]pyridazin-6-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

3-(3,7-Dimethyl-7H-pyrrolo[2,3-c]pyridazin-6-yl)-3-(3-(((S)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*S)-3-(3,7-Dimethyl-7H-pyrrolo[2,3-c]pyridazin-6-yl)-3-(3-(((S)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*R)-3-(3,7-Dimethyl-7H-pyrrolo[2,3-c]pyridazin-6-yl)-3-(3-(((S)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

3-(3,7-Dimethyl-7H-pyrrolo[2,3-c]pyridazin-6-yl)-3-(3-(((S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*S)-3-(3,7-Dimethyl-7H-pyrrolo[2,3-c]pyridazin-6-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(3,7-Dimethyl-7H-pyrrolo[2,3-c]pyridazin-6-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

3-(3,7-Dimethyl-7H-pyrrolo[2,3-c]pyridazin-6-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*S)-3-(3,7-Dimethyl-7H-pyrrolo[2,3-c]pyridazin-6-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(3,7-Dimethyl-7H-pyrrolo[2,3-c]pyridazin-6-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

3-(3-(Difluoromethyl)-8-methyl-[1,2,4]triazolo[4,3-a]pyridin-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*S)-3-(3-(Difluoromethyl)-8-methyl-[1,2,4]triazolo[4,3-a]pyridin-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(3-(Difluoromethyl)-8-methyl-[1,2,4]triazolo[4,3-a]pyridin-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

3-(3-(Difluoromethyl)-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*S)-3-(3-(Difluoromethyl)-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*R)-3-(3-(Difluoromethyl)-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

3-(3-((10,10-Difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-10,10-Difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-10,10-difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*R)-3-(3-(((*S)-10,10-Difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*R)-3-(3-(((*R)-10,10-Difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

3-(3-(Difluoromethyl)-8-methyl-[1,2,4]triazolo[4,3-a]pyridin-7-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid;

(*S)-3-(3-(Difluoromethyl)-8-methyl-[1,2,4]triazolo[4,3-a]pyridin-7-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid;

(*R)-3-(3-(Difluoromethyl)-8-methyl-[1,2,4]triazolo[4,3-a]pyridin-7-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid;

3-(3-(Difluoromethyl)-8-methyl-[1,2,4]triazolo[4,3-a]pyridin-7-yl)-3-(3-(((*S)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid;

(*S)-3-(3-(Difluoromethyl)-8-methyl-[1,2,4]triazolo[4,3-a]pyridin-7-yl)-3-(3-(((*S)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid;

(*R)-3-(3-(Difluoromethyl)-8-methyl-[1,2,4]triazolo[4,3-a]pyridin-7-yl)-3-(3-(((*S)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid;

3-(3-(Difluoromethyl)-8-methyl-[1,2,4]triazolo[4,3-a]pyridin-7-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic acid;

(*S)-3-(3-(Difluoromethyl)-8-methyl-[1,2,4]triazolo[4,3-a]pyridin-7-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic acid;

(*R)-3-(3-(Difluoromethyl)-8-methyl-[1,2,4]triazolo[4,3-a]pyridin-7-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic acid;

3-(3-(Difluoromethyl)-8-methyl-[1,2,4]triazolo[4,3-a]pyridin-7-yl)-3-(3-((1,1-dioxidospiro[benzo[b][1,4,5]oxathiazepine-4,3'-oxetan]-2(3H)-yl)methyl)-4-methylphenyl)propanoic acid;

(*S)-3-(3-(Difluoromethyl)-8-methyl-[1,2,4]triazolo[4,3-a]pyridin-7-yl)-3-(3-((1,1-dioxidospiro[benzo[b][1,4,5]oxathiazepine-4,3'-oxetan]-2(3H)-yl)methyl)-4-methylphenyl)propanoic acid;

(*R)-3-(3-(Difluoromethyl)-8-methyl-[1,2,4]triazolo[4,3-a]pyridin-7-yl)-3-(3-((1,1-dioxidospiro[benzo[b][1,4,5]oxathiazepine-4,3'-oxetan]-2(3N)-yl)methyl)-4-methylphenyl)propanoic acid;

3-(3-(Difluoromethyl)-8-methyl-[1,2,4]triazolo[4,3-a]pyridin-7-yl)-3-(3-((1',1'-dioxidospiro[oxetane-3,4'-pyrido[2,3-b][1,4,5]oxathiazepin]-2'(3'H)-yl)methyl)-4-methylphenyl)propanoic acid;

(*S)-3-(3-(Difluoromethyl)-8-methyl-[1,2,4]triazolo[4,3-a]pyridin-7-yl)-3-(3-((1',1'-dioxidospiro[oxetane-3,4'-pyrido[2,3-b][1,4,5]oxathiazepin]-2'(3'H)-yl)methyl)-4-methylphenyl)propanoic acid;

(*R)-3-(3-(Difluoromethyl)-8-methyl-[1,2,4]triazolo[4,3-a]pyridin-7-yl)-3-(3-((1',1'-dioxidospiro[oxetane-3,4'-pyrido[2,3-b][1,4,5]oxathiazepin]-2'(3'H)-yl)methyl)-4-methylphenyl)propanoic acid;

3-(3-(Difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)propanoic acid;

(*S)-3-(3-(Difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)propanoic acid;

(*R)-3-(3-(Difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)propanoic acid;

3-(3-(Difluoromethyl)-8-methyl-[1,2,4]triazolo[4,3-a]pyridin-7-yl)-3-(4-methyl-3-(((*S) 7a-methyl-5,5-dioxido-7a,8,9,10-tetrahydropyrido[2,3-f]pyrrolo[2,1-d][1,2,5]thiadiazepin-6(7N)-yl)methyl)phenyl)propanoic acid;

(*S)-3-(3-(Difluoromethyl)-8-methyl-[1,2,4]triazolo[4,3-a]pyridin-7-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(*R)-3-(3-(Difluoromethyl)-8-methyl-[1,2,4]triazolo[4,3-a]pyridin-7-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

3-(6-(((*S)-5,5-Dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

(*S)-3-(6-(((*S)-5,5-Dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

(*R)-3-(6-(((*S)-5,5-Dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

(R/S)-3-(6-((1',1'-Dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid;

(*S)-3-(6-((1',1'-Dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid;

(*R)-3-(6-((1',1'-Dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid;

3-(6-((1,1-Dioxidospiro[benzo[b][1,4,5]oxathiazepine-4,3'-oxetan]-2(3H)-yl)methyl)-5-methylpyridin-2-yl)-3-(8-methyl-3-(trifluoromethyl)-[1,2,4]triazolo[4,3-a]pyridin-7-yl)propanoic acid;

(*S)-3-(6-((1,1-dioxidospiro[benzo[b][1,4,5]oxathiazepine-4,3'-oxetan]-2(3H)-yl)methyl)-5-methylpyridin-2-yl)-3-(8-methyl-3-(trifluoromethyl)-[1,2,4]triazolo[4,3-a]pyridin-7-yl)propanoic acid;

(*R)-3-(6-((1,1-dioxidospiro[benzo[b][1,4,5]oxathiazepine-4,3'-oxetan]-2(3H)-yl)methyl)-5-methylpyridin-2-yl)-3-(8-methyl-3-(trifluoromethyl)-[1,2,4]triazolo[4,3-a]pyridin-7-yl)propanoic acid;

3-(8-Methyl-3-(trifluoromethyl)-[1,2,4]triazolo[4,3-a]pyridin-7-yl)-3-(5-methyl-6-(((*S)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic acid;

(*S)-3-(8-Methyl-3-(trifluoromethyl)-[1,2,4]triazolo[4,3-a]pyridin-7-yl)-3-(5-methyl-6-(((*S)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic acid;

(*R)-3-(8-Methyl-3-(trifluoromethyl)-[1,2,4]triazolo[4,3-a]pyridin-7-yl)-3-(5-methyl-6-(((*S)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic acid;

3-(8-Methyl-3-(trifluoromethyl)-[1,2,4]triazolo[4,3-a]pyridin-7-yl)-3-(5-methyl-6-(((*R)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic acid;

(*S)-3-(8-Methyl-3-(trifluoromethyl)-[1,2,4]triazolo[4,3-a]pyridin-7-yl)-3-(5-methyl-6-(((*R)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic acid;

(*R)-3-(8-Methyl-3-(trifluoromethyl)-[1,2,4]triazolo[4,3-a]pyridin-7-yl)-3-(5-methyl-6-(((*R)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic acid;

3-(6-((1',1'-Dioxidospiro[oxetane-3,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid;

(*S)-3-(6-((1',1'-Dioxidospiro[oxetane-3,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid;

(*R)-3-(6-((1',1'-Dioxidospiro[oxetane-3,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid;

3-(6-(((*S)-3-Fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

(*S)-3-(6-(((*S)-3-Fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

(*R)-3-(6-(((*S)-3-Fluoro-5,5-dioxido-7,7a,8,9,10,11-hexahydro-6H-dipyrido[2,1-d:2',3-1f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

3-(3-(Difluoromethyl)-8-methyl-[1,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic acid;

(*S)-3-(3-(Difluoromethyl)-8-methyl-[1,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3-f][1,2,5]thiadiazepin-6-yl)methyl)phenyl)propanoic acid;

(*R)-3-(3-(Difluoromethyl)-8-methyl-[1,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3-f][1,2,5]thiadiazepin-6-yl)methyl)phenyl)propanoic acid;

3-(3-(Difluoromethyl)-8-methyl-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic acid;

(*S)-3-(3-(Difluoromethyl)-8-methyl-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3-f][1,2,5]thiadiazepin-6-yl)methyl)phenyl)propanoic acid;

(*R)-3-(3-(Difluoromethyl)-8-methyl-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3-f][1,2,5]thiadiazepin-6-yl)methyl)phenyl)propanoic acid;

3-(6-(((*S)-3-Fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-2-methyl-3-(8-methyl-3-(trifluoromethyl)-[1,2,4]triazolo[4,3-a]pyridin-7-yl)propanoic acid;

(3*S)-3-(6-(((S)-3-fluoro-5,5-dioxido-7,7a,8,9,10,11-hexahydro-6H-dipyrido[2,1-d:2',3-f][1,2,5]thiadiazepin-6-yl)methyl)-5-methylpyridin-2-yl)-2-methyl-3-(8-methyl-3-(trifluoromethyl)-[1,2,4]triazolo[4,3-a]pyridin-7-yl)propanoic acid;

(3*R)-3-(6-(((*S)-3-Fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-2-methyl-3-(8-methyl-3-(trifluoromethyl)-[1,2,4]triazolo[4,3-a]pyridin-7-yl)propanoic acid;

3-(6-((8'-Fluoro-1',1'-dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid;

(*S)-3-(6-((8'-Fluoro-1',1'-dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid;

(*R)-3-(6-((8'-Fluoro-1',1'-dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid;

(*S)-3-(3-(Difluoromethyl)-8-methyl-[1,2,4]triazolo[4,3-a]pyridin-7-yl)-3-(3-(((*S)-3-fluoro-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*S)-3-(3-(Difluoromethyl)-8-methyl-[1,2,4]triazolo[4,3-a]pyridin-7-yl)-3-(3-(((*R)-3-fluoro-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(3*S)-3-(8-Ethyl-3-(trifluoromethyl)-[1,2,4]triazolo[4,3-a]pyridin-7-yl)-2-methyl-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic acid;

(3*S)-2-Methyl-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(3*S)-3-(8-Ethyl-3-(trifluoromethyl)-[1,2,4]triazolo[4,3-a]pyridin-7-yl)-2-methyl-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic acid;

(*S)-3-(8-Ethyl-3-(trifluoromethyl)-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic acid;

(*S)-3-(8-Ethyl-3-(trifluoromethyl)-[1,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic acid;

3-(6-((3-Chloro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

(*S)-3-(6-(((*S)-3-Chloro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

(*S)-3-(6-(((*R)-3-Chloro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

(*R)-3-(6-(((*S)-3-Chloro-5,5-dioxido-7,7a,8,9,10,11-hexahydro-6H-dipyrido[2,1-d:2',3'-f][1,2,5]thiadiazepin- 6-yl)methyl)-5-methylpyridin-2-yl)-3-(8-methyl-3-(trifluoromethyl)-[1,2,4]triazolo[4,3-a]pyridin-7-yl)propanoic acid;

(*R)-3-(6-(((*R)-3-Chloro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

3-(3-(Difluoromethyl)-8-methyl-[1,2,4]triazolo[4,3-a]pyridin-7-yl)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)propanoic acid;

(*S)-3-(3-(Difluoromethyl)-8-methyl-[1,2,4]triazolo[4,3-a]pyridin-7-yl)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)propanoic acid;

(*R)-3-(3-(Difluoromethyl)-8-methyl-[1,2,4]triazolo[4,3-a]pyridin-7-yl)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)propanoic acid;

3-(3-(Difluoromethyl)-8-methyl-[1,2,4]triazolo[4,3-a]pyridin-7-yl)-3-(3-((8'-fluoro-1',1'-dioxidospiro[cyclopropane-1,4'-pyrido[2,3-b][1,4,5]oxathiazepin]-2'(3'H)-yl)methyl)-4-methylphenyl)propanoic acid;

(*S)-3-(3-(Difluoromethyl)-8-methyl-[1,2,4]triazolo[4,3-a]pyridin-7-yl)-3-(3-((8'-fluoro-1',1'-dioxidospiro[cyclopropane-1,4'-pyrido[2,3-b][1,4,5]oxathiazepin]-2'(3'H)-yl)methyl)-4-methylphenyl)propanoic acid;

(*R)-3-(3-(Difluoromethyl)-8-methyl-[1,2,4]triazolo[4,3-a]pyridin-7-yl)-3-(3-((8'-fluoro-1',1'-dioxidospiro[cyclopropane-1,4'-pyrido[2,3-b][1,4,5]oxathiazepin]-2'(3'H)-yl)methyl)-4-methylphenyl)propanoic acid;

3-(3-((8'-Chloro-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic acid;

(*S)-3-(3-((8'-Chloro-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic acid;

(*R)-3-(3-((8'-Chloro-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic acid;

3-(3-(Difluoromethyl)-8-methyl-[1,2,4]triazolo[4,3-a]pyridin-7-yl)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)propanoic acid;

(*S)-3-(3-(Difluoromethyl)-8-methyl-[1,2,4]triazolo[4,3-a]pyridin-7-yl)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)propanoic acid;

(*R)-3-(3-(Difluoromethyl)-8-methyl-[1,2,4]triazolo[4,3-a]pyridin-7-yl)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)propanoic acid;

3-(3-(Difluoromethyl)-8-methyl-[1,2,4]triazolo[4,3-a]pyridin-7-yl)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;

(*S)-3-(3-(Difluoromethyl)-8-methyl-[1,2,4]triazolo[4,3-a]pyridin-7-yl)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;

(*R)-3-(3-(Difluoromethyl)-8-methyl-[1,2,4]triazolo[4,3-a]pyridin-7-yl)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;

(*S)-3-(4-Methyl-3-((7'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

3-(3-(((*R)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoic acid;

(*S)-3-(3-(((*R)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoic acid;

(*R)-3-(3-(((*R)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoic acid;

3-(3-(((S)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoic acid;

(*S)-3-(3-(((S)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoic acid;

(*R)-3-(3-(((S)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoic acid;

(2*S,3*R)-2-Methyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(2*R,3*R)-2-Methyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanamide;

(*S)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanamide;

(*R)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanamide;

3-(3-((8'-Carbamoyl-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic acid;

(*S)-3-(3-((8'-Carbamoyl-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic acid;

(*R)-3-(3-((8'-Carbamoyl-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic acid;

(2S,3*R)-3-(3-(Trifluoromethyl)-8-methyl-[1,2,4]triazolo[4,3-a]pyridin-7-yl)-3-(3-(((1',1'-dioxidospiro[cyclopropane-1,4'-pyrido[2,3-b][1,4,5]oxathiazepin]-2'(3'H)-yl)
methyl)-4-methylphenyl)-2-methylpropanoic acid;

(*S)-3-(6-((1',1'-Dioxido-2,3,5,6-tetrahydrospiro[pyran-4,
4'-pyrido[2,3-b][1,4,5]oxathiazepin]-2'(3'H)-yl)methyl)-
5-methylpyridin-2-yl)-3-(1-ethyl-4-methyl-1H-benzo[d]
[1,2,3]triazol-5-yl)-2,2-dimethylpropanoic acid;

(*R)-3-(6-((1',1'-Dioxido-2,3,5,6-tetrahydrospiro[pyran-4,
4'-pyrido[2,3-b][1,4,5]oxathiazepin]-2'(3'H)-yl)methyl)-
5-methylpyridin-2-yl)-3-(1-ethyl-4-methyl-1H-benzo[d]
[1,2,3]triazol-5-yl)-2,2-dimethylpropanoic acid;

(*S)-3-(1-Ethyl-4-methyl-1H-benzo[d][1,2,3]triazol-5-yl)-
2,2-dimethyl-3-(5-methyl-6-((8'-methyl-1',1'-dioxido-2,
3,5,6-tetrahydrospiro[pyran-4,4'-pyrido[2,3-b][1,4,5]ox-
athiazepin]-2'(3'H)-yl)methyl)pyridin-2-yl)propanoic
acid;

(*R)-3-(1-Ethyl-4-methyl-1H-benzo[d][1,2,3]triazol-5-yl)-
2,2-dimethyl-3-(5-methyl-6-((8'-methyl-1',1'-dioxido-2,
3,5,6-tetrahydrospiro[pyran-4,4'-pyrido[2,3-b][1,4,5]ox-
athiazepin]-2'(3'H)-yl)methyl)pyridin-2-yl)propanoic
acid;

(R/S)-3-(3-(Difluoromethyl)-8-methyl-[1,2,4]triazolo[4,3-
a]pyridin-7-yl)-2,2-dimethyl-3-(4-methyl-3-((8'-methyl-
1',1'-dioxidospiro[cyclopropane-1,4'-pyrido[2,3-b][1,4,5]
oxathiazepin]-2'(3'H)-yl)methyl)phenyl)propanoic acid;

(*S)-3-(3-(Difluoromethyl)-8-methyl-[1,2,4]triazolo[4,3-a]
pyridin-7-yl)-2,2-dimethyl-3-(4-methyl-3-((8'-methyl-1',
1'-dioxidospiro[cyclopropane-1,4'-pyrido[2,3-b][1,4,5]
oxathiazepin]-2'(3'H)-yl)methyl)phenyl)propanoic acid;

(*R)-3-(3-(Difluoromethyl)-8-methyl-[1,2,4]triazolo[4,3-a]
pyridin-7-yl)-2,2-dimethyl-3-(4-methyl-3-((8'-methyl-1',
1'-dioxidospiro[cyclopropane-1,4'-pyrido[2,3-b][1,4,5]
oxathiazepin]-2'(3'H)-yl)methyl)phenyl)propanoic acid;

(*S)-3-(5-((1',1'-Dioxido-2,3,5,6-tetrahydrospiro[pyran-4,
4'-pyrido[2,3-b][1,4,5]oxathiazepin]-2'(3'H)-yl)methyl)-
6-methylpyridin-3-yl)-3-(8-methyl-3-(trifluoromethyl)-
[1,2,4]triazolo[4,3-a]pyridin-7-yl)propanoic acid;

(*S)-3-(8-Methyl-3-(trifluoromethyl)-[1,2,4]triazolo[4,3-a]
pyridin-7-yl)-3-(6-methyl-5-((8'-methyl-1',1'-dioxi-
dospiro[cyclopropane-1,4'-pyrido[2,3-b][1,4,5]oxathiaz-
epin]-2'(3'H)-yl)methyl)pyridin-3-yl)propanoic acid;

(*R)-3-(5-((1',1'-Dioxido-2,3,5,6-tetrahydrospiro[pyran-4,
4'-pyrido[2,3-b][1,4,5]oxathiazepin]-2'(3'H)-yl)methyl)-
6-methylpyridin-3-yl)-3-(8-methyl-3-(trifluoromethyl)-
[1,2,4]triazolo[4,3-a]pyridin-7-yl)propanoic acid;

(*R)-3-(8-Methyl-3-(trifluoromethyl)-[1,2,4]triazolo[4,3-a]
pyridin-7-yl)-3-(6-methyl-5-((8'-methyl-1',1'-dioxi-
dospiro[cyclopropane-1,4'-pyrido[2,3-b][1,4,5]oxathiaz-
epin]-2'(3'H)-yl)methyl)pyridin-3-yl)propanoic acid;

(R/S)-3-(3-(Difluoromethyl)-8-methyl-[1,2,4]triazolo[4,3-
a]pyridin-7-yl)-3-(3-((1',1'-dioxidospiro[cyclopropane-1,
4'-pyrido[2,3-b][1,4,5]oxathiazepin]-2'(3'H)-yl)methyl)-
4-methylphenyl)-2,2-dimethylpropanoic acid;

(*S)-3-(3-(Difluoromethyl)-8-methyl-[1,2,4]triazolo[4,3-a]
pyridin-7-yl)-3-(3-((1',1'-dioxidospiro[cyclopropane-1,4'-
pyrido[2,3-b][1,4,5]oxathiazepin]-2'(3'H)-yl)methyl)-4-
methylphenyl)-2,2-dimethylpropanoic acid;

(*R)-3-(3-(Difluoromethyl)-8-methyl-[1,2,4]triazolo[4,3-a]
pyridin-7-yl)-3-(3-((1',1'-dioxidospiro[cyclopropane-1,4'-
pyrido[2,3-b][1,4,5]oxathiazepin]-2'(3'H)-yl)methyl)-4-
methylphenyl)-2,2-dimethylpropanoic acid;

(R/S)-3-(5-((1',1'-Dioxido-2,3,5,6-tetrahydrospiro[pyran-4,
4'-pyrido[2,3-b][1,4,5]oxathiazepin]-2'(3'H)-yl)methyl)-
6-methylpyridin-3-yl)-2,2-dimethyl-3-(8-methyl-3-(trif-
luoromethyl)-[1,2,4]triazolo[4,3-a]pyridin-7-yl)
propanoic acid;

(*S)-3-(5-((1',1'-Dioxido-2,3,5,6-tetrahydrospiro[pyran-4,
4'-pyrido[2,3-b][1,4,5]oxathiazepin]-2'(3'H)-yl)methyl)-
6-methylpyridin-3-yl)-2,2-dimethyl-3-(8-methyl-3-(trif-
luoromethyl)-[1,2,4]triazolo[4,3-a]pyridin-7-yl)
propanoic acid;

(R/S)-2,2-Dimethyl-3-(8-methyl-3-(trifluoromethyl)-[1,2,4]
triazolo[4,3-a]pyridin-7-yl)-3-(6-methyl-5-((8'-methyl-1',
1'-dioxidospiro[cyclopropane-1,4'-pyrido[2,3-b][1,4,5]
oxathiazepin]-2'(3'H)-yl)methyl)pyridin-3-yl)propanoic
acid;

(*S)-2,2-Dimethyl-3-(8-methyl-3-(trifluoromethyl)-[1,2,4]
triazolo[4,3-a]pyridin-7-yl)-3-(6-methyl-5-((8'-methyl-1',
1'-dioxidospiro[cyclopropane-1,4'-pyrido[2,3-b][1,4,5]
oxathiazepin]-2'(3'H)-yl)methyl)pyridin-3-yl)propanoic
acid;

(*R)-2,2-Dimethyl-3-(8-methyl-3-(trifluoromethyl)-[1,2,4]
triazolo[4,3-a]pyridin-7-yl)-3-(6-methyl-5-((8'-methyl-1',
1'-dioxidospiro[cyclopropane-1,4'-pyrido[2,3-b][1,4,5]
oxathiazepin]-2'(3'H)-yl)methyl)pyridin-3-yl)propanoic
acid;

(R/S)-3-(3-(Difluoromethyl)-8-methyl-[1,2,4]triazolo[4,3-
a]pyridin-7-yl)-2,2-dimethyl-3-(4-methyl-3-((8'-methyl-
1',1'-dioxido-2,3,5,6-tetrahydrospiro[pyran-4,4'-pyrido[2,
3-b][1,4,5]oxathiazepin]-2'(3'H)-yl)methyl)phenyl)
propanoic acid;

(*S)-3-(3-(Difluoromethyl)-8-methyl-[1,2,4]triazolo[4,3-a]
pyridin-7-yl)-2,2-dimethyl-3-(4-methyl-3-((8'-methyl-1',
1'-dioxido-2,3,5,6-tetrahydrospiro[pyran-4,4'-pyrido[2,3-
b][1,4,5]oxathiazepin]-2'(3'H)-yl)methyl)phenyl)
propanoic acid;

(*R)-3-(3-(Difluoromethyl)-8-methyl-[1,2,4]triazolo[4,3-a]
pyridin-7-yl)-2,2-dimethyl-3-(4-methyl-3-((8'-methyl-1',
1'-dioxido-2,3,5,6-tetrahydrospiro[pyran-4,4'-pyrido[2,3-
b][1,4,5]oxathiazepin]-2'(3'H)-yl)methyl)phenyl)
propanoic acid;

3-(3-(Difluoromethyl)-8-methyl-[1,2,4]triazolo[4,3-a]pyri-
din-7-yl)-2,2-dimethyl-3-(4-methyl-3-((7'-(2-morpholi-
noethoxy)-1',1'-dioxido-2,3,5,6-tetrahydrospiro[pyran-4,
4'-pyrido[2,3-b][1,4,5]oxathiazepin]-2'(3'H)-yl)methyl)
phenyl)propanoic acid;

(*S)-3-(3-(Difluoromethyl)-8-methyl-[1,2,4]triazolo[4,3-a]
pyridin-7-yl)-2,2-dimethyl-3-(4-methyl-3-((7'-(2-mor-
pholinoethoxy)-1',1'-dioxido-2,3,5,6-tetrahydrospiro
[pyran-4,4'-pyrido[2,3-b][1,4,5]oxathiazepin]-2'(3'H)-yl)
methyl)phenyl)propanoic acid;

(*R)-3-(3-(Difluoromethyl)-8-methyl-[1,2,4]triazolo[4,3-a]
pyridin-7-yl)-2,2-dimethyl-3-(4-methyl-3-((7'-(2-mor-
pholinoethoxy)-1',1'-dioxido-2,3,5,6-tetrahydrospiro
[pyran-4,4'-pyrido[2,3-b][1,4,5]oxathiazepin]-2'(3'H)-yl)
methyl)phenyl)propanoic acid;

3-(3-(difluoromethyl)-8-methyl-[1,2,4]triazolo[4,3-a]pyri-
din-7-yl)-3-(3-((7'-methoxy-1',1'-dioxido-2,3,5,6-tetrahy-
drospiro[pyran-4,4'-pyrido[2,3-b][1,4,5]oxathiazepin]-2'
(3'H)-yl)methyl)-4-methylphenyl)-2,2-
dimethylpropanoic acid;

(*S)-3-(3-(Difluoromethyl)-8-methyl-[1,2,4]triazolo[4,3-a]
pyridin-7-yl)-3-(3-((7'-methoxy-1',1'-dioxido-2,3,5,6-tet-
rahydrospiro[pyran-4,4'-pyrido[2,3-b][1,4,5]oxathiaz-
epin]-2'(3'H)-yl)methyl)-4-methylphenyl)-2,2-
dimethylpropanoic acid;

(*R)-3-(3-(Difluoromethyl)-8-methyl-[1,2,4]triazolo[4,3-a]
pyridin-7-yl)-3-(3-((7'-methoxy-1',1'-dioxido-2,3,5,6-tet-
rahydrospiro[pyran-4,4'-pyrido[2,3-b][1,4,5]oxathiaz-
epin]-2'(3'H)-yl)methyl)-4-methylphenyl)-2,2-
dimethylpropanoic acid;

(R/S)-2,2-Dimethyl-3-(8-methyl-3-(trifluoromethyl)-[1,2,4]
triazolo[4,3-a]pyridin-7-yl)-3-(6-methyl-5-((8'-methyl-1', 1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*S)-2,2-Dimethyl-3-(8-methyl-3-(trifluoromethyl)-[1,2,4]triazolo[4,3-a]pyridin-7-yl)-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*R)-2,2-Dimethyl-3-(8-methyl-3-(trifluoromethyl)-[1,2,4]triazolo[4,3-a]pyridin-7-yl)-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(R/S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid;

(*S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid;

(*R)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid;

(*S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid;

(*S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid;

(*S)-3-(1-Ethyl-4-methyl-1H-benzo[d][1,2,3]triazol-5-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid;

(*S)-3-(1-Ethyl-4-methyl-1H-benzo[d][1,2,3]triazol-5-yl)-2,2-dimethyl-3-(5-methyl-4-((8'-methyl-1',1'-dioxidospiro[azetidine-3,4'-pyrido[2,3-b][1,4,5]oxathiazepin]-2'(3'H)-yl)methyl)pyridin-2-yl)propanoic acid;

(*S)-3-(3-((7'-(2-(3-fluoroazetidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-2,2-dimethyl-3-(4-methyl-3-((8'-methyl-7'-(2-morpholinoethoxy)-1',1'-dioxidospiro[cyclopropane-1,4'-pyrido[2,3-b][1,4,5]oxathiazepin]-2',(3'H)-yl)methyl)phenyl)-3-(8-methyl-3-(trifluoromethyl)-[1,2,4]triazolo[4,3-a]pyridine-7-yl)propanoic acid;

(*S)-3-(3-((1',1'-dioxido-7'-(2-(pyrrolidine-1-yl)ethoxy)spiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-3-(3-((7'-(3-amino-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-2,2-Dimethyl-3-(4-methyl-3-((8'-methyl-1',1'-dioxido-7'-((1-(piperidin-1-yl)propan-2-yl)oxy)-2,3,5,6-tetrahydrospiro[pyran-4,4'-pyrido[2,3-b][1,4,5]oxathiazepin]-2',(3'H)-yl)methyl)phenyl)-3-(8-methyl-3-(trifluoromethyl)-[1,2,4]triazolo[4,3-a]pyridine-7-yl)propanoic acid;

(*S)-2,2-Dimethyl-3-(4-methyl-3-((8'-methyl-1',1'-dioxido-7'-(((*R)-1-(piperidin-1-yl)propan-2-yl)oxy)-2,3,5,6-tetrahydrospiro[pyran-4,4'-pyrido[2,3-b][1,4,5]oxathiazepin]-2',(3'H)-yl)methyl)phenyl)-3-(8-methyl-3-(trifluoromethyl)-[1,2,4]triazolo[4,3-a]pyridine-7-yl)propanoic acid;

(*S)-2,2-Dimethyl-3-(4-methyl-3-((8'-methyl-1',1'-dioxido-7'-(((*S)-1-(piperidin-1-yl)propan-2-yl)oxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-2,2-Dimethyl-3-(4-methyl-3-((8'-methyl-1',1'-dioxido-7'-(((*R)-1-(piperidin-1-yl)propan-2-yl)amino)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*S)-3-(3-((7'-(2-(Azetidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-3-(3-((7'-(3-Cyclobutylamino-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-3-(3-((7'-(2-Hydroxyethoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-3-(3-((7'-(3-(3-Hydroxypropoxy)propoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*R)-3-(3-((7'-(3-(3-Hydroxypropoxy)propoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*R)-2,2-Dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-3-(3-(Difluoromethyl)-8-methyl-[1,2,4]triazolo[4,3-a]pyridin-7-yl)-3-(6-((1',1'-dioxidospiro[oxetane-3,4'- pyrido[2,3-b][1,4,5]oxathiazepin]-2'(3'H)-yl)methyl)-5-methylpyridin-2-yl)-2,2-dimethylpropanoic acid;

(*R)-3-(3-(Difluoromethyl)-8-methyl-[1,2,4]triazolo[4,3-a]pyridin-7-yl)-3-(6-((1',1'-dioxidospiro[oxetane-3,4'-pyrido[2,3-b][1,4,5]oxathiazepin]-2'(3'H)-yl)methyl)-5-methylpyridin-2-yl)-2,2-dimethylpropanoic acid;

(*S)-3-(1-Cyclopropyl-4-methyl-1H-benzo[d][1,2,3]triazol-5-yl)-3-(5-((1',1'-dioxidospiro[oxetane-3,4'-pyrido[2,3-b][1,4,5]oxathiazepin]-2'(3'H)-yl)methyl)-6-methylpyridin-3-yl)-2,2-dimethylpropanoic acid;

(*R)-3-(1-Cyclopropyl-4-methyl-1H-benzo[d][1,2,3]triazol-5-yl)-3-(5-((1',1'-dioxidospiro[oxetane-3,4'-pyrido[2,3-b][1,4,5]oxathiazepin]-2'(3'H)-yl)methyl)-6-methylpyridin-3-yl)-2,2-dimethylpropanoic acid;

(*S)-2,2-dimethyl-3-(4-methyl-3-((8'-methyl-1',1'-dioxidospiro[oxetane-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*S)-3-(3-((1',1'-dioxidospiro[oxetane-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-3-(3-(difluoromethyl)-8-methyl-[1,2,4]triazolo[4,3-a]pyridine-7-yl)-3-((1',1'-dioxidospiro[oxetane-3,4'-pyrido[2,3-b][1,4,5]oxathiazepin]-2'(3'H)-yl)methyl)-4-methylphenyl)-2,2-dimethylpropanoic acid;

(*S)-3-(3-(Difluoromethyl)-8-methyl-[1,2,4]triazolo[4,3-a]pyridin-7-yl)-2,2-dimethyl-3-(4-methyl-3-((8'-methyl-1',1'-dioxidospiro[oxetane-3,4'-pyrido[2,3-b][1,4,5]oxathiazepin]-2'(3'H)-yl)methyl)phenyl)propanoic acid;

(R/S)-3-(1-Cyclopropyl-4-methyl-1H-benzo[d][1,2,3]triazol-5-yl)-2,2-dimethyl-3-(4-methyl-3-((8'-methyl-1',1'-dioxido-7'-(((S)-1-(piperidin-1-yl)propan-2-yl)amino)spiro[cyclopropane-1,4'-pyrido[2,3-b][1,4,5]oxathiazepin]-2'(3'H)-yl)methyl)phenyl)propanoic acid;

(*R)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[oxetane-3,4'-pyrido[2,3-b][1,4,5]oxathiazepin]-2'(3'H)-yl)methyl)phenyl)propanoic acid;

(*R)-3-(3-Cyclopropyl-8-methyl-[1,2,4]triazolo[4,3-a]pyridin-7-yl)-3-(3-((1',1'-dioxidospiro[oxetane-3,4'-pyrido[2,3-b][1,4,5]oxathiazepin]-2'(3'H)-yl)methyl)-4-methylphenyl)-2,2-dimethylpropanoic acid;

(*S)-3-(3-Cyclopropyl-8-methyl-[1,2,4]triazolo[4,3-a]pyridin-7-yl)-3-(3-((1',1'-dioxidospiro[oxetane-3,4'-pyrido[2,3-b][1,4,5]oxathiazepin]-2'(3'H)-yl)methyl)-4-methylphenyl)-2,2-dimethylpropanoic acid;

(*S)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[oxetane-3,4'-pyrido[2,3-b][1,4,5]oxathiazepin]-2'(3'H)-yl)methyl)phenyl)propanoic acid;

(*R)-3-(1-Cyclopropyl-4-methyl-1H-benzo[d][1,2,3]triazol-5-yl)-2,2-dimethyl-3-(6-methyl-5-((8'-methyl-1',1'-dioxidospiro[oxetane-3,4'-pyrido[2,3-b][1,4,5]]oxathiazepin]-2'(3'H)-yl)methyl)pyridine-3-yl)propanoic acid;

(*S)-3-(1-Cyclopropyl-4-methyl-1H-benzo[d][1,2,3]triazol-5-yl)-2,2-dimethyl-3-(6-methyl-5-((8'-methyl-1',1'-dioxidospiro[oxetane-3,4'-pyrido[2,3-b][1,4,5]]oxathiazepin]-2'(3'H)-yl)methyl)pyridine-3-yl)propanoic acid;

(*R)-3-(1-Cyclopropyl-4-methyl-1H-benzo[d][1,2,3]triazol-5-yl)-2,2-dimethyl-3-(6-methyl-5-((8'-methyl-1',1'-dioxido-7'-(2-(pyrrolidine-1-yl)ethoxy)spiro[cyclopropane-1,4'-pyrido[2,3-b][1,4,5]]oxathiazepin]-2'(3'H)-yl)methyl)pyridine-3-yl)propanoic acid;

(*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[oxetane-3,4'-pyrido[2,3-b][1,4,5]oxathiazepin]-2'(3'H)-yl)methyl)pyridin-2-yl)propanoic acid;

(*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[oxetane-3,4'-pyrido[2,3-b][1,4,5]oxathiazepin]-2'(3'H)-yl)methyl)pyridin-2-yl)propanoic acid;

(*S)-3-(1-Cyclopropyl-4-methyl-1H-benzo[d][1,2,3]triazol-5-yl)-2,2-dimethyl-3-(6-methyl-5-((8'-methyl-1',1'-dioxido-7'-(2-(pyrrolidine-1-yl)ethoxy)spiro[cyclopropane-1,4'-pyrido[2,3-b][1,4,5]]oxathiazepin]-2'(3'H)-yl)methyl)pyridine-3-yl)propanoic acid;

(*R)-2,2-Dimethyl-3-(8-methyl-3-(trifluoromethyl)-[1,2,4]triazolo[4,3-a]pyridin-7-yl)-3-(5-methyl-6-((8'-methyl-1',1'-dioxidospiro[azetidine-3,4'-pyrido[2,3-b][1,4,5]oxathiazepin]-2'(3'H)-yl)methyl)pyridin-2-yl)propanoic acid;

(*S)-2,2-Dimethyl-3-(8-methyl-3-(trifluoromethyl)-[1,2,4]triazolo[4,3-a]pyridin-7-yl)-3-(5-methyl-6-((8'-methyl-1',1'-dioxidospiro[azetidine-3,4'-pyrido[2,3-b][1,4,5]oxathiazepin]-2'(3'H)-yl)methyl)pyridin-2-yl)propanoic acid;

(*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[azetidine-3,4'-pyrido[2,3-b][1,4,5]oxathiazepin]-2'(3'H)-yl)methyl)pyridin-2-yl)propanoic acid;

(*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[azetidine-3,4'-pyrido[2,3-b][1,4,5]oxathiazepin]-2'(3'H)-yl)methyl)pyridin-2-yl)propanoic acid;

(*R)-2,2-Dimethyl-3-(8-methyl-3-(trifluoromethyl)-[1,2,4]triazolo[4,3-a]pyridin-7-yl)-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*S)-2,2-Dimethyl-3-(8-methyl-3-(trifluoromethyl)-[1,2,4]triazolo[4,3-a]pyridin-7-yl)-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid (*R)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*S)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*R)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*S)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*R)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid;

(*S)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid;

(*R)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid;

(*S)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid;

(*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid;

(*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid;

(*R)-3-(1-Cyclopropyl-4-methyl-1H-benzo[d][1,2,3]triazol-5-yl)-2,2-dimethyl-3-(4-methyl-3-((8'-methyl-1',1'-dioxidospiro[azetidine-3,4'-pyrido[2,3-b][1,4,5]oxathiazepin]-2'(3'H)-yl)methyl)phenyl)propanoic acid;

(*S)-3-(1-Cyclopropyl-4-methyl-1H-benzo[d][1,2,3]triazol-5-yl)-2,2-dimethyl-3-(4-methyl-3-((8'-methyl-1',1'-dioxidospiro[azetidine-3,4'-pyrido[2,3-b][1,4,5]oxathiazepin]-2'(3'H)-yl)methyl)phenyl)propanoic acid;

(*R)-3-(1-Cyclopropyl-4-methyl-1H-benzo[d][1,2,3]triazol-5-yl)-3-(3-((1',1'-dioxidospiro[piperidine-4,4'-pyrido[2,3-b][1,4,5]oxathiazepin]-2'(3'H)-yl)methyl)-4-methylphenyl)-2,2-dimethylpropanoic acid;

(*S)-3-(1-Cyclopropyl-4-methyl-1H-benzo[d][1,2,3]triazol-5-yl)-3-(3-((1',1'-dioxidospiro[piperidine-4,4'-pyrido[2,3-b][1,4,5]oxathiazepin]-2'(3'H)-yl)methyl)-4-methylphenyl)-2,2-dimethylpropanoic acid;

(*R)-3-(1-Cyclopropyl-4-methyl-1H-benzo[d][1,2,3]triazol-5-yl)-2,2-dimethyl-3-(4-methyl-3-((8'-methyl-1',1'-dioxidospiro[piperidine-4,4'-pyrido[2,3-b][1,4,5]oxathiazepin]-2'(3'H)-yl)methyl)phenyl)propanoic acid;

(*S)-3-(1-Cyclopropyl-4-methyl-1H-benzo[d][1,2,3]triazol-5-yl)-2,2-dimethyl-3-(4-methyl-3-((8'-methyl-1',1'-dioxidospiro[piperidine-4,4'-pyrido[2,3-b][1,4,5]oxathiazepin]-2'(3'H)-yl)methyl)phenyl)propanoic acid;

(R/S)-3-(1-Cyclopropyl-4-methyl-1H-benzo[d][1,2,3]triazol-5-yl)-2,2-dimethyl-3-(4-methyl-3-((8'-methyl-1',1'-dioxidospiro[azetidine-3,4'-pyrido[2,3-b][1,4,5]oxathiazepin]-2'(3'H)-yl)methyl)phenyl)propanoic acid;

(R/S)-3-(1-Cyclopropyl-4-methyl-1H-benzo[d][1,2,3]triazol-5-yl)-3-(3-((1',1'-dioxidospiro[piperidine-4,4'-pyrido[2,3-b][1,4,5]oxathiazepin]-2'(3'H)-yl)methyl)-4-methylphenyl)-2,2-dimethylpropanoic acid;

(R/S)-3-(1-Cyclopropyl-4-methyl-1H-benzo[d][1,2,3]triazol-5-yl)-2,2-dimethyl-3-(4-methyl-3-((8'-methyl-1',1'-dioxidospiro[piperidine-4,4'-pyrido[2,3-b][1,4,5]oxathiazepin]-2'(3'H)-yl)methyl)phenyl)propanoic acid;

(*R)-3-(5-(((*R)-3-Cyano-5,5-dioxido-7,7a,8,9,10,11-hexahydro-6H-dipyrido[2,1-d:2',3'-f][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoic acid;

(*R)-3-(5-(((*S)-3-Cyano-5,5-dioxido-7,7a,8,9,10,11-hexahydro-6H-dipyrido[2,1-d:2',3'-f][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoic acid;

(*S)-3-(5-(((*R)-3-Cyano-5,5-dioxido-7,7a,8,9,10,11-hexahydro-6H-dipyrido[2,1-d:2',3'-f][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoic acid;

(*S)-3-(5-(((*S)-3-Cyano-5,5-dioxido-7,7a,8,9,10,11-hexahydro-6H-dipyrido[2,1-d:2',3'-f][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoic acid;

(*R)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid (*S)-3-(1-Cyclopropyl-4-methyl-1H-benzo[d][1,2,3]triazol-5-yl)-2,2-dimethyl-3-(4-methyl-3-((8'-methyl-1',1'-dioxido-7'-(((S)-1-(piperidin-1-yl)propan-2-yl)amino)spiro[cyclopropane-1,4'-pyrido[2,3-b][1,4,5]oxathiazepin]-2'(3'H)-yl)methyl)phenyl)propanoic acid;

(*R)-3-(1-Cyclopropyl-4-methyl-1H-benzo[d][1,2,3]triazol-5-yl)-2,2-dimethyl-3-(4-methyl-3-((8'-methyl-1',1'-dioxido-7'-(((S)-1-(piperidin-1-yl)propan-2-yl)amino)spiro[cyclopropane-1,4'-pyrido[2,3-b][1,4,5]oxathiazepin]-2'(3'H)-yl)methyl)phenyl)propanoic acid;

(*S)-3-(3-((7'-(2-(4-fluoropiperidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-3-(3-((7'-(2-(4-fluoropiperidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-3-(3-Cyclopropyl-8-methyl-[1,2,4]triazolo[4,3-a]pyridin-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoic acid;

(*R)-3-(3-Cyclopropyl-8-methyl-[1,2,4]triazolo[4,3-a]pyridin-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoic acid;

(*R)-3-(1-Ethyl-4-methyl-1H-benzo[d][1,2,3]triazol-5-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid; and pharmaceutically acceptable salts, and combinations thereof.

DETAILED DESCRIPTION OF THE INVENTION

As used herein, the terms "including", "containing" and "comprising" are used in their open, non-limiting sense.

Unless qualified specifically in particular instances of use, the term "alkyl" refers to a straight- or branched-chain alkyl group having from 1 to 8 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. "C$_1$-C$_4$alkyl" refers to straight- or branched-chain alkyl group having from 1 to 4 carbon atoms in the chain.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

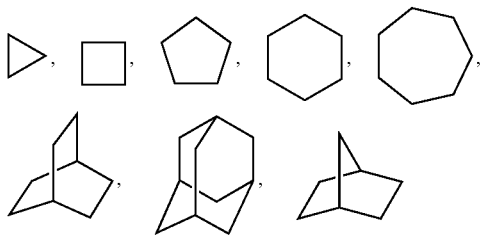

The term "halogen" or "halo" represents chlorine, fluorine, bromine, or iodine.

The term "perhaloalkyl" or "haloalkyl" refers to a straight- or branched-chain alkyl group having from 1 to 6 carbon atoms in the chain optionally substituting hydrogens with halogens. The term "C$_1$-C$_4$ haloalkyl" as used here refers to a straight- or branched-chain alkyl group having from 1 to 4 carbon atoms in the chain, optionally substituting hydrogens with halogens. Examples of "perhaloalkyl", "haloalkyl" groups include trifluoromethyl (CF$_3$), difluoromethyl (CF$_2$H), monofluoromethyl (CH$_2$F), pentafluoroethyl (CF$_2$CF$_3$), tetrafluoroethyl (CHFCF$_3$), monofluoroethyl (CH$_2$CH$_2$F), trifluoroethyl (CH$_2$CF$_3$), tetrafluorotrifluoromethylethyl (CF(CF$_3$)$_2$), and groups that in light of the ordinary skill in the art and the teachings provided herein would be considered equivalent to any one of the foregoing examples.

Those of ordinary skill in the art will recognize that the species of cycloalkyl groups listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of such formula. The compounds of this invention may possess one or more asymmetric centers; such compounds can therefore be produced as individual (R)- or (S)-stereoisomers or as mixtures thereof. Thus, any formula given herein is intended to represent a racemate, one or more of its enantiomeric forms, one or more of its diastereomeric forms, and mixtures thereof. Additionally, any formula given herein is intended to refer also to any one of hydrates, solvates, polymorphs of such compounds, and mixtures thereof, even if such forms are not listed explicitly.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number in an enriched form. Examples of isotopes that can be incorporated into compounds of the invention in a form that exceeds natural abundances include isotopes of hydrogen, carbon, nitrogen, oxygen, phosphorous, fluorine, chlorine, and iodine, such as $^2$H, $^3$H, $^{11}$C, $^{13}$C, 14C, $^{15}$N, $^{18}$O, $^{17}$O, $^{31}$P, $^{32}$P, $^{35}$S, 18F, $^{36}$C$_1$, and $^{125}$I, respectively. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^{2}$H) may afford certain therapeutic advantages resulting from greater metabolic stability, for example increased in vivo half-life or reduced dosage requirements. Isotopically labeled compounds of this invention can generally be prepared by carrying out the procedures disclosed in the schemes or in the examples and preparations described below by substituting a readily available isotopically labeled reagent for a non-isotopically labeled reagent.

The term $C_{n-m}$ alkyl refers to an aliphatic chain, whether straight or branched, with a total number N of carbon members in the chain that satisfies n≤N≤m, with m>n.

When the same plurality of substituents is assigned to various groups, the specific individual substituent assignment to each of such groups is meant to be independently made with respect to the specific individual substituent assignments to the remaining groups. By way of illustration, but not as a limitation, if each of groups Q and R can be H or F, the choice of H or F for Q is made independently of the choice of H or F for R, so the choice of assignment for Q does not determine or condition the choice of assignment for R, or vice-versa, unless it is expressly indicated otherwise. Illustrative claim recitation in this regard would read as "each of Q and R is independently H or F", or "each of Q and R is independently selected from the group consisting of H and F".

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

In another example, a zwitterionic compound would be encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well-established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein.

The nomenclature "$C_i$-$C_j$" with j>i, when applied herein to a class of substituents, is meant to refer to embodiments of this invention for which each and every one of the number of carbon members, from i to j including i and j, is independently realized. By way of example, the term $C_1$-$C_3$ refers independently to embodiments that have one carbon member ($C_1$), embodiments that have two carbon members ($C_2$), and embodiments that have three carbon members ($C_3$).

A "pharmaceutically acceptable salt" is intended to mean a salt of an acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response.

A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

Compounds of Formula (I) may contain at least one nitrogen of basic character, so desired pharmaceutically acceptable salts may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents.

Since compounds of Formula (I) contain a carboxylic acid moiety, a desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, piperazine, N-methyl-glucamine and tromethamine and inorganic salts derived from sodium, calcium, potassium, magnesium, manganese, iron, copper, zinc, aluminum, and lithium.

The compounds of the invention, including their pharmaceutically acceptable salts, whether alone or in combination, (collectively, "active agent" or "active agents") of the present invention are useful as KEAP1-Nrf2 inhibitors in the methods of the invention. Such methods for modulating KEAP1-Nrf2 interaction comprise the use of an effective amount of at least one chemical compound of the invention.

In some embodiments, the KEAP1-Nrf2 inhibitor is used in a subject diagnosed with or suffering from a disease, disorder, or medical condition associated with KEAP1-Nrf2 interaction, such as those described herein. Symptoms or disease states are intended to be included within the scope of "disease, disorders or medical conditions."

Accordingly, the invention relates to methods of using the active agents described herein to treat subjects diagnosed with or suffering from a disease, disorder, or medical condition associated with the KEAP1-Nrf2 interaction. The term "treat" or "treating" as used herein is intended to refer to administration of an active agent or composition of the invention to a subject for the purpose of effecting a therapeutic or prophylactic benefit through modulation of KEAP1-Nrf2 interaction. Treating includes reversing, ameliorating, alleviating, inhibiting the progress of, lessening the severity of, or preventing a disease, disorder, or condition, or one or more symptoms of such disease, disorder or condition associated with the KEAP1-Nrf2 interaction. The term "subject" refers to a mammalian patient in need of such treatment, such as a human. The term "inhibitors" or "inhibitor" refers to compounds that decrease, prevent, inactivate, desensitize or down-regulate the KEAP1-Nrf2 interaction.

In treatment methods according to the invention, an effective amount of at least one active agent according to the invention is administered to a subject suffering from or diagnosed as having such a disease, disorder, or medical condition. An "effective amount" means an amount or dose sufficient to generally bring about the desired therapeutic or prophylactic benefit in patients in need of such treatment for the designated disease, disorder, or condition. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. For a 70-kg human, an illustrative range for a suitable dosage amount is from about 1 to 1000 mg/day in single or multiple dosage units (e.g., BID, TID, QID or as required by modality).

Once improvement of the patient's disease, disorder, or condition has occurred, the dose may be adjusted for preventive or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention are envisaged for use alone, in combination with one or more of other compounds of this invention, or in combination with additional active ingredients in the treatment of the conditions discussed below. The additional active ingredients may be co-administered separately with at least one compound of the invention, with active agents of the invention or included with such an agent in a pharmaceutical composition according to the invention. In an illustrative embodiment, additional active ingredients are those that are known or discovered to be effective in the treatment of conditions, disorders, or diseases associated with the KEAP1-Nrf2 interaction, such as another KEAP1-Nrf2 inhibitor or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

When referring to inhibiting the target, an "effective amount" means an amount sufficient to affect KEAP1-Nrf2 interaction.

The active agents of the invention are envisaged for use, alone or in combination with one or more additional active ingredients, to formulate pharmaceutical compositions of the invention. A pharmaceutical composition of the invention comprises an effective amount of at least one active agent in accordance with the invention.

Pharmaceutically acceptable excipients commonly used in pharmaceutical compositions are substances that are non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of such excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using pharmaceutically acceptable excipients and compounding techniques known or that become available to those of ordinary skill in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. The compositions may be formulated for any one of a plurality of administration routes, such as intravenous infusion, topical administration, or oral administration. Preferably, the compositions may be formulated for oral administration.

For oral administration, the active agents of the invention can be provided in the form of tablets or capsules, or as a solution, emulsion, or suspension. To prepare the oral compositions, the active agents may be formulated to yield a dosage of, e.g., for a 70-kg human, an illustrative range for a suitable dosage amount is from about 1 to 1000 mg/day in single or multiple dosage units.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Illustrative examples of liquid oral excipients include ethanol, glycerol, water, and the like. Starch, polyvinyl-pyrrolidone (PVP), sodium starch glycolate, microcrystalline cellulose, and alginic acid are examples of disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin or (hydroxypropyl)methyl cellulose capsules. To prepare hard gelatin capsules, active ingredient(s) may be mixed with a solid, semi-solid, or liquid diluent. Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository, enema or foam. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.01% to about 20% of drug to vehicle, preferably 0.1% to 10%. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

In a further embodiment, the invention is directed to a method of treating a subject suffering from or diagnosed with a disease, disorder, or medical condition associated with KEAP1-Nrf2 interaction, comprising administering to the subject in need of such treatment an effective amount of the active agent.

In certain embodiments of the inventive method, the disease, disorder, or medical condition is an inflammatory bowel disease, such as Crohn's disease and ulcerative colitis.

Other embodiments of this invention provide for a method for modulating KEAP1-Nrf2 interaction, including when KEAP1-Nrf2 interaction is in a subject, comprising exposing KEAP1-Nrf2 to an effective amount of at least one compound selected from compounds of the invention.

Embodiments of this invention are compounds of Formula (I), and pharmaceutically acceptable salts thereof

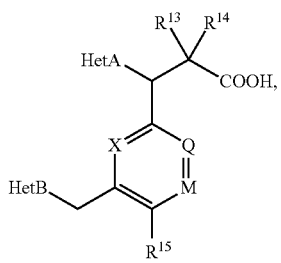

(I)

wherein

X is CH or N;

Q is CH or N;

M is CH or N;

wherein when X is N, each of Q and M is CH;

when Q is N, each of X and M is CH; and when M is N, each of X and Q are CH;

$R^{15}$ is $CH_3$ or Cl;

$R^{13}$ is H, F or $C_1$-$C_4$alkyl;

$R^{14}$ is H, F or $C_1$-$C_4$alkyl;

HetA is selected from the group consisting of

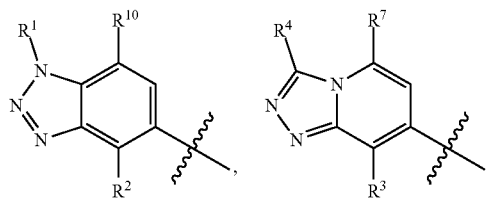

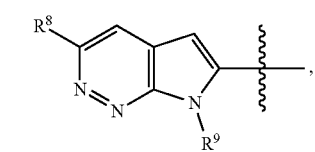

wherein $R^1$ is selected from the group consisting of $C_3$-$C_4$cycloalkyl, $C_1$-$C_4$alkyl and $C_1$-$C_4$alkyl monosubstituted with cyclopropyl or cyclobutyl;

$R^2$ is selected from the group consisting of H, $C_1$-$C_4$alkyl and $C_1$-$C_4$perhaloalkyl;

$R^3$ is H or $C_1$-$C_4$alkyl;

$R^4$ is selected from the group consisting of $C_1$-$C_4$alkyl, $C_1$-$C_4$perhaloalkyl and $C_3$-$C_4$cycloalkyl;

$R^7$ is H or $C_1$-$C_4$alkyl;

$R^8$ is $C_1$-$C_4$alkyl;

$R^9$ is $C_1$-$C_4$alkyl;

$R^{10}$ is selected from the group consisting of H, —$OC_3$-$C_4$cycloalkyl and —$OC_1$-$C_4$perhaloalkyl;

HetB is selected from the group consisting of

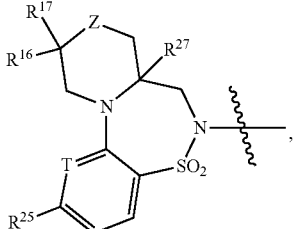

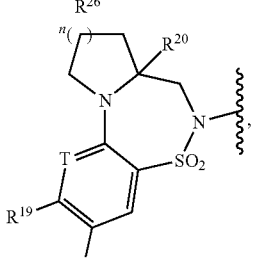

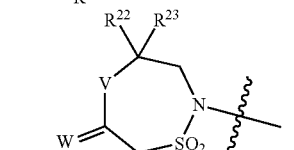

and

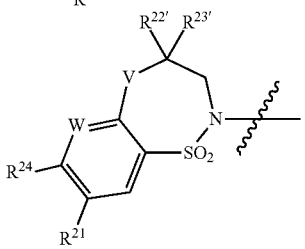

wherein

T is CH or N;

Y is CH or N;

W is CH or N;

V is O or N($CH_3$);

$R^{16}$ is H or F;

$R^{17}$ is H or F;

n is 0, 1 or 2;

$R^{18}$ is selected from the group consisting of H, —CN, halo, C(O)$NH_2$, $C_1$-$C_4$alkyl and $C_1$-$C_4$perhaloalkyl;

$R^{19}$ is selected from the group consisting of H; CN; halo; C(O)$NH_2$; N($R^{38}$)$C_1$-$C_6$alkyl; $C_1$-$C_4$alkyl; $C_1$-$C_4$perhaloalkyl;

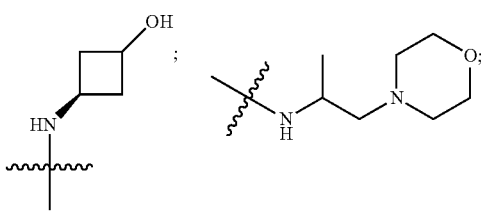

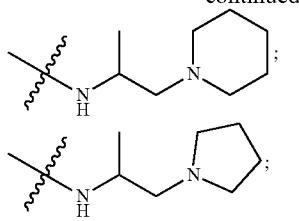

$OC_1$-$C_6$alkyl;

$OC_1$-$C_6$alkyl substituted with one or two substituents selected from the group consisting of —OH, —OCH$_3$, —O(CH$_2$)$_3$OH, —N(R$^{36}$)R$^{37}$, C$_1$-C$_4$alkyl,

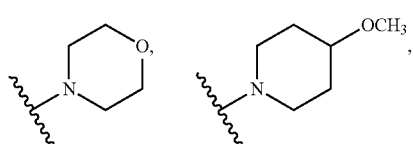

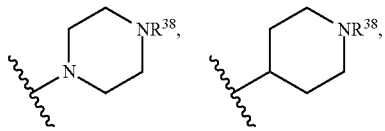

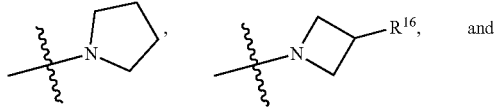

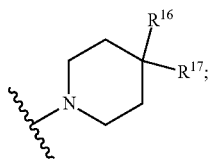

—N(R$^{38}$)C$_1$-C$_6$alkyl substituted with one or two substituents selected from the group consisting of OH, —OCH$_3$, —N(R$^{36}$)R$^{37}$, C$_1$-C$_4$alkyl,

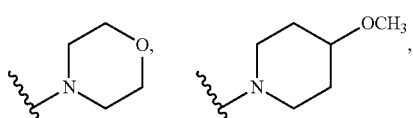

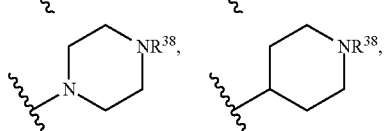

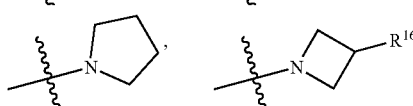

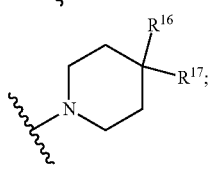

and

C$_1$-C$_4$alkyl monosubstituted with a substituent selected from the group consisting of —C(O)NHCH$_2$CH$_2$OH, —C(O)NHCH$_2$CH$_2$OCH$_2$CH$_2$NH$_2$, C(O)NH$_2$ and OH;

R$^{20}$ is H or C$_1$-C$_4$alkyl;

R$^{21}$ is selected from the group consisting of H, —CN, halo, C$_1$-C$_4$alkyl and C$_1$-C$_4$perhaloalkyl;

R$^{22}$ and R$^{23}$ are taken together with the carbon to which they are attached to form (a) the moiety

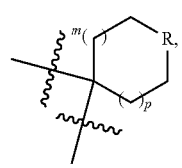

wherein R is selected from the group consisting of CH$_2$, NR$^{38}$ and O, m is 0 or 1, and p is 0 or 1; or (b) the moiety

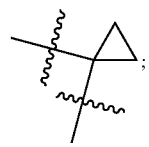 [SMILES: *C1(*)CC1]

R$^{22'}$ is selected from the group consisting of H, C$_1$-C$_4$alkyl and C$_3$-C$_4$cycloalkyl, and R$^{23'}$ is selected from the group consisting of H, C$_1$-C$_4$alkyl and C$_3$-C$_4$cycloalkyl;

R$^{24}$ is selected from the group consisting of H; CN; halo; C(O)NH$_2$;

C(O)(NH)C$_3$-C$_4$cycloalkyl; N(R$^{38}$)C$_1$-C$_6$alkyl; C$_1$-C$_4$alkyl; C$_1$-C$_4$perhaloalkyl;

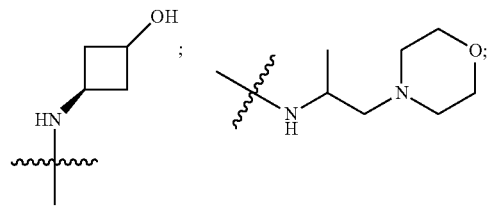

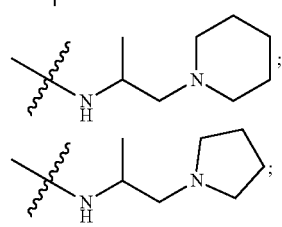

$OC_1$-$C_6$alkyl substituted with one or two substituents selected from the group consisting of —OH, —OCH$_3$, —O(CH$_2$)$_3$OH, —N(R$^{36}$)R$^{37}$, C$_1$-C$_4$alkyl;

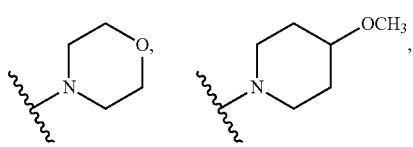

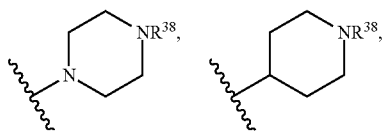

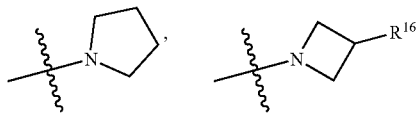

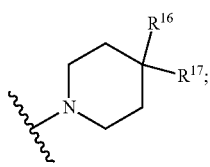

—N(R$^{38}$)C$_1$-C$_6$alkyl substituted with one or two substituents selected from the group consisting of OH, —OCH$_3$, —N(R$^{36}$)R$^{37}$, C$_1$-C$_4$alkyl,

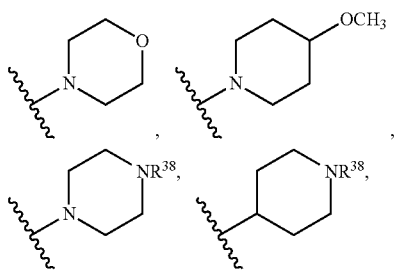

and

C$_1$-C$_4$alkyl monosubstituted with a substituent selected from the group consisting of —C(O)NHCH$_2$CH$_2$OH, —C(O)NHCH$_2$CH$_2$OCH$_2$CH$_2$NH$_2$, C(O)NH$_2$ and OH;

R$^{25}$ is selected from the group consisting of H; CN; halo; C(O)NH$_2$;

N(R$^{38}$)C$_1$-C$_6$alkyl; C$_1$-C$_4$alkyl; C$_1$-C$_4$perhaloalkyl;

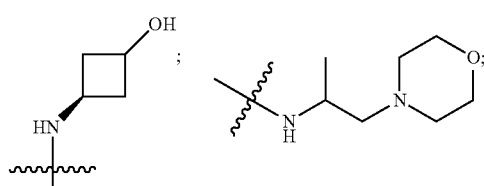

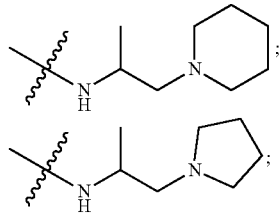

OC$_1$-C$_6$alkyl;

OC$_1$-C$_6$alkyl substituted with one or two substituents selected from the group consisting of —OH, —OCH$_3$, —O(CH$_2$)$_3$OH, —N(R$^{36}$)R$^{37}$, C$_1$-C$_4$alkyl,

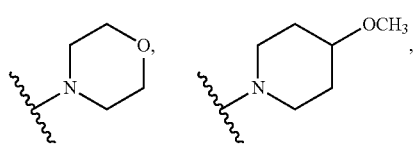

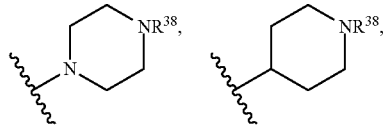

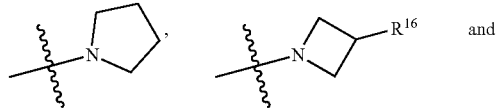

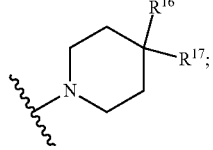

—N(R$^{38}$)C$_1$-C$_6$alkyl substituted with one or two substituents selected from the group consisting of OH, —OCH$_3$, —N(R$^{36}$)R$^{37}$, C$_1$-C$_4$alkyl,

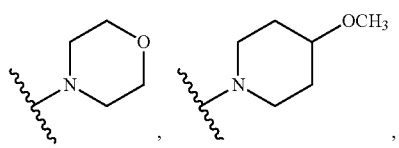

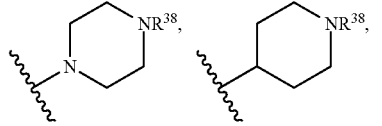

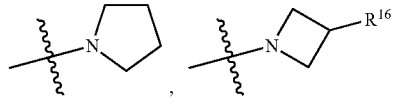

and

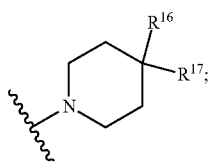

and

C$_1$-C$_4$alkyl monosubstituted with a substituent selected from the group consisting of —C(O)NHCH$_2$CH$_2$OH, —C(O)NHCH$_2$CH$_2$OCH$_2$CH$_2$NH$_2$, C(O)NH$_2$ and OH;

R$^{26}$ is selected from the group consisting of H, —CN, halo, C$_1$-C$_4$alkyl and C$_1$-C$_4$perhaloalkyl;

R$^{27}$ is H or C$_1$-C$_4$alkyl;

R$^{36}$ and R$^{37}$ are independently selected from the group consisting of H and C$_1$-C$_4$alkyl;

R$^{38}$ is H or C$_1$-C$_4$alkyl;

provided that when HetA is

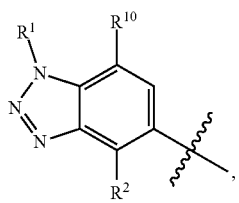

then HetB is not

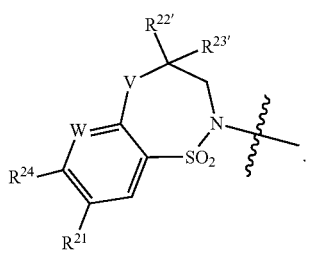

An additional illustrative embodiment of the invention is a compound of Formula (I), wherein HetA is

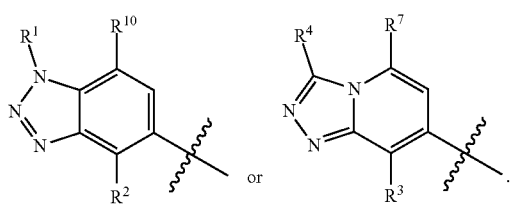

An additional illustrative embodiment of the invention is a compound of Formula (I), wherein HetA is

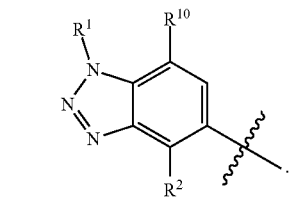

An additional illustrative embodiment of the invention is a compound of Formula (I), wherein HetA is

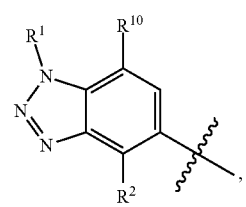

R$^1$ is C$_1$-C$_4$alkyl, R$^{10}$ is H and R$^2$ is C$_1$-C$_4$alkyl.

An additional illustrative embodiment of the invention is a compound of Formula (I), wherein HetA is

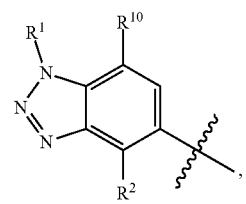

R$^1$ is C$_1$-C$_4$alkyl, R$^{10}$ is H and R$^2$ is CH$_3$.

An additional illustrative embodiment of the invention is a compound of Formula (I), wherein HetA is

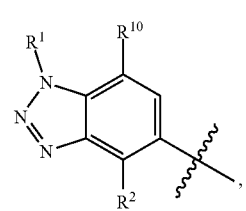

R$^1$ is C$_1$-C$_2$alkyl, R$^{10}$ is H and R$^2$ is CH$_3$.

An additional illustrative embodiment of the invention is a compound of Formula (I), wherein HetA is

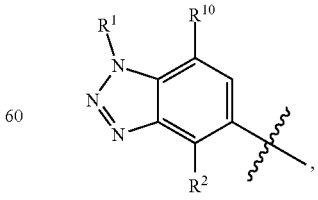

R$^1$ is CH$_2$CH$_3$, R$^{10}$ is H and R$^2$ is CH$_3$.

An additional illustrative embodiment of the invention is a compound of Formula (I), wherein HetA is

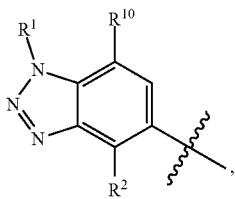

$R^1$ is $CH_3$, $R^{10}$ is H and $R^2$ is $CH_3$.

An additional illustrative embodiment of the invention is a compound of Formula (I), wherein HetA is

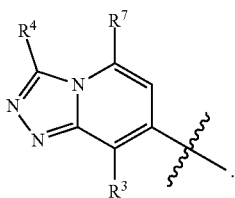

An additional illustrative embodiment of the invention is a compound of Formula (I), wherein HetA is

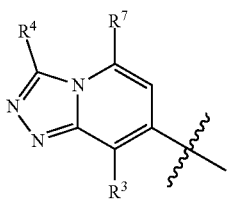

and $R^4$ is $C_1$-$C_4$alkyl or $C_1$-$C_4$perhaloalkyl.

An additional illustrative embodiment of the invention is a compound of Formula (I), wherein HetA is

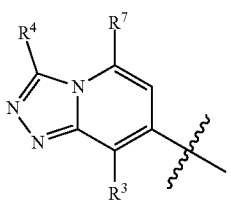

and $R^4$ is $C_1$-$C_4$perhaloalkyl.

An additional illustrative embodiment of the invention is a compound of Formula (I), wherein HetA is

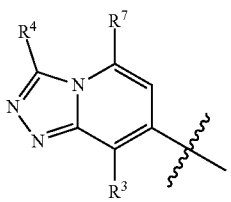

and $R^4$ is $C_1$-$C_2$perhaloalkyl.

An additional illustrative embodiment of the invention is a compound of Formula (I), wherein HetA is

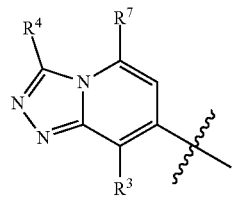

and $R^4$ is $CF_3$.

An additional illustrative embodiment of the invention is a compound of Formula (I), wherein HetA is

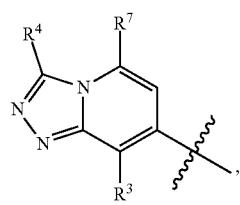

$R^4$ is $C_1$-$C_4$perhaloalkyl, $R^3$ is $C_1$-$C_4$alkyl and $R^7$ is H.

An additional illustrative embodiment of the invention is a compound of Formula (I), wherein HetA is

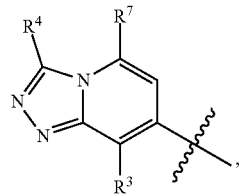

$R^4$ is $C_1$-$C_2$perhaloalkyl, $R^3$ is $C_1$-$C_4$alkyl and $R^7$ is H.

An additional illustrative embodiment of the invention is a compound of Formula (I), wherein HetA is

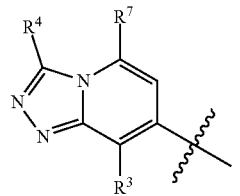

$R^4$ is $C_1$-$C_2$perhaloalkyl, $R^3$ is $C_1$-$C_2$alkyl and $R^7$ is H.

An additional illustrative embodiment of the invention is a compound of Formula (I), wherein HetA is

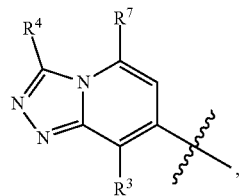

$R^4$ is $C_1$-$C_2$perhaloalkyl, $R^3$ is $CH_3$ and $R^7$ is H.

An additional illustrative embodiment of the invention is a compound of Formula (I), wherein HetA is

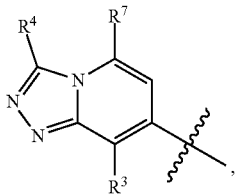

$R^4$ is $CF_3$, $R^3$ is $CH_3$ and $R^7$ is H.

An additional illustrative embodiment of the invention is a compound of Formula (I), wherein X is N.

An additional illustrative embodiment of the invention is a compound of Formula (I), wherein X is CH.

An additional illustrative embodiment of the invention is a compound of Formula (I), wherein Q is N.

An additional illustrative embodiment of the invention is a compound of Formula (I), wherein Q is CH.

An additional illustrative embodiment of the invention is a compound of Formula (I), wherein M is N.

An additional illustrative embodiment of the invention is a compound of Formula (I), wherein M is CH.

An additional illustrative embodiment of the invention is a compound of Formula (I), wherein $R^{15}$ is $CH_3$.

An additional illustrative embodiment of the invention is a compound of Formula (I), wherein $R^{15}$ is Cl.

An additional illustrative embodiment of the invention is a compound of Formula (I), wherein $R^{13}$ is $CH_3$.

An additional illustrative embodiment of the invention is a compound of Formula (I), wherein $R^{13}$ is $CH_3$ and $R^{14}$ is H.

An additional illustrative embodiment of the invention is a compound of Formula (I), wherein $R^{13}$ is $CH_3$ and $R^{14}$ is $CH_3$.

An additional illustrative embodiment of the invention is a compound of Formula (I), wherein $R^{13}$ is H and $R^{14}$ is H.

An additional illustrative embodiment of the invention is a compound of Formula (I), wherein HetA is

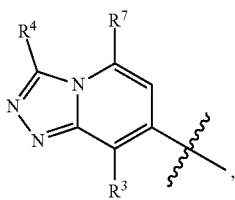

$R^4$ is $CF_3$, $R^3$ is $CH_3$, $R^7$ is H and X is N.

An additional illustrative embodiment of the invention is a compound of Formula (I), wherein HetA is

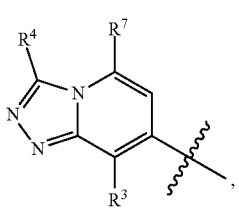

$R^4$ is $CF_3$, $R^3$ is $CH_3$, $R^7$ is H, X is N and $R^{15}$ is $CH_3$.

An additional illustrative embodiment of the invention is a compound of Formula (I), wherein HetA is

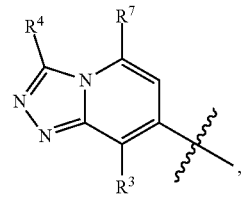

$R^4$ is $CF_3$, $R^3$ is $CH_3$, $R^7$ is H, X is N, $R^{15}$ is $CH_3$, $R^{13}$ is H and $R^{14}$ is H.

An additional illustrative embodiment of the invention is a compound of Formula (I), wherein HetA is

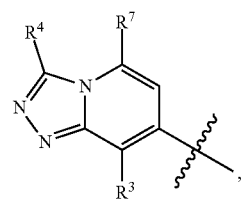

$R^4$ is $CF_3$, $R^3$ is $CH_3$, $R^7$ is H, X is N, $R^{15}$ is $CH_3$, $R^{13}$ is $CH_3$ and $R^{14}$ is $CH_3$.

An additional illustrative embodiment of the invention is a compound of Formula (I), wherein HetA is

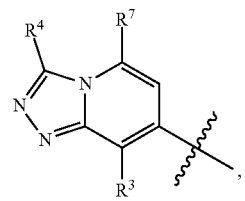

$R^4$ is $CF_3$, $R^3$ is $CH_3$, $R^7$ is H and X is CH.

An additional illustrative embodiment of the invention is a compound of Formula (I), wherein HetA is

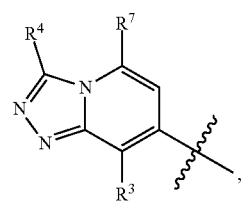

$R^4$ is $CF_3$, $R^3$ is $CH_3$, $R^7$ is H, X is CH, and $R^{15}$ is Cl.

An additional illustrative embodiment of the invention is a compound of Formula (I), wherein HetA is

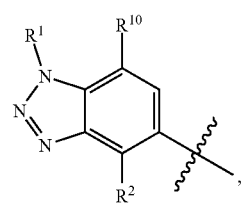

$R^1$ is $CH_2CH_3$, $R^{10}$ is H, $R^2$ is $CH_3$ and X is N.

An additional illustrative embodiment of the invention is a compound of Formula (I), wherein HetA is

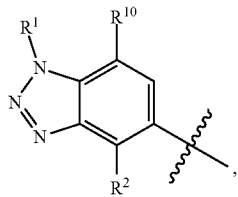

$R^1$ is $CH_2CH_3$, $R^{10}$ is H, $R^2$ is $CH_3$, X is N, $R^{15}$ is $CH_3$, $R^{13}$ is H and $R^{14}$ is H.

An additional illustrative embodiment of the invention is a compound of Formula (I), wherein HetA is

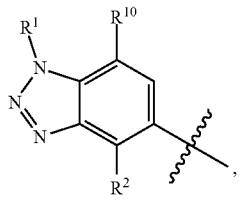

$R^1$ is $CH_2CH_3$, $R^{10}$ is H, $R^2$ is $CH_3$, X is N and $R^{15}$ is Cl.

An additional illustrative embodiment of the invention is a compound of Formula (I), wherein HetA is

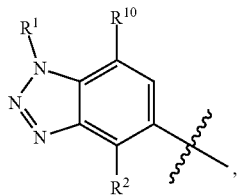

$R^1$ is $CH_2CH_3$, $R^{10}$ is H, $R^2$ is $CH_3$, X is CH, $R^{15}$ is $CH_3$, $R^{13}$ is H and $R^{14}$ is H.

An additional illustrative embodiment of the invention is a compound of Formula (I), wherein HetA is

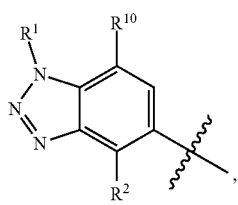

$R^1$ is $CH_2CH_3$, $R^{10}$ is H, $R^2$ is $CH_3$, X is CH and $R^5$ is Cl.

An additional illustrative embodiment of the invention is a compound of Formula (I), wherein HetB is selected from the group consisting of

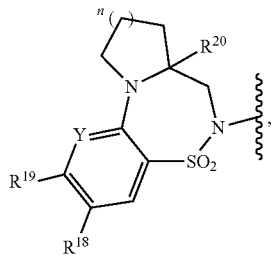

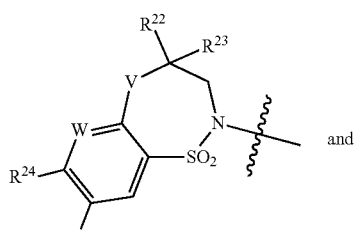

and

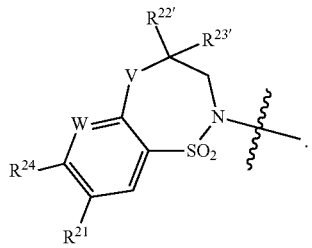

An additional illustrative embodiment of the invention is a compound of Formula (I), wherein HetB is selected from the group consisting of

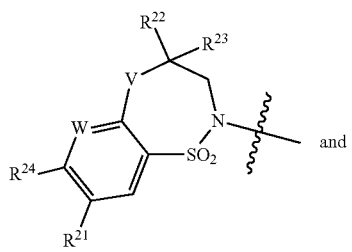

and

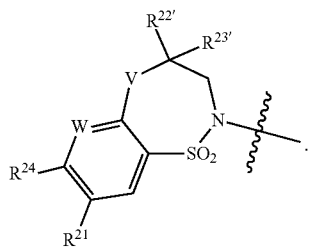

An additional illustrative embodiment of the invention is a compound of Formula (I), wherein HetB is

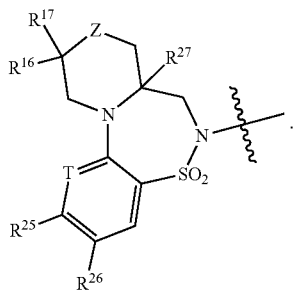

An additional illustrative embodiment of the invention is a compound of Formula (I), wherein HetB is

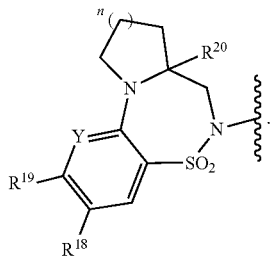

An additional illustrative embodiment of the invention is a compound of Formula (I), wherein HetB is

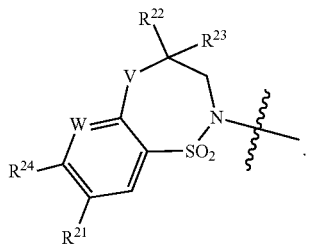

An additional illustrative embodiment of the invention is a compound of Formula (I), wherein HetB is

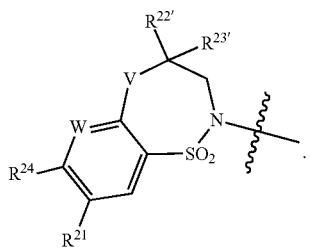

An additional illustrative embodiment of the invention is a compound of Formula (I), wherein HetB is

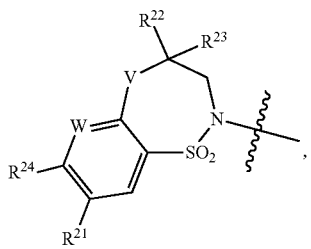

$R^{22}$ and $R^{23}$ are taken together with the carbon to which they are attached to form the moiety

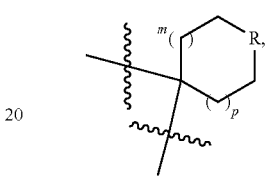

wherein R is $CH_2$ or O, m is 0 or 1, and p is 0 or 1.

An additional illustrative embodiment of the invention is a compound of Formula (I), wherein HetB is

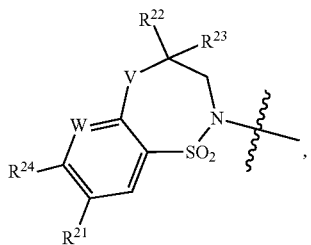

$R^{22}$ and $R^{23}$ are taken together with the carbon to which they are attached to form the moiety

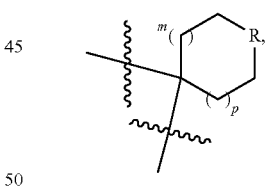

wherein R is O, m is 0 or 1, and p is 0 or 1.

An additional illustrative embodiment of the invention is a compound of Formula (I), HetB is

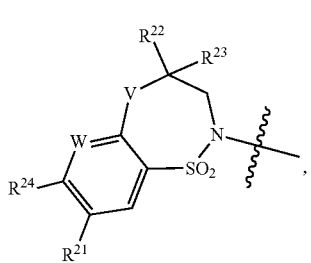

$R^{22}$ and $R^{23}$ are taken together with the carbon to which they are attached to form the moiety

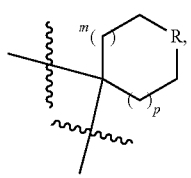

wherein R is O, m is 1, and p is 1.

An additional illustrative embodiment of the invention is a compound of Formula (I), wherein HetB is

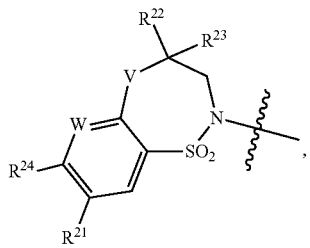

$R^{22}$ and $R^{23}$ are taken together with the carbon to which they are attached to form the moiety

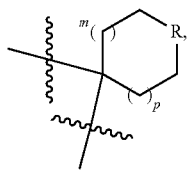

wherein R is O, m is 1, p is 1, $R^{13}$ is $C_1$-$C_4$alkyl, and $R^{14}$ is $C_1$-$C_4$alkyl.

An additional illustrative embodiment of the invention is a compound of Formula (I), wherein HetB is

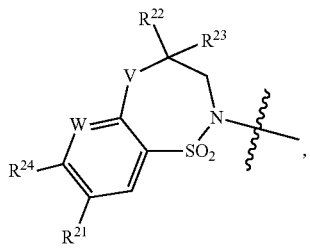

$R^{22}$ and $R^{23}$ are taken together with the carbon to which they are attached to form the moiety

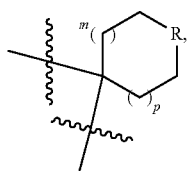

wherein 1 is O, m is 1, p is 1, $R^{13}$ is $CH_3$, and $R^{14}$ is $CH_3$.

An additional illustrative embodiment of the invention is a compound of Formula (I), wherein HetA is

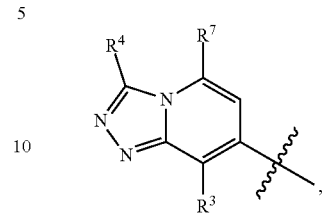

HetB is

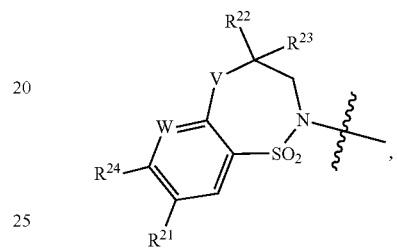

$R^4$ is $CF_3$, $R^3$ is $CH_3$, $R^7$ is H, X is CH, $R^{15}$ is $CH_3$, $R^{22}$ and $R^{23}$ are taken together with the carbon to which they are attached to form the moiety

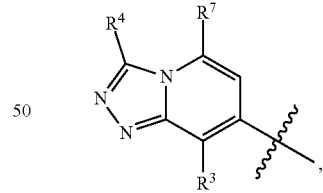

wherein R is O, m is 1, p is 1, $R^{13}$ is $CH_3$, and $R^{14}$ is $CH_3$

An additional illustrative embodiment of the invention is a compound of Formula (I), wherein HetA is

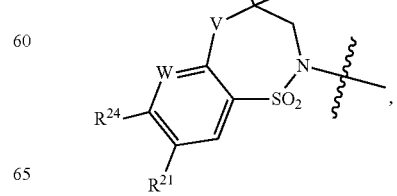

HetB is $R^4$ is $CHF_2$, $R^3$ is $CH_3$, $R^7$ is H, X is CH, Q is CH, M is CH, W is N, $R^{24}$ is H, $R^{21}$ is H, $R^{15}$ is $CH_3$, $R^{22}$ and $R^{23}$ are taken together with the carbon to which they are attached to form the moiety

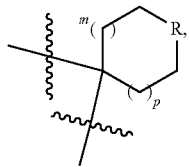

wherein R is O, m is 1, p is 1, $R^{13}$ is $CH_3$, and $R^{14}$ is $CH_3$.

An additional illustrative embodiment of the invention is a compound of Formula (I), wherein HetA is

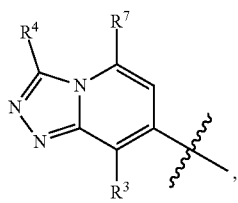

HetB is

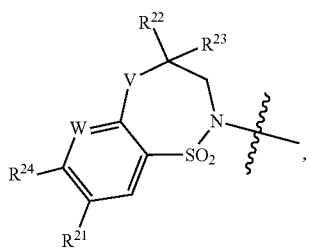

$R^4$ is $CF_3$, $R^3$ is $CH_3$, $R^7$ is H, X is CH, $R^{15}$ is $CH_3$, $R^{22}$ and $R^{23}$ are taken together with the carbon to which they are attached to form the moiety

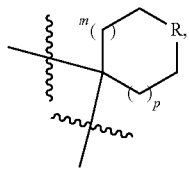

wherein R is O, m is 1, p is 1, $R^{13}$ is $CH_3$, $R^{14}$ is $CH_3$ and $R^{24}$ is $OC_2$-$C_4$alkyl or $OC_2$-$C_4$alkyl is substituted with

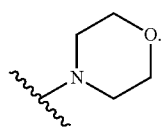 [SMILES: *N1CCOCC1]

An additional illustrative embodiment of the invention is a compound of Formula (I), wherein HetA is

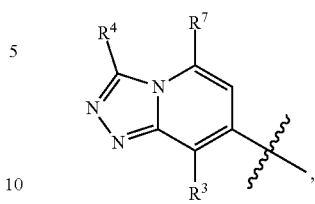

HetB is

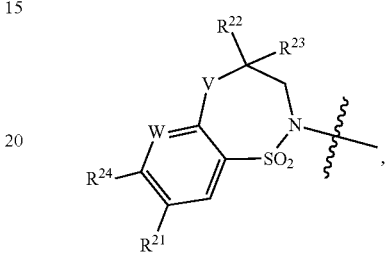

$R^4$ is cyclopropyl, $R^3$ is $CH_3$, $R^7$ is H, X is CH, Q is CH, M is CH, $R^{15}$ is $CH_3$, $R^{22}$ and $R^{23}$ are taken together with the carbon to which they are attached to form the moiety

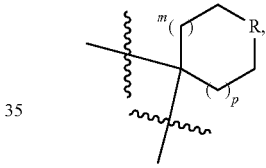

wherein R is O, m is 1, p is 1, $R^{13}$ is $CH_3$, and $R^{14}$ is $CH_3$.

An additional illustrative embodiment of the invention is a compound of Formula (I), wherein HetA is

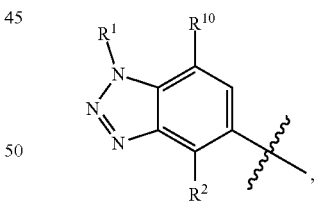

HetB is

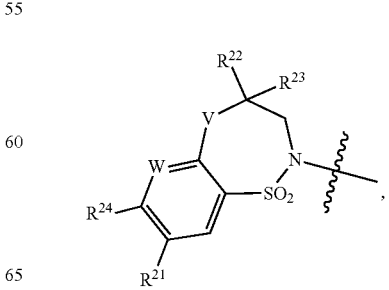

$R^1$ is $CH_2CH_3$, $R^2$ is $CH_3$, $R^{10}$ is H, X is CH, Q is CH, M is N, $R^{15}$ is $CH_3$, $R^{22}$ and $R^{23}$ are taken together with the carbon to which they are attached to form the moiety

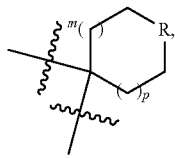

wherein R is O, m is 1, p is 1, $R^{13}$ is $CH_3$, and $R^{14}$ is $CH_3$.

An additional illustrative embodiment of the invention is a compound of Formula (I), wherein
HetA is

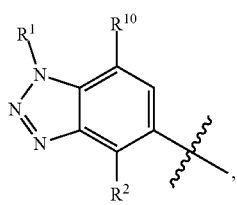

HetB is

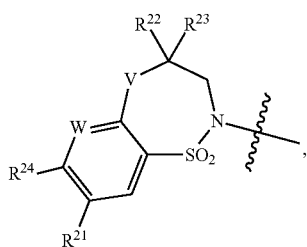

$R^1$ is cyclopropyl, $R^2$ is $CH_3$, $R^{10}$ is H, X is CH, Q is CH, M is N, $R^{15}$ is $CH_3$, $R^{22}$ and $R^{23}$ are taken together with the carbon to which they are attached to form the moiety

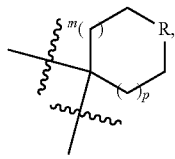

wherein R is O, m is 1, p is 1, $R^{13}$ is $CH_3$, and $R^{14}$ is $CH_3$.

An additional illustrative embodiment of the invention is a compound of Formula (I), wherein $R^1$ is $C_1$-$C_4$alkyl that is substituted with one of cyclopropyl and cyclobutyl.

An additional illustrative embodiment of the invention is a compound of Formula (I), wherein $R^{18}$ is $OC_1$-$C_4$alkyl substituted with one of —OH, —N($R^{36}$)$R^{37}$ and

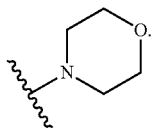

An additional illustrative embodiment of the invention is a compound of Formula (I), wherein $R^{18}$ is $NHC_1$-$C_4$alkyl substituted with one of OH and $CH_3$.

An additional illustrative embodiment of the invention is a compound of Formula (I), wherein $R^{18}$ is $C_1$-$C_4$alkyl is substituted with one of $C(O)NHCH_2CH_2OH$ and OH.

An additional illustrative embodiment of the invention is a compound of Formula (I), wherein $R^{24}$ is $OC_1$-$C_4$alkyl substituted with one of —OH, —N($R^{36}$)$R^{37}$ and

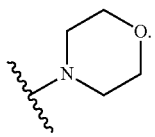 [SMILES: *N1CCOCC1]

An additional illustrative embodiment of the invention is a compound of Formula (I), wherein $R^{24}$ is $NHC_1$-$C_4$alkyl substituted with one of OH and $CH_3$.

An additional illustrative embodiment of the invention is a compound of Formula (I), wherein $R^{24}$ is $C_1$-$C_4$alkyl is substituted with one of $C(O)NHCH_2CH_2OH$ and OH.

An additional illustrative embodiment of the invention is a compound of Formula (I), wherein $R^{25}$ is $OC_1$-$C_4$alkyl substituted with one of —OH, —N($R^{36}$)$R^{37}$ and

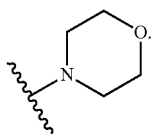 [SMILES: *N1CCOCC1]

An additional illustrative embodiment of the invention is a compound of Formula (I), wherein $R^{25}$ is $NHC_1$-$C_4$alkyl substituted with one of OH and $CH_3$.

An additional illustrative embodiment of the invention is a compound of Formula (I), wherein $R^{25}$ is $C_1$-$C_4$alkyl is substituted with one of $C(O)NHCH_2CH_2OH$ and OH.

Additional illustrative embodiments of the invention are compounds of Formula (I) selected from the group consisting of 3-(7-(Difluoromethoxy)-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*S)-3-(7-(Difluoromethoxy)-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(7-(Difluoromethoxy)-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

3-(7-Cyclopropoxy-1-methyl-1H-benzo[d][1,2,3]triazol-5-yl)-3-(3-(((R)-5,5-dioxido-7a, 8,9,10-tetrahydropyrido[2, 3-f]pyrrolo[2,1-d][1,2,5]thiadiazepin-6(7H)-yl)methyl)-4-methylphenyl)propanoic acid
(*S)-3-(7-Cyclopropoxy-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;
(*R)-3-(7-Cyclopropoxy-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;
(*S)-3-(3-((1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;
(*R)-3-(3-((1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;
(*S)-3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;
(*S)-3-(3-(((*S)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;
3-(1-(Cyclopropylmethyl)-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;
(*S)-3-(1-(cyclopropylmethyl)-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;
(*R)-3-(1-(cyclopropylmethyl)-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;
3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic acid;
(*S)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic acid;
(R)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic acid;
2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;
(*S)-2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;
2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;
3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;
(*S)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;
(*R)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;
3-(1-Cyclopropyl-4-methyl-1H-benzo[d][1,2,3]triazol-5-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid;
(*S)-3-(1-Cyclopropyl-4-methyl-1H-benzo[d][1,2,3]triazol-5-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid;
(*R)-3-(1-Cyclopropyl-4-methyl-1H-benzo[d][1,2,3]triazol-5-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid;
(*S)-3-(3-((1,1-Dioxidospiro[benzo[b][1,4,5]oxathiazepine-4,3'-oxetan]-2(3H)-yl)methyl)-4-methylphenyl)-3-(8-methyl-3-(trifluoromethyl)-[1,2,4]triazolo[4,3-a]pyridin-7-yl)propanoic acid;
(*S)-3-(4-Methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;
3-(3-((3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid;
(*R)-3-(3-(((*S)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid;
(*R)-3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid;
(*S)-3-(3-(((*S)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid;
(*S)-3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid;
3-(6-((3-cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;
(*S)-3-(6-(((*S)-3-cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;
(*S)-3-(6-(((*R)-3-cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

(*R)-3-(6-(((*R)-3-cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

(*R)-3-(6-(((*S)-3-cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid;

(*S)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl) propanoic acid;

(*R)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl) propanoic acid;

(R/S)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*S)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*R)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(R/S)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid;

(*S)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid;

(*R)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid;

2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

(*S)-2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

(*R)-2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-trifluoromethyl)-[1,2,4]triazolo[4,3-a]pyridine-7-yl)propanoic acid;

(*S)-3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methy-3-trifluoromethyl)-[1,2,4]triazolo[4,3-a]pyridine-7-yl)propanoic acid;

(*R) 3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methyl-3-trifluoromethyl)-[1,2,4]triazolo[4,3-a]pyridine-7-yl)propanoic acid;

(R/S)-3-(3-(Difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*S)-3-(3-(Difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*R)-3-(3-(Difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(R/S)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl) propanoic acid;

(*S)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl) propanoic acid;

(*R)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl) propanoic acid;

(R/S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic acid;

(*S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic acid;

(*R)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic acid;

(R/S)-3-(1-Ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*S)-3-(1-Ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*R)-3-(1-Ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*R)-3-(4-methyl-3-((8'-methyl-1',1'-dioxidospiro[cyclopropane-1,4'-pyrido[2,3-b][1,4,5]oxathiazepin]-2'(3'H)- yl)methyl)phenyl)-3-(8-methyl-3-(trifluoromethyl)-[1,2,4]triazolo[4,3-a]pyridin-7-yl)propanoic acid;

3-(1-(Cyclopropylmethyl)-4-(difluoromethyl-1H-benzo[d][1,2,3]triazol-5-yl)-3-(3-((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid;

(*S)-3-(1-(Cyclopropylmethyl)-4-(difluoromethyl-1H-benzo[d][1,2,3]triazol-5-yl)-3-(3-((R-5,5-dioxido-7a,8,9,10-tetrahydropyridi[2,3-f]pyrrolo[2, 1-d][1,2,5]thiadiazepin-6(7H)-yl)methyl)-4-methylphenyl)propanoic acid;

3-(1-(Cyclopropylmethyl)-4-methyl-1H-benzo[d][1,2,3]triazol-5-yl)-3-(3-((1',1'-dioxidospiro[oxetane-3,3'-pyrido[2,3-b][1,4,5]oxathiazepin]-2'(3'H)-yl)methyl)-4-methylphenyl)propanoic acid;

(*R)-3-(1-(Cyclopropylmethyl)-4-(difluoromethyl-1H-benzo[d][1,2,3]triazol-5-yl)-3-(3-((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid;

(*S)-3-(1-(Cyclopropylmethyl)-4-methyl-1H-benzo[d][1,2,3]triazol-5-yl)-3-(3-((1',1'-dioxidospiro[oxetane-3,4'-pyrido[2,3-b][1,4,5]oxathiazepin]-2'(3'H)-yl)methyl)-4-methylphenyl)propanoic acid;

(*R)-3-(1-(Cyclopropylmethyl)-4-methyl-1H-benzo[d][1,2,3]triazol-5-yl)-3-(3-((1',1'-dioxidospiro[oxetane-3,4'-pyrido[2,3-b][1,4,5]oxathiazepin]-2'(3'H)-yl)methyl)-4-methylphenyl)propanoic acid;

3-(4-(Difluoromethyl-1-methyl-1H-benzo[d][1,2,3]triazol-5-yl)-3-(3-(((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid;

(*S)-3-(4-(Difluoromethyl-1-methyl-1H-benzo[d][1,2,3]triazol-5-yl)-3-(3-(((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid;

(*R) 3-(4-(Difluoromethyl-1-methyl-1H-benzo[d][1,2,3]triazol-5-yl)-3-(3-(((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid;

3-(1-(Cyclopropylmethyl)-4-methyl-1H-benzo[d][1,2,3]triazol-5-yl)-3-(3-((1',1'-dioxidospiro[benzo[b][1,4,5]oxathiazepin-4,3'-oxetan]-2, (3H)-yl)methyl)-4-methylphenyl)propanoic acid;

3-(1-(Cyclopropylmethyl)-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid;

(*R)-3-(1-(cyclopropylmethyl)-4-methyl-1H-benzo[d][1,2,3]triazol-5-yl)-3-(3-((1',1'-dioxidospiro[benzo[b][1,4,5]oxathiazepin-4,3'-oxetan]-2(3H)-yl)methyl)-4-methylphenyl)propanoic acid;

(*S)-3-(1-(Cyclopropylmethyl)-4-methyl-1H-benzo[d][1,2,3]triazol-5-yl)-3-(3-((1',1'-dioxidospiro[benzo[b][1,4,5]oxathiazepin-4,3'-oxetan]-2, (3H)-yl)methyl)-4-methylphenyl)propanoic acid;

(*S)-3-(1-(Cyclopropylmethyl)-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid;

(*R)-3-(1-(Cyclopropylmethyl)-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid;

3-(1-(Cyclopropylmethyl)-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(*R)-3-(1-(Cyclopropylmethyl)-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(*S)-3-(1-(Cyclopropylmethyl)-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

3-(4-Chloro-3-(((*S)-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid;

(*S)-3-(4-Chloro-3-(((*S)-5,5-dioxido-7,7a,8,9,10,11-hexahydro-6H-dipyrido[2,1-d:2',3'-][1,2,5]thiadiazepin-6-yl)methyl)phenyl)-3-(8-methyl-3-(trifluoromethyl)-[1,2,4]triazolo[4,3-a]pyridine-7-yl)propanoic acid;

(*R)-3-(4-Chloro-3-(((*S)-5,5-dioxido-7,7a,8,9,10,11-hexahydro-6H-dipyrido[2,1-d:2',3'-f][,2,5]thiadiazepin-6-yl)methyl)phenyl)-3-(8-methyl-3-(trifluoromethyl)-[1,2,4]triazolo[4,3-a]pyridine-7-yl)propanoic acid;

3-(4-Chloro-3-((1',1'-dioxidospiro[oxetane-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-3-(4-Chloro-3-((1',1'-dioxidospiro[oxetane-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*S)-3-(4-Chloro-3-((1',1'-dioxidospiro[oxetane-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

3-(4-Chloro-3-(((*S)-3-methyl-5,5-dioxido-7,7a,8,9,10,11-hexahydro-6H-dipyrido[2,1-d:2',3'-f][,2,5]thiadiazepin-6-yl)methyl)phenyl)-3-(8-methyl-3-(trifluoromethyl)-[1,2,4]triazolo[4,3-a]pyridine-7-yl)propanoic acid;

(*R)-3-(4-Chloro-3-(((*S)-3-methyl-5,5-dioxido-7,7a,8,9,10,11-hexahydro-6H-dipyrido[2,1-d:2',3'-][1,2,5]thiadiazepin-6-yl)methyl)phenyl)-3-(8-methyl-3-(trifluoromethyl)-[1,2,4]triazolo[4,3-a]pyridine-7-yl)propanoic acid;

(*S)-3-(4-Chloro-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid;

3-(4-Chloro-3-(((*S)-3-fluoro-5,5-dioxido-7,7a,8,9,10,11-hexahydro-6H-dipyrido[2,1-d:2',3'-f][,2,5]thiadiazepin-6-yl)methyl)phenyl)-3-(8-methyl-3-(trifluoromethyl)-[1,2,4]triazolo[4,3-a]pyridine-7-yl)propanoic acid;

(*R)-3-(4-Chloro-3-(((*S)-3-fluoro-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid;

(*S)-3-(4-Chloro-3-(((*S)-3-fluoro-5,5-dioxido-7,7a,8,9,10,11-hexahydro-6H-dipyrido[2,1-d:2',3'-][1,2,5]thiadiazepin-6-yl)methyl)phenyl)-3-(8-methyl-3-(trifluoromethyl)-[1,2,4]triazolo[4,3-a]pyridine-7-yl)propanoic acid;

3-(4-Chloro-3-((1',1'-dioxidospiro[benzo[b]]oxethiazepine-4,3'-oxetan]-2(3H)-yl)methyl)phenyl)-3-(8-methyl-3-(trifluoromethyl)-[1,2,4]triazolo[4,3-a]pyridine-7-yl)propanoic acid;

(*R)-3-(4-Chloro-3-((1',1'-dioxidospiro[benzo[b]]oxethiazepine-4,3'-oxetan]-2(3H)-yl)methyl)phenyl)-3-(8-methyl-3-(trifluoromethyl)-[1,2,4]triazolo[4,3-a]pyridine-7-yl)propanoic acid;

(*S)-3-(4-Chloro-3-((1',1'-dioxoidospiro[benzo[b]]oxethi-azepine-4,3'-oxetan]-2(3H)-yl)methyl)phenyl)-3-(8-methyl-3-(trifluoromethyl)-[1,2,4]triazolo[4,3-a]pyridine-7-yl)propanoic acid;

(*S)-3-(3-((8-Fluoro-1,1-dioxidospiro[benzo[b][1,4,5]oxathiazepin]-4,1'-cyclopropan]-2(3H)-yl)methyl)-4-methylphenyl)-3-(8-methyl-3-(trifluoromethyl)-[1,2,4]triazolo[4,3-a]pyridin-7-yl)propanoic acid;

(*S)-3-(3-((8-Fluoro-1,1-dioxidospiro[benzo[b][1,4,5]oxathiazepine-4,3'-oxetan]-2(3H)-yl)methyl]-4-methylphenyl)-3-(8-methyl-3-(trifluoromethyl)-[1,2,4]triazolo[4,3-a]pyridin-7-yl)propanoic acid;

(*S)-3-(3-((7'-Chloro-1',1'-dioxidospiro(cyclopropane-1.4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-((7'-((2-Hydroxyethyl)amino)-1',1'-dioxidospiro[cyclopropane-1.4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridinn-7-yl)propanoic acid;

(*S)-3-(3-((7'-(2-Hydroxypropyl)amino-1',1'-dioxidospiro[cyclopropane-1.4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridinn-7-yl)propanoic acid;

(*S)-3-(3-((7'-Hydroxy-1',1'-dioxidospiro[cyclopropane-1,4'-pyrido[2,3,-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

3-(4-Cyano-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]trizolo[4,3-a]pyridine-7-yl)propanoic acid;

(*S)-3-(4-Cyano-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]trizolo[4,3-a]pyridine-7-yl)propanoic acid;

(*R)-3-(4-Cyano-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]trizolo[4,3-a]pyridine-7-yl)propanoic acid;

(*S)-3-(3-((7'-((3-Methoxypropyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

(*S)-3-(-3-((7'-((3-Hydroxypropyl)(methyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

(*S)-3-(-3-((7'-((3-Methoxypropoxy)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

(*S)-3-(-3-((7'-((3-Hydroxyethyl)(methyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

(*S)-3-(4-Methyl-((7'-((2-morpholinoethyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

(*S)-3-(3-((1',1'-Dioxido-7'-((2-(piperidin-1-yl)ethyl)amino)spiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

(*S)-3-(3-((7'-(Butylamino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

3-(3-((7'-((3-Hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-3-(3-((7'-((3-Hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*R)-3-(3-((7'-((3-Hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

3-(3-((7'-(((R)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

3-(3-((7'-(((S)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-3-(3-((7'-(((R)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4][triazolo[4,3-a]pyridine-7-yl)propanoic acid;

(*R)-3-(3-((7'-(((R)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4][triazolo[4,3-a]pyridine-7-yl)propanoic acid;

(*S)-3-(3-((7'-(((S)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4][triazolo[4,3-a]pyridine-7-yl)propanoic acid;

(*R)-3-(3-((7'-(((S)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4][triazolo[4,3-a]pyridine-7-yl)propanoic acid;

(*S)-3-(3-((7'-(((S)-4-Hydroxybutan-2-yl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-3-(3-((7'-(((R)-3-Hydroxy-3-methylbutan-2-yl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*R)-3-(3-((7'-(((1s,3S)-3-Hydroxycyclobutyl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

2,2-Dimethyl-3-(4-methyl-3-((8'-methyl-1',1'-dioxido3-(3-((7'-(((*S)-4-hydroxybutan-2-yl)amino)-8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

2,2-Dimethyl-3-(4-methyl-3-((8'-methyl-1',1'-dioxido-3-(3-((7'-(((*S)-4-hydroxybutan-2-yl)amino)-8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-3-(3-((7'-(3-((2-Hydroxyethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoic acid;

(3*R)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoic acid;

(3*S)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoic acid;

3-(5,8-Dimethyl-3)-(trifluoromethyl)-[1,2,4-triazolo[4,3-a]pyridine-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methylpropanoic acid;

(3*R)-3-(5,8-Dimethyl-3)-(trifluoromethyl)-[1,2,4-triazolo[4,3-a]pyridine-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methylpropanoic acid; and (3*S)-3-(5,8-Dimethyl-3)-(trifluoromethyl)-[1,2,4-triazolo[4,3-a]pyridine-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methylpropanoic acid; and pharmaceutically acceptable salts, and combinations thereof.

Additional illustrative embodiments of the invention are compounds of Formula (I) selected from the group consisting of (*S)-3-(3-((1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic acid;

(*S)-3-(4-Methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*R)-3-(6-(((*R)-3-cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid; and pharmaceutically acceptable salts, and combinations thereof.

An additional illustrative embodiment of the invention is a compound of Formula (I), wherein the compound is selected from the group consisting of (*S)-3-(3-((1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic acid;

(*S)-3-(4-Methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid; and pharmaceutically acceptable salts, and combinations thereof.

An additional illustrative embodiment of the invention is a compound of Formula (I), wherein the compound is selected from the group consisting of (*S)-3-(3-((1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic acid;

(*S)-3-(4-Methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid; and pharmaceutically acceptable salts, and combinations thereof.

An additional illustrative embodiment of the invention is a compound of Formula (I), wherein the compound is selected from the group consisting of (*S)-3-(3-((1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic acid (*S)-3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid; and pharmaceutically acceptable salts, and combinations thereof.

An additional illustrative embodiment of the invention is a compound of Formula (I), wherein the compound is (*S)-3-(3-((1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid; and
pharmaceutically acceptable salts thereof.

An additional illustrative embodiment of the invention is a compound of Formula (I), wherein the compound is (*S)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic acid; and
pharmaceutically acceptable salts thereof.

An additional illustrative embodiment of the invention is a compound of Formula (I), wherein the compound is selected from the group consisting of (*S)-2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid; and
pharmaceutically acceptable salts thereof.

An additional illustrative embodiment of the invention is a compound of Formula (I), wherein the compound is (*S)-3-(4-Methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid; and
pharmaceutically acceptable salts thereof.

An additional illustrative embodiment of the invention is a compound of Formula (I), wherein the compound is (*S)-3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid; and
pharmaceutically acceptable salts thereof.

An additional illustrative embodiment of the invention is a compound of Formula (I), wherein the compound is selected from the group consisting of (*S)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid;

(*R)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid;

(R/S)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*S)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*R)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(R/S)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid;

(*S)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid;

(*R)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid;

2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

(*S)-2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

(*R)-2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methyl-3-trifluoromethyl)-[1,2,4]triazolo[4,3-a]pyridine-7-yl)propanoic acid;

(*S)-3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methy-3-trifluoromethyl)-[1,2,4]triazolo[4,3-a]pyridine-7-yl)propanoic acid;

(*R) 3-(3-((7'-(3-Hydroxypropoxy)-1',1'dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methyl-3-trifluoromethyl)-[1,2,4]triazolo[4,3-a]pyridine-7-yl)propanoic acid;

(R/S)-3-(3-(Difluoromethyl)-8-methyl-[1,2,4]triazolo[4,3-a]pyridin-7-yl)-3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*S)-3-(3-(Difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*R)-3-(3-(Difluoromethyl)-8-methyl-[1,2,4]triazolo[4,3-a]pyridin-7-yl)-3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(R/S)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid;

(*S)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid;

(*R)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid;

(R/S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic acid;

(*S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic acid;

(*R)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic acid;

(R/S)-3-(1-Ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*S)-3-(1-Ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*R)-3-(1-Ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*R)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid; and pharmaceutically acceptable salts, and combinations thereof.

An additional illustrative embodiment of the invention is a compound of Formula (I), wherein the compound is selected from the group consisting of (*S)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid;

(*R)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid;

(R/S)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*S)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*R)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(R/S)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid;

(*S)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid;

(*R)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid;

2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

(*S)-2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

(*R)-2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methyl-3-trifluoromethyl)-[1,2,4]triazolo[4,3-a]pyridine-7-yl)propanoic acid;

(*S)-3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methy-3-trifluoromethyl)-[1,2,4]triazolo[4,3-a]pyridine-7-yl)propanoic acid;

(*R) 3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methyl-3-trifluoromethyl)-[1,2,4]triazolo[4,3-a]pyridine-7-yl)propanoic acid; and pharmaceutically acceptable salts, and combinations thereof.

An additional illustrative embodiment of the invention is a compound of Formula (I), wherein the compound is selected from the group consisting of 2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

(*S)-2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

(*R)-2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methyl-3-trifluoromethyl)-[1,2,4]triazolo[4,3-a]pyridine-7-yl)propanoic acid;

(*S)-3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methy-3-trifluoromethyl)-[1,2,4]triazolo[4,3-a]pyridine-7-yl)propanoic acid;

(*R) 3-(3-((7'-(3-Hydroxypropoxy)-1',1'dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methyl-3-trifluoromethyl)-[1,2,4]triazolo[4,3-a]pyridine-7-yl)propanoic acid; and pharmaceutically acceptable salts, and combinations thereof.

An additional illustrative embodiment of the invention is a compound of Formula (I), wherein the compound is selected from the group consisting of (*S)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*S)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid;

(*S)-2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid;

(*S)-3-(3-(Difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid;

(*S)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl) propanoic acid;

(*S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic acid; and pharmaceutically acceptable salts, and combinations thereof.

An additional illustrative embodiment of the invention is a compound of Formula (I), wherein the compound is (*S)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid; and pharmaceutically acceptable salts thereof.

An additional illustrative embodiment of the invention is a compound of Formula (I), wherein the compound is (*S)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid; and pharmaceutically acceptable salts thereof.

An additional illustrative embodiment of the invention is a compound of Formula (I), wherein the compound is (*S)-2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid; and pharmaceutically acceptable salts thereof.

An additional illustrative embodiment of the invention is a compound of Formula (I), wherein the compound is (*S)-3-(3-(Difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid; and pharmaceutically acceptable salts thereof.

An additional illustrative embodiment of the invention is a compound of Formula (I), wherein the compound is (*S)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl) propanoic acid; and pharmaceutically acceptable salts, thereof.

An additional illustrative embodiment of the invention is a compound of Formula (I), wherein the compound is (*S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic acid; and pharmaceutically acceptable salts thereof.

An additional illustrative embodiment of the invention is a compound of Formula (I), wherein the compound is selected from the group consisting of 3-(1-(Cyclopropylmethyl)-4-(difluoromethyl-1H-benzo[d][[1,2,3]triazol-5-yl)-3-(3-((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid;

(*S)-3-(1-(Cyclopropylmethyl)-4-(difluoromethyl-1H-benzo[d][1,2,3]triazol-5-yl)-3-(3-((R-5,5-dioxido-7a,8,9,10-tetrahydropyridi[2,3-f]pyrrolo[2, 1-d][1,2,5]thiadiazepin-6(7H)-yl)methyl)-4-methylphenyl)propanoic acid;

3-(1-(Cyclopropylmethyl)-4-methyl-1H-benzo[d][1,2,3]triazol-5-yl)-3-(3-((1',1'-dioxidospiro[oxetane-3,3'-pyrido[2,3-b][1,4,5]oxathiazepin]-2'(3'H)-yl)methyl)-4-methylphenyl)propanoic acid;

(*R)-3-(1-(Cyclopropylmethyl)-4-(difluoromethyl-1H-benzo[d][1,2,3]triazol-5-yl)-3-(3-((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid;

(*S)-3-(1-(Cyclopropylmethyl)-4-methyl-1H-benzo[d][1,2,3]triazol-5-yl)-3-(3-((1',1'-dioxidospiro[oxetane-3,4'-pyrido[2,3-b][1,4,5]oxathiazepin-2'(3'H)-yl)methyl)-4-methylphenyl)propanoic acid;

(*R)-3-(1-(Cyclopropylmethyl)-4-methyl-1H-benzo[d][1,2,3]triazol-5-yl)-3-(3-((1',1'-dioxidospiro[oxetane-3,4'-pyrido[2,3-b][1,4,5]oxathiazepin-2'(3'H)-yl)methyl)-4-methylphenyl)propanoic acid;

3-(4-(Difluoromethyl-1-methyl-1H-benzo[d][1,2,3]triazol-5-yl)-3-(3-(((R-5,5-dioxido-7a,8,9,10-tetrahydropyridi[2,3-f]pyrrolo[2, 1-d][1,2,5]thiadiazepin-6(7H)-yl)methyl)-4-methylphenyl)propanoic acid;

(*S)-3-(4-(Difluoromethyl-1-methyl-1H-benzo[d][1,2,3]triazol-5-yl)-3-(3-(((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid;

(*R) 3-(4-(Difluoromethyl-1-methyl-1H-benzo[d][1,2,3]triazol-5-yl)-3-(3-(((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid;

3-(1-(Cyclopropylmethyl)-4-methyl-1H-benzo[d][1,2,3]triazol-5-yl)-3-(3-((1',1'-dioxidospiro[benzo[b][1,4,5]oxathiazepin-4,3'-oxetan]-2, (3H)-yl)methyl)-4-methylphenyl)propanoic acid;

3-(1-(Cyclopropylmethyl)-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid;

(*R)-3-(1-(cyclopropylmethyl)-4-methyl-1H-benzo[d][1,2,3]triazol-5-yl)-3-(3-((1',1'-dioxidospiro[benzo[b][1,4,5]oxathiazepin-4,3'-oxetan]-2,(3H)-yl)methyl)-4-methylphenyl)propanoic acid;

(*S)-3-(1-(Cyclopropylmethyl)-4-methyl-1H-benzo[d][1,2,3]triazol-5-yl)-3-(3-((1',1'-dioxidospiro[benzo[b][1,4,5]oxathiazepin-4,3'-oxetan]-2, (3H)-yl)methyl)-4-methylphenyl)propanoic acid;

(*S)-3-(1-(Cyclopropylmethyl)-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid;

(*R)-3-(1-(Cyclopropylmethyl)-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid;

3-(1-(Cyclopropylmethyl)-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(*R)-3-(1-(Cyclopropylmethyl)-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2, 1-d][1,2,5]thiadiazepin-6(7H)-yl)methyl)phenyl)propanoic acid;

(*S)-3-(1-(Cyclopropylmethyl)-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

3-(4-Chloro-3-(((*S)-5,5-dioxido-7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid;

(*S)-3-(4-Chloro-3-(((*S)-5,5-dioxido-7a,8,9,10,11-hexahydro-6H-dipyrido[2,1-d:2',3'-f][,2,5]thiadiazepin-6-yl)methyl)phenyl)-3-(8-methyl-3-(trifluoromethyl)-[1,2,4]triazolo[4,3-a]pyridine-7-yl)propanoic acid;

(*R)-3-(4-Chloro-3-(((*S)-5,5-dioxido-7a,8,9,10,11-hexahydro-6H-dipyrido[2,1-d:2',3'-f][,2,5]thiadiazepin-6-yl)methyl)phenyl)-3-(8-methyl-3-(trifluoromethyl)-[1,2,4]triazolo[4,3-a]pyridine-7-yl)propanoic acid;

3-(4-Chloro-3-((1',1'-dioxidospiro[oxetane-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-3-(4-Chloro-3-((1',1'-dioxidospiro[oxetane-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*S)-3-(4-Chloro-3-((1',1'-dioxidospiro[oxetane-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

3-(4-Chloro-3-(((*S)-3-methyl-5,5-dioxido-7,7a,8,9,10,11-hexahydro-6H-dipyrido[2,1-d:2',3'-][,2,5]thiadiazepin-6-yl)methyl)phenyl)-3-(8-methyl-3-(trifluoromethyl)-[1,2,4]triazolo[4,3-a]pyridine-7-yl)propanoic acid;

(*R)-3-(4-Chloro-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid;

(*S)-3-(4-Chloro-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid;

3-(4-Chloro-3-(((*S)-3-fluoro-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid;

(*R)-3-(4-Chloro-3-(((*S)-3-fluoro-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid;

(*S)-3-(4-Chloro-3-(((*S)-3-fluoro-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid;

3-(4-Chloro-3-((1',1'-dioxidospiro[benzo[b]]oxethiazepine-4,3'-oxetan]-2(3H)-yl)methyl)phenyl)-3-(8-methyl-3-(trifluoromethyl)-[1,2,4]triazolo[4,3-a]pyridine-7-yl)propanoic acid;

(*R)-3-(4-Chloro-3-((1',1'-dioxidospiro[benzo[b]]oxethiazepine-4,3'-oxetan]-2(3H)-yl)methyl)phenyl)-3-(8-methyl-3-(trifluoromethyl)-[1,2,4]triazolo[4,3-a]pyridine-7-yl)propanoic acid;

(*S)-3-(4-Chloro-3-((1',1'-dioxidospiro[benzo[b]]oxethiazepine-4,3'-oxetan]-2(3H)-yl)methyl)phenyl)-3-(8-methyl-3-(trifluoromethyl)-[1,2,4]triazolo[4,3-a]pyridine-7-yl)propanoic acid;

(*S)-3-(3-((8-Fluoro-1,1-dioxidospiro[benzo[b][1,4,5]oxathiazepin]-4,1'-cyclopropan]-2(3H)-yl)methyl)-4-methylphenyl)-3-(8-methyl-3-(trifluoromethyl)-[1,2,4]triazolo[4,3-a]pyridin-7-yl)propanoic acid;

(*S)-3-(3-((8-Fluoro-1,1-dioxidospiro[benzo[b][1,4,5]oxathiazepine-4,3'-oxetan]-2(3H)-yl)methyl]-4-methylphenyl)-3-(8-methyl-3-(trifluoromethyl)-[1,2,4]triazolo[4,3-a]pyridin-7-yl)propanoic acid;

(*S)-3-(3-((7'-Chloro-1',1'-dioxidospiro(cyclopropane-1.4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-((7'-((2-Hydroxyethyl)amino-1',1'-dioxidospiro[cyclopropane-1.4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridinn-7-yl)propanoic acid;

(*S)-3-(3-((7'-((2-Hydroxypropyl)amino-1',1'-dioxidospiro[cyclopropane-1.4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridinn-7-yl)propanoic acid;

(*S)-3-(3-((7'-Hydroxy-1',1'-dioxidospiro[cyclopropane-1,4'-pyrido[2,3,-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

3-(4-Cyano-3-((8'-methyl-1',1'-dioxidospiro[cyclopropane-1,4'-pyrido[2,3-b][1,4,5]oxathiazepin]-2'(3'H)-yl)methyl phenyl)-3-(8-methyl-3-(trifluoromethyl)-[1,2,4]trizolo[4,3-a]pyridine-7-yl)propanoic acid;

(*S)-3-(4-Cyano-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]trizolo[4,3-a]pyridine-7-yl)propanoic acid;

(*R)-3-(4-Cyano-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]trizolo[4,3-a]pyridine-7-yl)propanoic acid;

(*S)-3-(3-((7'-((3-Methoxypropyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

(*S)-3-(-3-((7'-((3-Hydroxypropyl)(methyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4[triazolo[4,3-a]pyridine-7-yl)propanoic acid;

(*S)-3-(-3-((7'-((3-Methoxypropoxy)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

(*S)-3-(-3-((7'-((3-Hydroxyethyl)(methyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4[triazolo[4,3-a]pyridine-7-yl)propanoic acid;

(*S)-3-(4-Methyl-((7'-((2-morpholinoethyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4[triazolo[4,3-a]pyridine-7-yl)propanoic acid;

(*S)-3-(3-((1',1'-Dioxido-7'-((2-(piperidin-1-yl)ethyl)amino)spiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4[triazolo[4,3-a]pyridine-7-yl)propanoic acid;

(*S)-3-(3-((7'-(Butylamino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid;

3-(3-((7'-((3-Hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoic acid;

(*S)-3-(3-((7'-((3-Hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoic acid;

(*R)-3-(3-((7'-((3-Hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoic acid;

3-(3-((7'-(((R)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoic acid;

3-(3-((7'-(((S)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoic acid;

(*S)-3-(3-((7'-(((R)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoic acid;

(*R)-3-(3-((7'-(((R)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoic acid;

(*S)-3-(3-((7'-(((S)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoic acid;

(*R)-3-(3-((7'-(((S)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoic acid;

(*S)-3-(3-((7'-(((S)-4-Hydroxybutan-2-yl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoic acid;

(*S)-3-(3-((7'-(((R)-3-Hydroxy-3-methylbutan-2-yl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*R)-3-(3-((7'-(((1s,3S)-3-Hydroxycyclobutyl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

2,2-Dimethyl-3-(4-methyl-3-((8'-methyl-1',1'-dioxido3-(3-((7'-(((*S)-4-hydroxybutan-2-yl)amino)-8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

2,2-Dimethyl-3-(4-methyl-3-((8'-methyl-1',1'-dioxido-3-(3-((7'-(((*S)-4-hydroxybutan-2-yl)amino)-8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-3-(3-((7'-(3-((2-Hydroxyethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoic acid;

(3*R)-3-(3-(((*S)-5,5-Dioxido-7,7a,8,9,10,11-hexahydro-6H-dipyrido[2,1-d:2',3'-f][1,2,5]thiadiazepin-6-yl)

methyl)-4-methylphenyl)-2-methyl-3-(8-methyl-3-(trifluoromethyl)-[1,2,4]triazolo[4,3-a]pyridine-7-yl)propanoic acid;

(3*S)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoic acid;

3-(5,8-Dimethyl-3)-(trifluoromethyl)-[1,2,4-triazolo[4,3-a]pyridine-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methylpropanoic acid;

(3*R)-3-(5,8-Dimethyl-3)-(trifluoromethyl)-[1,2,4-triazolo[4,3-a]pyridine-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methylpropanoic acid; and (3*S)-3-(5,8-Dimethyl-3)-(trifluoromethyl)-[1,2,4-triazolo[4,3-a]pyridine-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methylpropanoic acid; and pharmaceutically acceptable salts, and combinations thereof.

An additional illustrative embodiment of the invention is a compound of Formula (I), wherein the compound is selected from the group consisting of (R/S)-3-(3-(((*S)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(1-ethyl-4-methyl-1H-benzo[d][1,2,3]triazol-5-yl)propanoic acid;

(*S)-3-(3-(((*S)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(1-ethyl-4-methyl-1H-benzo[d][1,2,3]triazol-5-yl)propanoic acid;

(*R)-3-(3-(((*S)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(1-ethyl-4-methyl-1H-benzo[d][1,2,3]triazol-5-yl)propanoic acid;

(R/S)-3-(3-(((*R)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(1-ethyl-4-methyl-1H-benzo[d][1,2,3]triazol-5-yl)propanoic acid;

(*S)-3-(3-(((*R)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(1-ethyl-4-methyl-1H-benzo[d][1,2,3]triazol-5-yl)propanoic acid;

(*R)-3-(3-(((*R)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(1-ethyl-4-methyl-1H-benzo[d][1,2,3]triazol-5-yl)propanoic acid;

(R/S)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(1-ethyl-4-methyl-1H-benzo[d][1,2,3]triazol-5-yl)propanoic acid;

(*S)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(1-ethyl-4-methyl-1H-benzo[d][1,2,3]triazol-5-yl)propanoic acid;

(*R)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(1-ethyl-4-methyl-1H-benzo[d][1,2,3]triazol-5-yl)propanoic acid;

(R/S)-3-(3-(((*R)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(1-ethyl-4-methyl-1H-benzo[d][1,2,3]triazol-5-yl)propanoic acid;

(*S)-3-(3-(((*R)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(1-ethyl-4-methyl-1H-benzo[d][1,2,3]triazol-5-yl)propanoic acid;

(*R)-3-(3-(((*R)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(1-ethyl-4-methyl-1H-benzo[d][1,2,3]triazol-5-yl)propanoic acid;

(R/S)-3-(3-(((S)-5,5-Dioxido-7a,8,9,10-tetrahydrobenzo[f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;

(*S)-3-[3-[(5,5-Dioxo-7a,8,9,10-tetrahydro-7H-pyrrolo[2,1-d][1,2,5]benzothiadiazepin-6-yl)methyl]-4-methylphenyl]-3-(1-ethyl-4-methyl-benzotriazol-5-yl)propanoic acid;

(*R)-3-[3-[(5,5-Dioxo-7a,8,9,10-tetrahydro-7H-pyrrolo[2,1-d][1,2,5]benzothiadiazepin-6-yl)methyl]-4-methylphenyl]-3-(1-ethyl-4-methyl-benzotriazol-5-yl)propanoic acid;

(R/S)-3-[3-[(4,4-Dimethyl-1,1-dioxo-3H-pyrido[2,3-b][1,4,5]oxathiazepin-2-yl)methyl]-4-methyl-phenyl]-3-(1-ethyl-4-methyl-benzotriazol-5-yl)propanoic acid;

(R/S)-3-(3-((4,4-Dimethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic acid;

(R/S)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;

(*S)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;

(*R)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;

(R/S)-3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;

(*S)-3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;

(*R)-3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid;

(*S)-3-(3-((4,4-Dimethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic acid;

(*R)-3-(3-((4,4-Dimethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic acid;

(R/S)-3-(3-((4,4-Dimethyl-1,1-dioxido-3,4-dihydro-2H-pyrido[2,3-b][1,4,5]oxathiazepin-2-yl)methyl)-4-methylphenyl)-3-(3-methyl-[1,2,4]triazolo[4,3-a]pyridin-7-yl)propanoic acid;

(R/S)-3-(3-((4,4-Dimethyl-1,1-dioxido-3,4-dihydro-2H-benzo[b][1,4,5]oxathiazepin-2-yl)methyl)-4-methylphenyl)-3-(3-methyl-[1,2,4]triazolo[4,3-a]pyridin-7-yl)propanoic acid;

(R/S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(3-methyl-[1,2,4]triazolo[4,3-a]pyridin-7-yl)propanoic acid;

(*S)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(3-methyl-[1,2,4]triazolo[4,3-a]pyridin-7-yl)propanoic acid;

(*R)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(3-methyl-[1,2,4]triazolo[4,3-a]pyridin-7-yl)propanoic acid;

(*S)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(3-methyl-[1,2,4]triazolo[4,3-a]pyridin-7-yl)propanoic acid;

(*R)-3-(3-(((R)-5,5-Dioxido-7a, 8,9,10-tetrahydrobenzo[f]pyrrolo[2,1-d][1,2,5]thiadiazepin-6(7H)-yl)methyl)-4-methylphenyl)-3-(3-methyl-[1,2,4]triazolo[4,3-a]pyridin-7-yl)propanoic acid;

(R/S)-3-(3-Cyclopropyl-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7N)-yl)methyl)-4-methylphenyl)propanoic acid;

(*s)-3-(3-Cyclopropyl-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*R)-3-(3-Cyclopropyl-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*S)-3-(1-(Cyclopropylmethyl)-4-(difluoromethyl)-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(1-(Cyclopropylmethyl)-4-(difluoromethyl)-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*S)-3-(1-(Cyclopropylmethyl)-4-(difluoromethyl)-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(1-(Cyclopropylmethyl)-4-(difluoromethyl)-1H-benzo[d][1,2,3]triazol-5-yl)-3-(3-(((R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(R/S)-3-(1-Cyclopropyl-4-methyl-1H-benzo[d][1,2,3]triazol-5-yl)-3-(6-(((R)-4-ethyl-1,1-dioxido-3,4-dihydro-2H-pyrido[2,3-b][1,4,5]oxathiazepin-2-yl)methyl)-5-methylpyridin-2-yl)propanoic acid;

(*S)-3-(1-Cyclopropyl-4-methyl-1H-benzo[d][1,2,3]triazol-5-yl)-3-(6-(((R)-4-ethyl-1,1-dioxido-3,4-dihydro-2H-pyrido[2,3-b][1,4,5]oxathiazepin-2-yl)methyl)-5-methylpyridin-2-yl)propanoic acid;

(*R)-3-(1-Cyclopropyl-4-methyl-1H-benzo[d][1,2,3]triazol-5-yl)-3-(6-(((R)-4-ethyl-1,1-dioxido-3,4-dihydro-2H-pyrido[2,3-b][1,4,5]oxathiazepin-2-yl)methyl)-5-methylpyridin-2-yl)propanoic acid;

(R/S)-3-(4-Methyl-3-(((*S)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(*S)-3-(4-Methyl-3-(((S)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(*R)-3-(4-Methyl-3-(((*S)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(R/S)-3-(4-Methyl-3-(((*R)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(*S)-3-(4-Methyl-3-(((*R)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(*R)-3-(4-Methyl-3-(((*R)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(R/S)-3-(4-Methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-3-(4-Methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)-3-(8-methyl-3-(t*rifluoromethyl)-[1,2,4]triazolo[4,3-a]pyridin-7-yl)propanoic acid;

(*R)-3-(4-Methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-3-(4-Methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)-3-(8-methyl-3-(trifluoromethyl)-[1,2,4]triazolo[4,3-a]pyridin-7-yl)propanoic acid;

(*R)-3-(4-Methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)-3-(8-methyl-3-(trifluoromethyl)-[1,2,4]triazolo[4,3-a]pyridin-7-yl)propanoic acid;

(R/S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid;

(*S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid;

(*R)-3-(3-(((R)-4-Ethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid;

(3*S)-3-(3-((3-Chloro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-3-Chloro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-3-Chloro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-4-Ethyl-8-methyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid;

(*S)-3-(3-((8'-Chloro-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-3-Cyano-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-3-Chloro-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-5,5-Dioxido-3-(trifluoromethyl)-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-5,5-Dioxido-3-(trifluoromethyl)-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-((8'-Cyano-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-((8'-Carbamoyl-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-2-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-2-Carbamoyl-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-2-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-2-Carbamoyl-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((S)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*S)-3-(3-(((R)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*S)-3-(4-Methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(R/S)-3-(1-Cyclopropyl-4-methyl-1H-benzo[d][1,2,3]triazol-5-yl)-3-(3-(((R)-5,5-dioxido-7a, 8,9,10-tetrahydropyrido[2,3-f]pyrrolo[2,1-d][1,2,5]thiadiazepin-6(7H)-yl)methyl)-4-methylphenyl)propanoic acid;

(*S)-3-(1-Cyclopropyl-4-methyl-1H-benzo[d][1,2,3]triazol-5-yl)-3-(3-(((R)-5,5-dioxido-7a, 8,9,10-tetrahydropyrido[2,3-f]pyrrolo[2,1-d][1,2,5]thiadiazepin-6(7H)-yl)methyl)-4-methylphenyl)propanoic acid;

(*R)-3-(1-Cyclopropyl-4-methyl-1H-benzo[d][1,2,3]triazol-5-yl)-3-(3-(((R)-5,5-dioxido-7a, 8,9,10-tetrahydropyrido[2,3-f]pyrrolo[2,1-d][1,2,5]thiadiazepin-6(7H)-yl)methyl)-4-methylphenyl)propanoic acid;

(*S)-3-(1-Cyclopropyl-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(1-Cyclopropyl-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(R/S)-3-(1-Cyclopropyl-4-methyl-1H-benzo[d][1,2,3]triazol-5-yl)-3-(3-((1,1-dioxidospiro[benzo[b][1,4,5]oxathiazepine-4,3'-oxetan]-2(3H)-yl)methyl)-4-methylphenyl)propanoic acid;

(*S)-3-(1-Cyclopropyl-4-methyl-1H-benzo[d][1,2,3]triazol-5-yl)-3-(3-((1,1-dioxidospiro[benzo[b][1,4,5]oxathiazepine-4,3'-oxetan]-2(3H)-yl)methyl)-4-methylphenyl)propanoic acid;

(*R)-3-(1-Cyclopropyl-4-methyl-1H-benzo[d][1,2,3]triazol-5-yl)-3-(3-((1,1-dioxidospiro[benzo[b][1,4,5]oxathiazepine-4,3'-oxetan]-2(3H)-yl)methyl)-4-methylphenyl)propanoic acid;

(R/S)-3-(1-Cyclopropyl-4-methyl-1H-benzo[d][1,2,3]triazol-5-yl)-3-(3-(((*S)-5,5-dioxido-7,7a,8,9,10,11-hexahydro-6H-benzo[f]pyrido[2,1-d][1,2,5]thiadiazepin-6-yl)methyl)-4-methylphenyl)propanoic acid;

(R/S)-3-(1-Cyclopropyl-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(*S)-3-(1-Cyclopropyl-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(*R)-3-(1-Cyclopropyl-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(R/S)-3-(1-Cyclopropyl-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(*S)-3-(1-Cyclopropyl-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid;

(*R)-3-(1-Cyclopropyl-4-methyl-1H-benzo[d][1,2,3]triazol-5-yl)-3-(4-methyl-3-(((*R)-7a-methyl-5,5-dioxido- 7a,8,9,10-tetrahydropyrido[2,3-f]pyrrolo[2,1-d][1,2,5]thiadiazepin-6(7H)-yl)methyl)phenyl)propanoic acid;

(R/S)-3-(1-Cyclopropyl-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid;

(*S)-3-(1-Cyclopropyl-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid;

(*R)-3-(1-Cyclopropyl-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid;

(R/S)-3-(1-Cyclopropyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*S)-3-(1-Cyclopropyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*R)-3-(1-Cyclopropyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;

(*S)-3-(3-Cyclopropyl-8-methyl-[1,2,4]triazolo[4,3-a]pyridin-7-yl)-3-(3-((8'-fluoro-1',1'-dioxidospiro[cyclopropane-1,4'-pyrido[2,3-b][1,4,5]oxathiazepin]-2'(3'H)-yl)methyl)-4-methylphenyl)propanoic acid;

(R/S)-3-(1-(Cyclopropylmethyl)-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*S)-3-(1-(Cyclopropylmethyl)-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(1-(Cyclopropylmethyl)-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(R/S)-3-(1-(Cyclopropylmethyl)-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(1-(Cyclopropylmethyl)-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*S)-3-(1-(Cyclopropylmethyl)-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(R/S)-3-(6-((1,1-Dioxidospiro[benzo[b][1,4,5]oxathiazepine-4,3'-oxetan]-2(3H)-yl)methyl)-5-methylpyridin-2-yl)-3-(1-ethyl-4-methyl-1H-benzo[d][1,2,3]triazol-5-yl)propanoic acid;

(*S)-3-(6-((1,1-Dioxidospiro[benzo[b][1,4,5]oxathiazepine-4,3'-oxetan]-2(3H)-yl)methyl)-5-methylpyridin-2-yl)-3-(1-ethyl-4-methyl-1H-benzo[d][1,2,3]triazol-5-yl)propanoic acid;

(*R)-3-(6-((1,1-Dioxidospiro[benzo[b][1,4,5]oxathiazepine-4,3'-oxetan]-2(3H)-yl)methyl)-5-methylpyridin-2-yl)-3-(1-ethyl-4-methyl-1H-benzo[d][1,2,3]triazol-5-yl)propanoic acid;

(R/S)-3-(6-((1',1'-Dioxidospiro[oxetane-3,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic acid;

(*S)-3-(6-((1',1'-Dioxidospiro[oxetane-3,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic acid;

(*R)-3-(6-((1',1'-Dioxidospiro[oxetane-3,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic acid;

(R/S)-3-(6-((1',1'-Dioxidospiro[cyclopropane-1,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic acid;

(*S)-3-(6-((1',1'-Dioxidospiro[cyclopropane-1,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic acid; and (*R)-3-(6-((1',1'-Dioxidospiro[cyclopropane-1,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic acid; and pharmaceutically acceptable salts, and combinations thereof.

An additional illustrative embodiment of the invention is a compound of Formula (I), wherein the compound is selected from the group consisting of 3-(7-(Difluoromethoxy)-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*S)-3-(7-(Difluoromethoxy)-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*R)-3-(7-(Difluoromethoxy)-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

3-(7-(Difluoromethoxy)-1-methyl-1H-benzo[d][1,2,3]triazol-5-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic acid;

(*S)-3-(7-(Difluoromethoxy)-1-methyl-1H-benzo[d][1,2,3]triazol-5-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic acid;

(*R)-3-(7-(Difluoromethoxy)-1-methyl-1H-benzo[d][1,2,3]triazol-5-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic acid;

3-(3-((1',1'-Dioxidospiro[oxetane-3,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)propanoic acid;

3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(3-(trifluoromethyl)-[1,2,4]triazolo[4,3-a]pyridin-7-yl)propanoic acid;

(*S)-3-(3-(((S)-5,5-Dioxido-7a,8,9,10-tetrahydropyrido[2,3-f]pyrrolo[2,1-d][1,2,5]thiadiazepin-6(7H)-yl)methyl)-

4-methylphenyl)-3-(3-(trifluoromethyl)-[1,2,4]triazolo[4,3-a]pyridin-7-yl)propanoic acid;

(*R)-3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(3-(trifluoromethyl)-[1,2,4]triazolo[4,3-a]pyridin-7-yl)propanoic acid;

3-(3-(((R)-4-Ethyl-1,1-dioxido-3,4-dihydro-2H-pyrido[2,3-b][1,4,5]oxathiazepin-2-yl)methyl)-4-methylphenyl)-3-(3-(trifluoromethyl)-[1,2,4]triazolo[4,3-a]pyridin-7-yl)propanoic acid;

(*S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(3-(trifluoromethyl)-[1,2,4]triazolo[4,3-a]pyridin-7-yl)propanoic acid;

(*R)-3-(3-(((R)-4-Ethyl-1,1-dioxido-3,4-dihydro-2H-pyrido[2,3-b][1,4,5]oxathiazepin-2-yl)methyl)-4-methylphenyl)-3-(3-(trifluoromethyl)-[1,2,4]triazolo[4,3-a]pyridin-7-yl)propanoic acid;

3-(3-((1',1'-Dioxidospiro[oxetane-3,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-((1',1'-Dioxidospiro[oxetane-3,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*R)-3-(3-((1',1'-Dioxidospiro[oxetane-3,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*R)-3-(3-(((*S)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*S)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*R)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

3-(3-((4,4-Dimethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid;

(*S)-3-(3-((4,4-Dimethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid;

(*R)-3-(3-((4,4-Dimethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid;

3-(3-(((*R)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*R)-3-(3-(((*R)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((S)-5,5-Dioxido-7a,8,9,10-tetrahydrobenzo[f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*R)-3-(3-(((S)-5,5-Dioxido-7a,8,9,10-tetrahydrobenzo[f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*R)-3-(3-(((*R)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic acid;

(*S)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic acid;

(*R)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic acid;

3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic acid;

(*S)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic acid;

(*R)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic acid;

3-(3-((4,4-Dimethyl-1,1-dioxido-3,4-dihydro-2H-benzo[b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid;

(*S)-3-(3-((4,4-Dimethyl-1,1-dioxido-3,4-dihydro-2H-benzo[b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid;

(*R)-3-(3-((4,4-Dimethyl-1,1-dioxido-3,4-dihydro-2H-benzo[b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid;

3-(3-((1,1-Dioxidospiro[benzo[b][1,4,5]oxathiazepine-4,3'-oxetan]-2(3H)-yl)methyl)-4-methylphenyl)-3-(8-methyl-3-(trifluoromethyl)-[1,2,4]triazolo[4,3-a]pyridin-7-yl)propanoic acid;

(*R)-3-(3-((1,1-dioxidospiro[benzo[b][1,4,5]oxathiazepine-4,3'-oxetan]-2(3H)-yl)methyl)-4-methylphenyl)-3-(8-methyl-3-(trifluoromethyl)-[1,2,4]triazolo[4,3-a]pyridin-7-yl)propanoic acid;

3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*R)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*S)-5,5-Dioxido-7,7a,8,9-tetrahydro-6H-azeto[2,1-d]pyrido[2,3-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*R)-3-(3-(((*S)-5,5-Dioxido-7,7a,8,9-tetrahydro-6H-azeto[2,1-d]pyrido[2,3-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-5,5-Dioxido-7,7a,8,9-tetrahydro-6H-azeto[2,1-d]pyrido[2,3-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*R)-3-(3-(((*R)-5,5-Dioxido-7,7a,8,9-tetrahydro-6H-azeto[2,1-d]pyrido[2,3-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

3-(6-(((R)-5,5-Dioxido-7a,8,9,10-tetrahydropyrido[2,3-f]pyrrolo[2,1-d][1,2,5]thiadiazepin-6(7H)-yl)methyl)-5-methylpyridin-2-yl)-3-(1-ethyl-4-methyl-1H-benzo[d][1,2,3]triazol-5-yl)propanoic acid;

(*S)-3-(6-(((R)-5,5-Dioxido-7a,8,9,10-tetrahydropyrido[2,3-f]pyrrolo[2,1-d][1,2,5]thiadiazepin-6(7H)-yl)methyl)-5-methylpyridin-2-yl)-3-(1-ethyl-4-methyl-1H-benzo[d][1,2,3]triazol-5-yl)propanoic acid;

(*R)-3-(6-(((R)-5,5-Dioxido-7a,8,9,10-tetrahydropyrido[2,3-f]pyrrolo[2,1-d][1,2,5]thiadiazepin-6(7H)-yl)methyl)-5-methylpyridin-2-yl)-3-(1-ethyl-4-methyl-1H-benzo[d][1,2,3]triazol-5-yl)propanoic acid;

(*S)-3-(3-(((*S)-5,5-Dioxido-7,7a,8,9,10,11-hexahydro-6H-benzo[f]pyrido[2,1-d][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-5,5-Dioxido-7,7a,8,9,10,11-hexahydro-6H-benzo[f]pyrido[2,1-d][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

3-(6-(((*S)-5,5-Dioxido-7,7a,8,9,10,11-hexahydro-6H-dipyrido[2,1-d:2',3'-f][1,2,5]thiadiazepin-6-yl)methyl)-5-methylpyridin-2-yl)-3-(1-ethyl-4-methyl-1H-benzo[d][1,2,3]triazol-5-yl)propanoic acid;

(*S)-3-(6-(((*S)-5,5-Dioxido-7,7a,8,9,10,11-hexahydro-6H-dipyrido[2,1-d:2',3'-f][1,2,5]thiadiazepin-6-yl)methyl)-5-methylpyridin-2-yl)-3-(1-ethyl-4-methyl-1H-benzo[d][1,2,3]triazol-5-yl)propanoic acid;

(*R)-3-(6-(((*S)-5,5-Dioxido-7,7a,8,9,10,11-hexahydro-6H-dipyrido[2,1-d:2',3'-f][1,2,5]thiadiazepin-6-yl)methyl)-5-methylpyridin-2-yl)-3-(1-ethyl-4-methyl-1H-benzo[d][1,2,3]triazol-5-yl)propanoic acid;

3-(6-(((*R)-5,5-Dioxido-7,7a,8,9,10,11-hexahydro-6H-dipyrido[2,1-d:2',3'-f][1,2,5]thiadiazepin-6-yl)methyl)-5-methylpyridin-2-yl)-3-(1-ethyl-4-methyl-1H-benzo[d][1,2,3]triazol-5-yl)propanoic acid;

(*S)-3-(6-(((*R)-5,5-Dioxido-7,7a,8,9,10,11-hexahydro-6H-dipyrido[2,1-d:2',3'-f][1,2,5]thiadiazepin-6-yl)methyl)-5-methylpyridin-2-yl)-3-(1-ethyl-4-methyl-1H-benzo[d][1,2,3]triazol-5-yl)propanoic acid;

(*R)-3-(6-(((*R)-5,5-Dioxido-7,7a,8,9,10,11-hexahydro-6H-dipyrido[2,1-d:2',3'-f][1,2,5]thiadiazepin-6-yl)methyl)-5-methylpyridin-2-yl)-3-(1-ethyl-4-methyl-1H-benzo[d][1,2,3]triazol-5-yl)propanoic acid;

(*S)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(*S)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoic acid;

(*S)-3-(3-(((*S)-3-fluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-(((*R)-3-fluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

(*S)-3-(3-((8'-Fluoro-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid;

(*S)-3-(3-((3-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid;

2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*R)-2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

3-(3-((1',1'-Dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*S)-3-(3-((1',1'-Dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*R)-3-(3-((1',1'-Dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

3-(3-((1',1'-Dioxido-2,3,5,6-tetrahydrospiro[pyran-4,4'-pyrido[2,3-b][1,4,5]oxathiazepin]-2'(3'H)-yl)methyl)-4- methylphenyl)-2,2-dimethyl-3-(3-(trifluoromethyl)-[1,2,4]triazolo[4,3-a]pyridin-7-yl)propanoic acid;
(*S)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(3-(trifluoromethyl)-[1,2,4]triazolo[4,3-a]pyridin-7-yl)propanoic acid;
(*R)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(3-(trifluoromethyl)-[1,2,4]triazolo[4,3-a]pyridin-7-yl)propanoic acid;
2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(3-(trifluoromethyl)-[1,2,4]triazolo[4,3-a]pyridin-7-yl)propanoic acid;
(*S)-2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(3-(trifluoromethyl)-[1,2,4]triazolo[4,3-a]pyridin-7-yl)propanoic acid;
(*R)-2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(3-(trifluoromethyl)-[1,2,4]triazolo[4,3-a]pyridin-7-yl)propanoic acid;
(*S)-2,2-Dimethyl-3-(8-methyl-3-(trifluoromethyl)-[1,2,4]triazolo[4,3-a]pyridin-7-yl)-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid;
(*R)-2,2-Dimethyl-3-(8-methyl-3-(trifluoromethyl)-[1,2,4]triazolo[4,3-a]pyridin-7-yl)-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid;
3-(1-(Cyclopropylmethyl)-4-methyl-1H-benzo[d][1,2,3]triazol-5-yl)-2,2-dimethyl-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid;
(*S)-3-(1-(Cyclopropylmethyl)-4-methyl-1H-benzo[d][1,2,3]triazol-5-yl)-2,2-dimethyl-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid;
(*R)-3-(1-(Cyclopropylmethyl)-4-methyl-1H-benzo[d][1,2,3]triazol-5-yl)-2,2-dimethyl-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid;
(*S)-3-(3,7-Dimethyl-7H-pyrrolo[2,3-c]pyridazin-6-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;
(*R)-3-(3,7-Dimethyl-7H-pyrrolo[2,3-c]pyridazin-6-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;
(*S)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid;
(*R)-3-(3-(difluoromethyl)-8-methyl-[1,2,4]triazolo[4,3-a]pyridin-7-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid;
(*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid;
(*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid;
(*S)-3-(3-((1',1'-Dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;
(*R)-3-(3-((1',1'-Dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;
(*S)-3-(3-((1',1'-Dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;
(*R)-3-(3-((1',1'-Dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;
(*S)-2,2-Dimethyl-3-(4-methyl-3-((8'-methyl-1',1'-dioxidospiro[piperidine-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;
(*R)-2,2-Dimethyl-3-(4-methyl-3-((8'-methyl-1',1'-dioxidospiro[piperidine-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;
(*S)-2,2-Dimethyl-3-(4-methyl-3-((8'-methyl-1',1'-dioxidospiro[azetidine-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;
(*R)-2,2-Dimethyl-3-(4-methyl-3-((8'-methyl-1',1'-dioxidospiro[azetidine-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;
(*R)-3-(3-((7'-(3-((2-(2-Aminoethoxy)ethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;
(*S)-3-(3-((7'-(3-((2-(2-aminoethoxy)ethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;
(*S)-3-(3,7-Dimethyl-7H-pyrrolo[2,3-c]pyridazin-6-yl)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoic acid;
(*R)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(pyrrolidine-1-yl)-ethoxy)2,3,5,6-tetrahydrospiro[pyran-4,4'-pyrido[2,3-b][1,4,5]oxathiazepin]-2',(3'H)-yl)methyl)phenyl)propanoic acid;
(*S)-3-(3,7-Dimethyl-7H-pyrrolo[2,3-c]pyridazine-6-yl)-2,2-dimethyl-3-(4-methyl-3-((8'-methyl-1',1'-dioxido-7'-(2-

(piperidine-1-yl)-ethoxy)2,3,5,6-tetrahydrospiro[pyran-4,4'-pyrido[2,3-b][1,4,5]oxathiazepin]-2',(3'H)-yl)methyl)phenyl)propanoic acid;

(*R)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)2,3,5,6-tetrahydrospiro[pyran-4,4'-pyrido[2,3-b][1,4,5]oxathiazepin]-2',(3'H)-yl)methyl)phenyl)propanoic acid;

(*S)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)spiro[cyclopropane-1,4'-pyrido[2,3-b][1,4,5]oxathiazepin]-2',(3'H)-yl)methyl)phenyl)propanoic acid;

(*R)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)spiro[cyclopropane-1,4'-pyrido[2,3-b][1,4,5]oxathiazepin]-2',(3'H)-yl)methyl)phenyl)propanoic acid;

(*S)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(pyrrolidin-1-yl)-ethoxy)spiro[cyclopropane-1,4'-pyrido[2,3-b][1,4,5]oxathiazepin]-2',(3'H)-yl)methyl)phenyl)propanoic acid;

(*R)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(pyrrolidin-1-yl)-ethoxy)spiro[cyclopropane-1,4'-pyrido[2,3-b][1,4,5]oxathiazepin]-2'-(3'H)-yl)methyl)phenyl)propanoic acid;

(*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid;

(*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid;

(*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*R)-3-(3-(difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid;

(*R)-3-(3-((7'-(2-(4,4-Difluoropiperidin-1-yl)ethoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic acid;

(*R)-3-(3-((7'-(((1R,3R)-3-Hydroxycyclobutyl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*R)-2,2-Dimethyl-3-(4-methyl-3-((8'-methyl-7'-(((R-1-morpholinopropan-2-yl)amino)-1',1'-dioxido-2,3,5,6-tetrahydrospiro [pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-2,2-Dimethyl-3-(4-methyl-3-((8'-methyl-7'-(((S-1-morpholinopropan-2-yl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-2,2-Dimethyl-3-(4-methyl-3-((8'-methyl-7'-(((1-morpholinopropan-2-yl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-2,2-Dimethyl-3-(4-methyl-3-((8'-methyl-7'-((2-morpholinoethyl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-2,2-Dimethyl-3-(4-methyl-3-((8'-methyl-7'-((2-morpholinoethyl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-2,2-Dimethyl-3-(4-methyl-3-((8'-methyl-1',1'-dioxido-7'-(((S)-1-(pyrrolidine-1-yl)propan-2-yl)amino)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*R)-3-(3-((1',1'-Dioxido-7'-(2-(piperazin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic acid;

(*R)-2,2-Dimethyl-3-(4-methyl-3-(8'-methyl-1',1'-dioxido-7'-(2-(piperidin-4-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic acid;

(*S)-2,2-Dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic acid;

(*S)-3-(3-1',1'-Dioxido-7'-(2-(piperidin-1-yl)ethoxy)spiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic acid;

(*S)-2,2-Dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*S)-2,2-Dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl)propanoic acid;

(*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoic acid;

3-(*R)-2,2-Dimethyl-3-(4-methyl-3-((8'-methyl-1',1'-dioxido-7'-((1-piperidin-1-yl)propan-2-yl)amino)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoic acid;

(*S)-3-(3-((7'-(2-(4-Methoxypiperidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;

(*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoic acid;

(*R)-2,2-Dimethyl-3-(4-methyl-3-((8'-methyl-1',1'-dioxido-7'-(((S)-1-piperidin-1-yl)propan-2-yl)amino)spiro[cyclopropane-1,4'-pyrido [2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;

(*S)-3-(3-(((*S)-1',1'-Dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*S)-3-(3-(((*R)-1',1'-Dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*S)-2,2-Dimethyl-3-(4-methyl-3-(((*S)-8'-methyl-1',1'-dioxido-4,5-dihydro-2H-spiro[furan-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-2,2-Dimethyl-3-(4-methyl-3-(((*R)-8'-methyl 1',1'-dioxido-4,5-dihydro-2H-spiro[furan-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*R)-3-(3-(((*S)-1',1'-Dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*R)-3-(3-(((*R)-1',1'-Dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;

(*R)-2,2-Dimethyl-3-(4-methyl-3-(((*S)-8'-methyl-1',1'-dioxido-4,5-dihydro-2H-spiro[furan-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*R)-2,2-Dimethyl-3-(4-methyl-3-(((*R)-8'-methyl-1',1'-dioxido-4,5-dihydro-2H-spiro[furan-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;

(*S)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(*R)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid;

(R/S)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;

(*S)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;

(*R)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;

(R/S)-3-(1-Cyclopropyl-4-methyl-1H-benzo[d][1,2,3]triazol-5-yl)-2,2-dimethyl-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic acid;

(*S)-3-(1-Cyclopropyl-4-methyl-1H-benzo[d][1,2,3]triazol-5-yl)-2,2-dimethyl-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic acid;

(*R)-3-(1-Cyclopropyl-4-methyl-1H-benzo[d][1,2,3]triazol-5-yl)-2,2-dimethyl-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic acid;

(R/S)-3-(1-Cyclopropyl-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*S)-3-(1-Cyclopropyl-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

(*R)-3-(1-Cyclopropyl-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;

3-(1-(cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;

(*R)-3-(1-(Cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;
(*S)-3-(1-(Cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;
3-(7-Cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;
(*R)-3-(7-Cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;
(*S)-3-(7-Cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid; and
pharmaceutically acceptable salts, and combinations thereof.

An additional illustrative embodiment of the invention is a compound of Formula (I), wherein the compound is selected from the group consisting of
(*R)-3-(1-ethyl-4-methyl-1H-benzo[d][1,2,3]triazol-5-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoic acid;
(*S)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)-2,2-dimethylpropanoic acid;
(*S)-3-(3-(Difluoromethyl)-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;
(*R)-3-(3-(((*S)-1',1'-Dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid;
(*S)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid;
(*S)-2,2-Dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;
(*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoic acid;
(*S)-3-(1-Ethyl-4-methyl-1H-benzo[d][1,2,3]triazol-5-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid;
(*S)-2,2-Dimethyl-3-(8-methyl-3-(trifluoromethyl)-[1,2,4]triazolo[4,3-a]pyridin-7-yl)-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid; and
pharmaceutically acceptable salts thereof.

An additional illustrative embodiment of the invention is a compound of Formula (I), wherein the compound is
(*R)-3-(1-ethyl-4-methyl-1H-benzo[d][1,2,3]triazol-5-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoic acid; and
pharmaceutically acceptable salts thereof.

An additional illustrative embodiment of the invention is a compound of Formula (I), wherein the compound is
(*S)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)-2,2-dimethylpropanoic acid; and
pharmaceutically acceptable salts thereof.

An additional illustrative embodiment of the invention is a compound of Formula (I), wherein the compound is
(*S)-3-(3-(Difluoromethyl)-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid; and
pharmaceutically acceptable salts thereof.

An additional illustrative embodiment of the invention is a compound of Formula (I), wherein the compound is
(*R)-3-(3-(((*S)-1',1'-Dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid; and
pharmaceutically acceptable salts thereof.

An additional illustrative embodiment of the invention is a compound of Formula (I), wherein the compound is
(*S)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid; and
pharmaceutically acceptable salts thereof.

An additional illustrative embodiment of the invention is a compound of Formula (I), wherein the compound is
(*S)-2,2-Dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid; and
pharmaceutically acceptable salts thereof.

An additional illustrative embodiment of the invention is a compound of Formula (I), wherein the compound is
(*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoic acid; and
pharmaceutically acceptable salts thereof.

An additional illustrative embodiment of the invention is a compound of Formula (I), wherein the compound is
(*S)-3-(1-Ethyl-4-methyl-1H-benzo[d][1,2,3]triazol-5-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid; and
pharmaceutically acceptable salts thereof.

An additional illustrative embodiment of the invention is a compound of Formula (I), wherein the compound is
(*S)-2,2-Dimethyl-3-(8-methyl-3-(trifluoromethyl)-[1,2,4]triazolo[4,3-a]pyridin-7-yl)-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid; and
pharmaceutically acceptable salts thereof.

Abbreviations and acronyms used herein include those listed in Table 1.

TABLE 1

Table of Abbreviations

| Acronym | Term |
|---|---|
| Ac | Acyl or Acetyl |
| ACN or MeCN | Acetonitrile |
| AcOH, HOAc | Acetic acid |
| AcOK or KOAc | Potassium acetate |
| Ar | Argon |
| $B_2Pin_2$ | Bis(pinacolato)diboron |
| HATU | 1-[Bis(dimethylamino)methylene]-1H-1,2,3-triazolo[4,5-b]pyridinium 3-oxid hexafluorophosphate |
| $BF_3$—$Et_2O$ | Boron trifluoride diethyl etherate |
| Boc | Tert-butylcarbamoyl |
| $Boc_2O$ | Di-tert-butyl dicarbonate |
| br | Broad |
| t-BuOK or KtOBu | Potassium tert-butoxide |
| CSA | Camphorsulfonic acid |
| dccp•2HBF$_4$ | 1,3-Bis(dicyclohexylphosphino)propane bis(tetrafluoroborate) |
| DBAD | Di-tert-butyl azodicarboxylate |
| DBU | 1,8-Diazabicyclo[5.4.0]undec-7-ene |
| DCE | Dichloroethane |
| DCM | Dichloromethane |
| DIAD | Diisopropyl azodicarboxylate |
| DIBAL-H | Diisobutylaluminum hydride |
| DIPEA | Diisopropylethylamine |
| DMA | Dimethylacetamide |
| DMAP | 4-Dimethylaminopyridine |
| DMF | N,N-Dimethylformamide |
| DMSO | Dimethyl sulfoxide |
| DPPF | 1,1'-Ferrocenediyl-bis(diphenylphosphine) |
| EtOAc | Ethyl acetate |
| EtOH | Ethanol |
| ESI | Electrospray ionization |
| HATU | 1-[Bis(dimethylamino)methylene]-1H-1,2,3-triazolo[4,5-b]pyridinium 3-oxid hexafluorophosphate, N-[(Dimethylamino)-1H-1,2,3-triazolo-[4,5-b]pyridin-1-ylmethylene]-N-methylmethanaminium hexafluorophosphate N-oxide |
| Herrmann's catalyst | trans-Bis(acetato)bis[o-(di-o-tolylphosphino)benzyl]dipalladium(II) |
| HPLC | High-pressure liquid chromatography |
| iPrNH$_2$ | Isopropyl amine |
| Josiphos Pd(0) pre-catalyst G3 | {(R)-1-[(Sp)-2-(Dicyclohexylphosphino)ferrocenyl]ethyldi-tert-butylphosphine}[2-(2'-amino-1,1'-biphenyl)]palladium(II) methanesulfonate |
| LCMS | Liquid chromatography and mass spectrometry |
| LAH | Lithium aluminium hydrideabbre |
| LDA | Lithium diisopropylamide |
| LG | Leaving Group |
| m/z | Mass to charge ratio |
| MeOH | Methanol |
| MeI | Methyl iodide |
| MS | Mass spectrometry |
| MTBE | Methyl tert-butyl ether |
| NaOAc | Sodium acetate |
| NaOMe | Sodium methoxide |
| NBS | N-Bromosuccinimide |
| NCS | N-Chlorosuccinimide |
| NMP | N-Methyl-2-pyrrolidone |
| NMR | Nuclear magnetic resonance |
| OMs | O—$CH_3S(O)_2$ |
| OTf or triflate | $CF_3$ $S(O)_2O$— |
| OTs | O—$S(O)_2$—p-$CH_3$—$C_6H_5$ |
| Pd(t-Bu$_3$P)$_2$ | Bis(tri-tert-butylphosphine)palladium(0) |
| Pd$_2$(dba)$_3$ | Tris(dibenzylideneacetone)dipalladium(0) |
| Pd(dppf)Cl$_2$ | [1,1'-Bis(diphenylphosphino)-ferrocene]dichloropalladium (II) |

TABLE 1-continued

Table of Abbreviations

| Acronym | Term |
|---|---|
| Pd(dppf)Cl$_2$—$CH_2Cl_2$ | [1,1'-Bis(diphenylphosphino)-ferrocene]dichloropalladium(II), complex with dichloromethane |
| Pd(PPh$_3$)$_2$Cl$_2$ | Palladium(II)bis(triphenylphosphine) dichloride |
| Pd(PPh$_3$)$_4$ | Tetrakis(triphenylphosphine)palladium(0) |
| Pd(dtbpf)Cl$_2$ | [1,1'-Bis(di-tert-butylphosphino)ferrocene]dichloro-palladium(II) |
| P(1-nap)$_3$ | Tri-1-naphthylphosphine |
| Pd(OAc)$_2$ | Palladium(II) acetate |
| P(o-tol)$_3$ | Tri(o-tolyl)phosphine |
| PG | Protecting Group |
| POBr$_3$ | Phosphorus(V) oxybromide |
| [Rh(COD)Cl]$_2$ | Chloro(1,5-cyclooctadiene)rhodium(I) dimer |
| RockPhos Pd G3 | [(2-Di-tert-butylphosphino-3-methoxy-6-methyl-2',4',6'-triisopropyl-1,1'-biphenyl)-2-(2-aminobiphenyl)]palladium(II) methanesulfonate |
| SFC | Supercritical Fluid Chromatography |
| Me$_3$Si | Trimethylsilyl |
| TMSCN | Trimethylsilyl cyanide |
| TBAF | Tetra-n-butylammonium fluoride |
| TBAB | Tetrabutylammonium bromide |
| TBS | Tert-butyldimethylsilyl |
| TBSCl | Tert-butyldimethylsilyl chloride |
| TBSOTf | Tert-butyldimethylsilyl triflate |
| TEA or Et$_3$N | Triethylamine |
| TFA | Trifluoroacetic acid |
| TFAA | Trifluoroacetic anhydride |
| tosyl | p-toluenesulfonyl |
| THF | Tetrahydrofuran |
| TLC | Thin layer chromatography |
| tol-BINAP | 2,2'-Bis(di-p-tolylphosphino)-1,1'-binaphthyl |
| X-Phos | 2-Dicyclohexylphosphino-2',4',6'-triisopropylbiphenyl |
| X-Phos Pd G2 | Chloro(2-dicyclohexylphosphino-2',4',6'-triisopropyl-1,1'-biphenyl)[2-(2'-amino-1,1'-biphenyl)]palladium(II) |
| Zn(CN)$_2$ | Zinc cyanide |

Illustrative compounds useful in methods of this invention are described below by reference to the illustrative synthetic schemes ("Schemes") and specific examples for their preparation. Compounds of Formula (I)

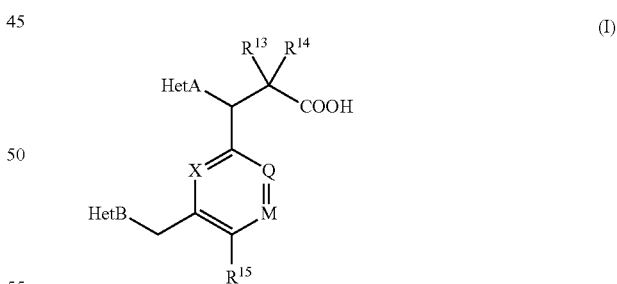

are synthesized in accordance with the Schemes. By way of illustration, but not as a limitation, compounds according to this invention are prepared according to the following general preparation procedures given by Schemes 1-12. One of ordinary skill in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent.

Unless otherwise specified, the variables in Schemes 1-12 are as defined above in reference to Formula (I). The following general features concerning reaction temperatures, protecting groups PG, leaving groups LG, and substituent $R^{35}$ refer, as applicable, to all the Schemes 1-12.

If no temperature or temperature range is stated, it is to be understood that the reaction is to be run at room temperature.

The term PG in the following schemes represents a protecting group such as an acetyl (Ac), or a t-butyldimethylsilyl (TBS).

The conditions to protect an alcohol as an acetyl include treatment of the alcohol with (i) acetyl chloride in the presence of a base such as triethylamine, DIPEA or pyridine in a reaction medium provided by solvents such as dichloromethane, DMF or THF at a temperature ranging from about 0° C. to about room temperature wherein DMAP may optionally be added, or (ii) acetic anhydride in the presence of a base such as triethylamine, DIPEA or pyridine in a reaction medium provided by solvents such as dichloromethane, DMF or THF at a temperature ranging from about 0° C. to about room temperature, wherein DMAP may optionally be added. These conditions are referred to as "acetyl protection conditions". The conditions to remove an acetyl group include using a base such as potassium carbonate in a reaction medium provided by solvents such as THF, methanol, ethanol, water, or mixtures thereof. These deprotection conditions are referred to as "acetyl group deprotection conditions".

Other conditions to protect an alcohol rely on its protection as a TBS ether by coupling the alcohol with TBS-Cl or TBS-OTf in the presence of a base such as imidazole, 2,6-lutidine, triethylamine, DIPEA or pyridine in a reaction medium provided by solvents such as dichloromethane, DMF or THF at a temperature ranging from about 0° C. to about room temperature, wherein DMAP may optionally be added. These conditions are referred to as "TBS protecting group conditions". The TBS group is removed by (i) TBAF in a solvent such as THF or DMF at a temperature ranging from about 0° C. to about 70° C., or (ii) HCl or CSA in a reaction medium provided by solvents such as THF, ethanol, methanol, water or mixtures thereof at a temperature ranging from about 0° C. to about room temperature. These deprotection conditions are referred to as "TBS group deprotection conditions".

$R^{35}$ is defined as $C_1$-$C_4$alkyl.

The term LG refers to a leaving group. Examples of leaving groups include I, Cl, Br, OMs and OTs.

When isomerically pure samples are desired, isomeric mixtures of compounds synthesized according to Scheme 1 can be separated by chiral SFC or HPLC.

Scheme 1

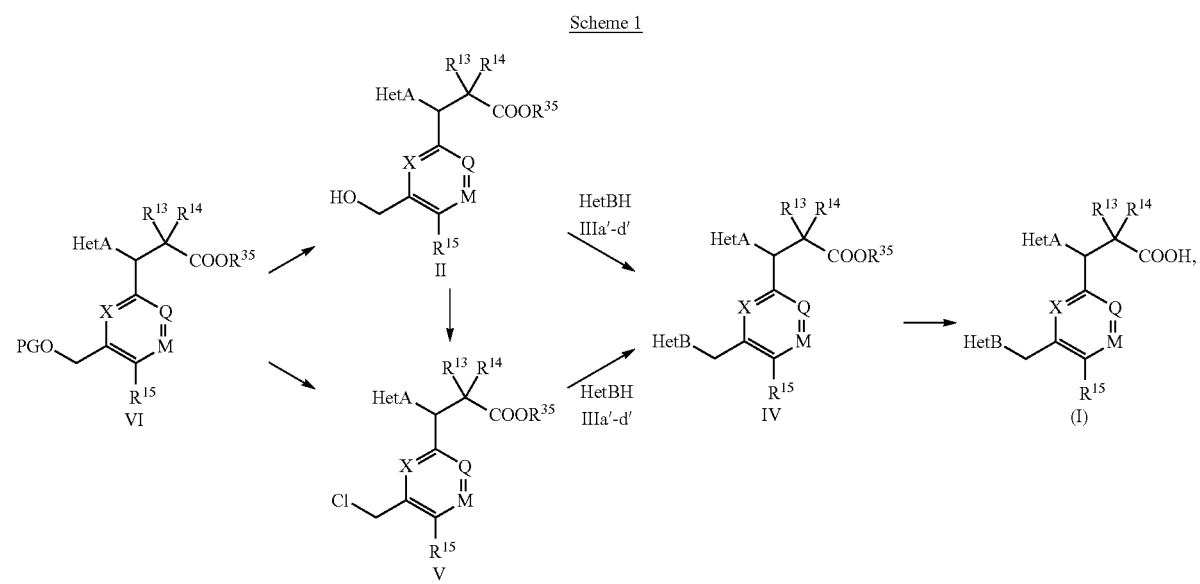

wherein HetB is

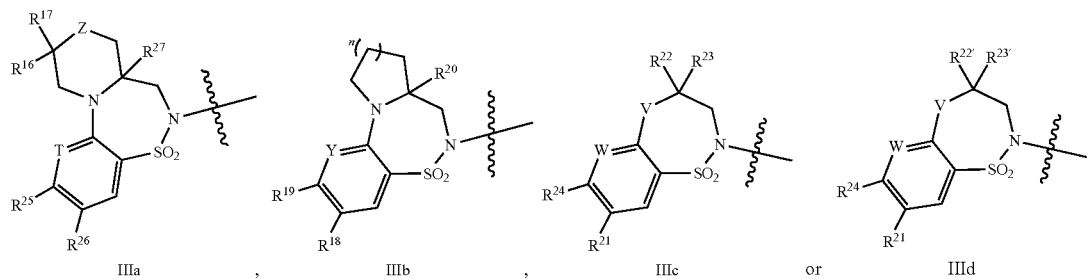

and HetB is

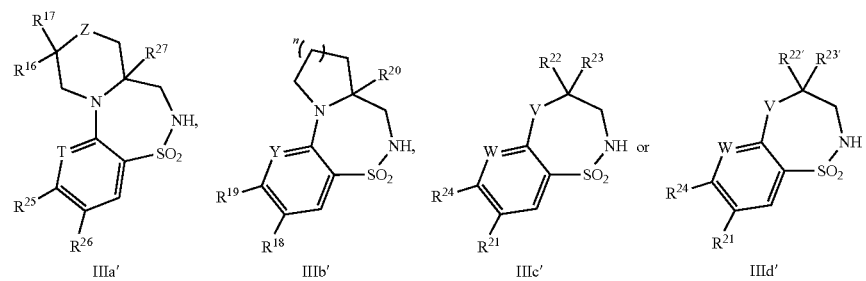

As shown in Scheme 1, compound II is converted to compound IV by coupling it with one of compounds IIIa'-d' (HetBH) under Mitsunobu reaction conditions. This Mitsunobu reaction is performed by using diisopropyl azodicarboxylate or di-tert-butyl azodicarboxylate in the presence of triphenylphosphine or solid-supported triphenylphosphine in a reaction medium provided by solvents such as THF, DMF, dichloromethane, or mixtures thereof, at a temperature range from about room temperature to about the reflux temperature of the solvent. These conditions are referred to as "Mitsunobu reaction conditions". Compound IIIa' is made as shown in Schemes 10a and 12a, compound IIIb' is made as shown in Schemes 10b and 12b, compound IIIc' is made as shown in Scheme 10c and compound IIId' is made as shown in Scheme 10d. Compound V is converted to compound IV by coupling it with one of compounds IIIa'-d' (HetBH) in an alkylation reaction. This alkylation reaction is performed by using a base such as sodium hydride or potassium tert-butoxide, in a reaction medium provided by solvents such as THF or DMF. Alternatively, compound IV is made as shown in Scheme 3b. Compound IV is converted to compound (I) under hydrolysis reaction conditions, employing an aqueous solution of NaOH or LiOH, in a reaction medium provided by solvents such as water, THF, 1,4-dioxane, methanol, ethanol, or mixtures thereof, at a temperature range from about room temperature to about the reflux temperature of the solvent. These conditions are referred to as "basic hydrolysis reaction conditions" Compound VI (PG is Ac) is converted to compound II under acetyl group deprotection conditions. Alternatively, compound II is made as shown in Scheme 3b. Compound VI (PG is TBS) is converted to compound V by treatment with a chlorinating agent such as thionyl chloride with or without DMF as an additive in a reaction medium provided by solvents such as dichloromethane or dichloroethane, to yield compound V. Compound VI is made as shown in Schemes 2, 3b and 4.

Scheme 2

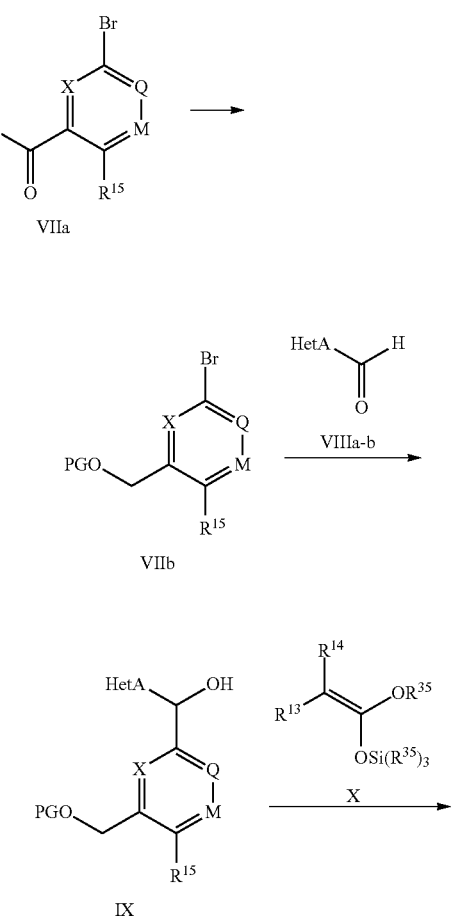

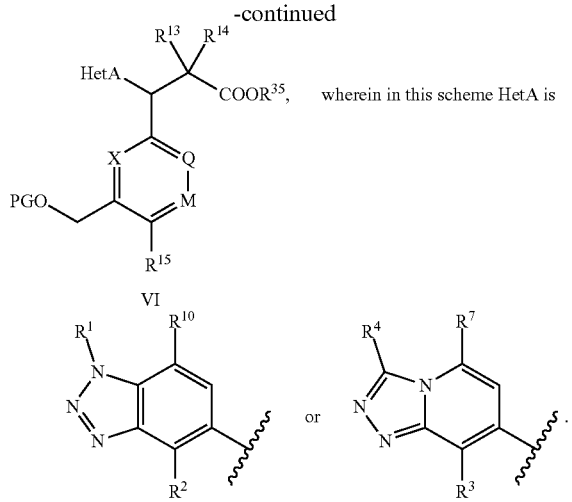

As shown in Scheme 2, compound VIIa is converted to compound VIIb by a two-step process. The first step in this two-step process is reduction of benzoate VIIa to a benzyl alcohol (structure not shown) with a reducing agent such as LiAlH$_4$ in a reaction medium provided by a solvent such as THF at a temperature ranging from about 0° C. to about 15° C. The second step in this two-step protocol is the protection of the benzyl alcohol as a TBS ether under TBS protection conditions. Compound VIIb is converted to compound IX by initially treating compound VIIB with a reagent such as n-butyllithium at a low temperature such as about −78° C. in a reaction medium provided by a solvent such as THF, forming an organolithium intermediate (structure not shown), this organolithium intermediate is then treated with compound VIIIa (made as shown in Schemes 4 and 9) or VIIIb (made as shown in Scheme 5) to form compound IX. Compound IX is converted to compound VI by coupling with a silylketene acetal X, using trichloroacetonitrile in the presence of the additives DBU and trifluoromethanesulfonamide in a reaction medium provided by a solvent such as acetonitrile, at a temperature ranging from about room temperature to about the reflux temperature of the reaction solvent. Alternatively, this coupling can also be accomplished by using a compound X and a reagent such as BF$_3$-Et$_2$O or TiCl$_4$ in a reaction medium provided by a solvent such as dichloromethane. Compound XIV is also made with a different HetA group as shown in Scheme 8.

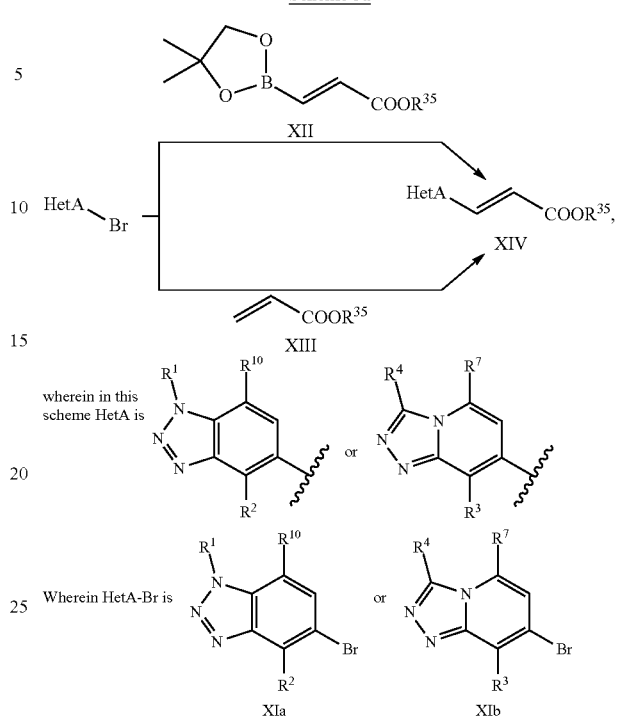

As shown in Scheme 3a, HetA-Br (XIa or XIb) is converted to compound XIV by a palladium catalyzed coupling with compound XII with a palladium catalyst such as Pd(dppf)Cl$_2$ or Pd(dppf)Cl$_2$.CH$_2$Cl$_2$ in the presence of a base additive such as potassium carbonate or sodium carbonate in a reaction medium provided by a solvent such as mixture of 1,4-dioxane and water at a temperature ranging from about room temperature to about the reflux temperature of the solvent. When compound XIII is used, compounds XIa (made as shown in Schemes 6 and 7) or XIb (as made as shown in Scheme 5) are treated with a palladium catalyst such as Herrmann's palladacycle, Pd(dppf)Cl$_2$, Pd(dtbpf)Cl$_2$, Pd(PPh$_3$)$_4$ or Pd(OAc)$_2$ in the presence of additives such as tetrabutylammonium chloride hydrate or P(o-tol)$_3$ and bases such as sodium acetate, triethylamine, diisopropylethyl amine or N,N-dicyclohexylmethyl amine in a reaction medium provided by a solvent such as DMF or DMA, at a temperature ranging from about room temperature to about the reflux temperature of the solvent.

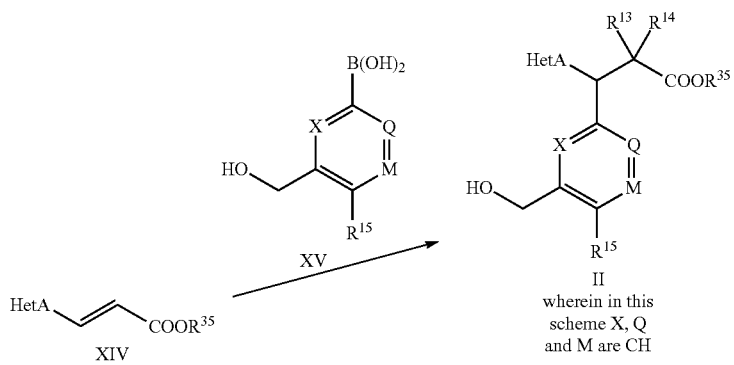

-continued

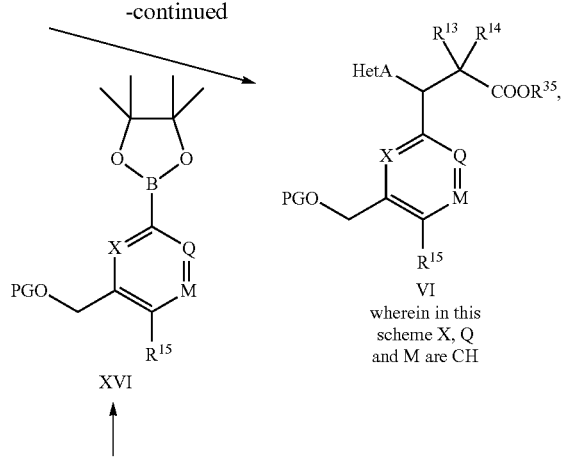

VI
wherein in this scheme X, Q and M are CH

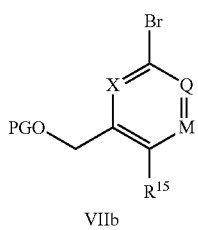

VIIb wherein in this scheme HetA is

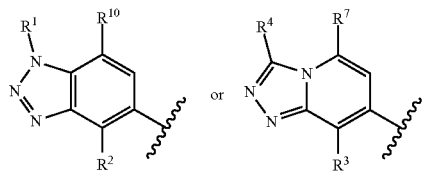

As shown in Scheme 3b, Compound XIV (made as shown in Scheme 3a) is converted into compound II, by coupling it to compound XV, using a rhodium-catalyzed conjugate addition reaction. This conjugate addition reaction is accomplished with a rhodium catalyst such as [Rh(COD)Cl]$_2$ in the presence of a base such as triethylamine, sodium carbonate, or KOH; in a reaction medium provided by a solvent such as 1,4-dioxane, water, THF, isopropanol, or mixtures thereof; at a temperature ranging from about room temperature to about the reflux temperature of the solvent. These reaction condition are herein referred to as "rhodium-catalyzed conjugate addition reaction conditions". Compound XIV is converted to compound VI by treating it with compound XVI under rhodium-catalyzed conjugate addition reaction conditions. Compound VIIb is converted to compound XVI by treating it with bis(pinacolato)diboron, a catalyst such as Pd(dppf)Cl$_2$, an additive such as KOAc in a reaction medium provided by a solvent such as DMF, DMSO, toluene, or 1,4-dioxane at a temperature ranging from about room temperature to about the reflux temperature of the solvent.

Scheme 4

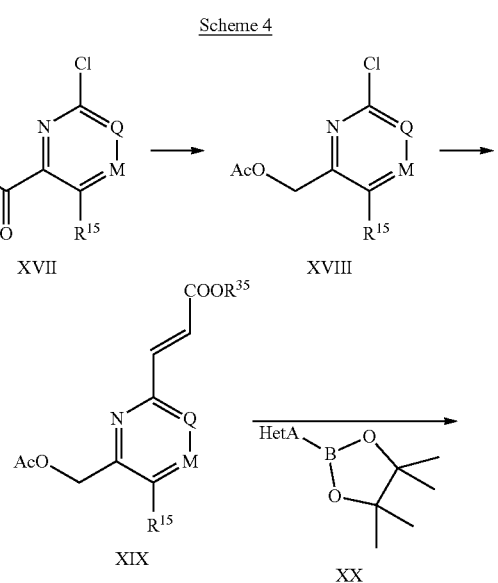

-continued

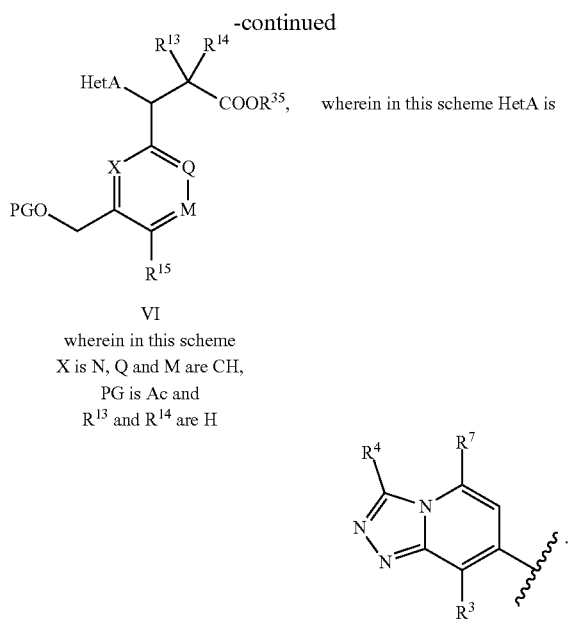

VI
wherein in this scheme
X is N, Q and M are CH,
PG is Ac and
R[13] and R[14] are H As illustrated in Scheme 4, compound XVII is converted to compound XVIII by a three-step process. In the first step, compound XVII is converted into an ester (structure not shown) using a reagent such as thionyl chloride in a reaction medium provided by a solvent such as methanol or ethanol at a temperature ranging from about 0° C. to about 50° C. In the second step, the ester group formed in step one is converted to the corresponding alcohol by reduction (structure not shown) with a reagent such as sodium borohydride in a reaction medium provided by a solvent such as THF at a temperature ranging from about 0° C. to about 30° C. In the third step, the alcohol formed in step two is converted into compound XVIII using acetyl protection conditions. Compound XVIII is converted into compound XIX under Heck reaction conditions using compound XIII, a catalyst such as Pd(OAc)$_2$, additives such as triethylamine and TBAB, in a reaction medium provided by a solvent such as DMF at a temperature of about 120° C. Compound XIX is converted to compound VI by coupling it with compound XX using rhodium-catalyzed conjugate addition reaction conditions.

Scheme 5

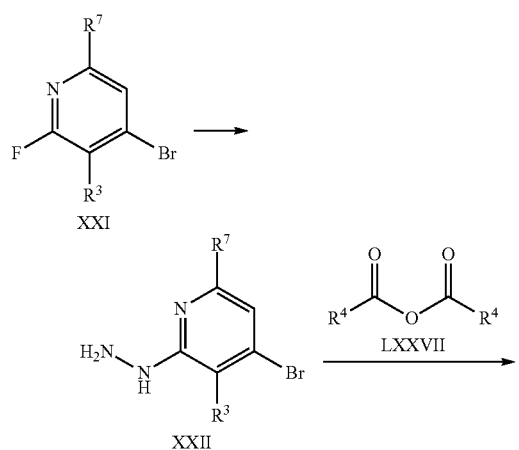

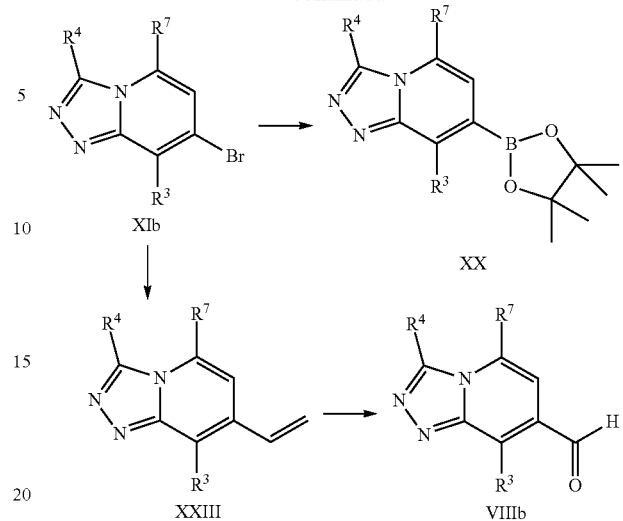

As shown in Scheme 5, compound XXI is converted to compound XXII by treatment with aqueous hydrazine at a temperature from about room temperature to about 65° C. Compound XXII is converted to compound XIb by a cyclization reaction with an acid anhydride such as LXXVII. Alternatively, compound XXII is treated with R[4]CO$_2$H (LXXVIII) in a reaction medium provided by a solvent such as propionic acid at a temperature from about room temperature to about 140° C. to provide XIb. Compound XIb is converted to compound XX by treating with bis(pinacolato)diboron, Pd(dppf)Cl$_2$, and KOAc in a reaction medium provided by a solvent such as DMF, DMSO, toluene, or 1,4-dioxane, at a temperature of about 70° C.-100° C. Compound XIb is converted to compound XXIII by treatment with potassium vinyltrifluoroborate, a palladium catalyst such as (Ph$_3$P)$_4$Pd, Pd(OAc)$_2$, Pd(dppf)Cl$_2$ or Pd(dppf)Cl$_2$OCH$_2$Cl$_2$, a base such as K$_3$PO$_4$, TEA, K$_2$CO$_3$ or NaOAc in a reaction medium provided by a solvent such as a mixture of 1,4-dioxane and water, at a temperature of about 100° C.-110° C. Compound XXIII is converted to compound VIIIb by (i) treatment with ozone in a reaction medium provided by a solvent such as dichloromethane, MeOH, or mixtures thereof, at a temperature of about −78° C. followed by the addition of triphenylphosphine or dimethylsulfide, or (ii) treatment with OsO$_4$ in a reaction medium provided by a solvent such as mixture of 1,4-dioxane and water, followed by sodium periodate or (iii) treatment with K$_2$OsO$_4$*2H$_2$O in the presence of sodium periodate in a reaction medium provided by a solvent such as mixture of 1,4-dioxane and water.

Scheme 6

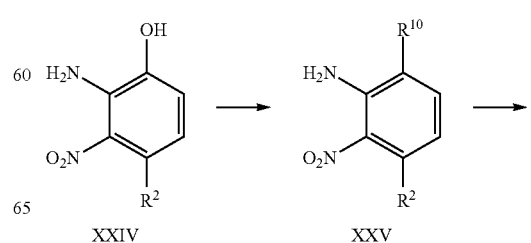

-continued

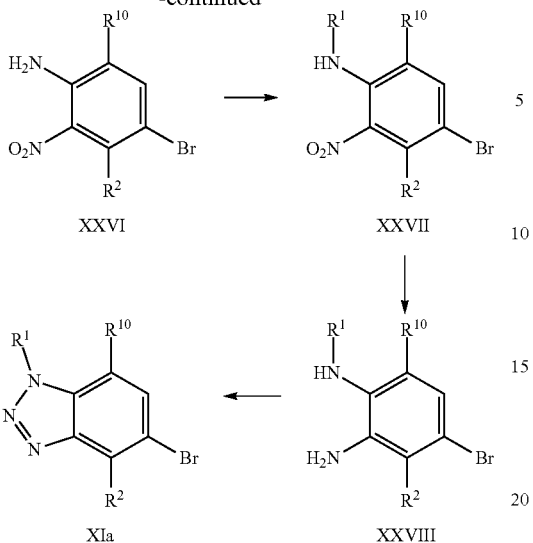

XXVI, XXVII, XXVIII, XIa

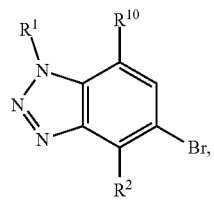

XIa wherein in this scheme
$R^1$ is $CH_3$, $CH_2CH_3$,
cyclopropyl or $CH_2$cyclopropyl,
$R^{10}$ is H and
$R^2$ is $CH_3$ As depicted in Scheme 6, compound XXIV is converted to compound XXV by treatment with $R^{36}$-LG (LXXVI), wherein $R^{36}$ is $-C_3$-$C_4$cycloalkyl or $-C_1$-$C_4$perhaloalkyl and LG is defined above, in the presence of a base such as cesium hydroxide hydrate or potassium carbonate in a reaction medium provided by a solvent such as DMSO, DMF and water or mixtures thereof at a temperature of about 150° C. Compound XXV is converted to compound XXVI by (i) a halogenation reaction with bromine in the presence of sodium acetate in a reaction medium provided by a solvent such as acetic acid or (ii) with NBS in a reaction medium provided by a solvent such as acetic acid. Compound XXVI is converted to compound XXVII by alkylation of the aniline with $R^1$-LG (LXXIX), wherein LG is a leaving group as defined above, in the presence of a base such as sodium hydride in a reaction medium provided by a solvent such as DMF. Compound XXVII is converted to compound XXVIII by a reduction of the nitro group with iron or zinc in a reaction medium provided by a solvent such as acetone, ethanol, water, acetic acid, aqueous ammonium chloride solution, or mixtures thereof, at a temperature of about 0° C. to a temperature of about room temperature. Alternatively, this reduction is accomplished by hydrogenation using a catalyst which is a finely grained solid composed mostly of nickel derived from a nickel-aluminum alloy, such as Raney nickel, in a reaction medium provided by a solvent such as ethanol under an atmosphere of hydrogen gas. Compound XXVIII is converted to compound XIa by cyclization with sodium nitrate in the presence of an acid such as aqueous sulfuric acid or aqueous HCl in a reaction medium provided by a solvent such as water, acetic acid, or methanol, or mixture thereof.

As illustrated in Scheme 7, compound XXIX is converted to compound XXV by displacement of the fluorine atom with $R^1$—$NH_2$ (LXXX); with or without a base such as triethylamine; with or without a reaction medium provided by a solvent such as ethanol or acetonitrile at a temperature ranging between about 50° C. to about 150° C. for an amount of time ranging between 4-48 hours. Compound XXV is converted to compound XIa by a three-step process which includes a bromination reaction, a nitro group reduction reaction, and a cyclization reaction. The conditions for these reactions are as described in Scheme 6 as follows: the bromination reaction conditions are as described in the conversion of XXV to XXVI, the nitro group conditions are as described in the conversion of XXVII to XXVIII and the cyclization reaction conditions are as described in the conversion of XXVIII to XIa. Alternatively, compound XXV is converted to compound XIa using a similar three-step process wherein the order of the reaction steps is a nitro group reduction reaction then a cyclization reaction, followed by a bromination reaction.

Scheme 8

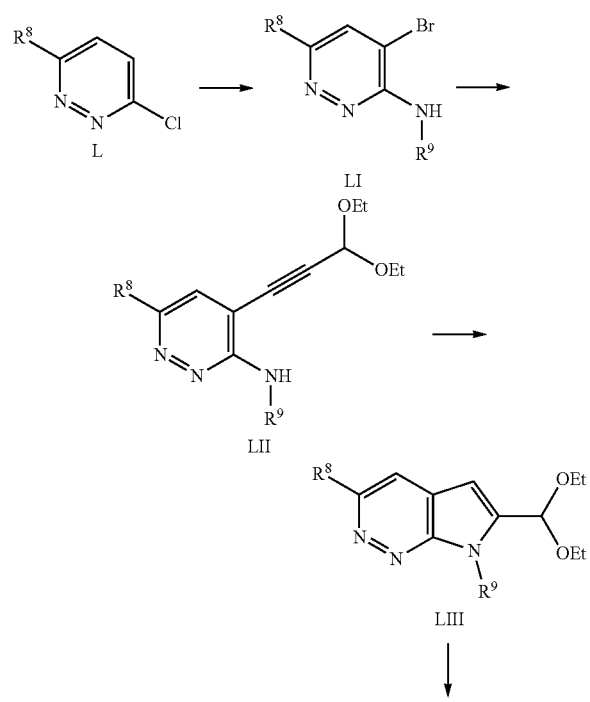

L, LI, LII, LIII

Scheme 7

XXIX, XXV

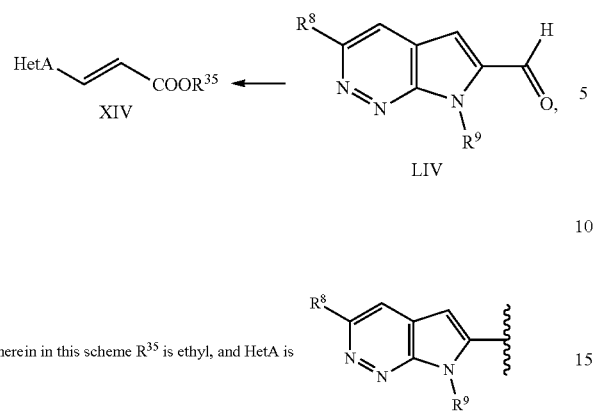

wherein in this scheme $R^{35}$ is ethyl, and HetA is

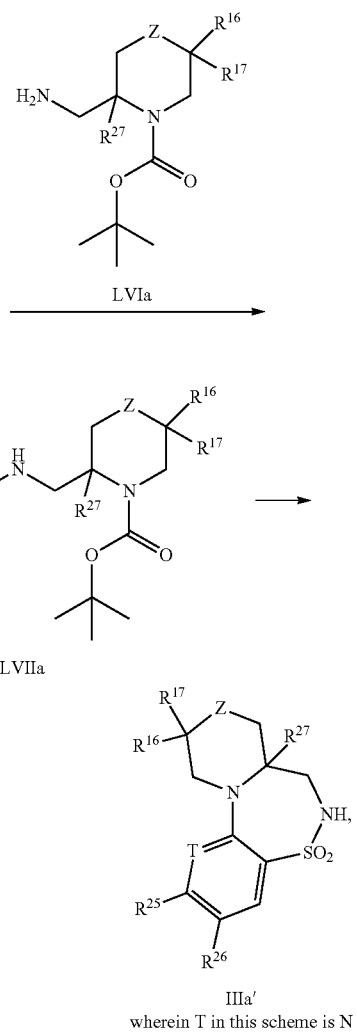

As described in Scheme 8, compound L is converted to compound LI by a two-step process. In the first step, the chlorine atom is displaced by $R^9$—$NH_2$ (LXXXI) in a reaction medium provided by a solvent such as methanol at temperature of about 110° C. In the second step, the aniline produced in the first step (structure not shown) is treated with bromine in a reaction medium provided by a solvent such as acetic acid to provide compound LI. Compound LI is converted to compound LII by coupling to 3,3-diethoxy-prop-1-yne (structure not shown) using a palladium catalyst such as $Pd(PPh_3)_2Cl_2$ in the presence of an additives such as CuI and triethylamine at a temperature of about 65° C. for about 1.5 hours. Compound LII is converted to compound LIII by treatment with a reagent such as TBAF in a reaction medium provided by a solvent such as THF at a temperature of about 65° C. Compound LIII is converted to compound LIV using an acid such as HCl in a reaction medium provided by a solvent such as 1,4-dioxane. Compound LIV is converted to compound XIV with a reagent such as ethyl 2-(diethoxyphosphoryl)acetate (structure not shown) using a base such as sodium hydride in a reaction medium provided by a solvent such as THF.

Scheme 9

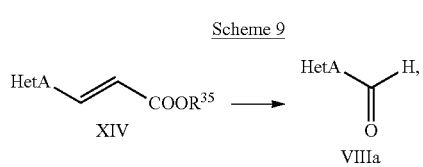

wherein in this scheme HetA is

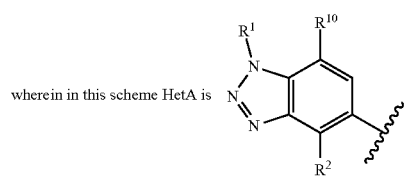

As shown in Scheme 9, compound XIV is converted to compound VIIIa by treatment with ozone in a reaction medium provided by a solvent such as dichloromethane, MeOH, or mixtures thereof, at a temperature of about −78° C. to about 15° C. followed by the addition of triphenylphosphine or dimethylsulfide.

As depicted in Scheme 10a, compound LVa is converted to compound LVIIa by coupling to an amine reagent LVIa using a base such as potassium carbonate in a reaction medium provided by mixture of solvents such as THF and water. These conditions are referred to as "sulfonamide forming reaction conditions". Compound LVIIa is converted to compounds IIIa' via a two-step process. The first step of this two-step process is removal of the tert-butyl carboxy protecting group to produce the free amine (free amine structure not shown). In this first step compound LVIIa is treated with TFA in a reaction medium provided by a solvent such as dichloromethane. These conditions are referred to as "tert-butyl carboxy protecting group removal conditions". In the second step of this two-step process, the free amine produced in step one is cyclized to IIIa' by treating with a base such as triethylamine or DIPEA at a temperature ranging from about reflux temperature of THF or toluene to about 160° C. in a reaction medium provided by a solvent such as toluene, DMSO, or THF. These conditions are referred to as "base cyclization conditions". When this reaction is conducted with compound LVIa wherein Z is N-Cbz, then the Cbz group of compound IIIa' can be removed using hydrogenolysis conditions such as $Pd(OH)_2$/C under $H_2$ in a solvent such as MeOH from a temperature ranging from about room temperature to about 50° C. These conditions are referred to as "Cbz protecting group removal conditions". The free amine that is produced from this Cbz removal can then be methylated by treatment with 37% aqueous HCHO and NaBH$_3$CN in a solvent mixture such as MeOH:DCM (2:1) at a temperature range of about room temperature to about 50° C. to provide compound IIIa' wherein Z is NMe.

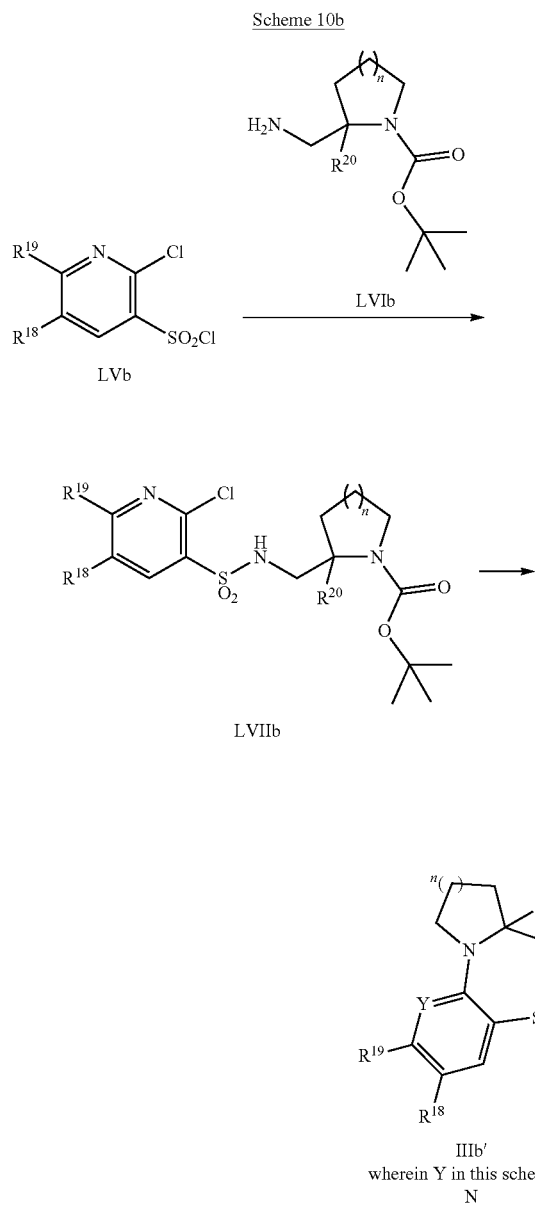

Scheme 10b

As depicted in Scheme 10b, compound LVb is converted to compound LVIIb by coupling to an amine reagent LVIb (made as shown in Scheme 11) using sulfonamide forming reaction conditions. Compound LVIIb is converted to compound IIIb via a two-step process. In this first step, compound LVIIb is subjected to tert-butyl carboxy protecting group removal conditions. In the second step of this two-step process, the free amine produced in step one is cyclized to IIIb' using base cyclization conditions.

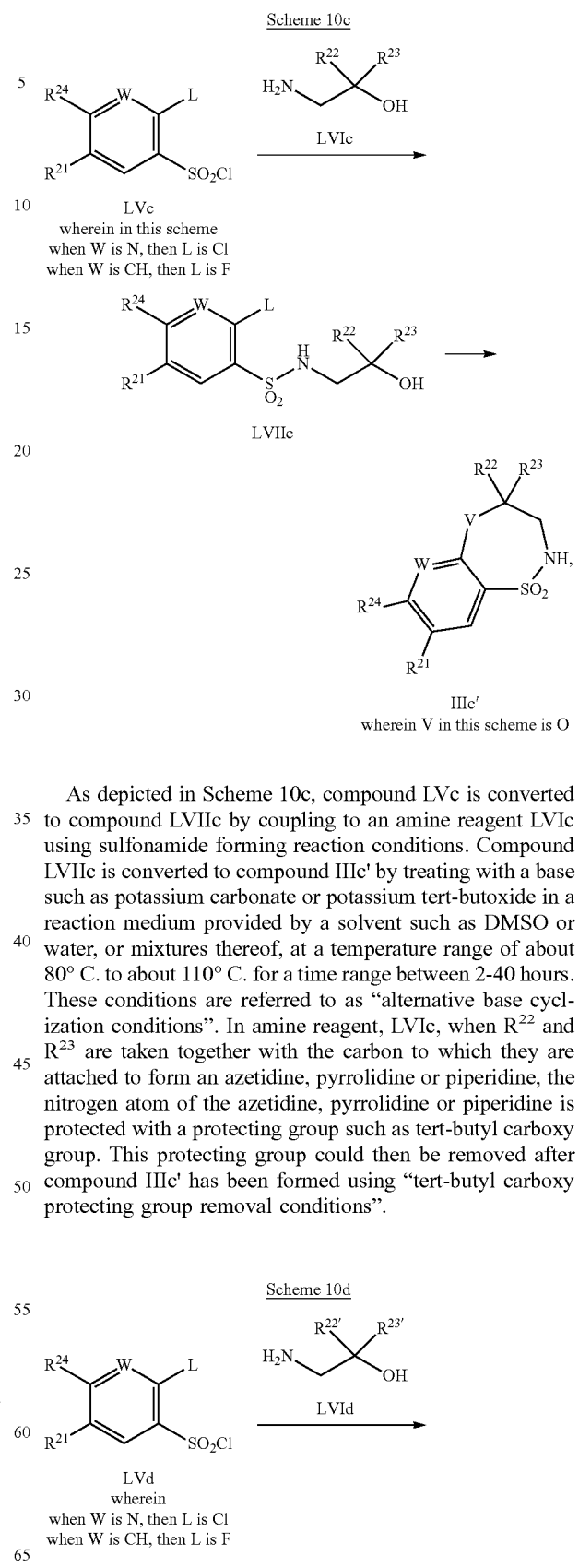

As depicted in Scheme 10c, compound LVc is converted to compound LVIIc by coupling to an amine reagent LVIc using sulfonamide forming reaction conditions. Compound LVIIc is converted to compound IIIc' by treating with a base such as potassium carbonate or potassium tert-butoxide in a reaction medium provided by a solvent such as DMSO or water, or mixtures thereof, at a temperature range of about 80° C. to about 110° C. for a time range between 2-40 hours. These conditions are referred to as "alternative base cyclization conditions". In amine reagent, LVIc, when $R^{22}$ and $R^{23}$ are taken together with the carbon to which they are attached to form an azetidine, pyrrolidine or piperidine, the nitrogen atom of the azetidine, pyrrolidine or piperidine is protected with a protecting group such as tert-butyl carboxy group. This protecting group could then be removed after compound IIIc' has been formed using "tert-butyl carboxy protecting group removal conditions".

-continued

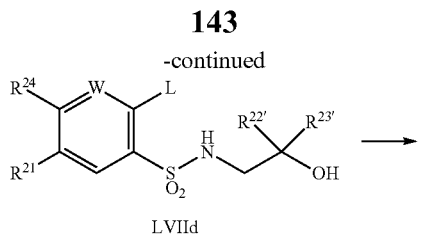

LVIId

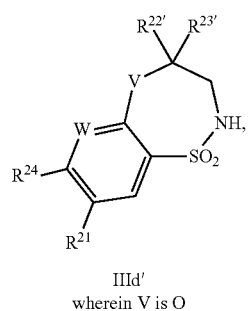

IIId'
wherein V is O

As depicted in Scheme 10d, compound LVd is converted to compound LVIId by coupling to an amine reagent LVId using sulfonamide forming reaction conditions. Compound LVII is converted to compound III' using alternative base cyclization conditions.

Scheme 10e

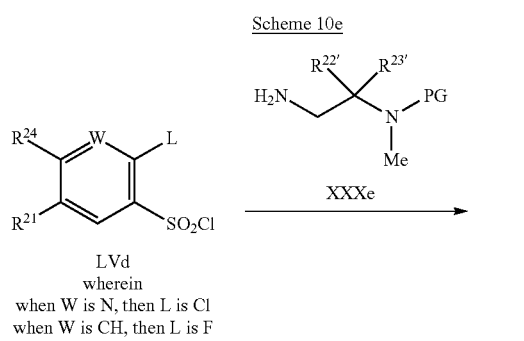

LVd
wherein
when W is N, then L is Cl
when W is CH, then L is F

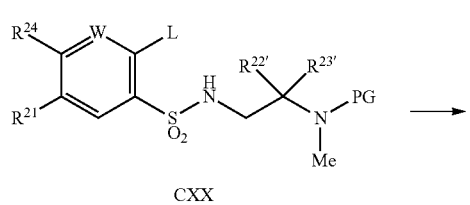

CXX

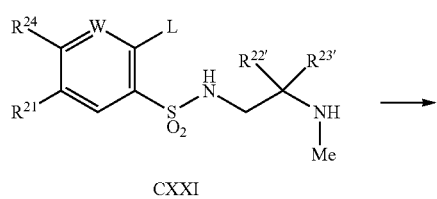

CXXI

-continued

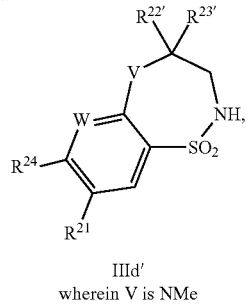

IIId'
wherein V is NMe

As depicted in Scheme 10e, compound LVd is converted to compound CXX by coupling to an amine reagent XXXe using sulfonamide forming reaction conditions. Compound CXX is converted to compound CXXI by removal of the protecting group (PG) using Cbz protecting group removal conditions when PG is Cbz. Compound CXXI is converted to compound III'd using alternative base cyclization conditions.

Scheme 11

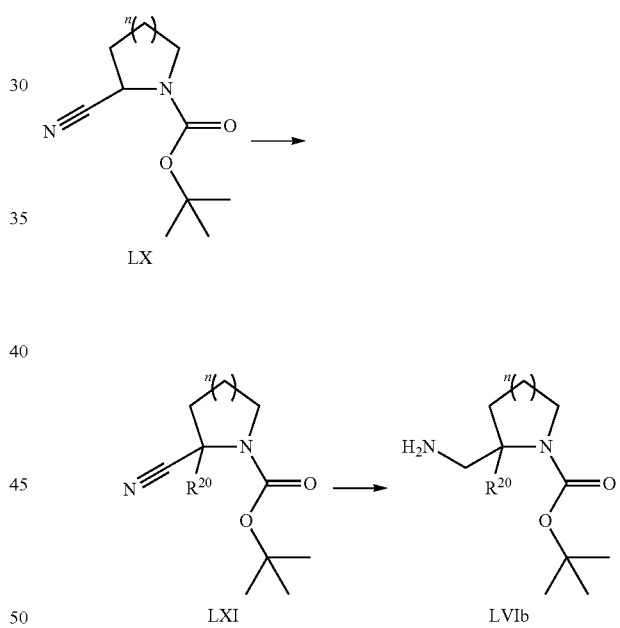

As described in Scheme 11, compound LX is converted to compound LXI by treating compound LX with a base such as LDA in a reaction medium provided by a solvent such as THF, ether, hexanes, toluene, and mixtures thereof and then adding an alkyl halide reagent $R^{20}$-LG (LXXXII). Compound LXI is converted to compound LVIb using a catalyst which is a finely grained solid composed mostly of nickel derived from a nickel-aluminum alloy, such as Raney nickel, in a reaction medium provided by a solvent mixture such as methanol and aqueous ammonia, under a hydrogen atmosphere.

Scheme 12a

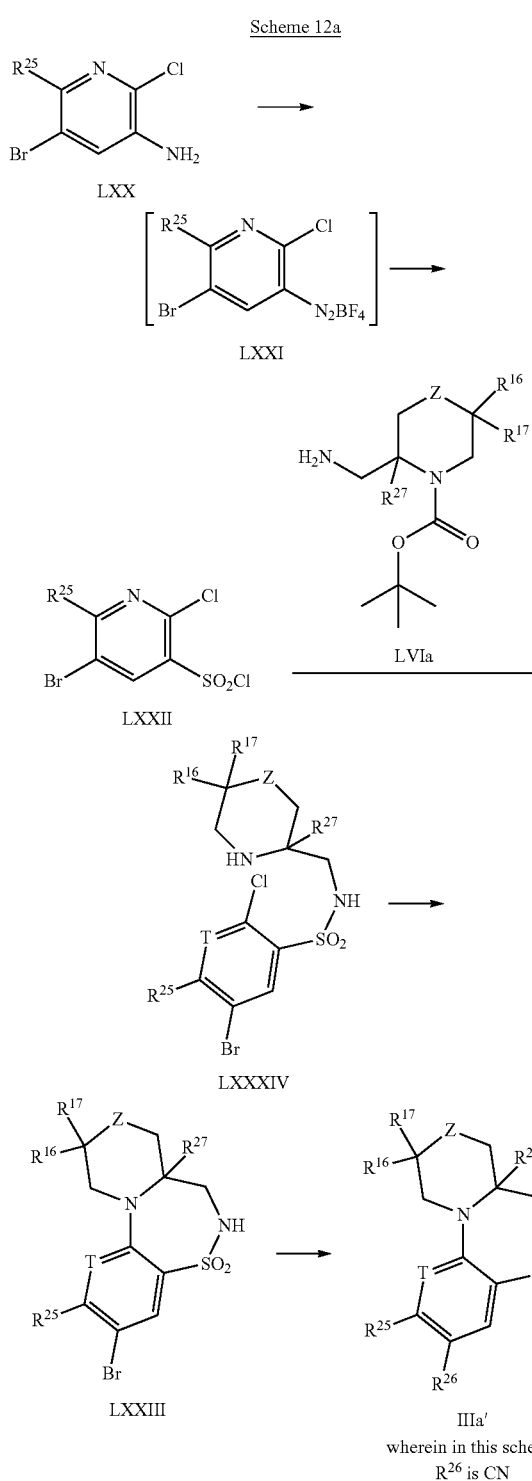

As shown in Scheme 12a, compound LXX is converted to compound LXXI by treating with $HBF_4$ and tert-butyl nitrite in a reaction medium provided by a solvent such as acetonitrile at a temperature of about 0° C. Compound LXXI, shown in brackets above, is not isolated, and is converted to compound LXXII by adding the reaction solution containing LXXI to a separate solution of CuCl in a reaction medium provided by a solvent such as acetic acid which is saturated by bubbling with $SO_2$ gas. Compound LXXII is converted to compound LXXXIV using a two-step process wherein compound LXXII is coupled with compound LVIa using sulfonamide forming reaction conditions. This product is then subjected to tert-butyl carboxy protecting group removal conditions to provide compound LXXXIV. Compound LXXXIV is converted to compound LXXIII using base catalyzed cyclization condition or alternative base catalyzed cyclization condition. Compound LXXIII is converted to compounds IIIa', wherein $R^{26}$ is —CN, by a palladium-catalyzed cyanation reaction. This cyanation reaction is achieved by using a palladium catalyst such as $Pd(dppf)Cl_2$ or $Pd_2(dba)_3$, using zinc cyanide, zinc as an additive, and with or without X-Phos added, in a reaction medium provided by a solvent such as DMF or DMA, at a temperature of about 110° C. to about 140° C. for a time range of 3-16 hours. These conditions are referred to as "palladium-catalyzed cyanation reaction conditions".

Scheme 12b

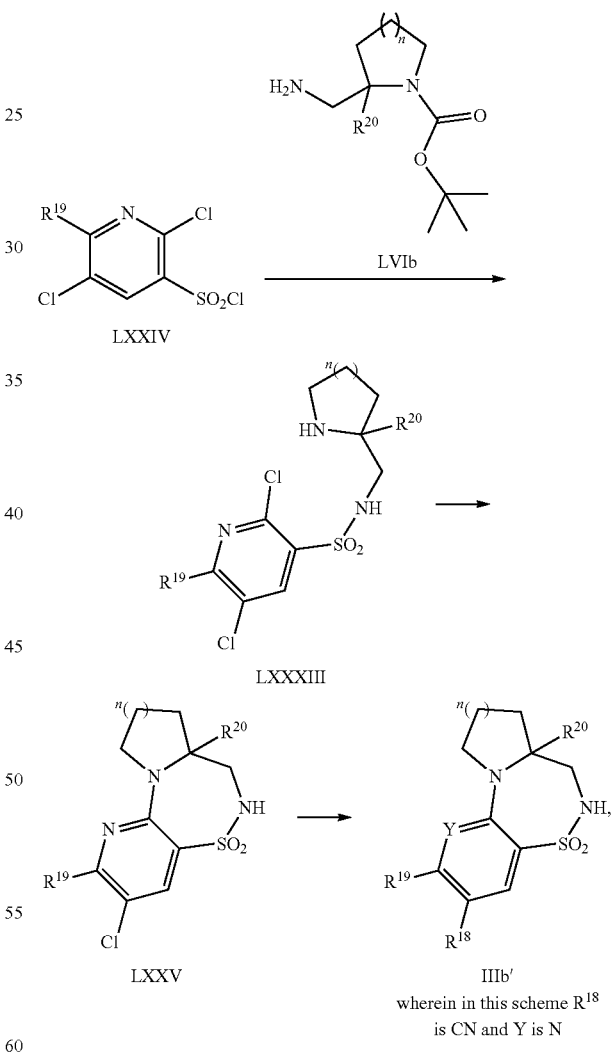

As shown in Scheme 12b, compound LXXIV is converted to compound LXXXIII using a two-step process wherein compound LXXIV is coupled with compound LVIb (made as shown in Scheme 11) using sulfonamide forming reaction conditions. This product is then subjected to tert-butyl carboxy protecting group removal conditions to provide compound LXXXIII. Compound LXXXIII is converted to compound LXXV using base catalyzed cyclization condition or alternative base catalyzed cyclization condition. Compound LXXV is converted to compound IIIb', wherein $R^{18}$ is —CN, using palladium-catalyzed cyanation reaction conditions.

Scheme 13

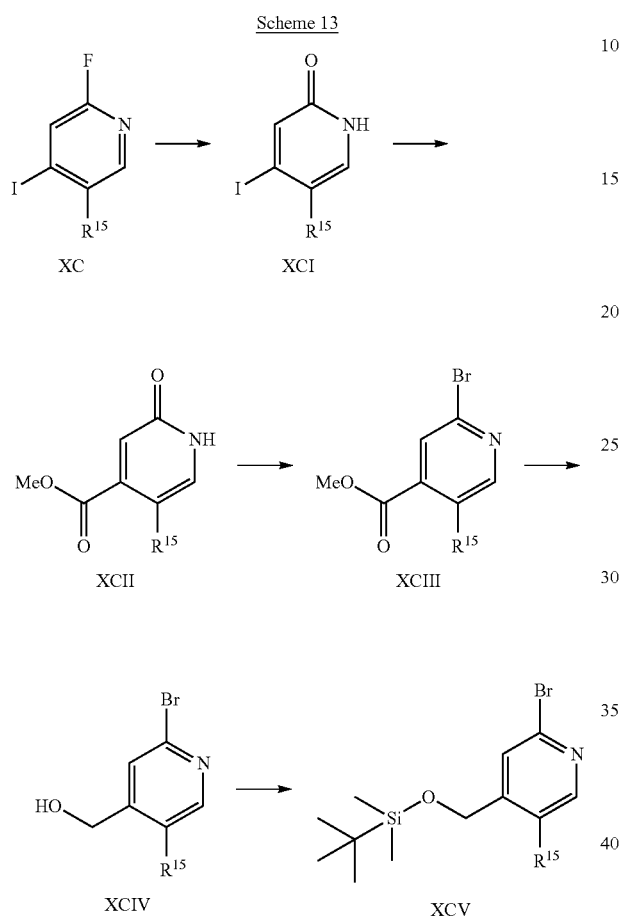

As shown in Scheme 13, compound XC is converted to compound XCI by subjecting it to acidic hydrolysis conditions such as aqueous HCl in a reaction medium provided by solvents such as water, dioxane, THF or mixtures thereof at a temperature range from about room temperature to about reflux temperature of the solvent. Compound XCI is converted to compound XCII under carbonylation conditions, employing a catalyst such as Pd(OAc)$_2$, an additive such as dccp.2HBF$_4$ in the presence of a base such as K$_2$CO$_3$ in a reaction medium provided by a solvent such as MeOH at a temperature range from about room temperature to about reflux temperature of the solvent under an atmosphere of CO at a pressure range of about 15 psi to about 50 psi. Compound XCII is converted to XCIII by treating it with POBr$_3$ in a reaction medium provided by a solvent such as toluene at a temperature range from about room temperature to about reflux temperature of the solvent. Compound XCIII is converted to compound XCIV by reduction with a reagent such as sodium borohydride in a reaction medium provided by a solvent such as THF at a temperature ranging from about 0° C. to about 30° C. Compound XCIV is converted to compound XCV by subjecting it to TBS protecting group conditions.

Scheme 14

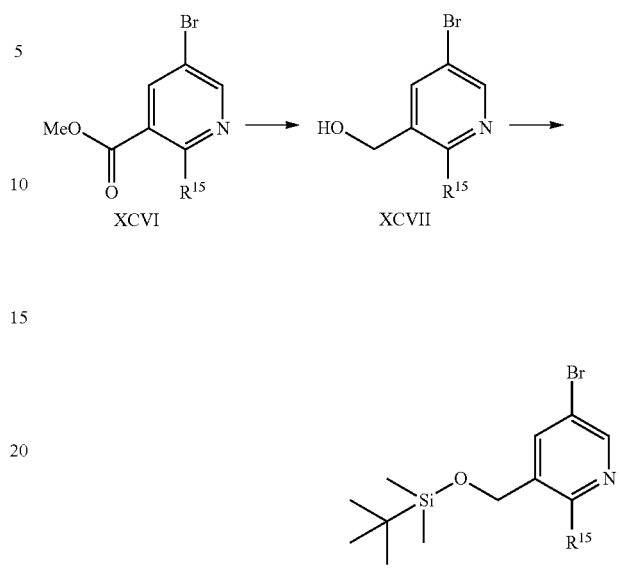

As shown in Scheme 14, compound XCVI is converted to compound XCVII by reduction with a reagent such as sodium borohydride in a reaction medium provided by a solvent such as THF at a temperature ranging from about 0° C. to about 30° C. Compound XCVII is converted to compound XCVIII subjecting XCVII to TBS protecting group conditions.

Scheme 15

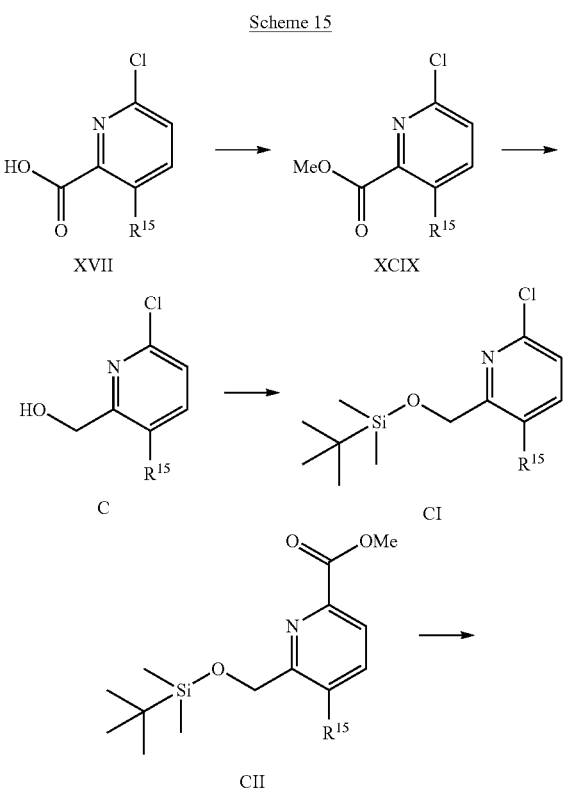

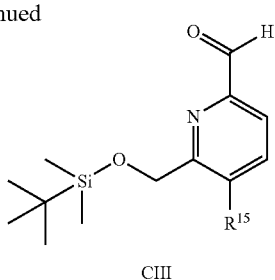

CIII

As shown in Scheme 15, compound XVII is converted to compound XCIX using thionyl chloride in a reaction medium provided by a solvent such as methanol at a temperature ranging from about 0° C. to about 50° C. XCIX is converted to compound C by reduction with a reagent such as sodium borohydride in a reaction medium provided by a solvent such as THF at a temperature ranging from about 0° C. to about 30° C. Compound C is converted to compound CI by subjecting C to TBS protecting group conditions. Compound CI is converted to compound CII under carbonylation conditions, employing a catalyst such as Pd(dppf)$_2$Cl$_2$ in the presence of a base such as TEA in a reaction medium provided by solvents such as MeOH, DMF or mixtures thereof at a temperature range from about room temperature to about 100° C. under an atmosphere of CO at a pressure range of about 15 psi to about 50 psi. Compound CII is converted to CIII by treating with DIBAL-H in a reaction medium provided by a solvent such as dichloromethane at a temperature ranging from about −78° C. to about −50° C.

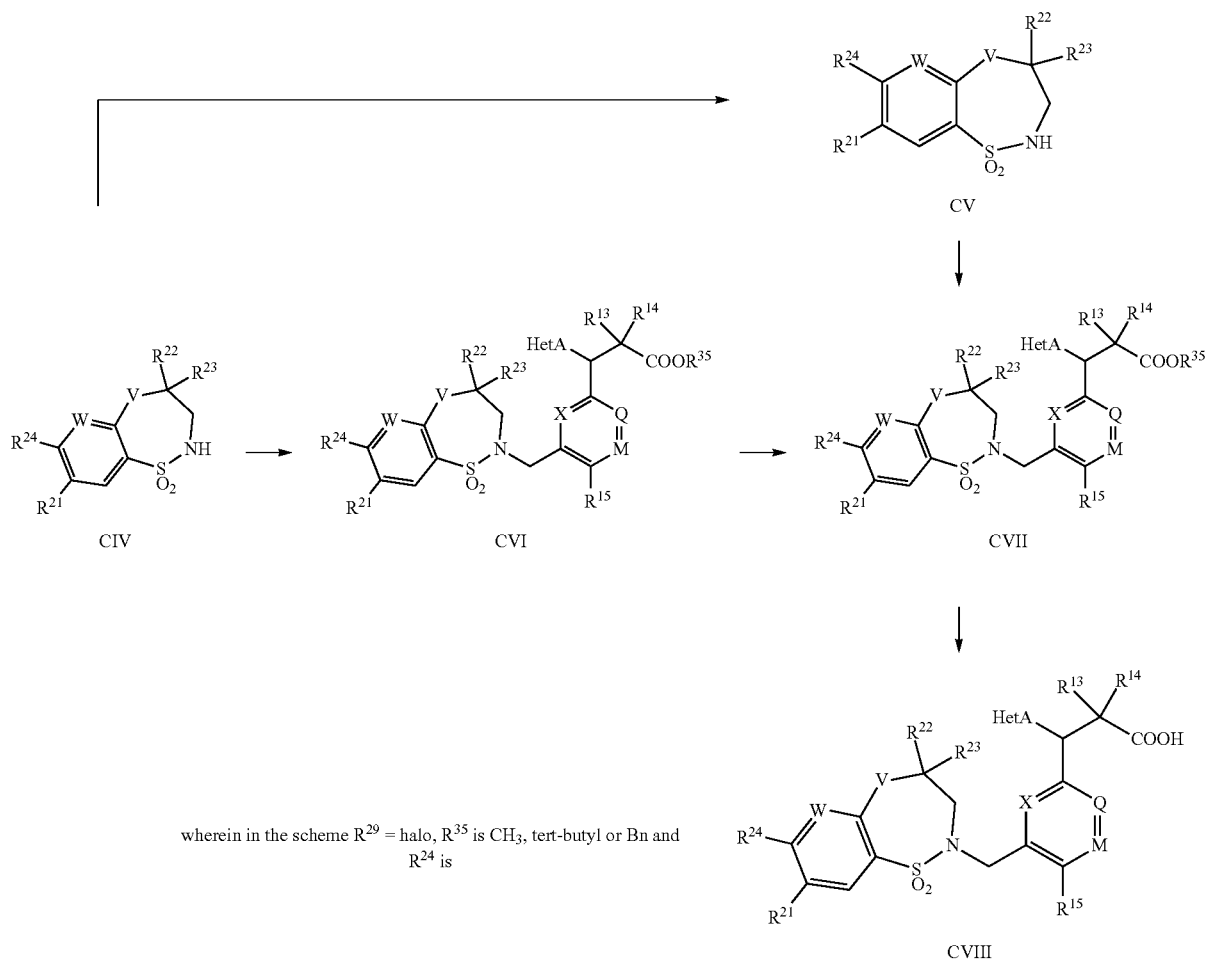

wherein in the scheme $R^{29}$ = halo, $R^{35}$ is CH$_3$, tert-butyl or Bn and $R^{24}$ is

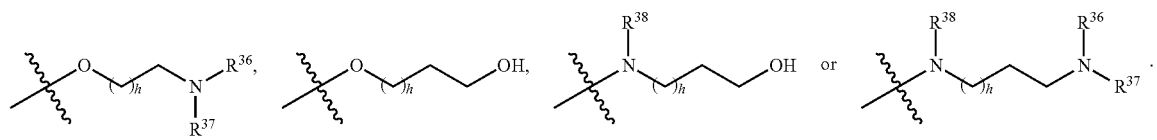

-continued

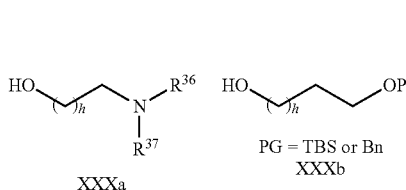

XXXa

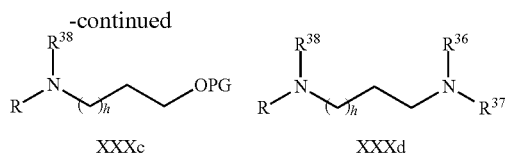

PG = TBS or Bn
XXXb

XXXc

XXXd

As shown in Scheme 16, compound CVIII is prepared from compound CIV through several different pathways depending on the conditions used and on the choice of the $R^{24}$ substituent. For example, compound CIV is converted to compound CV through a two-step reaction. In the first step, compound XXXa or XXXb is treated with tBuOK or NaH in a reaction medium provided by a solvent such as t-butanol when using tBuOK or THF when using NaH. The product from this first step is then added to a solution of compound CIV in a in a reaction medium provided by solvent such as DMSO at a temperature ranging from about room temperature to about 100° C. Alternatively, compound CIV is converted to compound CV through a different two-step process. In the first step, compound XXXa or XXXb is treated with tBuOK or NaH in a reaction medium provided by a solvent such as t-butanol when using tBuOK or THF when using NaH. The product from this first step is then added to a solution of compound CIV in a solvent medium such as toluene under palladium catalysis conditions using reagents such as NaH, $Pd_2dba_3$, racemic 2-(di-t-butylphosphino)-1,1'-binaphthyl, at a temperature ranging from about room temperature to about reflux temperature of solvent. Alternatively, compound CIV is converted to compound CV by treating compound CIV with compound XXXc or XXXd in a reaction medium provided by a solvent such as DMSO at a temperature ranging from about room temperature to about 100° C. Compound CV is converted to compound CVII by coupling it with compound II under Mitsunobu reaction conditions. Alternatively, compound CV is converted to compound CVII by coupling with compound V in an alkylation reaction. This alkylation reaction is performed by treating compound CV with a base such as sodium hydride, potassium tert-butoxide or $K_2CO_3$, in a reaction medium provided by solvents such as THF, DMF, $CH_3CN$ or mixtures thereof. Compound V is then added to this mixture to provide compound CVII. These conditions are referred to as "alkylation reaction conditions". Compound CIV is converted to compound CVI by coupling it with II under Mitsunobu reaction conditions. Alternatively, compound CIV is converted to compound CVI by coupling with compound V under alkylation reaction conditions. Compound CVI is converted to CVII using conditions described above for conversion of compound CIV to compound CV. Compound CVII is converted to compound CVIII under basic hydrolysis reaction conditions. Alternatively, the hydrolysis is also performed under acidic conditions using TFA in a reaction medium provided by solvent such as DCM at a temperature range from about room temperature to about the reflux temperature of the solvent. These conditions are referred to as "acidic hydrolysis conditions". In instances where the $R^{35}$ is Bn, hydrogenation conditions are employed for removal of the benzyl group such as transfer hydrogenation conditions using Pd/C as the catalyst and cyclohexadiene in a reaction medium provided by a solvent such as ethanol at a temperature range of about room temperature to about reflux temperature of the solvent. Alternatively, the benzyl group is removed using 10% $Pd(OH)_2/C$ or 10% Pd/C in a reaction medium such as methanol as the solvent at a temperature range of about room temperature to about 50° C. under an atmosphere of $H^2$ gas wherein the reaction may be conducted in a conventional reaction flask or using a continuous flow hydrogenation reactor. The above conditions to remove a benzyl group are referred to as "benzyl deprotection conditions". When compounds XXXb and XXXc are used, the protecting group, PG, is removed using TBS deprotection conditions when PG is TBS or benzyl protecting group conditions when PG is benzyl.

Scheme 17

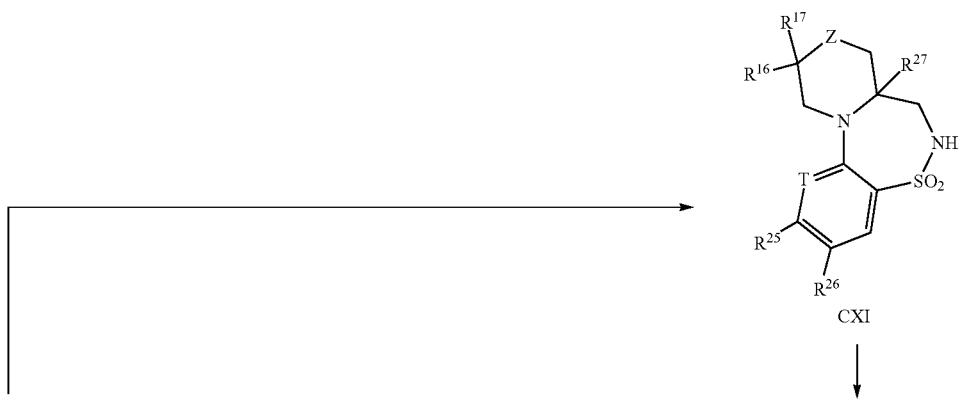

CXI

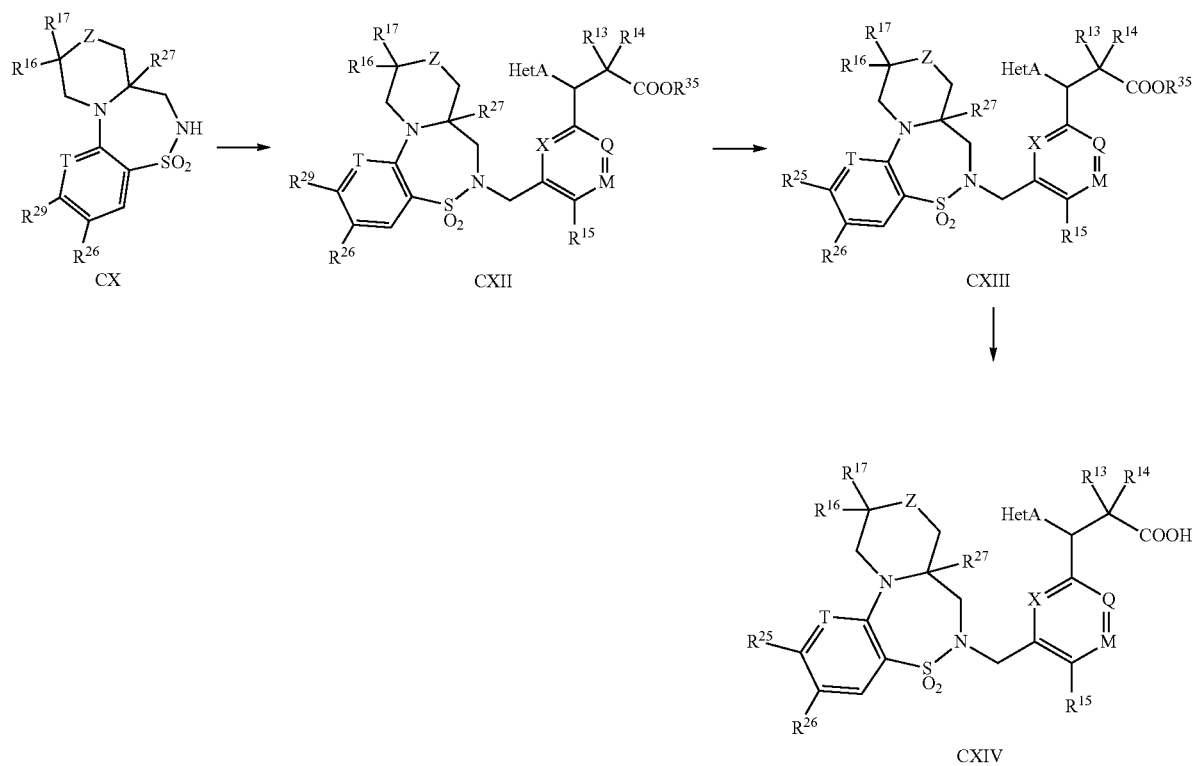
wherein in the scheme $R^{29}$ = halo, $R^{35}$ is $CH_3$, tert-butyl or Bn and $R^{25}$ is
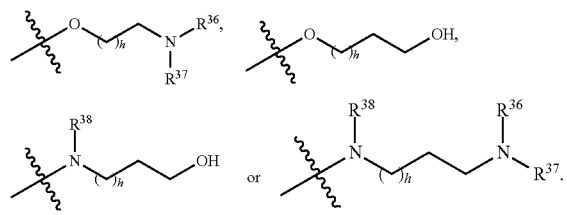
Scheme 18
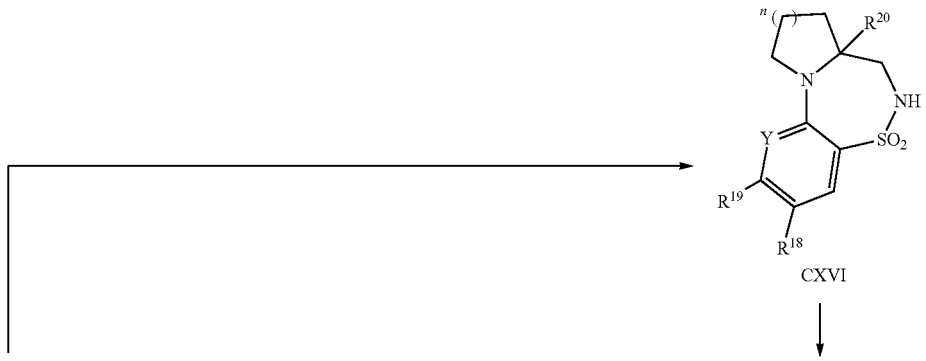

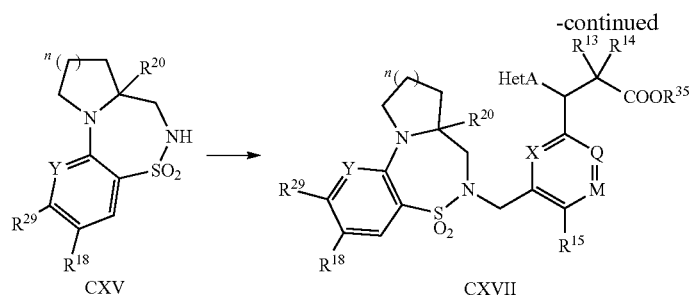
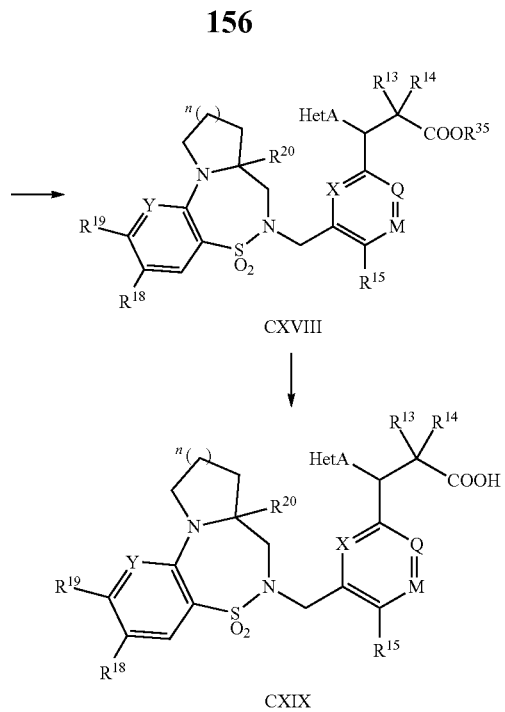
wherein in the scheme $R^{29}$ = halo, $R^{35}$ is $CH_3$, tert-butyl or Bn and $R^{18}$ is
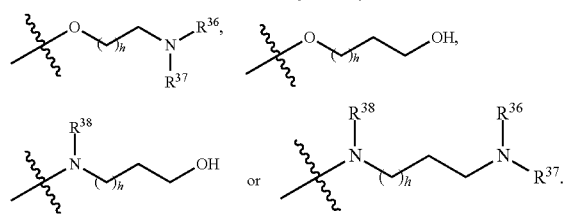
Scheme 19
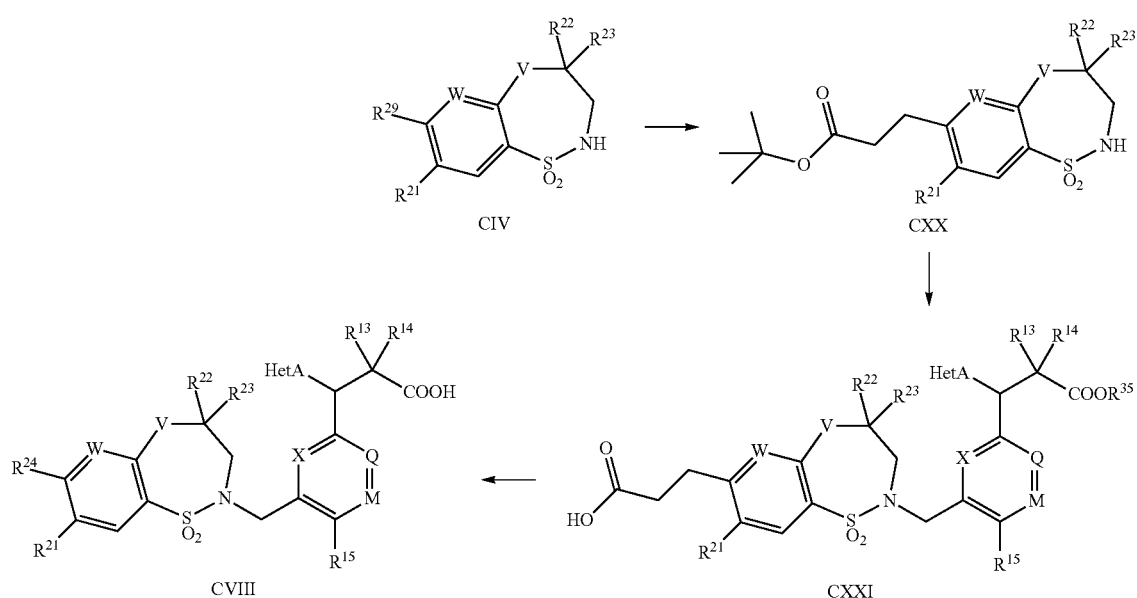

where in the scheme $R^{29}$ = halo, $R^{35}$ is $CH_3$ or Bn and $R^{24}$ is:

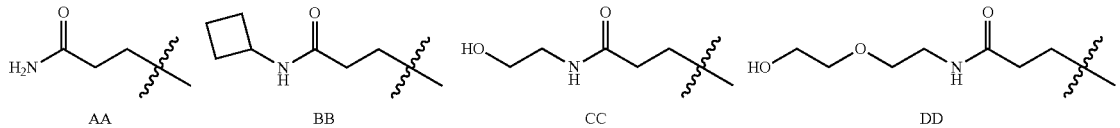

AA  BB  CC  DD

As shown in Scheme 19, compound CVIII is prepared from compound CIV by a pathway that proceeds through key intermediates CXX and CXXI. Compound CIV is transformed into compound CXX by a two-step sequence. In the first step, using Heck reaction conditions, compound CIV where $R^{29}$ is halo is converted to compound CIV where $R^{29}$ is $(CH_3)_3(C)C(O)CH=CH$ (structure not shown), using tert-butyl acrylate, a catalyst such as palladium acetate, additives such as triethylamine and 2-(di-tert-butylphosphino)biphenyl, in a reaction medium provided by a solvent such as DMF at a temperature of about 120° C. In the second step, compound CIV where $R^{29}$ is $(CH_3)_3(C)C(O)CH=CH-$ is reduced to compound CIV where $R^{29}$ is $(CH_3)_3(C)C(O)CH_2CH_2$ (Compound CXX) under an atmosphere of hydrogen gas, at a pressure of about 50 psi, using a catalyst such as palladium on carbon, in a reaction medium provided by a solvent such as methanol at a temperature of about room temperature. Compound CXX is transformed into compound CXXI by a two-step sequence. In the first step, compound CXX and compound II (shown in Scheme 1) are coupled under Mitsunobu reaction conditions as described above in Scheme 1. In the second step, the tert-butyl carboxy protecting group is removed under reaction conditions described above in Scheme 10a. Compound CXXI is transformed into compound CVIII by either a two-step reaction sequence or a three-step reaction sequence depending on the $R^{24}$ substituent. If the $R^{24}$ substituent contains a primary amide (substituent AA), a secondary cyclobutyl-substituted amide (substituent BB), or an ethanolamine amide group (substituent CC), then the two-step reaction sequence is used. In the first step of the two-step reaction sequence, an amide bond is formed with the appropriate amine in the presence of additives such as HATU and DIPEA in a reaction medium provided by a solvent such as DMF at a temperature of about room temperature. In the second step of the two-step reaction sequence, the $R^{35}$ acid protective group is removed under basic hydrolysis conditions ($R^{35}$=methyl) or under hydrogenation conditions ($R^{35}$=Bn) as described in Scheme 16. In the instance where the $R^{24}$ substituent is the N-(2-(2-aminoethoxy)ethyl)propionamide group (substituent DD), the three-step reaction sequence is followed. This three-step reaction sequence consists of the above two-step reaction sequence followed by the addition of a third step wherein the terminal $NH_2$ of substituent DD is deprotected. The deprotection of the Boc group under the tert-butyl carboxy protecting group removal conditions described in Scheme 10a.

The following examples are provided to further illustrate aspects of the invention and various preferred embodiments.

In obtaining the compounds described in the examples below and the corresponding analytical data, the following experimental and analytical protocols were followed unless otherwise indicated.

Reaction mixtures were magnetically stirred at room temperature. Where solutions are characterized as "dried," they were generally dried over a drying agent such as $Na_2SO_4$ or $MgSO_4$. Where mixtures, solutions, and extracts were "concentrated", they were typically concentrated on a rotary evaporator under reduced pressure.

Thin-layer chromatography was performed using Merck silica gel 60 F254 2.5 cm×7.5 cm, 250 μm or 5.0 cm×10.0 cm, 250 μm pre-coated silica gel plates.

Normal-phase flash column chromatography was performed on silica gel ($SiO_2$) eluting with 2 M $NH_3$ in MeOH/$CH_2Cl_2$, unless otherwise noted.

Mass spectra (MS) were obtained on an Agilent series 1100 MSD using electrospray ionization (ESI) in positive mode unless otherwise indicated. Calculated (calcd.) mass corresponds to the exact mass.

High Performance Liquid Chromatography was performed as described for the individual compounds. Compound purification was made in some cases by acidic HPLC that entailed purification on a reverse phase HPLC system using different mobile phases that started initially with a mobile phase of 5% ACN in $H_2O$ (both with 0.05% TFA) that was held for 1 min, then changed to a gradient of 5-99% ACN over 6 min, which was held at 99% ACN for 3 min, with a flow rate of 80 mL/min. The following endcapped columns were used: Waters Xbridge Prep OBD $C_{18}$ (pore size 130 Å, surface area 185 $m^2/g$, carbon load of 18%), Phenomenex Luna C18, (pore size 100 Å, surface area 440 $m^2/g$, carbon load of 19%), Phenomenex Synergi-Max $C_{18}$ (pore size 100 Å, surface area 475 $m^2/g$, carbon load of 11-19%), SunFire Prep $C_{18}$ OBD (pore size 100 Å, surface area 340 $m^2/g$, carbon load of 16%), and Phenomenex Gemini (pore size 110 Å, surface area 375 $m^2/g$, carbon load of 14%).

SFC was performed as described for individual compounds using the following stationary phase columns Chiralpak AD-H, Chiralpak IG, Chiralpak IC, Chiralpak AS-H, Chiralcel OJ-H, Chiralcel OZ-H, Phenomenex cellulose-2, Whelk O1 (S,S). The mobile phases used are described in the individual experimental write ups and usually consisted of varying amounts of $CO_2$ and alcoholic solvents such as methanol, ethanol, isopropanol, EtOH/$H_2O$ containing 0.1% $NH_3$.

Nuclear magnetic resonance (NMR) spectra were obtained on Bruker model DRX spectrometers. The format of the $^1H$ NMR data below is: chemical shift in ppm downfield of the tetramethylsilane reference or to residual protium in the solvent (multiplicity, coupling constant J in Hz, integration).

Chemical names were generated by either using ChemDraw (CambridgeSoft, Cambridge, Mass.) or ACD/ Name Version 9 (Advanced Chemistry Development, Toronto, Ontario, Canada).

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

Whenever a yield is given as a percentage, such yield refers to a mass of the entity for which the yield is given with respect to the maximum amount of the same entity that could be obtained under the particular stoichiometric conditions. Reagent concentrations that are given as percentages refer to mass ratios, unless indicated differently.

Intermediate 1: 7,7a,8,9,10,11-Hexahydro-6H-dipyrido[2,1-d:2',3'-f][1,2,5]thiadiazepine 5,5-dioxide

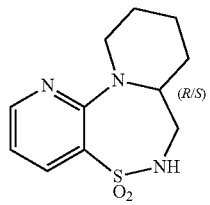 [SMILES: O=S1(=O)NCC2CCCCN2c2ncccc21]

Step A: tert-Butyl 2-((2-chloropyridine-3-sulfonamido)methyl)piperidine-1-carboxylate. $K_2CO_3$ (22.6 g, 163 mmol) was added to a mixture of tert-butyl 2-(aminomethyl)piperidine-1-carboxylate (50.08 g, 233.7 mmol), in THF (525 mL) and $H_2O$ (105 mL). 2-Chloropyridine-3-sulfonyl chloride (33.0 g, 156 mmol) was then added and the mixture was stirred at room temperature for 6.5 hours. The mixture was concentrated to dryness under reduced pressure and partitioned between ethyl acetate and water. The aqueous layer was extracted with ethyl acetate. These extractions resulted in several organic solvent fractions which were combined, dried over anhydrous $MgSO_4$, filtered and concentrated to dryness under reduced pressure and purified by flash column chromatography (eluent: hexanes/ethyl acetate, 1:0 to 1:1, gradient elution) to afford the title compound (60 g, 99%) as a white solid. MS (ESI): mass calcd. for $C_{16}H_{24}ClN_3O_4S$, 389.1; m/z found, 290.1 [M-BOC+H]$^+$. $^1$H NMR (400 MHz, CDCl$_3$) δ 8.57 (dd, J=4.8, 1.9 Hz, 1H), 8.40 (dd, J=7.8, 1.9 Hz, 1H), 7.44 (dd, J=7.8, 4.8 Hz, 1H), 5.73 (s, 1H), 4.38 (dt, J=10.2, 5.5 Hz, 1H), 3.93 (d, J=14.2 Hz, 1H), 3.34 (s, 1H), 2.93 (dt, J=12.3, 5.1 Hz, 1H), 2.74-2.69 (m, 1H), 2.05 (s, 1H), 1.62-1.52 (m, 3H), 1.48 (s, 9H), 1.39 (tdd, J=10.1, 4.8, 2.5 Hz, 2H).

Step B: 7,7a,8,9,10,11-Hexahydro-6H-dipyrido[2,1-d:2',3'-f][1,2,5]thiadiazepine 5,5-dioxide. A solution of 20% TFA in DCM (165 mL, 2.15 mol) was added to tert-butyl 2-((2-chloropyridine-3-sulfonamido)methyl)piperidine-1-carboxylate (55.0 g, 141 mmol). The resulting mixture was stirred for 2.5 hours at room temperature, concentrated to dryness under reduced pressure and re-dissolved in toluene (645 mL). TEA (119.1 mL, 857.2 mmol) was added and the resulting mixture was heated to reflux for 15 hours, cooled to room temperature, and concentrated to dryness under reduced pressure. The residue was purified by flash column chromatography (eluent: hexanes/ethyl acetate, 1:0 to 0:1, gradient elution)) to afford the title compound (31 g, 82% (95% purity)). MS (ESI): mass calcd. for $C_{11}H_{15}N_3O_2S$, 253.1; m/z found, 254.2 [M+H]$^+$. $^1$H NMR (500 MHz, CDCl$_3$) δ 8.24 (dd, J=4.7, 1.9 Hz, 1H), 7.92 (dd, J=7.8, 1.8 Hz, 1H), 6.77 (dd, J=7.8, 4.6 Hz, 1H), 5.30 (s, 1H), 4.36-4.20 (m, 2H), 3.49 (t, J=12.7 Hz, 1H), 3.44-3.31 (m, 2H), 1.84-1.74 (m, 3H), 1.71-1.55 (m, 3H).

Intermediate 2: (*S)-7,7a,8,9,10,11-Hexahydro-6H-dipyrido[2,1-d:2',3'-f][1,2,5]thiadiazepine 5,5-dioxide

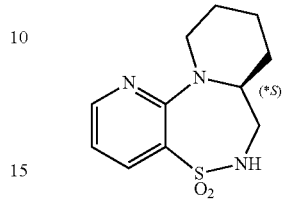

The racemic mixture of 7,7a,8,9,10,11-hexahydro-6H-dipyrido[2,1-d:2',3'-f][1,2,5]thiadiazepine 5,5-dioxide enantiomers (Intermediate 1, 31 g) was separated by chiral SFC (stationary phase: Chiralpak AD-H 5 μm 250×30 mm, Mobile phase: 70% $CO_2$, 30% MeOH) to afford two enantiomers. The first eluting isomer (14.6 g) was designated (*S). MS (ESI): mass calcd. for $C_{11}H_{15}N_3O_2S$, 253.1; m/z found, 254.2 [M+H]$^+$. $^1$H NMR (500 MHz, CDCl$_3$) δ 8.25 (dd, J=4.6, 1.8 Hz, 1H), 7.93 (dd, J=7.8, 1.8 Hz, 1H), 6.77 (dd, J=7.8, 4.6 Hz, 1H), 5.24 (t, J=6.0 Hz, 1H), 4.37-4.28 (m, 1H), 4.24 (dt, J=13.3, 4.9 Hz, 1H), 3.50 (ddd, J=13.4, 11.9, 6.4 Hz, 1H), 3.47-3.32 (m, 2H), 1.87-1.75 (m, 3H), 1.72-1.56 (m, 3H).

Intermediate 3: (*R)-7,7a,8,9,10,11-Hexahydro-6H-dipyrido[2,1-d:2',3'-f][1,2,5]thiadiazepine 5,5-dioxide

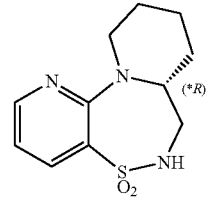 [SMILES: O=S1(=O)NC[C@H]2CCCCN2c2ncccc21]

The second eluting isomer from the separation of isomers by chiral SFC described in Intermediate 2 (15.2 g) was designated (*R). MS (ESI): mass calcd. for $C_{11}H_{15}N_3O_2S$, 253.1; m/z found, 254.0 [M+H]$^+$. $^1$H NMR (500 MHz, CDCl$_3$) δ 8.23 (dd, J=4.7, 1.9 Hz, 1H), 7.90 (dd, J=7.8, 1.8 Hz, 1H), 6.75 (dd, J=7.8, 4.6 Hz, 1H), 5.42 (t, J=5.9 Hz, 1H), 4.31 (dq, J=12.0, 4.7 Hz, 1H), 4.23 (dt, J=13.3, 4.8 Hz, 1H), 3.50 (ddd, J=13.5, 12.0, 6.4 Hz, 1H), 3.47-3.31 (m, 2H), 1.85-1.73 (m, 3H), 1.69-1.55 (m, 3H).

Intermediate 4: (R)-6,7,7a, 8,9,10-Hexahydropyrido[2,3-f]pyrrolo[2,1-d][1,2,5]thiadiazepine 5,5-dioxide

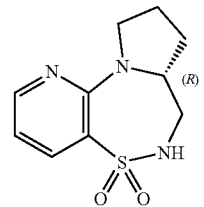

Step A: tert-Butyl (R)-2-(((2-chloropyridine)-3-sulfonamido)methyl)pyrrolidine-1-carboxylate. Water (17 mL) was added to a solution of tert-butyl (R)-2-(aminomethyl)pyrrolidine-1-carboxylate (7.50 g, 37.4 mmol) in THF. $K_2CO_3$ (3.67 g, 26.6 mmol) and 2-chloropyridine-3-sulfonyl chloride (5.25 g, 24.8 mmol) were sequentially added and the resulting mixture was stirred at room temperature for 2 hours. THF was removed under reduced pressure and the mixture was partitioned between ethyl acetate and water. The aqueous layer was extracted with ethyl acetate. These extractions resulted in several organic solvent fractions which were combined, washed with brine, dried over anhydrous $MgSO_4$, filtered and concentrated to dryness under reduced pressure. The residue was purified by flash column chromatography (eluent: 0 to 20% EtOAc/DCM, gradient elution) to afford the title compound (8.9 g, 95%). $^1$H NMR (500 MHz, DMSO-$d_6$) δ 8.64 (dd, J=4.8, 1.8 Hz, 1H), 8.39-8.26 (m, 2H), 7.66 (dd, J=7.8, 4.8 Hz, 1H), 3.74-3.51 (m, 1H), 3.12 (t, J=14.1 Hz, 3H), 2.93-2.78 (m, 1H), 1.94-1.63 (m, 4H), 1.36 (s, 9H).

Step B: (R)-6,7,7a,8,9,10-Hexahydropyrido[2,3-f]pyrrolo[2,1-d][1,2,5]thiadiazepine 5,5-dioxide. TFA in DCM (1:4 v/v, 80 mL) was added to tert-butyl (R)-2-(((2-chloropyridine)-3-sulfonamido)methyl)pyrrolidine-1-carboxylate (8.50 g, 22.6 mmol) at room temperature. The resulting mixture was stirred for 1 hour and the solvents were removed under reduced pressure. THF (80 mL) and TEA (20 mL, 143.8 mmol) were added and the resulting mixture was heated to reflux for 18 hours. The reaction mixture was cooled to room temperature and the solvents were removed under reduced pressure. Ethyl acetate was added to the residue. The resulting solution was washed with brine, dried over anhydrous $MgSO_4$, filtered and concentrated to dryness under reduced pressure. The residue was purified by flash column chromatography (eluent: 0 to 30% EtOAc/DCM, gradient elution) to afford the title compound (4.7 g, 86%). MS (ESI): mass calcd. for $C_{10}H_{13}N_3O_2S$, 239.1; m/z found, 240.1 [M+H]$^+$. $^1$H NMR (600 MHz, DMSO-$d_6$) δ 8.27 (dd, J=4.7, 1.8 Hz, 1H), 8.06 (s, 1H), 7.94 (dd, J=7.7, 1.8 Hz, 1H), 6.85 (dd, J=7.7, 4.7 Hz, 1H), 4.25-4.15 (m, 1H), 3.66-3.56 (m, 1H), 3.56-3.48 (m, 1H), 3.29 (dd, J=13.2, 3.4 Hz, 1H), 3.03 (dd, J=13.2, 11.9 Hz, 1H), 2.15-2.02 (m, 1H), 1.94-1.84 (m, 2H), 1.74-1.65 (m, 1H).

Intermediate 5: 2',3'-Dihydrospiro[cyclopropane-1,4'-pyrido[2,3-b][1,4,5]oxathiazepine]1',1'-dioxide

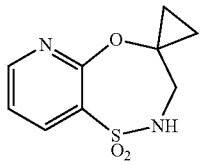 [SMILES: O=S1(=O)NCC2(CC2)Oc2ncccc21]

Step A: 2-Chloro-N-((1-hydroxycyclopropyl)methyl)pyridine-3-sulfonamide. A solution of 2-chloropyridine-3-sulfonyl chloride (13.0 g, 61.3 mmol) in THF (30 mL) was added dropwise to a mixture of 1-(aminomethyl)cyclopropanol (5.0 g, 57 mmol), $K_2CO_3$ (15.0 g, 109 mmol), THF (20 mL), and $H_2O$ (10 mL) at 0° C. The resulting mixture was stirred for 12 hours with gradual warming to room temperature before concentrating to dryness under reduced pressure. The residue was diluted with water (150 mL) and the aqueous layer was extracted with ethyl acetate (100 mL×3). These extractions resulted in several organic solvent fractions which were combined, dried over anhydrous $Na_2SO_4$, filtered and concentrated to dryness under reduced pressure to afford the title compound (10 g) as a yellow oil, which was used in the next step without further purification. MS (ESI): mass calcd. for $C_9H_{11}ClN_2O_3S$, 262.0; m/z found, 262.8 [M+H]$^+$.

Step B: 2',3'-Dihydrospiro[cyclopropane-1,4'-pyrido[2,3-b][1,4,5]oxathiazepine] 1',1'-dioxide. t-BuOK (10 g, 89 mmol) was added in portions to a solution of 2-chloro-N-((1-hydroxycyclopropyl)methyl)pyridine-3-sulfonamide (10 g) in DMSO (50 mL) at 0° C. The resulting mixture was heated to 80° C. for 4 hours before concentrating to dryness under reduced pressure. The residue was diluted with $H_2O$ (100 mL), and the pH adjusted to pH ~6 with 1 N aqueous HCl. The aqueous layer was extracted with ethyl acetate (100 mL×3). These extractions resulted in several organic solvent fractions which were combined, dried over anhydrous $Na_2SO_4$, filtered and concentrated to dryness under reduced pressure. The residue was purified by flash column chromatography (eluent:petroleum ether/ethyl acetate, 1:0 to 1:4, gradient elution) to afford the title compound (4.3 g, 47%) as a yellow solid. MS (ESI): mass calcd. for $C_9H_{10}N_2O_3S$, 226.0; m/z found, 227.0 [M+H]$^+$. $^1$H NMR (400 MHz, DMSO-$d_6$) δ 8.44-8.35 (m, 1H), 8.24-8.13 (m, 2H), 7.42-7.37 (m, 1H), 3.54-3.43 (m, 2H), 0.91-0.84 (m, 2H), 0.77-0.70 (m, 2H).

Intermediate 6: 8'-Methyl-2',3'-dihydrospiro[cyclopropane-1,4'-pyrido[2,3-b][1,4,5]oxathiazepine] 1',1'-dioxide

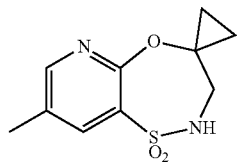 [SMILES: Cc1cnc2c(c1)S(=O)(=O)NCC1(CC1)O2]

Step A: 2-Chloro-N-((1-hydroxycyclopropyl)methyl)-5-methylpyridine-3-sulfonamide. 2-Chloro-5-methylpyridine-3-sulfonyl chloride (89.0 g, 394 mmol) in THF (300 mL) was added dropwise to a mixture of 1-(aminomethyl)cyclopropanol (68.5 g, 413 mmol) and $K_2CO_3$ (136 g, 984 mmol) in THF (1.3 L) and $H_2O$ (400 mL) while keeping the inner temperature around 0-5° C. The reaction mixture was allowed to warm to room temperature and stirred at 25° C. for 16 hours. The reaction mixture was diluted with water (500 mL) and the aqueous layer was extracted with ethyl acetate (500 mL×1, 300 mL×2). These extractions resulted in several organic solvent fractions which were combined, washed with brine (800 mL), dried over $Na_2SO_4$, filtered and concentrated under reduced pressure. The residue was purified by column chromatography (eluent:petroleum ether/ethyl acetate/ethanol, 9:3:1 to 3:1:0, gradient elution), followed by trituration in MTBE (120 mL) to afford the title compound (42 g, 39%). MS (ESI): mass calcd. for $C_{10}H_{13}ClN_2O_3S$, 276.1; m/z found, 276.8 [M+H]$^+$.

Step B: 8'-Methyl-2',3'-dihydrospiro[cyclopropane-1,4'-pyrido[2,3-b][1,4,5]oxathiazepine] 1',1'-dioxide. An aqueous solution of $K_2CO_3$ (3 M, 152 mL) was added to a mixture of 2-chloro-N-((1-hydroxycyclopropyl)methyl)-5-methylpyridine-3-sulfonamide (42.0 g, 152 mmol) in DMSO (800 mL) and the solution was stirred at 95° C. for 40 hours under N$_2$. A black brown suspension was obtained. The mixture was diluted with H$_2$O (1.5 L) and 4 N HCl in MeOH was added to the solution until the pH was ~7. The aqueous layer was extracted with EtOAc (1 L and then 500 mL×6). These extractions resulted in several organic solvent fractions which were combined, washed with brine (1 L), dried over anhydrous Na$_2$SO$_4$ and concentrated under reduced pressure. The residue was purified by flash column chromatography (eluent:petroleum ether/ethyl acetate, 1:1 to 1:4, gradient elution) and triturated in MTBE (100 mL) for 0.5 hours to afford the title compound (21.5 g, 59%). MS (ESI): mass calcd. for C$_{10}$H$_{12}$N$_2$O$_3$S, 240.1; m/z found, 241.3. [M+H]$^+$. $^1$H NMR (400 MHz, DMSO-d$_6$) δ 8.24 (d, J=1.8 Hz, 1H) 8.13 (br s, 1H) 8.05 (d, J=2.0 Hz, 1H) 3.49 (s, 2H) 2.34 (s, 3H) 0.86-0.93 (m, 2H) 0.69-0.79 (m, 2H).

Intermediate 7: 2,3-Dihydrospiro[benzo[b][1,4,5]oxathiazepine-4,3'-oxetane] 1,1-dioxide

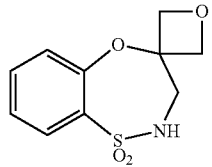 [SMILES: O=S1(=O)NCC2(COC2)Oc2ccccc21]

Step A: 2-Fluoro-N-((3-hydroxyoxetan-3-yl)methyl)benzenesulfonamide. A mixture of 3-(aminomethyl)oxetan-3-ol (30.0 g, 291 mmol), 2-fluorobenzene-1-sulfonyl chloride (38.0 g, 195 mmol), K$_2$CO$_3$ (23.0 g, 217 mmol), THF (240 mL) and H$_2$O (60 mL) were stirred at room-temperature for 2.5 hours. The reaction mixture was poured into H$_2$O (50 mL) and extracted with ethyl acetate (50 mL×3). These extractions resulted in several organic solvent fractions which were combined, washed with brine (20 mL), dried over anhydrous MgSO$_4$, filtered and concentrated to dryness under reduced pressure to afford the title compound (40 g) which was used in the next step without further purification. MS (ESI): mass calcd. for C$_{10}$H$_{12}$FNO$_4$S, 261.1; m/z found, 262.2 [M+H]$^+$.

Step B: 2,3-Dihydrospiro[benzo[b][1,4,5]oxathiazepine-4,3'-oxetane]1,1-dioxide. A mixture of 2-fluoro-N-((3-hydroxyoxetan-3-yl)methyl)benzenesulfonamide (40 g), t-BuOK (47.0 g, 419 mmol), and DMSO (150 mL) was sparged with N$_2$ for 5 minutes and was stirred at 95° C. for 4 hours. The reaction mixture was cooled to room temperature, acidified to pH ~2 with 5 N aqueous HCl, and poured into H$_2$O (50 mL). The resulting suspension was filtered and washed with H$_2$O (30 mL) and petroleum ether (20 mL). The solid was triturated with petroleum ether/ethyl acetate (4:1, 50 mL) and filtered, dried under reduced pressure to afford the title compound (23.6 g, 62%) as a yellow solid. To obtain a second portion of the title compound, the filtrate was extracted with ethyl acetate (50 mL×3). The combined organic extracts were washed with brine (30 mL), dried over anhydrous MgSO$_4$, filtered and concentrated to dryness under reduced pressure to give a second portion of the title compound, which was purified by preparative HPLC using a Phenomenex Synergi Max-RP, 250×50 mm×10 μm column (eluent: 10% to 40% (v/v) CH$_3$CN and H$_2$O with 0.225% HCOOH) to afford pure product. The product was suspended in water (20 mL), the mixture frozen using dry ice/acetone, and then lyophilized to dryness to afford the title compound (6.35 g) as a yellow solid. Total compound obtained from this experiment was 30.0 g. LC-MS (ESI): RT=3.27 min, mass calcd. for C$_{10}$H$_{11}$NO$_4$S 241.0, m/z found 242.0 [M+H]$^+$. $^1$H NMR (400 MHz, DMSO-d$_6$) δ 8.13 (t, J=6.7 Hz, 1H), 7.71 (dd, J=7.8, 1.7 Hz, 1H), 7.61 (dt, J=7.8, 1.7 Hz, 1H), 7.44-7.40 (m, 1H), 7.35-7.30 (m, 1H), 4.43 (d, J=7.3 Hz, 2H), 4.33 (d, J=7.5 Hz, 2H), 3.74 (d, J=6.6 Hz, 2H).

Intermediate 8: 7a-Methyl-6,7,7a,8,9,10-hexahydropyrido[2,3-f]pyrrolo[2,1-d][1,2,5]thiadiazepine 5,5-dioxide

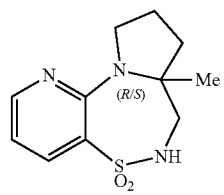 [SMILES: CC12CCCN1c1ncccc1S(=O)(=O)NC2]

Step A: tert-Butyl 2-cyano-2-methylpyrrolidine-1-carboxylate. n-BuLi (20 mL, 2.5 M in n-hexane, 50 mmol) was added dropwise to a solution of diisopropylamine (8.6 mL, 61 mmol) and THF (120 mL) at −78° C. The resulting mixture was stirred at −78° C. for 30 minutes and was added dropwise to a solution of tert-butyl 2-cyanopyrrolidine-1-carboxylate (8.0 g, 41 mmol) in THF (150 mL) at −78° C. The resulting mixture was stirred at −78° C. for 2 hours and then it was treated with MeI (5.0 mL, 80 mmol). This mixture was stirred at 0° C. for 2 hours before it was quenched with water (100 mL). The aqueous layer was extracted with ethyl acetate (100 mL×3). These extractions resulted in several organic solvent fractions which were combined, dried over anhydrous Na$_2$SO$_4$, filtered and concentrated to dryness under reduced pressure. The residue was purified by flash column chromatography (eluent:petroleum ether/ethyl acetate, 50:1 to 5:1, gradient elution) to afford the title compound (5 g, 58%) as a yellow oil. $^1$H NMR (400 MHz, CDCl$_3$) δ 3.59 (br s, 1H), 3.48-3.36 (m, 1H), 2.58-2.45 (m, 1H), 2.04-1.85 (m, 3H), 1.70 (br s, 3H), 1.52 (br s, 9H).

Step B: tert-Butyl 2-(aminomethyl)-2-methylpyrrolidine-1-carboxylate. Raney Ni (1 g) was added to a mixture of tert-butyl 2-cyano-2-methylpyrrolidine-1-carboxylate (1.0 g, 4.8 mmol), methanol (20 mL), and 25% aqueous NH$_3$ (5 mL) under Ar. The resulting mixture was stirred under H$_2$ (15 psi) at room temperature for 2 hours. The suspension was filtered through diatomaceous earth such as Celite® and the filtrate was concentrated to dryness under reduced pressure to afford the title compound (750 mg, 74%) as a yellow oil. $^1$H NMR (400 MHz, CDCl$_3$) δ 3.61 (d, J=5.1 Hz, 1H), 3.41-3.28 (m, 1H), 3.23 (d, J=13.0 Hz, 1H), 3.08 (d, J=13.0 Hz, 1H), 2.72-2.59 (m, 1H), 2.12-1.96 (m, 1H), 1.69-1.54 (m, 2H), 1.47 (d, J=13.9 Hz, 12H).

Step C: tert-Butyl 2-((2-chloropyridine-3-sulfonamido)methyl)-2-methylpyrrolidine-1-carboxylate. 2-Chloropyridine-3-sulfonyl chloride (3.5 g, 16 mmol) was added in portions to a mixture of tert-butyl 2-(aminomethyl)-2-methylpyrrolidine-1-carboxylate (3.6 g, 17 mmol), K$_2$CO$_3$ (2.74 g, 20.0 mmol) in THF (60 mL) and H$_2$O (15 mL). The resulting mixture was stirred at room temperature for 16 hours before diluting with H$_2$O (25 mL) and extracting the aqueous layer with ethyl acetate (50 mL×2). These extractions resulted in several organic solvent fractions which were combined, dried over anhydrous Na$_2$SO$_4$, filtered and concentrated to dryness under reduced pressure. The residue was purified by flash column chromatography (eluent:petroleum ether/ethyl acetate, 10:1 to 5:1, gradient elution) to afford the title compound (5.5 g, 85%). MS (ESI): mass calcd. for C$_{16}$H$_{24}$ClN$_3$O$_4$S, 389.1; m/z found, 412.0 [M+Na]$^+$.

Step D: 2-Chloro-N-((2-methylpyrrolidin-2-yl)methyl)pyridine-3-sulfonamide. TFA (6.5 mL, 85 mmol) was added to a solution of tert-butyl 2-((2-chloropyridine-3-sulfonamido)methyl)-2-methylpyrrolidine-1-carboxylate (5.5 g, 14 mmol) in dichloromethane (20 mL). The resulting mixture was stirred at room temperature for 5 hours and concentrated to dryness under reduced pressure to afford the title compound (4 g) as a yellow oil, which was used in the next step without further purification. MS (ESI): mass calcd. for C$_{11}$H$_{16}$ClN$_3$O$_2$S, 289.1; m/z found, 289.9 [M+H]$^+$.

Step E: 7a-Methyl-6,7,7a,8,9,10-hexahydropyrido[2,3-f]pyrrolo[2,1-d][1,2,5]thiadiazepine 5,5-dioxide. DIPEA (9.1 mL, 55 mmol) was added to a solution of 2-chloro-N-((2-methylpyrrolidin-2-yl)methyl)pyridine-3-sulfonamide (4.0 g, 14 mmol) and DMSO (30 mL). The resulting mixture was stirred at 160° C. for 6 hours before cooling to room temperature and concentrating to dryness under reduced pressure. The residue was dissolved in ethyl acetate (200 mL) and the resulting mixture was washed with H$_2$O (100 mL×3). The organic layer was dried over anhydrous Na$_2$SO$_4$, filtered and concentrated to dryness under reduced pressure. The residue was purified by preparative HPLC using a Phenomenex Gemini column, 150×25 mm×5 μm (eluent: 15% to 35% (v/v) CH$_3$CN and H$_2$O with 0.05% NH$_3$) to afford the title compound. The product was suspended in water (50 mL), the mixture frozen using dry ice/acetone, and then lyophilized to dryness to afford the title compound (2.9 g, 82%). MS (ESI): mass calcd. for C$_{11}$H$_{15}$N$_3$O$_2$S, 253.1; m/z found, 254.0 [M+H]$^+$. $^1$H NMR (400 MHz, DMSO-d$_6$) δ 8.39-8.32 (m, 1H), 8.04-7.99 (m, 1H), 7.98-7.92 (m, 1H), 7.02-6.96 (m, 1H), 3.92-3.82 (m, 1H), 3.31-3.20 (m, 2H), 3.17-3.08 (m, 1H), 2.01-1.68 (m, 4H), 0.78 (s, 3H).

Intermediate 9: 7,7a,8,9,10,11-Hexahydro-6H-dipyrido[2,1-d:2',3'-f][1,2,5]thiadiazepine-3-carbonitrile 5,5-dioxide

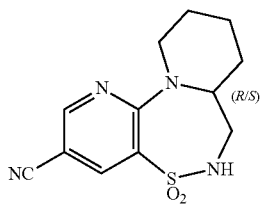 [SMILES: N#Cc1cnc2c(c1)S(=O)(=O)NCC1CCCCN21]

Step A: 5-Bromo-2-chloropyridine-3-sulfonyl chloride. HBF$_4$ (29.0 mL, 189 mmol) was added dropwise to a solution of 5-bromo-2-chloropyridin-3-amine (25.0 g, 121 mmol) in acetonitrile (200 mL) and the temperature of the solution was kept between 0° C. to 5° C. The resulting mixture was stirred at 0° C. for 10 minutes before adding tert-butyl nitrite (22.0 mL, 185 mmol) dropwise under an atmosphere of N$_2$. The resulting mixture was stirred at 0° C. for another 2 hours to afford solution one. While solution one was stirring, a separate second solution was prepared wherein a mixture of copper (I) chloride (18.0 g, 182 mmol) and acetic acid (200 mL) was cooled to 0° C., and SO$_2$ gas was bubbled through the solution (>1.3 M) for 1 hour. Solution one was then added dropwise to solution two at 0° C. under N$_2$ atmosphere. The resulting mixture was stirred for 16 hours with gradual warming to room temperature. The suspension was filtered and washed with ethyl acetate (30 mL×2). The filtrate was concentrated to dryness under reduced pressure. The residue was purified by flash column chromatography (eluent:petroleum ether) to afford the title compound (24.5 g, 71%) as a brown liquid. $^1$H NMR (400 MHz, DMSO-d$_6$) δ 8.50 (d, J=2.6 Hz, 1H), 8.27 (d, J=2.4 Hz, 1H).

Step B: tert-Butyl 2-(((5-bromo-2-chloropyridine)-3-sulfonamido)methyl)piperidine-1-carboxylate. tert-Butyl 2-(aminomethyl)piperidine-1-carboxylate (18.1 g, 84.5 mmol) was added to a suspension of K$_2$CO$_3$ (34.9 g, 253 mmol) in THF (150 mL) and H$_2$O (30 mL) at 0° C. The reaction mixture was stirred for 10 minutes at 0° C. and then treated with 5-bromo-2-chloropyridine-3-sulfonyl chloride (24.5 g, 84.2 mmol). The resulting mixture was stirred at 0° C. for 2.5 hours and concentrated to dryness under reduced pressure. The residue was dissolved in water (50 mL) and the aqueous layer was extracted with ethyl acetate (50 mL×3). These extractions resulted in several organic solvent fractions which were combined, washed with brine (50 mL), dried over anhydrous Na$_2$SO$_4$, filtered and concentrated to dryness under reduced pressure. The residue was purified by flash column chromatography (eluent:petroleum ether/ethyl acetate, 1:0 to 7:3, gradient elution) to afford the title compound (31 g, 74%) as a yellow solid. MS (ESI): mass calcd. for C$_{16}$H$_{23}$BrClN$_3$O$_4$S, 467.0; m/z found, 490.1 [M+Na]$^+$.

Step C: 5-Bromo-2-chloro-N-(piperidin-2-ylmethyl)pyridine-3-sulfonamide. TFA (69.0 mL, 995 mmol) was added dropwise to a solution of tert-butyl 2-((5-bromo-2-chloropyridine-3-sulfonamido)methyl)piperidine-1-carboxylate (31 g, 66 mmol) in dichloromethane (120 mL) at 0° C. The resulting mixture was stirred for 16 hours with gradual warming to room temperature. It was then concentrated to dryness under reduced pressure to afford the title compound (35 g), which was used in the next step without further purification. MS (ESI): mass calcd. for C$_{11}$H$_{15}$BrClN$_3$O$_2$S, 367.0; m/z found, 367.8 [M+H]$^+$.

Step D: 3-Bromo-7,7a,8,9,10,11-hexahydro-6H-dipyrido[2,1-d:2',3'-f][1,2,5]thiadiazepine 5,5-dioxide. DIPEA (120 mL, 881 mol) was added to a mixture of 5-bromo-2-chloro-N-(piperidin-2-ylmethyl)pyridine-3-sulfonamide (35 g) in toluene (120 mL). The resulting solution was stirred at 130° C. for 2 hours before cooling to room temperature and concentrating to dryness under reduced pressure. The residue was purified by flash column chromatography (eluent: petroleum ether/ethyl acetate, 1:0 to 3:1, gradient elution) to afford the title compound (19 g, 96%) as a yellow solid. MS (ESI): mass calcd. for C$_{11}$H$_{14}$BrN$_3$O$_2$S, 331.0; m/z found, 331.7 [M+H]$^+$.

Step E: 7,7a,8,9,10,11-Hexahydro-6H-dipyrido[2,1-d:2',3'-f][1,2,5]thiadiazepine-3-carbonitrile 5,5-dioxide. Zn(CN)$_2$ (16.7 g, 142 mmol) was added to a mixture of 3-bromo-7,7a,8,9,10,11-hexahydro-6H-dipyrido[2,1-d:2',3'-f][1,2,5]thiadiazepine 5,5-dioxide (23.0 g, 69.2 mmol), Zn (906 mg, 13.9 mmol), and DMF (100 mL). The mixture was sparged with Ar for 5 minutes and then treated with Pd(dppf)Cl$_2$ (5.07 g, 6.93 mmol). The resultant mixture was sparged with Ar for another 5 minutes and then stirred at 140° C. for 3 hours before cooling to room temperature. The reaction mixture was filtered and the solid was rinsed with ethyl acetate (10 mL×2). The filtrate was concentrated to dryness under reduced pressure and purified by flash column chromatography (eluent:petroleum ether/ethyl acetate, 1:0 to 1:1) to afford the title compound as a brown solid. MS (ESI): mass calcd. for $C_{12}H_{14}N_4O_2S$, 278.1; m/z found, 278.9 [M+H]$^+$.

Intermediate 10: (*R)-7,7a,8,9,10,11-Hexahydro-6H-dipyrido[2,1-d:2',3'-f][1,2,5]thiadiazepine-3-carbonitrile 5,5-dioxide

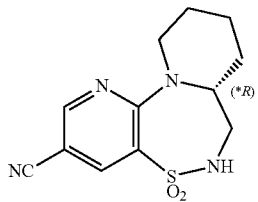 [SMILES: N#Cc1cnc2c(c1)S(=O)(=O)NC[C@H]1CCCCN21]

The mixture of 7,7a,8,9,10,11-hexahydro-6H-dipyrido[2,1-d:2',3'-f][1,2,5]thiadiazepine-3-carbonitrile 5,5-dioxide enantiomers (Intermediate 9, 30.0 g) was separated by chiral SFC (stationary phase: Phenomenex cellulose-2, 10 m 250× 50 mm, Mobile phase: 60% $CO_2$, 40% EtOH/$H_2O$ with 0.1% $NH_3$) to provide 2 enantiomers. The first eluting enantiomer (12.9 g) was designated (*R). MS (ESI): mass calcd. for $C_{12}H_{14}N_4O_2S$, 278.1; m/z found, 279.0 [M+H]$^+$. $^1$H NMR (400 MHz, DMSO-$d_6$) δ 8.62 (d, J=2.0 Hz, 1H), 8.32 (d, J=2.0 Hz, 1H), 8.48-8.00 (m, 1H), 4.45-4.33 (m, 2H), 3.54 (t, J=13.0 Hz, 1H), 3.42-3.35 (m, 1H), 3.26 (dd, J=13.6, Hz, 1H), 1.79-1.49 (m, 6H).

Intermediate 11: (*S)-7,7a,8,9,10,11-Hexahydro-6H-dipyrido[2,1-d:2',3'-f][1,2,5]thiadiazepine-3-carbonitrile 5,5-dioxide

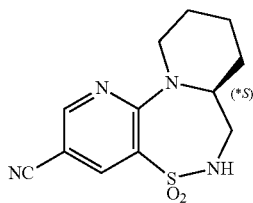 [SMILES: N#Cc1cnc2c(c1)S(=O)(=O)NC[C@@H]1CCCCN21]

The second eluting enantiomer from the separation of isomers by chiral SFC described in Intermediate 10 was designated (*S) (13.1 g, 43%). MS (ESI): mass calcd. for $C_{12}H_{14}N_4O_2S$, 278.08; m/z found, 279.0 [M+H]$^+$. $^1$H NMR (400 MHz, DMSO-$d_6$) δ 8.62 (d, J=2.0 Hz, 1H), 8.33-8.30 (m, 1H), 8.32 (d, J=2.0 Hz, 1H), 4.44-4.34 (m, 2H), 3.54 (t, J=13.2 Hz, 1H), 3.42-3.35 (m, 1H), 3.26 (dd, J=13.2, 3.6 Hz, 1H), 1.79-1.49 (m, 6H).

Intermediate 12: 6,7,7a,8,10,11-Hexahydro-[1,4]oxazino[3,4-d]pyrido[2,3-f][1,2,5]thiadiazepine 5,5-dioxide

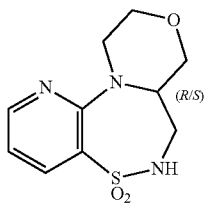 [SMILES: O=S1(=O)NCC2COCCN2c2ncccc21]

Step A: tert-Butyl 4-(((2-chloropyridine)-3-sulfonamido)methyl)-1,3-oxazinane-3-carboxylate. 2-Chloropyridine-3-sulfonyl chloride (8.9 g, 42 mmol) was added to a mixture of tert-butyl 4-(aminomethyl)-1,3-oxazinane-3-carboxylate (10 g, 46 mmol) and potassium carbonate (6.8 g, 49 mmol) in THF (150 mL) at room temperature. After 5 hours, the mixture was concentrated under reduced pressure and the residue was partitioned between water and ethyl acetate. The layers were separated and the aqueous layer was extracted with ethyl acetate. These extractions resulted in several organic solvent fractions which were combined, dried over $Na_2SO_4$, and filtered. Upon standing a solid crashed out of the filtrate. Ethyl ether was added and the slurry was stirred at room temperature, the solids were filtered off to provide the title compound (16.5 g, 100%) as a solid. MS (ESI): mass calcd. for $C_{15}H_{22}ClN_3O_5S$, 391.1; m/z found, 292.0 [M-$CO_2{}^t$Bu]$^+$. $^1$H NMR (500 MHz, CDCl$_3$) δ 8.61-8.55 (m, 1H), 8.45-8.39 (m, 1H), 7.44 (dd, J=7.8, 4.8 Hz, 1H), 5.85-5.32 (m, 1H), 4.28-4.04 (m, 1H), 3.92-3.67 (m, 3H), 3.60-3.55 (m, 1H), 3.48-3.40 (m, 1H), 3.23-2.97 (m, 2H), 1.50 (s, 9H).

Step B: 6,7,7a,8,10,11-Hexahydro-[1,4]oxazino[3,4-d]pyrido[2,3-f][1,2,5]thiadiazepine 5,5-dioxide. Trifluoroacetic acid in DCM (165 mL) was added to tert-butyl 4-(((2-chloropyridine)-3-sulfonamido)methyl)-1,3-oxazinane-3-carboxylate (23 g, 58.7 mmol) at room temperature. After 2.5 hours, the mixture was concentrated under reduced pressure and the residue was dissolved in toluene (270 mL). TEA (50.0 mL, 357 mmol) was added and the reaction mixture was stirred at 130° C. for 15 hours. The reaction was allowed to cool to room temperature and concentrated under reduced pressure. The residue was purified by flash column chromatography (0 to 100% ethyl acetate/hexanes, gradient elution) to provide the title compound (18.0 g) as a white solid. MS (ESI): mass calcd. for $C_{10}H_{13}N_3O_3S$, 255.3; m/z found, 256.1 [M+H]$^+$. $^1$H NMR (400 MHz, CDCl$_3$) δ 8.25 (dd, J=4.6, 1.8 Hz, 1H), 7.94 (dd, J=7.8, 1.8 Hz, 1H), 6.82 (dd, J=7.9, 4.6 Hz, 1H), 5.46 (t, J=5.7 Hz, 1H), 4.38 (ddt, J=12.0, 4.7, 2.7 Hz, 2H), 4.20-3.98 (m, 1H), 3.89-3.65 (m, 4H), 3.58-3.38 (m, 2H).

Intermediate 13: (*S)-6,7,7a,8,10,11-Hexahydro-[1,4]oxazino[3,4-d]pyrido[2,3-f][1,2,5]thiadiazepine 5,5-dioxide

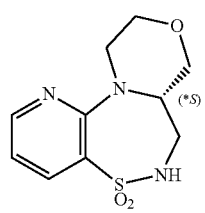 [SMILES: O=S1(=O)NC[C@H]2COCCN2c2ncccc21]

The mixture of 6,7,7a,8,10,11-hexahydro-[1,4]oxazino[3,4-d]pyrido[2,3-f][1,2,5]thiadiazepine 5,5-dioxide enantiomers (Intermediate 12, 18 g) was separated by chiral SFC (stationary phase: Chiralpak AS-H 5 μm 250×20 mm, Mobile phase: 60% $CO_2$, 40% MeOH) to afford two enantiomers. The first eluting isomer (8.25 g) was designated (*S). MS (ESI): mass calcd. for $C_{10}H_{13}N_3O_3S$, 255.3; m/z found, 256.1 [M+H]$^+$. $^1$H NMR (500 MHz, CDCl$_3$) δ 8.28 (dd, J=4.6, 1.8 Hz, 1H), 7.96 (dd, J=7.8, 1.8 Hz, 1H), 6.84 (dd, J=7.9, 4.6 Hz, 1H), 5.29 (t, J=5.6 Hz, 1H), 4.46-4.37 (m, 2H), 4.05 (dt, J=11.2, 3.7 Hz, 1H), 3.91-3.82 (m, 1H), 3.85-3.76 (m, 2H), 3.74 (dd, J=12.2, 2.0 Hz, 1H), 3.60-3.45 (m, 2H).

Intermediate 14: (*R)-6,7,7a,8,10,11-Hexahydro-[1,4]oxazino[3,4-d]pyrido[2,3-f][1,2,5]thiadiazepine 5,5-dioxide

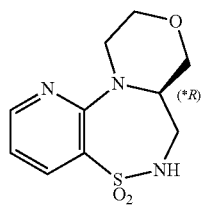 [SMILES: O=S1(=O)NC[C@@H]2COCCN2c2ncccc21]

The second eluting isomer (8.25 g) from the separation of isomers by chiral SFC described in Intermediate 13 was designated (*R). MS (ESI): mass calcd. for $C_{10}H_{13}N_3O_3S$, 255.3; m/z found, 256.1 [M+H]⁺. ¹H NMR (500 MHz, CDCl₃) δ 8.28 (dd, J=4.6, 1.8 Hz, 1H), 7.97 (dd, J=7.8, 1.8 Hz, 1H), 6.85 (dd, J=7.8, 4.6 Hz, 1H), 5.23 (t, J=5.6 Hz, 1H), 4.46-4.38 (m, 2H), 4.05 (dt, J=11.3, 3.7 Hz, 1H), 3.92-3.83 (m, 1H), 3.86-3.77 (m, 2H), 3.74 (dd, J=12.2, 2.0 Hz, 1H), 3.60-3.46 (m, 2H).

Intermediate 15: Ethyl (E)-3-(6-(acetoxymethyl)-5-methylpyridin-2-yl)acrylate

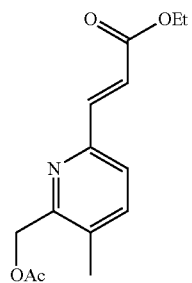 [SMILES: CCOC(=O)/C=C/c1ccc(C)c(COC(C)=O)n1]

Step A: Methyl 6-chloro-3-methylpicolinate. SOCl₂ (90.1 g, 757.6 mmol) was added to a solution of 6-chloro-3-methylpicolinic acid (65.0 g, 379 mmol) in MeOH (300 mL) at 0° C. The resulting solution was stirred for 15 minutes at 0° C., 0.5 hours at 20-30° C., and 6 hours at 50° C. The reaction mixture was concentrated under reduced pressure and diluted with EtOAc (300 mL). The organic fraction was washed with saturated aqueous Na₂CO₃ solution (100 mL×3), brine (300 mL), dried over Na₂SO₄, filtered and concentrated to afford the title compound (133.0 g, 94%) as a yellow oil. ¹H NMR (400 MHz CDCl₃) δ 7.53 (d, J=8.0 Hz, 1H), 7.31 (d, J=12 Hz, 1H), 3.89 (s, 3H), 2.49 (s, 3H).

Step B: 6-Chloro-3-methylpyridin-2-yl)methanol. To a suspension of methyl 6-chloro-3-methylpicolinate (65.0 g, 350 mmol) in THF (300 mL) at 0° C. under N₂, was added NaBH₄ (79.5 g, 2.1 mol) in portions. The resulting mixture was heated to 70° C. and stirred for 20 minutes. The reaction was then cooled to 20-30° C. and MeOH (60.0 mL) was added dropwise over 15 minutes and effervescence was observed. This mixture was stirred at 60° C. for 3 hours. The reaction was then cooled to room temperature, quenched with saturated aqueous NH₄Cl solution (500 mL) and stirred for 1.5 hours. The organic layer was separated and the aqueous layer was extracted with EtOAc (250 mL×3). These extractions resulted in several organic solvent fractions which were combined, washed with brine (100 mL), dried over Na₂SO₄, filtered and concentrated to afford the title compound (104.0 g, 94%) as a yellow oil. ¹H NMR (400 MHz CDCl₃) δ 7.34 (d, J=8.0 Hz, 1H), 7.06 (d, J=8 Hz, 1H), 4.57 (s, 2H), 2.12 (s, 3H).

Step C: 6-Chloro-3-methylpyridin-2-yl)methyl acetate. Acetyl chloride (213.8 g, 2.09 mol) was added to a solution of 6-chloro-3-methylpyridin-2-yl)methanol (110.0 g, 697.9 mmol) and TEA (353 g, 3.49 mol) in THF (1.0 L) at 0° C. The reaction mixture was stirred for 16 hours and gradually warmed to 40° C. over a period of 24 hours. The mixture was concentrated under reduced pressure and diluted with EtOAc (350 mL). The organic portion was washed with saturated aqueous NaHCO₃ solution (250 mL×3), brine (300 mL×3), dried over Na₂SO₄, filtered and concentrated under reduced pressure to afford the title compound. The residue was purified by flash column chromatography (petroleum ether/ethyl acetate, 100:1 to 50:1, gradient elution) to afford the title compound (95.0 g, 68%) as a yellow solid. ¹H NMR (400 MHz, CDCl₃) δ 7.42 (d, J=8.0 Hz, 1H), 7.16 (d, J=8 Hz, 1H), 5.10 (s, 2H), 2.28 (s, 3H), 2.07 (s, 3H).

Step D: Ethyl (E)-3-(6-(acetoxymethyl)-5-methylpyridin-2-yl)acrylate. DMF (500 mL) was added to a suspension of 6-chloro-3-methylpyridin-2-yl)methyl acetate (56.0 g, 280 mmol), ethyl acrylate (112 g, 1.12 mol), TEA (56.77 g, 561.0 mmol), TBAB (78.40 g, 243.2 mmol), DPPF (22.40 g, 40.41 mmol) and Pd(OAc)₂ (9.07 g, 40.4 mmol). The mixture was sparged with N₂ for 10 minutes, heated to 120° C. and stirred at this temperature under N₂ atmosphere for 24 hours. The reaction mixture was cooled to room temperature, diluted with EtOAc (100 mL) and the organic portion was washed sequentially with 10% aqueous NaHCO₃ solution (500 mL) and brine (500 mL). The resulting organic portion was dried over Na₂SO₄ and concentrated under reduced pressure. The residue was purified by flash column chromatography (petroleum ether/ethyl acetate, 60:1 to 15:1, gradient elution) to afford the title compound (47 g, 63%) as a green oil. MS (ESI): mass calcd. for $C_{14}H_{17}NO_4$, 263.1; m/z found, 263.9 [M+H]⁺. ¹H NMR: (400 MHz CDCl₃) δ 7.65 (d, J=15.6 Hz, 1H), 7.50 (d, J=8.0 Hz, 1H), 7.30 (d, J=8 Hz, 1H), 6.87 (d, J=16 Hz, 1H), 5.24 (s, 2H), 4.29-4.24 (m, 2H), 2.36 (s, 3H), 2.16 (s, 3H), 1.33 (t, J=8 Hz, 3H).

Intermediate 16: 5-Bromo-1-ethyl-4-methyl-1H-benzo[d][1,2,3]triazole

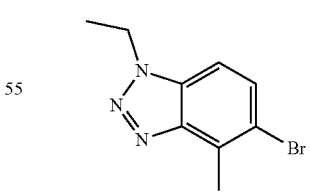

Step A: N-Ethyl-3-methyl-2-nitroaniline. Ethylamine (210 mL, 3.22 mol) was added to a solution of 1-fluoro-3-methyl-2-nitrobenzene (50.0 g, 322 mmol) in ethanol (500 mL). The reaction mixture was stirred at 50° C. for 48 hours. The reaction mixture was concentrated under reduced pressure and the red oil residue (57.0 g, 98%) was used in the next step without purification. ¹H NMR: (400 MHz, CDCl₃) δ

7.22 (t, J=8.0 Hz, 1H), 6.66 (d, J=8.6 Hz, 1H), 6.52 (d, J=7.4 Hz, 1H), 6.46 (br s, 1H), 3.21-3.30 (m, 2H), 2.48 (s, 3H), 1.28-1.36 (m, 3H).

Step B: 4-Bromo-N-ethyl-3-methyl-2-nitroaniline. Two batches of this reaction sequence were carried out in parallel. NBS (23.4 g, 131 mmol) was added in one portion to a mixture of N-ethyl-3-methyl-2-nitroaniline (25.0 g, 138 mmol) in AcOH (125 mL) at 15° C. The mixture was stirred for 12 hours. The reaction mixtures from the two parallel batches were combined. The resulting mixture was concentrated under reduced pressure. DCM (500 mL) was added. The organic phase was washed with $H_2O$ (300 mL×2), aqueous saturated $NaHCO_3$ solution (300 mL), dried over anhydrous $Na_2SO_4$, filtered and concentrated under reduced pressure to afford the title compound (70.0 g, 97%) as a red solid which was used in the next step without further purification.

Step C: 4-Bromo-$N^1$-ethyl-3-methylbenzene-1,2-diamine. In one portion, Fe (32.3 g, 578 mmol) was added to a mixture of 4-bromo-N-ethyl-3-methyl-2-nitroaniline (50.0 g, 192 mmol) and $NH_4Cl$ (62.1 g, 1.16 mol) in a mixture of ethanol (400 mL) and $H_2O$ (100 mL) at 50° C. The resulting mixture was stirred for 12 hours. The reaction mixture was filtered and concentrated under reduced pressure. The residue was then treated with $H_2O$ (200 mL) and the aqueous layer was extracted with DCM (200 mL×3). These extractions resulted in several organic solvent fractions which were combined and washed with brine (100 mL×2), dried over anhydrous $Na_2SO_4$, filtered and concentrated under reduced pressure to afford the title compound (42.0 g, 94%) as a red solid which was used in the next step without further purification. $^1$H NMR: (400 MHz, $CDCl_3$) δ 7.02 (d, J=8.4 Hz, 1H), 6.46 (d, J=8.4 Hz, 1H), 3.45 (br s, 2H), 3.12 (d, J=6.6 Hz, 2H), 2.32 (br s, 3H), 1.31 (t, J=6.4 Hz, 3H).

Step D: 5-Bromo-1-ethyl-4-methyl-1H-benzo[d][1,2,3]triazole. To a mixture of 4-bromo-$N^1$-ethyl-3-methylbenzene-1,2-diamine (42.0 g, 183 mmol) in AcOH (200 mL) at 10° C. was added in one portion a solution of $NaNO_2$ (13.9 g, 201 mmol) in water (10.9 mL). The mixture was stirred at 15° C. for 12 hours. The reaction mixture was concentrated under reduced pressure and added to $H_2O$ (200 mL). This mixture was extracted with DCM (200 mL×3).

These extractions resulted in several organic solvent fractions which were combined, washed with brine (100 mL×2), dried over anhydrous $Na_2SO_4$, filtered and concentrated under reduced pressure. The residue was purified by flash column chromatography (eluent:petroleum ether/ethyl acetate, 10:1 to 5:1, gradient elution) to afford the title compound (25.0 g, 40%) as a brown solid. MS (ESI): mass calcd. for $C_9H_{10}BrN_3$, 239.0; m/z found, 240.0 [M+H]$^+$. $^1$H NMR: (400 MHz, $CDCl_3$) δ 7.60 (d, J=8.8 Hz, 1H), 7.24 (d, J=8.8 Hz, 1H), 4.66 (q, J=7.6 Hz, 2H), 2.84 (s, 3H), 1.55-1.67 (m, 3H).

Intermediate 17: Ethyl (E)-3-(1-ethyl-4-methyl-1H-benzo[d][1,2,3]triazol-5-yl)acrylate

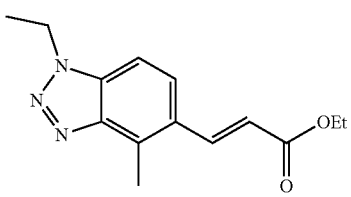 [SMILES: CCOC(=O)/C=C/c1ccc2c(nnn2CC)c1C]

A mixture of 5-bromo-1-ethyl-4-methyl-1H-benzo[d][1,2,3]triazole (Intermediate 16, 13.0 g, 54.1 mmol), ethyl prop-2-enoate (6.51 g, 64.9 mmol, 7.08 mL), Pd(PPh$_3$)$_4$ (5.0 g, 4.33 mmol), TEA (10.9 g, 108 mmol, 15.0 mL) in DMF (65 mL) was sparged with $N_2$ and then heated to 130° C. for 12 hours under $N_2$. The residue was poured into water (200 mL) and stirred for 10 minutes. The aqueous layer was extracted with ethyl acetate (200 mL×3). These extractions resulted in several organic solvent fractions which were combined, washed with brine (100 mL×2), dried with anhydrous $Na_2SO_4$, filtered and concentrated under reduced pressure. The residue was purified by flash column chromatography (eluent:petroleum ether/ethyl acetate, 10:1 to 3:1, gradient elution) to afford the title compound (13.0 g, 92%) as a yellow solid. MS (ESI): mass calcd. for $C_{14}H_{17}N_3O_2$, 259.1; m/z found, 260.1 [M+H]$^+$. $^1$H NMR: (400 MHz, $CDCl_3$) δ 8.15 (d, J=15.4 Hz, 1H), 7.71 (d, J=8.8 Hz, 1H), 7.36 (d, J=8.4 Hz, 1H), 6.42 (d, J=15.8 Hz, 1H), 4.63-4.74 (m, 2H), 4.31 (d, J=6.6 Hz, 2H), 2.93 (br s, 3H), 1.64 (t, J=6.6 Hz, 3H), 1.37 (t, J=6.2 Hz, 3H).

Intermediate 18: (5-Bromo-2-methylphenyl)methanol

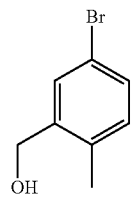

Two batches of the reaction were carried out in parallel. LiAlH$_4$ (4.74 g, 124 mmol) was added to a solution of methyl 5-bromo-2-methylbenzoate (26.0 g, 113 mmol) in THF (260 mL) at 0° C. over a period of 10 minutes under $N_2$. The reaction mixture was warmed to 15° C. and stirred for 12 hours. The reaction mixture was quenched by sequential addition of the following: water (4.75 mL), 15% aqueous NaOH (4.75 mL), and water (14.2 mL). The aqueous phase was extracted with DCM (300 mL), and this organic solvent fraction was dried over anhydrous $Na_2SO_4$ and filtered. The filtrate from the two batches were combined and concentrated under reduced pressure to afford the title compound (42.0 g, 92%) as a white solid which was used in the next step without purification. $^1$H NMR: (400 MHz, $CDCl_3$) δ 7.54 (s, 1H), 7.33 (dd, J=7.8, 1.6 Hz, 1H), 7.00-7.09 (m, 1H), 4.67 (s, 2H), 2.28 (s, 3H).

Intermediate 19: ((5-Bromo-2-methylbenzyl)oxy)(tert-butyl)dimethylsilane

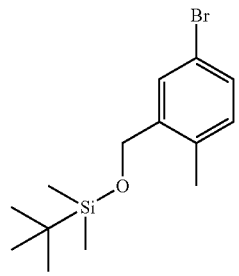 [SMILES: Cc1ccc(Br)cc1CO[Si](C)(C)C(C)(C)C]

TBSCl (89.96 g, 596.8 mmol) was added to a solution of 5-bromo-2-methylphenyl)methanol (80.0 g, 398 mmol) and imidazole (54.2 g, 796 mmol) in DMF (1.5 L) and the reaction mixture was stirred at 25° C. for 16 hour under $N_2$. The reaction mixture was poured into $H_2O$ (2 L) and extracted with EtOAc (1 L×3). These extractions resulted in several organic solvent fractions which were combined, washed with brine (2 L), dried over anhydrous $Na_2SO_4$ and concentrated under reduced pressure. The residue was purified by flash column chromatography (eluent:petroleum ether/ethyl acetate) to afford the title compound (106 g, 83%) as a colorless liquid. $^1$H NMR (500 MHz, $CDCl_3$) δ 7.44 (d, J=2.1 Hz, 1H), 7.16 (dd, J=8.0, 2.3 Hz, 1H), 6.87 (dd, J=8.1, 0.8 Hz, 1H), 4.53 (s, 2H), 2.08 (s, 3H), 0.84 (s, 9H).

Intermediate 20: 2-Methyl-5-(4,4,5,5-tetramethyl-1,3,2-dioxaborolan-2-yl)benzyl acetate

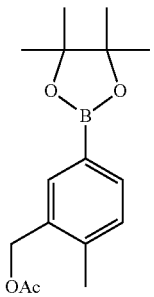 [SMILES: CC(=O)OCc1cc(B2OC(C)(C)C(C)(C)O2)ccc1C]

Step A: 5-Bromo-2-methylbenzyl acetate. A solution of acetyl chloride (10.6 mL, 149 mmol) in DCM (30 mL) was added dropwise at 0° C. over a period of 30 minutes to a mixture of (5-bromo-2-methylphenyl)methanol (25.0 g, 124 mmol) and $Et_3N$ (25.1 g, 248 mmol) in DCM (200 mL). After the addition, the reaction mixture was stirred at 15° C. for 3 hours. Water (200 mL) was added to the reaction mixture and the aqueous layer was extracted with DCM (200 mL×2). These extractions resulted in several organic solvent fractions which were combined, dried over $Na_2SO_4$, filtered and concentrated under reduced pressure. The residue was purified by flash column chromatography (petroleum ether/ethyl acetate, 1:0 to 15:1, gradient elution) to afford the title compound (26.0 g, 86%) as a light yellow oil. $^1$H NMR: (400 MHz, $CDCl_3$) δ 7.48 (d, J=0.8 Hz, 1H), 7.36 (dd, J=8.2, 1.6 Hz, 1H), 7.07 (d, J=8.2 Hz, 1H), 5.08 (s, 2H), 2.29 (s, 3H), 2.13 (s, 3H).

Step B: 2-Methyl-5-(4,4,5,5-tetramethyl-1,3,2-dioxaborolan-2-yl)benzyl acetate. $B_2Pin_2$ (32.6 g, 128 mmol), AcOK (15.7 g, 160 mmol) and $Pd(dppf)Cl_2$ (7.83 g, 10.7 mmol) were sequentially added to a solution of 5-bromo-2-methylbenzyl acetate (26.0 g, 106 mmol) in 1,4-dioxane (150 mL). The mixture was stirred at 90° C. for 12 hours. The reaction mixture was concentrated under reduced pressure and purified by flash column chromatography (eluent: petroleum ether/ethyl acetate, 1:0 to 15:1, gradient elution) to afford the title compound (5.0 g, 16%) as a white solid. $^1$H NMR: (400 MHz, $CDCl_3$) δ 7.76 (s, 1H), 7.70 (d, J=7.4 Hz, 1H), 7.22 (d, J=7.4 Hz, 1H), 5.14 (s, 2H), 2.38 (s, 3H), 2.10 (s, 3H), 1.35 (s, 12H).

Intermediate 21: Ethyl 3-(1-ethyl-4-methyl-1H-benzo[d][1,2,3]triazol-5-yl)-3-(3-(hydroxymethyl)-4-methylphenyl)propanoate

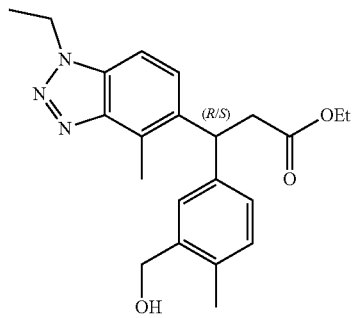 [SMILES: CCOC(=O)CC(c1ccc(C)c(CO)c1)c1ccc2c(nnn2CC)c1C]

Step A: Ethyl 3-(3-(acetoxymethyl)-4-methylphenyl)-3-(1-ethyl-4-methyl-1H-benzo[d][1,2,3]triazol-5-yl)propanoate. Five batches of this reaction sequence were carried out in parallel. $[Rh(COD)Cl]_2$ (1.33 g, 2.7 mmol) was added to a mixture of ethyl (E)-3-(1-ethyl-4-methyl-1H-benzo[d][1,2,3]triazol-5-yl)acrylate (Intermediate 17, 7.0 g, 27 mmol), 2-methyl-5-(4,4,5,5-tetramethyl-1,3,2-dioxaborolan-2-yl) benzyl acetate (Intermediate 20, 15.6 g, 54.0 mmol) and KOH (1.51 g, 27 mmol) in 1,4-dioxane (80 mL) and $H_2O$ (8 mL). The mixture was stirred at 110° C. for 12 hours under $N_2$. The five batches of reaction mixtures were combined, filtered and concentrated under reduced pressure and purified by flash column chromatography (eluent: petroleum ether/ethyl acetate, 2:1) to afford the title compound (30.0 g, 52%) as a yellow oil. $^1$H NMR: (400 MHz, $CDCl_3$) δ 7.26-7.37 (m, 2H), 7.04-7.16 (m, 3H), 5.02 (s, 2H), 4.96 (t, J=7.5 Hz, 1H), 4.62 (q, J=7.6 Hz, 2H), 3.95-4.07 (m, 2H), 2.94-3.15 (m, 2H), 2.83 (br s, 3H), 2.22-2.31 (m, 3H), 2.03-2.09 (m, 3H), 1.58 (t, J=7.2 Hz, 3H), 1.08 (t, J=7.0 Hz, 3H).

Step B: Ethyl 3-(1-ethyl-4-methyl-1H-benzo[d][1,2,3]triazol-5-yl)-3-(3-(hydroxymethyl)-4-methylphenyl)propanoate. A mixture of ethyl 3-(3-(acetoxymethyl)-4-methylphenyl)-3-(1-ethyl-4-methyl-1H-benzo[d][1,2,3]triazol-5-yl) propanoate (1.39 g, 3.00 mmol) and potassium carbonate (870.4 mg, 6.298 mmol) in ethanol (15 mL) was stirred at room temperature overnight. The reaction mixture was concentrated to dryness under reduced pressure, then dissolved in water and DCM. The resulting biphasic mixture was separated and the aqueous layer was extracted with DCM. These extractions resulted in several organic solvent fractions which were combined, dried over $MgSO_4$, filtered and concentrated to dryness under reduced pressure to provide the title compound (1.14 g, 96%) as a foam that was used without further purification. MS (ESI): mass calcd. for $C_{22}H_{27}N_3O_3$, 381.2; m/z found, 382.1 $[M+H]^+$.

Intermediate 22: 1-Ethyl-4-methyl-1H-benzo[d][1,2,3]triazole-5-carbaldehyde

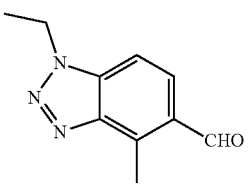

Ozone was bubbled into a solution of ethyl (E)-3-(1-ethyl-4-methyl-1H-benzo[d][1,2,3]triazol-5-yl)acrylate (Intermediate 17, 13.0 g, 50.1 mmol) in DCM (130 mL) at −78° C. for 45 minutes. The reaction mixture was warmed to 15° C. and the ozone was purged from the reaction mixture by bubbling oxygen through the solution. Me$_2$S (30 mL) was added and the mixture was stirred at 15° C. for 12 hours. The reaction mixture was concentrated and purified by flash column chromatography (petroleum ether/ethyl acetate, 10:1 to 1:1, gradient elution) to afford the title compound (5.6 g, 58%) as a yellow solid. MS (ESI): mass calcd. for $C_{10}H_{11}N_3O$, 189.1; m/z found, 190.1 [M+H]$^+$. $^1$H NMR: (400 MHz, CDCl$_3$) δ 10.53 (s, 1H), 8.01 (d, J=8.4 Hz, 1H), 7.44 (d, J=8.4 Hz, 1H), 4.63-4.77 (m, 2H), 3.18 (s, 3H), 1.66 (t, J=6.6 Hz, 3H).

Intermediate 23:
4-Bromo-2-hydrazinyl-3-methylpyridine

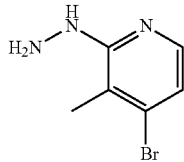

A mixture of hydrazine hydrate (87.4 g, 1.75 mol) and 4-bromo-2-fluoro-3-methylpyridine (32.50 g, 171.0 mmol) was stirred at 25° C. for 6 days. Then aqueous NaOH solution (70 mL, 3 M) and water (70 mL) were added to the mixture and the suspension was stirred at 25° C. for 1 hour. The solid was filtered, washed with water (100 mL), and the solid was dried under reduced pressure to afford the title compound (28.9 g, 84%) as a white solid, which was used in the next step without further purification. $^1$H NMR: (400 MHz, CD$_3$OD) δ 7.78 (d, J=5.6 Hz, 1H), 6.88 (d, J=5.6 Hz, 1H), 2.20 (s, 3H).

Intermediate 24: 7-Bromo-8-methyl-3-(trifluoromethyl)-[1,2,4]triazolo[4,3-a]pyridine

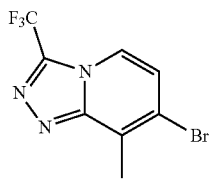

TFAA (151.5 mL, 1.1 mol) was slowly added to 4-bromo-2-hydrazinyl-3-methylpyridine (Intermediate 23, 10.0 g, 49.5 mmol) and the mixture was heated to reflux for 24 hours under an atmosphere of N$_2$. The residue was dissolved in EtOAc (100 mL). The resulting solution washed with aqueous saturated NaHCO$_3$ solution (50 mL×2), brine (80 mL), dried over Na$_2$SO$_4$, and concentrated under reduced pressure to afford the title compound (13.0 g, 93.8%) as a yellow solid, which was used in the next step without further purification. $^1$H NMR: (400 MHz, CDCl$_3$) δ 7.95 (d, J=7.2 Hz, 1H), 7.19 (d, J=7.2 Hz, 1H), 2.79 (s, 3H).

Intermediate 25: Ethyl 3-(3-(hydroxymethyl)-4-methylphenyl)-3-(8-methyl-3-(trifluoromethyl)-[1,2,4]triazolo[4,3-a]pyridin-7-yl)propanoate

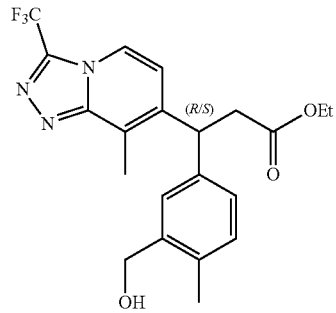 [SMILES: CCOC(=O)CC(c1ccc(C)c(CO)c1)c1ccn2c(C(F)(F)F)nnc2c1C]

Step A: Ethyl (E)-3-(8-methyl-3-(trifluoromethyl)-[1,2,4]triazolo[4,3-a]pyridin-7-yl)acrylate. A suspension of 7-bromo-8-methyl-3-(trifluoromethyl)-[1,2,4]triazolo[4,3-a]pyridine (Intermediate 24, 10.0 g, 35.7 mmol), ethyl acrylate (10.7 g, 107.1 mmol), Pd(PPh$_3$)$_4$ (3.3 g, 2.9 mmol) and TEA (10.8 g, 107.1 mmol) in DMF (100 mL) was sparged with N$_2$ for 10 minutes and then the mixture was heated to 110° C. and stirred under an atmosphere of N$_2$ for 58 hours. Water (100 mL) was added and the mixture was stirred at 25° C. for 10 minutes. The aqueous layer was extracted with CH$_2$Cl$_2$ (80 mL×2). These extractions resulted in several organic solvent fractions which were combined, washed with water (50 mL×4), brine (50 mL), dried over Na$_2$SO$_4$, filtered and concentrated under reduced pressure. The residue was purified by flash column chromatography (eluent:petroleum ether/ethyl acetate, 6:1) to afford the title compound (10.7 g, 84%) as a white solid. $^1$H NMR: (400 MHz, CDCl$_3$) δ 8.07 (d, J=7.2 Hz, 1H), 7.98 (d, J=16.0 Hz, 1H), 7.21 (d, J=7.2 Hz, 1H), 6.50 (d, J=16.0 Hz, 2H), 4.31 (q, J=7.2 Hz, 2H), 2.86 (s, 3H), 1.36 (t, J=7.2 Hz, 3H).

Step B: Ethyl 3-(3-(acetoxymethyl)-4-methylphenyl)-3-(8-methyl-3-(trifluoromethyl)-[1,2,4]triazolo[4,3-a]pyridin-7-yl)propanoate. Eight batches of the reaction were carried out in parallel. A mixture of ethyl (E)-3-(8-methyl-3-(trifluoromethyl)-[1,2,4]triazolo[4,3-a]pyridin-7-yl)acrylate (2.0 g, 6.7 mmol), 2-methyl-5-(4,4,5,5-tetramethyl-1,3,2-dioxaborolan-2-yl)benzyl acetate (Intermediate 20, 2.91 g, 10.0 mmol), [Rh(COD)Cl]$_2$ (329.5 mg, 0.668 mmol) and Na$_2$CO$_3$ (708.4 mg, 6.7 mmol) in 1,4-dioxane (18 mL) and water (3 mL), was sparged with N$_2$ for 10 minutes and stirred at 80° C. under an atmosphere of N$_2$ for 25 hours. The eight batches of the reaction were combined. The resulting mixture was filtered to remove solids and the filtrate was collected. The filtrate was concentrated under reduced pressure and the residue was purified by flash column chromatography (eluent:petroleum ether/ethyl acetate, 15:1 to 8:1, gradient elution) to afford the title compound (18.0 g, 75%) as a yellow gum. $^1$H NMR: (400 MHz, CDCl$_3$) δ 8.01 (d, J=7.2 Hz, 1H), 7.18-7.07 (m, 3H), 6.95 (d, J=7.2 Hz, 1H), 5.07 (s, 2H), 4.97 (t, J=8.0 Hz, 1H), 4.08 (q, J=7.2 Hz, 2H), 3.14 (dd, J=15.6, 6.8 Hz, 1H), 3.01 (dd, J=15.6, 6.8 Hz, 1H), 2.86 (s, 3H), 2.31 (s, 3H), 2.09 (s, 3H), 1.17 (t, J=7.2 Hz, 3H).

Step C: Ethyl 3-(3-(hydroxymethyl)-4-methylphenyl)-3-(8-methyl-3-(trifluoromethyl)-[1,2,4]triazolo[4,3-a]pyridin-7-yl)propanoate. Two batches of the reaction were carried out in parallel. Ethyl 3-(3-(acetoxymethyl)-4-methylphenyl)-3-(8-methyl-3-(trifluoromethyl)-[1,2,4]triazolo[4,3-a]

pyridin-7-yl)propanoate (8.5 g, 18.3 mmol) was dissolved in ethanol (200 mL) and stirred at 25° C. 2 M Aqueous HCl (90 mL) was added to the above solution and the mixture was stirred at 25° C. for 24 hours. The two batches of the reaction were combined and the resulting reaction mixture was slowly quenched with aqueous saturated NaHCO$_3$ solution. Ethanol was removed under reduced pressure and the aqueous layer was extracted with CH$_2$Cl$_2$ (200 mL×3). These extractions resulted in several organic solvent fractions which were combined, dried over Na$_2$SO$_4$, filtered and concentrated under reduced pressure. The residue was purified by column chromatography on silica gel (eluent:petroleum ether/ethyl acetate, 8:1 to 4:1, gradient elution) to afford the title compound (10.0 g, 65%) as a yellow gum. MS (ESI): mass calcd. for C$_{21}$H$_{22}$F$_3$N$_3$O$_3$, 421.2; m/z found, 422.2 [M+H]$^+$. $^1$H NMR: (400 MHz, CDCl$_3$) δ 7.99 (d, J=7.2 Hz, 1H), 7.25 (s, 1H), 7.13 (d, J=7.6 Hz, 1H), 7.06 (d, J=8.0 Hz, 1H), 6.92 (d, J=7.2 Hz, 1H), 4.96 (t, J=8.0 Hz, 1H), 4.67 (s, 2H), 4.06 (q, J=7.2 Hz, 2H), 3.15 (dd, J=15.6, 6.8 Hz, 1H), 3.01 (dd, J=15.6, 6.8 Hz, 1H), 2.85 (s, 3H), 2.29 (s, 3H), 1.16 (t, J=7.2 Hz, 3H).

Intermediate 26: Ethyl (*S)-3-(3-(hydroxymethyl)-4-methylphenyl)-3-(8-methyl-3-(trifluoromethyl)-[1,2,4]triazolo[4,3-a]pyridin-7-yl)propanoate

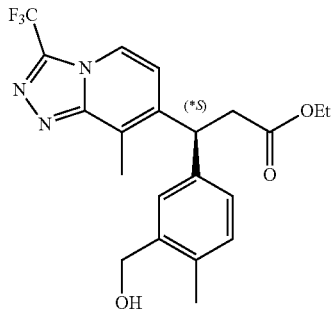 [SMILES: CCOC(=O)C[C@@H](c1ccc(C)c(CO)c1)c1ccn2c(C(F)(F)F)nnc2c1C]

The mixture of ethyl 3-(3-(hydroxymethyl)-4-methylphenyl)-3-(8-methyl-3-(trifluoromethyl)-[1,2,4]triazolo[4,3-a]pyridin-7-yl)propanoate enantiomers (Intermediate 25, 16 g) was separated by chiral SFC (stationary phase: Chiralpak AD-H 5 μm 250×30 mm, Mobile phase: 65% CO$_2$, 35% MeOH) to afford two enantiomers. The first eluting isomer (8.04 g) was designated (*S). MS (ESI): mass calcd. for C$_{21}$H$_{22}$F$_3$N$_3$O$_3$, 421.2; m/z found, 422.2 [M+H]$^+$. $^1$H NMR (500 MHz, CDCl$_3$) δ 7.99 (d, J=7.2 Hz, 1H), 7.27-7.26 (m, 1H), 7.14-7.10 (m, 1H), 7.07-7.03 (m, 1H), 6.93 (d, J=7.3 Hz, 1H), 5.01-4.91 (m, 1H), 4.67 (d, J=3.2 Hz, 2H), 4.11-4.02 (m, 2H), 3.20-3.11 (m, 1H), 3.08-2.98 (m, 1H), 2.84 (s, 3H), 2.28 (s, 3H), 2.15-2.06 (m, 1H), 1.20-1.13 (m, 3H).

Intermediate 27: Ethyl (*R)-3-(3-(hydroxymethyl)-4-methylphenyl)-3-(8-methyl-3-(trifluoromethyl)-[1,2,4]triazolo[4,3-a]pyridin-7-yl)propanoate

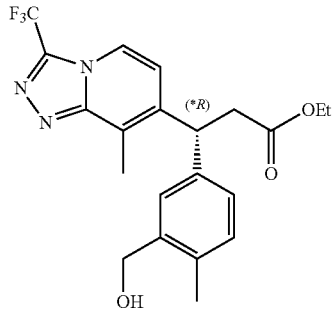 [SMILES: CCOC(=O)C[C@H](c1ccc(C)c(CO)c1)c1ccn2c(C(F)(F)F)nnc2c1C]

The second eluting isomer (7.94 g) from the separation of isomers by chiral SFC described in Intermediate 26 was designated (*R). MS (ESI): mass calcd. for C$_{21}$H$_{22}$F$_3$N$_3$O$_3$, 421.2; m/z found, 422.2 [M+H]$^+$. $^1$H NMR (500 MHz, CDCl$_3$) δ 7.99 (d, J=7.2 Hz, 1H), 7.29-7.24 (m, 1H), 7.14-7.10 (m, 1H), 7.08-7.03 (m, 1H), 6.93 (d, J=7.3 Hz, 1H), 4.99-4.94 (m, 1H), 4.67 (d, J=5.0 Hz, 2H), 4.12-4.01 (m, 2H), 3.20-3.11 (m, 1H), 3.08-2.97 (m, 1H), 2.84 (s, 3H), 2.28 (s, 3H), 2.15-2.09 (m, 1H), 1.16 (t, J=7.1 Hz, 3H).

Intermediate 28: 8-Methyl-3-(trifluoromethyl)-[1,2,4]triazolo[4,3-a]pyridine-7-carbaldehyde

Step A: 8-Methyl-3-(trifluoromethyl)-7-vinyl-[1,2,4]triazolo[4,3-a]pyridine. A mixture of 7-bromo-8-methyl-3-(trifluoromethyl)-[1,2,4]triazolo[4,3-a]pyridine (Intermediate 24, 38.0 g, 136 mmol), potassium trifluoro(vinyl)borate (36.3 g, 271 mmol), K$_3$PO$_4$ (86.0 g, 405 mmol), 1,4-dioxane (400 mL), and H$_2$O (80 mL) was sparged with Ar for 5 minutes and then treated with Pd(dppf)Cl$_2$ (5.0 g, 6.8 mmol). The resulting mixture was sparged with Ar for another 5 minutes and then stirred at 110° C. for 16 hours. After cooling to room temperature, the resulting suspension was filtered. The filtrate was poured into H$_2$O (100 mL) and the aqueous layer was extracted with ethyl acetate (200 mL×3). These extractions resulted in several organic solvent fractions which were combined, dried over anhydrous Na$_2$SO$_4$, filtered and concentrated to dryness under reduced pressure. The residue was purified by flash column chromatography (eluent:petroleum ether/ethyl acetate, 10:1 to 1:1, gradient elution) to afford the title compound (33 g, 99%) as a brown solid. MS (ESI): mass calcd. for C$_{10}$H$_8$F$_3$N$_3$ 227.1 m/z, found 227.9 [M+H]$^+$.

Step B: 8-Methyl-3-(trifluoromethyl)-[1,2,4]triazolo[4,3-a]pyridine-7-carbaldehyde. K$_2$OsO$_4$*2H$_2$O (1.6 g, 4.3 mmol) was added to a solution of 8-methyl-3-(trifluoromethyl)-7-vinyl-[1,2,4]triazolo[4,3-a]pyridine (25.0 g, 110 mmol) and 1,4-dioxane (600 mL) in distilled H₂O (600 mL). The resulting mixture was treated with NaIO₄ (75.0 g, 351 mmol), stirred at room temperature for 2 hours and then concentrated to dryness under reduced pressure. The residue was diluted with H₂O (100 mL) and the aqueous layer was extracted with ethyl acetate (150 mL×3). These extractions resulted in several organic solvent fractions which were combined, dried over anhydrous Na₂SO₄, filtered and concentrated to dryness under reduced pressure. The residue was purified by flash column chromatography (eluent:petroleum ether/ethyl acetate, 10:1 to 1:1, gradient elution) to afford the title compound (22 g, 87%) as a gray solid. MS (ESI): mass calcd. for C₉H₆F₃N₃O, 229.1 m/z; found 230.0 [M+H]⁺. ¹H NMR (400 MHz, DMSO-d₆) δ 10.44 (s, 1H), 8.52 (d, J=6.4 Hz, 1H), 7.42 (d, J=7.2 Hz, 1H), 2.98 (s, 3H).

Intermediate 29: 5-Bromo-1-cyclopropyl-4-methyl-1H-benzo[d][1,2,3]triazole

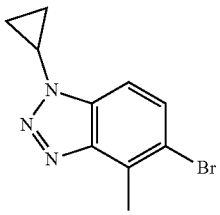

Step A: N-Cyclopropyl-3-methyl-2-nitroaniline. Three batches of the reaction were carried out in parallel. A mixture of 1-fluoro-3-methyl-2-nitrobenzene (10 g, 64.46 mmol), cyclopropanamine (18.40 g, 322.3 mmol, 22.33 mL) and TEA (13.05 g, 128.9 mmol) in MeCN (30 mL) was stirred at 112° C. for 16 hours. After cooling to room temperature, the reaction mixtures from the three batches were combined, diluted with EtOAc (200 mL) and sequentially washed with 10% aqueous NaHCO₃ solution (100 mL) and brine (100 mL). The organic layer was concentrated under reduced pressure to afford the title compound (35 g, 94%) as a yellow solid, which was used without further purification.

Step B: 4-Bromo-N-cyclopropyl-3-methyl-2-nitroaniline. NBS (30.79 g, 172.9 mmol) was added to a mixture of N-cyclopropyl-3-methyl-2-nitroaniline (35.0 g, 182 mmol) in AcOH (300 mL) at 20° C., and the reaction was stirred at 20° C. for 6 hours. The reaction was poured into water (1000 mL) and the aqueous layer was extracted with EtOAc (500 mL×2). These extractions resulted in several organic solvent fractions which were combined, washed with aqueous saturated NaHCO₃ (500 mL×3) solution, dried over Na₂SO₄, filtered and concentrated under reduced pressure to afford the title compound (46 g, 93%) as a red solid. MS (ESI): mass calcd. for C₁₀H₁₁BrN₂O₂, 270.0; m/z found, 270.9 [M+H]⁺.

Step C: 4-Bromo-N¹-cyclopropyl-3-methylbenzene-1,2-diamine. A mixture of Raney Ni (8.60 g, 100 mmol) and 4-bromo-N-cyclopropyl-3-methyl-2-nitroaniline (30.0 g, 110 mmol) in ethanol (300 mL) was stirred at room temperature under H₂ (50 psi) for 6 hours. The reaction mixture was filtered, washed with ethanol (50 mL×2) and the solvents were removed under reduced pressure to afford the title compound (21 g, 61%) as a red solid. MS (ESI): mass calcd. for C₁₀H₁₃BrN₂, 240.0; m/z found, 240.7 [M+H]⁺.

Step D: 5-Bromo-1-cyclopropyl-4-methyl-1H-benzo[d][1,2,3]triazole. A solution of NaNO₂ (7.76 g, 112 mmol) in H₂O (30 mL) was added to a solution of 4-bromo-N¹-cyclopropyl-3-methylbenzene-1,2-diamine (26.0 g, 107 mmol) in 2 M HCl (250 mL, 500 mmol) at 0° C. and the reaction was stirred at 0-10° C. for 1 hour. CH₂Cl₂ (300 mL) was added to the reaction mixture, and the aqueous phase was extracted with CH₂Cl₂ (200 mL×2). These extractions resulted in several organic solvent fractions which were combined, washed with brine (200 mL), dried with anhydrous Na₂SO₄, filtered and concentrated under reduced pressure. The residue was purified by flash column chromatography (eluent:petroleum ether/CH₂Cl₂, 10:1 to 3:1, gradient elution) to afford the title compound (8.4 g, 27%) as an off white solid. MS (ESI): mass calcd. for C₁₀H₁₀BrN₃, 251.0; m/z found, 251.8 [M+H]⁺. ¹H NMR (500 MHz, CDCl₃) δ 7.61 (d, J=8.7 Hz, 1H), 7.38-7.35 (m, 1H), 3.80-3.69 (m, 1H), 2.82 (s, 3H), 1.38-1.27 (m, 4H).

Intermediate 30: 8-Methyl-7-(4,4,5,5-tetramethyl-1,3,2-dioxaborolan-2-yl)-3-(trifluoromethyl)-[1,2,4]triazolo[4,3-a]pyridine

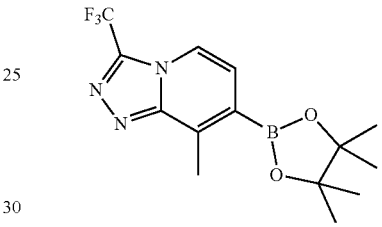

A mixture of 7-bromo-8-methyl-3-(trifluoromethyl)-[1,2,4]triazolo[4,3-a]pyridine (Intermediate 24, 1.2 g, 4.3 mmol), 4,4,4',4',5,5,5',5'-octamethyl-2,2'-bi(1,3,2-dioxaborolane) (5.4 g, 21 mmol), KOAc (1.26 g, 12.8 mmol) and toluene (15 mL) was sparged with N₂ for 5 minutes and then treated with Pd(dppf)Cl₂ (314 mg, 0.429 mmol). The mixture was sparged with N₂ for another 5 minutes and then stirred at 80° C. for 36 hours. After cooling to room temperature, the suspension was filtered through diatamaceous earth such as Celite® and washed with ethyl acetate (30 mL). The filtrate was concentrated to dryness under reduced pressure and the residue was purified by flash column chromatography (eluent:petroleum ether/ethyl acetate, 50:1 to 5:1, gradient elution) to afford the title compound (1.1 g, 63%) as a white solid. ¹H NMR (400 MHz, CDCl₃) δ 7.98 (d, J=6.8 Hz, 1H), 7.30 (d, J=7.1 Hz, 1H), 2.95 (s, 3H), 1.36 (s, 12H).

Intermediate 31: Ethyl 3-(3-(chloromethyl)-4-methylphenyl)-3-(1-ethyl-4-methyl-1H-benzo[d][1,2,3]triazol-5-yl)propanoate

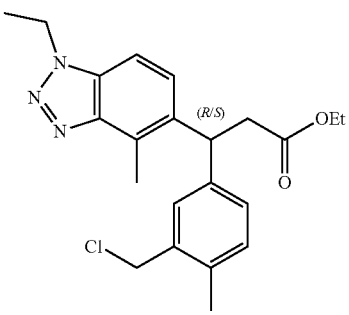 [SMILES: CCOC(=O)CC(c1ccc(C)c(CCl)c1)c1ccc2c(nnn2CC)c1C]

Thionyl chloride (0.85 mL, 12 mmol) was added to a solution of ethyl 3-(1-ethyl-4-methyl-1H-benzo[d][1,2,3]triazol-5-yl)-3-(3-(hydroxymethyl)-4-methylphenyl)propanoate (Intermediate 21, 2.94 g, 7.71 mmol) in DCM (38 mL). Five drops of DMF were added to the solution, and the reaction was stirred at room temperature for 4 hours. The reaction was quenched with saturated aqueous NaHCO$_3$, then extracted with DCM. These extractions resulted in several organic solvent fractions which were combined, dried over MgSO$_4$, filtered, and concentrated to dryness under reduced pressure to provide the title compound (3.05 g, 99%) as an oil which was used without further purification. MS (ESI): mass calcd. for C$_{22}$H$_{26}$ClN$_3$O$_2$, 399.2; m/z found, 400.0 [M+H]$^+$.

Intermediate 32: Ethyl 3-(3-(chloromethyl)-4-methylphenyl)-3-(1-cyclopropyl-4-methyl-1H-benzo[d][1,2,3]triazol-5-yl)propanoate

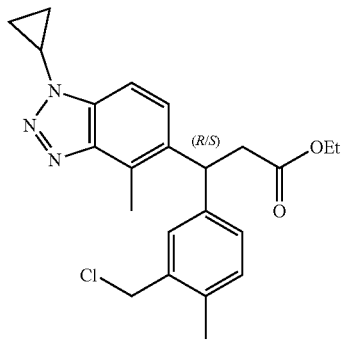 [SMILES: CCOC(=O)CC(c1ccc(C)c(CCl)c1)c1ccc2c(nnn2C2CC2)c1C]

Step A: Ethyl (E)-3-(1-cyclopropyl-4-methyl-1H-benzo[d][1,2,3]triazol-5-yl)acrylate. 1,4-Dioxane (17 mL) and water (5 mL) were added to a mixture of 5-bromo-1-cyclopropyl-4-methyl-1H-benzo[d][1,2,3]triazole (Intermediate 29, 1.25 g, 4.96 mmol), potassium carbonate (1.38 g, 9.99 mmol), Pd(dppf)Cl$_2$ (364 mg, 0.497 mmol), and ethyl (E)-3-(4,4,5,5-tetramethyl-1,3,2-dioxaborolan-2-yl)acrylate (1.37 g, 6.05 mmol). The mixture was heated to 90° C. and stirred for 4.5 hours. After this time, the reaction was cooled to room temperature, then filtered through a pad of diatomaceous earth such as Celite®. The pad was rinsed with ethyl acetate. The filtrate was collected, washed with brine, then dried over MgSO$_4$, filtered and concentrated to dryness under reduced pressure. The product was purified by flash column chromatography (0 to 20% ethyl acetate/DCM, gradient elution) to afford the title compound (980 mg, 73%). MS (ESI): mass calcd. for C$_{15}$H$_{17}$N$_3$O$_2$, 271.1; m/z found, 272.2 [M+H]$^+$.

Step B: Ethyl 3-(1-cyclopropyl-4-methyl-1H-benzo[d][1,2,3]triazol-5-yl)-3-(3-(hydroxymethyl)-4-methylphenyl)propanoate. (3-(Hydroxymethyl)-4-methylphenyl)boronic acid (907 mg, 5.46 mmol), triethylamine (0.76 mL, 5.5 mmol), and [Rh(COD)Cl]$_2$ (92 mg, 0.19 mmol) were added to a solution of ethyl (E)-3-(1-cyclopropyl-4-methyl-1H-benzo[d][1,2,3]triazol-5-yl)acrylate (980 mg, 3.6 mmol) in 1,4-dioxane (25 mL) and water (12 mL). The mixture was stirred at 95° C. for 2 hours. Additional (3-(hydroxymethyl)-4-methylphenyl)boronic acid (905 mg, 5.45 mmol) and [Rh(COD)Cl]$_2$ (92 mg, 0.19 mmol) were then added and the reaction was stirred at 95° C. for 1 hour. After this time, the reaction was cooled to room temperature, then diluted with water and ethyl acetate. The resulting biphasic mixture was separated and the aqueous layer was extracted with ethyl acetate. These extractions resulted in several organic solvent fractions which were combined, dried over MgSO$_4$, filtered and concentrated to dryness under reduced pressure. The product was purified by flash column chromatography (0 to 50% ethyl acetate/hexanes, gradient elution) to afford the title compound (1.2 g, 84%). MS (ESI): mass calcd. for C$_{23}$H$_{27}$N$_3$O$_3$, 393.2; m/z found, 394.1 [M+H]$^+$.

Step C: Ethyl 3-(3-(chloromethyl)-4-methylphenyl)-3-(1-cyclopropyl-4-methyl-1H-benzo[d][1,2,3]triazol-5-yl)propanoate. The title compound (1.2 g, 97%) was prepared using analogous conditions as described in Intermediate 31 where ethyl 3-(1-cyclopropyl-4-methyl-1H-benzo[d][1,2,3]triazol-5-yl)-3-(3-(hydroxymethyl)-4-methylphenyl)propanoate was used instead of ethyl 3-(1-ethyl-4-methyl-1H-benzo[d][1,2,3]triazol-5-yl)-3-(3-(hydroxymethyl)-4-methylphenyl)propanoate. MS (ESI): mass calcd. for C$_{23}$H$_{26}$ClN$_3$O$_2$, 411.2; m/z found, 412.1 [M+H]$^+$.

Intermediate 33: 5-Bromo-7-(difluoromethoxy)-1-methyl-1H-benzo[d][1,2,3]triazole

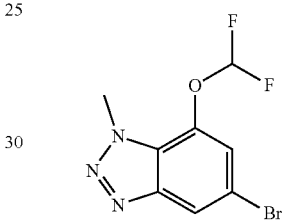

Step A: 2-(Difluoromethoxy)-6-nitroaniline. To a solution of 2-amino-3-nitrophenol (20.2 g, 131 mmol) in DMF (130 mL) and water (13 mL) was added sodium chlorodifluoroacetate (49.8 g, 327 mmol) and K$_2$CO$_3$ (27.1 g, 196 mmol). The reaction mixture was heated under Ar to 100° C. under a reflux condenser for 2.5 hours. The reaction mixture was diluted with water (300 mL) and extracted with EtOAc (300 mL). The organic phase was washed with 1 N aqueous NaOH (200 mL). The basic aqueous phase was extracted with EtOAc (200 mL). These extractions resulted in several organic solvent fractions which were combined, dried over Na$_2$SO$_4$, filtered, and concentrated to dryness under reduced pressure. The residue was purified by flash column chromatography (eluent: 40% DCM/heptane), to afford the title compound (14.6 g, 55%) as a yellow oil. $^1$H NMR (400 MHz, CDCl$_3$) δ 8.02 (dd, J=8.8, 1.3 Hz, 1H), 7.30-7.25 (m, 1H), 6.67 (dd, J=8.8, 7.8 Hz, 1H), 6.54 (t, J=72.8 Hz, 1H), 6.47-6.25 (m, 2H).

Step B: 4-Bromo-2-(difluoromethoxy)-6-nitroaniline. To a solution of 2-(difluoromethoxy)-6-nitroaniline (14.6 g, 71.3 mmol) in AcOH (182 mL) was added sodium acetate (9.36 g, 114 mmol) followed by bromine (4.05 mL, 78.5 mmol). The reaction mixture was stirred at room temperature under air for 20 minutes. Water (180 mL) was added and the precipitate was collected by vacuum filtration and air-dried. This yellow solid was further dried under vacuum, to afford the title compound (15.3 g, 76%). MS (ESI): mass calcd. for C$_7$H$_5$BrF$_2$N$_2$O$_3$, 284.0; m/z found, 284.9 [M+H]$^+$. $^1$H NMR (400 MHz, CDCl$_3$) δ 8.19 (d, J=2.0 Hz, 1H), 7.39 (d, J=2.5 Hz, 1H), 6.56 (t, J=72.0 Hz, 1H), 6.49-6.26 (m, 2H).

Step C: 4-Bromo-2-(difluoromethoxy)-N-methyl-6-nitroaniline. To a solution of 4-bromo-2-(difluoromethoxy)-

6-nitroaniline (15.3 g, 54.2 mmol) in DMF (100 mL) at 0° C. was added NaH (60% dispersion in mineral oil, 2.60 g, 65.0 mmol) and the reaction mixture was stirred at 0° C. under Ar for 45 minutes. Iodomethane (3.71 mL, 59.6 mmol) was then added and the reaction mixture was stirred for 30 minutes at 0° C. The reaction mixture was poured into water (250 mL). The mixture was filtered and the precipitate was washed with water, air-dried, and dried under vacuum to yield the title compound (15.7 g) which was used without further purification in the next reaction. MS (ESI): mass calcd. for $C_8H_7BrF_2N_2O_3$, 298.0; m/z found, 299.0 [M+H]$^+$.

Step D: 4-Bromo-6-(difluoromethoxy)-N$^1$-methylbenzene-1,2-diamine. To a solution of 4-bromo-2-(difluoromethoxy)-N-methyl-6-nitroaniline (15.7 g, 52.9 mmol) in AcOH (160 mL) was added zinc (10.4 g, 159 mmol). The reaction mixture was stirred for 16 hours under Ar at room temperature. The reaction mixture was filtered through a bed of diatomaceous earth such as Celite®, washing thoroughly with EtOAc. The filtrate was concentrated to provide a residue. The residue was concentrated twice from toluene under reduced pressure to remove residual AcOH. The residue was purified by flash column chromatography (eluent: 0 to 40% EtOAc/heptanes, gradient elution), to afford the title compound (6.34 g, 45%) as a red oil. MS (ESI): mass calcd. for $C_8H_9BrF_2N_2O$, 268.0; m/z found, 269.0 [M+H]$^+$. $^1$H NMR (400 MHz, CDCl$_3$) δ 6.72 (d, J=2.0 Hz, 1H), 6.65-6.63 (m, 1H), 6.47 (t, J=73.8 Hz, 1H), 3.88-4.16 (m, 2H), 2.66 (s, 3H).

Step E: 5-Bromo-7-(difluoromethoxy)-1-methyl-1H-benzo[d][1,2,3]triazole. To 4-bromo-6-(difluoromethoxy)-N$^1$-methylbenzene-1,2-diamine (6.34 g, 23.7 mmol) was added H$_2$SO$_4$ (10% aqueous solution, 24 mL, 450 mmol). The resulting suspension was cooled to 0° C. Sodium nitrite (2.29 g, 33.2 mmol) was added slowly over 6 minutes, and the reaction mixture was stirred at 0° C. for 30 minutes. Water (50 mL) was added and the mixture was filtered. The collected tan solid was washed with water (twice) and air-dried. It was subsequently dried further under vacuum to provide the title compound (6.71 g) which was used without further purification in the next step. MS (ESI): mass calcd. for $C_8H_6BrF_2N_3O$, 279.0; m/z found, 280.0 [M+H]$^+$. $^1$H NMR (400 MHz, CDCl$_3$) δ 8.05 (d, J=1.0 Hz, 1H), 7.28-7.27 (m, 1H), 6.72 (t, J=72.0 Hz, 1H), 4.45 (s, 3H).

Intermediate 34: 5-Bromo-7-cyclopropoxy-1-methyl-1H-benzo[d][1,2,3]triazole

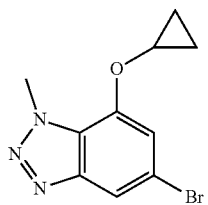

Step A: 2-Cyclopropoxy-6-nitroaniline. A mixture of cesium hydroxide monohydrate (16.08 g, 95.76 mmol), DMSO (50 mL), 2-amino-3-nitrophenol (14.71 g, 95.44 mmol), and cyclopropyl bromide (21.1 g, 174 mmol) was placed in a 500 mL high pressure flask with a screw cap, flushed with argon for 1 minute, then sealed and stirred at 150° C. After 16 hours, the reaction was cooled to room temperature, treated with additional cyclopropyl bromide (24.44 g, 202.0 mmol), argon was bubbled through the solution for 30 seconds, then the reaction vessel was re-sealed and stirred at 150° C. After 24 hours, the reaction was cooled to room temperature and the reaction mixture was allowed to sit for 9 weeks. The reaction mixture was then poured into water (400 mL) and 5:1 diethyl ether:DCM (600 mL) was added. A dark emulsion formed and it was filtered through diatomaceous earth such as Celite® to allow the organic and aqueous layers to separate. The aqueous layer of the filtrate was separated and was extracted with DCM (1×600 mL). The combined organic layers were dried over Na$_2$SO$_4$, filtered, and concentrated to dryness under reduced pressure. The residue was initially purified by flash column chromatography (eluent: heptanes/ethyl acetate, 95:5 to 70:30, gradient elution). Since impurities were still present, the residue was subsequently purified again by flash column chromatography (eluent: heptanes/ethyl acetate, 95:5 to 80:20, gradient elution) to provide the title compound (2.22 g, 12%). MS (ESI): mass calcd. for $C_9H_{10}N_2O_3$, 194.1; m/z found, 195.0 [M+H]$^+$. $^1$H NMR (400 MHz, CDCl$_3$) δ 7.75 (dd, J=1.3, 8.8 Hz, 1H), 7.28-7.24 (m, 1H), 6.62 (t, J=8.2 Hz, 1H), 6.33 (br s, 2H), 3.83-3.78 (m, 1H), 0.90-0.80 (m, 4H).

Step B: 4-Bromo-2-cyclopropoxy-6-nitroaniline. A mixture of 4-bromo-2-cyclopropoxy-6-nitroaniline (2.10 g, 10.8 mmol), HOAc (23 mL), and sodium acetate (1.405 g, 17.13 mmol) was stirred at 10-15° C. while a solution of bromine (1.92 g, 12.0 mmol) in HOAc (5 mL) was added dropwise over 6 minutes. The cooling bath was immediately removed and the reaction stirred at room temperature. After 2.5 hours, the reaction was treated with water (90 mL) over 3-4 minutes, filtered, and the filter cake washed with water (2×25 mL) and dried under reduced pressure to provide the title compound (2.92 g, 99%). MS (ESI): mass calcd. for $C_9H_9BrN_2O_3$, 272.0; m/z found, 273.0, 275.0 [M+H]$^+$. $^1$H NMR (400 MHz, CDCl$_3$) δ 7.92 (d, J=2.0 Hz, 1H), 7.32 (d, J=2.0 Hz, 1H), 6.36 (br s, 2H), 3.80 (tt, J=5.8, 3.0 Hz, 1H), 0.95-0.82 (m, 5H).

Step C: 4-Bromo-2-cyclopropoxy-N-methyl-6-nitroaniline. A solution of 4-bromo-2-cyclopropoxy-6-nitroaniline (2.79 g, 10.2 mmol) and DMF (41 mL) was stirred at 0° C. under argon while NaH (60.8% dispersion in mineral oil, 0.451 g, 11.4 mmol) was added in one portion. The reaction was stirred for 30 minutes. While keeping the reaction mixture at 0° C., a solution of MeI (1.605 g, 11.31 mmol) in DMF (8.5 mL, 10.2 mmol) was added dropwise over 10 minutes. The reaction was stirred at 0° C. for an additional 40 minutes, and was then treated with water (60 mL) dropwise over 6 minutes. Stirring was stopped while still at 0° C. for ~30 minutes and the reaction mixture was then filtered. The filter cake was washed with water (2×25 mL), dried under reduced pressure, and purified by flash column chromatography (eluent: heptanes/ethyl acetate, 100:0 to 80:20, gradient elution) to provide the title compound (1.54 g, 53%). MS (ESI): mass calcd. for $C_{10}H_{11}BrN_2O_3$, 286.0; m/z found, 287.1, 289.1 [M+H]$^+$. $^1$H NMR (400 MHz, CDCl$_3$) δ 7.87 (d, J=2.0 Hz, 1H), 7.65 (br s, 1H), 7.32 (d, J=2.5 Hz, 1H), 3.72 (tt, J=5.9, 3.0 Hz, 1H), 3.13 (d, J=5.1 Hz, 3H), 0.90-0.80 (m, 4H).

Step D: 4-Bromo-6-cyclopropoxy-Ni-methylbenzene-1,2-diamine. A solution of 4-bromo-2-cyclopropoxy-N-methyl-6-nitroaniline (1.51 g, 5.26 mmol) and HOAc (26 mL) was stirred at room temperature while iron powder (1.47 g, 26.3 mmol) was added in one portion. The reaction was stirred for 2 hours and then diluted with EtOAc (30 mL) and filtered through diatomaceous earth such as Celite®. The filter cake was washed with EtOAc (4×30 mL), the combined filtrates were concentrated to dryness under reduced pressure, and the residue was partitioned between EtOAc (100 mL) and 10 M NaOH (20 mL). The resulting emulsion was filtered through diatomaceous earth such as Celite® and the filter cake washed with EtOAc (2×50 mL). The aqueous layer was extracted with EtOAc (1×100 mL) and the organic solvent fractions were combined, dried over $Na_2SO_4$, filtered and concentrated to dryness under reduced pressure to provide the title compound. MS (ESI): mass calcd. for $C_{10}H_{13}BrN_2O$, 256.0; m/z found, 257.0, 259.0 $[M+H]^+$. $^1H$ NMR (400 MHz, $CDCl_3$) δ 6.78 (d, J=2.0 Hz, 1H), 6.53 (d, J=2.0 Hz, 1H), 3.94-3.82 (m, 2H), 3.82-3.58 (m, 1H), 2.65-2.57 (m, 3H), 0.84-0.70 (m, 4H).

Step E: 5-Bromo-7-cyclopropoxy-1-methyl-1H-benzo[d][1,2,3]triazole. A thick slurry of 4-bromo-6-cyclopropoxy-N1-methylbenzene-1,2-diamine (1.39 g, 5.41 mmol) in water (4.9 mL) and $H_2SO_4$ (1.2 mL, 23 mmol) at 0° C. was treated with a solution of sodium nitrite (0.536 g, 7.77 mmol) in water (4.9 mL) as an intermittent thin stream by syringe over 4 minutes with periodic spatula stirring of the thick mixture. The mixture was intermittently stirred with a spatula and shaken at 0° C. for an additional 10 minutes, at which point the reaction thinned to an easily stirring mixture. After 35 minutes at 0° C., the reaction was quenched with water (10 mL), allowed to chill in the ice bath, and filtered. The filter cake was washed with water (4×10 mL) and the filter cake was dried under reduced pressure to provide the title compound (1.31 g, 90%) which was used without further purification. MS (ESI): mass calcd. for $C_{10}H_{10}BrN_3O$, 267.0; m/z found, 268.0, 270.0 $[M+H]^+$. $^1H$ NMR (400 MHz, $CDCl_3$) δ 7.77 (d, J=1.5 Hz, 1H), 7.21 (d, J=1.0 Hz, 1H), 4.39 (s, 3H), 3.94-3.88 (m, 1H), 0.98-0.85 (m, 4H).

Intermediate 35: Ethyl (E)-3-(1-(cyclopropylmethyl)-4-methyl-1H-benzo[d][1,2,3]triazol-5-yl)acrylate

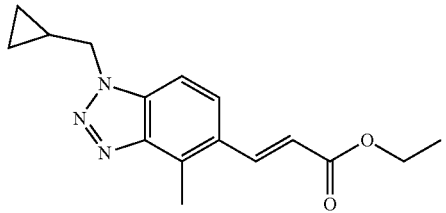 [SMILES: CCOC(=O)/C=C/c1ccc2c(nnn2CC2CC2)c1C]

Step A: N-(Cyclopropylmethyl)-3-methyl-2-nitroaniline. A solution of 3-fluoro-2-nitrotoluene (6.92 g, 44.6 mmol), cyclopropylmethylamine (4.45 g, 62.6 mmol) and TEA (6.2 mL, 45 mmol) was heated in a sealed tube to 150° C. under argon. After 4 hours, the reaction was cooled to room temperature, combined, and partitioned between EtOAc (80 mL) and 1 M $NaH_2PO_4$ (80 mL). The organic solvent fraction was dried over $Na_2SO_4$, filtered, and concentrated to dryness under reduced pressure to provide the title compound contaminated with 7 mol % EtOAc (9.36 g, 102%). MS (ESI): mass calcd. for $C_{11}H_{14}N_2O_2$, 206.2; m/z found, 207.1 $[M+H]^+$. $^1H$ NMR (400 MHz, $CDCl_3$) δ 7.21 (t, J=7.8 Hz, 1H), 6.62 (d, J=8.6 Hz, 2H), 6.51 (d, J=7.6 Hz, 1H), 3.04 (dd, J=7.1, 5.1 Hz, 2H), 2.47 (s, 3H), 1.18-1.08 (m, 1H), 0.66-0.55 (m, 2H), 0.33-0.24 (m, 2H).

Step B: 4-Bromo-N-(cyclopropylmethyl)-3-methyl-2-nitroaniline. A mixture of N-(cyclopropylmethyl)-3-methyl-2-nitroaniline (9.2 g, 44.6 mmol), HOAc (90 mL), and N-bromosuccinimide (7.93 g, 44.6 mmol) was stirred at 0° C. for 4 minutes and then was warmed to room temperature. After 3 hours, the reaction was concentrated under reduced pressure to give 35 g of a clear orange-red oil. 10 M NaOH (40 mL) was added in portions to the clear orange-red oil, and then the reaction mixture was partitioned between water (60 mL) and EtOAc (100 mL). The aqueous layer (pH ~14) was extracted with EtOAc (1×50 mL), and the organic solvent fractions were combined, dried over $Na_2SO_4$, filtered, and concentrated to dryness under reduced pressure to provide the title compound (12.1 g, 95%). MS (ESI): mass calcd. for $C_{11}H_{13}BrN_2O_2$, 284.0; m/z found, 285.0, 287.0 $[M+H]^+$. $^1H$ NMR (400 MHz, $CDCl_3$) δ 7.46 (d, J=9.1 Hz, 1H), 6.52 (d, J=9.1 Hz, 1H), 5.78 (br s, 1H), 2.99 (dd, J=7.1, 5.1 Hz, 2H), 2.44 (s, 3H), 1.14-1.04 (m, 1H), 0.63-0.54 (m, 2H), 0.29-0.22 (m, 2H).

Step C: 4-Bromo-$N^1$-(cyclopropylmethyl)-3-methylbenzene-1,2-diamine. A mixture of 4-bromo-N-(cyclopropylmethyl)-3-methyl-2-nitroaniline (11.71 g, 41.07 mmol), HOAc (123 mL), and iron powder (11.48 g, 205.6 mmol) was stirred at room temperature for 2.5 hours. The reaction was then filtered through diatomaceous earth such as Celite®, and the filter cake was washed with EtOAc (2×50 mL). The filtrate was concentrated under reduced pressure to provide 33.7 g of a dark oil. Then, 3 M NaOH (133 mL) and EtOAc (1×100 mL) was added to the residue, the resulting emulsion was filtered through diatomaceous earth such as Celite® and the filter cake washed with EtOAc (2×50 mL). This resulted in several organic solvent fractions which were combined, dried over $Na_2SO_4$, filtered and concentrated to dryness under reduced pressure to provide the title compound (9.6 g, 91%). MS (ESI): mass calcd. for $C_{11}H_{15}BrN_2$, 255.2; m/z found, 255.1, 257.1 $[M+H]^+$. $^1H$ NMR (400 MHz, $CDCl_3$) δ 6.99 (d, J=8.6 Hz, 1H), 6.41 (d, J=8.6 Hz, 1H), 3.51 (br s, 3H), 2.90 (d, J=6.6 Hz, 2H), 2.31 (s, 3H), 1.21-1.07 (m, 1H), 0.63-0.50 (m, 2H), 0.29-0.14 (m, 2H).

Step D: 5-Bromo-1-(cyclopropylmethyl)-4-methyl-1H-benzo[d][1,2,3]triazole. A solution containing 4-bromo-$N^1$-(cyclopropylmethyl)-3-methylbenzene-1,2-diamine (9.34 g, 36.6 mmol), HOAc (110 mL), and MeOH (110 mL) was stirred at 0° C. while a solution of sodium nitrite (3.55 g, 51.4 mmol) in water (50 mL) was added dropwise over 5 minutes via pressure-equalizing addition funnel. The reaction was stirred at room temperature for 2 hours, and then partially concentrated under reduced pressure to remove the volatile organic solvents. The remaining solution was poured onto ice (300 mL), neutralized with solid $K_2CO_3$ to pH ~7, and extracted with EtOAc (2×100 mL). These extractions resulted in multiple organic solvent fractions which were combined, dried over $Na_2SO_4$, filtered, and concentrated to dryness under reduced pressure. The residue was purified by flash column chromatography using two different sets of conditions. The first column used heptanes/ethyl acetate, 80:20 to 60:40, gradient elution as the eluent and the second column used heptanes/ethyl acetate 90:10 to 75:25, gradient elution as the eluent to provide the title compound (3.9 g, 40%). MS (ESI): mass calcd. for $C_{11}H_{12}BrN_3$, 265.0; m/z found, 266.0, 268.0 $[M+H]^+$. $^1H$ NMR (400 MHz, $CDCl_3$) δ 7.60 (d, J=8.6 Hz, 1H), 7.28 (d, J=9.6 Hz, 1H), 4.49 (d, J=7.1 Hz, 2H), 2.84 (s, 3H), 1.43-1.33 (m, 1H), 0.70-0.59 (m, 2H), 0.54-0.46 (m, 2H).

Step E: Ethyl (E)-3-(1-(cyclopropylmethyl)-4-methyl-1H-benzo[d][1,2,3]triazol-5-yl)acrylate. A mixture of 5-bromo-1-(cyclopropylmethyl)-4-methyl-1H-benzo[d][1,2,3]triazole (3.9 g, 14.7 mmol), DMF (7.3 mL), DIPEA (7.6 mL, 44 mmol), tri-o-tolylphosphine (0.894 g, 2.94 mmol), ethyl acrylate (3.2 mL, 29 mmol), and $Pd(OAc)_2$ (0.331 g, 1.47 mmol) was stirred under argon at 80° C. After 60 hours, the reaction was cooled to room temperature, partitioned between 0.5 M NaH$_2$PO$_4$ (100 mL) and 1:1 EtOAc:diethyl ether (100 mL). The organic solvent fraction was separated and washed with 0.5 M NaH$_2$PO$_4$ (1×100 mL), dried over Na$_2$SO$_4$, filtered, and concentrated to dryness under reduced pressure. The residue was purified by flash column chromatography (eluent: heptanes/ethyl acetate, 60:40 to 80:20, gradient elution) to provide 2.9 g of the title compound which still contained some impurities. To further purify the title compound it was heated to reflux in 200 mL diethyl ether for ~10 minutes, cooled to room temperature, and filtered. The filtrate was concentrated to dryness under reduced pressure to provide the title compound (2.49 g, 60%). MS (ESI): mass calcd. for C$_{16}$H$_{19}$N$_3$O$_2$, 285.2; m/z found, 286.2 [M+H]$^+$. $^1$H NMR (400 MHz, CDCl$_3$) δ 8.15 (d, J=15.7 Hz, 1H), 7.71 (d, J=9.1 Hz, 1H), 7.39 (d, J=9.1 Hz, 1H), 6.42 (d, J=15.7 Hz, 1H), 4.50 (d, J=7.1 Hz, 2H), 4.30 (q, J=7.1 Hz, 2H), 2.93 (s, 3H), 1.44-1.34 (m, 4H), 0.69-0.62 (m, 2H), 0.52-0.47 (m, 2H).

Intermediate 36: 2,2',3,3',5,6-Hexahydrospiro[pyran-4,4'-pyrido[2,3-b][1,4,5]oxathiazepine] 1',1'-dioxide

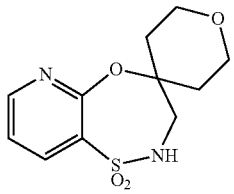 [SMILES: O=S1(=O)NCC2(CCOCC2)Oc2ncccc21]

Step A: 2-Chloropyridine-3-sulfonyl chloride (4.24 g, 20.0 mmol) was added to a mixture of 4-(aminomethyl) tetrahydro-2H-pyran-4-ol (2.62 g, 20.0 mmol) and K$_2$CO$_3$ (4.14 g, 30.0 mmol) in THF (70 mL) and water (15 mL) at room temperature. After 2 hours, H$_2$O (30 mL) was added and the aqueous layer was extracted with EtOAc (60 mL×2). These extractions resulted in several organic solvent fractions which were combined and concentrated under reduced pressure to provide 2-chloro-N-((1-hydroxycyclohexyl) methyl)pyridine-3-sulfonamide. MS (ESI): mass calcd. for C$_{21}$H$_{17}$ClN$_2$O$_3$S, 304.1; m/z found, 307.1 [M+H]$^+$.

Step B: 2-Chloro-N-((1-hydroxycyclohexyl)methyl)pyridine-3-sulfonamide was re-dissolved in DMF (20 mL), and K$^t$OBu (5.60 g, 50 mmol) was added and the mixture was heated at 110° C. for 2 hours. The mixture was cooled to room temperature and pH was adjusted to ~3-4 by adding 1 M aqueous HCl solution. The precipitated solid was filtered and dried under reduced pressure to afford the tile compound (3.20 g, 59%). MS (ESI): mass calcd. for C$_{11}$H$_{14}$N$_2$O$_4$S, 270.1; m/z found, 271.0 [M+H]$^+$. $^1$H NMR (500 MHz, CD$_3$OD) δ 8.56-8.37 (m, 1H), 8.25 (dd, J=7.7, 1.9 Hz, 1H), 7.49-7.29 (m, 1H), 4.01 (s, 2H), 3.75-3.52 (m, 4H), 1.84-1.57 (m, 4H).

Intermediate 37: 8'-Methyl-2,2',3,3',5,6-Hexahydrospiro[pyran-4,4'-pyrido[2,3-b][1,4,5]oxathiazepine] 1',1'-dioxide

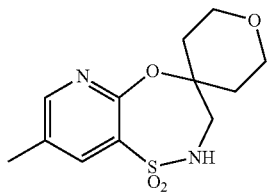 [SMILES: Cc1cnc2c(c1)S(=O)(=O)NCC1(CCOCC1)O2]

Step A: 2-Chloro-N-((4-hydroxytetrahydro-2H-pyran-4-yl)methyl)-5-methylpyridine-3-sulfonamide. 2-Chloro-5-methylpyridine-3-sulfonyl chloride (2.60 g, 20 mmol) was added to a mixture of 4-(aminomethyl)tetrahydro-2H-pyran-4-ol (2.62 g, 20.0 mmol) and K$_2$CO$_3$ (4.14 g, 30.0 mmol) in THF (70 mL) and water (15 mL) at room temperature. After 2 hours, H$_2$O (30 mL) and ethyl acetate were added. The layers were separated and the aqueous layer was further extracted with ethyl acetate (60 mL×2). These extractions resulted in several organic solvent fractions which were combined and concentrated to provide the title compound (4.30 g, 68%). MS (ESI): mass calcd. for Cl$_2$H$_{17}$ClN$_2$O$_4$S, 320.1; m/z found, 321.1 [M+H]$^+$. $^1$H NMR (500 MHz, CD$_3$OD) δ 8.51-8.36 (m, 1H), 8.34-8.24 (m, 1H), 3.81-3.57 (m, 4H), 2.99 (s, 2H), 2.45 (s, 3H), 1.76-1.60 (m, 2H), 1.54-1.37 (m, 2H).

Step B: 8'-Methyl-2,2',3,3',5,6-hexahydrospiro[pyran-4,4'-pyrido[2,3-b][1,4,5]oxathiazepine] 1',1'-dioxide. 2-Chloro-N-((4-hydroxytetrahydro-2H-pyran-4-yl)methyl)-5-methylpyridine-3-sulfonamide (4.20 g, 13.2 mmol) was dissolved into DMSO (12 mL), and K$^t$OBu (3.68 g, 32.8 mmol) was added. The mixture was heated to 95° C. for 2 hours. The mixture was then cooled, the pH of the mixture was adjusted to 5 by adding 5 M aqueous HCl solution. Ethyl acetate was added to the solution. The aqueous layer was separated and extracted with ethyl acetate (50 mL×3). These extractions resulted in several organic solvent fractions which were combined and concentrated. The residue was purified by flash column chromatography (10% EtOAc/hexanes) to provide the title compound (1.70 g, 45%). MS (ESI): mass calcd. for Cl$_2$H$_{16}$N$_2$O$_4$S, 284.1; m/z found, 285.1 [M+H]$^+$. $^1$H NMR (500 MHz, CD$_3$OD) δ 8.29 (d, J=2.2 Hz, 1H), 8.07 (d, J=2.2 Hz, 1H), 4.14-3.90 (m, 2H), 3.79-3.63 (m, 2H), 3.54 (s, 2H), 2.41 (s, 3H), 1.67 (d, J=6.0 Hz, 4H).

Intermediate 38: 7-Bromo-3-(difluoromethyl)-8-methyl-[1,2,4]triazolo[4,3-a]pyridine

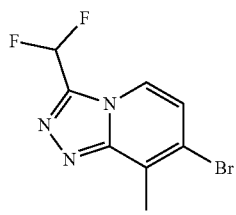

2,2-Difluoroacetic anhydride (34.50 g, 197.9 mmol) was added slowly to 4-bromo-2-hydrazinyl-3-methylpyridine (Intermediate 23, 2.00 g, 9.99 mmol). The reaction initially started to reflux and the solids turned yellow, but within 5 minutes the reaction was homogeneous. The reaction mixture was warmed to 50° C. After 18 hours, the reaction mixture was concentrated under reduced pressure. Ethyl acetate (100 mL) was added, followed by saturated aqueous NaHCO$_3$ until the pH of the solution was 7-8 and the layers were separated. The aqueous layer was extracted with ethyl acetate. These extractions resulted in several organic solvent fractions which were combined and washed sequentially with water and brine solution. The organics were dried over MgSO$_4$, filtered, and concentrated under reduced pressure. The residue was purified by flash column chromatography (0 to 100% EtOAc/hexanes, gradient elution) to afford the title compound (2.50 g, 96%) as a white solid. MS (ESI): mass calcd. for $C_8H_6BrF_2N_3$, 262.1; m/z found, 262.0 [M+H]$^+$. $^1$H NMR (400 MHz, CDCl$_3$) δ 8.11 (d, J=7.2 Hz, 1H), 7.18-7.09 (m, 2H), 2.76 (d, J=0.8 Hz, 3H).

Intermediate 39: (*S)-7a-Methyl-6,7,7a,8,9,10-hexahydropyrido[2,3-f]pyrrolo[2,1-d][1,2,5]thiadiazepine 5,5-dioxide

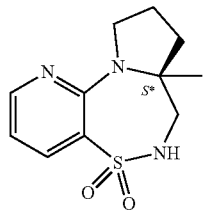 [SMILES: C[C@@]12CCCN1c1ncccc1S(=O)(=O)NC2]

The mixture of 7a-methyl-6,7,7a,8,9,10-hexahydropyrido[2,3-f]pyrrolo[2,1-d][1,2,5]thiadiazepine 5,5-dioxide enantiomers (Intermediate 8, 2.9 g) was separated by chiral SFC (stationary phase: Whelk 01 (S,S) 5 μm 250×21.1 mm, Mobile phase: 65% CO$_2$, 35% isopropanol) to afford two enantiomers. The first eluting isomer (1.3 g) was designated (*S). MS (ESI): mass calcd. for $C_{11}H_{15}N_3O_2S$, 253.1; m/z found, 254.1 [M+H]$^+$. $^1$H NMR (500 MHz, CDCl$_3$) δ 8.40-8.36 (m, 1H), 8.13-8.10 (m, 1H), 6.93-6.88 (m, 1H), 4.85-4.72 (m, 1H), 4.06-3.97 (m, 1H), 3.67-3.56 (m, 2H), 3.18-3.11 (m, 1H), 2.07-1.88 (m, 4H), 0.94 (s, 3H).

Intermediate 40: (*R)-7a-Methyl-6,7,7a,8,9,10-hexahydropyrido[2,3-f]pyrrolo[2,1-d][1,2,5]thiadiazepine 5,5-dioxide

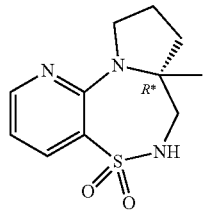 [SMILES: C[C@]12CCCN1c1ncccc1S(=O)(=O)NC2]

The second eluting isomer (1.25 g) from the separation of isomers by chiral SFC described in Intermediate 39 was designated (*R). MS (ESI): mass calcd. for $C_{11}H_{15}N_3O_2S$, 253.1; m/z found, 254.1 [M+H]$^+$. $^1$H NMR (500 MHz, CDCl$_3$) δ 8.41-8.36 (m, 1H), 8.14-8.09 (m, 1H), 6.92-6.89 (m, 1H), 4.90-4.74 (m, 1H), 4.07-3.94 (m, 1H), 3.69-3.56 (m, 2H), 3.19-3.09 (m, 1H), 2.07-1.88 (m, 4H), 0.94 (s, 3H).

Intermediate 41: 5-bromo-2-methylbenzyl Pivalate

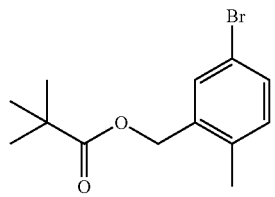 [SMILES: Cc1ccc(Br)cc1COC(=O)C(C)(C)C]

Pivaloyl chloride (119 mL, 966 mmol) was added dropwise to a solution of (5-bromo-2-methylphenyl)methanol (87.8 g, 437 mmol), triethylamine (243 mL, 1.75 mol), and dichloromethane (800 mL) that had been cooled to 0° C. The resulting mixture was allowed to slowly warm to room temperature and stirred for 4 hours before pouring it into water (600 mL). The aqueous layer was extracted with dichloromethane (300 mL×2). These extractions resulted in several organic solvent fractions which were combined, washed with brine (300 mL), dried over anhydrous Na$_2$SO$_4$, filtered, and concentrated to dryness under reduced pressure. The residue was purified by flash column chromatography (eluent:petroleum ether) to afford the title compound (160 g, 96%) as a yellow solid. $^1$H NMR (400 MHz, DMSO-d$_6$) δ 7.44 (d, J=2.2 Hz, 1H), 7.39 (dd, J=8.1, 2.2 Hz, 1H), 7.15 (d, J=8.1 Hz, 1H), 5.03 (s, 2H), 2.21 (s, 3H), 1.13 (s, 9H).

Intermediate 42: 2-methyl-5-(4,4,5,5-tetramethyl-1,3,2-dioxaborolan-2-yl)benzyl Pivalate

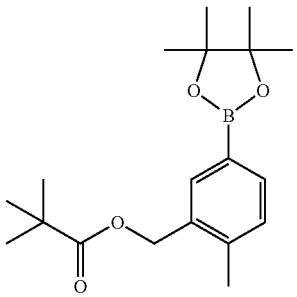 [SMILES: Cc1ccc(B2OC(C)(C)C(C)(C)O2)cc1COC(=O)C(C)(C)C]

A mixture of 5-bromo-2-methylbenzyl pivalate (Intermediate 41, 40.0 g, 140 mmol), 4,4,4',4',5,5,5',5'-octamethyl-2,2'-bi(1,3,2-dioxaborolane) (53.5 g, 211 mmol), KOAc (55.1 g, 561 mmol), and 1,4-dioxane (600 mL) was sparged with N$_2$ for 5 minutes and then treated with Pd(dppf)Cl$_2$ (8.2 g, 11 mmol). The mixture was sparged with N$_2$ for another 5 minutes and then heated to 90° C. for 4 hours before cooling to room-temperature. This mixture was then poured into H$_2$O (200 mL), and extracted with ethyl acetate (200 mL×3). These extractions resulted in several organic solvent fractions which were combined, washed with brine (50 mL), dried over anhydrous Na$_2$SO$_4$, filtered, and concentrated to dryness under reduced pressure. This residue was initially purified by flash column chromatography (eluent:petroleum ether/ethyl acetate, 10:1) and further purified by preparative HPLC using a SANPONT C$_{18}$, 250 mm×50 mm×5 Lm column (eluent: 50% to 95% (v/v) CH$_3$CN and H$_2$O with 0.1% TFA) to afford the title compound as a white solid. $^1$H NMR (400 MHz, DMSO-d$_6$) δ 7.60 (s, 1H), 7.54 (d, J=7.5 Hz, 1H), 7.24 (d, J=7.5 Hz, 1H), 5.09 (s, 2H), 2.31 (s, 3H), 1.28 (s, 12H), 1.14 (s, 9H).

Intermediate 43: Tert-butyldimethyl((2-methyl-5-(4,4,5,5-tetramethyl-1,3,2-dioxaborolan-2-yl)benzyl)oxy)silane

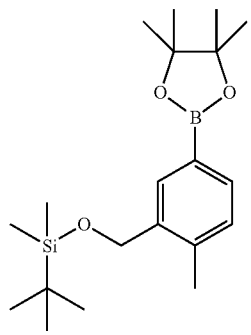

1,1'-Bis(diphenylphosphino)ferrocene-palladium(II) dichloride dichloromethane complex (655 mg, 0.79 mmol) was added to a mixture of ((5-bromo-2-methylbenzyl)oxy)(tert-butyl)dimethylsilane (Intermediate 19, 5.00 g, 15.9 mmol), bis(pinacolato)diboron (8.19 g, 32.3 mmol), potassium acetate (4.64 g, 47.3 mmol) and 1,4-dioxane (45.0 mL). The reaction mixture was stirred at 90° C. under nitrogen for 4 hours. After filtration of the mixture through a pad of diatomaceous earth, the filtrate was concentrated under reduced pressure. The resulting residue was partitioned between ethyl acetate and water and the aqueous layer was further extracted with ethyl acetate. These extractions resulted in several organic solvent fractions which were combined and dried over $Na_2SO_4$, filtered, and concentrated to dryness under reduced pressure. The residue was purified by flash column chromatography (eluent: 0 to 50% ethyl acetate/hexanes, gradient elution) to afford the title compound (4.00 g, 70%). $^1$H NMR (400 MHz, $CDCl_3$) δ 7.67 (d, J=1.3 Hz, 1H), 7.55-7.51 (m, 1H), 7.06 (d, J=7.4 Hz, 1H), 4.61 (s, 2H), 2.25 (s, 3H), 1.24 (s, 12H), 0.84 (s, 9H), 0.10 (s, 6H).

Intermediate 45: 3-(difluoromethyl)-8-methyl-[1,2,4]triazolo[4,3-a]pyridine-7-carbaldehyde

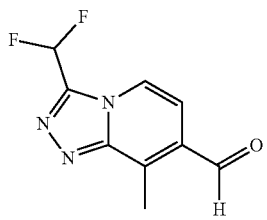

Step A: 3-(Difluoromethyl)-8-methyl-7-vinyl-[1,2,4]triazolo[4,3-a]pyridine. Pd(dppf)Cl$_2$ (11.1 g, 15.2 mmol) was added to a mixture of 7-bromo-3-(difluoromethyl)-8-methyl-[1,2,4]triazolo[4,3-a]pyridine (Intermediate 38, 40.0 g, 152 mmol), potassium vinyl trifluoroborate (40.9 g, 305 mmol) and $K_3PO_4$ (97.2 g, 457 mmol) in $H_2O$ (100 mL) and 1,4-dioxane (400 mL) at 25° C. The mixture was heated to 80° C. and stirred for 1 hour under $N_2$. The brownish suspension was filtered, the filtrate was poured into $H_2O$ (200 mL) and this aqueous suspension was extracted with DCM (300 mL×3). These extractions resulted in several organic solvent fractions which were combined and washed with brine (300 mL×3), dried with anhydrous $Na_2SO_4$, filtered and concentrated to dryness under reduced pressure. The product was triturated with petroleum ether (300 mL) and filtered, dried under vacuum to afford the title compound (30 g, 89%) as an off white solid.

Step B: 3-(Difluoromethyl)-8-methyl-[1,2,4]triazolo[4,3-a]pyridine-7-carbaldehyde. $K_2OsO_4.2H_2O$ (2.11 g, 5.74 mmol) was added to a solution consisting of 3-(difluoromethyl)-8-methyl-7-vinyl-[1,2,4]triazolo[4,3-a]pyridine (30.0 g, 143 mmol) in 1,4-dioxane (450 mL) and $H_2O$ (450 mL) at 25° C., and then $NaIO_4$ (92.0 g, 430 mmol) was added. The resulting suspension was stirred at 25° C. for 2 hours then filtered and the filtrate was concentrated to dryness under reduced pressure. The resulting residue was diluted with water and the aqueous phase was extracted with $CH_2Cl_2$ (500 mL×3). These extractions resulted in several organic solvent fractions which were combined, washed with brine (500 mL×2), dried with anhydrous $Na_2SO_4$, filtered and concentrated to dryness under reduced pressure. The residue was triturated with petroleum ether (500 mL), then the solvent was filtered off and the solid was dried in a vacuum oven to afford the title compound (20.6 g, 67%) as an off white solid. MS (ESI): mass calcd. for $C_9H_7F_2N_3O$, 211.1; m/z found, 211.9 [M+H]$^+$. $^1$H NMR (400 MHz, $CDCl_3$) δ 10.55 (s, 1H), 8.28 (d, J=7.2 Hz, 1H), 7.47 (d, J=7.2 Hz, 1H), 7.40-7.17 (m, 1H), 3.12 (s, 3H).

Intermediate 46: 5-Bromo-3-(((tert-butyldimethylsilyl)oxy)methyl)-2-methylpyridine

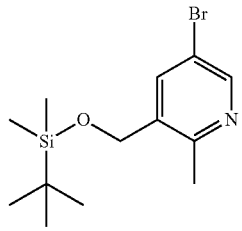 [SMILES: Cc1ncc(Br)cc1CO[Si](C)(C)C(C)(C)C]

Step A: (5-Bromo-2-methylpyridin-3-yl)methanol. $NaBH_4$ (9.40 g, 248 mmol) was added in portions to a solution of ethyl 5-bromo-2-methylnicotinate (20.2 g, 82.8 mmol) and MeOH (100 mL) at 0° C. The resulting mixture was stirred for 4 hours with gradual warming to room temperature. The mixture was quenched with $H_2O$ (80 mL) and extracted with dichloromethane (120 mL×3). These extractions resulted in several organic solvent fractions which were combined, and dried over anhydrous $Na_2SO_4$, filtered and concentrated to dryness under reduced pressure. The residue was purified by flash column chromatography (eluent:petroleum ether/ethyl acetate, 100:0 to 4:1, gradient elution) to afford the title compound (14.2 g) as an oil. $^1$H NMR (400 MHz, DMSO-d$_6$) δ 8.39 (d, J=2.0 Hz, 1H), 7.86 (d, J=1.3 Hz, 1H), 5.47 (t, J=5.5 Hz, 1H), 4.50 (d, J=5.5 Hz, 2H), 2.34 (s, 3H).

Step B: 5-Bromo-3-(((tert-butyldimethylsilyl)oxy)methyl)-2-methylpyridine. TBSCl (14.5 g, 96.2 mmol) was added to a solution of (5-bromo-2-methylpyridin-3-yl)methanol (13 g, 64 mmol), 1H-imidazole (13.1 g, 192 mmol), and dichloromethane (120 mL). The mixture was stirred at room temperature for 20 minutes. The reaction mixture was filtered through a pad of diatomaceous earth and the pad was washed with ethyl acetate (60 mL). The combined organic extracts were concentrated to dryness under reduced pressure and purified by flash column chromatography (eluent:petroleum ether/ethyl acetate, 100:0 to 10:1, gradient elution) to afford the title compound (16.8 g). The still impure product (16.8 g) was combined with another batch prepared from (5-bromo-2-methylpyridin-3-yl)methanol (14.2 g, 70.3 mmol) to give a total of 35.4 g which was dissolved in ethyl acetate and washed with saturated aqueous NaHCO$_3$(200 mL×2), dried over anhydrous Na$_2$SO$_4$, filtered, and concentrated to dryness under reduced pressure. The residue was further purified by flash column chromatography (eluent:petroleum ether/ethyl acetate, 100:0 to 10:1, gradient elution) and further purified by preparative HPLC using a Phenomenex Synergi Max-RP, 250 mm×50 mm×10 μm column (eluent: 50% to 99% (v/v) CH$_3$CN and H$_2$O with 10 mM NH$_4$HCO$_3$) to afford the title compound. The product was suspended in water (50 mL), the mixture frozen using dry ice/acetone, and then lyophilized to dryness to afford the title compound (26 g, 58%). MS (ESI): mass calcd. for C$_{13}$H$_{22}$BrNOSi, 315.1; m/z found, 316 [M+H]+; $^1$H NMR (400 MHz, DMSO-d$_6$) δ 8.41 (d, J=2.2 Hz, 1H), 7.83 (d, J=2.2 Hz, 1H), 4.67 (s, 2H), 2.35 (s, 3H), 0.89 (s, 9H), 0.08 (s, 6H).

Intermediate 47: 2-Bromo-4-(((tert-butyldimethylsilyl)oxy)methyl)-5-methylpyridine

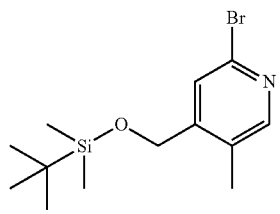 [SMILES: Cc1cnc(Br)cc1CO[Si](C)(C)C(C)(C)C]

Step A: 4-Iodo-5-methylpyridin-2(1H)-one. Concentrated HCl (200 mL) was added to 2-fluoro-4-iodo-5-methylpyridine (100 g, 422 mmol) in 1,4-dioxane:water (1:1, 400 mL). The resulting mixture was heated to 100° C. for 2 hours and then cooled to room-temperature. The reaction was then quenched with water (400 mL) and stirred at room-temperature for 1 hour. The mixture was then cooled to 0° C., and the solids were isolated via filtration. The filter cake was washed with diethyl ether (100 mL) before drying under reduced pressure to afford the title compound (79 g, 80%). MS (ESI): mass calcd. for C$_6$H$_6$INO, 234.9; m/z found, 235.8 [M+H]$^+$. $^1$H NMR (400 MHz, DMSO-d$_6$) δ 7.47 (s, 1H), 7.23 (s, 1H), 2.10 (s, 3H).

Step B: Methyl 5-methyl-2-oxo-1,2-dihydropyridine-4-carboxylate. 4-Iodo-5-methylpyridin-2(1H)-one (59.5 g, 253 mmol), MeOH (1 L), and K$_2$CO$_3$ (35.0 g, 253 mmol) were added to a 2 L hydrogenation bottle. The resultant mixture was purged with N$_2$ for 5 minutes and then treated with Pd(OAc)$_2$ (11.4 g, 50.8 mmol) and dcpp.2HBF$_4$ (31.0 g, 50.6 mmol). The resultant mixture was stirred under CO (50 psi) at 80° C. for 36 hours. The suspension was filtered through a pad of diatomaceous earth and the filtrate concentrated to dryness under reduced pressure. The residue was triturated with ethyl acetate (500 mL) and the solids isolated by filtration. The filter cake was washed with ethyl acetate (50 mL) before drying under reduced pressure to afford the title compound (58 g), which was used in the next step without further purification.

Step C: Methyl 2-bromo-5-methylisonicotinate. POBr$_3$ (222.3 g, 775.4 mmol) was added to a solution of 5-methyl-2-oxo-1,2-dihydropyridine-4-carboxylate (45.0 g) in toluene (500 mL). The resulting mixture was heated to 120° C. for 15 hours before cooling to room-temperature. The mixture was combined with another batch prepared from methyl-2-oxo-1,2-dihydropyridine-4-carboxylate (13.0 g) and the resulting mixture was poured into ice/water (500 mL). The pH of resultant solution was adjusted to pH=8 with aqueous NaOH (5 N). and then the solution was extracted with ethyl acetate (500 mL×2). These extractions resulted in several organic solvent fractions which were combined, washed with brine (400 mL×2), dried over anhydrous Na$_2$SO$_4$, filtered, and concentrated to dryness under reduced pressure. The product was purified by flash column chromatography (eluent:petroleum ether/ethyl acetate, 100:1 to 20:1, gradient elution) to afford the title compound (18 g) as a light yellow solid. $^1$H NMR (400 MHz, CDCl$_3$) δ 8.32 (s, 1H), 8.39-8.23 (m, 1H), 7.89 (s, 1H), 3.94 (s, 3H), 2.51 (s, 3H).

Step D: (2-Bromo-5-methylpyridin-4-yl)methanol. NaBH$_4$ (5.92 g, 157 mmol) was added to a solution of methyl 2-bromo-5-methylisonicotinate (18 g, 78 mmol) in MeOH (400 mL) at 0° C. The resulting mixture was stirred at 0° C. for 1 hour before quenching with H$_2$O (50 mL). The solvent was removed under reduced pressure and the resulting mixture was extracted with ethyl acetate (150 mL×3). These extractions resulted in several organic solvent fractions which were combined, dried over anhydrous Na$_2$SO$_4$, filtered, and concentrated to dryness under reduced pressure to afford the title compound (17 g) as a white solid. MS (ESI): mass calcd. for C$_7$H$_8$BrNO, 200.9; m/z found, 201.8 [M+H]$^+$; $^1$H NMR (400 MHz, DMSO-d$_6$) δ 8.10 (s, 1H), 7.54 (s, 1H), 5.55 (br s, 1H), 4.51 (s, 2H), 2.18-2.09 (m, 3H).

Step E: 2-Bromo-4-(((tert-butyldimethylsilyl)oxy)methyl)-5-methylpyridine. TBSCl (7.76 g, 51.5 mmol) was added to a solution of (2-bromo-5-methylpyridin-4-yl)methanol (8.00 g, 39.6 mmol), 1H-imidazole (8.08 g, 119 mmol), and dichloromethane (100 mL). The resulting mixture was stirred at room-temperature for 1 hour. The mixture was combined with another batch prepared from (2-bromo-5-methylpyridin-4-yl)methanol (1.6 g, 7.9 mmol). The combined mixture was concentrated to dryness under reduced pressure to give a residue that was purified by preparative HPLC using a SANPONT C$_{18}$, 250 mm×80 mm×10 μm column (eluent: 70% to 100% (v/v) CH$_3$CN and H$_2$O with 10 mM NH$_4$HCO$_3$). The fractions that contained the desired product were collected, suspended in water (25 mL), the mixture frozen using dry ice/acetone, and then lyophilized to dryness to afford the title compound (10 g, 67%) as a white solid. MS (ESI): mass calcd. for C$_{13}$H$_{22}$BrNOSi, 315.1 m/z found 316.0 [M+H]+; $^1$H NMR (400 MHz, CDCl$_3$) δ 8.07 (s, 1H), 7.59 (s, 1H), 4.64 (s, 2H), 2.15 (s, 3H), 0.97 (s, 9H), 0.14 (s, 6H).

Intermediate 48: Methyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate

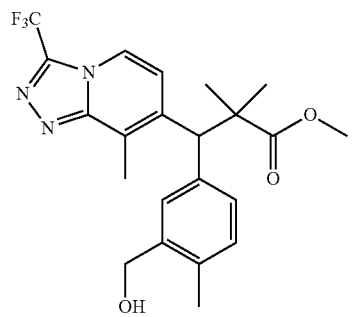 [SMILES: COC(=O)C(C)(C)C(c1ccc(C)c(CO)c1)c1ccn2c(C(F)(F)F)nnc2c1C]

Step A: 5-(Hydroxy(3-(trifluoromethyl)-[1,2,4]triazolo[4,3-a]pyridine-7-yl)methyl)-2-methylbenzyl pivalate. To a mixture of 3-(trifluoromethyl)-[1,2,4]triazolo[4,3-a]pyridine-7-carbaldehyde (Intermediate 28, 2.00 g, 8.73 mmol), 2-methyl-5-(4,4,5,5-tetramethyl-1,3,2-dioxaborolan-2-yl) benzyl pivalate (Intermediate 42, 3.80 g, 11.4 mmol), and K$_2$CO$_3$ (3.74 g, 27.1 mmol) in THF was added tri(1-naphthyl)phosphine (106 mg, 0.60 mmol) and palladium II chloride (285 mg, 0.67 mmol). After heating at 60° C. for 24 hours, the reaction mixture was cooled, poured into water and extracted with ethyl acetate. These extractions resulted in several organic solvent fractions which were combined, washed with brine, dried over Na$_2$SO$_4$, filtered, and concentrated to dryness under reduced pressure. The residue was purified by flash silica gel chromatography (eluent: 0-60% ethyl acetate/hexanes) to afford the title compound (1.90 g, 50.0%). MS (ESI): mass calcd. for C$_{22}$H$_{24}$F$_3$N$_3$O$_3$, 435.2; m/z found, 436.1 [M+H]$^+$.

Step B: 5-(Chloro-(3-(trifluoromethyl)-[1,2,4]triazolo[4,3-a]pyridine-7-yl)methyl)-2-methylbenzyl pivalate. To a solution of 5-(hydroxy(3-(trifluoromethyl)-[1,2,4]triazolo[4,3-a]pyridine-7-yl)methyl)-2-methylbenzyl pivalate (1.80 g, 4.13 mmol) in DCM (50 mL) was added dropwise thionyl chloride (3.50 mL, 47.8 mmol). After 24 hours the reaction mixture was slowly added to saturated aqueous bicarbonate and extracted with diethyl ether. These extractions resulted in several organic solvent fractions which were combined, washed with brine, dried over Na$_2$SO$_4$, filtered, and concentrated to dryness under reduced pressure. The residue was purified by flash silica gel chromatography (eluent: 0-50% ethyl acetate/hexanes) to afford the title compound (1.40 g, 75%). MS (ESI): mass calcd. for C$_{22}$H$_{23}$ClF$_3$N$_3$O$_2$, 453.1; m/z found, 454.1 [M+H]$^+$.

Step C: Methyl 2,2-dimethyl-3-(4-methyl-3-((pivaloyloxy)methyl)phenyl)-3-(8-methyl-3-(trifluoromethyl)-[1,2,4]triazolo[4,3-a]pyridine-7-yl)propanoate. To a mixture of 5-(chloro-(3-(trifluoromethyl)-[1,2,4]triazolo[4,3-a]pyridine-7-yl)methyl)-2-methylbenzyl pivalate (1.10 g, 2.42 mmol), dimethylketene methyl trimethylsilyl acetal (1.61 mL, 7.93 mmol) in DCM (32 mL) was added indium III bromide (200 mg, 0.56 mmol). After 18 hours the reaction was poured into saturated aqueous sodium bicarbonate and extracted with DCM. These extractions resulted in several organic solvent fractions which were combined, washed with brine, dried over MgSO$_4$, filtered, and concentrated to dryness under reduced pressure. The residue was purified by flash silica gel chromatography (eluent: 0-50% ethyl acetate/hexanes) to afford the title compound (760 mg, 60%). MS (ESI): mass calcd. for C$_{27}$H$_{32}$F$_3$N$_3$O$_4$, 519.2; m/z found, 520.2 [M+H]$^+$.

Step D: 3-(3-(Hydroxymethyl)-4-methylphenyl)-2,2-dimethyl-3-(8-methyl-3-(trifluomethyl)-[1,2,4]triazolo[4,3-a]pyridine-7-yl)propanoate. A solution of sodium methoxide in methanol (1.0 mL, 4.37 mmol, 25% w/w) was added to a solution of methyl 2,2-dimethyl-3-(4-methyl-3-((pivaloyloxy)methyl)phenyl)-3-(8-methyl-3-(trifluoromethyl)-[1,2,4]triazolo[4,3-a]pyridine-7-yl)propanoate (760 mg, 1.46 mmol) in methanol and stirred for 2 hours. The reaction was poured into saturated aqueous ammonium chloride and extracted three times with DCM. These extractions resulted in several organic solvent fractions which were combined, washed with brine, dried over Na$_2$SO$_4$, filtered, and concentrated to dryness under reduced pressure. The residue was purified by flash silica gel chromatography (eluent: 0-80% ethyl acetate/hexanes) to afford the title compound (630 mg, 99%). An alternative preparation of this compound is described in the preparation of Intermediate 48, steps A-I.

MS (ESI): mass calcd. for C$_{27}$H$_{32}$F$_3$N$_3$O$_4$, 435.2; m/z found, 436.2 [M+H]$^+$. $^1$H NMR (400 MHz, DMSO-d$_6$) δ 8.41 (d, J=7.3 Hz, 1H), 7.27 (d, J=7.4 Hz, 2H), 7.12 (dd, J=7.8, 2.1 Hz, 1H), 7.06 (d, J=7.9 Hz, 1H), 5.03 (t, J=5.4 Hz, 1H), 4.76 (s, 1H), 4.43 (d, J=5.4 Hz, 2H), 3.52 (s, 3H), 2.68 (s, 3H), 2.18 (s, 3H), 1.33 (s, 3H), 1.28 (s, 3H).

Intermediate 49: Methyl 3-(3-(difluoromethyl)-8-methyl-[1,2,4]triazolo[4,3-a]pyridin-7-yl)-3-(3-(hydroxymethyl)-4-methylphenyl)-2,2-dimethylpropanoate

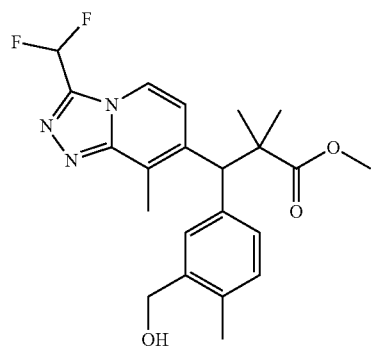 [SMILES: COC(=O)C(C)(C)C(c1ccc(C)c(CO)c1)c1ccn2c(C(F)F)nnc2c1C]

Step A: (3-(((Tert-butyldimethylsilyl)oxy)methyl)-4-methylphenyl)(3-(difluoromethyl)-8-methyl-[1,2,4]triazolo[4,3-a]pyridin-7-yl)methanol. A mixture of 3-(difluoromethyl)-8-methyl-[1,2,4]triazolo[4,3-a]pyridine-7-carbaldehyde (Intermediate 19, 0.5 g, 2.4 mmol), tert-butyldimethyl((2-methyl-5-(4,4,5,5-tetramethyl-1,3,2-dioxaborolan-2-yl)benzyl)oxy)silane (Intermediate 45, 1.3 g, 3.5 mmol), palladium (II) chloride (22 mg, 0.1 mmol), potassium carbonate (1.0 g, 7.3 mmol), and tri-1-naphthylphosphine (57 mg, 0.1 mmol) were charged to a reaction vessel, followed by addition of THF (15 mL). The vial was caped and degassed by bubbling argon through the reaction for 5 minutes, then the reaction was stirred overnight in a pre-heated block at 75° C. The reaction was cooled to room temperature, then filtered through diatomaceous earth and concentrated to dryness under reduced pressure. The residue was purified by flash column chromatography (0-100% ethyl acetate/hexanes, gradient elution) to afford the title compound (0.9 g, 85%). MS (ESI): mass calcd. for C$_{23}$H$_{31}$F$_2$N$_3$O$_2$Si, 447.2; m/z found, 448.3 [M+H]$^+$. $^1$H NMR (500 MHz, CDCl$_3$) δ 8.15 (d, J=7.2 Hz, 1H), 7.38 (d, J=7.2 Hz, 1H), 7.29 (d, J=2.0 Hz, 1H), 7.20 (dd, J=7.7, 2.0 Hz, 1H), 7.15 (s, 1H), 7.09-7.02 (m, 1H), 6.08 (s, 1H), 4.61 (s, 2H), 3.26 (s, 1H), 2.57 (s, 3H), 2.17 (s, 3H), 0.80 (s, 9H), 0.00 (d, J=4.7 Hz, 6H).

Step B: 7-((3-(((Tert-butyldimethylsilyl)oxy)methyl)-4-methylphenyl)chloromethyl)-3-(difluoromethyl)-8-methyl-[1,2,4]triazolo[4,3-a]pyridine. Thionyl chloride (1.6 mL, 23 mmol) was added to a solution of (3-(((tert-butyldimethylsilyl)oxy)methyl)-4-methylphenyl)(3-(difluoromethyl)-8-methyl-[1,2,4]triazolo[4,3-a]pyridin-7-yl)methanol (7.8 g, 17 mmol) and 2,6-di-tert-butylpyridine (7.8 ml, 35 mmol) in DCM (86 mL). The reaction was stirred at room temperature for 1 hour. The reaction was quenched with saturated aqueous NaHCO$_3$, then extracted twice with DCM. These extractions resulted in several organic solvent fractions which were combined, dried over MgSO$_4$, filtered, and concentrated to dryness under reduced pressure. The product was purified by flash column chromatography (0-100% ethyl acetate/hexanes, gradient elution) to provide the title compound (7.5 g, 92%). MS (ESI): mass calcd. for $C_{23}H_{30}ClF_2N_3OSi$, 465.2; m/z found, 466.2 [M+H]+. $^1$H NMR (500 MHz, CDCl$_3$) δ 8.15 (d, J=7.3 Hz, 1H), 7.42-7.36 (m, 1H), 7.31 (s, 1H), 7.26-7.03 (m, 4H), 6.42 (s, 1H), 4.62 (s, 2H), 4.08 (q, J=7.1 Hz, 1H), 2.74 (d, J=0.7 Hz, 3H), 2.19 (s, 3H), 0.79 (s, 9H), 0.29--0.22 (m, 6H).

Step C: Methyl 3-(3-(((tert-butyldimethylsilyl)oxy)methyl)-4-methylphenyl)-3-(3-(difluoromethyl)-8-methyl-[1,2,4]triazolo[4,3-a]pyridin-7-yl)-2,2-dimethylpropanoate. ((1-Methoxy-2-methylprop-1-en-1-yl)oxy)trimethylsilane (16 ml, 79 mmol) was added to a solution of 7-((3-(((tert-butyldimethyl silyl)oxy)methyl)-4-methylphenyl)chloromethyl)-3-(difluoromethyl)-8-methyl-[1,2,4]triazolo[4,3-a]pyridine (7.5 g, 16 mmol) in DCM (80 ml). Indium(III) bromide (1.7 g, 4.9 mmol) was added and the reaction was stirred at room temperature for 3 hours. The reaction was filtered, concentrated and purified by flash column chromatography (0-100% ethyl acetate/hexanes, gradient elution) to afford the title compound (6.0 g, 70%). MS (ESI): mass calcd. for $C_{28}H_{39}F_2N_3O_3Si$, 531.3; m/z found, 532.3 [M+H]+. $^1$H NMR (500 MHz, CDCl$_3$) δ 8.09 (d, J=7.3 Hz, 1H), 7.23 (d, J=1.7 Hz, 1H), 7.18 (s, 1H), 7.14-7.06 (m, 1H), 7.06-6.96 (m, 2H), 4.79 (s, 1H), 4.60 (s, 2H), 3.54 (s, 3H), 2.73-2.67 (m, 3H), 2.16 (s, 3H), 1.39 (s, 3H), 1.32 (s, 3H), 1.23 (t, J=7.1 Hz, 0H), 0.83 (s, 9H), 0.00 (dd, J=16.9, 5.9 Hz, 6H).

Step D: Methyl 3-(3-(difluoromethyl)-8-methyl-[1,2,4]triazolo[4,3-a]pyridin-7-yl)-3-(3-(hydroxymethyl)-4-methylphenyl)-2,2-dimethylpropanoate. Tetrabutylammonium fluoride (1 M in THF, 23 ml, 23 mmol) was added to a solution of methyl 3-(3-(((tert-butyldimethylsilyl)oxy)methyl)-4-methylphenyl)-3-(3-(difluoromethyl)-8-methyl-[1,2,4]triazolo[4,3-a]pyridin-7-yl)-2,2-dimethylpropanoate (6.0 g, 11 mmol) in THF (62 ml). The reaction was stirred at room temperature for 1 hour. The reaction was quenched with saturated aqueous NH$_4$C$_1$, then extracted twice with ethyl acetate. These extractions resulted in several organic solvent fractions which were combined, dried over MgSO$_4$, filtered, concentrated to and purified by flash column chromatography (0-100% ethyl acetate/hexanes, gradient elution) to afford the title compound (4.6, 98%). MS (ESI): mass calcd. for $C_{22}H_{25}F_2N_3O_3$, 417.2; m/z found, 418.2 [M+H]+. $^1$H NMR (500 MHz, CDCl$_3$) δ 8.14 (d, J=7.3 Hz, 1H), 7.29 (d, J=4.7 Hz, 1H), 7.18 (d, J=7.7 Hz, 2H), 7.09 (d, J=1.3 Hz, 2H), 4.81 (s, 1H), 4.68 (d, J=3.8 Hz, 2H), 4.13 (q, J=7.1 Hz, 1H), 3.58 (s, 3H), 2.73 (s, 3H), 2.28 (s, 3H), 1.35 (s, 6H).

Intermediate 50: Methyl 3-(4-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate

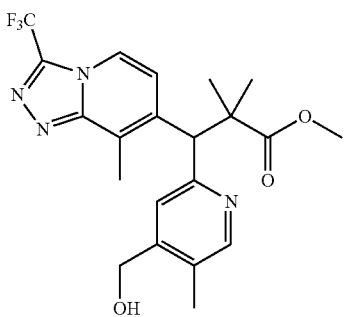

Step A: (4-(((Tert-butyldimethylsilyl)oxy)methyl)-5-methylpyridin-2-yl)(8-methyl-3-(trifluoromethyl)-[1,2,4]triazolo[4,3-a]pyridin-7-yl)methanol. n-Butyllithium (2.0 M, 3.1 ml, 6.2 mmol) was added dropwise to a stirring solution of 2-bromo-4-(((tert-butyldimethylsilyl)oxy)methyl)-5-methylpyridine (Intermediate 47, 2.0 g, 6.3 mmol) in THF (14 ml) at −78° C. under nitrogen. This reaction was stirred at −78° C. for 2 minutes to prepare the lithiate reaction mixture. A solution 3-(trifluoromethyl)-8-methyl-[1,2,4]triazolo[4,3-a]pyridine-7-carbaldehyde (Intermediate 28, 1.2 g, 5.1 mmol) in THF (10 ml) was added to the lithiate reaction mixture dropwise. The resulting reaction mixture was stirred at −78° C. for 5 minutes. The reaction was then quenched with saturated aqueous NaHCO$_3$, and then extracted twice with EtOAc. These extractions resulted in several organic solvent fractions which were combined, dried over MgSO$_4$, filtered, and concentrated to dryness under reduced pressure. The product was purified by flash column chromatography (0-100% ethyl acetate/hexanes, gradient elution) to provide the title compound (1.0 g, 42%). MS (ESI): mass calcd. for $C_{22}H_{29}F_3N_4O_2Si$, 466.2; m/z found, 467.3 [M+H]+. $^1$H NMR (500 MHz, CDCl$_3$) δ 8.30 (t, J=0.8 Hz, 1H), 8.05-7.99 (m, 1H), 7.25 (s, 1H), 7.16 (d, J=7.2 Hz, 1H), 6.19 (s, 1H), 5.94 (s, 1H), 4.65 (dd, J=15.6, 1.1 Hz, 1H), 4.60 (dd, J=15.6, 1.0 Hz, 1H), 2.86 (s, 3H), 2.20 (s, 3H), 2.06 (s, 1H), 1.27 (t, J=7.1 Hz, 1H), 0.78 (s, 9H), 0.84-0.72 (m, 1H), 0.05 (s, 3H).

Step B: 7-((4-(((Tert-butyldimethylsilyl)oxy)methyl)-5-methylpyridin-2-yl)chloromethyl)-8-methyl-3-(trifluoromethyl)-[1,2,4]triazolo[4,3-a]pyridine. Thionyl chloride (0.3 mL, 4.2 mmol) was added to a solution of (4-(((tert-butyldimethylsilyl)oxy)methyl)-5-methylpyridin-2-yl)(8-methyl-3-(trifluoromethyl)-[1,2,4]triazol o[4,3-a]pyridin-7-yl)methanol (1.5 g, 3.2 mmol) and 2,6-di-tert-butylpyridine (1.4 ml, 6.4 mmol) in DCM (16 mL). The reaction was stirred at room temperature for 1 hour. The reaction was quenched with saturated aqueous NaHCO$_3$, then extracted twice with DCM. These extractions resulted in several organic solvent fractions which were combined, dried over MgSO$_4$, filtered, and concentrated to dryness under reduced pressure. The product was purified by flash column chromatography (0-100% ethyl acetate/hexanes, gradient elution) to provide the title compound (1.0 g, 64% yield). MS (ESI): mass calcd. for $C_{22}H_{28}ClF_3N_4OSi$, 484.2; m/z found, 485.2 [M+H]+. $^1$H NMR (500 MHz, CDCl$_3$) δ 8.15 (t, J=0.8 Hz, 1H), 7.96 (d, J=7.2 Hz, 1H), 7.62 (s, 1H), 7.25 (d, J=7.3 Hz, 1H), 6.35 (s, 1H), 4.58 (d, J=1.0 Hz, 2H), 3.98 (q, J=7.1 Hz, 1H), 2.71 (d, J=0.7 Hz, 3H), 2.08 (s, 3H), 1.12 (t, J=7.1 Hz, 1H), 0.80 (s, 9H), 0.86-0.74 (m, 1H), 0.05 (s, 3H).

Step C: Methyl 3-(4-(((tert-butyldimethylsilyl)oxy)methyl)-5-methylpyridin-2-yl)-2,2-dimethyl-3-(8-methyl-3-(trifluoromethyl)-[1,2,4]triazolo[4,3-a]pyridin-7-yl)propanoate. ((1-Methoxy-2-methylprop-1-en-1-yl)oxy)trimethylsilane (6.1 ml, 30 mmol) was added to a solution of 7-((4-(((tert-butyldimethylsilyl)oxy)methyl)-5-methylpyridin-2-yl)chloromethyl)-8-methyl-3-(trifluoromethyl)-[1,2,4]triazolo[4,3-a]pyridine (3.0 g, 6.2 mmol) in DCM (31 ml). Indium(III) bromide (0.67 g, 1.9 mmol) was added and the reaction was stirred at room temperature for 3 hours. The reaction was filtered, concentrated and purified by flash column chromatography (0-100% ethyl acetate/hexanes, gradient elution) to afford the title compound (0.5 g, 15% yield). MS (ESI): mass calcd. for $C_{27}H_{37}F_3N_4O_3Si$, 550.2; m/z found, 551.2 [M+H]+. $^1$H NMR (500 MHz, CDCl$_3$) δ 8.22 (d, J=0.8 Hz, 1H), 7.91 (d, J=7.4 Hz, 1H), 7.28 (d, J=7.3 Hz, 1H), 7.06 (s, 1H), 5.04 (s, 1H), 4.60-4.49 (m, 2H), 3.59

(s, 3H), 2.86 (s, 3H), 2.11 (s, 3H), 2.01 (s, 1H), 1.28 (s, 3H), 1.22 (t, J=7.1 Hz, 1H), 0.74 (s, 9H), 0.76-0.70 (m, 1H), 0.14-0.07 (m, 6H).

Step D: Methyl 3-(4-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate. Tetrabutylammonium fluoride (1 M in THF, 1.4 ml, 1.4 mmol) was added to a solution of methyl 3-(4-(((tert-butyldimethylsilyl)oxy)methyl)-5-methylpyridin-2-yl)-2,2-dimethyl-3-(8-methyl-3-(trifluoromethyl)-[1,2,4]triazolo[4,3-a]pyridin-7-yl)propanoate (0.5 g, 0.9 mmol) in THF (5 ml). The reaction was stirred at room temperature for 1 hour. The reaction was quenched with saturated aqueous NH$_4$Cl, then extracted twice with ethyl acetate. These extractions resulted in several organic solvent fractions which were combined, dried over MgSO$_4$, filtered, concentrated and purified by flash column chromatography (0-100% ethyl acetate/hexanes, gradient elution) to afford the title compound (280 mg, 71% yield). MS (ESI): mass calcd. for C$_{21}$H$_{23}$F$_3$N$_4$O$_3$, 436.2; m/z found, 437.2 [M+H]$^+$. $^1$H NMR (500 MHz, CDCl$_3$) δ 8.28 (d, J=0.8 Hz, 1H), 7.92 (d, J=7.3 Hz, 1H), 7.47 (d, J=7.4 Hz, 1H), 7.23 (s, 1H), 5.00 (s, 1H), 4.71-4.66 (m, 2H), 3.60 (s, 4H), 2.86-2.82 (m, 3H), 2.19 (s, 3H), 1.40 (s, 3H), 1.32 (s, 3H).

Intermediate 51: Methyl 3-(1-ethyl-4-methyl-1H-benzo[d][1,2,3]triazol-5-yl)-3-(5-(hydroxymethyl)-6-methylpyridin-3-yl)-2,2-dimethylpropanoate

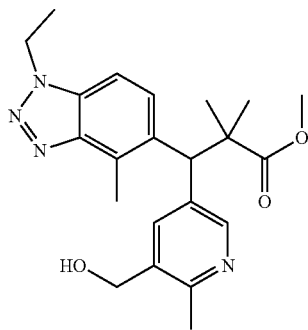 [SMILES: CCn1nnc2c(C)c(C(c3cnc(C)c(CO)c3)C(C)(C)C(=O)OC)ccc21]

Step A: (5-(((Tert-butyldimethylsilyl)oxy)methyl)-6-methylpyridin-3-yl)(1-ethyl-4-methyl-1H-benzo[d][1,2,3]triazol-5-yl)methanol. n-Butyllithium (2.5 M, 9.2 ml, 23 mmol) was added dropwise to a stirring solution of 5-bromo-3-(((tert-butyldimethylsilyl)oxy)methyl)-2-methylpyridine (Intermediate 46, 4.8 g, 15 mmol) in THF (20 ml) at −78° C. under nitrogen. The reaction mixture was stirred at −78° C. for 2 minutes to prepare the lithiate reaction mixture. A solution 1-ethyl-4-methyl-1H-benzo[d][1,2,3]triazole-5-carbaldehyde (Intermediate 22, 2.9 g, 15 mmol) in THF (10 ml) was added to the lithiate reaction mixture dropwise. The reaction was stirred at −78° C. for 5 minutes. The reaction was quenched with saturated aqueous NaHCO$_3$, and then extracted twice with EtOAc. These extractions resulted in several organic solvent fractions which were combined, dried over MgSO$_4$, filtered, and concentrated to dryness under reduced pressure. The product was purified by flash column chromatography (0-100% ethyl acetate/hexanes, gradient elution) to provide the title compound (4.0 g, 61%). MS (ESI): mass calcd. for C$_{23}$H$_{34}$N$_4$O$_2$Si, 426.2; m/z found, 427.2 [M+H]$^+$. $^1$H NMR (600 MHz, CDCl$_3$) δ 7.25 (dd, J=8.3, 1.7 Hz, 2H), 7.16 (d, J=8.7 Hz, 1H), 6.66 (d, J=7.8 Hz, 1H), 6.04 (s, 1H), 5.64 (s, 1H), 4.79 (d, J=0.9 Hz, 2H), 4.53 (q, J=7.3 Hz, 2H), 2.80 (s, 3H), 2.28 (s, 3H), 1.47 (t, J=7.3 Hz, 3H), 0.81 (s, 9H), 0.00 (d, J=1.1 Hz, 6H).

Step B: Methyl 3-(5-(((tert-butyldimethylsilyl)oxy)methyl)-6-methylpyridin-3-yl)-3-(1-ethyl-4-methyl-1H-benzo[d][1,2,3]triazol-5-yl)-2,2-dimethylpropanoate. Trichloroacetonitrile (1.4 g, 9.4 mmol) and DBU (0.1 g, 0.7 mmol) were added to a solution of (5-(((tert-butyldimethylsilyl)oxy)methyl)-6-methylpyridin-3-yl)(1-ethyl-4-methyl-1H-benzo[d][1,2,3]triazol-5-yl)methanol (2.0 g, 4.7 mmol) in ACN (25 ml). The reaction was stirred at room temperature under nitrogen for 1 hour. ((1-Methoxy-2-methylprop-1-en-1-yl)oxy)trimethylsilane (1.6 g, 9.4 mmol) was then added to the reaction, followed by trifluoromethanesulfonamide (0.7 g, 2.3 mmol), and the reaction was stirred at room temperature under nitrogen for 3 hours. The reaction was quenched with saturated aqueous NaHCO$_3$, then extracted twice with EtOAc. These extractions resulted in several organic solvent fractions which were combined, dried over MgSO$_4$, filtered, and concentrated to dryness under reduced pressure. The product was purified by flash column chromatography (0-50% EtOAc/hexanes, gradient elution) to provide the title compound that was carried forward without further purification (1.5 g, 63% yield). MS (ESI): mass calcd. for C$_{28}$H$_{42}$N$_4$O$_3$Si, 510.3; m/z found, 511.3 [M+H]$^+$.

Step C: Methyl 3-(1-ethyl-4-methyl-1H-benzo[d][1,2,3]triazol-5-yl)-3-(5-(hydroxymethyl)-6-methylpyridin-3-yl)-2,2-dimethylpropanoate. Tetrabutylammonium fluoride (1 M in THF, 11.7 ml, 11.7 mmol) was added to a solution of methyl 3-(5-(((tert-butyldimethylsilyl)oxy)methyl)-6-methylpyridin-3-yl)-3-(1-ethyl-4-methyl-1H-benzo[d][1,2,3]triazol-5-yl)-2,2-dimethylpropanoate (3.0 g, 5.8 mmol) and 3 drops of DMF in THF (60 ml). The reaction was stirred at room temperature for 1.5 hours. The reaction was quenched with saturated aqueous NaHCO$_3$, then extracted twice with EtOAc. These extractions resulted in several organic solvent fractions which were combined, dried over MgSO$_4$, filtered, and concentrated to an oil under reduced pressure. The product was purified by flash column chromatography (0-100% ethyl acetate/hexanes, gradient elution) to provide the title compound (1.8 g, 77% yield). MS (ESI): mass calcd. for C$_{22}$H$_{28}$N$_4$O$_3$, 396.2; m/z found, 397.2 [M+H]$^+$. $^1$H NMR (500 MHz, CDCl$_3$) δ 8.28 (d, J=2.3 Hz, 1H), 7.67 (d, J=2.4 Hz, 1H), 7.58 (d, J=8.8 Hz, 1H), 7.29 (d, J=8.7 Hz, 1H), 4.83 (s, 1H), 4.69-4.56 (m, 4H), 4.35 (s, 1H), 3.50 (s, 3H), 2.74 (s, 3H), 2.37 (s, 3H), 1.57 (t, J=7.3 Hz, 3H), 1.36 (s, 3H), 1.29 (s, 3H).

Intermediate 52: 2-hydrazinyl-4-iodo-3-methylpyridine

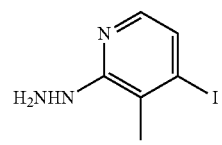

A mixture of hydrazine hydrate (47.0 mL, 630 mmol) and 2-fluoro-4-iodo-3-methylpyridine (23.39 g, 98.69 mmol) was stirred at 60° C. for 24 hours. The mixture was cooled to room temperature and then aqueous NaOH solution (60 mL, 3M) and water (60 mL) were added to the mixture and the suspension was stirred at 25° C. for 45 minutes. The solid was filtered, washed with water, and the solid was dried under reduced pressure to afford the title compound as a white solid (20.4 g, 83%), which was used in the next step without further purification. MS (ESI): mass calcd. for $C_6H_8IN_3$, 249.05; m/z found, 250 $[M+H]^+$. $^1$H NMR (400 MHz, DMSO-$d_6$) δ 7.57 (d, J=5.3 Hz, 1H), 7.44 (s, 1H), 7.03 (d, J=5.3 Hz, 1H), 4.17 (s, 2H), 2.19-2.11 (m, 3H).

Intermediate 53: 7-iodo-8-methyl-3-(trifluoromethyl)-[1,2,4]triazolo[4,3-a]pyridine

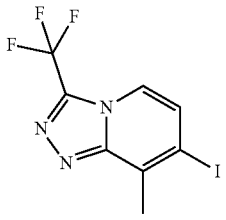

TFAA (53.0 mL, 375 mmol) was slowly added to a mixture of 2-hydrazinyl-4-iodo-3-methylpyridine (Intermediate 52, 20.4 g, 81.9 mmol) in toluene (40 mL). The mixture was heated to 60° C. for 22 hours under an atmosphere of nitrogen. The solvents were removed under reduced pressure, and the residue was dissolved in ethyl acetate. The resulting solution was washed with saturated aqueous NaHCO$_3$ solution, brine, dried and concentrated under reduced pressure. The residue was triturated with DCM/hexanes to afford the title compound as a white solid. MS (ESI): mass calcd. for $C_8H_5F_3IN_3$, 327.0; m/z found, 328.0 $[M+H]^+$. $^1$H NMR (400 MHz, DMSO-$d_6$) δ 8.24 (d, J=7.2 Hz, 1H), 7.52 (d, J=7.2 Hz, 1H), 2.68 (d, J=0.8 Hz, 3H).

Intermediate 54: 7-Bromo-3-cyclopropyl-8-methyl-[1,2,4]triazolo[4,3-a]pyridine

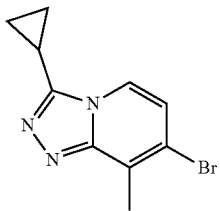

Step A: 4-Bromo-2-hydrazinyl-3-methylpyridine. Hydrazine hydrate (391 mL, 8.04 mol) was added to 4-bromo-2-fluoro-3-methylpyridine (240 g, 1.3 mol) and the white suspension was heated to 60° C. for 7 hours. The white suspension was concentrated under reduced pressure and the resulting white precipitate was collected by filtration. The solid was triturated with methyl tert-butyl ether (200 mL) to provide the title compound (255 g, 99.7% yield) as a white solid, which was used in the next step without further purification, MS (ESI): mass calcd. for $C_6H_8BrN_3$, 203.0; m/z found, 203.8 $[M+H]^+$.

Step B: 7-Bromo-3-cyclopropyl-8-methyl-[1,2,4]triazolo[4,3-a]pyridine. Cyclopropanecarbaldehyde (28.5 mL, 381 mmol) was added to a solution of 4-bromo-2-hydrazinyl-3-methylpyridine (70.0 g, 346 mmol) in EtOH (700 mL), and the light yellow mixture was stirred at 30° C. for 3 hours. H$_2$O (175 mL), CuBr$_2$ (1.62 mL, 34.6 mmol), and oxone (255.5 g, 415.7 mmol) were then added portion-wise and the resulting yellow solution was stirred for an additional 3 hours at 30° C. The mixture was filtered and the filtrate was concentrated under reduced pressure. Water (200 mL) was added to the reaction mixture, the pH was adjusted to 8 with saturated aqueous NaHCO$_3$, and the aqueous layer was extracted with dichloromethane (200 mL×3). These extractions resulted in several organic solvent fractions which were combined and washed with brine (500 mL), dried over anhydrous sodium sulfate, filtered, and concentrated under reduced pressure. The product was triturated with EtOAc (200 mL) and filtered. The resulting solid cake was dried under reduced pressure to afford the title compound (48 g, 52% yield) as a solid, which was used without further purification, MS (ESI): mass calcd. for $C_{10}H_{10}BrN_3$, 253.0; m/z found, 253.8 $[M+H]^+$.

Intermediate 55: Methyl 3-(3-cyclopropyl-8-methyl-[1,2,4]triazolo[4,3-a]pyridin-7-yl)-3-(3-(hydroxymethyl)-4-methylphenyl)-2,2-dimethylpropanoate

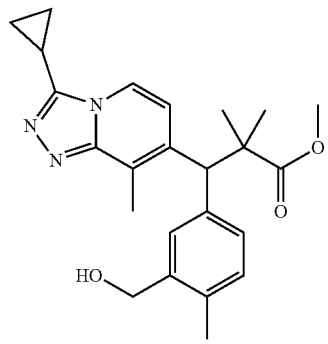 [SMILES: COC(=O)C(C)(C)C(c1ccc(C)c(CO)c1)c1ccn2c(C3CC3)nnc2c1C]

Step A: 3-Cyclopropyl-8-methyl-7-vinyl-[1,2,4]triazolo[4,3-a]pyridine. A mixture of 7-bromo-3-cyclopropyl-8-methyl-[1,2,4]triazolo[4,3-a]pyridine (Intermediate 54, 48.0 g, 190 mmol), potassium trifluoro(vinyl)borate (25.5 g, 190 mmol), potassium phosphate (121.6 g, 573.1 mmol), and Pd(dppf)Cl$_2$ (16.1 g, 19.8 mmol) in EtOH (720 mL) was degassed and purged with nitrogen 3 times and then the suspension was stirred at 85° C. for 12 hours under nitrogen. The mixture was concentrated under reduced pressure and the resulting residue was filtered through diatomaceous earth, and rinsed with DCM (200 mL). The filtrate was concentrated, and purified by FCC (5% MeOH/DCM) to afford the title compound (38.0 g, 80%, 80% purity). MS (ESI): mass calcd. for $Cl_2H_{13}N_3$, 199.1; m/z found, 200.2 $[M+H]^+$.

Step B: 3-Cyclopropyl-8-methyl-[1,2,4]triazolo[4,3-a]pyridine-7-carbaldehyde. Potassium osmate (2.44 g, 6.62 mmol) was added to a solution of 3-cyclopropyl-8-methyl-7-vinyl-[1,2,4]triazolo[4,3-a]pyridine (33.0 g, 166 mmol), dioxane (825 mL) and H$_2$O (825 mL). Then sodium periodate (113.3 g, 530 mmol) was added and the suspension was stirred at 30° C. for 2 hours. The reaction mixture was filtered through a plug of diatomaceous earth and the filtrate was concentrated under reduced pressure. The resulting residue was then diluted by addition of H$_2$O (200 mL) and the aqueous layer was extracted with DCM (200 mL×3). These extractions resulted in several organic solvent fractions which were combined, washed with brine, dried over sodium sulfate, filtered, and concentrated to dryness under reduced pressure. The product was triturated with DCM/hexanes (50 ml/250 ml) and further purified by flash column chromatography (5% EtOAc/DCM) to afford the title compound (20.9 g, 62%). MS (ESI): mass calcd. for $C_{11}H_{11}N_3O$, 201.1; m/z found, 202.0 $[M+H]^+$.

Step C: (3-(((Tert-butyldimethylsilyl)oxy)methyl)-4-methylphenyl)(3-cyclopropyl-8-methyl-[1,2,4]triazolo[4,3-a]pyridin-7-yl)methanol. 3-Cyclopropyl-8-methyl-[1,2,4]triazolo[4,3-a]pyridine-7-carbaldehyde (3.0 g, 15 mmol), tert-butyldimethyl((2-methyl-5-(4,4,5,5-tetramethyl-1,3,2-dioxaborolan-2-yl)benzyl)oxy)silane (Intermediate 43, 6.9 g, 18 mmol), palladium (II) chloride (0.26 g, 1.5 mmol), potassium carbonate (6.2 g, 45 mmol), and tri-1-naphthylphosphine (0.93 g, 2.2 mmol) were charged to a flask. The flask was evacuated and back-filled with nitrogen. THF (75 ml) was degassed with argon, then added via syringe. Argon was bubbled through the reaction mixture for 1 minute, then the reaction was stirred overnight in a pre-heated block at 75° C. under a reflux condenser and nitrogen. The reaction was cooled to room temperature, then filtered through diatomaceous earth and concentrated to dryness under reduced pressure. The product was purified by flash column chromatography (dry loaded with silica gel, 0-5% MeOH/DCM, gradient elution) to afford the title compound that was carried forward without further purification (0.66 g, 10%). MS (ESI): mass calcd. for $C_{25}H_{35}N_3O_2Si$, 437.2; m/z found, 438.3 $[M+H]^+$. An alternative method that was used to prepare (3-(((tert-butyldimethylsilyl)oxy)methyl)-4-methylphenyl)(3-cyclopropyl-8-methyl-[1,2,4]triazolo[4,3-a]pyridin-7-yl)methanol is shown below: 3-Cyclopropyl-7-iodo-8-methyl-[1,2,4]triazolo[4,3-a]pyridine (Intermediate 162, 5.05 g, 16.9 mmol) in 2-methyltetrahydrofuran (60 mL) was cooled in an ice bath under nitrogen, resulting in a suspension. Isopropylmagnesium chloride lithium chloride complex solution (1.3 M, 17 mL, 22 mmol) was added dropwise to the suspension and the reaction was removed from the ice bath and allowed to warm to room temperature for 30 minutes. 3-(((Tert-butyldimethylsilyl)oxy)methyl)-4-methylbenzaldehyde (Intermediate 163, 5.34 g, 20.2 mmol) was then added to the reaction via syringe using 2-methyltetrahydrofuran (4 mL). The suspension was stirred for 2 hours and became an orange solution, then was diluted with water and ethyl acetate. The resulting biphasic mixture was separated and the aqueous layer was extracted with ethyl acetate. These extractions resulted in several organic solvent fractions which were combined, dried over $MgSO_4$, filtered, and concentrated to dryness under reduced pressure. The material was purified by flash column chromatography (0-10% MeOH/DCM) to afford the title compound (5.99 g, 81% yield). MS (ESI): mass calcd. for $C_{25}H_{35}N_3O_2Si$, 437.2; m/z found, 438.3 $[M+H]^+$.

Step D: 7-((3-(((Tert-butyldimethylsilyl)oxy)methyl)-4-methylphenyl)chloromethyl)-3-cyclopropyl-8-methyl-[1,2,4]triazolo[4,3-a]pyridine. Thionyl chloride (0.2 mL, 3 mmol) was added to a solution of (3-(((tert-butyldimethylsilyl)oxy)methyl)-4-methylphenyl)(3-cyclopropyl-8-methyl-[1,2,4]triazolo[4,3-a]pyridin-7-yl)methanol (0.59 g, 1.3 mmol) and 2,6-di-tert-butylpyridine (0.7 ml, 3.1 mmol) in DCM (7 mL). The reaction was stirred at room temperature for 1 hour. The reaction was quenched with saturated aqueous $NaHCO_3$, then extracted twice with DCM. These extractions resulted in several organic solvent fractions which were combined, dried over $MgSO_4$, filtered, and concentrated to dryness under reduced pressure. The product was purified by flash column chromatography (dry loaded with silica gel, 0-50% ethyl acetate/hexanes, gradient elution) to provide the title compound (200 mg, 32%). MS (ESI): mass calcd. for $C_{25}H_{34}ClN_3OSi$, 455.2; m/z found, 456.2 $[M+H]^+$.

Step E: Methyl 3-(3-(((tert-butyldimethylsilyl)oxy)methyl)-4-methylphenyl)-3-(3-cyclopropyl-8-methyl-[1,2,4]triazolo[4,3-a]pyridin-7-yl)-2,2-dimethylpropanoate. ((1-Methoxy-2-methylprop-1-en-1-yl)oxy)trimethylsilane (0.6 ml, 3.0 mmol) was added to a solution of 7-((3-(((tert-butyldimethylsilyl)oxy)methyl)-4-methylphenyl)chloromethyl)-3-cyclopropyl-8-methyl-[1,2,4]triazolo[4,3-a]pyridine (267 mg, 0.585 mmol) in DCM (3 mL). Indium(III) bromide (114 mg, 0.322 mmol) was added and the reaction was stirred at room temperature for 3 hours. The reaction mixture was filtered, concentrated under a stream of nitrogen, and purified by flash column chromatography (0-10% MeOH/EtOAc, gradient elution) to afford the title compound (197 mg, 64%). MS (ESI): mass calcd. for $C_{30}H_{43}N_3O_3Si$, 521.3; m/z found, 522.3 $[M+H]^+$.

Step F: Methyl 3-(3-cyclopropyl-8-methyl-[1,2,4]triazolo[4,3-a]pyridin-7-yl)-3-(3-(hydroxymethyl)-4-methylphenyl)-2,2-dimethylpropanoate. Tetrabutylammonium fluoride (1 M in THF, 0.5 ml, 0.5 mmol) was added to a solution of methyl 3-(3-(((tert-butyldimethylsilyl)oxy)methyl)-4-methylphenyl)-3-(3-cyclopropyl-8-methyl-[1,2,4]triazolo[4,3-a]pyridin-7-yl)-2,2-dimethylpropanoate (197 mg, 0.38 mmol) in THF (2 ml). The reaction was stirred at room temperature for 1 hour. Additional tetrabutylammonium fluoride (1 M in THF, 0.1 ml, 0.1 mmol) was added and the reaction was stirred at room temperature for an additional 3.5 hours. The reaction was quenched with saturated aqueous $NH_4Cl$, then extracted twice with ethyl acetate. These extractions resulted in several organic solvent fractions which were combined, dried over $MgSO_4$, filtered, and concentrated to dryness under reduced pressure to provide the title compound (145 mg, 94%) which was used without further purification. MS (ESI): mass calcd. for $C_{24}H_{29}N_3O_3$, 407.2; m/z found, 408.2 $[M+H]^+$.

Intermediate 56: Methyl 3-(1-cyclopropyl-4-methyl-1H-benzo[d][1,2,3]triazol-5-yl)-3-(5-(hydroxymethyl)-6-methylpyridin-3-yl)-2,2-dimethylpropanoate

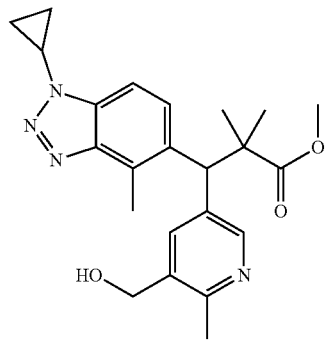 [SMILES: COC(=O)C(C)(C)C(c1cnc(C)c(CO)c1)c1ccc2c(nnn2C2CC2)c1C]

Step A: 1-Cyclopropyl-4-methyl-5-vinyl-1H-benzo[d][1,2,3]triazole. A mixture of 5-bromo-1-cyclopropyl-4-methyl-1H-benzo[d][1,2,3]triazole (Intermediate 29, 17 g, 67.4 mmol), potassium trifluoro(vinyl)borate (18.1 g, 135 mmol), potassium phosphate (42.9 g, 202 mmol), and $Pd(dppf)Cl_2$ (2.75 g, 3.37 mmol) were added to a flask, which was then evacuated and back-filled with nitrogen. 1,4-Dioxane (170 ml) and water (30 ml) were bubbled with nitrogen for 10 minutes, then added to the solid reagents. The reaction mixture was heated to 100° C. under a reflux condenser and nitrogen for 4 hours. The reaction was then cooled to room temperature and filtered through diatomaceous earth, rinsing with EtOAc. The filtrate was washed with brine, then dried over MgSO$_4$, filtered, and concentrated to dryness under reduced pressure. The product was purified by FCC (0-20% EtOAc/hexanes) to afford the title compound that was carried forward without further purification (2.1 g, 52%). MS (ESI): mass calcd. for $C_{12}H_{13}N_3$, 199.1; m/z found, 200.2 [M+H]$^+$.

Step B: 1-Cyclopropyl-4-methyl-1H-benzo[d][1,2,3]triazole-5-carbaldehyde. Potassium osmate (2.22 g, 6.0 mmol) was added to a solution of 1-cyclopropyl-4-methyl-5-vinyl-1H-benzo[d][1,2,3]triazole (30 g, 150 mmol), 1,4-dioxane (750 ml) and H$_2$O (750 ml). Then sodium periodate (103 g, 482 mmol) was added. The suspension was stirred at 25° C. for 2 hours. The reaction mixture was filtered through a plug of diatomaceous earth, rinsing with EtOAc. The filtrate was extracted twice with EtOAc. These extractions resulted in several organic solvent fractions which were washed with brine, combined, dried over sodium sulfate, filtered, and concentrated to dryness under reduced pressure. The residue was purified by FCC (10-30% EtOAc/hexanes) to provide a residue. This residue was then stirred with hexanes (100 ml) for 2 hours, filtered, and the filter cake was dried under reduced pressure to afford the title compound (21.2 g, 70%). MS (ESI): mass calcd. for $C_{11}H_{11}N_3O$, 201.1; m/z found, 201.9 [M+H]$^+$.

Step C: (5-(((Tert-butyldimethylsilyl)oxy)methyl)-6-methylpyridin-3-yl)(1-cyclopropyl-4-methyl-1H-benzo[d][1,2,3]triazol-5-yl)methanol. n-Butyllithium (1.6 M, 9 ml, 14 mmol) was added dropwise to a solution of 5-bromo-3-(((tert-butyldimethylsilyl)oxy)methyl)-2-methylpyridine (Intermediate 46, 4.05 g, 12.8 mmol) in THF under nitrogen (95 ml) which was cooled to −78° C. to prepare the lithiate reaction mixture. In a separate flask, 1-cyclopropyl-4-methyl-1H-benzo[d][1,2,3]triazole-5-carbaldehyde (2.81 g, 14 mmol) was mixed with THF (70 ml) and the resulting suspension was stirred and heated to form a solution. After all the solids had dissolved, this 1-cyclopropyl-4-methyl-1H-benzo[d][1,2,3]triazole-5-carbaldehyde solution was cooled to room temperature, then added to the lithiate reaction mixture as a stream. The resulting reaction mixture was then removed from the −78° C. bath and allowed to warm to room temperature for 30 minutes. The reaction was quenched with saturated aqueous NaHCO$_3$, and then extracted twice with EtOAc. These extractions resulted in several organic solvent fractions which were combined, dried over MgSO$_4$, filtered, and concentrated to dryness under reduced pressure. The product was purified by flash column chromatography (dry loaded with silica gel, 0-5% MeOH/DCM, gradient elution) to provide the title compound (1.96 g, 35%). MS (ESI): mass calcd. for $C_{24}H_{34}N_4O_2Si$, 438.2; m/z found, 439.3 [M+H]$^+$.

Step D: Methyl 3-(5-(((tert-butyldimethylsilyl)oxy)methyl)-6-methylpyridin-3-yl)-3-(1-cyclopropyl-4-methyl-1H-benzo[d][1,2,3]triazol-5-yl)-2,2-dimethylpropanoate. Trichloroacetonitrile (0.9 ml, 9 mmol) and DBU (0.15 ml, 1 mmol) were added to a solution of (5-(((tert-butyldimethylsilyl)oxy)methyl)-6-methylpyridin-3-yl)(1-cyclopropyl-4-methyl-1H-benzo[d][1,2,3]triazol-5-yl)methanol (1.91 g, 4.4 mmol) in ACN (22 ml). The reaction was stirred at room temperature under nitrogen for 1 hour. ((1-Methoxy-2-methylprop-1-en-1-yl)oxy)trimethylsilane (4.4 ml, 22 mmol) was then added to the reaction, followed by trifluoromethanesulfonamide (1.28 g, 4.6 mmol), and the reaction was stirred at room temperature under nitrogen for 3 hours. The reaction was quenched with saturated aqueous NaHCO$_3$, then extracted twice with EtOAc. These extractions resulted in several organic solvent fractions which were combined, dried over MgSO$_4$, filtered, and concentrated to dryness under reduced pressure. The product was purified by flash column chromatography (0-50% EtOAc/hexanes, gradient elution) to provide the title compound that was carried forward without further purification (1.5 g, 66%). MS (ESI): mass calcd. for $C_{29}H_{42}N_4O_3Si$, 522.3; m/z found, 523.4 [M+H]$^+$.

Step E: Methyl 3-(1-cyclopropyl-4-methyl-1H-benzo[d][1,2,3]triazol-5-yl)-3-(5-(hydroxymethyl)-6-methylpyridin-3-yl)-2,2-dimethylpropanoate. Tetrabutylammonium fluoride (1 M in THF, 5.7 ml, 5.7 mmol) was added to a solution of methyl 3-(5-(((tert-butyldimethylsilyl)oxy)methyl)-6-methylpyridin-3-yl)-3-(1-cyclopropyl-4-methyl-1H-benzo[d][1,2,3]triazol-5-yl)-2,2-dimethylpropanoate (1.5 g, 2.9 mmol) and 3 drops of DMF in THF (29 ml). The reaction was stirred at room temperature for 1.5 hours. The reaction was quenched with saturated aqueous NaHCO$_3$, then extracted twice with EtOAc. These extractions resulted in several organic solvent fractions which were combined, dried over MgSO$_4$, filtered, and concentrated to an oil under reduced pressure. The product was purified by flash column chromatography (0-100% EtOAc/hexanes, gradient elution) to provide the title compound (0.77 g, 66%). MS (ESI): mass calcd. for $C_{23}H_{28}N_4O_3$, 408.2; m/z found, 409.2 [M+H]$^+$, $^1$H NMR (400 MHz, CDCl$_3$) δ 8.33-8.28 (m, 1H), 7.63-7.56 (m, 2H), 7.42 (d, J=8.7 Hz, 1H), 4.82 (s, 1H), 4.68-4.57 (m, 2H), 3.77-3.66 (m, 1H), 3.51 (s, 3H), 3.26 (s, 1H), 2.74 (s, 3H), 2.40 (s, 3H), 1.39-1.23 (m, 10H).

Intermediate 57: 6-(((tert-Butyldimethylsilyl)oxy) methyl)-5-methylpicolinaldehyde

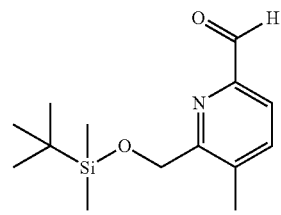 [SMILES: Cc1ccc(C=O)nc1CO[Si](C)(C)C(C)(C)C]

Step A: Methyl 6-chloro-3-methylpicolinate. Thionyl chloride (208 g, 1.75 mol) was added to a solution of 6-chloro-3-methylpicolinic acid (200 g, 1.17 mol) in methanol (300 mL) and the reaction mixture was warmed to 65° C. After 3 hours, the reaction mixture was concentrated under reduced pressure, and saturated aqueous NaHCO$_3$ solution (1 L) was added. The aqueous layer was extracted twice with ethyl acetate which resulted in several organic solvent fractions which were combined, dried over Na$_2$SO$_4$, filtered, and concentrated to dryness under reduced pressure to provide the title compound as a dark-brown solid (210 g, 97%). $^1$H NMR (400 MHz, CDCl$_3$) 7.57 (d, J=8.0 Hz, 1H) 7.36 (d, J=8.0 Hz, 1H) 3.95 (s, 3H) 2.53 (s, 3H).

Step B: (6-Chloro-3-methylpyridin-2-yl)methanol. Sodium borohydride (257 g, 6.79 mol) was added to a stirring solution of methyl 6-chloro-3-methylpicolinate (210 g, 1.13 mol) in THF (200 mL) and the mixture was warmed to 66° C. After 30 minutes, the mixture was cooled to room temperature and methanol (50 mL) was added dropwise. The resulting solution was warmed to 66° C. After 2 hours, the reaction mixture was cooled to room temperature, saturated aqueous NH₄Cl solution was added and the biphasic mixture was stirred for 1.5 hours. The mixture was filtered and the aqueous layer was extracted twice with ethyl acetate. This resulted in several organic solvent fractions which were combined, washed with saturated aqueous NaCl solution, dried over Na₂SO₄, filtered, and concentrated to dryness under reduced pressure to provide the title compound as a light yellow oil (140 g, 78%). ¹H NMR (400 MHz, CDCl₃) δ 7.35-7.33 (d, J=8.0 Hz, 1H), 7.07-7.05 (d, J=8 Hz, 1H), 4.57 (s, 2H), 2.12 (s, 3H).

Step C: 2-(((tert-Butyldimethylsilyl)oxy)methyl)-6-chloro-3-methylpyridine. TBSCl (36.8 g, 244 mmol) was added to a stirring solution of (6-chloro-3-methylpyridin-2-yl)methanol (35 g, 222 mmol) and imidazole (30.2 g, 444 mmol) in dichloromethane (450 mL). After 16 hours, dichloromethane (400 mL) was added and the mixture was washed sequentially with water and saturated aqueous NaCl solution. The organic layer was dried over Na₂SO₄, filtered, and concentrated to dryness under reduced pressure to provide a residue. The residue was purified by flash column chromatography (petroleum ether (containing 1% triethylamine)/ethyl acetate (50:1 to 5:1) gradient elution) to afford the title compound as a colorless liquid (58 g, 94%). MS (ESI): mass calcd. for C₁₃H₂₂ClNOSi, 271.1; m/z found, 271.9 [M+H]⁺. ¹H NMR (400 MHz, CDCl₃) 7.39 (d, J=7.6 Hz, 1H) 7.12 (d, J=7.6 Hz, 1H) 4.75 (s, 2H) 2.36 (s, 3H) 0.87 (s, 9H) 0.07 (s, 6H).

Step D: Methyl 6-(((tert-butyldimethylsilyl)oxy)methyl)-5-methylpicolinate. A mixture containing 2-(((tert-butyldimethylsilyl)oxy)methyl)-6-chloro-3-methylpyridine (65 g, 239 mmol), triethylamine (66.6 mL), and Pd(dppf)₂Cl₂ (17.5 g, 23.9 mmol) in DMF (350 mL) and methanol (350 mL) was stirred at 80° C. under a 50 psi atmosphere of carbon monoxide. After 16 hours, the reaction mixture was filtered, concentrated under reduced pressure, and the residue was dissolved in ethyl acetate. This mixture was washed with water and the aqueous layers were extracted with ethyl acetate. This resulted in several organic fractions which were combined, dried over Na₂SO₄, filtered, and concentrated to dryness under reduced pressure. The residue was purified by flash column chromatography (petroleum ether-ethyl acetate containing 1% triethylamine) to afford the title compound as a light yellow solid (60 g, 84%). ¹H NMR (400 MHz, CDCl₃) 7.95 (d, J=7.6 Hz, 1H) 7.58 (d, J=7.8 Hz, 1H) 4.88 (s, 2H) 3.97 (s, 3H) 2.47 (s, 3H) 0.88 (s, 9H) 0.07 (s, 6H).

Step E. 6-(((tert-Butyldimethylsilyl)oxy)methyl)-5-methylpicolinaldehyde. A 1 M solution of DIBAL-H in dichloromethane (264 mL, 264 mmol) was added dropwise to a stirring mixture of methyl 6-(((tert-butyldimethylsilyl)oxy)methyl)-5-methylpicolinate (68 g, 219 mmol) in dichloromethane (1.5 L) at a rate that maintained an internal temperature of less than −60° C. After 2 hours, methanol (20 mL) was added and the reaction allowed to warm to room temperature. Saturated aqueous potassium sodium tartrate solution (1 L) was added and the resulting biphasic mixture was stirred for 1 hour. The mixture was extracted twice with dichloromethane which resulted in several organic solvent fractions which were combined, washed with saturated aqueous NaCl solution, dried over Na₂SO₄, filtered, and concentrated to dryness under reduced pressure. The residue was purified by flash column chromatography (petroleum ether-ethyl acetate) to afford the title compound as a light yellow solid (33.1 g, 53%). MS (ESI): mass calcd. for C₁₄H₂₃NO₂Si, 265.2; m/z found, 266.1[M+H]⁺. ¹H NMR (400 MHz, CDCl₃) 10.03 (s, 1H) 7.81 (d, J=7.8 Hz, 1H) 7.62 (d, J=7.8 Hz, 1H) 4.91 (s, 2H) 2.50 (s, 3H) 0.90 (s, 9H) 0.09 (s, 6H).

Intermediate 58: ethyl 3-(1-(cyclopropylmethyl)-4-(difluoromethyl)-1H-benzo[d][1,2,3]triazol-5-yl)-3-(3-(hydroxymethyl)-4-methylphenyl)propanoate

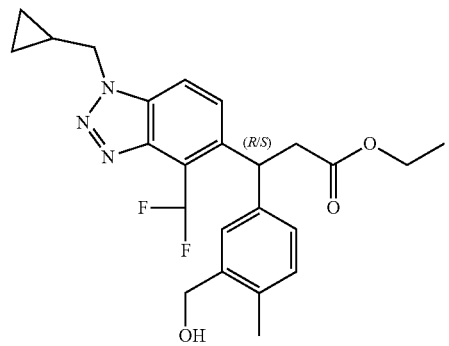 [SMILES: CCOC(=O)CC(c1ccc(C)c(CO)c1)c1ccc2c(nnn2CC2CC2)c1C(F)F]

Step A: 1-chloro-3-(difluoromethyl)-2-nitrobenzene. Diethylamino sulfurtrifluoride (32.6 g, 202 mmol) was added to a 0° C. (ice/water) solution consisting of 3-chloro-2-nitrobenzaldehyde (15 g, 81 mmol) and dichloromethane (200 mL). The resultant mixture was stirred for 3 hours with gradual warming to room-temperature before quenching with H₂O (200 mL) and extracting with dichloromethane (3×). These extractions resulted in several fractions which were combined, dried over sodium sulfate and concentrated to dryness under reduced pressure. The residue was purified by flash column chromatography (eluent:petroleum ether/ethyl acetate, 1:0 to 20:1, gradient elution) to give the title compound (12 g, 64%). ¹H NMR (400 MHz, DMSO-d₆) δ 8.06-7.95 (m, 1H), 7.86-7.77 (m, 2H), 7.42-7.11 (m, 1H).

Step B: N-(Cyclopropylmethyl)-3-(difluoromethyl)-2-nitroaniline. 1-Chloro-3-(difluoromethyl)-2-nitrobenzene (2.0 g, 9.6 mmol) and cyclopropylmethanamine (10 mL) were added to a 20 mL sealed tube. The resultant mixture was stirred at 80° C. for 16 hours before cooling to room-temperature, quenching with water (60 mL), and extracting with ethyl acetate (3×). These extractions resulted in several fractions which were combined, dried over sodium sulfate and concentrated to dryness under reduced pressure. The residue was purified by flash column chromatography (eluent:petroleum ether/ethyl acetate, 1:0 to 5:1, gradient elution) to give the title compound (2.1 g, 90%). MS (ESI): mass calcd. for C₁₁H₁₂F₂N₂O₂ 242.1, m/z found 242.7 [M+H]⁺.

Step C: 4-Bromo-N-(cyclopropylmethyl)-3-(difluoromethyl)-2-nitroaniline. N-(Cyclopropylmethyl)-3-(difluoromethyl)-2-nitroaniline (2.1 g, 8.7 mmol), NBS (1.54 g, 8.65 mmol), and DMF (10 mL) were added to a 50 mL round-bottomed flask. The resultant mixture was stirred at room-temperature for 4 hours before quenching with water (50 mL) and extracting with ethyl acetate (3×). These extractions resulted in several fractions which were combined, dried over sodium sulfate and concentrated to dryness under reduced pressure. The resulting residue was purified by flash column chromatography (eluent:petroleum ether/ethyl acetate, 1:0 to 5:1, gradient elution) to give the title compound (2.1 g, 68%). ¹H NMR (400 MHz, DMSO-d₆) δ 7.47

(d, J=9.0 Hz, 1H), 7.09-6.79 (m, 2H), 6.22 (t, J=5.6 Hz, 1H), 2.86 (t, J=6.2 Hz, 2H), 0.91-0.79 (m, 1H), 0.28-0.18 (m, 2H), 0.05-0.04 (m, 2H).

Step D: 4-Bromo-$N^1$-(cyclopropylmethyl)-3-(difluoromethyl)benzene-1,2-diamine. Zn (3.4 g, 52 mmol) was added to a solution of 4-bromo-N-(cyclopropylmethyl)-3-(difluoromethyl)-2-nitroaniline (2.1 g, 6.5 mmol), $NH_4Cl$ (5.6 g, 105 mmol), and THF (20 mL). The resultant mixture was stirred at room-temperature for 16 hours. The suspension was filtered through a pad of diatomaceous earth and the pad was washed with ethyl acetate (1×). The filtrate was concentrated to dryness under reduced pressure to afford the title product (1.8 g, 95%). MS (ESI): mass calcd. for $C_{11}H_{13}BrF_2N_2$ 290.0, m/z found 292.8 [M+H]$^+$.

Step E: 5-Bromo-1-(cyclopropylmethyl)-4-(difluoromethyl)-1H-benzo[d][1,2,3]triazole. A solution of $NaNO_2$ (5.7 g, 83 mmol) and $H_2O$ (10 mL) were added to a 0° C. (ice/water) mixture of 4-bromo-$N^1$-(cyclopropylmethyl)-3-(difluoromethyl)benzene-1,2-diamine (8.0 g, 27 mmol), 4-methylbenzenesulfonic acid hydrate (18.3 g, 96.2 mmol), and $CH_3CN$ (100 mL). The resultant mixture was stirred at 0° C. for 3 hours before quenching with aq. $NaHCO_3$(300 mL) and extracting with ethyl acetate (3×). These extractions resulted in several fractions which were combined, dried over sodium sulfate and concentrated to dryness under reduced pressure. The residue was purified by flash column chromatography (eluent:petroleum ether/ethyl acetate, 1:0 to 5:1) to give the title compound (6.2 g, 75%). MS (ESI): mass calcd. for $C_{11}H_{10}BrF_2N_3$ 301.0, m/z found 303.7 [M+H]$^+$.

Step F: (E)-Ethyl 3-(1-(cyclopropylmethyl)-4-(difluoromethyl)-1H-benzo[d][1,2,3]triazol-5-yl)acrylate. 5-Bromo-1-(cyclopropylmethyl)-4-(difluoromethyl)-1H-benzo[d][1,2,3]triazole (2.0 g, 6.6 mmol), (E)-ethyl 3-(4,4,5,5-tetramethyl-1,3,2-dioxaborolan-2-yl)acrylate (3.0 g, 13 mmol), and $Na_2CO_3$ (1.4 g, 13 mmol) were added to a 100 mL three-necked round-bottomed flask and the resulting mixture dissolved in 1,4-dioxane (30 mL) and $H_2O$ (6 mL). The mixture was sparged with $N_2$ for 5 minutes and then treated with Pd(dppf)$Cl_2$ (484 mg, 0.661 mmol). The mixture was sparged with $N_2$ for another 5 minutes and then stirred and heated at 100° C. for 16 hours before cooling to room-temperature, quenching with water (60 mL) and extracting with ethyl acetate (3×). These extractions resulted in several fractions which were combined, dried over sodium sulfate and concentrated to dryness under reduced pressure. The resulting residue was purified by flash column chromatography (eluent:petroleum ether/ethyl acetate, 20:1 to 5:1, gradient elution) to give the title compound (2.0 g, 80%) as a black solid. MS (ESI): mass calcd. for $C_{16}H_{17}F_2N_3O_2$ 321.1, m/z found 321.9 [M+H]$^+$.

Step G: Ethyl 3-(1-(cyclopropylmethyl)-4-(difluoromethyl)-1H-benzo[d][1,2,3]triazol-5-yl)-3-(3-(hydroxymethyl)-4-methylphenyl)propanoate. (E)-Ethyl 3-(1-(cyclopropylmethyl)-4-(difluoromethyl)-1H-benzo[d][1,2,3]triazol-5-yl)acrylate (1.5 g, 4.7 mmol), (3-(hydroxymethyl)-4-methylphenyl)boronic acid (2.3 g, 14 mmol), aqueous KOH (5.6 mL, 1.0 M, 5.6 mmol), and 1,4-dioxane (20 mL) were added to a 100 mL round-bottomed flask. The mixture was sparged with $N_2$ for 5 minutes and then treated with chloro(1,5-cyclooctadiene)rhodium(I) dimer (230 mg, 0.47 mmol). The reaction mixture was stirred at room-temperature for 16 hours before quenching with $H_2O$ (60 mL) and extracting with ethyl acetate (3×). These extractions resulted in several fractions which were combined, dried over sodium sulfate and concentrated to dryness under reduced pressure. The resulting residue was purified by reverse phase preparative HPLC (eluent: MeCN/water with 0.05% $NH_3$, 3:7 to 7:3, gradient elution). The product was suspended in water (10 mL), the mixture frozen using dry ice/acetone, and then lyophilized to dryness to afford the title compound (510 mg, 24%). MS (ESI): mass calcd. for $C_{24}H_{27}F_2N_3O_3$ 443.20, m/z found 444.0 [M+H]$^+$. $^1$H NMR (400 MHz, DMSO-$d_6$) δ 8.07-7.75 (m, 2H), 7.57 (d, J=8.8 Hz, 1H), 7.31 (s, 1H), 7.18-7.12 (m, 1H), 7.07-7.01 (m, 1H), 5.17-5.07 (m, 1H), 5.01 (t, J=5.3 Hz, 1H), 4.58 (d, J=7.3 Hz, 2H), 4.43-4.35 (m, 2H), 3.97-3.88 (m, 2H), 3.28-3.19 (m, 1H), 3.14-3.05 (m, 1H), 2.14 (s, 3H), 1.38-1.26 (m, 1H), 1.01 (t, J=7.2 Hz, 3H), 0.55-0.39 (m, 4H).

Intermediate 59: 2',3'-dihydrospiro[oxetane-3,4'-pyrido[2,3-b][1,4,5]oxathiazepine] 1',1'-dioxide

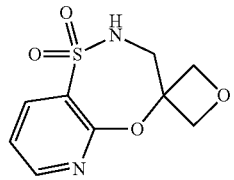 [SMILES: O=S1(=O)NCC2(COC2)Oc2ncccc21]

Step A: 3-(Nitromethyl)oxetan-3-ol. $Et_3N$ (0.5 mL) was added drop-wise to a solution consisting of oxetan-3-one (10.0 g, 139 mmol) and $MeNO_2$ (25 mL). The resultant mixture was stirred at room-temperature for 16 hours before concentrating to dryness to give the product, which was purified by flash column chromatography (eluent:petroleum ether/ethyl acetate, 10:1 to 1:1 gradient elution) to afford the title compound (15 g, 81%). $^1$H NMR (400 MHz, CDCl$_3$) δ 4.76 (s, 2H), 4.68-4.59 (m, 4H), 4.26 (s, 1H).

Step B: 3-(Aminomethyl)oxetan-3-ol. Dry Pd/C (1.0 g, 10 wt. %, 0.95 mmol) was added to a solution of 3-(nitromethyl)oxetan-3-ol (10 g, 75 mmol) and ethanol (50 mL) under $N_2$. The resultant mixture was stirred under $H_2$ (1 atm) at room-temperature for 16 hours. The suspension was filtered through a pad of diatomaceous earth and the pad washed with ethanol (50 mL). The filtrate was concentrated to dryness under reduced pressure to afford the product (8 g), which was used in the next step without further purification. $^1$H NMR (400 MHz, DMSO-$d_6$) δ 5.52 (br s, 2H), 4.45 (d, J=6.6 Hz, 2H), 4.37-4.32 (m, 2H), 2.97 (s, 2H), 2.69 (s, 1H).

Step C: 2-Chloro-N-((3-hydroxyoxetan-3-yl)methyl)pyridine-3-sulfonamide. 2-Chloropyridine-3-sulfonyl chloride (10 g, 47 mmol) was added to a solution of 3-(aminomethyl)oxetan-3-ol (7.3 g), $K_2CO_3$ (7.8 g, 56 mmol), THF (90 mL), and $H_2O$ (20 mL). The resultant mixture was stirred at room-temperature for 16 hours before concentrating to dryness under reduced pressure. The residue was dissolved water (30 mL) and extracted with ethyl acetate (3×). These extractions resulted in several fractions which were combined, dried over sodium sulfate and concentrated to dryness under reduced pressure to afford the title compound (7 g), which was used in the next step without further purification. MS (ESI): mass calcd. for $C_9H_{11}ClN_2O_4S$, 278.01, m/z found 279.1[M+H]$^+$.

Step D: 2',3'-dihydrospiro[oxetane-3,4'-pyrido[2,3-b][1,4,5]oxathiazepine] 1',1'-dioxide. t-BuOK (7.1 g, 63 mmol) was added to a solution consisting of 2-chloro-N-((3-hydroxyoxetan-3-yl)methyl)pyridine-3-sulfonamide (6.5 g) and DMSO (24 mL). The resultant mixture was stirred while heating at 95° C. for 2 hours before cooling to room-temperature, diluting with water (20 mL), acidifying pH to 4 with 1 N HCl, and extracting with ethyl acetate (50 mL×4). These extractions resulted in several fractions which were combined, dried over sodium sulfate and concentrated to dryness under reduced pressure, which was purified by preparative HPLC using a preparative HPLC (eluent: CH$_3$CN/H$_2$O with 0.225% HCOOH, 1:99 to 1:4 gradient elution) to afford pure product. The product was suspended in water (20 mL), the mixture was frozen using dry ice/acetone, and then lyophilized to dryness to afford the title compound (2.1 g). MS (ESI): mass calcd. for C$_9$H$_{10}$N$_2$O$_4$S, 242.0, m/z found 243.0 [M+H]$^+$. $^1$H NMR (400 MHz, DMSO-d$_6$) δ 8.52 (dd, J=2.0, 4.9 Hz, 1H), 8.36 (br s, 1H), 8.16 (dd, J=2.0, 7.7 Hz, 1H), 7.50-7.35 (m, 1H), 4.40 (s, 4H), 3.90-3.77 (m, 2H).

Intermediate 60: ethyl 3-(4-difluoromethyl)-1-methyl-1H-benzo[d][1,2,3]triazol-5-yl)-3-(3-hydroxymethyl)-4-methylphenyl)propanoate

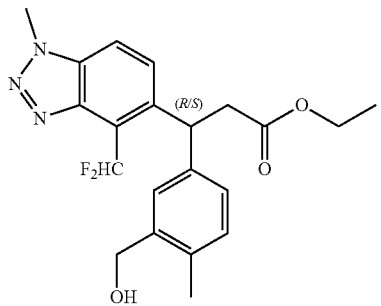 [SMILES: CCOC(=O)CC(c1ccc(C)c(CO)c1)c1ccc2c(nnn2C)c1C(F)F]

Step A: 3-(Difluoromethyl)-N-methyl-2-nitroaniline. 1-Chloro-3-(difluoromethyl)-2-nitrobenzene (9.0 g, 43 mmol) and methanamine (30 mL, 33% purity in ethanol) were added to a 100 mL sealed tube. The resultant mixture was stirred at 70° C. for 16 hours before cooling to room-temperature and concentrating to dryness under reduced pressure to afford the title compound (10 g), which was used in the next step without further purification. $^1$H NMR (400 MHz, CDCl$_3$) δ 7.51-7.45 (m, 1H), 7.43-7.13 (m, 1H), 7.07 (d, J=7.3 Hz, 1H), 6.98 (d, J=8.6 Hz, 1H), 3.01 (d, J=5.1 Hz, 3H).

Step B: 4-Bromo-3-(difluoromethyl)-N-methyl-2-nitroaniline. NBS (8.8 g, 49 mmol) was added to a solution of 3-(difluoromethyl)-N-methyl-2-nitroaniline (10.0 g, 49.5 mmol) and DMF (100 mL). The resultant mixture was stirred at room-temperature for 16 hours before pouring it into water (300 mL) and extracting with ethyl acetate (3×). These extractions resulted in several fractions which were combined, dried over sodium sulfate and concentrated to dryness under reduced pressure. The residue was purified by flash chromatography (eluent:petroleum ether/ethyl acetate 1:0 to 5:1, gradient elution) to afford the title compound (13 g, 93%). $^1$H NMR (400 MHz, CDCl$_3$) δ 8.00 (br s, 2H), 7.56 (d, J=9.0 Hz, 1H), 7.06-6.80 (m, 1H), 6.78 (d, J=2.6 Hz, 1H), 5.63 (br s, 1H), 2.91 (d, J=5.1 Hz, 3H).

Step C: 4-Bromo-3-(difluoromethyl)-N$^1$-methylbenzene-1,2-diamine. Zn (22.3 g, 341 mmol) was added to a mixture of 4-bromo-3-(difluoromethyl)-N-methyl-2-nitroaniline (12.0 g, 42.7 mmol), NH$_4$Cl (36.5 g, 682 mmol), and THF (300 mL). The resultant mixture was stirred at room-temperature for 16 hours. The suspension was filtered through a pad of diatomaceous earth and the pad washed with ethyl acetate (200 mL). The filtrate was concentrated to dryness under reduced pressure to give the product, which was purified by flash chromatography (eluent: petroleum ether/ethyl acetate, 50:1 to 10:1, gradient elution) to afford the title compound (9.5 g, 89%). $^1$H NMR (400 MHz, DMSO-d$_6$) δ 7.40-7.06 (m, 1H), 7.03-6.95 (m, 1H), 6.58 (d, J=8.6 Hz, 1H), 2.91-2.82 (m, 3H).

Step D: 5-Bromo-4-(difluoromethyl)-1-methyl-1H-benzo[d][1,2,3]triazole. A solution consisting of NaNO$_2$ (7.4 g, 0.11 mol) and H$_2$O (20 mL) was added to a 0° C. (ice/water) mixture consisting of 4-bromo-3-(difluoromethyl)-N$^1$-methylbenzene-1,2-diamine (9.0 g, 36 mmol), p-toluenesulfonic acid monohydrate (23.9 g, 126 mmol), and CH$_3$CN (300 mL). The resultant mixture was stirred at 0° C. for 3 hours before quenching with sat. NaHCO$_3$ (500 mL) and extracting with ethyl acetate (3×). These extractions resulted in several fractions which were combined, dried over sodium sulfate and concentrated to dryness under reduced pressure. The residue was purified by flash chromatography (eluent:petroleum ether/ethyl acetate, 1:0 to 5:1, gradient elution) to afford the title compound (5.0 g, 47%). $^1$H NMR (400 MHz, DMSO-d$_6$) δ (d, J=8.8 Hz, 1H), 7.83 (d, J=8.8 Hz, 1H), 7.55 (t, J=52.4 Hz, 1H), 4.40-4.26 (m, 3H).

Step E: (E)-Ethyl 3-(4-(difluoromethyl)-1-methyl-1H-benzo[d][1,2,3]triazol-5-yl)acrylate. 5-Bromo-4-(difluoromethyl)-1-methyl-1H-benzo[d][1,2,3]triazole (3.2 g, 12 mmol), (E)-ethyl 3-(4,4,5,5-tetramethyl-1,3,2-dioxaborolan-2-yl)acrylate (5.5 g, 24 mmol), and Na$_2$CO$_3$ (3.9 g, 37 mmol) were dissolved in 1,4-dioxane (100 mL) and H$_2$O (20 mL). The mixture was sparged with nitrogen for 5 minutes and then treated with Pd(dppf)Cl$_2$ (0.89 g, 1.2 mmol). The mixture was sparged with nitrogen for another 5 minutes and then stirred at 100° C. for 16 hours under nitrogen before cooling to room-temperature and diluting with ethyl acetate (100 mL). The organic layer was dried over anhydrous Na$_2$SO$_4$, filtered, and concentrated to dryness under reduced pressure to give the product, which was purified by flash chromatography (eluent: petroleum ether/ethyl acetate, 1:0 to 1:2, gradient elution) to afford the title compound (2.3 g, 93%). MS (ESI): mass calcd. for C$_{13}$H$_{13}$F$_2$N$_3$O$_2$ 281.1 m/z 281.9.

Step F: Ethyl 3-(4-(difluoromethyl)-1-methyl-1H-benzo[d][1,2,3]triazol-5-yl)-3-(3-(hydroxymethyl)-4-methylphenyl)propanoate. (E)-Ethyl 3-(4-(difluoromethyl)-1-methyl-1H-benzo[d][1,2,3]triazol-5-yl)acrylate (500 mg, 1.78 mmol), (3-(hydroxymethyl)-4-methylphenyl)boronic acid (885 mg, 5.33 mmol), and aq. KOH (1.8 mL, 1 M, 1.8 mmol) were added to a sealed tube and the resulting mixture dissolved in 1,4-dioxane (15 mL). The mixture was sparged with Ar for 20 minutes and then treated with [Rh(cod)Cl]$_2$ (88 mg, 0.18 mmol). The mixture was sparged with Ar for another 20 minutes. The resultant mixture was stirred at room-temperature for 16 hours under Ar. The suspension was filtered and the filtrate concentrated to dryness under reduced pressure to give the product, which was purified by flash chromatography (eluent:petroleum ether/ethyl acetate, 10:1 to 0:1, dichloromethane/methanol, 20:1, isocratic) to afford the title compound (378.7 mg, 52%). MS (ESI): mass calcd. for C$_{21}$H$_{23}$F$_2$N$_3$O$_3$ 403.17 m/z, found 404.0 [M+H]$^+$. $^1$H NMR (400 MHz, DMSO-d$_6$) δ 8.07-7.75 (m, 2H), 7.60 (d, J=8.8 Hz, 1H), 7.33-7.30 (m, 1H), 7.19-7.12 (m, 1H), 7.06 (d, J=8.0 Hz, 1H), 5.14 (t, J=7.8 Hz, 1H), 5.01 (t, J=5.3 Hz, 1H), 4.46-4.36 (m, 2H), 4.30 (s, 3H), 3.99-3.90 (m, 2H), 3.30-3.21 (m, 1H), 3.15-3.06 (m, 1H), 2.16 (s, 3H), 1.04 (t, J=7.2 Hz, 3H).

Intermediate 61: 5'-methyl-2',3'-dihydro-5'H-spiro[cyclopropane-1,4'-pyrido[2,3-f][1,2,5]thiadiazepine] 1',1'-dioxide

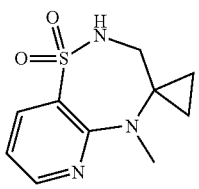 [SMILES: CN1c2ncccc2S(=O)(=O)NCC12CC2]

Step A: tert-Butyl (1-carbamoylcyclopropyl)carbamate. Pyridine (11.8 g, 149 mmol) was added drop-wise to a mixture of 1-((tertbutoxycarbonyl)amino)cyclopropanecarboxylic acid (50.0 g, 248 mmol), Boc$_2$O (70.5 g, 323 mmol), NH$_4$HCO$_3$ (24.6 g, 311 mmol), and MeCN (500 mL) over a period of 10 minutes. The mixture was stirred at room temperature for 16 hours before concentrating to dryness under reduced pressure. The residue was diluted with H$_2$O (100 mL), pH adjusted to 7 with 1 N HCl, and then the resultant mixture extracted with ethyl acetate (3×). The combined organic extracts were dried over anhydrous Na$_2$SO$_4$, filtered, and concentrated to dryness under reduced pressure to afford the title compound (40.1 g, 80%), which was used in the next step without further purification. $^1$H NMR (400 MHz, DMSO-d$_6$) δ 6.42 (br s, 1H), 5.71 (br s, 1H), 5.18 (br s, 1H), 1.61-1.56 (m, 2H), 1.46-1.45 (m, 9H), 1.09-0.98 (m, 2H).

Step B: tert-Butyl (1-cyanocyclopropyl)carbamate. TFAA (47.3 g, 225 mmol) was added drop-wise to solution of tert-butyl (1-carbamoylcyclopropyl)carbamate (30.0 g, 150 mmol), triethylamine (62.7 g, 450 mmol), and dichloromethane (180 mL) over a period of 1 hour. The resultant mixture was stirred at room-temperature for 4 hours before concentrating to dryness under reduced pressure to give the product, which was purified by FCC (eluent:petroleum ether/ethyl acetate, 1:0 to 5:1, gradient elution) to afford the title compound (22.5 g, 82.3%). $^1$H NMR (400 MHz, CDCl$_3$) δ 6.60 (br s, 1H), 2.63 (s, 9H), 1.28 (s, 2H), 1.24-1.20 (m, 1H), 1.07-1.01 (m, 1H).

Step C: tert-Butyl (1-cyanocyclopropyl)(methyl)carbamate. Sodium hydride in mineral oil (15.0 g, 60% purity, 375 mmol) was added in portions to a 0° C. (ice/water) solution of tert-butyl (1-cyanocyclopropyl)carbamate (22.5 g, 123 mmol) and THF (150 mL). The resultant mixture was treated with iodomethane (34.7 g, 244 mmol) by drop-wise addition at 0° C. and then stirred for 12 hours with gradual warming to room-temperature before quenching with sat. NH$_4$Cl (100 mL) and extracting with ethyl acetate (3×). These extractions resulted in several fractions which were combined, washed with brine, dried over sodium sulfate and concentrated to dryness under reduced pressure to afford the title compound (23.0 g), which was used in the next step without further purification. $^1$H NMR (400 MHz, CDCl$_3$) δ 2.90 (s, 3H), 1.48 (s, 9H), 1.27-1.26 (m, 2H), 0.86-0.82 (m, 2H).

Step D: tert-Butyl (1-(aminomethyl)cyclopropyl)(methyl)carbamate. Raney Ni (2 g) was added to a 1 L round-bottomed flask containing a mixture of tert-butyl (1-cyanocyclopropyl)carbamate (23 g), methanol (200 mL), and 25% aqueous NH$_3$(aq) (5 mL) under Ar. The resultant mixture was stirred under H$_2$ (15 psi) at room-temperature for 15 hours. The suspension was filtered through a pad of diatomaceous earth and the pad was washed with ethyl acetate. The filtrate was concentrated to dryness under reduced pressure to afford the title product (25 g), which was used in the next step without further purification. $^1$H NMR (400 MHz, CDCl$_3$) δ 2.86 (br s, 3H), 1.84-1.80 (m, 2H), 1.44 (br s, 9H), 1.23-1.22 (m, 2H), 0.85-0.81 (m, 2H).

Step E: tert-Butyl (1-((2-chloropyridine-3-sulfonamido)methyl)cyclopropyl)(methyl)carbamate. A solution of 2-chloropyridine-3-sulfonyl chloride (20 g, 94 mmol) and THF (50 mL) was added drop-wise to a 0° C. mixture of tert-butyl (1-(aminomethyl)cyclopropyl)(methyl)carbamate (20 g), K$_2$CO$_3$ (20.0 g, 145 mmol), THF (150 mL), and H$_2$O (40 mL). The mixture was stirred for 12 hours with gradual warming to room-temperature before concentrating to dryness under reduced pressure. The residue was diluted with water (100 mL) and extracted with ethyl acetate (2×). These extractions resulted in several fractions which were combined, dried over sodium sulfate and concentrated to dryness under reduced pressure to afford the title compound (30 g), which was used in the next step without purification. MS (ESI): mass calcd. for C$_{15}$H$_{22}$ClN$_3$O$_4$S, 375.1 m/z, found 398.0 [M+Na]$^+$. $^1$H NMR (400 MHz, CDCl$_3$) δ 8.58-8.54 (m, 1H), 8.40-8.35 (m, 1H), 7.45-7.36 (m, 1H), 6.83 (br s, 1H), 3.07-2.98 (m, 2H), 2.82 (s, 3H), 1.47 (s, 9H), 0.97-0.93 (m, 2H), 0.85-0.78 (m, 2H).

Step F: 2-Chloro-N-((1-(methylamino)cyclopropyl)methyl)pyridine-3-sulfonamide. TFA (30.0 mL, 433 mmol) was added to a 0° C. solution of tert-butyl (1-((2-chloropyridine-3-sulfonamido)methyl)cyclopropyl)(methyl)carbamate (35 g) and dichloromethane (100 mL). The mixture was stirred for 2 hours with gradual warming to room-temperature before concentrating to dryness under reduced pressure to afford the title compound (30 g), which was used in the next step without further purification. MS (ESI): calcd. for C$_{10}$H$_{14}$ClN$_3$O$_2$S, 275.1, m/z found 275.9 [M+H]$^+$.

Step G: 5'-Methyl-3',5'-dihydro-2'H-spiro[cyclopropane-1,4'-pyrido[2,3-f][1,2,5]thiadiazepine] 1',1'-dioxide. DIPEA (30.0 mL, 172 mmol) was added drop-wise to a solution of 2-chloro-N-((1-(methylamino)cyclopropyl)methyl)pyridine-3-sulfonamide (10 g) and DMSO (60 mL). The resultant mixture was stirred while heating at 160° C. for 2 hours before cooling to room-temperature and concentrating to dryness under reduced pressure. The residue was diluted with H$_2$O (200 mL) and extracted with ethyl acetate (3×). These extractions resulted in several fractions which were combined, dried over sodium sulfate and concentrated to dryness under reduced pressure. The resulting residue was triturated with ethyl acetate:petroleum ether (1:10, 80 mL). The suspension was isolated via filtration and the filter cake washed with ethyl acetate:petroleum ether (1:30, 30 mL) before drying under reduced pressure to afford the title compound (3.58 g, 41%). MS (ESI): mass calcd. For C$_{10}$H$_{13}$N$_3$O$_2$S, 239.1 m/z, found 240.0 [M+H]$^+$. $^1$H NMR (400 MHz, DMSO-d$_6$) δ 8.30-8.19 (m, 1H), 8.15-7.79 (m, 2H), 6.98-6.89 (m, 1H), 3.32-3.06 (m, 2H), 3.02 (s, 3H), 0.99-0.57 (m, 4H).

Intermediate 62: (2-Chloro-5-(4,4,5,5-tetramethyl-1,3,2-dioxaborolan-2-yl)phenyl)methanol

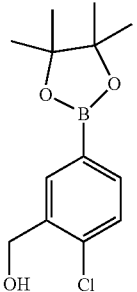

(5-Bromo-2-chlorophenyl)methanol (15.0 g, 67.7 mmol), 4,4,4',4',5,5,5',5'-octamethyl-2,2'-bi(1,3,2-dioxaborolane) (27.5 g, 108 mmol), KOAc (19.9 g, 203 mmol), and 1,4-dioxane (100 mL) were added to a 250 mL round-bottomed flask under $N_2$. The mixture was sparged with $N_2$ for 5 minutes and then treated with Pd(dppf)$Cl_2$.$CH_2Cl_2$ (4.96 g, 6.07 mmol). The mixture was sparged with $N_2$ for another 5 minutes and then stirred at 100° C. for 16 hours before cooling to room-temperature. The resultant mixture was filtered, and the filtrate was concentrated to dryness under reduced pressure to afford the product, which was purified by preparative HPLC (eluent: $CH_3CN/H_2O$ and $H_2O$ with 0.04% $NH_3$, 1:5 to 1:1, gradient elution) to afford pure product. The product was suspended in water (10 mL), the mixture frozen using dry ice/acetone, and then lyophilized to dryness to afford the title product (6.8 g) as a white solid. The white solid (6.8 g) was further purified by FCC (eluent: petroleum ether/ethyl acetate, 20:1 to 0:1) to afford the title compound (4.0 g, 22%). MS (ESI): mass calcd. for $C_{13}H_{18}BClO_3$ 268.1 m/z, found 251.0 $[M–H_2O+H]^+$. $^1$H NMR (400 MHz, $CDCl_3$) δ 7.88 (s, 1H), 7.68-7.63 (m, 1H), 7.35 (d, J=7.9 Hz, 1H), 4.77 (d, J=6.4 Hz, 2H), 1.90 (t, J=6.6 Hz, 1H), 1.33 (s, 12H).

Intermediate 63: (S*)-3-Methyl-7,7a,8,9,10,11-hexahydro-6H-dipyrido[2,1-d:2',3'-f][1,2,5]thiadiazepine 5,5-dioxide

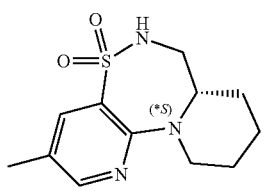 [SMILES: Cc1cnc2c(c1)S(=O)(=O)NC[C@@H]1CCCCN21]

Step A: 2-Chloro-5-methylpyridine-3-sulfonyl chloride. $HBF_4$ (7.6 mL, 48 mmol) was added drop-wise to a 100 mL three-necked round-bottomed flask containing a 0° C. solution of 2-chloro-5-methylpyridin-3-amine (5.0 g, 35 mmol) and acetonitrile (30 mL). The resultant mixture was stirred at 0° C. for 10 minutes before adding tert-Butyl nitrite (6.3 mL, 53 mmol) drop-wise at 0° C. The resultant mixture was stirred at 0° C. for another 1 hour. Copper(I) chloride (5.5 g, 56 mmol) and acetic acid (50 mL) were added to a 250 mL three-necked round-bottomed flask. The resultant mixture was cooled to 0° C., bubbled with $SO_2$ gas (>1.3 M) at 0° C. for 1 hour, and then treated with the above 2-chloro-5-methylpyridine-3-diazonium tetrafluoroborate solution by drop-wise addition at 0° C. The resultant mixture was stirred for 4 hours with gradual warming to room-temperature before quenching with sat. $NaHCO_3$(100 mL). The resultant mixture was stirred for 20 minutes and then extracted with ethyl acetate (3×). These extractions resulted in several fractions which were combined, washed with water (2×), dried over sodium sulfate and concentrated to dryness under reduced pressure to give the product, which was purified by FCC (eluent: petroleum ether/ethyl acetate, 1:0 to 10:1, gradient elution) to afford the title compound (3 g, 38%). $^1$H NMR (400 MHz, $CDCl_3$) δ 8.51 (s, 1H), 8.27-8.19 (m, 1H), 2.46 (s, 3H).

Step B: tert-Butyl 2-((2-chloro-5-methylpyridine-3-sulfonamido)methyl)piperidine-1-carboxylate. A solution consisting of 2-chloro-5-methylpyridine-3-sulfonyl chloride (2.5 g, 11 mmol) and THF (10 mL) was added drop-wise to a 0° C. mixture of tert-butyl 2-(aminomethyl)piperidine-1-carboxylate (2.5 g, 12 mmol), $K_2CO_3$ (2.5 g, 18 mmol), THF (10 mL), and $H_2O$ (5 mL). The resultant mixture was stirred for 2 hours with gradual warming to room-temperature before concentrated to dryness under reduced pressure. The residue was diluted with water (100 mL) and the resultant mixture extracted with ethyl acetate (2×). These extractions resulted in several fractions which were combined, dried over sodium sulfate and concentrated to dryness under reduced pressure to afford the title compound (3.5 g, 77%). MS (ESI): mass calcd. for $C_{17}H_{26}ClN_3O_4S$, 403.1, found 426.0 $[M+Na]^+$.

Step C: 2-Chloro-5-methyl-N-(piperidin-2-ylmethyl)pyridine-3-sulfonamide. TFA (5.0 mL, 72 mmol) was added to a 0° C. solution consisting of tert-butyl 2-((2-chloro-5-methylpyridine-3-sulfonamido)methyl)piperidine-1-carboxylate (3.5 g, 8.7 mmol) and dichloromethane (20 mL). The resultant mixture was stirred for 12 hours with gradual warming to room-temperature before concentrated to dryness under reduced pressure to afford the title compound (3.1 g), which was used in the next step without further purification. MS (ESI): mass calcd. for $C_{12}H_{18}ClN_3O_2S$, 303.1, found 303.9 $[M+H]^+$.

Step D: 3-Methyl-7,7a,8,9,10,11-hexahydro-6H-dipyrido[2,1-d:2',3'-f][1,2,5]thiadiazepine 5,5-dioxide. DIPEA (8.0 mL, 46 mmol) was added drop-wise to a solution of 2-chloro-5-methyl-N-(piperidin-2-ylmethyl)pyridine-3-sulfonamide (3.0 g) and DMSO (20 mL). The resultant mixture was stirred and heated at 160° C. for 2 hours before concentrating to dryness under reduced pressure. The residue was diluted with $H_2O$ (200 mL), and the resultant mixture extracted with ethyl acetate (3×). These extractions resulted in several fractions which were combined, dried over sodium sulfate and concentrated to dryness under reduced pressure to give the product, which was purified by FCC (eluent: petroleum ether/ethyl acetate, 1:0 to 3:1, gradient elution) to afford the title compound (1.6 g). MS (ESI): mass calcd. for $C_{12}H_{17}N_3O_2S$, 267.1, m/z found 267.9 $[M+H]^+$.

Step E: (S*)-3-Methyl-7,7a,8,9,10,11-hexahydro-6H-dipyrido[2,1-d:2',3'-f][1,2,5]thiadiazepine 5,5-dioxide. The mixture of 3-Methyl-7,7a,8,9,10,11-hexahydro-6H-dipyrido[2,1-d:2',3'-f][1,2,5]thiadiazepine 5,5-dioxide (1.6 g, 6.0 mmol) isomers were separated by purified by chiral SFC (stationary phase: AD 250 mm×50 mm, mobile phase: 40% $CO_2$, 40% EtOH and $H_2O$ with 0.1% $NH_3$) to afford two diastereomers. The first eluting isomer (370 mg) was designated *S: $^1$H NMR (400 MHz, DMSO-$d_6$) δ 8.11-8.07 (m, 1H), 8.05-7.99 (m, 1H), 7.72-7.66 (m, 1H), 4.19-4.06 (m, 2H), 3.47-3.38 (m, 1H), 3.32-3.24 (m, 1H), 3.19-3.10 (m, 1H), 2.18 (s, 3H), 1.72-1.49 (m, 6H).

Intermediate 64: (S*)-3-fluoro-7,7a,8,9,10,11-hexahydro-6H-dipyrido[2,1-d:2',3'-f][1,2,5]thiadiazepine 5,5-dioxide

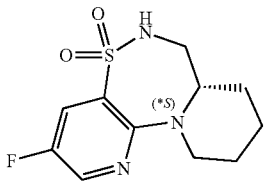 [SMILES: O=S1(=O)NC[C@@H]2CCCCN2c2ncc(F)cc21]

Step A: 2-Chloro-5-fluoropyridin-3-amine. Fe (15.2 g, 272 mmol) was added in portions to a solution of 2-chloro-5-fluoro-3-nitropyridine (12 g, 68 mmol) and HOAc (200 mL). The reaction mixture was stirred at 80° C. for 0.5 hours before cooling to room-temperature and concentrating to dryness under reduced pressure. The residue was suspended in ethyl acetate (100 mL), the resultant suspension filtered through a pad of Celite®, and the pad washed with ethyl acetate (20 mL). The filtrate was neutralized with sat. NaHCO$_3$(200 mL) and the resultant mixture extracted with ethyl acetate (3×). These extractions resulted in several fractions which were combined, dried over sodium sulfate and concentrated to dryness under reduced pressure to give the product (11 g), which was used in the next step without further purification. MS (ESI): mass calcd. for $C_5H_4ClFN_2$ 146.0, found 146.8 [M+H]$^+$.

Step B: 2-Chloro-5-fluoropyridine-3-sulfonyl chloride. HBF$_4$ (59.2 mL, 380 mmol) was added drop-wise to a 1 L three-necked round-bottomed flask containing a 0° C. mixture of 2-chloro-5-fluoropyridin-3-amine (40.0 g, 273 mmol) and acetonitrile (300 mL). The resultant mixture was stirred at 0° C. for 10 minutes before drop-wise addition of tert-butyl nitrite (48.8 mL, 410 mmol) at 0° C. The resultant mixture was stirred at 0° C. for another 1 hour. Copper(I) chloride (30.3 g, 303 mmol) and acetic acid (100 mL) were added to a 1 L three-necked round-bottomed flask. The resultant mixture was cooled to 0° C., bubbled with SO$_2$ gas (>1.3 M) at 0° C. for 1 hour followed by drop-wise addition of the 2-chloro-5-fluoropyridine-3-diazonium tetrafluoroborate solution at 0° C. The resultant mixture was stirred for 4 hours with gradual warming to room-temperature before quenching with sat. NaHCO$_3$(100 mL). The resultant mixture was stirred for 20 minutes and then extracted with ethyl acetate (3×). These extractions resulted in several fractions which were combined, washed with water (2×), brine (1×), dried over sodium sulfate and concentrated to dryness under reduced pressure to afford the product which was purified by FCC (eluent:petroleum ether/ethyl acetate, 1:0 to 9:1, gradient) to afford the title compound (30 g).

Step C: tert-Butyl 2-((2-chloro-5-fluoropyridine-3-sulfonamido)methyl)piperidine-1-carboxylate. A solution consisting of tert-butyl 2-(aminomethyl)piperidine-1-carboxylate (30.7 g, 143 mmol) and THF (100 mL) was added drop-wise to a 0° C. mixture consisting of 2-chloro-5-fluoropyridine-3-sulfonyl chloride (30 g), K$_2$CO$_3$ (28.8 g, 208 mmol), THF (100 mL), and H$_2$O (40 mL). The resultant mixture was stirred for 2 hours with gradual warming to room-temperature before concentrating to dryness under reduced pressure. The residue was diluted with water (80 mL) and extracted with ethyl acetate (3×). These extractions resulted in several fractions which were combined, dried over sodium sulfate and concentrated to dryness under reduced pressure to afford the product, which was purified by FCC (eluent:petroleum ether/ethyl acetate, 1:0 to 5:1, gradient) to afford the title compound (35 g, 64%). MS (ESI): mass calcd. for $C_{16}H_{23}ClFN_3O_4S$, 407.1, found 308.1 [M+H-Boc]$^+$.

Step D: 2-Chloro-5-fluoro-N-(piperidin-2-ylmethyl)pyridine-3-sulfonamide. TFA (40 mL) was added to a solution of tert-butyl 2-((2-chloro-5-fluoropyridine-3-sulfonamido)methyl)piperidine-1-carboxylate (23.0 g, 56.4 mmol) and dichloromethane (80 mL). The resultant mixture was stirred at room temperature for 3 hours before concentrating to dryness under reduced pressure to afford the title product (17 g), which was used in the next step without purification. MS (ESI): mass calcd. for $C_{11}H_{15}ClFN_3O_2S$, 307.1, found 308.0 [M+H]$^+$.

Step E: 3-Fluoro-7,7a,8,9,10,11-hexahydro-6H-dipyrido[2,1-d:2',3'-f][1,2,5]thiadiazepine 5,5-dioxide. DIPEA (50.0 mL, 287 mmol) was added drop-wise to a solution of 2-chloro-5-fluoro-N-(piperidin-2-ylmethyl)pyridine-3-sulfonamide (17 g) and DMSO (150 mL) at room temperature. The resultant mixture was stirred at 160° C. for 2 hours before concentrating to dryness under reduced pressure. The residue was diluted with H$_2$O (200 mL), and the resultant mixture extracted with ethyl acetate (3×). These extractions resulted in several fractions which were combined, dried over sodium sulfate and concentrated to dryness under reduced pressure to give the product, which was purified by FCC (eluent:petroleum ether/ethyl acetate, 1:0 to 3:1, gradient) to afford the title compound (11 g). MS (ESI): mass calcd. for $C_{11}H_{14}FN_3O_2S$, 271.1, m/z found 271.9 [M+H]$^+$.

Step F: (*S)-3-Fluoro-7,7a,8,9,10,11-hexahydro-6H-dipyrido[2,1-d:2',3'-f][1,2,5]thiadiazepine 5,5-dioxide. The mixture of 3-Fluoro-7,7a,8,9,10,11-hexahydro-6H-dipyrido[2,1-d:2',3'-f][1,2,5]thiadiazepine 5,5-dioxide (11 g, 40 mmol) isomers were separated by purified by chiral SFC (AS 250 mm×50 mm, mobile phase: 30% CO$_2$, 30% EtOH and H$_2$O with 0.1% NH$_3$) to afford two diastereomers. The first eluting isomer (5.2 g) was designated *S. MS (ESI): mass calcd. for $C_{11}H_{14}FN_3O_2S$, 271.1, m/z found 272.0 [M+H]$^+$. $^1$H NMR (400 MHz, DMSO-d$_6$) δ 8.29 (d, J=3.2 Hz, 1H), 8.22 (br s, 1H), 7.86-7.74 (m, 1H), 4.20-4.08 (m, 2H), 3.47 (t, J=12.8 Hz, 1H), 3.30-3.22 (m, 1H), 3.21-3.11 (m, 1H), 1.71-1.48 (m, 6H).

Intermediate 65: 8-fluoro-2,3-dihydrospiro[benzo][b][1,4,5]oxathiazepine-4,1'-cyclopropane]1',1'-dioxide

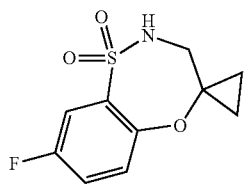 [SMILES: O=S1(=O)NCC2(CC2)Oc2ccc(F)cc21]

Step A: 2,5-difluoro-N-((1-hydroxycyclopropyl)methyl)benzenesulfonamide. In a 250 mL round bottom flask was added 1-(aminomethyl))cyclopropanol (3.1 g, 35 mmol), THF (90 mL) and water (21 mL). To this mixture was added potassium carbonate (3.9 g, 28 mmol) and 2,5-difluorobenzenesulfonyl chloride (5.0 g, 23 mmol). After stirring at r.t.

for 18 h. the mixture was partitioned between ethyl acetate/water and the aqueous layer extracted once more with ethyl acetate. These extractions resulted in several fractions which were combined, dried over sodium sulfate and concentrated to dryness under reduced pressure. The residue was purified by flash column chromatography (eluent: ethyl acetate/hexanes, 0:1 to 1:0, gradient elution) providing the title product. MS (ESI): mass calcd. for $C_{10}H_{11}F_2NO_3S$, 263.0, m/z found 264.0 [M+H]$^+$.

Step B: 8-fluoro-2,3-dihydrospiro[benzo][b][1,4,5]oxathiazepine-4,1'-cyclopropane]1',1'-dioxide. To a 100 mL round bottom flask was added 2,5-difluoro-N-((1-hydroxycyclopropyl)methyl)benzenesulfonamide (938 mg, 3.6 mmol), potassium carbonate (3.5 mL, 10.5 mmol, 3M solution in water), and DMSO (15 mL). The reaction was heated to 90° C. and allowed to stir for 20 h. The reaction was cooled, volume reduced to about half, poured into water and extracted with ethyl acetate (5×). These extractions resulted in several fractions which were combined, dried over sodium sulfate and concentrated to dryness under reduced pressure. The residue was purified by flash column chromatography (eluent: ethyl acetate/hexanes, 0:1 to 1:0, gradient elution) to afford the title compound (365 mg, 42%). MS (ESI): mass calcd. for $C_{10}H_{10}FNO_3S$, 243.0, m/z found 243.9 [M+H]$^+$.

Intermediate 66: 8-fluoro-2,3-dihydrospiro[benzo][b][1,4,5]oxathiazepine-4,3'-oxetane]1',1'-dioxide

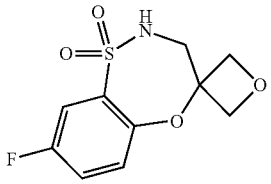 [SMILES: O=S1(=O)NCC2(COC2)Oc2ccc(F)cc21]

The title compound (820 mg, 34%) was prepared using analogous conditions as described in Intermediate 65 where 3-(aminomethyl)oxetan-3-ol was used instead of 1-(aminomethyl))cyclopropanol in step A. MS (ESI): mass calcd. for $C_{10}H_{10}FNO_4S$, 259.0, m/z found 260.0 [M+H]$^+$. $^1$H NMR (400 MHz, CDCl$_3$) δ 7.47 (dd, J=7.4, 3.0 Hz, 1H), 7.34 (dd, J=8.8, 4.3 Hz, 1H), 7.25-7.20 (m, 1H), 5.08 (s, 1H), 4.67 (d, J=7.5 Hz, 2H), 4.38-4.27 (m, 2H), 3.95 (d, J=5.7 Hz, 2H).

Intermediate 67: 7'-chloro-2',3'-dihydrospiro[cyclopropane-1,4'-pyrido[2,3-b][1,4,5]oxathiazepine] 1',1'-dioxide

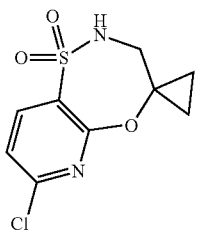 [SMILES: O=S1(=O)NCC2(CC2)Oc2nc(Cl)ccc21]

Step A: 2,6-dichloropyridine-3-sulfonyl chloride. SOCl$_2$ (365 g, 3.07 mol) was added dropwise to H$_2$O (1.6 L) chilled to 0-5° C. and allowed to stir at 0-15° C. for 16 h. To a second flask was added 2,6-dichloropyridin-3-amine (100 g, 613 mmol) and HCl (745 g, 7.36 mol, 36% purity). To this mixture was added a solution of NaNO$_2$ (50.8 g, 736 mmol) in H$_2$O (160 mL) at 0° C. After addition, the orange suspension was stirred at 0° C. for 0.5 h. CuCl (6.07 g, 61.3 mmol) was added to the first flask followed by immediate drop-wise addition of the suspension from the second flask at 0-5° C. The suspension was stirred at 0-5° C. for 1 h. The suspension was extracted with EtOAc (3×). These extractions resulted in several fractions which were washed with brine (2×), combined, dried over sodium sulfate and concentrated to dryness under reduced pressure. The residue was stirred in petroleum ether (300 mL) for 1 hr. The mixture was filtered, and the cake was washed with petroleum ether (50 mL). The cake was dried in vacuum to give the desired product (94.1 g, 48% yield). MS (ESI): mass calcd. for $C_5H_2Cl_3NO_2S$, 244.9, m/z found 297.1. $^1$H NMR (400 MHz, CDCl$_3$) δ 8.39 (d, J=8.4 Hz, 1H), 7.54 (d, J=8.4 Hz, 1H).

Step B: 2,6-dichloro-N-((1-hydroxycyclopropyl)methyl)pyridine-3-sulfonamide. To a mixture of 1-(aminomethyl)cyclopropane-1-ol (18.5 g, 212 mmol) and K$_2$CO$_3$ (42.0 g, 304.2 mmol) in THF (500 mL) and H$_2$O (150 mL) was added 2,6-dichloropyridine-3-sulfonyl chloride (50.0 g, 202 mmol) in THF (150 mL) drop-wise while keeping the reaction temperature between 0-5° C. The reaction mixture was stirred at 20° C. for 16 hrs. followed by extraction of the suspension with EtOAc (3×). These extractions resulted in several fractions which were combined, washed with water (1×), brine (1×), dried over sodium sulfate and concentrated to dryness under reduced pressure. The residue was purified by flash silica gel chromatography (eluent: ethyl acetate/petroleum ether, 0:1 to 1:3, gradient elution) to afford the title compound (63.1 g, 86.9%). MS (ESI): mass calcd. for $C_9H_{10}Cl_2N_2O_3S$, 296.0, m/z found 296.9 [M+H]$^+$.

Step C: 7'-chloro-2',3'-dihydrospiro[cyclopropane-1,4'-pyrido[2,3-b][1,4,5]oxathiazepine] 1',1'-dioxide. To a solution of 2,6-dichloro-N-((1-hydroxycyclopropyl)methyl)pyridine-3-sulfonamide (61.3 g, 173 mmol) in DMSO (1.2 L) was added K$_2$CO$_3$ (71.8 g, 519 mmol). The yellow suspension was stirred at 60° C. for 4 hrs. The suspension was poured into water (3 L), and extracted with EtOAc (3×). These extractions resulted in several fractions which were combined, washed with water (2×) and brine (1×), dried over anhydrous Na$_2$SO$_4$, filtered and concentrated under reduced pressure. The residue was purified by prep-HPLC (eluent: MeCN/water (0.1% TFA), 1:9 to 2:3, gradient elution) to afford the title compound (18.5 g, 40.0%). MS (ESI): mass calcd. for $C_9H_{19}ClN_2O_3S$, 260.0, m/z found 261.0 [M+H]$^+$.

Intermediate 68: 7'-chloro-2,2',3,3',5,6-hexahydrospiro[pyran-4,4'-pyrido[2,3-b][1,4,5]oxathiazepine] 1',1'-dioxide

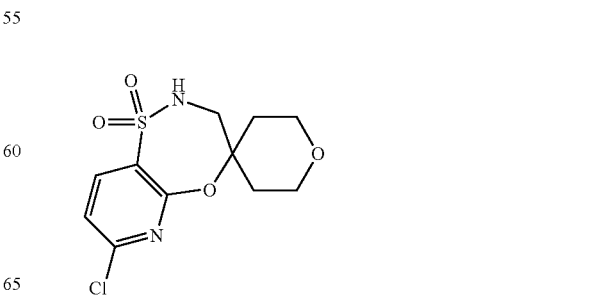

Step A: 4-hydroxytetrahydro-2H-4-carbonitrile. To a solution of tetrahydro-4H-4-one (50.0 g, 499 mmol) in THF (1.5 L) was added TMSCN (49.5 g, 499 mmol) followed by BF$_3$.Et$_2$O (74.4 g, 524 mmol). The internal temperature of the reaction was maintained below 10° C. during the addition of the BF$_3$.Et$_2$O. The reaction mixture was stirred at 20° C. for 3 hrs. The reaction mixture was diluted with sat. aq. NaHCO$_3$(1.5 L) and extracted with EtOAc (3×). These extractions resulted in several fractions which were combined, washed with brine (1×), dried over anhydrous Na$_2$SO$_4$, filtered and concentrated under reduced pressure. The residue was purified by flash silica gel chromatography (eluent: ethyl acetate/petroleum ether, 0:1 to 3:7, gradient elution) to afford the title compound (56.4 g, 88.8%).

Step B: 4-(aminomethyl)tetrahydro-2H-pyran-4-ol. To a solution of LAH (19.0 g, 487 mmol) in THF (500 mL) at 0° C. under N$_2$ was added dropwise 4-hydroxytetrahydropyran-4-carbonitrile (56.4 g, 443 mmol) in THF (100 mL). The reaction was allowed to warm to 20° C. followed by addition of H$_2$O (19 mL), 15% NaOH (19 mL) and H$_2$O (19 mL). The reaction was filtered and concentrated under reduced pressure to give the title compound (43.6 g, 74.9%), which was used directly in the next step without purification.

Step C. 2,6-dichloro-N-((4-hydroxytetrahydro-2H-pyran-4-yl)methyl)pyridine-3-sulfonamide. To a mixture of 4-(aminomethyl)tetrahydro-2H-pyran-4-ol (30.0 g, 229 mmol) and K$_2$CO$_3$ (45.2 g, 327 mmol) in THF (300 mL) and H$_2$O (90 mL) was added drop-wise 2,6-dichloropyridine-3-sulfonyl chloride (63.1 g, 217 mmol) in THF (90 mL) keeping the inner temperature between 0° C. and 5° C. The reaction mixture was then stirred at 15° C. for 13 hrs. The suspension was poured into water (200 mL) and extracted with EtOAc (3×). These extractions resulted in several fractions which were combined, washed with brine (1×), dried over anhydrous Na$_2$SO$_4$, filtered and concentrated under reduced pressure. The residue was purified by flash silica gel chromatography (eluent: ethyl acetate/petroleum ether, 0:1 to 3:7, gradient elution) to afford the title compound (45.4 g, 58.0%). MS (ESI): mass calcd. for C$_{11}$H$_{14}$Cl$_2$N$_2$O$_4$S, 340.0, m/z found 341.1 [M+H]$^+$.

Step D: 7'-chloro-2,2',3,3',5,6-hexahydrospiro[pyran-4,4'-pyrido[2,3-b][1,4,5]oxathiazepine] 1',1'-dioxide. To a solution of 2,6-dichloro-N-((4-hydroxytetrahydro-2H-pyran-4-yl)methyl)pyridine-3-sulfonamide (14.6 g, 42.8 mmol) in THF (300 mL) was added t-BuOK (4.80 g, 42.8 mmol). The mixture was stirred at 10° C. for 1.5 hrs. The suspension was poured into water (50 mL), extracted with EtOAc (5×). These extractions resulted in several fractions which were combined, washed with brine (1×), dried over anhydrous Na$_2$SO$_4$, filtered and concentrated under reduced pressure washed. The residue was stirred in 30 mL mixture of petroleum ether:ethyl acetate (3:1, 50 mL) for 30 min. The mixture was filtered off and the cake was washed with petroleum ether and ethyl acetate (5:1, 20 mL) and dried under vacuum to give the title compound (10.7 g, 48.4%). MS (ESI): mass calcd. for C$_{11}$H$_{13}$ClN$_2$O$_4$S, 304.0, m/z found 304.8 [M+H]$^+$. $^1$H NMR (400 MHz, DMSO) δ 8.55 (s, 1H) 8.17 (d, J=8.0, 1H) 7.5 (d, J=8.0 Hz, 1H) 3.75 (m, 2H) 3.62 (d, J=11.3 Hz, 2H) 3.53 (s, 2H) 1.64 (m, 4H)

Intermediate 69: Methyl 3-(3-((7'-chloro-1',1'-dioxido-2,3,5,6-tetrahydrospiropyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate

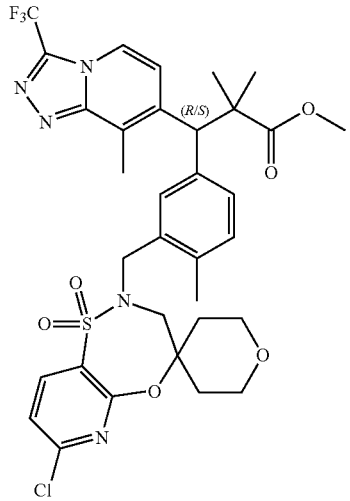 [SMILES: COC(=O)C(C)(C)C(c1ccc(C)c(CN2CC3(CCOCC3)Oc3nc(Cl)ccc3S2(=O)=O)c1)c1ccn2c(C(F)(F)F)nnc2c1C]

The title compound (760 mg, 73%) was prepared using analogous conditions as described in Example 11 where methyl 3-(3-(hydroxy methyl)-4-methylphenyl)-2,2-dimethyl-3-(8-methyl-3-(trifluoromethyl)-[1,2,4]triazolo[4,3-a]pyridine-7-yl)propanoate (Intermediate 48) was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and 7'-chloro-2,2',3,3',5,6-hexahydrospiro[pyran-4,4'-pyrido[2,3-b][1,4,5]oxathiazepine] 1',1'-dioxide (Intermediate 68) was used instead of (*S)-7a-methyl-6,7,7a,8,9,19-hexahydropyrido[2,3-f]pyrollo[2,1-d][1,2,5]thiadiazepine 5,5-dioxide (Intermediate 39) in step B. MS (ESI): mass calcd. for C$_{33}$H$_{35}$ClF$_3$N$_5$O$_6$S, 721.2; m/z found, 722.1 [M+H]$^+$. $^1$H NMR (400 MHz, CDCl$_3$) δ 8.05 (d, J=8.0 Hz, 1H), 7.96 (d, J=7.3 Hz, 1H), 7.17-7.10 (m, 2H), 7.03 (d, J=1.2 Hz, 2H), 4.72 (s, 1H), 4.47-4.33 (m, 2H), 3.98-3.90 (m, 2H), 3.60-3.45 (m, 6H), 3.38-3.32 (m, 1H), 2.71 (s, 3H), 2.16 (s, 3H), 1.71-1.57 (m, 2H), 1.49-1.37 (m, 2H), 1.35 (s, 3H), 1.29 (s, 3H).

Intermediate 71: Benzyl (*S)-3-(3-(3-hydroxymethyl)-4-methylphenyl)-2,2-dimethyl-3-(8-methyl-3-(trifluoromethyl)-[1,2,4]triazolo[4,3-a]pyridine-7-yl)propanoate

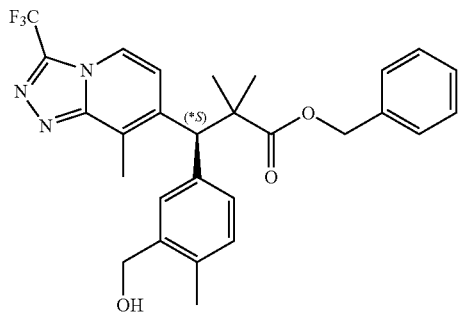 [SMILES: Cc1ccc([C@@H](c2ccn3c(C(F)(F)F)nnc3c2C)C(C)(C)C(=O)OCc2ccccc2)cc1CO]

Step A: (*S)-3-(3-hydroxymethyl)-4-methylphenyl)-2,2-dimethyl)-3-(8-methyl-3-(trifluoromethyl)-[1,2,4]triazolo[4,3-a]pyridine-7-yl)propanoic acid. To a solution of methyl (*S)-3-(3-hydroxymethyl)-4-methylphenyl)-2,2-dimethyl)-3-(8-methyl-3-(trifluoromethyl)-[1,2,4]triazolo[4,3-a]pyridine-7-yl)propanoate (Intermediate 145, 2.64 g, 5.9 mmol) in a 1:1 mixture of methanol (24 mL) and THF (24 mL) was added a 1M solution of LiOH in water (42 mL). The mixture was heated at 60° C. for 18 h, cooled, and the pH adjusted to ~5 with 1M HCl. The resulting precipitate was collected and washed with water. The aqueous filtrate was extracted with ethyl acetate (4×) resulting in several fractions which were combined, dried over sodium sulfate and concentrated to dryness under reduced pressure. The precipitate and the residue from extraction were combined to afford the title compound (2.48 g, 99%). MS (ESI): mass calcd. for $C_{21}H_{22}F_3N_3O_3$, 421.2; m/z found, 422.2 [M+H]+. 1H NMR (400 MHz, DMSO-$d_6$) δ 12.43 (s, 1H), 8.43 (d, J=7.3 Hz, 1H), 7.35-7.25 (m, 2H), 7.15 (dd, J=7.9, 2.1 Hz, 1H), 7.06 (d, J=7.9 Hz, 1H), 5.02 (s, 1H), 4.79 (s, 1H), 4.43 (s, 2H), 2.67 (s, 3H), 2.18 (s, 3H), 1.32-1.24 (m, 6H).

Step B: benzyl (*S)-3-(3-hydroxymethyl)-4-methylphenyl)-2,2-dimethyl)-3-(8-methyl-3-(trifluoromethyl)-[1,2,4]triazolo[4,3-a]pyridine-7-yl)propanoate. To a flask under $N_2$ was added (*S)-3-(3-hydroxymethyl)-4-methylphenyl)-2,2-dimethyl)-3-(8-methyl-3-(trifluoromethyl)-[1,2,4]triazolo[4,3-a]pyridine-7-yl)propanoic acid (500 mg, 1.19 mmol), potassium carbonate (410 mg, 2.97 mmol) and acetonitrile (5.0 mL). After stirring for 5 minutes, benzyl bromide (0.17 mL, 1.43 mmol) was added to the mixture followed by stirring at r.t. for an additional 24 h. The reaction was poured into water and extracted with ethyl acetate (3×). These extractions resulted in several fractions which were combined, dried over sodium sulfate and concentrated to dryness under reduced pressure. The residue was purified by flash column chromatography (eluent: ethyl acetate/hexanes, 0:1 to 1:0, gradient elution) to afford the title compound (540 mg, 89%). MS (ESI): mass calcd. for $C_{28}H_{28}F_3N_3O_3$, 511.2; m/z found, 512.3 [M+H]+. 1H NMR (600 MHz, DMSO-$d_6$) δ 8.25 (d, J=7.2 Hz, 1H), 7.28-7.22 (m, 2H), 7.10-7.00 (m, 7H), 5.09-5.00 (m, 2H), 4.87 (d, J=12.1 Hz, 1H), 4.71 (s, 1H), 4.41 (d, J=5.4 Hz, 2H), 2.54 (s, 3H), 2.16 (s, 3H), 1.35 (s, 3H), 1.29 (s, 3H).

Intermediate 72: 8'-Methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide

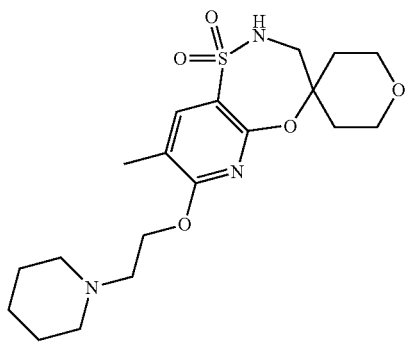 [SMILES: Cc1cc2c(nc1OCCN1CCCCC1)OC1(CCOCC1)CNS2(=O)=O]

Step A: 6-Bromo-2-chloro-N-((4-hydroxytetrahydro-2H-pyran-4-yl)methyl)-5-methylpyridine-3-sulfonamide. A solution of 4-(aminomethyl)tetrahydro-2H-pyran-4-ol (14.0 g, 83.5 mmol) in THF:$H_2O$ (230 mL, 4:1) was cooled to 0° C. and $K_2CO_3$ (26.2 g, 189 mmol) was added in portions to it. The resultant mixture was stirred for 5 min at 0° C. and then treated with 6-bromo-2-chloro-5-methylpyridine-3-sulfonyl chloride (23.1 g, 75.7 mmol). This mixture was stirred at room-temperature for 12 hours before pouring it into water (80 mL) and extracting with ethyl acetate (3×). These extractions resulted in several organic fractions which were combined, washed with brine (100 mL), dried over anhydrous $Na_2SO_4$, filtered, and concentrated to dryness under reduced pressure to afford the title compound (27.8 g). MS (ESI): mass calcd. for $C_{12}H_{16}BrClN_2O_4S$, 399.7 m/z found 400.8 [M+H]+. 1H NMR (400 MHz, DMSO-$d_6$) δ 8.25 (m, 1H), 8.05 (m, 1H), 4.39 (s, 1H), 3.57-3.51 (m, 4H), 2.89 (d, J=5.1 Hz, 2H), 2.40 (s, 3H), 1.55-1.45 (m, 2H), 1.33 (d, J=13.0 Hz, 2H).

Step B: 7'-Bromo-8'-methyl-2,2',3,3',5,6-hexahydrospiro[pyran-4,4'-pyrido[2,3-b][1,4,5]oxathiazepine] 1',1'-dioxide. t-BuOK (7.91 g, 70.5 mmol) was added in portions to a solution of 6-bromo-2-chloro-N-((4-hydroxytetrahydro-2H-pyran-4-yl)methyl)pyridine-3-sulfonamide (14.1 g, 35.2 mmol) and DMSO (110 mL) at 0° C. The resultant mixture was stirred at 100° C. for 2 hours before cooling to room-temperature and concentrating to dryness under reduced pressure. The residue was diluted with $H_2O$ (60 mL), the mixture acidified with 1 N HCl (100 mL) to pH=6, and the suspension isolated via filtration. The filter cake was washed with petroleum ether (60 mL) before drying under reduced pressure to give the product (10.08 g, 79%). The product (8.28 g) was purified by preparative HPLC (stationary phase: YMC Triart C18, 250 mm×50 mm×7 μm column; eluent: 10% to 40% (v/v) $CH_3CN$ and $H_2O$ with 0.225% HCOOH) to afford the title compound (7.13 g, 56%). MS (ESI): mass calcd. for $C_{12}H_{15}BrN_2O_4S$ 363.2 m/z found 363.0 [M+H]+. 1H NMR (400 MHz, DMSO-$d_6$) δ 8.50 (m, 1H), 8.09 (m, 1H), 3.79-3.70 (m, 2H), 3.61 (d, J=11.2 Hz, 2H), 3.50 (s, 2H), 2.36 (s, 3H), 1.69-1.55 (m, 4H).

Step C: 8'-Methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide. $Cs_2CO_3$ (6.72 g, 20.6 mmol) was added to a mixture of 7'-bromo-8'-methyl-2,2',3,3',5,6-hexahydrospiro[pyran-4,4'-pyrido[2,3-b][1,4,5]oxathiazepine] 1',1'-dioxide (2.5 g, 6.9 mmol), 2-(pyrrolidin-1-yl)ethanol (2.67 g, 20.7 mmol), JosiPhos pre-catalyst G3 (0.64 g, 0.70 mmol), and DMA (30 mL) under $N_2$. The resultant mixture was stirred at 95° C. for 16 hours before quenching with $H_2O$ and extracting with ethyl acetate (2×). These extractions resulted in several fractions which were combined dried over anhydrous $Na_2SO_4$, filtered, and concentrated to dryness under reduced pressure. The residue was purified by flash chromatography (eluent:petroleum ether/ethyl acetate; 1:0 to 0:1, gradient) to afford the title compound (2.1 g, 69.5%). MS (ESI): mass calcd. for $C_{19}H_{29}N_3O_5S$, 411.5 m/z found 412.2 [M+H]+. 1H NMR (400 MHz, DMSO-$d_6$) δ 8.15 (m, 1H), 7.83 (m, 1H), 4.39 (t, J=6.1 Hz, 2H), 3.87-3.76 (m, 2H), 3.62 (d, J=11.0 Hz, 2H), 3.43 (s, 2H), 2.66 (t, J=6.1 Hz, 2H), 2.44 (s, 4H), 2.12 (s, 3H), 1.60 (s, 4H), 1.51-1.45 (m, 4H), 1.40-1.33 (m, 2H).

225

Intermediate 73: 7'-(2-(Piperidin-1-yl)ethoxy)-2,2',3,3',5,6-hexahydrospiro[pyran-4,4'-pyrido[2,3-b][1,4,5]oxathiazepine] 1',1'-dioxide

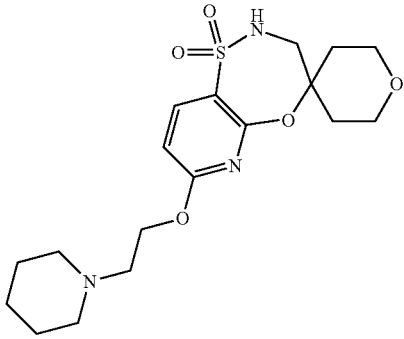 [SMILES: O=S1(=O)NCC2(CCOCC2)Oc2nc(OCCN3CCCCC3)ccc21]

To a solution of 2-piperidin-1-yl)ethan-1-ol (2.00 mL, 14.9 mmol) in DMSO (20 mL), which had been cooled to 0° C., was added NaH (558 mg, 13.9 mmol). The mixture was stirred at 0° C. for 2 minutes then allowed to warm to room temperature and stirred for an additional 45 minutes. 7'-chloro-2,2',3,3',5,6-hexahydrospiro[pyran-4,4'-pyrido[2,3-b][1,4,5]oxathiazepine] 1',1'-dioxide (1.00 g, 3.28 mmol, Intermediate 68) was then added as a solid in one portion and the reaction was stirred for an additional 15 h. The reaction was then quenched with saturated $NH_4Cl$ and the pH adjusted to about 7 with 1M aqueous HCl solution. The aqueous layer was extracted with ethyl acetate (5×) resulting in several organic fractions that were combined, washed with brine (1×), dried over $MgSO_4$ and concentrated to dryness under reduced pressure. The residue was purified by flash chromatography (eluent: ethyl acetate/methanol; 1:0 to 9:1, gradient elution) to afford the title compound (1.00 g, 77%). MS (ESI): mass calcd. for $C_{18}H_{27}N_3O_5S$, 397.2 m/z found 398.2 [M+H]$^+$. $^1$H NMR (400 MHz, DMSO-$d_6$) δ 8.18 (s, 1H), 7.98 (d, J=8.4 Hz, 1H), 6.72 (d, J=8.4 Hz, 1H), 4.38 (t, J=6.0 Hz, 2H), 3.85-3.78 (m, 2H), 3.67-3.60 (m, 2H), 3.47 (s, 2H), 2.65 (t, J=6.0 Hz, 2H), 2.45-2.38 (m, 4H), 1.69-1.58 (m, 4H), 1.52-1.45 (m, 4H), 1.41-1.33 (m, 2H).

Intermediate 74: (*R)-Methyl 3-(3-((7'-(3-(tert-butoxy)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate

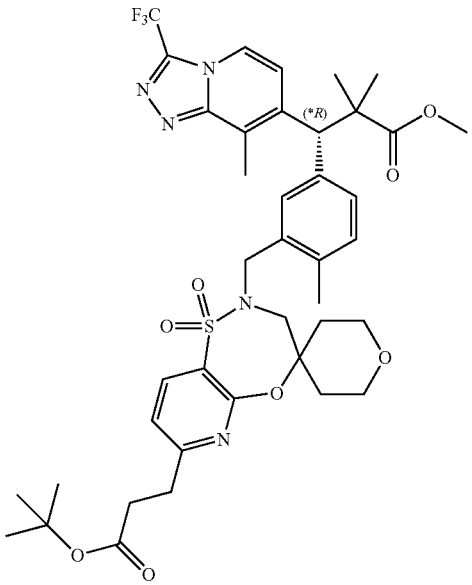 [SMILES: COC(=O)C(C)(C)[C@H](c1ccc(C)c(CN2CC3(CCOCC3)Oc3nc(CCC(=O)OC(C)(C)C)ccc3S2(=O)=O)c1)c1ccn2c(C(F)(F)F)nnc2c1C]

226

Step A: (E)-tert-Butyl 3-(1',1'-dioxido-2,2',3,3',5,6-hexahydrospiro[pyran-4,4'-pyrido[2,3-b][1,4,5]oxathiazepin]-7'-yl)acrylate. tert-Butyl acrylate (477 mg, 3.72 mmol), Pd(OAc)$_2$ (32.1 mg, 0.143 mmol), 2-(di-tert-butylphosphino)biphenyl (85.5 mg, 0.287 mmol), and Et$_3$N (580 mg, 5.73 mmol) were added to a solution of 7'-bromo-2,2',3,3',5,6-hexahydrospiro[pyran-4,4'-pyrido[2,3-b][1,4,5]oxathiazepine] 1',1'-dioxide (1.00 g, 2.86 mmol) and DMF (18 mL). The resultant mixture was sparged with N$_2$ for 5 minutes and then stirred while heating at 120° C. for 3 hours before cooling to room-temperature and concentrating to dryness under reduced pressure. The residue was diluted with sat. NH$_4$Cl (7 mL) and the resultant mixture was extracted with ethyl acetate (2×). These extractions resulted in several fractions which were combined, dried over sodium sulfate and concentrated to dryness under reduced pressure. The residue was purified by flash column chromatography (eluent:petroleum ether/ethyl acetate, 10:1 to 1:5, gradient elution) to afford the title compound (805 mg, 71%). MS (ESI): mass calcd. for $C_{18}H_{24}N_2O_6S$, 396.1 m/z found 396.9 [M+H]$^+$.

Step B: tert-Butyl 3-(1',1'-dioxido-2,2',3,3',5,6-hexahydrospiro[pyran-4,4'-pyrido[2,3-b][1,4,5]oxathiazepin]-7'-yl)propanoate. (E)-tert-Butyl 3-(1',1'-dioxido-2,2',3,3',5,6-hexahydrospiro[pyran-4,4'-pyrido[2,3-b][1,4,5]oxathiazepin]-7'-yl)acrylate (805 mg, 2.03 mmol), MeOH (10 mL), and dry Pd/C (200 mg, 10 wt. %, 0.189 mmol) were added to a 75 mL hydrogenation bottle. The resultant mixture was stirred at room-temperature for 16 hours under H$_2$ (50 psi). The suspension was filtered through a pad of diatomaceous earth and the pad washed with MeOH (20 mL). The filtrate was concentrated to dryness under reduced pressure to give the product, which was purified by flash column chromatography (eluent:petroleum ether/ethyl acetate, 10:1 to 1:5, gradient elution) to afford the title compound (780.5 mg). MS (ESI): mass calcd. for $C_{18}H_{26}N_2O_6S$, 398.1 m/z found 399.2 [M+H]$^+$. $^1$H NMR (400 MHz, DMSO-$d_6$) δ 8.60-8.10 (m, 1H), 8.02 (d, J=7.83 Hz, 1H), 7.24 (d, J=7.83 Hz, 1H), 3.81 (t, J=9.78 Hz, 2H), 3.57 (d, J=10.76 Hz, 2H), 3.47 (s, 2H), 2.97 (t, J=6.97 Hz, 2H), 2.64 (t, J=6.97 Hz, 2H), 1.72-1.46 (m, 4H), 1.34 (s, 9H).

Step C: (*R)-Methyl 3-(3-((7'-(3-(tert-butoxy)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate. DIAD (2.33 g, 11.5 mmol) was added to a solution of (*R)-methyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate (Intermediate 141, 2.5 g, 5.7 mmol), tert-butyl 3-(1',1'-dioxido-2,2',3,3',5,6-hexahydrospiro[pyran-4,4'-pyrido[2,3-b][1,4,5]oxathiazepin]-7'-yl)propanoate (2.75 g, 6.90 mmol), PPh$_3$ (3.02 g, 11.5 mmol), and THF (30 mL). The resultant mixture was stirred at room temperature for 3 hours before concentrating to dryness under reduced pressure to give the product, which was purified by flash column chromatography (eluent:petroleum ether/ethyl acetate, 10:1 to 1:3, gradient elution) to afford the title compound (6.1 g, 47%). MS (ESI): mass calcd. for $C_{40}H_{48}F_3N_5O_8S$, 815.32 m/z found 816.3 [M+H]$^+$. $^1$H NMR (400 MHz, DMSO-$d_6$) δ 8.41 (d, J=7.09 Hz, 1H), 8.05 (d, J=7.83 Hz, 1H), 7.29 (d, J=7.83 Hz, 1H), 7.25-7.16 (m, H), 7.16-7.09 (m, 1H), 4.80 (s, 1H), 4.54-4.24 (m, 2H), 3.76 (d, J=9.05 Hz, 2H), 3.55-3.40 (m, 6H), 2.99 (t, J=6.85 Hz, 2H), 2.76-2.59 (m, 5H), 2.15 (s, 3H), 2.07 (s, 1H), 1.52-1.40 (m, 4H), 1.36 (s, 12H), 1.29 (s, 3H).

Intermediate 75: (S)-6,7,7a,8,9,10-Hexahydropyrido[2,3-f]pyrrolo[2,1-d][1,2,5]thiadiazepine 5,5-dioxide

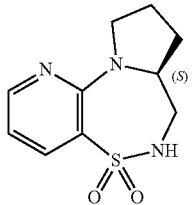

The title compound (4.3 g) was prepared using analogous conditions as described in Intermediate 4 using tert-butyl (S)-2-(aminomethyl)pyrrolidine-1-carboxylate instead of tert-butyl (R)-2-(aminomethyl)pyrrolidine-1-carboxylate in Step A. MS (ESI): mass calcd. for $C_{10}H_{13}N_3O_2S$, 239.1; m/z found, 240.1 $[M+H]^+$.

Intermediate 76: (*S)-7,7a,8,9,10,11-Hexahydro-6H-benzo[f]pyrido[2,1-d][1,2,5]thiadiazepine 5,5-dioxide

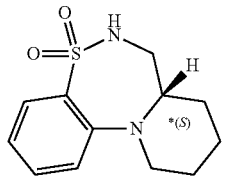 [SMILES: O=S1(=O)NC[C@@H]2CCCCN2c2ccccc21]

Step A: tert-Butyl 2-(((2-fluorophenyl)sulfonamido)methyl)piperidine-1-carboxylate. 2-Fluorobenzene-1-sulfonyl chloride (15 g, 77 mmol) was added in portions to a mixture of tert-butyl 2-(aminomethyl)piperidine-1-carboxylate (17 g, 81 mmol) and potassium carbonate (13 g, 93 mmol) in THF (150 mL) and water (38 mL). After 16 hours, sodium sulfate was added and the suspension was filtered through diatomaceous earth. The filtrate was concentrated to dryness under reduced pressure. The residue was purified by flash column chromatography (petroleum ether-ethyl acetate) to provide the title compound as a yellow oil (28 g, 93%). $^1$H NMR (400 MHz, CDCl$_3$) δ 7.89 (dt, J=7.5, 1.8 Hz, 1H), 7.61-7.53 (m, 1H), 7.30-7.25 (m, 1H), 7.21 (t, J=9.5 Hz, 1H), 5.14 (br s, 1H), 4.33 (br s, 1H), 3.88 (br d, J=12.6 Hz, 1H), 3.34 (br s, 1H), 2.59 (br s, 1H), 1.69-1.52 (m, 5H), 1.47 (s, 9H), 1.41-1.33 (m, 2H).

Step B: 2-Fluoro-N-(piperidin-2-ylmethyl)benzenesulfonamide hydrochloride. tert-Butyl 2-(((2-fluorophenyl)sulfonamido)methyl)piperidine-1-carboxylate (24 g, 64 mmol) was dissolved in a mixture of 4 M HCl in methanol (81 mL, 320 mmol). After 2 hours, the mixture was concentrated to dryness under reduced pressure to afford the title compound as a white solid which was used in the next step without further purification (19.9 g). $^1$H NMR (400 MHz, DMSO-d$_6$) δ 9.26-9.05 (m, 2H), 8.38 (br t, J=5.7 Hz, 1H), 7.82 (dt, J=7.6, 1.5 Hz, 1H), 7.77-7.70 (m, 1H), 7.51-7.38 (m, 2H), 3.24-3.16 (m, 2H), 3.10-2.98 (m, 2H), 2.87-2.73 (m, 1H), 1.88-1.56 (m, 4H), 1.40 (br s, 2H).

Step C: (*S)-7,7a,8,9,10,11-Hexahydro-6H-benzo[f]pyrido[2,1-d][1,2,5]thiadiazepine 5,5-dioxide. The below reaction was run three times on 2 different scale: twice using 5 g of 2-fluoro-N-(piperidin-2-ylmethyl)benzenesulfonamide hydrochloride and once using 13.2 g. The 13.2 g scale reaction details are provided. A solution containing 2-fluoro-N-(piperidin-2-ylmethyl)benzenesulfonamide hydrochloride (13.2 g, 42.7 mmol), DIPEA (27.6 g, 214 mmol) and DMSO (240 mL) was degassed by bubbling nitrogen through the solution for 5 minutes. The mixture was warmed to 160° C. After 6 hours, the solution was cooled to room temperature. At this point, the cooled reaction mixture was combined with the two additional reaction mixtures referred to above for further processing. The combined mixture was concentrated to dryness under reduced pressure. The residue was dissolved in ethyl acetate and washed with water. The organics extracts were dried over sodium sulfate, filtered and concentrated to dryness under reduced pressure. The residue was triturated with a mixture of petroleum ether and ethyl acetate (4:1, 40 mL) to afford a suspension. The solids were isolated by filtration and then dried to provide the title compound as a mixture of enantiomers (5.73 g). The mixture of isomers was separated by chiral SFC (stationary phase: Chiralcel OD-H 5 μm 3×25 cm; mobile phase: 25% methanol, 75% CO$_2$ with 0.3% iPrNH$_2$) to afford two enantiomers. The first eluting isomer (2.16 g) was designated (*S): $^1$H NMR (400 MHz, DMSO-d$_6$) δ 7.79-7.69 (m, 1H), 7.61-7.56 (m, 1H), 7.42-7.35 (m, 1H), 7.19-7.14 (m, 1H), 7.03-6.96 (m, 1H), 3.73 (s, 1H), 3.52-3.33 (m, 3H), 3.10-2.98 (m, 1H), 1.74-1.51 (m, 6H).

Intermediate 77: (*S)-3-Methyl-7,7a,8,9,10,11-hexahydro-6H-dipyrido[2,1-d:2',3'-f][1,2,5]thiadiazepine 5,5-dioxide

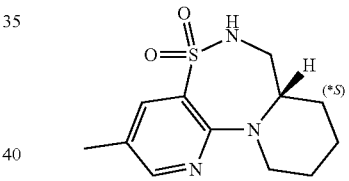

Step A: 2-Chloro-5-methylpyridine-3-sulfonyl chloride. HBF$_4$ (7.6 mL, 48 mmol) was added dropwise to a solution of 2-chloro-5-methylpyridin-3-amine (5.0 g, 35 mmol) in acetonitrile (30 mL) at 0° C. After 10 minutes, tert-butyl nitrite (6.3 mL, 53 mmol) was added dropwise. After 1 hour, this solution was added to mixture of copper chloride (5.5 g, 56 mmol) and acetic acid (50 mL) that had been degassed by bubbling SO$_2$ through it for 1 hour at 0° C. After 4 hours, the mixture was warmed to room temperature, and then saturated aqueous sodium bicarbonate solution was added. After 20 minutes, the aqueous portion was extracted with ethyl acetate and these extractions resulted in several organic fractions which were combined, washed with brine, dried over anhydrous Na$_2$SO$_4$, filtered, and concentrated to dryness under reduced pressure. The residue was purified by flash column chromatography (petroleum ether-ethyl acetate) to provide the title compound as a yellow oil (3 g, 38%). $^1$H NMR (400 MHz, CDCl$_3$) δ 8.51 (s, 1H), 8.27-8.19 (m, 1H), 2.46 (s, 3H).

Step B: 3-Methyl-7,7a,8,9,10,11-hexahydro-6H-dipyrido[2,1-d:2',3'-f][1,2,5]thiadiazepine 5,5-dioxide. The title compound (1.6 g) was prepared using analogous conditions as described the preparation of in Intermediate 76 using 2-chloro-5-methylpyridine-3-sulfonyl chloride instead of 2-fluorobenzene-1-sulfonyl chloride in Step A and TFA in dichloromethane instead of 4 M HCl in methanol in Step B. MS (ESI): mass calcd. for $C_{12}H_{17}N_3O_2S$, 267.1; m/z found, 267.9 $[M+H]^+$.

Step C: (*S)-3-Methyl-7,7a,8,9,10,11-hexahydro-6H-dipyrido[2,1-d:2',3'-f][1,2,5]thiadiazepine 5,5-dioxide. The mixture of 3-methyl-7,7a,8,9,10,11-hexahydro-6H-dipyrido[2,1-d:2',3'-f][1,2,5]thiadiazepine 5,5-dioxide isomers from Step B were separated by chiral SFC (stationary phase: Chiralpak AD 10 m 5×25 cm; mobile phase: 40% ethanol, 60% $CO_2$ with 0.1% $NH_3$) to afford two enantiomers. The first eluting isomer (370 mg) was designated (*S): MS (ESI): mass calcd. for $C_{12}H_{17}N_3O_2S$, 267.1; m/z found, 268.0 $[M+H]^+$. $^1$H NMR (400 MHz, DMSO-$d_6$) δ 8.11-8.07 (m, 1H), 8.05-7.99 (m, 1H), 7.72-7.66 (m, 1H), 4.19-4.06 (m, 2H), 3.47-3.38 (m, 1H), 3.32-3.24 (m, 1H), 3.19-3.10 (m, 1H), 2.18 (s, 3H), 1.72-1.49 (m, 6H).

Intermediate 78: (*S)-3-Fluoro-7,7a,8,9,10,11-hexahydro-6H-dipyrido[2,1-d:2',3'-f][1,2,5]thiadiazepine 5,5-dioxide

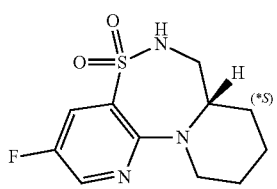 [SMILES: O=S1(=O)NC[C@@H]2CCCCN2c2ncc(F)cc21]

Step A: 2-Chloro-5-fluoropyridin-3-amine. Iron (15 g, 270 mmol) was added in portions to a solution of 2-chloro-5-fluoro-3-nitropyridine (12 g, 68 mmol) and acetic acid (200 mL). The mixture was warmed to 80° C. After 30 minutes, the mixture was cooled to room temperature and concentrated to dryness under reduced pressure. The residue was suspended in ethyl acetate and the suspension filtered through a pad of diatomaceous earth. The filtrate was brought to neutral pH by the addition of saturated aqueous sodium bicarbonate solution. The aqueous layer was extracted with ethyl acetate and these extractions resulted in several organic fractions which were combined, dried over anhydrous $Na_2SO_4$, filtered, and concentrated to dryness under reduced pressure to afford the title compound as a white solid which was used in the next step without further purification (11 g). MS (ESI): mass calcd. for $C_5H_4ClFN_2$, 146.0; m/z found, 146.8 $[M+H]^+$.

Step B: 3-Fluoro-7,7a,8,9,10,11-hexahydro-6H-dipyrido[2,1-d:2',3'-f][1,2,5]thiadiazepine 5,5-dioxide. The title compound (11 g) was prepared using analogous conditions as described in Intermediate 77 using 2-chloro-5-fluoropyridin-3-amine instead of 2-chloro-5-methylpyridin-3-amine in Step A. MS (ESI): mass calcd. for $C_{11}H_{14}FN_3O_2S$, 271.1; m/z found, 271.9 $[M+H]^+$.

Step C: (*S)-3-Fluoro-7,7a,8,9,10,11-hexahydro-6H-dipyrido[2,1-d:2',3'-f][1,2,5]thiadiazepine 5,5-dioxide. The mixture of 3-fluoro-7,7a,8,9,10,11-hexahydro-6H-dipyrido[2,1-d:2',3'-f][1,2,5]thiadiazepine 5,5-dioxide isomers prepared in Step B were separated by chiral SFC (stationary phase: Chiralpak AS 10 m 5×25 cm; mobile phase: 30% ethanol, 70% $CO_2$ with 0.1% $NH_3$) to afford two enantiomers. The first eluting isomer (5.22 g) was designated (*S): MS (ESI): mass calcd. for $C_{11}H_{14}FN_3O_2S$, 271.1; m/z found, 272.0 $[M+H]^+$. $^1$H NMR (400 MHz, DMSO-$d_6$) δ 8.29 (d, J=3.2 Hz, 1H), 8.22 (br s, 1H), 7.86-7.74 (m, 1H), 4.20-4.08 (m, 2H), 3.47 (t, J=12.8 Hz, 1H), 3.30-3.22 (m, 1H), 3.21-3.11 (m, 1H), 1.71-1.48 (m, 6H).

Intermediate 79: (*R)-3-Fluoro-7,7a,8,9,10,11-hexahydro-6H-dipyrido[2,1-d:2',3'-f][1,2,5]thiadiazepine 5,5-dioxide

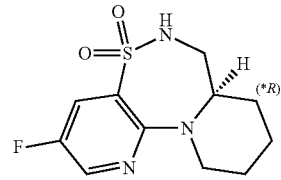

The second eluting isomer (4.95 g) from the separation of isomers by chiral SFC described in Intermediate 78 was designated (*R): MS (ESI): mass calcd. for $C_{11}H_{14}FN_3O_2S$, 271.1; m/z found, 272.0 $[M+H]^+$. $^1$H NMR (400 MHz, DMSO-$d_6$) δ 8.29 (d, J=2.8 Hz, 1H), 8.26-8.19 (m, 1H), 7.85-7.78 (m, 1H), 4.22-4.07 (m, 2H), 3.53-3.42 (m, 1H), 3.31-3.23 (m, 1H), 3.22-3.12 (m, 1H), 1.72-1.49 (m, 6H).

Intermediate 80: 8'-Fluoro-2',3'-dihydrospiro[cyclopropane-1,4'-pyrido[2,3-b][1,4,5]oxathiazepine] 1',1'-dioxide

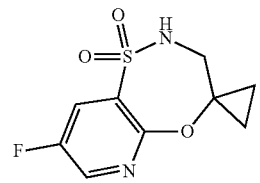 [SMILES: O=S1(=O)NCC2(CC2)Oc2ncc(F)cc21]

The title compound (2.2 g) was prepared using analogous conditions as described in Intermediate 78 using 1-(aminomethyl)cyclopropan-1-ol instead of tert-butyl 2-(aminomethyl)piperidine-1-carboxylate in Step B. MS (ESI): mass calcd. for $C_9H_9FN_2O_3S$, 244.0; m/z found, 245.0 $[M+H]^+$. $^1$H NMR (400 MHz, CDCl$_3$) δ 8.24 (d, J=3.0 Hz, 1H), 7.99-7.95 (m, 1H), 5.02-4.87 (m, 1H), 3.70 (d, J=7.0 Hz, 2H), 1.29-1.17 (m, 2H), 0.82-0.67 (m, 2H).

Intermediate 81: 4,4-Dimethyl-3,4-dihydro-2H-benzo[b][1,4,5]oxathiazepine 1,1-dioxide

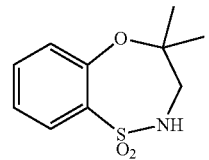

The title compound (238 mg) was prepared using analogous conditions as described in Intermediate 7 using 1-amino-2-methylpropan-2-ol instead of 3-(aminomethyl) oxetan-3-ol in Step A. MS (ESI): mass calcd. for $C_{10}H_{13}NO_3S$, 227.1; m/z found, 228.1 $[M+H]^+$. $^1$H NMR (400 MHz, CDCl$_3$) δ 7.80 (dd, J=7.8, 1.7 Hz, 1H), 7.45 (td, J=7.8, 1.7 Hz, 1H), 7.20 (td, J=7.7, 1.2 Hz, 1H), 7.09 (dd, J=8.0, 1.2 Hz, 1H), 4.85-4.74 (m, 1H), 3.61-3.40 (m, 2H), 1.29 (s, 6H).

Intermediate 82: 4,4-Dimethyl-3,4-dihydro-2H-pyrido[2,3-b][1,4,5]oxathiazepine 1,1-dioxide

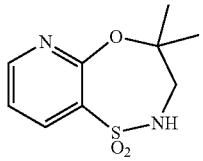

The title compound (139 mg) was prepared using analogous conditions as described in Intermediate 5 using 1-amino-2-methylpropan-2-ol instead of 1-(aminomethyl)cyclopropanol in Step A. MS (ESI): mass calcd. for $C_9H_{12}N_2O_3S$, 228.1; m/z found, 229.1 [M+H]+. 1H NMR (400 MHz, DMSO-$d_6$) δ 8.45 (dd, J=4.9, 2.0 Hz, 1H), 8.30 (s, 1H), 8.11 (dd, J=7.6, 2.0 Hz, 1H), 7.36 (dd, J=7.6, 4.8 Hz, 1H), 3.43 (s, 2H), 1.21 (s, 6H).

Intermediate 83: (R)-6,7,7a,8,9,10-Hexahydrobenzo[f]pyrrolo[2,1-d][1,2,5]thiadiazepine 5,5-dioxide

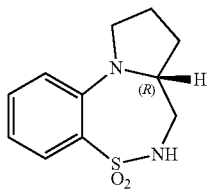

Step A: (R)-2-Fluoro-N-(pyrrolidin-2-ylmethyl)benzenesulfonamide. A mixture of 2-fluorobenzenesulfonamide (11.2 g, 64.2 mmol), (R)-pyrrolidin-2-ylmethanol (19 g, 188 mmol) in DMSO (33 mL) was warmed to 150° C. After 2.5 hours, the mixture was cooled to room temperature and then ethyl acetate was added. The organic layer was washed with saturated aqueous sodium bicarbonate solution and then with saturated sodium chloride solution. The organic layers were dried over anhydrous sodium sulfate, filtered, and then concentrated under reduced pressure. The residue was purified by flash column chromatography (dichloromethane-ethyl acetate) to provide the title compound (5.5 g, 33%). Impure product fractions were concentrated, triturated with dichloromethane, filtered, and the solids collected to obtain an additional portion of the title compound (5.4 g, 33%). MS (ESI): mass calcd. for $C_{11}H_{16}N_2O_3S$, 256.1; m/z found, 257.1 [M+H]+. 1H NMR (400 MHz, CDCl3) δ 8.08-7.99 (m, 1H), 7.60 (t, J=7.7 Hz, 1H), 7.44 (d, J=8.1 Hz, 1H), 7.37-7.27 (m, 1H), 5.96 (s, 2H), 3.78-3.51 (m, 4H), 2.88 (s, 1H), 2.66 (s, 1H), 2.19-1.91 (m, 4H).

Step B: (R)-6,7,7a,8,9,10-Hexahydrobenzo[f]pyrrolo[2,1-d][1,2,5]thiadiazepine 5,5-dioxide. Di-tert-butyl azodicarboxylate (5.6 g, 24 mmol) was added to a stirring slurry of (R)-2-fluoro-N-(pyrrolidin-2-ylmethyl)benzenesulfonamide (5.2 g, 20 mmol) and triphenylphosphine (8 g, 30 mmol) in dichloromethane (104 mL). After 30 minutes, the mixture was concentrated under reduced pressure and the residue was purified by flash column chromatography (dichloromethane-ethyl acetate) to provide the title compound (1.5 g, 31%). MS (ESI): mass calcd. for $C_{11}H_{14}N_2O_2S$, 238.1; m/z found, 238.9 [M+H]+. 1H NMR (400 MHz, CDCl3) δ 7.90 (dd, J=8.0, 1.7 Hz, 1H), 7.40 (ddd, J=8.6, 7.1, 1.6 Hz, 1H), 7.00-6.90 (m, 2H), 4.84 (s, 1H), 4.16 (s, 1H), 3.55-3.35 (m, 3H), 3.18-3.02 (m, 1H), 2.21-1.99 (m, 3H), 1.83-1.73 (m, 1H).

Intermediate 84: (S)-6,7,7a,8,9,10-Hexahydrobenzo[f]pyrrolo[2,1-d][1,2,5]thiadiazepine 5,5-dioxide

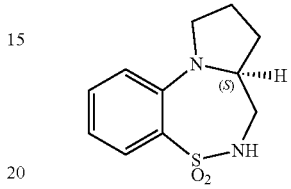

The title compound (1.7 g) was prepared using analogous conditions as described in Intermediate 83 using (S)-pyrrolidin-2-ylmethanol instead of (R)-pyrrolidin-2-ylmethanol in Step A. MS (ESI): mass calcd. for $C_{11}H_{14}N_2O_2S$, 238.1; m/z found, 239.1 [M+H]+. 1H NMR (400 MHz, DMSO-$d_6$) δ 7.79-7.71 (m, 1H), 7.67 (dd, J=7.9, 1.6 Hz, 1H), 7.38 (ddd, J=8.6, 7.1, 1.7 Hz, 1H), 7.00-6.94 (m, 1H), 6.90 (ddd, J=8.0, 7.1, 1.1 Hz, 1H), 3.86-3.74 (m, 1H), 3.37-3.24 (m, 2H), 3.17 (ddd, J=13.4, 4.7, 3.3 Hz, 1H), 2.95 (ddd, J=13.3, 11.6, 7.8 Hz, 1H), 2.12-1.82 (m, 3H), 1.67 (ddt, J=12.2, 6.0, 1.8 Hz, 1H).

Intermediate 85: (*S)-9-Methyl-7,7a,8,9,10,11-hexahydro-6H-pyrazino[2,1-d]pyrido[2,3-f][1,2,5]thiadiazepine 5,5-dioxide

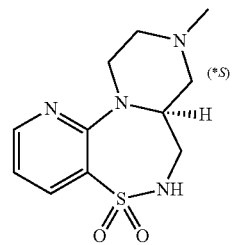

Step A: 4-Benzyl 1-(tert-butyl) 2-carbamoylpiperazine-1,4-dicarboxylate. NH4HCO3 (9 g, 114 mmol) was added to a solution of 4-((benzyloxy)carbonyl)-1-(tert-butoxycarbonyl)piperazine-2-carboxylic acid (33 g, 91 mmol), Boc2O (25.7 g, 118 mmol), pyridine (4.3 g, 54 mmol), and 1,4-dioxane (462 mL). After 14 hours, the mixture was concentrated under reduced pressure. The residue was dissolved in ethyl acetate (300 mL) and the solution was washed with brine. The organic layer was dried over anhydrous Na2SO4, filtered, and concentrated under reduced pressure to afford the title compound (36 g). This material was used in the next step without further purification. MS (ESI): mass calcd. for $C_{18}H_{25}N_3O_5$, 363.2; m/z found, 386.0 [M+Na]+.

Step B: 4-Benzyl 1-(tert-butyl) 2-cyanopiperazine-1,4-dicarboxylate. The below reaction was run twice on 2 different scales: once using 10 g of 4-benzyl 1-tert-butyl 2-carbamoylpiperazine-1,4-dicarboxylate and once using 26 g. The 26 g scale reaction details are provided. TFAA (19.5 g, 93.0 mmol) was added to an ice-water cooled solution of 4-benzyl 1-tert-butyl 2-carbamoylpiperazine-1,4-dicarboxylate (26 g, 72 mmol), Et$_3$N (23 g, 230 mmol), and THF (260 mL). The resulting mixture was stirred for 2 hours with gradual warming to room-temperature and then combined with a similar reaction mixture as described above starting with 10 g of 4-benzyl 1-tert-butyl 2-carbamoylpiperazine-1,4-dicarboxylate. The combined mixture was concentrated under reduced pressure. The residue was purified by column chromatography (petroleum ether-ethyl acetate, 10:1 to 2:1, gradient elution) to afford the title compound (26 g) as a light yellow oil. MS (ESI): mass calcd. for C$_{18}$H$_{23}$N$_3$O$_4$, 345.2; m/z found, 345.9 [M+H]$^+$. $^1$H NMR (400 MHz, CDCl$_3$) δ 7.42-7.29 (m, 5H), 5.24-4.98 (m, 3H), 4.54-4.16 (m, 2H), 3.95 (br s, 1H), 3.24-3.01 (m, 2H), 2.88 (br s, 1H), 1.49 (s, 9H).

Step C: 4-Benzyl 1-(tert-butyl) 2-(aminomethyl)piperazine-1,4-dicarboxylate. The below reaction was run twice on 2 different scales: 4-benzyl 1-tert-butyl 2-cyanopiperazine-1,4-dicarboxylate and a second using 16 g of 4-benzyl 1-tert-butyl 2-cyanopiperazine-1,4-dicarboxylate. The details for the 16 g reaction are shown below. NaBH$_4$ (17.5 g, 463 mmol) was added in portions to an ice-water cooled solution of 4-benzyl 1-tert-butyl 2-cyanopiperazine-1,4-dicarboxylate (16 g, 46 mmol) and CoCl$_2$ (22 g, 93 mmol), and MeOH (347 mL). The mixture was allowed to warm to room temperature. After 2 hours, the mixture was combined with the reaction mixture as described above starting with 10 g of 4-benzyl 1-tert-butyl 2-cyanopiperazine-1,4-dicarboxylate. The mixture was diluted with ethyl acetate (300 mL) and the suspension filtered through a pad of diatomaceous earth. The filtrate was concentrated under reduced pressure and water was added to the residue. The mixture was extracted with dichloromethane which resulted in several organic fractions. These fractions were combined, dried over anhydrous Na$_2$SO$_4$, filtered, and concentrated under reduced pressure to afford the title compound (21 g) as a dark yellow oil, which was used in the next step without further purification. MS (ESI): mass calcd. for C$_{18}$H$_{27}$N$_3$O$_4$, 349.2; m/z found, 350.0 [M+H]$^+$.

Step D: 4-Benzyl 1-(tert-butyl) 2-(((2-chloropyridine)-3-sulfonamido)methyl)piperazine-1,4-dicarboxylate. K$_2$CO$_3$ (5.44 g, 39.4 mmol) was added to a mixture of 4-benzyl 1-tert-butyl 2-(aminomethyl)piperazine-1,4-dicarboxylate (11.5 g), THF (124 mL), and H$_2$O (31 mL). After 5 minutes, 2-chloropyridine-3-sulfonyl chloride (6.96 g, 32.8 mmol) was added in portions. After 2 hours, the mixture was extracted with ethyl acetate which resulted in numerous organic fractions. These fractions were combined, dried over anhydrous Na$_2$SO$_4$, filtered, and concentrated under reduced pressure to afford the title compound (18 g) which was used in the next step without further purification. MS (ESI): mass calcd. for C$_{23}$H$_{29}$ClN$_4$O$_6$S, 524.2; m/z found, 547.0 [M+Na]+.

Step E: Benzyl 3-(((2-chloropyridine)-3-sulfonamido)methyl)piperazine-1-carboxylate 2,2,2-trifluoroacetate. TFA (20.0 mL, 269 mmol) was added to a solution of 4-benzyl 1-tert-butyl 2-((2-chloropyridine-3-sulfonamido)methyl)piperazine-1,4-dicarboxylate (13.0 g, 24.8 mmol) and methylene chloride (100 mL). After 2 hours, the mixture was concentrated under reduced pressure to afford the title compound (14.5 g) as a yellow oil, which was used in the next step without further purification. MS (ESI): mass calcd. for C$_{18}$H$_{21}$ClN$_4$O$_4$S, 424.1; m/z found, 425.0 [M+H]$^+$.

Step F: Benzyl 6,7,7a,8,10,11-hexahydro-9H-pyrazino[2,1-d]pyrido[2,3-f][1,2,5]thiadiazepine-9-carboxylate 5,5-dioxide. Cs$_2$CO$_3$ (43.8 g, 134 mmol) was added to a solution of benzyl 3-((2-chloropyridine-3-sulfonamido)methyl)piperazine-1-carboxylate 2,2,2-trifluoroacetate (14.5 g) and DMSO (250 mL). The mixture was warmed to 160° C. After 6 hours, the mixture was cooled to room temperature and then concentrated under reduced pressure. The residue was dissolved in ethyl acetate (350 mL) and washed with water. The organic layer was dried over anhydrous Na$_2$SO$_4$, filtered, and concentrated under reduced pressure. The residue was purified by column chromatography (petroleum ether: ethyl acetate=10:1 to 2:1, gradient elution) to afford the title compound (4.5 g, 43%) as a yellow oil. MS (ESI): mass calcd. for C$_{18}$H$_{20}$N$_4$O$_4$S, 388.1; m/z found, 389.0 [M+H]$^+$.

Step G: 7,7a,8,9,10,11-Hexahydro-6H-pyrazino[2,1-d]pyrido[2,3-f][1,2,5]thiadiazepine 5,5-dioxide. Benzyl 6,7,7a,8,10,11-hexahydro-9H-pyrazino[2,1-d]pyrido[2,3-f][1,2,5]thiadiazepine-9-carboxylate 5,5-dioxide (4.0 g, 10 mmol), MeOH (200 mL), and Pd(OH)$_2$ on carbon (2.0 g, 10 wt. %, 1.4 mmol) were added to a 500-mL round-bottomed flask. The mixture was stirred under a H$_2$ atmosphere (15 psi) at room temperature. After 1 hour, the suspension was filtered through a pad of diatomaceous earth and the pad washed with MeOH. The filtrate was concentrated under reduced pressure to afford the title compound (2.5 g) as a white solid, which was used in the next step without further purification. MS (ESI): mass calcd. for C$_{10}$H$_{14}$N$_4$O$_2$S, 254.1; m/z found, 255.1 [M+H]$^+$.

Step H: (*S)-9-Methyl-7,7a,8,9,10,11-hexahydro-6H-pyrazino[2,1-d]pyrido[2,3-f][1,2,5]thiadiazepine 5,5-dioxide. NaBH$_3$CN (3.7 g, 59 mmol) was added in portions to an ice-water cooled solution of 7,7a,8,9,10,11-Hexahydro-6H-pyrazino[2,1-d]pyrido[2,3-f][1,2,5]thiadiazepine 5,5-dioxide (2.5 g), 37% aqueous formaldehyde (16 g, 197 mmol), MeOH (100 mL), and dichloromethane (50 mL). The mixture was allowed to warm to room temperature. After 1 hour, the mixture was concentrated under reduced pressure. Water was added to the residue and the aqueous layer was extracted with ethyl acetate. This resulted in several organic fractions which were combined, washed with brine, dried over anhydrous Na$_2$SO$_4$, filtered, and concentrated under reduced pressure. The residue was purified by preparative HPLC (Waters Xbridge Prep OBD C18 250×50 mm×10 μm column, eluent: 5% to 25% (v/v) CH$_3$CN in H$_2$O with 0.05% NH$_3$) to afford the title compound as a racemic mixture as a pink solid (900 mg, 33%). This was combined with an additional 750 mg of the racemic mixture (1.6 g total). A second purification was performed by preparative liquid chromatography (irregular bare silica, 5% methanol in dichloromethane with 0.5% NH$_4$OH) to provide the title compound (1.4 g) as the racemic mixture. The isomers were separated by chiral SFC (stationary phase: Chiralcel OD-H 5 μm 250×30 mm, mobile phase: 80% CO$_2$ and 20% ethanol) to afford two enantiomers. The first eluting enantiomer (625 mg) was designated (*S). MS (ESI): mass calcd. for C$_{11}$H$_{16}$N$_4$O$_2$S, 268.1; m/z found, 268.9 [M+H]$^+$.

Intermediate 86: (*R)-9-Methyl-7,7a,8,9,10,11-hexahydro-6H-pyrazino[2,1-d]pyrido[2,3-][1,2,5]thiadiazepine 5,5-dioxide

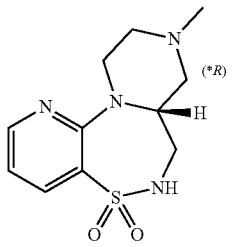

The second eluting isomer (650 mg) from the separation of isomers by chiral SFC described in Intermediate 85 was designated (*R). MS (ESI): mass calcd. for $C_{11}H_{16}N_4O_2S$, 268.1; m/z found, 268.9 [M+H]$^+$.

Intermediate 87: (R)-6,7,7a,8,9,10-hexahydropyrido[2,3-f]pyrrolo[2,1-d][1,2,5]thiadiazepine-3-carbonitrile 5,5-dioxide

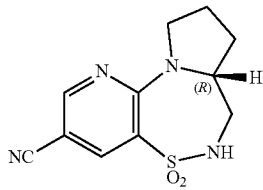

Step A: tert-Butyl (R)-2-(((2,5-dichloropyridine)-3-sulfonamido)methyl)pyrrolidine-1-carboxylate. tert-Butyl (R)-2-(aminomethyl)pyrrolidine-1-carboxylate (2.44 g, 12.2 mmol) was added to a suspension consisting of $K_2CO_3$ (1.18 g, 8.52 mmol), THF (27 mL), and $H_2O$ (5.5 mL) at 0° C. The reaction mixture was stirred for 10 minutes at 0° C. and then treated with 2,5-dichloropyridine-3-sulfonyl chloride (2.0 g, 8.1 mmol). The resulting mixture was stirred at room temperature for 6.5 hours and concentrated to dryness under reduced pressure. The residue was dissolved in water (20 mL) and the aqueous layer was extracted with ethyl acetate (20 mL×3). These extractions resulted in several organic solvent fractions which were combined, washed with brine (20 mL), dried over anhydrous $Na_2SO_4$, filtered, and concentrated to dryness under reduced pressure. The residue was purified by flash column chromatography (eluent: 0-100% ethyl acetate/hexanes, gradient elution) to afford the title compound (3.0 g, 90%) as a yellow solid. MS (ESI): mass calcd. for $C_{15}H_{21}Cl_2N_3O_4S$, 409.1; m/z found, 310.1 [M-100]$^+$. $^1$H NMR (500 MHz, CDCl$_3$) δ 8.47 (d, J=2.5 Hz, 1H), 8.33 (d, J=2.6 Hz, 1H), 7.51 (s, 1H), 4.09 (q, J=7.1 Hz, 1H), 4.01-3.95 (m, 1H), 3.42-3.33 (m, 1H), 3.25 (dt, J=11.5, 6.3 Hz, 1H), 3.20-3.12 (m, 1H), 2.94-2.85 (m, 1H), 2.08-1.96 (m, 2H), 1.85-1.72 (m, 1H), 1.43 (s, 9H).

Step B: (R)-3-Chloro-6,7,7a, 8,9,10-hexahydropyrido[2,3-f]pyrrolo[2,1-d][1,2,5]thiadiazepine 5,5-dioxide. TFA (5 mL) was added dropwise to a solution of tert-butyl (R)-2-(((2,5-dichloropyridine)-3-sulfonamido)methyl)pyrrolidine-1-carboxylate (3.0 g, 7.3 mmol) and dichloromethane (20 mL) at 0° C. The resulting mixture was stirred for 16 hours with gradual warming to room temperature. It was then concentrated to dryness under reduced pressure. TEA (6.2 mL, 44 mol) was added to the residue in toluene (33 mL). The resulting solution was stirred at refluxing temperature for 16 hours before cooling to room-temperature and concentrating to dryness under reduced pressure. The residue was purified by flash column chromatography (eluent: 0-100% ethyl acetate/hexanes, gradient elution) to afford the title compound (2.0 g, 99%) as a yellow solid. MS (ESI): mass calcd. for $C_{10}H_{12}ClN_3O_2S$, 273.0; m/z found, 274.1 [M+H]$^+$. $^1$H NMR (500 MHz, CDCl$_3$) δ 8.16-8.09 (m, 1H), 7.83 (dd, J=5.3, 2.5 Hz, 1H), 5.84 (d, J=11.6 Hz, 1H), 4.46-4.35 (m, 1H), 4.15-4.00 (m, 2H), 3.61 (p, J=4.8 Hz, 2H), 3.49-3.39 (m, 1H), 3.17-3.03 (m, 1H), 2.15-2.05 (m, 1H), 1.76-1.68 (m, 1H).

Step C: (R)-6,7,7a,8,9,10-Hexahydropyrido[2,3-f]pyrrolo[2,1-d][1,2,5]thiadiazepine-3-carbonitrile 5,5-dioxide. Zn(CN)$_2$ (1.47 g, 12.5 mmol) was added to a mixture of (R)-3-chloro-6,7,7a,8,9,10-hexahydropyrido[2,3-f]pyrrolo[2,1-d][1,2,5]thiadiazepine 5,5-dioxide (2.0 g, 7.3 mmol), Zn (185 mg, 2.83 mmol), and DMA (42 mL). The mixture was sparged with Ar for 5 minutes and then treated with Pd(dppf)Cl$_2$ (631 mg, 0.69 mmol) and X-Phos (526 mg, 1.10 mmol). The resultant mixture was sparged with Ar for another 5 minutes and then stirred at 110° C. for 18 hours before cooling to room temperature. The reaction mixture was filtered and the solid was rinsed with ethyl acetate (10 mL×2). The filtrate was concentrated to dryness under reduced pressure and purified by flash column chromatography (eluent: 0-100% ethyl acetate/hexanes, gradient elution) to afford the title compound (1.7 g, 88%) as a brown solid. MS (ESI): mass calcd. for $C_{11}H_{12}N_4O_2S$, 264.1; m/z found, 264.9 [M+H]$^+$. $^1$H NMR (500 MHz, CDCl$_3$) δ 8.39 (d, J=2.2 Hz, 1H), 8.06 (d, J=2.1 Hz, 1H), 5.65 (dd, J=6.6, 3.8 Hz, 1H), 4.85-4.75 m, 1H), 3.86-3.65 (m, 2H), 3.56 (dt, J=12.9, 3.7 Hz, 1H), 3.20 (td, J=12.6, 6.5 Hz, 1H), 2.11-1.94 (m, 3H), 1.84-1.74 (m, 1H).

Intermediate 88: (S)-6,7,7a,8,9,10-Hexahydropyrido[2,3-f]pyrrolo[2,1-d][1,2,5]thiadiazepine-3-carbonitrile 5,5-dioxide

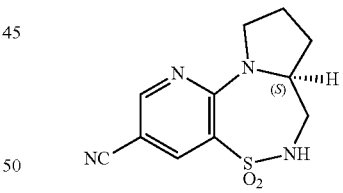

Step A: tert-Butyl (S)-2-(((2,5-dichloropyridine)-3-sulfonamido)methyl)pyrrolidine-1-carboxylate. tert-Butyl (S)-2-(aminomethyl)pyrrolidine-1-carboxylate (2.44 g, 12.2 mmol) was added to a suspension consisting of $K_2CO_3$ (1.18 g, 8.52 mmol), THF (27 mL), and $H_2O$ (5.5 mL) at 0° C. The reaction mixture was stirred for 10 minutes at 0° C. and then treated with 2,5-dichloropyridine-3-sulfonyl chloride (2.0 g, 8.1 mmol). The resulting mixture was stirred at room temperature for 6.5 hours and concentrated to dryness under reduced pressure. The residue was dissolved in water (20 mL) and the aqueous layer was extracted with ethyl acetate (20 mL×3). These extractions resulted in several organic solvent fractions which were combined, washed with brine (20 mL), dried over anhydrous $Na_2SO_4$, filtered, and concentrated to dryness under reduced pressure. The residue was purified by flash column chromatography (eluent: 0-100% ethyl acetate/hexanes, gradient elution) to afford the title compound (3.0 g, 90%) as a yellow solid. MS (ESI): mass calcd. for $C_{15}H_{21}Cl_2N_3O_4S$, 409.1; m/z found, 310.1 [M-100]$^+$. $^1$H NMR (500 MHz, CDCl$_3$) δ 8.44 (d, J=2.5 Hz, 1H), 8.29 (d, J=2.5 Hz, 1H), 7.49 (dd, J=6.4, 3.1 Hz, 1H), 3.93 (tt, J=8.4, 4.1 Hz, 1H), 3.33 (dt, J=10.9, 7.5 Hz, 1H), 3.22 (dt, J=11.6, 6.3 Hz, 1H), 3.15-3.07 (m, 1H), 2.92-2.83 (m, 1H), 2.04-1.91 (m, 2H), 1.83-1.69 (m, 2H), 1.39 (s, 9H).

Step B: (S)-3-Chloro-6,7,7a,8,9,10-hexahydropyrido[2,3-f]pyrrolo[2,1-d][1,2,5]thiadiazepine 5,5-dioxide. TFA (5 mL) was added dropwise to a solution of tert-butyl (S)-2-(((2,5-dichloropyridine)-3-sulfonamido)methyl)pyrrolidine-1-carboxylate (3.0 g, 7.3 mmol) and dichloromethane (20 mL) at 0° C. The resulting mixture was stirred for 16 hours with gradual warming to room temperature. It was then concentrated to dryness under reduced pressure. TEA (6.2 mL, 44 mol) was added to the residue in toluene (33 mL). The resulting solution was stirred at 130° C. for 16 hours before cooling to room-temperature and concentrating to dryness under reduced pressure. The residue was purified by flash column chromatography (eluent: 0-100% ethyl acetate/hexanes, gradient elution) to afford the title compound (2.0 g, 99%) as a yellow solid. MS (ESI): mass calcd. for $C_{10}H_{12}ClN_3O_2S$, 273.0; m/z found, 273.9 [M+H]$^+$. $^1$H NMR (500 MHz, CDCl$_3$) δ 8.12 (d, J=2.5 Hz, 1H), 7.80 (d, J=2.5 Hz, 1H), 6.00 (s, 1H), 4.44-4.35 (m, 1H), 3.68-3.53 (m, 2H), 3.43 (dd, J=13.1, 3.6 Hz, 1H), 3.10 (dd, J=13.1, 12.1 Hz, 1H), 2.03-1.88 (m, 3H), 1.76-1.67 (m, 1H).

Step C: (S)-6,7,7a,8,9,10-Hexahydropyrido[2,3-f]pyrrolo[2,1-d][1,2,5]thiadiazepine-3-carbonitrile 5,5-dioxide. Zn(CN)$_2$ (1.47 g, 12.5 mmol) was added to a mixture of (R)-3-chloro-6,7,7a,8,9,10-hexahydropyrido[2,3-f]pyrrolo[2,1-d][1,2,5]thiadiazepine 5,5-dioxide (2.0 g, 7.3 mmol), Zn (185 mg, 2.83 mmol), and DMA (42 mL). The mixture was sparged with Ar for 5 minutes and then treated with Pd(dppf)Cl$_2$ (631 mg, 0.69 mmol) and X-Phos (526 mg, 1.10 mmol). The resultant mixture was sparged with Ar for another 5 minutes and then stirred at 110° C. for 18 hours before cooling to room temperature. The reaction mixture was filtered and the solid was rinsed with ethyl acetate (10 mL×2). The filtrate was concentrated to dryness under reduced pressure and purified by flash column chromatography (eluent: 0-100% ethyl acetate/hexanes, gradient elution) to afford the title compound (1.7 g, 87%) as a brown solid. MS (ESI): mass calcd. for $C_{11}H_{12}N_4O_2S$, 264.1; m/z found, 264.9 [M+H]$^+$. $^1$H NMR (500 MHz, CDCl$_3$) δ 8.42 (d, J=2.1 Hz, 1H), 8.09 (d, J=2.2 Hz, 1H), 5.50 (s, 1H), 4.87-4.75 (m, 1H), 3.86-3.64 (m, 2H), 3.58 (dt, J=12.9, 3.5 Hz, 1H), 3.20 (td, J=12.5, 6.2 Hz, 1H), 2.25-2.15 (m, J=12.7, 11.4, 8.6, 6.7 Hz, 1H), 2.12-1.93 (m, 2H), 1.84-1.75 (m, 1H).

Intermediate 89: (*S)-3-Chloro-6,7,7a,8,10,11-hexahydro-[1,4]oxazino[3,4-d]pyrido[2,3-f][1,2,5]thiadiazepine 5,5-dioxide

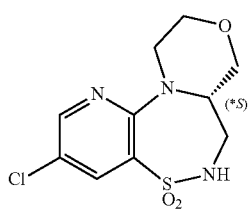

(*S)-6,7,7a,8,10,11-hexahydro-[1,4]oxazino[3,4-d]pyrido[2,3-f][1,2,5]thiadiazepine 5,5-dioxide (Intermediate 13, 300 mg, 1.18 mmol) was dissolved in DCM (24 mL). At room temperature, N-chlorosuccinimide (314 mg, 2.35 mmol) was added. The resulting mixture was stirred at room temperature for 2 hours. The reaction mixture was dissolved in water (10 mL) and the aqueous layer was extracted with ethyl acetate (10 mL×3). These extractions resulted in several organic solvent fractions which were combined, washed with brine (10 mL), dried over anhydrous Na$_2$SO$_4$, filtered, and concentrated to dryness under reduced pressure. The residue was purified by flash column chromatography (eluent: 0-100% ethyl acetate/hexanes) to afford the title compound (200 mg, 59%) as a yellow solid. MS (ESI): mass calcd. for $C_{10}H_{12}ClN_3O_3S$, 289.0; m/z found, 290.0 [M+1]$^+$. $^1$H NMR (600 MHz, CDCl$_3$) δ 8.14 (d, J=2.5 Hz, 1H), 7.77 (d, J=2.5 Hz, 1H), 5.88-5.83 (m, 1H), 4.37-4.28 (m, 2H), 4.10-4.00 (m, 1H), 3.84 (td, J=13.0, 6.4 Hz, 1H), 3.79-3.71 (m, 2H), 3.70 (dd, J=12.2, 2.0 Hz, 1H), 3.55-3.47 (m, 1H), 3.42 (dt, J=13.4, 4.5 Hz, 1H).

Intermediate 90: Ethyl 3-(6-(acetoxymethyl)-5-methylpyridin-2-yl)-3-(1-cyclopropyl-4-methyl-1H-benzo[d][1,2,3]triazol-5-yl)propanoate

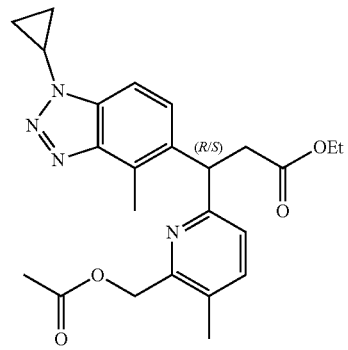 [SMILES: CCOC(=O)CC(c1ccc(C)c(COC(C)=O)n1)c1ccc2c(nnn2C2CC2)c1C]

Step A: 1-Cyclopropyl-4-methyl-5-(4,4,5,5-tetramethyl-1,3,2-dioxaborolan-2-yl)-1H-benzo[d][1,2,3]triazole. A mixture of 5-bromo-1-cyclopropyl-4-methyl-1H-benzo[d][1,2,3]triazole (Intermediate 29, 135 mg, 0.54 mmol), 4,4,4',4',5,5,5',5'-octamethyl-2,2'-bi(1,3,2-dioxaborolane) (166 mg, 0.64 mmol), KOAc (158 mg, 1.61 mmol), and dioxane (15 mL) was sparged with N$_2$ for 5 minutes and then treated with Pd(dppf)Cl$_2$ (12 mg, 0.02 mmol). The mixture was sparged with N$_2$ for another 5 minutes and then stirred at 90° C. for 4 hours. After cooling to room temperature, the suspension was filtered through diatamaceous earth and washed with ethyl acetate (10 mL). The filtrate was concentrated to dryness under reduced pressure and the residue was purified by flash column chromatography (eluent: 0-100% ethyl acetate/hexanes, gradient elution) to afford the title compound (150 mg, 94%) as a white solid. MS (ESI): mass calcd. for $C_{16}H_{22}BN_3O_2$, 299.2; m/z found, 299.0 [M]$^+$.

Step B: Ethyl 3-(6-(acetoxymethyl)-5-methylpyridin-2-yl)-3-(1-cyclopropyl-4-methyl-1H-benzo[d][1,2,3]triazol-5-yl)propanoate. 1-Cyclopropyl-4-methyl-5-(4,4,5,5-tetramethyl-1,3,2-dioxaborolan-2-yl)-1H-benzo[d][1,2,3]triazole (258 mg, 0.86 mmol), triethylamine (0.12 mL, 0.86 mmol), and [Rh(COD)Cl]$_2$ (14 mg, 0.03 mmol) were added to a solution of ethyl (E)-3-(6-(acetoxymethyl)-5-methylpyridin- 2-yl)acrylate (Intermediate 15, 150 mg, 0.57 mmol) in 1,4-dioxane (4 mL) and water (2 mL). The reaction mixture was stirred at 95° C. for 2 hours. After this time, the reaction was cooled to room temperature, then diluted with water and ethyl acetate. The resulting biphasic mixture was separated and the aqueous layer was extracted with ethyl acetate. These extractions resulted in several organic solvent fractions which were combined, dried over MgSO$_4$, filtered, and concentrated to dryness under reduced pressure. The material was purified by flash column chromatography (eluent: 0-20% ethyl acetate/hexanes) to afford the title compound (50 mg, 20% yield). MS (ESI): mass calcd. for $C_{24}H_{28}N_4O_4$, 436.2; m/z found, 437.0 [M+H]$^+$.

Intermediate 91: (R)-4-Ethyl-3,4-dihydro-2H-pyrido [2,3-b][1,4,5]oxathiazepine 1,1-dioxide

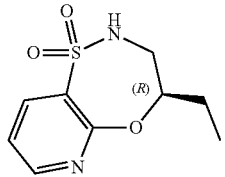

Step A: (R)-1-Aminobutan-2-ol. (R)-2-Ethyloxirane (6.0 g, 83 mmol) and 28% aqueous NH$_3$ (100 mL, 727 mmol) were added to a 250 mL three-necked round-bottomed flask. The mixture was stirred at room temperature for 18 hours before concentrating to dryness under reduced pressure to afford the title compound (8 g) as a yellow oil, which was used in the next step without purification. $^1$H NMR (400 MHz, CDCl$_3$) δ 3.47-3.38 (m, 1H), 2.85-2.74 (m, 1H), 2.57-2.48 (m, 4H), 1.50-1.35 (m, 2H), 0.93 (t, J=7.6 Hz, 3H).

Step B: (R)-2-Chloro-N-(2-hydroxybutyl) pyridine-3-sulfonamide. A solution of 2-chloropyridine-3-sulfonyl (20 g, 94 mmol) and THF (80 mL) was added dropwise to a 0° C. mixture of (R)-1-aminobutan-2-ol (8.0 g), K$_2$CO$_3$ (24.0 g, 173 mmol), THF (80 mL), and H$_2$O (40 mL). The mixture was stirred at room temperature for 12 hours, then concentrated to dryness under reduced pressure. The residue was diluted with water (150 mL) and the resultant mixture extracted with ethyl acetate (100 mL×3). These extractions resulted in several organic solvent fractions which were combined, dried over anhydrous Na$_2$SO$_4$, filtered, and concentrated to dryness under reduced pressure to afford the title compound (20 g) as a yellow oil, which was used in the next step without further purification. MS (ESI): mass calcd. C$_9$H$_{13}$ClN$_2$O$_3$S, 264.03 m/z, found 264.8 [M+H]$^+$.

Step C: (R)-4-Ethyl-3,4-dihydro-2H-pyrido[2,3-b][1,4,5] oxathiazepine 1,1-dioxide. t-BuOK (25.0 g, 223 mmol) was added in portions to a 0° C. solution of (R)-2-chloro-N-(2-hydroxybutyl)pyridine-3-sulfonamide (20 g) and DMSO (100 ml). The mixture was heated at 80° C. for 12 hours before cooling to room temperature and concentrating to dryness under reduced pressure. The residue was diluted with H$_2$O (200 mL), and the resultant mixture acidified to pH 6 with 1 N HCl, and extracted with ethyl acetate (100 mL×3). These extractions resulted in several organic solvent fractions which were combined, dried over anhydrous Na$_2$SO$_4$, filtered, and concentrated to dryness under reduced pressure. The material was purified by preparative acidic HPLC using a Xtimate C18, 150×25 mm×5 μm column (eluent: 5% to 35% (v/v) CH$_3$CN and H$_2$O with 0.225% HCOOH) to afford the title compound (6 g). The product contained impurities and was triturated with petroleum ether:ethyl acetate (30:1, 100 mL) and the suspension isolated via filtration. The filter cake was washed with petroleum ether (50 mL) before drying under reduced pressure to afford the title compound (5.67 g) as a white solid. MS (ESI): mass calcd. for C$_9$H$_{12}$N$_2$O$_3$S, 228.06 m/z, found 229.0 [M+H]$^+$. $^1$H NMR (400 MHz, DMSO-d$_6$) δ 9.04 (s, 1H), 8.85 (d, J=5.2 Hz, 1H), 7.72-7.67 (m, 2H), 6.76-6.70 (m, 1H), 6.68-6.65 (m, 1H), 5.40 (s, 2H), 4.49 (t, J=6.4 Hz, 2H), 2.69 (t, J=6.4 Hz, 2H).

Intermediate 92: Ethyl 3-(3-(chloromethyl)-4-methylphenyl)-3-(1-(cyclopropylmethyl)-4-(difluoromethyl)-1H-benzo[d][1,2,3]triazol-5-yl)propanoate

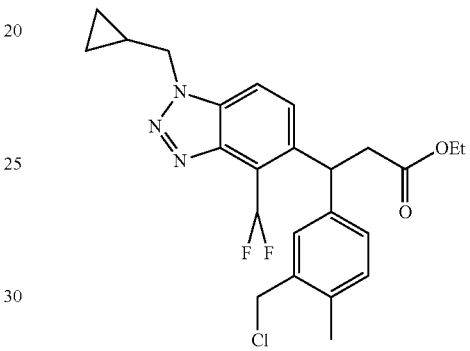

Step A: 1-Chloro-3-(difluoromethyl)-2-nitrobenzene. Diethylamino sulfurtrifluoride (32.6 g, 202 mmol) was added to a 0° C. solution of 3-chloro-2-nitrobenzaldehyde (15 g, 81 mmol) and dichloromethane (200 mL). The mixture was stirred for 3 hours with gradual warming to room temperature before quenching with H$_2$O (200 mL) and extracting with dichloromethane (100 mL×3). These extractions resulted in several organic solvent fractions which were combined, dried over anhydrous Na$_2$SO$_4$, filtered, and concentrated to dryness under reduced pressure. The material was purified by FCC (petroleum ether:ethyl acetate=1:0 to 20:1, gradient elution) to provide the title compound (12 g, 64%) as a yellow oil. $^1$H NMR (400 MHz, DMSO-d$_6$) δ 8.06-7.95 (m, 1H), 7.86-7.77 (m, 2H), 7.42-7.11 (m, 1H).

Step B: N-(Cyclopropylmethyl)-3-(difluoromethyl)-2-nitroaniline. 1-Chloro-3-(difluoromethyl)-2-nitrobenzene (2.0 g, 9.6 mmol) and cyclopropylmethanamine (10 mL) were added to a 20 mL sealed tube. The mixture was stirred at 80° C. for 16 hours before cooling to room temperature. At that time the reaction mixture was quenched with water (60 mL), and extracted with ethyl acetate (50 mL×3). These extractions resulted in several organic solvent fractions which were combined, dried over anhydrous Na$_2$SO$_4$, filtered, and concentrated to dryness under reduced pressure. The material was purified by FCC (petroleum ether:ethyl acetate, 1:0 to 5:1, gradient elution) to give the title compound (2.1 g, 90%) as a red solid.

Step C: 4-Bromo-N-(cyclopropylmethyl)-3-(difluoromethyl)-2-nitroaniline. N-(Cyclopropylmethyl)-3-(difluoromethyl)-2-nitroaniline (2.1 g, 8.7 mmol), NBS (1.54 g, 8.65 mmol), and DMF (10 mL) were added to a 50 mL round-bottomed flask. The mixture was stirred at room temperature for 4 hours before quenching with water (50 mL) and extracting with ethyl acetate (30 mL×3). These extractions resulted in several organic solvent fractions which were combined, dried over anhydrous $Na_2SO_4$, filtered, and concentrated to dryness under reduced pressure. The material was purified by FCC (petroleum ether:ethyl acetate, 1:0 to 5:1, gradient elution) to give the title compound (2.1 g, 68%) as yellow solid. $^1$H NMR (400 MHz, DMSO-$d_6$) δ 7.47 (d, J=9.0 Hz, 1H), 7.09-6.79 (m, 2H), 6.22 (t, J=5.6 Hz, 1H), 2.86 (t, J=6.2 Hz, 2H), 0.91-0.79 (m, 1H), 0.28-0.18 (m, 2H), 0.05-0.04 (m, 2H).

Step D: 4-Bromo-$N^1$-(cyclopropylmethyl)-3-(difluoromethyl)benzene-1,2-diamine. Zn (3.4 g, 52 mmol) was added to a solution of 4-bromo-N-(cyclopropylmethyl)-3-(difluoromethyl)-2-nitroaniline (2.1 g, 6.5 mmol), $NH_4Cl$ (5.60 g, 105 mmol), and THF (20 mL). The resultant mixture was stirred at room temperature for 16 hours. The suspension was filtered through a pad of diatomaceous earth and the pad was washed with ethyl acetate (60 mL). The filtrate was concentrated to dryness under reduced pressure to afford the title product (1.8 g, 95%) as a yellow solid. MS (ESI): mass calcd. for $C_{11}H_{13}BrF_2N_2$ 290.02, m/z found 292.8 [M+H]$^+$.

Step E: 5-Bromo-1-(cyclopropylmethyl)-4-(difluoromethyl)-1H-benzo[d][1,2,3]triazole.

A solution of $NaNO_2$ (5.7 g, 83 mmol) and $H_2O$ (10 mL) were added to a 0° C. mixture of 4-bromo-$N^1$-(cyclopropylmethyl)-3-(difluoromethyl)benzene-1,2-diamine (8.0 g, 27 mmol), 4-methylbenzenesulfonic acid hydrate (18.3 g, 96.2 mmol), and $CH_3CN$ (100 mL). The resultant mixture was stirred at 0° C. for 3 hours before quenching with aq. $NaHCO_3$ (300 mL) and extracting with ethyl acetate (100 mL×3). These extractions resulted in several organic solvent fractions which were combined, dried over anhydrous $Na_2SO_4$, filtered, and concentrated to dryness under reduced pressure. The material was purified by FCC (petroleum ether:ethyl acetate, 1:0 to 5:1, gradient elution) to give the title compound (6.2 g, 75%) as a brown solid.

Step F: (E)-Ethyl 3-(1-(cyclopropylmethyl)-4-(difluoromethyl)-1H-benzo[d][1,2,3]triazol-5-yl)acrylate. 5-Bromo-1-(cyclopropylmethyl)-4-(difluoromethyl)-1H-benzo[d][1,2,3]triazole (2.0 g, 6.6 mmol), (E)-ethyl 3-(4,4,5,5-tetramethyl-1,3,2-dioxaborolan-2-yl)acrylate (3.0 g, 13 mmol), and $Na_2CO_3$ (1.4 g, 13 mmol) were added to a 100 mL three-necked round-bottomed flask and the mixture dissolved in 1,4-dioxane (30 mL) and $H_2O$ (6 mL). The mixture was sparged with $N_2$ for 5 minutes and then treated with Pd(dppf)$Cl_2$ (484 mg, 0.661 mmol). The mixture was sparged with $N_2$ for another 5 minutes and then stirred and heated at 100° C. for 16 hours before cooling to room temperature, quenching with water (60 mL) and extracting with ethyl acetate (40 mL×3). These extractions resulted in several organic solvent fractions which were combined, dried over anhydrous $Na_2SO_4$, filtered, and concentrated to dryness under reduced pressure. The material was purified by FCC (petroleum ether:ethyl acetate, 20:1 to 5:1, gradient elution) to give the title compound (2.0 g, 80%) as a black solid. MS (ESI): mass calcd. for $C_{16}H_{17}F_2N_3O_2$ 321.13, m/z found 321.9 [M+H]$^+$.

Step G: Ethyl 3-(1-(cyclopropylmethyl)-4-(difluoromethyl)-1H-benzo[d][1,2,3]triazol-5-yl)-3-(3-(hydroxymethyl)-4-methylphenyl)propanoate. (E)-Ethyl 3-(1-(cyclopropylmethyl)-4-(difluoromethyl)-1H-benzo[d][1,2,3]triazol-5-yl)acrylate (1.5 g, 4.7 mmol), (3-(hydroxymethyl)-4-methylphenyl)boronic acid (2.3 g, 14 mmol), aq. KOH (5.6 mL, 1.0 M, 5.6 mmol), and 1,4-dioxane (20 mL) were added to a 100 mL round-bottomed flask. The mixture was sparged with $N_2$ for 5 minutes and then treated with chloro(1,5-cyclooctadiene)rhodium(I) dimer (230 mg, 0.466 mmol). The reaction mixture was stirred at room temperature for 16 hours before quenching with $H_2O$ (60 mL) and extracting with ethyl acetate (50 mL×3). These extractions resulted in several organic solvent fractions which were combined, dried over anhydrous $Na_2SO_4$, filtered, and concentrated to dryness under reduced pressure. The material was purified by preparative basic HPLC using a Phenomenex Gemini C18 250 mm×50 mm, 10 m column (eluent: 30% to 70% (v/v) $CH_3CN$ and $H_2O$ with 0.05% $NH_3$) to afford the title compound. MS (ESI): mass calcd. for $C_{24}H_{27}F_2N_3O_3$ 443.20, m/z found 444.0 [M+H]$^+$. $^1$H NMR (400 MHz, DMSO-$d_6$) δ 8.07-7.75 (m, 2H), 7.57 (d, J=8.8 Hz, 1H), 7.31 (s, 1H), 7.18-7.12 (m, 1H), 7.07-7.01 (m, 1H), 5.17-5.07 (m, 1H), 5.01 (t, J=5.3 Hz, 1H), 4.58 (d, J=7.3 Hz, 2H), 4.43-4.35 (m, 2H), 3.97-3.88 (m, 2H), 3.28-3.19 (m, 1H), 3.14-3.05 (m, 1H), 2.14 (s, 3H), 1.38-1.26 (m, 1H), 1.01 (t, J=7.2 Hz, 3H), 0.55-0.39 (m, 4H).

Step H: Ethyl 3-(3-(chloromethyl)-4-methylphenyl)-3-(1-(cyclopropylmethyl)-4-(difluoromethyl)-1H-benzo[d][1,2,3]triazol-5-yl)propanoate. Thionyl chloride (0.16 mL, 2.2 mmol) was added to a solution of ethyl 3-(1-(cyclopropylmethyl)-4-(difluoromethyl)-1H-benzo[d][1,2,3]triazol-5-yl)-3-(3-(hydroxymethyl)-4-methylphenyl)propanoate. (502 mg, 1.1 mmol) in DCM (5.5 mL) and 2 drops of DMF. The reaction was stirred at room temperature for 5 minutes. The reaction was quenched with saturated aqueous $NaHCO_3$, then extracted with DCM. These extractions resulted in several organic solvent fractions which were combined, dried over $MgSO_4$, filtered, and concentrated to dryness under reduced pressure, to provide the title compound which was used without further purification. MS (ESI): mass calcd. for $C_{24}H_{26}ClF_2N_3O_2$, 461.9; m/z found, 462.3 [M+H]$^+$.

Intermediate 93: 5'-Methyl-2',3'-dihydro-5'H-spiro [cyclopropane-1,4'-pyrido[2,3-f][1,2,5]thiadiazepine] 1',1'-dioxide

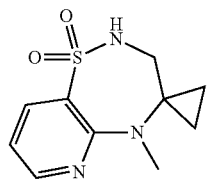 [SMILES: CN1c2ncccc2S(=O)(=O)NCC12CC2]

Step A: tert-Butyl (1-carbamoylcyclopropyl)carbamate. Pyridine(11.8 g, 149 mmol) was added drop-wise to a mixture consisting of 1-((tert-butoxycarbonyl)amino)cyclopropanecarboxylic acid (50.0 g, 248 mmol), $Boc_2O$ (70.5 g, 323 mmol), $NH_4HCO_3$ (24.6 g, 311 mmol), and MeCN (500 mL) over a period of 10 minutes. The resultant mixture was stirred at room temperature for 16 hours before concentrating to dryness under reduced pressure. The residue was diluted with $H_2O$ (100 mL), adjusted to pH 7 with 1 N HCl, and then the resultant mixture was extracted with ethyl acetate (300 mL×3). These extractions resulted in several organic solvent fractions which were combined, dried over $MgSO_4$, filtered, and concentrated to dryness under reduced pressure, to provide the title compound (40.1 g, 80%) as a white solid, which was used in the next step without further purification. $^1$H NMR (400 MHz, DMSO-$d_6$) δ 6.42 (br. s, 1H), 5.71 (br. s, 1H), 5.18 (br. s, 1H), 1.61-1.56 (m, 2H), 1.46-1.45 (m, 9H), 1.09-0.98 (m, 2H).

Step B: tert-Butyl (1-cyanocyclopropyl)carbamate. TFAA (47.3 g, 225 mmol) was added drop-wise to solution consisting of tert-butyl (1-carbamoylcyclopropyl)carbamate (30.0 g, 150 mmol), triethylamine (62.7 g, 450 mmol), and dichloromethane (180 mL) over a period of 1 hour. The resultant mixture was stirred at room temperature for 4 hours before concentrating to dryness under reduced pressure to give the title compound, which was purified by FCC (petroleum ether:ethyl acetate, 1:0 to 5:1, gradient elution) to afford the title compound (22.5 g, 82.3%) as a light yellow solid. $^1$H NMR (400 MHz, CDCl$_3$) δ 6.60 (br s, 1H), 2.63 (s, 9H), 1.28 (s, 2H), 1.24-1.20 (m, 1H), 1.07-1.01 (m, 1H).

Step C: tert-Butyl (1-cyanocyclopropyl)(methyl)carbamate. Sodium hydride in mineral oil (15.0 g, 60% purity, 375 mmol) was added in portions to a 0° C. solution of tert-butyl (1-cyanocyclopropyl)carbamate (22.5 g, 123 mmol) and THF (150 mL). The resultant mixture was treated with iodomethane (34.7 g, 244 mmol) by dropwise addition at 0° C. and then stirred for 12 hours with gradual warming to room temperature before quenching with saturated aqueous NH$_4$Cl (100 mL) and extracting with ethyl acetate (150 mL×3). These extractions resulted in several organic solvent fractions which were combined, washed with brine (100 mL), dried over MgSO$_4$, filtered, and concentrated to dryness under reduced pressure, to provide the title compound (23.0 g), which was used in the next step without further purification. $^1$H NMR (400 MHz, CDCl$_3$) δ 2.90 (s, 3H), 1.48 (s, 9H), 1.27-1.26 (m, 2H), 0.86-0.82 (m, 2H).

Step D: tert-Butyl (1-(aminomethyl)cyclopropyl)(methyl) carbamate. Raney Ni (2 g) was added to a 1 L round-bottomed flask containing a mixture of tert-butyl (1-cyanocyclopropyl)(methyl)carbamate (23 g), methanol (200 mL), and 25% aqueous NH$_3$ (5 mL) which had been degassed with argon. The mixture was stirred under an atmosphere of H$_2$ (15 psi) at room temperature for 15 hours. The suspension was filtered through a pad of diatomaceous earth and the pad was washed with ethyl acetate (150 mL). The filtrate was concentrated to dryness under reduced pressure to afford the title product (25 g), which was used in the next step without further purification. $^1$H NMR (400 MHz, CDCl$_3$) δ 2.86 (br s, 3H), 1.84-1.80 (m, 2H), 1.44 (br. s, 9H), 1.23-1.22 (m, 2H), 0.85-0.81 (m, 2H).

Step E: tert-Butyl (1-((2-chloropyridine-3-sulfonamido) methyl)cyclopropyl)(methyl)carbamate. A solution consisting of 2-chloropyridine-3-sulfonyl chloride (20 g, 94 mmol) and THF (50 mL) was added dropwise to a mixture of tert-butyl (1-(aminomethyl)cyclopropyl)(methyl)carbamate (20 g), K$_2$CO$_3$ (20.0 g, 145 mmol), THF (150 mL), and H$_2$O (40 mL) which had been cooled to 0° C. The resultant mixture was stirred for 12 hours with gradual warming to room temperature before concentrating to dryness under reduced pressure. The residue was diluted with water (100 mL) and extracted with ethyl acetate (200 mL×2). These extractions resulted in several organic solvent fractions which were combined, dried over MgSO$_4$, filtered, and concentrated to dryness under reduced pressure, to provide the title compound (30 g) as a yellow solid, which was used in the next step without purification. MS (ESI): mass calcd. for C$_{15}$H$_{22}$ClN$_3$O$_4$S, 375.10 m/z, found 398.0 [M+Na]$^+$. $^1$H NMR (400 MHz, CDCl$_3$) δ 8.58-8.54 (m, 1H), 8.40-8.35 (m, 1H), 7.45-7.36 (m, 1H), 6.83 (br. s, 1H), 3.07-2.98 (m, 2H), 2.82 (s, 3H), 1.47 (s, 9H), 0.97-0.93 (m, 2H), 0.85-0.78 (m, 2H).

Step F: 2-Chloro-N-((1-(methylamino)cyclopropyl) methyl)pyridine-3-sulfonamide. TFA (30.0 mL, 433 mmol) was added to a 0° C. solution consisting of tert-butyl (1-((2-chloropyridine-3-sulfonamido)methyl)cyclopropyl) (methyl)carbamate (35 g) and dichloromethane (100 mL). The mixture was stirred for 2 hours with gradual warming to room temperature before concentrating to dryness under reduced pressure to afford the title compound (30 g), which was used in the next step without further purification. MS (ESI): mass calcd. for C$_{10}$H$_{14}$ClN$_3$O$_2$S, 275.05, m/z found 275.9 [M+H]$^+$.

Step G: 5'-Methyl-3',5'-dihydro-2'H-spiro[cyclopropane-1,4'-pyrido[2,3-f][1,2,5]thiadiazepine] 1',1'-dioxide. DIPEA (30.0 mL, 172 mmol) was added dropwise to a solution of 2-chloro-N-((1-(methylamino)cyclopropyl)methyl)pyridine-3-sulfonamide (10 g) and DMSO (60 mL). The mixture was heated at 160° C. for 2 hours before cooling to room temperature and concentrating to dryness under reduced pressure. The residue was diluted with H$_2$O (200 mL) and the resultant solution extracted with ethyl acetate (150 mL×3). These extractions resulted in several organic solvent fractions which were combined, dried over MgSO$_4$, filtered, and concentrated to dryness under reduced pressure to give the product, which was triturated with ethyl acetate:petroleum ether (1:10). The suspension was isolated via filtration and the filter cake washed with ethyl acetate:petroleum ether (1:30) before drying under reduced pressure to afford the title compound (3.58 g, 41%). MS (ESI): mass calcd. for C$_{10}$H$_{13}$N$_3$O$_2$S, 239.07 m/z, found 240.0 [M+H]$^+$. $^1$H NMR (400 MHz, DMSO-d$_6$) δ 8.30-8.19 (m, 1H), 8.15-7.79 (m, 2H), 6.98-6.89 (m, 1H), 3.32-3.06 (m, 2H), 3.02 (s, 3H), 0.99-0.57 (m, 4H).

Intermediate 94: 2,5-Dichloropyridine-3-sulfonyl chloride

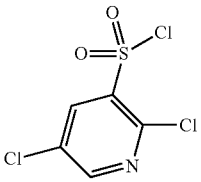 [SMILES: O=S(=O)(Cl)c1cc(Cl)cnc1Cl]

To a solution of 2,5-dichloropyridin-3-amine (50 g, 307 mmol) in CH$_3$CN (300 mL), which had been cooled to 0° C., was added fluoroboric acid (71.6 mL, 460 mmol, 40% purity) at 0° C., and the mixture was stirred at 0° C. for 10 minutes. Then tert-butyl nitrite (44.3 g, 429 mmol) was added dropwise and the mixture was stirred at 0° C. for 1 hour. The resulting solution was a diazonium salts solution. In a separate flask, H$_2$O (500 mL) was added to SOCl$_2$ (100 mL, 1.38 mol), dropwise, while keeping the inner temperature below 7° C., then the solution was stirred at 15° C. for 16 hours. CuCl (734 uL, 30.7 mmol) was added, then the previously prepared diazonium salts solution was added (diazonium salt solution was maintained at −5° C. during addition) dropwise at 0° C. The reaction was stirred at 0° C. for 1 hour. A gray suspension was obtained. The mixture was extracted with EtOAc (500 ml×3). These extractions resulted in several organic solvent fractions which were combined, washed with brine (600 mL), dried over Na$_2$SO$_4$, filtered, and concentrated to dryness under reduced pressure. The material was purified by FCC (petroleum ether/ethyl acetate=15:1) to afford the title compound (65.0 g, 81.7% yield) as a yellow oil.

Intermediate 95: 3-Chloro-7,7a,8,9,10,11-hexa-hydro-6H-dipyrido[2,1-d:2',3'-f][1,2,5]thiadiazepine 5,5-dioxide

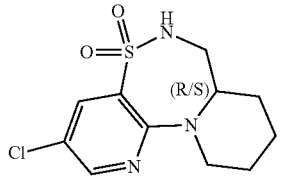 [SMILES: O=S1(=O)NCC2CCCCN2c2ncc(Cl)cc21]

Step A: tert-Butyl 2-(((2,5-dichloropyridine)-3-sulfona-mido)methyl)piperidine-1-carboxylate. To a solution of 2,5-dichloropyridine-3-sulfonyl chloride (Intermediate 94, 38.3 g, 179 mL) in THF (550 mL) and H$_2$O (200 mL) was added K$_2$CO$_3$ (35.9 g, 260 mmol). A solution of 2,5-dichloropyridine-3-sulfonyl chloride (40.0 g, 162 mmol) in THF (250 mL) was added to the reaction mixture which had been cooled to 0° C. After warming to 20° C., the reaction mixture was stirred at 20° C. for 2 hours. A yellow suspension was obtained. The reaction mixture was diluted with water (400 mL) and extracted with ethyl acetate. These extractions resulted in several organic solvent fractions which were combined, washed with brine (600 mL), dried over Na$_2$SO$_4$, filtered, and concentrated to dryness under reduced pressure. The material was purified by FCC (petroleum ether/ethyl acetate, 3:1 with 1% of Et$_3$N) to provide the title compound (55.0 g, 76% yield) as a yellow solid.

Step B: 2,5-Dichloro-N-(piperidin-2-ylmethyl)pyridine-3-sulfonamide. To a solution of tert-butyl 2-(((2,5-dichloropyridine)-3-sulfonamido)methyl)piperidine-1-carboxylate (55.0 g, 130 mmol) in DCM (500 mL) was added TFA (28.8 mL, 389 mmol), and the reaction mixture was stirred at 20° C. for 2 hours. The reaction mixture was concentrated under reduced pressure, the residue was dissolved in DCE (200 mL) and the solution was concentrated under reduced pressure again. The material was stirred in MTBE (100 mL) for 30 minutes and the solid was collected by filtration to provide the title compound as its TFA salt (40.0 g, 70% yield) as a white solid.

Step C: 3-Chloro-7,7a,8,9,10,11-hexahydro-6H-dipyrido [2,1-d:2',3'-f][1,2,5]thiadiazepine 5,5-dioxide. To a solution of 2,5-dichloro-N-(piperidin-2-ylmethyl)pyridine-3-sulfonamide as its TFA salt (40.0 g, 91.3 mmol) in DMF (600 mL) was added Cs$_2$CO$_3$ (89.2 g, 274 mmol) and the reaction mixture was stirred at 120° C. for 4 hours. The reaction mixture was diluted with water (400 mL) and extracted with ethyl acetate (500 mL×3). These extractions resulted in several organic solvent fractions which were combined, washed with water (500 mL) and brine (500 mL), dried over Na$_2$SO$_4$, filtered, and concentrated to dryness under reduced pressure. The material was purified by FCC (petroleum ether/ethyl acetate=5:1). The product was stirred in MTBE (60 mL) for 30 minutes and the solid was collected by filtration to provide the title compound (30 g).

Intermediate 96: 8'-Chloro-2',3'-dihydrospiro[cyclopropane-1,4'-pyrido[2,3-b][1,4,5]oxathiazepine] 1',1'-dioxide

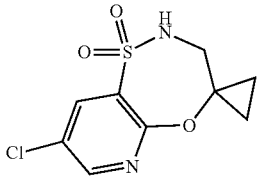 [SMILES: O=S1(=O)NCC2(CC2)Oc2ncc(Cl)cc21]

Step A: 2,5-Dichloro-N-((1-hydroxycyclopropyl)methyl) pyridine-3-sulfonamide. To a solution of 1-(aminomethyl) cyclopropan-1-ol (35.0 g, 283 mmol, as its HCl salt) in THF (1 L) and H$_2$O (200 mL) was added K$_2$CO$_3$ (126 g, 913 mmol). A solution of 2,5-dichloropyridine-3-sulfonyl chloride (Intermediate 94, 90.0 g, 365 mmol) in THF (500 mL) was added to the reaction mixture which had been cooled to 0° C. and then the reaction mixture was stirred at 20° C. for 16 hours. A yellow solution was obtained. The reaction mixture was extracted with EtOAc (1 L×3). These extractions resulted in several organic solvent fractions which were combined, washed with brine (1 L), dried over Na$_2$SO$_4$, filtered, and concentrated to dryness under reduced pressure. The residue was purified by FCC (petroleum ether/ethyl acetate, 5:1) to provide the title compound (66.0 g, 60% yield) as a white solid.

Step B: 8'-Chloro-2',3'-dihydrospiro[cyclopropane-1,4'-pyrido[2,3-b][1,4,5]oxathiazepine] 1',1'-dioxide. To a solution of 2,5-dichloro-N-((1-hydroxycyclopropyl)methyl) pyridine-3-sulfonamide (33.0 g, 111 mmol) in DMSO (500 mL) was added aqueous K$_2$CO$_3$ (3 M, 111 mL), the reaction mixture was stirred at 100° C. for 16 hours. A colorless solution was obtained. The reaction mixture was diluted with water (400 mL) and extracted with ethyl acetate (500 mL×3). These extractions resulted in several organic solvent fractions which were combined, washed with water (500 mL) and brine (500 mL), dried over Na$_2$SO$_4$, filtered, and concentrated to dryness under reduced pressure. The residue was stirred in MTBE (100 mL) for 30 minutes, and the solid was collected by filtration to provide the title compound (30.0 g, 51% yield, 98% purity) as a white solid.

Intermediate 97: 7,7a,8,9,10,11-hexahydro-6H-dipyrido[2,1-d:2',3'-f][1,2,5]thiadiazepine-2-carbonitrile 5,5-dioxide

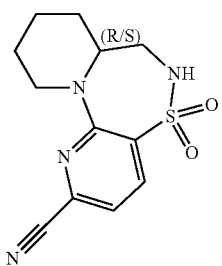 [SMILES: N#Cc1ccc2c(n1)N1CCCCC1CNS2(=O)=O]

Step A: 6-Bromo-2-chloropyridine-3-sulfonyl chloride. HBF$_4$ (22.2 mL, 40 wt. % in water, 145 mmol) was added dropwise to a solution of 6-bromo-2-chloropyridin-3-amine (20.0 g, 96.4 mmol) and acetonitrile (100 mL) which had been cooled to 0° C. This mixture was stirred at 0° C. for 10 minutes before treating it with tert-butyl nitrite (17.2 mL, 145 mmol) dropwise. The resultant mixture was stirred at room temperature for another 2 hours. Copper(I) chloride (14.3 g, 144 mmol) and acetic acid (100 mL) were mixed in a separate flask. This mixture was cooled to 0° C., bubbled with $SO_2$ gas (>1.3 M) at 0° C. for 1 hour. The copper(I) chloride in acetic acid mixture was cooled to 0° C. and was then treated with the above 6-bromo-2-chloropyridine-3-diazonium tetrafluoroborate solution dropwise. This mixture was stirred for 16 hours with gradual warming to room temperature. The suspension was filtered through a pad of diatomaceous earth and the pad was washed with ethyl acetate (50 mL×3). The filtrate was concentrated to dryness under reduced pressure to give the product, which was purified by FCC (petroleum ether:ethyl acetate, 1:0 to 10:1, gradient elution) to afford the title compound (11.4 g) as a brown liquid, which was used in the next step without further purification. $^1$H NMR (400 MHz, DMSO-$d_6$) δ 13.52 (br s, 1H), 8.29-7.95 (m, 2H), 7.74-7.46 (m, 2H).

Step B: tert-Butyl 2-((6-bromo-2-chloropyridine-3-sulfonamido)methyl)piperidine-1-carboxylate. 6-Bromo-2-chloropyridine-3-sulfonyl chloride (11.4 g, 39.2 mmol) was added to a 250 mL three-necked round-bottomed flask containing a mixture of $K_2CO_3$ (16.3 g, 118 mmol), THF (50 mL), and $H_2O$ (10 mL) which had been cooled to 0° C. The resultant mixture was stirred for 10 minutes at 0° C. before treating with tert-butyl 2-(aminomethyl)piperidine-1-carboxylate (8.4 g, 39 mmol). This mixture was stirred at room temperature for 8 hours and then concentrated to dryness under reduced pressure. The residue was diluted with water (100 mL) and extracted with ethyl acetate (100 mL×3). These extractions resulted in several organic solvent fractions which were combined, dried over $Na_2SO_4$, filtered, and concentrated to dryness under reduced pressure. The material was purified by FCC (petroleum ether:ethyl acetate, 1:0 to 3:2, gradient elution) to afford the title compound (10.7 g) as a yellow solid. MS (ESI): mass calcd. for $C_{16}H_{23}BrClN_3O_4S$, 467.03 m/z found 369.8 [M-100+H]$^+$.

Step C: 6-Bromo-2-chloro-N-(piperidin-2-ylmethyl)pyridine-3-sulfonamide. TFA (11.4 mL, 164 mmol) was added dropwise to a 100 mL round-bottomed flask containing a solution consisting of tert-butyl 2-((6-bromo-2-chloropyridine-3-sulfonamido)methyl)piperidine-1-carboxylate (7.70 g, 16.4 mmol) and dichloromethane (20 mL) which had been cooled to 0° C. The resultant mixture was stirred for 6 hours with gradual warming to room temperature before concentrating to dryness under reduced pressure to afford the title compound (8.3 g) as a brown liquid, which was used in the next step without further purification. MS (ESI): mass calcd. for $C_{11}H_{15}BrClN_3O_2S$, 366.98 m/z found 369.8 [M+H]$^+$.

Step D: 2-Bromo-7,7a,8,9,10,11-hexahydro-6H-dipyrido[2,1-d:2',3'-f][1,2,5]thiadiazepine 5,5-dioxide. DIPEA (42.2 mL, 310 mmol) was added to a mixture of 6-bromo-2-chloro-N-(piperidin-2-ylmethyl)pyridine-3-sulfonamide (8.3 g, 17 mmol) and toluene (20 mL). The reaction mixture was heated at 130° C. for 2 hours before cooling to room temperature. The mixture was concentrated to dryness under reduced pressure and then purified by FCC (petroleum ether:ethyl acetate, 1:0 to 1:1, gradient elution) to afford the title compound (7.6 g) as a yellow solid. MS (ESI): mass calcd. for $C_{11}H_{14}BrN_3O_2S$, 331.00 m/z found 333.7 [M+H]$^+$.

Step E: 7,7a,8,9,10,11-Hexahydro-6H-dipyrido[2,1-d:2',3'-f][1,2,5]thiadiazepine-2-carbonitrile 5,5-dioxide. $Zn(CN)_2$ (5.4 g, 46 mmol) was added to a 250 mL round-bottomed flask containing a mixture of 2-bromo-7,7a,8,9,10,11-hexahydro-6H-dipyrido[2,1-d:2',3'-f][1,2,5]thiadiazepine 5,5-dioxide (7.6 g, 23 mmol), Zn (310 mg, 4.74 mmol), and DMF (30 mL). The mixture was sparged with argon for 5 minutes and then treated with Pd(dppf)Cl$_2$ (1.8 g, 2.5 mmol). The mixture was then sparged with argon for another 5 minutes and heated at 140° C. for 3 hours before cooling to room temperature. The suspension was filtered through a pad of diatomaceous earth, the filtrate poured into water (50 mL), and the filtrate water mixture was extracted with ethyl acetate (50 mL×3). These extractions resulted in several organic solvent fractions which were combined, washed with brine (50 mL), dried over $Na_2SO_4$, filtered, concentrated to dryness under reduced pressure and purified by FCC (petroleum ether:ethyl acetate, 10:1 to 3:7, gradient elution) to afford the title compound (5.6 g, 86%) as a green solid. MS (ESI): mass calcd. for $C_{12}H_{14}N_4O_2S$, 278.08 m/z found 278.9 [M+H]$^+$.

Intermediate 98: (*S)-7,7a,8,9,10,11-Hexahydro-6H-dipyrido[2,1-d:2',3'-f][1,2,5]thiadiazepine-2-carbonitrile 5,5-dioxide

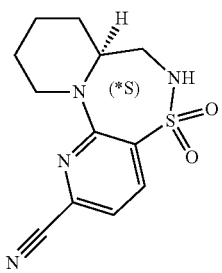 [SMILES: N#Cc1ccc2c(n1)N1CCCC[C@H]1CNS2(=O)=O]

7,7a,8,9,10,11-Hexahydro-6H-dipyrido[2,1-d:2',3'-f][1,2,5]thiadiazepine-2-carbonitrile 5,5-dioxide (Intermediate 97) was purified by SFC over AD 250 mm×50 mm, 10 m (eluent: 40% to 40% (v/v) supercritical $CO_2$ in EtOH and $H_2O$ with 0.1% $NH_3$) to afford two diastereomers. The first eluting isomer (1.974 g) was designated (*S): MS (ESI): mass calcd. for $C_{12}H_{14}N_4O_2S$, 278.08 m/z found 279.0 [M+H]$^+$. $^1$H NMR (400 MHz, CDCl$_3$) 8.00 (d, J=8.0 Hz, 1H), 7.08 (d, J=7.6 Hz, 1H), 5.25-5.14 (m, 1H), 4.49-4.37 (m, 1H), 4.37-4.26 (m, 1H), 3.57-3.42 (m, 2H), 3.40-3.27 (m, 1H), 1.87-1.73 (m, 3H), 1.69-1.58 (m, 3H).

Intermediate 99: (*R)-7,7a,8,9,10,11-Hexahydro-6H-dipyrido[2,1-d:2',3'-f][1,2,5]thiadiazepine-2-carbonitrile 5,5-dioxide

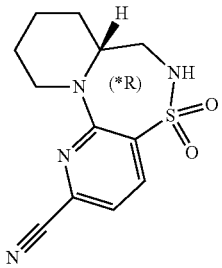 [SMILES: N#Cc1ccc2c(n1)N1CCCC[C@@H]1CNS2(=O)=O]

The second eluting isomer (1.9 g) from the separation of isomers by chiral SFC described in Intermediate 98 was designated (*R): MS (ESI): mass calcd. for $Cl_2H_{14}N_4O_2S$, 278.08 m/z found 279.0 $[M+H]^+$. $^1H$ NMR (400 MHz, $CDCl_3$) 8.00 (d, J=7.6 Hz, 1H), 7.08 (d, J=7.6 Hz, 1H), 5.22-5.15 (m, 1H), 4.46-4.38 (m, 1H), 4.35-4.28 (m, 1H), 3.53-3.41 (m, 2H), 3.38-3.28 (m, 1H), 1.87-1.73 (m, 3H), 1.68-1.58 (m, 3H). Alternatively, the $^1H$ NMR was run in DMSO-$d_6$ and the data is as follows: $^1H$ NMR (400 MHz, DMSO-$d_6$) δ 8.39-8.32 (m, 1H), 8.07 (d, J=8.0 Hz, 1H), 7.37 (d, J=8.0 Hz, 1H), 4.29-4.12 (m, 2H), 3.53-3.43 (m, 1H), 3.30-3.25 (m, 1H), 3.23-3.15 (m, 1H), 1.74-1.46 (m, 5H), 1.76-1.45 (m, 1H).

Intermediate 100: 3-(Trifluoromethyl)-7,7a,8,9,10,11-hexahydro-6H-dipyrido[2,1-d:2',3'-f][1,2,5]thiadiazepine 5,5-dioxide

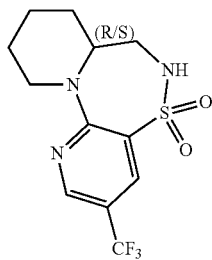 [SMILES: O=S1(=O)NCC2CCCCN2c2ncc(C(F)(F)F)cc21]

Step A: 2-Chloro-5-(trifluoromethyl)pyridine-3-diazonium tetrafluoroborate. $HBF_4$ (11.7 mL, 40 wt. % in water, 76.2 mmol) was added dropwise to a mixture of 2-chloro-5-(trifluoromethyl)pyridin-3-amine (10 g, 51 mmol) and acetonitrile (80 mL) that had been cooled to 0° C. After 10 minutes, tert-butyl nitrite (9.1 mL, 77 mmol) was added drop-wise under $N_2$ atmosphere. The resultant mixture was stirred at room temperature for 2 hours. The mixture was used in the next step without further purification.

Step B: 2-Chloro-5-(trifluoromethyl)pyridine-3-sulfonyl chloride. Copper(I) chloride (7.6 g, 77 mmol) and acetic acid (150 mL) was cooled to 0° C., bubbled with $SO_2$ gas (>1.3 M) at 0° C. for 1 hour, and then treated with the 2-chloro-5-(trifluoromethyl)pyridine-3-diazonium tetrafluoroborate solution dropwise at 0° C. under $N_2$ atmosphere. This reaction mixture was stirred for 16 hours with gradual warming to room temperature. The suspension was filtered through a pad of diatomaceous earth and the filtrate concentrated to dryness under reduced pressure to give the product, which was further purified by FCC (petroleum ether:ethyl acetate, 1:0) to afford the title compound (12.1 g) as a brown liquid. $^1H$ NMR (400 MHz, DMSO-$d_6$) δ 8.80-8.76 (m, 1H), 8.38 (d, J=2.0 Hz, 1H).

Step C: tert-Butyl 2-((2-chloro-5-(trifluoromethyl)pyridine-3-sulfonamido)methyl)piperidine-1-carboxylate. tert-Butyl 2-(aminomethyl)piperidine-1-carboxylate (7.35 g, 34.3 mmol) was added to a suspension of $K_2CO_3$ (17.8 g, 129 mmol), THF (80 mL), and $H_2O$ (16 mL) which had been cooled to 0° C. This reaction mixture was stirred for 10 minutes at 0° C. and then treated with 2-chloro-5-(trifluoromethyl)pyridine-3-sulfonyl chloride (12 g, 43 mmol). The mixture was stirred at 0° C. for 2.5 hours before concentrating to dryness under reduced pressure. The residue was diluted with water (50 mL) and extracted with ethyl acetate (50 mL×3). These extractions resulted in several organic solvent fractions which were combined, washed with brine (50 mL), dried over $Na_2SO_4$, filtered, and concentrated to dryness under reduced pressure to give the product, which was purified by FCC (petroleum ether:ethyl acetate, 1:0 to 3:2, gradient elution) to afford the title compound (12 g, 61%) as a brown liquid. MS (ESI): mass calcd. for $C_{17}H_{23}ClF_3N_3O_4S$, 457.10 m/z found 357.9 $[M-100+H]^+$.

Step D: 2-Chloro-N-(piperidin-2-ylmethyl)-5-(trifluoromethyl)pyridine-3-sulfonamide. TFA (18.2 mL, 263 mmol) was added dropwise to solution consisting of tert-butyl 2-((2-chloro-5-(trifluoromethyl)pyridine-3-sulfonamido)methyl)piperidine-1-carboxylate (12 g, 26 mmol) and dichloromethane (30 mL) that had been cooled to a 0° C. This mixture was stirred for 16 hours with gradual warming to room temperature before concentrating to dryness under reduced pressure to give the product (14 g) as a brown liquid, which was used in the next step without further purification. MS (ESI): mass calcd. for $Cl_2H_{15}ClF_3N_3O_2S$, 357.05 m/z found 357.9 $[M+H]^+$.

Step E: 3-(Trifluoromethyl)-7,7a,8,9,10,11-hexahydro-6H-dipyrido[2,1-d:2',3'-f][1,2,5]thiadiazepine 5,5-dioxide. DIPEA (48.0 mL, 352 mmol) was added to a mixture of 2-chloro-N-(piperidin-2-ylmethyl)-5-(trifluoromethyl)pyridine-3-sulfonamide (14 g) and toluene (30 mL). The resultant mixture was stirred at 130° C. for 2 hours before cooling to room temperature and concentrating to dryness under reduced pressure. The material was purified by FCC (petroleum ether:ethyl acetate, 1:0 to 3:1, gradient elution) to provide the title compound (7.2 g, 94%) as a yellow solid. MS (ESI): mass calcd. for $Cl_2H_{14}F_3N_3O_2S$, 321.08 m/z found 321.9 $[M+H]^+$.

Intermediate 101: (*S)-3-(Trifluoromethyl)-7,7a,8,9,10,11-hexahydro-6H-dipyrido[2,1-d:2',3'-f][1,2,5]thiadiazepine 5,5-dioxide

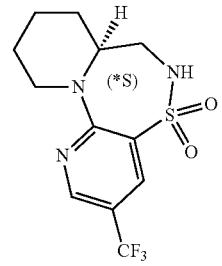 [SMILES: O=S1(=O)NC[C@@H]2CCCCN2c2ncc(C(F)(F)F)cc21]

3-(Trifluoromethyl)-7,7a,8,9,10,11-hexahydro-6H-dipyrido[2,1-d:2',3'-f][1,2,5]thiadiazepine 5,5-dioxide (Intermediate 100, 7.2 g, 17 mmol) was purified by SFC over OD 250 mm×50 mm, 10 m (eluent: 20% to 20% (v/v) supercritical $CO_2$ in EtOH and $H_2O$ with 0.1% $NH_3$) to afford two diastereomers. The first eluting isomer (3.0 g) was designated (*S): MS (ESI): mass calcd. for $Cl_2H_{14}F_3N_3O_2S$, 321.08 m/z found 322.0 $[M+H]^+$. $^1H$ NMR (400 MHz, DMSO-$d_6$) δ 8.58-8.53 (m, 1H), 8.31 (s, 1H), 8.05 (d, J=2.0 Hz, 1H), 4.39-4.29 (m, 2H), 3.50 (t, J=13.2 Hz, 1H), 3.38-3.31 (m, 1H), 3.22 (dd, J=3.6, 3.6 Hz, 1H), 1.76-1.45 (m, 6H).

Intermediate 102: (*R)-3-(Trifluoromethyl)-7,7a,8,9,10,11-hexahydro-6H-dipyrido[2,1-d:2',3'-f][1,2,5]thiadiazepine 5,5-dioxide

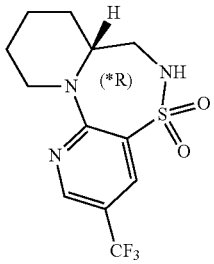 [SMILES: O=S1(=O)NC[C@H]2CCCCN2c2ncc(C(F)(F)F)cc21]

The second eluting isomer (3.6 g) from the separation of isomers by chiral SFC described in Intermediate 101 was designated (*R): MS (ESI): mass calcd. for $C_{12}H_{14}F_3N_3O_2S$, 321.08 m/z found 322.0 [M+H]$^+$. $^1$H NMR (400 MHz, DMSO-d$_6$) δ 8.56-8.54 (m, 1H), 8.30 (br s, 1H), 8.05 (d, J=2.4 Hz, 1H), 4.39-4.30 (m, 2H), 3.50 (t, J=13.2 Hz, 1H), 3.39-3.31 (m, 1H), 3.22 (dd, J=3.6, 3.6 Hz, 1H), 1.75-1.46 (m, 6H).

Intermediate 103: Ethyl (E)-3-(3-methyl-[1,2,4]triazolo[4,3-a]pyridin-7-yl)acrylate

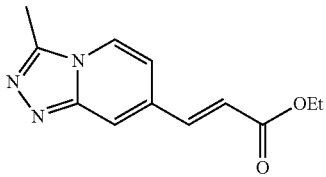 [SMILES: CCOC(=O)/C=C/c1ccn2c(C)nnc2c1]

Step A: 4-Bromo-2-hydrazinylpyridine. An emulsion of 4-bromo-2-fluoropyridine (33 g, 188 mmol) and hydrazine monohydrate (91 mL, 1876 mmol) was stirred at room temperature for 16 hours. 4M aqueous NaOH (81 mL) and water (165 mL) were added and the mixture was stirred at room temperature for 10 minutes. The precipitate was collected and washed with water (200 mL) to provide the title compound (34 g, 97%) as a white powder which was used in the next step without further purification.

Step B: N-(4-Bromopyridin-2-yl)acetohydrazide. Acetic anhydride (17 mL, 180 mmol) was added dropwise to a solution of 4-bromo-2-hydrazinylpyridine (33.9 g, 180 mmol) and triethyl amine (27.7 mL, 199 mmol) in DCM (340 mL) that had been cooled to 0° C. The reaction was stirred at 0° C. for 1 hour. After this period of time, the reaction mixture was diluted with saturated aqueous NaHCO$_3$(400 mL). The precipitate was collected and washed with saturated aqueous NaHCO$_3$(600 mL) to provide the title compound (37.6 g, 91%%) as a white powder which was used in the next step without further purification.

Step C: 7-Bromo-3-methyl-[1,2,4]triazolo[4,3-a]pyridine. A solution of N-(4-bromopyridin-2-yl)acetohydrazide (37.5 g, 163 mmol) in acetic acid (380 mL) was stirred at 100° C. for 72 hours. The reaction mixture was then concentrated under reduced pressure and the resulting residue was triturated with saturated aqueous NaHCO$_3$(300 mL). The solid was washed with water (100 mL) and diethyl ether (50 mL) to provide the title compound (31 g, 90%) as a pale yellow solid which was used in the next step without further purification.

Step D: Ethyl (E)-3-(3-methyl-[1,2,4]triazolo[4,3-a]pyridin-7-yl)acrylate. A mixture of 7-bromo-3-methyl-[1,2,4]triazolo[4,3-a]pyridine (5 g, 24 mmol), ethyl acrylate (5.1 mL, 47 mmol), Pd(dppf)Cl$_2$ (1.73 g, 2.36 mmol), and triethyl amine (13.2 mL, 94.7 mmol) was stirred in DMF (50 mL) at 120° C. for 4 hours. The reaction mixture was cooled to room temperature and the precipitate was collected. The solid was washed with DMF (10 mL) to provide the title compound (5.12 g, 94%) as an off-white solid. MS (ESI): mass calcd. for $C_{12}H_{13}N_3O_2$, 231.1; m/z found, 232.2 [M+H]$^+$. $^1$H NMR (300 MHz, DMSO-d$_6$) δ 8.36 (d, J=7.3 Hz, 1H), 8.11-8.04 (m, 1H), 7.71 (d, J=16.0 Hz, 1H), 7.41 (dd, J=7.3, 1.6 Hz, 1H), 6.84 (d, J=16.0 Hz, 1H), 4.22 (q, J=7.1 Hz, 2H), 2.69 (s, 3H), 1.27 (t, J=7.1 Hz, 3H).

Intermediate 104: Ethyl 3-(3-(chloromethyl)-4-methylphenyl)-3-(8-methyl-3-(trifluoromethyl)-[1,2,4]triazolo[4,3-a]pyridin-7-yl)propanoate

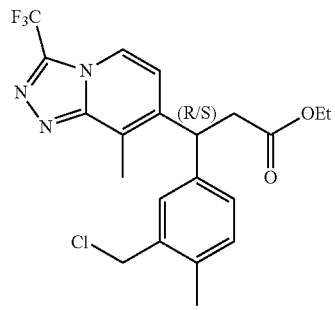 [SMILES: CCOC(=O)CC(c1ccc(C)c(CCl)c1)c1ccn2c(C(F)(F)F)nnc2c1C]

Thionyl chloride (0.17 mL, 2.3 mmol) was added to a solution of ethyl 3-(3-(hydroxymethyl)-4-methylphenyl)-3-(8-methyl-3-(trifluoromethyl)-[1,2,4]triazolo[4,3-a]pyridin-7-yl)propanoate (Intermediate 25, 480 mg, 1.14 mmol) and 2 drops of DMF in DCM (6 mL). The reaction was stirred at room temperature for 30 minutes. The reaction was quenched with saturated aqueous NaHCO$_3$, then extracted with DCM. These extractions resulted in several organic solvent fractions which were combined, dried over MgSO$_4$, filtered, and concentrated to dryness under reduced pressure, to provide the title compound which was used without further purification. MS (ESI): mass calcd. for $C_{21}H_{21}ClF_3N_3O_2$, 439.1; m/z found, 440.2 [M+H]$^+$.

Intermediate 105: Ethyl 3-(3-(chloromethyl)-4-methylphenyl)-3-(3-methyl-[1,2,4]triazolo[4,3-a]pyridin-7-yl)propanoate

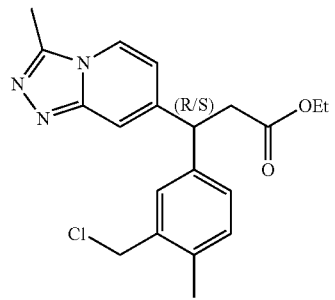 [SMILES: CCOC(=O)CC(c1ccc(C)c(CCl)c1)c1ccn2c(C)nnc2c1]

Step A: Ethyl 3-(3-(acetoxymethyl)-4-methylphenyl)-3-(3-methyl-[1,2,4]triazolo[4,3-a]pyridin-7-yl)propanoate. 1M Aqueous potassium hydroxide (2.2 mL, 2.2 mmol) was added to a mixture of 2-methyl-5-(4,4,5,5-tetramethyl-1,3,2-dioxaborolan-2-yl)benzyl acetate (Intermediate 20, 1.89 g, 6.50 mmol), ethyl (E)-3-(3-methyl-[1,2,4]triazolo[4,3-a]pyridin-7-yl)acrylate (Intermediate 103, 501 mg, 2.17 mmol), and [Rh(COD)Cl]$_2$ (107.8 mg, 0.219 mmol) in 1,4-dioxane (7.5 mL). The reaction was heated at 110° C. overnight. After this time, the reaction mixture was cooled to room temperature, filtered, and concentrated. The residue was diluted in water, ethyl acetate, and brine. The resulting biphasic mixture was separated and the aqueous layer was extracted with ethyl acetate. These extractions resulted in several organic solvent fractions which were combined, dried over MgSO$_4$, filtered, and concentrated to dryness under reduced pressure. The material was purified by flash column chromatography (0-5% MeOH/DCM) to afford the title compound (360 mg, 42% yield). MS (ESI): mass calcd. for $C_{22}H_{25}N_3O_4$, 395.2; m/z found, 396.1 [M+H]$^+$.

Step B: Ethyl 3-(3-(hydroxymethyl)-4-methylphenyl)-3-(3-methyl-[1,2,4]triazolo[4,3-a]pyridin-7-yl)propanoate. A mixture of ethyl 3-(3-(chloromethyl)-4-methylphenyl)-3-(3-methyl-[1,2,4]triazolo[4,3-a]pyridin-7-yl)propanoate (360 mg, 0.91 mmol) and potassium carbonate (260 mg, 1.88 mmol) in ethanol (9 mL) was stirred at room temperature overnight. The reaction mixture was concentrated to dryness under reduced pressure, then dissolved in water and DCM. The resulting biphasic mixture was separated and the aqueous layer was extracted with DCM. These extractions resulted in several organic solvent fractions which were combined, dried over MgSO$_4$, filtered, and concentrated to dryness under reduced pressure to provide the title compound which was used without further purification (259 mg, 80% yield). MS (ESI): mass calcd. for $C_{20}H_{23}N_3O_3$, 353.2; m/z found, 354.3 [M+H]$^+$.

Step C: Ethyl 3-(3-(chloromethyl)-4-methylphenyl)-3-(3-methyl-[1,2,4]triazolo[4,3-a]pyridin-7-yl)propanoate. The title compound (260 mg, 95% yield) was prepared using analogous conditions as described in Intermediate 104 where ethyl 3-(3-(hydroxymethyl)-4-methylphenyl)-3-(3-methyl-[1,2,4]triazolo[4,3-a]pyridin-7-yl)propanoate was used instead of ethyl 3-(3-(hydroxymethyl)-4-methylphenyl)-3-(8-methyl-3-(trifluoromethyl)-[1,2,4]triazolo[4,3-a]pyridin-7-yl)propanoate (Intermediate 25). MS (ESI): mass calcd. for $C_{20}H_{22}ClN_3O_2$, 371.1; m/z found, 372.1 [M+H]$^+$.

Intermediate 106: Ethyl 3-(3-(chloromethyl)-4-methylphenyl)-3-(3-cyclopropyl-8-methyl-[1,2,4]triazolo[4,3-a]pyridin-7-yl)propanoate

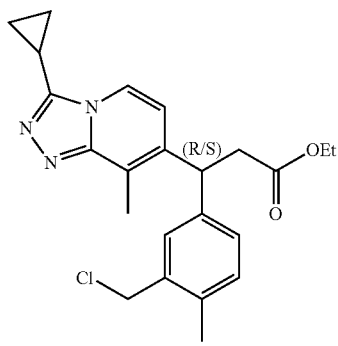 [SMILES: CCOC(=O)CC(c1ccc(C)c(CCl)c1)c1ccn2c(C3CC3)nnc2c1C]

Step A: 4-Bromo-2-hydrazinyl-3-methylpyridine. 4-Bromo-2-fluoro-3-methylpyridine (100 g, 526 mmol), pyridine (1000 mL), and hydrazine hydrate (300 mL) were combined under an atmosphere of nitrogen stirred for 4 hours at 75° C. The resulting mixture was concentrated under vacuum, then diluted with 2000 mL of H$_2$O and stirred for 30 minutes. The solids were collected by filtration and washed with H$_2$O to provide the title compound which was used without further purification (90 g, 85% yield).

Step B: 7-Bromo-3-cyclopropyl-8-methyl-[1,2,4]triazolo[4,3-a]pyridine. 4-Bromo-2-hydrazinyl-3-methylpyridine (25 g, 124 mmol), DCM (250 mL), and cyclopropanecarbaldehyde (9.96 g, 142 mmol) were combined under an atmosphere of nitrogen and stirred for 30 minutes at room temperature. This was followed by the addition of iodobenzene diacetate (47.8 g, 148 mmol), in portions at 0° C. The resulting solution was stirred for 12 hours at room temperature. The reaction was then quenched by the addition of 300 mL of water. The reaction mixture was partitioned between DCM and water. The resulting biphasic mixture was separated and the aqueous layer was extracted with DCM. These extractions resulted in several organic solvent fractions which were combined, washed with water, dried over Na$_2$SO$_4$, filtered, and concentrated to dryness under reduced pressure to provide the title compound which was re-crystallized from DCM/hexane in the ratio of 1:3 to provide an orange solid (20 g, 65% yield). MS (ESI): mass calcd. for $C_{20}H_{10}BrN_3$, 251.0; m/z found, 252.0 [M+H]$^+$.

Step C: Ethyl (E)-3-(3-cyclopropyl-8-methyl-[1,2,4]triazolo[4,3-a]pyridin-7-yl)acrylate. Anhydrous DMF (7 mL) was added to a mixture of 7-bromo-3-cyclopropyl-8-methyl-[1,2,4]triazolo[4,3-a]pyridine (1.25 g, 4.96 mmol) and Pd(OAc)$_2$ (96 mg, 0.43 mmol) under an atmosphere of nitrogen. Ethyl acrylate (2.3 mL, 21 mmol) and triethylamine (0.59 mL mg, 4.2 mmol) were added and the mixture was heated at 110° C. overnight. After this time, the reaction was cooled to room temperature, then filtered through a pad of diatomaceous earth, rinsing with ethyl acetate. The filtrate was collected, washed with water and brine, then dried over MgSO$_4$, filtered, and concentrated to dryness under reduced pressure. The material was purified by flash column chromatography (0-5% MeOH/DCM) to afford the title compound (140 mg, 24% yield). MS (ESI): mass calcd. for $C_{15}H_{17}N_3O_2$ 271.1; m/z found, 272.0 [M+H]$^+$.

Step D: Ethyl 3-(3-(acetoxymethyl)-4-methylphenyl)-3-(3-cyclopropyl-8-methyl-[1,2,4]triazolo[4,3-a]pyridin-7-yl)propanoate. The title compound (149 mg, 54% yield) was prepared using analogous conditions as described in Intermediate 105, Step A where ethyl (E)-3-(3-cyclopropyl-8-methyl-[1,2,4]triazolo[4,3-a]pyridin-7-yl)acrylate was used instead of ethyl (E)-3-(3-methyl-[1,2,4]triazolo[4,3-a]pyridin-7-yl)acrylate. MS (ESI): mass calcd. for $C_{25}H_{29}N_3O_4$, 435.2; m/z found, 436.0 [M+H]$^+$.

Step E: Ethyl 3-(3-cyclopropyl-8-methyl-[1,2,4]triazolo[4,3-a]pyridin-7-yl)-3-(3-(hydroxymethyl)-4-methylphenyl)propanoate. The title compound (193 mg, 93% yield) was prepared using analogous conditions as described in Intermediate 105, Step B where ethyl 3-(3-(acetoxymethyl)-4-methylphenyl)-3-(3-cyclopropyl-8-methyl-[1,2,4]triazolo[4,3-a]pyridin-7-yl)propanoate was used instead of ethyl 3-(3-(chloromethyl)-4-methylphenyl)-3-(3-methyl-[1,2,4]triazolo[4,3-a]pyridin-7-yl)propanoate. MS (ESI): mass calcd. for $C_{23}H_{27}N_3O_3$, 393.2; m/z found, 394.0 [M+H]$^+$.

Step F: Ethyl 3-(3-(chloromethyl)-4-methylphenyl)-3-(3-cyclopropyl-8-methyl-[1,2,4]triazolo[4,3-a]pyridin-7-yl)propanoate. The title compound (186 mg, 92% yield) was prepared using analogous conditions as described in Intermediate 104 where ethyl 3-(3-cyclopropyl-8-methyl-[1,2,4]triazolo[4,3-a]pyridin-7-yl)-3-(3-(hydroxymethyl)-4-methylphenyl)propanoate was used instead of ethyl 3-(3-(hydroxymethyl)-4-methylphenyl)-3-(8-methyl-3-(trifluoromethyl)-[1,2,4]triazolo[4,3-a]pyridin-7-yl)propanoate (Intermediate 25). MS (ESI): mass calcd. for $C_{23}H_{26}ClN_3O_2$, 411.2; m/z found, 412.0 [M+H]$^+$.

Intermediate 107: Ethyl 3-(1-cyclopropyl-4-methyl-1H-benzo[d][1,2,3]triazol-5-yl)-3-(6-(hydroxymethyl)-5-methylpyridin-2-yl)propanoate

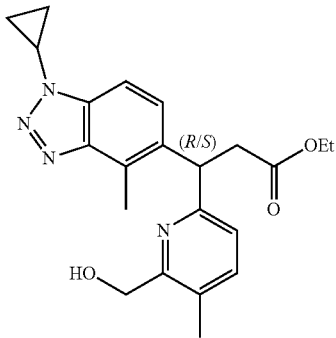 [SMILES: CCOC(=O)CC(c1ccc(C)c(CO)n1)c1ccc2c(nnn2C2CC2)c1C]

The title compound (53.2 mg, 118% yield) was prepared using analogous conditions as described in Intermediate 105, Step B where ethyl 3-(6-(acetoxymethyl)-5-methylpyridin-2-yl)-3-(1-cyclopropyl-4-methyl-1H-benzo[d][1,2,3]triazol-5-yl)propanoate (Intermediate 90) was used instead of ethyl 3-(3-(chloromethyl)-4-methylphenyl)-3-(3-methyl-[1,2,4]triazolo[4,3-a]pyridin-7-yl)propanoate and the reaction was heated to 50° C. instead of performing the reaction at room temperature. MS (ESI): mass calcd. for $C_{22}H_{26}N_4O_3$, 394.2; m/z found, 395.2 [M+H]$^+$.

Intermediate 108: (R/S)-Ethyl 3-(1-ethyl-4-methyl-1H-benzo[d][1,2,3]triazol-5-yl)-3-(6-(hydroxymethyl)-5-methylpyridin-2-yl)propanoate

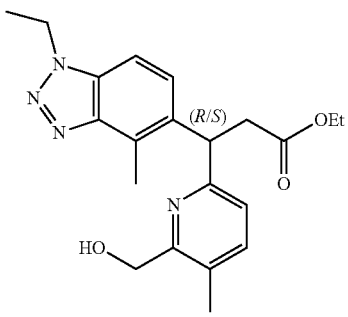 [SMILES: CCOC(=O)CC(c1ccc(C)c(CO)n1)c1ccc2c(nnn2CC)c1C]

Step A: (E)-Ethyl 3-(6-(acetoxymethyl)-5-methylpyridin-2-yl)-3-(1-ethyl-4-methyl-1H-benzo[d][1,2,3]triazol-5-yl)acrylate. (E)-Ethyl 3-(6-(acetoxymethyl)-5-methylpyridin-2-yl)acrylate (Intermediate 15, 3.5 g, 13 mmol), 5-bromo-1-ethyl-4-methyl-1H-benzo[d][1,2,3]triazole (Intermediate 16, 4.1 g, 17 mmol), DIPEA (5.2 g, 40 mmol), and 1,4-dioxane (30 mL) were added to a 100 mL round-bottomed flask. The mixture was sparged with $N_2$ for 5 minutes and then treated with Pd(t-Bu$_3$P)$_2$ (680 mg, 1.33 mmol). The resultant mixture was stirred and heated to 80° C. for 16 hours under $N_2$ before cooling to room temperature, pouring it into water (100 mL), and extracting with ethyl acetate (60 mL×3). These extractions resulted in several organic solvent fractions which were combined, dried over Na$_2$SO$_4$, filtered, and concentrated to dryness under reduced pressure. The material was purified by FCC (petroleum ether:ethyl acetate, 20:1 to 1:1, gradient elution) to afford the title compound (3.9 g, 68%) as a yellow oil. MS (ESI): mass calcd. for $C_{23}H_{26}N_4O_4$ 422.20, m/z found 423.1 [M+H]$^+$.

Step B: (E)-Ethyl 3-(1-ethyl-4-methyl-1H-benzo[d][1,2,3]triazol-5-yl)-3-(6-(hydroxymethyl)-5-methylpyridin-2-yl)acrylate. (E)-Ethyl 3-(6-(acetoxymethyl)-5-methylpyridin-2-yl)-3-(1-ethyl-4-methyl-1H-benzo[d][1,2,3]triazol-5-yl)acrylate (3.9 g, 9.2 mmol), K$_2$CO$_3$ (3.83 g, 27.7 mmol), EtOH (30 mL), and THF (10 mL) were added to a 100 mL round-bottomed flask. The resultant mixture was stirred at room temperature for 3 hours before pouring it into H$_2$O (100 mL) and extracting with ethyl acetate (80 mL×3). These extractions resulted in several organic solvent fractions which were combined, dried over Na$_2$SO$_4$, filtered, and concentrated to dryness under reduced pressure to provide the title product (3.6 g, 88%) as an oil. MS (ESI): mass calcd. for $C_{21}H_{24}N_4O_3$ 380.18, m/z found 381.1 [M+H]$^+$.

Step C: (R/S)-Ethyl 3-(1-ethyl-4-methyl-1H-benzo[d][1,2,3]triazol-5-yl)-3-(6-(hydroxymethyl)-5-methylpyridin-2-yl)propanoate. Raney Ni (3.0 g) was added to a solution of (E)-ethyl 3-(1-ethyl-4-methyl-1H-benzo[d][1,2,3]triazol-5-yl)-3-(6-(hydroxymethyl)-5-methylpyridin-2-yl)acrylate (3.6 g, 9.5 mmol) and ethyl acetate (30 mL). The resultant mixture was stirred under H$_2$ atmosphere (50 psi) at room temperature for 36 hours. The suspension was filtered through a pad of diatomaceous earth and the pad washed with ethyl acetate (100 mL). The filtrate was concentrated to dryness under reduced pressure. The material was purified by preparative acidic HPLC using a Phenomenex Synergi Max-RP, 250×50 mm×10 m column (eluent: 5% to 55% (v/v) CH$_3$CN and H$_2$O with 0.225% HCOOH) to afford the title compound (2.12 g). MS (ESI): mass calcd. for $C_{21}H_{26}N_4O_3$ 382.20, m/z found 383.1 [M+H]$^+$. $^1$H NMR (400 MHz, DMSO-d$_6$) δ 7.54 (d, J=8.8 Hz, 1H), 7.40 (d, J=7.9 Hz, 1H), 7.37 (d, J=8.8 Hz, 1H), 7.00 (d, J=7.7 Hz, 1H), 5.00-4.89 (m, 2H), 4.62 (q, J=7.3 Hz, 2H), 4.53 (d, J=5.1 Hz, 2H), 3.92 (q, J=7.1 Hz, 2H), 3.39-3.32 (m, 1H), 3.06-2.97 (m, 1H), 2.79 (s, 3H), 2.18 (s, 3H), 1.42 (t, J=7.3 Hz, 3H), 1.01 (t, J=7.1 Hz, 3H).

Intermediate 109: 4-Bromo-2-hydrazinylpyridine

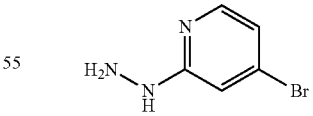

A mixture containing 4-bromo-2-fluoropyridine (50 g, 280 mmol) and hydrazine hydrate (414 mL, 8.54 mol) was heated to 50° C. After 16 hours, the suspension was cooled to room temperature, filtered, and the solids were washed with water. The washed solids were dried under reduced pressure to afford the title compound (50.5 g, 95%) as a white solid. $^1$H NMR (400 MHz, DMSO-d$_6$) δ 7.81 (d, J=5.4 Hz, 1H), 7.70 (br s, 1H), 6.89 (d, J=1.5 Hz, 1H), 6.67 (dd, J=1.7, 5.4 Hz, 1H).

Intermediate 110: 7-Bromo-3-(trifluoromethyl)-[1,2,4]triazolo[4,3-a]pyridine

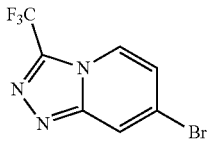

TFAA (758 mL, 5.38 mol) was added dropwise to the stirring solid 4-bromo-2-hydrazinylpyridine (Intermediate 109, 50.5 g, 269 mmol). The resulting mixture was stirred at 50° C. After 16 hours, the mixture was poured slowly into water (200 mL) and then brought to pH 7-8 by addition of aqueous NaOH. The resulting suspension was filtered, and the filter cake was washed with water and then dried under reduced pressure to afford the title compound (62.8 g, 88%) as a white solid. MS (ESI): mass calcd. for $C_7H_3BrF_3N_3$, 264.9; m/z found, 267.7 [M+H]$^+$. $^1$H NMR (400 MHz, DMSO-d$_6$): 8.58 (d, J=7.3 Hz, 1H), 8.48 (d, J=7.0 Hz, 1H), 7.40 (dd, J=1.7, 7.3 Hz, 1H).

Intermediate 111: 7-Bromo-3-ethyl-8-methyl-[1,2,4]triazolo[4,3-a]pyridine

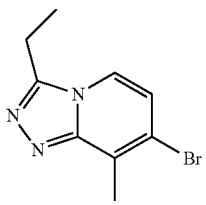

The title compound (3.05 g) was prepared using analogous conditions as described in Intermediate 24 using propionic acid instead of TFAA. MS (ESI): mass calcd. for $C_9H_{10}BrN_3$, 239.0; m/z found, 240.0 [M+H]$^+$. $^1$H NMR (400 MHz, CDCl$_3$) δ 7.61 (d, J=7.2 Hz, 1H), 6.95 (d, J=7.3 Hz, 1H), 3.12-3.03 (m, 2H), 2.72 (s, 3H), 1.52-1.45 (m, 3H).

Intermediate 112: Ethyl (E)-3-(3-ethyl-8-methyl-[1,2,4]triazolo[4,3-a]pyridin-7-yl)acrylate

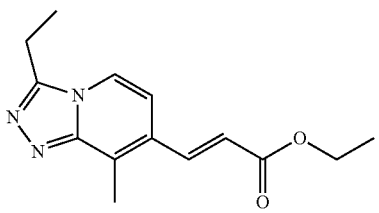 [SMILES: CCOC(=O)/C=C/c1ccn2c(CC)nnc2c1C]

A mixture of 7-bromo-3-ethyl-8-methyl-[1,2,4]triazolo[4,3-a]pyridine (Intermediate 111, 1.05 g, 4.37 mmol), ethyl acrylate (2.1 mL, 19.4 mmol), triethylamine (1.6 mL, 11.5 mmol), and Pd(OAc)$_2$ (338 mg, 1.51 mmol) in DMA (12 mL) was degassed by bubbling nitrogen through the mixture. The mixture was then heated at 125° C. After 18 hours, the mixture was cooled to room temperature, diluted with ethyl acetate, and then filtered through diatomaceous earth. The filtrate was partitioned between ethyl acetate and water. The layers were separated. The organic extracts were washed with brine, dried over anhydrous sodium sulfate, and then absorbed onto diatomaceous earth for purification by flash column chromatography (hexanes-ethyl acetate) to provide the title compound (494 mg, 44%). MS (ESI): mass calcd. for $C_{14}H_{17}N_3O_2$, 259.1; m/z found, 260.1 [M+H]$^+$. $^1$H NMR (400 MHz, DMSO-d$_6$) δ 8.26 (d, J=7.3 Hz, 1H), 7.89 (d, J=15.9 Hz, 1H), 7.35 (d, J=7.3 Hz, 1H), 6.78 (d, J=15.8 Hz, 1H), 4.28-4.19 (m, 2H), 3.14-3.04 (m, 2H), 2.66 (s, 3H), 1.39-1.31 (m, 3H), 1.31-1.25 (m, 3H).

Intermediate 113: (*S)-7,7a,8,9-Tetrahydro-6H-azeto[2,1-d]pyrido[2,3-f][1,2,5]thiadiazepine 5,5-dioxide

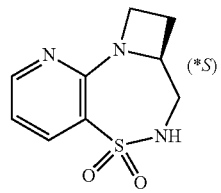 [SMILES: O=S1(=O)NC[C@@H]2CCN2c2ncccc21]

Step A: tert-Butyl 2-(((2-chloropyridine)-3-sulfonamido)methyl)azetidine-1-carboxylate. tert-Butyl (azetidin-2-ylmethyl)carbamate (9.2 g, 49.5 mmol) and potassium carbonate (7.8 g, 56.6 mmol) were suspended in a mixture of THF (100 mL) and water (25 mL). After 5 minutes, 2-chloropyridine-3-sulfonyl chloride (10 g, 47.2 mmol) was added. After stirring overnight, the solvents were removed under reduced pressure. The residue was partitioned between water and ethyl acetate and the layers were separated. The aqueous layer was extracted with ethyl acetate and these extractions resulted in several organic fractions which were combined, dried over anhydrous Na$_2$SO$_4$, filtered, and concentrated to dryness under reduced pressure to afford the title compound (17.9 g, 89%). This material was used in the next step without further purification. MS (ESI): mass calcd. for $C_{14}H_{20}ClN_3O_4S$, 361.1; m/z found, 261.7 [M-CO$_2$t-Bu]$^-$.

Step B: N-(Azetidin-2-ylmethyl)-2-chloropyridine-3-sulfonamide. TFA (17.4 mL, 251 mmol) was added to a solution of tert-butyl 2-(((2-chloropyridine)-3-sulfonamido)methyl)azetidine-1-carboxylate (17.9 g, 41.9 mmol) in DCM (80 mL) which had been cooled to 0° C. The mixture was allowed to warm to room temperature. After 15 hours, TLC analysis indicated complete consumption of starting material and then the reaction mixture was concentrated to afford the title compound as a yellow oil (10.5 g, 96%). This material was used in the next step without further purification.

Step C: (*S)-7,7a,8,9-Tetrahydro-6H-azeto[2,1-d]pyrido[2,3-f][1,2,5]thiadiazepine 5,5-dioxide. Cs$_2$CO$_3$ (38.5 g, 118 mmol) was added to a solution of N-(azetidin-2-ylmethyl)-2-chloropyridine-3-sulfonamide (10.3 g, 39.4 mmol) in DMSO (150 mL). The mixture was heated at 130° C. After 2 hours, the mixture was cooled to room temperature and then poured onto water. The aqueous layer was extracted with ethyl acetate and these extractions resulted in several organic fractions which were combined, washed with brine, dried over anhydrous Na$_2$SO$_4$, filtered, and concentrated to dryness under reduced pressure. The residue was purified by flash column chromatography (petroleum ether-ethyl acetate) to provide the title compound as a white solid (4.35 g, 49%). MS (ESI): mass calcd. for $C_9H_{11}N_3O_2S$, 449.2; m/z found, 226.0 [M+H]$^+$. $^1$H NMR (400 MHz, DMSO-d$_6$) δ 8.33 (dd, J=1.8, 4.9 Hz, 1H), 7.97 (dd, J=1.7, 7.6 Hz, 1H), 7.71 (br s, 1H), 6.95 (dd, J=4.9, 7.7 Hz, 1H), 4.16-4.06 (m, 1H), 4.04-3.93 (m, 1H), 3.67-3.56 (m, 1H), 3.34-3.26 (m, 2H), 2.31-2.19 (m, 1H), 2.18-2.09 (m, 1H). The mixture of 7,7a,8,9-Tetrahydro-6H-azeto[2,1-d]pyrido[2,3-f][1,2,5]thiadiazepine 5,5-dioxide isomers were separated by chiral SFC (stationary phase: Chiralpak AS-H 5 μm 250×20 mm, mobile phase: 70% CO$_2$, 30% MeOH) to afford two enantiomers. The first eluting enantiomer (2.05 g) was designated (*S). MS (ESI): mass calcd. for $C_9H_{11}N_3O_2S$, 449.2; m/z found, 226.0 [M+H]$^+$. $^1$H NMR (400 MHz, DMSO-d$_6$) δ 8.35-8.30 (m, 1H), 7.99-7.93 (m, 1H), 7.69 (s, 1H), 6.97-6.91 (m, 1H), 4.15-4.07 (m, 1H), 4.04-3.94 (m, 1H), 3.65-3.57 (m, 1H), 3.41-3.26 (m, 2H), 2.30-2.19 (m, 1H), 2.19-2.09 (m, 1H).

Intermediate 114: (*R)-7,7a, 8,9-Tetrahydro-6H-azeto[2,1-d]pyrido[2,3-f][1,2,5]thiadiazepine 5,5-dioxide

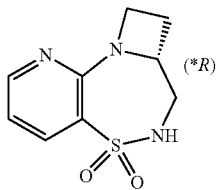 [SMILES: O=S1(=O)NC[C@H]2CCN2c2ncccc21]

The second eluting isomer (2.09 g) from the chiral separation described in Intermediate 113 was designated (*R). MS (ESI): mass calcd. for $C_9H_{11}N_3O_2S$, 449.2; m/z found, 226.1 [M+H]$^+$. $^1$H NMR (400 MHz, DMSO-d$_6$) δ 8.35-8.30 (m, 1H), 7.96 (dd, J=7.6, 1.7 Hz, 1H), 7.69 (s, 1H), 6.94 (dd, J=7.7, 4.8 Hz, 1H), 4.14-4.06 (m, 1H), 4.04-3.94 (m, 1H), 3.66-3.57 (m, 1H), 3.42-3.26 (m, 2H), 2.30-2.18 (m, 1H), 2.18-2.09 (m, 1H).

Intermediate 115: Ethyl 3-(1-ethyl-4-methyl-1H-benzo[d][1,2,3]triazol-5-yl)-3-(6-(hydroxymethyl)-5-methylpyridin-2-yl)propanoate

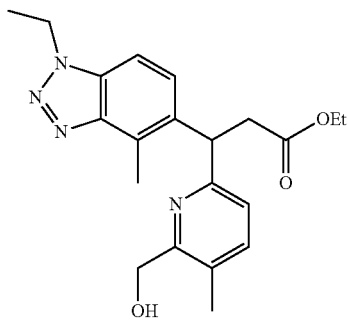 [SMILES: CCOC(=O)CC(c1ccc(C)c(CO)n1)c1ccc2c(nnn2CC)c1C]

Step A: Ethyl (E)-3-(6-(acetoxymethyl)-5-methylpyridin-2-yl)-3-(1-ethyl-4-methyl-1H-benzo[d][1,2,3]triazol-5-yl)acrylate. A mixture of ethyl (E)-3-(6-(acetoxymethyl)-5-methylpyridin-2-yl)acrylate (Intermediate 15, 3.5 g, 13 mmol), 5-bromo-1-ethyl-4-methyl-1H-benzo[d][1,2,3]triazole (Intermediate 16, 4.1 g, 17 mmol), DIPEA (5.2 g, 40 mmol), and 1,4-dioxane (30 mL) was degassed by bubbling nitrogen gas through the mixture. After 5 minutes, Pd(t-Bu$_3$P)$_2$ (680 mg, 1.3 mmol) was added and then the resulting mixture was heated at 80° C. After 16 hours, the mixture was cooled to room temperature and then poured onto water. The aqueous was extracted with ethyl acetate and these extractions resulted in several organic fractions which were combined, washed with brine, dried over anhydrous Na$_2$SO$_4$, filtered, and concentrated to dryness under reduced pressure. The residue was purified by flash column chromatography (petroleum ether-ethyl acetate) to provide the title compound as a yellow oil (3.9 g, 68%). MS (ESI): mass calcd. for $C_{23}H_{26}N_4O_4$, 422.2; m/z found, 423.1 [M+H]$^+$.

Step B: Ethyl (E)-3-(1-ethyl-4-methyl-1H-benzo[d][1,2,3]triazol-5-yl)-3-(6-(hydroxymethyl)-5-methylpyridin-2-yl)acrylate. A mixture of ethyl (E)-3-(6-(acetoxymethyl)-5-methylpyridin-2-yl)-3-(1-ethyl-4-methyl-1H-benzo[d][1,2,3]triazol-5-yl)acrylate (3.9 g, 9.2 mmol), K$_2$CO$_3$ (3.8 g, 28 mmol), EtOH (30 mL), and THF (10 mL) was stirred at room temperature. After 3 hours, the mixture was poured onto water. The aqueous portion was extracted with ethyl acetate and these extractions resulted in several organic fractions which were combined, washed with brine, dried over anhydrous Na$_2$SO$_4$, filtered, and concentrated to dryness under reduced pressure to afford the title compound as an oil (3.6 g, 88%). MS (ESI): mass calcd. for $C_{21}H_{24}N_4O_3$, 380.2; m/z found, 381.1 [M+H]$^+$.

Step C: Ethyl 3-(1-ethyl-4-methyl-1H-benzo[d][1,2,3]triazol-5-yl)-3-(6-(hydroxymethyl)-5-methylpyridin-2-yl)propanoate. A mixture of ethyl (E)-3-(1-ethyl-4-methyl-1H-benzo[d][1,2,3]triazol-5-yl)-3-(6-(hydroxymethyl)-5-methylpyridin-2-yl)acrylate (3.6 g, 9.5 mmol) and Raney nickel (3 g) in ethyl acetate (30 mL) was stirred under an atmosphere of hydrogen gas at room temperature. After 36 hours, the suspension was filtered through diatomaceous earth and the filtrate was concentrated to dryness to afford the title compound (3.5 g) which was combined with a second batch of the title compound which had been prepared in an analogous manner (2 g). The 5.5 g of the title compound was purified by preparative HPLC (Phenomenex Synergi Max-RP, 250×50 mm×10 μm column (eluent: 5% to 55% (v/v) CH$_3$CN and H$_2$O with 0.225% formic acid) to afford pure product (3.3 g). MS (ESI): mass calcd. for $C_{21}H_{26}N_4O_3$, 382.2; m/z found, 383.1 [M+H]$^+$. $^1$H NMR (400 MHz, DMSO-d$_6$) δ 7.54 (d, J=8.8 Hz, 1H), 7.40 (d, J=7.9 Hz, 1H), 7.37 (d, J=8.8 Hz, 1H), 7.00 (d, J=7.7 Hz, 1H), 5.00-4.89 (m, 2H), 4.62 (q, J=7.3 Hz, 2H), 4.53 (d, J=5.1 Hz, 2H), 3.92 (q, J=7.1 Hz, 2H), 3.39-3.32 (m, 1H), 3.06-2.97 (m, 1H), 2.79 (s, 3H), 2.18 (s, 3H), 1.42 (t, J=7.3 Hz, 3H), 1.01 (t, J=7.1 Hz, 3H).

Intermediate 116: (*R)-7,7a,8,9,10,11-Hexahydro-6H-benzo[f]pyrido[2,1-d][1,2,5]thiadiazepine 5,5-dioxide

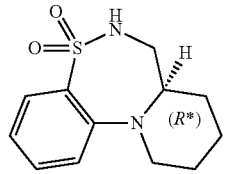 [SMILES: O=S1(=O)NC[C@H]2CCCCN2c2ccccc21]

The second eluting isomer (2.16 g) from the chiral separation described in Intermediate 76 was designated (*R): $^1$H NMR (400 MHz, DMSO-d$_6$) δ 7.80-7.67 (m, 1H), 7.61-7.57 (m, 1H), 7.43-7.34 (m, 1H), 7.19-7.13 (m, 1H), 7.03-6.95 (m, 1H), 3.79-3.67 (m, 1H), 3.55-3.33 (m, 3H), 3.08-2.98 (m, 1H), 1.75-1.50 (m, 6H).

Intermediate 117: (*R)-3-Methyl-7,7a,8,9,10,11-hexahydro-6H-dipyrido[2,1-d:2',3'-f][1,2,5]thiadiazepine 5,5-dioxide

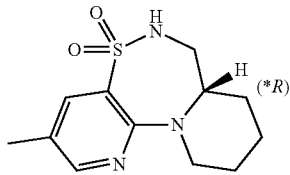 [SMILES: Cc1cnc2c(c1)S(=O)(=O)NC[C@@H]1CCCCN21]

The second eluting isomer (289 mg) from the chiral separation described in Intermediate 77 was designated (*R): MS (ESI): mass calcd. for C$_{12}$H$_{17}$N$_3$O$_2$S, 267.1; m/z found, 268.0 [M+H]$^+$. $^1$H NMR (400 MHz, DMSO-d$_6$) δ 8.11 (s, 1H), 8.07-8.00 (m, 1H), 7.71 (s, 1H), 4.20-4.09 (m, 2H), 3.49-3.39 (m, 1H), 3.34-3.25 (m, 1H), 3.21-3.13 (m, 1H), 2.20 (s, 3H), 1.74-1.52 (m, 6H).

Intermediate 118: 5-Bromo-1-(cyclopropylmethyl)-4-methyl-1H-benzo[d][1,2,3]triazole

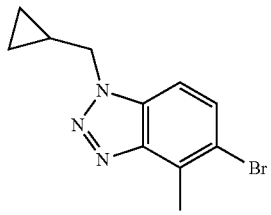

The title compound (84 g) was prepared using analogous conditions as described in Intermediate 16 using cyclopropylmethanamine instead of ethylamine in Step A, DMF instead of acetic acid as solvent in Step B, SnCl$_2$.2H$_2$O instead of iron in Step C, acetonitrile/water instead of acetic acid/water in Step D, and 4-methylbenzenesulfonic acid hydrate as an additive in Step D. $^1$H NMR (400 MHz, DMSO-d$_6$) δ 7.76-7.72 (m, 1H), 7.70-7.65 (m, 1H), 4.59 (d, J=7.3 Hz, 2H), 2.71 (s, 3H), 1.40-1.28 (m, 1H), 0.56-0.49 (m, 2H), 0.48-0.42 (m, 2H).

Intermediate 119: 1-(Cyclopropylmethyl)-4-methyl-1H-benzo[d][1,2,3]triazole-5-carbaldehyde

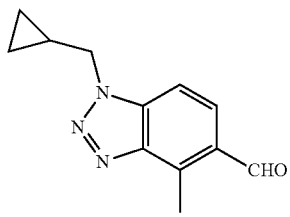 [SMILES: Cc1c(C=O)ccc2c1nnn2CC1CC1]

The title compound (34.3 g) was prepared using analogous conditions as described in Intermediate 28 using 5-bromo-1-(cyclopropylmethyl)-4-methyl-1H-benzo[d][1,2,3]triazole (Intermediate 118) instead of 7-bromo-8-methyl-3-(trifluoromethyl)-[1,2,4]triazolo[4,3-a]pyridine, triethylamine instead of K$_3$PO$_4$ as base, and ethanol instead of dioxane/water as solvent in Step A. MS (ESI): mass calcd. for C$_{12}$H$_{13}$N$_3$O, 215.1; m/z found, 216.1 [M+H]$^+$. $^1$H NMR (400 MHz, DMSO-d$_6$) δ 10.44 (s, 1H), 7.93 (d, J=8.4 Hz, 1H), 7.87 (d, J=8.8 Hz, 1H), 4.62 (d, J=6.8 Hz, 2H), 3.05 (s, 3H), 1.43-1.32 (m, 1H), 0.58-0.52 (m, 2H), 0.51-0.45 (m, 2H).

Intermediate 120: 6-Bromo-2-(((tert-butyldimethylsilyl)oxy)methyl)-3-methylpyridine

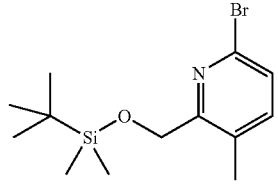 [SMILES: Cc1ccc(Br)nc1CO[Si](C)(C)C(C)(C)C]

Step A. (6-Bromo-3-methylpyridin-2-yl)methanol. This reaction was run in two batches starting with 30 g of 6-bromo-3-methylpicolinic acid for each batch. Borane tetrahydrofuran complex (1 M in THF, 280 mL, 280 mmol) was added dropwise to a solution of 6-bromo-3-methylpicolinic acid (30 g, 139 mmol) in THF (100 mL) at 0° C. The mixture was then heated at 50° C. After 16 hours, the reaction mixture was cooled to 0° C. and water (500 mL) was added slowly until gas evolution ceased. This mixture was stirred for 1 hour with warming to room temperature. At this point the two batches where combined. The combined mixture was extracted with ethyl acetate which resulted in several organic fractions. These fractions were combined, dried over sodium sulfate, filtered, and concentrated to dryness under reduced pressure to afford the title compound as a colorless oil (50 g). $^1$H NMR (400 MHz, DMSO-d$_6$) δ 7.54 (d, J=8.0 Hz, 1H), 7.45 (d, J=8.0 Hz, 1H), 4.50 (s, 2H), 2.29 (s, 3H).

Step B: 6-Bromo-2-(((tert-butyldimethylsilyl)oxy)methyl)-3-methylpyridine. TBSCl (56 g, 372 mmol) was added to an ice-cooled solution of (6-bromo-3-methylpyridin-2-yl)methanol (50 g, 247 mmol) and imidazole (37.2 g, 546 mmol) in DCM (500 mL). The mixture was allowed to warm to room temperature over the course of 2 hours which resulted in a suspension being formed. The solids where removed by filtration through diatomaceous earth. The filtrate was concentrated to dryness under reduced pressure and the residue was purified by flash column chromatography (eluent:petroleum ether-ethyl acetate) to afford the title compound as a colorless oil (30 g, 37%).

Intermediate 121: ((1-(tert-Butoxy)-2-methylprop-1-en-1-yl)oxy)trimethylsilane

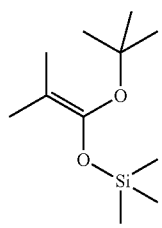

Step A: tert-Butyl isobutyrate. A solution of tert-butanol (19 mL, 200 mmol) in DCM (40 mL) was added dropwise over five minutes to a solution of isobutyryl chloride (20 mL, 190 mmol) in DCM (90 mL). Triethylamine (40 mL, 290 mmol) was then added dropwise, slowly. Additional DCM (40 mL) was added followed by the addition of DMAP (1.1 g, 10 mmol). After 18 hours, 1 M aqueous HCl solution was added until the mixture was biphasic and each layer was homogeneous. The layers were separated and the aqueous portion was extracted with DCM. The organic layers were combined and washed with saturated aqueous sodium bicarbonate solution and brine. The organic extracts were dried over anhydrous sodium sulfate, filtered, and concentrated under reduced pressure. The residue was purified by distillation (bath temperature of 125° C. and head temperature of 85-90° C. with ice-water cooling of the collection flask) to provide the title compound as a clear, colorless liquid (18.3 g, 67%). $^1$H NMR (400 MHz, CDCl$_3$) δ 2.42 (dt, J=13.9, 7.0 Hz, 1H), 1.43 (s, 9H), 1.12 (s, 3H), 1.11 (s, 3H).

Step B: ((1-(tert-Butoxy)-2-methylprop-1-en-1-yl)oxy) trimethylsilane. A 1.6 M solution of n-butyllithium in hexanes (20.5 mL, 32.8 mmol) was added to a solution of diisopropylamine (5 mL, 35.7 mmol) in THF (25 mL) which had been cooled to 0° C. After 10 minutes, a solution of tert-butyl isobutyrate (4.3 g, 30 mmol) in THF (10 mL) was added dropwise. After 30 minutes, chlorotrimethylsilane (4.5 mL, 35.5 mmol) was added. The reaction flask was removed from the cooling bath and allowed to warm to room temperature. After 1.5 hours, the mixture was poured into a solution of ice water and hexanes. The layers were separated. The organic portion was washed with brine, dried over anhydrous sodium sulfate, filtered, and concentrated under reduced pressure to provide the title compound as a light-yellow liquid. $^1$H NMR (400 MHz, CDCl$_3$) δ 1.38 (s, 3H), 1.35 (s, 3H), 1.10 (s, 9H), 0.01 (s, 9H).

Intermediate 122: Methyl 2,2-dimethyl-3-(4-methyl-3-((pivaloyloxy)methyl)phenyl)-3-(3-(trifluoromethyl)-[1,2,4]triazolo[4,3-a]pyridin-7-yl)propanoate

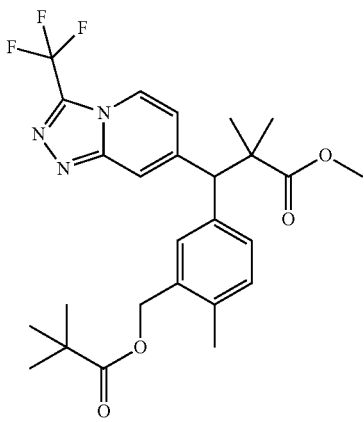 [SMILES: COC(=O)C(C)(C)C(c1ccc(C)c(COC(=O)C(C)(C)C)c1)c1ccn2c(C(F)(F)F)nnc2c1]

Step A: 3-(Trifluoromethyl)-7-vinyl-[1,2,4]triazolo[4,3-a] pyridine. To vial equipped with a stir bar was added 3-(trifluoromethyl)-7-vinyl-[1,2,4]triazolo[4,3-a]pyridine, (Intermediate 110, 8.98 g, 33.8 mmol), potassium vinyltrifluoroborate (9.63 g, 71.9 mmol), potassium phosphate (31.1 g, 144 mmol), 1,1'-bis(diphenylphosphino)ferrocene-palladium (II) dichloride dichloromethane complex (1.41 g, 1.71 mmol), 1,4-dioxane (88 mL) and distilled water (16 mL). The solution was degassed by bubbling nitrogen gas through it for 10 minutes, the vial was then capped and placed in a sand bath which had been heated at 100° C. After 1 hour, the vial was removed from the hot sand and allowed to cool to room temperature. The mixture was partitioned between ether and brine. The layers were separated and the organic layer was dried over anhydrous Na$_2$SO$_4$, filtered, and concentrated to dryness under reduced pressure. The residue was purified by flash column chromatography (eluent: hexanes/ethyl acetate) to afford the title compound (5.74 g, 80%). MS (ESI): mass calcd. for C$_9$H$_6$F$_3$N$_3$, 213.1; m/z found, 214.1 [M+H]$^+$.

Step B: 3-(Trifluoromethyl)-[1,2,4]triazolo[4,3-a]pyridine-7-carbaldehyde. To a solution of 3-(trifluoromethyl)-7-vinyl-[1,2,4]triazolo[4,3-a]pyridine (5.72 g, 26.8 mmol) in 1,4-dioxane (120 mL) and distilled water (40 mL) under positive pressure of nitrogen at room temperature, was added osmium tetroxide (2.5 wt. % in tert-butanol solution, 14 mL, 1.38 mmol) followed immediately by addition of sodium periodate (17 mL, 81.4 mmol) resulting in the formation of a white ppt. After stirring for 18 hours, the reaction mixture was cooled to room temperature and partitioned between ether and water. Brine was added and the aqueous was extracted three times with DCM. These extractions resulted in several organic solvent fractions which were combined, dried over anhydrous Na$_2$SO$_4$, filtered, and concentrated to dryness under reduced pressure. The residue was purified by flash column chromatography (eluent: hexanes/ethyl acetate) to afford a white foam. The foam was dissolved with minimal DCM and then hexanes were added until a white solid crashed out of solution. The white solids were isolated by vacuum filtration to afford the title compound (3.23 g, 56%). MS (ESI): mass calcd. for C$_8$H$_4$F$_3$N$_3$O, 215.1; m/z found, 216.1 [M+H]$^+$.

Step C: 5-(Hydroxy(3-(trifluoromethyl)-[1,2,4]triazolo[4,3-a]pyridin-7-yl)methyl)-2-methylbenzyl pivalate. To an oven-dried flask fitted with a reflux condenser and an argon gas inlet was added 3-(trifluoromethyl)-[1,2,4]triazolo[4,3-a]pyridine-7-carbaldehyde. (1.7 g, 8 mmol), 2-methyl-5-(4,4,5,5-tetramethyl-1,3,2-dioxaborolan-2-yl)benzylpivalate (Intermediate 42, 3.1 g, 9.3 mmol), potassium carbonate (3.6 g, 26 mmol), palladium chloride (106 mg, 0.598 mmol), tri(1-naphthyl)phosphine (169 mg, 0.397 mmol) and THF (86 mL). The reaction was heated in a sand bath set at 75° C. After 17 hours, the reaction mixture was allowed to cool to room temperature and additional 2-methyl-5-(4,4,5,5-tetramethyl-1,3,2-dioxaborolan-2-yl)benzylpivalate, potassium carbonate, palladium chloride, and tri(1-naphthyl) phosphine were added. The reaction was heated in a sand bath set at 75° C. After 6 hours, the reaction was cooled to room temperature and the mixture was partitioned between ether and water. The layers were separated. The organic layer was dried over anhydrous Na$_2$SO$_4$, filtered, and concentrated to dryness under reduced pressure. The residue was purified by flash column chromatography (hexanes to ethyl acetate) to afford the title compound (2.5 g, 75%). MS (ESI): mass calcd. for C$_{21}$H$_{22}$F$_3$N$_3$O$_3$, 421.2; m/z found, 422.1 [M+H]$^+$.

Step D: 5-(Chloro(3-(trifluoromethyl)-[1,2,4]triazolo[4,3-a]pyridin-7-yl)methyl)-2-methylbenzyl pivalate. To a vial under a positive pressure of nitrogen, was added 5-(hydroxy(3-(trifluoromethyl)-[1,2,4]triazolo[4,3-a]pyridin-7-yl) methyl)-2-methylbenzyl pivalate (1.35 g, 3.20 mmol) and DCM (39 mL) followed by thionyl chloride (0.20 mL, 2.73 mmol). After 20 minutes, the mixture was partitioned between DCM and distilled water. The pH of the aqueous layer was adjusted to pH 7 by the addition of saturated aqueous NaHCO₃. The layers were separated. The organic layer was dried over anhydrous Na₂SO₄, filtered, and concentrated to dryness under reduced pressure to afford the title compound (1.40 g, 99%). MS (ESI): mass calcd. for C₂₁H₂₁ClF₃N₃O₂, 439.1; m/z found, 440.1 [M+H]⁺.

Step E: Methyl 2,2-dimethyl-3-(4-methyl-3-((pivaloyloxy)methyl)phenyl)-3-(3-(trifluoromethyl)-[1,2,4]triazolo[4,3-a]pyridin-7-yl)propanoate. To a flask under argon, was added 5-(chloro(3-(trifluoromethyl)-[1,2,4]triazolo[4,3-a]pyridin-7-yl)methyl)-2-methylbenzyl pivalate (1.40 g, 3.18 mmol), DCM (82 mL), dimethyl ketene methyl trimethylsilyl acetal (0.970 mL, 4.77 mmol) and indium (III) bromide (228 mg, 0.637 mmol). After 18 hours, an additional equivalent of each dimethyl ketene methyl trimethylsilyl acetal and indium (III) bromide was added. After 4 days, the mixture was partitioned between hexanes-DCM (1:1) and saturated aqueous NaHCO₃. The layers were separated. The organic layer was dried over anhydrous Na₂SO₄, filtered, and concentrated to dryness under reduced pressure. The bright orange residue was purified by flash column chromatography (hexanes to ethyl acetate) to afford the title compound (438 mg, 27%) as a light orange foam. MS (ESI): mass calcd. for C₂₆H₃₀F₃N₃O₄, 505.2; m/z found, 506.5 [M+H]⁺.

Intermediate 123:
3-(3-(Benzyloxy)propoxy)propan-1-ol

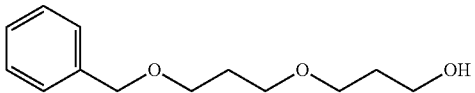 [SMILES: OCCCOCCCOCc1ccccc1]

Step A: 3-(Benzyloxy)propyl-4-methylbenzenesulfonate. 3-(Benzyloxy)propan-1-ol (10.0 g, 60.2 mmol), p-toluenesulfonyl chloride (17.2 g, 90.2 mmol), triethylamine (25.0 mL, 179 mmol), and dichloromethane (100 mL) were stirred at 20° C. for 3 hours before pouring into water (50 mL) and extracting with dichloromethane (2×). These extractions resulted in several organic fractions which were combined, dried over anhydrous Na₂SO₄, filtered, and concentrated under reduced pressure to give the product, which was purified by FCC (eluent:petroleum ether:ethyl acetate=1:0 to 5:1, gradient elution) to afford the title compound (18 g) as a brown oil, which was used in the next step without further purification. ¹H NMR (400 MHz, CDCl₃) δ 7.78 (d, J=8.4 Hz, 2H), 7.38-7.22 (m, 7H), 4.40 (s, 2H), 4.19-4.14 (m, 2H), 3.50 (t, J=6.0 Hz, 2H), 2.42 (s, 3H), 1.98-1.90 (m, 2H).

Step B: 3-(3-(benzyloxy)propoxy)propan-1-ol. Sodium hydride in mineral oil (6.0 g, 60% purity, 0.15 mmol) was added in portions to a solution of propane-1,3-diol (17.0 g, 223 mmol) and DMF (40 mL) at 0° C. The resulting mixture was stirred for 2 hours with gradual warming to room-temperature. The reaction mixture was again cooled to 0° C. and then a solution of 3-(benzyloxy)propyl 4-methylbenzenesulfonate (18.0 g) and DMF (40 mL) was added. This mixture was stirred while heating at 80° C. for 12 hours before cooling to room temperature, pouring into aqueous saturated NH₄Cl (40 mL) solution, and extracting with ethyl acetate (2×). These extractions resulted in several organic fractions which were combined, dried over anhydrous Na₂SO₄, filtered, and concentrated under reduced pressure to give the product, which was purified by FCC (eluent: petroleum ether:ethyl acetate=1:0 to 1:1, gradient elution) to afford the title compound (9.0 g, 71%) as a yellow solid. ¹H NMR (400 MHz, CDCl₃) δ 7.37-7.25 (m, 4H), 4.49 (s, 2H), 3.78-3.71 (m, 2H), 3.71-3.66 (m, 1H), 3.59 (t, J=5.6 Hz, 2H), 3.54 (t, J=6.4 Hz, 4H), 2.05 (s, 2H), 1.92-1.82 (m, 4H).

Intermediate 124: 7'-Bromo-2,2',3,3',5,6-hexahydrospiro[pyran-4,4'-pyrido[2,3-b][1,4,5]oxathiazepine] 1',1'-dioxide

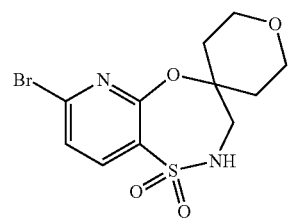 [SMILES: O=S1(=O)NCC2(CCOCC2)Oc2nc(Br)ccc21]

Step A: 6-Bromo-2-chloropyridine-3-sulfonyl chloride. HBF₄ (32.0 mL, 206 mmol) was added drop-wise to a solution of 6-bromo-2-chloropyridin-3-amine (30.0 g, 145 mmol) and acetonitrile (150 mL) which had been cooled to 0° C. The resulting mixture was stirred at 0° C. for 10 minutes before adding tert-butyl nitrite (26.0 mL, 219 mmol) drop-wise. The resulting mixture was stirred at 0° C. for 1 hour which resulted in the preparation of a 6-bromo-2-chloropyridine-3-diazonium tetrafluoroborate solution. In a separate 1 L three-necked round-bottomed flask was added copper(I) chloride (22.0 g, 222 mmol) and acetic acid (120 mL). This mixture was cooled to 0° C., SO₂ gas (>1.3 M) bubbled through it at 0° C. for 1 hour to prepare a sulfur solution. At this time, the above 6-bromo-2-chloropyridine-3-diazonium tetrafluoroborate solution, which had also been cooled to 0° C., was added drop-wise to the sulfur solution which had been cooled to 0° C. The resulting mixture was stirred for 12 hours with gradual warming to room temperature. The suspension was filtered through a pad of diatomaceous earth and the pad washed with ethyl acetate (100 mL). The filtrate was quenched with aqueous saturated NaHCO₃ (200 mL) solution, stirred for 20 minutes, and then extracted with ethyl acetate (3×). These extractions resulted in several organic fractions that were combined, washed with water (2×) and brine (50 mL), dried over anhydrous Na₂SO₄, filtered, and concentrated to dryness under reduced pressure. The residue was purified by flash chromatography (eluent: petroleum ether/ethyl acetate; 1:0 to 10:1, gradient elution) to afford the title compound (24 g), which was used in the next step without further purification.

Step B: 6-Bromo-2-chloro-N-((4-hydroxytetrahydro-2H-pyran-4-yl)methyl)pyridine-3-sulfonamide. A solution of 6-bromo-2-chloropyridine-3-sulfonyl chloride (48 g) and THF (100 mL) was added drop-wise to a mixture of 4-(aminomethyl)tetrahydro-2H-pyran-4-ol (20.0 g, 152 mmol), K₂CO₃ (65.0 g, 470 mmol), THF (100 mL), and H₂O (50 mL). The resulting mixture was stirred for 12 hours with gradual warming to room temperature before concentrating to dryness under reduced pressure. The residue was diluted with water (50 mL) and extracted with ethyl acetate (3×). These extractions resulted in several organic fractions that were combined, dried over anhydrous Na₂SO₄, filtered, and concentrated to dryness under reduced pressure. The residue was purified by flash chromatography (eluent:petroleum ether/ethyl acetate; 1:0 to 1:1, gradient elution) to afford the title compound (35 g), which was used in the next step without further purification.

Step C: 7'-bromo-2,2',3,3',5,6-hexahydrospiro[pyran-4,4'-pyrido[2,3-b][1,4,5]oxathiazepine] 1',1'-dioxide. t-BuOK (5.5 g, 49 mmoL) was added in portions to a solution of 6-bromo-2-chloro-N-((4-hydroxytetrahydro-2H-pyran-4-yl)methyl)pyridine-3-sulfonamide (10 g) and DMSO (40 mL) which had been cooled to 0° C. This mixture was then heated at 100° C. for 2 hours before concentrating to dryness under reduced pressure. The residue was diluted with H$_2$O (50 mL) and the pH of the solution was adjusted to pH=6 with 1 N HCl (20 mL) which resulted in the formation of a suspension. The solid of the suspension was isolated via filtration and the filter cake washed with petroleum ether (20 mL) before drying under reduced pressure to give the product (7.0 g), which was combined with another batch of 7'-bromo-2,2',3,3',5,6-hexahydrospiro[pyran[2,3-b][1,4,5]oxathiazepine] 1',1'-dioxide (14 g) to afford 21 g of product to be purified. The 21 g of product was then triturated with ethyl acetate (30 mL) and the solids were isolated via filtration. The filter cake was washed with petroleum ether/ethyl acetate (10:1, 50 mL) before drying under reduced pressure to afford the title compound (18.5 g) as a gray solid. MS (ESI): mass calcd. for C$_{11}$H$_{13}$BrN$_2$O$_4$S, 348.0, m/z found 349.0 [M+H]$^+$. $^1$H NMR (400 MHz, DMSO-d$_6$) δ 8.54-8.47 (m, 1H), 8.01 (d, J=8.0 Hz, 1H), 7.60 (d, J=8.0 Hz, 1H), 3.76-3.66 (m, 2H), 3.62-3.55 (m, 2H), 3.49 (d, J=6.4 Hz, 2H), 1.68-1.53 (m, 4H).

Intermediate 125: 7'-(2-(4,4-Difluoropiperidin-1-yl)ethoxy)-2,2',3,3',5,6-hexahydrospiro[pyran-4,4'-pyrido[2,3-b][1,4,5]oxathiazepine] 1',1'-dioxide

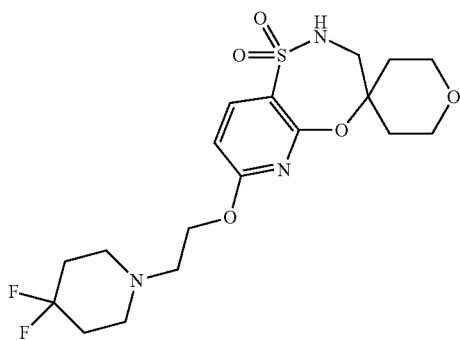 [SMILES: O=S1(=O)NCC2(CCOCC2)Oc2nc(OCCN3CCC(F)(F)CC3)ccc21]

To a solution of (4,4-difluoropiperidin-1-yl)ethan-1-ol (655 mg, 3.97 mmol) in toluene (5.0 mL) under N$_2$ which had been cooled to 0° C. was added NaH (164 mg, 60% dispersion in oil, 4.1 mmol) in two batches. After stirring at 0° C. for 10 minutes, the reaction was warmed to room temperature and the mixture stirred an additional 50 minutes. This solution was then transferred via syringe to a 48 mL screw-capped pressure vessel under N$_2$ containing 7'-bromo-2,2',3,3',5,6-hexahydrospiro[pyran-4,4'-pyrido[2,3-b][1,4,5]oxathiazepine] 1',1'-dioxide (500 mg, 1.32 mmol, Intermediate 124), tris(dibenzylidienaceton)dipalladium(0) (121 mg, 0.13 mmol) and [1,1'-binaphthalen]-2-yl-di-tert-butylphosphine (105 mg, 0.26 mmol). The reaction was heated to 100° C. for 18 h. After that time, the reaction was allowed to cool to room temperature, and 0.15 mL of AcOH was added. The mixture was then diluted with ethyl acetate and filtered through a pad of diatomaceous earth. The filtrate was concentrated to dryness under reduced pressure to give the product, which was purified by flash column chromatography (eluent: methanol/DCM, 0:1 to 1:10, gradient elution) to afford the title compound (202 mg, 35%). MS (ESI): mass calcd. for C$_{18}$H$_{25}$F$_2$N$_3$O$_5$S, 433.1, m/z found 434.1 [M+H]$^+$. $^1$H NMR (400 MHz, DMSO-d$_6$) δ 8.21 (s, 1H), 7.99 (d, J=8.4 Hz, 1H), 6.73 (d, J=8.4 Hz, 1H), 4.40 (t, J=5.8 Hz, 2H), 3.85-3.76 (m, 2H), 3.64 (d, J=11.3 Hz, 2H), 3.47 (s, 2H), 2.78 (t, J=5.8 Hz, 2H), 2.62 (t, J=5.7 Hz, 4H), 1.99-1.90 (m, 4H), 1.62 (d, J=4.3 Hz, 4H).

Intermediate 126: tert-Butyl 4-(2-((1',1'-dioxido-2,2',3,3',5,6-hexahydrospiro[pyran-4,4'-pyrido[2,3-b][1,4,5]oxathiazepin]-7'-yl)oxy)ethyl)piperazine-1-carboxylate

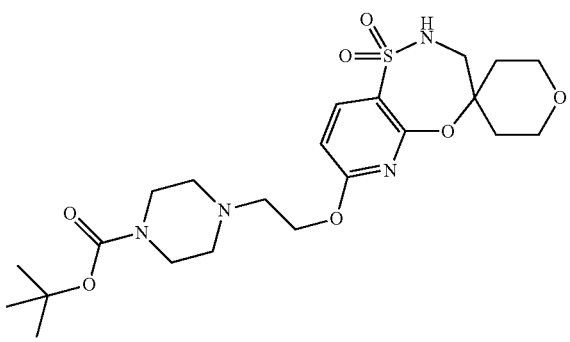 [SMILES: CC(C)(C)OC(=O)N1CCN(CCOc2ccc3c(n2)OC2(CCOCC2)CNS3(=O)=O)CC1]

To a solution of tert-butyl 4-(2-hydroxyethyl)piperazine-1-carboxylate (1020 mg, 4.4 mmol) in DMSO (6.0 mL) under N$_2$ was added sodium hydride (65 mg, 1.6 mmol) and the resulting mixture was allowed to stir at room temperature for 45 minutes. 7'-chloro-2,2',3,3',5,6-hexahydrospiro[pyran-4,4'-pyrido[2,3-b][1,4,5]oxathiazepine] 1',1'-dioxide (300 mg, 0.98 mmol, Intermediate 68) was then added and the reaction stirred at room temperature for 18 h. The reaction was quenched with aqueous saturated NH$_4$Cl solution and extracted with ethyl acetate (4×). These extractions resulted in several organic fractions which were combined, dried over sodium sulfate and concentrated to dryness under reduced pressure. The residue was purified by flash column chromatography (eluent: MeOH/DCM; 0:100 to 1:10, gradient elution) to afford the title compound (382 mg, 78%). $^1$H NMR (400 MHz, DMSO-d$_6$) δ 8.20 (s, 1H), 7.98 (d, J=8.4 Hz, 1H), 6.73 (d, J=8.4 Hz, 1H), 4.40 (t, J=5.8 Hz, 2H), 3.81 (ddd, J=13.1, 9.2, 4.2 Hz, 2H), 3.63 (dd, J=10.8, 3.9 Hz, 2H), 3.46 (s, 2H), 2.71 (t, J=5.8 Hz, 2H), 2.42 (t, J=5.1 Hz, 4H), 1.62 (t, J=4.4 Hz, 4H), 1.39 (s, 9H).

Intermediate 127: 7'-(2-(Piperidin-1-yl)ethoxy)-2',3'-dihydrospiro[cyclopropane-1,4'-pyrido[2,3-b][1,4,5]oxathiazepine] 1',1'-dioxide

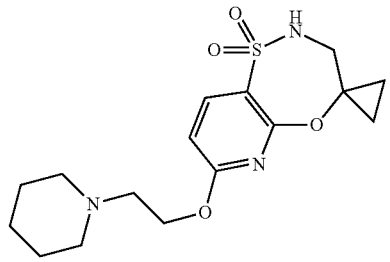 [SMILES: O=S1(=O)NCC2(CC2)Oc2nc(OCCN3CCCCC3)ccc21]

To a 48-mL screw capped pressure vessel under N₂ was added 7'-chloro-2',3'-dihydrospiro[cyclopropane-1,4'-pyrido[2,3-b][1,4,5]oxathiazepine] 1',1'-dioxide (400 mg, 1.5 mmol, Intermediate 67), 2-(piperidin-1-yl)ethan-1-ol (595 mg, 4.6 mmol), cesium carbonate (1.5 g, 4.6 mmol), Josiphos Pd(0) pre-catalyst G3 (142 mg, 0.15 mmol) and DMA (10 mL). The mixture was sparged with N₂ for 5 minutes and then heated to 100° C. for 18 h. The reaction mixture was allowed to cool to room temperature and poured into a 50/50 mixture of brine/water and extracted with ethyl acetate. These extractions resulted in several organic fractions which were combined, dried over sodium sulfate and concentrated to dryness under reduced pressure. The residue purified by flash column chromatography (eluent, MeOH/DCM; 0:100 to 3:20, gradient elution) to afford the title compound (240 mg, 44%). LC-MS (ESI): mass calcd. for $C_{16}H_{23}N_3O_4S$, 353.1, m/z found 354.2 [M+H]⁺. ¹H NMR (400 MHz, CDCl₃) δ 7.98 (d, J=8.5 Hz, 1H), 6.52 (d, J=8.5 Hz, 1H), 4.33 (t, J=6.0 Hz, 2H), 3.56 (s, 2H), 2.69 (t, J=6.0 Hz, 2H), 2.47 (s, 4H), 1.59 (s, 4H), 1.43-1.34 (m, 2H), 1.17-1.10 (m, 2H), 0.71-0.66 (m, 2H).

Intermediate 128: tert-Butyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate

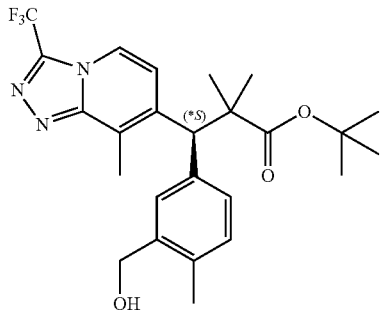 [SMILES: Cc1ccc([C@@H](c2ccn3c(C(F)(F)F)nnc3c2C)C(C)(C)C(=O)OC(C)(C)C)cc1CO]

Step A: 8-Methyl-3-(trifluoromethyl)-7-vinyl-[1,2,4]triazolo[4,3-a]pyridine. A mixture of 7-bromo-8-methyl-3-(trifluoromethyl)-[1,2,4]triazolo[4,3-a]pyridine (60.0 g, 214 mmol, Intermediate 24), potassium trifluoro(vinyl)borate (57.0 g, 426 mmol), K₃PO₄ (136 g, 641 mmol), 1,4-dioxane (500 mL), and H₂O (100 mL) was sparged with Ar for 5 minutes and then treated with Pd(dppf)Cl₂ (9.4 g, 13 mmol). The resultant mixture was sparged with Ar again for another 5 minutes and then heated at 110° C. for 16 hours before cooling to room-temperature. The suspension was filtered, and the solids were washed with ethyl acetate (200 mL). The filtrate was poured into H₂O (500 mL), and extracted with ethyl acetate (3×). These extractions resulted in several organic fractions that were combined, dried over anhydrous Na₂SO₄, filtered, and concentrated to dryness under reduced pressure. The residue was purified by flash chromatography (petroleum ether/ethyl acetate; 10:1 to 1:1, gradient elution) to afford the title compound (42 g, 86%). MS (ESI): mass calcd. for $C_{10}H_8F_3N_3$ 227.1, m/z found 228.1 [M+H]⁺.

Step B: 8-Methyl-3-(trifluoromethyl)-[1,2,4]triazolo[4,3-a]pyridine-7-carbaldehyde. K₂OsO₄*2H₂O (1.36 g, 3.69 mmol) was added to a solution of 8-methyl-3-(trifluoromethyl)-7-vinyl-[1,2,4]triazolo[4,3-a]pyridine (21 g, 92 mmol) 1,4-dioxane (700 mL) and H₂O (distilled, 700 mL). NaIO4 (59 g, 276 mmol) was added and the resulting mixture stirred at room-temperature for 2 hours. The mixture was filtered, quenched with H₂O (600 mL) and extracted with ethyl acetate (3×). These extractions resulted in several organic fractions that were combined, dried over anhydrous Na₂SO₄, filtered, and concentrated to dryness under reduced pressure. The residue was purified by flash chromatography (eluent:petroleum ether:/ethyl acetate; 10:1 to 3:1, gradient elution) to afford the title compound. MS (ESI): mass calcd. for $C_9H_6F_3N_3O$, 229.1, m/z found 230.1 [M+H]⁺.

Step C: (3-(((tert-Butyldimethylsilyl)oxy)methyl)-4-methylphenyl)(8-methyl-3-(trifluoromethyl)-[1,2,4]triazolo[4,3-a]pyridin-7-yl)methanol. i-PrMgCl.LiCl (80.6 mL, 1.3 M in THF, 105 mmol) was added drop-wise to a mixture of tert-butyl-((5-iodo-2-methylbenzyl)oxy)dimethylsilane (27.8 g, 76.7 mmol) and THF (200 mL) which had been cooled to −15° C. The reaction mixture was stirred at −15° C. for 1 hour followed by drop-wise addition of a solution of 8-methyl-3-(trifluoromethyl)-[1,2,4]triazolo[4,3-a]pyridine-7-carbaldehyde (16 g, 70 mmol) in THF (100 mL). The reaction mixture was stirred for 2 hours with gradual warming to room-temperature before quenching with saturated NH₄Cl (500 mL) and extracting with ethyl acetate (3×). These extractions resulted in several organic fractions that were combined, dried over anhydrous Na₂SO₄, filtered, and concentrated to dryness under reduced pressure. The residue was purified by flash chromatography (eluent:petroleum ether/ethyl acetate; 20:1 to 2:1, gradient elution) to afford the title compound (24 g, 73%). MS (ESI): mass calcd. for $C_{23}H_{30}F_3N_3O_2Si$, 465.2, m/z found 466.3 [M+H]⁺.

Step D: tert-Butyl 3-(3-(((tert-butyldimethylsilyl)oxy)methyl)-4-methylphenyl)-2,2-dimethyl-3-(8-methyl-3-(trifluoromethyl)-[1,2,4]triazolo[4,3-a]pyridin-7-yl)propanoate. 2,2,2-Trichloroacetonitrile (431 µL, 4.30 mmol) was added to a solution of (3-(((tert-butyldimethylsilyl)oxy)methyl)-4-methylphenyl)(8-methyl-3-(trifluoromethyl)-[1,2,4]triazolo[4,3-a]pyridin-7-yl)methanol (1.0 g, 2.1 mmol), DBU (64 µL, 0.43 mmol), and 1,2-dichloroethane (5 mL) under N₂. After stirring for 1 hour at room-temperature ((1-(tert-butoxy)-2-methylprop-1-en-1-yl)oxy)trimethylsilane (4.65 g, 21.5 mmol) and BF₃.Et₂O (0.24 mL, 1.9 mmol) were added and the reaction stirred for an additional 1.5 hours before quenching with H₂O (30 mL) and extracting with dichloromethane (3×). These extractions resulted in several organic fractions that were combined, dried over anhydrous Na₂SO₄, filtered, and concentrated to dryness under reduced pressure. The residue was purified by flash chromatography (eluent:petroleum ether/ethyl acetate; 20:1 to 5:1, gradient elution) to afford the title compound (380 mg, 27.9%). MS (ESI): mass calcd. for $C_{31}H_{44}F_3N_3O_3Si$, 591.3, m/z found 592.3 [M+H]⁺.

Step E: tert-Butyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate. TBAF (7.3 mL, 1 M in THF, 7.3 mmol) was added to a solution of tert-butyl 3-(3-(((tert-butyldimethylsilyl)oxy)methyl)-4-methylphenyl)-2,2-dimethyl-3-(8-methyl-3-(trifluoromethyl)-[1,2,4]triazolo[4,3-a]pyridin-7-yl)propanoate (2.15 g, 3.63 mmol) and THF (20 mL). The resulting mixture was stirred at room-temperature for 2 hours before quenching with H₂O (50 mL) and extracting with ethyl acetate (3×). These extractions resulted in several organic fractions that were combined, washed with brine (3×), dried over anhydrous Na₂SO₄, and concentrated to dryness under reduced pressure. The residue was purified by flash chromatography (eluent:petroleum ether/ethyl acetate; 10:1 to 1:1, gradient elution) to afford the title compound (1.3 g, 75%). MS (ESI): mass calcd. for $C_{25}H_{30}F_3N_3O_3$ 477.2, m/z found 478.2 [M+H]$^+$.

Step F: tert-butyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate. The mixture of tert-butyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate (1.3 g, 2.7 mmol) isomers were separated by chiral SFC (stationary phase: REGIS (s,s) WHELK-O1 250 mm×50 mm, 10 am; eluent: 35% to 35% (v/v) supercritical $CO_2$ in i-PrOH and $H_2O$ with 0.1% $NH_3$). The first eluting isomer (561 mg, 43%) was designated (*S). MS (ESI): mass calcd. for $C_{25}H_{30}F_3N_3O_3$ 477.2, m/z found 478.3 [M+H]$^+$. $^1$H NMR (400 MHz, DMSO-d$_6$) δ 8.46 (d, J=7.3 Hz, 1H), 7.32-7.26 (m, 2H), 7.12-7.08 (m, 1H), 7.07-7.04 (m, 1H), 5.04 (t, J=5.3 Hz, 1H), 4.72 (s, 1H), 4.43 (d, J=5.1 Hz, 2H), 2.65 (s, 3H), 2.17 (s, 3H), 1.29 (s, 3H), 1.21 (s, 3H), 1.17 (s, 9H).

Intermediate 129: tert-Butyl (*S)-3-(3-(difluoromethyl)-8-methyl-[1,2,4]triazolo[4,3-a]pyridine-7-yl)-3-(3-(hydroxymethyl)-4-methylphenyl)-2,2-dimethylpropanoate

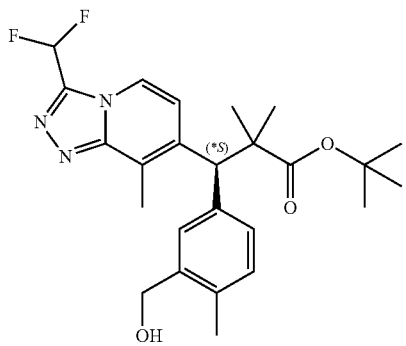 [SMILES: Cc1ccc([C@@H](c2ccn3c(C(F)F)nnc3c2C)C(C)(C)C(=O)OC(C)(C)C)cc1CO]

Step A: (5-Iodo-2-methylphenyl)methanol. Borane tetrahydrofuran complex (276 mL, 1 M in THF, 276 mmol) was added drop-wise to a solution of 5-iodo-2-methylbenzoic acid (60.0 g, 229 mmol) and THF (500 mL) that had been cooled to 0° C. The resulting mixture was stirred for 20 minutes at room temperature and then heated at 50° C. for 3 hours before cooling to 0° C.

This mixture was treated with $H_2O$ (250 mL) dropwise, stirred for another 1 hour with gradual warming to room temperature, and then extracted with ethyl acetate (3×). These extractions resulted in several organic fractions that were combined, washed with brine (200 mL), dried over anhydrous $Na_2SO_4$, filtered, and concentrated to dryness under reduced pressure to give the title compound (55 g, 97%). $^1$H NMR (400 MHz, DMSO-d$_6$) δ 7.66 (s, 1H), 7.50-7.39 (m, 1H), 6.90 (d, J=7.8 Hz, 1H), 4.41 (s, 2H), 2.19-2.07 (m, 3H).

Step B: tert-Butyl((5-iodo-2-methylbenzyl)oxy)dimethylsilane. TBSCl (37.0 g, 245 mmol) was added to a solution of (5-iodo-2-methylphenyl)methanol (55.0 g, 222 mmol), imidazole (30.6 g, 449 mmol), and dichloromethane (600 mL) which had been cooled to 0° C. The resulting mixture was stirred for 16 hours with gradual warming to room-temperature. After such time, the reaction mixture was heated at 75° C. for 3 hours before cooling to room temperature. Solids that had formed during the above described procedure were isolated via filtration and the filtrate concentrated to dryness under reduced pressure to give the product, which was purified by flash chromatography (eluent:petroleum ether/ethyl acetate, 1:0, gradient elution) to afford the title compound (67 g, 83%). $^1$H NMR (400 MHz, DMSO-d$_6$) δ 7.60 (s, 1H), 7.41 (dd, J=7.9, 1.8 Hz, 1H), 6.87 (d, J=7.8 Hz, 1H), 4.55 (s, 2H), 2.08 (s, 3H), 0.82 (s, 9H), 0.08 (s, 6H).

Step C: tert-Butyldimethyl((2-methyl-5-vinylbenzyl)oxy)silane. Pd(dppf)Cl$_2$ (5.5 g, 7.5 mmol) was added to a mixture of tert-butyl((5-iodo-2-methylbenzyl)oxy)dimethylsilane (67.0 g, 185 mmol), potassium trifluoro(vinyl)borate (50.0 g, 373 mmol), $K_3PO_4$ (119 g, 561 mmol), 1,4-dioxane (700 mL), and $H_2O$ (140 mL) under $N_2$. The mixture was stirred at 100° C. for 3 hours before cooling to room-temperature, pouring it into water (100 mL), and extracting with ethyl acetate (3×). These extractions resulted in several organic fractions that were washed with brine (100 mL), dried over anhydrous $Na_2SO_4$, filtered, and concentrated to dryness under reduced pressure. The residue was purified by flash chromatography (eluent:petroleum ether/ethyl acetate, 1:0 to 1:0, gradient elution) to afford the title compound (42.1 g, 87%). $^1$H NMR (400 MHz, DMSO-d$_6$) δ 7.44 (s, 1H), 7.24 (dd, J=7.7, 1.6 Hz, 1H), 7.11 (d, J=7.6 Hz, 1H), 6.69 (dd, J=17.6, 11.0 Hz, 1H), 5.72 (dd, J=17.6, 0.7 Hz, 1H), 5.21-5.16 (m, 1H), 4.67 (s, 2H), 2.22 (s, 3H), 0.91 (s, 9H), 0.08 (s, 6H).

Step D: 3-(((tert-Butyldimethylsilyl)oxy)methyl)-4-methylbenzaldehyde. $K_2OsO_4$·2$H_2O$ (2.91 g, 7.90 mmol) was added to a solution of tert-butyldimethyl((2-methyl-5-vinylbenzyl)oxy)silane (42.0 g, 158 mmol), 1,4-dioxane (500 mL), and $H_2O$ (500 mL). The mixture was treated with $NaIO_4$ (102 g, 477 mmol) slowly and then stirred at room-temperature for 2 hours. The resulting suspension was isolated via filtration and the filter cake washed with ethyl acetate (3×). The aqueous layer was extracted with ethyl acetate (2×). These extractions resulted in several organic fractions that were washed with brine (100 mL), dried over anhydrous $Na_2SO_4$, filtered, and concentrated to dryness under reduced pressure The residue was purified by flash chromatography (eluent:petroleum ether/ethyl acetate; 1:0 to 10:1, gradient elution) to afford the title compound (34.7 g, 83%). $^1$H NMR (400 MHz, DMSO-d$_6$) δ 9.95 (s, 1H), 7.90 (s, 1H), 7.72 (dd, J=7.7, 1.6 Hz, 1H), 7.38 (d, J=7.8 Hz, 1H), 4.75 (s, 2H), 2.32 (s, 3H), 0.92 (s, 9H), 0.10 (s, 6H).

Step E: 2-Hydrazinyl-4-iodo-3-methylpyridine. 2-Fluoro-4-iodo-3-methylpyridine (50.0 g, 211 mmol) was added to a 1 L round-bottomed flask containing hydrazine hydrate (345 mL, 7.11 mol). The resulting mixture was heated at 50° C. for 16 hours before cooling to the room temperature. The resulting suspension was isolated via filtration and the filter cake washed with water (3×) before drying under reduced pressure to afford the title compound (50.2 g, 96%).

Step F: 3-(Difluoromethyl)-7-iodo-8-methyl-[1,2,4]triazolo[4,3-a]pyridine. 2,2,2-Trifluoroacetic anhydride (502 mL, 4.04 mmol) was added drop-wise to 2-hydrazinyl-4-iodo-3-methylpyridine (50.2 g, 202 mmol). The resulting mixture was heated at 75° C. for 32 hours before cooling to room-temperature. The pH of the solution was adjusted to pH 7-8 with 5 N aqueous NaOH solution. The resulting suspension was filtered, and the filter cake washed with water (3×) before drying under reduced pressure to afford the title compound (56.8 g, 79%). MS (ESI): mass calcd. for $C_8H_6F_2IN_3$ 309.0 m/z found 310.0 [M+H]$^+$. $^1$H NMR (400 MHz, DMSO-d$_6$) δ 8.23 (d, J=7.3 Hz, 1H), 7.86-7.58 (m, 1H), 7.45 (d, J=7.0 Hz, 1H), 2.64 (s, 3H).

Step G: (3-(((tert-Butyldimethylsilyl)oxy)methyl)-4-methylphenyl)(3-(difluoromethyl)-8-methyl-[1,2,4]triazolo[4,3-a]pyridin-7-yl)methanol. i-PrMgCl.LiCl (33.5 mL, 1.3 M in THF, 43.6 mmol) was added drop-wise to a solution of 3-(difluoromethyl)-7-iodo-8-methyl-[1,2,4]triazolo[4,3-a]pyridine (12.3 g, 39.8 mmol) and THF (150 mL) which had been cooled to −20° C. This mixture was stirred at −20° C. for 1 hour. At such time a solution of 3-(((tert-butyldimethylsilyl)oxy)methyl)-4-methylbenzaldehyde (9.6 g, 36 mmol) and THF (50 mL) was added dropwise. The resulting mixture was stirred for 16 hours with gradual warming to room-temperature before quenching with aqueous saturated $NH_4Cl$ solution (50 mL), pouring into $H_2O$ (30 mL), and extracting with ethyl acetate (3×). These extractions resulted in several organic fractions that were combined, washed with brine (50 mL), dried over anhydrous $Na_2SO_4$, filtered, and concentrated to dryness under reduced pressure. The residue was purified by flash chromatography (eluent:petroleum ether/ethyl acetate, 10:1 to 1:1, gradient elution) to afford the title compound (5 g) which was used without further purification. MS (ESI): mass calcd. for $C_{23}H_{31}F_2N_3O_2Si$, 447.2 m/z found 448.2 [M+H]⁺.

Step H: 7-((3-(((tert-Butyldimethylsilyl)oxy)methyl)-4-methylphenyl)chloromethyl)-3-(difluoromethyl)-8-methyl-[1,2,4]triazolo[4,3-a]pyridine. $SOCl_2$ (3.6 mL, 50 mmol) was added dropwise to a solution of (3-(((tert-butyldimethylsilyl)oxy)methyl)-4-methylphenyl)(3-(difluoromethyl)-8-methyl-[1,2,4]triazolo[4,3-a]pyridin-7-yl)methanol (27.3 g, 40.9 mmol), 2,6-di-tert-butylpyridine (23 mL), and dichloromethane (180 mL) which had been cooled to 0° C. The resulting mixture was stirred at 0° C. for 20 minutes before adjusting the pH with aqueous saturated $NaHCO_3$ solution to pH=7. The organic layer was dried over anhydrous $Na_2SO_4$, filtered, and concentrated to dryness under reduced pressure. The residue was purified by FCC (eluent:petroleum ether/ethyl acetate, 10:1 to 5:1, gradient elution) to afford the title compound (18.5 g).

Step I: tert-Butyl 3-(3-(((tert-butyldimethylsilyl)oxy)methyl)-4-methylphenyl)-3-(3-(difluoromethyl)-8-methyl-[1,2,4]triazolo[4,3-a]pyridin-7-yl)-2,2-dimethylpropanoate. $InBr_3$ (3.06 g, 8.63 mmol) was added to a solution of 7-((3-(((tert-butyldimethylsilyl)oxy)methyl)-4-methylphenyl)chloromethyl)-3-(difluoromethyl)-8-methyl-[1,2,4]triazolo[4,3-a]pyridine (17.5 g, 37.6 mmol), ((1-(tert-butoxy)-2-methylprop-1-en-1-yl)oxy)trimethylsilane (81.28 g, 375.6 mmol), and dichloromethane (200 mL) under $N_2$. The resulting mixture was sparged with $N_2$ for another 5 minutes and then stirred at room temperature under $N_2$ for 3 days before quenching with $H_2O$ (50 mL). The mixture was combined with another batch of tert-butyl 3-(3-(((tert-butyldimethylsilyl)oxy)methyl)-4-methylphenyl)-3-(3-(difluoromethyl)-8-methyl-[1,2,4]triazolo[4,3-a]pyridin-7-yl)-2,2-dimethylpropanoate and the organic and aqueous portions were separated. The aqueous layer extracted with ethyl acetate (3×). These extractions resulted in several organic fractions that were combined, dried over anhydrous $Na_2SO_4$, filtered, and concentrated to dryness under reduced pressure. The residue was purified by FCC (eluent: petroleum ether/ethyl acetate, 10:1 to 3:1, gradient elution) to afford 23 g of the title compound. This material was further purified by preparative HPLC (stationary phase: YMC-Triart Prep C18, 150 mm×40 mm×7 μm column, eluent: 70% to 100% (v/v) $CH_3CN$ and $H_2O$ with 0.225% HCOOH) to afford the title compound (7.6 g). ¹H NMR (400 MHz, DMSO-d₆) δ 8.42 (d, J=7.3 Hz, 1H), 7.89-7.57 (m, 1H), 7.18-7.12 (m, 3H), 7.12-7.06 (m, 1H), 4.73 (s, 1H), 4.60 (s, 2H), 2.59 (s, 3H), 2.16 (s, 3H), 1.31 (s, 3H), 1.20 (d, J=2.0 Hz, 3H), 1.19-1.16 (m, 9H), 0.75 (s, 9H), −0.02--0.09 (m, 6H).

Step J: tert-Butyl 3-(3-(difluoromethyl)-8-methyl-[1,2,4]triazolo[4,3-a]pyridin-7-yl)-3-(3-(hydroxymethyl)-4-methylphenyl)-2,2-dimethylpropanoate. TBAF (28.3 mL, 1 M in THF, 28.3 mmol) was added to a solution of tert-butyl 3-(3-(((tert-butyldimethylsilyl)oxy)methyl)-4-methylphenyl)-3-(3-(difluoromethyl)-8-methyl-[1,2,4]triazolo[4,3-a]pyridin-7-yl)-2,2-dimethylpropanoate (8.1 g, 14 mmol) and THF (80 mL). The resulting mixture was stirred for 5 hours at room-temperature before pouring into water (50 mL) and extracting with ethyl acetate (3×). These extractions resulted in several organic fractions that were combined, washed with brine (50 mL), dried over anhydrous $Na_2SO_4$, filtered, and concentrated to dryness under reduced pressure. The residue was purified by flash chromatography (eluent:petroleum ether/ethyl acetate, 1:0 to 2:3, gradient elution) to afford the title compound (5.4 g, 84%). MS (ESI): mass calcd. for $C_{25}H_{31}F_2N_3O_3$ 459.2 m/z found 460.3 [M+H]⁺.

Step K: (*S)-tert-Butyl 3-(3-(difluoromethyl)-8-methyl-[1,2,4]triazolo[4,3-a]pyridin-7-yl)-3-(3-(hydroxymethyl)-4-methylphenyl)-2,2-dimethylpropanoate. The mixture of 2,2-dimethyl-3-(8-methyl-3-(trifluoromethyl)-[1,2,4]triazolo[4,3-a]pyridin-7-yl)-3-(6-methyl-4-(3-(morpholine-4-carbonyl)phenyl)benzofuran-2-yl)propanoic acid isomers were separated by chiral SFC (stationary phase: REGIS (s,s) WHELK-O1 250 mm×50 mm, 10 μm, eluent: 35% to 35% (v/v) supercritical $CO_2$ in IPA with 0.1% $NH_3$). The first eluting isomer (2.46 g, 37%) was designated (*S). MS (ESI): mass calcd. for $C_{25}H_{31}F_2N_3O_3$ 459.2 m/z found 460.2 [M+H]⁺. ¹H NMR (400 MHz, DMSO-d₆) δ 8.43 (d, J=7.6 Hz, 1H), 7.86-7.58 (m, 1H), 7.29-7.23 (m, 2H), 7.12-7.08 (m, 1H), 7.07-7.03 (m, 1H), 5.05 (t, J=5.4 Hz, 1H), 4.68 (s, 1H), 4.42 (d, J=5.4 Hz, 2H), 2.61 (s, 3H), 2.17 (s, 3H), 1.28 (s, 3H), 1.21 (s, 3H), 1.16 (s, 9H).

Intermediate 130: Ethyl 3-(3-(((*S)-5,5-dioxido-7,7a,8,9,10,11-hexahydro-6H-dipyrido[2,1-d:2',3'-d][1,2,5]thiadiazepin-6-yl)methyl)-4-methylphenyl)-3-(8-methyl-3-(trifluoromethyl)-[1,2,4]triazolo[4,3-a]pyridine-7-yl)propanoate

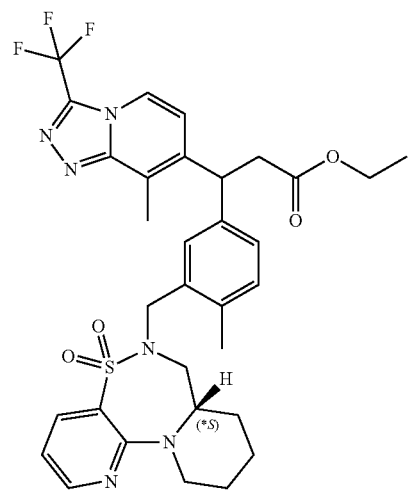 [SMILES: CCOC(=O)CC(c1ccc(C)c(CN2C[C@@H]3CCCCN3c3ncccc3S2(=O)=O)c1)c1ccn2c(C(F)(F)F)nnc2c1C]

To a solution of ethyl 3-(3-(hydroxymethyl)-4-methylphenyl)-3-(8-methyl-3-(trifluoromethyl)-[1,2,4]triazolo[4,3-a]pyridine-7-yl)propanoate (1.5 g, 3.56 mmol, Intermediate 25) in THF (25 mL) was added (*S)-7,7a,8,9,10,11-hexahydro-6H-dipyrido[2,1-d:2',3'-d][1,2,5]thiadiazepine 5,5-dioxide (1.3 g, 4.97 mmol) and triphenylphosphine (1.4 g, 5.34 mmol). After the reaction mixture was homogenous, diisopropyl azodicarboxylate (1.2 mL, 5.94 mmol) was added and the mixture stirred at room temperature for 18 h. The reaction mixture was then poured into saturated bicarbonate and extracted with ethyl acetate (3×). These extractions resulted in several organic fractions which were combined, dried over sodium sulfate and concentrated to dryness under reduced pressure. The residue was dissolved in DCM and purified by flash column chromatography (eluent: EtOAc/Hexanes; 0:100 to 40:60, gradient elution) to afford the title compound (1450 mg, 62%). MS (ESI): mass calcd. for $C_{32}H_{35}F_3N_6O_4S$, 656.2, m/z found 657.3 [M+H]$^+$.

Intermediate 131: 7'-Chloro-8'-methyl-2',3'-dihydrospiro[cyclopropane-1,4'-pyrido[2,3-b][1,4,5]oxathiazepine] 1',1'-dioxide

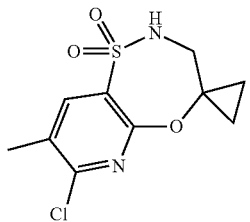 [SMILES: Cc1cc2c(nc1Cl)OC1(CC1)CNS2(=O)=O]

Step A: 2,6-Dichloro-5-methylpyridin-3-amine. NCS (32.9 g, 246 mmol) was added in portions to a solution of 2-chloro-5-methylpyridin-3-amine (35.0 g, 245 mmol) and acetonitrile (250 mL). The resulting mixture was heated at 35° C. for 16 hours before cooling to room temperature. The resulting suspension was filtered, and the filtrate concentrated to dryness under reduced pressure. The residue was purified by flash chromatography (eluent:petroleum ether/ethyl acetate; 1:0 to 4:1, gradient elution) to afford the title compound (45 g, 99%). MS (ESI): mass calcd. For $C_6H_6Cl_2N_2$ 176.0 m/z found 176.8 [M+H]$^+$. $^1$H NMR (400 MHz, DMSO-d$_6$) δ 7.07 (s, 1H), 5.65 (br s, 2H), 2.53 (s, 3H).

Step B: 2,6-Dichloro-5-methylpyridine-3-sulfonyl chloride. HBF$_4$ (56.0 mL, 365 mmol) was added drop-wise to a solution of 2,6-dichloro-5-methylpyridin-3-amine (43.0 g, 243 mmol) and acetonitrile (300 mL) at which had been cooled to 0° C. This mixture was stirred at 0° C. for 10 minutes, treated with tert-butyl nitrite (44.0 mL, 370 mmol) drop-wise, followed by additional stirring at 0° C. for another 2 hours to prepare a 2,6-dichloro-5-methylpyridine-3-diazonium tetrafluoroborate solution. In a separate flask, copper(I) chloride (36.0 g, 364 mmol) and acetic acid (300 mL) were mixed and cooled to 0° C. This copper chloride/acetic acid was then treated with the above 2,6-dichloro-5-methylpyridine-3-diazonium tetrafluoroborate solution which had also been cooled to 0° C. The resulting mixture was stirred for 16 hours with gradual warming to room-temperature. The suspension was filtered through a pad of diatomaceous and the pad washed with ethyl acetate. The filtrate was concentrated to dryness under reduced pressure and then purified by flash chromatography (eluent:petroleum ether/ethyl acetate; 1:0 to 1:1, gradient elution) to afford the title compound (39.5 g) as a yellow oil, which was used in the next step without further purification. $^1$H NMR (400 MHz, DMSO-d$_6$) δ 8.13 (s, 1H), 2.28 (s, 3H).

Step C: 2,6-Dichloro-N-((1-hydroxycyclopropyl)methyl)-5-methylpyridine-3-sulfonamide. To a mixture of K$_2$CO$_3$ (28.7 g, 208 mmol), THF (100 mL) and H$_2$O (20 mL) which had been cooled to 0° C. was added 1-(aminomethyl)cyclopropanol (4.30 g, 49.4 mmol). The resulting mixture was stirred for 10 minutes at 0° C. and then treated with 2,6-dichloro-5-methylpyridine-3-sulfonyl chloride (18.0 g, 69.1 mmol). This mixture was stirred for 2 hours at 0° C. before concentrating to dryness under reduced pressure. The residue was poured into water and extracted with ethyl acetate (5×). These extractions resulted in several organic fractions that were combined, dried over anhydrous Na$_2$SO$_4$, filtered, and concentrated to dryness under reduced pressure. The residue was purified by flash chromatography (eluent:petroleum ether/ethyl acetate; 1:0 to 1:1, gradient elution) to afford the title compound (12 g, 49%). MS (ESI) mass calcd. for $C_{10}H_{12}Cl_2N_2O_3S$, 310.0 m/z found 310.8 [M+H]$^+$. $^1$H NMR (400 MHz, DMSO-d$_6$) δ 8.32 (s, 1H), 8.23-8.17 (m, 1H), 5.17 (s, 1H), 3.04-2.98 (m, 2H), 2.35 (s, 3H), 0.42 (s, 4H).

Step D: 7'-Chloro-8'-methyl-2',3'-dihydrospiro[cyclopropane-1,4'-pyrido[2,3-b][1,4,5]oxathiazepine] 1',1'-dioxide. To a solution of 2,6-dichloro-N-((4-hydroxytetrahydro-2H-pyran-4-yl)methyl)-5-methylpyridine-3-sulfonamide (11.0 g, 35.3 mmol) and DMSO (80 mL) was added t-BuOK (10.0 g, 89.1 mmol). This mixture was heated at 90° C. for 16 hours before cooling to room-temperature, and concentrating to dryness under reduced pressure to give the product, which was purified by flash chromatography (eluent:petroleum ether/ethyl acetate; 1:0 to 3:2, gradient elution). This product was further purified by reverse phase preparative HPLC (stationary phase: PREPL-M Xbridge BEH C18 250 mm×50 mm×10 m column; eluent, CH$_3$CN/H$_2$O (with 0.04% NH$_3$ and 10 mM NH$_4$HCO$_3$) 10% to 43%, gradient elution) to afford the title product (2.3 g, 23%). MS (ESI) mass calcd. for $C_{10}H_{11}ClN_2O_3S$, 274.0 m/z found 275.0 [M+H]$^+$. $^1$H NMR (400 MHz, DMSO-d$_6$) δ 8.31 (s, 1H), 8.24 (s, 1H), 3.52 (br s, 2H), 2.37 (s, 3H), 0.97-0.91 (m, 2H), 0.82-0.76 (m, 2H).

Intermediate 132: 7'-Chloro-8'-methyl-2,2',3,3',5,6-hexahydrospiro[pyran-4,4'-pyrido[2,3-b][1,4,5]oxathiazepine] 1',1'-dioxide

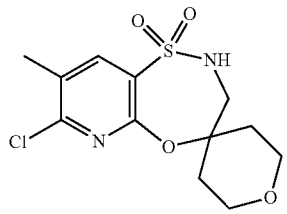 [SMILES: Cc1cc2c(nc1Cl)OC1(CCOCC1)CNS2(=O)=O]

The title compound (8.48 g, 63%) was prepared using analogous conditions as described in Intermediate 131 where 4-(aminomethyl)tetrahydro-2H-pyran-4-ol was used instead of 1-(aminomethyl)cyclopropan-1-ol in step C. MS (ESI): mass calcd. for $C_{12}H_{15}ClN_2O_4S$, 318.0 m/z found 318.9 [M+H]$^+$. $^1$H NMR (400 MHz, DMSO-d$_6$) δ 8.50 (br s, 1H), 8.14 (s, 1H), 3.83-3.69 (m, 2H), 3.67-3.56 (m, 2H), 3.50 (s, 2H), 2.36 (s, 3H), 1.71-1.51 (m, 4H).

Intermediate 133: tert-Butyl 4-(2-((1',1'-dioxido-2,2',3,3',5,6-hexahydrospiro[pyran-4,4'-pyrido[2,3-b][1,4,5]oxathiazepin]-7'-yl)oxy)ethyl)piperidine-1-carboxylate

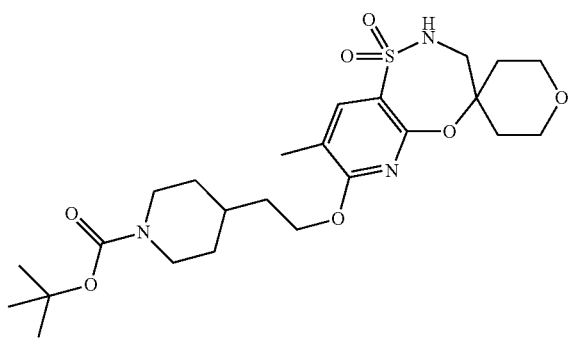 [SMILES: Cc1cc2c(nc1OCCC1CCN(C(=O)OC(C)(C)C)CC1)OC1(CCOCC1)CNS2(=O)=O]

The title compound (450 mg, 93%) was prepared using analogous conditions as described in Intermediate 126 where tert-butyl 4-(2-hydroxyethyl-piperidine)-1-carboxylate was used instead of tert-butyl 4-(2-hydroxyethyl)piperazine-1-carboxylate and 7'-chloro-8'-methyl-2,2',3,3',5,6-hexahydrospiro[pyran-4,4'-pyrido[2,3-b][1,4,5]oxathiazepine] 1',1'-dioxide (Intermediate 132) was used instead of 7'-chloro-2,2',3,3',5,6-hexahydrospiro[pyran-4,4'-pyrido[2,3-b][1,4,5]oxathiazepine] 1',1'-dioxide (Intermediate, 68). MS (ESI): mass calcd. for $C_{24}H_{37}N_3O_7S$, 511.2, m/z found 412.1 [M+H-boc]$^+$.

Intermediate 134: 8'-Methyl-7'-(2-(pyrrolidin-1-yl)ethoxy)-2,2',3,3',5,6-hexahydrospiro[pyran-4,4'-pyrido[2,3-b][1,4,5]oxathiazepine] 1',1'-dioxide

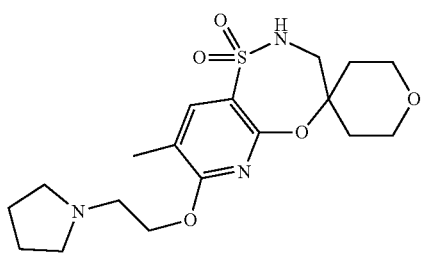 [SMILES: Cc1cc2c(nc1OCCN1CCCC1)OC1(CCOCC1)CNS2(=O)=O]

The title compound (1405 mg, 51%) was prepared using analogous conditions as described in Intermediate 126 where 2-(pyrrolidin-1-yl)ethan-1-ol was used instead of tert-butyl 4-(2-hydroxyethyl)piperazine-1-carboxylate and 7'-chloro-8'-methyl-2,2',3,3',5,6-hexahydrospiro[pyran-4,4'-pyrido[2,3-b][1,4,5]oxathiazepine] 1',1'-dioxide (Intermediate 132) was used instead of 7'-chloro-2,2',3,3',5,6-hexahydrospiro[pyran-4,4'-pyrido[2,3-b][1,4,5]oxathiazepine] 1',1'-dioxide (Intermediate 68). MS (ESI): mass calcd. for $C_{18}H_{27}N_3O_5S$, 397.2, m/z found 398.2 [M+H]$^+$.

Intermediate 135: tert-Butyl (*R)-3-(3-(hydroxymethyl)-4-methylphenyl)-2,2-dimethyl-3-(8-methyl-3-(trifluoromethyl) [1,2,4]triazolo[4,3-a]pyridine-7-yl)propanoate

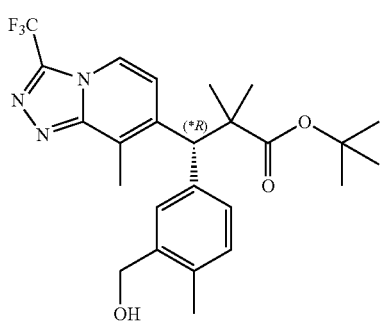 [SMILES: Cc1ccc([C@H](c2ccn3c(C(F)(F)F)nnc3c2C)C(C)(C)C(=O)OC(C)(C)C)cc1CO]

The mixture of tert-Butyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate (1.3 g, 2.7 mmol, Intermediate 128, step E) isomers were separated by chiral SFC (stationary phase: REGIS (s,s) WHELK-O1 250 mm×50 mm, 10 m; eluent: 35% to 35% (v/v) supercritical $CO_2$ in i-PrOH and $H_2O$ with 0.1% $NH_3$). The second eluting isomer (535 mg, 41%) was designated (*R). MS (ESI): mass calcd. for $C_{25}H_{30}F_3N_3O_3$ 477.2, m/z found 478.3 [M+H]$^+$. $^1$H NMR (400 MHz, DMSO-d$_6$) δ 8.46 (d, J=7.1 Hz, 1H), 7.33-7.26 (m, 2H), 7.12-7.07 (m, 1H), 7.07-7.04 (m, 1H), 5.03 (t, J=5.4 Hz, 1H), 4.72 (s, 1H), 4.43 (d, J=5.1 Hz, 2H), 2.65 (s, 3H), 2.17 (s, 3H), 1.29 (s, 3H), 1.21 (s, 3H), 1.17 (s, 9H).

Intermediate 136: 8'-Methyl-7'-(2-(piperidin-1-yl)ethoxy)-2',3'-dihydrospiro[cyclopropane-1,4'-pyrido[2,3-b][1,4,5]oxathiazepine] 1',1'-dioxide

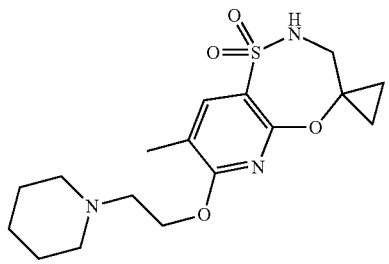 [SMILES: Cc1cc2c(nc1OCCN1CCCCC1)OC1(CC1)CNS2(=O)=O]

The title compound (274 mg, 42%) was prepared using analogous conditions as described in Intermediate 127 where 7'-chloro-8'-methyl-2',3'-dihydrospiro[cyclopropane-1,4'-pyrido[2,3-b][1,4,5]oxathiazepine] 1',1'-dioxide (Intermediate 131) was used instead of 7'-chloro-2',3'-dihydrospiro[cyclopropane-1,4'-pyrido[2,3-b][1,4,5]oxathiazepine] 1',1'-dioxide (Intermediate 67). MS (ESI): mass calcd. for $C_{17}H_{25}N_3O_4S$, 367.2; m/z found, 368.1 [M+H]$^+$. 1H NMR (400 MHz, CDCl$_3$) δ 7.80 (d, J=1.0 Hz, 1H), 4.98 (s, 1H), 4.44-4.33 (m, 2H), 3.55 (s, 2H), 2.75 (s, 2H), 2.52 (s, 4H), 2.08 (d, J=0.9 Hz, 3H), 1.65-1.53 (m, 4H), 1.45-1.35 (m, 2H), 1.17-1.08 (m, 2H), 0.71-0.61 (m, 2H).

Intermediate 137: 8'-Methyl-7'-(2-(pyrrolidin-1-yl)ethoxy)-2',3'-dihydrospiro[cyclopropane-1,4'-pyrido[2,3-b][1,4,5]oxathiazepine] 1',1'-dioxide

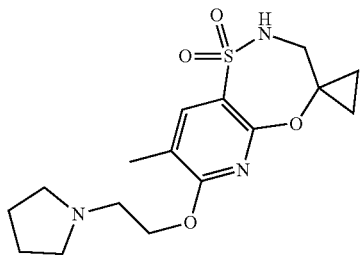 [SMILES: Cc1cc2c(nc1OCCN1CCCC1)OC1(CC1)CNS2(=O)=O]

The title compound (512 mg, 41%) was prepared using analogous conditions as described in Intermediate 127 where 7'-chloro-8'-methyl-2',3'-dihydrospiro[cyclopropane-1,4'-pyrido[2,3-b][1,4,5]oxathiazepine] 1',1'-dioxide (Intermediate 131) was used instead of 7'-chloro-2',3'-dihydrospiro[cyclopropane-1,4'-pyrido[2,3-b][1,4,5]oxathiazepine] 1',1'-dioxide (Intermediate 67) and 2-(pyrrolidine-1-yl)ethan-1-ol instead of 2-(piperidin-1-yl)ethan-1-ol. MS (ESI): mass calcd. for $C_{16}H_{23}N_3O_4S$, 353.1; m/z found, 354.2 $[M+H]^+$.

Intermediate 138: 7'-(2-(4-Methoxypiperidine-1-yl)ethoxy)-8'-methyl-2',3'-dihydrospiro[cyclopropane-1,4'-pyrido[2,3-b][1,4,5]oxathiazepine] 1',1'-dioxide

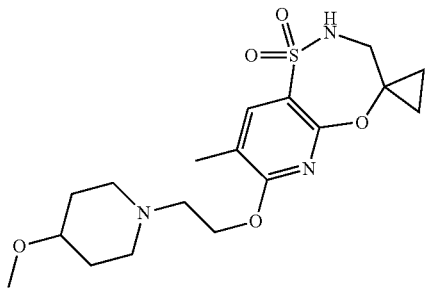 [SMILES: COC1CCN(CCOc2nc3c(cc2C)S(=O)(=O)NCC2(CC2)O3)CC1]

The title compound (250 mg, 71%) was prepared using analogous conditions as described in Intermediate 127 where 7'-chloro-8'-methyl-2',3'-dihydrospiro[cyclopropane-1,4'-pyrido[2,3-b][1,4,5]oxathiazepine] 1',1'-dioxide (Intermediate 131) was used instead of 7'-chloro-2',3'-dihydrospiro[cyclopropane-1,4'-pyrido[2,3-b][1,4,5]oxathiazepine] 1',1'-dioxide (Intermediate 67) and 2-(4-methoxypiperidin-1-yl)ethan-1-ol instead of 2-(piperidin-1-yl)ethan-1-ol. MS (ESI): mass calcd. for $C_{18}H_{27}N_3O_5S$, 397.2; m/z found, 398.2 $[M+H]^+$.

Intermediate 139: Benzyl (*R)-3-(3-hydroxymethyl)-4-methylphenyl)-2,2-dimethyl)-3-(8-methyl-3-(trifluoromethyl)-[1,2,4]triazolo[4,3-a]pyridine-7-yl)propanoate

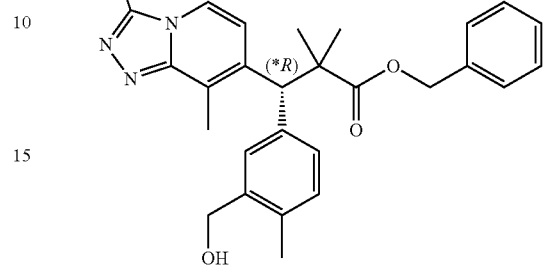

The title compound (2.48 g, 99%) was prepared using analogous conditions as described in Intermediate 71 where methyl (*R)-3-(3-hydroxymethyl)-4-methylphenyl)-2,2-dimethyl)-3-(8-methyl-3-(trifluoromethyl)-[1,2,4]triazolo[4,3-a]pyridine-7-yl)propanoate (Intermediate 141) was used instead of methyl (*S)-3-(3-hydroxymethyl)-4-methylphenyl)-2,2-dimethyl)-3-(8-methyl-3-(trifluoromethyl)-[1,2,4]triazolo[4,3-a]pyridine-7-yl)propanoate in step A. MS (ESI): mass calcd. for $C_{21}H_{22}F_3N_3O_3$ 421.2 m/z found 422.1 $[M+H]^+$. $^1H$ NMR (400 MHz, DMSO-$d_6$) δ 12.43 (s, 1H), 8.43 (d, J=7.3 Hz, 1H), 7.35-7.25 (m, 2H), 7.15 (dd, J=7.9, 2.1 Hz, 1H), 7.06 (d, J=7.9 Hz, 1H), 5.02 (s, 1H), 4.79 (s, 1H), 4.43 (s, 2H), 2.67 (s, 3H), 2.18 (s, 3H), 1.33-1.22 (m, 6H).

Intermediate 140: 8'-Methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide

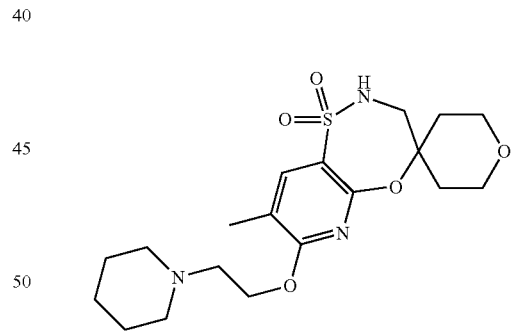

Step A: 6-Bromo-2-chloro-N-((4-hydroxytetrahydro-2H-pyran-4-yl)methyl)-5-methylpyridine-3-sulfonamide.

$K_2CO_3$ (26.2 g, 189 mmol) was added in portions to a solution of 4-(aminomethyl)tetrahydro-2H-pyran-4-ol (14.0 g, 83.5 mmol) and THF:$H_2O$ (230 mL, 4:1) which had been cooled to 0° C. The resulting mixture was stirred for 5 min at 0° C. and then 6-bromo-2-chloro-5-methylpyridine-3-sulfonyl chloride (23.1 g, 75.7 mmol) was added. This mixture was allowed to slowly warm to room temperature and stirred for 12 hours before pouring it into water (80 mL) and extracting with ethyl acetate (3x). These extractions resulted in several organic fractions that were combined, washed with brine (100 mL), dried over anhydrous $Na_2SO_4$, filtered, and concentrated to dryness under reduced pressure to afford the title compound (27.8 g, 83%). MS (ESI): mass calcd. for $C_{12}H_{16}BrClN_2O_4S$, 399.7 m/z found 400.8 $[M+H]^+$. $^1H$ NMR (400 MHz, DMSO-$d_6$) δ 8.25 (m, 1H), 8.05 (m, 1H), 4.39 (s, 1H), 3.57-3.51 (m, 4H), 2.89 (d, J=5.1 Hz, 2H), 2.40 (s, 3H), 1.55-1.45 (m, 2H), 1.33 (d, J=13.0 Hz, 2H).

Step B: 7'-Bromo-8'-methyl-2,2',3,3',5,6-hexahydrospiro[pyran-4,4'-pyrido[2,3-b][1,4,5]oxathiazepine] 1',1'-dioxide. t-BuOK (7.91 g, 70.5 mmol) was added in portions to a solution of 6-bromo-2-chloro-N-((4-hydroxytetrahydro-2H-pyran-4-yl)methyl)pyridine-3-sulfonamide (14.1 g, 35.2 mmol) in DMSO (110 mL) which had been cooled to 0° C. This mixture was then heated at 100° C. for 2 hours before cooling to room temperature and concentrating to dryness under reduced pressure. The residue was diluted with $H_2O$ (60 mL) and the pH adjusted with 1 N HCl (100 mL) to pH=6. The resulting suspension was isolated via filtration and the filter cake washed with petroleum ether (60 mL) before drying under reduced pressure to give the title compound (10.08 g). This solid was further purified by preparative HPLC (stationary phase: YMC Triart C18, 250 mm×50 mm×7 μm column; eluent: 10% to 40% (v/v) $CH_3CN$ and $H_2O$ with 0.225% HCOOH) to afford the title compound (7.13 g, 56%). MS (ESI): mass calcd. for $C_{12}H_{15}BrN_2O_4S$, 363.2 m/z found 363.0 $[M+H]^+$. $^1H$ NMR (400 MHz, DMSO-$d_6$) δ 8.50 (m, 1H), 8.09 (m, 1H), 3.79-3.70 (m, 2H), 3.61 (d, J=11.2 Hz, 2H), 3.50 (s, 2H), 2.36 (s, 3H), 1.69-1.55 (m, 4H).

Step C: 8'-Methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide. $Cs_2CO_3$ (6.72 g, 20.6 mmol) was added to a mixture of 7'-bromo-8'-methyl-2,2',3,3',5,6-hexahydrospiro[pyran-4,4'-pyrido[2,3-b][1,4,5]oxathiazepine] 1',1'-dioxide (2.5 g, 6.9 mmol), 2-(piperidin-1-yl)ethanol (2.67 g, 20.7 mmol), JosiPhos pre-catalyst G3 (0.64 g, 0.70 mmol), and DMA (30 mL) under $N_2$. This mixture was heated at 95° C. for 16 hours before quenching with $H_2O$ and extracting with ethyl acetate (2×). These extractions resulted in several organic fractions that were combined, dried over anhydrous $Na_2SO_4$, filtered, and concentrated to dryness under reduced pressure. The residue was purified by flash chromatography (eluent:petroleum ether/ethyl acetate, 1:0 to 0:1, gradient elution) to afford the title compound (2.1 g, 69%). MS (ESI): mass calcd. for $C_{19}H_{29}N_3O_5S$, 411.5 m/z found 412.2 $[M+H]^+$. $^1H$ NMR (400 MHz, DMSO-$d_6$) δ 8.15 (m, 1H), 7.83 (m, 1H), 4.39 (t, J=6.1 Hz, 2H), 3.87-3.76 (m, 2H), 3.62 (d, J=11.0 Hz, 2H), 3.43 (s, 2H), 2.66 (t, J=6.1 Hz, 2H), 2.44 (s, 4H), 2.12 (s, 3H), 1.60 (s, 4H), 1.51-1.45 (m, 4H), 1.40-1.33 (m, 2H).

Intermediate 141: Methyl (*R)-3-(3-(3-hydroxymethyl)-4-methylphenyl)-2,2-dimethyl)-3-(8-methyl-3-(trifluoromethyl)-[1,2,4]triazolo[4,3-a]pyridine-7-yl)propanoate

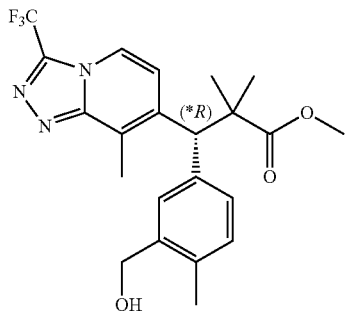

Step A: (5-Bromo-2-methylphenyl)methanol. Borane tetrahydrofuran complex (250 mL, 1 M in THF, 250 mmol) was added drop-wise to a solution of 5-bromo-2-methylbenzoic acid (45.0 g, 209 mmol) and THF (400 mL) which had been cooled to 0° C. The mixture was heated at 50° C. for 2 hours before allowing to cool to room-temperature. The mixture was then further cooled to 0° C. and quenched by slow addition of MeOH (250 mL) and it was combined with another batch of (5-bromo-2-methylphenyl)methanol and concentrated to dryness under reduced pressure. The residue was diluted with ethyl acetate (200 mL) and washed with water (200 mL). The aqueous layer was extracted with ethyl acetate (2×) resulting in several organic fractions that were combined, dried over anhydrous $Na_2SO_4$, filtered, and concentrated to dryness under reduced pressure to afford the title compound (87.8 g), which was used in the next step without further purification. $^1H$ NMR (400 MHz, DMSO-$d_6$) δ 7.48 (d, J=2.0 Hz, 1H), 7.28 (dd, J=8.1, 2.2 Hz, 1H), 7.06 (d, J=8.1 Hz, 1H), 4.44 (s, 2H), 2.13 (s, 3H).

Step B: 5-Bromo-2-methylbenzyl pivalate. Pivaloyl chloride (119 mL, 966 mmol) was added drop-wise to a solution of (5-bromo-2-methylphenyl)methanol (87.8 g, 437 mmol), triethylamine (243 mL, 1.75 mol), and dichloromethane (800 mL) which had been cooled to 0° C. The resulting mixture was allowed to warm to room-temperature and stirred for 4 hours before pouring into water (600 mL). The aqueous layer was extracted with dichloromethane (2×). These extractions resulted in several organic fractions that were combined, washed with brine (300 mL), dried over anhydrous $Na_2SO_4$, filtered, and concentrated to dryness under reduced pressure. The residue was purified by flash chromatography (eluent:petroleum ether, isocratic) to afford the title compound (160 g, 96%). $^1H$ NMR (400 MHz, DMSO-$d_6$) δ 7.44 (d, J=2.2 Hz, 1H), 7.39 (dd, J=8.1, 2.2 Hz, 1H), 7.15 (d, J=8.1 Hz, 1H), 5.03 (s, 2H), 2.21 (s, 3H), 1.13 (s, 9H).

Step C: 2-Methyl-5-(4,4,5,5-tetramethyl-1,3,2-dioxaborolan-2-yl)benzyl pivalate. 5-Bromo-2-methylbenzyl pivalate (40.0 g, 140 mmol), 4,4,4',4',5,5,5',5'-octamethyl-2,2'-bi(1,3,2-dioxaborolane) (53.5 g, 211 mmol), KOAc (55.1 g, 561 mmol), and 1,4-dioxane (600 mL) were mixed and sparged with $N_2$ for 5 minutes and Pd(dppf)$Cl_2$ (8.2 g, 11 mmol) was added. The mixture was sparged again with $N_2$ for another 5 minutes and then heated at 90° C. for 4 hours before cooling to room-temperature, pouring it into $H_2O$ (200 mL), and extracting with ethyl acetate (3×). These extractions resulted in several organic fractions that were combined, washed with brine (50 mL), dried over anhydrous $Na_2SO_4$, filtered, and concentrated to dryness under reduced pressure. This material was combined with another batch of 2-methyl-5-(4,4,5,5-tetramethyl-1,3,2-dioxaborolan-2-yl)benzyl pivalate and purified by flash chromatography (eluent:petroleum ether/ethyl acetate, 10:1, isocratic) to give the product (120 g), which was further purified by preparative HPLC (stationary phase: SANPONT C18, 250 mm×50 mm×5 Lm column, eluent: 50% to 95% (v/v) $CH_3CN$ and $H_2O$ with 0.1% TFA) to afford the title compound (77.1 g) as a white solid. $^1H$ NMR (400 MHz, DMSO-$d_6$) δ 7.60 (s, 1H), 7.54 (d, J=7.5 Hz, 1H), 7.24 (d, J=7.5 Hz, 1H), 5.09 (s, 2H), 2.31 (s, 3H), 1.28 (s, 12H), 1.14 (s, 9H).

Step D: 8-Methyl-3-(trifluoromethyl)-7-vinyl-[1,2,4]triazolo[4,3-a]pyridine. 7-Bromo-8-methyl-3-(trifluoromethyl)-[1,2,4]triazolo[4,3-a]pyridine (36.5 g, 130 mmol), potassium trifluoro(vinyl)borate (34.9 g, 261 mmol), $K_3PO_4$ (83.0 g, 391 mmol), 1,4-dioxane (350 mL), and $H_2O$ (70 mL) were mixed and sparged with Ar for 5 minutes and then Pd(dppf)$Cl_2$ (4.8 g, 6.6 mmol) was added. This mixture was sparged with Ar for another 5 minutes and heated at 110° C. for 16 hours. The reaction was cooled to room-temperature, combined with another batch of 8-methyl-3-(trifluoromethyl)-7-vinyl-[1,2,4]triazolo[4,3-a]pyridine and filtered through a pad of diatomaceous earth. The filtrate was poured into H$_2$O (160 mL), and extracted with ethyl acetate (3×). These extractions resulted in several organic fractions that were combined, dried over anhydrous Na$_2$SO$_4$, filtered, and concentrated to dryness under reduced pressure. The residue was purified by FCC (eluent:petroleum ether/ethyl acetate, 10:1 to 3:1, gradient elution) to afford the title compound (48.4 g).

Step E: 8-Methyl-3-(trifluoromethyl)-[1,2,4]triazolo[4,3-a]pyridine-7-carbaldehyde. K$_2$OsO$_4$.2H$_2$O (1.6 g, 4.3 mmol) was added to a solution of 8-methyl-3-(trifluoromethyl)-7-vinyl-[1,2,4]triazolo[4,3-a]pyridine (24.0 g, 105 mmol), 1,4-dioxane (700 mL), and distilled H$_2$O (700 mL). NaIO4 (72.3 g, 338 mmol) was then added and the reaction mixture allowed to stir at room-temperature for 2 hours. The suspension was filtered through a pad of diatomaceous earth, the filtrate combined with another batch of 8-methyl-3-(trifluoromethyl)-[1,2,4]triazolo[4,3-a]pyridine-7-carbaldehyde, and concentrated to dryness under reduced pressure. The residue was diluted with water (100 mL) and extracted with ethyl acetate (3×). These extractions resulted in several organic fractions that were dried over anhydrous Na$_2$SO$_4$, filtered, and concentrated to dryness under reduced pressure. The residue was purified by flash chromatography (eluent: petroleum ether:/ethyl acetate, 10:1 to 3:1, gradient elution) to afford the title compound (45.2 g). MS (ESI): mass calcd. for C$_9$H$_6$F$_3$N$_3$O, 229.1 m/z found 229.8 [M+H]$^+$.

Step F: 5-(Hydroxy(8-methyl-3-(trifluoromethyl)-[1,2,4]triazolo[4,3-a]pyridin-7-yl)methyl)-2-methylbenzyl pivalate. 8-Methyl-3-(trifluoromethyl)-[1,2,4]triazolo[4,3-a]pyridine-7-carbaldehyde (25.6 g, 112 mmol), 2-methyl-5-(4,4,5,5-tetramethyl-1,3,2-dioxaborolan-2-yl)benzyl pivalate (44.54 g, 134.1 mmol), P(1-nap)$_3$ (18.4 g, 44.6 mmol), K$_2$CO$_3$ (77.2 g, 559 mmol), and THF (600 mL) were mixed and sparged with Ar for 5 minutes followed by addition of PdCl$_2$ (3.96 g, 22.3 mmol). The mixture was sparged with N$_2$ for another 5 minutes and then heated at 75° C. for 1 hour before cooling to room-temperature. The suspension was combined with two additional batches of 5-(hydroxy(8-methyl-3-(trifluoromethyl)-[1,2,4]triazolo[4,3-a]pyridin-7-yl)methyl)-2-methylbenzyl pivalate, filtered, and the filter cake washed with methanol (2×). The filtrate was concentrated to dryness under reduced pressure and the residue purified by flash chromatography (eluent:petroleum ether/ethyl acetate, 1:0 to 2:3, gradient elution) to afford the title compound (61 g). $^1$H NMR (400 MHz, DMSO-d$_6$) δ 8.48 (d, J=7.1 Hz, 1H), 7.35-7.26 (m, 2H), 7.21-7.16 (m, 2H), 6.28 (d, J=4.2 Hz, 1H), 6.07 (d, J=4.2 Hz, 1H), 5.04 (s, 2H), 2.23 (s, 3H), 1.05 (s, 9H).

Step G: 5-(Chloro(8-methyl-3-(trifluoromethyl)-[1,2,4]triazolo[4,3-a]pyridin-7-yl)methyl)-2-methylbenzyl pivalate. Thionyl chloride (117 mL, 1.61 mol) was added to a solution of 5-(hydroxy(8-methyl-3-(trifluoromethyl)-[1,2,4]triazolo[4,3-a]pyridin-7-yl)methyl)-2-methylbenzyl pivalate (61.0 g, 140 mmol) and dichloromethane (1 L). The resulting mixture was stirred at room-temperature for 15 hours before concentrating to dryness under reduced pressure to afford the title compound (74 g), which was used in the next step without further purification.

Step H: Methyl 2,2-dimethyl-3-(4-methyl-3-((pivaloyloxy)methyl)phenyl)-3-(8-methyl-3-(trifluoromethyl)-[1,2,4]triazolo[4,3-a]pyridin-7-yl)propanoate. 5-(Chloro(8-methyl-3-(trifluoromethyl)-[1,2,4]triazolo[4,3-a]pyridin-7-yl)methyl)-2-methylbenzyl pivalate (69.0 g, 129 mmol), ((1-methoxy-2-methylprop-1-en-1-yl)oxy)trimethylsilane (74.3 g, 426 mmol), dichloromethane (1 L), and InBr$_3$ (10.54 g, 29.73 mmol) were mixed, sparged with Ar for 5 minutes and then stirred at room temperature under Ar for 18 hours. The reaction mixture was poured into aqueous saturated NaHCO$_3$ solution (250 mL) and extracted with dichloromethane (2×). These extractions resulted in several organic fractions that were dried over anhydrous MgSO$_4$, filtered, and concentrated to dryness under reduced pressure. The residue was purified by flash chromatography (eluent: petroleum ether/ethyl acetate, 100:1 to 3:1, gradient elution) to provide the title compound (31 g, 46%). MS (ESI): mass calcd. For C$_{27}$H$_{32}$F$_3$N$_3$O$_4$ 519.2 m/z found 520.1 [M+H]$^+$. $^1$H NMR (400 MHz, DMSO-d$_6$) δ 8.41 (d, J=7.3 Hz, 1H), 7.20 (d, J=7.3 Hz, 2H), 7.15 (d, J=7.8 Hz, 2H), 5.02 (s, 2H), 4.79 (s, 1H), 3.51 (s, 3H), 2.66 (s, 3H), 2.23 (s, 3H), 1.32 (s, 3H), 1.26 (s, 3H), 1.06 (s, 9H).

Step I: Methyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate. Sodium methoxide (37.0 mL, 25 wt % in MeOH, 162 mmol) was added drop-wise to a solution of methyl 2,2-dimethyl-3-(4-methyl-3-((pivaloyloxy)methyl)phenyl)-3-(8-methyl-3-(trifluoromethyl)-[1,2,4]triazolo[4,3-a]pyridin-7-yl)propanoate (26 g, 50 mmol) and MeOH (250 mL). The resulting mixture was stirred at room-temperature for 2 hours, combined with another batch of methyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate, poured into aqueous saturated NH$_4$Cl solution (200 mL), and extracted with DCM (3×). These extractions resulted in several organic fractions that were combined, dried over anhydrous Na$_2$SO$_4$, filtered, and concentrated to dryness under reduced pressure. The residue was purified by flash chromatography (eluent:petroleum ether/ethyl acetate, 100:1 to 1:1, gradient elution) to give the title compound (21 g) which was used in the next step without further purification.

Step J: (*R)-Methyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate. The mixture of methyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate isomers were separated by chiral SFC (stationary phase: REGIS (s,s) WHELK-O1 250 mm×50 mm, 5 am; eluent: 35% to 35% (v/v) supercritical CO$_2$ in IPA and H$_2$O with 0.1% NH$_3$). The second eluting isomer (8.5 g, 39%) was designated (*R). MS (ESI): mass calcd. For C$_{22}$H$_{24}$F$_3$N$_3$O$_3$ 435.2 m/z found 436.2 [M+H]$^+$. $^1$H NMR (400 MHz, DMSO-d$_6$) δ 8.41 (d, J=7.1 Hz, 1H), 7.30-7.25 (m, 2H), 7.13-7.09 (m, 1H), 7.06 (d, J=8.4 Hz, 1H), 5.04 (t, J=5.3 Hz, 1H), 4.76 (s, 1H), 4.43 (d, J=5.4 Hz, 2H), 3.51 (s, 3H), 2.68 (s, 3H), 2.17 (s, 3H), 1.32 (s, 3H), 1.28 (s, 3H).

Intermediate 142: Methyl (*R)-3-(3-((7'-chloro-8'-methyl-1',1'-dioxido-2,3,5,6-tetrahydrospiropyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate

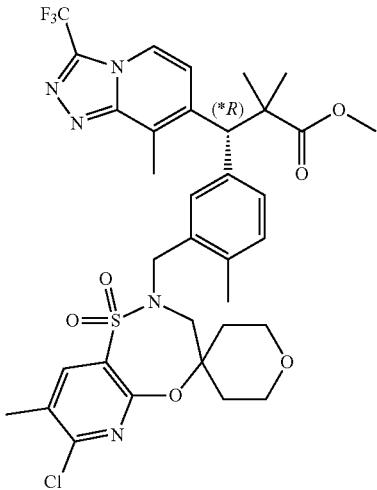

The title compound (230 mg, 91%) was prepared using analogous conditions as described in Example 11 where methyl (*R) 3-(3-(hydroxy methyl)-4-methylphenyl)-2,2-dimethyl-3-(8-methyl-3-(trifluoromethyl)-[1,2,4]triazolo[4,3-a]pyridine-7-yl)propanoate (Intermediate 141) was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and 7'-chloro-8'-methyl-2,2',3,3',5,6-hexahydrospiro[pyran-4,4'-pyrido[2,3-b][1,4,5]oxathiazepine] 1',1'-dioxide (Intermediate 132) instead of (*S)-7a-methyl-6,7,7a, 8,9,19-hexahydropyrido[2,3-f]pyrollo[2,1-d][1,2,5]thiadiazepine 5,5-dioxide (Intermediate 39) in step B. MS (ESI): mass calcd. for $C_{34}H_{37}ClF_3N_5O_6S$, 735.2; m/z found, 736.1 [M+H]⁺. ¹H NMR (400 MHz, CDCl₃) δ 8.03 (d, J=7.4 Hz, 1H), 8.00 (d, J=0.9 Hz, 1H), 7.24 (s, 1H), 7.21 (d, J=7.4 Hz, 1H), 7.10 (d, J=1.4 Hz, 2H), 5.30 (s, 1H), 4.79 (s, 1H), 4.53-4.40 (m, 2H), 4.07-3.96 (m, 2H), 3.65-3.50 (m, 5H), 3.40 (d, J=15.4 Hz, 1H), 2.78 (s, 3H), 2.42 (s, 3H), 2.23 (s, 3H), 1.70 (ddd, J=19.5, 14.0, 2.6 Hz, 2H), 1.51 (ddd, J=13.5, 11.4, 4.9 Hz, 2H), 1.42 (s, 3H), 1.36 (s, 3H).

Intermediate 143: Methyl (*R)-3-(3-((7'-chloro-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate

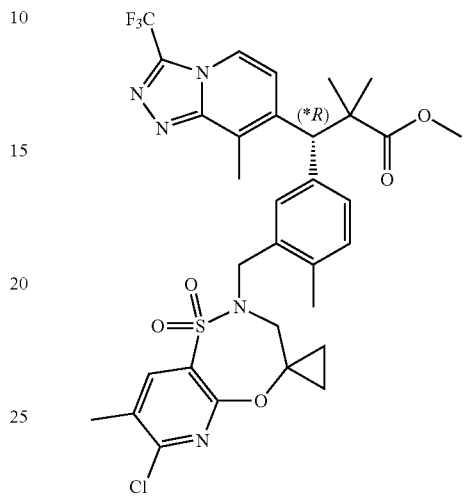

The title compound (726 mg, 93%) was prepared using analogous conditions as described in Example 11 where methyl (*R) 3-(3-(hydroxy methyl)-4-methylphenyl)-2,2-dimethyl-3-(8-methyl-3-(trifluoromethyl)-[1,2,4]triazolo[4,3-a]pyridine-7-yl)propanoate (Intermediate 141) was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and 7'-chloro-8'-methyl-2',3'-dihydrospiro[cyclopropane-1,4'-pyrido[2,3-b][1,4,5]oxathiazepine] 1',1'-dioxide (Intermediate 131) instead of (*S)-7a-methyl-6,7,7a, 8,9,19-hexahydropyrido[2,3-f]pyrollo[2,1-d][1,2,5]thiadiazepine 5,5-dioxide (Intermediate 39) in step B. MS (ESI): mass calcd. for $C_{32}H_{33}ClF_3N_5O_5S$, 691.2; m/z found, 692.2 [M+H]⁺.

Intermediate 144: 8'-Methyl-7'-(2-(pyrrolidin-1-yl)ethoxy)-2,2',3,3',5,6-hexahydropsiro[pyran-4,4'-pyrido[2,3-b][1,4,5]oxathiazepine] 1',1'-dioxide

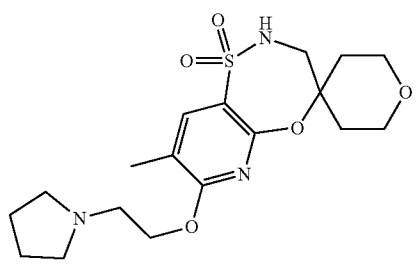 [SMILES: Cc1cc2c(nc1OCCN1CCCC1)OC1(CCOCC1)CNS2(=O)=O]

The title compound (667 mg, 61%) was prepared using analogous conditions as described in Intermediate 140 where 2-(pyrrolidin-1-yl)ethanol was used instead of 2-(piperidin-1-yl)ethanol in step C. MS (ESI): mass calcd. for $C_{18}H_{27}N_3O_5S$, 397.5 m/z found 398.2 [M+H]⁺. ¹H NMR (400 MHz, DMSO-d₆) δ 8.19 (m, 1H), 7.84 (m, 1H), 4.43 (t, J=5.7 Hz, 2H), 3.87-3.74 (m, 2H), 3.62 (d, J=11.0 Hz, 2H), 3.44 (d, J=4.6 Hz, 2H), 2.92 (t, J=5.7 Hz, 2H), 2.68-2.63 (m, 4H), 2.14 (s, 3H), 1.75-1.67 (m, 4H), 1.60 (s, 4H).

Intermediate 145: Methyl (*S)-3-(3-hydroxymethyl)-4-methylphenyl)-2,2-dimethyl-3-(8-methyl-3-(trifluoromethyl)-[1,2,4]triazolo[4,3-a]pyridine-7-yl)propanoate

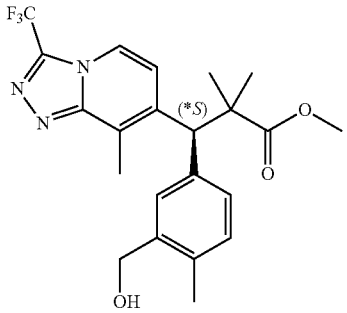

The mixture of methyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate isomers (Intermediate 48) were separated by chiral SFC (stationary phase: REGIS (s,s) WHELK-O1 250 mm×50 mm, 5 m; eluent: 35% to 35% (v/v) supercritical $CO_2$ in IPA and $H_2O$ with 0.1% $NH_3$). The first eluting isomer (8.5 g, 39%) was designated (*S). MS (ESI): mass calcd. For $C_{22}H_{24}F_3N_3O_3$ 435.2 m/z found 436.2 [M+H]$^+$. $^1$H NMR (400 MHz, DMSO-d$_6$) δ 8.41 (d, J=7.3 Hz, 1H), 7.31-7.25 (m, 2H), 7.13-7.09 (m, 1H), 7.06 (d, J=7.6 Hz, 1H), 5.03 (t, J=5.3 Hz, 1H), 4.76 (s, 1H), 4.43 (d, J=5.0 Hz, 2H), 3.51 (s, 3H), 2.68 (s, 3H), 2.17 (s, 3H), 1.32 (s, 3H), 1.28 (s, 2H), 1.30-1.25 (m, 1H).

Intermediate 146: 7'-(2-Morpholinoethoxy)-2,2',3,3',5,6-hexahydrospiro[pyran-4,4'-pyrido[2,3-b][1,4,5]oxathiazepine] 1',1'-dioxide

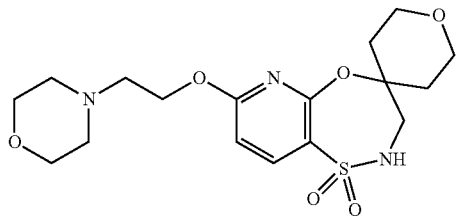 [SMILES: O=S1(=O)NCC2(CCOCC2)Oc2nc(OCCN3CCOCC3)ccc21]

Step A: 6-Bromo-2-chloropyridine-3-sulfonyl chloride. HBF$_4$ (32.0 mL, 206 mmol) was added drop-wise to a solution of 6-bromo-2-chloropyridin-3-amine (30.0 g, 145 mmol) and acetonitrile (150 mL) which had been cooled to 0° C. The resulting mixture was stirred at 0° C. for 10 minutes. Then tert-butyl nitrite (26.0 mL, 219 mmol) was added drop-wise and the reaction mixture was allowed to stir at 0° C. for 1 hour to form a 6-bromo-2-chloropyridine-3-diazonium tetrafluoroborate solution. In a separate flask, copper(I) chloride (22.0 g, 222 mmol) and acetic acid (120 mL) were mixed and cooled to 0° C. SO$_2$ gas (>1.3 M) was bubbled through the mixture which was maintained at 0° C. for 1 hour. At this time the 6-bromo-2-chloropyridine-3-diazonium tetrafluoroborate solution, which had been cooled to 0° C., was added dropwise. The resulting mixture was stirred for 12 hours with gradual warming to room-temperature. The suspension was filtered through a pad of diatomaceous earth and the pad washed with ethyl acetate (1×). The resulting mixture was quenched with aqueous saturated NaHCO$_3$ solution (200 mL), stirred for 20 minutes, and then extracted with ethyl acetate (3×). These extractions resulted in several organic fractions that were combined, washed with water (2×) and brine (1×), dried over anhydrous Na$_2$SO$_4$, filtered, and concentrated to dryness under reduced pressure. The resulting residue was purified by flash chromatography (eluent:petroleum ether/ethyl acetate; 1:0 to 10:1, gradient elution) to afford the title compound (24 g), which was used in the next step without further purification.

Step B: 6-Bromo-2-chloro-N-((4-hydroxytetrahydro-2H-pyran-4-yl)methyl)pyridine-3-sulfonamide. A solution of 6-bromo-2-chloropyridine-3-sulfonyl chloride (48 g) and THF (100 mL) was added drop-wise to a mixture of 4-(aminomethyl)tetrahydro-2H-pyran-4-ol (20.0 g, 152 mmol), K$_2$CO$_3$ (65.0 g, 470 mmol), THF (100 mL), and H$_2$O (50 mL) which had been cooled to 0° C. This reaction mixture was stirred for 12 hours with gradual warming to room-temperature before concentrating to dryness under reduced pressure. The residue was diluted with water (50 mL) and extracted with ethyl acetate (3×). These extractions resulted in several organic fractions that were combined, dried over anhydrous Na$_2$SO$_4$, filtered, and concentrated to dryness under reduced pressure. The resulting residue was purified by flash chromatography (eluent:petroleum ether/ethyl acetate; 1:0 to 1:1, gradient elution) to afford the title compound (35 g), which was used in the next step without further purification.

Step C: 7'-Bromo-2,2',3,3',5,6-hexahydrospiro[pyran-4,4'-pyrido[2,3-b][1,4,5]oxathiazepine]1',1'-dioxide. t-BuOK (5.5 g, 49 mmoL) was added in portions to a solution of 6-bromo-2-chloro-N-((4-hydroxytetrahydro-2H-pyran-4-yl)methyl)pyridine-3-sulfonamide (10 g) and DMSO (40 mL) which had been cooled to 0° C. The resulting mixture was heated at 100° C. for 2 hours before concentrating to dryness under reduced pressure. The residue was diluted with H$_2$O (50 mL) and the pH of the solution was adjusted to pH=6 with 1 N HCl (20 mL). The suspension was isolated via filtration and the filter cake washed with petroleum ether (20 mL) before drying under reduced pressure to provide the product (7.0 g), which was combined with another batch of the title compound (14 g), to provide 21 g of the title compound. The product (21 g) was then triturated with ethyl acetate (30 mL) and the suspension isolated via filtration. The filter cake was washed with petroleum ether/ethyl acetate (10:1, 50 mL) before drying under reduced pressure to afford the title compound (18.5 g). MS (ESI): mass calcd. for $C_{11}H_{13}BrN_2O_4S$, 348.0, m/z found 349.0 [M+H]$^+$. $^1$H NMR (400 MHz, DMSO-d$_6$) δ 8.54-8.47 (m, 1H), 8.01 (d, J=8.0 Hz, 1H), 7.60 (d, J=8.0 Hz, 1H), 3.76-3.66 (m, 2H), 3.62-3.55 (m, 2H), 3.49 (d, J=6.4 Hz, 2H), 1.68-1.53 (m, 4H).

Step D: 7'-(2-Morpholinoethoxy)-2,2',3,3',5,6-hexahydrospiro[pyran-4,4'-pyrido[2,3-b][1,4,5]oxathiazepine] 1',1'-dioxide. Sodium hydride in mineral oil (5.20 g, 60% purity, 130 mmol) was added in portions to a solution of 2-morpholinoethanol (14.0 g, 107 mmol) and toluene (150 mL) which had been cooled to 0° C. The resulting mixture was stirred for 0.5 hours with gradual warming to room-temperature and was then treated with 7'-bromo-2,2',3,3',5,6-hexahydrospiro[pyran-4,4'-pyrido[2,3-b][1,4,5]oxathiazepine] 1',1'-dioxide (18 g, 52 mmol), S-tol-BINAP (1.4 g, 2.1 mmol), and Pd$_2$(dba)$_3$ (930 mg, 1.02 mmol). This reaction mixture was heated at 110° C. for 16 hours before quenching with acetic acid (8 mL). The suspension was filtered through a pad of diatomaceous earth and the pad washed with ethyl acetate (500 mL). The filtrate was concentrated to dryness under reduced pressure to give the product, which was purified by flash chromatography (eluent:petroleum ether/ethyl acetate, 10:1 to 0:1, gradient elution) to afford the title compound (8.0 g, 38%). The mixture was combined with another batch of the title compound and triturated with petroleum ether/ethyl acetate, 10:1 (50 mL) and the suspension was isolated via filtration. The filter cake was washed with petroleum ether (50 mL) before drying under reduced pressure to afford the title compound (14.2 g). MS (ESI): mass calcd. for C$_{17}$H$_{25}$N$_3$O$_6$S, 399.5 m/z found 400.2 [M+H]$^+$. $^1$H NMR (400 MHz, DMSO-d$_6$) δ 8.22-8.14 (m, 1H), 7.95 (d, J=8.8 Hz, 1H), 6.70 (d, J=8.4 Hz, 1H), 4.42-4.30 (m, 2H), 3.83-3.71 (m, 2H), 3.64-3.56 (m, 2H), 3.55-3.50 (m, 4H), 3.46-3.40 (m, 2H), 2.68-2.61 (m, 2H), 2.45-2.38 (m, 4H), 1.65-1.51 (m, 4H).

Intermediate 147: 4-(((tert-Butyldimethylsilyl)oxy)methyl)-5-methylpicolinaldehyde

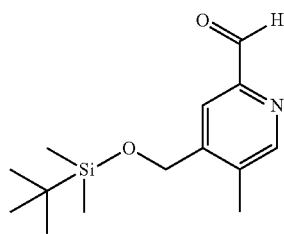 [SMILES: Cc1cnc(C=O)cc1CO[Si](C)(C)C(C)(C)C]

Step A: 4-Iodo-5-methylpyridin-2(1H)-one. Concentrated HCl (12 M, 400 mL, 4.80 mol) was added to a mixture of 2-fluoro-4-iodo-5-methylpyridine (200 g, 844 mmol), 1,4-dioxane (400 mL), and H$_2$O (400 mL). The resulting mixture was heated at 100° C. for 2 hours, then cooled to room temperature and poured into H$_2$O (1200 mL). The resulting suspension was stirred for 16 hours and then isolated via filtration. The filter cake was washed with water (100 mL×3) and dried under reduced pressure to give the title compound (116 g). MS (ESI): mass calcd. for C$_6$H$_6$INO 234.95; m/z found, 235.9 [M+H]$^+$. $^1$H NMR (400 MHz, DMSO-d$_6$) δ 11.66 (br. s., 1H), 7.26 (s, 1H), 7.00 (s, 1H), 2.04 (s, 3H).

Step B: Methyl 5-methyl-2-oxo-1,2-dihydropyridine-4-carboxylate. 4-Iodo-5-methylpyridin-2(1H)-one (60.0 g, 255 mmol) and K$_2$CO$_3$ (70.57 g, 510.6 mmol) were added to a 2 L round-bottomed flask and the resulting mixture was treated with MeOH (1000 mL). The mixture was sparged with Argon for 5 minutes and then treated with Pd(OAc)$_2$ (6.88 g, 30.6 mmol) and dcpp.BF$_4$ (31.26 g, 51.06 mmol). The resulting mixture was heated at 80° C. for 48 hours under CO (50 psi) atmosphere, then the reaction mixture was cooled to room temperature. The mixture was combined with another batch of methyl 5-methyl-2-oxo-1,2-dihydropyridine-4-carboxylate and then filtered and washed with MeOH (100 mL). The filtrate was concentrated under reduced pressure. The resulting mixture was poured into H$_2$O (1500 mL) and the pH of the mixture was adjusted to pH=5 with concentrated HCl. The mixture was then filtered and extracted with ethyl acetate (1 L×3). These extractions resulted in several organic solvent fractions which were combined and concentrated to dryness under reduced pressure to give the title compound (34 g), which was used in the next step without further purification. MS (ESI): mass calcd. for C$_8$H$_9$NO$_3$ 167.06; m/z found, 167.8 [M+H]$^+$.

Step C: Methyl 2-chloro-5-methylisonicotinate. Methyl 5-methyl-2-oxo-1,2-dihydropyridine-4-carboxylate (68 g) was added to a 1 L round-bottomed flask containing POCl$_3$ (600 g, 3.91 mol). The resulting mixture was stirred at 110° C. for 16 hours, then was cooled to room temperature and concentrated under reduced pressure. The mixture was poured into H$_2$O (600 mL) and extracted with ethyl acetate (600 mL×3). These extractions resulted in several organic solvent fractions which were combined, dried over anhydrous Na$_2$SO$_4$, filtered, and concentrated to dryness under reduced pressure. The material was purified by FCC (eluent: petroleum ether/ethyl acetate=1:0 to 10:1) to give the title compound (38 g, 48% yield). MS (ESI): mass calcd. for C$_8$H$_8$ClNO$_2$ 185.02; m/z found, 186.0 [M+H]$^+$.

Step D: (2-chloro-5-methylpyridin-4-yl)methanol. NaBH$_4$ (11.4 g, 301 mmol) was added to a solution of methyl 2-chloro-5-methylisonicotinate (28.0 g, 151 mmol), NaOMe (407 mg, 7.53 mmol), and MeOH (400 mL) at room temperature. The resulting mixture was stirred at room temperature for 1 hour, then was quenched with H$_2$O (400 mL) and extracted with ethyl acetate (400 mL×3). These extractions resulted in several organic solvent fractions which were combined, dried over anhydrous Na$_2$SO$_4$, filtered, and concentrated to dryness under reduced pressure to give the title compound (21 g), which was used in next step without further purification. MS (ESI): mass calcd. for C$_7$H$_8$ClNO 157.03; m/z found, 157.8 [M+H]$^+$.

Step E: 4-(((tert-Butyldimethylsilyl)oxy)methyl)-2-chloro-5-methylpyridine. TBSCl (26.1 g, 173 mmol) was added to a solution of (2-chloro-5-methylpyridin-4-yl)methanol (21.0 g, 133 mmol), 1H-imidazole (27.2 g, 400 mmol), and dichloromethane (500 mL). The resulting mixture was stirred at room temperature for 1 hour. The mixture was filtered and the filtrate was concentrated under reduced pressure. The material was purified by FCC (eluent:petroleum ether/ethyl acetate=1:0 to 10:1) to give the title compound (35 g, 97% yield). MS (ESI): mass calcd. for C$_{13}$H$_{22}$ClNOSi, 271.1; m/z found, 272.1 [M+H]$^+$.

Step F: 4-(((tert-Butyldimethylsilyl)oxy)methyl)-5-methyl-2-vinylpyridine. 4-(((tert-Butyldimethyl silyl)oxy)methyl)-2-chloro-5-methylpyridine (35.0 g, 129 mmol) was added to a mixture of potassium trifluoro(vinyl)borate (34.4 g, 257 mmol), K$_3$PO$_4$ (82.0 g, 386 mmol), 1,4-dioxane (400 mL), and H$_2$O (100 mL). The resulting mixture was sparged with N$_2$ for 5 minutes and then treated with Pd(dppf)Cl$_2$ (4.71 g, 6.44 mmol). The resulting mixture was sparged with N$_2$ for another 5 minutes and then stirred and heated at 90° C. for 13 hours under an atmosphere of N$_2$. After this period of time, the reaction was cooled to room temperature, filtered through a pad diatomaceous earth, such as of Celite®, and the pad was washed with ethyl acetate (200 mL). The filtrate was poured into water (500 mL) and the resulting mixture was extracted with ethyl acetate (500 mL×3). These extractions resulted in several organic solvent fractions which were combined, washed with brine, dried over anhydrous Na$_2$SO$_4$, filtered, and concentrated to dryness under reduced pressure. The material was purified in two batches by FCC (eluent: petroleum ether/ethyl acetate=1:0 to 10:1) to give the title compound (batch 1:22 g, 65% yield; batch 2: 10 g, 27% yield). MS (ESI): mass calcd. for C$_{13}$H$_{22}$ClNOSi, 263.17; m/z found, 264.3 [M+H]$^+$.

Step G: 4-(((tert-Butyldimethylsilyl)oxy)methyl)-5-methylpicolinaldehyde. $K_2OsO_4 \cdot H_2O$ (559 mg, 1.52 mmol) was added to a solution of 4-(((tert-butyldimethylsilyl)oxy)methyl)-5-methyl-2-vinylpyridine (10.0 g, 38.0 mmol), 1,4-dioxane (200 mL), and $H_2O$ (200 mL). The resulting mixture was treated with $NaIO_4$ (26.0 g, 122 mmol) and stirred at room temperature for 5 hours. The mixture was then filtered through a pad diatomaceous earth, such as of Celite® and the pad washed with ethyl acetate (100 mL). The filtrate was quenched with $H_2O$ (200 mL) and extracted with ethyl acetate (200 mL×3). These extractions resulted in several organic solvent fractions which were combined, dried over anhydrous $Na_2SO_4$, filtered, and concentrated to dryness under reduced pressure. The material was combined with another batch of the same compound and purified by FCC (eluent:petroleum ether/ethyl acetate=1:0 to 10:1) to give the title compound (5.9 g). MS (ESI): mass calcd. for $C_{14}H_{23}NO_2Si$, 265.15; m/z found, 266.2 $[M+H]^+$. $^1H$ NMR (400 MHz, DMSO-$d_6$) δ 9.94 (s, 1H), 8.55 (s, 1H), 7.95 (s, 1H), 4.79 (s, 2H), 2.29 (s, 3H), 0.93 (s, 9H), 0.12 (s, 6H).

Intermediate 148: 3-(Difluoromethyl)-7-iodo-8-methyl-[1,2,4]triazolo[4,3-a]pyridine

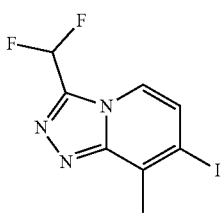

Step A: 2-Hydrazinyl-4-iodo-3-methylpyridine. To 2-fluoro-4-iodo-3-methylpyridine (23.4 g, 98.7 mmol) was added hydrazine hydrate (47 mL, 630 mmol). The resulting mixture was heated at 60° C. for 24 hours before being allowed to cool to room temperature. 3N NaOH solution (60 mL) and water (60 mL) were added to the reaction mixture and stirred for 30 minutes. The resulting precipitate was isolated by filtration and the filter cake was washed with water and dried under reduced pressure to afford the title compound (20.4 g, 83% yield). MS (ESI): mass calcd. for $C_6H_8IN_3$ 249.0; m/z found, 250.0 $[M+H]^+$.

Step B: 3-(Difluoromethyl)-7-iodo-8-methyl-[1,2,4]triazolo[4,3-a]pyridine. 2,2,2-Trifluoroacetic anhydride (18.9 mL, 162 mmol) was added dropwise to 2-hydrazinyl-4-iodo-3-methylpyridine (26.9 g, 108 mmol). The resulting mixture was stirred at 90° C. for 20 hours before being allowed to cool to room temperature. The pH of the reaction mixture was adjusted to pH=8 with aqueous saturated $Na_2CO_3$. The resulting biphasic mixture was separated and the organic layer was washed with water and brine. The organic layer was then dried over $MgSO_4$, filtered, and concentrated to dryness under reduced pressure. The product was triturated with hexanes and ethyl acetate, and the solid was filtered to provide the title compound (29.6 g, 88.7% yield). MS (ESI): mass calcd. for $C_8H_6F_2IN_3$ 308.96; m/z found, 310.0 $[M+H]^+$. $^1H$ NMR (400 MHz, CDCl$_3$) δ 7.99-7.95 (m, 1H), 7.35-7.30 (m, 1H), 7.39-7.10 (m, 1H), 2.86-2.81 (m, 3H).

Intermediate 149: 3,7-Dimethyl-7H-pyrrolo[2,3-c]pyridazine-6-carbaldehyde

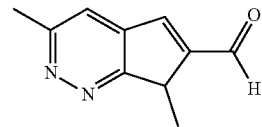

Step A: N,6-Dimethylpyridazin-3-amine. Into a 5000-mL pressure tank reactor, was placed 3-chloro-6-methylpyridazine (200 g, 1.56 mol) and $CH_3NH_2$/MeOH (3000 mL, 30% wt). The resulting solution was heated overnight at 110° C. After this time, the reaction mixture was cooled and concentrated under reduced pressure. The residue was washed with 1000 mL of petroleum ether and dried in an oven under reduced pressure to provide the title compound (210 g), which was used in the next step without further purification.

Step B: 4-Bromo-N,6-dimethylpyridazin-3-amine. Into a 5000-mL 3-necked round-bottom flask, purged and maintained with an inert atmosphere of nitrogen, was placed N,6-dimethylpyridazin-3-amine (210 g, 1.71 mol), acetic acid (2100 mL), sodium acetate (140 g, 1.71 mol), and bromine (809 g, 5.06 mol). The resulting solution was heated overnight at 65° C. After this time, the reaction mixture was allowed to cool to room temperature and concentrated under reduced pressure. The reaction was then quenched by the addition of 2000 mL of saturated aqueous $NaHCO_3$ solution. The pH of the solution was adjusted to pH=9 using additional aqueous saturated sodium bicarbonate solution and then the solution was extracted with ethyl acetate. These extractions resulted in several organic solvent fractions which were combined, dried over anhydrous $Na_2SO_4$, filtered, and concentrated to dryness under reduced pressure. The material was purified by FCC (dichloromethane/methanol, 40:1) to give the title compound (64 g, 19% yield over two steps).

Step C: 4-(3,3-Diethoxyprop-1-yn-1-yl)-N,6-dimethylpyridazin-3-amine. Into a 250-mL 3-necked round-bottom flask, was placed 4-bromo-N,6-dimethylpyridazin-3-amine (10 g, 49.49 mmol), N,N-dimethylformamide (100 mL), TEA (25.12 g, 248.25 mmol), and 3,3-diethoxyprop-1-yne (7.64 g, 59.61 mmol). The solution was sparged with $N_2$ for 5 min. Then, dichloropalladium bis(triphenylphosphane) (1.74 g, 2.48 mmol) and copper iodide (940 mg, 4.94 mmol) were added. The resulting solution was heated at 50° C. for 2 hours. After this time, the reaction mixture was allowed to cool to room temperature. The reaction was then quenched with 400 mL of saturated aqueous $NaHCO_3$ solution and extracted with ethyl acetate. These extractions resulted in several organic solvent fractions which were combined, dried over anhydrous $Na_2SO_4$, filtered, and concentrated to dryness under reduced pressure. The material was purified by FCC (ethyl acetate/petroleum ether, 1:2) to give the title compound (9.9 g, 80% yield).

Step D: 6-(Diethoxymethyl)-3,7-dimethyl-7H-pyrrolo[2,3-c]pyridazine. Into a 250-mL 3-necked round-bottom flask purged and maintained with an inert atmosphere of nitrogen, was placed 4-(3,3-diethoxyprop-1-yn-1-yl)-N,6-dimethylpyridazin-3-amine (10 g, 40.11 mmol) and NMP (100 mL) then the solution was cooled to 0° C. KO$^t$Bu (1.8 g, 16.04 mmol) was then added and the reaction mixture was allowed to warm to room temperature. The resulting solution was stirred for 1 hour. The reaction was then quenched by the addition of 200 mL of water/ice and extracted with ethyl acetate (3×100 mL). These extractions resulted in several organic solvent fractions which were combined, washed with saturated aqueous NaCl (2×100 mL), dried over anhydrous $Na_2SO_4$, filtered, and concentrated to dryness under reduced pressure. The material was purified by preparative basic HPLC (CombiFlash-1, C18 silica gel, mobile phase: $ACN/H_2O$ (5 mmol/L $NH_4HCO_3$)=30/70 increasing to $ACN/H_2O$ (5 mmol/L $NH_4HCO_3$)=40/70), to give the title compound (6.0 g, 60% yield).

Step E: 3,7-Dimethyl-7H-pyrrolo[2,3-c]pyridazine-6-carbaldehyde. Into a 250-mL 3-necked round-bottom flask purged and maintained with an inert atmosphere of nitrogen, was placed 6-(diethoxymethyl)-3,7-dimethyl-7H-pyrrolo[2,3-c]pyridazine (10 g, 40.11 mmol) and 1,4-dioxane (100 mL) which had been cooled to 0° C. 6N Hydrogen chloride (100 mL) was the added and the reaction mixture was allowed to warm to room temperature. The resulting solution was stirred for 4 hours. The resulting solution was extracted with ethyl acetate (2×200 mL) and the pH of the aqueous layer was adjusted to pH=9 using saturated aqueous $NaHCO_3$ solution. The resulting aqueous solution was extracted with ethyl acetate (3×200 mL). These extractions resulted in several organic solvent fractions which were combined, dried over anhydrous $Na_2SO_4$, filtered, and concentrated to dryness under reduced pressure to give the title compound (6.0 g, 85% yield). MS (ESI): mass calcd. for $C_9H_9N_3O$, 175.07; m/z found, 176.1 $[M+H]^+$. $^1H$ NMR (400 MHz, DMSO-$d_6$) δ 10.11 (s, 1H), 7.90 (s, 1H), 7.39 (s, 1H), 4.15 (s, 3H), 2.73 (s, 3H).

Intermediate 150: tert-Butyl 2',3'-dihydrospiro[piperidine-4,4'-pyrido[2,3-b][1,4,5]oxathiazepine]-1-carboxylate 1',1'-dioxide

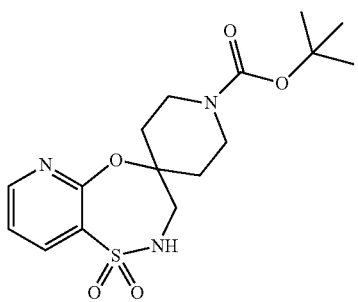 [SMILES: CC(C)(C)OC(=O)N1CCC2(CC1)CNS(=O)(=O)c1cccnc1O2]

Step A: tert-Butyl 4-((2-chloropyridine-3-sulfonamido)methyl)-4-hydroxypiperidine-1-carboxylate. 2-Chloropyridine-3-sulfonyl chloride (6.0 g, 28 mmol) was added dropwise to mixture of tert-butyl 4-(aminomethyl)-4-hydroxypiperidine-1-carboxylate (6.52 g, 28.3 mmol), $K_2CO_3$ (9.78 g, 70.8 mmol), THF (100 mL), and $H_2O$ (20 mL) which had been cooled to a 0° C.

The resulting mixture was stirred at 0° C. for 4 hours, then was poured into water (50 mL) and extracted with ethyl acetate (50 mL×3). These extractions resulted in several organic solvent fractions which were combined, washed with brine (30 mL), dried over anhydrous $Na_2SO_4$, filtered, and concentrated to dryness under reduced pressure. The residue was triturated with petroleum ether/ethyl acetate (10:1, 50 mL) and the solid was isolated via filtration. The filter cake was washed with petroleum ether/ethyl acetate (10:1, 5 mL×2) and dried under reduced pressure to give the title compound (6.8 g, 52% yield). MS (ESI): mass calcd. for $C_{16}H_{24}ClN_3O_5S$, 405.11; m/z found, 305.9 [M-Boc+H]$^+$. $^1H$ NMR (400 MHz, DMSO-$d_6$) δ 8.62 (dd, J=4.8, 1.8 Hz, 1H), 8.33 (dd, J=7.8, 2.0 Hz, 1H), 8.01 (t, J=6.3 Hz, 1H), 7.63 (dd, J=7.8, 4.8 Hz, 1H), 3.61 (d, J=11.0 Hz, 2H), 2.99 (br s, 2H), 2.88 (d, J=6.3 Hz, 2H), 1.41 (br s, 1H), 1.38 (s, 9H), 1.36-1.29 (m, 3H).

Step B: tert-Butyl 2',3'-dihydrospiro[piperidine-4,4'-pyrido[2,3-b][1,4,5]oxathiazepine]-1-carboxylate 1',1'-dioxide. t-BuOK (4.7 g, 42 mmol) was added to a solution of tert-butyl 4-((2-chloropyridine-3-sulfonamido)methyl)-4-hydroxypiperidine-1-carboxylate (6.8 g, 17 mmol) and DMSO (70 mL) which had been cooled to 0° C. The resulting mixture was stirred at 90° C. for 16 hours, then was allowed to cool to room temperature and concentrated to dryness under reduced pressure at 110° C. The residue was diluted with water (50 mL) and the mixture extracted with ethyl acetate (60 mL×4). These extractions resulted in several organic solvent fractions which were combined, washed with brine (50 mL), dried over anhydrous $Na_2SO_4$, filtered, and concentrated to dryness under reduced pressure. The material was purified by FCC (petroleum ether/ethyl acetate=1:0 to 2:3, gradient elution) to give the title compound (4.8 g, 74% yield). MS (ESI): mass calcd. for $C_{16}H_{23}N_3O_5S$, 369.14; m/z found, 370.2 $[M+H]^+$. $^1H$ NMR (400 MHz, DMSO-$d_6$) δ 8.53-8.46 (m, 1H), 8.45-8.38 (m, 1H), 8.19-8.12 (m, 1H), 7.44-7.36 (m, 1H), 3.70-3.55 (m, 2H), 3.54-3.43 (m, 2H), 3.33-3.14 (m, 2H), 1.70-1.57 (m, 2H), 1.56-1.45 (m, 2H), 1.38 (s, 9H).

Intermediate 151: tert-Butyl 2',3'-dihydrospiro[azetidine-3,4'-pyrido[2,3-b][1,4,5]oxathiazepine]-1-carboxylate 1',1'-dioxide

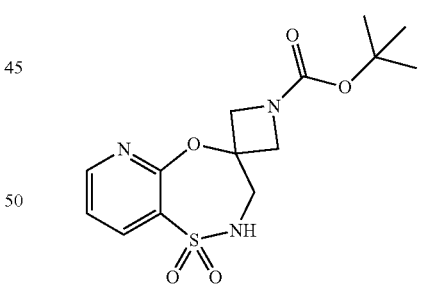

The title compound (6.3 g, 55% yield) was prepared using analogous conditions as described in Intermediate 150 where tert-butyl 3-(aminomethyl)-3-hydroxyazetidine-1-carboxylate was used instead of tert-butyl 4-(aminomethyl)-4-hydroxypiperidine-1-carboxylate. MS (ESI): mass calcd. for $C_{14}H_{20}ClN_3O_5S$, 341.10; m/z found, 286.1 [M-t-Bu+H]$^+$. $^1H$ NMR (400 MHz, DMSO-$d_6$) δ 8.58-8.51 (m, 1H), 8.36-8.26 (m, 1H), 8.24-8.16 (m, 1H), 7.53-7.44 (m, 1H), 3.93-3.83 (m, 2H), 3.82-3.75 (m, 2H), 3.71-3.59 (m, 2H), 1.37 (s, 9H).

Intermediate 152: tert-Butyl 8'-methyl-2',3'-dihydrospiro[piperidine-4,4'-pyrido[2,3-b][1,4,5]oxathiazepine]-1-carboxylate 1',1'-dioxide

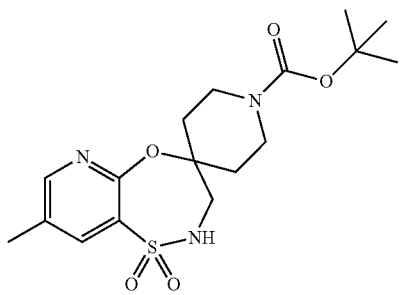 [SMILES: Cc1cnc2c(c1)S(=O)(=O)NCC1(CCN(C(=O)OC(C)(C)C)CC1)O2]

The title compound (8.3 g, 67% yield) was prepared using analogous conditions as described in Intermediate 150 where 2-chloro-5-methylpyridine-3-sulfonyl chloride was used instead of 2-chloropyridine-3-sulfonyl chloride. MS (ESI): mass calcd. for $C_{17}H_{25}N_3O_5S$, 383.15; m/z found, 384.2 [M+H]$^+$. $^1$H NMR (400 MHz, DMSO-$d_6$) δ 8.37-8.32 (m, 1H), 8.31-8.29 (m, 1H), 7.98-7.94 (m, 1H), 3.73-3.54 (m, 2H), 3.51-3.41 (m, 2H), 3.32-3.16 (m, 2H), 2.34 (s, 3H), 1.66-1.57 (m, 2H), 1.55-1.44 (m, 2H), 1.39 (s, 9H).

Intermediate 153: tert-Butyl 8'-methyl-2',3'-dihydrospiro[azetidine-3,4'-pyrido[2,3-b][1,4,5]oxathiazepine]-1-carboxylate 1',1'-dioxide

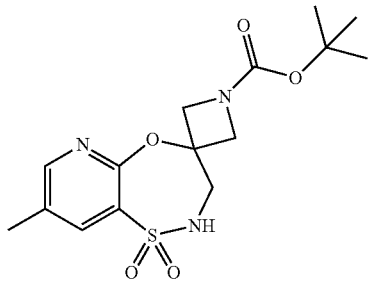 [SMILES: Cc1cnc2c(c1)S(=O)(=O)NCC1(CN(C(=O)OC(C)(C)C)C1)O2]

The title compound (3.8 g, 62% yield) was prepared using analogous conditions as described in Intermediate 150 where 2-chloro-5-methylpyridine-3-sulfonyl chloride was used instead of 2-chloropyridine-3-sulfonyl chloride and tert-butyl 3-(aminomethyl)-3-hydroxyazetidine-1-carboxylate was used instead of tert-butyl 4-(aminomethyl)-4-hydroxypiperidine-1-carboxylate. MS (ESI): mass calcd. for $C_{15}H_{21}N_3O_5S$, 355.12; m/z found, 300.1 [M-t-Bu+H]$^+$. $^1$H NMR (400 MHz, DMSO-$d_6$) δ 8.35 (d, J=2.0 Hz, 1H), 8.26 (s, 1H), 8.01 (d, J=2.0 Hz, 1H), 3.84 (d, J=9.0 Hz, 2H), 3.76 (s, 2H), 3.65 (d, J=8.8 Hz, 2H), 2.35 (s, 3H), 1.37 (s, 9H).

Intermediate 154: (*S)-2',3',4,5-Tetrahydro-2H-spiro[furan-3,4'-pyrido[2,3-b][1,4,5]oxathiazepine] 1',1'-dioxide

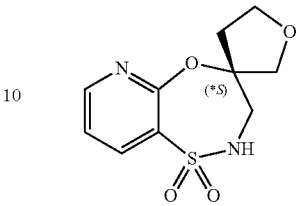

Step A: 3-Hydroxytetrahydrofuran-3-carbonitrile. BF$_3$.Et$_2$O (105 g, 738 mmol) was added to a stirring solution of dihydrofuran-3(2H)-one (60.5 g, 703 mmol) and TMSCN (73.2 g, 738 mmol) in THF (1.2 L) while maintaining the temperature below 20° C. After 16 hours, saturated aqueous sodium bicarbonate solution was added until the pH was 7. The mixture was concentrated under reduced pressure and the residue was extracted with ethyl acetate. This resulted in several organic fractions which were combined, washed with saturated aqueous sodium chloride solution, dried over anhydrous sodium sulfate, filtered, and then concentrated under reduced pressure. The residue was purified by flash column chromatography (petroleum ether-ethyl acetate) to provide the title compound (45 g, 57%). $^1$H NMR (400 MHz, CDCl$_3$) δ 4.09-3.91 (m, 4H), 2.52-2.42 (m, 1H), 2.37-2.28 (m, 1H).

Step B: 3-(Aminomethyl)tetrahydrofuran-3-ol. A solution of 3-hydroxytetrahydrofuran-3-carbonitrile (20.5 g, 181 mmol) in THF (80 mL) was added dropwise to a stirring solution of LAH (7.57 g, 199 mmol) in THF (200 mL) at 0° C. After 3 hours, water (7.6 mL), 15% aqueous sodium hydroxide solution (7.6 mL), and then water (7.6 mL) were added dropwise, sequentially. The mixture was filtered and the filtrate was concentrated under reduced pressure to provide the title compound as a colorless liquid (15 g). This material was used in the next step without further purification.

Step C: 2-Chloro-N-((3-hydroxytetrahydrofuran-3-yl)methyl)pyridine-3-sulfonamide. 2-Chloropyridine-3-sulfonyl chloride (25.9 g, 122 mmol) was added to a stirring solution of 3-(aminomethyl)tetrahydrofuran-3-ol (15 g, 128 mmol) and potassium carbonate (42.1 g, 305 mmol) in a mixture of THF (300 mL) and water (75 mL) at 0° C. The mixture was allowed to warm to room temperature. After 16 hours, water (150 mL) was added and the mixture was concentrated under reduced pressure and the concentrate was extracted with ethyl acetate. This resulted in numerous organic fractions which were combined, washed with saturated aqueous sodium chloride solution, dried over anhydrous sodium sulfate, filtered, and then concentrated under reduced pressure. The residue was purified by flash column chromatography (petroleum ether-ethyl acetate) to provide the title compound (16.7 g, 46%). MS (ESI): mass calcd. for $C_{10}H_{13}ClN_2O_4S$, 292.0; m/z found, 293.2 [M+H]$^+$. $^1$H NMR (400 MHz, CDCl$_3$) δ 8.58 (dd, J=4.8, 1.9 Hz, 1H), 8.40 (dd, J=7.8, 1.9 Hz, 1H), 7.45 (dd, J=7.8, 4.8 Hz, 1H), 5.95 (t, J=6.2 Hz, 1H), 4.05-3.94 (m, 1H), 3.91-3.82 (m, 1H), 3.69 (d, J=9.7 Hz, 1H), 3.62 (d, J=9.7 Hz, 1H), 3.18-3.07 (m, 2H), 2.88 (s, 1H), 1.99-1.92 (m, 2H).

Step D: (*S)-2',3',4,5-Tetrahydro-2H-spiro[furan-3,4'-pyrido[2,3-b][1,4,5]oxathiazepine]1',1'-dioxide. A mixture of 2-chloro-N-((3-hydroxytetrahydrofuran-3-yl)methyl)pyridine-3-sulfonamide (3 g, 10 mmol) and potassium tert-butoxide (3.45 g, 30.7 mmol) in DMF (60 mL) was warmed to 80° C. After 1 hour, the mixture was cooled to room temperature and then a solution of 4 M HCl in methanol was added until the pH was 7. The mixture was concentrated under reduced pressure to afford a mixture of 2',3',4,5-tetrahydro-2H-spiro[furan-3,4'-pyrido[2,3-b][1,4,5]oxathiazepine] 1',1'-dioxide enantiomers (4 g). This was combined with an additional batch of 2',3',4,5-tetrahydro-2H-spiro[furan-3,4'-pyrido[2,3-b][1,4,5]oxathiazepine] 1',1'-dioxide enantiomers (2.9 g). The isomers were separated by chiral SFC (stationary phase: Chiralcel OJ m 250×50 mm, mobile phase: 60% $CO_2$ and 40% methanol with 0.1% $NH_3$) to afford two enantiomers. The first eluting enantiomer (2.8 g) was designated (*S). MS (ESI): mass calcd. for $C_{10}H_{12}N_2O_4S$, 256.1; m/z found, 256.9 [M+H]$^+$. $^1$H NMR (400 MHz, DMSO-$d_6$) δ 8.51 (dd, J=4.8, 2.0 Hz, 1H), 8.32 (s, 1H), 8.19 (dd, J=7.6, 2.0 Hz, 1H), 7.43 (dd, J=7.6, 4.8 Hz, 1H), 4.02-3.94 (m, 1H), 3.89-3.81 (m, 1H), 3.77-3.58 (m, 4H), 2.02-1.90 (m, 1H), 1.86-1.78 (m, 1H).

Intermediate 155: (*R)-2',3',4,5-Tetrahydro-2H-spiro[furan-3,4'-pyrido[2,3-b][1,4,5]oxathiazepine] 1',1'-dioxide

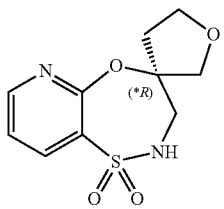 [SMILES: O=S1(=O)NC[C@@]2(CCOC2)Oc2ncccc21]

The second eluting isomer (2.8 g) from the chiral separation described in Intermediate 154 was designated (*R). MS (ESI): mass calcd. for $C_{10}H_{12}N_2O_4S$, 256.1; m/z found, 256.8 [M+H]$^+$. $^1$H NMR (400 MHz, DMSO-$d_6$) δ 8.49 (dd, J=4.8, 1.9 Hz, 1H), 8.30 (s, 1H), 8.17 (dd, J=7.7, 1.9 Hz, 1H), 7.41 (dd, J=7.6, 4.9 Hz, 1H), 4.00-3.92 (m, 1H), 3.87-3.78 (m, 1H), 3.74-3.56 (m, 4H), 1.99-1.90 (m, 1H), 1.85-1.76 (m, 1H).

Intermediate 156: (*S)-8'-Methyl-2',3',4,5-tetrahydro-2H-spiro[furan-3,4'-pyrido[2,3-b][1,4,5]oxathiazepine] 1',1'-dioxide

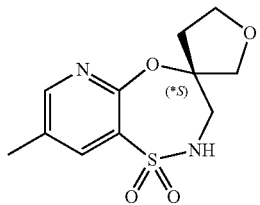 [SMILES: Cc1cnc2c(c1)S(=O)(=O)NC[C@]1(CCOC1)O2]

The title compound (2.6 g) was prepared using analogous conditions as described in Intermediate 154 using 2-chloro-5-methylpyridine-3-sulfonyl chloride instead of 2-chloro-pyridine-3-sulfonyl chloride in Step C. MS (ESI): mass calcd. for $C_{11}H_{14}N_2O_4S$, 270.1; m/z found, 270.9 [M+H]$^+$. $^1$H NMR (400 MHz, DMSO-$d_6$) δ 8.31 (d, J=2.4 Hz, 1H), 8.26 (s, 1H), 8.00 (d, J=2.4 Hz, 1H), 4.02-3.92 (m, 1H), 3.87-3.80 (m, 1H), 3.74-3.56 (m, 4H), 2.35 (s, 3H), 2.00-1.88 (m, 1H), 1.85-1.76 (m, 1H).

Intermediate 157: (*R)-8'-Methyl-2',3',4,5-tetrahydro-2H-spiro[furan-3,4'-pyrido[2,3-b][1,4,5]oxathiazepine] 1',1'-dioxide

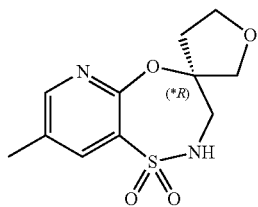 [SMILES: Cc1cnc2c(c1)S(=O)(=O)NC[C@@]1(CCOC1)O2]

The second eluting isomer (2.8 g) from the chiral separation described in Intermediate 156 was designated (*R). MS (ESI): mass calcd. for $C_{11}H_{14}N_2O_4S$, 270.1; m/z found, 270.9 [M+H]$^+$. $^1$H NMR (400 MHz, DMSO-$d_6$) δ 8.31 (d, J=2.4 Hz, 1H), 8.25 (s, 1H), 8.00 (d, J=2.4 Hz, 1H), 4.02-3.92 (m, 1H), 3.87-3.80 (m, 1H), 3.73-3.53 (m, 4H), 2.35 (s, 3H), 1.99-1.88 (m, 1H), 1.87-1.76 (m, 1H).

Intermediate 160: Methyl (*S)-3-(3-(chloromethyl)-4-methylphenyl)-2,2-dimethyl-3-(8-methyl-3-(trifluoromethyl)-[1,2,4]triazolo[4,3-a]pyridin-7-yl)propanoate

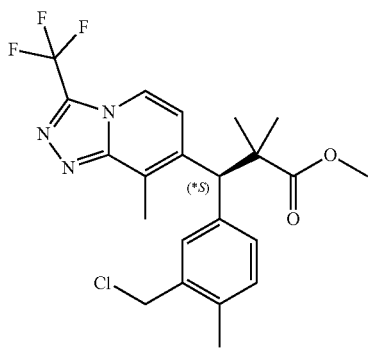 [SMILES: COC(=O)C(C)(C)[C@@H](c1ccc(C)c(CCl)c1)c1ccn2c(C(F)(F)F)nnc2c1C]

Thionyl chloride (1.5 mL, 21 mmol) was added to a stirring solution of methyl (*S)-3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate (Intermediate 141, 400 mg, 0.919 mmol) in dichloromethane (5 mL). After 16 hours, the mixture was concentrated under reduced pressure to afford the title compound (420 mg). This material was used in the next step without further purification. $^1$H NMR (400 MHz, DMSO-$d_6$) δ 8.39 (d, J=7.3 Hz, 1H), 7.33 (s, 1H), 7.28-7.22 (m, 2H), 7.18-7.14 (m, 1H), 4.76 (s, 1H), 4.72 (s, 2H), 3.51 (s, 3H), 2.68 (s, 3H), 2.31 (s, 3H), 1.31 (s, 3H), 1.27 (s, 3H).

Intermediate 161: Methyl (*R)-3-(3-(chloromethyl)-4-methylphenyl)-2,2-dimethyl-3-(8-methyl-3-(trifluoromethyl)-[1,2,4]triazolo[4,3-a]pyridin-7-yl)propanoate

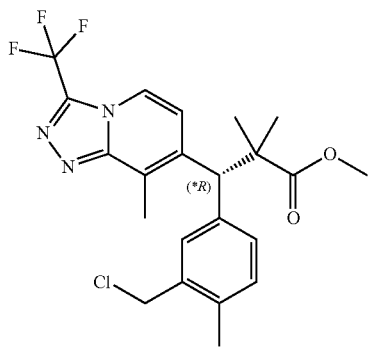 [SMILES: COC(=O)C(C)(C)[C@H](c1ccc(C)c(CCl)c1)c1ccn2c(C(F)(F)F)nnc2c1C]

The title compound (420 mg) was prepared using analogous conditions as described in Intermediate 160 using methyl (*R)-3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate (Intermediate 145) instead of methyl (*S)-3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate. $^1$H NMR (400 MHz, DMSO-$d_6$) δ 8.40 (d, J=7.3 Hz, 1H), 7.33 (s, 1H), 7.29-7.22 (m, 2H), 7.19-7.15 (m, 1H), 4.76 (s, 1H), 4.73 (s, 2H), 3.50 (s, 3H), 2.69 (s, 3H), 2.32 (s, 3H), 1.31 (s, 3H), 1.27 (s, 3H).

Intermediate 162: 3-Cyclopropyl-7-iodo-8-methyl-[1,2,4]triazolo[4,3-a]pyridine

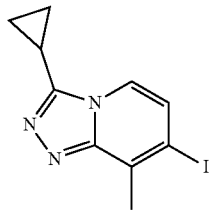

Cyclopropanecarbaldehyde (6.9 mL, 92 mmol) was added to a suspension of 2-hydrazinyl-4-iodo-3-methylpyridine (Intermediate 52, 20 g, 80 mmol) in DCM (80 mL) at room temperature. The mixture was stirred for 30 minutes at room temperature, then was cooled in an ice bath. Phenyl-13-iodanediyl diacetate (31 g, 96 mmol) was added portionwise over 2 minutes, then the reaction was removed from the ice bath and allowed to warm to room temperature overnight. The mixture became a solution while stirring overnight. The reaction was diluted with water and DCM. The resulting biphasic mixture was separated and the aqueous layer was extracted with DCM. These extractions resulted in several organic solvent fractions which were combined, washed with brine, dried over MgSO$_4$, filtered, and concentrated to dryness under reduced pressure. A mixture of DCM and hexanes was used to precipitate the title compound (18.4 g, 77% yield). MS (ESI): mass calcd. for $C_{10}H_{10}IN_3$, 299.0; m/z found, 300.0 [M+H]$^+$. $^1$H NMR (400 MHz, DMSO-$d_6$) δ 8.21-8.17 (m, 1H), 7.27 (d, J=7.1 Hz, 1H), 2.58 (s, 3H), 2.40-2.30 (m, 1H), 1.16-0.94 (m, 4H).

Intermediate 163: 3-(((tert-Butyldimethylsilyl)oxy)methyl)-4-methylbenzaldehyde

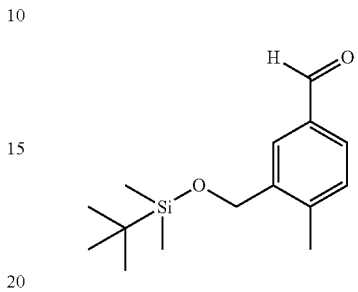

Step A: tert-Butyldimethyl((2-methyl-5-vinylbenzyl)oxy)silane. A mixture of ((5-bromo-2-methylbenzyl)oxy)(tert-butyl)dimethylsilane (Intermediate 19, 75 g, 238 mmol), potassium trifluoro(vinyl)borate (65 g, 485 mmol), and potassium phosphate (150 g, 707 mmol) in water (100 mL) and 1,4-dioxane (500 mL) was sparged with argon for 5 minutes. Pd(dppf)Cl$_2$ (9 g, 12 mmol) was added to the reaction and the resulting mixture was sparged with argon for 5 minutes. The reaction was then heated to 110° C. overnight. After this period of the time, the reaction was allowed to cool to room temperature and the suspension was filtered. The filtrate was diluted with water and extracted with ethyl acetate. These extractions resulted in several organic solvent fractions which were combined, dried over Na$_2$SO$_4$, filtered, and concentrated to dryness under reduced pressure. The material was purified by flash column chromatography (5-10% EtOAc/hexanes) to afford the title compound (50 g, 80% yield). $^1$H NMR (400 MHz, CDCl$_3$) δ 7.39 (s, 1H), 7.13-7.03 (m, 1H), 7.01-6.91 (m, 1H), 6.59 (m, 1H), 5.60 (m, 1H), 5.07 (m, 1H), 4.64-4.51 (m, 2H), 2.14 (s, 3H), 0.90-0.80 (m, 9H), 0.08--0.03 (m, 6H)

Step B: 3-(((tert-Butyldimethylsilyl)oxy)methyl)-4-methylbenzaldehyde. Potassium dioxidodioxoosmium dihydrate (9 g, 24 mmol) was added to a solution of tert-butyldimethyl((2-methyl-5-vinylbenzyl)oxy)silane (Intermediate 163, Step A, 110 g, 419 mmol) in water (500 mL) and 1,4-dioxane (500 mL). Sodium periodate (270 g, 1262 mmol) was added and the resultant mixture stirred at room temperature for 3 hours. The reaction was diluted with water and extracted with ethyl acetate. These extractions resulted in several organic solvent fractions which were combined, dried over Na$_2$SO$_4$, filtered, and concentrated to dryness under reduced pressure. The material was purified by flash column chromatography (5-10% EtOAc/hexanes) and then purified by preparative basic HPLC (SANPONT C18, acetonitrile-water, 10 mM NH$_4$HCO$_3$) to afford the title compound (82.7 g, 74% yield). $^1$H NMR (400 MHz, CDCl$_3$) δ 9.85 (s, 1H), 7.81 (s, 1H), 7.61-7.51 (m, 1H), 7.18-7.13 (m, 1H), 4.62 (s, 2H), 2.22 (s, 3H), 0.83 (s, 9H), 0.03--0.10 (m, 6H).

Intermediate 164: 7-(Difluoromethoxy)-1-methyl-1H-benzo[d][1,2,3]triazole-5-carbaldehyde

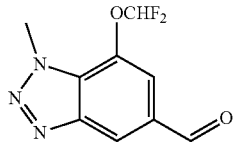 [SMILES: Cn1nnc2cc(C=O)cc(OC(F)F)c21]

Et$_3$N (2.8 g, 28 mmol) and triethylsilane (4.9 g, 42 mmol) were added 5-bromo-7-(difluoromethoxy)-1-methyl-1H-benzo[d][1,2,3]triazole (3.8 g, 14 mmol), 1,3-bis(diphenylphosphino)propane (620 mg, 1.50 mmol), and DMF (60 mL). The resultant mixture was sparged with N$_2$ for 5 minutes and then treated with Pd(OAc)$_2$ (307 mg, 1.37 mmol) and Pd(dppf)$_2$Cl$_2$ (440 mg, 0.601 mmol). The mixture was stirred while heating at 80° C. under CO atmosphere (50 Psi) for 16 hours before cooling to room-temperature, pouring it into water (60 mL) and extracting with dichloromethane (50 mL×3). The combined organic extracts were washed with brine (50 mL), dried over anhydrous Na$_2$SO$_4$, filtered, and concentrated to dryness under reduced pressure to give the title product, which was purified by FCC (eluent:petroleum ether:ethyl acetate=10:1 to 2:1) to afford the title compound (1.38 g, 44%) as a yellow solid. MS (ESI) mass calcd. for C$_9$H$_7$F$_2$N$_3$O$_2$ 227.05 m/z found 228.0 [M+H]$^+$. $^1$H NMR (400 MHz, DMSO-d$_6$) δ 10.16-10.03 (m, 1H), 8.63 (s, 1H), 7.80-7.33 (m, 2H), 4.44 (s, 3H)

Intermediate 165: 8-fluoro-2,2',3,3',5',6'-hexahydrospiro[benzo[b][1,4,5]oxathiazepine-4,4'-pyran] 1,1-dioxide

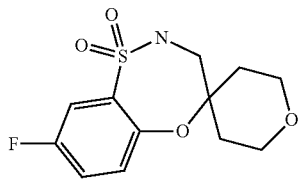 [SMILES: O=S1(=O)NCC2(CCOCC2)Oc2ccc(F)cc21]

8-Fluoro-2,2',3,3',5',6'-hexahydrospiro[benzo[b][1,4,5]oxathiazepine-4,4'-pyran] 1,1-dioxide (1.4 g, 50% yield) was prepared using analogous conditions as described in Intermediate 36 where 2,5-difluorobenzenesulfonyl chloride was used instead of 2-chloropyridine-3-sulfonyl chloride in Step A. MS (ESI): mass calcd. for C$_{12}$H$_{14}$FNO$_4$S, 287.06; m/z found, 288.1 [M+H]$^+$. $^1$H NMR (400 MHz, CD$_3$OD) Q 7.54-7.45 (m, 1H), 7.45-7.36 (m, 1H), 7.36-7.22 (m, 1H), 4.67-4.49 (m, 1H), 3.90-3.78 (m, 2H), 3.77-3.65 (m, 2H), 3.59-3.45 (s, 2H), 1.77-1.62 (m, 4H).

Intermediate 166: 8'-fluoro-2,2',3,3',5,6-hexahydrospiro[pyran-4,4'-pyrido[2,3-b][1,4,5]oxathiazepine] 1',1'-dioxide

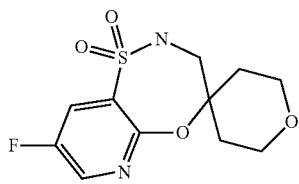 [SMILES: O=S1(=O)NCC2(CCOCC2)Oc2ncc(F)cc21]

8'-Fluoro-2,2',3,3',5,6-hexahydrospiro[pyran-4,4'-pyrido[2,3-b][1,4,5]oxathiazepine] 1',1'-dioxide (350 mg, 24.4% yield) was prepared using analogous conditions as described in Intermediate 36 where 2-chloro-5-fluoropyridine-3-sulfonyl chloride was used instead of 2-chloropyridine-3-sulfonyl chloride in Step A. MS (ESI): mass calcd. for C$_{11}$H$_{13}$FN$_2$O$_4$S, 288.06; m/z found, 289.1 [M+H]$^+$. $^1$H NMR (400 MHz, CD$_3$OD) Q 8.53 (t, J=3.1 Hz, 1H), 8.34-8.15 (m, 1H), 4.59 (s, 2H), 3.79-3.64 (m, 3H), 3.08-2.95 (m, 2H), 1.74-1.59 (m, 2H), 1.59-1.39 (m, 2H).

Intermediate 167: Ethyl (*S)-3-(3-(difluoromethyl)-8-methyl-[1,2,4]triazolo[4,3-a]pyridin-7-yl)-3-(3-(hydroxymethyl)-4-methylphenyl)propanoate

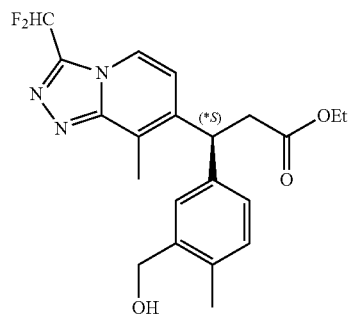 [SMILES: CCOC(=O)C[C@@H](c1ccc(C)c(CO)c1)c1ccn2c(C(F)F)nnc2c1C]

The mixture of ethyl 3-(3-(difluoromethyl)-8-methyl-[1,2,4]triazolo[4,3-a]pyridin-7-yl)-3-(3-(hydroxymethyl)-4-methylphenyl)propanoate isomers (Example 28, Step C) were separated by chiral SFC (Stationary phase: Chiralpak AD-H 5 μm 250×30 mm, Mobile phase: 70% CO$_2$, 30% MeOH) to afford two enantiomers. The first eluting isomer (2.42 g) was designated (*S): MS (ESI): mass calcd. for C$_{21}$H$_{22}$F$_2$N$_3$O$_3$, 403.4; m/z found, 404.2 [M+H]$^+$. The second eluting isomer was designated as (*R), however this Intermediate was not used further.

Intermediate 168: Methyl 3-(1-ethyl-4-methyl-1H-benzo[d][1,2,3]triazol-5-yl)-3-(6-(hydroxymethyl)-5-methylpyridin-2-yl)-2,2-dimethylpropanoate

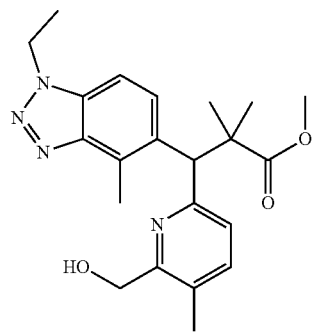 [SMILES: CCn1nnc2c(C)c(C(c3ccc(C)c(CO)n3)C(C)(C)C(=O)OC)ccc21]

Step A: 1-Ethyl-4-methyl-1H-benzo[d][1,2,3]triazole-5-carbaldehyde. Osmium tetroxide (0.40 mL, 1.56 mmol) was added to a stirring mixture of ethyl (E)-3-(1-ethyl-4-methyl-1H-benzo[d][1,2,3]triazol-5-yl)acrylate (Intermediate 17, 1.0 g, 3.86 mmol) in dioxane (25 mL) and water (25 mL) at room temperature. Then sodium periodate (2.61 g, 12.2 mmol) was added immediately. After one and half hours, ethyl acetate and water were added until all solids dissolved. The layers were separated, dried over Na$_2$SO$_4$, filtered and concentrated to dryness under reduced pressure. The residue was purified by flash column chromatography (eluent: 0-100% ethyl acetate/hexanes) to provide the title compound (500 mg, 68%) as a white foam. MS (ESI): mass calcd. for C$_{10}$H$_{11}$N$_3$O, 189.1; m/z found, 190.2 [M+H]$^+$. $^1$H NMR (600 MHz, CDCl$_3$) δ 10.50 (s, 1H), 7.97 (d, J=8.7 Hz, 1H), 7.45 (dt, J=8.6, 0.7 Hz, 1H), 4.72 (q, J=7.4 Hz, 2H), 3.14 (s, 3H), 1.66 (t, J=7.4 Hz, 3H).

Step B: (6-(((tert-Butyldimethylsilyl)oxy)methyl)-5-methylpyridin-2-yl)(1-ethyl-4-methyl-1H-benzo[d][1,2,3]triazol-5-yl)methanol. n-Butyllithium (2.0 M, 3.1 ml, 6.2 mmol) was added dropwise to a solution of 6-bromo-2-(((tert-butyldimethylsilyl)oxy)methyl)-3-methylpyridine (Intermediate 120, 1.25 g, 3.96 mmol) in THF (14 ml) at −78° C. under nitrogen. The reaction was stirred at −78° C. for 2 minutes to prepare the lithiate reaction mixture. A solution 1-ethyl-4-methyl-1H-benzo[d][1,2,3]triazole-5-carbaldehyde (750 mg, 3.96 mmol) in THF (10 ml) was added to the lithiate reaction mixture dropwise. The resulting reaction mixture was stirred at −78° C. for 5 minutes. The reaction was then quenched with saturated aqueous NaHCO$_3$, and then extracted with EtOAc. These extractions resulted in several organic solvent fractions which were combined, dried over MgSO$_4$, filtered, and concentrated to dryness under reduced pressure. The product was purified by flash column chromatography (eluent: 0-100% ethyl acetate/hexanes) to provide the title compound (800 mg, 47%). MS (ESI): mass calcd. for C$_{23}$H$_{34}$N$_4$O$_2$Si, 426.2; m/z found, 427.2 [M+H]$^+$. $^1$H NMR (600 MHz, CDCl$_3$) δ 7.25 (dd, J=8.3, 1.7 Hz, 2H), 7.16 (d, J=8.7 Hz, 1H), 6.66 (d, J=7.8 Hz, 1H), 6.04 (s, 1H), 5.64 (s, 1H), 4.79 (d, J=0.9 Hz, 2H), 4.53 (q, J=7.3 Hz, 2H), 2.80 (s, 3H), 2.28 (s, 3H), 1.47 (t, J=7.3 Hz, 3H), 0.81 (s, 9H), 0.00 (d, J=1.1 Hz, 6H).

Step C: Methyl 3-(6-(((tert-butyldimethylsilyl)oxy)methyl)-5-methylpyridin-2-yl)-3-(1-ethyl-4-methyl-1H-benzo[d][1,2,3]triazol-5-yl)-2,2-dimethylpropanoate. Trichloroacetonitrile (0.49 ml, 4.88 mmol) and DBU (0.04 ml, 0.28 mmol) were added to a solution of (6-(((tert-butyldimethylsilyl)oxy)methyl)-5-methylpyridin-2-yl)(1-ethyl-4-methyl-1H-benzo[d][1,2,3]triazol-5-yl)methanol (800 mg, 1.88 mmol) in ACN (22 ml). The reaction was stirred at room temperature under nitrogen for 1 hour. ((1-Methoxy-2-methylprop-1-en-1-yl)oxy)trimethylsilane (0.76 ml, 3.75 mmol) was then added to the reaction, followed by trifluoromethanesulfonamide (263 mg, 0.94 mmol), and the reaction was stirred at room temperature under nitrogen for 3 hours. The reaction was quenched with saturated aqueous NaHCO$_3$, then extracted twice with EtOAc. These extractions resulted in several organic solvent fractions which were combined, dried over MgSO$_4$, filtered, and concentrated to dryness under reduced pressure. The product was purified by flash column chromatography (eluent: 0-50% ethyl acetate/hexanes) to provide the title compound that was carried forward without further purification (600 mg, 63%). MS (ESI): mass calcd. for C$_{28}$H$_{42}$N$_4$O$_3$Si, 510.3; m/z found, 511.3 [M+H]$^+$.

Step D: Methyl 3-(1-ethyl-4-methyl-1H-benzo[d][1,2,3]triazol-5-yl)-3-(6-(hydroxymethyl)-5-methylpyridin-2-yl)-2,2-dimethylpropanoate. Tetrabutylammonium fluoride (1 M in THF, 2.35 ml, 2.35 mmol) was added to a solution of methyl 3-(6-(((tert-butyldimethyl silyl)oxy)methyl)-5-methylpyridin-2-yl)-3-(1-ethyl-4-methyl-1H-benzo[d][1,2,3]triazol-5-yl)-2,2-dimethylpropanoate (600 mg, 1.18 mmol) and 3 drops of DMF in THF (25 ml). The reaction was stirred at room temperature for 1.5 hours. The reaction was quenched with saturated aqueous NaHCO$_3$, then extracted twice with EtOAc. These extractions resulted in several organic solvent fractions which were combined, dried over MgSO$_4$, filtered, and concentrated to an oil under reduced pressure. The product was purified by flash column chromatography (eluent: 0-100% ethyl acetate/hexanes) to provide the title compound (350 mg, 75%). MS (ESI): mass calcd. for C$_{22}$H$_{28}$N$_4$O$_3$, 396.2; m/z found, 397.2 [M+H]$^+$.

Intermediate 169: Methyl 3-(5-(hydroxymethyl)-6-methylpyridin-3-yl)-2,2-dimethyl-3-(8-methyl-3-(trifluoromethyl)-[1,2,4]triazolo[4,3-a]pyridin-7-yl)propanoate

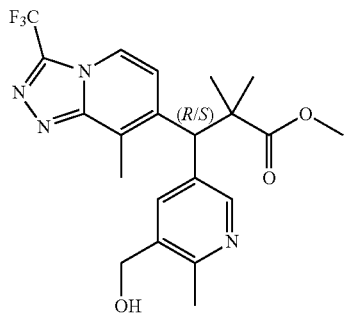 [SMILES: COC(=O)C(C)(C)C(c1cnc(C)c(CO)c1)c1ccn2c(C(F)(F)F)nnc2c1C]

Step A: (4-(((tert-Butyldimethylsilyl)oxy)methyl)-5-methylpyridin-2-yl)(8-methyl-3-(trifluoromethyl)-[1,2,4]triazolo[4,3-a]pyridin-7-yl)methanol. n-Butyllithium (2.0 M, 3.1 ml, 6.2 mmol) was added dropwise to a solution of 5-bromo-3-(((tert-butyldimethylsilyl)oxy)methyl)-2-methylpyridine (Intermediate 46, 4.0 g, 12.6 mmol) in THF (47 ml) at −78° C. under nitrogen. The reaction was stirred at −78° C. for 2 minutes to prepare the lithiate reaction mixture. A solution of 3-(trifluoromethyl)-8-methyl-[1,2,4]triazolo[4,3-a]pyridine7-carbaldehyde (Intermediate 28, 2.6 g, 10.3 mmol) in THF (10 ml) was added to the lithiate reaction mixture dropwise. The resulting reaction mixture was stirred at −78° C. for 5 minutes. The reaction was then quenched with saturated aqueous NaHCO$_3$, and then extracted twice with EtOAc. These extractions resulted in several organic solvent fractions which were combined, dried over MgSO$_4$, filtered, and concentrated to dryness under reduced pressure. The product was purified by flash column chromatography (eluent: 0-100% EtOAc/hexanes) to provide the title compound (3.0 g, 63%). MS (ESI): mass calcd. for C$_{22}$H$_{29}$F$_3$N$_4$O$_2$Si, 466.2; m/z found, 467.3 [M+H]$^+$. $^1$H NMR (500 MHz, CDCl$_3$) δ 8.35 (d, J=2.3 Hz, 1H), 8.12-7.98 (m, 1H), 7.61-7.53 (m, 1H), 7.48-7.39 (m, 1H), 6.22 (s, 1H), 4.57 (s, 2H), 2.60 (s, 3H), 2.33 (s, 3H), 0.76 (s, 9H), 0.82-0.70 (m, 6H).

Step B: 7-((5-(((tert-Butyldimethylsilyl)oxy)methyl)-6-methylpyridin-3-yl)chloromethyl)-8-methyl-3-(trifluoromethyl)-[1,2,4]triazolo[4,3-a]pyridine. Thionyl chloride (3.03 mL, 41.8 mmol) was added to a solution of (4-(((tert-butyldimethylsilyl)oxy)methyl)-5-methylpyridin-2-yl)(8-methyl-3-(trifluoromethyl)-[1,2,4]triazolo[4,3-a]pyridin-7-yl)methanol (15 g, 32 mmol) and 2,6-di-tert-butylpyridine (14 ml, 64 mmol) in DCM (160 mL). The reaction was stirred at room temperature for 1 hour. The reaction was quenched with saturated aqueous NaHCO$_3$, then extracted twice with DCM. These extractions resulted in several organic solvent fractions which were combined, dried over MgSO₄, filtered, and concentrated to dryness under reduced pressure. The product was purified by flash column chromatography (eluent: 0-100% ethyl acetate/hexanes) to provide the title compound (11.6 g, 74% yield). MS (ESI): mass calcd. for C₂₂H₂₈ClF₃N₄OSi, 484.2; m/z found, 485.2 [M+H]⁺.

Step C: Methyl 3-(5-(((tert-butyldimethylsilyl)oxy) methyl)-6-methylpyridin-3-yl)-2,2-dimethyl-3-(8-methyl-3-(trifluoromethyl)-[1,2,4]triazolo[4,3-a]pyridin-7-yl)propanoate. ((1-Methoxy-2-methylprop-1-en-1-yl)oxy) trimethylsilane (23.7 ml, 117 mmol) was added to a solution of 7-((5-(((tert-butyldimethylsilyl)oxy)methyl)-6-methylpyridin-3-yl)chloromethyl)-8-methyl-3-(trifluoromethyl)-[1,2,4]triazolo[4,3-a]pyridine (11.6 g, 23.9 mmol) in DCM (119 ml). Indium(III) bromide (2.6 g, 7.3 mmol) was added and the reaction was stirred at room temperature for 16 hours. The reaction was filtered, concentrated and purified by flash column chromatography (eluent: 0-100% ethyl acetate/hexanes) to afford the title compound (5.0 g, 40% yield). MS (ESI): mass calcd. for C₂₇H₃₇F₃N₄O₃Si, 550.3; m/z found, 551.3 [M+H]⁺.

Step D: Methyl 3-(5-(hydroxymethyl)-6-methylpyridin-3-yl)-2,2-dimethyl-3-(8-methyl-3-(trifluoromethyl)-[1,2,4]triazolo[4,3-a]pyridin-7-yl)propanoate. Tetrabutylammonium fluoride (1 M in THF, 27 ml, 27 mmol) was added to a solution of methyl 3-(5-(((tert-butyldimethylsilyl)oxy)methyl)-6-methylpyridin-3-yl)-2,2-dimethyl-3-(8-methyl-3-(trifluoromethyl)-[1,2,4]triazolo[4,3-a]pyridin-7-yl)propanoate (5.0 g, 9.1 mmol) in THF (50 ml). The reaction was stirred at room temperature for 1 hour. The reaction was quenched with saturated aqueous NH₄C₁, then extracted twice with ethyl acetate. These extractions resulted in several organic solvent fractions which were combined, dried over MgSO₄, filtered, concentrated, purified by flash column chromatography (eluent: 0-100% ethyl acetate/hexanes) and further purified by preparative acidic HPLC (0.05% TFA in water, 0.05% TFA in acetonitrile) to provide the title compound (3.8 g, 96% yield). MS (ESI): mass calcd. for C₂₁H₂₃F₃N₄O₃, 436.2; m/z found, 437.0 [M+H]⁺. ¹H NMR (500 MHz, CDCl₃) δ 8.60 (d, J=2.1 Hz, 1H), 8.38 (d, J=2.2 Hz, 1H), 8.13 (d, J=7.2 Hz, 1H), 7.19 (d, J=7.4 Hz, 1H), 4.90 (s, 1H), 4.74 (s, 2H), 3.63 (s, 3H), 2.71 (s, 3H), 2.64 (s, 3H), 1.37 (d, J=19.6 Hz, 6H).

Intermediate 170: Methyl (*S)-3-(4-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate

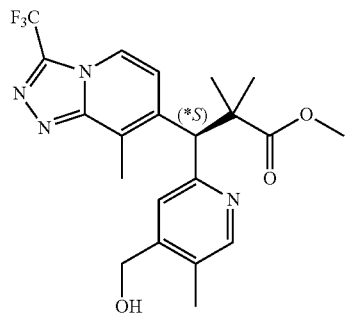 [SMILES: COC(=O)C(C)(C)[C@@H](c1cc(CO)c(C)cn1)c1ccn2c(C(F)(F)F)nnc2c1C]

Step A: (4-(((tert-Butyldimethylsilyl)oxy)methyl)-5-methylpyridin-2-yl)(8-methyl-3-(trifluoromethyl)-[1,2,4]triazolo[4,3-a]pyridin-7-yl)methanol. n-Butyllithium (2.0 M, 3.1 ml, 6.2 mmol) was added dropwise to a stirring solution of 2-bromo-4-(((tert-butyldimethylsilyl)oxy) methyl)-5-methylpyridine (Intermediate 47, 2.0 g, 6.3 mmol) in THF (14 ml) at −78° C. under nitrogen. The reaction was stirred at −78° C. for 2 minutes. A solution 3-(trifluoromethyl)-8-methyl-[1,2,4]triazolo[4,3-a]pyridine-7-carbaldehyde (Intermediate 28, 1.2 g, 5.1 mmol) in THF (10 ml) was added to the lithiate reaction mixture dropwise. The reaction was stirred at −78° C. for 5 minutes. The reaction was quenched with saturated aqueous NaHCO₃, and then extracted with EtOAc. These extractions resulted in several organic solvent fractions which were combined, dried over MgSO₄, filtered, and concentrated to dryness under reduced pressure. The material was purified by flash column chromatography (eluent: 0-100% ethyl acetate/ hexanes) to provide the title compound (1.0 g, 42%). MS (ESI): mass calcd. for C₂₂H₂₉F₃N₄O₂Si, 466.2; m/z found, 467.3 [M+H]⁺. ¹H NMR (500 MHz, CDCl₃) δ 8.30 (t, J=0.8 Hz, 1H), 8.05-7.99 (m, 1H), 7.25 (s, 1H), 7.16 (d, J=7.2 Hz, 1H), 6.19 (s, 1H), 5.94 (s, 1H), 4.65 (dd, J=15.6, 1.1 Hz, 1H), 4.60 (dd, J=15.6, 1.0 Hz, 1H), 2.86 (s, 3H), 2.20 (s, 3H), 2.06 (s, 1H), 1.27 (t, J=7.1 Hz, 1H), 0.78 (s, 9H), 0.84-0.72 (m, 1H), 0.05 (s, 3H).

Step B: 7-((4-(((tert-Butyldimethylsilyl)oxy)methyl)-5-methylpyridin-2-yl)chloromethyl)-8-methyl-3-(trifluoromethyl)-[1,2,4]triazolo[4,3-a]pyridine. Thionyl chloride (0.3 mL, 4.2 mmol) was added to a solution of (4-(((tert-butyldimethylsilyl)oxy)methyl)-5-methylpyridin-2-yl)(8-methyl-3-(trifluoromethyl)-[1,2,4]triazolo[4,3-a]pyridin-7-yl)methanol (1.5 g, 3.2 mmol) and 2,6-di-tert-butylpyridine (1.4 ml, 6.4 mmol) in DCM (16 mL). The reaction was stirred at room temperature for 1 hour. The reaction was quenched with saturated aqueous NaHCO₃, then extracted with DCM. These extractions resulted in several organic solvent fractions which were combined, dried over MgSO₄, filtered, and concentrated to dryness under reduced pressure. The material was purified by flash column chromatography (eluent: 0-100% ethyl acetate/hexanes) to provide the title compound (1.0 g, 64% yield). MS (ESI): mass calcd. for C₂₂H₂₈ClF₃N₄OSi, 484.2; m/z found, 485.2 [M+H]⁺. ¹H NMR (500 MHz, CDCl₃) δ 8.15 (t, J=0.8 Hz, 1H), 7.96 (d, J=7.2 Hz, 1H), 7.62 (s, 1H), 7.25 (d, J=7.3 Hz, 1H), 6.35 (s, 1H), 4.58 (d, J=1.0 Hz, 2H), 3.98 (q, J=7.1 Hz, 1H), 2.71 (d, J=0.7 Hz, 3H), 2.08 (s, 3H), 1.12 (t, J=7.1 Hz, 1H), 0.80 (s, 9H), 0.86-0.74 (m, 1H), 0.05 (s, 3H).

Step C: Methyl 3-(4-(((tert-butyldimethylsilyl)oxy) methyl)-5-methylpyridin-2-yl)-2,2-dimethyl-3-(8-methyl-3-(trifluoromethyl)-[1,2,4]triazolo[4,3-a]pyridin-7-yl)propanoate. ((1-Methoxy-2-methylprop-1-en-1-yl)oxy) trimethylsilane (6.1 ml, 30 mmol) was added to a solution of 7-((4-(((tert-butyldimethylsilyl)oxy)methyl)-5-methylpyridin-2-yl)chloromethyl)-8-methyl-3-(trifluoromethyl)-[1,2,4]triazolo[4,3-a]pyridine (3.0 g, 6.2 mmol) in DCM (31 ml). Indium(III) bromide (0.67 g, 1.9 mmol) was added and the reaction was stirred at room temperature for 3 hours. The reaction was filtered, concentrated and purified by flash column chromatography (eluent: 0-100% ethyl acetate/ hexanes) to afford the title compound (0.5 g, 15% yield). MS (ESI): mass calcd. for C₂₇H₃₇F₃N₄O₃Si, 550.2; m/z found, 551.2 [M+H]⁺. ¹H NMR (500 MHz, CDCl₃) δ 8.22 (d, J=0.8 Hz, 1H), 7.91 (d, J=7.4 Hz, 1H), 7.28 (d, J=7.3 Hz, 1H), 7.06 (s, 1H), 5.04 (s, 1H), 4.60-4.49 (m, 2H), 3.59 (s, 3H), 2.86 (s, 3H), 2.11 (s, 3H), 2.01 (s, 1H), 1.28 (s, 3H), 1.22 (t, J=7.1 Hz, 1H), 0.74 (s, 9H), 0.76-0.70 (m, 1H), 0.14-0.07 (m, 6H).

Step D: Methyl 3-(4-(hydroxymethyl)-5-methylpyridin-2-yl)-2,2-dimethyl-3-(8-methyl-3-(trifluoromethyl)-[1,2,4] triazolo[4,3-a]pyridin-7-yl)propanoate. Tetrabutylammonium fluoride (1 M in THF, 1.4 ml, 1.4 mmol) was added to a solution of Methyl 3-(4-(((tert-butyldimethylsilyl)oxy) methyl)-5-methylpyridin-2-yl)-2,2-dimethyl-3-(8-methyl-3-(trifluoromethyl)-[1,2,4]triazolo[4,3-a]pyridin-7-yl)propanoate (0.5 g, 0.9 mmol) in THF (5 ml). The reaction was stirred at room temperature for 1 hour. The reaction was quenched with saturated aqueous NH$_4$C$_1$, then extracted with ethyl acetate. These extractions resulted in several organic solvent fractions which were combined, dried over MgSO$_4$, filtered, concentrated to and purified by flash column chromatography (eluent: 0-100% ethyl acetate/ hexanes) to afford the title compound (280 mg, 71% yield). This racemic mixture was used in the preparation of Example 587 and is designated as Intermediate 170-racemic. MS (ESI): mass calcd. for C$_{21}$H$_{23}$F$_3$N$_4$O$_3$, 436.2; m/z found, 437.2 [M+H]$^+$. $^1$H NMR (500 MHz, CDCl$_3$) δ 8.28 (d, J=0.8 Hz, 1H), 7.92 (d, J=7.3 Hz, 1H), 7.47 (d, J=7.4 Hz, 1H), 7.23 (s, 1H), 5.00 (s, 1H), 4.71-4.66 (m, 2H), 3.60 (s, 4H), 2.86-2.82 (m, 3H), 2.19 (s, 3H), 1.40 (s, 3H), 1.32 (s, 3H).

Step E: The mixture of (R/S)-methyl 3-(4-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate (1.5 g) was separated by chiral SFC (stationary phase: ADH 2*25 cm, Mobile phase: 60% CO$_2$, 40% EtOH) to afford two enantiomers. The second eluting isomer, designated (*R), was not isolated. The first eluting isomer (573 mg) was designated (*S): MS (ESI): mass calcd. for C$_{21}$H$_{23}$F$_3$N$_4$O$_3$, 436.2; m/z found, 437.2 [M+H]$^+$. $^1$H NMR (500 MHz, CDCl$_3$) δ 8.28 (d, J=0.8 Hz, 1H), 7.92 (d, J=7.3 Hz, 1H), 7.47 (d, J=7.4 Hz, 1H), 7.23 (s, 1H), 5.00 (s, 1H), 4.71-4.66 (m, 2H), 3.60 (s, 4H), 2.86-2.82 (m, 3H), 2.19 (s, 3H), 1.40 (s, 3H), 1.32 (s, 3H).

Intermediate 171: Methyl (*S)-3-(1-ethyl-4-methyl-1H-benzo[d][1,2,3]triazol-5-yl)-3-(4-(hydroxymethyl)-5-methylpyridin-2-yl)-2,2-dimethylpropanoate

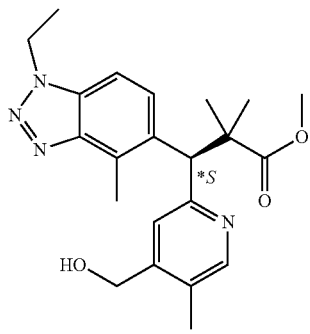 [SMILES: CCn1nnc2c(C)c([C@H](c3cc(CO)c(C)cn3)C(C)(C)C(=O)OC)ccc21]

Step A: (4-(((tert-Butyldimethylsilyl)oxy)methyl)-5-methylpyridin-2-yl)(1-ethyl-4-methyl-1H-benzo[d][1,2,3]triazol-5-yl)methanol. n-Butyllithium (1.6 M, 5.0 ml, 7.9 mmol) was added dropwise to a stirring solution of 2-bromo-4-(((tert-butyldimethylsilyl)oxy)methyl)-5-methylpyridine (Intermediate 47, 1.7 g, 5.3 mmol) in THF (11 ml) at −78° C. under nitrogen. The reaction mixture was stirred at −78° C. for 2 minutes. A solution 1-ethyl-4-methyl-1H-benzo[d][1,2,3]triazole-5-carbaldehyde (Intermediate 22, 1.0 g, 5.3 mmol) in THF (10 ml) was added to the lithiate reaction mixture dropwise. The reaction was stirred at −78° C. for 5 minutes. The reaction was quenched with saturated aqueous NaHCO$_3$, and then extracted with EtOAc. These extractions resulted in several organic solvent fractions which were combined, dried over MgSO$_4$, filtered, and concentrated to dryness under reduced pressure. The material was purified by flash column chromatography (eluent: 0-100% ethyl acetate/hexanes) to provide the title compound (1.2 g, 53%). MS (ESI): mass calcd. for C$_{23}$H$_{34}$N$_4$O$_2$Si, 426.2; m/z found, 427.2 [M+H]$^+$. $^1$H NMR (400 MHz, CDCl$_3$) δ 8.39 (s, 1H), 7.56 (d, J=8.6 Hz, 1H), 7.39 (d, J=8.6 Hz, 1H), 7.20 (s, 1H), 6.30 (s, 1H), 5.78 (s, 1H), 4.81-4.60 (m, 4H), 2.98 (s, 3H), 2.27 (s, 3H), 1.68 (t, J=7.3 Hz, 3H), 0.82 (s, 9H), 0.08 (s, 3H), 0.00 (s, 3H).

Step B: Methyl 3-(4-(((tert-butyldimethylsilyl)oxy) methyl)-5-methylpyridin-2-yl)-3-(1-ethyl-4-methyl-1H-benzo[d][1,2,3]triazol-5-yl)-2,2-dimethylpropanoate. Trichloroacetonitrile (0.7 mL, 7.3 mmol) and DBU (63 mL, 0.4 mmol) were added to a solution of (4-(((tert-butyldimethyl silyl)oxy)methyl)-5-methylpyridin-2-yl)(1-ethyl-4-methyl-1H-benzo[d][1,2,3]triazol-5-yl)methanol (1.2 g, 2.8 mmol) in ACN (14 ml). The reaction was stirred at room temperature under nitrogen for 1 hour. ((1-Methoxy-2-methylprop-1-en-1-yl)oxy)trimethylsilane (1.1 mL, 5.6 mmol) was then added to the reaction, followed by trifluoromethanesulfonamide (0.4 g, 1.4 mmol), and the reaction was stirred at room temperature under nitrogen for 2 hours. The reaction was quenched with saturated aqueous NaHCO$_3$, then extracted with EtOAc. These extractions resulted in several organic solvent fractions which were combined, dried over MgSO$_4$, filtered, and concentrated to dryness under reduced pressure. The material was purified by flash column chromatography (eluent: 0-100% ethyl acetate/ hexanes) to provide the title compound as an impure mixture that was carried forward without further purification (1.3 g, 90% yield). MS (ESI): mass calcd. for C$_{28}$H$_{42}$N$_4$O$_3$Si, 510.3; m/z found, 511.3 [M+H]$^+$. $^1$H NMR (400 MHz, CDCl$_3$) δ 8.27 (s, 1H), 7.48 (d, J=8.7 Hz, 1H), 7.29 (d, J=8.7 Hz, 1H), 7.02 (s, 1H), 5.28 (s, 1H), 4.69 (qd, J=7.2, 2.1 Hz, 2H), 4.67-4.51 (m, 2H), 4.16 (q, J=7.1 Hz, 0H), 3.65 (s, 3H), 3.00 (s, 3H), 2.17 (s, 3H), 1.64 (t, J=7.3 Hz, 3H), 1.27 (s, 6H), 0.73 (s, 9H), 0.01 (s, 3H), −0.06 (s, 3H).

Step C: Methyl 3-(1-ethyl-4-methyl-1H-benzo[d][1,2,3] triazol-5-yl)-3-(4-(hydroxymethyl)-5-methylpyridin-2-yl)-2,2-dimethylpropanoate. Tetrabutylammonium fluoride (1 M in THF, 5.1 ml, 5.1 mmol) was added to a solution of methyl 3-(4-(((tert-butyldimethylsilyl)oxy)methyl)-5-methylpyridin-2-yl)-3-(1-ethyl-4-methyl-1H-benzo[d][1,2,3]triazol-5-yl)-2,2-dimethylpropanoate (1.3 g, 2.5 mmol) in THF (28 ml) and 3 drops of DMF. The reaction was stirred at room temperature for 1.5 hours. The reaction was quenched with saturated aqueous NaHCO$_3$, then extracted with EtOAc. These extractions resulted in several organic solvent fractions which were combined, dried over MgSO$_4$, filtered, and concentrated to an oil under reduced pressure. The material was purified by flash column chromatography (eluent: 0-100% ethyl acetate/hexanes) to provide the title compound (0.6 g, 56% yield). MS (ESI): mass calcd. for C$_{22}$H$_{28}$N$_4$O$_3$, 396.2; m/z found, 397.2 [M+H]$^+$. $^1$H NMR (400 MHz, CDCl$_3$) δ 8.16 (s, 1H), 7.45 (d, J=8.8 Hz, 1H), 7.11 (d, J=8.7 Hz, 1H), 6.98 (s, 1H), 5.05 (s, 1H), 4.57-4.44 (m, 4H), 3.48 (s, 3H), 3.26 (s, 1H), 2.77 (s, 3H), 2.08 (s, 3H), 1.48 (t, J=7.3 Hz, 3H), 1.32 (s, 3H), 1.13 (s, 3H).

Step D: The mixture of (R/S)-methyl 3-(1-ethyl-4-methyl-1H-benzo[d][1,2,3]triazol-5-yl)-3-(4-(hydroxymethyl)-5-methylpyridin-2-yl)-2,2-dimethylpropanoate (590 mg) was purified and separated by chiral SFC (stationary phase: OD-H 2*25 cm, Mobile phase: 65% CO$_2$, 35% iPrOH, 0.1% DEA, stationary phase: IG 2*25 cm, Mobile phase: 70% CO$_2$, 30% EtOH, 0.1% DEA) to afford two enantiomers. The first eluting isomer (269 mg) was designated (*S): MS (ESI): mass calcd. for $C_{22}H_{28}N_4O_3$, 396.2; m/z found, 397.2 [M+H]$^+$. $^1$H NMR (600 MHz, CDCl$_3$) δ 8.16 (s, 1H), 7.46 (d, J=8.9 Hz, 1H), 7.11 (d, J=8.8 Hz, 1H), 6.98 (s, 1H), 5.06 (s, 1H), 4.57-4.43 (m, 4H), 3.48 (s, 3H), 2.80 (s, 3H), 2.08 (s, 3H), 1.47 (t, J=7.3 Hz, 3H), 1.32 (d, J=3.9 Hz, 3H), 1.13 (d, J=5.7 Hz, 3H).

Intermediate 172: Ethyl (*R)-3-(5-(hydroxymethyl)-6-methylpyridin-3-yl)-3-(8-methyl-3-(trifluoromethyl)-[1,2,4]triazolo[4,3-a]pyridin-7-yl)propanoate

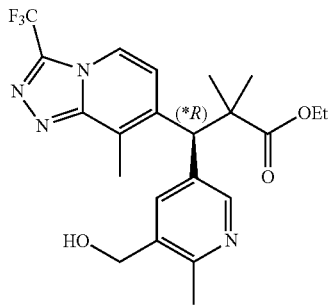 [SMILES: CCOC(=O)C(C)(C)[C@@H](c1cnc(C)c(CO)c1)c1ccn2c(C(F)(F)F)nnc2c1C]

Step A: Ethyl (E)-3-(8-methyl-3-(trifluoromethyl)-[1,2,4]triazolo[4,3-a]pyridin-7-yl)acrylate. 7-Bromo-8-methyl-3-(trifluoromethyl)-[1,2,4]triazolo[4,3-a]pyridine (Intermediate 24, 7.0 g, 25 mmol), (E)-ethyl 3-(4,4,5,5-tetramethyl-1,3,2-dioxaborolan-2-yl)acrylate (7.35 g, 32.5 mmol), and Na$_2$CO$_3$ (7.95 g, 75.0 mmol) were added to a 250-mL, three-necked round-bottom flask and then 1,4-dioxane (75 mL) and water (15 mL) were added. The mixture was sparged with nitrogen for 5 minutes and Pd(dppf)Cl$_2$ (1.83 g, 2.50 mmol) was added. The mixture was sparged with nitrogen for another 5 minutes and then stirred at 90° C. After 16 hours, the mixture was allowed to cool to room temperature. Water (100 mL) was added and the mixture was extracted numerous times with ethyl acetate which resulted in many organic fractions. The fractions were combined, dried over anhydrous Na$_2$SO$_4$, filtered, and concentrated under reduced pressure to afford a residue. The residue was purified by flash column chromatography (petroleum ether: ethyl acetate 20:1 to 5:1) to give the title compound (7.0 g, 76%) as a brown solid. MS (ESI): mass calcd. for $C_{13}H_{12}F_3N_3O_2$, 299.1; m/z found, 299.9 [M+H]$^+$.

Step B: Ethyl (E)-3-(5-(((tert-butyldimethylsilyl)oxy)methyl)-6-methylpyridin-3-yl)-3-(8-methyl-3-(trifluoromethyl)-[1,2,4]triazolo[4,3-a]pyridin-7-yl)acrylate. (E)-Ethyl 3-(8-methyl-3-(trifluoromethyl)-[1,2,4]triazolo[4,3-a]pyridin-7-yl)acrylate (6.8 g, 23 mmol), 5-bromo-3-(((tert-butyldimethylsilyl)oxy)methyl)-2-methylpyridine (Intermediate 46, 9.34 g, 29.5 mmol), DIPEA (8.81 g, 68.2 mmol), and 1,4-dioxane (80 mL) were added to a 250-mL round-bottomed flask. The mixture was sparged with nitrogen for 5 minutes and then Pd(t-Bu$_3$P)$_2$ (1.16 g, 2.27 mmol) was added. The mixture was stirred at 125° C. After 16 h, the mixture was allowed to cool to room temperature. The suspension was filtered and the filter cake washed with ethyl acetate (80 mL). The filtrate was dried over anhydrous Na$_2$SO$_4$, filtered, and concentrated under reduced pressure to afford a residue. The residue was purified by flash column chromatography (petroleum ether:ethyl acetate 10:1 to 2:1) to give the title compound (6.0 g, 49%) as a brown solid. MS (ESI): mass calcd. for $C_{26}H_{33}F_3N_4O_3Si$, 534.2; m/z found, 535.1 [M+H]$^+$.

Step C: Ethyl 3-(5-(((tert-butyldimethylsilyl)oxy)methyl)-6-methylpyridin-3-yl)-3-(8-methyl-3-(trifluoromethyl)-[1,2,4]triazolo[4,3-a]pyridin-7-yl)propanoate. Raney nickel (5.0 g, in water) was added to a solution of ethyl (E)-3-(5-(((tert-butyldimethylsilyl)oxy)methyl)-6-methylpyridin-3-yl)-3-(8-methyl-3-(trifluoromethyl)-[1,2,4]triazolo[4,3-a]pyridin-7-yl)acrylate (6.0 g, 11 mmol) in EtOH (60 mL). The reaction mixture was stirred under a hydrogen atmosphere (15 Psi) at room temperature. After 16 hours, the mixture was filtered through a pad of Celite® and the pad was washed with ethyl acetate (60 mL). The filtrate was dried over anhydrous Na$_2$SO$_4$, filtered, and concentrated under reduced pressure to afford the title product (5.2 g) as an oil which was used in the next step without further purification. MS (ESI): mass calcd. for $C_{26}H_{35}F_3N_4O_3Si$, 536.2; m/z found, 537.1 [M+H]$^+$.

Step D: Ethyl (*S)-3-(5-(hydroxymethyl)-6-methylpyridin-3-yl)-3-(8-methyl-3-(trifluoromethyl)-[1,2,4]triazolo[4,3-a]pyridin-7-yl)propanoate. TFA (6 mL) and ethyl 3-(5-(((tert-butyldimethylsilyl)oxy)methyl)-6-methylpyridin-3-yl)-3-(8-methyl-3-(trifluoromethyl)-[1,2,4]triazolo[4,3-a]pyridin-7-yl)propanoate (5.2 g) were added to a 100-mL, round-bottomed flask. The mixture was stirred at room temperature for 3 hours and then concentrated under reduced pressure. Aqueous NaHCO$_3$ (60 mL) was added to the residue and the mixture was extracted with ethyl acetate which resulted in numerous organic fractions. These fractions were combined, dried over anhydrous Na$_2$SO$_4$, filtered, and concentrated under reduced pressure to afford the product (4.6 g) as an oil. This material was combined with a second batch (2 g) made in a similar manner as above. This material was purified by preparative HPLC using a Phenomenex Gemini 250 mm×50 mm column (10 μm, eluent: 10% to 45% (v/v) CH$_3$CN in water with 0.05% v/v added ammonia). The pure fractions were combined and concentrated under reduced pressure. The residue was suspended in water (10 mL), frozen and lyophilized to afford the title compound (4.3 g, 51%) as a sticky oil. This racemic mixture was further purified by chiral SFC (AD column, 250 mm×50 mm, 10 am, EtOH—CO$_2$ containing 0.1% of 25% aq. NH$_3$) to afford two enantiomers. The first eluting isomer (1.62 g) was designated *R: MS (ESI): mass calcd. for $C_{20}H_{21}F_3N_4O_3$, 422.2; m/z found, 423.1 [M+H]$^+$. $^1$H NMR (400 MHz, DMSO-d$_6$) δ 8.44 (d, J=7.3 Hz, 1H), 8.38 (d, J=2.2 Hz, 1H), 7.65 (d, J=2.0 Hz, 1H), 7.27 (d, J=7.3 Hz, 1H), 5.22 (t, J=5.3 Hz, 1H), 4.89 (t, J=7.9 Hz, 1H), 4.45 (d, J=5.1 Hz, 2H), 4.02-3.94 (m, 2H), 3.28 (d, J=7.9 Hz, 2H), 2.75 (s, 3H), 2.36 (s, 3H), 1.07 (t, J=7.2 Hz, 3H).

Intermediate 173: Ethyl (*S)-3-(5-(hydroxymethyl)-6-methylpyridin-3-yl)-3-(8-methyl-3-(trifluoromethyl)-[1,2,4]triazolo[4,3-a]pyridin-7-yl)propanoate

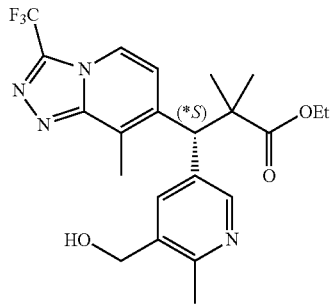 [SMILES: CCOC(=O)C(C)(C)[C@H](c1cnc(C)c(CO)c1)c1ccn2c(C(F)(F)F)nnc2c1C]

The second eluting isomer (1.72 g) from the chiral separation described in Intermediate 172 was designated *S: MS (ESI): mass calcd. for $C_{20}H_{21}F_3N_4O_3$, 422.2; m/z found, 423.1 [M+H]$^+$. $^1$H NMR (400 MHz, DMSO-$d_6$) δ 8.43 (d, J=7.1 Hz, 1H), 8.37 (d, J=2.4 Hz, 1H), 7.65 (d, J=2.2 Hz, 1H), 7.26 (d, J=7.3 Hz, 1H), 5.22 (t, J=5.3 Hz, 1H), 4.88 (t, J=7.8 Hz, 1H), 4.45 (d, J=5.3 Hz, 2H), 4.02-3.93 (m, 2H), 3.27 (d, J=7.9 Hz, 2H), 2.75 (s, 3H), 2.35 (s, 3H), 1.06 (t, J=7.1 Hz, 3H).

Intermediate 174: Ethyl (E)-3-(3,7-dimethyl-7H-pyrrolo[2,3-c]pyridazin-6-yl)acrylate

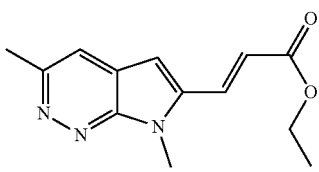 [SMILES: CCOC(=O)/C=C/c1cc2cc(C)nnc2n1C]

Step A: N,6-Dimethylpyridazin-3-amine. A 5-L pressure tank reactor was charged with 3-chloro-6-methylpyridazine (75 g, 580 mmol) and a 30% solution of methylamine in methanol (1.5 L). The resulting solution was stirred overnight at 110° C. The mixture was cooled and then concentrated under reduced pressure. The residue was purified by flash column chromatography (10:1 dichloromethane: methanol) to provide the title compound as a light yellow solid (55 g, 77%).

Step B: 4-Bromo-N,6-dimethylpyridazin-3-amine. A 1-L, round-bottom flask was charged with N,6-Dimethylpyridazin-3-amine (36 g, 290 mmol) and acetic acid (400 mL). This was followed by the dropwise addition of bromine (141 g, 880 mmol). The resulting solution was stirred overnight at 65° C. The solution was cooled and then diluted with dichloromethane (1.5 L). The pH of the solution was adjusted to 8-9 by adding aqueous ammonia solution (~800 mL). The resulting mixture was washed sequentially with aqueous $Na_2SO_3$ solution (600 mL) and water (600 mL). The organic phase was dried over anhydrous sodium sulfate, filtered, and then concentrated under reduced pressure. The residue was purified by flash column chromatography (petroleum ether-ethyl acetate) to provide the title compound (7.9 g, 13%) as a yellow solid.

Step C: 4-(3,3-Diethoxyprop-1-yn-1-yl)-N,6-dimethylpyridazin-3-amine. A 250-mL, round-bottom flask was purged with nitrogen and then charged with 4-bromo-N,6-dimethylpyridazin-3-amine (7.9 g, 39 mmol), 3,3-diethoxyprop-1-yne (6.0 g, 47 mmol), CuI (740 mg, 3.9 mmol), triethylamine (5.9 g, 58 mmol), Pd(PPh$_3$)$_2$Cl$_2$ (5.5 g, 7.8 mmol), and THF (80 mL). The resulting solution was stirred for 1.5 h at 65° C. The mixture was cooled and the solids removed by filtration. The filtrate was concentrated under reduced pressure and the residue was purified by flash column chromatography (petroleum ether-ethyl acetate) to provide the title compound (7.7 g, 79%) as a yellow solid.

Step D: 6-(Diethoxymethyl)-3,7-dimethyl-7H-pyrrolo[2, 3-c]pyridazine. A 500-mL, round-bottom flask was charged with 4-(3,3-diethoxyprop-1-yn-1-yl)-N,6-dimethylpyridazin-3-amine (7.7 g, 31 mmol) and a solution of TBAF in tetrahydrofuran (1 M, 230 mL). The resulting solution was stirred overnight at 65° C. The mixture was cooled and then concentrated under reduced pressure. The residue was diluted with ethyl acetate (200 mL) and then washed with water. The organic layer was dried over anhydrous sodium sulfate, filtered, and then concentrated under reduced pressure. The residue was purified by flash column chromatography (petroleum ether-ethyl acetate, 2:1) to provide the title compound (3.8 g, 49%) as a brown oil.

Step E: 3,7-Dimethyl-7H-pyrrolo[2,3-c]pyridazine-6-carbaldehyde. A 250-mL, 3-necked round bottom flask was charged with a solution of 6-(diethoxymethyl)-3,7-dimethyl-7H-pyrrolo[2,3-c]pyridazine (3.8 g, 15 mmol) in 1,4-dioxane (40 mL). This was followed by the addition of hydrogen chloride (40 mL, 6 N) dropwise at 0° C. The resulting solution was stirred for 2 h at room temperature and then water (100 mL) was added. The layers were separated and the aqueous washed with ethyl acetate. The pH of the aqueous layer was adjusted to 8-9 by addition of aqueous sodium bicarbonate solution. The basic solution was extracted with ethyl acetate which resulted in numerous organic layers which were combined, dried over anhydrous sodium sulfate and concentrated under reduced pressure to afford the title compound as a yellow solid (2.2 g) which was used in the next step without purification.

Step F: Ethyl (E)-3-(3,7-dimethyl-7H-pyrrolo[2,3-c]pyridazin-6-yl)acrylate. A 250-mL, 3-necked round bottom flask was charged with NaH (60% dispersion in oil, 0.6 g) and THF (10 mL) at 0° C. A solution of ethyl(diethoxyphosphoryl) acetate (3.4 g, 15 mmol) in THF (20 mL) was added dropwise. The resulting mixture was stirred at 0° C. for 0.5 h. A solution of 3,7-dimethyl-7H-pyrrolo[2,3-c]pyridazine-6-carbaldehyde (2.2 g, 13 mmol) in THF (30 mL) was added dropwise. The mixture was stirred at 0° C. for 0.5 h. The reaction mixture was quenched by addition of 5% aqueous NH$_4$Cl solution (200 mL) at 0° C. After warming to RT, the mixture was extracted with ethyl acetate which resulted in numerous organic layers which were combined, dried over anhydrous sodium sulfate and concentrated under reduced pressure. The residue was purified by flash column chromatography (petroleum ether-ethyl acetate, 2:1) to provide the title compound (2.0 g, 66%) as a light-yellow solid. MS (ESI): mass calcd. for $C_{13}H_{15}N_3O_2$, 245.1; m/z found, 246.2 [M+H]$^+$. $^1$H NMR (300 MHz, CDCl$_3$) δ 7.79 (d, J=16.2 Hz, 1H), 7.46 (s, 1H), 6.74 (s, 1H), 6.67 (d, J=15.9 Hz, 1H), 4.36-4.28 (m, 2H), 4.10 (s, 3H), 2.80 (s, 3H), 1.37 (t, J=6.9 Hz, 3H).

Intermediate 175: Methyl (2*S, 3*R)-3-(3-(hydroxymethyl)-4-methylphenyl)-2-methyl-3-(8-methyl-3-(trifluoromethyl)-[1,2,4]triazolo[4,3-a]pyridin-7-yl)propanoate

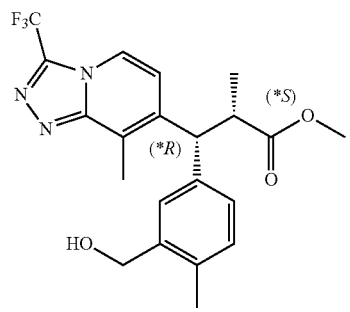 [SMILES: COC(=O)[C@@H](C)[C@H](c1ccc(C)c(CO)c1)c1ccn2c(C(F)(F)F)nnc2c1C]

Step A: Ethyl (*R)-3-(3-(((tert-butyldiphenylsilyl)oxy) methyl)-4-methylphenyl)-3-(8-methyl-3-(trifluoromethyl)-[1,2,4]triazolo[4,3-a]pyridin-7-yl)propanoate. TBDPSCl (3.33 mL, 12.8 mmol) was added to a solution consisting of ethyl (*R)-3-(3-(hydroxymethyl)-4-methylphenyl)-3-(8-methyl-3-(trifluoromethyl)-[1,2,4]triazolo[4,3-a]pyridin-7-yl)propanoate (Intermediate 27, 3.6 g, 8.5 mmol), 1H-imidazole (1.75 g, 25.7 mmol), and dichloromethane (50 mL). The mixture was stirred at room-temperature for 20 minutes which resulted in a suspension. The suspension was filtered through a pad of Celite® and the pad washed with ethyl acetate (20 mL). The filtrate was concentrated to dryness under reduced pressure and the residue was purified by flash column chromatography (petroleum ether-ethyl acetate, 50:1 to 5:1) to provide the title compound (5.2 g, 92%) as a white solid. MS (ESI): mass calcd. for $C_{37}H_{40}F_3N_3O_3Si$, 659.3; m/z found, 660.3 [M+H]$^+$.

Step B: (*R)-3-(3-(((tert-Butyldiphenylsilyl)oxy)methyl)-4-methylphenyl)-3-(8-methyl-3-(trifluoromethyl)-[1,2,4]triazolo[4,3-a]pyridin-7-yl)propanoic acid. Lithium hydroxide monohydrate (378 mg, 9.01 mmol) was added to a solution consisting of ethyl (*R)-3-(3-(((tert-butyldiphenylsilyl)oxy)methyl)-4-methylphenyl)-3-(8-methyl-3-(trifluoromethyl)-[1,2,4]triazolo[4,3-a]pyridin-7-yl)propanoate (3.3 g, 5.0 mmol), EtOH (12 mL), and $H_2O$ (3 mL). The mixture was stirred at room temperature for 2 hours. The pH was adjusted to 5 by the addition of 1 M aqueous HCl solution and then diluted with $H_2O$ (30 mL). The mixture was extracted with ethyl acetate which resulted in numerous organic layers which were combined, dried over anhydrous sodium sulfate and concentrated under reduced pressure to afford the title compound (3.0 g, 88%) as a white solid. MS (ESI): mass calcd. for $C_{35}H_{36}F_3N_3O_3Si$, 631.3; m/z found, 632.3 [M+H]$^+$.

Step C: (R)-4-Benzyl-3-((*R)-3-(3-(((tert-butyldiphenylsilyl)oxy)methyl)-4-methylphenyl)-3-(8-methyl-3-(trifluoromethyl)-[1,2,4]triazolo[4,3-a]pyridin-7-yl)propanoyl)oxazolidin-2-one. CDI (385 mg, 2.37 mmol) was added to a solution consisting of (*R)-3-(3-(((tert-butyldiphenylsilyl)oxy)methyl)-4-methylphenyl)-3-(8-methyl-3-(trifluoromethyl)-[1,2,4]triazolo[4,3-a]pyridin-7-yl)propanoic acid (1.0 g, 1.6 mmol) in tetrahydrofuran (10 mL). The mixture was stirred at room temperature for 6 hours. Tetrahydrofuran was allowed to evaporate with a stream of nitrogen and the residue was diluted with acetonitrile (10 mL). (R)-4-benzyloxazolidin-2-one (309 mg, 1.74 mmol) and DBU (47 µL, 0.31 mmol) were added to the mixture. After 16 hours, the mixture was concentrated under reduced pressure and the residue was purified by flash column chromatography (petroleum ether:ethyl acetate, 1:0 to 3:1) to afford the title compound (860 mg, 68%) as a white solid. MS (ESI): mass calcd. for $C_{45}H_{45}F_3N_4O_4Si$, 790.3; m/z found, 791.3 [M+H]$^+$.

Step D: (4R)-4-Benzyl-3-((3*R)-3-(3-(((tert-butyldiphenylsilyl)oxy)methyl)-4-methylphenyl)-2-methyl-3-(8-methyl-3-(trifluoromethyl)-[1,2,4]triazolo[4,3-a]pyridin-7-yl)propanoyl)oxazolidin-2-one. KHMDS (759 µL, 1 M in THF, 0.759 mmol) was added to a solution consisting of (R)-4-benzyl-3-((*R)-3-(3-(((tert-butyldiphenylsilyl)oxy)methyl)-4-methylphenyl)-3-(8-methyl-3-(trifluoromethyl)-[1,2,4]triazolo[4,3-a]pyridin-7-yl)propanoyl)oxazolidin-2-one (500 mg, 0.632 mmol) and tetrahydrofuran (5 mL) at −78° C. The reaction mixture was stirred at −78° C. for 1.5 hours before adding iodomethane (449 mg, 3.16 mmol). The reaction mixture was stirred −78° C. for 4 hours before quenching with saturated aqueous $NH_4Cl$ solution (0.5 mL) at −78° C. The mixture was allowed to warm to room temperature and then water (30 mL) was added. The mixture was extracted with ethyl acetate which resulted in numerous organic layers which were combined, dried over anhydrous sodium sulfate and concentrated under reduced pressure. The residue was purified by flash column chromatography (petroleum ether-ethyl acetate, 1:0 to 3:1) to provide the title compound as a mixture of diastereoisomers (420 mg, 83%) as a white solid. MS (ESI): mass calcd. for $C_{46}H_{47}F_3N_4O_4Si$, 804.3; m/z found, 805.3 [M+H]$^+$.

Step E: (3*R)-3-(3-(((tert-Butyldiphenylsilyl)oxy)methyl)-4-methylphenyl)-2-methyl-3-(8-methyl-3-(trifluoromethyl)-[1,2,4]triazolo[4,3-a]pyridin-7-yl)propanoic acid. Hydrogen peroxide (275 mg, 2.43 mmol) and lithium hydroxide monohydrate (969 µL, 1 M in water, 0.969 mmol) were added to a 0° C. solution of (4R)-4-benzyl-3-((3*R)-3-(3-(((tert-butyldiphenylsilyl)oxy)methyl)-4-methylphenyl)-2-methyl-3-(8-methyl-3-(trifluoromethyl)-[1,2,4]triazolo[4,3-a]pyridin-7-yl)propanoyl)oxazolidin-2-one (390 mg, 0.484 mmol) in THF (8 mL) and $H_2O$ (1.2 mL). The mixture was stirred at room temperature for 26 hours before quenching with saturated aqueous $Na_2SO_3$ solution (0.6 mL). The mixture was concentrated under reduced pressure and then diluted with water (20 mL). The pH was adjusted to 5 by adding 1 M aqueous HCl solution. The mixture was extracted with ethyl acetate which resulted in numerous organic layers which were combined, washed with brine solution, dried over anhydrous sodium sulfate and concentrated under reduced pressure to afford the title compound (330 mg) as a colorless oil which was used in the next step without purification. MS (ESI): mass calcd. for $C_{36}H_{38}F_3N_3O_3Si$, 645.3; m/z found, 646.3 [M+H]$^+$.

Step F: Methyl (3*R)-3-(3-(((tert-butyldiphenylsilyl)oxy)methyl)-4-methylphenyl)-2-methyl-3-(8-methyl-3-(trifluoromethyl)-[1,2,4]triazolo[4,3-a]pyridin-7-yl)propanoate. (Diazomethyl)trimethylsilane (0.50 mL, 2M in hexane, 1.0 mmol) was added drop-wise to a solution of (3*R)-3-(3-(((tert-butyldiphenylsilyl)oxy)methyl)-4-methylphenyl)-2-methyl-3-(8-methyl-3-(trifluoromethyl)-[1,2,4]triazolo[4,3-a]pyridin-7-yl)propanoic acid (320 mg, 0.496 mmol) in dichloromethane (8 mL) and methanol (4 mL) at room temperature. The reaction mixture was stirred for 6 hours and then TFA (0.1 mL) was added. The mixture was concentrated to dryness under reduced pressure and then dichloromethane (80 mL) was added. The mixture was washed with saturated aqueous $NaHCO_3$ solution (20 mL) and brine (20 mL). The organic layer was dried over anhydrous sodium sulfate, filtered, and concentrated under reduced pressure. The residue was purified by flash column chromatography (petroleum ether-ethyl acetate, 10:0 to 1:1) to provide the title compound (160 mg) as a white solid. MS (ESI): mass calcd. for $C_{37}H_{40}F_3N_3O_3Si$, 659.3; m/z found, 660.2 [M+H]$^+$.

Step G: Methyl (2*S, 3*R)-3-(3-(hydroxymethyl)-4-methylphenyl)-2-methyl-3-(8-methyl-3-(trifluoromethyl)-[1,2,4]triazolo[4,3-a]pyridin-7-yl)propanoate. TBAF (0.29 mL, 1 M in THF, 0.29 mmol) was added to a solution of methyl (3*R)-3-(3-(((tert-butyldiphenylsilyl)oxy)methyl)-4-methylphenyl)-2-methyl-3-(8-methyl-3-(trifluoromethyl)-[1,2,4]triazolo[4,3-a]pyridin-7-yl)propanoate (160 mg, 0.242 mmol) in THF (5 mL) at room temperature. After 6 hours, the reaction mixture was concentrated under reduced pressure and then ethyl acetate (90 mL) was added. The resulting mixture was washed with water (30 mL), brine (30 mL×2), dried over anhydrous sodium sulfate, filtered, and concentrated under reduced pressure. The residue was purified by flash column chromatography (petroleum ether-ethyl acetate, 10:0 to 1:1) to provide the title compound as a mixture of isomers (102 mg) as a white solid. MS (ESI): mass calcd. for $C_{21}H_{22}F_3N_3O_3$, 421.2; m/z found, 422.1 [M+H]$^+$. The title compound was further purified chiral SFC (stationary phase: Chiralpak AD, 250 mm×30 mm, 5 μm isocratic mobile phase: 25% $CO_2$, 75% MeOH with 0.1% aqueous $NH_3$) to afford two diastereoisomers. The first eluting isomer (50.1 mg) was designated (*S): MS (ESI): mass calcd. for $C_{21}H_{22}F_3N_3O_3$, 421.2; m/z found, 422.0 [M+H]$^+$. $^1$H NMR (400 MHz, CDCl$_3$) δ 7.99 (d, J=7.2 Hz, 1H), 7.29 (s, 1H), 7.15-7.06 (m, 2H), 6.96 (d, J=7.2 Hz, 1H), 4.67 (d, J=11.6 Hz, 1H), 4.64 (s, 2H), 3.57 (s, 3H), 3.42-3.33 (m, 1H), 2.89 (s, 3H), 2.25 (s, 3H), 1.15 (d, J=7.2 Hz, 3H).

Intermediate 176: Methyl (2*R, 3*R)-3-(3-(hydroxymethyl)-4-methylphenyl)-2-methyl-3-(8-methyl-3-(trifluoromethyl)-[1,2,4]triazolo[4,3-a]pyridin-7-yl)propanoate

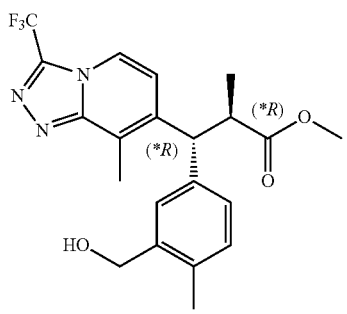 [SMILES: COC(=O)[C@H](C)[C@H](c1ccc(C)c(CO)c1)c1ccn2c(C(F)(F)F)nnc2c1C]

The second eluting isomer (81.1 mg) from the chiral SFC separation described in Intermediate 175 was designated (*R): MS (ESI): mass calcd. for $C_{21}H_{22}F_3N_3O_3$, 421.2; m/z found, 422.0 [M+H]$^+$. $^1$H NMR (400 MHz, CDCl$_3$) δ 8.01 (d, J=7.2 Hz, 1H), 7.31 (s, 1H), 7.16 (d, J=7.6 Hz, 1H), 7.13 (s, 2H), 4.69 (d, J=4.4 Hz, 2H), 4.50 (d, J=11.6 Hz, 1H), 3.53 (s, 3H), 3.46-3.33 (m, 1H), 2.83 (s, 3H), 2.28 (s, 3H), 1.79-1.73 (m, 1H), 1.24 (d, J=6.4 Hz, 3H).

Intermediate 177: 7'-(2-(3-fluoroazetidin-1-yl)ethoxy)-8'-methyl-2',3'-dihydrospiro[cyclopropane-1,4'-pyrido[2,3-b][1,4,5]oxathiazepine] 1',1'-dioxide

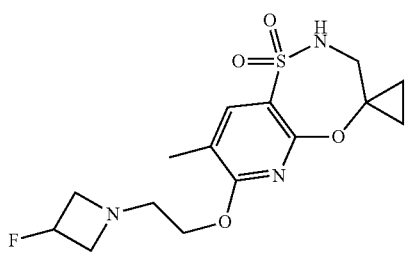 [SMILES: Cc1cc2c(nc1OCCN1CC(F)C1)OC1(CC1)CNS2(=O)=O]

The title compound (54 mg, 15%) was prepared using analogous conditions as described in Intermediate 127 where 7'-chloro-8'methyl-2',3'-dihydrospiro[cyclopropane-1,4'-pyrido[2,3-b][1,4,5]oxathiazepine] 1',1'-dioxide (Intermediate 131) was used instead of 7'-chloro-2',3'-dihydrospiro[cyclopropane-1,4'-pyrido[2,3-b][1,4,5]oxathiazepine] 1',1'-dioxide (Intermediate 67) and 2-(3-fluoroazetidin-1yl)ethan-1-ol was used instead of 2-(piperidin-1-yl)ethan-1-ol. MS (ESI): mass calcd. for $C_{15}H_{20}FN_3O_4S$, 357.1, m/z found 358.2 [M+H]$^+$.

Intermediate 178: 8'-methyl-7'-(2-morpholinoethoxy)-2',3'-dihydrospiro[cyclopropane-1,4'-pyrido[2,3-b][1,4,5]oxathiazepine] 1',1'-dioxide

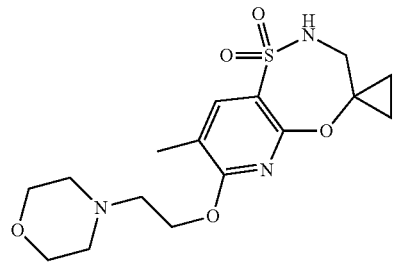 [SMILES: Cc1cc2c(nc1OCCN1CCOCC1)OC1(CC1)CNS2(=O)=O]

The title compound (510 mg, 95%) was prepared using analogous conditions as described in Intermediate 127 where 7'-chloro-8'methyl-2',3'-dihydrospiro[cyclopropane-1,4'-pyrido[2,3-b][1,4,5]oxathiazepine] 1',1'-dioxide (Intermediate 131) was used instead of 7'-chloro-2',3'-dihydrospiro[cyclopropane-1,4'-pyrido[2,3-b][1,4,5]oxathiazepine] 1',1'-dioxide (Intermediate 67) and 2-morpholinoethan-1-ol was used instead of 2-(piperidin-1-yl)ethan-1-ol. MS (ESI): mass calcd. for $C_{16}H_{23}N_3O_5S$, 369.1, m/z found 370.1 [M+H]$^+$.

Intermediate 179: 7'-(2-(pyrrolidin-1-yl)ethoxy)-2',3'-dihydrospiro[cyclopropane-1,4'-pyrido[2,3-b][1,4,5]oxathiazepine] 1',1'-dioxide

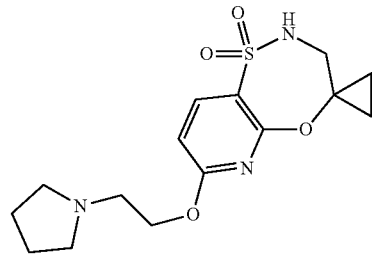 [SMILES: O=S1(=O)NCC2(CC2)Oc2nc(OCCN3CCCC3)ccc21]

The title compound (234 mg, 36%) was prepared using analogous conditions as described in Intermediate 25 where 2-(pyrolidin-1-yl)ethan-1-ol was used instead of 2-(piperidin-1-yl)ethan-1-ol MS (ESI): mass calcd. for $C_{15}H_{21}N_3O_4S$, 339.1, m/z found 340.2 [M+H]$^+$.

Intermediate 180: tert-Butyl 3-(1',1'-dioxido-2,2',3,3',5,6-hexahydrospiro[pyran-4,4'-pyrido[2,3-b][1,4,5 [oxathiazepin]-7'-yl)propanoate

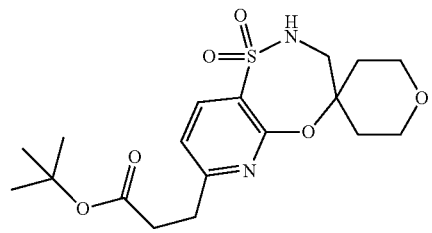 [SMILES: CC(C)(C)OC(=O)CCc1ccc2c(n1)OC1(CCOCC1)CNS2(=O)=O]

Step A: (E)-tert-Butyl 3-(1',1'-dioxido-2,2',3,3',5,6-hexahydrospiro[pyran-4,4'-pyrido[2,3-b][1,4,5]oxathiazepin]-7'-yl)acrylate. tert-Butyl acrylate (477 mg, 3.72 mmol), Pd(OAc)$_2$ (32.1 mg, 0.143 mmol), 2-(di-tert-butylphosphino)biphenyl (85.5 mg, 0.287 mmol), and Et$_3$N (580 mg, 5.73 mmol) were added to a solution of 7'-bromo-2,2',3,3',5,6-hexahydrospiro[pyran-4,4'-pyrido[2,3-b][1,4,5]oxathiazepine] 1',1'-dioxide (1.00 g, 2.86 mmol, Intermediate 124) and DMF (18 mL). The resulting mixture was sparged with N$_2$ for 5 minutes and then stirred while heating at 120° C. for 3 hours before cooling to room-temperature and concentrating to dryness under reduced pressure. The residue was diluted with aqueous saturated NH$_4$Cl solution (7 mL) and the resulting mixture extracted with ethyl acetate (2×). These extractions resulted in several fractions that were combined, dried over anhydrous Na$_2$SO$_4$, filtered, and concentrated to dryness under reduced pressure. The residue was purified by flash chromatography (eluent: petroleum ether/ethyl acetate, 10:1 to 1:5, gradient) to afford the title compound (805 mg, 71%) as a yellow solid. MS (ESI): mass calcd. for C$_{18}$H$_{24}$N$_2$O$_6$S, 396.1 m/z found 396.9 [M+H]$^+$.

Step B: tert-Butyl 3-(1',1'-dioxido-2,2',3,3',5,6-hexahydrospiro[pyran-4,4'-pyrido[2,3-b][1,4,5]oxathiazepin]-7'-yl)propanoate. (E)-tert-Butyl 3-(1',1'-dioxido-2,2',3,3',5,6-hexahydrospiro[pyran-4,4'-pyrido[2,3-b][1,4,5]oxathiazepin]-7'-yl)acrylate (805 mg, 2.03 mmol), MeOH (10 mL), and dry Pd/C (200 mg, 10 wt. %, 0.189 mmol) were added to 75 mL hydrogenation bottle and stirred at room temperature for 16 hours under H$_2$ (50 psi). The suspension was filtered through a pad of Celite® and the pad was washed with MeOH (20 mL). The filtrate was concentrated to dryness under reduced pressure to give the product, which was combined with another batch of tert-Butyl 3-(1',1'-dioxido-2,2',3,3',5,6-hexahydrospiro[pyran-4,4'-pyrido[2,3-b][1,4,5]oxathiazepin]-7'-yl)propanoate and purified by flash chromatography (eluent:petroleum ether/ethyl acetate, 10:1 to 1:5, gradient) to afford the title compound (781 mg). MS (ESI): mass calcd. for C$_{18}$H$_{26}$N$_2$O$_6$S, 398.2 m/z found 399.2 [M+H]$^+$. $^1$H NMR (400 MHz, DMSO-d$_6$) δ 8.60-8.10 (m, 1H), 8.02 (d, J=7.8 Hz, 1H), 7.24 (d, J=7.8 Hz, 1H), 3.81 (t, J=9.8 Hz, 2H), 3.57 (d, J=10.8 Hz, 2H), 3.47 (s, 2H), 2.97 (t, J=7.0 Hz, 2H), 2.64 (t, J=7.0 Hz, 2H), 1.72-1.46 (m, 4H), 1.34 (s, 9H).

Intermediate 181: 8'-methyl-7'-((1-(piperidin-1-yl)propan-2-yl)oxy)-2,2',3,3',5,6-hexahydrospiro[pyran-4,4'-pyrido[2,3-b][1,4,5]oxathiazepine] 1',1'-dioxide

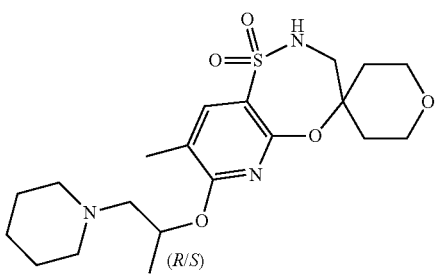 [SMILES: Cc1cc2c(nc1OC(C)CN1CCCCC1)OC1(CCOCC1)CNS2(=O)=O]

The title compound (230 mg, 79%) was prepared using analogous conditions as described in Intermediate 72 where 1-(piperidin-1-yl)propan-2-ol was used instead of 2-(pyrrolidin-1-yl)ethanol in step C. MS (ESI): mass calcd. for C$_{20}$H$_{31}$N$_3$O$_5$S, 425.2 m/z found 426.1 [M+H]$^+$. $^1$H NMR (400 MHz, DMSO-d$_6$) δ 8.13 (t, J=6.8 Hz, 1H), 7.82 (d, J=1.0 Hz, 1H), 5.33-5.25 (m, 1H), 3.89-3.76 (m, 2H), 3.66-3.61 (m, 2H), 3.50-3.38 (m, 2H), 2.62-2.56 (m, 1H), 2.50-2.35 (m, 5H), 2.11 (s, 3H), 1.65-1.55 (m, 4H), 1.50-1.42 (m, 4H), 1.39-1.26 (m, 5H).

Intermediate 182: 7'-(2-azetidin-1-yl)ethoxy)-8'-methyl-2',3'-dihydrospiro[cyclopropane-1,4'-pyrido[2,3-b][1,4,5]oxathiazepine] 1',1'-dioxide

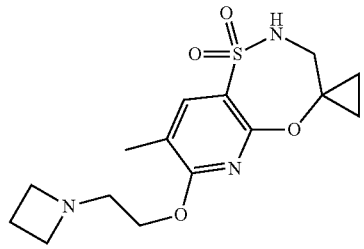 [SMILES: Cc1cc2c(nc1OCCN1CCC1)OC1(CC1)CNS2(=O)=O]

The title compound (214 mg, 32%) was prepared using analogous conditions as described in Intermediate 127 where 7'-chloro-8'methyl-2',3'-dihydrospiro[cyclopropane-1,4'-pyrido[2,3-b][1,4,5]oxathiazepine] 1',1'-dioxide (Intermediate 131) was used instead of 7'-chloro-2',3'-dihydrospiro[cyclopropane-1,4'-pyrido[2,3-b][1,4,5]oxathiazepine] 1',1'-dioxide (Intermediate 67) and 2-(azetidin-1yl)ethan-1-ol was used instead of 2-(piperidin-1-yl)ethan-1-ol. MS (ESI): mass calcd. for C$_{15}$H$_{21}$N$_3$O$_4$S, 339.1, m/z found 340.2 [M+H]$^+$.

Intermediate 183: 7'-(2-hydroxyethoxy)-2,2',3,3',5,6-hexahydrospiro[pyran-4,4'-pyrido[2,3-b][1,4,5]oxathiazepine] 1',1'-dioxide

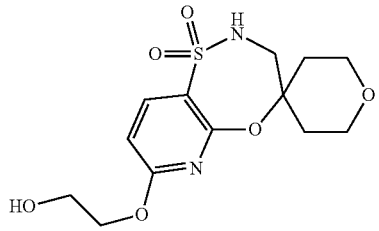 [SMILES: O=S1(=O)NCC2(CCOCC2)Oc2nc(OCCO)ccc21]

Step A: 7'-(2-(Benzyloxy)ethoxy)-2,2',3,3',5,6-hexahydrospiro[pyran-4,4'-pyrido[2,3-b][1,4,5]oxathiazepine] 1',1'-dioxide. Sodium hydride in mineral oil (860 mg, 60% purity, 21.5 mmol) was added in portions to a solution of 2-(benzyloxy)ethanol (2.6 g, 17 mmol) in toluene (30 mL) at 0° C. The resulting mixture was stirred for 0.5 hours with gradual warming to room-temperature and then treated with 7'-bromo-2,2',3,3',5,6-hexahydrospiro[pyran-4,4'-pyrido[2,3-b][1,4,5]oxathiazepine] 1',1'-dioxide (3.0 g, 8.6 mmol, Intermediate 124), o-tol-BiNAP (230 mg, 0.339 mmol), and Pd$_2$(dba)$_3$ (160 mg, 0.175 mmol). The resulting mixture was stirred at 100° C. for 16 hours before cooling to room-temperature and quenching the excess NaH with acetic acid (1.3 mL) to pH 6. The suspension was filtered through a pad of Celite® and the pad washed with ethyl acetate (50 mL). The filtrate was concentrated to dryness under reduced pressure and the resulting residue was purified by flash chromatography (eluent:petroleum ether/ethyl acetate, 10:1 to 1:2, gradient) to afford the title compound (2.5 g, 58%), which was used in the next step without further purification. MS (ESI): mass calcd. for $C_{20}H_{24}N_2O_6S$, 420.1 m/z found 443.1 [M+Na]$^+$.

Step B: 7'-(2-hydroxyethoxy)-2,2',3,3',5,6-hexahydrospiro[pyran-4,4'-pyrido[2,3-b][1,4,5]oxathiazepine] 1',1'-dioxide. Dry Pd/C (300 mg, 10%) was added to a solution of 7'-(2-(benzyloxy)ethoxy)-2,2',3,3',5,6-hexahydrospiro[pyran-4,4'-pyrido[2,3-b][1,4,5]oxathiazepine]1',1'-dioxide (2.5 g) and THF (50 mL). The resulting mixture was stirred at room temperature for 12 hours under 50 psi of hydrogen. The suspension was filtered through a pad of Celite® and the pad washed with THF (50 mL). The filtrate was concentrated to dryness under reduced pressure to give the still-impure product (2.0 g), which was triturated with 10:1 petroleum ether/ethyl acetate (30 mL) and the resulting suspension isolated via filtration. The filter cake was washed with petroleum ether (20 mL) and dried under reduced pressure to afford the title compound (1.7 g, 85%). MS (ESI): mass calcd. for $C_{13}H_{18}N_2O_6S$, 330.1 m/z found 331.1 [M+H]$^+$. $^1$H NMR (400 MHz, DMSO-d$_6$) δ 8.25-8.15 (m, 1H), 8.00-7.92 (m, 1H), 6.71 (d, J=8.4 Hz, 1H), 4.89 (t, J=5.6 Hz, 1H), 4.27 (t, J=4.8 Hz, 2H), 3.83-3.74 (m, 2H), 3.72-3.67 (m, 2H), 3.65-3.56 (m, 2H), 3.48-3.41 (m, 2H), 1.68-1.53 (m, 4H).

Intermediate 184: Methyl 3-(3-(chloromethyl)-4-methylphenyl)-3-(1-cyclopropyl-4-methyl-1H-benzo[d][1,2,3]triazol-5-yl)-2,2-dimethylpropanoate

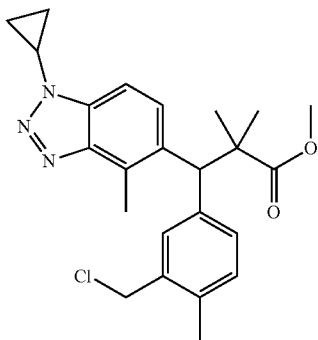 [SMILES: COC(=O)C(C)(C)C(c1ccc(C)c(CCl)c1)c1ccc2c(nnn2C2CC2)c1C]

Step A: (3-(((Tert-butyldimethylsilyl)oxy)methyl)-4-methylphenyl)(1-cyclopropyl-4-methyl-1H-benzo[d][1,2,3]triazol-5-yl)methanol. N-butyllithium (2.5 M, 4.8 ml, 12 mmol) was added dropwise to a stirring solution of 5-bromo-1-cyclopropyl-4-methyl-1H-benzo[d][1,2,3]triazole (Intermediate 29, 3.0 g, 12 mmol) in THF (50 ml) in a dry ice/acetone bath under nitrogen. 3-(((Tert-butyldimethylsilyl)oxy)methyl)-4-methylbenzaldehyde (Intermediate 163, 3.2 g, 12 mmol) was dissolved in THF (7 ml) and the resulting solution was added to the lithiate reaction dropwise. The reaction was then removed from the dry ice/acetone bath and allowed to warm to room temperature for 3 hours. The reaction was quenched with saturated aqueous NH$_4$Cl. Brine and EtOAc were added and the resulting biphasic mixture was separated. The aqueous layer was extracted with EtOAc. These extractions resulted in several organic solvent fractions which were combined, washed with brine, dried over MgSO$_4$, filtered, and concentrated to dryness under reduced pressure. The material was purified by flash column chromatography (0-20% EtOAc/hexanes) to provide the title compound (2.46 g, 47% yield). MS (ESI): mass calcd. for $C_{25}H_{35}N_3O_2Si$, 437.2; m/z found, 438.3 [M+H]$^+$.

Step B: Methyl 3-(3-(((tert-butyldimethylsilyl)oxy)methyl)-4-methylphenyl)-3-(1-cyclopropyl-4-methyl-1H-benzo[d][1,2,3]triazol-5-yl)-2,2-dimethylpropanoate. Trichloroacetonitrile (2 ml, 20 mmol) and DBU (0.3 ml, 2 mmol) were added to a solution of (3-(((tert-butyldimethylsilyl)oxy)methyl)-4-methylphenyl)(1-cyclopropyl-4-methyl-1H-benzo[d][1,2,3]triazol-5-yl)methanol (4.24 g, 9.69 mmol) in ACN (50 ml). The reaction was stirred at room temperature under nitrogen for 50 minutes. ((1-Methoxy-2-methylprop-1-en-1-yl)oxy)trimethylsilane (10 ml, 49 mmol) was then added to the reaction, followed by trifluoromethanesulfonamide (2.72 g, 9.69 mmol), and the reaction was stirred at room temperature under nitrogen for 45 minutes. The reaction was quenched with saturated aqueous NaHCO$_3$, then extracted with EtOAc. These extractions resulted in several organic solvent fractions which were combined, dried over MgSO$_4$, filtered, and concentrated to dryness under reduced pressure. The material was purified by flash column chromatography (0-20% EtOAc/DCM) to provide the title compound (4.82 g, 95% yield). MS (ESI): mass calcd. for $C_{30}H_{43}N_3O_3Si$, 521.3; m/z found, 522.3 [M+H]$^+$.

Step C: Methyl 3-(1-cyclopropyl-4-methyl-1H-benzo[d][1,2,3]triazol-5-yl)-3-(3-(hydroxymethyl)-4-methylphenyl)-2,2-dimethylpropanoate. Tetrabutylammonium fluoride (1 M in THF, 18 ml, 18 mmol) was added to a solution of methyl 3-(3-(((tert-butyldimethylsilyl)oxy)methyl)-4-methylphenyl)-3-(1-cyclopropyl-4-methyl-1H-benzo[d][1,2,3]triazol-5-yl)-2,2-dimethylpropanoate (4.82 g, 9.24 mmol) in THF (92 ml). The reaction was stirred at room temperature for 3 hours. The reaction was quenched with saturated aqueous NaHCO$_3$, then extracted with EtOAc. These extractions resulted in several organic solvent fractions which were combined, dried over MgSO$_4$, filtered, and concentrated to an oil under reduced pressure. The material was purified by flash column chromatography (0-100% EtOAc/hexanes) to provide the title compound (4.84 g, 128% yield) containing TBAF as an impurity. MS (ESI): mass calcd. for $C_{24}H_{29}N_3O_3$, 407.2; m/z found, 408.2 [M+H]$^+$. $^1$H NMR (400 MHz, CDCl$_3$) δ 7.52 (d, J=8.7 Hz, 1H), 7.31 (d, J=8.8 Hz, 1H), 7.12-7.08 (m, 1H), 7.03-6.97 (m, 1H), 6.97-6.92 (m, 1H), 4.76 (s, 1H), 4.51 (s, 2H), 3.66-3.57 (m, 1H), 3.39 (s, 3H), 2.70 (s, 3H), 2.18 (s, 3H), 1.30 (s, 3H), 1.27-1.22 (m, 2H), 1.21 (s, 3H), 1.19-1.13 (m, 2H).

Step D: Methyl 3-(3-(chloromethyl)-4-methylphenyl)-3-(1-cyclopropyl-4-methyl-1H-benzo[d][1,2,3]triazol-5-yl)-2,2-dimethylpropanoate. Thionyl chloride (0.7 mL, 9.6 mmol) was added to a solution of methyl 3-(1-cyclopropyl-4-methyl-1H-benzo[d][1,2,3]triazol-5-yl)-3-(3-(hydroxymethyl)-4-methylphenyl)-2,2-dimethylpropanoate (1.87 g, 4.59 mmol) in DCM (23 mL). The reaction was stirred at room temperature for 40 minutes. The reaction was quenched with saturated aqueous NaHCO$_3$, the resulting biphasic mixture was separated, and the aqueous layer was extracted with DCM. These extractions resulted in several organic solvent fractions which were combined, dried over MgSO$_4$, filtered, and concentrated to an oil under reduced pressure to provide the title compound without further purification (1.8 g, 92% yield). MS (ESI): mass calcd. for $C_{24}H_{28}ClN_3O_2$, 425.2; m/z found, 426.2 [M+H]$^+$.

Intermediate 185: Methyl 3-(5-(hydroxymethyl)-6-methylpyridin-3-yl)-2,2-dimethyl-3-(8-methyl-3-(trifluoromethyl)-[1,2,4]triazolo[4,3-a]pyridin-7-yl)propanoate

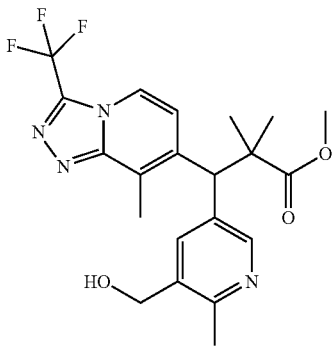 [SMILES: COC(=O)C(C)(C)C(c1cnc(C)c(CO)c1)c1ccn2c(C(F)(F)F)nnc2c1C]

Step A: (5-(((Tert-butyldimethylsilyl)oxy)methyl)-6-methylpyridin-3-yl)(8-methyl-3-(trifluoromethyl)-[1,2,4]triazolo[4,3-a]pyridin-7-yl)methanol. N-butyllithium (1.6 M, 7.8 ml, 12.5 mmol) was added dropwise to a stirring solution of 5-bromo-3-(((tert-butyldimethylsilyl)oxy)methyl)-2-methylpyridine (Intermediate 46, 4.0 g, 13 mmol) in THF (47 ml) in a dry ice/acetone bath under nitrogen. 8-Methyl-3-(trifluoromethyl)-[1,2,4]triazolo[4,3-a]pyridine-7-carbaldehyde (Intermediate 28, 2.35 g, 10.3 mmol) was dissolved in THF (47 ml) added to the lithiate reaction dropwise. The reaction was stirred for 5 minutes, then quenched with saturated aqueous NH$_4$Cl and extracted with EtOAc. These extractions resulted in several organic solvent fractions which were combined, dried over Na$_2$SO$_4$, filtered, and concentrated to dryness under reduced pressure. The material was purified by flash column chromatography (EtOAc/hexanes) to provide the title compound (3 g, 63% yield). This procedure was repeated five times, to yield a total of 15 g of the title compound. MS (ESI): mass calcd. for $C_{22}H_{29}F_3N_4O_2Si$, 466.2; m/z found, 467.2 [M+H]$^+$.

Step B: 7-((5-(((Tert-butyldimethylsilyl)oxy)methyl)-6-methylpyridin-3-yl)chloromethyl)-8-methyl-3-(trifluoromethyl)-[1,2,4]triazolo[4,3-a]pyridine. Thionyl chloride (3 mL, 41 mmol) was added to a solution of (5-(((tert-butyldimethylsilyl)oxy)methyl)-6-methylpyridin-3-yl)(8-methyl-3-(trifluoromethyl)-[1,2,4]triazolo[4,3-a]pyridin-7-yl)methanol (15 g, 32 mmol) and 2,6-di-tert-butylpyridine (14 ml, 62 mmol) in DCM (160 mL). The reaction was stirred at room temperature for 5 minutes. The reaction was quenched with saturated aqueous NaHCO$_3$, then extracted with ethyl acetate. These extractions resulted in several organic solvent fractions which were combined, dried over MgSO$_4$, filtered, and concentrated to dryness under reduced pressure. The material was purified by flash column chromatography (0-100% ethyl acetate/hexanes) to provide the title compound (11.6 g, 74% yield). MS (ESI): mass calcd. for $C_{22}H_{28}ClF_3N_4OSi$, 484.2; m/z found, 485.2 [M+H]$^+$.

Step C: Methyl 3-(5-(((tert-butyldimethylsilyl)oxy)methyl)-6-methylpyridin-3-yl)-2,2-dimethyl-3-(8-methyl-3-(trifluoromethyl)-[1,2,4]triazolo[4,3-a]pyridin-7-yl)propanoate. ((1-Methoxy-2-methylprop-1-en-1-yl)oxy)trimethylsilane (24 ml, 118 mmol) was added to a solution of 7-((5-(((tert-butyldimethylsilyl)oxy)methyl)-6-methylpyridin-3-yl)chloromethyl)-8-methyl-3-(trifluoromethyl)-[1,2,4]triazolo[4,3-a]pyridine (11.6 g, 24 mmol) in DCM (118 ml). Indium(III) bromide (2.6 g, 7.3 mmol) was added and the reaction was stirred at room temperature for 16 hours. Saturated aqueous NaHCO$_3$ was added and the resulting biphasic mixture was separated. The aqueous layer was extracted with DCM. These extractions resulted in several organic solvent fractions which were combined, dried over Na$_2$SO$_4$, filtered, and concentrated to dryness under reduced pressure to provide the title compound (5 g, 38% yield) without further purification. MS (ESI): mass calcd. for $C_{27}H_{37}F_3N_4O_3Si$, 550.2; m/z found, 551.3 [M+H]$^+$.

Step D: Methyl 3-(5-(hydroxymethyl)-6-methylpyridin-3-yl)-2,2-dimethyl-3-(8-methyl-3-(trifluoromethyl)-[1,2,4]triazolo[4,3-a]pyridin-7-yl)propanoate. Tetrabutylammonium fluoride (1 M in THF, 27 ml, 27 mmol) was added to a solution of methyl 3-(5-(((tert-butyldimethylsilyl)oxy)methyl)-6-methylpyridin-3-yl)-2,2-dimethyl-3-(8-methyl-3-(trifluoromethyl)-[1,2,4]triazolo[4,3-a]pyridin-7-yl)propanoate (5 g, 9 mmol) in THF (50 ml). The reaction was stirred at room temperature for 1 hour. The reaction was quenched with saturated aqueous NaHCO$_3$, the resulting biphasic mixture was separated, and the aqueous layer was extracted with DCM. These extractions resulted in several organic solvent fractions which were combined, dried over MgSO$_4$, filtered, and concentrated to dryness under reduced pressure. The material was purified by flash column chromatography (0-100% ethyl acetate/hexanes) to provide the title compound (3.8 g, 96% yield). MS (ESI): mass calcd. for $C_{21}H_{23}F_3N_4O_3$, 436.2; m/z found, 437.0 [M+H]$^+$. $^1$H NMR (500 MHz, CDCl$_3$) D 8.60 (d, J=2.1 Hz, 1H), 8.38 (d, J=2.2 Hz, 1H), 8.13 (d, J=7.2 Hz, 1H), 7.19 (d, J=7.4 Hz, 1H), 4.90 (s, 1H), 4.74 (s, 2H), 3.63 (s, 3H), 2.71 (s, 3H), 2.64 (s, 3H), 1.37 (d, J=19.6 Hz, 6H).

Intermediate 186: Methyl (*R)-3-(3-cyclopropyl-8-methyl-[1,2,4]triazolo[4,3-a]pyridin-7-yl)-3-(3-(hydroxymethyl)-4-methylphenyl)-2,2-dimethylpropanoate

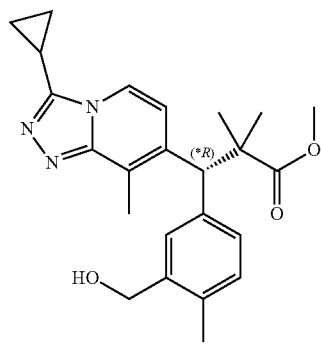 [SMILES: COC(=O)C(C)(C)[C@H](c1ccc(C)c(CO)c1)c1ccn2c(C3CC3)nnc2c1C]

The second eluting isomer (1.9 g) from the chiral separation described in Intermediate 184 was designated (*R): MS (ESI): mass calcd. for $C_{24}H_{29}N_3O_3$, 407.2; m/z found, 408.2 [M+H]$^+$.

Intermediate 187: 7'-(3-(3-Hydroxypropoxy)propoxy)-2,2',3,3',5,6-hexahydrospiro[pyran-4,4'-pyrido[2,3-b][1,4,5]oxathiazepine] 1',1'-dioxide

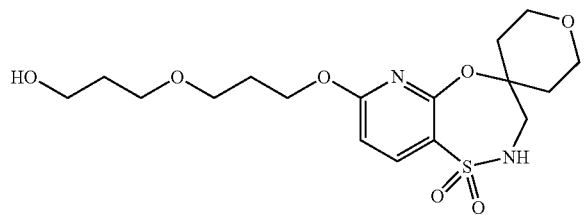 [SMILES: O=S1(=O)NCC2(CCOCC2)Oc2nc(OCCCOCCCO)ccc21]

Step A: 3-(Benzyloxy)propyl 4-methylbenzenesulfonate. 3-(Benzyloxy)propan-1-ol (10.0 g, 60.2 mmol), p-toluenesulfonyl chloride (17.2 g, 90.2 mmol), triethylamine (25.0 mL, 179 mmol), and dichloromethane (100 mL) were combined. The resultant mixture was stirred at 20° C. for 3 hours, then was poured into water (50 mL) and extracted with dichloromethane (50 mL×2). These organic solvent fractions were combined, dried over anhydrous $Na_2SO_4$, filtered, and concentrated under reduced pressure to give the product, which was purified by FCC (eluent: petroleum ether/ethyl acetate=1:0 to 5:1) to afford the title compound (18 g, 93%) as a brown oil, and was used in the next step without further purification. $^1$H NMR (400 MHz, CDCl$_3$) δ 7.78 (d, J=8.4 Hz, 2H), 7.38-7.22 (m, 7H), 4.40 (s, 2H), 4.19-4.14 (m, 2H), 3.50 (t, J=6.0 Hz, 2H), 2.42 (s, 3H), 1.98-1.90 (m, 2H).

Step B: 3-(3-(Benzyloxy)propoxy)propan-1-ol. Sodium hydride in mineral oil (6.0 g, 60% purity, 0.15 mmol) was added in portions to a 0° C. (ice/water) solution consisting of propane-1,3-diol (17.0 g, 223 mmol) and DMF (40 mL). The resultant mixture was stirred for 2 hours with gradual warming to room temperature and then treated with a solution consisting of 3-(benzyloxy)propyl 4-methylbenzenesulfonate (18.0 g, 56 mmol) and DMF (40 mL) at 0° C. The mixture was heated to 80° C. for 12 hours, then was cooled to room temperature, poured into saturated aqueous NH$_4$Cl (40 mL), and extracted with ethyl acetate (200 mL×2). These organic solvent fractions were combined, dried over anhydrous $Na_2SO_4$, filtered, and concentrated under reduced pressure to give the product, which was purified by FCC (eluent:petroleum ether/ethyl acetate=1:0 to 1:1) to afford the title compound (9 g, 71%) as a yellow solid. $^1$H NMR (400 MHz, CDCl$_3$) δ 7.37-7.25 (m, 4H), 4.49 (s, 2H), 3.78-3.71 (m, 2H), 3.71-3.66 (m, 1H), 3.59 (t, J=5.6 Hz, 2H), 3.54 (t, J=6.4 Hz, 4H), 2.05 (s, 2H), 1.92-1.82 (m, 4H).

Step C: 7'-(3-(3-(Benzyloxy)propoxy)propoxy)-2,2',3,3',5,6-hexahydrospiro[pyran-4,4'-pyrido[2,3-b][1,4,5]oxathiazepine] 1',1'-dioxide. Sodium hydride in mineral oil (460 mg, 60% purity, 11.5 mmol) was added in portions to a 0° C. (ice/water) solution consisting of 3-(3-(benzyloxy)propoxy)propan-1-ol (2.0 g, 8.9 mmol) and toluene (20 mL). The resultant mixture was stirred for 0.5 hours with gradual warming to room temperature and then treated with 7'-bromo-2,2',3,3',5,6-hexahydrospiro[pyran-4,4'-pyrido[2,3-b][1,4,5]oxathiazepine] 1',1'-dioxide (Intermediate 124, 1.5 g, 4.3 mmol), o-tol-BINAP (130 mg, 0.192 mmol), and Pd$_2$(dba)$_3$ (80 mg, 0.087 mmol). The resultant mixture was stirred at 100° C. for 16 hours, then was quenched with acetic acid (0.7 mL) (adjusted pH of the mixture to 6). The resulting suspension was filtered through a pad of Celite® and the pad washed with ethyl acetate (30 mL). The filtrate was concentrated to dryness under reduced pressure to give the product, which was combined with another batch of the same compound and then purified by FCC (eluent:petroleum ether/ethyl acetate=10:1 to 1:3) to afford the title compound (1.0 g) which was used in the next step without further purification. MS (ESI): mass calcd. for $C_{24}H_{32}N_2O_7S$, 492.19; m/z found, 493.1 [M+H]$^+$.

Step D: 7'-(3-(3-Hydroxypropoxy)propoxy)-2,2',3,3',5,6-hexahydrospiro[pyran-4,4'-pyrido[2,3-b][1,4,5]oxathiazepine] 1',1'-dioxide. 7'-(3-(3-(Benzyloxy)propoxy)propoxy)-2,2',3,3',5,6-hexahydrospiro[pyran-4,4'-pyrido[2,3-b][1,4,5]oxathiazepine] 1',1'-dioxide (1.0 g, 2 mmol), dry Pd/C (200 mg, 10%), and MeOH (20 mL) were added to a 100 mL hydrogenation bottle. The resultant mixture was stirred under H$_2$ (50 psi) at room temperature for 12 hours. The suspension was filtered through a pad of Celite® and the pad washed with ethyl acetate (30 mL). The filtrate was concentrated to dryness under reduced pressure to afford the title product (850 mg, 104%, as a yellow solid, which was used in the next step without further purification. MS (ESI): mass calcd. for $C_{17}H_{26}N_2O_7S$, 402.15; m/z found, 403.0 [M+H]$^+$.

Intermediate 188: Methyl (*S)-3-(5-(chloromethyl)-6-methylpyridin-3-yl)-3-(1-cyclopropyl-4-methyl-1H-benzo[d][1,2,3]triazol-5-yl)-2,2-dimethylpropanoate

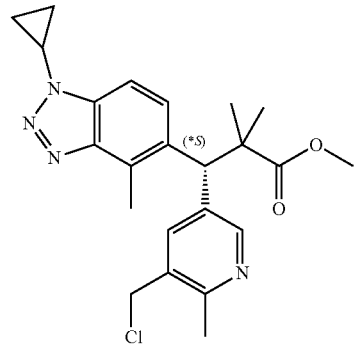 [SMILES: COC(=O)C(C)(C)[C@H](c1cnc(C)c(CCl)c1)c1ccc2c(nnn2C2CC2)c1C]

Step A: (5-(((tert-Butyldimethylsilyl)oxy)methyl)-6-methylpyridin-3-yl)(1-cyclopropyl-4-methyl-1H-benzo[d][1,2,3]triazol-5-yl)methanol. n-BuLi (4.1 mL, 10 mmol) was slowly added drop-wise to a −65° C. solution of 5-bromo-3-(((tert-butyldimethylsilyl)oxy)methyl)-2-methylpyridine (3.0 g, 9.5 mmol, Intermediate 46) and THF (30 mL). The resulting mixture was stirred at −65° C. for 5 minutes before treating drop-wise with a solution of 1-cyclopropyl-4-methyl-1H-benzo[d][1,2,3]triazole-5-carbaldehyde (2.0 g, 10 mmol, Intermediate 56 step B) in THF (50 mL) at −65° C. The resulting mixture was stirred at −65° C. for 2 hours then poured into the sat. NH$_4$Cl (60 mL) and extracting with ethyl acetate (3×). These extractions resulted in several fractions that were washed with brine (1×), dried over anhydrous Na$_2$SO$_4$, filtered, and concentrated to dryness under reduced pressure. The residue was purified by flash chromatography (eluent:petroleum ether/ethyl acetate, 1:0 to 0:1; gradient) to afford the title compound (1.8 g, 42%). MS (ESI): mass calcd. for $C_{24}H_{34}N_4O_2Si$, 438.3 m/z found 439.5 [M+H]$^+$.

Step B: Methyl 3-(5-(((tert-butyldimethylsilyl)oxy)methyl)-6-methylpyridin-3-yl)-3-(1-cyclopropyl-4-methyl-1H-benzo[d][1,2,3]triazol-5-yl)-2,2-dimethylpropanoate. DBU (0.13 mL, 0.87 mmol) and 2,2,2-trichloroacetonitrile (0.8 mL, 8.0 mmol) were added to a mixture of (5-(((tert-butyldimethylsilyl)oxy)methyl)-6-methylpyridin-3-yl)(1-cyclopropyl-4-methyl-1H-benzo[d][1,2,3]triazol-5-yl)methanol (1.6 g, 3.6 mmol) and MeCN (25 mL) under $N_2$ at room-temperature. The resulting mixture was stirred at room-temperature for 1 hour before treating with ((1-methoxy-2-methylprop-1-en-1-yl)oxy)trimethylsilane (3.2 g, 18 mmol) and a solution of $Tf_2N$ (1.1 g, 3.9 mmol) in MeCN (5 mL). The mixture was stirred at room-temperature for 3 hours then treated with another batch of ((1-methoxy-2-methylprop-1-en-1-yl)oxy)trimethylsilane (1.5 g, 8.6 mmol) and solution consisting of $Tf_2N$ (500 mg, 1.78 mmol) in MeCN (3 mL). The resultant mixture was stirred at room-temperature for another 3 hours, quenched with sat. $NaHCO_3$ (50 mL) and extracted with ethyl acetate (3×). These extractions resulted in several fractions that were dried over anhydrous $Na_2SO_4$, filtered, and concentrated to dryness under reduced pressure. The residue was purified by flash chromatography (eluent: petroleum ether/ethyl acetate, 10:1 to 1:2; gradient) to yield the compound (1.7 g, 82%). MS (ESI): mass calcd. for $C_{29}H_{42}N_4O_3Si$, 522.3 m/z found 523.6 $[M+H]^+$.

Step C: Methyl 3-(1-cyclopropyl-4-methyl-1H-benzo[d][1,2,3]triazol-5-yl)-3-(5-(hydroxymethyl)-6-methylpyridin-3-yl)-2,2-dimethylpropanoate. TBAF (6.5 mL, 1M in THF, 6.5 mmol) was added to a solution of methyl 3-(5-(((tert-butyldimethylsilyl)oxy)methyl)-6-methylpyridin-3-yl)-3-(1-cyclopropyl-4-methyl-1H-benzo[d][1,2,3]triazol-5-yl)-2,2-dimethylpropanoate (1.7 g, 3.3 mmol), and THF (20 mL). The resulting mixture was stirred for 1.5 hours at room-temperature before pouring into water (50 mL) and extracting with ethyl acetate (3×). These extractions resulted in several fractions that were combined, washed with brine (30 mL), dried over anhydrous $Na_2SO_4$, filtered, and concentrated to dryness under reduced pressure. The residue was purified by flash chromatography (eluent: ethyl acetate, 100%) to afford the title compound (580 mg, 43%). MS (ESI): mass calcd. for $C_{23}H_{28}N_4O_3$ 408.22 m/z found 409.2 $[M+H]^+$.

Step D: (*S) Methyl 3-(1-cyclopropyl-4-methyl-1H-benzo[d][1,2,3]triazol-5-yl)-3-(5-(hydroxymethyl)-6-methylpyridin-3-yl)-2,2-dimethylpropanoate. The mixture of methyl 3-(1-cyclopropyl-4-methyl-1H-benzo[d][1,2,3]triazol-5-yl)-3-(5-(hydroxymethyl)-6-methylpyridin-3-yl)-2,2-dimethylpropanoate isomers were separated by chiral SFC (Stationary phase: Daicel Chiralpak AD 10 μm 150×50 mm, Mobile phase: (75% $CO_2$, 25% EtOH (w/0.1% 25% aqueous $NH_3$)) to afford two enantiomers. The first eluting isomer (9.5 g, 38%) was designated *S. $^1H$ NMR (400 MHz, DMSO-$d_6$) δ 8.30-8.27 (m, 1H), 7.67-7.61 (m, 3H), 5.23 (t, J=5.3 Hz, 1H), 4.77 (s, 1H), 4.45-4.41 (m, 2H), 3.99-3.93 (m, 1H), 3.47 (s, 3H), 2.70 (s, 3H), 2.33 (s, 3H), 1.29 (s, 3H), 1.25 (s, 3H), 1.24-1.20 (m, 4H).

Step E: (*S)-Methyl 3-(5-(chloromethyl)-6-methylpyridin-3-yl)-3-(1-cyclopropyl-4-methyl-1H-benzo[d][1,2,3]triazol-5-yl)-2,2-dimethylpropanoate. $SOCl_2$ (0.52 mL, 7.2 mmol) was added to a solution of (*S) methyl 3-(1-cyclopropyl-4-methyl-1H-benzo[d][1,2,3]triazol-5-yl)-3-(5-(hydroxymethyl)-6-methylpyridin-3-yl)-2,2-dimethylpropanoate (580 mg, 1.42 mmol) and dichloromethane (8.0 mL) under $N_2$. The resulting mixture was stirred at room-temperature for 1 hour before concentrating to dryness under reduced pressure to afford the product (600 mg) which was used in the next step without further purification. MS (ESI): mass calcd. for $C_{23}H_{27}ClN_4O_2$ 426.2 m/z found 427.0 $[M+H]^+$.

Intermediate 189: Methyl (*R)-3-(5-(chloromethyl)-6-methylpyridin-3-yl)-3-(1-cyclopropyl-4-methyl-1H-benzo[d][1,2,3]triazol-5-yl)-2,2-dimethylpropanoate

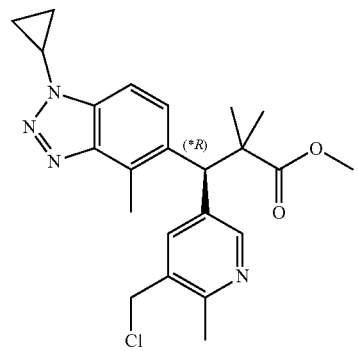 [SMILES: COC(=O)C(C)(C)[C@@H](c1cnc(C)c(CCl)c1)c1ccc2c(nnn2C2CC2)c1C]

Step A: (*R) Methyl 3-(1-cyclopropyl-4-methyl-1H-benzo[d][1,2,3]triazol-5-yl)-3-(5-(hydroxymethyl)-6-methylpyridin-3-yl)-2,2-dimethylpropanoate. The mixture of methyl 3-(1-cyclopropyl-4-methyl-1H-benzo[d][1,2,3]triazol-5-yl)-3-(5-(hydroxymethyl)-6-methylpyridin-3-yl)-2,2-dimethylpropanoate isomers (Intermediate 188, step C) were separated by chiral SFC (Stationary phase: Daicel Chiralpak AD 10 m 150×50 mm, Mobile phase: (75% $CO_2$, 25% EtOH (w/0.1% 25% aqueous $NH_3$)) to afford two enantiomers. The second eluting isomer (9.5 g, 38%) was designated *R. $^1H$ NMR (400 MHz, DMSO-$d_6$) δ 8.31-8.28 (m, 1H), 7.68-7.62 (m, 3H), 5.24 (t, J=5.3 Hz, 1H), 4.78 (s, 1H), 4.46-4.42 (m, 2H), 4.00-3.94 (m, 1H), 3.47 (s, 3H), 2.71 (s, 3H), 2.34 (s, 3H), 1.30 (s, 3H), 1.26 (s, 3H), 1.25-1.21 (m, 4H).

Step B: methyl (*R)-3-(5-(chloromethyl)-6-methylpyridin-3-yl)-3-(1-cyclopropyl-4-methyl-1H-benzo[d][1,2,3]triazol-5-yl)-2,2-dimethylpropanoate. The title compound (480 mg) was prepared using analogous conditions as described in Intermediate 188 where (*R) methyl 3-(1-cyclopropyl-4-methyl-1H-benzo[d][1,2,3]triazol-5-yl)-3-(5-(hydroxymethyl)-6-methylpyridin-3-yl)-2,2-dimethylpropanoate was used instead of (*S) methyl 3-(1-cyclopropyl-4-methyl-1H-benzo[d][1,2,3]triazol-5-yl)-3-(5-(hydroxymethyl)-6-methylpyridin-3-yl)-2,2-dimethylpropanoate in step E. MS (ESI): mass calcd. for $C_{23}H_{27}ClN_4O_2$ 426.2 m/z found 427.2 $[M+H]^+$.

Intermediate 190: 8'-methyl-2',3'-dihydrospiro[oxetane-3,4'-pyrido[2,3-b][1,4,5]oxathiazepine] 1',1'-dioxide

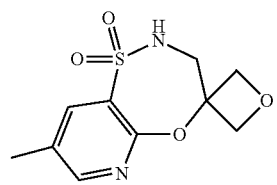 [SMILES: Cc1cnc2c(c1)S(=O)(=O)NCC1(COC1)O2]

The title compound (23.5 g, 60%) was prepared using analogous conditions as described in Intermediate 59 where 2-chloro-5-methylpyridine-3-sulfonyl chloride was used instead of 2-chloropyridine-3-sulfonyl chloride in step C. MS (ESI): mass calcd. for $C_{10}H_{12}N_2O_4S$, 256.1 m/z found 256.9 $[M+H]^+$. $^1$H NMR (400 MHz, DMSO-$d_6$) δ 8.36 (d, J=1.8 Hz, 1H) 8.31 (br s, 1H) 8.00 (d, J=2.0 Hz, 1H) 4.35-4.49 (m, 4H) 3.83 (s, 2H) 2.35 (s, 3H).

Intermediate 191: tert-Butyl 3-(3-(difluoromethyl)-8-methyl-[1,2,4]triazolo[4,3-a]pyridin-7-yl)-3-(4-(hydroxymethyl)-5-methylpyridin-2-yl)-2,2-dimethylpropanoate

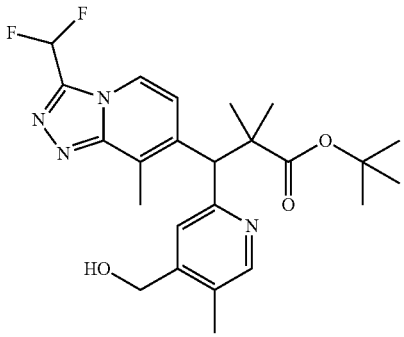 [SMILES: Cc1cnc(C(c2ccn3c(C(F)F)nnc3c2C)C(C)(C)C(=O)OC(C)(C)C)cc1CO]

Step A: (4-(((tert-Butyldimethylsilyl)oxy)methyl)-5-methylpyridin-2-yl)(3-(difluoromethyl)-8-methyl-[1,2,4]triazolo[4,3-a]pyridin-7-yl)methanol. A 1.3 M solution of i-PrMgCl.LiCl in THF (30 mL, 39 mmol) was added dropwise to a stirring solution of 3-(difluoromethyl)-7-iodo-8-methyl-[1,2,4]triazolo[4,3-a]pyridine (Intermediate 129, Step F, 10 g, 32 mmol) in THF (120 mL) at −10° C. After 1 hour, a solution of 4-(((tert-butyldimethylsilyl)oxy)methyl)-5-methylpicolinaldehyde (Intermediate 147, 9.5 g, 36 mmol) in THF (30 mL) was added dropwise and then the mixture was allowed to warm to room temperature. After 16 hours, the mixture was poured into saturated aqueous NH$_4$Cl solution and then extracted with ethyl acetate. These extractions resulted in several organic solvent fractions which were combined, dried over Na$_2$SO$_4$, filtered, and concentrated to dryness under reduced pressure. The residue was purified by flash column chromatography (petroleum ether:ethyl acetate=1:0 to 0:1) to provide the title compound as a yellow oil (7.5 g, 45%). MS (ESI): mass calcd. for $C_{22}H_{30}F_2N_4O_2Si$, 448.2; m/z found, 449.5 $[M+H]^+$.

Step B: 7-((4-(((tert-Butyldimethylsilyl)oxy)methyl)-5-methylpyridin-2-yl)chloromethyl)-3-(difluoromethyl)-8-methyl-[1,2,4]triazolo[4,3-a]pyridine. SOCl$_2$ (1.1 mL, 15 mmol) was added drop-wise to a 100 mL, three-necked round-bottomed flask containing a ice-water cooled solution of (4-(((tert-butyldimethylsilyl)oxy)methyl)-5-methylpyridin-2-yl)(3-(difluoromethyl)-8-methyl-[1,2,4]triazolo[4,3-a]pyridin-7-yl)methanol (6.0 g, 12 mmol) and 2,6-di-tert-butylpyridine (6.8 mL, 29 mmol) in dichloromethane (80 mL). After 40 minutes, the mixture was brought to pH 8 by adding saturated aqueous sodium bicarbonate solution and then extracted with dichloromethane. These extractions resulted in several organic solvent fractions which were combined, dried over Na$_2$SO$_4$, filtered, and concentrated to dryness under reduced pressure. The residue was purified by flash column chromatography (petroleum ether:ethyl acetate=1:0 to 0:1) to provide the title compound as a yellow oil (5 g, 86%). MS (ESI): mass calcd. for $C_{22}H_{29}ClF_2N_4OSi$, 466.2; m/z found, 467.4 $[M+H]^+$.

Step C: tert-Butyl 3-(4-(((tert-butyldimethylsilyl)oxy)methyl)-5-methylpyridin-2-yl)-3-(3-(difluoromethyl)-8-methyl-[1,2,4]triazolo[4,3-a]pyridin-7-yl)-2,2-dimethylpropanoate. A mixture containing InBr$_3$ (1.9 g, 5.4 mmol), 7-((4-(((tert-butyldimethylsilyl)oxy)methyl)-5-methylpyridin-2-yl)chloromethyl)-3-(difluoromethyl)-8-methyl-[1,2,4]triazolo[4,3-a]pyridine (5 g, 11 mmol), and ((1-(tert-butoxy)-2-methylprop-1-en-1-yl)oxy)trimethylsilane (Intermediate 121, 23.0 g, 106 mmol) in dichloromethane (80 mL) was stirred at room temperature. After 50 hours, additional ((1-(tert-butoxy)-2-methylprop-1-en-1-yl)oxy)trimethylsilane (Intermediate 121, 15 g, 69 mmol) and InBr$_3$ (1 g, 2.8 mmol) were added. After 30 hours, the mixture was poured into water and then extracted with dichloromethane. These extractions resulted in several organic solvent fractions which were combined, dried over Na$_2$SO$_4$, filtered, and concentrated to dryness under reduced pressure. The residue was purified by flash column chromatography (petroleum ether:ethyl acetate=100:1 to 2:1) to provide the title compound as a yellow oil (900 mg, 12%). MS (ESI): mass calcd. for $C_{30}H_{44}F_2N_4O_3Si$, 574.3 m/z found, 575.2 $[M+H]^+$.

Step D: tert-Butyl 3-(3-(difluoromethyl)-8-methyl-[1,2,4]triazolo[4,3-a]pyridin-7-yl)-3-(4-(hydroxymethyl)-5-methylpyridin-2-yl)-2,2-dimethylpropanoate. A 1 M solution of TBAF in THF (2.7 mL, 2.7 mmol) was added dropwise to a stirring solution of tert-butyl 3-(4-(((tert-butyldimethylsilyl)oxy)methyl)-5-methylpyridin-2-yl)-3-(3-(difluoromethyl)-8-methyl-[1,2,4]triazolo[4,3-a]pyridin-7-yl)-2,2-dimethylpropanoate (900 mg, 1.3 mmol) in THF (15 mL). After 4 hours, the mixture was poured into water and then extracted with ethyl acetate. These extractions resulted in several organic solvent fractions which were combined, dried over Na$_2$SO$_4$, filtered, and concentrated to dryness under reduced pressure. The residue was purified by flash column chromatography (ethyl acetate) to provide the title compound as a yellow oil (450 mg, 71%). MS (ESI): mass calcd. for $C_{24}H_{30}F_2N_4O_3$, 460.2 m/z found, 461.1 $[M+H]^+$.

Intermediate 192 tert-Butyl 3-(4-(chloromethyl)-5-methylpyridin-2-yl)-3-(3-(difluoromethyl)-8-methyl-[1,2,4]triazolo[4,3-a]pyridin-7-yl)-2,2-dimethylpropanoate

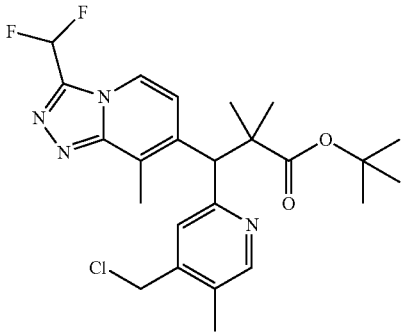 [SMILES: Cc1cnc(C(c2ccn3c(C(F)F)nnc3c2C)C(C)(C)C(=O)OC(C)(C)C)cc1CCl]

SOCl$_2$ (0.4 mL, 6 mmol) was added to a stirring solution of tert-butyl 3-(3-(difluoromethyl)-8-methyl-[1,2,4]triazolo[4,3-a]pyridin-7-yl)-3-(4-(hydroxymethyl)-5-methylpyridin-2-yl)-2,2-dimethylpropanoate (Intermediate 191, 450 mg, 0.98 mmol) in dichloromethane (8 mL). After 1 hour, the mixture was concentrated to dryness under reduced Intermediate 193 tert-Butyl 3-(3-(difluoromethyl)-8-methyl-[1,2,4]triazolo[4,3-a]pyridin-7-yl)-3-(6-(hydroxymethyl)-5-methylpyridin-2-yl)-2,2-dimethylpropanoate

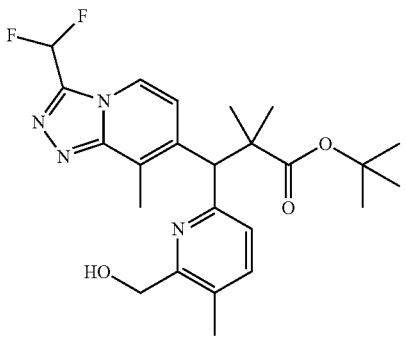 [SMILES: Cc1ccc(C(c2ccn3c(C(F)F)nnc3c2C)C(C)(C)C(=O)OC(C)(C)C)nc1CO]

The title compound (350 mg) was prepared using analogous conditions as described in Intermediate 191 where 6-(((tert-butyldimethylsilyl)oxy)methyl)-5-methylpicolinaldehyde (Intermediate 57) was used instead of 4-(((tert-butyldimethylsilyl)oxy)methyl)-5-methylpicolinaldehyde in Step A. MS (ESI): mass calcd. for $C_{24}H_{30}F_2N_4O_3$, 460.2 m/z found, 461.2 [M+H]$^+$.

Intermediate 194 tert-Butyl 3-(6-(chloromethyl)-5-methylpyridin-2-yl)-3-(3-(difluoromethyl)-8-methyl-[1,2,4]triazolo[4,3-a]pyridin-7-yl)-2,2-dimethylpropanoate

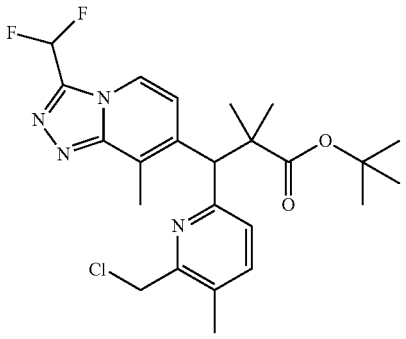 [SMILES: Cc1ccc(C(c2ccn3c(C(F)F)nnc3c2C)C(C)(C)C(=O)OC(C)(C)C)nc1CCl]

The title compound (320 mg) was prepared using analogous conditions as described in Intermediate 192 where tert-butyl 3-(3-(difluoromethyl)-8-methyl-[1,2,4]triazolo[4,3-a]pyridin-7-yl)-3-(6-(hydroxymethyl)-5-methylpyridin-2-yl)-2,2-dimethylpropanoate (Intermediate 193) was used instead of tert-butyl 3-(3-(difluoromethyl)-8-methyl-[1,2,4]triazolo[4,3-a]pyridin-7-yl)-3-(4-(hydroxymethyl)-5-methylpyridin-2-yl)-2,2-dimethylpropanoate. MS (ESI): mass calcd. for $C_{24}H_{29}ClF_2N_4O_3$, 478.2 m/z found, 479.2 [M+H]$^+$.

Intermediate 195 Methyl 3-(3-(difluoromethyl)-8-methyl-[1,2,4]triazolo[4,3-a]pyridin-7-yl)-3-(6-(hydroxymethyl)-5-methylpyridin-2-yl)-2,2-dimethylpropanoate

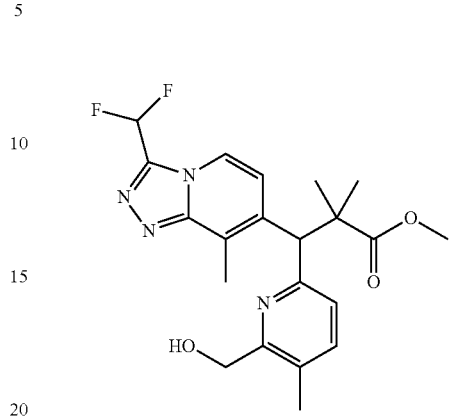

The title compound (330 mg) was prepared using analogous conditions as described in Intermediate 191 where 6-(((tert-butyldimethylsilyl)oxy)methyl)-5-methylpicolinaldehyde (Intermediate 57) was used instead of 4-(((tert-butyldimethylsilyl)oxy)methyl)-5-methylpicolinaldehyde in Step A and where ((1-methoxy-2-methylprop-1-en-1-yl)oxy)trimethylsilane was used instead of ((1-(tert-butoxy)-2-methylprop-1-en-1-yl)oxy)trimethylsilane in Step C. MS (ESI): mass calcd. for $C_{21}H_{24}F_2N_4O_3$, 418.2 m/z found, 419.2 [M+H]$^+$.

Intermediate 196 Methyl 3-(6-(chloromethyl)-5-methylpyridin-2-yl)-3-(3-(difluoromethyl)-8-methyl-[1,2,4]triazolo[4,3-a]pyridin-7-yl)-2,2-dimethylpropanoate

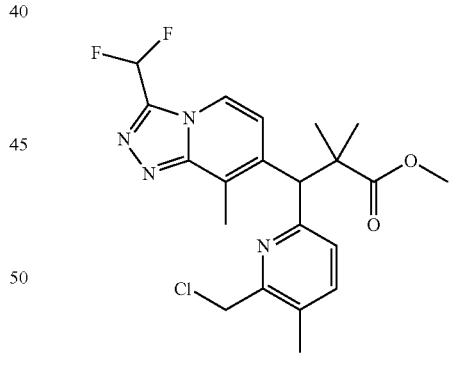

The title compound (350 mg) was prepared using analogous conditions as described in Intermediate 192 where methyl 3-(3-(difluoromethyl)-8-methyl-[1,2,4]triazolo[4,3-a]pyridin-7-yl)-3-(6-(hydroxymethyl)-5-methylpyridin-2-yl)-2,2-dimethylpropanoate (Intermediate 195) was used instead of tert-butyl 3-(3-(difluoromethyl)-8-methyl-[1,2,4]triazolo[4,3-a]pyridin-7-yl)-3-(4-(hydroxymethyl)-5-methylpyridin-2-yl)-2,2-dimethylpropanoate. MS (ESI): mass calcd. for $C_{21}H_{23}ClF_2N_4O_2$, 436.2 m/z found, 437.2 [M+H]$^+$.

331

Intermediate 197: tert-Butyl 3-(6-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate

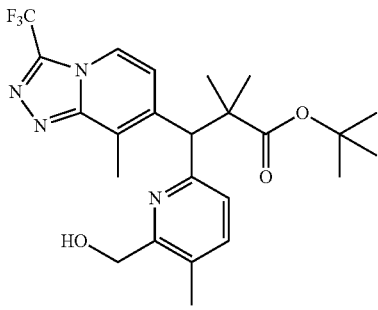 [SMILES: Cc1ccc(C(c2ccn3c(C(F)(F)F)nnc3c2C)C(C)(C)C(=O)OC(C)(C)C)nc1CO]

Step A: (6-(((tert-Butyldimethylsilyl)oxy)methyl)-5-methylpyridin-2-yl)(8-methyl-3-(trifluoromethyl)-[1,2,4]triazolo[4,3-a]pyridin-7-yl)methanol. The title compound was prepared using analogous conditions as described in Intermediate 191: Step A where 7-iodo-8-methyl-3-(trifluoromethyl)-[1,2,4]triazolo[4,3-a]pyridine (Intermediate 53) was used instead of 3-(difluoromethyl)-7-iodo-8-methyl-[1,2,4]triazolo[4,3-a]pyridine. MS (ESI): mass calcd. for $C_{22}H_{29}F_3N_4O_2Si$, 466.2 m/z found, 467.2 [M+H]$^+$.

Step B: tert-Butyl 3-(6-(((tert-butyldimethylsilyl)oxy)methyl)-5-methylpyridin-2-yl)-2,2-dimethyl-3-(8-methyl-3-(trifluoromethyl)-[1,2,4]triazolo[4,3-a]pyridin-7-yl)propanoate. The title compound was prepared using analogous conditions as described in Example 17: Step B where (6-(((tert-butyldimethylsilyl)oxy)methyl)-5-methylpyridin-2-yl)(8-methyl-3-(trifluoromethyl)-[1,2,4]triazolo[4,3-a]pyridin-7-yl)methanol was used instead of (3-(((tert-butyldimethylsilyl)oxy)methyl)-4-methylphenyl)(8-methyl-3-(trifluoromethyl)-[1,2,4]triazolo[4,3-a]pyridin-7-yl)methanol and ((1-(tert-butoxy)-2-methylprop-1-en-1-yl)oxy)trimethylsilane (Intermediate 121) was used instead of ((1-methoxy-2-methylprop-1-en-1-yl)oxy)trimethylsilane and dichloroethane was used instead of acetonitrile as solvent. MS (ESI): mass calcd. for $C_{30}H_{43}F_3N_4O_3Si$, 592.3 m/z found, 593.1 [M+H]$^+$.

Step C: tert-Butyl 3-(6-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate. The title compound was prepared using analogous conditions as described in Intermediate 191: Step D where tert-butyl 3-(6-(((tert-butyldimethylsilyl)oxy)methyl)-5-methylpyridin-2-yl)-2,2-dimethyl-3-(8-methyl-3-(trifluoromethyl)-[1,2,4]triazolo[4,3-a]pyridin-7-yl)propanoate was used instead of tert-butyl 3-(4-(((tert-butyldimethylsilyl)oxy)methyl)-5-methylpyridin-2-yl)-3-(3-(difluoromethyl)-8-methyl-[1,2,4]triazolo[4,3-a]pyridin-7-yl)-2,2-dimethylpropanoate. MS (ESI): mass calcd. for $C_{24}H_{29}F_3N_4O_3$, 478.2 m/z found, 479.1 [M+H]$^+$.

332

Intermediate 198: tert-Butyl 3-(6-(chloromethyl)-5-methylpyridin-2-yl)-2,2-dimethyl-3-(8-methyl-3-(trifluoromethyl)-[1,2,4]triazolo[4,3-a]pyridin-7-yl)propanoate

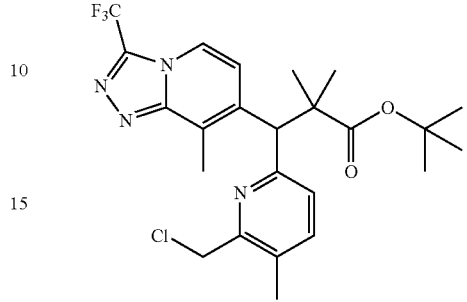

The title compound (700 mg) was prepared using analogous conditions as described in Intermediate 192 where tert-butyl 3-(6-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate (Intermediate 197) was used instead of tert-butyl 3-(3-(difluoromethyl)-8-methyl-[1,2,4]triazolo[4,3-a]pyridin-7-yl)-3-(4-(hydroxymethyl)-5-methylpyridin-2-yl)-2,2-dimethylpropanoate. MS (ESI): mass calcd. for $C_{24}H_{28}ClF_3N_4O_2$, 496.2 m/z found, 497.2 [M+H]$^+$.

Intermediate 199: Benzyl (*S)-3-(3-cyclopropyl-8-methyl-[1,2,4]triazolo[4,3-a]pyridin-7-yl)-3-(3-(hydroxymethyl)-4-methylphenyl)-2,2-dimethylpropanoate

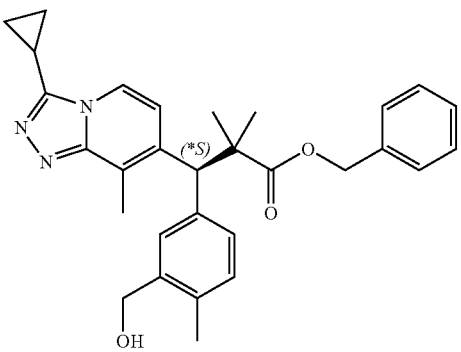 [SMILES: Cc1ccc([C@@H](c2ccn3c(C4CC4)nnc3c2C)C(C)(C)C(=O)OCc2ccccc2)cc1CO]

Step A: 3-(3-Cyclopropyl-8-methyl-[1,2,4]triazolo[4,3-a]pyridin-7-yl)-3-(3-(hydroxymethyl)-4-methylphenyl)-2,2-dimethylpropanoic acid. LiOH*H$_2$O (1.6 g, 38 mmol) was added to a solution of methyl 3-(3-(((tert-butyldimethylsilyl)oxy)methyl)-4-methylphenyl)-3-(3-cyclopropyl-8-methyl-[1,2,4]triazolo[4,3-a]pyridin-7-yl)-2,2-dimethylpropanoate (Intermediate 55, Step E, 4.0 g, 7.7 mmol) and 1,4-dioxane:H$_2$O (1:1, 60 mL). The resulting mixture was stirred at 75° C. for 16 hours, then was cooled to room temperature and adjusted to pH=6 using 1N HCl. The organic solvent was removed under reduced pressure and the mixture extracted with ethyl acetate (50 mL×5). These extractions resulted in several organic solvent fractions which were combined, dried over anhydrous Na$_2$SO$_4$, filtered, and concentrated to provide the title compound (2.2 g, 67%) as yellow solid. MS (ESI): mass calcd. for $C_{23}H_{27}N_3O_3$ 393.48; m/z found, 394.2 [M+H]+. 1H NMR (400 MHz, DMSO-$d_6$) δ 8.28 (d, J=6.6 Hz, 1H), 7.28 (s, 1H), 7.15 (d, J=7.3 Hz, 1H), 7.04 (br s, 2H), 5.03 (br s, 1H), 5.15-4.88 (m, 1H), 4.71 (s, 1H), 4.41 (s, 2H), 2.53 (s, 2H), 2.32 (s, 1H), 2.16 (s, 3H), 1.28 (s, 3H), 1.22 (s, 3H), 1.11-0.89 (m, 4H).

Step B: Benzyl 3-(3-cyclopropyl-8-methyl-[1,2,4]triazolo[4,3-a]pyridin-7-yl)-3-(3-(hydroxymethyl)-4-methylphenyl)-2,2-dimethylpropanoate. Benzyl bromide (0.16 mL, 1.3 mmol) was added to a mixture of 3-(3-cyclopropyl-8-methyl-[1,2,4]triazolo[4,3-a]pyridin-7-yl)-3-(3-(hydroxymethyl)-4-methylphenyl)-2,2-dimethylpropanoic acid (500 mg, 1.27 mmol), $K_2CO_3$ (439 mg, 3.18 mmol), and MeCN (10 mL). The resulting mixture was stirred at room temperature for 16 hours. The suspension was filtered, and the filter cake was washed with ethyl acetate (4 mL×3). The filtrate was concentrated to dryness under reduced pressure and purified by FCC (eluent:petroleum ether/ethyl acetate=1:0 to 0:1) to provide the title compound (330 mg, 53%) as a yellow oil. MS (ESI): mass calcd. for $C_{30}H_{33}N_3O_3$ 483.60; m/z found, 484.7 [M+H]+. 1H NMR (400 MHz, CDCl$_3$) δ 7.69 (d, J=7.3 Hz, 1H), 7.21-7.11 (m, 4H), 7.08-6.99 (m, 4H), 6.89 (d, J=7.3 Hz, 1H), 5.07-5.01 (m, 1H), 4.97-4.90 (m, 1H), 4.73 (s, 1H), 4.59 (s, 2H), 2.57 (s, 3H), 2.26 (s, 3H), 1.98-1.91 (m, 1H), 1.43 (s, 3H), 1.34 (s, 3H), 1.27-1.07 (m, 4H).

Step C: Benzyl (*S)-3-(3-cyclopropyl-8-methyl-[1,2,4]triazolo[4,3-a]pyridin-7-yl)-3-(3-(hydroxymethyl)-4-methylphenyl)-2,2-dimethylpropanoate. Benzyl 3-(3-cyclopropyl-8-methyl-[1,2,4]triazolo[4,3-a]pyridin-7-yl)-3-(3-(hydroxymethyl)-4-methylphenyl)-2,2-dimethylpropanoate (2.2 g, 4.5 mmol) was purified by chiral SFC (DAICEL CHIRALPAK AD, mobile phase: 60% $CO_2$, 40% EtOH containing 0.1% of 25% aq. $NH_3$ to afford two enantiomers. The first eluting isomer (980 mg, 45%) was designated (*S): MS (ESI): mass calcd. for $C_{30}H_{33}N_3O_3$ 483.60; m/z found, 484.3 [M+H]+.

Intermediate 200: Benzyl (*R)-3-(3-cyclopropyl-8-methyl-[1,2,4]triazolo[4,3-a]pyridin-7-yl)-3-(3-(hydroxymethyl)-4-methylphenyl)-2,2-dimethylpropanoate

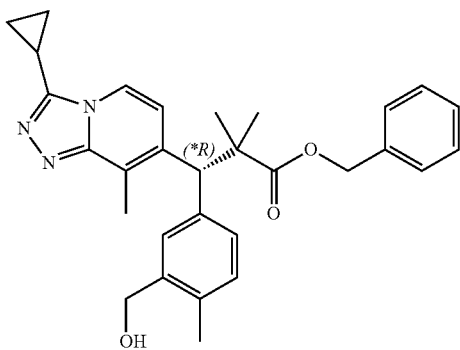 [SMILES: Cc1ccc([C@H](c2ccn3c(C4CC4)nnc3c2C)C(C)(C)C(=O)OCc2ccccc2)cc1CO]

The second eluting isomer (1.0 g, 44%) from the chiral separation described in Intermediate 199 was designated (*R): MS (ESI): mass calcd. for $C_{30}H_{33}N_3O_3$ 483.60; m/z found, 484.3 [M+H]+.

Intermediate 201: 7'-Bromo-8'-methyl-2',3'-dihydrospiro[cyclopropane-1,4'-pyrido[2,3-b][1,4,5]oxathiazepine] 1',1'-dioxide

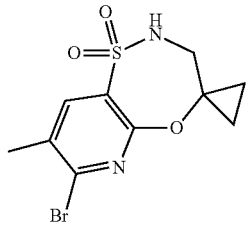 [SMILES: Cc1cc2c(nc1Br)OC1(CC1)CNS2(=O)=O]

The title compound (8.2 g) was prepared using analogous conditions as described in Intermediate 72, Steps A and B using 1-(aminomethyl)cyclopropan-1-ol instead of 4-(aminomethyl)tetrahydro-2H-pyran-4-ol in Step A. MS (ESI): mass calcd. for $C_{10}H_{11}BrN_2O_3S$, 318.0 m/z found 319.0 [M+H]+.

Intermediate 202: 7'-(2-(4-Fluoropiperidin-1-yl)ethoxy)-8'-methyl-2',3'-dihydrospiro[cyclopropane-1,4'-pyrido[2,3-b][1,4,5]oxathiazepine] 1',1'-dioxide

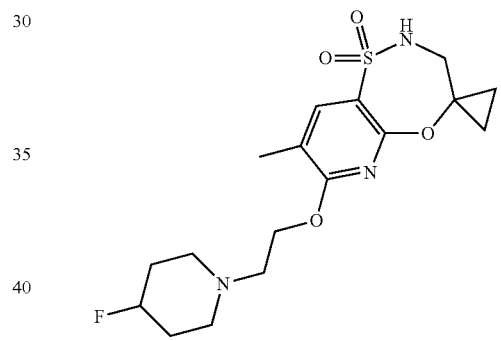

Step A: 2-(4-Fluoropiperidin-1-yl)ethanol. 2-Bromoethanol (5.10 mL, 72.0 mmol) was added to a solution of 4-fluoropiperidine hydrochloride (5.0 g, 35.8 mmol), $K_2CO_3$ (34.7 g, 251 mmol), and $CH_3CN$ (70 mL). The resulting mixture was stirred at 90° C. for 16 hours before concentrating to dryness under reduced pressure. $H_2O$ (20 mL) was added to the residue and the mixture extracted with ethyl acetate (3×). These extractions resulted in several fractions that were combined, dried over anhydrous $Na_2SO_4$, filtered, and concentrated to dryness under reduced pressure afford the title compound (4.5 g), which was used in the next step without further purification. MS (ESI): mass calcd. for $C_7H_{14}FNO$ 147.1 m/z found 148.0 [M+H]+.

Step B: 7'-(2-(4-Fluoropiperidin-1-yl)ethoxy)-8'-methyl-2',3'-dihydrospiro[cyclopropane-1,4'-pyrido[2,3-b][1,4,5]oxathiazepine] 1',1'-dioxide. 2-(4-Fluoropiperidin-1-yl)ethanol (922 mg, 6.25 mol) and $Cs_2CO_3$ (2.45 g, 7.52 mmol) were added to a solution of 7'-bromo-8'-methyl-2',3'-dihydrospiro[cyclopropane-1,4'-pyrido[2,3-b][1,4,5]oxathiazepine] 1',1'-dioxide (Intermediate 201, 800 mg, 2.51 mmol) and DMA (10 mL). The mixture was sparged with $N_2$ for 5 minutes and then treated with JosiPhos pre-catalyst G3 (116 mg, 0.126 mmol). The resulting mixture was sparged with $N_2$ for an additional 5 minutes and then stirred while heating at 100° C. for 18 hours before cooling to room-temperature and concentrating to dryness under reduced pressure. The residue was diluted with water (10 mL) and extracted with ethyl acetate (3×). These extractions resulted in several fractions that were combined, dried over anhydrous $Na_2SO_4$, filtered, and concentrated to dryness under reduced pressure. The residue was purified by flash chromatography (eluent: petroleum ether/ethyl acetate; 10:1 to 0:1, gradient) to afford the title compound (650 mg, 67%). MS (ESI): mass calcd. for $C_{17}H_{24}FN_3O_4S$, 385.2 m/z; 386.2 found $[M+H]^+$.

Intermediate 203: Benzyl (*S)-3-(3-(chloromethyl)-4-methylphenyl)-2,2-dimethyl-3-(8-methyl-3-(trifluoromethyl)-[1,2,4]triazolo[4,3-a]pyridin-7-yl)propanoate

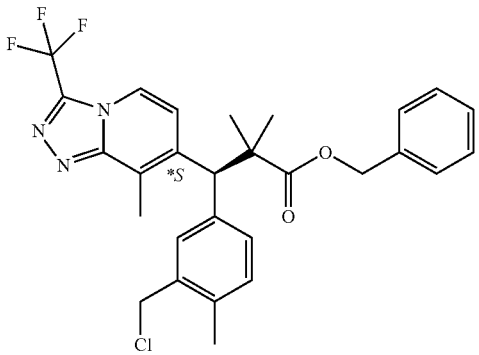 [SMILES: Cc1ccc([C@@H](c2ccn3c(C(F)(F)F)nnc3c2C)C(C)(C)C(=O)OCc2ccccc2)cc1CCl]

Step A: 3-(3-(Hydroxymethyl)-4-methylphenyl)-2,2-dimethyl-3-(8-methyl-3-(trifluoromethyl)-[1,2,4]triazolo[4,3-a]pyridin-7-yl)propanoic acid. The title compound (35.1 g) was prepared using analogous conditions as described in Example 330, Step F using methyl 3-(3-(((tert-butyldimethylsilyl)oxy)methyl)-4-methylphenyl)-2,2-dimethyl-3-(8-methyl-3-(trifluoromethyl)-[1,2,4]triazolo[4,3-a]pyridin-7-yl)propanoate (Example 17, Step B) instead of methyl 3-(3,7-dimethyl-7H-pyrrolo[2,3-c]pyridazin-6-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoate. MS (ESI): mass calcd. for $C_{21}H_{22}F_3N_3O_3$ 421.2; m/z found, 422.2 $[M+H]^+$. $^1H$ NMR (400 MHz, DMSO-$d_6$) δ 12.16 (br s, 1H), 8.42 (d, J=7.1 Hz, 1H), 7.29 (d, J=7.5 Hz, 2H), 7.14 (dd, J=1.7, 7.8 Hz, 1H), 7.05 (d, J=7.9 Hz, 1H), 5.07-5.00 (m, 1H), 4.78 (s, 1H), 4.41 (d, J=4.6 Hz, 2H), 2.66 (s, 3H), 2.16 (s, 3H), 1.29 (s, 3H), 1.24 (s, 3H).

Step B: Benzyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate. Benzyl bromide (9.9 mL, 83 mmol) was added to a stirring mixture containing 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoic acid (35.1 g, 75.7 mmol), $K_2CO_3$ (26.3 g, 190 mmol) in $CH_3CN$ (400 mL) at room temperature. After 16 hours, the mixture was filtered and the filter cake was washed with ethyl acetate. The filtrate was combined with an additional batch and concentrated to dryness under reduced pressure. The filtrate was purified by column chromatography (petroleum ether:ethyl acetate=1:0 to 1:1) to afford the title compound (37.2 g) as a yellow oil. MS (ESI): mass calcd. for $C_{28}H_{28}F_3N_3O_3$ 511.2; m/z found, 512.3 $[M+H]^+$. $^1H$ NMR (400 MHz, DMSO-$d_6$) δ 8.22 (d, J=7.3 Hz, 1H), 7.22 (d, J=6.8 Hz, 2H), 7.07-6.97 (m, 7H), 5.06-4.97 (m, 2H), 4.84 (d, J=12.1 Hz, 1H), 4.67 (s, 1H), 4.37 (d, J=5.3 Hz, 2H), 2.50 (s, 3H), 2.13 (s, 3H), 1.32 (s, 3H), 1.26 (s, 3H).

Step C: Benzyl (*S)-3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate and Benzyl (*R)-3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate. The mixture of benzyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate enantiomers were separated by chiral SFC (stationary phase: REGIS (s,s) WHELK-O1 250 mm×50 mm, 10 am; eluent: 35% to 35% (v/v) supercritical $CO_2$ in ethanol and $H_2O$ with 0.1% $NH_3$). The first eluting isomer (12.4 g) was designated (*S): MS (ESI): mass calcd. for $C_{28}H_{28}F_3N_3O_3$ 511.2; m/z found, 512.3 [M+H]+; $^1H$ NMR (400 MHz, DMSO-$d_6$) δ 8.25 (d, J=7.3 Hz, 1H), 7.27-7.21 (m, 2H), 7.09-7.01 (m, 7H), 5.09-5.00 (m, 2H), 4.87 (d, J=12.3 Hz, 1H), 4.70 (s, 1H), 4.40 (d, J=5.5 Hz, 2H), 2.53 (s, 3H), 2.16 (s, 3H), 1.35 (s, 3H), 1.29 (s, 3H) and the second eluting isomer (12.5 g) was designated (*R): MS (ESI): mass calcd. for $C_{28}H_{28}F_3N_3O_3$ 511.2; m/z found, 512.3 [M+H]+; $^1H$ NMR (400 MHz, DMSO-$d_6$) δ 8.25 (d, J=7.3 Hz, 1H), 7.27-7.23 (m, 2H), 7.10-7.00 (m, 7H), 5.09-5.00 (m, 2H), 4.87 (d, J=12.1 Hz, 1H), 4.71 (s, 1H), 4.40 (d, J=5.3 Hz, 2H), 2.53 (s, 3H), 2.16 (s, 3H), 1.35 (s, 3H), 1.29 (s, 3H).

Step D: Benzyl (*S)-3-(3-(chloromethyl)-4-methylphenyl)-2,2-dimethyl-3-(8-methyl-3-(trifluoromethyl)-[1,2,4]triazolo[4,3-a]pyridin-7-yl)propanoate. The title compound (1.0 g) was prepared using analogous conditions as described in Example 17, Step C using benzyl (*S)-3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate instead of methyl 3-(3-(((tert-butyldimethylsilyl)oxy)methyl)-4-methylphenyl)-2,2-dimethyl-3-(8-methyl-3-(trifluoromethyl)-[1,2,4]triazolo[4,3-a]pyridin-7-yl)propanoate. MS (ESI): mass calcd. for $C_{28}H_{27}ClF_3N_3O_2$ 529.2; m/z found, 530.2 $[M+H]^+$.

Intermediate 204: Benzyl (*R)-3-(3-(chloromethyl)-4-methylphenyl)-2,2-dimethyl-3-(8-methyl-3-(trifluoromethyl)-[1,2,4]triazolo[4,3-a]pyridin-7-yl)propanoate

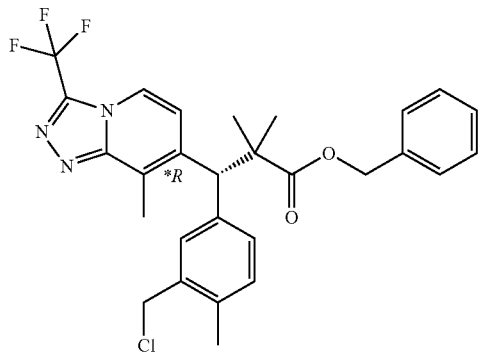 [SMILES: Cc1ccc([C@H](c2ccn3c(C(F)(F)F)nnc3c2C)C(C)(C)C(=O)OCc2ccccc2)cc1CCl]

The title compound (1.0 g) was prepared using analogous conditions as described in Example 17, Step C using benzyl (*R)-3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate (Intermediate 203, Step C: second eluting isomer) instead of methyl 3-(3-(((tert-butyldimethylsilyl)oxy)methyl)-4-methylphenyl)-2,2-dimethyl-3-(8-methyl-3-(trifluoromethyl)-[1,2,4]triazolo[4,3-a]pyridin-7-yl)propanoate. MS (ESI): mass calcd. for $C_{28}H_{27}ClF_3N_3O_2$ 529.2; m/z found, 530.2 $[M+H]^+$.

Example 1: 3-(7-(Difluoromethoxy)-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid and its trifluoroacetic Acid Salt

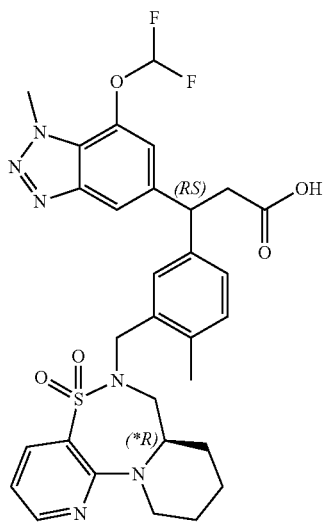 [SMILES: Cc1ccc(C(CC(=O)O)c2cc(OC(F)F)c3c(c2)nnn3C)cc1CN1C[C@H]2CCCCN2c2ncccc2S1(=O)=O]

Step A: Methyl (E)-3-(7-(difluoromethoxy)-1-methyl-1H-benzo[d][1,2,3]triazol-5-yl)acrylate. To a solution of 5-bromo-7-(difluoromethoxy)-1-methyl-1H-benzo[d][1,2,3]triazole (Intermediate 33, 6.71 g, 24.1 mmol) in DMF (6.5 mL) was added sequentially methyl acrylate (10.9 mL, 121 mmol), DIPEA (10.4 mL, 60.3 mmol), tri-o-tolylphosphine (1.47 g, 4.83 mmol), and Pd(OAc)$_2$ (542 mg, 2.41 mmol). The reaction vessel was evacuated and back-filled with Ar and was heated to 100° C. for 24 hours. The reaction mixture was then allowed to cool to room temperature and was stirred for 2 days. The reaction mixture was filtered through a pad of diatomaceous earth such as Celite®, and the pad was washed with EtOAc. The organic filtrate was washed with water (twice) and saturated aqueous NaCl (once). The organic phase was dried (Na$_2$SO$_4$), filtered, and concentrated onto silica gel. Flash column chromatography (eluent: 0 to 40% EtOAc/heptanes, gradient elution) provided the title compound (3.29 g) as brown solid which still contained some impurities. MS (ESI): mass calcd. for $Cl_2H_{11}F_2N_3O_3$, 283.1; m/z found, 284.1 $[M+H]^+$. $^1$H NMR (400 MHz, CDCl$_3$) δ 8.00 (s, 1H), 7.78 (d, J=15.7 Hz, 1H), 7.34 (s, 1H), 6.75 (t, J=72.0 Hz, 1H), 6.47 (d, J=16.2 Hz, 1H), 4.46 (s, 3H), 3.84 (s, 3H).

Step B: Methyl 3-(7-(difluoromethoxy)-1-methyl-1H-benzo[d][1,2,3]triazol-5-yl)-3-(3-(hydroxymethyl)-4-methylphenyl)propanoate. To a solution of methyl (E)-3-(7-(difluoromethoxy)-1-methyl-1H-benzo[d][1,2,3]triazol-5-yl)acrylate (327 mg, 1.16 mmol) in a mixture of 1,4-dioxane (8 mL) and water (deionized, 4 mL) was added sequentially 3-(hydroxymethyl)-4-methylphenyl)boronic acid (288 mg, 1.73 mmol), Et$_3$N (0.241 mL, 1.73 mmol) and chloro(1,5-cyclooctadiene)rhodium(I) dimer (28.5 mg, 0.0578 mmol). The reaction vessel was evacuated and back-filled with Ar. The mixture was heated to 95° C. for 50 minutes.

The reaction mixture was partitioned between EtOAc and water (25 mL each). The aqueous phase was extracted with EtOAc (2×25 mL). These extractions resulted in several organic solvent fractions which were combined, dried over Na$_2$SO$_4$, filtered, and concentrated to dryness under reduced pressure. The residue was purified by flash column chromatography (eluent: 0 to 100% EtOAc/heptanes, gradient elution) to provide the title compound (334 mg, 71%) as a light tan foam. MS (ESI): mass calcd. for $C_{20}H_{21}F_2N_3O_4$, 405.2; m/z found, 406.2 $[M+H]^+$. $^1$H NMR (400 MHz, CDCl$_3$) δ 7.76 (s, 1H), 7.23 (s, 1H), 7.14-7.09 (m, 1H), 7.09-7.05 (m, 1H), 7.00 (s, 1H), 6.64 (t, J=72.8 Hz, 1H), 4.70-4.64 (m, 3H), 4.41 (s, 3H), 3.60 (s, 3H), 3.18-3.04 (m, 2H), 2.30 (s, 3H).

Step C: Methyl 3-(3-(chloromethyl)-4-methylphenyl)-3-(7-(difluoromethoxy)-1-methyl-1H-benzo[d][1,2,3]triazol-5-yl)propanoate. To a solution of methyl 3-(7-(difluoromethoxy)-1-methyl-1H-benzo[d][1,2,3]triazol-5-yl)-3-(3-(hydroxymethyl)-4-methylphenyl)propanoate (272 mg, 0.671 mmol) in DCM (3 mL) was added SOCl$_2$ (0.073 mL, 1.01 mmol) followed by 2 drops of DMF. The reaction mixture was stirred under Ar at room temperature for 2.5 hours. The mixture was partitioned between DCM and saturated aqueous NaHCO$_3$. The aqueous phase was extracted with DCM. These extractions resulted in several organic solvent fractions which were combined, dried over Na$_2$SO$_4$, filtered, and concentrated to dryness under reduced pressure to provide the title compound (260 mg, 91%) as a light brown oil. MS (ESI): mass calcd. for $C_{20}H_{20}ClF_2N_3O_3$, 423.1; m/z found, 424.1 $[M+H]^+$. $^1$H NMR (400 MHz, CDCl$_3$) δ 7.75 (s, 1H), 7.19-7.07 (m, 3H), 6.98 (s, 1H), 6.63 (t, J=72.5 Hz, 1H), 4.66 (t, J=7.8 Hz, 1H), 4.55 (s, 2H), 4.41 (s, 3H), 3.61 (s, 3H), 3.18-3.03 (m, 2H), 2.38 (s, 3H).

Step D: 3-(7-(Difluoromethoxy)-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid. (*R)-7,7a,8,9,10,11-Hexahydro-6H-dipyrido[2,1-d:2',3'-f][1,2,5]thiadiazepine 5,5-dioxide (Intermediate 3, 83.6 mg, 0.330 mmol) was dissolved in DMF (0.75 mL). The solution was cooled to 0° C. and NaH (60% dispersion in mineral oil, 39.6 mg, 0.990 mmol) was added. The mixture was stirred at 0° C. for 10 minutes and a solution of methyl 3-(3-(chloromethyl)-4-methylphenyl)-3-(7-(difluoromethoxy)-1-methyl-1H-benzo[d][1,2,3]triazol-5-yl)propanoate in DMF (0.30 M, 1.0 mL, 0.30 mmol) was added. The reaction mixture was allowed to slowly warm to room temperature overnight. The reaction mixture was filtered, washing with a minimal volume of MeOH. The filtrate was purified by preparative HPLC (10 to 90% CH$_3$CN/H$_2$O, 0.1% TFA) to afford the title compound (54 mg, 23%) as a cream-colored powder and its trifluoroacetic acid salt. MS (ESI): mass calcd. for $C_{30}H_{32}F_2N_6O_5S$, 626.2; m/z found, 627.3 $[M+H]^+$. $^1$H NMR (400 MHz, CDCl$_3$) δ 8.46-8.26 (m, 2H), 7.71-7.62 (m, 1H), 7.19-6.90 (m, 5H), 6.88-6.45 (m, 1H), 4.71-4.51 (m, 2H), 4.45-4.29 (m, 5H), 4.06-3.80 (m, 1H), 3.47-3.24 (m, 2H), 3.17-2.62 (m, 2H), 2.35-2.25 (m, 3H), 1.83-1.23 (m, 7H).

Example 2: (*S)-3-(7-(Difluoromethoxy)-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

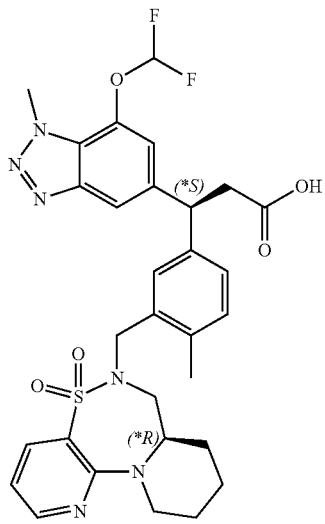 [SMILES: Cc1ccc([C@H](CC(=O)O)c2cc(OC(F)F)c3c(c2)nnn3C)cc1CN1C[C@H]2CCCCN2c2ncccc2S1(=O)=O]

The mixture of 3-(7-(difluoromethoxy)-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid isomers (Example 1, 45.6 mg) were separated by chiral SFC (stationary phase: Chiralpak AD-H 5 μm, 250×20 mm, mobile phase: 70% $CO_2$, 30% MeOH) to afford two diastereoisomers. The first eluting isomer (19 mg) was designated (*S). MS (ESI): mass calcd. for $C_{30}H_{32}F_2N_6O_5S$, 626.2; m/z found, 627.3 [M+H]$^+$. $^1$H NMR (400 MHz, MeOH-d$_4$) δ 8.25 (dd, J=4.8, 1.8 Hz, 1H), 8.00 (dd, J=7.8, 1.8 Hz, 1H), 7.77 (s, 1H), 7.33-7.03 (m, 5H), 6.92-6.82 (m, 1H), 4.73-4.57 (m, 1H), 4.41 (s, 3H), 4.38-4.21 (m, 3H), 4.06 (td, J=13.5, 4.6 Hz, 1H), 3.28-2.94 (m, 5H), 2.20 (s, 3H), 1.66-1.25 (m, 6H).

Example 3: (*R)-3-(7-(Difluoromethoxy)-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

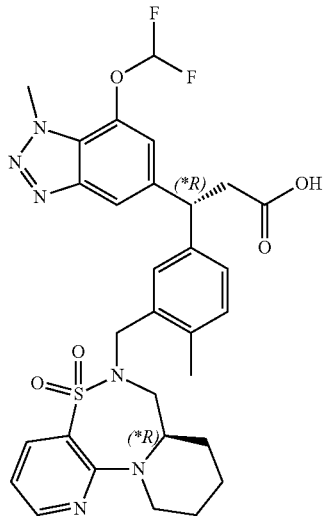

The second eluting isomer (20 mg) from the separation of isomers by chiral SFC described in Example 2 was designated (*R). MS (ESI): mass calcd. for $C_{30}H_{32}F_2N_6O_5S$, 626.2; m/z found, 627.3 [M+H]$^+$. $^1$H NMR (400 MHz, MeOH-d$_4$) δ 8.25 (dd, J=4.6, 1.5 Hz, 1H), 8.00 (dd, J=7.8, 1.8 Hz, 1H), 7.75 (br s, 1H), 7.32-7.03 (m, 5H), 6.93-6.82 (m, 1H), 4.66 (br s, 1H), 4.41 (s, 3H), 4.39-4.19 (m, 3H), 4.04 (td, J=13.3, 4.7 Hz, 1H), 3.28-2.98 (m, 5H), 2.21 (s, 3H), 1.72-1.27 (m, 6H).

Example 4: 3-(7-Cyclopropoxy-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid and its trifluoroacetic Acid Salt

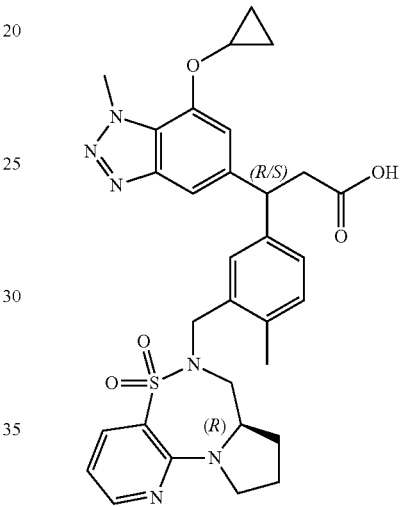

Step A: Methyl (E)-3-(7-cyclopropoxy-1-methyl-1H-benzo[d][1,2,3]triazol-5-yl)acrylate. A mixture containing 5-bromo-7-cyclopropoxy-1-methyl-1H-benzo[d][1,2,3]triazole (Intermediate 34, 1.21 g, 4.51 mmol), tetrabutylammonium chloride hydrate (0.134 g, 0.451 mmol), N,N-dicyclohexylmethylamine (1.4 mL, 6.6 mmol), methyl acrylate (0.81 mL, 9.0 mmol), PdCl$_2$(dtbpf) (0.296 g, 0.455 mmol), and DMA (7.5 mL) was heated to 120° C. under argon in a sealed tube. After 3 hours, the reaction was diluted with water (75 mL) and extracted with 1:1 diethyl ether: EtOAc (2×40 mL). These extractions resulted in multiple organic solvent fractions which were combined, washed sequentially with 0.1 M HCl (1×40 mL), 1 M NaHCO$_3$ (1×20 mL), dried over Na$_2$SO$_4$, filtered, and concentrated to dryness under reduced pressure. The residue was purified by flash column chromatography (eluent: heptanes/ethyl acetate, 90:10 to 20:80, gradient elution) to provide the title compound (1.04 g, 84%). MS (ESI): mass calcd. for $C_{14}H_{15}N_3O_3$, 273.1; m/z found, 274.2 [M+H]$^+$. $^1$H NMR (400 MHz, CDCl$_3$) δ 7.81 (d, J=15.7 Hz, 1H), 7.74 (s, 1H), 7.30 (d, J=1.0 Hz, 1H), 6.47 (d, J=15.7 Hz, 1H), 4.41 (s, 3H), 3.97-3.91 (m, 1H), 3.84 (s, 3H), 0.99-0.87 (m, 4H).

Step B: Methyl 3-(7-cyclopropoxy-1-methyl-1H-benzo[d][1,2,3]triazol-5-yl)-3-(3-(hydroxymethyl)-4-methylphenyl)propanoate. A solution of methyl (E)-3-(7-cyclopropoxy-1-methyl-1H-benzo[d][1,2,3]triazol-5-yl)acrylate (180.9 mg, 0.6619 mmol), 3-hydroxymethyl-4-methylphenylboronic acid (163.8 mg, 0.9868 mmol) and TEA (0.28 mL, 2.0 mmol) in 1,4-dioxane (2.6 mL) and water (1.3 mL, 0.65 mmol) was charged with [Rh(COD)Cl]$_2$ (33 mg, 0.067 mmol) and stirred under argon at 60° C. for 60 hours. The reaction was partitioned between EtOAc (6 mL) and 1 M NaH$_2$PO$_4$ (6 mL). The organic and aqueous layers were separated and the aqueous layer was extracted with EtOAc (1×3 mL). These extractions resulted in multiple organic solvent fractions which were combined, dried over Na$_2$SO$_4$, filtered, and concentrated to dryness under reduced pressure. The residue was purified by flash column chromatography (eluent: heptanes/ethyl acetate, 60:40 to 0:100, gradient elution) to provide the title compound (168 mg, 64%). MS (ESI): mass calcd. for C$_{22}$H$_{25}$N$_3$O$_4$, 395.2; m/z found, 396.1 [M+H]$^+$. $^1$H NMR (400 MHz, CDCl$_3$) δ 7.47 (br s, 1H), 7.28-7.27 (m, 1H), 7.11 (s, 2H), 7.01-6.97 (m, 1H), 4.70-4.63 (m, 3H), 4.35 (s, 3H), 3.86-3.80 (m, 1H), 3.86-3.80 (m, 1H), 3.61 (s, 3H), 3.12 (br s, 2H), 2.30 (s, 3H), 0.93-0.77 (m, 4H).

Step C: Methyl 3-(3-(chloromethyl)-4-methylphenyl)-3-(7-cyclopropoxy-1-methyl-1H-benzo[d][1,2,3]triazol-5-yl)propanoate. A solution containing methyl 3-(7-cyclopropoxy-1-methyl-1H-benzo[d][1,2,3]triazol-5-yl)-3-(3-(hydroxymethyl)-4-methylphenyl)propanoate (162.5 mg, 0.411 mmol) in DCM (1.7 mL) was treated with thionyl chloride (0.12 mL, 1.7 mmol) dropwise at room temperature over ~10 seconds followed by dropwise addition of DMF (22 μL, 0.28 mmol). After 35 minutes, the reaction was diluted with DCM (4 mL) and cooled to 0° C. while 1 M aqueous NaHCO$_3$ solution (6 mL) was added in one portion. After 5 minutes at 0° C., the mixture was warmed room temperature for 10 minutes and the aqueous layer was extracted with DCM (1×4 mL). These extractions resulted in multiple organic solvent fractions which were combined, dried over Na$_2$SO$_4$, filtered, and concentrated to dryness to provide the title compound (183 mg) which was carried on to the next step without further purification. MS (ESI): mass calcd. for C$_{22}$H$_{24}$ClN$_3$O$_3$, 413.2; m/z found, 414.1 [M+H]$^+$.

Step D: Methyl 3-(7-cyclopropoxy-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoate. A solution containing (R)-6,7,7a,8,9,10-hexahydropyrido[2,3-f]pyrrolo[2,1-d][1,2,5]thiadiazepine 5,5-dioxide (Intermediate 4, 54.7 mg, 0.229 mmol) and DMF (0.52 mL) was treated with NaH (60.8% dispersion in mineral oil, 13.2 mg, 0.334 mmol) in one portion at room temperature, and was then immediately cooled to 0° C. and stirred under argon for 10 minutes. The reaction was then treated dropwise with a solution of methyl 3-(3-(chloromethyl)-4-methylphenyl)-3-(7-cyclopropoxy-1-methyl-1H-benzo[d][1,2,3]triazol-5-yl)propanoate (91 mg, 0.22 mmol) in DMF (0.56 mL) over 2 minutes, and stirred at 0° C. for 20 minutes. The reaction was then quenched with 1 M NaH$_2$PO$_4$ (3 mL) and extracted with EtOAc (2×3 mL). These extractions resulted in multiple organic solvent fractions which were combined, dried over Na$_2$SO$_4$, filtered, and concentrated to dryness under reduced pressure to provide the title compound (141 mg) which was used in the next step without further purification. MS (ESI): mass calcd. for C$_{32}$H$_{36}$N$_6$O$_5$S, 616.3; m/z found, 617.3 [M+H]$^+$.

Step E: 3-(7-Cyclopropoxy-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid. A mixture containing methyl 3-(7-cyclopropoxy-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoate (127 mg, 0.206 mmol), 1.0 M LiOH (0.68 mL, 0.68 mmol), MeOH (0.91 mL) and THF (0.91 mL) was stirred at 60° C. for 40 minutes. The reaction mixture was then allowed to cool to room temperature and the pH adjusted to pH-2 with TFA (0.068 mL), diluted with MeOH (3 mL), and purified by C$_{18}$ reverse phase HPLC (30×100 mm Phenomenex Luna 5 μm column; 10 to 90% CH$_3$CN with 0.1% TFA) to provide, after lyophilization, the title compound and its trifluoroacetic acid salt. (85.2 mg, 58%). MS (ESI): mass calcd. for C$_{31}$H$_{34}$N$_6$O$_5$S, 602.2; m/z found, 603.3 [M+H]$^+$. $^1$H NMR (400 MHz, CD$_3$OD) δ 8.25-8.19 (m, 2H), 7.39 (d, J=12.1 Hz, 1H), 7.25 (td, J=7.7, 2.5 Hz, 1H), 7.20-7.12 (m, 3H), 6.95 (ddd, J=7.7, 5.2, 1.3 Hz, 1H), 4.69-4.59 (m, 2H), 4.44 (dd, J=14.1, 4.5 Hz, 1H), 4.36 (s, 3H), 4.20 (dd, J=14.4, 7.3 Hz, 1H), 3.98-3.93 (m, 1H), 3.64-3.51 (m, 2H), 3.24 (ddd, J=16.9, 13.4, 3.5 Hz, 1H), 3.17-3.06 (m, 2H), 3.02-2.90 (m, 1H), 2.27-2.26 (s, 3H), 2.06-1.92 (m, 1H), 1.86-1.61 (m, 2H), 1.53-1.44 (m, 1H), 0.90-0.75 (m, 4H).

Example 5: (*S)-3-(7-Cyclopropoxy-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

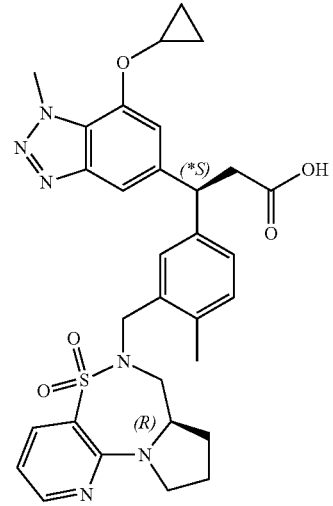

The mixture of 3-(7-cyclopropoxy-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid isomers (Example 4) was separated by chiral SFC (stationary phase: Chiralpak AD-H 5 μm 250×30 mm, Mobile phase: 70% CO$_2$, 30% EtOH) to afford two diastereomers. The first eluting isomer (30 mg, 44%) was designated (*S). MS (ESI): mass calcd. for C$_{31}$H$_{34}$N$_6$O$_5$S, 602.2; m/z found, 602.2 [M]$^+$. $^1$H NMR (400 MHz, CD$_3$OD) δ 8.26 (dd, J=4.8, 1.8 Hz, 1H), 8.04 (dd, J=7.6, 2.0 Hz, 1H), 7.41 (s, 1H), 7.25 (dd, J=7.6, 2.0 Hz, 1H), 7.18-7.13 (m, 3H), 6.86 (dd, J=7.8, 4.8 Hz, 1H), 4.62 (t, J=7.8 Hz, 1H), 4.46 (br s, 1H), 4.42-4.38 (m, 1H), 4.36 (s, 3H), 4.19 (d, J=14.1 Hz, 1H), 3.95 (tt, J=5.9, 2.9 Hz, 1H), 3.60 (dt, J=10.9, 6.1 Hz, 1H), 3.52-3.40 (m, 1H), 3.20 (dd, J=13.6, 3.5 Hz, 1H), 3.16-3.04 (m, 2H), 2.96-2.86 (m, 1H), 2.26 (s, 3H), 2.02-1.89 (m, 1H), 1.75-1.51 (m, 2H), 1.48-1.39 (m, 1H), 0.93-0.75 (m, 4H).

Example 6: (*R)-3-(7-Cyclopropoxy-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl) propanoic Acid

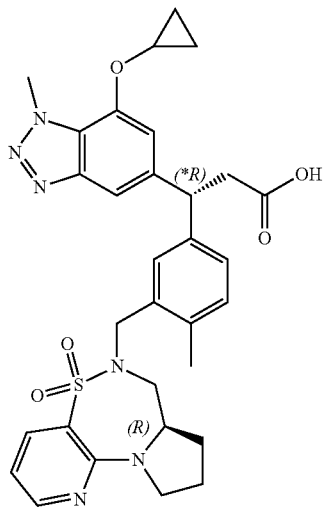

The second eluting isomer (26.1 mg, 39%) from the separation of isomers by chiral SFC described in Example 5 was designated (*R). MS (ESI): mass calcd. for $C_{31}H_{34}N_6O_5S$, 602.2; m/z found, 602.2 [M]+. $^1$H NMR (400 MHz, CD$_3$OD) δ 8.25 (dd, J=5.1, 1.5 Hz, 1H), 8.10 (dd, J=7.8, 1.8 Hz, 1H), 7.39 (s, 1H), 7.26-7.21 (m, 1H), 7.20-7.12 (m, 3H), 6.89 (dd, J=7.6, 5.1 Hz, 1H), 4.63 (t, J=7.8 Hz, 1H), 4.48 (br s, 1H), 4.40 (s, 1H), 4.36 (s, 3H), 4.22 (d, J=14.1 Hz, 1H), 3.96 (tt, J=6.0, 2.8 Hz, 1H), 3.67-3.57 (m, 1H), 3.57-3.47 (m, 1H), 3.18 (dd, J=13.6, 3.5 Hz, 1H), 3.15-3.08 (m, 2H), 2.99-2.91 (m, 1H), 2.27 (s, 3H), 1.99-1.88 (m, 1H), 1.81-1.55 (m, 2H), 1.53-1.33 (m, 1H), 0.92-0.75 (m, 4H).

Example 7: (*S)-3-(3-((1',1'-Dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl) propanoic Acid Step A: Ethyl 3-(3-((1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoate. Diisopropyl azodicarboxylate (0.1 mL, 0.5 mmol) was added to a mixture of ethyl 3-(3-(hydroxymethyl)-4-methylphenyl)-3-(8-methyl-3-(trifluoromethyl)-[1,2,4]triazolo[4,3-a]pyridin-7-yl)propanoate (Intermediate 25, 130 mg, 0.31 mmol), 2',3'-dihydrospiro[cyclopropane-1,4'-pyrido[2,3-b][1,4,5]oxathiazepine] 1',1'-dioxide (Intermediate 5, 97.7 mg, 0.432 mmol), and triphenyl phosphine (120 mg, 0.46 mmol) in THF (3.5 mL) at room temperature. After 3 hours, ethyl acetate was added and then the mixture was absorbed onto diatomaceous earth such as Celite® for purification by flash column chromatography (hexanes/ethyl acetate) to provide the title compound (205 mg, 106%). MS (ESI): mass calcd. for $C_{30}H_{30}F_3N_5O_5S$, 629.2; m/z found, 630.2 [M+H]+.

Step B: (*S)-3-(3-((1',1'-Dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid. A mixture of ethyl 3-(3-((1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoate (205 mg, 0.326 mmol) in 1 M aqueous NaOH solution (3 mL, 3 mmol) and THF (3 mL) was stirred at room temperature. After 18 hours, water was added and then 1 M aqueous HCl solution was added until the pH was 3-4. Ethyl acetate was added and the resulting biphasic mixture was separated. The organic layer was dried over Na$_2$SO$_4$, filtered, and concentrated to dryness under reduced pressure. The residue was purified by chiral SFC (stationary phase: Daicel Chiralpak AD-H 5 μm 300 gram, isocratic mobile phase: 70% CO$_2$, 30% MeOH) to afford two enantiomers. The first eluting isomer (55 mg) was designated (*S). MS (ESI): mass calcd. for $C_{28}H_{26}F_3N_5O_5S$, 601.2; m/z found, 602.1 [M+H]+. $^1$H NMR (500 MHz, DMSO-d$_6$) δ 12.3 (br s, 1H), 8.54-8.47 (m, 1H), 8.39 (d, J=7.2 Hz, 1H), 8.26 (dd, J=7.7, 1.9 Hz, 1H), 7.50 (dd, J=7.6, 4.9 Hz, 1H), 7.26-7.20 (m, 1H), 7.19-7.11 (m, 3H), 4.81 (t, J=7.8 Hz, 1H), 4.28-4.13 (m, 2H), 3.69-3.54 (m, 1H), 3.50-3.39 (m, 1H), 3.14-2.99 (m, 2H), 2.71 (s, 3H), 2.22 (s, 3H), 1.01-0.87 (m, 2H), 0.69-0.55 (m, 2H).

Example 8: (*R)-3-(3-((1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl) propanoic Acid

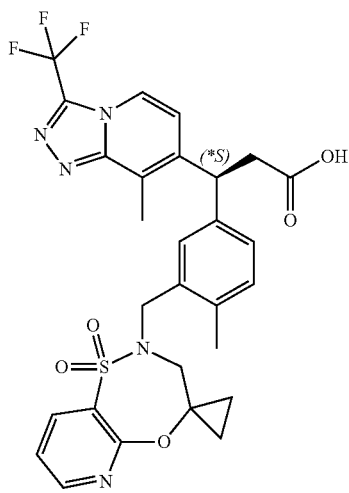
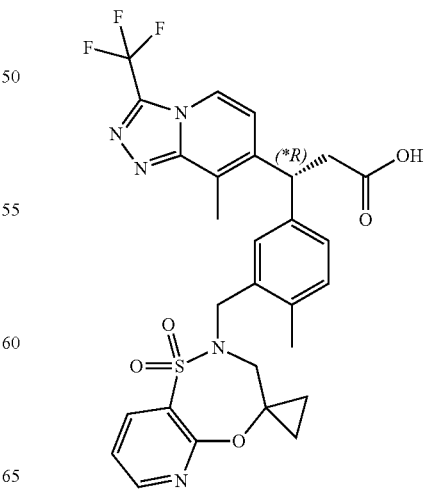

The second eluting isomer (53 mg) from the separation of isomers by chiral SFC described in Example 7 was designated (*R). MS (ESI): mass calcd. for $C_{28}H_{26}F_3N_5O_5S$, 601.2; m/z found, 602.1 [M+H]$^+$. $^1$H NMR (500 MHz, DMSO-$d_6$) δ 8.51 (dd, J=4.9, 1.9 Hz, 1H), 8.39 (d, J=7.1 Hz, 1H), 8.26 (dd, J=7.6, 1.9 Hz, 1H), 7.53-7.47 (m, 1H), 7.25-7.20 (m, 1H), 7.18-7.11 (m, 3H), 4.86-4.75 (m, 1H), 4.29-4.12 (m, 2H), 3.70-3.53 (m, 1H), 3.53-3.38 (m, 1H), 3.13-3.00 (m, 2H), 2.71 (s, 3H), 2.22 (s, 3H), 1.00-0.85 (m, 2H), 0.69-0.54 (m, 2H).

Example 9: (*S)-3-(3-(((*R)-3-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

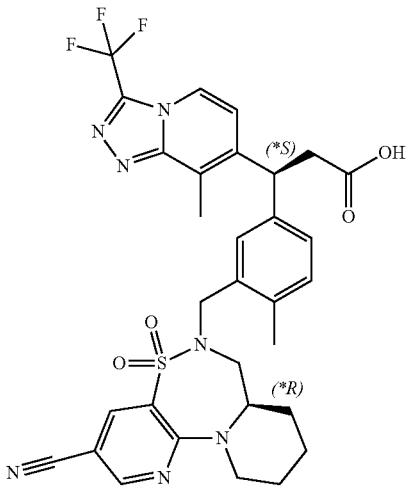 [SMILES: Cc1ccc([C@H](CC(=O)O)c2ccn3c(C(F)(F)F)nnc3c2C)cc1CN1C[C@H]2CCCCN2c2ncc(C#N)cc2S1(=O)=O]

Step A: Ethyl (*3S)-3-(3-((3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoate. Di-tert-butyl azodicarboxylate (601 mg, 2.61 mmol) was added to a solution of ethyl (*S)-3-(3-(hydroxymethyl)-4-methylphenyl)-3-(8-methyl-3-(trifluoromethyl)-[1,2,4]triazolo[4,3-a]pyridin-7-yl)propanoate (Intermediate 26, 693 mg, 1.64 mmol), 7,7a,8,9,10,11-hexahydro-6H-dipyrido[2,1-d:2',3'-f][1,2,5]thiadiazepine-3-carbonitrile 5,5-dioxide (Intermediate 9, 561 mg, 2.02 mmol), and triphenyl phosphine (691 mg, 2.63 mmol) in THF (24 mL) at room temperature. After 30 minutes, additional triphenyl phosphine (201 mg) and di-tert-butyl azodicarboxylate (170 mg) were added and the mixture was stirred overnight. The mixture was absorbed onto diatomaceous earth such as Celite® for purification by flash column chromatography (hexanes/ethyl acetate) to provide the title compound which still contained impurities. The residue was further purified by reverse phase-flash column chromatography ($C_{18}$ column, acetonitrile-water containing 0.05% TFA). The pure fractions resulting from the reverse phase-flash column chromatography were collected, concentrated under reduced pressure, and then extracted with dichloromethane. These extractions resulted in several organic solvent fractions which were combined, dried over $Na_2SO_4$, filtered, and concentrated to dryness under reduced pressure to provide the title compound as a white solid (1.01 g, 90%). MS (ESI): mass calcd. for $C_{33}H_{34}F_3N_7O_4S$, 681.2; m/z found, 682.2 [M+H]$^+$. $^1$H NMR (400 MHz, DMSO-$d_6$) δ 8.69-8.65 (m, 1H), 8.45-8.40 (m, 2H), 7.33-7.13 (m, 4H), 4.93-4.77 (m, 1H), 4.51-4.09 (m, 4H), 4.03-3.93 (m, 2H), 3.35-3.09 (m, 5H), 2.79-2.70 (m, 3H), 2.16-2.10 (m, 3H), 1.69-1.25 (m, 6H), 1.12-1.01 (m, 3H).

Step B: (*S)-3-(3-(((*R)-3-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid. A mixture containing ethyl (*3S)-3-(3-((3-cyano-5,5-dioxido-7,7a,8,9,10,11-hexahydro-6H-dipyrido[2,1-d:2',3'-][1,2,5]thiadiazepin-6-yl)methyl)-4-methylphenyl)-3-(8-methyl-3-(trifluoromethyl)-[1,2,4]triazolo[4,3-a]pyridin-7-yl)propanoate (1.01 g, 1.48 mmol), 1 M aqueous NaOH solution (4.4 mL, 4.4 mmol) and THF (8 mL) was stirred at room temperature. After 2 hours, additional 1 M aqueous NaOH solution (4.4 mL) and THF (4 mL) were added. After 6 hours, water was added and then 1 M aqueous HCl solution until the pH was 3-4. Ethyl acetate was added and the layers were separated. The aqueous layer was extracted with ethyl acetate. These extractions resulted in several organic solvent fractions which were combined, dried over $Na_2SO_4$, filtered, and then absorbed onto diatomaceous earth such as Celite® for purification by reverse phase-flash column chromatography ($C_{18}$ column, acetonitrile-water containing 0.05% TFA). The pure fractions resulting from the reverse phase-flash column chromatography were collected, concentrated under reduced pressure, and then extracted with dichloromethane. These extractions resulted in several organic solvent fractions which were combined, dried over $Na_2SO_4$, filtered, and concentrated to dryness under reduced pressure to afford a mixture of isomers (934 mg, 96%). The isomeric mixture was separated by chiral SFC (stationary phase: Daicel Chiralpak IG, 2×25 cm, mobile phase: 60% $CO_2$, 40% MeOH) to provide two diastereoisomers. The first eluting isomer (441 mg) was designated (*R). MS (ESI): mass calcd. for $C_{31}H_{30}F_3N_7O_4S$, 653.2; m/z found, 654.2 [M+H]$^+$. $^1$H NMR (400 MHz, DMSO-$d_6$) δ 12.37 (s, 1H), 8.67 (d, J=2.1 Hz, 1H), 8.48-8.37 (m, 2H), 7.33-7.10 (m, 4H), 4.87-4.76 (m, 1H), 4.46-4.36 (m, 1H), 4.36-4.20 (m, 2H), 4.20-4.09 (m, 1H), 3.38-3.03 (m, 5H), 2.73 (s, 3H), 2.12 (s, 3H), 1.65-1.21 (m, 6H).

Example 10: (*S)-3-(3-(((*S)-3-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

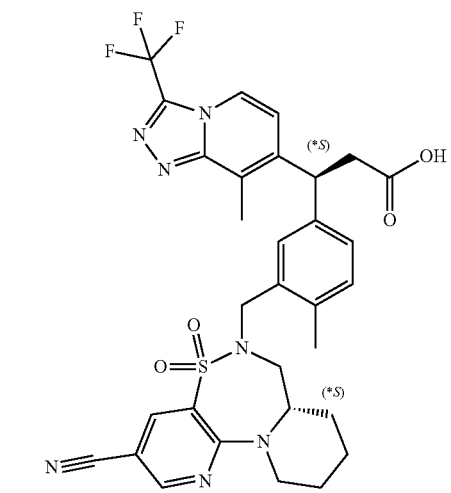 [SMILES: Cc1ccc([C@H](CC(=O)O)c2ccn3c(C(F)(F)F)nnc3c2C)cc1CN1C[C@@H]2CCCCN2c2ncc(C#N)cc2S1(=O)=O]

The second eluting isomer (449 mg) from the separation of isomers by chiral SFC described in Example 9 was designated (*S). MS (ESI): mass calcd. for $C_{31}H_{30}F_3N_7O_4S$, 653.2; m/z found, 654.1 [M+H]⁺. ¹H NMR (400 MHz, DMSO-d₆) δ 12.44 (s, 1H), 8.67 (d, J=2.2 Hz, 1H), 8.48-8.33 (m, 2H), 7.36-7.08 (m, 4H), 4.90-4.79 (m, 1H), 4.51-4.33 (m, 2H), 4.21-4.09 (m, 2H), 3.41-3.04 (m, 5H), 2.76 (s, 3H), 2.14 (s, 3H), 1.67-1.14 (m, 6H).

Example 11: 3-(1-(Cyclopropylmethyl)-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

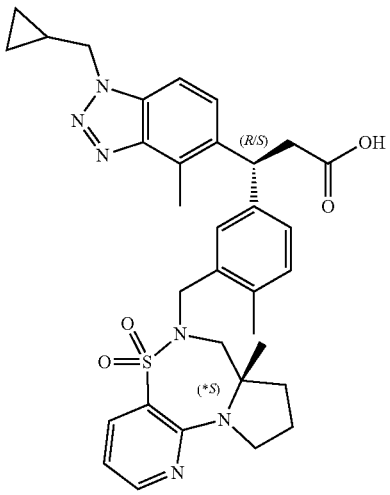

Step A: Ethyl 3-(1-(cyclopropylmethyl)-4-methyl-1H-benzo[d][1,2,3]triazol-5-yl)-3-(3-hydroxymethyl)-4-methylphenyl)propanoate. To a 100 mL round bottom flask under N₂ was added ethyl (E)-3-1-(cyclopropylmethyl)-4-methyl-1H-benzo[d][1,2,3]triazol-5-yl)acrylate (Intermediate 35, 1.00 g, 3.51 mmol), (3-(hydroxymethyl)-4-methylphenyl) boronic acid (934 mg, 5.63 mmol) and TEA (1.30 mL, 9.35 mmol) in 1,4-dioxane (17.0 mL) and water (7.00 mL). [Rh(COD)Cl]₂ (254 mg, 0.52 mmol) was added and the reaction mixture was stirred at room temperature for 18 hours. The reaction was poured into aqueous saturated sodium bicarbonate solution and extracted with ethyl acetate (3×). These extractions resulted in several organic solvent fractions which were combined, dried over sodium sulfate and concentrated to dryness under reduced pressure. The residue was purified by flash column chromatography (eluent: ethyl acetate/DCM, 1:1) to afford the title compound (1.15 g, 81%) as a colorless oil. MS (ESI): mass calcd. for C₂₄H₂₉N₃O₃, 407.2; m/z found, 408.2 [M+H]⁺.

Step B: Ethyl 3-(1-(cyclopropylmethyl)-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoate. To a reaction vessel under N₂ was added ethyl 3-(1-(cyclopropylmethyl)-4-methyl-1H-benzo[d][1,2,3]triazol-5-yl)-3-(3-hydroxymethyl)-4-methylphenyl)propanoate (200 mg, 0.49 mmol), (*S)-7a-methyl-6,7,7a,8,9,19-hexahydropyrido[2,3-]pyrollo[2,1-d[1,2,5]thiadiazepine 5,5-dioxide (Intermediate 39, 174 mg, 0.69 mmol), triphenyl phosphine (244 mg, 0.93 mmol) and THF (6.00 mL). Diisopropyl azodicarboxylate (0.18 mL, 0.91 mmol) was then added to this mixture, and the reaction was allowed to stir at room temperature for 18 hours. The reaction mixture was poured into aqueous saturated sodium bicarbonate solution and the aqueous layer was extracted with ethyl acetate (2×). These extractions resulted in several organic solvent fractions which were combined, dried over sodium sulfate and concentrated to dryness under reduced pressure. The residue was purified by flash column chromatography (eluent: ethyl acetate/DCM, 1:1) to afford the title compound (260 mg, 82%) as a colorless, solid. MS (ESI): mass calcd. for C₃₅H₄₂N₆O₄S, 642.3; m/z found, 642.9 [M+H]⁺.

Step C: 3-(1-(Cyclopropylmethyl)-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid. To a reaction vessel containing ethyl 3-(1-(cyclopropylmethyl)-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoate (260 mg, 0.40 mmol) was added 1 M NaOH (3.70 mL), THF (3.70 mL) and ethanol (0.40 mL). This mixture was stirred for 18 hours at room temperature followed by adjustment of the pH to ~pH 3-5 with 2 M HCl. The mixture was partitioned between water and ethyl acetate, the layers were separated, and the aqueous layer was extracted with ethyl acetate (3×). These extractions resulted in several organic solvent fractions which were combined, washed with brine (1x), dried over anhydrous sodium sulfate, filtered and concentrated under reduced pressure to afford the title compound (245 mg, 98%) as a white foam. MS (ESI): mass calcd. for C₃₃H₃₈N₆O₄S, 614.3; m/z found, 615.3 [M+H]⁺. ¹H NMR (400 MHz, CDCl₃) δ 8.37-8.35 (m, 1H), 8.16-8.12 (m, 1H), 7.38-7.34 (m, 2H), 7.16 (d, J=13.8 Hz, 1H), 7.12-7.04 (m, 2H), 6.92-6.89 (m, 1H), 4.99-4.95 (m, 1H), 4.73 (dd, J=14.9, 5.8 Hz, 1H), 4.45 (dd, J=7.1, 4.0 Hz, 2H), 4.27 (dd, J=14.9, 3.2 Hz, 1H), 3.93-3.85 (m, 1H), 3.60-3.44 (m, 2H), 3.24-3.03 (m, 2H), 2.89-2.70 (m, 4H), 2.26 (d, J=5.7 Hz, 3H), 1.88-1.59 (m, 4H), 1.42-1.14 (m, 3H), 0.76-0.70 (m, 2H), 0.66-0.57 (m, 2H), 0.49-0.44 (m, 2H).

Example 12: (*S)-3-(1-(Cyclopropylmethyl)-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

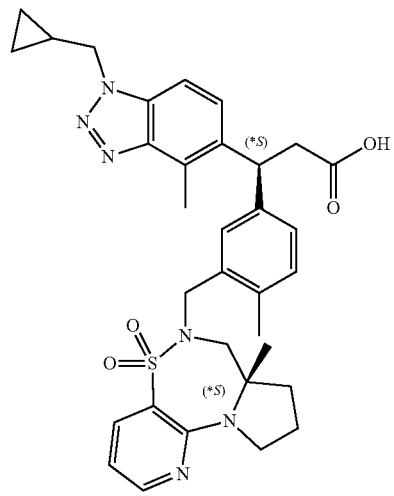 [SMILES: Cc1ccc([C@H](CC(=O)O)c2ccc3c(nnn3CC3CC3)c2C)cc1CN1C[C@]2(C)CCCN2c2ncccc2S1(=O)=O]

The mixture of 3-(1-(cyclopropylmethyl)-4-methyl)-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid isomers (Example 11, 245 mg) was separated by chiral SFC (stationary phase: Chiralpak AD-H 5 μm 250×30 mm, mobile phase: 50% CO₂, 50% MeOH) to afford two diastereoisomers. The first eluting isomer (99 mg) was designated (*S). MS (ESI): mass calcd. for $C_{33}H_{38}N_6O_4S$, 614.3; m/z found, 615.3 [M+H]⁺. ¹H NMR (400 MHz, CDCl₃) δ 8.35 (dd, J=4.8, 1.8 Hz, 1H), 8.14 (dd, J=7.7, 1.9 Hz, 1H), 7.37 (d, J=1.4 Hz, 2H), 7.15 (s, 1H), 7.08 (s, 2H), 6.91 (dd, J=7.7, 4.8 Hz, 1H), 4.97 (t, J=7.7 Hz, 1H), 4.73 (d, J=14.8 Hz, 1H), 4.45 (d, J=7.0 Hz, 2H), 4.27 (d, J=14.8 Hz, 1H), 3.90-3.83 (m, 1H), 3.75-3.70 (m, 0.5H), 3.58-3.44 (m, 1.5H), 3.21-3.11 (m, 2H), 2.86-2.70 (m, 4H), 2.27 (s, 3H), 1.81-1.54 (m, 4H), 1.42-1.15 (m, 2H), 0.75 (s, 3H), 0.66-0.56 (m, 2H), 0.47-0.43 (m, 2H).

Example 13: (*R)-3-(1-(Cyclopropylmethyl)-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

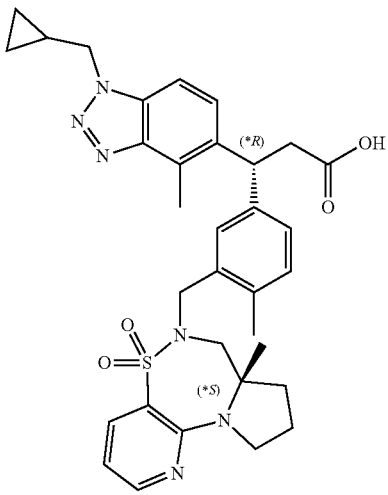 [SMILES: Cc1ccc([C@@H](CC(=O)O)c2ccc3c(nnn3CC3CC3)c2C)cc1CN1C[C@]2(C)CCCN2c2ncccc2S1(=O)=O]

The second eluting isomer (100 mg) from the separation of isomers by chiral SFC described in Example 12 was designated (*R). MS (ESI): mass calcd. for $C_{33}H_{38}N_6O_4S$, 614.3; m/z found, 615.3 [M+H]⁺. ¹H NMR (400 MHz, CDCl₃) δ 8.35 (dd, J=4.8, 1.8 Hz, 1H), 8.14 (dd, J=7.7, 1.9 Hz, 1H), 7.36-7.32 (m, 2H), 7.15 (s, 1H), 7.08-7.07 (m, 2H), 6.91 (dd, J=7.7, 4.8 Hz, 1H), 4.97 (t, J=7.7 Hz, 1H), 4.73 (d, J=14.8 Hz, 1H), 4.45 (d, J=7.0 Hz, 2H), 4.27 (d, J=14.8 Hz, 1H), 3.93-3.98 (m, 1H), 3.58-3.44 (m, 2H), 3.20-3.17 (m, 1H), 3.11-3.07 (m, 1H), 2.86-2.70 (m, 4H), 2.27 (s, 3H), 1.85-1.73 (m, 4H), 1.42-1.15 (m, 2H), 0.69 (s, 3H), 0.66-0.56 (m, 2H), 0.47-0.43 (m, 2H).

Example 14: 3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic Acid

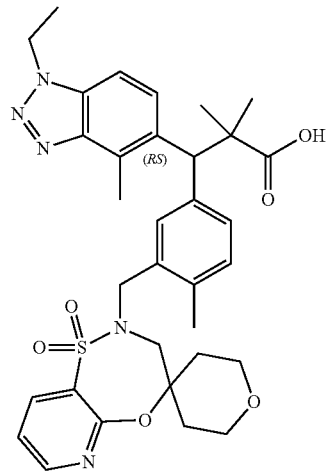 [SMILES: CCn1nnc2c(C)c(C(c3ccc(C)c(CN4CC5(CCOCC5)Oc5ncccc5S4(=O)=O)c3)C(C)(C)C(=O)O)ccc21]

Step A: (3-(((tert-Butyldimethylsilyl)oxy)methyl)-4-methylphenyl)(1-ethyl-4-methyl-1H-benzo[d][1,2,3]triazol-5-yl)methanol. A solution of n-BuLi (0.700 mL, 2.5 M in hexanes, 1.75 mmol) was added dropwise to ((5-bromo-2-methylbenzyl)oxy)(tert-butyl)dimethylsilane (Intermediate 19, 472 mg, 1.58 mmol) in THF at −78° C. (20 mL) and the resulting mixture was stirred for 1 hour. 1-Ethyl-4-methyl-1H-benzo[d][1,2,3]triazole-5-carbaldehyde (Intermediate 22, 298 mg, 1.50 mmol) in THF (5 mL) was added dropwise and the resulting solution was warmed to room temperature over a period of 4 hours. The mixture was quenched with aqueous saturated NaHCO₃ solution (10 mL) and the aqueous layer was extracted with EtOAc (15 mL×3). These extractions resulted in several organic solvent fractions which were combined and concentrated to dryness under reduced pressure. The residue was purified by flash column chromatography (eluent: 10% acetone in CH₂Cl₂) to provide the title compound (450 mg, 70%). MS (ESI): mass calcd. for $C_{24}H_{35}N_3O_2Si$, 425.2; m/z found, 426.0 [M+H]⁺. ¹H NMR (500 MHz, CDCl₃) δ 7.73 (d, J=8.6 Hz, 1H), 7.40-7.30 (m, 2H), 7.20 (dd, J=7.7, 2.0 Hz, 1H), 7.08 (d, J=7.8 Hz, 1H), 6.75 (br s, 1H), 6.23 (s, 1H), 4.69-4.62 (m, 4H), 2.74 (s, 3H), 2.21 (s, 3H), 1.59 (t, J=7.3 Hz, 3H), 0.82 (s, 9H), 0.10 (s, 6H).

Step B: Methyl 3-(3-(chloromethyl)-4-methylphenyl)-3-(1-ethyl-4-methyl-1H-benzo[d][1,2,3]triazol-5-yl)-2,2-dimethylpropanoate. 2,2,2-Trichloroacetonitrile (397 mg, 2.75 mmol) and DBU (7.60 mg, 0.0499 mmol) were added to (3-(((tert-butyldimethylsilyl)oxy)methyl)-4-methylphenyl)(1-ethyl-4-methyl-1H-benzo[d][1,2,3]triazol-5-yl)methanol (450 mg, 1.08 mmol) in acetonitrile (5 mL) at room temperature, and the mixture was stirred for 45 minutes. ((1-Methoxy-2-methylprop-1-en-1-yl)oxy)trimethylsilane (438 mg, 2.51 mmol) and bis(trifluoromethanesulfonyl)imide (32.0 mg, 0.114 mmol) were then added sequentially, and the mixture was stirred at room temperature for 2 hours. The reaction was quenched with aqueous saturated NaHCO₃ solution (20 mL), and extracted with DCM (15 mL×3). These extractions resulted in several organic solvent fractions which were combined and concentrated to dryness under reduced pressure. The residue was then dissolved in DCM (10 mL) and SOCl₂ (0.31 mL, 4.3 mmol) was added and the mixture was stirred at room temperature for 2 hours. The mixture was concentrated and the residue was purified by flash column chromatography (eluent: 10% acetone in CH$_2$Cl$_2$) to provide the title compound (250 mg, 57%). MS (ESI): mass calcd. for C$_{23}$H$_{28}$ClN$_3$O$_2$, 413.2; m/z found, 414.0 [M+H]$^+$. $^1$H NMR (500 MHz, CDCl$_3$) δ 7.60 (d, J=8.7 Hz, 1H), 7.32-7.27 (m, 1H), 7.17-7.09 (m, 2H), 7.08-7.04 (m, 1H), 4.86 (s, 1H), 4.69-4.60 (m, 2H), 4.57-4.50 (m, 2H), 2.72 (s, 3H), 3.50 (s, 3H), 2.34 (s, 3H), 1.66-1.54 (m, 3H), 1.40 (s, 3H), 1.31 (s, 3H).

Step C: 3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic acid. DMF (0.5 mL) was added to a mixture of 2,2',3,3',5,6-hexahydrospiro[pyran-4,4'-pyrido[2,3-b][1,4,5]oxathiazepine] 1',1'-dioxide (Intermediate 36, 33 mg, 0.12 mmol) and sodium hydride (60% dispersion in mineral oil, 9.0 mg, 0.24 mmol). After 10 minutes, a solution of methyl 3-(3-(chloromethyl)-4-methylphenyl)-3-(1-ethyl-4-methyl-1H-benzo[d][1,2,3]triazol-5-yl)-2,2-dimethylpropanoate (50 mg, 0.12 mmol) in DMF (0.5 mL) was added, and the mixture was stirred at room temperature for 1 hour. Water (20 mL) was added and the aqueous layer was extracted with EtOAc (15 mL×3). These extractions resulted in several organic solvent fractions which were combined and concentrated under reduced pressure. The residue was dissolved in THF (1 mL) and MeOH (1 mL) and then NaOH (3 M, 1 mL, 3 mmol) was added. The mixture was heated to 50° C. for 24 hours. Water (5 mL) was added, and the pH of the mixture was adjusted to ~3-4 by adding 1 M aqueous HCl solution. This reaction mixture was extracted with ethyl acetate and the organic and aqueous portion separated. The aqueous layer was extracted with EtOAc (15 mL×3). These extractions resulted in several organic solvent fractions which were combined and concentrated. The residue was purified by flash column chromatography (10% methanol/CH$_2$Cl$_2$) to provide the title compound (24 mg, 32%). MS (ESI): mass calcd. for C$_{33}$H$_{39}$N$_5$O$_6$S, 633.3; m/z found, 633.9 [M+H]$^+$. $^1$H NMR (500 MHz, CDCl$_3$) δ 8.50-8.32 (m, 1H), 8.19-8.09 (m, 1H), 7.41 (d, J=8.7 Hz, 1H), 7.22-7.14 (m, 3H), 6.99 (d, J=7.8 Hz, 1H), 6.86 (d, J=7.9 Hz, 1H), 5.04 (s, 1H), 4.59-4.50 (m, 2H), 4.47-4.20 (m, 2H), 4.03-3.87 (m, 2H), 3.65-3.56 (m, 1H), 3.49-3.44 (m, 2H), 3.42-3.25 (m, 1H), 2.74 (s, 3H), 2.07 (s, 3H), 1.64-1.33 (m, 7H), 1.20 (s, 3H), 0.95 (s, 3H).

Example 15: (*S)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic Acid The mixture of 3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic acid enantiomers (Example 14, 24 mg) was separated by chiral SFC (stationary phase: Chiralpak AD-H 5 μm 250×30 mm, mobile phase: 80% CO$_2$, 20% MeOH) to afford two enantiomers. The first eluting enantiomer (7 mg) was designated (*S). MS (ESI): mass calcd. for C$_{33}$H$_{39}$N$_5$O$_6$S, 633.3; m/z found, 633.9 [M+H]$^+$.

Example 16: (*R)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)-2,2-dimethylpropanoic Acid

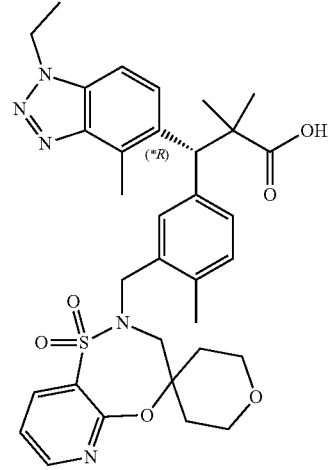 [SMILES: CCn1nnc2c(C)c([C@@H](c3ccc(C)c(CN4CC5(CCOCC5)Oc5ncccc5S4(=O)=O)c3)C(C)(C)C(=O)O)ccc21]

The second eluting enantiomer (7 mg) from the separation of isomers by chiral SFC described in Example 15 was designated (*R). MS (ESI): mass calcd. for C$_{33}$H$_{39}$N$_5$O$_6$S, 633.3; m/z found, 633.9 [M+H]$^+$.

Example 17: 2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

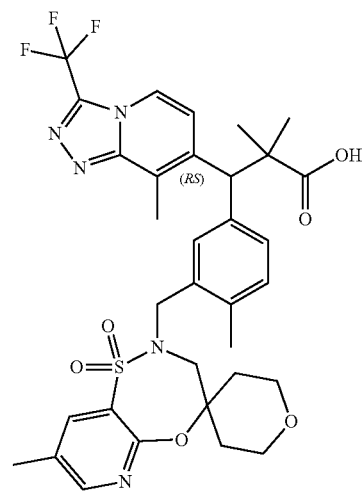 [SMILES: Cc1cnc2c(c1)S(=O)(=O)N(Cc1cc(C(c3ccn4c(C(F)(F)F)nnc4c3C)C(C)(C)C(=O)O)ccc1C)CC1(CCOCC1)O2]

Step A: (3-(((tert-Butyldimethylsilyl)oxy)methyl)-4-methylphenyl)(8-methyl-3-(trifluoromethyl)-[1,2,4]triazolo[4,3-a]pyridin-7-yl)methanol. A solution of n-BuLi (2.95 mL, 2.5 M in hexanes, 7.38 mmol) was added dropwise to ((5-bromo-2-methylbenzyl)oxy)(tert-butyl)dimethylsilane (Intermediate 19, 1.78 g, 5.67 mmol) in THF (80 mL) at −78° C. and the resulting mixture was stirred for 1 hour. 8-Methyl-3-(trifluoromethyl)-[1,2,4]triazolo[4,3-a]pyridine-7-carbaldehyde (Intermediate 22, 1.30 g, 5.67 mmol) in THF (5 mL) was then added dropwise and the resulting solution was warmed to room temperature over a period of 4 hours. Aqueous saturated NH$_4$Cl solution (40 mL) was added and the aqueous layer was extracted with EtOAc (60 mL×2). These extractions resulted in several organic solvent fractions which were combined and concentrated to dryness under reduced pressure. The residue was purified by flash column chromatography (10% EtOAc in hexanes) to provide the title compound (1.60 g, 61%). MS (ESI): mass calcd. for $C_{23}H_{30}F_3N_3O_2Si$, 465.2; m/z found, 466.2 [M+H]$^+$. $^1$H NMR (500 MHz, CDCl$_3$) δ 8.04 (d, J=7.2 Hz, 1H), 7.45 (d, J=7.2 Hz, 1H), 7.36-7.31 (m, 1H), 7.18 (dd, J=7.7, 2.0 Hz, 1H), 7.09 (d, J=7.8 Hz, 1H), 6.13 (d, J=3.2 Hz, 1H), 4.61 (s, 2H), 2.65-2.61 (m, 4H), 2.18 (s, 3H), 0.82 (s, 9H), 0.01 (d, J=8.5 Hz, 6H).

Step B: Methyl 3-(3-(((tert-butyldimethylsilyl)oxy)methyl)-4-methylphenyl)-2,2-dimethyl-3-(8-methyl-3-(trifluoromethyl)-[1,2,4]triazolo[4,3-a]pyridin-7-yl)propanoate. 2,2,2-Trichloroacetonitrile (1.29 g, 8.94 mmol) and DBU (80.0 mg, 0.525 mmol) were added to (3-(((tert-butyldimethylsilyl)oxy)methyl)-4-methylphenyl)(8-methyl-3-(trifluoromethyl)-[1,2,4]triazolo[4,3-a]pyridin-7-yl)methanol (1.60 g, 3.44 mmol) in acetonitrile (5 mL) at room temperature and the mixture was stirred for 45 minutes. ((1-Methoxy-2-methylprop-1-en-1-yl)oxy)trimethylsilane (1.38 g, 7.90 mmol) and bis(trifluoromethanesulfonyl)imide (96.6 mg, 0.344 mmol) were then added sequentially, and the mixture was stirred at room temperature for 16 hours. Another portion of ((1-methoxy-2-methylprop-1-en-1-yl)oxy)trimethyl silane (1.38 g, 7.90 mmol) and bis(trifluoromethanesulfonyl)imide (96.6 mg, 0.344 mmol) were then added sequentially, and the mixture was stirred at 50° C. for 16 hours. The reaction was quenched with aqueous saturated NaHCO$_3$ solution (20 mL), and extracted with EtOAc (50 mL×3). These extractions resulted in several organic solvent fractions which were combined and concentrated to dryness under reduced pressure. The residue was purified by flash column chromatography (10% EtOAc/hexanes) to provide the title compound (1.20 g, 64%). MS (ESI): mass calcd. for $C_{28}H_{38}F_3N_3O_3Si$, 549.3; m/z found, 550.3 [M+H]$^+$. $^1$H NMR (500 MHz, CDCl$_3$) δ 7.96 (d, J=7.3 Hz, 1H), 7.27-7.14 (m, 2H), 7.01 (d, J=1.3 Hz, 2H), 4.79 (s, 1H), 4.60 (s, 2H), 3.55 (s, 3H), 2.73 (d, J=0.8 Hz, 3H), 2.16 (s, 3H), 1.36 (d, J=32.8 Hz, 6H), 0.83 (s, 9H), 0.00 (d, J=3.6 Hz, 6H).

Step C: Methyl 3-(3-(chloromethyl)-4-methylphenyl)-2,2-dimethyl-3-(8-methyl-3-(trifluoromethyl)-[1,2,4]triazolo[4,3-a]pyridin-7-yl)propanoate. Methyl 3-(3-(((tert-butyldimethylsilyl)oxy)methyl)-4-methylphenyl)-2,2-dimethyl-3-(8-methyl-3-(trifluoromethyl)-[1,2,4]triazolo[4,3-a]pyridin-7-yl)propanoate (550 mg, 1.00 mmol) was dissolved in DCM (10 mL), and SOCl$_2$ (0.31 mL, 4.33 mmol) was added. The mixture was stirred at room temperature for 2 hours. The mixture was concentrated and purified by flash column chromatography (10% EtOAc/hexanes) to provide the title compound (400 mg, 88%). MS (ESI): mass calcd. for $C_{22}H_{23}ClF_3N_3O_2$, 453.1; m/z found, 453.3 [M+H]$^+$. $^1$H NMR (500 MHz, CDCl$_3$) δ 7.95 (d, J=7.3 Hz, 1H), 7.20-7.02 (m, 4H), 4.79 (s, 1H), 4.62-4.47 (m, 2H), 3.55 (s, 3H), 2.79 (s, 3H), 2.39 (s, 3H), 1.43 (s, 3H), 1.35 (s, 3H).

Step D: 2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid. DMF (0.5 mL) was added to a mixture of 8'-methyl-2,2',3,3',5,6-hexahydrospiro[pyran-4,4'-pyrido[2,3-b][1,4,5]oxathiazepine] 1',1'-dioxide (Intermediate 37, 200 mg, 0.703 mmol) and KO$^t$Bu (118 mg, 1.05 mmol). After 10 minutes, a solution of methyl 3-(3-(chloromethyl)-4-methylphenyl)-3-(1-ethyl-4-methyl-1H-benzo[d][1,2,3]triazol-5-yl)-2,2-dimethylpropanoate (319 mg, 0.703 mmol) in DMF (0.5 mL) was added and the mixture was stirred at room temperature for 1 hour. Water (20 mL) was added and the aqueous layer was extracted with EtOAc (15 mL×3). These extractions resulted in several organic solvent fractions which were combined and concentrated under reduced pressure. LiOH$_{(aq)}$ (3 M, 1 mL) was added to the residue which had been dissolved in THF (1 mL) and MeOH (1 mL) and the mixture was heated at 50° C. for 24 hours. Water (5 mL) was then added, and the pH of the mixture was adjusted to pH ~3-4 by adding a solution of 1 M aqueous HCl. The aqueous layer was extracted with EtOAc (15 mL×3). These extractions resulted in several organic solvent fractions which were combined and concentrated. The residue was purified by flash column chromatography (10% methanol/CH$_2$Cl$_2$) to provide the title compound (150 mg, 31%). MS (ESI): mass calcd. for $C_{33}H_{36}F_3N_5O_6S$, 687.2; m/z found, 688.3 [M+H]$^+$. $^1$H NMR (600 MHz, CD$_3$OD) δ 8.18 (m, 2H), 7.93 (d, J=2.3 Hz, 1H), 7.40 (d, J=7.3 Hz, 1H), 7.24 (d, J=7.9 Hz, 1H), 7.06 (d, J=7.4 Hz, 1H), 6.96 (s, 1H), 4.83 (s, 1H), 4.50-4.22 (m, 2H), 3.77-3.64 (m, 2H), 3.33-3.24 (m, 2H), 3.20-3.02 (m, 2H), 2.55 (s, 3H), 2.28 (s, 3H), 2.15 (s, 3H), 1.44-1.33 (m, 2H), 1.26 (s, 3H), 1.16 (s, 3H), 1.12-1.02 (m, 2H).

Example 18: (*S)-2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

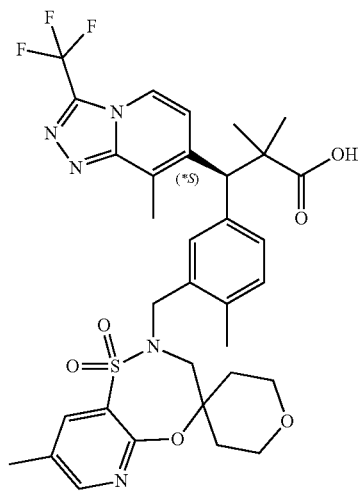 [SMILES: Cc1cnc2c(c1)S(=O)(=O)N(Cc1cc([C@@H](c3ccn4c(C(F)(F)F)nnc4c3C)C(C)(C)C(=O)O)ccc1C)CC1(CCOCC1)O2]

The mixture of 2,2-dimethyl-3-(4-methyl-3-((8'-methyl-1',1'-dioxido-2,3,5,6-tetrahydrospiro[pyran-4,4'-pyrido[2,3- b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid enantiomers (Example 17, 150 mg) was separated by chiral SFC (stationary phase: Chiralcel OZ-H 2×25 cm, mobile phase: 60% $CO_2$, 40% MeOH) to afford two enantiomers. The first eluting enantiomer (68 mg) was designated (*S). MS (ESI): mass calcd. for $C_{33}H_{36}F_3N_5O_6S$, 687.2; m/z found, 688.3 $[M+H]^+$.

Example 19: (*R)-2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

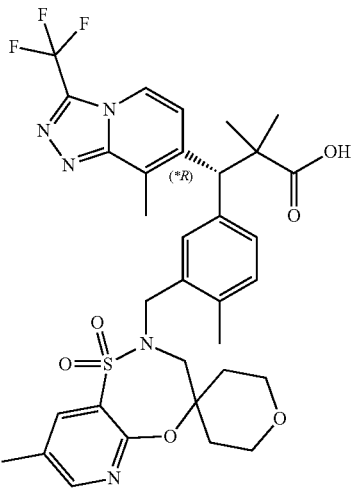 [SMILES: Cc1cnc2c(c1)S(=O)(=O)N(Cc1cc([C@H](c3ccn4c(C(F)(F)F)nnc4c3C)C(C)(C)C(=O)O)ccc1C)CC1(CCOCC1)O2]

The second eluting enantiomer (53 mg) from the separation of isomers by chiral SFC described in Example 18 was designated (*R). MS (ESI): mass calcd. for $C_{33}H_{36}F_3N_5O_6S$, 687.2; m/z found, 688.3 $[M+H]^+$.

Example 20: 3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic Acid and its Trifluoroacetic Acid Salt

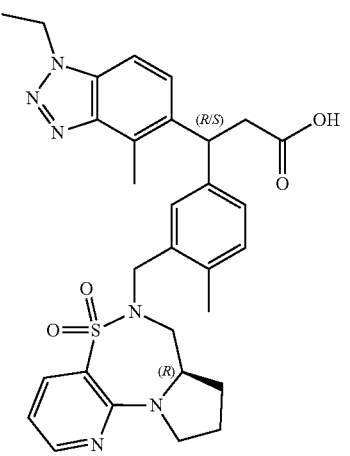

DMF (1.4 mL) was added to a mixture of (R)-6,7,7a,8,9,10-hexahydropyrido[2,3-f]pyrrolo[2,1-d][1,2,5]thiadiazepine 5,5-dioxide (Intermediate 4, 67 mg, 0.28 mmol) and sodium hydride (60% dispersion in mineral oil, 24 mg, 0.60 mmol) under nitrogen at 0° C. After 10 minutes, a solution of ethyl 3-(3-(chloromethyl)-4-methylphenyl)-3-(1-ethyl-4-methyl-1H-benzo[d][1,2,3]triazol-5-yl)propanoate (Intermediate 31, 0.7 ml, 0.4 M in DMF, 0.3 mmol) was added and the mixture was allowed to warm to room temperature for 2.5 hours. 1 M Aqueous sodium hydroxide solution (0.84 mL) was added and the reaction was stirred at room temperature overnight. An additional portion of 1 M aqueous sodium hydroxide (0.56 mL) was added and the reaction was stirred again overnight at room temperature. The mixture was filtered and the filtrate was purified by preparative acidic HPLC (XBridge C18, acetonitrile-water containing 0.05% TFA). The pure fractions resulting from the preparative acidic HPLC were collected and lyophilized to dryness to provide the title compound (108.2 mg, 67%) as its trifluoroacetic acid salt. MS (ESI): mass calcd. for $C_{30}H_{34}N_6O_4S$, 574.2; m/z found, 575.4 $[M+H]^+$.

Example 21: (*S)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic Acid

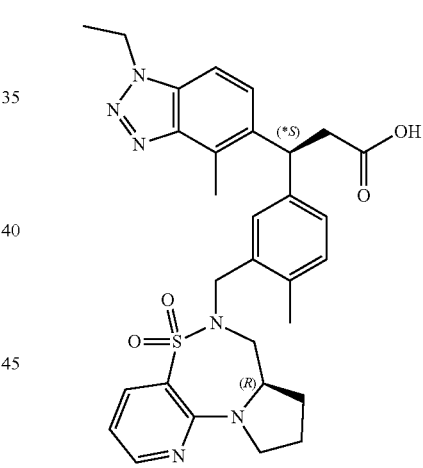

The mixture of 3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid isomers (Example 20, 108.2 mg) was separated by chiral SFC (stationary phase: Chiralcel OJ-H 5 m, 250×20 mm, mobile phase: 80% $CO_2$, 20% MeOH) to afford two diastereomers. The first eluting isomer (44 mg) was designated (*S). MS: mass calcd. for $C_{30}H_{34}N_6O_4S$, 574.2; m/z found, 575.0. $^1$H NMR (400 MHz, $CDCl_3$) δ 8.25-8.16 (m, 2H), 7.30-7.24 (m, 2H), 7.04-6.98 (m, 2H), 6.98-6.92 (m, 1H), 6.87-6.80 (m, 1H), 4.82-4.69 (m, 2H), 4.64-4.44 (m, 2H), 4.38-4.29 (m, 1H), 4.23-4.12 (m, 1H), 3.65-3.50 (m, 2H), 3.33-3.24 (m, 1H), 3.10-2.89 (m, 2H), 2.89-2.75 (m, 1H), 2.68 (s, 3H), 2.19 (s, 3H), 2.00-1.88 (m, 1H), 1.85-1.73 (m, 1H), 1.62-1.43 (m, 3H), 1.30-1.22 (m, 1H), 1.22-1.13 (m, 1H).

Example 22: (*R)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic Acid

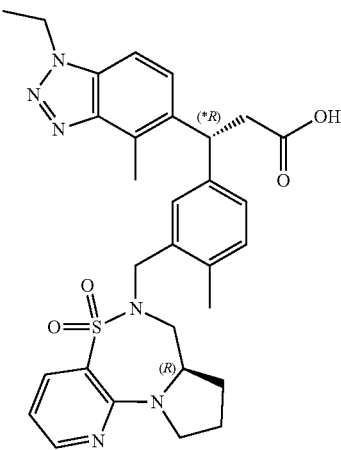

The second eluting isomer (41 mg) from the separation of isomers by chiral SFC described in Example 21 was designated (*R). MS: mass calcd. for $C_{30}H_{34}N_6O_4S$, 574.2; m/z found, 575.0. $^1$H NMR (500 MHz, CDCl$_3$) δ 8.29 (dd, J=4.8, 1.9 Hz, 1H), 8.07 (dd, J=7.7, 1.8 Hz, 1H), 7.35-7.30 (m, 2H), 7.11-7.06 (m, 3H), 6.80 (dd, J=7.7, 4.8 Hz, 1H), 4.95 (t, J=7.9 Hz, 1H), 4.64 (q, J=7.3 Hz, 2H), 4.61-4.53 (m, 1H), 4.39 (d, J=14.3 Hz, 1H), 4.13 (d, J=14.2 Hz, 1H), 3.66-3.59 (m, 1H), 3.56-3.49 (m, 1H), 3.32-3.24 (m, 1H), 3.18-3.04 (m, 3H), 2.82 (s, 3H), 2.26 (s, 3H), 2.00-1.92 (m, 1H), 1.83-1.75 (m, 1H), 1.65-1.58 (m, 4H), 1.47-1.40 (m, 1H).

Example 23: 3-(1-Cyclopropyl-4-methyl-1H-benzo[d][1,2,3]triazol-5-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic Acid

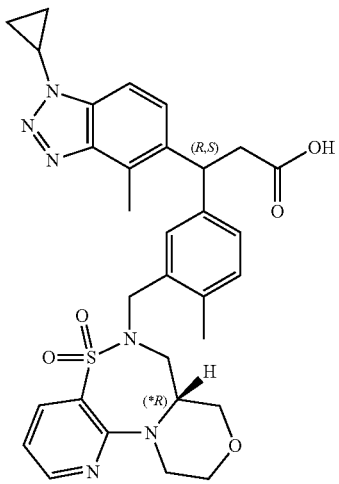

DMF (0.75 mL) was added to a mixture of (*R)-6,7,7a,8,10,11-hexahydro-[1,4]oxazino[3,4-d]pyrido[2,3-f][1,2,5]thiadiazepine 5,5-dioxide (Intermediate 12, 75 mg, 0.29 mmol) and sodium hydride (60% dispersion in mineral oil, 38 mg, 0.95 mmol) under nitrogen at 0° C. After 10 minutes, a solution of ethyl 3-(3-(chloromethyl)-4-methylphenyl)-3-(1-cyclopropyl-4-methyl-1H-benzo[d][1,2,3]triazol-5-yl)propanoate (Intermediate 32, 0.75 ml, 0.4 M in DMF, 0.29 mmol) was added and the mixture was allowed to warm to room temperature overnight. The mixture was filtered and the filtrate was purified by preparative acidic HPLC (XBridge C$_{18}$, acetonitrile-water containing 0.05% TFA). The pure fractions resulting from the preparative acidic HPLC were collected and lyophilized to dryness to provide the title compound. (104.7 mg, 59%). MS (ESI): mass calcd. for $C_{31}H_{34}N_6O_5S$, 602.2; m/z found, 603.3 [M+H]$^+$. $^1$H NMR (500 MHz, CDCl$_3$) δ 8.37-8.30 (m, 1H), 8.21-8.16 (m, 1H), 7.54-7.49 (m, 0.5H), 7.49-7.44 (m, 0.5H), 7.44-7.40 (m, 0.5H), 7.40-7.34 (m, 0.5H), 7.31-7.28 (m, 0.5H), 7.21-7.17 (m, 0.5H), 7.09-7.02 (m, 1.5H), 7.00-6.93 (m, 1H), 6.87-6.83 (m, 0.5H), 4.96-4.86 (m, 1H), 4.72-4.63 (m, 0.5H), 4.58-4.49 (m, 1.5H), 4.47-4.40 (m, 0.5H), 4.34-4.16 (m, 2H), 3.88-3.82 (m, 0.5H), 3.81-3.63 (m, 5H), 3.30-3.18 (m, 1.5H), 3.18-3.04 (m, 1H), 3.04-2.91 (m, 1.5H), 2.80 (s, 1.5H), 2.69 (s, 1.5H), 2.20 (s, 1.5H), 2.12 (s, 1.5H), 1.40-1.24 (m, 4H).

Example 24: (*S)-3-(1-Cyclopropyl-4-methyl-1H-benzo[d][1,2,3]triazol-5-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic Acid

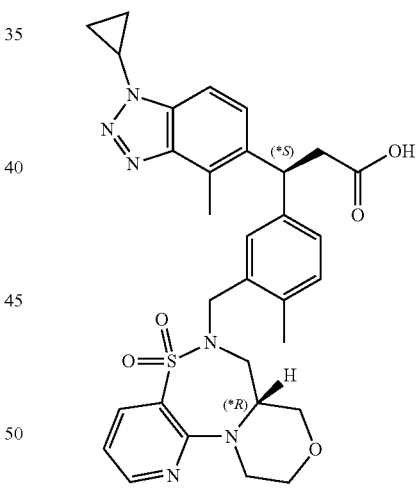

The mixture of 3-(1-cyclopropyl-4-methyl-1H-benzo[d][1,2,3]triazol-5-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid isomers (Example 23, 104.7 mg) was separated by chiral SFC (stationary phase: Chiralpak AD-H 2×25 cm, mobile phase: 60% CO$_2$, 40% MeOH) to afford two diastereomers. The first eluting isomer (34 mg) was designated (*S). MS: mass calcd. for $C_{31}H_{34}N_6O_5S$, 602.2; m/z found, 603.2 [M+H]$^+$. $^1$H NMR (500 MHz, CDCl$_3$) δ 8.30-8.26 (m, 1H), 8.11-8.06 (m, 1H), 7.46-7.42 (m, 1H), 7.40-7.36 (m, 1H), 7.22 (s, 1H), 7.08-7.02 (m, 2H), 6.89-6.84 (m, 1H), 4.95-4.89 (m, 1H), 4.59-4.49 (m, 2H), 4.38-4.31 (m, 1H), 4.28 (d, J=13.8 Hz, 1H), 3.93-3.85 (m, 1H), 3.76-3.59 (m, 5H), 3.26-3.20 (m, 1H), 3.20-3.11 (m, 1H), 3.01-2.88 (m, 2H), 2.82 (s, 3H), 2.08 (s, 3H), 1.35-1.29 (m, 2H), 1.29-1.23 (m, 2H).

Example 25: (*R)-3-(1-Cyclopropyl-4-methyl-1H-benzo[d][1,2,3]triazol-5-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic Acid

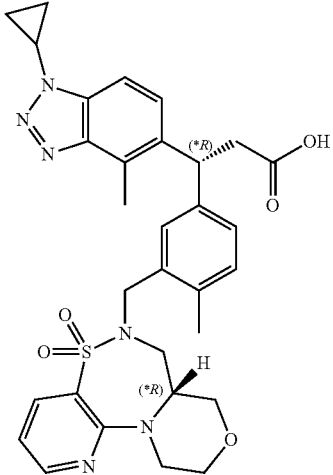 [SMILES: Cc1ccc([C@@H](CC(=O)O)c2ccc3c(nnn3C3CC3)c2C)cc1CN1C[C@@H]2COCCN2c2ncccc2S1(=O)=O]

The second eluting isomer (36 mg) from the separation of isomers by chiral SFC described in Example 24 was designated (*R). MS: mass calcd. for $C_{31}H_{34}N_6O_5S$, 602.2; m/z found, 603.2 [M+H]$^+$. $^1$H NMR (500 MHz, CDCl$_3$) δ 8.35-8.29 (m, 1H), 8.13-8.07 (m, 1H), 7.57-7.49 (m, 1H), 7.46-7.40 (m, 1H), 7.36-7.32 (m, 1H), 7.07-7.00 (m, 1H), 6.95-6.87 (m, 1H), 6.83-6.76 (m, 1H), 4.91 (dd, J=11.9, 3.8 Hz, 1H), 4.75-4.69 (m, 1H), 4.66-4.54 (m, 2H), 4.39-4.34 (m, 1H), 4.18 (d, J=13.1 Hz, 1H), 3.83-3.70 (m, 5H), 3.35-3.27 (m, 1H), 3.20 (dd, J=13.5, 4.1 Hz, 1H), 3.11-3.04 (m, 1H), 3.01-2.93 (m, 1H), 2.69 (s, 3H), 2.20 (s, 3H), 1.39-1.24 (m, 4H).

Example 26: (*S)-3-(3-((1,1-Dioxidospiro[benzo[b][1,4,5]oxathiazepine-4,3'-oxetan]-2(3H)-yl)methyl)-4-methylphenyl)-3-(8-methyl-3-(trifluoromethyl)-[1,2,4]triazolo[4,3-a]pyridin-7-yl)propanoic Acid

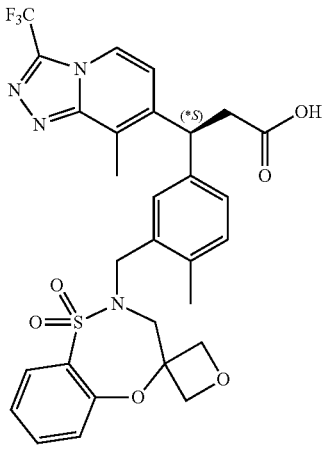 [SMILES: Cc1ccc([C@H](CC(=O)O)c2ccn3c(C(F)(F)F)nnc3c2C)cc1CN1CC2(COC2)Oc2ccccc2S1(=O)=O]

Step A: Ethyl (*S)-3-(3-((1,1-dioxidospiro[benzo[b][1,4,5]oxathiazepine-4,3'-oxetan]-2(3H)-yl)methyl)-4-methylphenyl)-3-(8-methyl-3-(trifluoromethyl)-[1,2,4]triazolo[4,3-a]pyridin-7-yl)propanoate. A solution of ethyl (*S)-3-(3-(hydroxymethyl)-4-methylphenyl)-3-(8-methyl-3-(trifluoromethyl)-[1,2,4]triazolo[4,3-a]pyridin-7-yl)propanoate (Intermediate 26, 122 mg, 0.289 mmol), 2,3-dihydrospiro[benzo[b][1,4,5]oxathiazepine-4,3'-oxetane] 1,1-dioxide (Intermediate 7, 87 mg, 0.36 mmol), and triphenylphosphine (116 mg, 0.444 mmol) in THF (4.5 mL) was stirred at room temperature for 1 minute. DBAD (107 mg, 0.465 mmol) was added and the solution was stirred at room temperature for 20 minutes. The reaction was then concentrated under a stream of nitrogen and purified by flash column chromatography (0 to 20% ethyl acetate/DCM, gradient elution) to afford the title compound (550 mg) which was contaminated with triphenylphosphine oxide byproduct and remaining solvent. MS (ESI): mass calcd. for $C_{31}H_{31}F_3N_4O_6S$, 644.2; m/z found, 645.3 [M+H]$^+$.

Step B: ((*S)-3-(3-((1,1-Dioxidospiro[benzo[b][1,4,5]oxathiazepine-4,3'-oxetan]-2(3H)-yl)methyl)-4-methylphenyl)-3-(8-methyl-3-(trifluoromethyl)-[1,2,4]triazolo[4,3-a]pyridin-7-yl)propanoic acid. Aqueous sodium hydroxide (1 M, 2.5 mL, 2.5 mmol) was added to a solution of ethyl (*S)-3-(3-((1,1-dioxidospiro[benzo[b][1,4,5]oxathiazepine-4,3'-oxetan]-2(3H)-yl)methyl)-4-methylphenyl)-3-(8-methyl-3-(trifluoromethyl)-[1,2,4]triazolo[4,3-a]pyridin-7-yl)propanoate (540 mg, 0.84 mmol) in THF (4 mL) and ethanol (1 mL). The reaction was stirred at room temperature for 4 hours, then concentrated under reduced pressure to remove THF. A small amount of DMF was added to form a solution, and the reaction was purified by preparative basic HPLC (XBridge C$_{18}$, acetonitrile-water, 20 mM NH$_4$OH). The pure fractions resulting from the preparative basic HPLC were collected and lyophilized to dryness to provide the title compound (88.2 mg, 17%). MS (ESI): mass calcd. for $C_{29}H_{27}F_3N_4O_6S$, 616.2; m/z found, 617.2 [M+H]$^+$. $^1$H NMR (500 MHz, CDCl$_3$) δ 8.04 (d, J=7.2 Hz, 1H), 7.87 (dd, J=7.8, 1.7 Hz, 1H), 7.60-7.55 (m, 1H), 7.37 (dd, J=8.1, 1.2 Hz, 1H), 7.34-7.29 (m, 1H), 7.25-7.22 (m, 1H), 7.12 (d, J=7.8 Hz, 1H), 6.98-6.93 (m, 2H), 4.91-4.84 (m, 1H), 4.71-4.63 (m, 2H), 4.52-4.45 (m, 1H), 4.32-4.22 (m, 3H), 3.87-3.80 (m, 1H), 3.76-3.70 (m, 1H), 3.08-3.01 (m, 1H), 2.96-2.88 (m, 1H), 2.73 (s, 3H), 2.26 (s, 3H).

Example 27: (*S)-3-(4-Methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

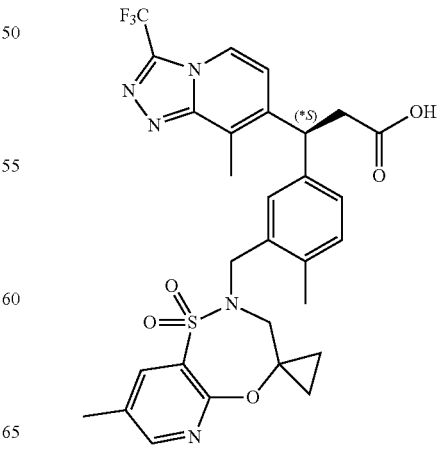

Step A: Ethyl (*S)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate. The title compound (254 mg, 85%) was prepared using analogous conditions as described in Example 26, Step A where 8'-methyl-2',3'-dihydrospiro[cyclopropane-1,4'-pyrido[2,3-b][1,4,5]oxathiazepine] 1',1'-dioxide (Intermediate 8) was used instead of 2,3-dihydrospiro[benzo[b][1,4,5]oxathiazepine-4,3'-oxetane] 1,1-dioxide (Intermediate 7) and (0 to 80% ethyl acetate/hexanes, gradient elution) was used for flash column chromatography instead of (0 to 20% ethyl acetate/DCM, gradient elution). MS (ESI): mass calcd. for $C_{31}H_{32}F_3N_5O_5S$, 643.2; m/z found, 644.2 [M+H]$^+$.

Step B: (*S)-3-(4-Methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid. Aqueous sodium hydroxide (1 M, 1.2 mL, 1.2 mmol) was added to a solution of ethyl (*S)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate (254 mg, 0.395 mmol) in THF (2 mL) and ethanol (0.2 mL). The reaction was stirred at 50° C. for 1 hour, then concentrated under a stream of nitrogen to remove THF. 1 M Aqueous HCl solution was added until the pH was 4. DCM was added and the resulting biphasic mixture was separated. The aqueous layer was extracted with DCM. These extractions resulted in several organic solvent fractions which were combined, dried over MgSO$_4$, filtered, and concentrated to dryness under reduced pressure. The product was purified by preparative basic HPLC (XBridge $C_{18}$, acetonitrile-water, 20 mM NH$_4$OH). The pure fractions resulting from the preparative basic HPLC were collected and lyophilized to dryness to provide the title compound (125 mg, 51%). MS (ESI): mass calcd. for $C_{29}H_{28}F_3N_5O_5S$, 615.2; m/z found, 616.2 [M+H]$^+$. $^1$H NMR (500 MHz, DMSO-d$_6$) δ 8.38 (d, J=7.1 Hz, 1H), 8.34-8.32 (m, 1H), 8.10-8.07 (m, 1H), 7.24-7.20 (m, 1H), 7.16-7.09 (m, 3H), 4.80 (t, J=7.8 Hz, 1H), 4.26-4.12 (m, 2H), 3.64-3.49 (m, 1H), 3.10-2.96 (m, 2H), 2.70 (s, 3H), 2.37 (s, 3H), 2.22 (s, 3H), 0.97-0.85 (m, 2H), 0.64-0.52 (m, 2H).

Example 28: 3-(3-((3-Cyano-5,5-dioxido-7,7a, 8,9, 10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic Acid

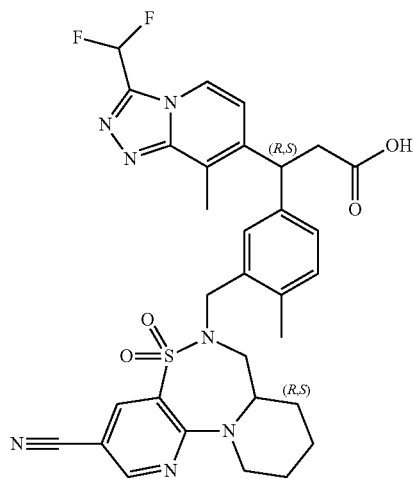 [SMILES: Cc1ccc(C(CC(=O)O)c2ccn3c(C(F)F)nnc3c2C)cc1CN1CC2CCCCN2c2ncc(C#N)cc2S1(=O)=O]

Step A: 7-Bromo-3-(difluoromethyl)-8-methyl-[1,2,4]triazolo[4,3-a]pyridine. 2,2-Difluoroacetic anhydride (34.50 g, 197.9 mmol) was added slowly to 4-bromo-2-hydrazinyl-3-methylpyridine (Intermediate 23, 2.00 g, 9.99 mmol). The reaction initially started to reflux and the solids turned yellow, but within 5 minutes the reaction was homogeneous. The reaction mixture was warmed to 50° C. After 18 hours, the reaction mixture was concentrated under reduced pressure. Ethyl acetate (100 mL) was added, followed by aqueous saturated NaHCO$_3$ solution until pH was about 7-8. The layers were separated and the aqueous layer was extracted with ethyl acetate. These extractions resulted in several organic solvent fractions which were combined and washed sequentially with water and brine solution, dried over MgSO$_4$, filtered, and concentrated under reduced pressure. The residue was purified by flash column chromatography (0 to 100% ethyl acetate/hexanes, gradient elution) to afford the title compound (2.5 g, 96%) as a white solid. MS (ESI): mass calcd. for $C_8H_6BrF_2N_3$, 261.0; m/z found, 262.0 [M+H]$^+$. $^1$H NMR (400 MHz, CDCl$_3$) δ 8.11 (d, J=7.2 Hz, 1H), 7.18-7.09 (m, 2H), 2.76 (d, J=0.8 Hz, 3H).

Step B: Ethyl (E)-3-(3-(difluoromethyl)-8-methyl-[1,2,4]triazolo[4,3-a]pyridin-7-yl)acrylate. A mixture containing 7-bromo-3-(difluoromethyl)-8-methyl-[1,2,4]triazolo[4,3-a]pyridine (2.50 g, 9.54 mmol), ethyl (E)-3-(4,4,5,5-tetramethyl-1,3,2-dioxaborolan-2-yl)acrylate (2.66 g, 11.77 mmol), potassium carbonate (2.64 g, 19.1 mmol), dichloro[1,1'-bis(diphenylphosphino)ferrocene]palladium(II), complex with dichloromethane (1:1) (705 mg, 0.96 mml) in 1,4-dioxane (33 mL) and water (10 mL) was sparged with N$_2$ for 15 minutes. The mixture was then heated to 90° C. After one hour, the reaction was allowed to cool to room temperature and filtered through diatomaceous earth such as Celite® and washed with ethyl acetate (100 mL). Water was added to the filtrate and the layers were separated. The aqueous layer was extracted with ethyl acetate. These extractions resulted in several organic solvent fractions which were combined and washed sequentially with water and brine solution, dried over Na$_2$SO$_4$, filtered, and concentrated under reduced pressure. The residue was purified by flash column chromatography (0 to 100% ethyl acetate/hexanes, gradient elution) to provide the title compound (1.58 g, 59%) as a reddish brown solid. MS (ESI): mass calcd. for $C_{13}H_6F_2N_3O_2$, 281.3; m/z found, 282.1 [M+H]$^+$. $^1$H NMR (400 MHz, CDCl$_3$) δ 8.22 (d, J=7.3 Hz, 1H), 8.00 (d, J=15.9 Hz, 1H), 7.48-7.07 (m, 2H), 6.51 (d, J=15.9 Hz, 1H), 4.32 (q, J=7.1 Hz, 2H), 2.84 (s, 3H), 1.37 (t, J=7.1 Hz, 3H).

Step C: Ethyl 3-(3-(difluoromethyl)-8-methyl-[1,2,4]triazolo[4,3-a]pyridin-7-yl)-3-(3-(hydroxymethyl)-4-methylphenyl)propanoate. TEA (1.18 mL, 8.50 mmol) and [Rh(COD)C$_1$]$_2$ (143 mg, 0.29 mmol) were added sequentially to a slurry of ethyl (E)-3-(3-(difluoromethyl)-8-methyl-[1,2,4]triazolo[4,3-a]pyridin-7-yl)acrylate (1.58 g, 5.62 mmol) and (3-(hydroxymethyl)-4-methylphenyl)boronic acid (1.41 g, 8.50 mmol) in 1,4-dioxane (30 mL) and water (15 mL). The reaction mixture was heated to 95° C. After 45 minutes, the reaction was allowed to cool to room temperature and a mixture of ethyl acetate/water was added and the biphasic mixture was separated. The aqueous layer was extracted with ethyl acetate. These extractions resulted in several organic solvent fractions which were combined, washed sequentially with water and brine solution, dried over Na$_2$SO$_4$, filtered and concentrated under reduced pressure. The residue was purified by flash column chromatography (eluent: 0 to 100% ethyl acetate/hexanes, gradient elution) to afford the title compound (1.80 g, 79%) as a yellow foam. MS (ESI): mass calcd. for $C_{21}H_{23}F_2N_3O_3$, 403.4; m/z found, 404.2 $[M+H]^+$.

Step D: Ethyl 3-(3-((3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoate. Diisopropyl azodicarboxylate (0.72 mL, 3.67 mmol) was added to a mixture of ethyl 3-(3-(difluoromethyl)-8-methyl-[1,2,4]triazolo[4,3-a]pyridin-7-yl)-3-(3-(hydroxymethyl)-4-methylphenyl)propanoate (900 mg, 2.23 mmol), 7,7a,8,9,10,11-hexahydro-6H-dipyrido[2,1-d:2',3'-f][1,2,5]thiadiazepine-3-carbonitrile 5,5-dioxide (Intermediate 9, 882 mg, 3.17 mmol) and triphenylphosphine (868 mg, 3.31 mmol) in THF (25 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organics were dried over $Na_2SO_4$, filtered and concentrated under reduced pressure. The residue was purified by flash column chromatography (0 to 100% ethyl acetate/hexanes, gradient elution) to provide the title compound (1.40 g, 95%) as a white foam. MS (ESI): mass calcd. for $C_{33}H_{35}F_2N_7O_4S$, 663.7; m/z found, 664.2 $[M+H]^+$. $^1H$ NMR (400 MHz, $CDCl_3$) δ 8.46 (d, J=2.1 Hz, 1H), 8.27-8.14 (m, 2H), 7.24-7.09 (m, 2H), 7.14-7.06 (m, 1H), 6.86 (dd, J=9.9, 7.2 Hz, 1H), 4.95 (ddd, J=8.6, 7.1, 4.0 Hz, 1H), 4.70-4.60 (m, 1H), 4.50 (dd, J=14.6, 11.8 Hz, 1H), 4.34 (ddt, J=13.9, 9.7, 4.9 Hz, 1H), 4.22-4.02 (m, 4H), 3.38-3.07 (m, 4H), 3.02 (ddd, J=15.7, 8.7, 5.5 Hz, 1H), 2.83 (d, J=7.6 Hz, 3H), 2.24 (d, J=10.5 Hz, 3H), 1.74-1.68 (m, 1H), 1.64-1.43 (m, 1H), 1.47-1.31 (m, 1H), 1.26 (t, J=7.1 Hz, 3H), 1.18 (td, J=7.2, 2.0 Hz, 3H).

Step E: 3-(3-((3-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid. A mixture containing ethyl 3-(3-((3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoate (1.40 g, 2.10 mmol), 1 M aqueous NaOH solution (10.0 mL, 10.0 mmol), and THF (10 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered, and concentrated to dryness under reduced pressure. The residue was purified by flash column chromatography (0 to 10% MeOH/DCM, gradient elution) to provide the title compound (1.27 g, 95%) as a white foam. MS (ESI): mass calcd. for $C_{31}H_{31}F_2N_7O_4S$, 635.6; m/z found, 636.2 $[M+H]^+$. $^1H$ NMR (500 MHz, $CDCl_3$) δ 8.46 (dd, J=2.2, 1.2 Hz, 1H), 8.23 (dd, J=2.2, 0.9 Hz, 1H), 8.21-8.09 (m, 1H), 7.14 (ddt, J=15.9, 7.2, 4.2 Hz, 3H), 6.90 (dd, J=11.4, 7.3 Hz, 1H), 4.99-4.90 (m, 1H), 4.65 (s, 1H), 4.57 (s, 3H), 4.48 (t, J=14.5 Hz, 1H), 4.33 (tt, J=13.3, 5.0 Hz, 1H), 4.16 (dd, J=24.2, 14.8 Hz, 1H), 3.37 (dd, J=13.3, 3.5 Hz, 1H), 3.31-3.19 (m, 1H), 3.19 (dt, J=6.1, 4.4 Hz, 1H), 3.20-3.12 (m, 1H), 3.07 (dt, J=16.0, 8.9 Hz, 1H), 2.76 (d, J=7.5 Hz, 3H), 2.23 (d, J=12.8 Hz, 3H), 1.77-1.61 (m, 3H), 1.55-1.41 (m, 1H), 1.36 (m, 1H).

Example 29: (*R)-3-(3-(((*S)-3-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic Acid

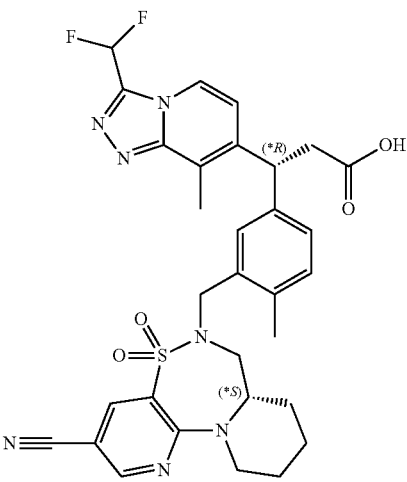 [SMILES: Cc1ccc([C@@H](CC(=O)O)c2ccn3c(C(F)F)nnc3c2C)cc1CN1C[C@@H]2CCCCN2c2ncc(C#N)cc2S1(=O)=O]

The mixture of 4 diastereoisomers of 3-(3-((3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid (Example 28, 1.27 g) were separated using two chiral separation methods. The mixture of 4 diastereomers was initially subjected to Chiral Separation Method I: chiral SFC (stationary phase: Chiralpak AD-H m 250×30 mm, Mobile phase: 45% $CO_2$, 55% EtOH) to provide Example 29 and Example 30 and a mixture of the two remaining diastereomers (Example 31 and Example 32). The mixture of Example 31 and Example 32 was subsequently separated using Chiral Separation Method II: chiral SFC (stationary phase: Chiralpak IG 5 μm 250×20 mm, Mobile phase: 60% $CO_2$, 40% EtOH) to afford Example 31 and Example 32. The separation of isomers by Chiral Separation Method, order of elution and designated stereochemistry is tabulated below in Table 2. When the stereochemical configuration is written as, for example (*R, *S), with the first configuration, (*R), corresponds to the configuration at the 3-propanoic carbon and the second configuration, (*S), corresponds to the stereochemistry at the sultam. The characterization for (*R)-3-(3-(((*S)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic acid (Example 29) is as follows: MS (ESI): mass calcd. for $C_{31}H_{31}F_2N_7O_4S$, 635.6; m/z found, 636.2 $[M+H]^+$. $^1H$ NMR (500 MHz, $CDCl_3$) δ 8.47 (d, J=2.2 Hz, 1H), 8.25 (d, J=2.2 Hz, 1H), 8.14 (d, J=7.2 Hz, 1H), 7.18-7.06 (m, 3H), 6.90 (d, J=7.3 Hz, 1H), 4.89 (t, J=7.8 Hz, 1H), 4.46 (d, J=15.0 Hz, 1H), 4.35 (dt, J=13.4, 4.9 Hz, 1H), 4.19 (d, J=15.1 Hz, 1H), 3.40 (dd, J=13.3, 3.5 Hz, 1H), 3.34 (s, 2H), 3.26-3.11 (m, 2H), 3.04 (dd, J=15.6, 6.8 Hz, 1H), 2.94 (dd, J=15.6, 8.9 Hz, 1H), 2.78 (s, 3H), 2.22 (s, 3H), 1.77-1.70 (m, 1H), 1.65 (d, J=6.1 Hz, 1H), 1.56-1.42 (m, 2H), 1.03 (d, J=6.3 Hz, 3H).

TABLE 2

Chiral separation method, Order of elution and Designated stereochemistry for Examples 29-32

| Example # | Chiral Separation method/order of elution | Configuration |
|---|---|---|
| 29 | Method I, first eluting | (*R, *S) |
| 30 | Method I, second eluting | (*R, *R) |
| 31 | Method II, first eluting | (*S, *S) |
| 32 | Method II, second eluting | (*S, *R) |

Example 30: (*R)-3-(3-(((*R)-3-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic Acid

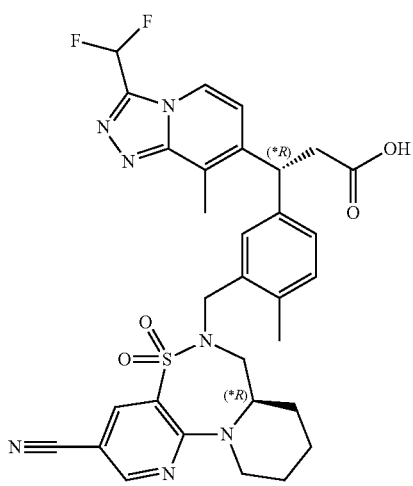 [SMILES: Cc1ccc([C@@H](CC(=O)O)c2ccn3c(C(F)F)nnc3c2C)cc1CN1C[C@H]2CCCCN2c2ncc(C#N)cc2S1(=O)=O]

The title compound (351 mg) was obtained as described in Example 29 and Table 2: MS (ESI): mass calcd. for $C_{31}H_{31}F_2N_7O_4S$, 635.6; m/z found, 636.2 [M+H]$^+$. $^1$H NMR (500 MHz, CDCl$_3$) δ 8.46 (d, J=2.3 Hz, 1H), 8.24 (d, J=2.1 Hz, 1H), 8.15 (d, J=6.6 Hz, 1H), 7.21-7.07 (m, 4H), 6.85 (d, J=7.0 Hz, 1H), 4.94 (s, 1H), 4.62 (dd, J=12.0, 5.2 Hz, 1H), 4.49 (d, J=14.7 Hz, 1H), 4.30 (dt, J=13.7, 5.2 Hz, 1H), 4.20 (d, J=14.7 Hz, 1H), 3.82 (s, 2H), 3.49 (s, 1H), 3.32-3.09 (m, 2H), 3.01 (s, 1H), 2.78 (s, 3H), 2.26 (s, 3H), 1.70 (dt, J=15.3, 5.7 Hz, 1H), 1.64-1.57 (m, 1H), 1.54-1.41 (m, 3H), 1.04 (s, 1H).

Example 31: (*S)-3-(3-(((*S)-3-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic Acid

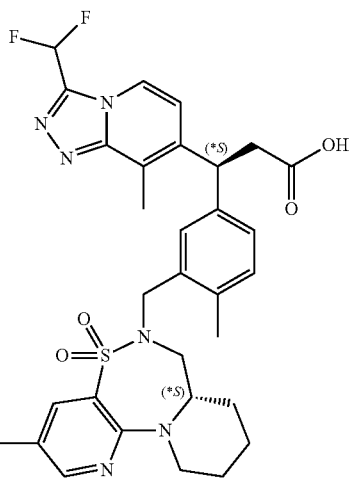

The title compound (199 mg) was obtained as described in Example 29 and Table 2: MS (ESI): mass calcd. for $C_{31}H_{31}F_2N_7O_4S$, 635.6; m/z found, 636.2 [M+H]$^+$. $^1$H NMR (500 MHz, CDCl$_3$) δ 8.47 (d, J=2.1 Hz, 1H), 8.25 (d, J=2.2 Hz, 1H), 8.15 (d, J=7.2 Hz, 1H), 7.13 (ddd, J=23.3, 5.8, 3.6 Hz, 3H), 6.89 (d, J=7.3 Hz, 1H), 4.93 (dd, J=9.0, 6.6 Hz, 1H), 4.71-4.63 (m, 1H), 4.57 (s, 3H), 4.47 (d, J=15.0 Hz, 1H), 4.35 (dt, J=13.5, 4.9 Hz, 1H), 4.19 (d, J=15.0 Hz, 1H), 3.38 (dd, J=13.3, 3.6 Hz, 1H), 3.26-3.11 (m, 2H), 3.04 (dd, J=15.9, 9.1 Hz, 1H), 2.78 (s, 3H), 2.23 (s, 3H), 1.74 (s, 2H), 1.64 (t, J=6.9 Hz, 1H), 1.54 (d, J=6.9 Hz, 1H), 1.52-1.41 (m, 1H), 1.00 (d, J=5.9 Hz, 1H).

Example 32: (*S)-3-(3-(((*R)-3-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(3-(difluoromethyl)-8-methyl-[1,2,4]triazolo[4,3-a]pyridin-7-yl)propanoic Acid

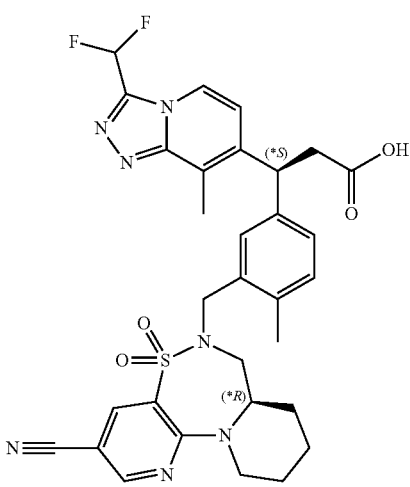 [SMILES: Cc1ccc([C@H](CC(=O)O)c2ccn3c(C(F)F)nnc3c2C)cc1CN1C[C@H]2CCCCN2c2ncc(C#N)cc2S1(=O)=O]

The title compound (260 mg) was obtained as described in Example 29 and Table 2: MS (ESI): mass calcd. for $C_{31}H_{31}F_2N_7O_4S$, 635.6; m/z found, 636.2 $[M+H]^+$. $^1H$ NMR (500 MHz, $CDCl_3$) δ 8.46 (d, J=2.3 Hz, 1H), 8.24 (d, J=2.1 Hz, 1H), 8.15 (d, J=6.6 Hz, 1H), 7.21-7.07 (m, 3H), 6.85 (d, J=7.0 Hz, 1H), 4.94 (s, 1H), 4.62 (dd, J=12.0, 5.2 Hz, 1H), 4.49 (d, J=14.7 Hz, 1H), 4.30 (dt, J=13.7, 5.2 Hz, 1H), 4.20 (d, J=14.7 Hz, 1H), 3.49 (s, 1H), 3.32-3.09 (m, 5H), 3.01 (s, 1H), 2.78 (s, 3H), 2.26 (s, 3H), 1.70 (dt, J=15.3, 5.7 Hz, 1H), 1.64-1.57 (m, 1H), 1.54-1.41 (m, 3H), 1.04 (s, 1H).

Example 33: 3-(6-((3-Cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

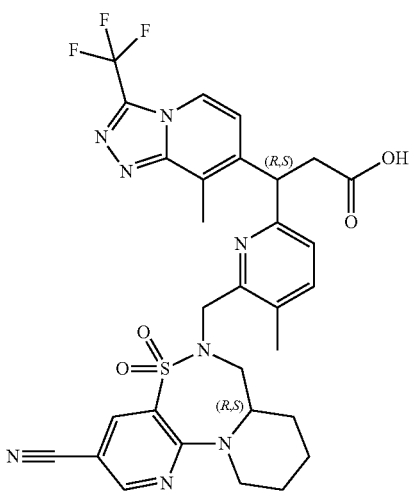 [SMILES: Cc1ccc(C(CC(=O)O)c2ccn3c(C(F)(F)F)nnc3c2C)nc1CN1CC2CCCCN2c2ncc(C#N)cc2S1(=O)=O]

Step A: Ethyl 3-(6-(acetoxymethyl)-5-methylpyridin-2-yl)-3-(8-methyl-3-(trifluoromethyl)-[1,2,4]triazolo[4,3-a]pyridin-7-yl)propanoate. A mixture of 8-methyl-7-(4,4,5,5-tetramethyl-1,3,2-dioxaborolan-2-yl)-3-(trifluoromethyl)-[1,2,4]triazolo[4,3-a]pyridine (Intermediate 30, 500 mg, 1.53 mmol), ethyl (Z)-3-(6-(acetoxymethyl)-5-methylpyridin-2-yl)acrylate (Intermediate 15, 268 mg, 1.02 mmol), potassium carbonate (434 mg, 3.14 mmol), $[Rh(COD)Cl]_2$ (51 mg, 0.10 mmol), THF (6 mL) and propan-2-ol (0.08 mL) was sparged with $N_2$ for 15 minutes. The mixture was then heated to 95° C. After one hour, the reaction was allowed to cool to room temperature, filtered through diatomaceous earth such as Celite®, which was rinsed with ethyl acetate (10 mL). Brine was added to the filtrate and the layers were separated. The aqueous layer was extracted with ethyl acetate. These extractions resulted in several organic solvent fractions which were combined, washed sequentially with water and brine, dried over $Na_2SO_4$, filtered, and concentrated under reduced pressure. The residue was purified by flash column chromatography (0 to 100% EtOAc/hexanes, gradient elution) to afford the title compound (125 mg, 26%) as a reddish brown solid. MS (ESI): mass calcd. for $C_{22}H_{23}F_3N_4O_4$, 464.4; m/z found, 465.2 $[M+H]^+$. $^1H$ NMR (500 MHz, $CD_3OD$) δ 8.31 (d, J=7.2 Hz, 1H), 7.60 (dd, J=7.8, 0.9 Hz, 1H), 7.25 (dd, J=7.6, 3.9 Hz, 2H), 5.31-5.21 (m, 2H), 5.13 (t, J=7.7 Hz, 1H), 4.05 (q, J=7.1 Hz, 2H), 3.42 (dd, J=16.5, 8.0 Hz, 1H), 3.10 (dd, J=16.5, 7.4 Hz, 1H), 2.84 (d, J=0.7 Hz, 3H), 2.33 (s, 3H), 2.13 (s, 3H), 1.14 (t, J=7.1 Hz, 3H).

Step B: Ethyl 3-(6-(hydroxymethyl)-5-methylpyridin-2-yl)-3-(8-methyl-3-(trifluoromethyl)-[1,2,4]triazolo[4,3-a]pyridin-7-yl)propanoate. Potassium carbonate (304 mg, 2.2 mmol) was added to a solution of ethyl 3-(3-(acetoxymethyl)-4-methylphenyl)-3-(3-(trifluoromethyl)-[1,2,4]triazolo[4,3-a]pyridin-7-yl)propanoate (390 mg, 0.868 mmol) in THF (10 mL) and ethanol (7 mL) at room temperature. The reaction mixture was heated to 50° C. After 16 hours, the mixture was partitioned between ethyl acetate and water. The layers were separated and the aqueous layer was extracted with ethyl acetate. These extractions resulted in several organic solvent fractions which were combined, washed sequentially with water and brine, dried over $Na_2SO_4$, filtered, and concentrated under reduced pressure. The residue was purified by flash column chromatography (0 to 100% EtOAc/hexanes, gradient elution) to provide the title compound (700 mg, 96%) as a clear oil. MS (ESI): mass calcd. for $C_{21}H_{22}F_3N_3O_3$, 421.4; m/z found, 422.9 $[M+H]^+$. $^1H$ NMR (500 MHz, $CDCl_3$) δ 7.99 (d, J=7.2 Hz, 1H), 7.35 (dd, J=1.9, 0.9 Hz, 1H), 7.11-6.98 (m, 3H), 4.93 (dd, J=9.3, 6.5 Hz, 1H), 4.64 (d, J=4.9 Hz, 2H), 4.11-3.96 (m, 3H), 3.76 (p, J=5.0 Hz, 1H), 3.13 (dd, J=15.9, 6.5 Hz, 1H), 2.80 (s, 3H), 2.21 (s, 3H), 1.12 (t, J=7.1 Hz, 3H).

Step C: Ethyl 3-(6-((3-cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoate. Diisopropyl azodicarboxylate (264 mg, 1.15 mmol) was added to a mixture of ethyl 3-(6-(hydroxymethyl)-5-methylpyridin-2-yl)-3-(8-methyl-3-(trifluoromethyl)-[1,2,4]triazolo[4,3-a]pyridin-7-yl)propanoate (320 mg, 0.76 mmol), 7,7a,8,9,10,11-hexahydro-6H-dipyrido[2,1-d:2',3'-f][1,2,5]thiadiazepine-3-carbonitrile 5,5-dioxide (Intermediate 9, 253 mg, 0.91 mmol), and triphenylphosphine (299 mg, 1.14 mmol) in THF (25 mL) at room temperature. After 1 hour, ethyl acetate and water were added. The biphasic mixture was separated and the aqueous layer was extracted with ethyl acetate. These extractions resulted in several organic solvent fractions which were combined, washed sequentially with water and brine, dried over $Na_2SO_4$, filtered and concentrated under reduced pressure. The residue was purified by flash column chromatography (0 to 100% EtOAc/hexanes, gradient elution) to provide the title compound (510 mg, 98%) as a white foam. MS (ESI): mass calcd. for $C_{32}H_{33}F_3N_8O_4S$, 682.7; m/z found, 683.2 $[M+H]^+$. $^1H$ NMR (400 MHz, $CDCl_3$) δ 8.43 (t, J=2.3 Hz, 1H), 8.21 (dd, J=8.9, 2.2 Hz, 1H), 8.00 (dd, J=7.2, 5.1 Hz, 1H), 7.43 (dd, J=17.0, 7.9 Hz, 1H), 7.38-7.25 (m, 1H), 7.12 (dd, J=22.9, 7.8 Hz, 1H), 5.03 (q, J=7.4 Hz, 1H), 4.86-4.64 (m, 2H), 4.54-4.39 (m, 1H), 4.26 (dd, J=26.6, 14.9 Hz, 1H), 4.15-3.96 (m, 1H), 3.68 (dd, J=12.8, 3.6 Hz, 1H), 3.62-3.47 (m, 2H), 3.47-3.27 (m, 2H), 3.04 (ddd, J=28.8, 16.4, 7.4 Hz, 1H), 2.88 (d, J=2.8 Hz, 3H), 2.25 (d, J=24.5 Hz, 4H), 1.79 (qt, J=15.2, 5.6 Hz, 3H), 1.62 (dq, J=10.7, 5.4 Hz, 1H), 1.58-1.41 (m, 1H), 1.15 (td, J=7.1, 1.0 Hz, 3H).

Step D: 3-(6-((3-Cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid. A mixture containing ethyl 3-(6-((3-cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoate (510 mg, 0.75 mmol), 1 M aqueous NaOH solution (2.2 mL, 2.2 mmol), and THF (3 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organics were dried over $Na_2SO_4$, filtered, concentrated to dryness under reduced pressure. The residue was purified by flash column chromatography (0 to 10% MeOH/DCM, gradient elution) to provide the title compound (477 mg, 97%) as a white foam. MS (ESI): mass calcd. for $C_{30}H_{29}F_3N_8O_4S$, 654.2; m/z found, 655.1 [M+H]$^+$. $^1$H NMR (500 MHz, CDCl$_3$) δ 9.14 (s, 1H), 8.46 (dd, J=4.5, 2.2 Hz, 1H), 8.23 (dd, J=10.3, 2.2 Hz, 1H), 8.02 (dd, J=9.6, 7.1 Hz, 1H), 7.50-7.37 (m, 1H), 7.28 (d, J=7.2 Hz, 1H), 7.10 (dd, J=21.8, 7.8 Hz, 1H), 5.05 (q, J=7.4 Hz, 1H), 4.88-4.68 (m, 2H), 4.49 (tt, J=13.1, 4.8 Hz, 1H), 4.34 (d, J=16.0 Hz, 1H), 3.78 (dd, J=12.9, 3.5 Hz, 1H), 3.68 (dd, J=16.6, 8.3 Hz, 1H), 3.63-3.31 (m, 3H), 3.17-3.01 (m, 1H), 2.86 (d, J=4.1 Hz, 3H), 2.23 (s, 3H), 1.82 (dq, J=13.8, 6.6 Hz, 2H), 1.79-1.63 (m, 1H), 1.67-1.59 (m, 1H), 1.63-1.44 (m, 1H).

Example 34: (*S)-3-(6-(((*S)-3-Cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

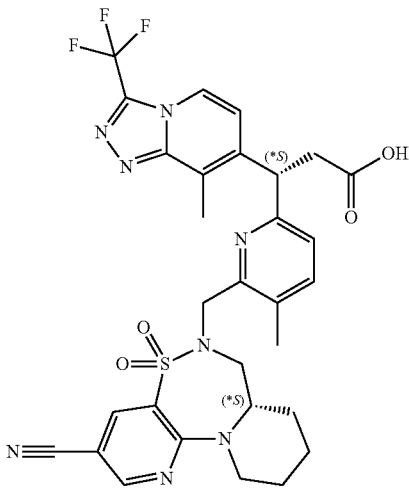 [SMILES: Cc1ccc([C@@H](CC(=O)O)c2ccn3c(C(F)(F)F)nnc3c2C)nc1CN1C[C@@H]2CCCCN2c2ncc(C#N)cc2S1(=O)=O]

The mixture of 4 diasteroisomers of 3-(6-((3-cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid (Example 33) were separated using two chiral separation methods. The mixture of 4 diastereomers was initially subjected to Chiral Separation Method III: chiral SFC (stationary phase: Chiralpak AD-H 5 μm 250×30 mm, Mobile phase: 45% $CO_2$, 55% EtOH) to provide Example 34 and Example 35 and a mixture of the two remaining diastereomers Example 36 and Example 37. The mixture of Example 36 and Example 37 was subsequently separated using Chiral Separation Method IV: chiral SFC (stationary phase: Chiralpak AS-H 5 μm 250×20 mm, Mobile phase: 70% $CO_2$, 30% EtOH) to afford Example 36 and Example 37. The chiral separation method, order of elution and designated stereochemistry is tabulated below in Table 3. When the stereochemical configuration is written as, for example (*R, *S), with the first configuration, (*R), corresponds to the configuration at the 3-propanoic carbon and the second configuration, (*S), corresponds to the stereochemistry at the sultam. The characterization for (*S)-3-(6-(((*S)-3-cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid (264 mg) is as follows: MS (ESI): mass calcd. for $C_{30}H_{29}F_3N_8O_4S$, 654.2; m/z found, 655.1 [M+H]$^+$. $^1$H NMR (500 MHz, CDCl$_3$) δ 8.45 (d, J=2.2 Hz, 1H), 8.25 (d, J=2.1 Hz, 1H), 8.00 (d, J=7.2 Hz, 1H), 7.40 (d, J=7.8 Hz, 1H), 7.29 (d, J=7.3 Hz, 1H), 7.04 (d, J=7.8 Hz, 1H), 5.03 (t, J=7.4 Hz, 1H), 4.85-4.76 (m, 2H), 4.50 (dt, J=13.5, 4.8 Hz, 1H), 4.30 (d, J=16.0 Hz, 1H), 3.75 (dd, J=12.7, 3.5 Hz, 1H), 3.63 (dd, J=16.6, 8.2 Hz, 1H), 3.52 (t, J=12.7 Hz, 1H), 3.37 (ddd, J=14.0, 9.1, 5.6 Hz, 1H), 3.03 (dd, J=16.5, 6.6 Hz, 1H), 2.87 (s, 3H), 2.23 (s, 3H), 1.86-1.77 (m, 3H), 1.63 (dd, J=12.8, 7.0 Hz, 3H), 1.48 (d, J=18.2 Hz, 1H).

TABLE 3

Chiral separation method, Order of elution and Designated stereochemistry for Examples 34-37

| Example # | Chiral Separation method/order of elution | Configuration |
|---|---|---|
| 34 | Method III, first eluting | (*S, *S) |
| 35 | Method III, second eluting | (*S, *R) |
| 36 | Method IV, first eluting | (*R, *R) |
| 37 | Method IV, second eluting | (*R, *S) |

Example 35: (*S)-3-(6-(((*R)-3-Cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

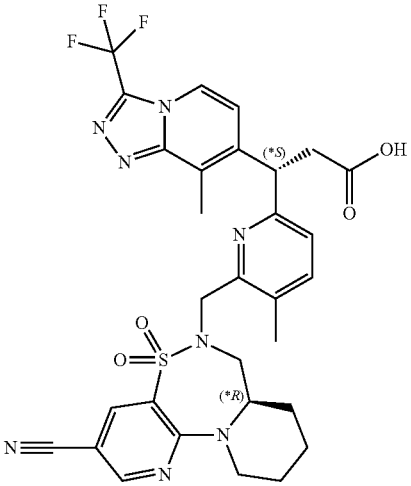 [SMILES: Cc1ccc([C@@H](CC(=O)O)c2ccn3c(C(F)(F)F)nnc3c2C)nc1CN1C[C@H]2CCCCN2c2ncc(C#N)cc2S1(=O)=O]

The title compound (114 mg) was obtained as described in Example 34 and Table 3: MS (ESI): mass calcd. for $C_{30}H_{29}F_3N_8O_4S$, 654.2; m/z found, 655.1 [M+H]$^+$. $^1$H NMR (500 MHz, CDCl$_3$) δ 8.46 (d, J=2.1 Hz, 1H), 8.23 (d, J=2.2 Hz, 1H), 7.96 (d, J=7.2 Hz, 1H), 7.44 (d, J=7.8 Hz, 1H), 7.17 (d, J=7.3 Hz, 1H), 7.08 (d, J=7.8 Hz, 1H), 4.99 (t, J=7.3 Hz, 1H), 4.75 (d, J=14.7 Hz, 2H), 4.47 (dt, J=13.5, 4.8 Hz, 1H), 4.22 (d, J=14.5 Hz, 1H), 3.72 (q, J=7.0 Hz, 1H), 3.54-3.35 (m, 4H), 3.05 (dd, J=16.4, 7.2 Hz, 1H), 2.86 (s, 3H), 2.30 (s, 3H), 1.80 (d, J=6.8 Hz, 1H), 1.80 (s, 2H), 1.81-1.70 (m, 1H), 1.59-1.45 (m, 1H), 1.24 (t, J=7.0 Hz, 1H).

Example 36: (*R)-3-(6-(((*R)-3-Cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

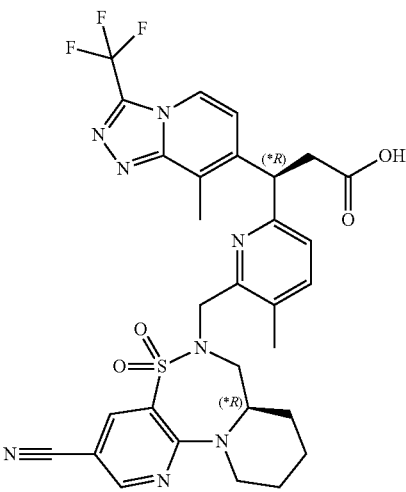 [SMILES: Cc1ccc([C@H](CC(=O)O)c2ccn3c(C(F)(F)F)nnc3c2C)nc1CN1C[C@H]2CCCCN2c2ncc(C#N)cc2S1(=O)=O]

The title compound (95 mg) was obtained as described in Example 34 and Table 3: MS (ESI): mass calcd. for $C_{30}H_{29}F_3N_8O_4S$, 654.2; m/z found, 655.1 [M+H]$^+$. $^1$H NMR (500 MHz, CDCl$_3$) δ 8.46 (d, J=2.2 Hz, 1H), 8.25 (d, J=2.1 Hz, 1H), 8.00 (d, J=7.2 Hz, 1H), 7.40 (dd, J=7.8, 0.8 Hz, 1H), 7.28 (d, J=7.3 Hz, 1H), 7.04 (d, J=7.8 Hz, 1H), 5.07-5.00 (m, 1H), 4.80 (dd, J=16.4, 10.8 Hz, 2H), 4.51 (dt, J=13.6, 4.8 Hz, 1H), 4.30 (d, J=16.0 Hz, 1H), 3.78-3.68 (m, 2H), 3.64 (dd, J=16.5, 8.3 Hz, 1H), 3.56-3.47 (m, 1H), 3.37 (ddd, J=13.5, 9.1, 5.7 Hz, 1H), 3.02 (dd, J=16.5, 6.5 Hz, 1H), 2.88 (s, 3H), 2.24 (s, 3H), 1.86-1.78 (m, 4H), 1.64 (d, J=5.8 Hz, 1H), 1.24 (t, J=7.0 Hz, 1H).

Example 37: (*R)-3-(6-(((*S)-3-Cyano-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

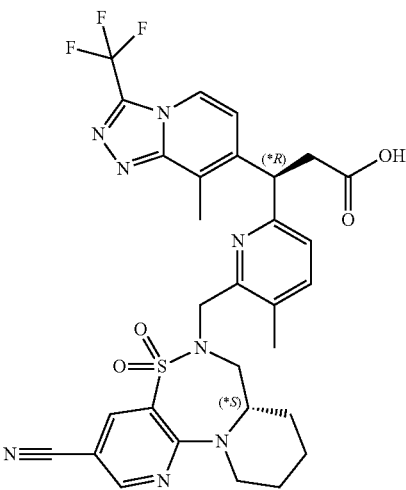 [SMILES: Cc1ccc([C@H](CC(=O)O)c2ccn3c(C(F)(F)F)nnc3c2C)nc1CN1C[C@@H]2CCCCN2c2ncc(C#N)cc2S1(=O)=O]

The title compound (128 mg) was obtained as described in Example 34 and Table 3: MS (ESI): mass calcd. for $C_{30}H_{29}F_3N_8O_4S$, 654.2; m/z found, 655.1 [M+H]$^+$. $^1$H NMR (500 MHz, CDCl$_3$) δ 8.46 (d, J=2.2 Hz, 1H), 8.23 (d, J=2.2 Hz, 1H), 7.97 (d, J=7.2 Hz, 1H), 7.47-7.42 (m, 1H), 7.19 (d, J=7.3 Hz, 1H), 7.09 (d, J=7.8 Hz, 1H), 5.00 (t, J=7.4 Hz, 1H), 4.80-4.71 (m, 2H), 4.47 (dt, J=13.5, 4.8 Hz, 1H), 4.22 (d, J=14.4 Hz, 1H), 3.73 (q, J=7.0 Hz, 1H), 3.56-3.33 (m, 4H), 3.08 (dd, J=16.5, 7.3 Hz, 1H), 2.86 (s, 3H), 2.31 (s, 3H), 1.85-1.70 (m, 4H), 1.58-1.45 (m, 1H), 1.24 (t, J=7.1 Hz, 1H).

Example 38: (*S)-3-(6-(((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic Acid

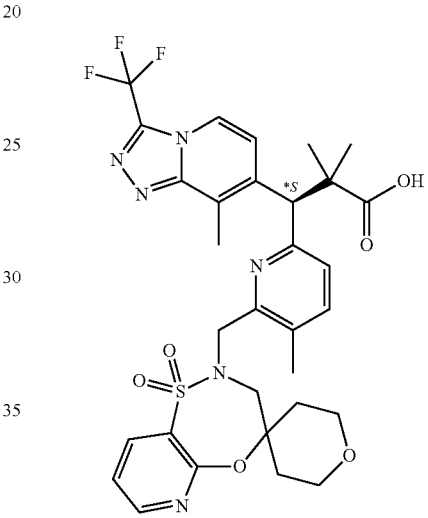

Step A: 7-((6-((((tert-Butyldimethylsilyl)oxy)methyl)-5-methylpyridin-2-yl)chloromethyl)-8-methyl-3-(trifluoromethyl)-[1,2,4]triazolo[4,3-a]pyridine. A 1.3 M solution of isopropylmagnesium chloride-lithium chloride complex in THF (8 mL, 10.4 mmol) was added dropwise to a stirring solution of 7-iodo-8-methyl-3-(trifluoromethyl)-[1,2,4]triazolo[4,3-a]pyridine (Intermediate 53, 3.3 g, 10.1 mmol) in THF (25 mL) at −20° C. After 15 minutes, the Grignard solution was added by cannula to a stirring solution of 6-(((tert-butyldimethylsilyl)oxy)methyl)-5-methylpicolinaldehyde (Intermediate 57, 2.5 g, 9.2 mmol) in THF (25 mL) at −20° C. After 20 minutes, during which time the bath temperature rose to −10° C., methanol (5 mL) was added. The round-bottomed flask was removed from the cooling bath and allowed to warm to room temperature. The pH of the mixture was adjusted to 7 by adding 1 M aqueous HCl solution and then partitioned between water and ethyl acetate. The layers were separated. The aqueous layer was extracted with ethyl acetate which resulted in several organic solvent fractions which were combined, dried over Na$_2$SO$_4$, filtered, and concentrated to dryness under reduced pressure to provide a yellow oil. The oil was dissolved in dichloromethane (44 mL) and then cooled in an ice-water bath; whereupon 2,6-di-tert-butylpyridine (3 mL, 13.4 mmol) and thionyl chloride (0.9 mL, 12.4 mmol) were added sequentially. The round-bottomed flask was removed from the cooling bath and allowed to warm to room temperature over 45 minutes. Saturated aqueous NaHCO$_3$ was added until the pH of the mixture was 7. The mixture was then poured into water and the aqueous layer extracted with dichloromethane which resulted in several organic solvent fractions which were combined, dried over Na$_2$SO$_4$, filtered, and concentrated to dryness under reduced pressure. The residue was purified by flash column chromatography (hexanes-ethyl acetate) to afford the title compound (3.87 g, 87%). MS (ESI): mass calcd. for C$_{22}$H$_{28}$ClF$_3$N$_4$OSi, 484.2; m/z found, 485.1 [M+H]$^+$. $^1$H NMR (400 MHz, CDCl$_3$) δ 8.01 (d, J=7.3 Hz, 1H), 7.55-7.45 (m, 2H), 7.32 (d, J=7.3 Hz, 1H), 6.42 (s, 1H), 4.72 (s, 2H), 2.86 (s, 3H), 2.39 (s, 3H), 0.79 (s, 9H) −0.06 (s, 3H), −0.09 (s, 3H).

Step B: Methyl 3-(6-(((tert-butyldimethylsilyl)oxy) methyl)-5-methylpyridin-2-yl)-2,2-dimethyl-3-(8-methyl-3-(trifluoromethyl)-[1,2,4]triazolo[4,3-a]pyridin-7-yl)propanoate. Indium tribromide (151 mg, 0.426 mmol) was added to a stirring mixture of 7-((6-(((tert-butyldimethylsilyl)oxy)methyl)-5-methylpyridin-2-yl)chloromethyl)-8-methyl-3-(trifluoromethyl)-[1,2,4]triazolo[4,3-a]pyridine (730 mg, 1.5 mmol) and methyl trimethylsilyl dimethylketene acetal (1.3 mL, 6.0 mmol) in dichloromethane (7.5 mL). After 16 hours, ethyl acetate and saturated aqueous NaCl solution were added and the resulting biphasic mixture was separated. The organic layer was dried over Na$_2$SO$_4$, filtered, and concentrated to dryness under reduced pressure to afford a residue. The residue was purified by flash column chromatography (hexanes-ethyl acetate) to afford the title compound which was contaminated with other by-products (406 mg). This material was taken onto the next step without further purification of characterization. MS (ESI): mass calcd. for C$_{27}$H$_{37}$F$_3$N$_4$O$_3$Si, 550.3; m/z found, 551.2 [M+H]$^+$.

Step C: Methyl 3-(6-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate. A 1 M solution of TBAF in THF (1.2 mL, 1.2 mmol) was added to a stirring solution of the impure methyl 3-(6-(((tert-butyldimethylsilyl)oxy)methyl)-5-methylpyridin-2-yl)-2,2-dimethyl-3-(8-methyl-3-(trifluoromethyl)-[1,2,4]triazolo[4,3-a]pyridin-7-yl)propanoate (406 mg) in THF (4 mL). After 5 minutes, the reaction mixture was partitioned between ethyl acetate and water. The layers were separated and the organic layer was dried over Na$_2$SO$_4$, filtered, and concentrated to dryness under reduced pressure to afford a residue. The residue was purified by RP-HPLC (SunFire Prep C$_{18}$ OBD column, 5 M, 30×250 mm, eluting with acetonitrile-water w/0.05% TFA. The pure fractions were combined and lyophilized to afford the title compound as an off-white powder (197 mg, 61%). MS (ESI): mass calcd. for C$_{21}$H$_{23}$F$_3$N$_4$O$_3$, 436.2; m/z found, 437.1 [M+H]$^+$. $^1$H NMR (400 MHz, DMSO-d$_6$) δ 8.33 (d, J=7.2 Hz, 1H), 7.47-7.43 (m, 1H), 7.11 (d, J=7.4 Hz, 1H), 6.96 (d, J=7.8 Hz, 1H), 5.04 (s, 1H), 4.71-4.63 (m, 1H), 4.60 (d, J=5.2 Hz, 2H), 3.55 (s, 3H), 2.79 (s, 3H), 2.24 (s, 3H), 1.31 (s, 3H), 1.22 (s, 3H).

Step D: Methyl 3-(6-((1',1'-dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoate. Di-tert-butyl azodicarboxylate (135 mg, 0.587 mmol) was added in one portion to a stirring mixture containing methyl 3-(6-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate (197 mg, 0.451 mmol), 2,2',3,3',5,6-hexahydrospiro[pyran-4,4'-pyrido[2,3-b][1,4,5]oxathiazepine] 1',1'-dioxide (Intermediate 36, 160 mg, 0.592 mmol), and triphenylphosphine (151 mg, 0.576 mmol) in THF (3 mL) and DMF (2 mL). After 12 hours, the mixture was partitioned between ethyl acetate and water. The layers were separated and the organic layer was dried over Na$_2$SO$_4$, filtered, and concentrated to dryness under reduced pressure to afford a residue. The residue was purified by three sequential chromatographic steps: first by flash column chromatography (hexanes-ethyl acetate), second by flash column chromatography (dichloromethane-methanol) and third by RP-HPLC (XBridge Prep OBD C$_{18}$ column, 5 m, 50×250 mm, eluent: 20 mM aqueous NH$_3$-acetonitrile) to afford the title compound as a white foam (250 mg, 80%). MS (ESI): mass calcd. for C$_{32}$H$_{35}$F$_3$N$_6$O$_6$S, 688.2; m/z found, 689.2 [M+H]$^+$. $^1$H NMR (400 MHz, DMSO-d$_6$) δ 8.58-8.54 (m, 1H), 8.27 (d, J=7.3 Hz, 1H), 8.20 (dd, J=7.6, 2.0 Hz, 1H), 7.66 (d, J=7.4 Hz, 1H), 7.53-7.49 (m, 1H), 7.45 (dd, J=7.6, 4.9 Hz, 1H), 7.20 (d, J=7.8 Hz, 1H), 4.99 (s, 1H), 4.68-4.49 (m, 2H), 3.94-3.70 (m, 4H), 3.66-3.54 (m, 2H), 3.51 (s, 3H), 2.78 (s, 3H), 2.24 (s, 3H), 1.80-1.53 (m, 4H), 1.38 (s, 3H), 1.30 (s, 3H).

Step E: (*S)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid. A mixture containing methyl 3-(6-((1',1'-dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoate (250 mg, 0.363 mmol), 2 M aqueous lithium hydroxide solution (1.5 mL, 3 mmol), THF (3 mL), and methanol (3 mL) was stirred at 60° C. After 12 hours, the reaction mixture was cooled to room temperature, diluted with water, and brought to pH 4-5 by dropwise addition of 1 M aqueous HCl solution. The mixture was extracted with ethyl acetate which resulted in several organic solvent fractions which were combined, dried over Na$_2$SO$_4$, filtered, and concentrated to dryness under reduced pressure to provide a mixture of 3-(6-((1',1'-dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid isomers (245 mg). These isomers were separated by chiral SFC (stationary phase: Chiralpak AD-H, 250×20 mm, mobile phase: 80% CO$_2$, 20% EtOH) to afford two enantiomers. The first eluting isomer (115 mg) was designated (*S). MS (ESI): mass calcd. for C$_{31}$H$_{33}$F$_3$N$_6$O$_6$S, 674.2; m/z found, 675.2 [M+H]$^+$. $^1$H NMR (500 MHz, DMSO-d$_6$) δ 12.40 (s, 1H), 8.58-8.54 (m, 1H), 8.27 (d, J=7.3 Hz, 1H), 8.20 (dd, J=7.6, 1.9 Hz, 1H), 7.78 (d, J=7.3 Hz, 1H), 7.52 (d, J=7.8 Hz, 1H), 7.47-7.42 (m, 1H), 7.26 (d, J=7.8 Hz, 1H), 4.99 (s, 1H), 4.59 (s, 2H), 3.91-3.69 (m, 4H), 3.65-3.53 (m, 2H), 2.78 (s, 3H), 2.24 (s, 3H), 1.77-1.63 (m, 2H), 1.63-1.51 (m, 2H), 1.34 (s, 3H), 1.31 (s, 3H).

Example 39: (*R)-3-(6-((1',1'-Dioxido-2,3,5,6-tetra-hydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic Acid

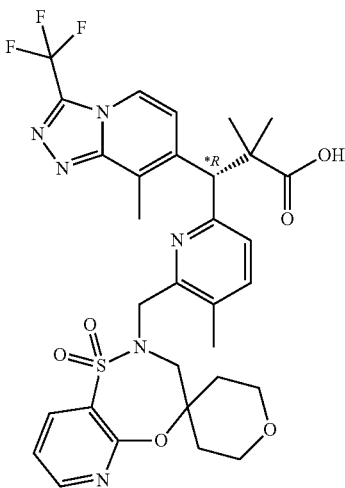 [SMILES: Cc1ccc([C@H](c2ccn3c(C(F)(F)F)nnc3c2C)C(C)(C)C(=O)O)nc1CN1CC2(CCOCC2)Oc2ncccc2S1(=O)=O]

The second eluting isomer (112 mg) from the separation of isomers by chiral SFC described in Example 38 was designated (*R). MS (ESI): mass calcd. for $C_{31}H_{33}F_3N_6O_6S$, 674.2; m/z found, 675.1 [M+H]+; $^1$H NMR (500 MHz, DMSO-$d_6$) δ 12.40 (s, 1H), 8.56 (dd, J=4.9, 1.9 Hz, 1H), 8.27 (d, J=7.3 Hz, 1H), 8.21-8.18 (m, 1H), 7.78 (d, J=7.4 Hz, 1H), 7.52 (d, J=7.8 Hz, 1H), 7.47-7.42 (m, 1H), 7.26 (d, J=7.8 Hz, 1H), 4.99 (s, 1H), 4.59 (s, 2H), 3.92-3.69 (m, 4H), 3.65-3.52 (m, 2H), 2.78 (s, 3H), 2.24 (s, 3H), 1.77-1.63 (m, 2H), 1.63-1.51 (m, 2H), 1.34 (s, 3H), 1.30 (s, 3H).

Example 40: (R/S)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic Acid Step A: Methyl 3-(3-cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoate.
A solution of methyl 3-(3-cyclopropyl-8-methyl-[1,2,4]triazolo[4,3-a]pyridin-7-yl)-3-(3-(hydroxymethyl)-4-methylphenyl)-2,2-dimethylpropanoate (Intermediate 55, 145 mg, 0.36 mmol), 2,2',3,3',5,6-hexahydrospiro[pyran-4,4'-pyrido[2,3-b][1,4,5]oxathiazepine] 1',1'-dioxide (Intermediate 36, 146 mg, 0.54 mmol), and triphenylphosphine (153 mg, 0.58 mmol) in THF (2 mL) and DMF (2 ml) was stirred at room temperature for 5 minutes. DBAD (131 mg, 0.57 mmol) was added and the solution was stirred at room temperature for 30 minutes. The reaction was then concentrated under a stream of nitrogen and purified by flash column chromatography (0-10% MeOH/DCM, gradient elution) to afford the title compound (174 mg, 74%). MS (ESI): mass calcd. for $C_{35}H_{41}N_5O_6S$, 659.3; m/z found, 660.4 [M+H]+.

Step B: (R/S)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid. 2 M Aqueous lithium hydroxide (0.54 mL, 1.1 mmol) was added to a solution of methyl 3-(3-cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoate (70 mg, 0.1 mmol) in MeOH (0.6 mL). The reaction was stirred at 75° C. overnight then allowed to cool to room temperature. 1 M aqueous HCl solution was added until the pH was 4. DCM was added and the resulting biphasic mixture was separated and the aqueous layer was extracted with DCM. These extractions resulted in several organic solvent fractions which were combined, dried over $MgSO_4$, filtered, and concentrated to dryness under reduced pressure. The product, (35 mg), was purified by preparative acidic HPLC (XBridge $C_{18}$, acetonitrile-water containing 0.05% TFA). MS (ESI): mass calcd. for $C_{34}H_{39}N_5O_6S$, 645.2; m/z found, 646.3 [M+H]+.

Example 41: (*S)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic Acid

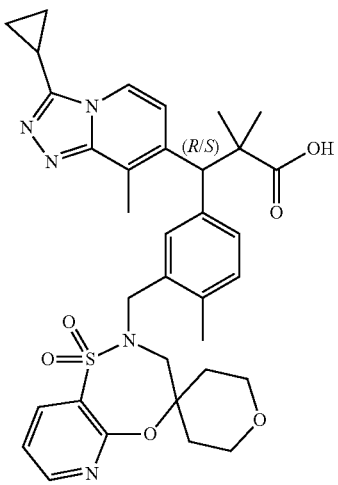 [SMILES: Cc1ccc(C(c2ccn3c(C4CC4)nnc3c2C)C(C)(C)C(=O)O)cc1CN1CC2(CCOCC2)Oc2ncccc2S1(=O)=O]

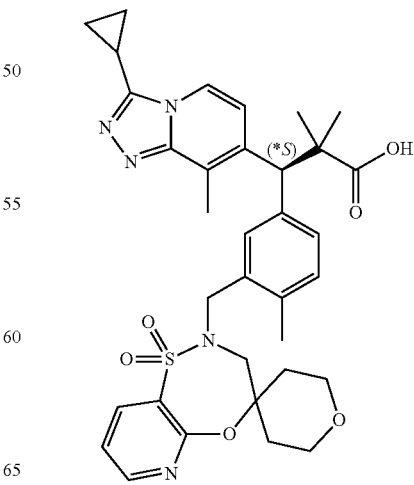

The mixture of 3-(3-cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid isomers (Example 40) was separated by chiral SFC (Chiralcel OJ-H, 2×25 cm, mobile phase: 80% CO$_2$, 20% MeOH with 0.1% diethylamine) to afford two enantiomers. The first eluting isomer (11 mg) was designated (*S): MS: mass calcd. for C$_{34}$H$_{39}$N$_5$O$_6$S, 645.3; m/z found, 646.2. $^1$H NMR (400 MHz, CDCl$_3$) δ 8.50-8.44 (m, 1H), 8.22-8.17 (m, 1H), 7.85 (d, J=6.9 Hz, 1H), 7.25-7.22 (m, 1H), 7.21-7.15 (m, 2H), 7.05 (d, J=7.6 Hz, 1H), 6.98 (d, J=7.2 Hz, 1H), 4.89 (s, 1H), 4.56-4.35 (m, 2H), 4.06-3.92 (m, 2H), 3.67-3.32 (m, 4H), 2.77-2.65 (m, 6H), 2.23 (s, 3H), 2.04-1.94 (m, 1H), 1.59 (d, J=32.5 Hz, 2H), 1.50-1.02 (m, 9H).

Example 42: (*R)-3-(3-Cyclopropyl-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic Acid

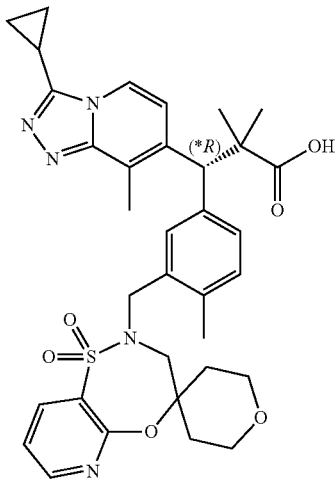 [SMILES: Cc1ccc([C@H](c2ccn3c(C4CC4)nnc3c2C)C(C)(C)C(=O)O)cc1CN1CC2(CCOCC2)Oc2ncccc2S1(=O)=O]

The second eluting isomer (11 mg) from the separation of isomers by chiral SFC described in Example 41 was designated (*R): MS: mass calcd. for C$_{34}$H$_{39}$N$_5$O$_6$S, 645.3; m/z found, 646.2. $^1$H NMR (400 MHz, CDCl$_3$) δ 8.51-8.44 (m, 1H), 8.23-8.15 (m, 1H), 7.95-7.78 (m, 1H), 7.26-6.90 (m, 5H), 4.98-4.81 (m, 1H), 4.60-4.33 (m, 2H), 4.09-3.89 (m, 2H), 3.77-3.28 (m, 4H), 2.88-2.53 (m, 6H), 2.23 (s, 3H), 2.06-1.93 (m, 1H), 1.69-1.51 (m, 2H), 1.49-0.95 (m, 9H).

Example 43: (R/S)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic Acid

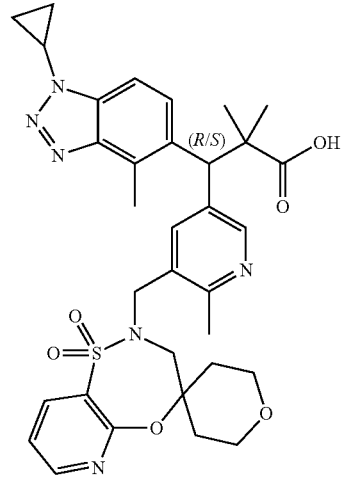 [SMILES: Cc1ncc(C(c2ccc3c(nnn3C3CC3)c2C)C(C)(C)C(=O)O)cc1CN1CC2(CCOCC2)Oc2ncccc2S1(=O)=O]

Step A: Methyl 3-(1-cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoate. A solution of methyl 3-(1-cyclopropyl-4-methyl-1H-benzo[d][1,2,3]triazol-5-yl)-3-(5-(hydroxymethyl)-6-methylpyridin-3-yl)-2,2-dimethylpropanoate (Intermediate 56, 0.68 g, 1.7 mmol), 2,2',3,3',5,6-hexahydrospiro[pyran-4,4'-pyrido[2,3-b][1,4,5]oxathiazepine] 1',1'-dioxide (Intermediate 36, 0.68 g, 2.5 mmol), and triphenylphosphine (0.70 g, 2.7 mmol) in THF (16 mL) and DMF (12 ml) was stirred at room temperature for 5 minutes. DBAD (0.61 g, 2.7 mmol) was added and the reaction mixture was stirred for 30 minutes. The mixture was then concentrated under a stream of nitrogen and purified by flash column chromatography (0-100% EtOAc/hexanes, gradient elution) to afford the title compound (1.1 g, 91%). MS (ESI): mass calcd. for C$_{34}$H$_{40}$N$_6$O$_6$S, 660.3; m/z found, 661.3 [M+H]$^+$.

Step B: (R/S)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid. 2 M Aqueous lithium hydroxide (2.6 mL, 5.2 mmol) was added to a solution of methyl 3-(1-cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoate (350 mg, 0.53 mmol) in MeOH (3 mL). The reaction mixture was stirred at 75° C. overnight and then allowed to cool to room temperature. 1 M aqueous HCl solution was added until the pH was approximately 6. DCM was then added and the resulting biphasic mixture was separated and the aqueous layer was extracted with DCM. These extractions resulted in several organic solvent fractions which were combined, dried over MgSO$_4$, filtered, concentrated to dryness under reduced pressure and purified by preparative acidic HPLC (XBridge C$_{18}$, acetonitrile-water containing 0.05% TFA). The fractions that contained product from such preparative acidic HPLC were collected and lyophilized to dryness to provide the title compound (241 mg). MS (ESI): mass calcd. for C$_{33}$H$_{38}$N$_6$O$_6$S, 646.2; m/z found, 647.2 [M+H]$^+$.

Example 44: (*S)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic Acid

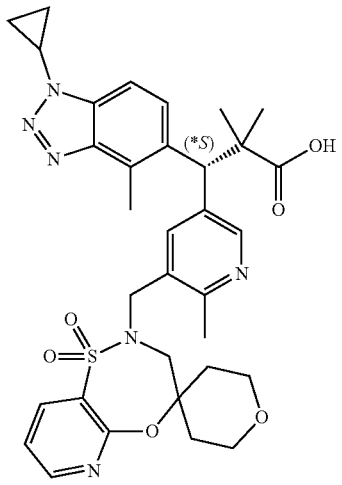 [SMILES: Cc1ncc([C@H](c2ccc3c(nnn3C3CC3)c2C)C(C)(C)C(=O)O)cc1CN1CC2(CCOCC2)Oc2ncccc2S1(=O)=O]

The mixture of (R/S)-3-(1-cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic acid (Example 43) was separated by chiral SFC (Chiralcel OJ-H, 2×25 cm, mobile phase: 80% $CO_2$, 20% MeOH with 0.1% diethylamine) to afford two enantiomers. The first eluting isomer (47 mg) was designated (*S): MS: mass calcd. for $C_{33}H_{38}N_6O_6S$, 646.2; m/z found, 647.2. $^1$H NMR (400 MHz, $CDCl_3$) δ 8.55-8.43 (m, 2H), 8.23-8.15 (m, 1H), 7.61 (s, 2H), 7.47 (s, 1H), 7.26-7.21 (m, 1H), 5.06-4.94 (m, 1H), 4.62-4.46 (m, 1H), 4.44-4.29 (m, 1H), 4.08-3.90 (m, 2H), 3.69-3.37 (m, 6H), 2.95-2.79 (m, 4H), 2.79-2.67 (m, 1H), 2.44 (s, 3H), 1.61-1.26 (m, 11H).

Example 45: (*R)-3-(1-Cyclopropyl-4-methyl-1H-benzo[d][1,2,3]triazol-5-yl)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethylpropanoic Acid

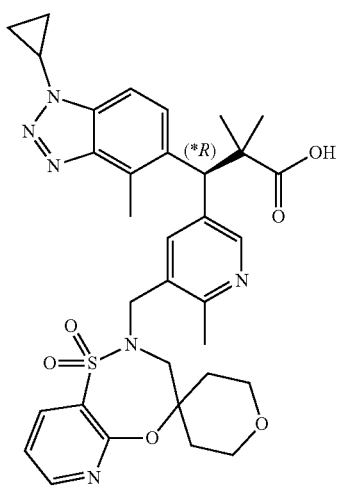 [SMILES: Cc1ncc([C@@H](c2ccc3c(nnn3C3CC3)c2C)C(C)(C)C(=O)O)cc1CN1CC2(CCOCC2)Oc2ncccc2S1(=O)=O]

The second eluting isomer (54 mg) from the separation of isomers by chiral SFC described in Example 44 was designated (*R): MS: mass calcd. for $C_{33}H_{38}N_6O_6S$, 646.2; m/z found, 647.3. $^1$H NMR (400 MHz, $CDCl_3$) δ 8.49 (d, J=4.5 Hz, 2H), 8.24-8.15 (m, 1H), 7.70-7.53 (m, 2H), 7.50-7.41 (m, 1H), 7.28-7.22 (m, 1H), 5.06-4.92 (m, 1H), 4.65-4.48 (m, 1H), 4.42-4.26 (m, 1H), 4.14-3.90 (m, 2H), 3.67-3.37 (m, 6H), 2.93-2.36 (m, 8H), 1.63-1.26 (m, 11H).

Example 46: 2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl) propanoic Acid

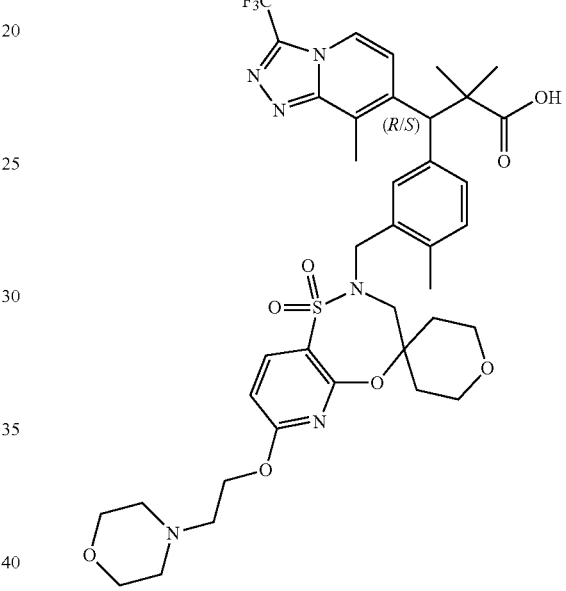

Step A: Methyl 3-(3-((7'-chloro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate. To a 100 mL round bottom flask under $N_2$ was added methyl 3-(3-(hydroxymethyl)-4-methylphenyl)-2,2-dimethyl-3-(8-methyl-3-(trifluoromethyl)-[1,2,4]triazolo[4,3-a]pyridine-7-yl)propanoate (Intermediate 48, 630 mg, 1.45 mmol), 7'-chloro-2,2',3,3',5,6-hexahydrospiro[pyran-4,4'-pyrido[2,3-b][1,4,5]oxathiazepine] 1',1'-dioxide (Intermediate 68, 618 mg, 2.01 mmol), triphenylphosphine (561 mg, 2.14 mmol), tetrahydrofuran (7.5 mL) and DMF (7.5 mL). Once the mixture was homogeneous, diisopropyl azodicarboxylate (0.48 mL, 2.4 mmol) was added and the reaction mixture was stirred at room temperature for 18 h. The reaction mixture was poured into saturated sodium bicarbonate solution and extracted with ethyl acetate. These extractions resulted in several organic fractions which were combined, dried over sodium sulfate and concentrated to dryness under reduced pressure. The residue was purified by flash column chromatography (eluent: 1:1 ethyl acetate/DCM) to afford the title compound (760 mg, 73%). MS (ESI): mass calcd. for $C_{33}H_{35}ClF_3N_5O_6S$, 721.2; m/z found, 722.1 [M+H]$^+$. $^1$H NMR (400 MHz, $CDCl_3$) δ 8.05 (d, J=8.0 Hz, 1H), 7.96 (d, J=7.3 Hz, 1H), 7.19 (s, 1H), 7.16 (s, 1H), 7.13 (d, J=7.3 Hz, 1H), 7.05-7.03 (m, 2H), 4.72 (s, 1H), 4.47-4.33 (m, 2H), 3.98-3.91 (m, 2H), 3.58-3.47 (m, 6H), 3.37-3.33 (m, 1H), 2.71 (s, 3H), 2.16 (s, 3H), 1.70-1.56 (m, 2H), 1.49-1.39 (m, 2H), 1.35 (s, 3H), 1.29 (s, 3H).

Step B: Methyl 2,2-dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoate. To a reaction vessel under N$_2$ was added methyl 3-(3-((7'-chloro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate (200 mg, 0.28 mmol), 2-morpholinoethan-1-ol (101 μL, 0.83 mmol), Cs$_2$CO$_3$ (271 mg, 0.83 mmol) and toluene (2.0 mL, which had been previously purged with N$_2$ for 30 minutes). RockPhos Pd G3 (11.6 mg, 0.014 mmol) was then added to this mixture and the reaction mixture was purged with N$_2$ for an additional 5 minutes. The reaction mixture was then heated to 90° C. for 18 hours. Afterwards, the reaction was cooled, partitioned between ethyl acetate and water and the aqueous layer extracted with ethyl acetate. These extractions resulted in several organic solvent fractions which were combined, dried over sodium sulfate and concentrated to dryness under reduced pressure. The residue was purified by flash column chromatography (eluent: 1:10 MeOH/DCM) to afford the title compound (75 mg, 33%) as a white solid. MS (ESI): mass calcd. for C$_{39}$H$_{47}$F$_3$N$_6$O$_8$S, 816.3; m/z found, 817.2 [M+H]$^+$.

Step C: 2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid. To a flask was added methyl 2,2-dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoate (190 mg, 0.23 mmol), lithium hydroxide (2M, 0.8 mL, 1.6 mmol), MeOH (1.6 mL), THF (1.6 mL) and water (0.8 mL). The mixture was heated to 75° C. and stirred for 6 h. The reaction was cooled to room temperature, pH adjusted to about 4 with 2 M HCl, poured into water and extracted with ethyl acetate (4×). These extractions resulted in several organic solvent fractions which were combined, dried over sodium sulfate and concentrated to dryness under reduced pressure. The resulting residue was purified by flash chromatography (eluent: 1:10 MeOH/DCM) to afford the title compound (40 mg, 21%). MS (ESI): mass calcd. for C$_{38}$H$_{45}$F$_3$N$_6$O$_8$S, 802.3; m/z found, 803.1 [M+H]$^+$. $^1$H NMR (400 MHz, CDCl$_3$) δ 8.00-7.92 (m, 2H), 7.22-7.19 (m, 1H), 7.17-7.14 (m, 1H), 7.13-7.08 (m, 1H), 7.03 (d, J=7.8 Hz, 1H), 6.54 (d, J=8.4 Hz, 1H), 4.81 (s, 1H), 4.50-4.30 (m, 4H), 3.93-3.83 (m, 2H), 3.69-3.52 (m, 7H), 3.40 (br s, 2H), 2.79-2.68 (m, 6H), 2.56-2.47 (m, 4H), 2.16 (s, 4H), 1.69-1.41 (m, 4H), 1.38 (s, 4H).

Example 47: (*S)-2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl) propanoic Acid

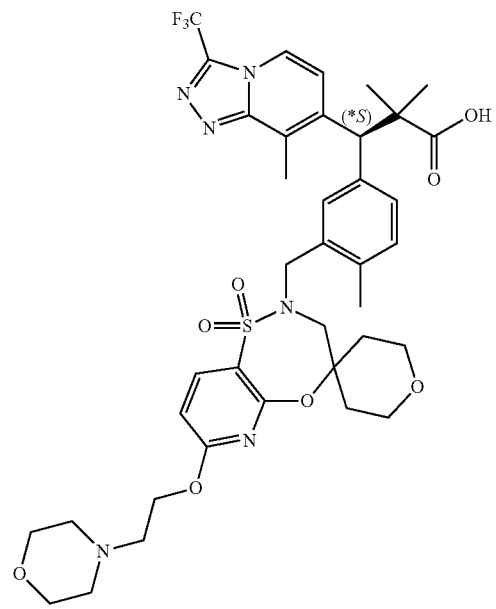 [SMILES: Cc1ccc([C@@H](c2ccn3c(C(F)(F)F)nnc3c2C)C(C)(C)C(=O)O)cc1CN1CC2(CCOCC2)Oc2nc(OCCN3CCOCC3)ccc2S1(=O)=O]

The mixture of 2,2-dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic acid enantiomers (Example 46, 40 mg) was separated by chiral SFC (Stationary phase: Chiralpak IG, 5 m, 250×20 mm, Mobile phase: 50% CO$_2$, 50% EtOH) to afford two enantiomers. The first eluting isomer (11 mg) was designated (*S): MS (ESI): mass calcd. for C$_{38}$H$_{45}$F$_3$N$_6$O$_8$S, 802.3; m/z found, 803.1 [M+H]$^+$, $^1$H NMR (400 MHz, CDCl$_3$) δ 8.05 (d, J=8.4 Hz, 1H), 8.00 (d, J=7.3 Hz, 1H), 7.24-7.14 (m, 3H), 7.11-7.07 (m, 1H), 6.63 (d, J=8.4 Hz, 1H), 4.90 (s, 1H), 4.60-4.51 (m, 1H), 4.48-4.38 (m, 3H), 4.04-3.86 (m, 2H), 3.82-3.37 (m, 8H), 2.86 (s, 3H), 2.82-2.75 (m, 2H), 2.60-2.54 (m, 4H), 2.22 (s, 3H), 1.65-1.49 (m, 4H), 1.46 (s, 3H), 1.34 (s, 3H).

Example 48: (*R)-2,2-Dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoic Acid

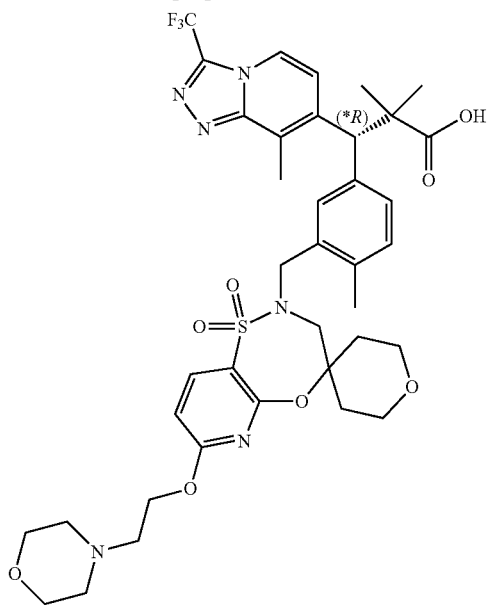 [SMILES: Cc1ccc([C@H](c2ccn3c(C(F)(F)F)nnc3c2C)C(C)(C)C(=O)O)cc1CN1CC2(CCOCC2)Oc2nc(OCCN3CCOCC3)ccc2S1(=O)=O]

The second eluting isomer (12 mg) from the separation of isomers by chiral SFC described in Example 47 was designated (*R): MS (ESI): mass calcd. for $C_{38}H_{45}F_3N_6O_8S$, 802.3; m/z found, 803.1 [M+H]$^+$.

Example 49: 3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methyl-3-trifluoromethyl)-[1,2,4]triazolo[4,3-a]pyridine-7-yl)propanoic Acid

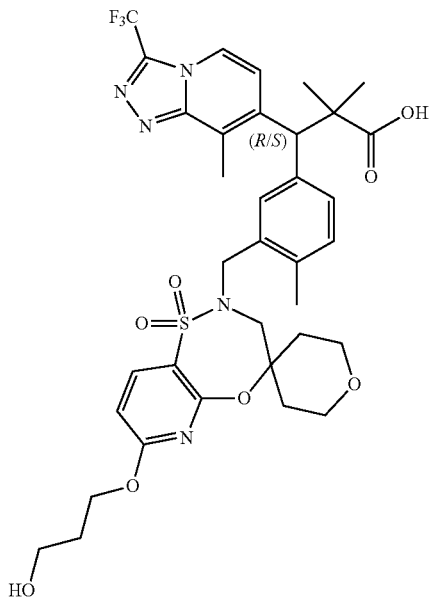 [SMILES: Cc1ccc(C(c2ccn3c(C(F)(F)F)nnc3c2C)C(C)(C)C(=O)O)cc1CN1CC2(CCOCC2)Oc2nc(OCCCO)ccc2S1(=O)=O]

The title compound (20 mg, 30%) was prepared using analogous conditions as described in Example 46 where 3-((2-(trimethylsilyl)propan-2-yl)oxy)propan-1-ol was used instead of 2-morpholinoethan-1-ol in step B. MS (ESI): mass calcd. for $C_{35}H_{40}F_3N_6O_8S$, 747.2; m/z found, 748.1 [M+H]$^+$. $^1$H NMR (400 MHz, CDCl$_3$) δ 7.99 (d, J=8.5 Hz, 1H), 7.94 (d, J=7.4 Hz, 1H), 7.21-7.16 (m, 1H), 7.16-7.08 (m, 2H), 7.03 (d, J=7.9 Hz, 1H), 6.54 (d, J=8.5 Hz, 1H), 4.83 (s, 1H), 4.50-4.32 (m, 4H), 3.93-3.79 (m, 2H), 3.73-3.67 (m, 3H), 3.62-3.35 (m, 3H), 2.78 (s, 3H), 2.16 (s, 3H), 1.94 (q, J=5.9 Hz, 3H), 1.60-1.52 (m, 3H), 1.45-1.37 (s, 4H), 1.28-1.20 (m, 4H).

Example 50: (*S)-3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methy-3-trifluoromethyl)-[1,2,4]triazolo[4,3-a]pyridine-7-yl)propanoic Acid

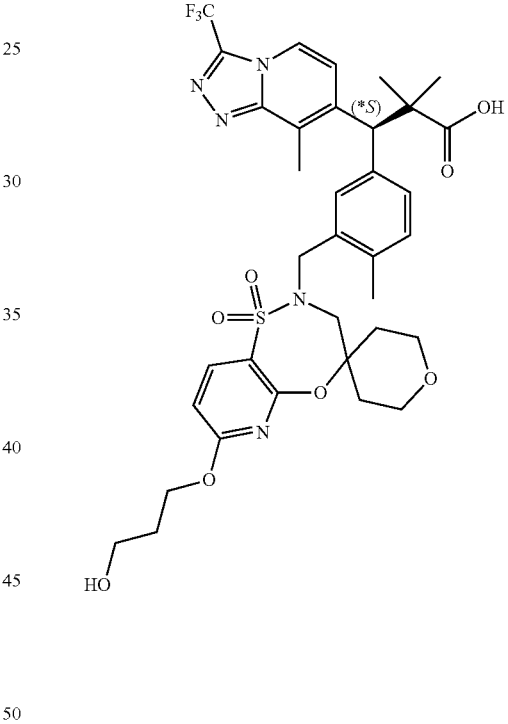

The mixture of 3-(3-((7'-(3-hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methyl-3-trifluoromethyl)-[1,2,4]triazolo[4,3-a]pyridine-7-yl)propanoic acid enantiomers (Example 49) was separated by chiral SFC (Stationary phase: Chiralpak AD-H, 5 m, 250×30 mm, Mobile phase: 75% CO$_2$, 25% EtOH) to afford two enantiomers. The first eluting isomer (8 mg) was designated (*S): MS (ESI): mass calcd. for $C_{35}H_{40}F_3N_6O_8S$, 747.2; m/z found, 748.1 [M+H]$^+$. $^1$H NMR (400 MHz, Chloroform-d) δ 8.01-7.95 (m, 1H), 7.93 (d, J=7.3 Hz, 1H), 7.18-7.11 (m, 2H), 7.09-6.98 (m, 2H), 6.56-6.52 (m, 1H), 4.82 (s, 1H), 4.48-4.34 (m, 4H), 3.94-3.83 (m, 2H), 3.75-3.55 (m, 4H), 3.37 (s, 3H), 2.75 (s, 3H), 2.16 (s, 3H), 2.04-1.93 (m, 2H), 1.61-1.45 (m, 3H), 1.37 (s, 4H), 1.27 (s, 3H).

Example 51: (*R) 3-(3-((7'-(3-Hydroxypropoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl-2,2'-dimethyl-3-(8-methyl-3-trifluoromethyl)-[1,2,4]triazolo[4,3-a]pyridine-7-yl) propanoic Acid

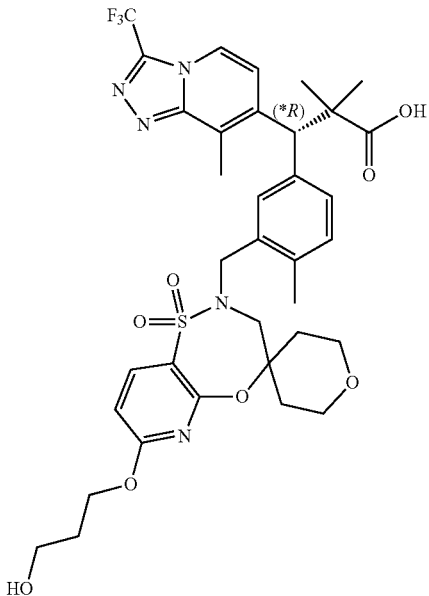 [SMILES: Cc1ccc([C@H](c2ccn3c(C(F)(F)F)nnc3c2C)C(C)(C)C(=O)O)cc1CN1CC2(CCOCC2)Oc2nc(OCCCO)ccc2S1(=O)=O]

The second eluting isomer (9 mg) from the separation of isomers by chiral SFC described in Example 50 was designated (*R): MS (ESI): mass calcd. for $C_{35}H_{40}F_3N_6O_8S$, 747.2; m/z found, 748.1 [M+H].

Example 52: (R/S)-3-(3-(Difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic Acid

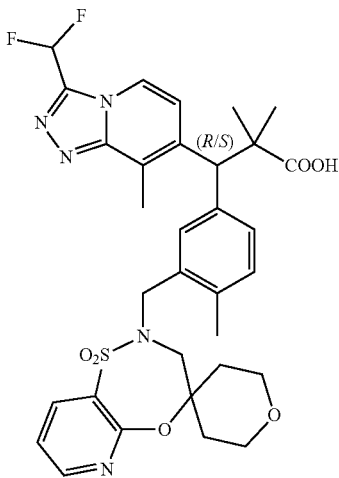 [SMILES: Cc1ccc(C(c2ccn3c(C(F)F)nnc3c2C)C(C)(C)C(=O)O)cc1CN1CC2(CCOCC2)Oc2ncccc2S1(=O)=O]

Step A: Methyl 3-(3-(difluoromethyl)-8-methyl-[1,2,4]triazolo[4,3-a]pyridin-7-yl)-3-(3-((1',1'-dioxido-2,3,5,6-tet-rahydrospiro[pyran-4,4'-pyrido[2,3-b][1,4,5]oxathiazepin]-2'(3'H)-yl)methyl)-4-methylphenyl)-2,2-dimethylpropanoate. A solution of methyl 3-(3-(difluoromethyl)-8-methyl-[1,2,4]triazolo[4,3-a]pyridin-7-yl)-3-(3-(hydroxymethyl)-4-methylphenyl)-2,2-dimethylpropanoate (Intermediate 49, 2.0 g, 4.8 mmol), 2,2',3,3',5,6-hexahydrospiro[pyran-4,4'-pyrido[2,3-b][1,4,5]oxathiazepine] 1',1'-dioxide (Intermediate 36, 1.6 g, 6.0 mmol), and triphenylphosphine (1.8 g, 7.1 mmol) in THF (133 mL) and DMF (13 ml) was stirred at room temperature for 5 minutes. DBAD (1.9 g, 7.9 mmol) was added and the reaction mixture was stirred at room temperature for 10 minutes. Water and ethyl acetate were added to the reaction mixture and the aqueous layer was extracted with ethyl acetate. These extractions resulted in several organic solvent fractions which were combined, dried over magnesium sulfate, filtered and concentrated to dryness under reduced pressure. The residue was purified by flash column chromatography (0-100% ethyl acetate/hexanes, gradient elution) to afford the title compound (3 g, 93% yield) which was carried on to the next step without further purification. MS (ESI): mass calcd. for $C_{33}H_{37}F_2N_5O_6S$, 669.2; m/z found, 670.3 [M+H]$^+$.

Step B: (R/S)-3-(3-(Difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid. Lithium hydroxide (0.65 g, 15.5 mmol) was added to a solution of methyl 3-(3-(difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoate (3.0 g, 3.9 mmol) in MeOH (25 mL) and water (17 mL). The reaction mixture was stirred at 75° C. overnight then allowed to cool to room temperature. 1 M aqueous HCl solution was then added until the pH was 4. Ethyl acetate was added and the resulting biphasic mixture was separated. The aqueous layer was extracted with ethyl acetate. These extractions resulted in several organic solvent fractions which were combined, dried over Na$_2$SO$_4$, filtered, and concentrated to dryness under reduced pressure. The product was purified by flash column chromatography (0-10% MeOH/DCM, gradient elution) to provide the title compound (2.5 g, 98% yield). MS (ESI): mass calcd. for $C_{32}H_{35}F_2N_5O_6S$, 655.2; m/z found, 656.3 [M+H]$^+$.

Example 53: (*S)-3-(3-(Difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic Acid

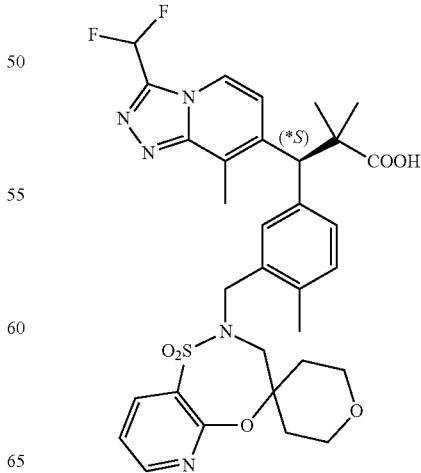

The mixture of 3-(3-(difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid isomers (Example 52, 2.5 g) was separated by chiral SFC (stationary phase: Chiralpak IC, 30×150 mm, Mobile phase: 35% ethanol, 65% $CO_2$) to afford two enantiomers. The first eluting isomer (1.2 g) was designated (*S): $^1$H NMR (500 MHz, $CDCl_3$) δ 8.52-8.45 (m, 1H), 8.23-8.18 (m, 1H), 8.14 (d, J=7.2 Hz, 1H), 7.33-7.15 (m, 5H), 7.12-7.06 (m, 1H), 4.86 (s, 1H), 4.54-4.43 (m, 2H), 4.03-3.88 (m, 2H), 3.73-3.36 (m, 4H), 2.74 (s, 3H), 2.21 (s, 3H), 1.64-1.47 (m, 3H), 1.47-1.30 (m, 7H).

Example 54: (*R)-3-(3-(Difluoromethyl)-8-methyl-[1,2,4]triazolo[4,3-a]pyridin-7-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic Acid

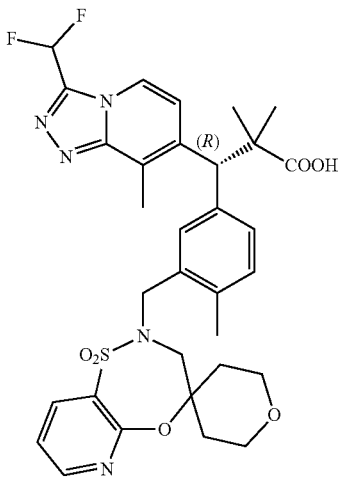

The second eluting isomer (1.1 g) from the separation of isomers by chiral SFC described in Example 53 was designated (*R): $^1$H NMR (600 MHz, $CDCl_3$) δ 8.51-8.46 (m, 1H), 8.23-8.19 (m, 1H), 8.13 (d, J=7.2 Hz, 1H), 7.29-7.07 (m, 6H), 4.86 (s, 1H), 4.57-4.50 (m, 1H), 4.48-4.40 (m, 1H), 4.06-3.92 (m, 2H), 3.68-3.57 (m, 2H), 3.57-3.36 (m, 2H), 2.75 (s, 3H), 2.23 (s, 3H), 1.63-1.32 (m, 10H).

Example 55: (R/S)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic Acid

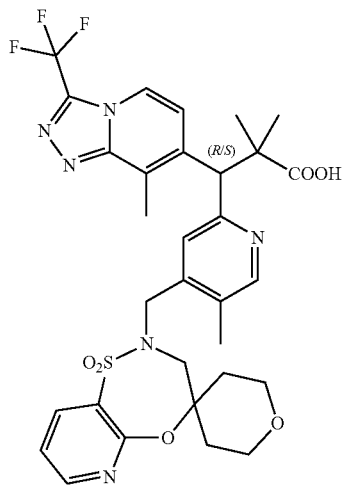 [SMILES: Cc1cnc(C(c2ccn3c(C(F)(F)F)nnc3c2C)C(C)(C)C(=O)O)cc1CN1CC2(CCOCC2)Oc2ncccc2S1(=O)=O]

Step A: Methyl 3-(4-((1',1'-dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoate. A solution of methyl 3-(4-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate (Intermediate 50, 480 mg, 1.1 mmol), 2,2',3,3',5,6-hexahydrospiro[pyran-4,4'-pyrido[2,3-b][1,4,5]oxathiazepine] 1',1'-dioxide (Intermediate 36, 420 mg, 1.55 mmol), DBAD (372 mg, 1.62 mmol) and triphenylphosphine (420 mg, 1.60 mmol) in THF (7.2 mL) and DMF (7.2 ml) was stirred at room temperature for 16 hours. The reaction was then concentrated and purified by flash column chromatography (0-100% ethyl acetate/hexanes, gradient elution) to afford the title compound (650 mg, 86% yield) which was taken on to the next step without further purification. MS (ESI): mass calcd. for $C_{32}H_{35}F_3N_6O_6S$, 688.2; m/z found, 689.2 $[M+H]^+$.

Step B: (R/S)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid. Lithium hydroxide (166 mg, 6.92 mmol) was added to a solution of methyl 3-(4-((1',1'-dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoate (650 mg, 0.94 mmol) in MeOH (43 mL) and water (13 mL). The reaction mixture was stirred at 70° C. overnight then allowed to cool to room temperature. 1 M aqueous HCl solution was added until the pH was 4. EtOAc was added and the resulting biphasic mixture was separated. The aqueous layer was extracted with EtOAc. These extractions resulted in several organic solvent fractions which were combined, dried over $Na_2SO_4$, filtered, and concentrated to dryness under reduced pressure. The product was purified by flash column chromatography (0-10% MeOH/DCM, gradient elution) to provide the title compound to provide the title compound (188 mg, 30% yield). MS (ESI): mass calcd. for $C_{32}H_{35}F_3N_6O_6S$, 674.2; m/z found, 675.3 [M+H]$^+$. $^1$H NMR (500 MHz, CDCl$_3$) δ 8.55-8.51 (m, 1H), 8.40 (s, 1H), 8.16-8.12 (m, 1H), 7.97-7.93 (m, 1H), 7.38-7.32 (m, 2H), 7.31-7.25 (m, 1H), 4.81 (s, 1H), 4.59-4.51 (m, 1H), 4.42-4.34 (m, 1H), 4.10-3.99 (m, 2H), 3.79-3.53 (m, 4H), 2.96 (s, 3H), 2.26 (s, 3H), 1.76-1.60 (m, 3H), 1.54-1.45 (m, 1H), 1.44-1.33 (m, 6H).

Example 56: (*S)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic Acid

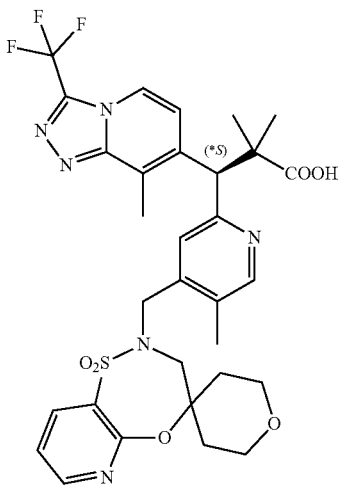 [SMILES: Cc1cnc([C@@H](c2ccn3c(C(F)(F)F)nnc3c2C)C(C)(C)C(=O)O)cc1CN1CC2(CCOCC2)Oc2ncccc2S1(=O)=O]

The mixture of (R/S)-3-(4-((1',1'-dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic acid isomers (Example 55, 280 mg) was separated by chiral SFC (stationary phase: Chiralpak IC, 5 m, 250×30 mm, mobile phase: 55% CO$_2$, 45% mixture of EtOH/DCM, 90/10, v/v) to afford two enantiomers. The first eluting isomer (54 mg) was designated (*S): MS (ESI): mass calcd. for $C_{32}H_{35}F_3N_6O_6S$, 674.2; m/z found, 675.3 [M+H]$^+$. $^1$H NMR (600 MHz, CDCl$_3$) δ 8.56-8.50 (m, 1H), 8.39 (s, 1H), 8.17-8.12 (m, 1H), 7.93 (d, J=7.3 Hz, 1H), 7.38-7.32 (m, 2H), 7.29-7.27 (m, 1H), 4.78 (s, 1H), 4.61-4.54 (m, 1H), 4.35-4.28 (m, 1H), 4.12-3.99 (m, 2H), 3.74-3.52 (m, 4H), 2.99 (s, 3H), 2.25 (s, 3H), 1.75-1.60 (m, 3H), 1.47-1.34 (m, 7H).

Example 57: (*R)-3-(4-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-2,2-dimethyl-3-(8-methyl-3-(trifluoromethyl)-[1,2,4]triazolo[4,3-a]pyridin-7-yl)propanoic Acid

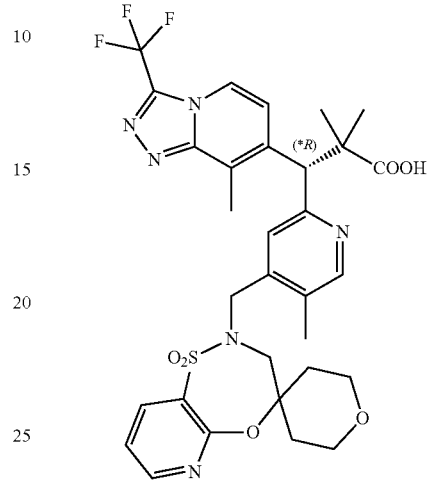

The second eluting isomer (58 mg) from the separation of isomers by chiral SFC described in Example 56 was designated (*R): MS (ESI): mass calcd. for $C_{32}H_{35}F_3N_6O_6S$, 674.2; m/z found, 675.3 [M+H]$^+$. $^1$H NMR (600 MHz, CDCl$_3$) δ 8.55-8.50 (m, 1H), 8.39 (s, 1H), 8.17-8.11 (m, 1H), 7.95-7.91 (m, 1H), 7.38-7.32 (m, 2H), 7.29-7.27 (m, 1H), 4.78 (s, 1H), 4.62-4.52 (m, 1H), 4.35-4.28 (m, 1H), 4.09-4.00 (m, 2H), 3.75-3.52 (m, 4H), 2.98 (s, 3H), 2.26 (s, 3H), 1.75-1.58 (m, 3H), 1.47-1.35 (m, 7H).

Example 58: (R/S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic Acid

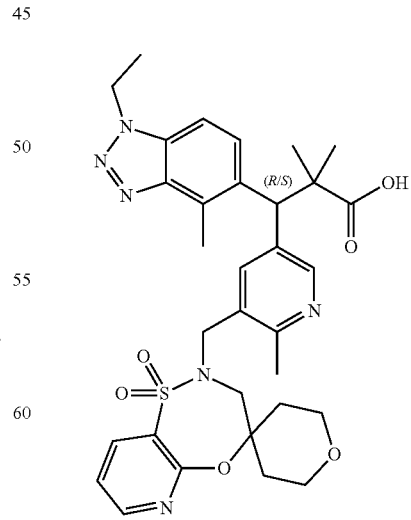

Step A: Methyl 3-(5-((1',1'-dioxido-2,3,5,6-tetrahydrospiro[pyran-4,4'-pyrido[2,3-b][1,4,5]oxathiazepin]-2'

(3'H)-yl)methyl)-6-methylpyridin-3-yl)-3-(1-ethyl-4-methyl-1H-benzo[d][1,2,3]triazol-5-yl)-2,2-dimethylpropanoate. A solution of methyl 3-(1-ethyl-4-methyl-1H-benzo[d][1,2,3]triazol-5-yl)-3-(5-(hydroxymethyl)-6-methylpyridin-3-yl)-2,2-dimethylpropanoate (Intermediate 51, 1.5 g, 3.8 mmol), 2,2',3,3',5,6-hexahydrospiro[pyran-4,4'-pyrido[2,3-b][1,4,5]oxathiazepine] 1',1'-dioxide (Intermediate 36, 1.3 g, 4.7 mmol), triphenylphosphine (1.6 g, 6.0 mmol), and DBAD (1.4 g, 6.1 mmol) in THF (41 mL) and DMF (5 ml) was stirred at room temperature for 10 minutes. Water and ethyl acetate were added to the reaction mixture and the aqueous layer was extracted with ethyl acetate. These extractions resulted in several organic solvent fractions which were combined, dried over magnesium sulfate, filtered and concentrated to dryness under reduced pressure. The residue was purified by flash column chromatography (0-100% ethyl acetate/hexanes, gradient elution) to afford the title compound (2.4 g, 98% yield) which was carried on to the next step without further purification. MS (ESI): mass calcd. for $C_{33}H_{40}N_6O_6S$, 648.3; m/z found, 649.3 $[M+H]^+$.

Step B: (R/S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic acid. Lithium hydroxide (0.44 g, 18.5 mmol) was added to a solution of methyl 3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoate (2.4 g, 3.7 mmol) in MeOH (30 mL), THF (60 mL) and water (30 mL). The reaction mixture was stirred at 70° C. overnight then allowed to cool to room temperature. 1 M aqueous HCl solution was added until the pH was approximately 3-4. EtOAc was added and the resulting biphasic mixture was separated. The aqueous layer was extracted with EtOAc. These extractions resulted in several organic solvent fractions which were combined, dried over MgSO₄, filtered, and concentrated to dryness under reduced pressure. The product was purified by flash column chromatography (0-10% MeOH/DCM, gradient elution) to provide the title compound (2.25 g, 96% yield). MS (ESI): mass calcd. for $C_{32}H_{38}N_6O_6S$, 634.3; m/z found, 635.3 $[M+H]^+$.

Example 59: (*S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic Acid

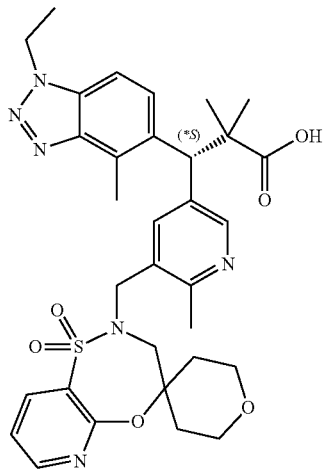 [SMILES: CCn1nnc2c(C)c([C@@H](c3cnc(C)c(CN4CC5(CCOCC5)Oc5ncccc5S4(=O)=O)c3)C(C)(C)C(=O)O)ccc21]

The mixture of (R/S)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic acid isomers (Example 58, 2.25 g) was separated by chiral SFC (stationary phase: Chiralpak AD-H, 2×25 cm, Mobile phase: 65% $CO_2$, 35% EtOH) to afford two enantiomers. The first eluting isomer (1.01 g) was designated (*S): $^1$H NMR (500 MHz, CDCl₃) δ 8.51-8.47 (m, 1H), 8.43-8.38 (m, 1H), 8.13-8.08 (m, 1H), 7.60-7.52 (m, 2H), 7.34-7.29 (m, 1H), 7.19-7.15 (m, 1H), 5.02 (s, 1H), 4.65-4.53 (m, 2H), 4.51-4.45 (m, 1H), 4.31-4.23 (m, 1H), 3.98-3.87 (m, 2H), 3.60-3.43 (m, 2H), 3.43-3.23 (m, 2H), 2.85 (s, 3H), 2.39 (s, 3H), 1.57-1.44 (m, 5H), 1.41-1.22 (m, 8H).

Example 60: (*R)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(1-ethyl-4-methyl-1H-benzo[d][1,2,3]triazol-5-yl)-2,2-dimethylpropanoic Acid

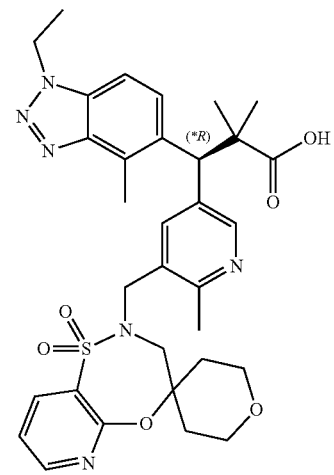 [SMILES: CCn1nnc2c(C)c([C@H](c3cnc(C)c(CN4CC5(CCOCC5)Oc5ncccc5S4(=O)=O)c3)C(C)(C)C(=O)O)ccc21]

The second eluting isomer (1.04 g) from the separation of isomers by chiral SFC described in Example 59 was designated (*R): $^1$H NMR (500 MHz, CDCl₃) δ 8.49-8.44 (m, 1H), 8.43-8.40 (m, 1H), 8.12-8.07 (m, 1H), 7.59-7.52 (m, 2H), 7.34-7.28 (m, 1H), 7.20-7.16 (m, 1H), 5.00 (s, 1H), 4.63-4.53 (m, 2H), 4.53-4.43 (m, 1H), 4.28-4.22 (m, 1H), 3.99-3.87 (m, 2H), 3.59-3.42 (m, 2H), 3.42-3.23 (m, 2H), 2.83 (s, 3H), 2.39 (s, 3H), 1.56-1.45 (m, 5H), 1.41-1.21 (m, 8H).

Example 61: (R/S)-3-(1-Ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic Acid

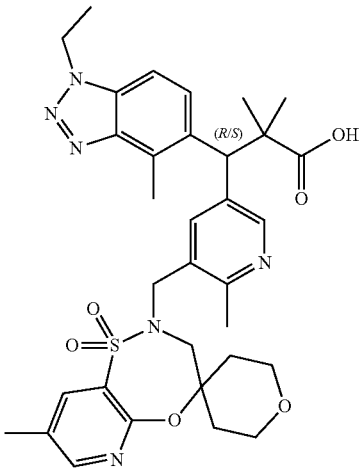 [SMILES: CCn1nnc2c(C)c(C(c3cnc(C)c(CN4CC5(CCOCC5)Oc5ncc(C)cc5S4(=O)=O)c3)C(C)(C)C(=O)O)ccc21]

Step A: Methyl 2,2-dimethyl-3-(8-methyl-3-(trifluoromethyl)-[1,2,4]triazolo[4,3-a]pyridin-7-yl)-3-(5-methyl-4-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoate. A solution of methyl 3-(1-ethyl-4-methyl-1H-benzo[d][1,2,3]triazol-5-yl)-3-(5-(hydroxymethyl)-6-methylpyridin-3-yl)-2,2-dimethylpropanoate (Intermediate 51, 1.5 g, 3.8 mmol), 8'-methyl-2,2',3,3',5,6-hexahydrospiro[pyran-4,4'-pyrido[2,3-b][1,4,5]oxathiazepine] 1',1'-dioxide (Intermediate 37, 1.3 g, 4.7 mmol), and triphenylphosphine (1.6 g, 6.0 mmol) in THF (41 mL) and DMF (5 ml) was stirred at room temperature for 5 minutes. DBAD (1.4 g, 6.1 mmol) was added and the solution was stirred at room temperature for 30 minutes. The reaction mixture was then concentrated and purified by flash column chromatography (0-100% ethyl acetate/hexanes, gradient elution) to afford the title compound (2.5 g, 99% yield). MS (ESI): mass calcd. for $C_{34}H_{43}N_6O_6S$, 662.3; m/z found, 663.3 $[M+H]^+$.

Step B: (R/S)-3-(1-Ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid. Lithium hydroxide (0.45 g, 18.9 mmol) was added to a solution of methyl 2,2-dimethyl-3-(8-methyl-3-(trifluoromethyl)-[1,2,4]triazolo[4,3-a]pyridin-7-yl)-3-(5-methyl-4-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoate (2.5 g, 3.8 mmol) in MeOH (30 mL), THF (60 mL) and water (30 mL). The reaction was stirred at 75° C. overnight then allowed to cool to room temperature. 1 M aqueous HCl solution was added until the pH was approximately 6. DCM was then added and the resulting biphasic mixture was separated. The aqueous layer was extracted with DCM. These extractions resulted in several organic solvent fractions which were combined, dried over MgSO$_4$, filtered, and concentrated to dryness under reduced pressure. The product was purified by flash column chromatography (0-10% MeOH/DCM, gradient elution) to provide the title compound to provide the title compound (2.35 g, 96% yield). MS (ESI): mass calcd. for $C_{33}H_{40}N_6O_6S$, 648.3; m/z found, 649.3 $[M+H]^+$. $^1$H NMR (600 MHz, CDCl$_3$) δ 8.52 (d, J=2.2 Hz, 1H), 8.28 (d, J=2.4 Hz, 1H), 7.97 (d, J=2.4 Hz, 1H), 7.72-7.66 (m, 2H), 7.40 (d, J=8.7 Hz, 1H), 5.07 (s, 1H), 4.65 (qd, J=7.1, 3.5 Hz, 2H), 4.52 (d, J=15.5 Hz, 1H), 4.35 (d, J=15.6 Hz, 1H), 4.03-3.93 (m, 2H), 3.63-3.57 (m, 1H), 3.51 (dd, J=12.0, 4.4 Hz, 1H), 3.45 (s, 1H), 3.41-3.37 (m, 2H), 2.87 (s, 3H), 2.38 (s, 3H), 1.63-1.53 (m, 6H), 1.39-1.33 (m, 1H), 1.32 (s, 3H), 1.27 (dd, J=12.3, 4.3 Hz, 1H), 1.24 (s, 3H), 1.20-1.14 (m, 1H).

Example 62: (*S)-3-(1-Ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic Acid

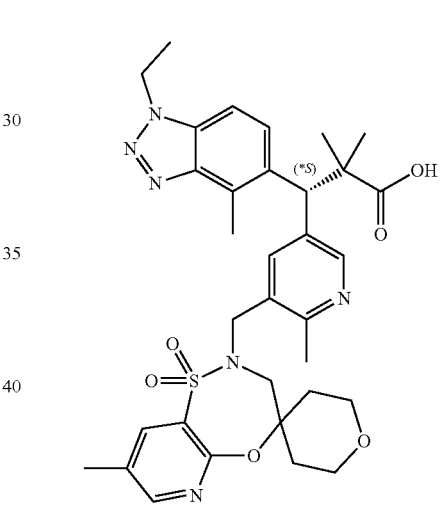

The mixture of (R/S)-3-(1-ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid isomers (Example 61, 2.35 g) was separated by chiral SFC (stationary phase: Chiralpak IC 5 μm 2×25 cm, Mobile phase: 60% CO$_2$, 40% MeOH) to afford two enantiomers. The first eluting isomer (1.1 g) was designated (*S): MS: mass calcd. $C_{33}H_{40}N_6O_6S$, 648.3; m/z found, 649.3 $[M+H]^+$. $^1$H NMR (600 MHz, CDCl$_3$) δ 8.48 (d, J=2.2 Hz, 1H), 8.22-8.18 (m, 1H), 7.89 (d, J=2.4 Hz, 1H), 7.60-7.53 (m, 2H), 7.31 (d, J=8.7 Hz, 1H), 5.02 (s, 1H), 4.58 (qd, J=7.0, 5.3 Hz, 2H), 4.46 (d, J=15.4 Hz, 1H), 4.26 (d, J=15.4 Hz, 1H), 3.91-3.83 (m, 2H), 3.56 (d, J=10.9 Hz, 1H), 3.43 (d, J=21.4 Hz, 1H), 3.33 (s, 2H), 2.85 (s, 3H), 2.39 (s, 3H), 2.31 (s, 3H), 1.56-1.44 (m, 4H), 1.39 (s, 4H), 1.27 (dd, J=12.3, 4.3 Hz, 1H), 1.24 (s, 3H), 1.20-1.14 (m, 1H).

Example 63: (*R)-3-(1-Ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic Acid

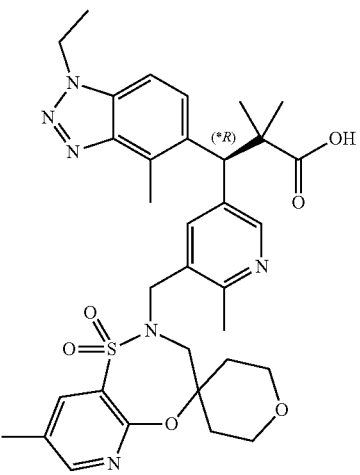 [SMILES: CCn1nnc2c(C)c([C@H](c3cnc(C)c(CN4CC5(CCOCC5)Oc5ncc(C)cc5S4(=O)=O)c3)C(C)(C)C(=O)O)ccc21]

The second eluting isomer (1.1 g) from the separation of isomers by chiral SFC described in Example 62 was designated (*R): MS: mass calcd. $C_{33}H_{40}N_6O_6S$, 648.3; m/z found, 649.3 [M+H]$^+$. $^1$H NMR (600 MHz, CDCl$_3$) δ 8.48 (d, J=2.2 Hz, 1H), 8.22-8.18 (m, 1H), 7.89 (d, J=2.4 Hz, 1H), 7.60-7.53 (m, 2H), 7.31 (d, J=8.7 Hz, 1H), 5.02 (s, 1H), 4.58 (qd, J=7.0, 5.3 Hz, 2H), 4.46 (d, J=15.4 Hz, 1H), 4.26 (d, J=15.4 Hz, 1H), 3.91-3.83 (m, 2H), 3.56 (d, J=10.9 Hz, 1H), 3.43 (d, J=21.4 Hz, 1H), 3.33 (s, 2H), 2.85 (s, 3H), 2.39 (s, 3H), 2.31 (s, 3H), 1.56-1.44 (m, 4H), 1.39 (s, 4H), 1.27 (dd, J=12.3, 4.3 Hz, 1H), 1.24 (s, 3H), 1.20-1.14 (m, 1H).

Example 64: (*R)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

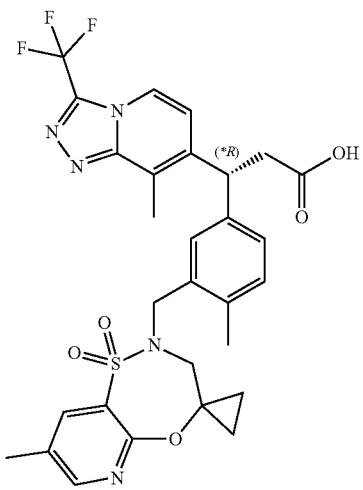 [SMILES: Cc1cnc2c(c1)S(=O)(=O)N(Cc1cc([C@@H](CC(=O)O)c3ccn4c(C(F)(F)F)nnc4c3C)ccc1C)CC1(CC1)O2]

A solution of ethyl (*R)-3-(3-(hydroxymethyl)-4-methylphenyl)-3-(8-methyl-3-(trifluoromethyl)-[1,2,4]triazolo[4,3-a]pyridin-7-yl)propanoate (Intermediate 27, 240 mg, 0.570 mmol), 8'-methyl-2',3'-dihydrospiro[cyclopropane-1,4'-pyrido[2,3-5 b][1,4,5]oxathiazepine]1',1'-dioxide (Intermediate 6, 137 mg, 0.570 mmol), and triphenylphosphine (131 mg, 0.570 mmol) in THF (10 mL) was stirred at room temperature for 5 minutes. DBAD (149 mg, 0.570 mmol) was added and the solution was stirred at room temperature for 2 hours. Saturated NaHCO$_3$(10 mL) was added and the aqueous layer was extracted with EtOAc (15 mL×3). These extractions resulted in several organic solvent fractions which were combined and concentrated under reduced pressure. The resulting residue was dissolved in THF (2 mL) and NaOH (2M, 2 mL) was added to it. The mixture was stirred at room temperature for 24 hours. Water (5 mL) was then added, and the pH of the mixture was adjusted to about 3-4 by adding 1 M aqueous HCl solution. This solution was extracted with EtOAc (4 mL×3). These extractions resulted in several organic solvent fractions which were combined and concentrated. The residue was purified by flash column chromatography (10% methanol/CH$_2$Cl$_2$, gradient elution) to provide the title compound (180 mg, 51%). MS (ESI): mass calcd. for $C_{29}H_{28}F_3N_5O_5S$, 615.2; m/z found, 616.2 [M+H]$^+$. $^1$H NMR (500 MHz, CD$_3$OD) δ 8.30 (d, J=7.2 Hz, 1H), 8.25 (dd, J=2.4, 0.8 Hz, 1H), 8.14 (dd, J=2.4, 0.8 Hz, 1H), 7.22 (dd, J=7.9, 2.0 Hz, 1H), 7.16 (dd, J=7.7, 2.5 Hz, 2H), 7.02 (d, J=2.0 Hz, 1H), 5.01-4.91 (m, 1H), 4.37-4.21 (m, 2H), 3.57-3.37 (m, 2H), 3.03-2.83 (m, 2H), 2.73 (s, 3H), 2.41 (s, 3H), 2.29 (s, 3H), 1.09-0.82 (m, 2H), 0.52-0.40 (m, 2H).

Example 65: 3-(1-(Cyclopropylmethyl)-4-(difluoromethyl-1H-benzo[d][1,2,3]triazol-5-yl)-3-(3-((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic Acid

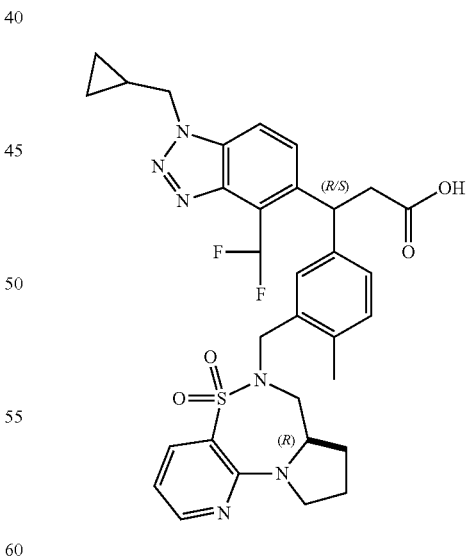

The title compound (240 mg, 82%) was prepared using analogous conditions as described in Example 11 where ethyl 3-(1-(cyclopropylmethyl)-4-(difluoromethyl)-1H-benzo[d][1,2,3]triazol-5-yl)-3-(3-(hydroxymethyl)-4-methylphenyl)propanoate (Intermediate 58) was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and (R)-6,7,7a,8,9,10-hexahydropyrido[2,3-f]pyrrolo[2,1-d][1,2,5]thiadiazepine 5,5-dioxide (Intermediate 4) was used instead of (*S)-7a-methyl-6,7,7a,8,9,19-hexahydropyrido[2,3-f]pyrollo[2,1-d][1,2,5]thiadiazepine 5,5-dioxide (Intermediate 39) in step B. MS (ESI): mass calcd. for $C_{32}H_{34}F_2N_6O_4S$, 636.2; m/z found, 637.1 [M+H]$^+$. $^1$H NMR (400 MHz, CDCl$_3$) δ 8.30-8.27 (m, 1H), 8.09-8.05 (m, 1H), 8.03 (d, J=2.1 Hz, 1H), 7.90-7.76 (m, 1H), 7.58 (d, J=8.57 Hz, 1H), 7.36 (dd, J=8.7, 3.1 Hz, 1H), 7.25-7.17 (m, 1H), 7.18-7.09 (m, 1H), 6.83-6.76 (m, 1H), 5.40-5.34 (m, 1H), 4.65-4.37 (m, 4H), 4.10 (d, J=14.0 Hz, 1H), 3.65-3.56 (m, 2H), 3.37-2.97 (m, 3H), 2.94-2.76 (m, 1H), 2.28 (d, J=11.0 Hz, 3H), 2.09-1.44 (m, 3H), 1.26 (d, J=6.3 Hz, 2H), 0.70-0.59 (m, 2H), 0.53-0.41 (m, 2H).

Example 66: (*S)-3-(1-(Cyclopropylmethyl)-4-(difluoromethyl-1H-benzo[d][1,2,3]triazol-5-yl)-3-(3-((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic Acid

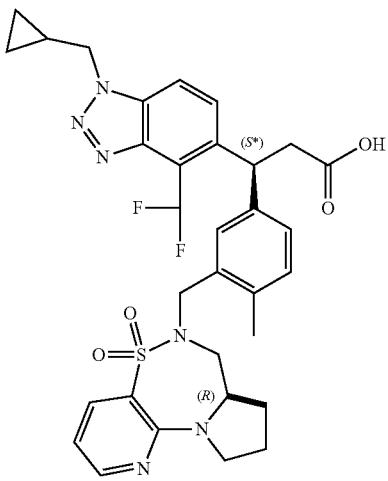

The mixture of 3-(1-(cyclopropylmethyl)-4-(difluoromethyl-1H-benzo[d][1,2,3]triazol-5-yl)-3-(3-((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid isomers (Example 65) was separated by chiral SFC (Stationary phase: Chiralpak AD-H 5 μm 250*30 mm, Mobile phase: 50% CO$_2$, 50% EtOH) to afford two diastereomers. The first eluting isomer (78 mg) was designated *S: MS (ESI): mass calcd. for $C_{32}H_{34}F_2N_6O_4S$, 636.2; m/z found, 637.1 [M+H]$^+$. $^1$H NMR (400 MHz, CDCl$_3$) δ 8.29 (dd, J=4.7, 1.8 Hz, 1H), 8.07 (dd, J=7.7, 1.8 Hz, 1H), 8.03-7.75 (m, 1H), 7.58 (d, J=8.7 Hz, 1H), 7.35 (d, J=8.7 Hz, 1H), 7.24-7.09 (m, 3H), 6.80 (dd, J=7.7, 4.7 Hz, 1H), 5.36 (t, J=7.7 Hz, 1H), 4.59-4.37 (m, 4H), 4.10 (d, J=14.0 Hz, 1H), 3.65-3.54 (m, 2H), 3.22-3.15 (m, 2H), 3.07-2.96 (m, 1H), 2.90-2.73 (m, 1H), 2.29 (s, 3H), 1.99-1.85 (m, 1H), 1.77-1.52 (m, 2H), 1.42-1.20 (m, 2H), 0.68-0.62 (m, 2H), 0.53-0.43 (m, 2H).

Example 67: 3-(1-(Cyclopropylmethyl)-4-methyl-1H-benzo[d][1,2,3]triazol-5-yl)-3-(3-((1',1'-dioxidospiro[oxetane-3,3'-pyrido[2,3-b][1,4,5]oxathiazepin]-2'(3'H)-yl)methyl)-4-methylphenyl)propanoic Acid

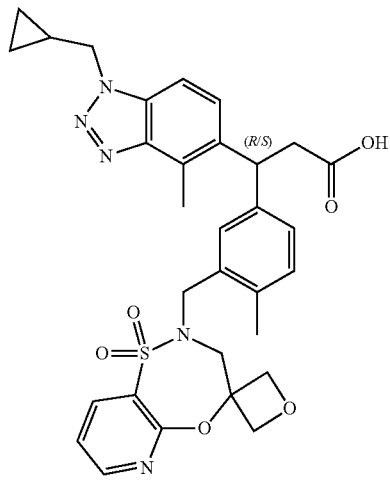 [SMILES: Cc1ccc(C(CC(=O)O)c2ccc3c(nnn3CC3CC3)c2C)cc1CN1CC2(COC2)Oc2ncccc2S1(=O)=O]

The title compound (190 mg, 90% yield) was prepared using analogous conditions as described in Example 11 where 2',3'-dihydrospiro[oxetane-3,4'-pyrido[2,3-b][1,4,5]oxathiazepine] 1',1'-dioxide (Intermediate 59) was used instead of (*S)-7a-methyl-6,7,7a,8,9,19-hexahydropyrido[2,3-f]pyrollo[2,1-d][1,2,5]thiadiazepine 5,5-dioxide (Intermediate 39) in step B. MS (ESI): mass calcd. for $C_{31}H_{33}N_5O_6S$, 603.2; m/z found, 604.1 [M+H]$^+$. $^1$H NMR (400 MHz, CDCl$_3$) δ 8.56-8.55 (m, 1H), 8.27-8.24 (m, 1H), 7.46-7.38 (m, 2H), 7.36-7.34 (m, 1H), 7.23 (d, J=1.9 Hz, 1H), 7.09 (d, J=7.8 Hz, 1H), 6.97 (dd, J=7.8, 1.9 Hz, 1H), 4.92-4.76 (m, 3H), 4.69 (d, J=13.7 Hz, 1H), 4.48 (d, J=7.1 Hz, 2H), 4.44-4.29 (m, 2H), 4.22-4.02 (m, 1H), 4.00-3.76 (m, 2H), 3.14-2.98 (m, 2H), 2.72 (s, 3H), 2.25 (s, 3H), 1.42-1.35 (m, 1H), 0.67-0.60 (m, 2H), 0.50-0.46 (m, 2H).

Example 68: (*R)-3-(1-(Cyclopropylmethyl)-4-(difluoromethyl-1H-benzo[d][1,2,3]triazol-5-yl)-3-(3-((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic Acid

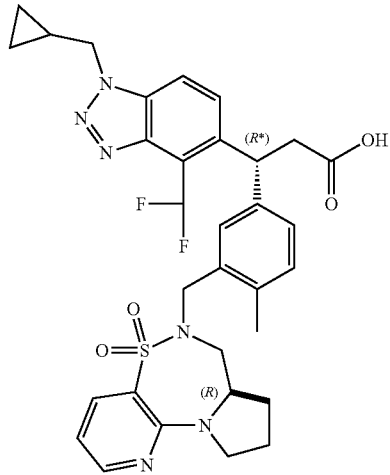

The mixture of 3-(1-(cyclopropylmethyl)-4-(difluoromethyl-1H-benzo[d][1,2,3]triazol-5-yl)-3-(3-((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid isomers (Example 65) was separated by chiral SFC (Stationary phase: Chiralpak AD-H 5 μm 250*30 mm, Mobile phase: 50% CO₂, 50% EtOH) to afford two diastereomers. The second eluting isomer (72 mg) was designated *R: MS (ESI): mass calcd. for $C_{32}H_{34}F_2N_6O_4S$, 636.2; m/z found, 637.1 [M+H]⁺. ¹H NMR (400 MHz, CDCl₃) δ 8.28 (dd, J=4.7, 1.8 Hz, 1H), 8.06 (dd, J=7.8, 1.8 Hz, 1H), 8.03-7.75 (m, 1H), 7.58 (d, J=8.8 Hz, 1H), 7.36 (d, J=8.8 Hz, 1H), 7.24-7.09 (m, 3H), 6.79 (dd, J=7.8, 4.8 Hz, 1H), 5.37 (t, J=7.7 Hz, 1H), 4.68-4.35 (m, 4H), 4.10 (d, J=14.2 Hz, 1H), 3.65-3.55 (m, 2H), 3.39-3.15 (m, 2H), 3.10-2.96 (m, 1H), 2.87 (t, J=12.7 Hz, 1H), 2.27 (s, 3H), 2.04-1.69 (m, 2H), 1.49 (dd, J=12.4, 6.5 Hz, 1H), 1.42-1.19 (m, 2H), 0.70-0.61 (m, 2H), 0.47 (dt, J=6.1, 4.9 Hz, 2H).

Example 69: (*S)-3-(1-(Cyclopropylmethyl)-4-methyl-1H-benzo[d][1,2,3]triazol-5-yl)-3-(3-((1',1'-dioxidospiro[oxetane-3,4'-pyrido[2,3-b][1,4,5]oxathiazepin-2'(3'H)-yl)methyl)-4-methylphenyl) propanoic Acid

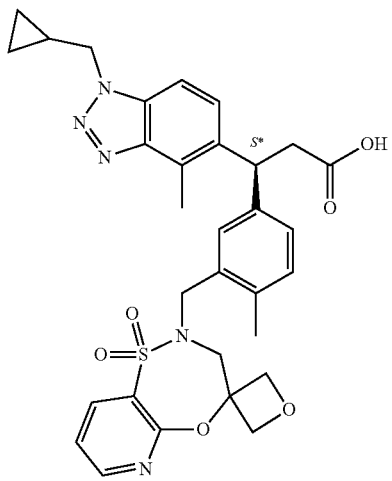 [SMILES: Cc1ccc([C@H](CC(=O)O)c2ccc3c(nnn3CC3CC3)c2C)cc1CN1CC2(COC2)Oc2ncccc2S1(=O)=O]

3-(1-(cyclopropylmethyl)-4-methyl-1H-benzo[d][1,2,3]triazol-5-yl)-3-(3-((1',1'-dioxidospiro[oxetane-3,3'-pyrido[2,3-b][1,4,5]oxathiazepin]-2'(3'H)-yl)methyl)-4-methylphenyl)propanoic acid isomers (Example 67) were separated by chiral SFC (Stationary phase: Chiralpak AD-H 5 μm 250*30 mm, Mobile phase: 50% CO₂, 50% EtOH) to afford two enantiomers. The first eluting isomer (63 mg) was designated *S: MS (ESI): mass calcd. for $C_{31}H_{33}N_5O_6S$, 603.2; m/z found, 604.2 [M+H]⁺. ¹H NMR (600 MHz, CDCl₃) δ 8.56 (dd, J=4.9, 1.9 Hz, 1H), 8.26 (dd, J=7.6, 2.0 Hz, 1H), 7.46-7.38 (m, 2H), 7.35 (dd, J=7.6, 4.9 Hz, 1H), 7.24 (d, J=1.9 Hz, 1H), 7.09 (d, J=7.9 Hz, 1H), 6.97 (dd, J=7.8, 1.9 Hz, 1H), 4.91-4.80 (m, 3H), 4.71 (d, J=13.6 Hz, 1H), 4.48 (d, J=7.1 Hz, 2H), 4.42 (d, J=7.6 Hz, 1H), 4.34 (d, J=7.5 Hz, 1H), 4.16 (d, J=13.6 Hz, 1H), 3.98-3.91 (m, 1H), 3.84-3.78 (m, 1H), 3.14-2.99 (m, 2H), 2.72 (s, 3H), 2.26 (s, 3H), 1.43-1.33 (m, 1H), 0.69-0.60 (m, 2H), 0.54-0.45 (m, 2H).

Example 70: (*R)-3-(1-(Cyclopropylmethyl)-4-methyl-1H-benzo[d][1,2,3]triazol-5-yl)-3-(3-((1',1'-dioxidospiro[oxetane-3,4'-pyrido[2,3-b][1,4,5]oxathiazepin-2'(3'H)-yl)methyl)-4-methylphenyl) propanoic Acid

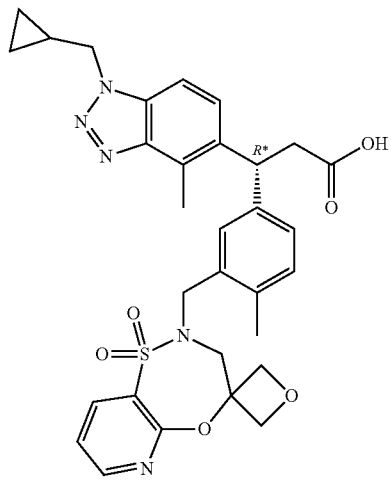 [SMILES: Cc1ccc([C@@H](CC(=O)O)c2ccc3c(nnn3CC3CC3)c2C)cc1CN1CC2(COC2)Oc2ncccc2S1(=O)=O]

The mixture of 3-(4-(difluoromethyl-1-methyl-1H-benzo[d][1,2,3]triazol-5-yl)-3-(3-(((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid isomers (Example 67) was separated by chiral SFC (Stationary phase: Chiralpak AD-H 5 μm 250*30 mm, Mobile phase: 50% CO₂, 50% EtOH) to afford two enantiomers. The second eluting isomer (70 mg) was designated *R: MS (ESI): mass calcd. for $C_{31}H_{33}N_5O_6S$, 603.2; m/z found, 604.2 [M+H]⁺. ¹H NMR (600 MHz, CDCl₃) δ 8.56 (dd, J=4.9, 1.9 Hz, 1H), 8.26 (dd, J=7.6, 2.0 Hz, 1H), 7.46-7.38 (m, 2H), 7.35 (dd, J=7.6, 4.9 Hz, 1H), 7.24 (d, J=1.9 Hz, 1H), 7.09 (d, J=7.9 Hz, 1H), 6.97 (dd, J=7.8, 1.9 Hz, 1H), 4.91-4.80 (m, 3H), 4.71 (d, J=13.6 Hz, 1H), 4.48 (d, J=7.1 Hz, 2H), 4.42 (d, J=7.6 Hz, 1H), 4.34 (d, J=7.5 Hz, 1H), 4.16 (d, J=13.6 Hz, 1H), 3.98-3.91 (m, 1H), 3.84-3.78 (m, 1H), 3.14-2.99 (m, 2H), 2.72 (s, 3H), 2.26 (s, 3H), 1.43-1.33 (m, 1H), 0.69-0.60 (m, 2H), 0.54-0.45 (m, 2H).

Example 71: 3-(4-(Difluoromethyl-1-methyl-1H-benzo[d][1,2,3]triazol-5-yl)-3-(3-(((R-5,5-dioxido-7a,8,9,10-tetrahydropyridi[2,3-f]pyrrolo[2,1-d][1,2,5]thiadiazepin-6(7H)-yl)methyl)-4-methylphenyl) propanoic Acid

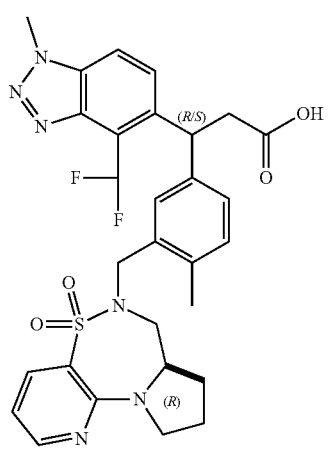

The title compound (202 mg, 98% yield) was prepared using analogous conditions as described in Example 11 where ethyl 3-(4-difluoromethyl)-1-methyl-1H-benzo[d][1,2,3]triazol-5-yl)-3-(3-hydroxymethyl)-4-methylphenyl)propanoate (Intermediate 60) was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and (R)-6,7,7a,8,9,10-hexahydropyrido[2,3-f]pyrrolo[2,1-d][1,2,5]thiadiazepine 5,5-dioxide (Intermediate 4) was used instead of (*S)-7a-methyl-6,7,7a,8,9,19-hexahydropyrido[2,3-f]pyrollo[2,1-d[1,2,5]thiadiazepine 5,5-dioxide (Intermediate 39), in step B. MS (ESI): mass calcd. for $C_{29}H_{30}F_2N_6O_4S$, 596.2; m/z found, 597.1 [M+H]$^+$. $^1$H NMR (400 MHz, CDCl$_3$) δ 8.32-8.24 (m, 1H), 8.10-8.01 (m, 1H), 8.00-7.72 (m, 1H), 7.53 (dd, J=8.6, 1.3 Hz, 1H), 7.38 (dd, J=8.7, 1.4 Hz, 1H), 7.22-7.09 (m, 3H), 6.84-6.74 (m, 1H), 5.38-5.32 (m, 1H), 4.66-4.37 (m, 2H), 4.28 (d, J=3.1 Hz, 3H), 4.18-4.05 (m, 1H), 3.74-3.50 (m, 3H), 3.39-2.97 (m, 3H), 2.92-2.78 (m, 1H), 2.28 (d, J=10.3 Hz, 1H), 2.30-2.10 (m, 2H), 2.03-1.73 (m, 2H), 1.55-1.32 (m, 1H).

Example 72: (*S)-3-(4-(Difluoromethyl-1-methyl-1H-benzo[d][1,2,3]triazol-5-yl)-3-(3-(((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic Acid

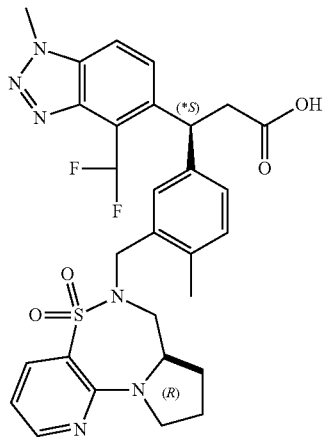

The mixture of 3-(4-(difluoromethyl-1-methyl-1H-benzo[d][1,2,3]triazol-5-yl)-3-(3-(((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid isomers (Example 71) was separated by chiral SFC (Stationary phase: Chiralpak AD-H 5 μm 250*30 mm, Mobile phase: 60% CO$_2$, 40% EtOH) to afford two enantiomers. The first eluting isomer (88 mg) was designated *S: MS (ESI): mass calcd. for $C_{29}H_{30}F_2N_6O_4S$, 596.2; m/z found, 597.1 [M+H]$^+$. $^1$H NMR (400 MHz, CDCl$_3$) δ 8.32-8.24 (m, 1H), 8.08-7.99 (m, 1H), 8.00-7.69 (m, 1H), 7.52 (d, J=8.7 Hz, 1H), 7.37 (d, J=8.8 Hz, 1H), 7.15 (d, J=5.0 Hz, 2H), 7.07 (d, J=8.2 Hz, 1H), 6.80-6.75 (m, 1H), 5.26 (t, J=7.6 Hz, 1H), 4.52-4.43 (m, 1H), 4.38 (d, J=14.0 Hz, 1H), 4.30-4.05 (s, 3H), 3.75-3.50 (m, 2H), 3.25-2.75 (m, 3H), 2.25 (s, 3H), 2.04-1.85 (m, 1H), 1.79-1.52 (m, 2H), 1.41-1.18 (m, 1H), 0.93 (s, 2H).

Example 73: (*R) 3-(4-(Difluoromethyl-1-methyl-1H-benzo[d][1,2,3]triazol-5-yl)-3-(3-(((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic Acid

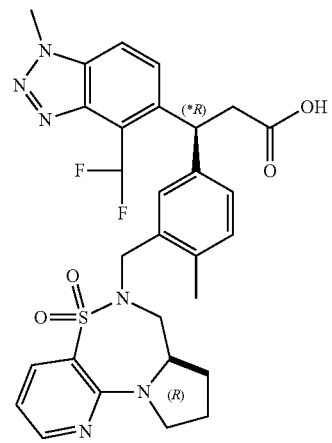

The mixture of 3-(4-(difluoromethyl-1-methyl-1H-benzo[d][1,2,3]triazol-5-yl)-3-(3-(((R-5,5-dioxido-7a,8,9,10-tetrahydropyridi[2,3-f]pyrrolo[2,1-d][1,2,5]thiadiazepin-6(7H)-yl)methyl)-4-methylphenyl)propanoic acid isomers (Example 71) was separated by chiral SFC (Stationary phase: Chiralpak AD-H 5 μm 250*30 mm, Mobile phase: 60% CO$_2$, 40% EtOH) to afford two enantiomers. The second eluting isomer (82 mg) was designated *R: MS (ESI): mass calcd. for $C_{29}H_{30}F_2N_6O_4S$, 596.2; m/z found, 597.1 [M+H]$^+$. $^1$H NMR (400 MHz, CDCl$_3$) δ 8.32-8.24 (m, 1H), 8.08-7.99 (m, 1H), 8.00-7.69 (m, 1H), 7.52 (d, J=8.7 Hz, 1H), 7.37 (d, J=8.8 Hz, 1H), 7.15 (d, J=5.0 Hz, 2H), 7.07 (d, J=8.2 Hz, 1H), 6.80-6.75 (m, 1H), 5.26 (t, J=7.6 Hz, 1H), 4.52-4.43 (m, 1H), 4.38 (d, J=14.0 Hz, 1H), 4.30-4.05 (s, 3H), 3.75-3.50 (m, 2H), 3.25-2.75 (m, 3H), 2.25 (s, 3H), 2.04-1.85 (m, 1H), 1.79-1.52 (m, 2H), 1.41-1.18 (m, 1H), 0.93 (s, 2H).

Example 74: 3-(1-(Cyclopropylmethyl)-4-methyl-1H-benzo[d][1,2,3]triazol-5-yl)-3-(3-((1',1'-dioxidospiro[benzo[b][1,4,5]oxathiazepin-4,3'-oxetan]-2,(3H)-yl)methyl)-4-methylphenyl)propanoic Acid

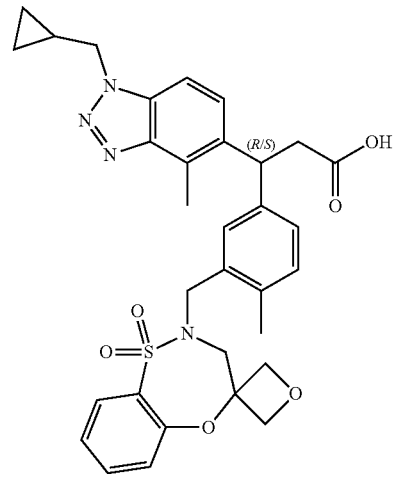 [SMILES: Cc1ccc(C(CC(=O)O)c2ccc3c(nnn3CC3CC3)c2C)cc1CN1CC2(COC2)Oc2ccccc2S1(=O)=O]

The title compound (360 mg, 93% yield) was prepared using analogous conditions as described in Example 11 where 2,3-dihydrospiro[benzo[b][1,4,5]oxathiazepine-4,3'-oxetane]1,1'-dioxide (Intermediate 7) was used instead of (*S)-7a-methyl-6,7,7a,8,9,19-hexahydropyrido[2,3-f]pyrollo[2,1-d][1,2,5]thiadiazepine 5,5-dioxide (Intermediate 39) in step B. MS (ESI): mass calcd. for $C_{32}H_{34}N_4O_6S$, 602.2; m/z found, 603.1 [M+H]⁺. $^1$H NMR (400 MHz, CDCl$_3$) δ 7.90 (dd, J=7.8, 1.7 Hz, 1H), 7.61-7.51 (m, 1H), 7.47-7.20 (m, 4H), 7.23-7.21 (m, 1H), 7.08 (d, J=7.8 Hz, 1H), 6.93 (dd, J=7.8, 1.9 Hz, 1H), 5.00-4.82 (m, 1H), 4.76-4.69 (m, 3H), 4.48 (d, J=7.0 Hz, 2H), 4.41 (d, J=7.7 Hz, 1H), 4.37-4.26 (m, 1H), 4.10-3.70 (m, 3H), 3.14-2.96 (m, 2H), 2.71 (s, 3H), 2.27 (s, 3H), 1.46-1.34 (m, 1H), 0.70-0.59 (m, 2H), 0.53-0.44 (m, 2H).

Example 75: 3-(1-(Cyclopropylmethyl)-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic Acid

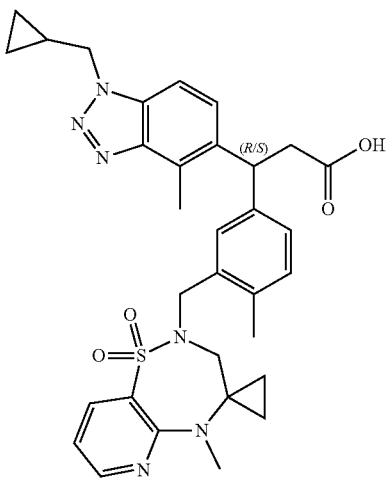 [SMILES: Cc1ccc(C(CC(=O)O)c2ccc3c(nnn3CC3CC3)c2C)cc1CN1CC2(CC2)N(C)c2ncccc2S1(=O)=O]

The title compound (351 mg) was prepared using analogous conditions as described in Example 11 where 5'-methyl-2',3'-dihydro-5'H-spiro[cyclopropane-1,4'-pyrido[2,3-f][1,2,5]thiadiazepine] 1',1'-dioxide (Intermediate 61) was used instead of (*S)-7a-methyl-6,7,7a,8,9,19-hexahydropyrido[2,3-]pyrollo[2,1-d][1,2,5]thiadiazepine 5,5-dioxide (Intermediate 39) in step B. MS (ESI): mass calcd. for $C_{32}H_{36}N_6O_4S$, 600.2; m/z found, 600.9 [M+H]⁺. $^1$H NMR (400 MHz, CDCl$_3$) δ 8.27-8.22 (m, 1H), 8.12-8.06 (m, 1H), 7.39-7.30 (m, 2H), 7.14 (d, J=1.6 Hz, 1H), 7.07 (s, 2H), 6.87 (dd, J=7.8, 4.7 Hz, 1H), 4.97 (t, J=7.8 Hz, 1H), 4.46 (d, J=7.0 Hz, 2H), 4.34 (s, 1H), 3.24-3.01 (m, 4H), 2.94 (s, 3H), 2.82 (s, 3H), 2.23 (s, 3H), 1.43-1.13 (m, 2H), 0.96-0.80 (m, 4H), 0.67-0.57 (m, 2H), 0.50-0.43 (m, 2H).

Example 76: (*R)-3-(1-(cyclopropylmethyl)-4-methyl-1H-benzo[d][1,2,3]triazol-5-yl)-3-(3-((1',1'-dioxidospiro[benzo[b][1,4,5]oxathiazepin-4,3'-oxetan]-2,(3H)-yl)methyl)-4-methylphenyl)propanoic Acid

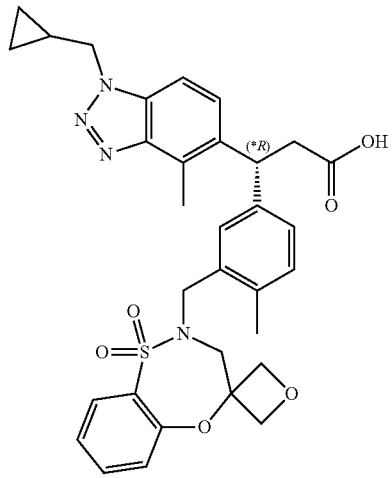 [SMILES: Cc1ccc([C@@H](CC(=O)O)c2ccc3c(nnn3CC3CC3)c2C)cc1CN1CC2(COC2)Oc2ccccc2S1(=O)=O]

The mixture of 3-(1-(cyclopropylmethyl)-4-methyl-1H-benzo[d][1,2,3]triazol-5-yl)-3-(3-((1',1'-dioxidospiro[benzo[b][1,4,5]oxathiazepin-4,3'-oxetan]-2,(3H)-yl)methyl)-4-methylphenyl)propanoic acid isomers (Example 74) was separated by chiral SFC (Stationary phase: Chiralpak AD-H 5 μm 250*30 mm, Mobile phase: 55% CO$_2$, 45% MeOH) to afford two enantiomers. The second eluting isomer (145 mg) was designated *R: MS (ESI): mass calcd. for $C_{32}H_{34}N_4O_6S$, 602.2; m/z found, 603.1 [M+H]⁺. $^1$H NMR (400 MHz, CDCl$_3$) δ 7.89 (dd, J=7.8, 1.7 Hz, 1H), 7.60-7.53 (m, 1H), 7.45-7.35 (m, 3H), 7.34-7.28 (m, 1H), 7.22 (d, J=2.0 Hz, 1H), 7.07 (d, J=7.8 Hz, 1H), 6.95 (dd, J=7.8, 1.9 Hz, 1H), 4.87 (dd, J=11.0, 5.2 Hz, 1H), 4.77-4.59 (m, 3H), 4.47 (d, J=7.0 Hz, 2H), 4.39 (d, J=7.6 Hz, 1H), 4.30 (d, J=7.4 Hz, 1H), 4.11 (d, J=13.7 Hz, 1H), 3.87-3.66 (m, 2H), 3.27-2.79 (m, 1H), 2.73 (s, 3H), 2.26 (s, 3H), 1.44-1.20 (m, 2H), 0.68-0.59 (m, 2H), 0.51-0.44 (m, 2H).

Example 77: (*S)-3-(1-(Cyclopropylmethyl)-4-methyl-1H-benzo[d][1,2,3]triazol-5-yl)-3-(3-((1',1'-dioxidospiro[benzo[b][1,4,5]oxathiazepin-4,3'-oxetan]-2,(3H)-yl)methyl)-4-methylphenyl)propanoic Acid

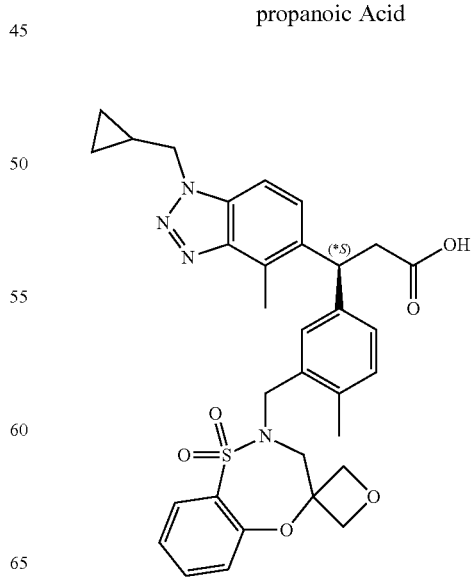

The mixture of 3-(1-(cyclopropylmethyl)-4-methyl-1H-benzo[d][1,2,3]triazol-5-yl)-3-(3-((1',1'-dioxidospiro[benzo[b][1,4,5]oxathiazepin-4,3'-oxetan]-2,(3H)-yl)methyl)-4-methylphenyl)propanoic acid isomers (Example 74) was separated by chiral SFC (Stationary phase: Chiralpak AD-H 5 μm 250*30 mm, Mobile phase: 55% $CO_2$, 45% MeOH) to afford two enantiomers. The first eluting isomer (137 mg) was designated *S: MS (ESI): mass calcd. for $C_{32}H_{34}N_4O_6S$, 602.2; m/z found, 603.1 [M+H]$^+$. $^1$H NMR (400 MHz, CDCl$_3$) δ 7.89 (dd, J=7.8, 1.7 Hz, 1H), 7.60-7.53 (m, 1H), 7.45-7.35 (m, 3H), 7.34-7.28 (m, 1H), 7.22 (d, J=2.0 Hz, 1H), 7.07 (d, J=7.8 Hz, 1H), 6.95 (dd, J=7.8, 1.9 Hz, 1H), 4.87 (dd, J=11.0, 5.2 Hz, 1H), 4.77-4.59 (m, 3H), 4.47 (d, J=7.0 Hz, 2H), 4.39 (d, J=7.6 Hz, 1H), 4.30 (d, J=7.4 Hz, 1H), 4.11 (d, J=13.7 Hz, 1H), 3.85 (d, J=15.4 Hz, 1H), 3.77-3.66 (m, 1H), 3.27-2.79 (m, 1H), 2.73 (s, 3H), 2.26 (s, 3H), 1.44-1.20 (m, 2H), 0.68-0.59 (m, 2H), 0.51-0.44 (m, 2H).

Example 78: (*S)-3-(1-(Cyclopropylmethyl)-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic Acid

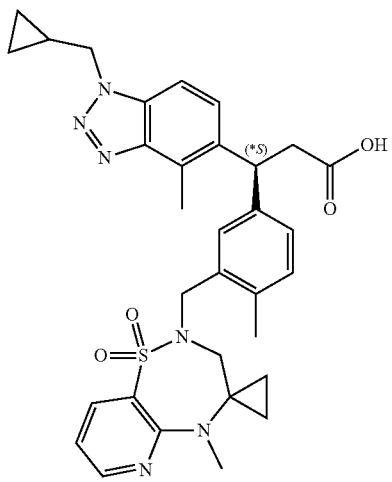 [SMILES: Cc1ccc([C@H](CC(=O)O)c2ccc3c(nnn3CC3CC3)c2C)cc1CN1CC2(CC2)N(C)c2ncccc2S1(=O)=O]

The mixture of 3-(1-(cyclopropylmethyl)-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid (Example 75) was separated by chiral SFC (Stationary phase: Chiralpak AD-H 5 μm 250*30 mm, Mobile phase: 55% $CO_2$, 45% MeOH) to afford two enantiomers. The first eluting isomer (116 mg) was designated *S: MS (ESI): mass calcd. for $C_{32}H_{36}N_6O_4S$, 600.2; m/z found, 600.9 [M+H]$^+$. $^1$H NMR (400 MHz, CDCl$_3$) δ 8.24 (dd, J=4.8, 1.8 Hz, 1H), 8.10 (dd, J=7.8, 1.8 Hz, 1H), 7.38-7.29 (m, 2H), 7.13 (d, J=1.7 Hz, 1H), 7.07 (s, 2H), 6.90-6.84 (m, 1H), 4.97 (t, J=7.9 Hz, 1H), 4.45 (d, J=7.0 Hz, 2H), 4.34 (s, 2H), 3.23-3.02 (m, 4H), 2.95 (s, 3H), 2.83 (s, 3H), 2.23 (s, 3H), 1.44-1.20 (m, 1H), 0.95-0.79 (m, 4H), 0.68-0.58 (m, 2H), 0.52-0.41 (m, 2H).

Example 79: (*R)-3-(1-(Cyclopropylmethyl)-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic Acid

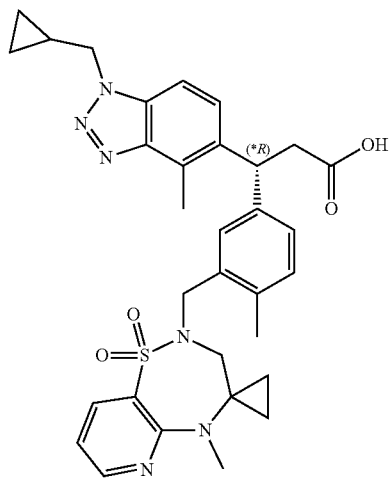 [SMILES: Cc1ccc([C@@H](CC(=O)O)c2ccc3c(nnn3CC3CC3)c2C)cc1CN1CC2(CC2)N(C)c2ncccc2S1(=O)=O]

The mixture of 3-(1-(cyclopropylmethyl)-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid (Example 75) was separated by chiral SFC (Stationary phase: Chiralpak AD-H 5 μm 250*30 mm, Mobile phase: 55% $CO_2$, 45% MeOH) to afford two enantiomers. The second eluting isomer (134 mg) was designated *R: MS (ESI): mass calcd. for $C_{32}H_{36}N_6O_4S$, 600.2; m/z found, 600.9 [M+H]$^+$. $^1$H NMR (400 MHz, CDCl$_3$) δ 8.24 (dd, J=4.6, 1.8 Hz, 1H), 8.10 (dd, J=7.8, 1.8 Hz, 1H), 7.34 (d, J=2.0 Hz, 2H), 7.14 (s, 1H), 7.07 (s, 2H), 6.87 (dd, J=7.8, 4.7 Hz, 1H), 4.96 (t, J=7.7 Hz, 1H), 4.45 (d, J=7.0 Hz, 2H), 4.34 (s, 2H), 3.27-3.00 (m, 4H), 2.95 (s, 3H), 2.82 (s, 3H), 2.23 (s, 3H), 1.42-1.22 (m, 1H), 0.91-0.81 (m, 4H), 0.67-0.59 (m, 2H), 0.51-0.42 (m, 2H).

Example 80: 3-(1-(Cyclopropylmethyl)-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

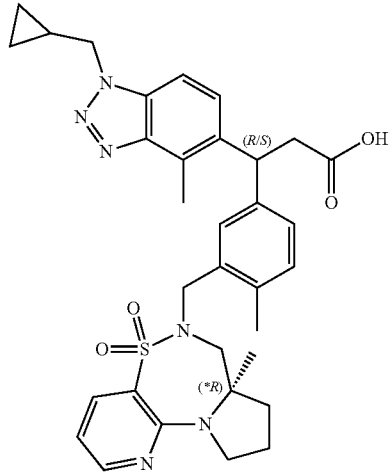 [SMILES: Cc1ccc(C(CC(=O)O)c2ccc3c(nnn3CC3CC3)c2C)cc1CN1C[C@@]2(C)CCCN2c2ncccc2S1(=O)=O]

The title compound (260 mg, 88%) was prepared using analogous conditions as described in Example 11 where (*R)-7a-methyl-6,7,7a,8,9,19-hexahydropyrido[2,3-f]pyrollo[2,1-d][1,2,5]thiadiazepine 5,5-dioxide (Intermediate 40) instead of (*S)-7a-methyl-6,7,7a,8,9,19-hexahydropyrido[2,3-f]pyrollo[2,1-d][1,2,5]thiadiazepine 5,5-dioxide (Intermediate 39) in step B. MS (ESI): mass calcd. for $C_{33}H_{38}N_6O_4S$, 614.3; m/z found, 615.3 [M+H]$^+$. $^1$H NMR (400 MHz, CDCl$_3$) δ 8.35 (dt, J=4.6, 2.2 Hz, 1H), 8.14 (ddd, J=7.7, 3.7, 1.9 Hz, 1H), 7.41-7.31 (m, 2H), 7.16 (d, J=13.7 Hz, 1H), 7.08 (dd, J=6.8, 1.2 Hz, 2H), 6.90 (ddd, J=7.6, 4.8, 1.3 Hz, 1H), 5.30 (s, 1H), 4.97 (td, J=7.9, 2.3 Hz, 1H), 4.72 (dd, J=14.9, 5.9 Hz, 1H), 4.45 (dd, J=7.1, 4.1 Hz, 2H), 4.27 (dd, J=14.9, 3.0 Hz, 1H), 3.95-3.79 (m, 1H), 3.58-3.43 (m, 2H), 3.25-3.03 (m, 2H), 2.87-2.68 (m, 4H), 2.26 (d, J=5.7 Hz, 3H), 1.89-1.57 (m, 4H), 1.42-1.12 (m, 1H), 0.75 (s, 1.5H), 0.69 (s, 1.5H), 0.67-0.57 (m, 2H), 0.46 (dtd, J=6.9, 4.8, 2.4 Hz, 2H).

Example 81: (*R)-3-(1-(Cyclopropylmethyl)-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

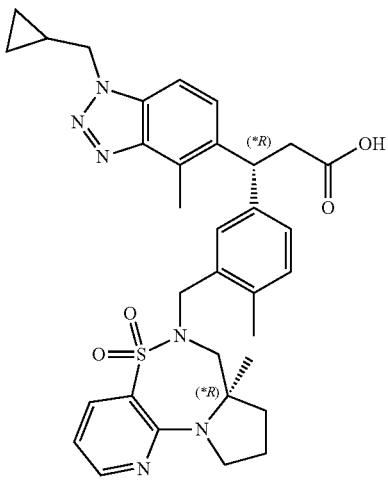 [SMILES: Cc1ccc([C@@H](CC(=O)O)c2ccc3c(nnn3CC3CC3)c2C)cc1CN1C[C@@]2(C)CCCN2c2ncccc2S1(=O)=O]

The mixture of 3-(1-(Cyclopropylmethyl)-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl) propanoic acid (Example 80) was separated by chiral SFC (Stationary phase: Chiralpak AD-H 5 μm 250*30 mm, Mobile phase: 55% CO$_2$, 45% MeOH) to afford two enantiomers. The first eluting isomer (104 mg) was designated *R: MS (ESI): mass calcd. for $C_{33}H_{38}N_6O_4S$, 614.3; m/z found, 615.3 [M+H]$^+$. $^1$H NMR (400 MHz, CDCl$_3$) δ 8.35 (dd, J=4.8, 1.9 Hz, 1H), 8.14 (dd, J=7.7, 1.8 Hz, 1H), 7.43-7.32 (m, 2H), 7.16 (s, 1H), 7.08-7.05 (m, 2H), 6.91 (dd, J=7.7, 4.8 Hz, 1H), 4.96 (t, J=7.7 Hz, 1H), 4.73 (d, J=14.9 Hz, 1H), 4.45 (d, J=7.0 Hz, 2H), 4.26 (d, J=14.8 Hz, 1H), 3.92-3.83 (m, 1H), 3.64-3.27 (m, 2H), 3.20-3.03 (m, 2H), 2.86-2.70 (m, 4H), 2.26 (s, 3H), 1.82-1.70 (m, 1H), 1.68-1.61 (m, 2H), 1.40-1.31 (m, 1H), 0.89 (d, J=6.2 Hz, 1H), 0.76 (s, 3H), 0.68-0.57 (m, 2H), 0.54-0.40 (m, 2H).

Example 82: (*S)-3-(1-(Cyclopropylmethyl)-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

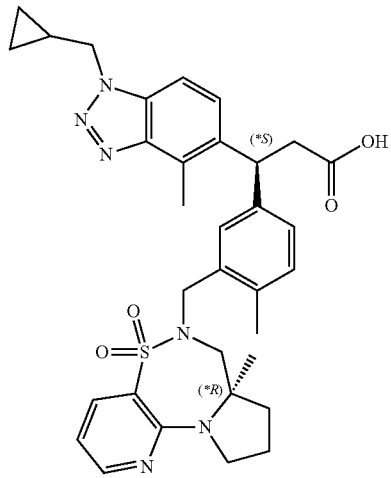 [SMILES: Cc1ccc([C@H](CC(=O)O)c2ccc3c(nnn3CC3CC3)c2C)cc1CN1C[C@@]2(C)CCCN2c2ncccc2S1(=O)=O]

The mixture of 3-(1-(Cyclopropylmethyl)-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl) propanoic acid (Example 80) was separated by chiral SFC (Stationary phase: Chiralpak AD-H 5 μm 250*30 mm, Mobile phase: 55% CO$_2$, 45% MeOH) to afford two enantiomers. The second eluting isomer (107 mg) was designated *S: MS (ESI): mass calcd. for $C_{33}H_{38}N_6O_4S$, 614.3; m/z found, 615.3 [M+H]$^+$. $^1$H NMR (400 MHz, CDCl$_3$) δ 8.36 (dd, J=4.8, 1.8 Hz, 1H), 8.12 (dd, J=7.7, 1.9 Hz, 1H), 7.42-7.29 (m, 2H), 7.19 (s, 1H), 7.08-7.02 (m, 2H), 6.90 (dd, J=7.7, 4.7 Hz, 1H), 4.96 (t, J=7.6 Hz, 1H), 4.72 (d, J=15.1 Hz, 1H), 4.44 (d, J=7.0 Hz, 2H), 4.25 (d, J=15.1 Hz, 1H), 3.97-3.84 (m, 1H), 3.77-3.63 (m, 2H), 3.56-3.50 (m, 1H), 3.45-2.93 (m, 2H), 2.85-2.78 (m, 4H), 2.24 (s, 3H), 1.90-1.62 (m, 2H), 1.41-1.18 (m, 1H), 0.92 (d, J=6.1 Hz, 1H), 0.70 (s, 3H), 0.66-0.56 (m, 2H), 0.52-0.40 (m, 2H).

Example 83: 3-(4-Chloro-3-((((*S)-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl) propanoic Acid

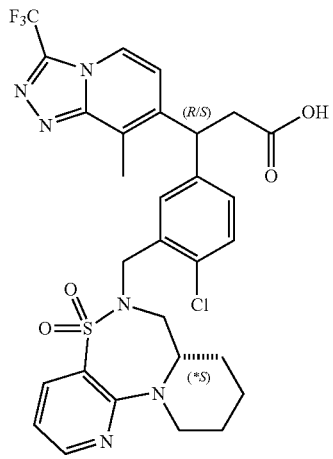

Step A: Ethyl 3-(4-chloro-3-(hydroxymethyl)phenyl)-3-(8-methyl-3-(trifluoromethyl)-[1,2,4]triazolo[4,3-a]pyridine-7-yl)propanoate. To a 20 mL vial under $N_2$ was added ethyl (E)-3-(8-methyl-3-(trifluoromethyl)-[1,2,4]triazolo[4,3-a]pyridine-7-yl)acrylate (200 mg, 0.67 mmol, Intermediate 25, step A), (2-chloro-5-(4,4,5,5-tetramethyl-1,3,2-dioxaborolan-2-yl)phenyl)methanol (288 mg, 1.07 mmol), potassium hydroxide (41 mg, 0.73 mmol), dioxane (3.0 mL), water (1.4 mL) and chloro(1,5-cyclooctadiene)rhodium(I) dimer (48 mg, 0.098 mmol). The vial was capped and stirred at r.t. for 18 h. The reaction was poured into aqueous saturated sodium bicarbonate solution and extracted with ethyl acetate (3×). These extractions resulted in several fractions which were combined, dried over sodium sulfate and concentrated to dryness under reduced pressure. The residue was purified by flash column chromatography (eluent: 1:1 ethyl acetate/DCM) to afford the title compound (150 mg, 53%). MS (ESI): mass calcd. for $C_{20}H_{19}ClF_3N_3O_3$, 441.1; m/z found, 442.1 $[M+H]^+$.

Step B: The title compound (153 mg, 89%) was prepared using analogous conditions as described in Example 11 where ethyl 3-(4-chloro-3-(hydroxymethyl)phenyl)-3-(8-methyl-3-(trifluoromethyl)-[1,2,4]triazolo[4,3-a]pyridine-7-yl)propanoate was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and (*S)-7,7a,8,9,10-hexahydro-6H-dipyrido[2,1-d:2',3'-f][1,2,5]thiadiazepine 5,5-dioxide (Intermediate 2) instead of (*S)-7a-methyl-6,7,7a,8,9,19-hexahydropyrido[2,3-]pyrollo[2,1-d[1,2,5]thiadiazepine 5,5-dioxide (Intermediate 39) in step B. MS (ESI): mass calcd. for $C_{29}H_{28}ClF_3N_6O_4S$, 648.1; m/z found, 649.0 $[M+H]^+$. $^1H$ NMR (400 MHz, $CDCl_3$) δ 8.32-8.28 (m, 1H), 8.05-8.00 (m, 2H), 7.46-7.42 (m, 1H), 7.30 (dd, J=8.3, 1.4 Hz, 1H), 7.08-7.02 (m, 1H), 6.89-6.79 (m, 2H), 4.95-4.88 (m, 1H), 4.62-4.43 (m, 3H), 4.33-4.23 (m, 1H), 3.54-3.34 (m, 2H), 3.31-2.94 (m, 5H), 1.81-1.70 (m, 3H), 1.65-1.50 (m, 3H), 1.33-1.16 (m, 1H).

Example 84: (*S)-3-(4-Chloro-3-(((*S)-5,5-dioxido-7,7a,8,9,10,11-hexahydro-6H-dipyrido[2,1-d:2',3'-][1,2,5]thiadiazepin-6-yl)methyl)phenyl)-3-(8-methyl-3-(trifluoromethyl)-[1,2,4]triazolo[4,3-a]pyridine-7-yl)propanoic Acid

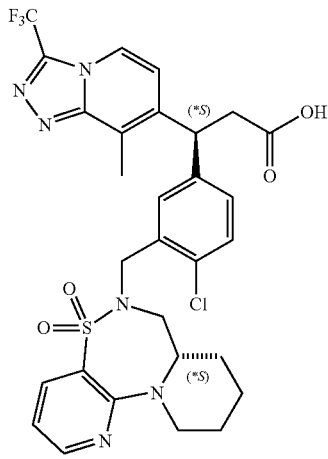

The mixture of 3-(4-chloro-3-(((*S)-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid (Example 83) isomers was separated by chiral SFC (Stationary phase: Chiralpak AD-H 5 μm 250*30 mm, Mobile phase: 50% $CO_2$, 50% MeOH) to afford two enantiomers. The first eluting isomer (69 mg) was designated *S: MS (ESI): mass calcd. for $C_{29}H_{28}ClF_3N_6O_4S$, 648.1; m/z found, 649.0 $[M+H]^+$. $^1H$ NMR (400 MHz, $CDCl_3$) δ 8.31-8.28 (m, 1H), 8.05-8.00 (m, 2H), 7.44 (s, 1H), 7.30-7.25 (m, 1H), 7.05-7.02 (m, 1H), 6.89-6.79 (m, 2H), 4.93-4.86 (m, 1H), 4.62-4.43 (m, 3H), 4.33-4.23 (m, 1H), 3.54-3.34 (m, 2H), 3.31-2.75 (m, 5H), 1.81-1.69 (m, 3H), 1.65-1.50 (m, 3H), 1.33-1.16 (m, 1H).

Example 85: (*R)-3-(4-Chloro-3-(((*S)-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic Acid

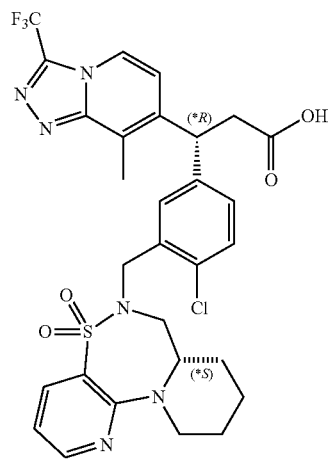

The mixture of 3-(4-chloro-3-(((*S)-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid (Example 83) isomers was separated by chiral SFC (Stationary phase: Chiralpak AD-H 5 μm 250*30 mm, Mobile phase: 50% $CO_2$, 50% MeOH) to afford two enantiomers. The second eluting isomer (69 mg) was designated *R: MS (ESI): mass calcd. for $C_{29}H_{28}ClF_3N_6O_4S$, 648.1; m/z found, 649.0 $[M+H]^+$. $^1H$ NMR (400 MHz, $CDCl_3$) δ 8.31-8.28 (m, 1H), 8.05-8.00 (m, 2H), 7.44 (s, 1H), 7.30-7.25 (m, 1H), 7.05-7.02 (m, 1H), 6.92-6.79 (m, 2H), 4.93-4.86 (m, 1H), 4.62-4.43 (m, 3H), 4.33-4.23 (m, 1H), 3.54-3.34 (m, 2H), 3.31-2.75 (m, 5H), 1.81-1.69 (m, 3H), 1.65-1.50 (m, 3H), 1.33-1.16 (m, 1H).

Example 86: 3-(4-Chloro-3-((1',1'-dioxoidospiro[oxetane-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

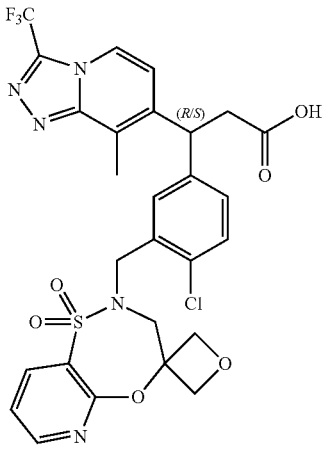 [SMILES: Cc1c(C(CC(=O)O)c2ccc(Cl)c(CN3CC4(COC4)Oc4ncccc4S3(=O)=O)c2)ccn2c(C(F)(F)F)nnc12]

The title compound (68 mg, 22%) was prepared using analogous conditions as described in Example 11 where ethyl 3-(4-chloro-3-(hydroxymethyl)phenyl)-3-(8-methyl-3-(trifluoromethyl)-[1,2,4]triazolo[4,3-a]pyridine-7-yl)propanoate (Example 83, step A) was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and 2'3'-dihydrospiro[oxetane-3,4'-pyrido[2,3-b][1,4,5]oxathiazepine] 1',1'-dioxide (Intermediate 59) was used instead of (*S)-7a-methyl-6,7,7a,8,9,19-hexahydropyrido[2,3-f]pyrollo[2,1-d[1,2,5]thiadiazepine 5,5-dioxide (Intermediate 39) in step B. MS (ESI): mass calcd. for $C_{27}H_{23}ClF_3N_5O_6S$, 637.1; m/z found, 638.0 [M+H]$^+$. $^1$H NMR (400 MHz, CDCl$_3$) δ 8.55 (dd, J=4.9, 1.9 Hz, 1H), 8.21 (dd, J=7.7, 1.9 Hz, 1H), 8.05 (d, J=7.1 Hz, 1H), 7.48 (d, J=2.3 Hz, 1H), 7.37-7.29 (m, 2H), 7.08 (dd, J=8.3, 2.2 Hz, 1H), 6.93 (d, J=7.3 Hz, 1H), 4.94 (t, J=7.9 Hz, 1H), 4.80-4.73 (m, 2H), 4.54 (d, J=3.3 Hz, 2H), 4.41-4.36 (m, 2H), 4.04-3.94 (m, 2H), 3.35-2.85 (m, 2H), 2.80 (s, 3H).

Example 87: (*R)-3-(4-Chloro-3-((1',1'-dioxoidospiro[oxetane-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

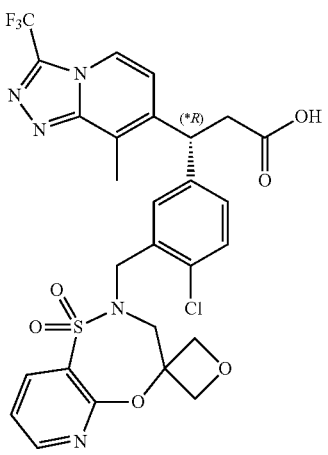 [SMILES: Cc1c([C@H](CC(=O)O)c2ccc(Cl)c(CN3CC4(COC4)Oc4ncccc4S3(=O)=O)c2)ccn2c(C(F)(F)F)nnc12]

The mixture of 3-(4-chloro-3-((1',1'-dioxoidospiro[oxetane-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid (Example 86) isomers was separated by chiral SFC (Stationary phase: Chiralpak AD-H 5 μm 250*30 mm, Mobile phase: 60% CO$_2$, 40% i-PrOH) to afford two enantiomers. The first eluting isomer (27 mg) was designated *R: MS (ESI): mass calcd. for $C_{27}H_{23}ClF_3N_5O_6S$, 637.1; m/z found, 638.0 [M+H]$^+$. $^1$H NMR (400 MHz, CDCl$_3$) δ 8.55 (dd, J=4.9, 1.9 Hz, 1H), 8.21 (dd, J=7.7, 1.9 Hz, 1H), 8.05 (d, J=7.1 Hz, 1H), 7.48 (s, 1H), 7.37-7.29 (m, 2H), 7.08 (dd, J=8.3, 2.2 Hz, 1H), 6.93 (d, J=7.3 Hz, 1H), 4.94 (t, J=7.9 Hz, 1H), 4.79-4.72 (m, 2H), 4.54 (d, J=3.3 Hz, 2H), 4.42-4.33 (m, 2H), 4.05-3.90 (m, 2H), 3.35-2.85 (m, 2H), 2.80 (s, 3H).

Example 88: (*S)-3-(4-Chloro-3-((1',1'-dioxoidospiro[oxetane-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

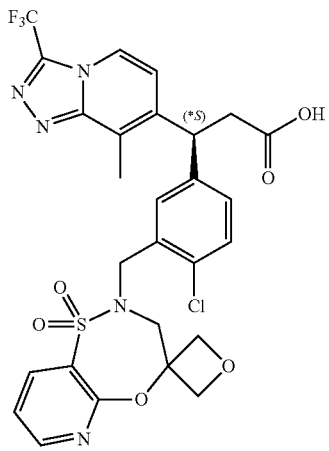 [SMILES: Cc1c([C@@H](CC(=O)O)c2ccc(Cl)c(CN3CC4(COC4)Oc4ncccc4S3(=O)=O)c2)ccn2c(C(F)(F)F)nnc12]

The mixture of 3-(4-chloro-3-((1',1'-dioxoidospiro[oxetane-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid (Example 86) isomers was separated by chiral SFC (Stationary phase: Chiralpak AD-H 5 μm 250*30 mm, Mobile phase: 60% CO$_2$, 40% i-PrOH) to afford two enantiomers. The second eluting isomer (28 mg) was designated *S: MS (ESI): mass calcd. for $C_{27}H_{23}ClF_3N_5O_6S$, 637.1; m/z found, 638.0 [M+H]$^+$. $^1$H NMR (400 MHz, CDCl$_3$) δ 8.55 (dd, J=4.9, 1.9 Hz, 1H), 8.21 (dd, J=7.7, 1.9 Hz, 1H), 8.05 (d, J=7.1 Hz, 1H), 7.48 (s, 1H), 7.37-7.29 (m, 2H), 7.08 (dd, J=8.3, 2.2 Hz, 1H), 6.93 (d, J=7.3 Hz, 1H), 4.94 (t, J=7.9 Hz, 1H), 4.79-4.72 (m, 2H), 4.54 (d, J=3.3 Hz, 2H), 4.42-4.33 (m, 2H), 4.05-3.90 (m, 2H), 3.35-2.85 (m, 2H), 2.80 (s, 3H).

Example 89: 3-(4-Chloro-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic Acid

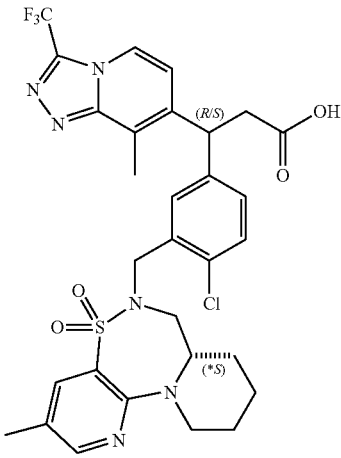

The title compound (51 mg, 31%) was prepared using analogous conditions as described in Example 11 where ethyl 3-(4-chloro-3-(hydroxymethyl)phenyl)-3-(8-methyl-3-(trifluoromethyl)-[1,2,4]triazolo[4,3-a]pyridine-7-yl)propanoate (Example 83, step A) was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and (*S)-3-methyl-7,7a,8,9,10,11-hexahydro-6H-dipyrido[2,1-d:2',3'-f][1,2,5]thiadiazepine 5,5-dioxide (Intermediate 63) was used instead of (*S)-7a-methyl-6,7,7a,8,9,19-hexahydropyrido[2,3-f]pyrollo[2,1-d][1,2,5]thiadiazepine 5,5-dioxide (Intermediate 39) in step B. MS (ESI): mass calcd. for $C_{30}H_{30}ClF_3N_6O_4S$, 662.2; m/z found, 663.0 [M+H]$^+$. $^1$H NMR (400 MHz, CDCl$_3$) δ 8.15-8.12 (m, 1H), 8.03 (d, J=7.2 Hz, 1H), 7.87-7.84 (m, 1H), 7.46-7.42 (m, 1H), 7.30 (dd, J=8.3, 1.4 Hz, 1H), 7.07-7.02 (m, 1H), 6.88 (dd, J=7.3, 4.2 Hz, 1H), 4.95-4.86 (m, 1H), 4.58-4.37 (m, 3H), 4.21-4.09 (m, 1H), 3.50-3.31 (m, 2H), 3.29-2.94 (m, 3H), 2.80 (m, 3H), 2.27 (s, 3H), 1.79-1.67 (m, 3H) 1.63-1.45 (m, 3H).

Example 90: (*R)-3-(4-Chloro-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic Acid

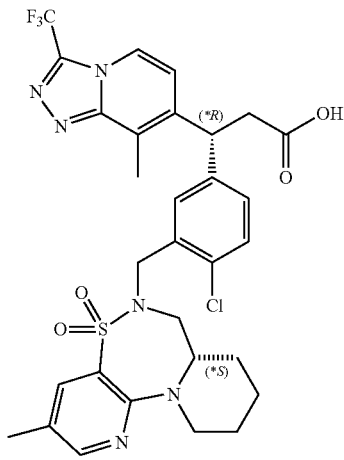

The mixture of 3-(4-chloro-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid (Example 89) isomers was separated by chiral SFC (Stationary phase: Chiralpak AD-H 5 µm 250*30 mm, Mobile phase: 60% CO$_2$, 40% i-PrOH) to afford two enantiomers. The first eluting isomer (27 mg) was designated *R: MS (ESI): mass calcd. for $C_{30}H_{30}ClF_3N_6O_4S$, 662.2; m/z found, 663.0 [M+H]$^+$. $^1$H NMR (400 MHz, CDCl$_3$) δ 8.13 (d, J=2.5 Hz, 1H), 8.02 (d, J=7.2 Hz, 1H), 7.85 (d, J=2.3 Hz, 1H), 7.44 (d, J=2.3 Hz, 1H), 7.30 (d, J=8.3 Hz, 1H), 7.07 (dd, J=8.3, 2.3 Hz, 1H), 6.91 (d, J=7.3 Hz, 1H), 4.97-4.90 (m, 1H), 4.55-4.36 (m, 3H), 4.20-4.13 (m, 1H), 3.50-3.30 (m, 2H), 3.26-3.18 (m, 1H), 3.11-2.96 (m, 2H), 2.80 (s, 3H), 2.27 (s, 3H), 1.79-1.45 (m, 6H).

Example 91: (*S)-3-(4-Chloro-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic Acid

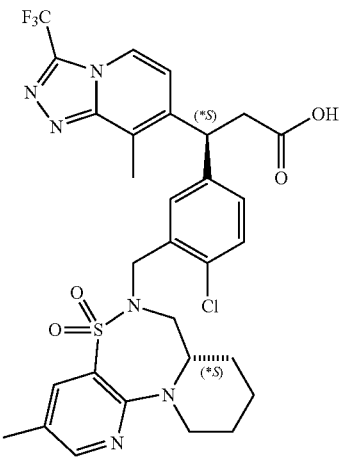

The mixture of 3-(4-chloro-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid (Example 89) isomers was separated by chiral SFC (Stationary phase: Chiralpak AD-H 5 µm 250*30 mm, Mobile phase: 60% CO$_2$, 40% i-PrOH) to afford two enantiomers. The second eluting isomer (24 mg) was designated *S: MS (ESI): mass calcd. for $C_{30}H_{30}ClF_3N_6O_4S$, 662.2; m/z found, 663.0 [M+H]$^+$. $^1$H NMR (400 MHz, CDCl$_3$) δ 8.13 (d, J=2.5 Hz, 1H), 8.02 (d, J=7.2 Hz, 1H), 7.85 (d, J=2.3 Hz, 1H), 7.44 (d, J=2.3 Hz, 1H), 7.30 (d, J=8.3 Hz, 1H), 7.07 (dd, J=8.3, 2.3 Hz, 1H), 6.91 (d, J=7.3 Hz, 1H), 4.97-4.90 (m, 1H), 4.55-4.36 (m, 3H), 4.20-4.13 (m, 1H), 3.50-3.30 (m, 2H), 3.26-3.18 (m, 1H), 3.11-2.96 (m, 2H), 2.80 (s, 3H), 2.27 (s, 3H), 1.79-1.45 (m, 6H).

Example 92: 3-(4-Chloro-3-(((*S)-3-fluoro-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic Acid

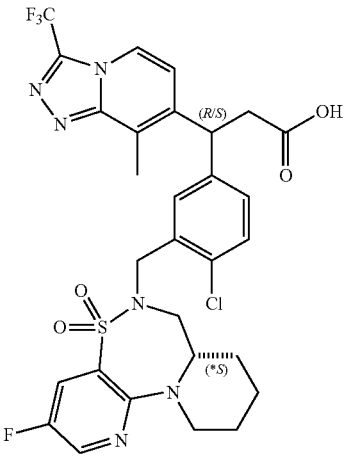

The title compound (125 mg, 65%) was prepared using analogous conditions as described in Example 11 where ethyl 3-(4-chloro-3-(hydroxymethyl)phenyl)-3-(8-methyl-3-(trifluoromethyl)-[1,2,4]triazolo[4,3-a]pyridine-7-yl)propanoate (Example 83, step A) was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and (*S)-3-fluoro-7,7a,8,9,10,11-hexahydro-6H-dipyrido[2,1-d:2',3'-f][1,2,5]thiadiazepine 5,5-dioxide (Intermediate 64) was used instead of (*S)-7a-methyl-6,7,7a,8,9,19-hexahydropyrido[2,3-f]pyrollo[2,1-d][1,2,5]thiadiazepine 5,5-dioxide (Intermediate 39) in step B. MS (ESI): mass calcd. for $C_{29}H_{27}ClF_4N_6O_4S$, 666.1; m/z found, 667.1 [M+H]$^+$. $^1$H NMR (400 MHz, CDCl$_3$) δ 8.19 (d, J=2.9 Hz, 1H), 8.06-8.01 (m, 1H), 7.80-7.76 (m, 1H), 7.45 (dd, J=7.8, 2.3 Hz, 1H), 7.31 (dd, J=8.2, 2.3 Hz, 1H), 7.10-7.02 (m, 1H), 6.92-6.84 (m, 1H), 5.02-4.88 (m, 1H), 4.56-4.38 (m, 3H), 4.25-4.40 (m, 1H), 3.52-2.97 (m, 5H), 2.81 (d, J=2.1 Hz, 3H), 1.80-1.70 (m, 3H), 1.68-1.47 (m, 3H).

Example 93: (*R)-3-(4-Chloro-3-(((*S)-3-fluoro-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic Acid

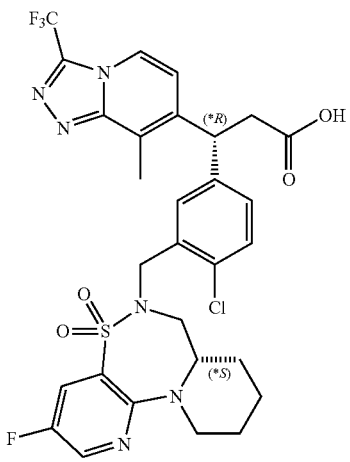

The mixture of 3-(4-chloro-3-(((*S)-3-fluoro-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid (Example 92) isomers was separated by chiral SFC (Stationary phase: Chiralpak AD-H 5 μm 250*30 mm, Mobile phase: 50% CO$_2$, 50% i-PrOH) to afford two diastereomers. The first eluting isomer (70 mg) was designated *R: MS (ESI): mass calcd. for $C_{29}H_{27}ClF_4N_6O_4S$, 666.1; m/z found, 667.0 [M+H]$^+$. $^1$H NMR (400 MHz, CDCl$_3$) δ 8.19 (d, J=3.0 Hz, 1H), 8.03 (d, J=7.3 Hz, 1H), 7.78 (dd, J=7.4, 2.9 Hz, 1H), 7.46 (d, J=2.3 Hz, 1H), 7.31 (d, J=8.2 Hz, 1H), 7.06 (dd, J=8.3, 2.3 Hz, 1H), 6.87 (d, J=7.3 Hz, 1H), 5.04-4.88 (m, 1H), 4.52-4.43 (m, 3H), 4.24-4.16 (m, 1H), 3.50-3.38 (m, 2H), 3.30-3.00 (m, 3H), 2.82 (s, 3H), 1.81-1.69 (m, 3H), 1.68-1.47 (m, 3H).

Example 94: (*S)-3-(4-Chloro-3-(((*S)-3-fluoro-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic Acid

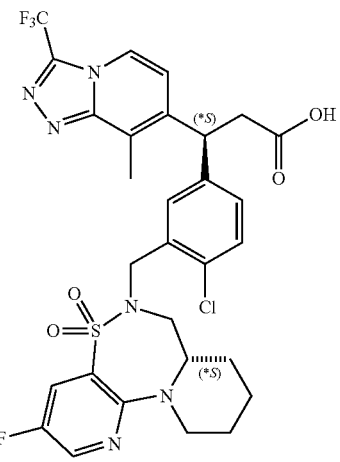

The mixture of 3-(4-chloro-3-(((*S)-3-fluoro-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid (Example 92) isomers was separated by chiral SFC (Stationary phase: Chiralpak AD-H 5 μm 250*30 mm, Mobile phase: 50% CO$_2$, 50% i-PrOH) to afford two diastereomers. The second eluting isomer (55 mg) was designated *S: MS (ESI): mass calcd. for $C_{29}H_{27}ClF_4N_6O_4S$, 666.1; m/z found, 667.0 [M+H]$^+$. $^1$H NMR (400 MHz, CDCl$_3$) δ 8.19 (d, J=3.0 Hz, 1H), 8.04 (d, J=7.1 Hz, 1H), 7.79 (dd, J=7.4, 3.0 Hz, 1H), 7.44 (d, J=2.3 Hz, 1H), 7.31 (d, J=8.3 Hz, 1H), 7.08 (dd, J=8.3, 2.3 Hz, 1H), 6.88 (d, J=7.3 Hz, 1H), 4.94 (dd, J=8.8, 6.8 Hz, 1H), 4.57-4.38 (m, 3H), 4.19 (dt, J=13.2, 4.7 Hz, 1H), 3.50-3.32 (m, 2H), 3.25 (ddd, J=13.7, 9.5, 4.7 Hz, 1H), 3.16-2.99 (m, 2H), 2.82 (s, 3H), 1.74 (dd, J=9.5, 4.2 Hz, 3H), 1.65-1.47 (m, 3H).

Example 95: 3-(4-Chloro-3-((1',1'-dioxoidospiro[benzo[b]]oxethiazepine-4,3'-oxetan]-2(3H)-yl)methyl)phenyl)-3-(8-methyl-3-(trifluoromethyl)-[1,2,4]triazolo[4,3-a]pyridine-7-yl)propanoic Acid

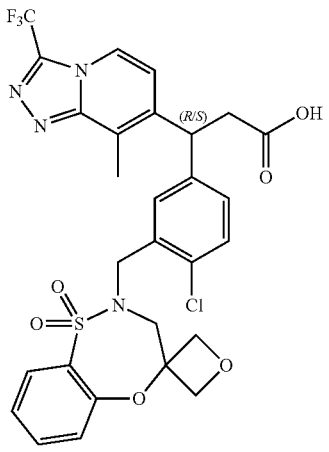 [SMILES: Cc1c(C(CC(=O)O)c2ccc(Cl)c(CN3CC4(COC4)Oc4ccccc4S3(=O)=O)c2)ccn2c(C(F)(F)F)nnc12]

The title compound (120 mg, 84%) was prepared using analogous conditions as described in Example 11 where ethyl 3-(4-chloro-3-(hydroxymethyl)phenyl)-3-(8-methyl-3-(trifluoromethyl)-[1,2,4]triazolo[4,3-a]pyridine-7-yl)propanoate (Example 83, step A) was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and 2,3-dihydrospiro[benzo[b][1,4,5]oxathiazepine-4,3'-oxetane] 1,1-dioxide (Intermediate 7) was used instead of (*S)-7a-methyl-6,7,7a,8,9,19-hexahydropyrido[2,3-f]pyrollo[2,1-d[1,2,5]thiadiazepine 5,5-dioxide (Intermediate 39) in step B. MS (ESI): mass calcd. for $C_{28}H_{24}ClF_3N_4O_6S$, 636.1; m/z found, 637.0 [M+H]$^+$. $^1$H NMR (400 MHz, CDCl$_3$) δ 8.05 (d, J=7.3 Hz, 1H), 7.84 (dd, J=7.8, 1.7 Hz, 1H), 7.60-7.54 (m, 1H), 7.51 (d, J=2.3 Hz, 1H), 7.37 (dd, J=8.1, 1.1 Hz, 1H), 7.34-7.28 (m, 2H), 7.06 (dd, J=8.3, 2.3 Hz, 1H), 6.94 (d, J=7.3 Hz, 1H), 4.93 (t, J=7.9 Hz, 1H), 4.70-4.64 (m, 2H), 4.58-4.40 (m, 2H), 4.37-4.33 (m, 2H), 3.95-3.81 (m, 2H), 3.18-2.96 (m, 2H), 2.78 (s, 3H).

Example 96: (*R)-3-(4-Chloro-3-((1',1'-dioxoidospiro[benzo[b]]oxethiazepine-4,3'-oxetan]-2(3H)-yl)methyl)phenyl)-3-(8-methyl-3-(trifluoromethyl)-[1,2,4]triazolo[4,3-a]pyridine-7-yl)propanoic Acid

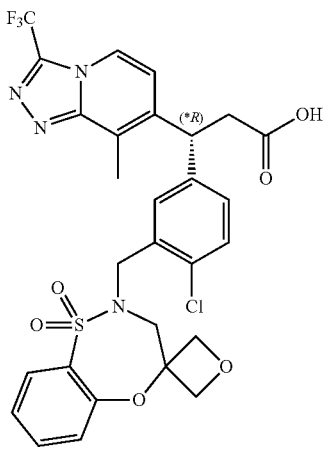 [SMILES: Cc1c([C@H](CC(=O)O)c2ccc(Cl)c(CN3CC4(COC4)Oc4ccccc4S3(=O)=O)c2)ccn2c(C(F)(F)F)nnc12]

The mixture of 3-(4-chloro-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid (Example 95) isomers was separated by chiral SFC (Stationary phase: Chiralpak AD-H 5 μm 250*30 mm, Mobile phase: 60% CO$_2$, 40% i-PrOH) to afford two enantiomers. The first eluting isomer (44 mg) was designated *R: MS (ESI): mass calcd. for $C_{28}H_{24}ClF_3N_4O_6S$, 636.1; m/z found, 637.0 [M+H]$^+$. $^1$H NMR (400 MHz, CDCl$_3$) δ 8.04 (d, J=7.1 Hz, 1H), 7.83 (dd, J=7.8, 1.7 Hz, 1H), 7.61-7.55 (m, 1H), 7.52 (d, J=2.3 Hz, 1H), 7.38 (dd, J=8.1, 1.0 Hz, 1H), 7.34-7.27 (m, 2H), 7.06 (dd, J=8.3, 2.3 Hz, 1H), 6.94 (d, J=7.3 Hz, 1H), 4.94 (t, J=7.9 Hz, 1H), 4.70-4.63 (m, 2H), 4.54-4.34 (m, 4H), 3.95-3.82 (m, 2H), 3.16-2.93 (m, 2H), 2.79 (s, 3H).

Example 97: (*S)-3-(4-Chloro-3-((1',1'-dioxoidospiro[benzo[b]]oxethiazepine-4,3'-oxetan]-2(3H)-yl)methyl)phenyl)-3-(8-methyl-3-(trifluoromethyl)-[1,2,4]triazolo[4,3-a]pyridine-7-yl)propanoic Acid

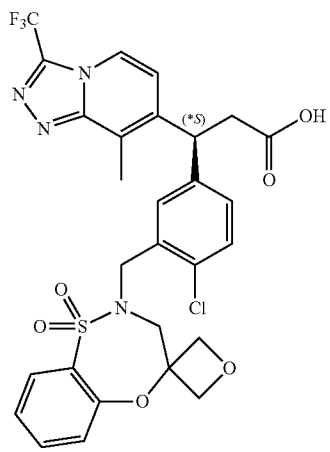 [SMILES: Cc1c([C@@H](CC(=O)O)c2ccc(Cl)c(CN3CC4(COC4)Oc4ccccc4S3(=O)=O)c2)ccn2c(C(F)(F)F)nnc12]

The mixture of 3-(4-chloro-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridine-7-yl)propanoic acid (Example 95) isomers was separated by chiral SFC (Stationary phase: Chiralpak AD-H 5 μm 250*30 mm, Mobile phase: 60% CO$_2$, 40% i-PrOH) to afford two enantiomers. The second eluting isomer (40 mg) was designated *S: MS (ESI): mass calcd. for $C_{28}H_{24}ClF_3N_4O_6S$, 636.1; m/z found, 637.0 [M+H]$^+$. $^1$H NMR (400 MHz, CDCl$_3$) δ 8.04 (d, J=7.1 Hz, 1H), 7.83 (dd, J=7.8, 1.7 Hz, 1H), 7.60-7.55 (m, 1H), 7.52 (d, J=2.3 Hz, 1H), 7.38 (dd, J=8.1, 1.0 Hz, 1H), 7.34-7.27 (m, 2H), 7.06 (dd, J=8.3, 2.3 Hz, 1H), 6.94 (d, J=7.3 Hz, 1H), 4.94 (t, J=7.9 Hz, 1H), 4.70-4.63 (m, 2H), 4.54-4.34 (m, 4H), 3.95-3.82 (m, 2H), 3.16-2.93 (m, 2H), 2.79 (s, 3H).

Example 98: (*S)-3-(3-((8-Fluoro-1,1-dioxidospiro[benzo[b][1,4,5]oxathiazepin]-4,1'-cyclopropan]-2(3H)-yl)methyl)-4-methylphenyl)-3-(8-methyl-3-(trifluoromethyl)-[1,2,4]triazolo[4,3-a]pyridin-7-yl)propanoic Acid

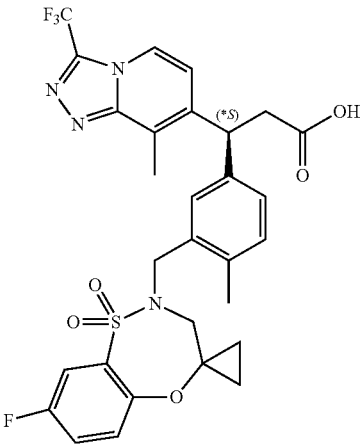 [SMILES: Cc1ccc([C@H](CC(=O)O)c2ccn3c(C(F)(F)F)nnc3c2C)cc1CN1CC2(CC2)Oc2ccc(F)cc2S1(=O)=O]

The title compound (531 mg, 89%) was prepared using analogous conditions as described in Example 11 where ethyl (*S)-3-(3-(hydroxymethyl)-4-methylphenyl)-3-(8-methyl-3-(trifluoromethyl)-[1,2,4]triazolo[4,3-a]pyridine-7-yl)propanoate (Intermediate 26) was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and 8-flouro-2,3-dihydrospiro[benzo[b][1,4,5]oxathiazepine-4,1'-cyclopropane] 1,1-dioxide (Intermediate 65) was used instead of (*S)-7a-methyl-6,7,7a,8,9,19-hexahydropyrido[2,3-f]pyrollo[2,1-d][1,2,5]thiadiazepine 5,5-dioxide (Intermediate 39) in step B. MS (ESI): mass calcd. for $C_{29}H_{26}F_4N_4O_5S$, 618.2; m/z found, 619.0 [M+H]$^+$. $^1$H NMR (400 MHz, CDCl$_3$) δ 8.01 (d, J=7.1 Hz, 1H), 7.60 (dd, J=7.4, 3.1 Hz, 1H), 7.22-7.03 (m, 4H), 6.94 (dd, J=8.8, 4.3 Hz, 1H), 6.89 (d, J=7.3 Hz, 1H), 4.26 (s, 2H), 3.22-2.97 (m, 2H), 2.79 (s, 3H), 2.28 (s, 3H), 1.05-0.98 (m, 2H), 0.51-0.41 (m, 2H).

Example 99: (*S)-3-(3-((8-Fluoro-1,1-dioxidospiro[benzo[b][1,4,5]oxathiazepine-4,3'-oxetan]-2(3H)-yl)methyl]-4-methylphenyl)-3-(8-methyl-3-(trifluoromethyl)-[1,2,4]triazolo[4,3-a]pyridin-7-yl)propanoic Acid

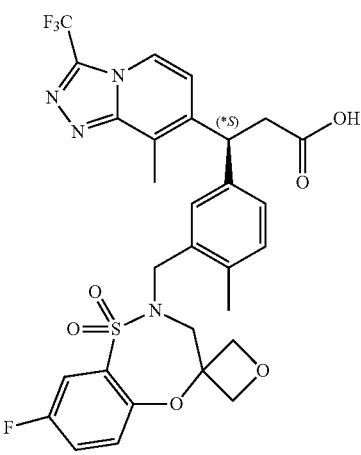 [SMILES: Cc1ccc([C@H](CC(=O)O)c2ccn3c(C(F)(F)F)nnc3c2C)cc1CN1CC2(COC2)Oc2ccc(F)cc2S1(=O)=O]

The title compound (123 mg, 43%) was prepared using analogous conditions as described in Example 11 where ethyl (*S)-3-(3-(hydroxymethyl)-4-methylphenyl)-3-(8-methyl-3-(trifluoromethyl)-[1,2,4]triazolo[4,3-a]pyridine-7-yl)propanoate (Intermediate 26) was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and 8-flouro-2,3-dihydrospiro[benzo[b][1,4,5]oxathiazepine-4,3'-oxetane] 1,1-dioxide (Intermediate 66) was used instead of (*S)-7a-methyl-6,7,7a,8,9,19-hexahydropyrido[2,3-]pyrollo[2,1-d[1,2,5]thiadiazepine 5,5-dioxide (Intermediate 39) in step B. MS (ESI): mass calcd. for $C_{29}H_{26}F_4N_4O_6S$, 634.2; m/z found, 635.1 [M+H]$^+$. $^1$H NMR (400 MHz, CDCl$_3$) δ 8.08 (d, J=7.1 Hz, 1H), 7.60 (dd, J=7.3, 3.1 Hz, 1H), 7.36 (dd, J=8.8, 4.3 Hz, 1H), 7.30-7.23 (m, 1H), 7.21 (d, J=2.0 Hz, 1H), 7.15 (d, J=8.0 Hz, 1H), 7.05-6.95 (m, 2H), 4.85 (dd, J=10.4, 5.9 Hz, 1H), 4.70 (dd, J=7.6, 5.0 Hz, 2H), 4.59 (d, J=13.9 Hz, 1H), 4.34-4.20 (m, 3H), 3.92-3.68 (m, 2H), 3.11-2.92 (m, 2H), 2.72 (m, 3H), 2.27 (s, 3H).

Example 100: (*S)-3-(3-((7'-Chloro-1',1'-dioxidospiro(cyclopropane-1.4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic Acid

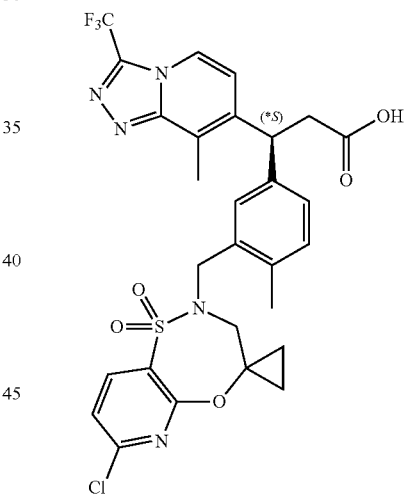

The title compound (212 mg, 76%) was prepared using analogous conditions as described in Example 11 where methyl (*S)-3-(3-(hydroxymethyl)-4-methylphenyl)-3-(8-methyl-3-(trifluoromethyl)[1,2,4]triazolo[4,3-a]pyridine-7-yl)propanoate (Intermediate 26) was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and 7'-chloro-2',3'-dihydrospiro[cyclopropane-1,4'-pyridio[2,3-b][1,4,5]oxathiazepine] 1',1'-dioxide (Intermediate 67) was used instead of (*S)-7a-methyl-6,7,7a,8,9,19-hexahydropyrido[2,3-f]pyrollo[2,1-d][1,2,5]thiadiazepine 5,5-dioxide (Intermediate 39) in step B. MS (ESI): mass calcd. for $C_{28}H_{25}ClF_3N_5O_5S$, 635.1; m/z found, 636.1 [M+H]$^+$. $^1$H NMR (500 MHz, CDCl$_3$) δ 8.21 (d, J=8.1 Hz, 1H), 8.01 (d, J=7.2 Hz, 1H), 7.32 (d, J=8.0 Hz, 1H), 7.17 (d, J=1.9 Hz, 1H), 7.13 (d, J=7.9 Hz, 1H), 7.04 (dd, J=7.8, 1.9 Hz, 1H), 6.87 (d, J=7.3 Hz, 1H), 4.93 (t, J=7.8

Hz, 1H), 4.34 (s, 2H), 3.59-3.49 (m, 2H), 3.01 (dd, J=16.1, 7.3 Hz, 2H), 2.80 (s, 3H), 2.27 (s, 3H), 1.26-1.19 (m, 2H), 0.68-0.59 (m, 2H).

Example 101: (*S)-3-(3-(((7'-((2-Hydroxyethyl) amino-1',1'-dioxidospiro[cyclopropane-1.4'-pyrido [2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridinn-7-yl)propanoic Acid

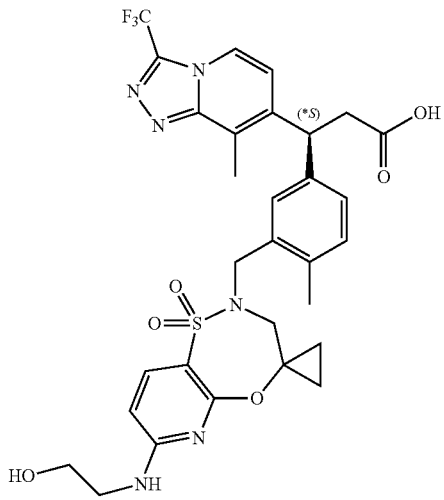 [SMILES: Cc1ccc([C@H](CC(=O)O)c2ccn3c(C(F)(F)F)nnc3c2C)cc1CN1CC2(CC2)Oc2nc(NCCO)ccc2S1(=O)=O]

A vial was charged with (*S)-3-(3-(((7'-chloro-1',1'-dioxidospiro(cyclopropane-1.4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl) propanoic acid (50 mg, 0.079 mmol, Example 100), 2-aminoethan-1-ol (29 mg, 0.47 mmol) and DMSO (0.5 mL). The vial heated to 130° C. for 1.5 h in a microwave reactor. The reaction was cooled, diluted with 1.0 mL of methanol and purified by reverse phase HPLC (5-70% MeCN-water with 20 mM NH$_4$OH) to afford the title compound as a white powder (23 mg, 44%) after lyophilization. MS (ESI): mass calcd. for $C_{30}H_{31}F_3N_6O_6S$, 660.2; m/z found, 661.3 [M+H]$^+$. $^1$H NMR (400 MHz, DMSO-d$_6$) δ 8.32 (d, J=7.3 Hz, 1H), 7.61 (d, J=8.1 Hz, 2H), 7.15 (dd, J=7.8, 1.9 Hz, 1H), 7.11-6.99 (m, 3H), 6.34 (d, J=8.6 Hz, 1H), 4.73 (t, J=7.7 Hz, 1H), 4.03 (q, J=14.4 Hz, 2H), 3.44 (t, J=5.9 Hz, 2H), 3.35-3.18 (m, 5H), 2.98 (dd, J=7.8, 3.0 Hz, 2H), 2.64 (s, 3H), 2.16 (s, 3H), 0.85 (s, 2H), 0.44 (s, 2H).

Example 102: (*S)-3-(3-(((7'-((2-Hydroxypropyl) amino-1',1'-dioxidospiro[cyclopropane-1.4'-pyrido [2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridinn-7-yl)propanoic Acid

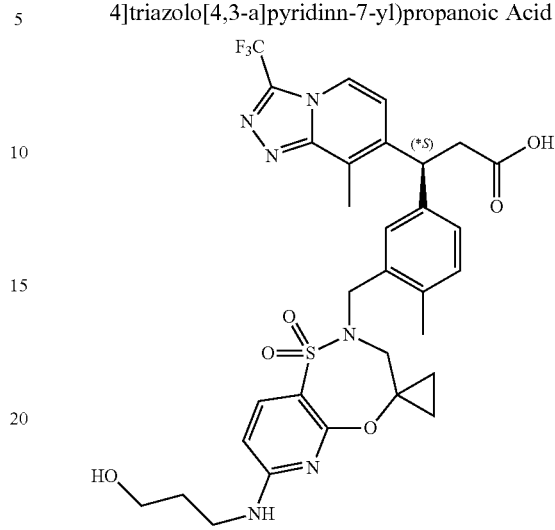

The title compound (11 mg, 21%) was prepared using analogous conditions as described in Example 101 where 3-aminopropan-1-ol was used instead of 2-aminoethan-1-ol. MS (ESI): mass calcd. for $C_{31}H_{33}F_3N_6O_6S$, 674.2; m/z found, 675.2 [M+H]$^+$. $^1$H NMR (500 MHz, CDCl$_3$) δ 8.30 (d, J=7.3 Hz, 1H) 8.01 (d, J=7.2 Hz, 1H), 7.84 (d, J=8.5 Hz, 1H), 7.12-7.10 (m, 2H), 7.07-7.04 (m, 1H), 6.90 (d, J=7.2 Hz, 1H), 6.27 (d, J=8.7 Hz, 1H), 5.96 (s, 1H), 4.92 (t, J=7.8 Hz, 1H), 4.28 (s, 2H), 3.67 (t, J=5.6 Hz, 2H), 3.50-3.46 (m, 4H), 3.09 (dd, J=15.9, 6.9 Hz, 1H), 2.96 (dd, J=15.8, 8.6 Hz, 1H), 2.82 (s, 3H), 2.30 (s, 3H), 1.84-1.73 (m, 2H), 1.22-1.16 (m, 2H), 0.53 (s, 2H).

Example 103: (*S)-3-(3-(((7'-Hydroxy-1',1'-dioxidospiro[cyclopropane-1,4'-pyrido[2,3,-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic Acid

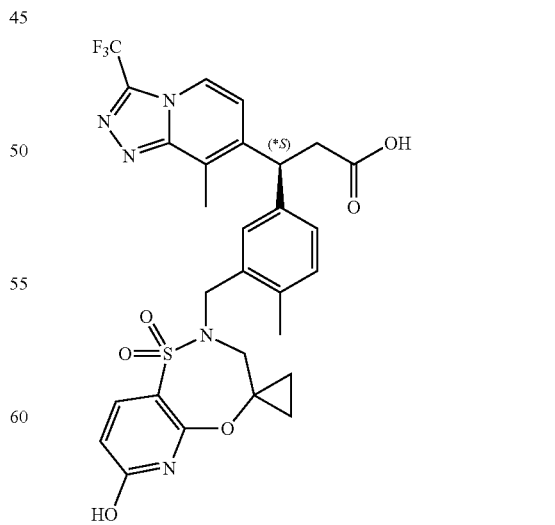

A vial was charged with (*S)-3-(3-(((7'-chloro-1',1'-dioxidospiro(cyclopropane-1.4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl) propanoic acid (50 mg, 0.079 mmol, Example 100), ethane-1,2-diol (29 mg, 0.47 mmol), cesium carbonate (38 mg, 0.12 mmol) and DMSO (0.5 ml). The vial heated to 130° C. for 1.5 h in a microwave reactor. The reaction was cooled, diluted with 1.0 mL of methanol and purified by reverse phase HPLC (eluent: MeCN/water with 20 mM NH$_4$OH, 5:95 to 70:30, gradient) to afford the title compound (8.5 mg, 18%) after lyophilization. MS (ESI): mass calcd. for C$_{28}$H$_{26}$F$_3$N$_5$O$_6$S, 617.1; m/z found, 618.0 [M+H]$^+$. $^1$H NMR (400 MHz, CDCl$_3$) δ 8.03 (d, J=7.3 Hz, 1H), 7.93 (d, J=9.0 Hz, 1H), 7.16-7.10 (m, 2H), 7.05 (dd, J=7.8, 2.0 Hz, 1H), 6.90 (d, J=7.3 Hz, 1H), 6.46 (d, J=9.1 Hz, 1H), 4.93 (t, J=7.8 Hz, 1H), 4.33 (s, 2H), 3.53-3.45 (m, 2H), 3.47-3.38 (m, 1H), 3.11 (dd, J=15.9, 7.3 Hz, 1H), 2.97 (dd, J=15.9, 8.3 Hz, 1H), 2.81 (s, 3H), 2.30 (s, 3H), 1.35-1.25 (m, 2H), 0.68-0.61 (m, 2H).

Example 104: 3-(4-Cyano-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]trizolo[4,3-a]pyridine-7-yl)propanoic Acid

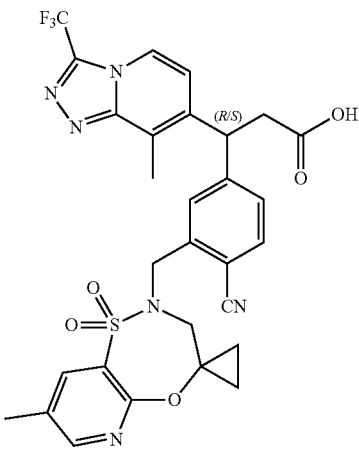 [SMILES: Cc1cnc2c(c1)S(=O)(=O)N(Cc1cc(C(CC(=O)O)c3ccn4c(C(F)(F)F)nnc4c3C)ccc1C#N)CC1(CC1)O2]

Step A: ethyl 3-(4-chloro-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoate. The title compound (150 mg, 18%) was prepared using analogous conditions as described in example 11 where ethyl 3-(4-chloro-3-(hydroxymethyl)phenyl)-3-(8-methyl-3-(trifluoromethyl)-[1,2,4]triazolo[4,3-a]pyridine-7-yl)propanoate (Example 83, step A) was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and 8'-methyl-2',3'-dihydrospiro[cyclopropane-1,4'pyrido[2,3-b][1,4,5]oxathiazepine] 1',1'-dioxide (Intermediate 6) was used instead of (*S)-7a-methyl-6,7,7a,8,9,19-hexahydropyrido[2,3-f]pyrollo[2,1-d][1,2,5]thiadiazepine 5,5-dioxide (Intermediate 39) in step B. MS (ESI): mass calcd. for C$_{30}$H$_{29}$ClF$_3$N$_5$O$_5$S, 663.1; m/z found, 664.0 [M+H]$^+$.

Step B: ethyl 3-(4-cyano-3-((8'-methyl-1',1'-dioxidospiro[cyclopropane-1,4'-pyrido[2,3-b][1,4,5]oxathiazepin]-2'(3'H-yl)methyl)phenyl)-3-(8-methyl-3-(trifluoromethyl)-[1,2,4]triazolo-4,3-a]pyridine-7-yl)propanoate. To a 9 mL screw capped pressure vessel under N$_2$ was added ethyl 3-(4-chloro-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-trifluoromethyl)-[1,2,4]triazolo[4,3-a]pyridine-7-yl)propanoate (150 mg, 0.23 mmol), zinc cyanide (53 mg, 0.45 mmol), X-Phos (22 mg, 0.046 mmol), zinc powder (6 mg, 0.092 mmol), Pd$_2$(dba)$_3$ (21 mg, 0.023 mmol) and DMA (2.0 mL). N$_2$ was bubbled through this mixture for 20 min. and then heated to 110° C. for 72 h. The reaction was cooled, poured into saturated bicarbonate solution and extracted with ethyl acetate (3×). These extractions resulted in several fractions which were combined, dried over sodium sulfate and concentrated to dryness under reduced pressure. The residue was purified by flash column chromatography (eluent: ethyl acetate/hexanes, 0:1 to 30:10, gradient elution) to afford the title compound. MS (ESI): mass calcd. for C$_{31}$H$_{29}$F$_3$N$_6$O$_5$S, 654.2; m/z found, 665.0 [M+H]$^+$.

Step C: 3-(4-cyano-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]trizolo[4,3-a]pyridine-7-yl)propanoic acid. The title compound (43 mg, 90%) was prepared using analogous conditions as described in example 11 where ethyl 3-(4-cyano-3-((8'-methyl-1',1'-dioxidospiro[cyclopropane-1,4'-pyrido[2,3-b][1,4,5]oxathiazepin]-2'(3'H-yl)methyl)phenyl)-3-(8-methyl-3-(trifluoromethyl)-[1,2,4]triazolo-4,3-a]pyridine-7-yl)propanoate was used instead of ethyl 3-(1-(cyclopropylmethyl)-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoate in Step C. MS (ESI): mass calcd. for C$_{29}$H$_{25}$F$_3$N$_6$O$_5$S, 626.2; m/z found, 627.0 [M+H]$^+$.

Example 105: (*S)-3-(4-Cyano-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]trizolo[4,3-a]pyridine-7-yl)propanoic Acid

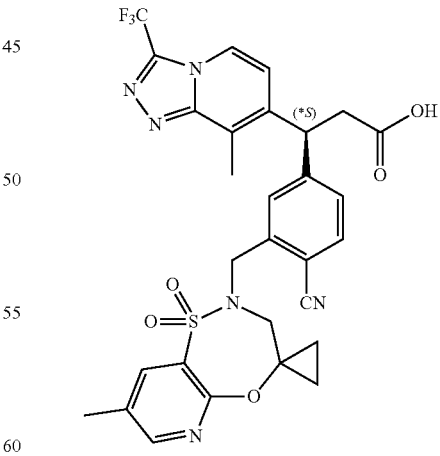

The mixture of 3-(4-cyano-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]trizolo[4,3-a]pyridine-7-yl)propanoic acid isomers (Example 104) was separated by chiral SFC (Stationary phase: Chiralpak AD-H 5 µm 25*2 mm, Mobile phase: 60% CO$_2$, 40% EtOH) to afford two enantiomers. The first eluting isomer (17.5 mg) was designated *S: MS (ESI): mass calcd. for C$_{29}$H$_{25}$F$_3$N$_6$O$_5$S, 626.2; m/z found, 627.1 [M+H]$^+$. $^1$H NMR (400 MHz, CDCl$_3$) δ 8.28 (s, 1H), 8.09-8.00 (m, 2H), 7.74 (s, 1H), 7.56 (d, J=7.9 Hz, 1H), 7.23 (d, J=8.1 Hz, 1H), 6.97-6.86 (m, 1H), 5.04 (s, 1H), 4.50 (s, 2H), 3.90-3.50 (m, 2H), 3.23-2.97 (m, 2H), 2.82 (s, 3H), 2.43 (s, 3H), 1.30-1.19 (m, 2H), 0.80-0.72 (m, 2H).

Example 106: (*R)-3-(4-Cyano-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]trizolo[4,3-a]pyridine-7-yl)propanoic Acid

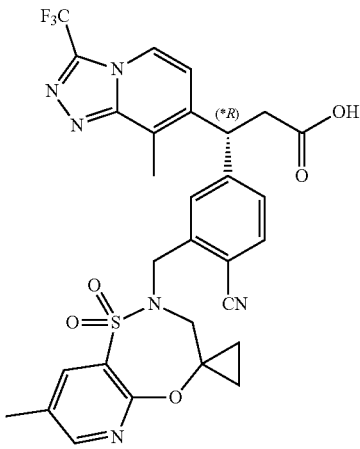 [SMILES: Cc1cnc2c(c1)S(=O)(=O)N(Cc1cc([C@@H](CC(=O)O)c3ccn4c(C(F)(F)F)nnc4c3C)ccc1C#N)CC1(CC1)O2]

The mixture of 3-(4-cyano-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]trizolo[4,3-a]pyridine-7-yl)propanoic acid isomers (Example 104) was separated by chiral SFC (Stationary phase: Chiralpak AD-H 5 μm 25*2 mm, Mobile phase: 60% CO$_2$, 40% EtOH) to afford two enantiomers. The second eluting isomer (10.4 mg) was designated *R: MS (ESI): mass calcd. for C$_{29}$H$_{25}$F$_3$N$_6$O$_5$S, 626.2; m/z found, 627.1 [M+H]$^+$. $^1$H NMR (400 MHz, CDCl$_3$) δ 8.28 (s, 1H), 8.09-8.00 (m, 2H), 7.74 (s, 1H), 7.56 (d, J=7.9 Hz, 1H), 7.23 (d, J=8.1 Hz, 1H), 6.97-6.86 (m, 1H), 5.04 (s, 1H), 4.50 (s, 2H), 3.90-3.50 (m, 2H), 3.23-2.97 (m, 2H), 2.82 (s, 3H), 2.43 (s, 3H), 1.30-1.19 (m, 2H), 0.80-0.72 (m, 2H).

Example 107: (*S)-3-(3-((7'-((3-Methoxypropyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic Acid

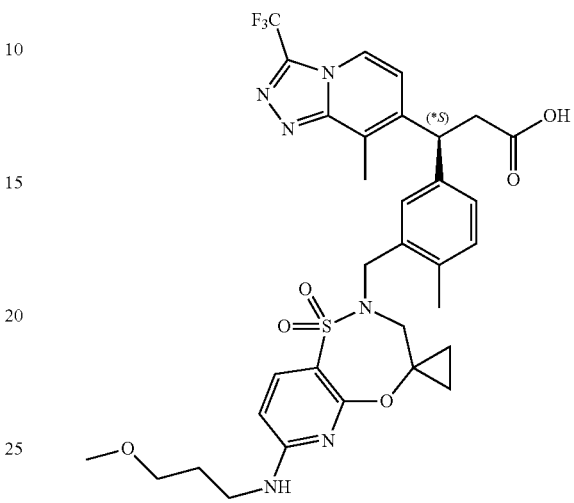

Step A: ethyl (*S)-3-(3-((7'-((3-methoxypropyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoate. A vial was charged with ethyl (*S)-3-(3-((7'-chloro-1',1'-dioxidospiro(cyclopropane-1.4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoate (50 mg, 0.075 mmol, Example 100), 3-methoxypropan-1-amine (40 mg, 0.45 mmol) and DMSO (0.5 mL). The vial was capped then heated to 110° C. for 1 h in a microwave reactor. The reaction was cooled, poured into water and extracted with ethyl acetate (3×). These extractions resulted in several fractions which were combined, dried over sodium sulfate and concentrated to dryness under reduced pressure. The residue was purified by flash column chromatography (eluent: ethyl acetate/hexanes, 0:100 to 70:30, gradient elution) to afford the title compound (54 mg, 100%). MS (ESI): mass calcd. for C$_{34}$H$_{39}$F$_3$N$_6$O$_6$S, 716.3; m/z found, 717.2 [M+H]$^+$.

Step B: (*S)-3-(3-((7'-((3-methoxypropyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoic acid. To a 20 mL vial was added ethyl (*S)-3-(3-((7'-((3-methoxypropyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridine-7-yl)propanoate (54 mg, 0.075 mmol), THF (1.0 mL), 1M NaOH (1.0 mL) and ethanol (0.1 mL). This mixture was stirred at r.t. for 6 h followed by adjustment of the pH to between 3-5. The reaction was then poured into water and extracted with ethyl acetate (3×). These extractions resulted in several fractions which were combined, dried over sodium sulfate and concentrated to dryness under reduced pressure to afford the title compound (49 mg, 94%). MS (ESI): mass calcd. for C$_{32}$H$_{35}$F$_3$N$_6$O$_6$S, 688.2; m/z found, 689.1 [M+H]$^+$. $^1$H NMR (500 MHz, CDCl$_3$) δ 8.02 (d, J=7.2 Hz, 1H), 7.91 (d, J=8.6 Hz, 1H), 7.16-7.09 (m, 2H), 7.02 (dd, J=7.8, 2.0 Hz, 1H), 6.89 (d, J=7.3 Hz, 1H), 6.23 (d, J=8.7 Hz, 1H), 4.95 (t, J=7.7 Hz, 1H), 4.33 (d, J=14.4 Hz, 1H), 4.24 (d, J=14.5 Hz, 1H), 3.48 (t, J=5.7 Hz, 3H), 3.34 (s, 4H), 3.16 (dd, J=15.9, 7.0 Hz, 1H), 3.03 (dd, J=15.9, 8.6 Hz, 1H), 2.84 (s, 3H), 2.30 (s, 3H), 1.91-1.84 (m, 2H), 1.30-1.23 (m, 3H), 1.10-1.05 (m, 1H), 1.02-0.93 (m, 1H), 0.50-0.44 (m, 1H), 0.42-0.37 (m, 1H).

Example 108: (*S)-3-(-3-((7'-((3-Hydroxypropyl)(methyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4[triazolo[4,3-a]pyridine-7-yl)propanoic Acid

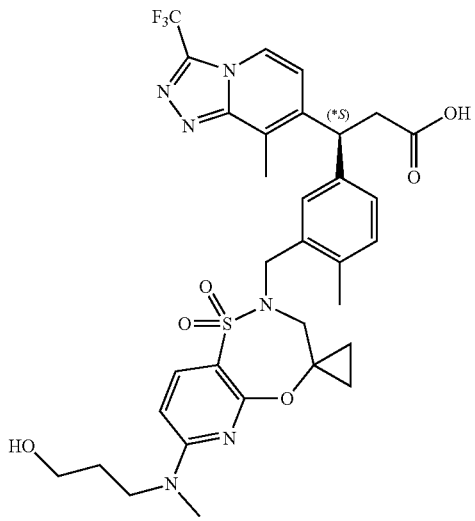 [SMILES: Cc1ccc([C@H](CC(=O)O)c2ccn3c(C(F)(F)F)nnc3c2C)cc1CN1CC2(CC2)Oc2nc(N(C)CCCO)ccc2S1(=O)=O]

The title compound (44 mg, 86%) was prepared using analogous conditions as described in Example 107 where 3-(methylamino)propan-1-ol was used instead of 3-methoxypropan-1-amine in Step A. MS (ESI): mass calcd. for C₃₂H₃₅F₃N₆O₆S, 688.2; m/z found, 689.1 [M+H]⁺. ¹H NMR (500 MHz, CDCl₃) δ 8.01 (d, J=7.2 Hz, 1H), 7.94 (d, J=8.7 Hz, 1H), 7.17 (d, J=2.1 Hz, 1H), 7.11 (d, J=7.9 Hz, 1H), 7.00 (dd, J=7.8, 2.0 Hz, 1H), 6.90 (d, J=7.3 Hz, 1H), 6.35 (d, J=8.8 Hz, 1H), 4.95 (t, J=7.8 Hz, 1H), 4.31 (s, 2H), 3.71-3.66 (m, 2H), 3.55-3.38 (m, 4H), 3.16 (dd, J=16.0, 7.4 Hz, 1H), 3.06-2.95 (m, 4H), 2.82 (s, 3H), 2.30 (s, 3H) 1.82-1.72 (m, 2H), 1.30-1.24 (m, 2H), 1.16-1.10 (m, 2H), 0.57-0.48 (m, 2H).

Example 109: (*S)-3-(-3-((7'-((3-Methoxypropoxy)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4[triazolo[4,3-a]pyridine-7-yl)propanoic Acid

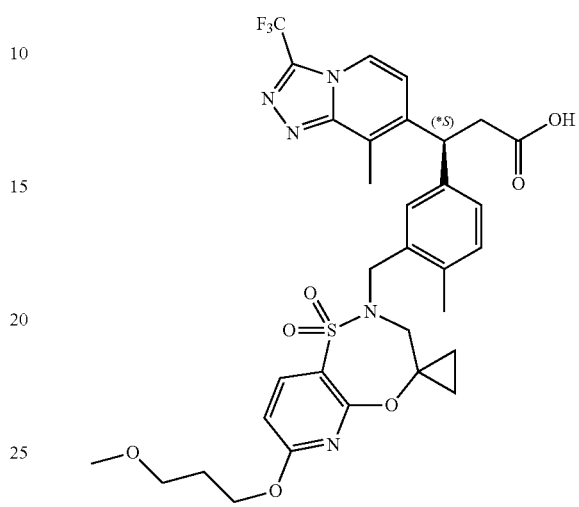

Step A: ethyl (*S)-3-(-3-((7'-((3-methoxypropoxy)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4[triazolo[4,3-a]pyridine-7-yl)propanoate. To a 9 mL screw cap pressure vial under nitrogen was added (*S)-3-(-3-((7'-chloro-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4[triazolo[4,3-a]pyridine-7-yl)propanoate (100 mg, 0.15 mmol, Example 100), propane-1,3-diol (27 mg, 0.3 mmol), cesium carbonate (103 mg, 0.32 mmol), RockPhos Pd G3 (6.3 mg, 0.007 mmol) and toluene (1.0 mL). Nitrogen was bubbled through the reaction mixture for 10 min, and then heated to 90° C. for 18 h. The reaction was cooled, partitioned between ethyl acetate/water and the aqueous layer extracted with ethyl acetate (3×). These extractions resulted in several fractions which were combined, dried over sodium sulfate and concentrated to dryness under reduced pressure. The residue was purified by flash column chromatography (eluent: ethyl acetate/hexanes, 0:100 to 70:30, gradient elution) to afford the title compound (30 mg, 28%). MS (ESI): mass calcd. for C₃₄H₃₈F₃N₅O₇S, 717.2; m/z found, 718.2 [M+H]⁺.

Step B: (*S)-3-(-3-((7'-((3-methoxypropoxy)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4[triazolo[4,3-a]pyridine-7-yl)propanoic acid. To a 20 mL scintillation vial was added ethyl (*S)-3-(-3-((7'-((3-methoxypropoxy)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4[triazolo[4,3-a]pyridine-7-yl)propanoate (30 mg, 0.042 mmol), THF (0.6 mL), 1M NaOH (0.6 mL) and ethanol (0.06 mL). This mixture was stirred at r.t. for 18 h followed by adjustment of the pH to between 3-5. The reaction was then poured into water and extracted with ethyl acetate (4×). These extractions resulted in several fractions which were combined, dried over sodium sulfate and concentrated to dryness under reduced pressure to afford the title compound (38 mg). MS (ESI): mass calcd. for C$_{32}$H$_{34}$F$_3$N$_5$O$_7$S, 689.2; m/z found, 690.2 [M+H]$^+$. $^1$H NMR (500 MHz, CDCl$_3$) δ 8.04 (d, J=8.4 Hz, 1H), 7.96-7.91 (m, 1H), 7.25-7.21 (m, 1H), 7.02 (d, J=7.7 Hz, 1H), 6.95 (d, J=7.7 Hz, 1H), 6.86 (d, J=7.3 Hz, 1H), 6.61 (d, J=8.5 Hz, 1H), 4.86 (s, 1H), 4.36 (t, J=6.4 Hz, 2H), 3.53 (t, J=6.1 Hz, 2H), 3.34 (s, 3H), 3.02-2.92 (m, 1H), 2.88-2.73 (m, 1H), 2.72 (s, 3H), 2.33-2.28 (m, 1H), 2.20 (s, 3H), 2.08-1.95 (m, 2H), 1.71-1.58 (m, 1H), 1.45-1.10 (m, 2H), 0.97-0.75 (m, 2H), 0.57 (br s, 2H).

Example 110: (*S)-3-(-3-((7'-((3-Hydroxyethyl)(methyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4[triazolo[4,3-a]pyridine-7-yl)propanoic Acid

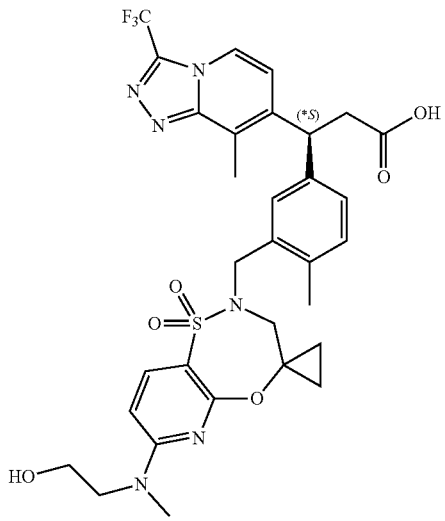 [SMILES: Cc1ccc([C@H](CC(=O)O)c2ccn3c(C(F)(F)F)nnc3c2C)cc1CN1CC2(CC2)Oc2nc(N(C)CCO)ccc2S1(=O)=O]

The title compound (36 mg, 97%) was prepared using analogous conditions as described in Example 107 where 2-(methylamino)ethyan-1-ol was used instead of 3-methoxypropan-1-amine in Step A. MS (ESI): mass calcd. for C$_{31}$H$_{33}$F$_3$N$_6$O$_6$S, 674.2; m/z found, 675.2 [M+H]$^+$. $^1$H NMR (500 MHz, CDCl$_3$) δ 8.00 (d, J=7.2 Hz, 1H), 7.92 (d, J=8.7 Hz, 1H), 7.14 (d, J=2.0 Hz, 1H), 7.11 (d, J=7.9 Hz, 1H), 7.02 (dd, J=7.9, 2.0 Hz, 1H), 6.89 (d, J=7.3 Hz, 1H), 6.37 (d, J=8.8 Hz, 1H), 4.92 (t, J=7.8 Hz, 1H), 4.28 (s, 2H), 3.87-3.83 (m, 2H), 3.76-3.71 (m, 2H), 3.46 (s, 2H), 3.18-3.12 (m, 4H), 3.00 (dd, J=16.1, 8.4 Hz, 1H), 2.79 (s, 3H), 2.28 (s, 3H), 1.13-1.07 (m, 2H), 0.54-0.45 (m, 2H).

Example 111: (*S)-3-(4-Methyl-((7'-((2-morpholinoethyl)amino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4 [triazolo[4,3-a]pyridine-7-yl)propanoic Acid

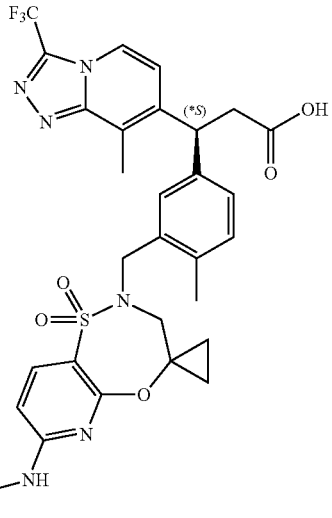

The title compound (69 mg, 93%) was prepared using analogous conditions as described in Example 107 where 2-morpholinoethan-1-amine was used instead of 3-methoxypropan-1-amine in Step A. MS (ESI): mass calcd. for C$_{34}$H$_{38}$F$_3$N$_7$O$_6$S, 729.2; m/z found, 730.2 [M+H]$^+$. $^1$H NMR (500 MHz, CDCl$_3$) δ 8.01 (d, J=7.1 Hz, 1H), 7.75-7.67 (m, 1H), 7.24 (d, J=1.8 Hz, 1H), 7.12 (d, J=8.0 Hz, 1H), 7.09-7.05 (m, 1H), 6.90 (d, J=7.3 Hz, 1H), 6.62-6.50 (m, 1H), 6.00-5.90 (m, 1H), 4.94 (t, J=7.8 Hz, 1H), 4.29 (s, 2H), 3.75-3.70 (m, 4H), 3.52-3.37 (m, 4H), 3.12 (dd, J=15.9, 8.2 Hz, 1H), 2.92 (dd, J=15.9, 7.4 Hz, 1H), 2.83-2.60 (m, 9H), 2.28 (s, 3H), 1.13-1.07 (m, 2H), 0.49-0.43 (m, 2H).

Example 112: (*S)-3-(3-((1',1'-Dioxido-7'-((2-(piperidin-1-yl)ethyl)amino)spiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4[triazolo[4,3-a]pyridine-7-yl)propanoic Acid

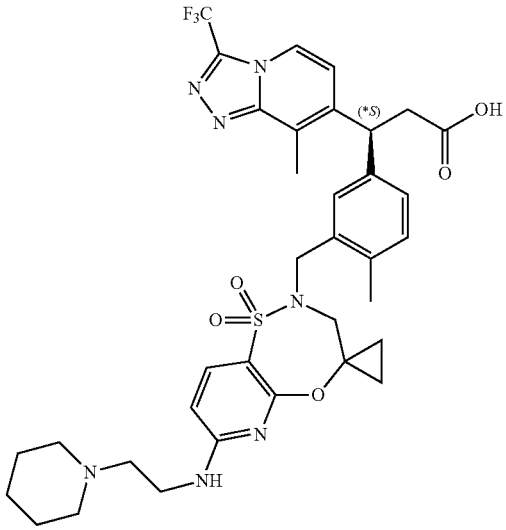 [SMILES: Cc1ccc([C@H](CC(=O)O)c2ccn3c(C(F)(F)F)nnc3c2C)cc1CN1CC2(CC2)Oc2nc(NCCN3CCCCC3)ccc2S1(=O)=O]

The title compound (65 mg, 84%) was prepared using analogous conditions as described in Example 107 where 2-(piperidin-1-yl)ethan-1-amine was used instead of 3-methoxypropan-1-amine in Step A. MS (ESI): mass calcd. for $C_{35}H_{40}F_3N_7O_5S$, 727.2; m/z found, 728.2 [M+H]$^+$. $^1$H NMR (600 MHz, Methanol-$d_4$) δ 8.31 (d, J=7.2 Hz, 1H), 7.84 (d, J=8.6 Hz, 1H), 7.24 (dd, J=7.9, 2.0 Hz, 1H), 7.19 (d, J=8.1 Hz, 1H), 7.15 (d, J=7.3 Hz, 1H), 7.06 (d, J=1.9 Hz, 1H), 6.46 (d, J=8.6 Hz, 1H), 4.97 (t, J=7.8 Hz, 1H), 4.32 (d, J=14.4 Hz, 1H), 4.22 (d, J=14.5 Hz, 1H), 3.74 (t, J=5.9 Hz, 2H), 3.55-3.49 (m, 1H), 3.35-3.23 (m, 4H), 3.14 (dd, J=15.8, 7.1 Hz, 1H), 3.07-2.96 (m, 1H), 2.77 (s, 3H), 2.31 (s, 3H), 1.90-1.82 (m, 4H), 1.74-1.65 (m, 2H), 1.42-1.27 (m, 2H), 1.03-0.88 (m, 4H), 0.52-0.40 (m, 2H).

Example 113: (*S)-3-(3-((7'-(Butylamino)-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4[triazolo[4,3-a]pyridine-7-yl)propanoic Acid

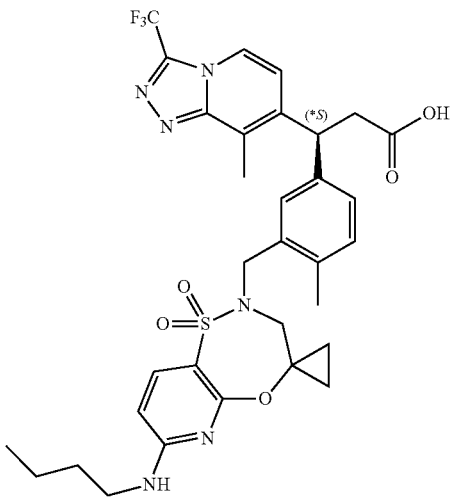 [SMILES: CCCCNc1ccc2c(n1)OC1(CC1)CN(Cc1cc([C@H](CC(=O)O)c3ccn4c(C(F)(F)F)nnc4c3C)ccc1C)S2(=O)=O]

The title compound (35 mg, 91%) was prepared using analogous conditions as described in Example 107 where butan-1-amine was used instead of 3-methoxypropan-1-amine in Step A. MS (ESI): mass calcd. for $C_{32}H_{35}F_3N_6O_5S$, 672.2; m/z found, 673.2 [M+H]$^+$. $^1$H NMR (400 MHz, CDCl$_3$) δ 7.95 (d, J=7.1 Hz, 1H), 7.86 (d, J=8.7 Hz, 1H), 7.08-7.02 (m, 2H), 6.95 (dd, J=8.0, 2.0 Hz, 1H), 6.82 (d, J=7.3 Hz, 1H), 6.14 (d, J=8.7 Hz, 1H), 4.89 (t, J=7.7 Hz, 1H), 4.26 (d, J=14.4 Hz, 1H), 4.16 (d, J=14.4 Hz, 1H), 3.43 (d, J=15.4 Hz, 1H), 3.28 (d, J=15.4 Hz, 1H), 3.19-3.06 (m, 3H), 2.97 (dd, J=15.9, 8.5 Hz, 1H), 2.78 (s, 3H), 2.24 (s, 3H), 1.58-1.47 (m, 2H), 1.39-1.27 (m, 2H), 1.26-1.15 (m, 1H), 1.02-0.95 (m, 1H), 0.90-0.82 (m, 4H), 0.48-0.28 (m, 2H).

Example 114: 3-(3-((7'-((3-Hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoic Acid

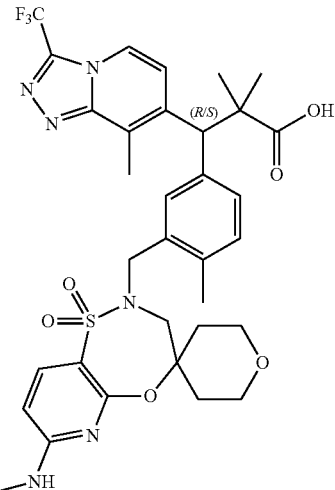

Step A: Methyl-3-(3-((7'-((3-hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoate. The title compound (133 mg, 100%) was prepared using analogous conditions as described in Example 107 where 3-aminopropan-1-ol was used instead of 3-methoxypropan-1-amine and methyl 3-(3-((7'-chloro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(3-(trifluoromethyl)-[1,2,4]triazoo[4,3-a]pyridine-7-yl)propanoate (Intermediate 69) instead of ethyl (*S)-3-(3-((7'-chloro-1',1'-dioxidospiro(cyclopropane-1.4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoate (Example 100) in Step A. MS (ESI): mass calcd. for $C_{36}H_{43}F_3N_6O_7S$, 760.3; m/z found, 761.3 [M+H]$^+$.

Step B: 3-(3-((7'-((3-hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoic acid. In a 20 mL scintillation vial was added Methyl-3-(3-((7'-((3-hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoate (133 mg, 0.18 mmol), LiOH (2.0M solution in water, 0.6 mL, 1.2 mmol), MeOH (1.2 mL) and water (0.6 mL). The reaction was heated to 75 C for 6 h, followed by cooling to room temperature and pH adjustment to ~4 with 2M HCl. The mixture was then further diluted with water and extracted with ethyl acetate (4×). These extractions resulted in several fractions which were combined, dried over sodium sulfate and concentrated to dryness under reduced pressure to afford the title compound (100 mg, 77%). MS (ESI): mass calcd. for $C_{35}H_{41}F_3N_6O_7S$, 746.3; m/z found, 747.2 [M+H]$^+$. $^1$H NMR (400 MHz, CDCl$_3$) δ 7.95 (d, J=7.3 Hz, 1H), 7.76 (d, J=8.5 Hz, 1H), 7.22-7.15 (m, 2H), 7.08-7.00 (m, 2H), 6.14 (d, J=8.6 Hz, 1H), 5.51 (br s, 1H), 4.82 (s, 1H), 4.47-4.31 (m, 2H), 3.90-3.80 (m, 2H), 3.71-3.24 (m, 8H), 2.74 (s, 3H), 2.18 (s, 3H), 1.79-1.41 (m, 5H), 1.37 (s, 3H), 1.32-1.25 (m, 4H), 1.22-1.17 (m, 1H).

Example 115: (*S)-3-(3-((7'-((3-Hydroxypropyl)
amino)-1',1'-dioxido-2,3,5,6-tetrahydrospiro[pyran-
4,4'-pyrido[2,3-b][1,4,5]oxathiazepin]-2'(3'H)-yl)
methyl)-4-methylphenyl)-2,2-dimethyl-3-(8-methyl-
3-(trifluoromethyl)-[1,2,4]triazolo[4,3-a]pyridine-7-
yl)propanoic Acid

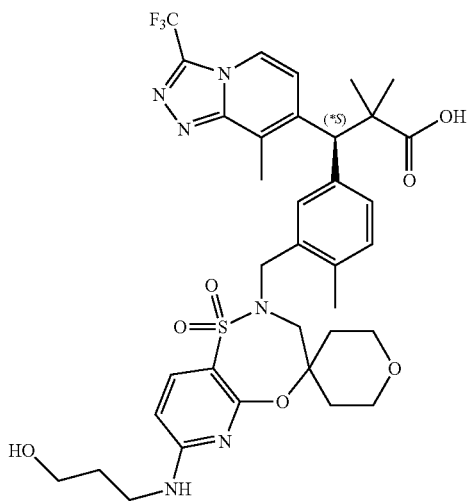 [SMILES: Cc1ccc([C@@H](c2ccn3c(C(F)(F)F)nnc3c2C)C(C)(C)C(=O)O)cc1CN1CC2(CCOCC2)Oc2nc(NCCCO)ccc2S1(=O)=O]

The mixture of 3-(3-((7'-((3-hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid isomers (Example 114) were separated by chiral SFC (Chiralpak IC 5 μM, 250×21.2 mm, 65% $CO_2$, 35% MeOH). The first eluting isomer (14 mg) was designated *S: MS (ESI): mass calcd. for $C_{35}H_{41}F_3N_6O_7S$, 746.3; m/z found, 747.5 [M+H]$^+$.

Example 116: (*R)-3-(3-((7'-((3-Hydroxypropyl)
amino)-1',1'-dioxido-2,3,5,6-tetrahydrospiro[pyran-
4,4'-pyrido[2,3-b][1,4,5]oxathiazepin]-2'(3'H)-yl)
methyl)-4-methylphenyl)-2,2-dimethyl-3-(8-methyl-
3-(trifluoromethyl)-[1,2,4]triazolo[4,3-a]pyridine-7-
yl)propanoic Acid

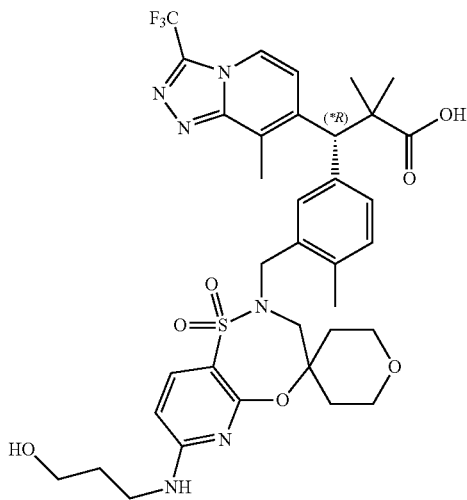 [SMILES: Cc1ccc([C@H](c2ccn3c(C(F)(F)F)nnc3c2C)C(C)(C)C(=O)O)cc1CN1CC2(CCOCC2)Oc2nc(NCCCO)ccc2S1(=O)=O]

The mixture of 3-(3-((7'-((3-hydroxypropyl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid isomers (Example 115) were separated by chiral SFC (Chiralpak IC 5 μM, 250×21.2 mm, 65% $CO_2$, 35% MeOH). The second eluting isomer (19 mg) was designated *R: MS (ESI): mass calcd. for $C_{35}H_{41}F_3N_6O_7S$, 746.3; m/z found, 747.0 [M+H]$^+$.

Example 117: 3-(3-((7'-(((R)-4-Hydroxybutan-2-yl)
amino)-1',1'-dioxido-2,3,5,6-tetrahydrospiro[pyran-
4,4'-pyrido[2,3-b][1,4,5]oxathiazepin]-2'(3'H)-yl)
methyl)-4-methylphenyl)-2,2-dimethyl-3-(8-methyl-
3-(trifluoromethyl)-[1,2,4]triazolo[4,3-a]pyridine-7-
yl)propanoic Acid

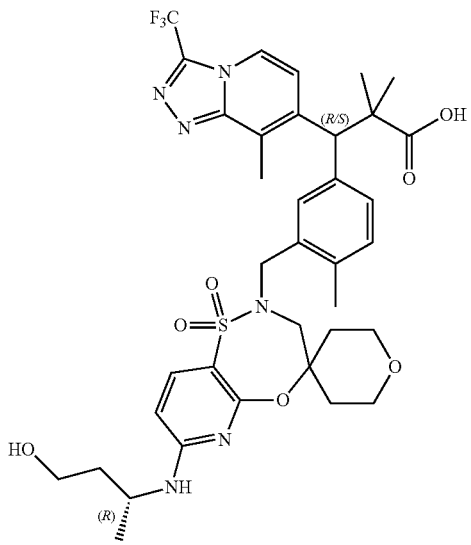

The title compound (110 mg, 86%) was prepared using analogous conditions as described in Example 114 where (R)-3-aminobutan-1-ol was used instead of 3-aminopropan-1-ol and in Step A. MS (ESI): mass calcd. for $C_{36}H_{43}F_3N_6O_7S$, 760.3; m/z found, 761.2 [M+H]$^+$. $^1$H NMR (600 MHz, CDCl$_3$) δ 7.94 (dd, J=7.3, 2.5 Hz, 1H), 7.74 (dd, J=8.5, 1.5 Hz, 1H), 7.23-7.16 (m, 1.5H), 7.13 (d, J=2.1 Hz, 0.5H), 7.08 (dd, J=7.9, 2.0 Hz, 0.5H), 7.05-6.95 (m, 1.5H), 6.15 (dd, J=11.4, 8.5 Hz, 1H), 4.98 (br s, 1H), 4.82 (d, J=16.1 Hz, 1H), 4.44-4.30 (m, 2H), 4.07 (br s, 1H), 3.90-3.76 (m, 2H), 3.69-3.38 (m, 5H), 3.12 (s, 1H), 2.74 (d, J=6.6 Hz, 3H), 2.19 (d, J=2.1 Hz, 3H), 1.87 (br s, 1H), 1.74-1.38 (m, 4H), 1.37-1.33 (m, 3H), 1.30-1.10 (m, 8H).

Example 118: 3-(3-((7'-(((S)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

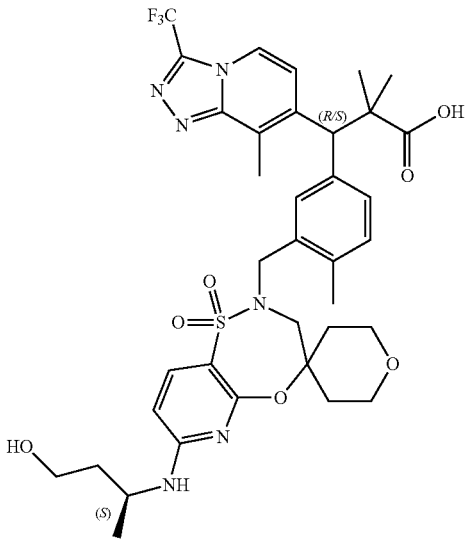

The title compound (110 mg, 86%) was prepared using analogous conditions as described in Example 114 where (S)-3-aminobutan-1-ol was used instead of 3-aminopropan-1-ol in Step A. MS (ESI): mass calcd. for $C_{36}H_{43}F_3N_6O_7S$, 760.3; m/z found, 761.1 [M+H]$^+$. $^1$H NMR (600 MHz, CDCl$_3$) δ 7.95 (dd, J=7.3, 2.1 Hz, 1H), 7.74 (dd, J=8.6, 1.4 Hz, 1H), 7.22-7.16 (m, 1.5H), 7.13 (d, J=2.2 Hz, 0.5H), 7.08 (dd, J=8.0, 2.0 Hz, 0.5H), 7.06-6.98 (m, 1.5H), 6.15 (dd, J=10.9, 8.6 Hz, 1H), 5.00 (br s, 1H), 4.82 (d, J=15.1 Hz, 1H), 4.45-4.31 (m, 2H), 4.12-4.00 (m, 1H), 3.91-3.77 (m, 2H), 3.68-3.39 (m, 5H), 3.16 (br s, 1H), 2.74 (d, J=6.4 Hz, 3H), 2.19 (d, J=1.9 Hz, 3H), 1.87 (br s, 1H), 1.73-1.41 (m, 4H), 1.36 (d, J=5.0 Hz, 3H), 1.30-1.13 (m, 8H).

Example 119: (*S)-3-(3-((7'-(((R)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

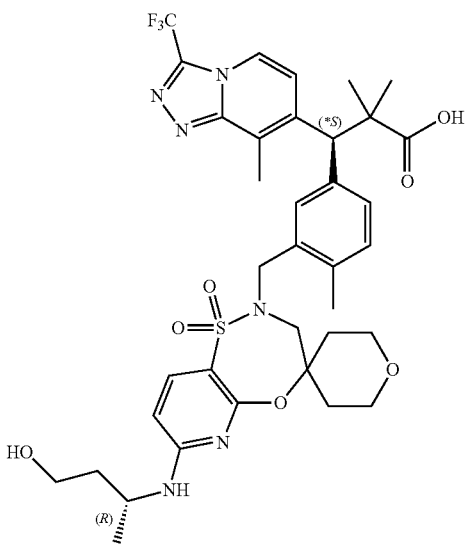

The mixture of 3-(3-((7'-(((R)-4-hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4triazolo[4,3-a]pyridine-7-yl) propanoic acid isomers (Example 117) were separated by chiral SFC (Stationary phase: Chiralpak AD-H 5 μm 25*2 mm, Mobile phase: 60% CO$_2$, 40% EtOH). The first eluting isomer (31 mg) was designated *S: MS (ESI): mass calcd. for $C_{36}H_{43}F_3N_6O_7S$, 760.3; m/z found, 761.2 [M+H]$^+$.

Example 120: (*R)-3-(3-((7'-(((R)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

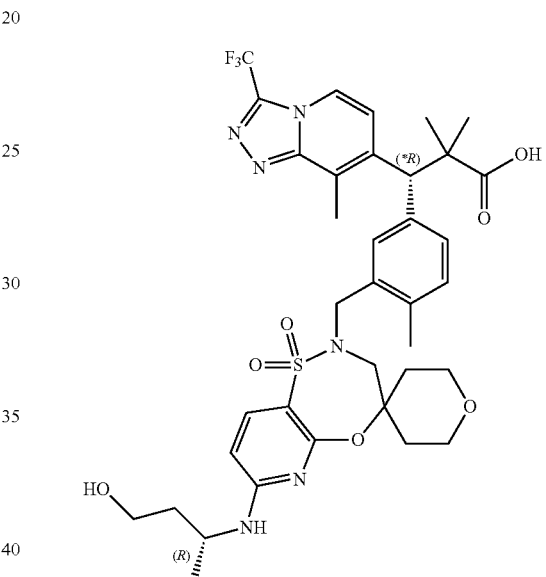

The mixture of 3-(3-((7'-(((R)-4-hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl) propanoic acid isomers (Example 117) were separated by chiral SFC (Stationary phase: Chiralpak AD-H 5 μm 25*2 mm, Mobile phase: 60% CO$_2$, 40% EtOH). The second eluting isomer (31 mg) was designated *R: MS (ESI): mass calcd. for $C_{36}H_{43}F_3N_6O_7S$, 760.3; m/z found, 761.2 [M+H]$^+$.

Example 121: (*S)-3-(3-((7'-(((S)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

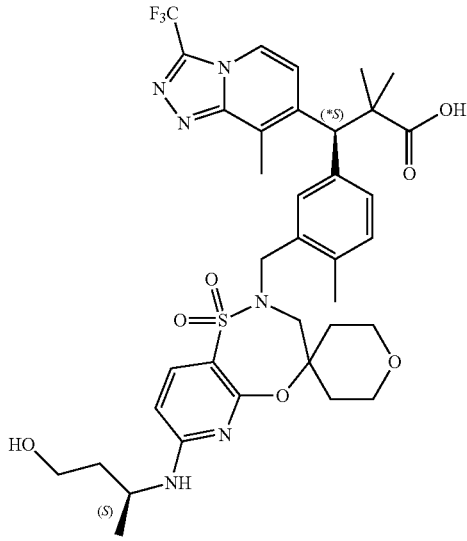

The mixture of 3-(3-((7'-(((S)-4-hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl)propanoic acid isomers (Example 118) were separated by chiral SFC (Stationary phase: Chiralpak AD-H 5 μm 25*2 mm, Mobile phase: 60% CO$_2$, 40% EtOH). The first eluting isomer (36 mg) was designated *S: MS (ESI): mass calcd. for C$_{36}$H$_{43}$F$_3$N$_6$O$_7$S, 760.3; m/z found, 761.2 [M+H]$^+$.

Example 122: (*R)-3-(3-((7'-(((S)-4-Hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

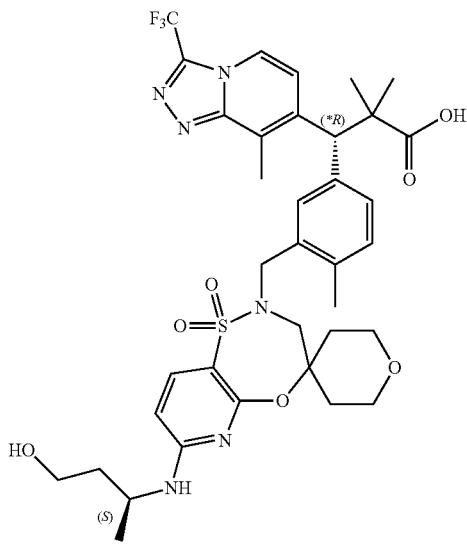

The mixture of 3-(3-((7'-(((S)-4-hydroxybutan-2-yl)amino)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4[triazolo[4,3-a]pyridine-7-yl) propanoic acid isomers (Example 118) were separated by chiral SFC (Stationary phase: Chiralpak AD-H 5 μm 25*2 mm, Mobile phase: 60% CO$_2$, 40% EtOH). The second eluting isomer (31 mg) was designated *R: MS (ESI): mass calcd. for C$_{36}$H$_{43}$F$_3$N$_6$O$_7$S, 760.3; m/z found, 761.2 [M+H]$^+$.

Example 123: (*R)-3-(3-((7'-(((S)-4-Hydroxybutan-2-yl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4][triazolo[4,3-a]pyridine-7-yl)propanoic Acid

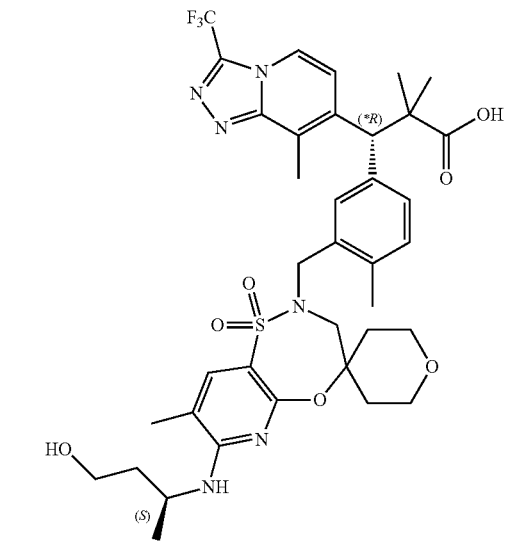

The title compound (76 mg, 87%) was prepared using analogous conditions as described in example 114 where (S)-3-aminobutan-1-ol was used instead of 3-aminopropan-1-ol and methyl (*R)-3-(3((7'-chloro-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]]pyridine-7-yl)propanoate (Intermediate 142) instead of methyl 3-(3-((7'-chloro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate (Example 36) in Step A. MS (ESI): mass calcd. for C$_{37}$H$_{45}$F$_3$N$_6$O$_7$S, 774.3; m/z found, 775.4 [M+H]$^+$. $^1$H NMR (400 MHz, CDCl$_3$) δ 7.93 (d, J=7.4 Hz, 1H), 7.61 (s, 1H), 7.23-7.19 (m, 1H), 7.13-7.07 (m, 2H), 7.03 (d, J=8.3 Hz, 1H), 4.83 (s, 1H), 4.47-4.31 (m, 3H), 3.95-3.68 (m, 3H), 3.66-3.44 (m, 4H), 3.07 (d, J=15.4 Hz, 1H), 2.78 (s, 3H), 2.19 (s, 3H), 2.03 (d, J=0.8 Hz, 3H), 1.90-1.83 (m, 1H), 1.71-1.48 (m, 3H), 1.44-1.39 (m, 1H), 1.37 (s, 3H), 1.31-1.23 (m, 6H) 1.20-1.13 (m, 2H).

Example 124: (*R)-3-(3-((7'-(((R)-3-Hydroxy-methylbutan-2-yl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

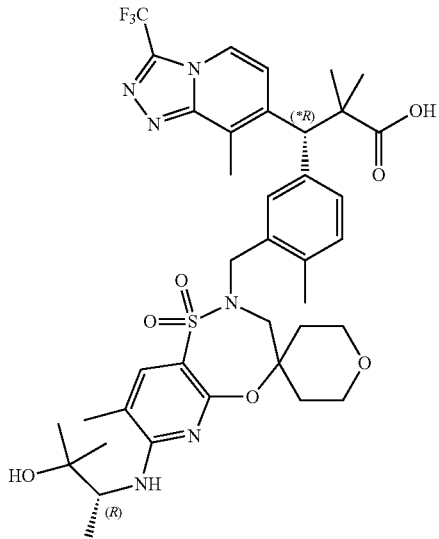

The title compound (113 mg, 69%) was prepared using analogous conditions as described in Example 114 where (R)-3-amino-2-methylbutan-2-ol was used instead of 3-aminopropan-1-ol in Step A and methyl (*R)-3-(3-((7'-chloro-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]]pyridine-7-yl)propanoate (Intermediate 142) instead of methyl 3-(3-((7'-chloro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(3-(trifluoromethyl)-[1,2,4]triazolo[4,3-a]pyridine-7-yl)propanoate (Example 36). MS (ESI): mass calcd. for $C_{38}H_{47}F_3N_6O_7S$, 788.3; m/z found, 789.3 [M+H]$^+$. $^1$H NMR (400 MHz, DMSO-d$_6$) δ 12.42 (s, 1H), 8.33 (d, J=7.2 Hz, 1H), 7.44 (s, 1H), 7.22-7.11 (m, 3H), 7.07 (d, J=7.9 Hz, 1H), 5.73 (d, J=8.9 Hz, 1H), 4.73 (s, 1H), 4.58 (s, 1H), 4.31 (d, J=15.2 Hz, 1H), 4.20 (d, J=15.2 Hz, 1H), 4.10-4.04 (m, 1H), 3.79-3.58 (m, 2H), 3.35 (d, J=10.2 Hz, 1H), 3.28-3.15 (m, 2H), 2.58 (s, 3H), 2.13 (s, 3H), 2.01 (s, 3H), 1.42 (d, J=13.9 Hz, 2H), 1.30-1.13 (m, 9H), 1.10-0.97 (m, 9H).

Example 125: (*R)-3-(3-((7'-(((1s,3S)-3-Hydroxy-cyclobutyl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

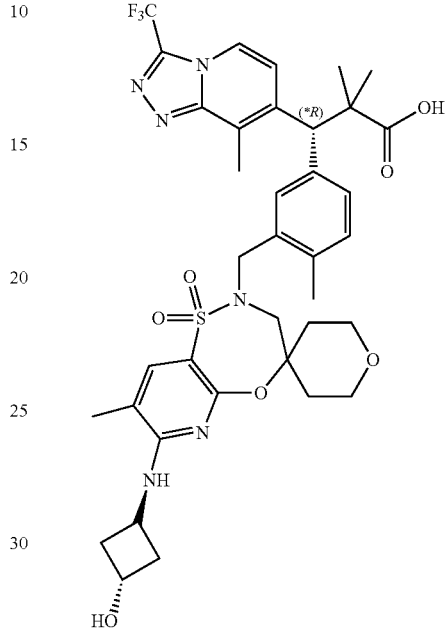

The title compound (61 mg, 50%) was prepared using analogous conditions as described in Example 114 where (1s,3s)-3-aminocyclobutan-1-ol was used instead of 3-aminopropan-1-ol in Step A and methyl (*R)-3-(3-((7'-chloro-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]]pyridine-7-yl)propanoate (Intermediate 142) instead of methyl 3-(3-((7'-chloro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(3-(trifluoromethyl)-[1,2,4]triazolo[4,3-a]pyridine-7-yl)propanoate (Example 36). MS (ESI): mass calcd. for $C_{37}H_{43}F_3N_6O_7S$, 772.3; m/z found, 773.3 [M+H]$^+$. $^1$H NMR (400 MHz, DMSO-d$_6$) δ 8.37 (d, J=7.2 Hz, 1H), 7.48 (d, J=0.9 Hz, 1H), 7.32-7.22 (m, 2H), 7.17 (s, 1H), 7.12 (d, J=7.9 Hz, 1H), 6.77 (d, J=5.9 Hz, 1H), 5.00 (br s, 1H), 4.80 (s, 1H), 4.51-4.17 (m, 5H), 3.81-3.72 (m, 3H), 3.60-3.10 (m, 2H), 2.63 (s, 3H), 2.36-2.23 (m, 2H), 2.21-2.13 (m, 5H), 2.08 (s, 3H), 1.46 (d, J=14.0 Hz, 2H), 1.30-1.16 (m, 8H).

Example 126: 2,2-Dimethyl-3-(4-methyl-3-((8'-methyl-1',1'-dioxido3-(3-((7'-(((*S)-4-hydroxybutan-2-yl)amino)-8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

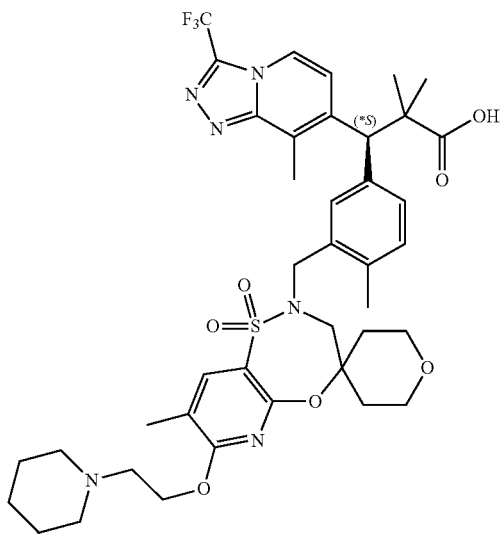 [SMILES: Cc1ccc([C@@H](c2ccn3c(C(F)(F)F)nnc3c2C)C(C)(C)C(=O)O)cc1CN1CC2(CCOCC2)Oc2nc(OCCN3CCCCC3)c(C)cc2S1(=O)=O]

Step A: Benzyl (*S)-2,2-dimethyl-3-(4-methyl-3-((8'-methyl-1',1'-dioxido-7'-(2-(piperidin-1-yl)ethyoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl]propanoate. The title compound (130 mg, 59%) was prepared using analogous conditions as described Example 11 where benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 17) was used instead of ethyl 3-(1-(cyclopropylmethyl)-4-methyl-1H-benzo[d][1,2,3]triazol-5-yl)-3-(3-hydroxymethyl)-4-methylphenyl)propanoate (Example 11, step A) and 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide was used instead of (*S)-7a-methyl-6,7,7a,8,9,19-hexahydropyrido[2,3-f]pyrollo[2,1-d][1,2,5]thiadiazepine 5,5-dioxide (Intermediate 39) in step B. MS (ESI): mass calcd. for $C_{47}H_{55}F_3N_6O_7S$, 904.4; m/z found, 905.3 [M+H]⁺.

Step B: (*S)-2,2-dimethyl-3-(4-methyl-3-((8'-methyl-1',1'-dioxido3-(3-((7'-(((S)-4-hydroxybutan-2-yl)amino)-8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid. Benzyl (*S)-2,2-dimethyl-3-(4-methyl-3-((8'-methyl-1',1'-dioxido-7'-(2-(piperidin-1-yl)ethyoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoate (85 mg, 0.09 mmol) was dissolved in methanol (3.0 mL) and continuously flowed through a hydrogenation flow system fitted with a 20% Pd(OH)₂ on carbon cartridge at a flow rate of 1.0 mL/min. and a temperature of 50° C. for 20 minutes. The eluent from the hydrogenation flow system was collected in a 20 mL scintillation vial and solvent removed under reduced pressure. The residue was dried in a vacuum oven at 60° C. for 24 h giving the title compound (30 mg, 39%). MS (ESI): mass calcd. for $C_{40}H_{49}F_3N_6O_7S$, 814.3; m/z found, 815.2 [M+H]⁺. ¹H NMR (400 MHz, DMSO-d₆) δ 8.42 (d, J=7.2 Hz, 1H), 7.86 (s, 1H), 7.28-7.23 (m, 2H), 7.21 (s, 1H), 7.15 (d, J=7.9 Hz, 1H), 4.81 (s, 1H), 4.48-4.41 (m, 3H), 4.36-4.28 (m, 1H), 3.80-3.68 (m, 2H), 3.50-3.40 (m, 7H), 2.78-2.68 (m, 2H), 2.66 (s, 3H), 2.19 (s, 3H), 2.15 (s, 3H), 1.56-1.45 (m, 6H), 1.42-1.22 (m, 11H).

Example 127: 2,2-Dimethyl-3-(4-methyl-3-((8'-methyl-1',1'-dioxido-3-(3-((7'-(((*S)-4-hydroxybutan-2-yl)amino)-8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

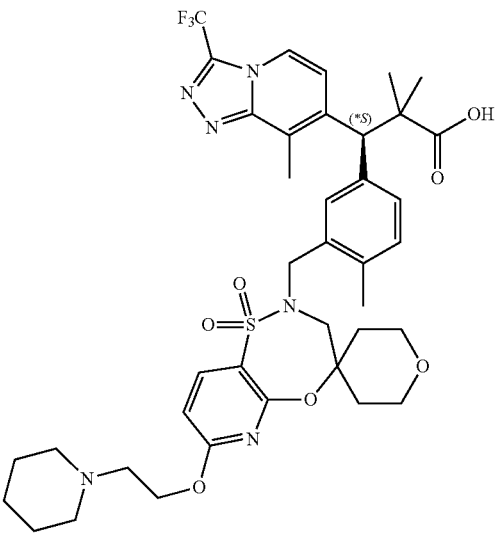 [SMILES: Cc1ccc([C@@H](c2ccn3c(C(F)(F)F)nnc3c2C)C(C)(C)C(=O)O)cc1CN1CC2(CCOCC2)Oc2nc(OCCN3CCCCC3)ccc2S1(=O)=O]

The title compound (130 mg, 83%) was prepared using analogous conditions as described in Example 126 where 7'-(2-(piperidin-1-yl)ethoxy)-2,2',3,3',5,6-hexahydrospiro[pyran-4,4'-pyrido[2,3-b][1,4,5]oxathiazepine] 1',1'-dioxide was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide in step A. MS (ESI): mass calcd. for $C_{39}H_{47}F_3N_6O_7S$, 800.3; m/z found, 801.3 [M+H]⁺. ¹H NMR (500 MHz, CDCl₃) δ 7.98-7.93 (m, 2H), 7.27 (d, J=7.4 Hz, 1H), 7.12-7.05 (m, 2H), 7.02 (d, J=7.9 Hz, 1H), 6.51 (d, J=8.4 Hz, 1H), 4.75 (s, 1H), 4.52-4.31 (m, 4H), 3.92-3.79 (m, 2H), 3.61-3.47 (m, 2H), 3.43-3.23 (m, 2H), 2.99-2.86 (m, 2H), 2.75-2.64 (m, 6H), 2.19 (s, 3H), 1.95 (s, 2H), 1.62-1.41 (m, 6H), 1.40-1.20 (m, 9H).

Example 128: (*R)-3-(3-((7'-(3-((2-Hydroxyethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

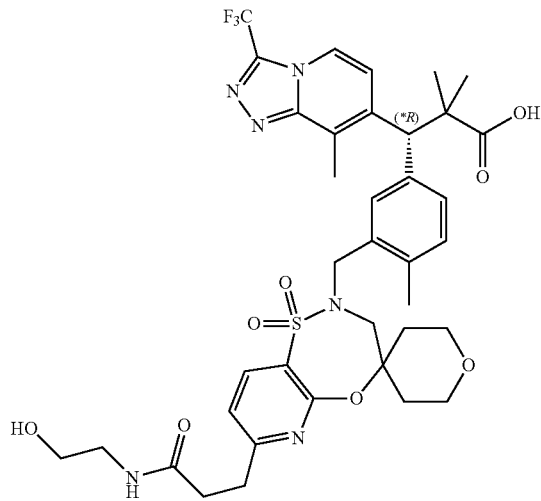 [SMILES: Cc1ccc([C@H](c2ccn3c(C(F)(F)F)nnc3c2C)C(C)(C)C(=O)O)cc1CN1CC2(CCOCC2)Oc2nc(CCC(=O)NCCO)ccc2S1(=O)=O]

Step A: (*R)-3-(2'-(5-(3-methoxy-2,2-dimethyl-1-(8-methyl-3-(trifluoromethyl)-[1,2,4-triazolo[4,3-a]pyridine-7-yl)-3-oxopropyl)-2-methylbenzyl)-1',1'-dioxido-2,2',3,3',5,6-hexahydrospiro[pyran-4,4'-pyrido[2,3-b][1,4,5]oxathiazepin]-7'-yl)propanoic acid. methyl (*R)-3-(3-((7'-(3-(tert-butoxy)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl]propanoate (100 mg, 0.12 mmol, Intermediate 74) was added to a 20 mL scintillation vial and dissolved in a 1:1 solution of DCM/TFA (1.0 mL). The mixture was stirred for 1 h then the solvent removed under reduced pressure. The resulting residue was dissolved in 1:1 DCM/MeCN and the solvent removed under reduced pressure. This process was repeated twice, and the final residue dried overnight at 60° C. in a vacuum oven producing the title compound (118 mg, 116% yield). MS (ESI): mass calcd. for $C_{36}H_{40}F_3N_5O_8S$, 760.2; m/z found, 761.2 [M+H]$^+$.

Step B: methyl (*R)-3-(3-((7'-(3-((2-hydroxyethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate. To a 15 mL round bottom flask under $N_2$ was added (*R)-3-(2'-(5-(3-methoxy-2,2-dimethyl-1-(8-methyl-3-(trifluoromethyl)-[1,2,4]triazolo[4,3-a]pyridine-7-yl)-3-oxopropyl)-2-methylbenzyl)-1',1'-dioxido-2,2',3,3',5,6-hexahydrospiro[pyran-4,4'-pyrido[2,3-b][1,4,5]oxathiazepin]-7'-yl)propanoic acid (118 mg, 0.16 mmol), DMF (2.0 mL), TEA (0.07 mL) and HATU (88 mg, 0.23 mmol). This mixture was stirred for 15 min. followed by addition of ethanolamine (28 mg, 0.46 mmol). The reaction was stirred for 24 h at r.t. then poured into saturated bicarbonate and extracted with ethyl acetate (3×). These extractions resulted in several fractions which were combined, dried over sodium sulfate and concentrated to dryness under reduced pressure. The residue was dissolved in DCM and purified by silica gel chromatography (eluent: MeOH/DCM, 0:100 to 10:90, gradient) to afford the title compound (60 mg, 48%). MS (ESI): mass calcd. for $C_{38}H_{45}F_3N_6O_8S$, 802.3; m/z found, 803.3 [M+H]$^+$.

Step C: (*R)-3-(3-((7'-(3-((2-hydroxyethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid. In a 20 mL scintillation was added methyl (*R)-3-(3-((7'-(3-((2-hydroxyethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate (60 mg, 0.07 mmol), methanol (1.0 mL), THF (1.0 mL), aqueous LiOH (0.34 mL, 2M) and water (0.34 mL). This mixture was heated to 40 C for 24 h. The reaction was then cooled to r.t., pH adjusted to ~4.0 with 1N HCl and extracted with ethyl acetate (4×). These extractions resulted in several fractions which were combined, dried over sodium sulfate and concentrated to dryness under reduced pressure. The residue was dissolved in 1:1 MeOH/DMSO and purified by reverse phase HPLC (eluent, MeCN/water with 20 mM $NH_4OH$, 5:95 to 70:30, gradient) to afford the title compound (35 mg, 59%). MS (ESI): mass calcd. for $C_{37}H_{43}F_3N_6O_8S$, 788.3; m/z found, 789.3 [M+H]$^+$. $^1$H NMR (400 MHz, DMSO-$d_6$) δ 12.50 (s, 1H), 8.43 (d, J=7.2 Hz, 1H), 8.03 (d, J=7.8 Hz, 1H), 7.90 (t, J=5.6 Hz, 1H), 7.31-7.21 (m, 4H), 7.15 (d, J=7.7 Hz, 1H), 4.81 (s, 1H), 4.63 (t, J=5.4 Hz, 1H), 4.45 (d, J=15.6 Hz, 1H), 4.35 (d, J=15.6 Hz, 1H), 3.81-3.71 (m, 2H), 3.53-3.34 (m, 5H), 3.34-3.27 (m, 2H), 3.15-3.05 (m, 2H), 3.00-2.95 (m, 2H), 2.66 (s, 3H), 2.18 (s, 3H), 1.51-1.21 (m, 11H).

Example 129: 3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoic Acid

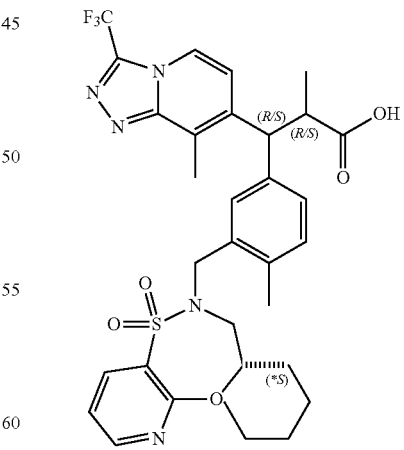

Step A: Ethyl 3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoate. To a 25-mL round bottom flask under nitrogen was added ethyl 3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridine-7-yl)propanoate (475 mg, 0.72 mmol) and THF (9 mL). The mixture was cooled to −78° C. followed by addition of LDA (0.43 mL, 2.0 M solution in THF/heptane/ethylbenzene) dropwise. After stirring for 30 minutes at −78° C., MeI (0.09 mL, 1.45 mmol) was added to the reaction neat. The reaction was stirred for an additional 1 h at −78° C., then quenched with aqueous saturated NH$_4$Cl solution and allowed to warm to r.t. The mixture was poured into aqueous saturated NH$_4$Cl and extracted with ethyl acetate (3×). These extractions resulted in several fractions which were combined, dried over sodium sulfate and concentrated to dryness under reduced pressure. The residue was purified by flash chromatography (eluent: ethyl acetate/hexanes: 0:100 to 1:1, gradient) to afford the title compound (85 mg, 17%). MS (ESI): mass calcd. for $C_{33}H_{37}F_3N_6O_4S$, 670.3; m/z found, 671.3 [M+H]$^+$.

Step B: 3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoic acid. In a 20 mL scintillation vial was added ethyl 3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoate (165 mg, 0.25 mmol), aqueous sodium hydroxide (1M, 2.2 mL) and THF (2.2 mL). The mixture was heated to 50° C. and stirred overnight. After cooling, the reaction mixture pH was adjusted to ~4 with 1M aqueous HCl and then extracted with ethyl acetate (4×). These extractions resulted in several fractions which were combined, dried over sodium sulfate and concentrated to dryness under reduced pressure. The residue was purified by SFC (Chiralcel OD-H 5 μM, 250×21.2 mm, 50% CO$_2$/50% i-PrOH) to afford the title compound (127 mg, 80%). MS (ESI): mass calcd. for $C_{31}H_{33}F_3N_6O_4S$, 642.2; m/z found, 643.3 [M+H]$^+$.

Example 130: (3*R)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoic Acid

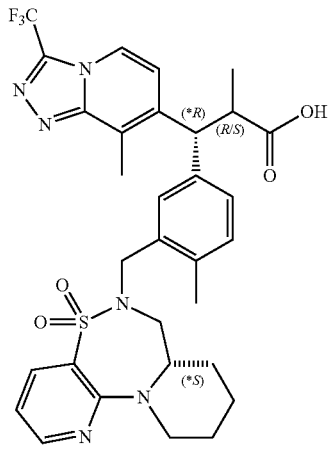 [SMILES: Cc1ccc([C@H](c2ccn3c(C(F)(F)F)nnc3c2C)C(C)C(=O)O)cc1CN1C[C@@H]2CCCCN2c2ncccc2S1(=O)=O]

The mixture of 3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoic acid isomers (Example 129) were separated by chiral SFC (Chiralcel OD-H 5 μM 250×21.2 mm, eluent 80% CO$_2$/20% MeOH). The first eluting isomer (67 mg) was designated *R: MS (ESI): mass calcd. for $C_{31}H_{33}F_3N_6O_4S$, 642.2; m/z found, 643.3 [M+H]$^+$. $^1$H NMR (400 MHz, CDCl$_3$) δ 8.30 (dd, J=4.7, 1.9 Hz, 1H), 8.04 (dd, J=7.8, 1.9 Hz, 1H), 7.98 (d, J=7.1 Hz, 1H), 7.32-7.22 (m, 2H), 7.18-7.12 (m, 2H), 6.83 (dd, J=7.8, 4.6 Hz, 1H), 4.60-4.37 (m, 3H), 4.34-4.17 (m, 2H), 3.36-3.15 (m, 4H), 2.76 (s, 3H), 2.23 (s, 3H), 1.82-1.60 (m, 2H), 1.55-1.22 (m, 2H), 1.13 (d, J=6.6 Hz, 3H), 0.94-0.71 (m, 2H).

Example 131: (3*S)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoic Acid

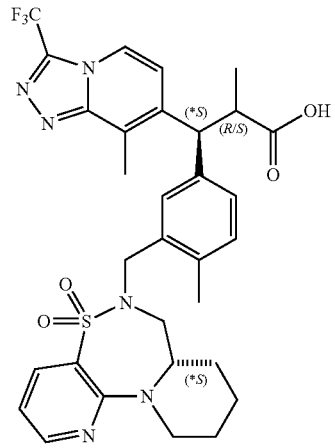 [SMILES: Cc1ccc([C@@H](c2ccn3c(C(F)(F)F)nnc3c2C)C(C)C(=O)O)cc1CN1C[C@@H]2CCCCN2c2ncccc2S1(=O)=O]

The mixture of 3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoic acid isomers (Example 129) were separated by chiral SFC (Chiralcel OD-H 5 μM 250×21.2 mm, eluent 80% CO$_2$/20% MeOH). The second eluting isomer (43 mg) was designated *S: MS (ESI): mass calcd. for $C_{31}H_{33}F_3N_6O_4S$, 642.2; m/z found, 643.3 [M+H]$^+$. $^1$H NMR (400 MHz, CDCl$_3$) δ 8.30 (dd, J=4.6, 1.9 Hz, 1H), 8.05 (dd, J=7.8, 1.8 Hz, 1H), 8.00 (d, J=7.1 Hz, 1H), 7.31-7.23 (m, 2H), 7.14 (s, 2H), 6.84 (dd, J=7.8, 4.6 Hz, 1H), 4.60-4.53 (m, 1H), 4.50-4.40 (m, 2H), 4.33-4.19 (m, 2H), 3.38-3.16 (m, 4H), 2.75 (s, 3H), 2.23 (s, 3H), 1.84-1.61 (m, 3H), 1.58-1.33 (m, 2H), 1.23-1.18 (m, 3H), 0.90-0.80 (m, 1H).

Example 132: 3-(5,8-Dimethyl-3)-(trifluoromethyl)-[1,2,4-triazolo[4,3-a]pyridine-7-yl)-3-(3-(((*S)-5,5-dioxido-7,7a,8,9,10,11-hexahydro-6H-dipyrido[2,1-d:2',3'-j][1,2,5]thiadiazepin-6-yl)methyl)-4-methylphenyl)-2-methylpropanoic Acid

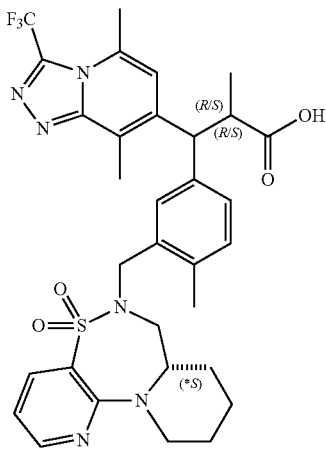 [SMILES: Cc1ccc(C(c2cc(C)n3c(C(F)(F)F)nnc3c2C)C(C)C(=O)O)cc1CN1C[C@@H]2CCCCN2c2ncccc2S1(=O)=O]

Step A: ethyl 3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoate. To a 25-mL round bottom flask under nitrogen was added ethyl 3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridine-7-yl)propanoate (500 mg, 0.76 mmol), and THF (10 mL). The mixture was cooled to −78° C. followed by addition of LDA (0.46 mL, 2.0 M solution in THF/heptane/ethylbenzene) dropwise. After stirring for 30 minutes at −78° C., MeI (0.19 mL, 3.05 mmol) was added to the reaction neat. The reaction was stirred for an additional 1 h at −78° C., then quenched with aqueous saturated NH$_4$Cl solution and allowed to warm to r.t. The mixture was poured into aqueous saturated NH$_4$Cl and extracted with ethyl acetate (3×). These extractions resulted in several fractions which were combined, dried over sodium sulfate and concentrated to dryness under reduced pressure. The residue was purified by flash chromatography (eluent: ethyl acetate/hexanes, 0:100 to 1:1 ethyl acetate/hexanes, gradient) to afford the title compound (150 mg, 29%). MS (ESI): mass calcd. for $C_{33}H_{37}F_3N_6O_4S$, 670.3; m/z found, 671.3 [M+H]$^+$.

Step B: ethyl 3-(5,8-dimethyl-3-(trifluoromethyl)-[1,2,4]triazolo[4,3-a]pyridine-7-yl)-3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methylpropanoate. To a 25 mL round bottom flask under nitrogen was added ethyl 3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methyl-3-(8-methyl-3-(trifluoromethyl)-[1,2,4]triazolo[4,3-a]pyridine-7-yl)propanoate (150 mg, 0.22 mmol), and THF (3.0 mL). The mixture was cooled to −78° C. followed by the addition of LDA solution (0.13 mL, 0.26 mmol, 2.0 M solution in THF/heptane/ethylbenzene) dropwise. The reaction was stirred at −78° C. for 1 h before it was quenched with saturated aqueous NH$_4$Cl and then allowed to warm to r.t. The quenched reaction mixture was then poured into saturated aqueous NH$_4$Cl and extracted with ethyl acetate (3×). These extractions resulted in several fractions which were combined, dried over sodium sulfate and concentrated to dryness under reduced pressure. The residue was purified by silica gel chromatography (eluent: ethyl acetate/hexanes, 0:100 to 1:1 ethyl acetate/hexanes, gradient) to afford the title compound (110 mg, 72%). MS (ESI): mass calcd. for $C_{34}H_{39}F_3N_6O_4S$, 684.3; m/z found, 685.2 [M+H]$^+$.

Step C: 3-(5,8-dimethyl-3)-(trifluoromethyl)-[1,2,4-triazolo[4,3-a]pyridine-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methylpropanoic acid. In a 20 mL vial was added ethyl 3-(5,8-dimethyl-3-(trifluoromethyl)-[1,2,4]triazolo[4,3-a]pyridine-7-yl)-3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methylpropanoate (110 mg, 0.16 mmol), aqueous sodium hydroxide (1M, 1.5 mL) and THF (1.5 mL). The mixture was heated to 50° C. and stirred overnight. After cooling, the reaction mixture pH was adjusted to ~4 with 1M aqueous HCl and then extracted with ethyl acetate (4×). These extractions resulted in several fractions which were combined, dried over sodium sulfate and concentrated to dryness under reduced pressure to afford the title compound (73 mg, 69%). MS (ESI): mass calcd. for $C_{32}H_{35}F_3N_6O_4S$, 656.2; m/z found, 657.2 [M+H]$^+$.

Example 133: (3*R)-3-(5,8-Dimethyl-3)-(trifluoromethyl)-[1,2,4-triazolo[4,3-a]pyridine-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methylpropanoic Acid

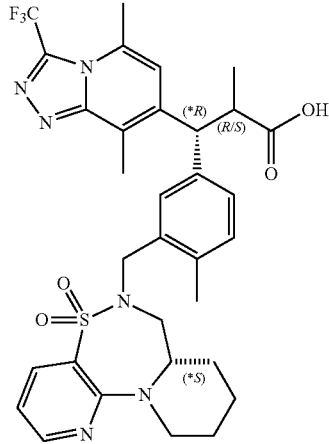 [SMILES: Cc1ccc([C@H](c2cc(C)n3c(C(F)(F)F)nnc3c2C)C(C)C(=O)O)cc1CN1C[C@@H]2CCCCN2c2ncccc2S1(=O)=O]

The mixture of 3-(5,8-dimethyl-3)-(trifluoromethyl)-[1,2,4-triazolo[4,3-a]pyridine-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methylpropanoic acid isomers (Example 132) were separated by chiral SFC (AD-H 2×25 cm, eluent 75% CO$_2$/25% i-PrOH). The first eluting isomer (26 mg) was designated *R: MS (ESI): mass calcd. for $C_{32}H_{35}F_3N_6O_4S$, 656.2; m/z found, 657.2 [M+H]$^+$. $^1$H NMR (400 MHz, CDCl$_3$) δ 8.30 (dd, J=4.6, 1.9 Hz, 1H), 8.05 (dd, J=7.8, 1.9 Hz, 1H), 7.31 (s, 1H), 7.15-7.12 (m, 2H), 7.00 (s, 1H), 6.84 (dd, J=7.8, 4.6 Hz, 1H), 4.64-4.52 (m, 1H), 4.50-4.39 (m, 2H), 4.33-4.18 (m, 2H), 3.45-3.18 (m, 4H), 2.75-2.65 (m, 6H), 2.21 (s, 3H), 1.84-1.34 (m, 6H), 1.27-1.20 (m, 3H).

Example 134: (3*S)-3-(5,8-Dimethyl-3)-(trifluoromethyl)-[1,2,4-triazolo[4,3-a]pyridine-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methylpropanoic Acid

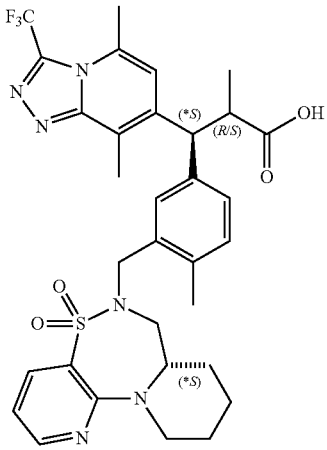 [SMILES: Cc1ccc([C@@H](c2cc(C)n3c(C(F)(F)F)nnc3c2C)C(C)C(=O)O)cc1CN1C[C@@H]2CCCCN2c2ncccc2S1(=O)=O]

The mixture of 3-(5,8-dimethyl-3)-(trifluoromethyl)-[1,2,4-triazolo[4,3-a]pyridine-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-2-methylpropanoic acid isomers (Example 132) were separated by chiral SFC (AD-H 2×25 cm, eluent 75% $CO_{2/25}$% i-PrOH). The second eluting isomer (30 mg) was designated *S: MS (ESI): mass calcd. for $C_{32}H_{35}F_3N_6O_4S$, 656.2; m/z found, 657.2 [M+H]⁺. ¹H NMR (400 MHz, CDCl₃) δ 8.30 (dd, J=4.6, 1.9 Hz, 1H), 8.05 (dd, J=7.8, 1.9 Hz, 1H), 7.31 (s, 1H), 7.15-7.12 (m, 2H), 7.00 (s, 1H), 6.84 (dd, J=7.8, 4.6 Hz, 1H), 4.58-4.40 (m, 3H), 4.32-4.18 (m, 2H), 3.40-3.16 (m, 4H), 2.75-2.65 (m, 6H), 2.21 (s, 3H), 1.81-1.60 (m, 3H), 1.57-1.46 (m, 1H), 1.43-1.32 (m, 2H), 1.25-1.16 (m, 3H).

Example 135: (R/S)-3-(3-(((*S)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(1-ethyl-4-methyl-1H-benzo[d][1,2,3]triazol-5-yl)propanoic Acid

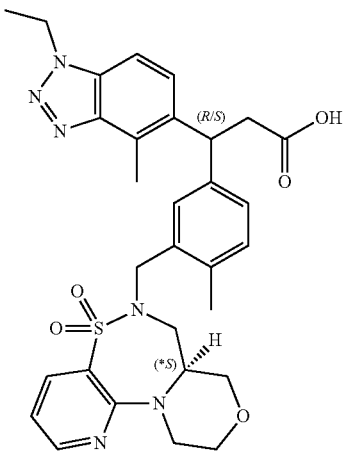 [SMILES: CCn1nnc2c(C)c(C(CC(=O)O)c3ccc(C)c(CN4C[C@H]5COCCN5c5ncccc5S4(=O)=O)c3)ccc21]

DMF (1.5 mL) was added to an ice-cooled, stirring mixture of (*S)-6,7,7a,8,10,11-hexahydro-[1,4]oxazino[3,4-d]pyrido[2,3-f][1,2,5]thiadiazepine 5,5-dioxide (Intermediate 13, 79 mg, 0.31 mmol) and sodium hydride (60% dispersion in mineral oil, 42 mg, 1.05 mmol) under nitrogen. After 30 minutes, ethyl 3-(3-(chloromethyl)-4-methylphenyl)-3-(1-ethyl-4-methyl-1H-benzo[d][1,2,3]triazol-5-yl)propanoate (Intermediate 31, 123 mg, 0.308 mmol) was added and the mixture was allowed to warm to room temperature for 2.5 hours. 1 M aqueous sodium hydroxide solution (0.62 mL) was added and the reaction was stirred at room temperature overnight. The mixture was filtered and the filtrate was purified by preparative acidic HPLC (XBridge $C_{18}$, acetonitrile-water containing 0.05% TFA) to provide the title compound (110.5 mg, 99% yield). MS (ESI): mass calcd. for $C_{30}H_{34}N_6O_5S$, 590.2; m/z found, 591.0 [M+H]⁺.

Example 136: (*S)-3-(3-(((*S)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(1-ethyl-4-methyl-1H-benzo[d][1,2,3]triazol-5-yl)propanoic Acid

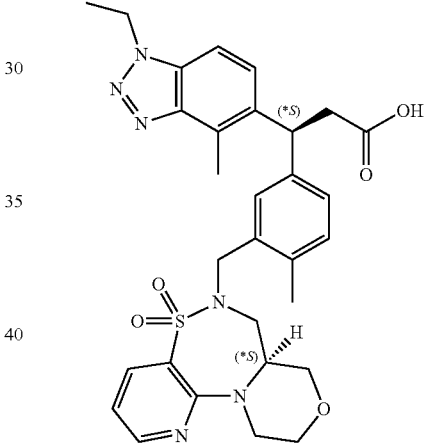

The mixture of (R/S)-3-(3-(((*S)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(1-ethyl-4-methyl-1H-benzo[d][1,2,3]triazol-5-yl)propanoic acid isomers (Example 135) was separated by chiral SFC (Daicel Chiralpak AD-H 5 μm, 300 gram, mobile phase: 70% $CO_2$, 30% MeOH) to afford two diastereomers. The first eluting isomer (41 mg) was designated (*S): MS (ESI): mass calcd. for $C_{30}H_{34}N_6O_5S$, 590.2; m/z found, 591.3 [M+H]⁺. ¹H NMR (500 MHz, CDCl₃) δ 8.24 (dd, J=4.6, 1.8 Hz, 1H), 8.02 (dd, J=7.8, 1.8 Hz, 1H), 7.37-7.26 (m, 3H), 6.96 (d, J=7.9 Hz, 1H), 6.83 (dd, J=7.8, 4.6 Hz, 1H), 6.74 (dd, J=7.8, 2.0 Hz, 1H), 4.86 (dd, J=12.0, 3.9 Hz, 1H), 4.68-4.49 (m, 5H), 4.28 (d, J=11.3 Hz, 1H), 4.11 (d, J=13.1 Hz, 1H), 3.75-3.64 (m, 4H), 3.29-3.21 (m, 1H), 3.14 (dd, J=13.6, 4.1 Hz, 1H), 3.05-2.97 (m, 1H), 2.94-2.88 (m, 1H), 2.64 (s, 3H), 2.13 (s, 3H), 1.58-1.52 (m, 3H).

Example 137: (*R)-3-(3-(((*S)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(1-ethyl-4-methyl-1H-benzo[d][1,2,3]triazol-5-yl) propanoic Acid

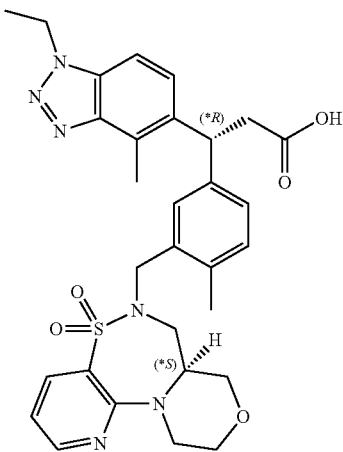 [SMILES: CCn1nnc2c(C)c([C@H](CC(=O)O)c3ccc(C)c(CN4C[C@H]5COCCN5c5ncccc5S4(=O)=O)c3)ccc21]

The second eluting isomer (41 mg) from the separation of isomers by chiral SFC described in Example 136 was designated (*R): MS (ESI): mass calcd. for $C_{30}H_{34}N_6O_5S$, 590.2; m/z found, 591.3 [M+H]$^+$. $^1$H NMR (500 MHz, CDCl$_3$) δ 8.32-8.28 (m, 1H), 8.11 (d, J=7.9, 1.8 Hz, 1H), 7.41-7.31 (m, 2H), 7.24 (s, 1H), 7.12-7.03 (m, 2H), 6.89 (dd, J=7.8, 4.6 Hz, 1H), 5.00-4.91 (m, 1H), 4.66 (q, J=7.3 Hz, 2H), 4.62-4.49 (m, 2H), 4.39-4.28 (m, 2H), 3.95-3.87 (m, 1H), 3.76-3.61 (m, 4H), 3.29-3.13 (m, 2H), 3.06-2.95 (m, 2H), 2.86 (s, 3H), 2.11 (s, 3H), 1.64-1.58 (m, 3H).

Example 138: (R/S)-3-(3-(((*R)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(1-ethyl-4-methyl-1H-benzo[d][1,2,3]triazol-5-yl) propanoic Acid

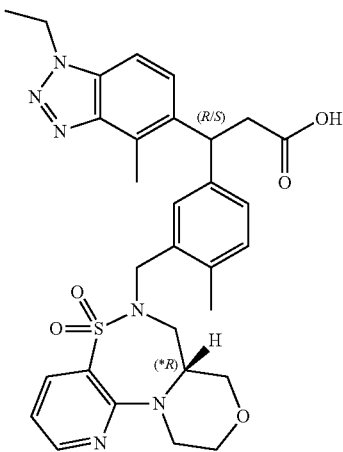 [SMILES: CCn1nnc2c(C)c(C(CC(=O)O)c3ccc(C)c(CN4C[C@@H]5COCCN5c5ncccc5S4(=O)=O)c3)ccc21]

The title compound (111 mg, 62% yield) was prepared using analogous conditions as described in Example 135 where (*R)-6,7,7a,8,10,11-hexahydro-[1,4]oxazino[3,4-d]pyrido[2,3-f][1,2,5]thiadiazepine 5,5-dioxide (Intermediate 14) was used instead of (*S)-6,7,7a,8,10,11-hexahydro-[1,4]oxazino[3,4-d]pyrido[2,3-f][1,2,5]thiadiazepine 5,5-dioxide. MS (ESI): mass calcd. for $C_{30}H_{34}N_6O_5S$, 590.2; m/z found, 591.0 [M+H]$^+$.

Example 139: (*S)-3-(3-(((*R)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(1-ethyl-4-methyl-1H-benzo[d][1,2,3]triazol-5-yl) propanoic Acid

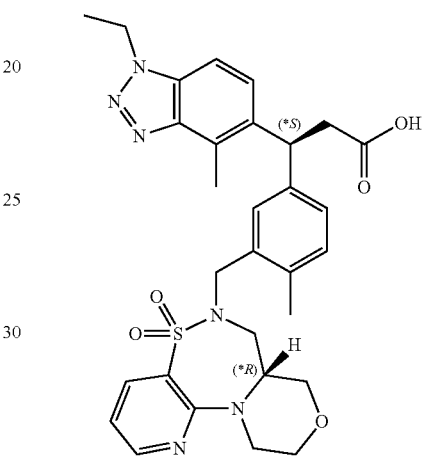

The mixture of (R/S)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(1-ethyl-4-methyl-1H-benzo[d][1,2,3]triazol-5-yl)propanoic acid isomers (Example 138) was separated by chiral SFC (Daicel Chiralpak AD-H 5 μm, 300 gram, mobile phase: 70% $CO_2$, 30% MeOH) to afford two diastereomers. The first eluting isomer (37 mg) was designated (*S): MS (ESI): mass calcd. for $C_{30}H_{34}N_6O_5S$, 590.2; m/z found, 591.3 [M+H]$^+$. $^1$H NMR (500 MHz, CDCl$_3$) δ 8.21 (dd, J=4.7, 1.8 Hz, 1H), 8.02 (dd, J=7.8, 1.9 Hz, 1H), 7.32-7.23 (m, 2H), 7.16 (s, 1H), 7.02-6.95 (m, 2H), 6.80 (dd, J=7.9, 4.6 Hz, 1H), 4.91-4.83 (m, 1H), 4.57 (q, J=7.3 Hz, 2H), 4.53-4.41 (m, 2H), 4.30-4.19 (m, 2H), 3.85-3.80 (m, 1H), 3.66-3.53 (m, 4H), 3.20-3.13 (m, 1H), 3.13-3.04 (m, 1H), 2.95-2.82 (m, 2H), 2.77 (s, 3H), 2.02 (s, 3H), 1.55-1.50 (m, 3H).

Example 140: (*R)-3-(3-(((*R)-5,5-Dioxido-7a,8,
10,11-tetrahydro-[1,4]oxazino[3,4-d]pyrido[2,3-f][1,
2,5]thiadiazepin-6(7H)-yl)methyl)-4-methylphenyl)-
3-(1-ethyl-4-methyl-1H-benzo[d][1,2,3]triazol-5-yl)
propanoic Acid

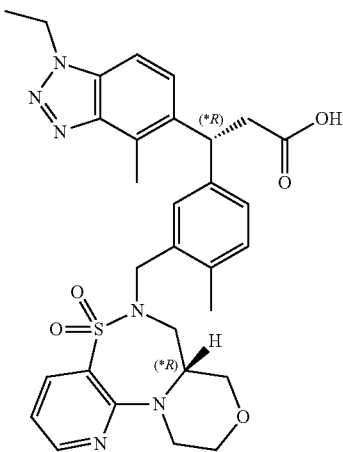 [SMILES: CCn1nnc2c(C)c([C@H](CC(=O)O)c3ccc(C)c(CN4C[C@@H]5COCCN5c5ncccc5S4(=O)=O)c3)ccc21]

The second eluting isomer (38 mg) from the separation of isomers by chiral SFC described in Example 139 was designated (*R): MS (ESI): mass calcd. for $C_{30}H_{34}N_6O_5S$, 590.2; m/z found, 591.3 [M+H]$^+$. $^1$H NMR (500 MHz, CDCl$_3$) δ 8.33 (dd, J=4.6, 1.8 Hz, 1H), 8.10 (dd, J=7.8, 1.8 Hz, 1H), 7.46-7.35 (m, 3H), 7.05 (d, J=7.8 Hz, 1H), 6.92 (dd, J=7.8, 4.7 Hz, 1H), 6.86-6.81 (m, 1H), 4.99-4.92 (m, 1H), 4.77-4.57 (m, 5H), 4.40-4.33 (m, 1H), 4.20 (d, J=13.1 Hz, 1H), 3.85-3.72 (m, 4H), 3.38-3.29 (m, 1H), 3.27-3.19 (m, 1H), 3.14-3.05 (m, 1H), 3.05-2.97 (m, 1H), 2.73 (s, 3H), 2.22 (s, 3H), 1.67-1.61 (m, 3H).

Example 141: (R/S)-3-(3-(((*S)-5,5-Dioxido-7,7a,8,
9,10,11-hexahydro-6H-dipyrido[2,1-d:2',3'-f][1,2,5]
thiadiazepin-6-yl)methyl)-4-methylphenyl)-3-(1-
ethyl-4-methyl-1H-benzo[d][1,2,3]triazol-5-yl)
propanoic Acid

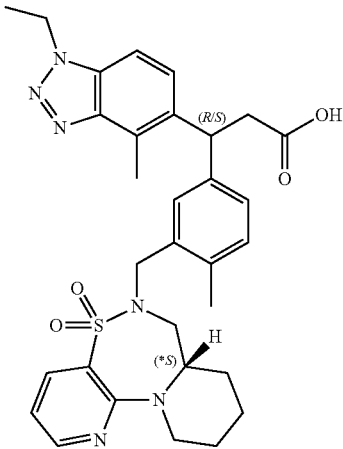

The title compound (120.6 mg, 67% yield) was prepared using analogous conditions as described in Example 135 where (S)-7,7a,8,9,10,11-hexahydro-6H-dipyrido[2,1-d:2',3'-f][1,2,5]thiadiazepine 5,5-dioxide (Intermediate 2) was used instead of (*S)-6,7,7a,8,10,11-hexahydro-[1,4]oxazino[3,4-d]pyrido[2,3-f][1,2,5]thiadiazepine 5,5-dioxide. MS (ESI): mass calcd. for $C_{31}H_{36}N_6O_4S$, 588.2; m/z found, 589.0 [M+H]$^+$.

Example 142: (*S)-3-(3-(((*S)-5,5-Dioxido-7,7a,8,
9,10,11-hexahydro-6H-dipyrido[2,1-d:2',3'-f][1,2,5]
thiadiazepin-6-yl)methyl)-4-methylphenyl)-3-(1-
ethyl-4-methyl-1H-benzo[d][1,2,3]triazol-5-yl)
propanoic Acid

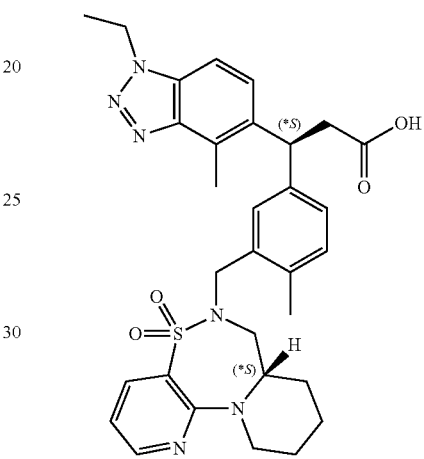

The mixture of (R/5)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-3-(1-ethyl-4-methyl-1H-benzo[d][1,2,3]triazol-5-yl)propanoic acid isomers (Example 141) was separated by chiral SFC (Daicel Chiralpak AD-H 5 μm, 300 gram, mobile phase: 70% CO$_2$, 30% MeOH) to afford two diastereomers. The first eluting isomer (39 mg) was designated (*S): MS (ESI): mass calcd. for $C_{31}H_{36}N_6O_4S$, 588.2; m/z found, 589.3 [M+H]$^+$. $^1$H NMR (500 MHz, CDCl$_3$) δ 8.29 (d, J=4.4 Hz, 1H), 8.05 (d, J=7.6 Hz, 1H), 7.39-7.31 (m, 2H), 7.15-7.07 (m, 3H), 6.85-6.80 (m, 1H), 4.98 (t, 1H), 4.66 (q, J=7.4 Hz, 2H), 4.54-4.48 (m, 1H), 4.44 (d, J=14.3 Hz, 1H), 4.22-4.13 (m, 2H), 3.23-3.14 (m, 3H), 3.14-3.04 (m, 2H), 2.84 (s, 3H), 2.26 (s, 3H), 1.70-1.59 (m, 4H), 1.54-1.25 (m, 5H).

Example 143: (*R)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(1-ethyl-4-methyl-1H-benzo[d][1,2,3]triazol-5-yl)propanoic Acid

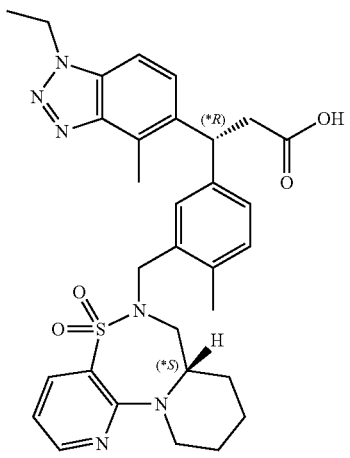

The second eluting isomer (38 mg) from the separation of isomers by chiral SFC described in Example 142 was designated (*R): MS (ESI): mass calcd. for $C_{31}H_{36}N_6O_4S$, 588.2; m/z found, 589.3 [M+H]$^+$. $^1$H NMR (500 MHz, CDCl$_3$) δ 8.31-8.27 (m, 1H), 8.06 (d, J=7.7 Hz, 1H), 7.33 (s, 2H), 7.15-7.08 (m, 3H), 6.85-6.81 (m, 1H), 5.04-4.94 (m, 1H), 4.65 (q, J=7.1 Hz, 2H), 4.52-4.44 (m, 2H), 4.24-4.11 (m, 2H), 3.18-3.07 (m, 5H), 2.86 (s, 3H), 2.27 (s, 3H), 1.71-1.50 (m, 5H), 1.43-1.17 (m, 4H).

Example 144: (R/S)-3-(3-(((*R)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(1-ethyl-4-methyl-1H-benzo[d][1,2,3]triazol-5-yl)propanoic Acid

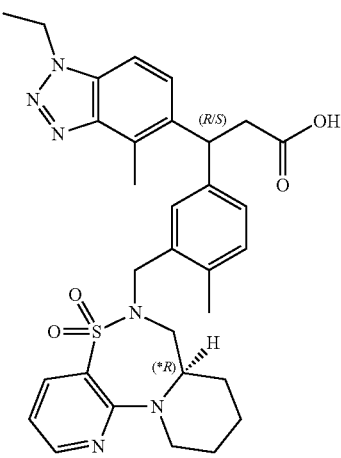

The title compound (99.8 mg, 56% yield) was prepared using analogous conditions as described in Example 135 where (*R)-7,7a,8,9,10,11-hexahydro-6H-dipyrido[2,1-d:2',3'-f][1,2,5]thiadiazepine 5,5-dioxide (Intermediate 3) was used instead of (*S)-6,7,7a,8,10,11-hexahydro-[1,4]oxazino[3,4-d]pyrido[2,3-f][1,2,5]thiadiazepine 5,5-dioxide. MS (ESI): mass calcd. for $C_{31}H_{36}N_6O_4S$, 588.2; m/z found, 589.0 [M+H]$^+$.

Example 145: (*S)-3-(3-(((*R)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(1-ethyl-4-methyl-1H-benzo[d][1,2,3]triazol-5-yl)propanoic Acid

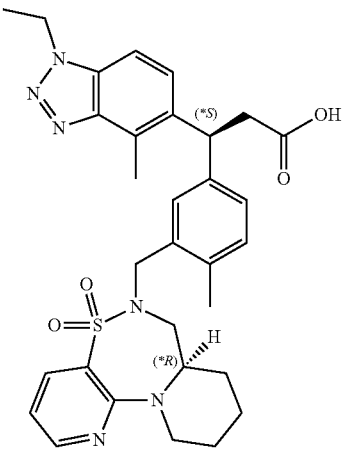 [SMILES: CCn1nnc2c(C)c([C@@H](CC(=O)O)c3ccc(C)c(CN4C[C@H]5CCCCN5c5ncccc5S4(=O)=O)c3)ccc21]

The mixture of (R/S)-3-(3-(((*R)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(1-ethyl-4-methyl-1H-benzo[d][1,2,3]triazol-5-yl)propanoic acid isomers (Example 144) was separated by chiral SFC (Daicel Chiralpak AD-H 5 μm, 300 gram, mobile phase: 70% CO$_2$, 30% MeOH) to afford two diastereomers. The first eluting isomer (26 mg) was designated (*S): MS (ESI): mass calcd. for $C_{31}H_{36}N_6O_4S$, 588.2; m/z found, 589.3 [M+H]$^+$. $^1$H NMR (500 MHz, CDCl$_3$) δ 8.29 (dd, J=4.6, 1.8 Hz, 1H), 8.06 (dd, J=7.8, 1.8 Hz, 1H), 7.33 (s, 2H), 7.15-7.08 (m, 3H), 6.86-6.80 (m, 1H), 4.98 (t, J=7.8 Hz, 1H), 4.65 (q, J=7.3 Hz, 2H), 4.51-4.43 (m, 2H), 4.23-4.11 (m, 2H), 3.22-3.04 (m, 5H), 2.86 (s, 3H), 2.27 (s, 3H), 1.71-1.49 (m, 5H), 1.44-1.14 (m, 4H).

Example 146: (*R)-3-(3-(((*R)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(1-ethyl-4-methyl-1H-benzo[d][1,2,3]triazol-5-yl)propanoic Acid

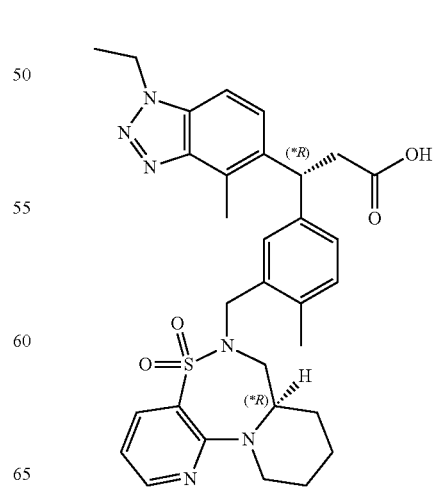

The second eluting isomer (25 mg) from the separation of isomers by chiral SFC described in Example 145 was designated (*R): MS (ESI): mass calcd. for $C_{31}H_{36}N_6O_4S$, 588.2; m/z found, 589.3 [M+H]+. $^1H$ NMR (500 MHz, CDCl$_3$) δ 8.29 (d, J=4.8, 1.7 Hz, 1H), 8.05 (dd, J=7.7, 1.8 Hz, 1H), 7.39-7.30 (m, 2H), 7.15-7.08 (m, 3H), 6.85-6.79 (m, 1H), 4.98 (t, 1H), 4.66 (q, J=7.3 Hz, 2H), 4.55-4.47 (m, 1H), 4.44 (d, J=14.4 Hz, 1H), 4.22-4.14 (m, 2H), 3.24-3.13 (m, 3H), 3.13-3.04 (m, 2H), 2.84 (s, 3H), 2.26 (s, 3H), 1.71-1.59 (m, 4H), 1.54-1.24 (m, 5H).

Example 147: (R/S)-3-(3-(((S)-5,5-Dioxido-7a,8,9,10-tetrahydrobenzo[f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic Acid

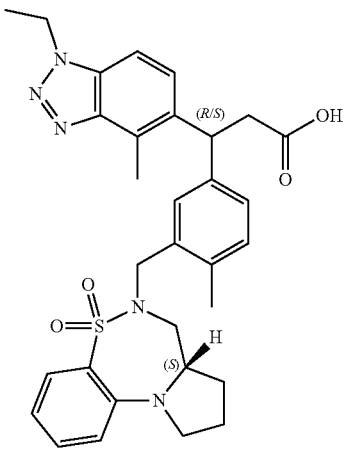

The title compound (34.4 mg, 50% yield) was prepared using analogous conditions as described in Example 135 where (S)-6,7,7a,8,9,10-hexahydrobenzo[f]pyrrolo[2,1-d][1,2,5]thiadiazepine 5,5-dioxide (Intermediate 84) was used instead of (*S)-6,7,7a,8,10,11-hexahydro-[1,4]oxazino[3,4-d]pyrido[2,3-f][1,2,5]thiadiazepine 5,5-dioxide. MS (ESI): mass calcd. for $C_{31}H_{35}N_5O_4S$, 573.2; m/z found, 574.2 [M+H]+.

Example 148: (*S)-3-[3-[(5,5-Dioxo-7a,8,9,10-tetrahydro-7H-pyrrolo[2,1-d][1,2,5]benzothiadiazepin-6-yl)methyl]-4-methyl-phenyl]-3-(1-ethyl-4-methyl-benzotriazol-5-yl)propanoic Acid

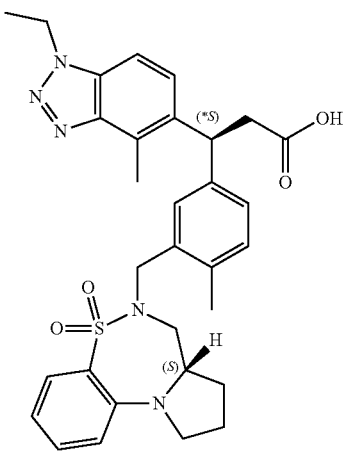

The mixture of (R/S)-3-(3-(((S)-5,5-dioxido-7a,8,9,10-tetrahydrobenzo[f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid isomers (Example 147) was separated by chiral SFC (Daicel Chiralpak AD-H 5 μm, mobile phase: 55% $CO_2$, 45% MeOH) to afford two diastereomers. The first eluting isomer (11 mg) was designated (*S): MS (ESI): mass calcd. for $C_{31}H_{35}N_5O_4S$, 573.2; m/z found, 574.2 [M+H]+. $^1H$ NMR (400 MHz, CDCl$_3$) δ 7.85-7.80 (m, 1H), 7.34-7.27 (m, 1H), 7.27-7.21 (m, 2H), 7.04-6.96 (m, 3H), 6.90-6.84 (m, 1H), 6.80 (d, J=8.2 Hz, 1H), 4.86 (t, J=7.7 Hz, 1H), 4.61-4.51 (m, 2H), 4.24-4.05 (m, 2H), 3.42 (s, 1H), 3.25-3.18 (m, 2H), 3.12-2.94 (m, 3H), 2.88-2.69 (m, 4H), 2.20 (s, 3H), 1.90-1.73 (m, 2H), 1.73-1.59 (m, 1H), 1.58-1.45 (m, 3H), 1.36-1.26 (m, 1H).

Example 149: (*R)-3-[3-[(5,5-Dioxo-7a,8,9,10-tetrahydro-7H-pyrrolo[2,1-d][1,2,5]benzothiadiazepin-6-yl)methyl]-4-methyl-phenyl]-3-(1-ethyl-4-methyl-benzotriazol-5-yl)propanoic Acid

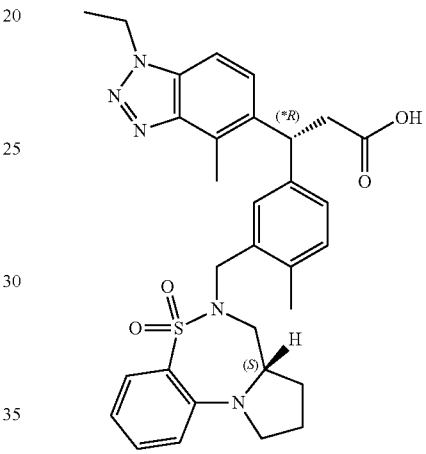

The second eluting isomer (13 mg) from the separation of isomers by chiral SFC described in Example 148 was designated (*R): MS (ESI): mass calcd. for $C_{31}H_{35}N_5O_4S$, 573.2; m/z found, 574.2 [M+H]+.

Example 150: (R/S)-3-[3-[(4,4-Dimethyl-1,1-dioxo-3H-pyrido[2,3-b][1,4,5]oxathiazepin-2-yl)methyl]-4-methyl-phenyl]-3-(1-ethyl-4-methyl-benzotriazol-5-yl)propanoic Acid

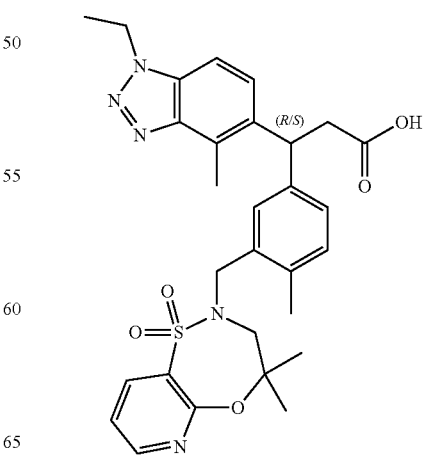

The title compound (11 mg, 44% yield) was prepared using analogous conditions as described in Example 135 where 4,4-dimethyl-3,4-dihydro-2H-pyrido[2,3-b][1,4,5]oxathiazepine 1,1-dioxide (Intermediate 82) was used instead of (*S)-6,7,7a,8,10,11-hexahydro-[1,4]oxazino[3,4-d]pyrido[2,3-f][1,2,5]thiadiazepine 5,5-dioxide. MS (ESI): mass calcd. for $C_{29}H_{33}N_5O_5S$, 563.2; m/z found, 564.3 [M+H]$^+$. $^1$H NMR (500 MHz, CDCl$_3$) δ 8.39 (dd, J=4.9, 2.0 Hz, 1H), 8.12 (dd, J=7.6, 2.0 Hz, 1H), 7.28 (q, J=8.7 Hz, 2H), 7.19-7.15 (m, 2H), 6.99-6.93 (m, 2H), 4.92 (t, J=7.7 Hz, 1H), 4.63-4.57 (m, 2H), 4.41 (s, 2H), 3.42 (s, 2H), 3.06-2.88 (m, 2H), 2.74 (s, 3H), 2.16 (s, 3H), 1.60-1.53 (m, 3H) 1.15-1.08 (m, 6H).

Example 151: (R/S)-3-(3-((4,4-Dimethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic Acid

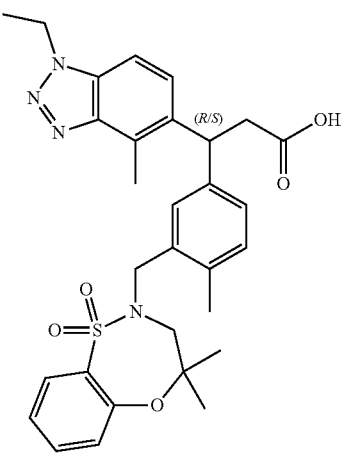 [SMILES: CCn1nnc2c(C)c(C(CC(=O)O)c3ccc(C)c(CN4CC(C)(C)Oc5ccccc5S4(=O)=O)c3)ccc21]

The title compound (26.6 mg, 47% yield) was prepared using analogous conditions as described in Example 135 where 4,4-dimethyl-3,4-dihydro-2H-benzo[b][1,4,5]oxathiazepine 1,1-dioxide (Intermediate 81) was used instead of (*S)-6,7,7a,8,10,11-hexahydro-[1,4]oxazino[3,4-d]pyrido[2,3-f][1,2,5]thiadiazepine 5,5-dioxide. MS (ESI): mass calcd. for $C_{30}H_{34}N_4O_5S$, 562.2; m/z found, 563.2 [M+H]$^+$. $^1$H NMR (400 MHz, CDCl$_3$) δ 7.80 (dd, J=7.8, 1.7 Hz, 1H), 7.45-7.40 (m, 1H), 7.35-7.27 (m, 2H), 7.21-7.14 (m, 2H), 7.07-6.98 (m, 3H), 4.93 (t, J=7.8 Hz, 1H), 4.66-4.36 (m, 2H), 4.44-4.36 (m, 2H), 3.37-3.24 (m, 2H), 3.16-2.96 (m, 2H), 2.77 (s, 3H), 2.20 (s, 3H), 1.61-1.55 (m, 3H), 1.10-0.99 (m, 6H).

Example 152: (R/S)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic Acid

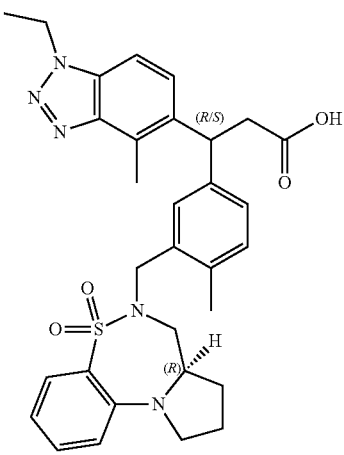

The title compound (34.1 mg, 59% yield) was prepared using analogous conditions as described in Example 135 where (R)-6,7,7a,8,9,10-hexahydrobenzo[f]pyrrolo[2,1-d][1,2,5]thiadiazepine 5,5-dioxide (Intermediate 83) was used instead of (*S)-6,7,7a,8,10,11-hexahydro-[1,4]oxazino[3,4-d]pyrido[2,3-f][1,2,5]thiadiazepine 5,5-dioxide. MS (ESI): mass calcd. for $C_{31}H_{35}N_5O_4S$, 573.2; m/z found, 574.2 [M+H]$^+$. $^1$H NMR (400 MHz, CDCl$_3$) δ 7.89-7.83 (m, 1H), 7.39-7.32 (m, 1H), 7.29 (d, J=1.2 Hz, 2H), 7.15 (d, J=6.6 Hz, 1H), 7.04-6.95 (m, 2H), 6.95-6.82 (m, 2H), 4.93 (t, J=7.8 Hz, 1H), 4.65-4.57 (m, 2H), 4.30-4.12 (m, 2H), 3.35-3.21 (m, 2H), 3.11-2.91 (m, 5H), 2.81-2.75 (m, 3H), 2.23 (d, J=4.5 Hz, 3H), 1.93-1.63 (m, 3H), 1.61-1.53 (m, 3H), 1.35 (t, J=10.1 Hz, 1H).

Example 153: (*S)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic Acid

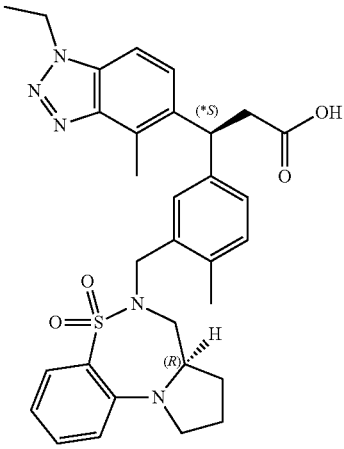

The mixture of (R/S)-3-(3-(((R)-5,5-dioxido-7a,8,9,10-tetrahydrobenzo[f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic acid isomers (Example 152) was separated by chiral SFC (Chiralpak AD-H 5 μm, mobile phase: 55% CO₂, 45% MeOH) to afford two diastereomers. The first eluting isomer (16 mg) was designated (*S): MS (ESI): mass calcd. for $C_{31}H_{35}N_5O_4S$, 573.2; m/z found, 574.2 [M+H]⁺. ¹H NMR (400 MHz, CDCl₃) δ 7.83 (d, J=7.8 Hz, 1H), 7.31 (t, J=7.6 Hz, 1H), 7.27-7.20 (m, 2H), 7.07-6.96 (m, 3H), 6.91-6.85 (m, 1H), 6.83-6.77 (m, 1H), 4.91-4.84 (m, 1H), 4.61-4.51 (m, 2H), 4.26-4.08 (m, 2H), 3.30-3.15 (m, 2H), 3.12-2.92 (m, 3H), 2.77 (s, 3H), 2.21 (s, 3H), 1.90-1.27 (m, 6H), 1.25-1.17 (m, 3H).

Example 154: (*R)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic Acid

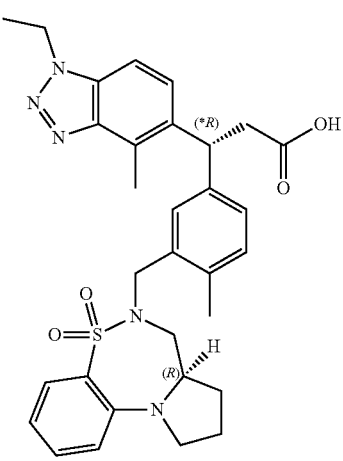

The second eluting isomer (14 mg) from the separation of isomers by chiral SFC described in Example 153 was designated (*R): MS (ESI): mass calcd. for $C_{31}H_{35}N_5O_4S$, 573.2; m/z found, 574.2 [M+H]⁺. ¹H NMR (400 MHz, CDCl₃) δ 7.85-7.79 (m, 1H), 7.34-7.21 (m, 3H), 7.06-6.96 (m, 3H), 6.91-6.85 (m, 1H), 6.84-6.77 (m, 1H), 4.94-4.82 (m, 1H), 4.62-4.52 (m, 2H), 4.22-4.08 (m, 2H), 3.28-3.17 (m, 2H), 3.14-2.95 (m, 3H), 2.78-2.70 (m, 3H), 2.25-2.17 (m, 3H), 1.89-1.29 (m, 6H), 1.18 (s, 3H).

Example 155: (R/S)-3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl) propanoic Acid

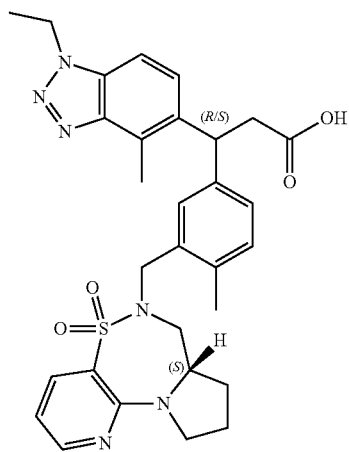

The title compound (15.5 mg, 11% yield) was prepared using analogous conditions as described in Example 135 where (S)-6,7,7a,8,9,10-hexahydropyrido[2,3-f]pyrrolo[2,1-d][1,2,5]thiadiazepine 5,5-dioxide (Intermediate 75) was used instead of (*S)-6,7,7a,8,10,11-hexahydro-[1,4]oxazino[3,4-d]pyrido[2,3-f][1,2,5]thiadiazepine 5,5-dioxide. MS (ESI): mass calcd. for $C_{30}H_{34}N_6O_4S$, 574.2; m/z found, 575.2 [M+H]⁺.

Example 156: (*S)-3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl) propanoic Acid

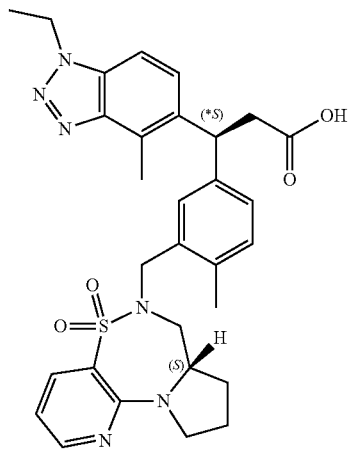

The mixture of (R/5S)-3-(3-(((S)-5,5-dioxido-7a,8,9,10-tetrahydropyrido[2,3-f]pyrrolo[2,1-d][1,2,5]thiadiazepin-6 (7H)-yl)methyl)-4-methylphenyl)-3-(1-ethyl-4-methyl-1H-benzo[d][1,2,3]triazol-5-yl)propanoic acid isomers (Example 155) was separated by chiral SFC (Chiralpak AD-H 5 μm, mobile phase: 50% CO₂, 50% MeOH) to afford two diastereomers. The first eluting isomer (9 mg) was designated (*S): MS (ESI): mass calcd. for C₃₀H₃₄N₆O₄S, 574.2; m/z found, 575.2 [M+H]⁺. ¹H NMR (400 MHz, CDCl₃) δ 8.28-8.18 (m, 1H), 8.06-7.97 (m, 1H), 7.34-7.22 (m, 2H), 7.09-6.94 (m, 3H), 6.74 (dd, J=7.7, 4.6 Hz, 1H), 4.90-4.79 (m, 1H), 4.62-4.46 (m, 3H), 4.32 (d, J=14.1 Hz, 1H), 4.05 (d, J=13.9 Hz, 1H), 3.61-3.39 (m, 2H), 3.24-3.14 (m, 1H), 3.12-2.92 (m, 2H), 2.80-2.67 (m, 4H), 2.19 (s, 3H), 1.93-1.81 (m, 1H), 1.76-1.65 (m, 1H), 1.57-1.43 (m, 4H), 1.41-1.31 (m, 1H).

Example 157: (*R)-3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(1-ethyl-4-methyl-1H-benzo[d][1,2,3]triazol-5-yl)propanoic Acid

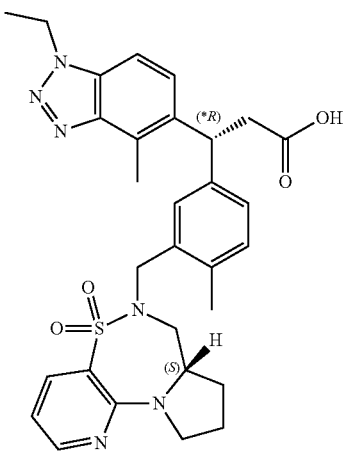

The second eluting isomer (9 mg) from the separation of isomers by chiral SFC described in Example 156 was designated (*R): MS (ESI): mass calcd. for C₃₀H₃₄N₆O₄S, 574.2; m/z found, 575.0 [M+H]⁺. ¹H NMR (400 MHz, CDCl₃) δ 8.24-8.17 (m, 1H), 8.02-7.95 (m, 1H), 7.29-7.20 (m, 2H), 7.06-6.93 (m, 3H), 6.77-6.68 (m, 1H), 4.92-4.79 (m, 1H), 4.55 (q, J=7.3 Hz, 2H), 4.50-4.39 (m, 1H), 4.34-4.26 (m, 1H), 4.06-3.99 (m, 1H), 3.58-3.42 (m, 2H), 3.18-3.08 (m, 1H), 3.06-2.82 (m, 2H), 2.80-2.65 (m, 4H), 2.17 (s, 3H), 1.90-1.74 (m, 1H), 1.74-1.63 (m, 1H), 1.63-1.43 (m, 4H), 1.37-1.26 (m, 1H).

Example 158: (*S)-3-(3-((4,4-Dimethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic Acid

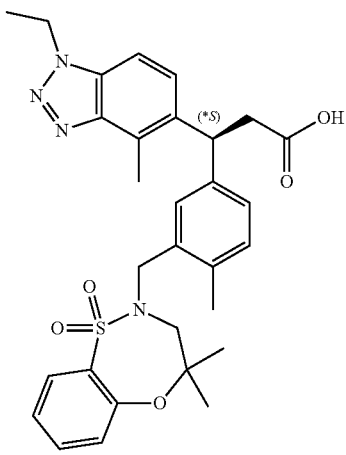 [SMILES: CCn1nnc2c(C)c([C@@H](CC(=O)O)c3ccc(C)c(CN4CC(C)(C)Oc5ccccc5S4(=O)=O)c3)ccc21]

The title compound (8 mg, 5% yield) was prepared using analogous conditions as described in Example 135 where 4,4-dimethyl-3,4-dihydro-2H-benzo[b][1,4,5]oxathiazepine 1,1-dioxide (Intermediate 81) was used instead of (*S)-6,7,7a,8,10,11-hexahydro-[1,4]oxazino[3,4-d]pyrido[2,3-f][1,2,5]thiadiazepine 5,5-dioxide, followed by separation of the mixture of isomers by chiral SFC (Chiralpak IC 5 μm, mobile phase: 60% CO₂, 40% MeOH) to afford two diastereomers. The first eluting isomer was designated (*S): MS (ESI): mass calcd. for C₃₀H₃₄N₄O₅S, 562.2; m/z found, 563.4 [M+H]⁺. ¹H NMR (400 MHz, CDCl₃) δ 7.75 (dd, J=7.8, 1.7 Hz, 1H), 7.37 (td, J=7.6, 1.7 Hz, 1H), 7.30-7.22 (m, 2H), 7.16-7.09 (m, 1H), 7.03 (s, 1H), 7.01-6.97 (m, 3H), 4.88 (t, J=7.7 Hz, 1H), 4.56 (q, J=7.3 Hz, 2H), 4.43-4.26 (m, 2H), 3.37-3.14 (m, 2H), 3.15-2.96 (m, 2H), 2.73 (s, 3H), 2.15 (s, 3H), 1.54-1.48 (m, 3H), 1.02-0.89 (m, 6H).

Example 159: (*R)-3-(3-((4,4-Dimethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)propanoic Acid

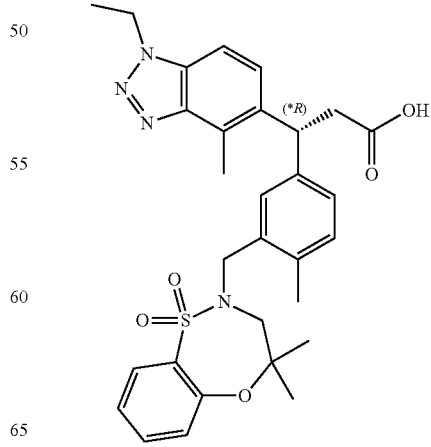

The second eluting isomer (9 mg) from the separation of isomers by chiral SFC described in Example 158 was designated (*R): MS (ESI): mass calcd. for $C_{30}H_{34}N_4O_5S$, 562.2; m/z found, 563.4 [M+H]+. 1H NMR (400 MHz, CDCl3) δ 7.75 (dd, J=7.8, 1.7 Hz, 1H), 7.37 (td, J=7.6, 1.7 Hz, 1H), 7.30-7.22 (m, 2H), 7.16-7.10 (m, 1H), 7.04-6.96 (m, 4H), 4.88 (t, J=7.7 Hz, 1H), 4.56 (q, J=7.3 Hz, 2H), 4.41-4.25 (m, 2H), 3.35-3.15 (m, 2H), 3.15-2.95 (m, 2H), 2.73 (s, 3H), 2.15 (s, 3H), 1.55-1.47 (m, 3H), 1.04-0.89 (m, 6H).

Example 160: (R/S)-3-(3-((4,4-Dimethyl-1,1-di-oxido-3,4-dihydro-2H-pyrido[2,3-b][1,4,5]oxathiaz-epin-2-yl)methyl)-4-methylphenyl)-3-(3-methyl-[1,2,4]triazolo[4,3-a]pyridin-7-yl)propanoic Acid

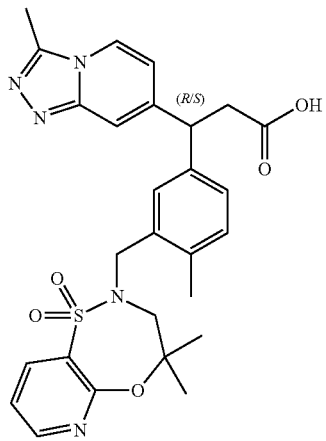 [SMILES: Cc1ccc(C(CC(=O)O)c2ccn3c(C)nnc3c2)cc1CN1CC(C)(C)Oc2ncccc2S1(=O)=O]

The title compound (24 mg, 42% yield) was prepared using analogous conditions as described in Example 135 where 4,4-dimethyl-3,4-dihydro-2H-pyrido[2,3-b][1,4,5]oxathiazepine 1,1-dioxide (Intermediate 82) was used instead of (*S)-6,7,7a,8,10,11-hexahydro-[1,4]oxazino[3,4-d]pyrido[2,3-f][1,2,5]thiadiazepine 5,5-dioxide and ethyl 3-(3-(chloromethyl)-4-methylphenyl)-3-(3-methyl-[1,2,4]triazolo[4,3-a]pyridin-7-yl)propanoate (Intermediate 105) was used instead of ethyl 3-(3-(chloromethyl)-4-methylphenyl)-3-(1-ethyl-4-methyl-1H-benzo[d][1,2,3]triazol-5-yl)propanoate. MS (ESI): mass calcd. for $C_{27}H_{29}N_5O_5S$, 535.2; m/z found, 536.2 [M+H]+. 1H NMR (400 MHz, CDCl3) δ 8.45 (dd, J=4.9, 2.0 Hz, 1H), 8.18 (dd, J=7.6, 2.0 Hz, 1H), 7.83 (s, 1H), 7.69 (d, J=7.2 Hz, 1H), 7.26-7.22 (m, 1H), 7.20 (s, 1H), 7.14-7.07 (m, 2H), 6.67 (d, J=7.3 Hz, 1H), 4.65 (t, J=7.7 Hz, 1H), 4.55-4.42 (m, 2H), 3.55 (s, 2H), 3.22-3.07 (m, 2H), 2.65 (s, 3H), 2.25 (s, 3H), 1.23 (s, 6H).

Example 161: (R/S)-3-(3-((4,4-Dimethyl-1,1-di-oxido-3,4-dihydro-2H-benzo[b][1,4,5]oxathiazepin-2-yl)methyl)-4-methylphenyl)-3-(3-methyl-[1,2,4]triazolo[4,3-a]pyridin-7-yl)propanoic Acid

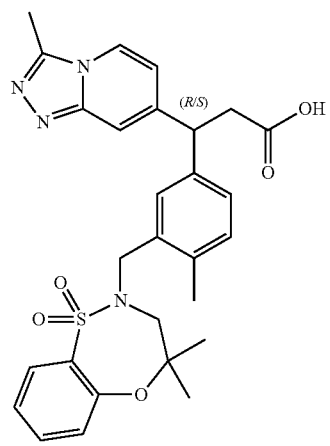 [SMILES: Cc1ccc(C(CC(=O)O)c2ccn3c(C)nnc3c2)cc1CN1CC(C)(C)Oc2ccccc2S1(=O)=O]

The title compound (23.6 mg, 41% yield) was prepared using analogous conditions as described in Example 135 where 4,4-dimethyl-3,4-dihydro-2H-benzo[b][1,4,5]oxathi-azepine 1,1-dioxide (Intermediate 81) was used instead of (*S)-6,7,7a,8,10,11-hexahydro-[1,4]oxazino[3,4-d]pyrido[2,3-f][1,2,5]thiadiazepine 5,5-dioxide and ethyl 3-(3-(chloromethyl)-4-methylphenyl)-3-(3-methyl-[1,2,4]triazolo[4,3-a]pyridin-7-yl)propanoate (Intermediate 105) was used instead of ethyl 3-(3-(chloromethyl)-4-methylphenyl)-3-(1-ethyl-4-methyl-1H-benzo[d][1,2,3]triazol-5-yl)propanoate. MS (ESI): mass calcd. for $C_{28}H_{30}N_4O_5S$, 534.2; m/z found, 535.2 [M+H]+. 1H NMR (400 MHz, CDCl3) δ 7.86-7.79 (m, 2H), 7.67 (d, J=7.2 Hz, 1H), 7.49-7.43 (m, 1H), 7.24-7.19 (m, 2H), 7.12-7.03 (m, 3H), 6.66 (d, J=7.3 Hz, 1H), 4.64 (t, J=7.6 Hz, 1H), 4.50-4.36 (m, 2H), 3.46 (s, 2H), 3.20-3.02 (m, 2H), 2.63 (s, 3H), 2.24 (s, 3H), 1.18 (s, 6H).

Example 162: (R/S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(3-methyl-[1,2,4]triazolo[4,3-a]pyridin-7-yl)propanoic Acid The title compound (9.9 mg, 11% yield) was prepared using analogous conditions as described in Example 135 where (R)-4-ethyl-3,4-dihydro-2H-pyrido[2,3-b][1,4,5]oxathiazepine 1,1-dioxide (Intermediate 91) was used instead of (*S)-6,7,7a,8,10,11-hexahydro-[1,4]oxazino[3,4-d]pyrido[2,3-f][1,2,5]thiadiazepine 5,5-dioxide and ethyl 3-(3-(chloromethyl)-4-methylphenyl)-3-(3-methyl-[1,2,4]triazolo[4,3-a]pyridin-7-yl)propanoate (Intermediate 105) was used instead of ethyl 3-(3-(chloromethyl)-4-methylphenyl)-3-(1-ethyl-4-methyl-1H-benzo[d][1,2,3]triazol-5-yl)propanoate. MS (ESI): mass calcd. for $C_{27}H_{29}N_5O_5S$, 535.2; m/z found, 536.2 $[M+H]^+$. $^1H$ NMR (400 MHz, $CDCl_3$) δ 8.40 (dd, J=4.8, 1.9 Hz, 1H), 8.17-8.12 (m, 1H), 8.11-8.04 (m, 2H), 7.22-7.19 (m, 1H), 7.16-7.09 (m, 2H), 7.08-6.99 (m, 2H), 4.61-4.54 (m, 1H), 4.43-4.29 (m, 2H), 4.03-3.97 (m, 1H), 3.58-3.45 (m, 1H), 3.21-3.09 (m, 2H), 3.03-2.94 (m, 1H), 2.73 (s, 3H), 2.18 (s 3H), 1.72-1.60 (m, 1H), 1.59-1.47 (m, 1H), 0.97 (t, J=7.3 Hz, 3H).

Example 163: (*S)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(3-methyl-[1,2,4]triazolo[4,3-a]pyridin-7-yl)propanoic Acid

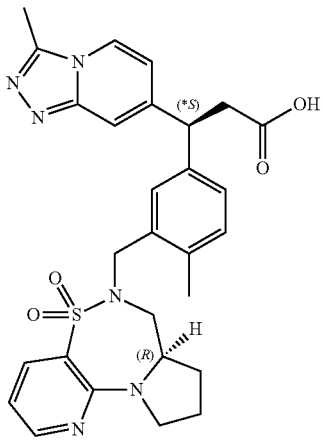

The title compound (4 mg, 7% yield) was prepared using analogous conditions as described in Example 135 where (R)-6,7,7a,8,9,10-hexahydropyrido[2,3-f]pyrrolo[2,1-d][1,2,5]thiadiazepine 5,5-dioxide (Intermediate 4) was used instead of (*S)-6,7,7a,8,10,11-hexahydro-[1,4]oxazino[3,4-d]pyrido[2,3-f][1,2,5]thiadiazepine 5,5-dioxide and ethyl 3-(3-(chloromethyl)-4-methylphenyl)-3-(3-methyl-[1,2,4]triazolo[4,3-a]pyridin-7-yl)propanoate (Intermediate 105) was used instead of ethyl 3-(3-(chloromethyl)-4-methylphenyl)-3-(1-ethyl-4-methyl-1H-benzo[d][1,2,3]triazol-5-yl)propanoate, followed by separation of the mixture of isomers by chiral SFC (Chiralpak AD-H 5 µm, mobile phase: 45% $CO_2$, 55% EtOH) to afford two diastereomers. The first eluting isomer was designated (*S): MS (ESI): mass calcd. for $C_{28}H_{30}N_6O_4S$, 546.2; m/z found, 547.3 $[M+H]^+$. $^1H$ NMR (400 MHz, $CDCl_3$) δ 8.30-8.21 (m, 1H), 8.03-7.96 (m, 1H), 7.96-7.86 (m, 1H), 7.77-7.65 (m, 1H), 7.14-6.94 (m, 3H), 6.81-6.71 (m, 1H), 6.71-6.60 (m, 1H), 4.64-4.51 (m, 2H), 4.38-4.29 (m, 1H), 4.16 (d, J=14.5 Hz, 1H), 3.65-3.55 (m, 2H), 3.37-3.30 (m, 1H), 3.15-3.05 (m, 1H), 3.05-2.94 (m, 1H), 2.94-2.81 (m, 1H), 2.61 (s, 3H), 2.21 (s, 3H), 2.03-1.93 (m, 1H), 1.91-1.82 (m, 1H), 1.80-1.71 (m, 1H), 1.57-1.47 (m, 1H).

Example 164: (*R)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(3-methyl-[1,2,4]triazolo[4,3-a]pyridin-7-yl)propanoic Acid

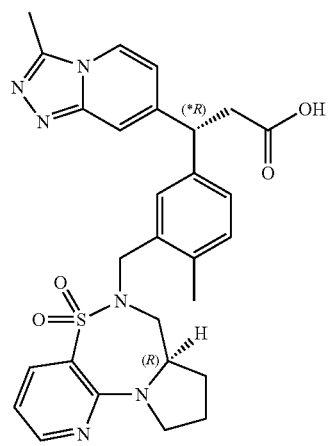

The second eluting isomer (4 mg) from the separation of isomers by chiral SFC described in Example 163 was designated (*R): MS (ESI): mass calcd. for $C_{28}H_{30}N_6O_4S$, 546.2; m/z found, 547.3 $[M+H]^+$. $^1H$ NMR (400 MHz, $CDCl_3$) δ 8.24 (dd, J=4.8, 1.8 Hz, 1H), 8.00 (dd, J=7.7, 1.8 Hz, 1H), 7.95-7.88 (m, 1H), 7.69-7.62 (m, 1H), 7.10-7.00 (m, 3H), 6.77-6.71 (m, 1H), 6.66-6.59 (m, 1H), 4.62-4.50 (m, 2H), 4.35 (d, J=14.6 Hz, 1H), 4.13 (d, J=14.6 Hz, 1H), 3.64-3.53 (m, 2H), 3.36-3.28 (m, 1H), 3.16-3.07 (m, 1H), 3.07-2.95 (m, 1H), 2.86 (t, J=12.5 Hz, 1H), 2.60 (s, 3H), 2.22 (s, 3H), 2.04-1.91 (m, 1H), 1.90-1.82 (m, 1H), 1.79-1.66 (m, 1H), 1.56-1.46 (m, 1H).

Example 165: (*S)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(3-methyl-[1,2,4]triazolo[4,3-a]pyridin-7-yl)propanoic Acid

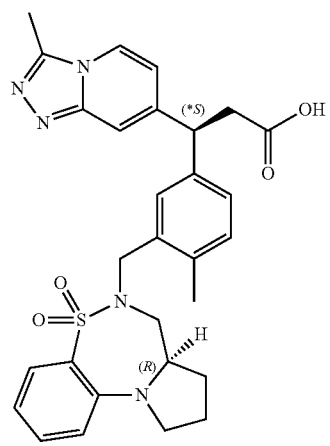

The title compound (7 mg, 13% yield) was prepared using analogous conditions as described in Example 135 where (R)-6,7,7a,8,9,10-hexahydrobenzo[f]pyrrolo[2,1-d][1,2,5]thiadiazepine 5,5-dioxide (Intermediate 83) was used instead of (*S)-6,7,7a,8,10,11-hexahydro-[1,4]oxazino[3,4-d]pyrido[2,3-f][1,2,5]thiadiazepine 5,5-dioxide and ethyl 3-(3-(chloromethyl)-4-methylphenyl)-3-(3-methyl-[1,2,4]triazolo[4,3-a]pyridin-7-yl)propanoate (Intermediate 105) was used instead of ethyl 3-(3-(chloromethyl)-4-methylphenyl)-3-(1-ethyl-4-methyl-1H-benzo[d][1,2,3]triazol-5-yl)propanoate, followed by separation of the mixture of isomers by chiral SFC (Chiralpak AD-H 5 μm, mobile phase: 45% $CO_2$, 55% EtOH) to afford two diastereomers. The first eluting isomer was designated (*S): MS (ESI): mass calcd. for $C_{29}H_{31}N_5O_4S$, 545.2; m/z found, 546.2 $[M+H]^+$. $^1H$ NMR (400 MHz, $CDCl_3$) δ 7.94-7.89 (m, 1H), 7.84-7.80 (m, 1H), 7.64-7.56 (m, 1H), 7.37-7.29 (m, 1H), 7.10-6.98 (m, 3H), 6.91-6.82 (m, 2H), 6.57-6.51 (m, 1H), 4.64-4.55 (m, 1H), 4.29-4.10 (m, 3H), 3.36-2.98 (m, 6H), 2.58 (s, 3H), 2.23 (s, 3H), 1.97-1.75 (m, 3H), 1.49-1.42 (m, 1H).

Example 166: (*R)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(3-methyl-[1,2,4]triazolo[4,3-a]pyridin-7-yl)propanoic Acid

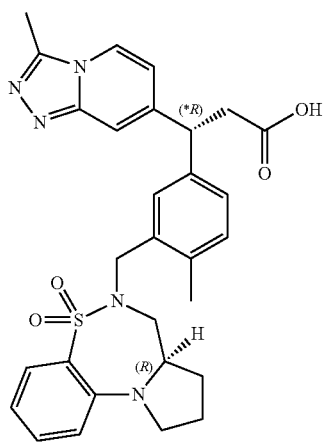

The second eluting isomer (6 mg) from the separation of isomers by chiral SFC described in Example 165 was designated (*R): MS (ESI): mass calcd. for $C_{29}H_{31}N_5O_4S$, 545.2; m/z found, 546.2 $[M+H]^+$. $^1H$ NMR (400 MHz, $CDCl_3$) δ 7.96-7.86 (m, 1H), 7.88-7.76 (m, 1H), 7.70-7.60 (m, 1H), 7.38-7.24 (m, 1H), 7.13-6.93 (m, 3H), 6.89-6.77 (m, 2H), 6.68-6.56 (m, 1H), 4.63-4.51 (m, 1H), 4.34-4.06 (m, 3H), 3.37-2.80 (m, 6H), 2.59 (s, 3H), 2.23 (s, 3H), 2.03-1.69 (m, 3H), 1.53-1.42 (m, 2H).

Example 167: (R/S)-3-(3-Cyclopropyl-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

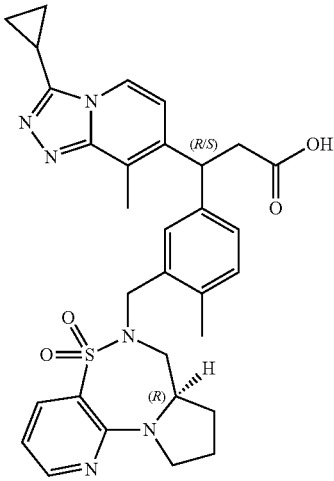

The title compound (200 mg, 75% yield) was prepared using analogous conditions as described in Example 135 where (R)-6,7,7a,8,9,10-hexahydropyrido[2,3-f]pyrrolo[2,1-d][1,2,5]thiadiazepine 5,5-dioxide (Intermediate 4) was used instead of (*S)-6,7,7a,8,10,11-hexahydro-[1,4]oxazino[3,4-d]pyrido[2,3-f][1,2,5]thiadiazepine 5,5-dioxide and ethyl 3-(3-(chloromethyl)-4-methylphenyl)-3-(3-cyclopropyl-8-methyl-[1,2,4]triazolo[4,3-a]pyridin-7-yl)propanoate (Intermediate 106) was used instead of ethyl 3-(3-(chloromethyl)-4-methylphenyl)-3-(1-ethyl-4-methyl-1H-benzo[d][1,2,3]triazol-5-yl)propanoate. MS (ESI): mass calcd. for $C_{31}H_{34}N_6O_4S$, 586.2; m/z found, 587.2 $[M+H]^+$. $^1H$ NMR (500 MHz, $CDCl_3$) δ 8.32 (d, J=4.9 Hz, 1H), 8.27-8.20 (m, 1H), 8.07 (d, J=7.7 Hz, 1H), 7.23-7.08 (m, 3H), 7.05 (s, 1H), 6.88-6.79 (m, 1H), 4.97-4.83 (m, 1H), 4.74-4.56 (m, 1H), 4.40 (d, J=14.6 Hz, 1H), 4.22 (d, J=15.8 Hz, 1H), 3.77-3.63 (m, 2H), 3.49-3.33 (m, 1H), 3.20-3.05 (m, 2H), 2.98-2.88 (m, 1H), 2.74-2.62 (m, 3H), 2.31-2.21 (m, 3H), 2.21-1.92 (m, 3H), 1.91-1.79 (m, 1H), 1.69-1.55 (m, 1H), 1.37-1.19 (m, 4H).

Example 168: (*S)-3-(3-Cyclopropyl-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

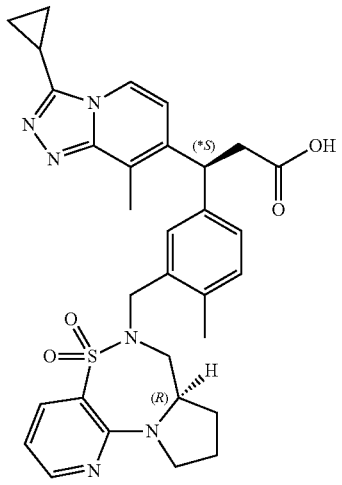

The mixture of (R/S)-3-(3-cyclopropyl-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid isomers (Example 167) was separated by chiral SFC (Chiralpak IA, mobile phase: 60% $CO_2$, 40% MeOH) to afford two diastereomers. The first eluting isomer (89 mg) was designated (*S): MS (ESI): mass calcd. for $C_{31}H_{34}N_6O_4S$, 586.2; m/z found, 587.2 [M+H]$^+$. $^1$H NMR (500 MHz, CDCl$_3$) δ 8.36-8.27 (m, 1H), 8.09 (dd, J=7.8, 1.7 Hz, 1H), 7.93 (s, 1H), 7.18-7.03 (m, 3H), 6.88-6.74 (m, 2H), 4.96 (s, 1H), 4.60 (t, J=10.8 Hz, 1H), 4.43 (d, J=14.4 Hz, 1H), 4.19 (d, J=14.4 Hz, 1H), 3.69-3.57 (m, 2H), 3.31 (dd, J=13.2, 3.6 Hz, 1H), 3.25-2.97 (m, 2H), 2.95-2.83 (m, 1H), 2.71 (s, 3H), 2.29 (s, 3H), 2.07-1.90 (m, 2H), 1.90-1.67 (m, 2H), 1.56-1.46 (m, 1H), 1.36-1.25 (m, 1H), 1.22-1.11 (m, 3H).

Example 169: (*R)-3-(3-Cyclopropyl-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

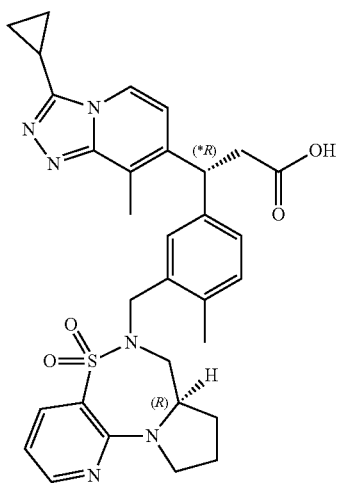

The second eluting isomer (85 mg) from the separation of isomers by chiral SFC described in Example 168 was designated (*R): MS (ESI): mass calcd. for $C_{31}H_{34}N_6O_4S$, 586.2; m/z found, 587.2 [M+H]$^+$. $^1$H NMR (500 MHz, CDCl$_3$) δ 8.31 (d, J=4.5 Hz, 1H), 8.08 (dd, J=7.8, 1.7 Hz, 1H), 7.98-7.89 (m, 1H), 7.18-7.06 (m, 3H), 6.82 (dd, J=7.8, 4.7 Hz, 2H), 5.00-4.87 (m, 1H), 4.69-4.57 (m, 1H), 4.42 (d, J=14.6 Hz, 1H), 4.20 (d, J=14.5 Hz, 1H), 3.71-3.59 (m, 2H), 3.43-3.34 (m, 1H), 3.23-2.99 (m, 2H), 2.91 (t, J=12.5 Hz, 1H), 2.70 (s, 3H), 2.28 (s, 3H), 2.10-1.88 (m, 3H), 1.87-1.74 (m, 1H), 1.60-1.52 (m, 1H), 1.39-1.13 (m, 4H).

Example 170: (*S)-3-(1-(Cyclopropylmethyl)-4-(difluoromethyl)-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

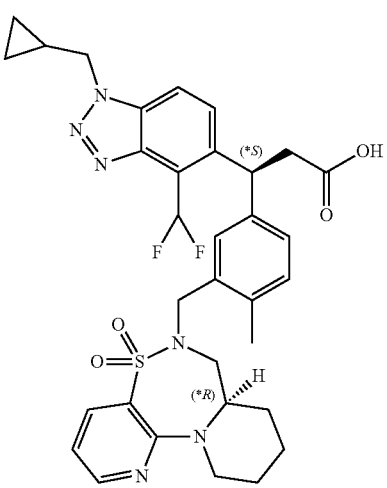

The title compound (15 mg) was prepared using analogous conditions as described in Example 135 where (R)-7,7a,8,9,10,11-hexahydro-6H-dipyrido[2,1-d:2',3'-f][1,2,5]thiadiazepine 5,5-dioxide (Intermediate 2) was used instead of (*S)-6,7,7a,8,10,11-hexahydro-[1,4]oxazino[3,4-d]pyrido[2,3-f][1,2,5]thiadiazepine 5,5-dioxide and ethyl 3-(3-(chloromethyl)-4-methylphenyl)-3-(1-(cyclopropylmethyl)-4-(difluoromethyl)-1H-benzo[d][1,2,3]triazol-5-yl)propanoate (Intermediate 92) was used instead of ethyl 3-(3-(chloromethyl)-4-methylphenyl)-3-(1-ethyl-4-methyl-1H-benzo[d][1,2,3]triazol-5-yl)propanoate, followed by separation of the mixture of isomers by chiral SFC (Chiralpak AD-H 5 μm, mobile phase: 50% $CO_2$, 50% EtOH) to afford two diastereomers. The first eluting isomer was designated (*S): MS (ESI): mass calcd. for $C_{33}H_{36}F_2N_6O_4S$, 650.2; m/z found, 651.5 [M+H]$^+$.

Example 171: (*R)-3-(1-(Cyclopropylmethyl)-4-(difluoromethyl)-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

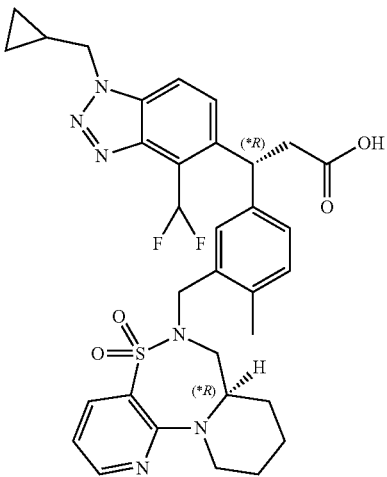

The second eluting isomer (16 mg) from the separation of isomers by chiral SFC described in Example 170 was designated (*R): MS (ESI): mass calcd. for $C_{33}H_{36}F_2N_6O_4S$, 650.2; m/z found, 651.5 [M+H]$^+$.

Example 172: (*S)-3-(1-(Cyclopropylmethyl)-4-(difluoromethyl)-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

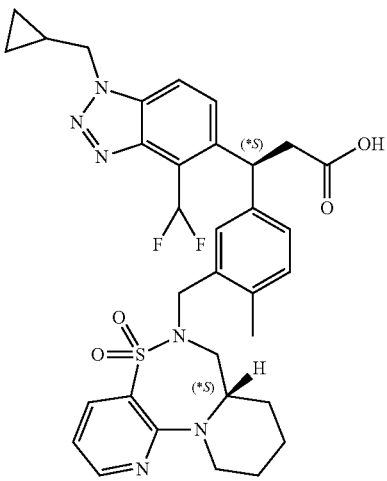

The title compound (15 mg) was prepared using analogous conditions as described in Example 135 where (S)-7,7a,8,9,10,11-hexahydro-6H-dipyrido[2,1-d:2',3'-f][1,2,5]thiadiazepine 5,5-dioxide (Intermediate 2) was used instead of (*S)-6,7,7a,8,10,11-hexahydro-[1,4]oxazino[3,4-d]pyrido[2,3-f][1,2,5]thiadiazepine 5,5-dioxide and ethyl 3-(3-(chloromethyl)-4-methylphenyl)-3-(1-(cyclopropylmethyl)-4-(difluoromethyl)-1H-benzo[d][,2,3]triazol-5-yl)propanoate (Intermediate 92) was used instead of ethyl 3-(3-(chloromethyl)-4-methylphenyl)-3-(1-ethyl-4-methyl-1H-benzo[d][1,2,3]triazol-5-yl)propanoate, followed by separation of the mixture of isomers by chiral SFC (Chiralpak AD-H 5 μm, mobile phase: 50% $CO_2$, 50% iPrOH) to afford two diastereomers. The first eluting isomer was designated (*S): MS (ESI): mass calcd. for $C_{33}H_{36}F_2N_6O_4S$, 650.2; m/z found, 651.5 [M+H]$^+$. $^1$H NMR (400 MHz, CDCl$_3$) δ 8.30-8.26 (m, 1H), 8.07-7.76 (m, 3H), 7.62-7.56 (d, J=8.5 Hz, 1H), 7.41-7.36 (d, J=8.7 Hz, 1H), 7.25-7.21 (m, 1H), 7.17-7.11 (m, 1H), 6.84-6.78 (m, 1H), 5.44-5.35 (t, J=7.9 Hz, 1H), 4.59-4.39 (m, 4H), 4.27-4.11 (m, 2H), 3.33-2.98 (m, 6H), 2.29-2.22 (s, 3H), 1.66-1.31 (m, 5H), 0.93-0.81 (m, 1H), 0.72-0.62 (m, 2H), 0.53-0.44 (m, 2H).

Example 173: (*R)-3-(1-(Cyclopropylmethyl)-4-(difluoromethyl)-1H-benzo[d][1,2,3]triazol-5-yl)-3-(3-(((R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

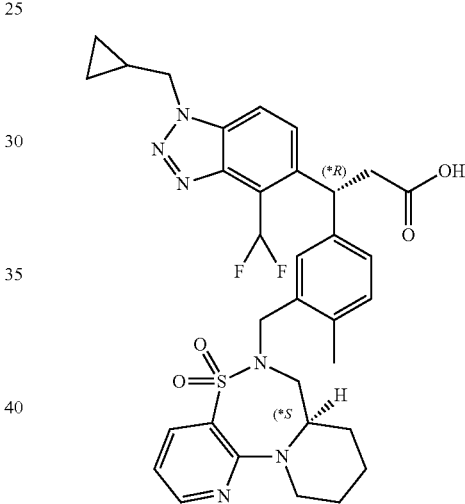

The second eluting isomer (15 mg) from the separation of isomers by chiral SFC described in Example 172 was designated (*R): MS (ESI): mass calcd. for $C_{33}H_{36}F_2N_6O_4S$, 650.2; m/z found, 651.5 [M+H]$^+$. $^1$H NMR (400 MHz, CDCl$_3$) δ 8.32-8.26 (m, 1H), 8.08-7.77 (m, 3H), 7.63-7.57 (m, 1H), 7.41-7.36 (m, 1H), 7.24-7.20 (m, 1H), 7.20-7.14 (m, 1H), 6.85-6.78 (m, 1H), 5.46-5.35 (m, 1H), 4.55-4.42 (m, 3H), 4.31-4.18 (m, 1H), 4.16-4.05 (m, 1H), 3.31-3.00 (m, 6H), 2.34-2.27 (s, 3H), 1.43-1.29 (m, 3H), 1.16-1.02 (m, 2H), 0.95-0.79 (m, 2H), 0.71-0.61 (m, 2H), 0.52-0.43 (m, 2H).

Example 174: (R/S)-3-(1-Cyclopropyl-4-methyl-1H-benzo[d][1,2,3]triazol-5-yl)-3-(6-(((R)-4-ethyl-1,1-dioxido-3,4-dihydro-2H-pyrido[2,3-b][1,4,5]oxathiazepin-2-yl)methyl)-5-methylpyridin-2-yl)propanoic Acid

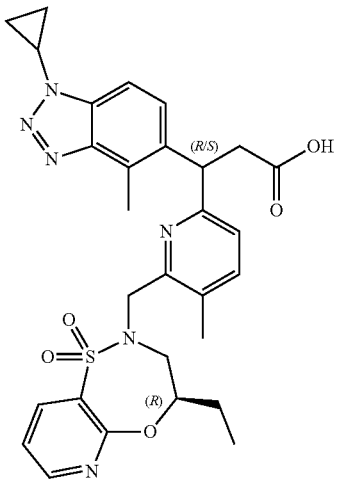

Step A: (R/S)-Ethyl 3-(1-cyclopropyl-4-methyl-1H-benzo[d][1,2,3]triazol-5-yl)-3-(6-(((R)-4-ethyl-1,1-dioxido-3,4-dihydro-2H-pyrido[2,3-b][1,4,5]oxathiazepin-2-yl)methyl)-5-methylpyridin-2-yl)propanoate. A solution ethyl 3-(1-cyclopropyl-4-methyl-1H-benzo[d][1,2,3]triazol-5-yl)-3-(6-(hydroxymethyl)-5-methylpyridin-2-yl)propanoate (Intermediate 107, 45.2 mg, 0.115 mmol), (R)-4-ethyl-3,4-dihydro-2H-pyrido[2,3-b][1,4,5]oxathiazepine 1,1-dioxide (Intermediate 91, 33.5 mg, 0.147 mmol), and triphenylphosphine (49.8 mg, 0.19 mmol) in THF (1.8 mL) was stirred at room temperature for 1 minute. DBAD (46.7 mg, 0.203 mmol) was added and the solution was stirred at room temperature for 30 minutes. The reaction was then concentrated under a stream of nitrogen and purified by flash column chromatography (0-20% EtOAc/DCM) to afford the title compound (64 mg, 92% yield) which contained a triphenylphosphine oxide impurity and was used without further purification. MS (ESI): mass calcd. for $C_{31}H_{36}N_6O_5S$, 604.2; m/z found, 605.2 [M+H]$^+$.

Step B: (R/S)-3-(1-Cyclopropyl-4-methyl-1H-benzo[d][1,2,3]triazol-5-yl)-3-(6-(((R)-4-ethyl-1,1-dioxido-3,4-dihydro-2H-pyrido[2,3-b][1,4,5]oxathiazepin-2-yl)methyl)-5-methylpyridin-2-yl)propanoic acid. 1M Aqueous sodium hydroxide (0.3 mL, 0.3 mmol) was added to a solution of (R 5)-ethyl 3-(1-cyclopropyl-4-methyl-1H-benzo[d][1,2,3]triazol-5-yl)-3-(6-(((R)-4-ethyl-1,1-dioxido-3,4-dihydro-2H-pyrido[2,3-b][1,4,5]oxathiazepin-2-yl)methyl)-5-methylpyridin-2-yl)propanoate (63.5 mg, 0.105 mmol) in THF (0.5 mL). The reaction was stirred at 50° C. overnight, then allowed to cool to room temperature. The reaction was then concentrated under a stream of nitrogen and purified by preparative basic HPLC (XBridge $C_{18}$, acetonitrile-water, 20 mM NH$_4$OH) to provide the title compound (44.5 mg, 73% yield). MS (ESI): mass calcd. for $C_{29}H_{32}N_6O_5S$, 576.2; m/z found, 577.2 [M+H]$^+$. $^1$H NMR (500 MHz, CDCl$_3$) δ 8.38-8.32 (m, 1H), 8.16-8.08 (m, 1H), 7.35-7.23 (m, 2H), 7.15-7.05 (m, 2H), 6.87 (dd, J=15.8, 7.9 Hz, 1H), 4.92-4.85 (m, 1H), 4.47-4.27 (m, 2H), 4.17-4.03 (m, 1H), 2.14-2.02 (m, 3H), 3.66-3.55 (m, 2H), 3.23-3.00 (m, 2H), 2.69-2.56 (m, 4H), 1.68-1.34 (m, 2H), 1.29 (dd, J=11.6, 4.9 Hz, 1H), 1.22-1.14 (m, 3H), 1.00-0.86 (m, 3H).

Example 175: (*S)-3-(1-Cyclopropyl-4-methyl-1H-benzo[d][1,2,3]triazol-5-yl)-3-(6-(((R)-4-ethyl-1,1-dioxido-3,4-dihydro-2H-pyrido[2,3-b][1,4,5]oxathiazepin-2-yl)methyl)-5-methylpyridin-2-yl)propanoic Acid

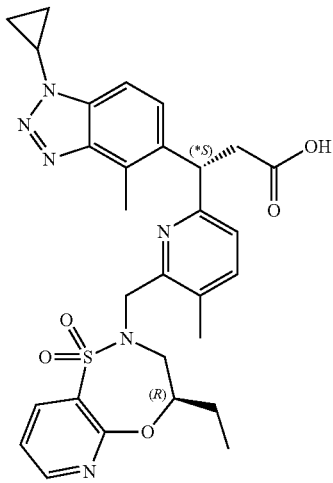

The mixture of (R/S)-3-(1-cyclopropyl-4-methyl-1H-benzo[d][1,2,3]triazol-5-yl)-3-(6-(((R)-4-ethyl-1,1-dioxido-3,4-dihydro-2H-pyrido[2,3-b][1,4,5]oxathiazepin-2-yl)methyl)-5-methylpyridin-2-yl)propanoic acid isomers (Example 174) was separated by chiral SFC (Chiralpak AD-H, mobile phase: 70% CO$_2$, 30% EtOH) to afford two diastereomers. The first eluting isomer (22 mg) was designated (*S): $^1$H NMR (400 MHz, CDCl$_3$) δ 8.46 (d, J=4.6 Hz, 1H), 8.24 (d, J=7.5 Hz, 1H), 7.39-7.32 (m, 2H), 7.25-7.17 (m, 2H), 6.87 (d, J=7.8 Hz, 1H), 5.05-4.96 (m, 1H), 4.65-4.50 (m, 2H), 4.25 (d, J=13.8 Hz, 1H), 3.90-3.78 (m, 1H), 3.74-3.66 (m, 1H), 3.38-3.27 (m, 2H), 2.91-2.77 (m, 4H), 2.34 (s, 3H), 1.84-1.73 (m, 1H), 1.66-1.54 (m, 1H), 1.36-1.27 (m, 2H), 1.26-1.23 (m, 2H), 1.11 (t, J=7.3 Hz, 3H).

Example 176: (*R)-3-(1-Cyclopropyl-4-methyl-1H-benzo[d][1,2,3]triazol-5-yl)-3-(6-(((R)-4-ethyl-1,1-dioxido-3,4-dihydro-2H-pyrido[2,3-b][1,4,5]oxathiazepin-2-yl)methyl)-5-methylpyridin-2-yl)propanoic Acid

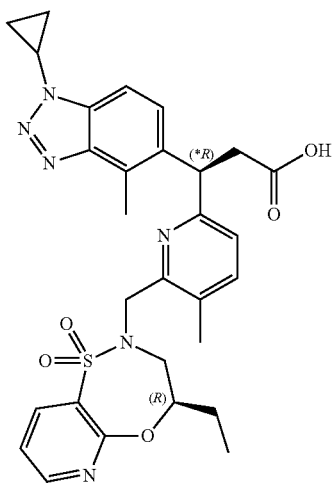

477

The second eluting isomer (22 mg) from the separation of isomers by chiral SFC described in Example 175 was designated (*R): ¹H NMR (400 MHz, CDCl₃) δ 8.35 (d, J=4.5 Hz, 1H), 8.12 (d, J=7.5 Hz, 1H), 7.32-7.23 (m, 2H), 7.17-7.09 (m, 2H), 6.92 (d, J=7.8 Hz, 1H), 4.93-4.84 (m, 1H), 4.44 (d, J=14.3 Hz, 1H), 4.39-4.28 (m, 1H), 4.07 (d, J=14.4 Hz, 1H), 3.66-3.55 (m, 2H), 3.19-3.01 (m, 2H), 2.69-2.56 (m, 4H), 2.11 (s, 3H), 1.57-1.45 (m, 1H), 1.36-1.29 (m, 2H), 1.22-1.15 (m, 3H), 0.96-0.90 (m, 3H).

Example 177: (R/S)-3-(4-Methyl-3-(((*S)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic Acid

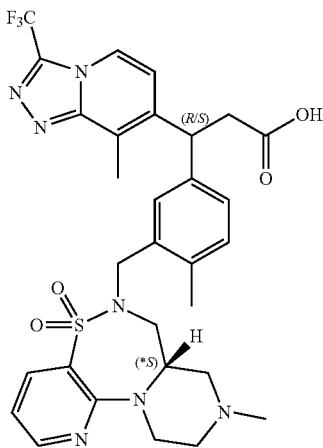

The title compound (44.6 mg, 19.8% yield) was prepared using analogous conditions as described in Example 135 where (*S)-9-methyl-7,7a,8,9,10,11-hexahydro-6H-pyrazino[2,1-d]pyrido[2,3-f][1,2,5]thiadiazepine 5,5-dioxide (Intermediate 85) was used instead of (*S)-6,7,7a,8,10,11-hexahydro-[1,4]oxazino[3,4-d]pyrido[2,3-f][1,2,5]thiadiazepine 5,5-dioxide and ethyl 3-(3-(chloromethyl)-4-methylphenyl)-3-(8-methyl-3-(trifluoromethyl)-[1,2,4]triazolo[4,3-a]pyridin-7-yl)propanoate (Intermediate 104) was used instead of ethyl 3-(3-(chloromethyl)-4-methylphenyl)-3-(1-ethyl-4-methyl-1H-benzo[d][1,2,3]triazol-5-yl)propanoate. MS (ESI): mass calcd. for $C_{30}H_{32}F_3N_7O_4S$, 643.2; m/z found, 644.2 [M+H]⁺. ¹H NMR (400 MHz, CDCl₃) δ 8.32-8.25 (m, 1H), 8.12-8.00 (m, 2H), 7.50-7.33 (m, 1H), 7.14-7.09 (m, 1H), 7.08-6.83 (m, 3H), 4.95-4.78 (m, 2H), 4.66-4.35 (m, 3H), 4.05-3.78 (m, 1H), 3.41-2.83 (m, 5H), 2.83-2.71 (m, 4H), 2.58-2.51 (m, 1H), 2.46-2.35 (m, 4H), 2.13-2.04 (m, 3H).

478

Example 178: (*S)-3-(4-Methyl-3-(((S)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic Acid

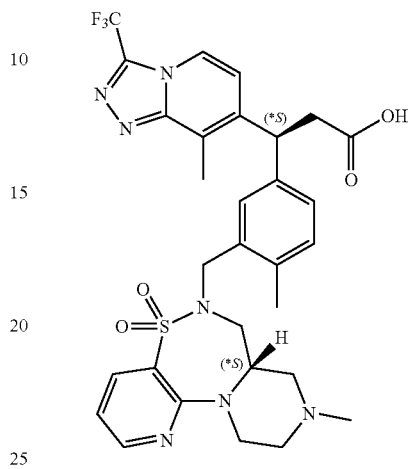

The mixture of (S)-3-(4-methyl-3-(((*S)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic acid isomers (Example 177) was separated by chiral SFC (Chiralpak AD-H, mobile phase: 55% CO₂, 45% iPrOH with 0.3% iPrNH₂) to afford two diastereomers. The first eluting isomer (20 mg) was designated (*S): MS (ESI): mass calcd. for $C_{30}H_{32}F_3N_7O_4S$, 643.2; m/z found, 644.4 [M+H]⁺. ¹H NMR (400 MHz, CDCl₃) δ 8.31-8.27 (m, 1H), 8.12-8.04 (m, 2H), 7.48-7.45 (m, 1H), 7.09-7.03 (m, 1H), 7.02-6.97 (m, 1H), 6.94-6.83 (m, 2H), 4.94-4.84 (m, 2H), 4.67-4.55 (m, 1H), 4.50-4.38 (m, 2H), 4.00 (t, J=13.5 Hz, 1H), 3.43-3.33 (m, 1H), 3.31-3.22 (m, 1H), 3.02-2.88 (m, 2H), 2.87-2.77 (m, 2H), 2.74 (s, 2H), 2.59-2.50 (m, 1H), 2.48-2.36 (m, 4H), 2.10-2.03 (m, 3H).

Example 179: (*R)-3-(4-Methyl-3-(((*S)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic Acid

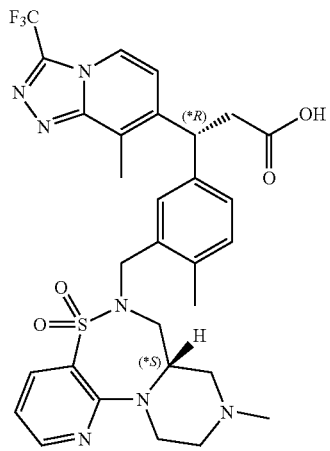

The second eluting isomer (21 mg) from the separation of isomers by chiral SFC described in Example 178 was designated (*R): MS (ESI): mass calcd. for $C_{30}H_{32}F_3N_7O_4S$, 643.2; m/z found, 644.4 [M+H]$^+$. $^1$H NMR (400 MHz, CDCl$_3$) δ 8.28 (dd, J=4.7, 2.0 Hz, 1H), 8.10 (dd, J=5.9, 2.1 Hz, 1H), 8.04 (d, J=7.2 Hz, 1H), 7.38-7.33 (m, 1H), 7.13-7.07 (m, 2H), 7.03-6.98 (m, 1H), 6.89 (dd, J=7.8, 4.6 Hz, 1H), 4.89-4.76 (m, 2H), 4.65-4.51 (m, 2H), 4.42-4.33 (m, 1H), 3.83 (t, J=13.2 Hz, 1H), 3.23-2.85 (m, 5H), 2.83-2.76 (m, 4H), 2.57-2.49 (m, 1H), 2.44-2.34 (m, 4H), 2.15-2.07 (m, 3H).

Example 180: (R/S)-3-(4-Methyl-3-(((*R)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic Acid

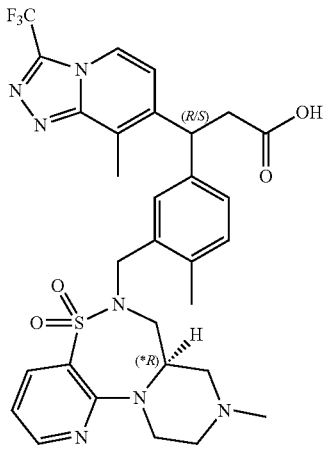

The title compound (57 mg, 25% yield) was prepared using analogous conditions as described in Example 135 where (*R)-9-methyl-7,7a,8,9,10,11-hexahydro-6H-pyrazino[2,1-d]pyrido[2,3-f][1,2,5]thiadiazepine 5,5-dioxide (Intermediate 86) was used instead of (*S)-6,7,7a,8,10,11-hexahydro-[1,4]oxazino[3,4-d]pyrido[2,3-f][1,2,5]thiadiazepine 5,5-dioxide and ethyl 3-(3-(chloromethyl)-4-methylphenyl)-3-(8-methyl-3-(trifluoromethyl)-[1,2,4]triazolo[4,3-a]pyridin-7-yl)propanoate (Intermediate 104) was used instead of ethyl 3-(3-(chloromethyl)-4-methylphenyl)-3-(1-ethyl-4-methyl-1H-benzo[d][1,2,3]triazol-5-yl)propanoate. MS (ESI): mass calcd. for $C_{30}H_{32}F_3N_7O_4S$, 643.2; m/z found, 644.2 [M+H]$^+$. $^1$H NMR (400 MHz, CDCl$_3$) δ 8.31-8.26 (m, 1H), 8.13-8.02 (m, 2H), 7.49-7.35 (m, 1H), 7.15-7.09 (m, 1H), 7.08-6.84 (m, 3H), 4.95-4.76 (m, 2H), 4.66-4.35 (m, 3H), 4.05-3.78 (m, 1H), 3.41-2.83 (m, 5H), 2.83-2.71 (m, 4H), 2.59-2.50 (m, 1H), 2.48-2.35 (m, 4H), 2.15-2.03 (m, 3H).

Example 181: (*S)-3-(4-Methyl-3-(((*R)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic Acid

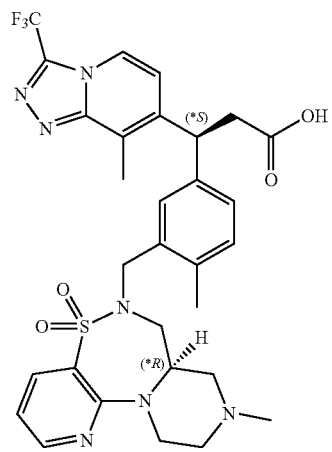

The mixture of (R/S)-3-(4-methyl-3-(((*R)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic acid isomers (Example 180) was separated by chiral SFC (Chiralpak AD-H, mobile phase: 60% CO$_2$, 40% iPrOH with 0.3% iPrNH$_2$) to afford two diastereomers. The first eluting isomer (29 mg) was designated (*S): MS (ESI): mass calcd. for $C_{30}H_{32}F_3N_7O_4S$, 643.2; m/z found, 644.4 [M+H]$^+$. $^1$H NMR (400 MHz, CDCl$_3$) δ 8.29-8.25 (m, 1H), 8.13-8.06 (m, 1H), 8.06-8.00 (m, 1H), 7.38-7.33 (m, 1H), 7.14-7.07 (m, 2H), 7.04-6.97 (m, 1H), 6.92-6.86 (m, 1H), 4.88-4.75 (m, 2H), 4.66-4.51 (m, 2H), 4.43-4.34 (m, 1H), 3.88-3.78 (m, 1H), 3.25-2.84 (m, 5H), 2.84-2.76 (m, 4H), 2.57-2.48 (m, 1H), 2.46-2.33 (m, 4H), 2.14-2.07 (m, 3H).

Example 182: (*R)-3-(4-Methyl-3-(((*R)-9-methyl-5,5-dioxido-7,7a,8,9,10,11-hexahydro-6H-pyrazino[2,1-d]pyrido[2,3-f][1,2,5]thiadiazepin-6-yl)methyl)phenyl)-3-(8-methyl-3-(trifluoromethyl)-[1,2,4]triazolo[4,3-a]pyridin-7-yl)propanoic Acid

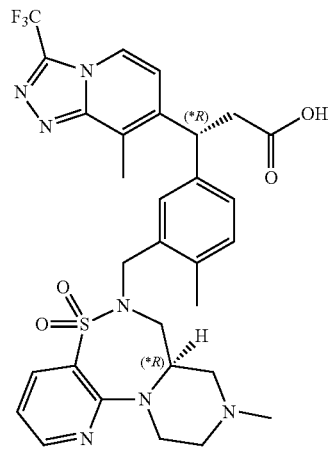

The second eluting isomer (25 mg) from the separation of isomers by chiral SFC described in Example 181 was designated (*R): MS (ESI): mass calcd. for $C_{30}H_{32}F_3N_7O_4S$, 643.2; m/z found, 644.4 [M+H]$^+$. $^1$H NMR (400 MHz, CDCl$_3$) δ 8.31-8.27 (m, 1H), 8.12-8.04 (m, 2H), 7.48-7.43 (m, 1H), 7.08-6.96 (m, 2H), 6.93-6.83 (m, 2H), 4.95-4.83 (m, 2H), 4.67-4.55 (m, 1H), 4.49-4.36 (m, 2H), 4.05-3.94 (m, 1H), 3.38 (d, J=11.4 Hz, 1H), 3.31-3.22 (m, 1H), 3.01-2.87 (m, 2H), 2.87-2.77 (m, 2H), 2.74 (s, 3H), 2.57-2.51 (m, 1H), 2.47-2.35 (m, 4H), 2.10-2.02 (m, 3H).

Example 183: (R/S)-3-(4-Methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)-3-(8-methyl-3-(trifluoromethyl)-[1,2,4]triazolo[4,3-a]pyridin-7-yl)propanoic Acid

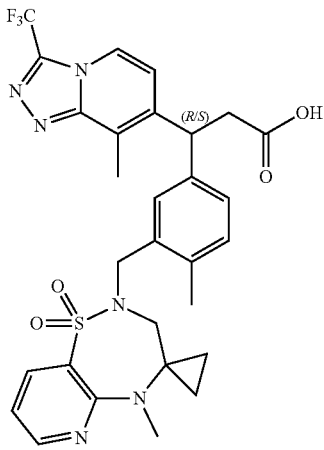 [SMILES: Cc1ccc(C(CC(=O)O)c2ccn3c(C(F)(F)F)nnc3c2C)cc1CN1CC2(CC2)N(C)c2ncccc2S1(=O)=O]

The title compound (123 mg, 57% yield) was prepared using analogous conditions as described in Example 135 where 5-methylspiro[2,3-dihydropyrido[2,3-f][1,2,5]thiadiazepine-4,1'-cyclopropane] 1,1-dioxide (Intermediate 93) was used instead of (*S)-6,7,7a,8,10,11-hexahydro-[1,4]oxazino[3,4-d]pyrido[2,3-f][1,2,5]thiadiazepine 5,5-dioxide and ethyl 3-(3-(chloromethyl)-4-methylphenyl)-3-(8-methyl-3-(trifluoromethyl)-[1,2,4]triazolo[4,3-a]pyridin-7-yl)propanoate (Intermediate 104) was used instead of ethyl 3-(3-(chloromethyl)-4-methylphenyl)-3-(1-ethyl-4-methyl-1H-benzo[d][1,2,3]triazol-5-yl)propanoate. MS (ESI): mass calcd. for $C_{29}H_{29}F_3N_6O_4S$, 614.2; m/z found, 615.3 [M+H]$^+$. $^1$H NMR (400 MHz, CDCl$_3$) 8.34-8.21 (m, 2H), 8.03 (d, J=7.2 Hz, 1H), 7.30-7.17 (m, 1H), 7.13 (d, J=7.7 Hz, 1H), 7.09-6.93 (m, 1H), 4.98-4.87 (m, 1H), 4.41 (s, 2H), 3.30 (s, 2H), 3.22-2.96 (m, 5H), 2.78 (s, 3H), 2.25 (s, 3H), 1.11-0.89 (m, 4H).

Example 184: (*S)-3-(4-Methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)-3-(8-methyl-3-(t*rifluoromethyl)-[1,2,4]triazolo[4,3-a]pyridin-7-yl)propanoic Acid

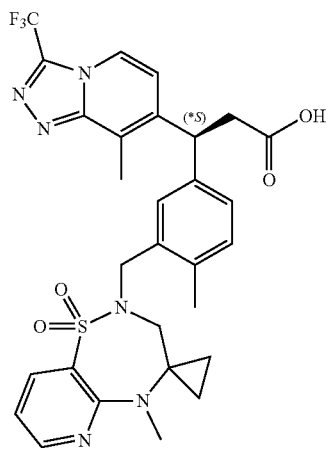

The mixture of (R/5)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)-3-(8-methyl-3-(trifluoromethyl)-[1,2,4]triazolo[4,3-a]pyridin-7-yl)propanoic acid isomers (Example 183) was separated by chiral SFC (Chiralpak AD-H, mobile phase: 55% CO$_2$, 45% iPrOH) to afford enantiomers. The first eluting isomer (51 mg) was designated (*S): MS (ESI): mass calcd. for $C_{29}H_{29}F_3N_6O_4S$, 614.2; m/z found, 615.3 [M+H]$^+$. $^1$H NMR (400 MHz, CDCl$_3$) δ 8.32-8.22 (m, 1H), 8.10 (dd, J=7.8, 1.8 Hz, 1H), 8.00 (d, J=7.1 Hz, 1H), 7.26-7.23 (m, 1H), 7.10 (d, J=7.8 Hz, 1H), 7.05-6.97 (m, 1H), 6.97-6.84 (m, 2H), 4.93 (t, J=7.7 Hz, 1H), 4.39 (s, 2H), 3.41-3.18 (m, 2H), 3.18-2.93 (m, 5H), 2.80 (s, 3H), 2.24 (s, 3H), 1.24-1.19 (m, 2H), 0.97-0.92 (m, 2H).

Example 185: (*R)-3-(4-Methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)-3-(8-methyl-3-(trifluoromethyl)-[1,2,4]triazolo[4,3-a]pyridin-7-yl)propanoic Acid

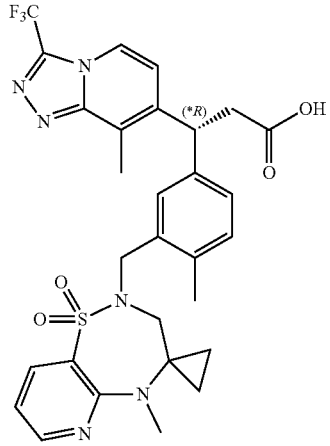

The second eluting isomer (51 mg) from the separation of isomers by chiral SFC described in Example 184 was designated (*R): MS (ESI): mass calcd. for $C_{29}H_{29}F_3N_6O_4S$, 614.2; m/z found, 615.4 [M+H]$^+$. $^1$H NMR (400 MHz, CDCl$_3$) δ 8.30-8.25 (m, 1H), 8.12-8.07 (m, 1H), 8.00 (d, J=7.2 Hz, 1H), 7.27-7.26 (m, 1H), 7.10 (d, J=7.8 Hz, 1H), 7.00 (d, J=7.7 Hz, 1H), 6.93-6.86 (m, 2H), 4.93 (t, J=7.7 Hz, 1H), 4.39 (s, 2H), 3.30-3.24 (m, 2H), 3.14-2.92 (m, 5H), 2.81 (s, 3H), 2.24 (s, 3H), 1.19-1.11 (m, 2H), 0.98-0.93 (m, 2H).

Example 186: (*S)-3-(4-Methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)-3-(8-methyl-3-(trifluoromethyl)-[1,2,4]triazolo[4,3-a]pyridin-7-yl)propanoic Acid

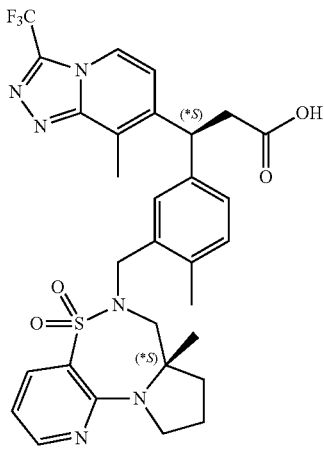

Step A: Ethyl (*S)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)-3-(8-methyl-3-(trifluoromethyl)-[1,2,4]triazolo[4,3-a]pyridin-7-yl)propanoate. A solution ethyl (*S)-3-(3-(hydroxymethyl)-4-methylphenyl)-3-(8-methyl-3-(trifluoromethyl)-[1,2,4]triazolo[4,3-a]pyridin-7-yl)propanoate (Intermediate 26, 169.2 mg, 0.402 mmol), (*S)-7a-methyl-6,7,7a,8,9,10-hexahydropyrido[2,3-f]pyrrolo[2,1-d][1,2,5]thiadiazepine 5,5-dioxide (Intermediate 39, 132.3 mg, 0.522 mmol), triphenylphosphine (162.2 mg, 0.618 mmol) and DBAD (141.9 mg, 0.616 mmol) in THF (5 mL) was stirred at room temperature for 3 hours. The reaction was then concentrated under a stream of nitrogen and purified by flash column chromatography (EtOAc/hexanes) to afford the title compound (210 mg, 79% yield). MS (ESI): mass calcd. for $C_{32}H_{35}F_3N_6O_4S$, 656.2; m/z found, 657.3 [M+H]$^+$.

Step B: (*S)-3-(4-Methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)-3-(8-methyl-3-(trifluoromethyl)-[1,2,4]triazolo[4,3-a]pyridin-7-yl)propanoic acid. 1M Aqueous sodium hydroxide (0.96 mL, 0.96 mmol) was added to a solution of ethyl (*S)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)-3-(8-methyl-3-(trifluoromethyl)-[1,2,4]triazolo[4,3-a]pyridin-7-yl)propanoate (209.5 mg, 0.319 mmol) in THF (1.6 mL) and EtOH (0.5 mL). The reaction was stirred at room temperature for 3 hours. 1 M aqueous HCl solution was added until the pH was 3-4. Ethyl acetate was added and the resulting biphasic mixture was separated. The aqueous layer was extracted with ethyl acetate. These extractions resulted in several organic solvent fractions which were combined, dried over MgSO$_4$, filtered, and concentrated to dryness under reduced pressure to provide the title compound (185 mg, 92% yield). MS (ESI): mass calcd. for $C_{30}H_{31}F_3N_6O_4S$, 628.2; m/z found, 629.2 [M+H]$^+$. $^1$H NMR (400 MHz, CDCl$_3$) δ 8.43-8.35 (m, 1H), 8.17-8.08 (m, 1H), 8.00 (d, J=7.1 Hz, 1H), 7.39-7.31 (m, 1H), 7.10 (d, J=7.7 Hz, 1H), 7.07-7.01 (m, 1H), 7.01-6.96 (m, 1H), 6.93 (dd, J=7.7, 4.8 Hz, 1H), 4.97 (t, J=8.8, 6.6 Hz, 1H), 4.82-4.72 (m, 1H), 4.33-4.22 (m, 1H), 4.01-3.90 (m, 1H), 3.83 (d, J=14.7 Hz, 1H), 3.62-3.51 (m, 1H), 3.28-3.15 (m, 1H), 3.15-3.03 (m, 1H), 3.00-2.88 (m, 1H), 2.82 (s, 3H), 2.24 (s, 3H), 1.95-1.79 (m, 4H), 0.88 (s, 3H).

Example 187: (*R)-3-(4-Methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)-3-(8-methyl-3-(trifluoromethyl)-[1,2,4]triazolo[4,3-a]pyridin-7-yl)propanoic Acid

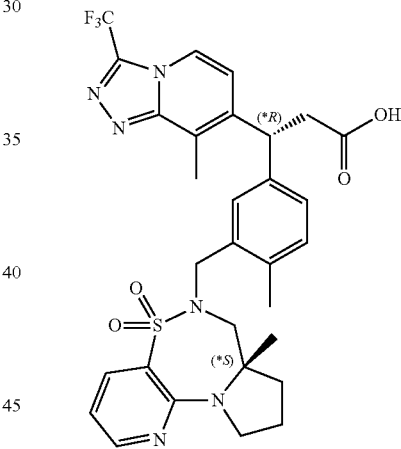

The title compound (117 mg, 84% yield) was prepared using analogous conditions as described in Example 186 where ethyl (*R)-3-(3-(hydroxymethyl)-4-methylphenyl)-3-(8-methyl-3-(trifluoromethyl)-[1,2,4]triazolo[4,3-a]pyridin-7-yl)propanoate (Intermediate 27) was used instead of ethyl (*S)-3-(3-(hydroxymethyl)-4-methylphenyl)-3-(8-methyl-3-(trifluoromethyl)-[1,2,4]triazolo[4,3-a]pyridin-7-yl)propanoate. MS (ESI): mass calcd. for $C_{30}H_{31}F_3N_6O_4S$, 628.2; m/z found, 629.2 [M+H]$^+$. $^1$H NMR (400 MHz, CDCl$_3$) δ 8.41-8.36 (m, 1H), 8.18-8.10 (m, 1H), 8.07-7.99 (m, 1H), 7.30-7.27 (m, 1H), 7.16-7.05 (m, 2H), 7.04-6.97 (m, 1H), 6.97-6.90 (m, 1H), 4.96 (t, J=8.8, 6.5 Hz, 1H), 4.78 (d, J=15.5 Hz, 1H), 4.25 (d, J=15.5 Hz, 1H), 3.96-3.89 (m, 1H), 3.66 (d, J=14.6 Hz, 1H), 3.59-3.48 (m, 1H), 3.25-3.03 (m, 2H), 2.89-2.74 (m, 4H), 2.26 (s, 3H), 1.89-1.66 (m, 4H), 0.86 (s, 3H).

Example 188: (R/S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic Acid

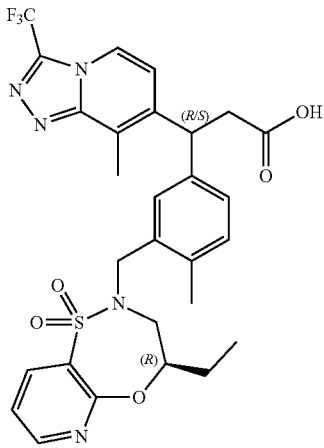

The title compound (115 mg, 81% yield) was prepared using analogous conditions as described in Example 186 where (R)-4-ethyl-3,4-dihydro-2H-pyrido[2,3-b][1,4,5]oxathiazepine 1,1-dioxide (Intermediate 91) was used instead of (*S)-7a-methyl-6,7,7a,8,9,10-hexahydropyrido[2,3-f]pyrrolo[2,1-d][1,2,5]thiadiazepine 5,5-dioxide, ethyl 3-(3-(hydroxymethyl)-4-methylphenyl)-3-(8-methyl-3-(trifluoromethyl)-[1,2,4]triazolo[4,3-a]pyridin-7-yl)propanoate (Intermediate 25) was used instead of ethyl (*S)-3-(3-(hydroxymethyl)-4-methylphenyl)-3-(8-methyl-3-(trifluoromethyl)-[1,2,4]triazolo[4,3-a]pyridin-7-yl)propanoate, and DIAD was used instead of DBAD. MS (ESI): mass calcd. for $C_{28}H_{28}F_3N_5O_5S$, 603.2; m/z found, 604.0 $[M+H]^+$.

Example 189: (*S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic Acid

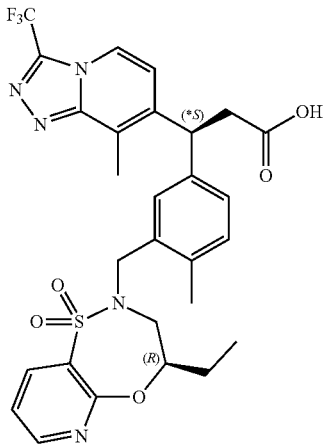

The mixture of (R/S)-3-(3-(((R)-4-ethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid isomers (Example 188) was separated by chiral SFC (Chiralpak AD-H, mobile phase: 60% $CO_2$, 40% EtOH) to afford two diastereomers. The first eluting isomer (53 mg) was designated (*S): MS (ESI): mass calcd. for $C_{28}H_{28}F_3N_5O_5S$, 603.2; m/z found, 604.4 $[M+H]^+$. $^1$H NMR (400 MHz, CDCl$_3$) δ 8.45-8.37 (m, 1H), 8.17 (dd, J=7.7, 1.9 Hz, 1H), 7.91 (d, J=7.1 Hz, 1H), 7.24-7.20 (m, 1H), 7.16 (s, 1H), 7.06-7.01 (m, 1H), 6.98-6.93 (m, 1H), 6.83 (d, J=7.2 Hz, 1H), 4.88-4.80 (m, 1H), 4.44-4.35 (m, 1H), 4.31 (d, J=14.7 Hz, 1H), 4.05 (d, J=14.6 Hz, 1H), 3.58-3.46 (m, 1H), 3.13 (dd, J=15.0, 2.4 Hz, 1H), 3.01-2.91 (m, 1H), 2.88-2.80 (m, 1H), 2.73 (s, 3H), 2.20 (s, 3H), 1.74-1.60 (m, 1H), 1.55-1.45 (m, 1H), 0.97 (t, J=7.3 Hz, 3H).

Example 190: (*R)-3-(3-(((R)-4-Ethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic Acid

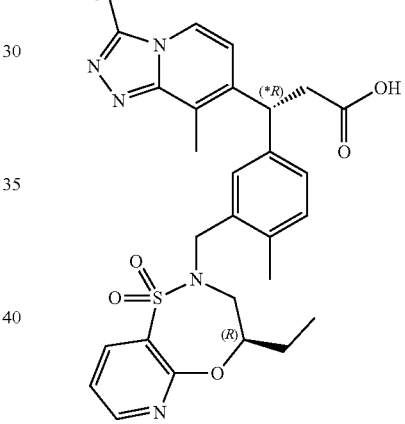

The second eluting isomer (55 mg) from the separation of isomers by chiral SFC described in Example 189 was designated (*R): MS (ESI): mass calcd. for $C_{28}H_{28}F_3N_5O_5S$, 603.2; m/z found, 604.4 $[M+H]^+$. $^1$H NMR (400 MHz, CDCl$_3$) δ 8.41 (s, 1H), 8.16 (dd, J=7.7, 1.9 Hz, 1H), 7.95-7.87 (m, 1H), 7.22-7.17 (m, 1H), 7.15 (s, 1H), 7.06-7.01 (m, 1H), 6.99-6.94 (m, 1H), 6.86 (d, J=7.3 Hz, 1H), 4.88-4.79 (m, 1H), 4.44-4.28 (m, 2H), 4.03 (d, J=14.7 Hz, 1H), 3.53-3.44 (m, 1H), 3.16-3.10 (m, 1H), 2.96-2.77 (m, 2H), 2.72 (s, 3H), 2.19 (s, 3H), 1.70-1.58 (m, 1H), 1.51-1.39 (m, 1H), 0.96-0.89 (m, 3H).

Example 191: (3*S)-3-(3-((3-Chloro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

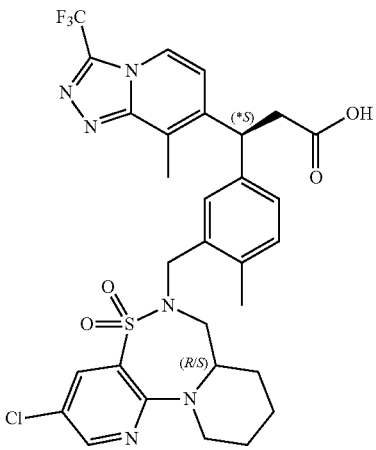

The title compound (215 mg, 57% yield) was prepared using analogous conditions as described in Example 186 where 3-chloro-7,7a,8,9,10,11-hexahydro-6H-dipyrido[2,1-d:2',3'-f][1,2,5]thiadiazepine 5,5-dioxide (Intermediate 95) was used instead of (*S)-7a-methyl-6,7,7a,8,9,10-hexahydropyrido[2,3-f]pyrrolo[2,1-d][1,2,5]thiadiazepine 5,5-dioxide. The product was purified by preparative basic HPLC (XBridge $C_{18}$, acetonitrile-water, 20 mM $NH_4OH$). MS (ESI): mass calcd. for $C_{30}H_{30}ClF_3N_6O_4S$, 662.2; m/z found, 663.1 [M+H]$^+$. $^1$H NMR (500 MHz, CDCl$_3$) δ 8.21 (s, 1H), 8.05-7.97 (m, 2H), 7.20-7.12 (m, 2H), 7.08 (t, J=8.7 Hz, 1H), 6.96-6.85 (m, 1H), 4.99-4.90 (m, 1H), 4.58-4.43 (m, 2H), 4.25-4.14 (m, 2H), 3.34-3.13 (m, 4H), 3.13-3.00 (m, 1H), 2.82 (d, J=5.5 Hz, 3H), 2.25 (d, J=11.1 Hz, 3H), 1.80-1.37 (m, 6H).

Example 192: (*S)-3-(3-(((*S)-3-Chloro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

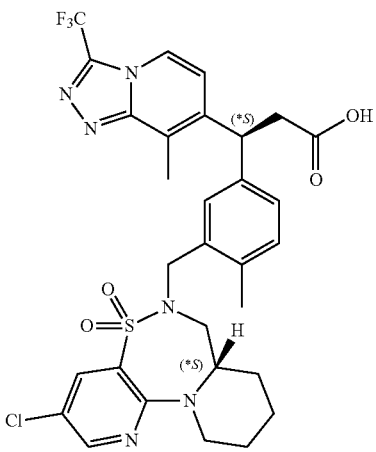

The mixture of (3*S)-3-(3-((3-chloro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid isomers (Example 191) was separated by chiral SFC (Chiralpak AD-H, mobile phase: 80% CO$_2$, 20% EtOH) to afford two diastereomers. The first eluting isomer (102 mg) was designated (*S): $^1$H NMR (500 MHz, CDCl$_3$) δ 8.21 (d, J=2.5 Hz, 1H), 8.03-7.96 (m, 2H), 7.20-7.16 (m, 1H), 7.16-7.11 (m, 1H), 7.09-7.04 (m, 1H), 6.92 (d, J=7.2 Hz, 1H), 4.93 (t, J=7.7 Hz, 1H), 4.55-4.48 (m, 1H), 4.44 (d, J=15.1 Hz, 1H), 4.25-4.14 (m, 2H), 3.35-3.26 (m, 1H), 3.26-3.12 (m, 3H), 3.12-2.99 (m, 1H), 2.81 (s, 3H), 2.24 (s, 3H), 1.78-1.58 (m, 3H), 1.58-1.38 (m, 3H).

Example 193: (*S)-3-(3-(((*R)-3-Chloro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

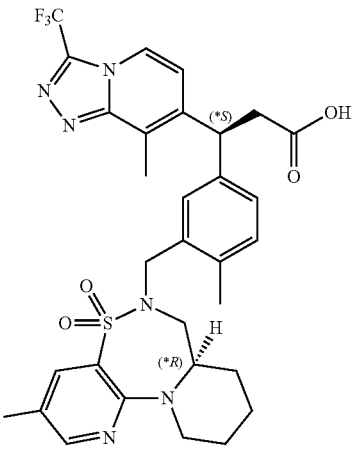

The second eluting isomer (110 mg) from the separation of isomers by chiral SFC described in Example 192 was designated (*R): $^1$H NMR (500 MHz, CDCl$_3$) δ 8.21 (d, J=2.5 Hz, 1H), 8.03-7.97 (m, 2H), 7.16-7.12 (m, 2H), 7.09-7.05 (m, 1H), 6.87 (d, J=7.3 Hz, 1H), 4.94 (t, J=7.8 Hz, 1H), 4.51-4.42 (m, 2H), 4.22-4.15 (m, 2H), 3.25-3.15 (m, 3H), 3.14-2.98 (m, 2H), 2.83 (s, 3H), 2.26 (s, 3H), 1.74-1.54 (m, 3H), 1.51-1.31 (m, 3H).

Example 194: (*S)-3-(3-(((*R)-4-Ethyl-8-methyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic Acid

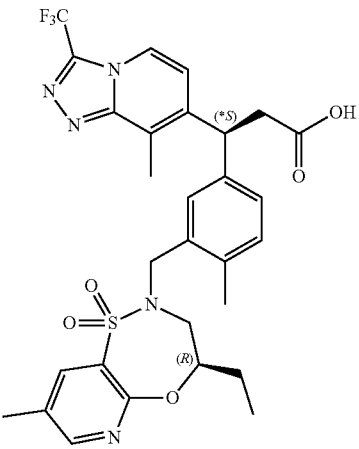

The title compound (71 mg, 49% yield) was prepared using analogous conditions as described in Example 186 where (R)-4-ethyl-3,4-dihydro-2H-pyrido[2,3-b][1,4,5]oxathiazepine 1,1-dioxide (Intermediate 91) was used instead of (*S)-7a-methyl-6,7,7a, 8,9,10-hexahydropyrido[2,3-f]pyrrolo[2,1-d][1,2,5]thiadiazepine 5,5-dioxide. In addition, the hydrolysis reaction was run at 50° C., and the title compound was purified by preparative basic HPLC (XBridge $C_{18}$, acetonitrile-water, 20 mM $NH_4OH$). MS (ESI): mass calcd. for $C_{29}H_{30}F_3N_5O_5S$, 617.2; m/z found, 618.3 $[M+H]^+$. $^1H$ NMR (500 MHz, $CDCl_3$) δ 8.28-8.25 (m, 1H), 8.05-8.00 (m, 1H), 7.98 (d, J=7.1 Hz, 1H), 7.25-7.21 (m, 1H), 7.11 (d, J=7.9 Hz, 1H), 7.05-7.01 (m, 1H), 6.89 (d, J=7.3 Hz, 1H), 4.92 (t, J=7.7 Hz, 1H), 4.42-4.31 (m, 2H), 4.08 (d, J=14.6 Hz, 1H), 3.64-3.53 (m, 1H), 3.18-3.05 (m, 1H), 2.96 (dd, J=15.9, 8.4 Hz, 1H), 2.78 (s, 3H), 2.38 (s, 3H), 2.26 (s, 3H), 1.72-1.61 (m, 1H), 1.57-1.45 (m, 1H), 0.99 (t, J=7.3 Hz, 3H).

Example 195: (*S)-3-(3-((8'-Chloro-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic Acid

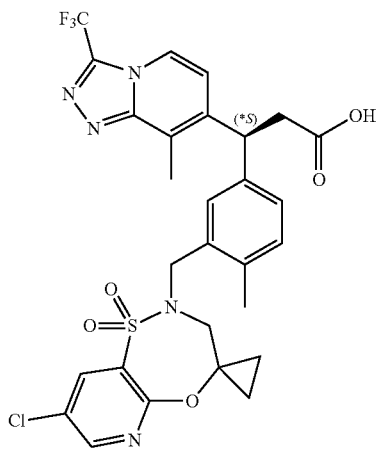 [SMILES: Cc1ccc([C@H](CC(=O)O)c2ccn3c(C(F)(F)F)nnc3c2C)cc1CN1CC2(CC2)Oc2ncc(Cl)cc2S1(=O)=O]

The title compound (119 mg, 85% yield) was prepared using analogous conditions as described in Example 186 where 8'-chloro-2',3'-dihydrospiro[cyclopropane-1,4'-pyrido[2,3-b][1,4,5]oxathiazepine] 1',1'-dioxide (Intermediate 96) was used instead of (*S)-7a-methyl-6,7,7a,8,9,10-hexahydropyrido[2,3-f]pyrrolo[2,1-d][1,2,5]thiadiazepine 5,5-dioxide and the hydrolysis reaction was run at 50° C. MS (ESI): mass calcd. for $C_{28}H_{25}ClF_3N_5O_5S$, 635.1; m/z found, 636.1 $[M+H]^+$. $^1H$ NMR (500 MHz, $CDCl_3$) δ 8.38 (d, J=2.6 Hz, 1H), 8.24 (d, J=2.6 Hz, 1H), 8.01 (d, J=7.2 Hz, 1H), 7.16-7.11 (m, 2H), 7.07-7.04 (m, 1H), 6.88 (d, J=7.3 Hz, 1H), 4.94 (t, J=7.8 Hz, 1H), 4.39-4.27 (m, 2H), 3.60-3.48 (m, 2H), 3.21-3.12 (m, 1H), 3.07-2.99 (m, 1H), 2.81 (s, 3H), 2.29 (s, 3H), 1.21-1.07 (m, 2H), 0.64-0.50 (m, 2H).

Example 196: (*S)-3-(3-(((*S)-3-Cyano-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

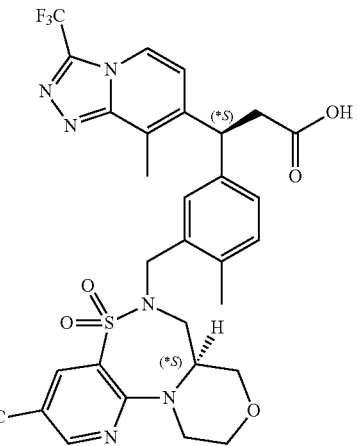

Step A: Ethyl (*S)-3-(3-(((*S)-3-chloro-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoate. The title compound (293.6 mg, 91% yield) was prepared using analogous conditions as described in Example 174, Step A where (*S)-3-chloro-6,7,7a,8,10,11-hexahydro-[1,4]oxazino[3,4-d]pyrido[2,3-f][1,2,5]thiadiazepine 5,5-dioxide (Intermediate 88) was used instead of (R)-4-ethyl-3,4-dihydro-2H-pyrido[2,3-b][1,4,5]oxathiazepine 1,1-dioxide and ethyl (*S)-3-(3-(hydroxymethyl)-4-methylphenyl)-3-(8-methyl-3-(trifluoromethyl)-[1,2,4]triazolo[4,3-a]pyridin-7-yl)propanoate (Intermediate 26) was used instead of ethyl 3-(1-cyclopropyl-4-methyl-1H-benzo[d][1,2,3]triazol-5-yl)-3-(6-(hydroxymethyl)-5-methylpyridin-2-yl)propanoate. MS (ESI): mass calcd. for $C_{31}H_{32}ClF_3N_6O_5S$, 692.2; m/z found, 693.1 $[M+H]^+$.

Step B: Ethyl (*S)-3-(3-(((*S)-3-cyano-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoate. DMA (1.4 mL) was added to a mixture of ethyl (*S)-3-(3-(((*S)-3-chloro-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoate (195.7 mg, 0.282 mmol), zinc cyanide (65.6 mg, 0.56 mmol), XPhos Pd G2 (22.8 mg, 0.029 mmol), and zinc powder (10 mg, 0.16 mmol). Nitrogen was bubbled through the reaction mixture for 1 minute, then the reaction was heated at 120° C. for 1 hour. After that time, the reaction was filtered, and the solids were rinsed with ethyl acetate. The filtrate was washed with saturated aqueous sodium bicarbonate, dried over $MgSO_4$, filtered, and concentrated to dryness under reduced pressure. The material was purified by flash column chromatography (0-50% EtOAc/hexanes) to afford the title compound (164 mg, 85% yield). MS (ESI): mass calcd. for $C_{32}H_{32}F_3N_7O_5S$, 683.2; m/z found, 684.1 $[M+H]^+$.

Step C: (*S)-3-(3-(((*S)-3-Cyano-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid. The title compound (42 mg, 27% yield) was prepared using analogous conditions as described in Example 186, Step B where ethyl (*S)-3-(3-(((*S)-3-cyano-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoate was used instead of ethyl (*S)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)-3-(8-methyl-3-(trifluoromethyl)-[1,2,4]triazolo[4,3-a]pyridin-7-yl)propanoate, the hydrolysis reaction was run starting at a temperature of 0° C. with slow warming to room temperature, and it was purified by preparative acidic HPLC (XBridge $C_{18}$, acetonitrile-water containing 0.05% TFA). MS (ESI): mass calcd. for $C_{30}H_{28}F_3N_7O_5S$, 655.2; m/z found, 656.2 $[M+H]^+$. $^1H$ NMR (500 MHz, $CDCl_3$) δ 8.49 (d, J=2.1 Hz, 1H), 8.29 (d, J=2.2 Hz, 1H), 8.10 (d, J=7.2 Hz, 1H), 7.30 (d, J=2.0 Hz, 1H), 7.12 (d, J=7.9 Hz, 1H), 7.01 (d, J=7.3 Hz, 1H), 6.95-6.90 (m, 1H), 4.95-4.88 (m, 1H), 4.78-4.72 (m, 1H), 4.68-4.61 (m, 1H), 4.49 (d, J=13.7 Hz, 1H), 4.34-4.22 (m, 2H), 3.80-3.77 (m, 2H), 3.77-3.70 (m, 2H), 3.35-3.29 (m, 1H), 3.14-3.04 (m, 2H), 2.99-2.93 (m, 1H), 2.73 (s, 3H), 2.13 (s, 3H).

Example 197: (*S)-3-(3-(((*S)-3-Chloro-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

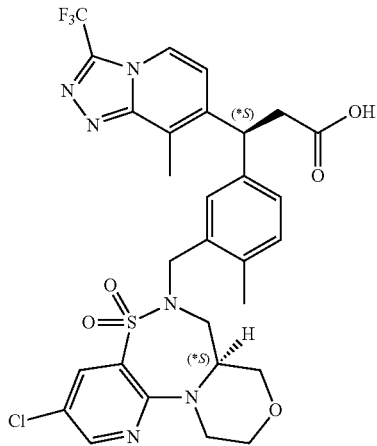 [SMILES: Cc1ccc([C@H](CC(=O)O)c2ccn3c(C(F)(F)F)nnc3c2C)cc1CN1C[C@H]2COCCN2c2ncc(Cl)cc2S1(=O)=O]

The title compound (68.6 mg, 73% yield) was prepared using analogous conditions as described in Example 186, Step B where ethyl (*S)-3-(3-(((*S)-3-chloro-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoate (prepared in Example 196, Step A) was used instead of ethyl (*S)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)-3-(8-methyl-3-(trifluoromethyl)-[1,2,4]triazolo[4,3-a]pyridin-7-yl)propanoate. MS (ESI): mass calcd. for $C_{29}H_{28}ClF_3N_6O_5S$, 664.1; m/z found, 665.2 $[M+H]^+$. $^1H$ NMR (500 MHz, $CDCl_3$) δ 8.23 (d, J=2.6 Hz, 1H), 8.10 (d, J=7.3 Hz, 1H), 8.04 (d, J=2.6 Hz, 1H), 7.34-7.29 (m, 1H), 7.11 (d, J=7.8 Hz, 1H), 6.99 (d, J=7.3 Hz, 1H), 6.90 (d, J=7.9 Hz, 1H), 4.94-4.87 (m, 1H), 4.70-4.62 (m, 1H), 4.57-4.44 (m, 2H), 4.33-4.22 (m, 2H), 3.80-3.67 (m, 4H), 3.28-3.22 (m, 1H), 3.19-3.04 (m, 2H), 2.99-2.92 (m, 1H), 2.72 (s, 3H), 2.18 (s, 3H).

Example 198: (*S)-3-(3-(((*S)-5,5-Dioxido-3-(trifluoromethyl)-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

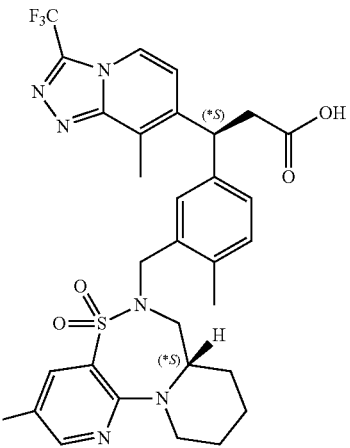

The title compound (102.4 mg, 60% yield) was prepared using analogous conditions as described in Example 186 where (*S)-3-(trifluoromethyl)-7,7a,8,9,10,11-hexahydro-6H-dipyrido[2,1-d:2',3'-f][1,2,5]thiadiazepine 5,5-dioxide (Intermediate 101) was used instead of (*S)-7a-methyl-6,7,7a,8,9,10-hexahydropyrido[2,3-f]pyrrolo[2,1-d][1,2,5]thiadiazepine 5,5-dioxide, the hydrolysis reaction was heated at 50° C., and it was purified by preparative acidic HPLC (XBridge $C_{18}$, acetonitrile-water containing 0.05% TFA). MS (ESI): mass calcd. for $C_{31}H_{30}F_6N_6O_4S$, 696.2; m/z found, 697.2 $[M+H]^+$. $^1H$ NMR (400 MHz, $CDCl_3$) δ 8.53-8.47 (m, 1H), 8.27-8.21 (m, 1H), 8.06 (d, J=7.2 Hz, 1H), 7.24-7.19 (m, 1H), 7.14 (d, J=7.9 Hz, 1H), 7.08-6.97 (m, 2H), 4.95 (t, J=7.8 Hz, 1H), 4.72-4.62 (m, 1H), 4.49 (d, J=15.3 Hz, 1H), 4.38-4.30 (m, 1H), 4.20 (d, J=15.4 Hz, 1H), 3.46-3.38 (m, 1H), 3.33-3.16 (m, 3H), 3.13-3.02 (m, 1H), 2.81 (s, 3H), 2.24 (s, 3H), 1.86-1.63 (m, 3H), 1.63-1.47 (m, 3H).

Example 199: (*S)-3-(3-(((*R)-5,5-Dioxido-3-(trifluoromethyl)-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

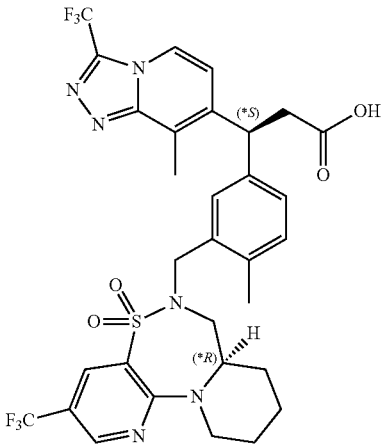 [SMILES: Cc1ccc([C@H](CC(=O)O)c2ccn3c(C(F)(F)F)nnc3c2C)cc1CN1C[C@H]2CCCCN2c2ncc(C(F)(F)F)cc2S1(=O)=O]

The title compound (68.3 mg, 47% yield) was prepared using analogous conditions as described in Example 186 where (*R)-3-(trifluoromethyl)-7,7a,8,9,10,11-hexahydro-6H-dipyrido[2,1-d:2',3'-f][1,2,5]thiadiazepine 5,5-dioxide (Intermediate 102) was used instead of (*S)-7a-methyl-6,7,7a,8,9,10-hexahydropyrido[2,3-f]pyrrolo[2,1-d][1,2,5]thiadiazepine 5,5-dioxide, the hydrolysis reaction was heated at 50° C., and it was purified by preparative acidic HPLC (XBridge $C_{18}$, acetonitrile-water containing 0.05% TFA). MS (ESI): mass calcd. for $C_{31}H_{30}F_6N_6O_4S$, 696.2; m/z found, 697.2 [M+H]$^+$. $^1$H NMR (400 MHz, CDCl$_3$) δ 8.53-8.45 (m, 1H), 8.28-8.19 (m, 1H), 8.04 (d, J=7.2 Hz, 1H), 7.19-7.11 (m, 2H), 7.11-7.04 (m, 1H), 6.94 (d, J=7.2 Hz, 1H), 5.00-4.91 (m, 1H), 4.67-4.55 (m, 1H), 4.49 (d, J=15.0 Hz, 1H), 4.40-4.27 (m, 1H), 4.18 (d, J=15.0 Hz, 1H), 3.33-2.98 (m, 5H), 2.82 (s, 3H), 2.26 (s, 3H), 1.82-1.58 (m, 3H), 1.58-1.35 (m, 3H).

Example 200: (*S)-3-(3-((8'-Cyano-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic Acid

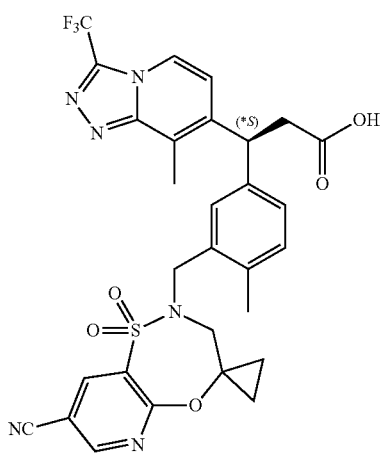 [SMILES: Cc1ccc([C@H](CC(=O)O)c2ccn3c(C(F)(F)F)nnc3c2C)cc1CN1CC2(CC2)Oc2ncc(C#N)cc2S1(=O)=O]

Step A: Ethyl (*S)-3-(3-((8'-Chloro-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoate. The title compound (979.6 mg, 78% yield) was prepared using analogous conditions as described in Example 186, Step A where 8'-chloro-2',3'-dihydrospiro[cyclopropane-1,4'-pyrido[2,3-b][1,4,5]oxathiazepine] 1',1'-dioxide (Intermediate 96) was used instead of (*S)-7a-methyl-6,7,7a,8,9,10-hexahydropyrido[2,3-f]pyrrolo[2,1-d][1,2,5]thiadiazepine 5,5-dioxide. MS (ESI): mass calcd. for $C_{30}H_{29}ClF_3N_6O_5S$, 663.1; m/z found, 664.2 [M+H]$^+$.

Step B: Ethyl (*S)-3-(3-((8'-cyano-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoate. The title compound (87.1 mg, 43% yield) was prepared using analogous conditions as described in Example 196, Step B where ethyl (*S)-3-(3-((8'-Chloro-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoate was used instead of ethyl (*S)-3-(3-(((*S)-3-chloro-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoate. MS (ESI): mass calcd. for $C_{31}H_{29}F_3N_6O_5S$, 654.2; m/z found, 655.2 [M+H]$^+$.

Step C: (*S)-3-(3-((8'-Cyano-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid. The title compound (7 mg, 8% yield) was prepared using analogous conditions as described in Example 186, Step B where ethyl (*S)-3-(3-((8'-cyano-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoate was used instead of ethyl (*S)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)-3-(8-methyl-3-(trifluoromethyl)-[1,2,4]triazolo[4,3-a]pyridin-7-yl)propanoate, the hydrolysis reaction was run overnight, and it was purified by preparative acidic HPLC (XBridge C18, acetonitrile-water containing 0.05% TFA). MS (ESI): mass calcd. for $C_{29}H_{25}F_3N_6O_5S$, 626.2; m/z found, 627.1 [M+H]$^+$. $^1$H NMR (500 MHz, CDCl$_3$) δ 8.71 (d, J=2.3 Hz, 1H), 8.54 (d, J=2.2 Hz, 1H), 8.05 (d, J=7.2 Hz, 1H), 7.17-7.13 (m, 2H), 7.09-7.05 (m, 1H), 6.94 (d, J=7.3 Hz, 1H), 4.95 (t, J=7.8 Hz, 1H), 4.38 (s, 2H), 3.62-3.50 (m, 2H), 3.22-3.15 (m, 1H), 3.08-3.01 (m, 1H), 2.83-2.80 (m, 3H), 2.28 (s, 3H), 1.25-1.17 (m, 2H), 0.80-0.69 (m, 2H). In addition to the title compound, (*S)-3-(3-((8'-Carbamoyl-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid was also produced in this reaction and its characterization is shown below in the description of Example 201.

Example 201: (*S)-3-(3-((8'-Carbamoyl-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic Acid

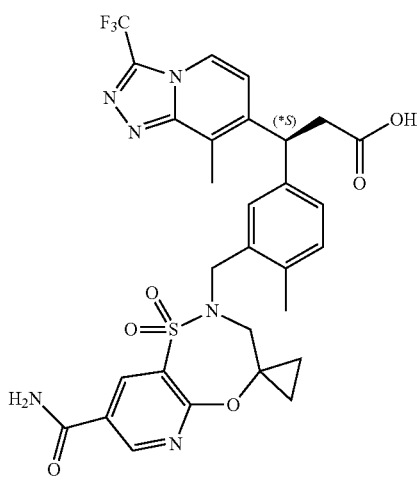 [SMILES: Cc1ccc([C@H](CC(=O)O)c2ccn3c(C(F)(F)F)nnc3c2C)cc1CN1CC2(CC2)Oc2ncc(C(N)=O)cc2S1(=O)=O]

The title compound (62.8 mg, 29% yield) was produced during the experiment described in Example 200, Step C. MS (ESI): mass calcd. for $C_{29}H_{27}F_3N_6O_6S$, 644.2; m/z found, 645.1 [M+H]$^+$. $^1$H NMR (500 MHz, DMSO-d$_6$) δ 13.10 (s, 1H), 8.46 (s, 1H), 8.40 (d, J=7.1 Hz, 1H), 7.95 (d, J=2.5 Hz, 1H), 7.25 (d, J=1.9 Hz, 1H), 7.20-7.08 (m, 2H), 7.03 (d, J=7.9 Hz, 1H), 4.81 (t, J=7.8 Hz, 1H), 4.66 (s, 2H), 3.34-3.25 (m, 2H), 3.10 (d, J=7.8 Hz, 2H), 2.75 (s, 3H), 2.15 (s, 3H), 0.45-0.36 (m, 2H), 0.26-0.14 (m, 2H).

Example 202: (*S)-3-(3-(((*S)-2-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

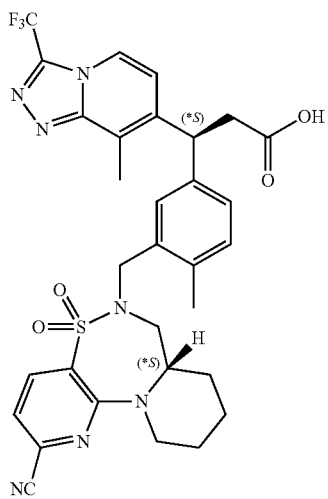 [SMILES: Cc1ccc([C@H](CC(=O)O)c2ccn3c(C(F)(F)F)nnc3c2C)cc1CN1C[C@@H]2CCCCN2c2nc(C#N)ccc2S1(=O)=O]

The title compound (22 mg, 7% yield) was prepared using analogous conditions as described in Example 186 where (*S)-7,7a,8,9,10,11-hexahydro-6H-dipyrido[2,1-d:2',3'-f][1,2,5]thiadiazepine-2-carbonitrile 5,5-dioxide (Intermediate 98) was used instead of (*S)-7a-methyl-6,7,7a,8,9,10-hexahydropyrido[2,3-f]pyrrolo[2,1-d][1,2,5]thiadiazepine 5,5-dioxide, the hydrolysis reaction was run from 0-50° C. with only 1 eq. of base, and the title compound was purified by preparative acidic HPLC (XBridge C$_{18}$, acetonitrile-water containing 0.05% TFA). MS (ESI): mass calcd. for $C_{31}H_{30}F_3N_7O_4S$, 653.2; m/z found, 654.3 [M+H]$^+$. $^1$H NMR (500 MHz, CDCl$_3$) δ 8.12 (d, J=7.8 Hz, 1H), 8.05 (d, J=7.2 Hz, 1H), 7.18-7.13 (m, 3H), 7.10-7.05 (m, 1H), 6.95 (d, J=7.3 Hz, 1H), 5.00-4.92 (m, 1H), 4.61-4.53 (m, 1H), 4.50 (d, J=15.0 Hz, 1H), 4.34-4.26 (m, 1H), 4.18 (d, J=15.0 Hz, 1H), 3.31-3.14 (m, 3H), 3.09-3.02 (m, 1H), 2.84 (s, 3H), 2.25 (s, 3H), 1.82-1.60 (m, 3H), 1.56-1.36 (m, 4H).

Example 203: (*S)-3-(3-(((*S)-2-Carbamoyl-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

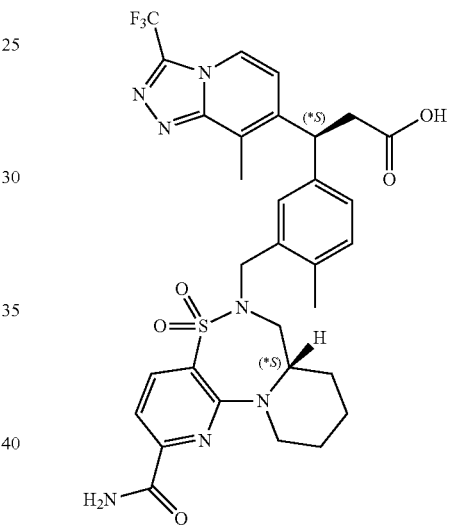

The title compound (40 mg, 13% yield) was produced during the experiment described in Example 202, Step C. MS (ESI): mass calcd. for $C_{31}H_{32}F_3N_7O_5S$, 671.2; m/z found, 672.3 [M+H]$^+$. $^1$H NMR (500 MHz, CDCl$_3$) δ 8.26 (d, J=8.0 Hz, 1H), 7.99 (d, J=7.2 Hz, 1H), 7.75-7.71 (m, 1H), 7.69 (d, J=7.9 Hz, 1H), 7.34-7.28 (m, 1H), 7.12 (d, J=7.9 Hz, 1H), 7.05-7.01 (m, 1H), 7.00-6.96 (m, 1H), 6.80 (d, J=7.3 Hz, 1H), 4.87 (t, J=7.8 Hz, 1H), 4.64-4.58 (m, 1H), 4.51-4.47 (m, 1H), 4.41-4.35 (m, 1H), 4.19-4.12 (m, 1H), 3.39-3.34 (m, 1H), 3.29-3.21 (m, 1H), 3.12-3.04 (m, 1H), 2.88 (d, J=7.8 Hz, 2H), 2.79 (s, 3H), 2.28 (s, 3H), 1.80-1.69 (m, 2H), 1.64-1.36 (m, 5H).

Example 204: (*S)-3-(3-(((*R)-2-Cyano-5,5-di-oxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

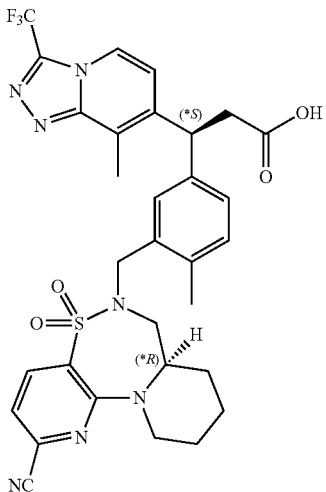 [SMILES: Cc1ccc([C@H](CC(=O)O)c2ccn3c(C(F)(F)F)nnc3c2C)cc1CN1C[C@H]2CCCCN2c2nc(C#N)ccc2S1(=O)=O]

The title compound (79 mg, 26% yield) was prepared using analogous conditions as described in Example 186 where (*R)-7,7a,8,9,10,11-hexahydro-6H-dipyrido[2,1-d:2',3'-f][1,2,5]thiadiazepine-2-carbonitrile 5,5-dioxide (Intermediate 99) was used instead of (*S)-7a-methyl-6,7,7a,8,9,10-hexahydropyrido[2,3-f]pyrrolo[2,1-d][1,2,5]thiadiazepine 5,5-dioxide, the hydrolysis reaction was run from 0-50° C. with only 1 eq. of base, and the title compound was purified by preparative acidic HPLC (XBridge $C_{18}$, acetonitrile-water containing 0.05% TFA). MS (ESI): mass calcd. for $C_{31}H_{30}F_3N_7O_4S$, 653.2; m/z found, 654.3 [M+H]$^+$. $^1$H NMR (500 MHz, CDCl$_3$) δ 8.12 (d, J=7.8 Hz, 1H), 8.05 (d, J=7.1 Hz, 1H), 7.21-7.18 (m, 1H), 7.18-7.13 (m, 2H), 7.08-7.04 (m, 1H), 6.99 (d, J=7.3 Hz, 1H), 4.97-4.92 (m, 1H), 4.65-4.57 (m, 1H), 4.47 (d, J=15.3 Hz, 1H), 4.34-4.26 (m, 1H), 4.22 (d, J=15.4 Hz, 1H), 3.44-3.36 (m, 1H), 3.26-3.14 (m, 3H), 3.11-3.03 (m, 1H), 2.80 (s, 3H), 2.22 (s, 3H), 1.84-1.62 (m, 3H), 1.62-1.44 (m, 3H).

Example 205: (*S)-3-(3-(((*R)-2-Carbamoyl-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

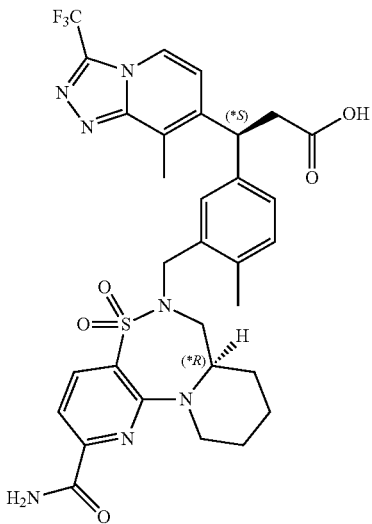 [SMILES: Cc1ccc([C@H](CC(=O)O)c2ccn3c(C(F)(F)F)nnc3c2C)cc1CN1C[C@H]2CCCCN2c2nc(C(N)=O)ccc2S1(=O)=O]

The title compound (53 mg, 17% yield) was produced during the experiment described in Example 204, Step C. MS (ESI): mass calcd. for $C_{31}H_{32}F_3N_7O_5S$, 671.2; m/z found, 672.3 [M+H]$^+$. $^1$H NMR (500 MHz, CDCl$_3$) δ 8.23 (d, J=7.9 Hz, 1H), 8.01 (d, J=7.1 Hz, 1H), 7.74-7.70 (m, 1H), 7.67 (d, J=7.9 Hz, 1H), 7.15 (d, J=7.8 Hz, 1H), 7.10-7.00 (m, 3H), 6.94 (d, J=7.3 Hz, 1H), 4.86-4.80 (m, 1H), 4.65-4.58 (m, 1H), 4.44-4.34 (m, 2H), 4.21-4.14 (m, 1H), 3.44-3.38 (m, 1H), 3.29-3.21 (m, 1H), 3.19-3.02 (m, 3H), 2.71 (s, 3H), 2.26 (s, 3H), 1.83-1.71 (m, 2H), 1.71-1.44 (m, 5H).

Example 206: (*S)-3-(3-(((S)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

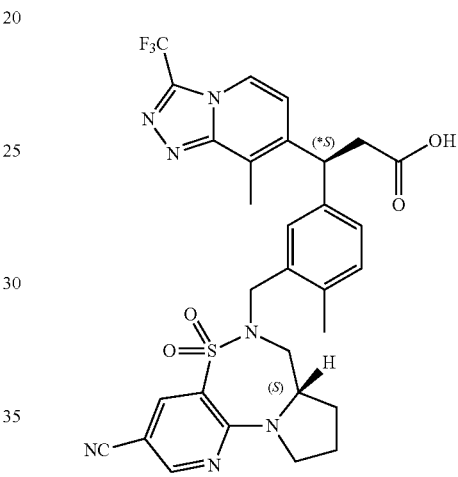

The title compound (97 mg, 52% yield) was prepared using analogous conditions as described in Example 174 where (S)-6,7,7a,8,9,10-hexahydropyrido[2,3-f]pyrrolo[2,1-d][1,2,5]thiadiazepine-3-carbonitrile 5,5-dioxide (Intermediate 88) was used instead of (R)-4-ethyl-3,4-dihydro-2H-pyrido[2,3-b][1,4,5]oxathiazepine 1,1-dioxide and ethyl (*S)-3-(3-(hydroxymethyl)-4-methylphenyl)-3-(8-methyl-3-(trifluoromethyl)-[1,2,4]triazolo[4,3-a]pyridin-7-yl)propanoate (Intermediate 26) was used instead of ethyl 3-(1-cyclopropyl-4-methyl-1H-benzo[d][1,2,3]triazol-5-yl)-3-(6-(hydroxymethyl)-5-methylpyridin-2-yl)propanoate. In addition, the hydrolysis reaction was run at room temperature and the title compound was purified by preparative acidic HPLC (XBridge $C_{18}$, acetonitrile-water containing 0.05% TFA). MS (ESI): mass calcd. for $C_{30}H_{28}F_3N_7O_4S$, 639.2; m/z found, 640.2 [M+H]$^+$. $^1$H NMR (500 MHz, CDCl$_3$) δ 8.49 (d, J=2.2 Hz, 1H), 8.23 (d, J=2.2 Hz, 1H), 8.04 (d, J=7.2 Hz, 1H), 7.21-7.17 (m, 1H), 7.14 (d, J=7.8 Hz, 1H), 7.05 (dd, J=7.8, 2.0 Hz, 1H), 6.96 (d, J=7.2 Hz, 1H), 4.99-4.88 (m, 2H), 4.52 (d, J=15.2 Hz, 1H), 4.10 (d, J=15.2 Hz, 1H), 3.76-3.69 (m, 2H), 3.48 (dd, J=13.0, 3.6 Hz, 1H), 3.24-3.14 (m, 1H), 3.11-2.99 (m, 1H), 2.88 (t, J=12.4 Hz, 1H), 2.81 (s, 3H), 2.24 (s, 3H), 2.20-2.07 (m, 1H), 2.06-1.94 (m, 1H), 1.92-1.79 (m, 1H), 1.68-1.57 (m, 1H).

Example 207: (*S)-3-(3-(((R)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

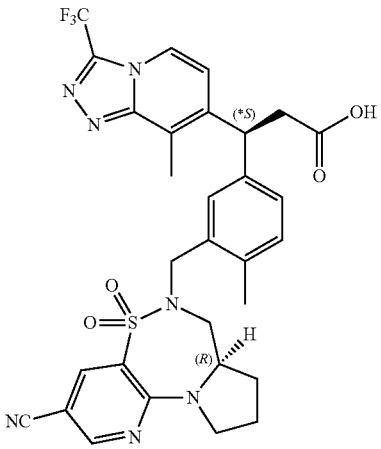

The title compound (156 mg, 60% yield) was prepared using analogous conditions as described in Example 186 where (R)-6,7,7a,8,9,10-hexahydropyrido[2,3-f]pyrrolo[2,1-d][1,2,5]thiadiazepine-3-carbonitrile 5,5-dioxide (Intermediate 87) was used instead of (*S)-7a-methyl-6,7,7a,8,9,10-hexahydropyrido[2,3-f]pyrrolo[2,1-d][1,2,5]thiadiazepine 5,5-dioxide and the title compound was purified by preparative basic HPLC (XBridge $C_{18}$, acetonitrile-water, 20 mM $NH_4OH$). MS (ESI): mass calcd. for $C_{30}H_{28}F_3N_7O_4S$, 639.2; m/z found, 640.2 [M+H]$^+$. $^1$H NMR (500 MHz, CDCl$_3$) δ 8.48 (d, J=2.2 Hz, 1H), 8.22 (d, J=2.2 Hz, 1H), 8.05 (d, J=7.1 Hz, 1H), 7.16-7.09 (m, 2H), 7.06 (dd, J=7.9, 2.0 Hz, 1H), 6.95 (d, J=7.2 Hz, 1H), 4.98-4.90 (m, 1H), 4.90-4.81 (m, 1H), 4.50 (d, J=15.0 Hz, 1H), 4.12 (d, J=15.0 Hz, 1H), 3.76-3.68 (m, 2H), 3.37 (dd, J=13.0, 3.5 Hz, 1H), 3.21-3.09 (m, 1H), 3.09-3.00 (m, 1H), 2.91-2.82 (m, 1H), 2.79 (s, 3H), 2.25 (s, 3H), 2.16-2.04 (m, 1H), 2.00-1.92 (m, 1H), 1.87-1.74 (m, 1H), 1.63-1.53 (m, 1H).

Example 208: (*S)-3-(4-Methyl-3-((8'-methyl-1',1'-dioxido-2,3,5,6-tetrahydrospiro[pyran-4,4'-pyrido[2,3-b][[,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

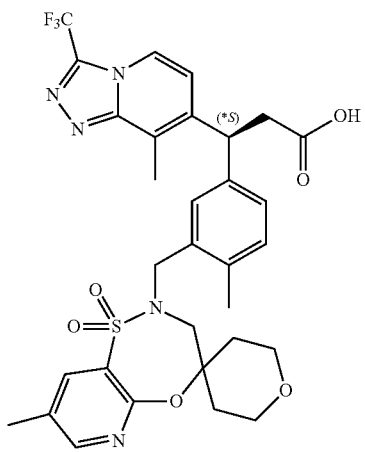 [SMILES: Cc1cnc2c(c1)S(=O)(=O)N(Cc1cc([C@H](CC(=O)O)c3ccn4c(C(F)(F)F)nnc4c3C)ccc1C)CC1(CCOCC1)O2]

Step A: Ethyl (*S)-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate. A solution of ethyl (*S)-3-(3-(hydroxymethyl)-4-methylphenyl)-3-(8-methyl-3-(trifluoromethyl)-[1,2,4]triazolo[4,3-a]pyridin-7-yl)propanoate (Intermediate 26, 145.8 mg, 0.346 mmol), 8'-methyl-2,2',3,3',5,6-hexahydrospiro[pyran-4,4'-pyrido[2,3-b][1,4,5]oxathiazepine] 1',1'-dioxide (Intermediate 37, 153.2 mg, 0.539 mmol), and triphenylphosphine (150 mg, 0.572 mmol) in DMF (3 mL) was stirred at room temperature for 1 minute. DBAD (127.5 mg, 0.554 mmol) was added and the solution was stirred at room temperature for 15 minutes. Additional triphenylphosphine (160.9 mg) and DBAD (128.2 mg) were added and the reaction was stirred at room temperature overnight. Additional triphenylphosphine (155.8 mg), DBAD (146.1 mg), and DMF (1 mL) were added and the reaction was stirred at 50° C. overnight. Additional triphenylphosphine (257.4 mg), DBAD (256.3 mg) and THF (7 mL) were added and the reaction was stirred at 50° C. overnight. The reaction was then concentrated under a stream of nitrogen and purified by flash column chromatography (EtOAc/hex) to afford the title compound (263.2 mg) which was used without further purification. MS (ESI): mass calcd. for $C_{33}H_{36}F_3N_5O_6S$, 687.2; m/z found, 688.3 [M+H]$^+$.

Step B: (*S)-3-(4-Methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid. 1M Aqueous sodium hydroxide (1.2 mL, 1.2 mmol) was added to a solution of ethyl (*S)-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate (263 mg, 0.382 mmol) in THF (2 mL). The reaction was stirred at room temperature overnight. After this time, the reaction was diluted with ethyl acetate and the resulting biphasic mixture was separated. 1 M aqueous HCl solution was added to the aqueous layer until the pH was 3-4. DCM was then added and the resulting biphasic mixture was separated. The aqueous layer was extracted with DCM. These extractions resulted in several organic solvent fractions which were combined, dried over MgSO$_4$, filtered, and concentrated to dryness under reduced pressure to provide the title compound (72.3 mg, 29% yield) which was used without further purification. MS (ESI): mass calcd. for $C_{31}H_{32}F_3N_5O_6S$, 659.2; m/z found, 660.1 [M+H]$^+$. $^1$H NMR (500 MHz, CDCl$_3$) δ 8.29-8.25 (m, 1H), 8.05 (d, J=7.2 Hz, 1H), 8.03-8.00 (m, 1H), 7.22-7.18 (m, 1H), 7.14-7.10 (m, 1H), 7.08-7.03 (m, 1H), 6.96 (d, J=7.3 Hz, 1H), 4.96-4.88 (m, 1H), 4.69 (d, J=14.4 Hz, 1H), 4.36 (d, J=14.4 Hz, 1H), 4.03-3.87 (m, 2H), 3.79-3.71 (m, 1H), 3.61-3.36 (m, 3H), 3.20-3.10 (m, 1H), 3.01-2.91 (m, 1H), 2.79 (s, 3H), 2.40 (s, 3H), 2.23 (s, 3H), 1.72-1.59 (m, 2H), 1.46-1.37 (m, 1H), 1.22-1.11 (m, 2H).

Example 209: (R/S)-3-(1-Cyclopropyl-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

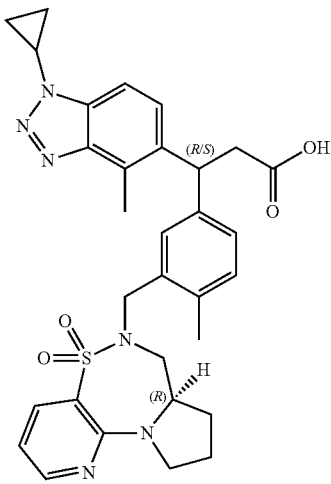

DMF (0.75 mL) was added to a mixture of (R)-6,7,7a,8,9,10-hexahydropyrido[2,3-f]pyrrolo[2,1-d][1,2,5]thiadiazepine 5,5-dioxide (Intermediate 4, 70.1 mg, 0.293 mmol) and sodium hydride (60% dispersion in mineral oil, 35.7 mg, 0.893 mmol) under nitrogen at 0° C. After 10 minutes, a solution of ethyl 3-(3-(chloromethyl)-4-methylphenyl)-3-(1-cyclopropyl-4-methyl-1H-benzo[d][1,2,3]triazol-5-yl)propanoate (Intermediate 32, 0.75 ml, 0.4 M in DMF, 0.29 mmol) was added and the mixture was allowed to warm to room temperature overnight. The mixture was filtered, the filtrate was concentrated and purified by preparative acidic HPLC (XBridge $C_{18}$, acetonitrile-water containing 0.05% TFA) to provide the title compound (64.4 mg, 38% yield). MS (ESI): mass calcd. for $C_{31}H_{34}N_6O_4S$, 586.2; m/z found, 587.2 [M+H]$^+$. $^1$H NMR (500 MHz, CDCl$_3$) δ 8.34-8.27 (m, 1H), 8.27-8.22 (m, 1H), 7.49-7.41 (m, 1H), 7.36-7.27 (m, 1H), 7.10-7.05 (m, 2H), 7.04-6.98 (m, 1H), 6.93 (ddd, J=14.3, 7.7, 5.5 Hz, 1H), 4.96-4.76 (m, 2H), 4.50-4.39 (m, 1H), 4.27-4.15 (m, 1H), 3.83-3.61 (m, 3H), 3.39-3.25 (m, 1H), 3.16-3.05 (m, 1H), 3.05-2.84 (m, 2H), 2.81-2.69 (m, 3H), 2.30-2.20 (m, 3H), 2.09-1.93 (m, 1.5H), 1.93-1.75 (m, 1H), 1.71-1.59 (m, 0.5H), 1.59-1.49 (m, 1H), 1.38-1.24 (m, 4H).

Example 210: (*S)-3-(1-Cyclopropyl-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

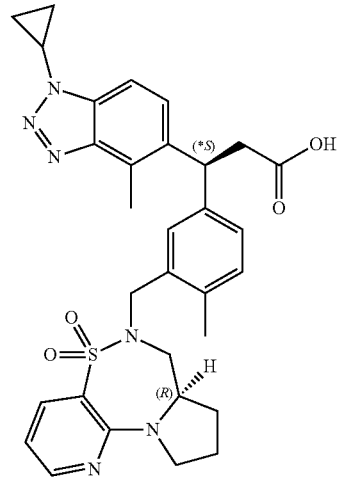

The mixture of 3-(1-cyclopropyl-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid isomers (Example 209) was separated by chiral SFC (Chiralpak AD-H, mobile phase: 60% CO$_2$, 40% EtOH) to afford two diastereomers. The first eluting isomer (19.9 mg) was designated (*S): MS (ESI): mass calcd. for $C_{31}H_{34}N_6O_4S$, 586.2; m/z found, 587.2 [M+H]$^+$. $^1$H NMR (500 MHz, CDCl$_3$) δ 8.21 (d, J=2.5 Hz, 1H), 8.03-7.96 (m, 2H), 7.20-7.16 (m, 1H), 7.16-7.11 (m, 1H), 7.09-7.04 (m, 1H), 6.92 (d, J=7.2 Hz, 1H), 4.93 (t, J=7.7 Hz, 1H), 4.55-4.48 (m, 1H), 4.44 (d, J=15.1 Hz, 1H), 4.25-4.14 (m, 2H), 3.35-3.26 (m, 1H), 3.26-3.12 (m, 3H), 3.12-2.99 (m, 1H), 2.81 (s, 3H), 2.24 (s, 3H), 1.78-1.58 (m, 3H), 1.58-1.38 (m, 3H).

Example 211: (*R)-3-(1-Cyclopropyl-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

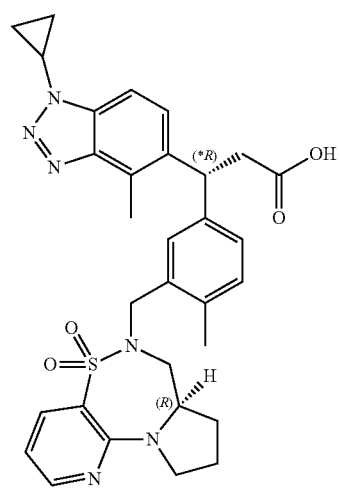

The second eluting isomer (19.7 mg) from the separation of isomers by chiral SFC described in Example 210 was designated (*R): MS (ESI): mass calcd. for $C_{31}H_{34}N_6O_4S$, 586.2; m/z found, 587.2 [M+H]$^+$. $^1$H NMR (500 MHz, CDCl$_3$) δ 8.31-8.27 (m, 1H), 8.07 (dd, J=7.8, 1.8 Hz, 1H), 7.46-7.42 (m, 1H), 7.34 (d, J=8.7 Hz, 1H), 7.10-7.05 (m, 3H), 6.82-6.76 (m, 1H), 4.93 (t, J=7.8 Hz, 1H), 4.62-4.53 (m, 1H), 4.39 (d, J=14.2 Hz, 1H), 4.11 (d, J=14.2 Hz, 1H), 3.75-3.68 (m, 1H), 3.66-3.57 (m, 1H), 3.57-3.49 (m, 1H), 3.27 (dd, J=13.2, 3.6 Hz, 1H), 3.17-3.01 (m, 2H), 2.84-2.76 (m, 4H), 2.26 (s, 3H), 1.98-1.90 (m, 1H), 1.82-1.75 (m, 1H), 1.64-1.56 (m, 1H), 1.47-1.39 (m, 1H), 1.36-1.27 (m, 4H).

Example 212: (*S)-3-(1-Cyclopropyl-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl) propanoic Acid

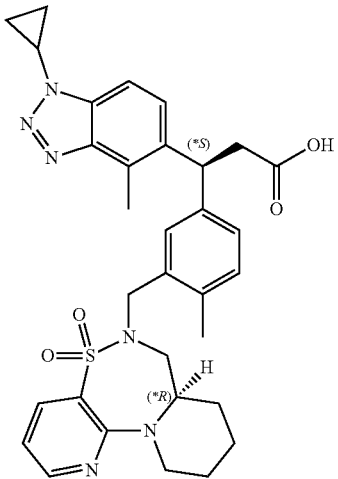 [SMILES: Cc1ccc([C@H](CC(=O)O)c2ccc3c(nnn3C3CC3)c2C)cc1CN1C[C@H]2CCCCN2c2ncccc2S1(=O)=O]

The title compound (112.5 mg, 64% yield) was prepared using analogous conditions as described in Example 209 where (*R)-7,7a,8,9,10,11-hexahydro-6H-dipyrido[2,1-d:2',3'-f][1,2,5]thiadiazepine 5,5-dioxide (Intermediate 3) was used instead of (R)-6,7,7a,8,9,10-hexahydropyrido[2,3-f]pyrrolo[2,1-d][1,2,5]thiadiazepine 5,5-dioxide. The mixture of isomers was separated by chiral SFC (Chiralpak AD-H, mobile phase: 60% CO$_2$, 40% EtOH) to afford two diastereomers. The first eluting isomer (41 mg) was designated (*S): MS (ESI): mass calcd. for $C_{32}H_{36}N_6O_4S$, 600.3; m/z found, 601.3 [M+H]$^+$. $^1$H NMR (500 MHz, CDCl$_3$) δ 8.28-8.26 (m, 1H), 8.05-8.01 (m, 1H), 7.45-7.41 (m, 1H), 7.32 (d, J=8.6 Hz, 1H), 7.11-7.08 (m, 2H), 7.07 (s, 1H), 6.83-6.78 (m, 1H), 4.95 (t, J=7.8 Hz, 1H), 4.49-4.39 (m, 2H), 4.21-4.15 (m, 1H), 4.12 (d, J=14.2 Hz, 1H), 3.74-3.69 (m, 1H), 3.19-3.00 (m, 5H), 2.82 (s, 3H), 2.25 (s, 3H), 1.70-1.47 (m, 3H), 1.39-1.24 (m, 6H), 1.21 (t, J=5.4 Hz, 1H).

Example 213: (*R)-3-(1-Cyclopropyl-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl) propanoic Acid

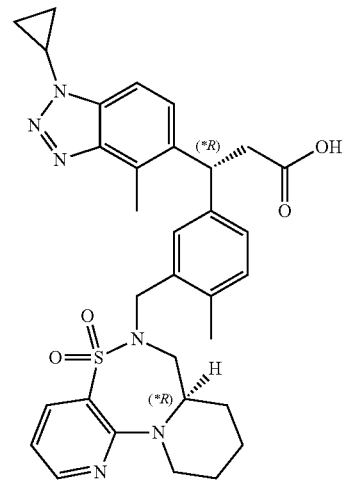 [SMILES: Cc1ccc([C@@H](CC(=O)O)c2ccc3c(nnn3C3CC3)c2C)cc1CN1C[C@H]2CCCCN2c2ncccc2S1(=O)=O]

The second eluting isomer (41 mg) from the separation of isomers by chiral SFC described in Example 212 was designated (*R): MS (ESI): mass calcd. for $C_{32}H_{36}N_6O_4S$, 600.3; m/z found, 601.3 [M+H]$^+$. $^1$H NMR (500 MHz, CDCl$_3$) δ 8.29-8.26 (m, 1H), 8.05-8.02 (m, 1H), 7.46-7.42 (m, 1H), 7.37-7.33 (m, 1H), 7.11-7.08 (m, 2H), 7.07 (s, 1H), 6.82-6.79 (m, 1H), 4.94 (t, J=7.9 Hz, 1H), 4.52-4.45 (m, 1H), 4.42 (d, J=14.3 Hz, 1H), 4.20-4.11 (m, 2H), 3.76-3.68 (m, 1H), 3.17-3.02 (m, 5H), 2.80 (s, 3H), 2.23 (s, 3H), 1.70-1.55 (m, 2H), 1.52-1.39 (m, 2H), 1.38-1.23 (m, 6H).

Example 214: (R/S)-3-(1-Cyclopropyl-4-methyl-1H-benzo[d][1,2,3]triazol-5-yl)-3-(3-((1,1-dioxidospiro[benzo[b][1,4,5]oxathiazepine-4,3'-oxetan]-2(3H)-yl)methyl)-4-methylphenyl)propanoic Acid

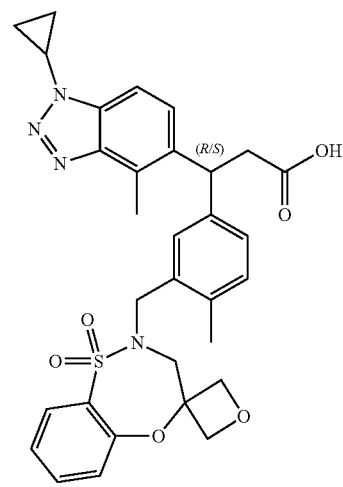 [SMILES: Cc1ccc(C(CC(=O)O)c2ccc3c(nnn3C3CC3)c2C)cc1CN1CC2(COC2)Oc2ccccc2S1(=O)=O]

DMF (0.75 mL) was added to a mixture of 2,3-dihydrospiro[benzo[b][1,4,5]oxathiazepine-4,3'-oxetane] 1,1-dioxide (Intermediate 7, 71.7 mg, 0.297 mmol) and sodium hydride (60% dispersion in mineral oil, 41 mg, 1.0 mmol) under nitrogen at 0° C. After 10 minutes, a solution of ethyl 3-(3-(chloromethyl)-4-methylphenyl)-3-(1-cyclopropyl-4-methyl-1H-benzo[d][1,2,3]triazol-5-yl)propanoate (Intermediate 32, 0.75 ml, 0.4 M in DMF, 0.29 mmol) was added and the mixture was allowed to warm to room temperature overnight. 1M aqueous NaOH (0.9 mL, 0.9 mmol) was added and the reaction was stirred for 2 hours. The mixture was filtered and the filtrate was purified by preparative basic HPLC (XBridge $C_{18}$, acetonitrile-water, 20 mM $NH_4OH$) to provide the title compound (60 mg, 35% yield). MS (ESI): mass calcd. for $C_{31}H_{32}N_4O_6S$, 588.2; m/z found, 589.2 $[M+H]^+$. $^1H$ NMR (500 MHz, $CDCl_3$) δ 7.86 (dd, J=7.8, 1.7 Hz, 1H), 7.56 (td, J=7.8, 1.7 Hz, 1H), 7.45-7.41 (m, 1H), 7.38-7.33 (m, 2H), 7.30 (t, J=7.6, 1.2 Hz, 1H), 7.18-7.15 (m, 1H), 7.06-7.03 (m, 1H), 7.00-6.96 (m, 1H), 4.93-4.85 (m, 1H), 4.65-4.54 (m, 2H), 4.45-4.38 (m, 1H), 4.31 (d, J=7.6 Hz, 1H), 4.24 (d, J=7.5 Hz, 1H), 4.17 (d, J=14.1 Hz, 1H), 3.75-3.63 (m, 3H), 3.09-3.00 (m, 1H), 2.96-2.89 (m, 1H), 2.74 (s, 3H), 2.24 (s, 3H), 1.36-1.21 (m, 4H).

Example 215: (*S)-3-(1-Cyclopropyl-4-methyl-1H-benzo[d][1,2,3]triazol-5-yl)-3-(3-((1,1-dioxidospiro[benzo[b][1,4,5]oxathiazepine-4,3'-oxetan]-2(3H)-yl)methyl)-4-methylphenyl)propanoic Acid

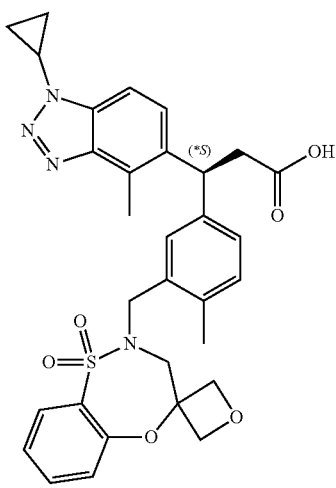 [SMILES: Cc1ccc([C@H](CC(=O)O)c2ccc3c(nnn3C3CC3)c2C)cc1CN1CC2(COC2)Oc2ccccc2S1(=O)=O]

The mixture of 3-(1-cyclopropyl-4-methyl-1H-benzo[d][1,2,3]triazol-5-yl)-3-(3-((1,1-dioxidospiro[benzo[b][1,4,5]oxathiazepine-4,3'-oxetan]-2(3H)-yl)methyl)-4-methylphenyl)propanoic acid isomers (Example 214) was separated by chiral SFC to afford two diastereomers. The first eluting isomer (24.2 mg) was designated (*S): MS (ESI): mass calcd. for $C_{31}H_{32}N_4O_6S$, 588.2; m/z found, 589.3 $[M+H]^+$. $^1H$ NMR (500 MHz, $CDCl_3$) δ 7.90-7.86 (m, 1H), 7.58-7.53 (m, 1H), 7.48-7.43 (m, 1H), 7.41-7.33 (m, 2H), 7.33-7.27 (m, 1H), 7.22 (s, 1H), 7.06-7.01 (m, 1H), 6.91 (d, J=7.8 Hz, 1H), 4.87-4.81 (m, 1H), 4.73-4.56 (m, 3H), 4.43-4.34 (m, 1H), 4.34-4.25 (m, 1H), 4.10 (d, J=13.7 Hz, 1H), 3.86-3.79 (m, 1H), 3.76-3.67 (m, 2H), 3.10-3.00 (m, 1H), 3.00-2.88 (m, 1H), 2.70 (s, 3H), 2.24 (s, 3H), 1.37-1.21 (m, 4H).

Example 216: (*R)-3-(1-Cyclopropyl-4-methyl-1H-benzo[d][1,2,3]triazol-5-yl)-3-(3-((1,1-dioxidospiro[benzo[b][1,4,5]oxathiazepine-4,3'-oxetan]-2(3H)-yl)methyl)-4-methylphenyl)propanoic Acid

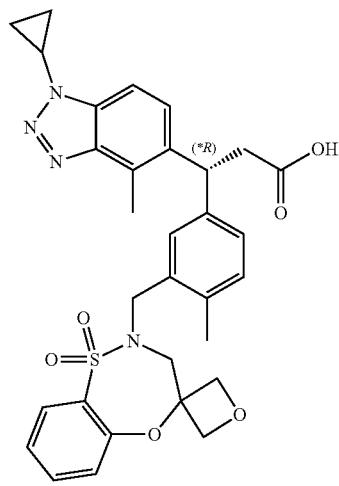 [SMILES: Cc1ccc([C@@H](CC(=O)O)c2ccc3c(nnn3C3CC3)c2C)cc1CN1CC2(COC2)Oc2ccccc2S1(=O)=O]

The second eluting isomer (24.9 mg) from the separation of isomers by chiral SFC described in Example 215 was designated (*R): MS (ESI): mass calcd. for $C_{31}H_{32}N_4O_6S$, 588.2; m/z found, 589.3 $[M+H]^+$. $^1H$ NMR (500 MHz, $CDCl_3$) δ 7.88 (d, J=7.8 Hz, 1H), 7.59-7.54 (m, 1H), 7.49-7.45 (m, 1H), 7.43-7.39 (m, 1H), 7.37-7.34 (m, 1H), 7.33-7.29 (m, 1H), 7.22 (s, 1H), 7.07-7.02 (m, 1H), 6.91 (d, J=7.7 Hz, 1H), 4.88-4.79 (m, 1H), 4.75-4.61 (m, 3H), 4.42-4.34 (m, 1H), 4.33-4.25 (m, 1H), 4.09 (d, J=13.8 Hz, 1H), 3.89-3.77 (m, 1H), 3.77-3.65 (m, 2H), 3.09-3.00 (m, 1H), 3.00-2.89 (m, 1H), 2.70 (s, 3H), 2.25 (s, 3H), 1.37-1.27 (m, 4H).

Example 217: (R/S)-3-(1-Cyclopropyl-4-methyl-1H-benzo[d][1,2,3]triazol-5-yl)-3-(3-(((*S)-5,5-dioxido-7,7a,8,9,10,11-hexahydro-6H-benzo[f]pyrido[2,1-d][1,2,5]thiadiazepin-6-yl)methyl)-4-methylphenyl)propanoic Acid

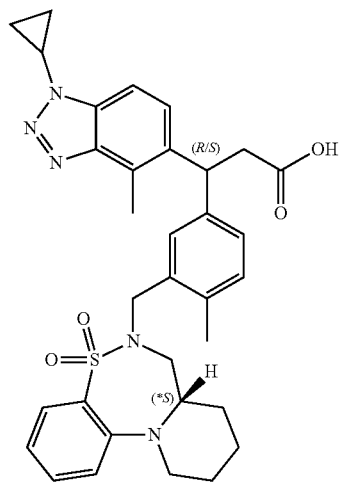 [SMILES: Cc1ccc(C(CC(=O)O)c2ccc3c(nnn3C3CC3)c2C)cc1CN1C[C@@H]2CCCCN2c2ccccc2S1(=O)=O]

The title compound (42.7 mg, 18% yield) was prepared using analogous conditions as described in Example 209 where (*S)-7,7a,8,9,10,11-hexahydro-6H-dipyrido[2,1-d:2',3'-f][1,2,5]thiadiazepine 5,5-dioxide (Intermediate 2) was used instead of (R)-6,7,7a,8,9,10-hexahydropyrido[2,3-f]pyrrolo[2,1-d][1,2,5]thiadiazepine 5,5-dioxide. MS (ESI): mass calcd. for $C_{32}H_{36}N_6O_4S$, 600.3; m/z found, 601.3 [M+H]$^+$.

Example 218: (R/S)-3-(1-Cyclopropyl-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

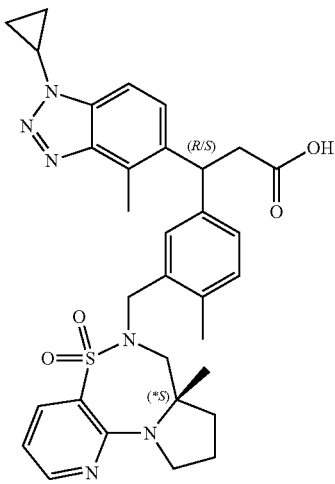 [SMILES: Cc1ccc(C(CC(=O)O)c2ccc3c(nnn3C3CC3)c2C)cc1CN1C[C@]2(C)CCCN2c2ncccc2S1(=O)=O]

The title compound (87 mg, 50% yield) was prepared using analogous conditions as described in Example 209 where (*S)-7a-methyl-6,7,7a,8,9,10-hexahydropyrido[2,3-f]pyrrolo[2,1-d][1,2,5]thiadiazepine 5,5-dioxide (Intermediate 39) was used instead of (R)-6,7,7a,8,9,10-hexahydropyrido[2,3-f]pyrrolo[2,1-d][1,2,5]thiadiazepine 5,5-dioxide. MS (ESI): mass calcd. for $C_{32}H_{36}N_6O_4S$, 600.3; m/z found, 601.3 [M+H]$^+$. $^1$H NMR (400 MHz, CDCl$_3$) δ 8.44-8.38 (m, 1H), 8.33-8.27 (m, 1H), 7.51-7.43 (m, 1H), 7.43-7.37 (m, 1H), 7.21-7.11 (m, 1H), 7.10-6.99 (m, 3H), 5.01-4.90 (t, J=7.8 Hz, 1H), 4.82-4.70 (dd, J=15.0, 7.0 Hz, 1H), 4.37-4.22 (t, J=15.1 Hz, 1H), 4.03-3.89 (m, 1H), 3.81-3.51 (m, 3H), 3.24-3.04 (m, 2H), 2.92-2.81 (m, 1H), 2.77 (d, J=4.9 Hz, 3H), 2.26 (d, J=4.6 Hz, 3H), 1.95-1.69 (m, 4H), 1.40-1.22 (m, 4H), 0.85 (d, J=19.7 Hz, 3H).

Example 219: (*S)-3-(1-Cyclopropyl-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

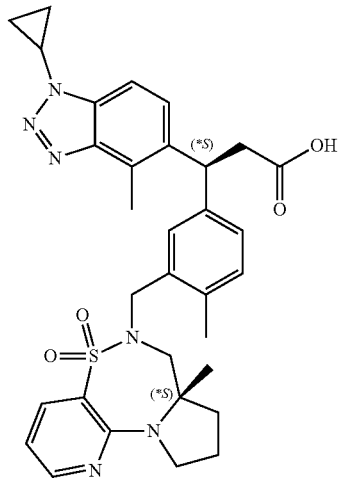 [SMILES: Cc1ccc([C@H](CC(=O)O)c2ccc3c(nnn3C3CC3)c2C)cc1CN1C[C@]2(C)CCCN2c2ncccc2S1(=O)=O]

The mixture of (R/S)-3-(1-cyclopropyl-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid isomers (Example 218) was separated by chiral SFC (Chiralpak AD-H, mobile phase: 55% $CO_2$, 45% EtOH) to afford two diastereomers. The first eluting isomer (45 mg) was designated (*S): MS (ESI): mass calcd. for $C_{32}H_{36}N_6O_4S$, 600.3; m/z found, 601.5 [M+H]$^+$. $^1$H NMR (400 MHz, CDCl$_3$) δ 8.39-8.36 (m, 1H), 8.13 (dd, J=7.7, 1.9 Hz, 1H), 7.45-7.35 (m, 2H), 7.22-7.19 (m, 1H), 7.07-7.01 (m, 2H), 6.95-6.88 (m, 1H), 4.96 (t, J=7.8 Hz, 1H), 4.72 (d, J=15.1 Hz, 1H), 4.27 (d, J=15.2 Hz, 1H), 3.98-3.88 (m, 1H), 3.75-3.66 (m, 2H), 3.59-3.51 (m, 1H), 3.22-3.00 (m, 2H), 2.85 (d, J=14.7 Hz, 1H), 2.80 (s, 3H), 2.24 (s, 3H), 1.93-1.80 (m, 2H), 1.80-1.68 (m, 2H), 1.37-1.19 (m, 4H), 0.74 (s, 3H).

Example 220: (*R)-3-(1-Cyclopropyl-4-methyl-1H-benzo[d][1,2,3]triazol-5-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

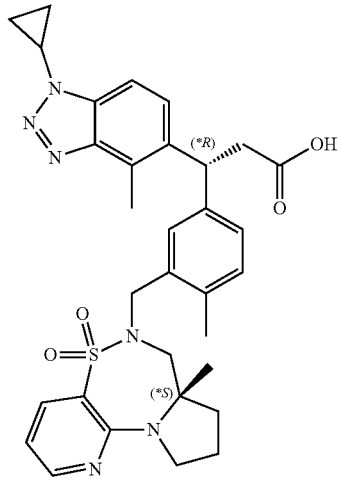 [SMILES: Cc1ccc([C@@H](CC(=O)O)c2ccc3c(nnn3C3CC3)c2C)cc1CN1C[C@]2(C)CCCN2c2ncccc2S1(=O)=O]

The second eluting isomer (44 mg) from the separation of isomers by chiral SFC described in Example 219 was designated (*R): MS (ESI): mass calcd. for $C_{32}H_{36}N_6O_4S$, 600.3; m/z found, 601.5 [M+H]$^+$. $^1$H NMR (400 MHz, CDCl$_3$) δ 8.36 (dd, J=4.8, 1.8 Hz, 1H), 8.15 (dd, J=7.7, 1.9 Hz, 1H), 7.49-7.43 (m, 1H), 7.42-7.36 (m, 1H), 7.21-7.16 (s, 1H), 7.10-7.01 (m, 2H), 6.92 (dd, J=7.7, 4.8 Hz, 1H), 5.00-4.89 (m, 1H), 4.76 (d, J=15.0 Hz, 1H), 4.25 (d, J=15.0 Hz, 1H), 3.98-3.86 (m, 1H), 3.76-3.67 (m, 1H), 3.59-3.49 (m, 2H), 3.44-3.30 (m, 1H), 3.24-3.04 (m, 2H), 2.79 (s, 3H), 2.26 (s, 3H), 1.88-1.76 (m, 2H), 1.72-1.65 (m, 2H), 1.37-1.18 (m, 4H), 0.80 (s, 3H).

Example 221: (R/S)-3-(1-Cyclopropyl-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

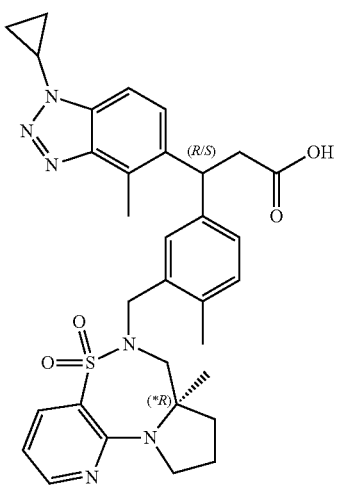 [SMILES: Cc1ccc(C(CC(=O)O)c2ccc3c(nnn3C3CC3)c2C)cc1CN1C[C@@]2(C)CCCN2c2ncccc2S1(=O)=O]

The title compound (55.2 mg, 31.4% yield) was prepared using analogous conditions as described in Example 209 where (*R)-7a-methyl-6,7,7a,8,9,10-hexahydropyrido[2,3-f]pyrrolo[2,1-d][1,2,5]thiadiazepine 5,5-dioxide (Intermediate 40) was used instead of (R)-6,7,7a,8,9,10-hexahydropyrido[2,3-f]pyrrolo[2,1-d][1,2,5]thiadiazepine 5,5-dioxide. MS (ESI): mass calcd. for $C_{32}H_{36}N_6O_4S$, 600.3; m/z found, 601.3 [M+H]$^+$. $^1$H NMR (400 MHz, CDCl$_3$) δ 8.44-8.38 (m, 1H), 8.31-8.24 (m, 1H), 7.50-7.37 (m, 2H), 7.21-7.11 (m, 1H), 7.09-6.98 (m, 3H), 4.95 (t, J=7.9 Hz, 1H), 4.81-4.69 (m, 1H), 4.36-4.21 (m, 1H), 4.01-3.87 (m, 1H), 3.77-3.49 (m, 3H), 3.23-3.02 (m, 2H), 2.90-2.79 (m, 1H), 2.77 (d, J=4.9 Hz, 3H), 2.25 (d, J=4.6 Hz, 3H), 1.91-1.66 (m, 4H), 1.38-1.22 (m, 4H), 0.83 (d, J=20.1 Hz, 3H).

Example 222: (*S)-3-(1-Cyclopropyl-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

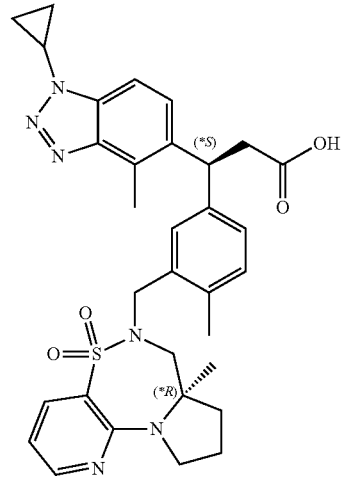 [SMILES: Cc1ccc([C@H](CC(=O)O)c2ccc3c(nnn3C3CC3)c2C)cc1CN1C[C@@]2(C)CCCN2c2ncccc2S1(=O)=O]

The mixture of (R/S)-3-(1-cyclopropyl-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid isomers (Example 221) was separated by chiral SFC (Chiralpak AD-H, mobile phase: 60% CO$_2$, 40% EtOH) to afford two diastereomers. The first eluting isomer (25 mg) was designated (*S): MS (ESI): mass calcd. for $C_{32}H_{36}N_6O_4S$, 600.3; m/z found, 601.6 [M+H]$^+$. $^1$H NMR (400 MHz, CDCl$_3$) δ 8.36 (dd, J=4.8, 1.8 Hz, 1H), 8.14 (dd, J=7.7, 1.9 Hz, 1H), 7.47-7.36 (m, 2H), 7.15 (s, 1H), 7.08-7.02 (m, 2H), 6.91 (dd, J=7.7, 4.8 Hz, 1H), 4.95 (t, J=7.8 Hz, 1H), 4.74 (d, J=14.9 Hz, 1H), 4.25 (d, J=14.9 Hz, 1H), 3.98-3.86 (m, 1H), 3.78-3.67 (m, 1H), 3.59-3.48 (m, 2H), 3.20-3.01 (m, 2H), 2.81-2.71 (m, 4H), 2.26 (s, 3H), 1.86-1.73 (m, 2H), 1.70-1.62 (m, 2H), 1.36-1.27 (m, 4H), 0.77 (s, 3H).

Example 223: (*R)-3-(1-Cyclopropyl-4-methyl-1H-benzo[d][1,2,3]triazol-5-yl)-3-(4-methyl-3-(((*R)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

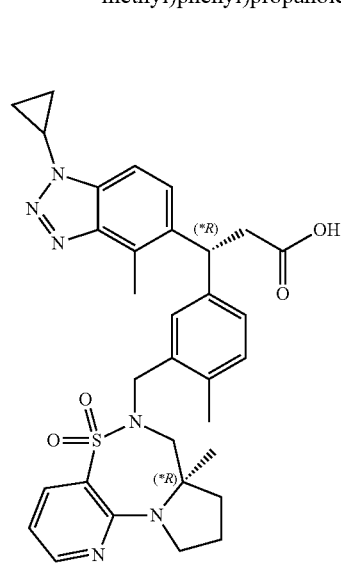

The second eluting isomer (22 mg) from the separation of isomers by chiral SFC described in Example 222 was designated (*R): MS (ESI): mass calcd. for $C_{32}H_{36}N_6O_4S$, 600.3; m/z found, 601.6 [M+H]+. $^1$H NMR (400 MHz, CDCl$_3$) δ 8.37 (dd, J=4.8, 1.8 Hz, 1H), 8.13 (dd, J=7.7, 1.9 Hz, 1H), 7.44-7.36 (m, 2H), 7.20 (s, 1H), 7.08-7.01 (m, 2H), 6.91 (dd, J=7.7, 4.8 Hz, 1H), 4.96 (t, J=7.9 Hz, 1H), 4.72 (d, J=15.2 Hz, 1H), 4.27 (d, J=15.1 Hz, 1H), 3.97-3.88 (m, 1H), 3.74-3.66 (m, 2H), 3.59-3.51 (m, 1H), 3.18-3.00 (m, 2H), 2.87-2.77 (m, 4H), 2.24 (s, 3H), 1.89-1.70 (m, 4H), 1.35-1.26 (m, 4H), 0.73 (s, 3H).

Example 224: (R/S)-3-(1-Cyclopropyl-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic Acid

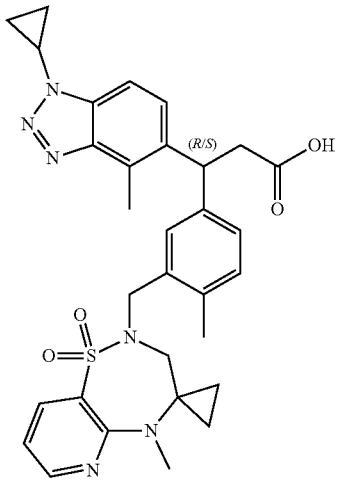 [SMILES: Cc1ccc(C(CC(=O)O)c2ccc3c(nnn3C3CC3)c2C)cc1CN1CC2(CC2)N(C)c2ncccc2S1(=O)=O]

The title compound (82.7 mg, 48% yield) was prepared using analogous conditions as described in Example 214 where 5'-methyl-2',3'-dihydro-5'H-spiro[cyclopropane-1,4'-pyrido[2,3-f][1,2,5]thiadiazepine] 1',1'-dioxide (Intermediate 93) was used instead of 2,3-dihydrospiro[benzo[b][1,4,5]oxathiazepine-4,3'-oxetane] 1,1-dioxide the title compound was purified by preparative acidic HPLC (XBridge C$_{18}$, acetonitrile-water containing 0.05% TFA). $^1$H NMR (400 MHz, CDCl$_3$) δ 8.30-8.22 (m, 2H), 7.45 (d, J=8.6 Hz, 1H), 7.32 (d, J=8.7 Hz, 1H), 7.13-7.03 (m, 3H), 6.99 (dd, J=7.7, 5.2 Hz, 1H), 4.90 (t, J=7.8 Hz, 1H), 4.43-4.30 (m, 2H), 3.77-3.68 (m, 1H), 3.27-2.98 (m, 4H), 2.97 (s, 3H), 2.77 (s, 3H), 2.23 (s, 3H), 1.38-1.22 (m, 4H), 1.01-0.82 (m, 4H).

Example 225: (*S)-3-(1-Cyclopropyl-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic Acid

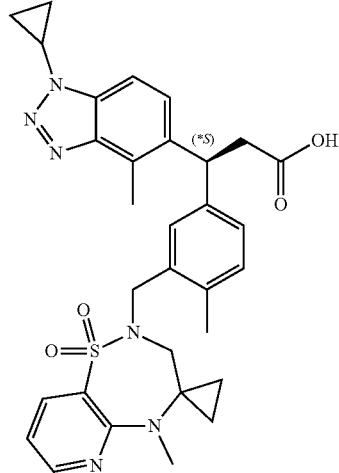 [SMILES: Cc1ccc([C@H](CC(=O)O)c2ccc3c(nnn3C3CC3)c2C)cc1CN1CC2(CC2)N(C)c2ncccc2S1(=O)=O]

The mixture of (R/S)-3-(1-cyclopropyl-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic acid isomers (Example 224) was separated by chiral SFC (Chiralpak AD-H, mobile phase: 55% CO$_2$, 45% EtOH) to afford two enantiomers. The first eluting isomer (34 mg) was designated (*S): MS (ESI): mass calcd. for $C_{31}H_{34}N_6O_4S$, 586.2; m/z found, 587.5 [M+H]+. $^1$H NMR (400 MHz, CDCl$_3$) δ 8.28-8.23 (m, 1H), 8.12-8.07 (m, 1H), 7.46-7.41 (m, 1H), 7.39-7.33 (m, 1H), 7.16-7.13 (m, 1H), 7.08-7.01 (m, 2H), 6.90-6.86 (m, 1H), 4.95 (t, J=7.8 Hz, 1H), 4.34 (s, 2H), 3.77-3.67 (m, 1H), 3.24-3.00 (m, 4H), 2.97 (s, 3H), 2.80 (s, 3H), 2.23 (s, 3H), 1.36-1.24 (m, 4H), 0.93-0.80 (m, 4H).

Example 226: (*R)-3-(1-Cyclopropyl-4-methyl-1H-benzo[d][1,2,3]triazol-5-yl)-3-(4-methyl-3-((5'-methyl-1',1'-dioxido-5'H-spiro[cyclopropane-1,4'-pyrido[2,3-f][1,2,5]thiadiazepin]-2'(3'H)-yl)methyl)phenyl)propanoic Acid

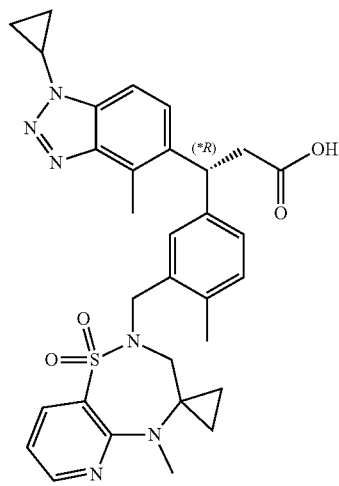 [SMILES: Cc1ccc([C@@H](CC(=O)O)c2ccc3c(nnn3C3CC3)c2C)cc1CN1CC2(CC2)N(C)c2ncccc2S1(=O)=O]

The second eluting isomer (30 mg) from the separation of isomers by chiral SFC described in Example 225 was designated (*R): MS (ESI): mass calcd. for $C_{31}H_{34}N_6O_4S$, 586.2; m/z found, 587.5 [M+H]$^+$. $^1$H NMR (400 MHz, CDCl$_3$) δ 8.27-8.23 (m, 1H), 8.12-8.06 (m, 1H), 7.46-7.41 (m, 1H), 7.39-7.34 (m, 1H), 7.16 (s, 1H), 7.07-7.00 (m, 2H), 6.88 (dd, J=7.8, 4.7 Hz, 1H), 4.95 (t, 1H), 4.34 (s, 2H), 3.75-3.68 (m, 1H), 3.22-3.01 (m, 4H), 2.97 (s, 3H), 2.80 (s, 3H), 2.23-2.21 (m, 3H), 1.36-1.20 (m, 4H), 0.93-0.82 (m, 4H).

Example 227: (R/S)-3-(1-Cyclopropyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic Acid

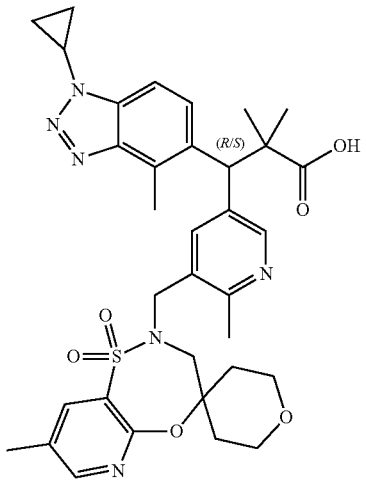 [SMILES: Cc1cnc2c(c1)S(=O)(=O)N(Cc1cc(C(c3ccc4c(nnn4C4CC4)c3C)C(C)(C)C(=O)O)cnc1C)CC1(CCOCC1)O2]

The title compound (36.4 mg, 87% yield) was prepared using analogous conditions as described in Example 43 where 8'-methyl-2,2',3,3',5,6-hexahydrospiro[pyran-4,-4'-pyrido[2,3-b][1,4,5]oxathiazepine] 1',1'-dioxide (Intermediate 37) was used instead of 2,2',3,3',5,6-hexahydrospiro [pyran-4,-4'-pyrido[2,3-b][1,4,5]oxathiazepine] 1',1'-dioxide. MS (ESI): mass calcd. for $C_{34}H_{40}N_6O_6S$, 660.3; m/z found, 661.3 [M+H]$^+$.

Example 228: (*S)-3-(1-Cyclopropyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic Acid

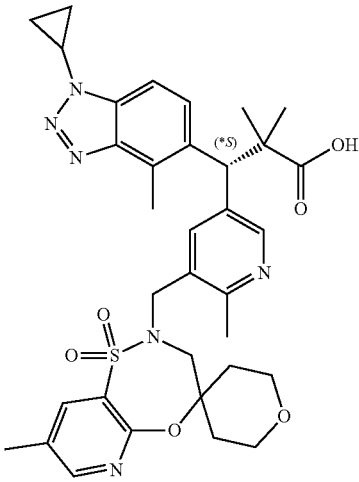 [SMILES: Cc1cnc2c(c1)S(=O)(=O)N(Cc1cc([C@H](c3ccc4c(nnn4C4CC4)c3C)C(C)(C)C(=O)O)cnc1C)CC1(CCOCC1)O2]

The mixture of (R/S)-3-(1-cyclopropyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid isomers (Example 227) was separated by chiral SFC (Chiralpak AS-H, mobile phase: 85% CO$_2$, 15% MeOH with 0.1% NH$_4$OH) to afford two enantiomers. The first eluting isomer (44 mg) was designated (*S): $^1$H NMR (500 MHz, CDCl$_3$) δ 8.52 (s, 1H), 8.30-8.25 (m, 1H), 8.00-7.95 (m, 1H), 7.68-7.56 (m, 2H), 7.48 (d, J=8.5 Hz, 1H), 5.04 (s, 1H), 4.52 (d, J=15.1 Hz, 1H), 4.37 (d, J=15.1 Hz, 1H), 4.05-3.91 (m, 2H), 3.80-3.73 (m, 1H), 3.65 (d, J=10.8 Hz, 1H), 3.56 (s, 1H), 3.42 (s, 2H), 2.90 (s, 3H), 2.45 (s, 3H), 2.39 (s, 3H), 1.60-1.49 (m, 2H), 1.48-1.25 (m, 12H).

Example 229: (*R)-3-(1-Cyclopropyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic Acid

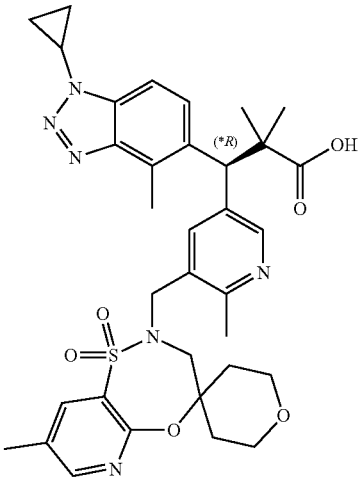 [SMILES: Cc1cnc2c(c1)S(=O)(=O)N(Cc1cc([C@@H](c3ccc4c(nnn4C4CC4)c3C)C(C)(C)C(=O)O)cnc1C)CC1(CCOCC1)O2]

The second eluting isomer (41 mg) from the separation of isomers by chiral SFC described in Example 228 was designated (*R): $^1$H NMR (500 MHz, CDCl$_3$) δ 8.49 (s, 1H), 8.29-8.26 (m, 1H), 8.00-7.96 (m, 1H), 7.64-7.57 (m, 2H), 7.47 (d, J=8.6 Hz, 1H), 5.04 (s, 1H), 4.54 (d, J=15.2 Hz, 1H), 4.36 (d, J=15.0 Hz, 1H), 4.05-3.93 (m, 2H), 3.78-3.72 (m, 1H), 3.69-3.62 (m, 1H), 3.60-3.53 (m, 1H), 3.51-3.32 (m, 2H), 2.90 (s, 3H), 2.44 (s, 3H), 2.39 (s, 3H), 1.59-1.50 (m, 2H), 1.47-1.19 (m, 12H).

Example 230: (*S)-3-(3-Cyclopropyl-8-methyl-[1,2,4]triazolo[4,3-a]pyridin-7-yl)-3-(3-((8'-fluoro-1',1'-dioxidospiro[cyclopropane-1,4'-pyrido[2,3-b][1,4,5]oxathiazepin]-2'(3'H)-yl)methyl)-4-methylphenyl)propanoic Acid

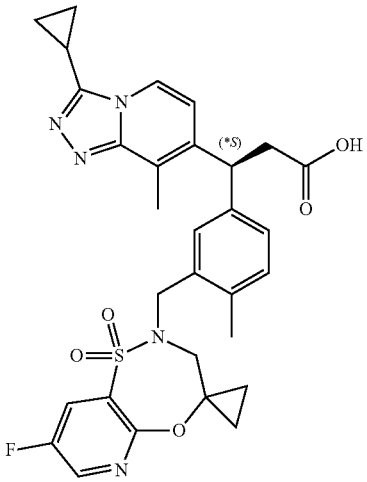 [SMILES: Cc1ccc([C@H](CC(=O)O)c2ccn3c(C4CC4)nnc3c2C)cc1CN1CC2(CC2)Oc2ncc(F)cc2S1(=O)=O]

The title compound (82.6 mg, 97% yield) was prepared using analogous conditions as described in Example 186 where ethyl 3-(3-cyclopropyl-8-methyl-[1,2,4]triazolo[4,3-a]pyridin-7-yl)-3-(3-(hydroxymethyl)-4-methylphenyl)propanoate (prepared in the synthesis of Intermediate 106, Step E) was used instead of ethyl (*S)-3-(3-(hydroxymethyl)-4-methylphenyl)-3-(8-methyl-3-(trifluoromethyl)-[1,2,4]triazolo[4,3-a]pyridin-7-yl)propanoate, 8'-fluoro-2',3'-dihydrospiro[cyclopropane-1,4'-pyrido[2,3-b][1,4,5]oxathiazepine] 1',1'-dioxide (Intermediate 80) was used instead of (*S)-7a-methyl-6,7,7a,8,9,10-hexahydropyrido[2,3-f]pyrrolo[2,1-d][1,2,5]thiadiazepine 5,5-dioxide and the hydrolysis reaction was run at 50° C. MS (ESI): mass calcd. for $C_{30}H_{30}FN_5O_5S$, 591.2; m/z found, 592.2 [M+H]+. 1H NMR (400 MHz, CDCl3) δ 8.27 (d, J=3.0 Hz, 1H), 8.05-7.98 (m, 1H), 7.89 (d, J=7.2 Hz, 1H), 7.15-7.10 (m, 1H), 7.10-7.04 (m, 2H), 6.69 (d, J=7.2 Hz, 1H), 4.91 (t, J=7.9 Hz, 1H), 4.32 (s, 2H), 3.62-3.44 (m, 2H), 3.23-3.10 (m, 1H), 3.03-2.94 (m, 1H), 2.65 (s, 3H), 2.30 (s, 3H), 2.01-1.93 (m, 1H), 1.22-1.06 (m, 6H), 0.57-0.46 (m, 2H).

Example 231: (R/S)-3-(1-(Cyclopropylmethyl)-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

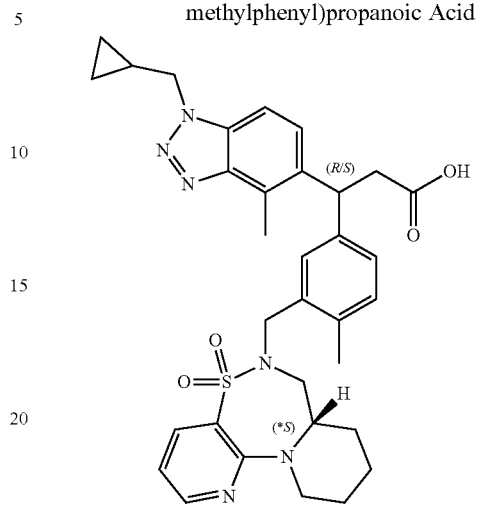

The title compound (223 mg, 71.6% yield) was prepared using analogous conditions as described in Example 11 where (*S)-7,7a,8,9,10,11-hexahydro-6H-dipyrido[2,1-d:2',3'-f][1,2,5]thiadiazepine 5,5-dioxide (Intermediate 2) was used instead of (*S)-7a-methyl 6,7,7a,8,9,19-hexahydropyrido[2,3-f]pyrollo[2,1-d[1,2,5]thiadiazepine 5,5-dioxide and the title compound was purified by preparative basic HPLC (XBridge $C_{18}$, acetonitrile-water, 20 mM NH4OH). MS (ESI): mass calcd. for $C_{33}H_{38}N_6O_4S$, 614.3; m/z found, 615.2 [M+H]+. 1H NMR (500 MHz, CDCl3) δ 8.21-8.14 (m, 1H), 7.94-7.87 (m, 1H), 7.25-7.07 (m, 3H), 6.95-6.88 (m, 1H), 6.80 (d, J=7.8 Hz, 1H), 6.63 (dt, J=8.3, 4.5 Hz, 1H), 4.89-4.75 (m, 1H), 4.43-4.21 (m, 4H), 4.21-4.06 (m, 1H), 3.99 (t, J=15.4 Hz, 1H), 3.23-2.95 (m, 3H), 2.95-2.76 (m, 1H), 2.66 (d, J=17.6 Hz, 3H), 2.00 (s, 3H), 1.64-1.04 (m, 8H), 0.60-0.46 (m, 2H), 0.46-0.31 (m, 2H).

Example 232: (*S)-3-(1-(Cyclopropylmethyl)-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid The mixture of (R/S)-3-(1-(cyclopropylmethyl)-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid isomers (Example 231) was separated by chiral SFC (Chiralpak OZ-H, mobile phase: 60% CO$_2$, 40% EtOH) to afford two diastereomers. The first eluting isomer (105 mg) was designated (*S): $^1$H NMR (400 MHz, CDCl$_3$) δ 8.22 (d, J=4.4 Hz, 1H), 7.95 (d, J=7.5 Hz, 1H), 7.30-7.24 (m, 2H), 7.21-7.16 (m, 1H), 6.97-6.90 (m, 2H), 6.70 (t, J=6.0 Hz, 1H), 4.95-4.85 (m, 1H), 4.47-4.33 (m, 4H), 4.17-4.01 (m, 2H), 3.29-3.01 (m, 3H), 2.99-2.77 (m, 2H), 2.76-2.65 (m, 3H), 2.11 (s, 3H), 1.63-1.28 (m, 7H), 0.64-0.54 (m, 2H), 0.49-0.37 (m, 2H).

Example 233: (*R)-3-(1-(Cyclopropylmethyl)-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

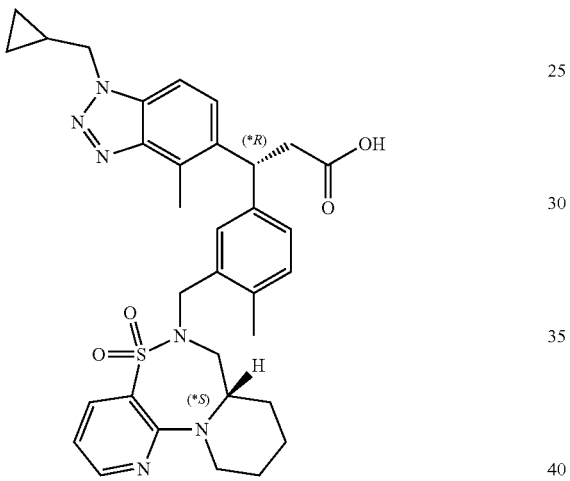

The second eluting isomer (120 mg) from the separation of isomers by chiral SFC described in Example 232 was designated (*R): $^1$H NMR (400 MHz, CDCl$_3$) δ 8.20-8.14 (m, 1H), 7.94-7.88 (m, 1H), 7.20-7.10 (m, 3H), 6.97 (d, J=7.7 Hz, 1H), 6.84-6.78 (m, 1H), 6.63 (dd, J=7.8, 4.6 Hz, 1H), 4.87-4.79 (m, 1H), 4.40-4.10 (m, 5H), 3.96 (d, J=14.8 Hz, 1H), 1.54-1.45 (m, 2H), 3.17-3.01 (m, 3H), 2.93-2.81 (m, 1H), 2.71-2.55 (m, 4H), 2.00 (s, 3H), 1.63-1.54 (m, 1H), 1.30-1.24 (m, 3H), 1.15-1.04 (m, 1H), 0.57-0.49 (m, 2H), 0.42-0.35 (m, 2H).

Example 234: (R/S)-3-(1-(Cyclopropylmethyl)-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

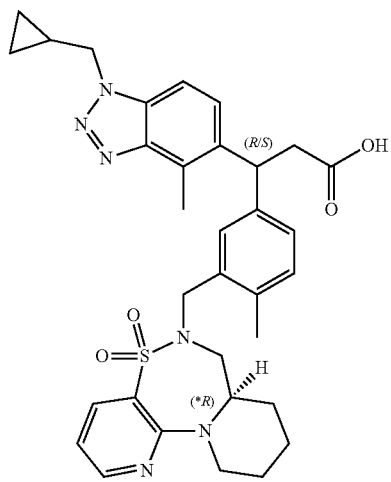 [SMILES: Cc1ccc(C(CC(=O)O)c2ccc3c(nnn3CC3CC3)c2C)cc1CN1C[C@H]2CCCCN2c2ncccc2S1(=O)=O]

The title compound (196 mg, 71% yield) was prepared using analogous conditions as described in Example 11 where (*R)-7,7a,8,9,10,11-hexahydro-6H-dipyrido[2,1-d:2',3'-f][1,2,5]thiadiazepine 5,5-dioxide (Intermediate 3) was used instead of (*S)-7a-methyl 6,7,7a,8,9,19-hexahydropyrido[2,3-f]pyrollo[2,1-d[1,2,5]thiadiazepine 5,5-dioxide and the title compound was purified by preparative basic HPLC (XBridge C$_{18}$, acetonitrile-water, 20 mM NH$_4$OH). MS (ESI): mass calcd. for C$_{33}$H$_{38}$N$_6$O$_4$S, 614.3; m/z found, 615.3 [M+H]$^+$. $^1$H NMR (500 MHz, CDCl$_3$) δ 8.17 (d, J=4.9 Hz, 1H), 7.95-7.87 (m, 1H), 7.25-7.08 (m, 3H), 6.94-6.86 (m, 1H), 6.84-6.77 (m, 1H), 6.63 (dt, J=7.7, 4.1 Hz, 1H), 4.83 (t, J=7.5 Hz, 1H), 4.42-4.21 (m, 4H), 4.21-4.07 (m, 1H), 4.07-3.92 (m, 1H), 3.23-2.76 (m, 5H), 2.74-2.59 (m, 4H), 2.01 (s, 3H), 1.66-1.07 (m, 6H), 0.61-0.48 (m, 2H), 0.40 (dd, J=9.5, 5.0 Hz, 2H). Example 235: (*R)-3-(1-(Cyclopropylmethyl)-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

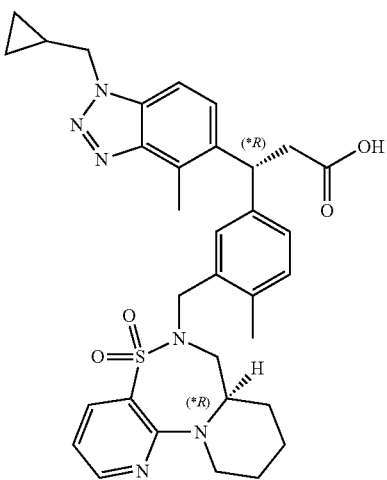 [SMILES: Cc1ccc([C@@H](CC(=O)O)c2ccc3c(nnn3CC3CC3)c2C)cc1CN1C[C@H]2CCCCN2c2ncccc2S1(=O)=O]

The mixture of (R/S)-3-(1-(cyclopropylmethyl)-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid isomers (Example 234) was separated by chiral SFC (Chiralpak AD-H, mobile phase: 60% CO₂, 40% MeOH) to afford two diastereomers. The first eluting isomer (100 mg) was designated (*R): MS (ESI): mass calcd. for C₃₃H₃₈N₆O₄S, 614.3; m/z found, 615.3 [M+H]⁺. ¹H NMR (400 MHz, CDCl₃) δ 8.29-8.25 (m, 1H), 8.05-8.00 (m, 1H), 7.37-7.28 (m, 2H), 7.14-7.07 (m, 3H), 6.80 (dd, J=7.8, 4.7 Hz, 1H), 4.97 (t, J=7.6 Hz, 1H), 4.49-4.40 (m, 4H), 4.21-4.08 (m, 2H), 3.19-2.98 (m, 5H), 2.84 (s, 3H), 2.24 (s, 3H), 1.70-1.46 (m, 3H), 1.40-1.09 (m, 4H), 0.65-0.59 (m, 2H), 0.51-0.42 (m, 2H).

Example 236: (*S)-3-(1-(Cyclopropylmethyl)-4-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

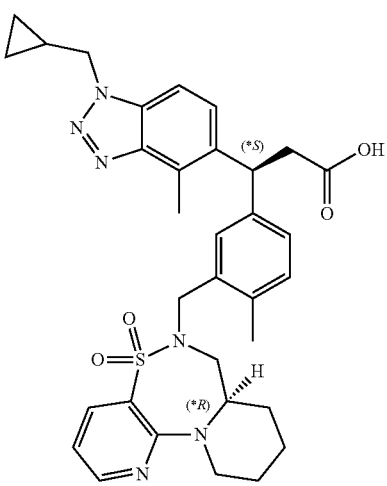 [SMILES: Cc1ccc([C@H](CC(=O)O)c2ccc3c(nnn3CC3CC3)c2C)cc1CN1C[C@H]2CCCCN2c2ncccc2S1(=O)=O]

The second eluting isomer (98 mg) from the separation of isomers by chiral SFC described in Example 235 was designated (*S): MS (ESI): mass calcd. for C₃₃H₃₈N₆O₄S, 614.3; m/z found, 615.3 [M+H]⁺. ¹H NMR (400 MHz, CDCl₃) δ 8.29-8.24 (m, 1H), 8.05-7.99 (m, 1H), 7.37-7.30 (m, 2H), 7.15-7.03 (m, 3H), 6.79 (s, 1H), 4.99-4.91 (m, 1H), 4.52-4.38 (m, 4H), 4.21-4.09 (m, 2H), 3.22-2.99 (m, 5H), 2.81 (s, 3H), 2.22 (s, 3H), 1.67-1.23 (m, 7H), 0.67-0.59 (m, 2H), 0.50-0.45 (m, 2H).

Example 237: (R S)-3-(6-((1,1-Dioxidospiro[benzo[b][1,4,5]oxathiazepine-4,3'-oxetan]-2(3H)-yl)methyl)-5-methylpyridin-2-yl)-3-(1-ethyl-4-methyl-1H-benzo[d][1,2,3]triazol-5-yl)propanoic Acid

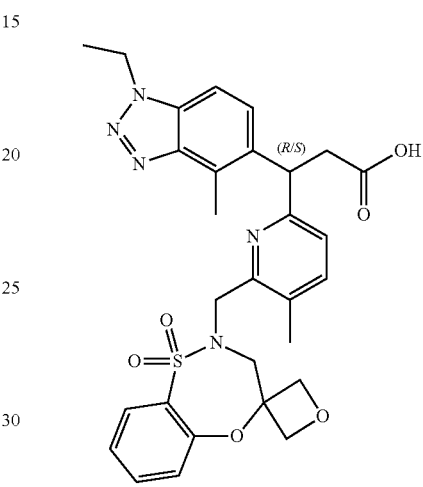

The title compound (129 mg, 91% yield) was prepared using analogous conditions as described in Example 186 where 2,3-dihydrospiro[benzo[b][1,4,5]oxathiazepine-4,3'-oxetane]1,1-dioxide (Intermediate 7) was used instead of (*S)-7a-methyl-6,7,7a,8,9,10-hexahydropyrido[2,3-f]pyrrolo[2,1-d][1,2,5]thiadiazepine 5,5-dioxide, ethyl 3-(1-ethyl-4-methyl-1H-benzo[d][1,2,3]triazol-5-yl)-3-(6-(hydroxymethyl)-5-methylpyridin-2-yl)propanoate (Intermediate 108) was used instead of ethyl (*S)-3-(3-(hydroxymethyl)-4-methylphenyl)-3-(8-methyl-3-(trifluoromethyl)-[1,2,4]triazolo[4,3-a]pyridin-7-yl)propanoate and the hydrolysis reaction was run overnight. MS (ESI): mass calcd. for C₂₉H₃₁N₅O₆S, 577.2; m/z found, 578.1 [M+H]⁺. ¹H NMR (400 MHz, CDCl₃) δ 7.99-7.87 (m, 1H), 7.67-7.57 (m, 1H), 7.50-7.42 (m, 1H), 7.42-7.27 (m, 3H), 7.24-7.17 (m, 1H), 6.85 (d, J=8.0 Hz, 1H), 5.16-5.04 (m, 1H), 4.92-4.75 (m, 3H), 4.75-4.52 (m, 3H), 4.40-4.25 (m, 1H), 4.04-3.78 (m, 2H), 3.38-3.26 (m, 1H), 2.96-2.73 (m, 4H), 2.43 (s, 3H), 1.69-1.52 (m, 3H), 1.52-1.43 (m, 1H).

Example 238: (*S)-3-(6-((1,1-Dioxidospiro[benzo[b][1,4,5]oxathiazepine-4,3'-oxetan]-2(3H)-yl)methyl)-5-methylpyridin-2-yl)-3-(1-ethyl-4-methyl-1H-benzo[d][1,2,3]triazol-5-yl)propanoic Acid

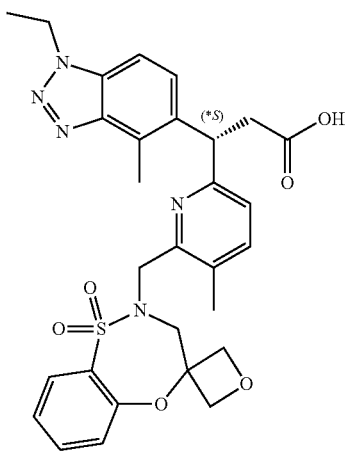 [SMILES: CCn1nnc2c(C)c([C@H](CC(=O)O)c3ccc(C)c(CN4CC5(COC5)Oc5ccccc5S4(=O)=O)n3)ccc21]

The mixture of (R/5)-3-(6-((1,1-dioxidospiro[benzo[b][1,4,5]oxathiazepine-4,3'-oxetan]-2(3H)-yl)methyl)-5-methylpyridin-2-yl)-3-(1-ethyl-4-methyl-1H-benzo[d][1,2,3]triazol-5-yl)propanoic acid isomers (Example 237) was separated by chiral SFC (Chiralpak AD-H, mobile phase: 70% $CO_2$, 30% MeOH) to afford two enantiomers. The first eluting isomer (50 mg) was designated (*S): MS (ESI): mass calcd. for $C_{29}H_{31}N_5O_6S$, 577.2; m/z found, 578.3 $[M+H]^+$. $^1$H NMR (500 MHz, CDCl$_3$) δ 7.92 (dd, J=7.8, 1.7 Hz, 1H), 7.63-7.59 (m, 1H), 7.47-7.44 (m, 1H), 7.39-7.32 (m, 2H), 7.31-7.28 (m, 1H), 7.20-7.15 (m, 1H), 6.85-6.82 (m, 1H), 5.09-5.03 (m, 1H), 4.91-4.79 (m, 4H), 4.68-4.59 (m, 3H), 4.34-4.28 (m, 1H), 4.00-3.92 (m, 1H), 3.88-3.82 (m, 1H), 3.30-3.21 (m, 1H), 2.86 (d, J=12.1 Hz, 1H), 2.79 (s, 3H), 2.44 (s, 3H), 1.62-1.57 (m, 3H).

Example 239: (*R)-3-(6-((1,1-Dioxidospiro[benzo[b][1,4,5]oxathiazepine-4,3'-oxetan]-2(3H)-yl)methyl)-5-methylpyridin-2-yl)-3-(1-ethyl-4-methyl-1H-benzo[d][1,2,3]triazol-5-yl)propanoic Acid

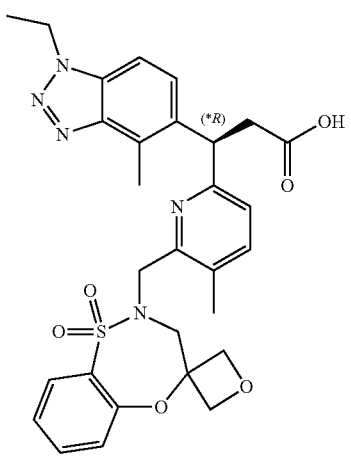 [SMILES: CCn1nnc2c(C)c([C@@H](CC(=O)O)c3ccc(C)c(CN4CC5(COC5)Oc5ccccc5S4(=O)=O)n3)ccc21]

The second eluting isomer (48 mg) from the separation of isomers by chiral SFC described in Example 238 was designated (*R): MS (ESI): mass calcd. for $C_{29}H_{31}N_5O_6S$, 577.2; m/z found, 578.4 $[M+H]^+$. $^1$H NMR (500 MHz, CDCl$_3$) δ 7.91 (dd, J=7.8, 1.6 Hz, 1H), 7.63-7.58 (m, 1H), 7.47-7.43 (m, 1H), 7.38-7.31 (m, 2H), 7.30-7.28 (m, 1H), 7.22-7.18 (m, 1H), 6.85 (d, J=7.9 Hz, 1H), 5.10-5.04 (m, 1H), 4.91-4.77 (m, 4H), 4.69-4.57 (m, 3H), 4.33-4.28 (m, 1H), 3.98-3.91 (m, 1H), 3.87-3.81 (m, 1H), 3.31-3.24 (m, 1H), 2.89-2.82 (m, 1H), 2.79 (s, 3H), 2.43 (s, 3H), 1.62-1.57 (m, 3H).

Example 240: (R/S)-3-(6-((1',1'-Dioxidospiro[oxetane-3,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic Acid

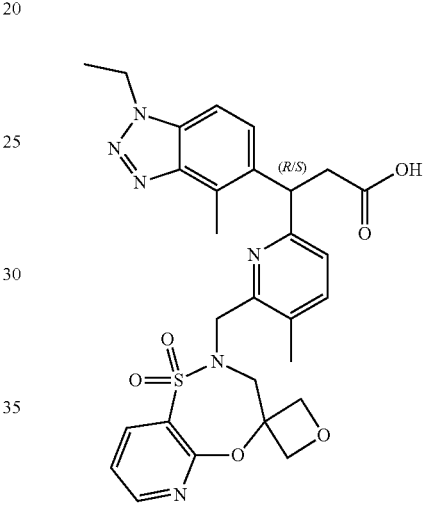

The title compound (118 mg, 85% yield) was prepared using analogous conditions as described in Example 186 where 2',3'-dihydrospiro[oxetane-3,4'-pyrido[2,3-b][1,4,5]oxathiazepine] 1',1'-dioxide (Intermediate 59) was used instead of (*S)-7a-methyl-6,7,7a,8,9,10-hexahydropyrido[2,3-f]pyrrolo[2,1-d][1,2,5]thiadiazepine 5,5-dioxide, ethyl 3-(1-ethyl-4-methyl-1H-benzo[d][1,2,3]triazol-5-yl)-3-(6-(hydroxymethyl)-5-methylpyridin-2-yl)propanoate (Intermediate 108) was used instead of ethyl (*S)-3-(3-(hydroxymethyl)-4-methylphenyl)-3-(8-methyl-3-(trifluoromethyl)-[1,2,4]triazolo[4,3-a]pyridin-7-yl)propanoate and the hydrolysis reaction was run overnight. MS (ESI): mass calcd. for $C_{28}H_{30}N_6O_6S$, 578.2; m/z found, 579.3 $[M+H]^+$. $^1$H NMR (500 MHz, CDCl$_3$) δ 8.63-8.51 (m, 1H), 8.31-8.17 (m, 1H), 7.70-7.43 (m, 1H), 7.41-7.28 (m, 2H), 7.20 (d, J=8.7 Hz, 1H), 6.86 (d, J=7.8 Hz, 1H), 5.17-5.03 (m, 1H), 5.03-4.88 (m, 2H), 4.88-4.76 (m, 2H), 4.76-4.61 (m, 3H), 4.41-4.34 (m, 1H), 4.18-3.91 (m, 2H), 3.37-3.26 (m, 1H), 2.97-2.77 (m, 4H), 2.42 (s, 3H), 1.64-1.55 (m, 3H).

Example 241: (*S)-3-(6-((1',1'-Dioxidospiro[oxetane-3,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic Acid

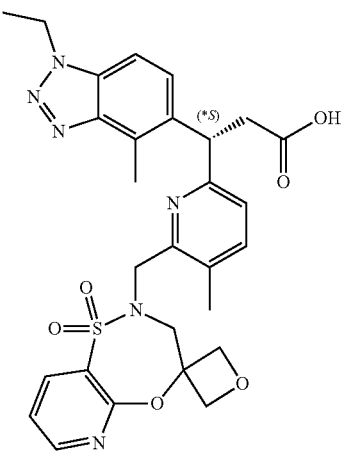 [SMILES: CCn1nnc2c(C)c([C@H](CC(=O)O)c3ccc(C)c(CN4CC5(COC5)Oc5ncccc5S4(=O)=O)n3)ccc21]

The mixture of (R S)-3-(6-((1',1'-dioxidospiro[oxetane-3,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic acid isomers (Example 240) was separated by chiral SFC (Chiralpak AD-H, mobile phase: 70% $CO_2$, 30% MeOH) to afford two enantiomers. The first eluting isomer (42 mg) was designated (*S): MS (ESI): mass calcd. for $C_{28}H_{30}N_6O_6S$, 578.2; m/z found, 579.3 $[M+H]^+$. $^1$H NMR (500 MHz, CDCl$_3$) δ 8.61-8.56 (m, 1H), 8.26 (d, J=7.6 Hz, 1H), 7.40-7.33 (m, 2H), 7.30-7.27 (m, 1H), 7.25-7.18 (m, 1H), 6.94-6.85 (m, 1H), 5.15-5.00 (m, 4H), 4.70-4.59 (m, 3H), 4.39-4.31 (m, 1H), 4.10-4.00 (m, 1H), 4.00-3.90 (m, 1H), 3.36-3.23 (m, 1H), 2.88-2.76 (m, 4H), 2.40 (s, 3H), 1.63-1.55 (m, 3H).

Example 242: (*R)-3-(6-((1',1'-Dioxidospiro[oxetane-3,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic Acid

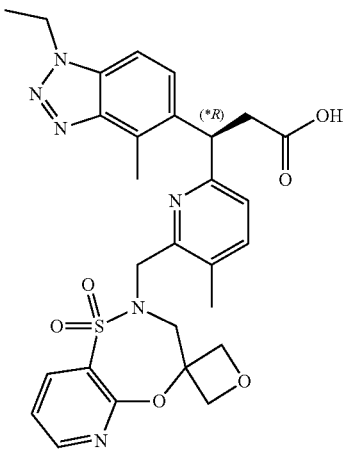

The second eluting isomer (44 mg) from the separation of isomers by chiral SFC described in Example 241 was designated (*R): MS (ESI): mass calcd. for $C_{28}H_{30}N_6O_6S$, 578.2; m/z found, 579.3 $[M+H]^+$. $^1$H NMR (500 MHz, CDCl$_3$) δ 8.61-8.54 (m, 1H), 8.29-8.23 (m, 1H), 7.41-7.33 (m, 2H), 7.30-7.27 (m, 1H), 7.23-7.16 (m, 1H), 6.92-6.84 (m, 1H), 5.13-5.01 (m, 1H), 4.94-4.74 (m, 4H), 4.69-4.60 (m, 3H), 4.36-4.26 (m, 1H), 4.06-3.90 (m, 2H), 3.33-3.25 (m, 1H), 2.85-2.76 (m, 4H), 2.42-2.38 (m, 3H), 1.62-1.55 (m, 3H).

Example 243: (R/S)-3-(6-((1',1'-Dioxidospiro[cyclopropane-1,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic Acid

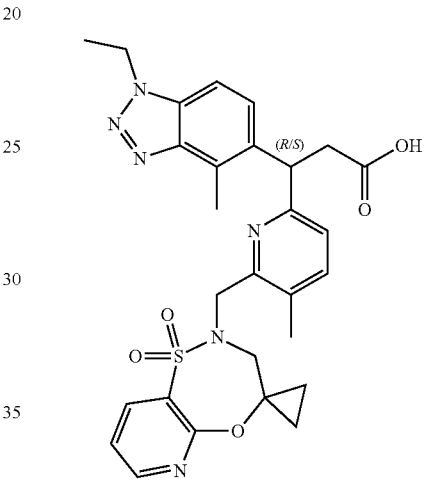

The title compound (63 mg, 33% yield) was prepared using analogous conditions as described in Example 186 where 2',3'-dihydrospiro[cyclopropane-1,4'-pyrido[2,3-b][1,4,5]oxathiazepine] 1',1'-dioxide (Intermediate 5) was used instead of (*S)-7a-methyl-6,7,7a,8,9,10-hexahydropyrido[2,3-f]pyrrolo[2,1-d][1,2,5]thiadiazepine 5,5-dioxide, ethyl 3-(1-ethyl-4-methyl-1H-benzo[d][1,2,3]triazol-5-yl)-3-(6-(hydroxymethyl)-5-methylpyridin-2-yl)propanoate (Intermediate 108) was used instead of ethyl (*S)-3-(3-(hydroxymethyl)-4-methylphenyl)-3-(8-methyl-3-(trifluoromethyl)-[1,2,4]triazolo[4,3-a]pyridin-7-yl)propanoateate and the hydrolysis reaction was run overnight. MS (ESI): mass calcd. for $C_{28}H_{30}N_6O_5S$, 562.2; m/z found, 563.2 $[M+H]^+$.

Example 244: (*S)-3-(6-((1',1'-Dioxidospiro[cyclopropane-1,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic Acid

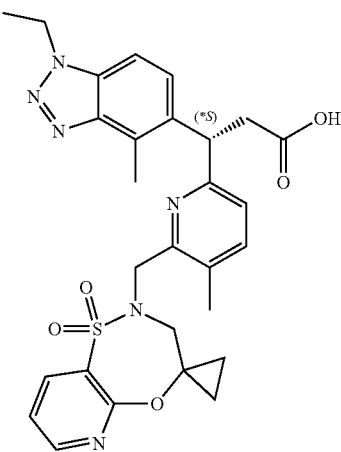 [SMILES: CCn1nnc2c(C)c([C@H](CC(=O)O)c3ccc(C)c(CN4CC5(CC5)Oc5ncccc5S4(=O)=O)n3)ccc21]

The mixture of (R/S)-3-(6-((1',1'-dioxidospiro[cyclopropane-1,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic acid isomers (Example 243) was separated by chiral SFC (Chiralpak AD-H, mobile phase: 80% $CO_2$, 20% EtOH) to afford two enantiomers. The first eluting isomer (29 mg) was designated (*S): $^1$H NMR (500 MHz, $CDCl_3$) δ 8.47 (dd, J=4.9, 2.0 Hz, 1H), 8.31 (dd, J=7.6, 2.0 Hz, 1H), 7.38 (d, J=7.8 Hz, 1H), 7.32 (dd, J=7.6, 4.9 Hz, 1H), 7.26-7.21 (m, 2H), 7.01 (d, J=7.9 Hz, 1H), 4.99 (t, J=7.4 Hz, 1H), 4.62 (q, J=7.3 Hz, 2H), 4.51-4.37 (m, 2H), 3.73-3.53 (m, 2H), 3.30-3.23 (m, 1H), 2.91-2.83 (m, 4H), 2.62-2.56 (m, 2H), 2.41-2.39 (m, 3H), 1.24-1.11 (m, 2H), 0.91 (t, J=7.3 Hz, 3H).

Example 245: (*R)-3-(6-((1',1'-Dioxidospiro[cyclopropane-1,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)propanoic Acid

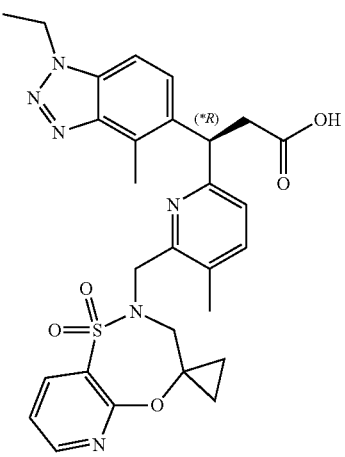 [SMILES: CCn1nnc2c(C)c([C@@H](CC(=O)O)c3ccc(C)c(CN4CC5(CC5)Oc5ncccc5S4(=O)=O)n3)ccc21]

The second eluting isomer (28 mg) from the separation of isomers by chiral SFC described in Example 244 was designated (*R): $^1$H NMR (500 MHz, $CDCl_3$) δ 8.47 (dd, J=4.9, 2.0 Hz, 1H), 8.31 (dd, J=7.6, 1.9 Hz, 1H), 7.37 (d, J=7.9 Hz, 1H), 7.32 (dd, J=7.6, 4.9 Hz, 1H), 7.30-7.21 (m, 2H), 7.02 (d, J=7.9 Hz, 1H), 4.99 (t, J=7.5 Hz, 1H), 4.62 (q, J=7.3 Hz, 2H), 4.50-4.36 (m, 2H), 3.71-3.52 (m, 2H), 3.28-3.20 (m, 1H), 2.90-2.82 (m, 4H), 2.62-2.55 (m, 2H), 2.40 (s, 3H), 1.23-1.11 (m, 2H), 0.91 (t, J=7.2 Hz, 3H).

Example 246: 3-(7-(Difluoromethoxy)-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid and its Trifluoroacetic Acid Salt

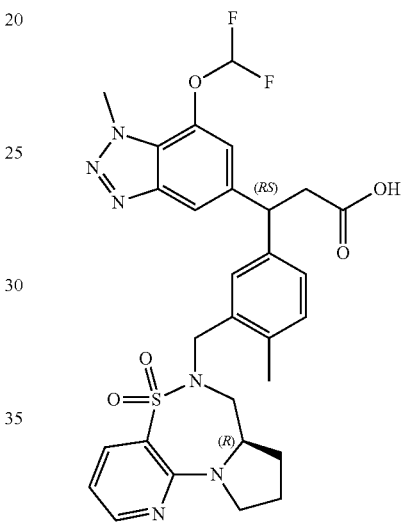

To a solution of methyl 3-(7-(difluoromethoxy)-1-methyl-1H-benzo[d][1,2,3]triazol-5-yl)-3-(3-(hydroxymethyl)-4-methylphenyl)propanoate (Example 1, Step B, 112 mg, 0.276 mmol) in THF (4.5 mL) was added sequentially (R)-6,7,7a,8,9,10-hexahydropyrido[2,3-f]pyrrolo[2,1-d][1,2,5]thiadiazepine 5,5-dioxide (Intermediate 4, 99.2 mg, 0.414 mmol), triphenylphosphine polystyrene resin (184 mg, 3 mmol/g, 0.552 mmol), and DIAD (0.108 mL, 0.553 mmol). The reaction mixture was stirred at room temperature under air for 18 hours. A second portion of triphenylphosphine polystyrene resin and DIAD (same amounts as above) was added and the reaction mixture was stirred at room temperature for 3 hours. A third portion of triphenylphosphine polystyrene resin and DIAD (same amounts as above) was added and the reaction mixture was stirred at room temperature for 2.5 hours. The reaction mixture was filtered and the filtrate was concentrated under reduced pressure. The residue was dissolved in a mixture of MeOH (4 mL) and aqueous NaOH solution (1.0 M, 0.83 mL, 0.83 mmol). The reaction mixture was then heated in an oil bath at 90° C. for 80 minutes. The pH of the reaction mixture was adjusted to pH 3 with 1 N aqueous HCl and then the reaction mixture was concentrated. The residue was purified by preparative HPLC (10-90% $CH_3CN$—$H_2O$, 0.1% TFA) to afford the title compound and its trifluoroacetic acid salt (72 mg). MS (ESI): mass calcd. for $C_{29}H_{30}F_2N_6O_5S$, 612.2; m/z found, 613.3 $[M+H]^+$. $^1$H NMR (400 MHz, $CDCl_3$) δ

8.42-8.27 (m, 1H), 8.24 (td, J=5.8, 2.2, Hz, 1H), 7.67 (s, 1H), 7.16-6.90 (m, 5H), 6.88-6.46 (m, 1H), 5.04-4.85 (m, 1H), 4.64-4.41 (m, 6H), 3.83-3.64 (m, 2H), 3.44 (ddd, J=15.9, 12.6, 3.8 Hz, 1H), 3.14-2.93 (m, 3H), 2.28 (d, J=9.1 Hz, 3H), 2.18-1.96 (m, 2H), 1.94-1.58 (m, 2H).

Example 247: (*S)-3-(7-(Difluoromethoxy)-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

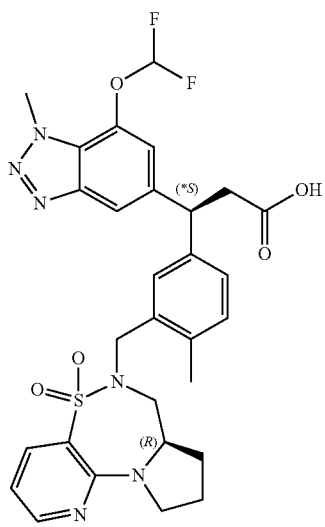

The mixture of 3-(7-(difluoromethoxy)-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid trifluoroacetate isomers (Example 246, 67 mg) were separated by chiral SFC (stationary phase: Chiralpak AD-H 5 µm, 250×20 mm, mobile phase: 70% CO$_2$, 30% EtOH) to afford two diastereoisomers. The first eluting isomer (20 mg, 36%) was designated (*S): MS (ESI): mass calcd. for C$_{29}$H$_{30}$F$_2$N$_6$O$_5$S, 612.2; m/z found, 613.3 [M+H]$^+$. $^1$H NMR (400 MHz, MeOH-d$_4$) δ 8.27 (dd, J=4.8, 1.8 Hz, 1H), 8.04 (dd, J=7.6, 2.0 Hz, 1H), 7.74 (s, 1H), 7.27-6.84 (m, 6H), 4.64 (t, J=7.8 Hz, 1H), 4.50-4.41 (m, 4H), 4.39-4.31 (m, 1H), 4.25-4.17 (m, 1H), 3.61 (dt, J=10.9, 5.6 Hz, 1H), 3.54-3.49 (m, 1H), 3.23-3.03 (m, 3H), 2.92 (t, J=12.9 Hz, 1H), 2.27 (s, 3H), 2.04-1.90 (m, 1H), 1.81-1.70 (m, 1H), 1.69-1.55 (m, 1H), 1.52-1.43 (m, 1H).

Example 248: (*R)-3-(7-(Difluoromethoxy)-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

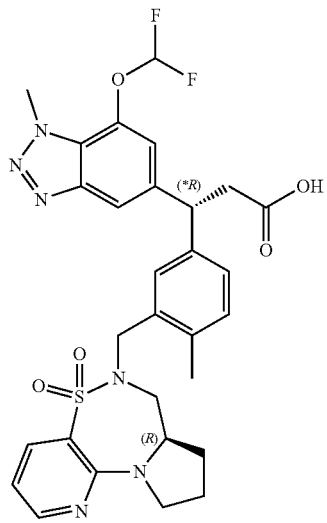

The second eluting isomer (22 mg, 39%) from the separation by chiral SFC described in Example 247 was designated (*R): MS (ESI): mass calcd. for C$_{29}$H$_{30}$F$_2$N$_6$O$_5$S, 612.2; m/z found, 613.3 [M+H]$^+$. $^1$H NMR (400 MHz, MeOH-d$_4$) δ 8.27 (dd, J=4.8, 1.8 Hz, 1H), 8.05 (dd, J=7.6, 2.0 Hz, 1H), 7.72 (s, 1H), 7.26-6.83 (m, 6H), 4.65 (t, J=8.1 Hz, 1H), 4.48-4.40 (m, 4H), 4.39-4.33 (m, 1H), 4.26-4.18 (m, 1H), 3.68-3.58 (m, 1H), 3.57-3.50 (m, 1H), 3.17 (dd, J=13.6, 3.5 Hz, 1H), 3.11 (d, J=8.1 Hz, 2H), 2.99-2.89 (m, 1H), 2.27 (s, 3H), 2.01-1.88 (m, 1H), 1.84-1.73 (m, 1H), 1.72-1.56 (m, 1H), 1.50-1.39 (m, 1H).

Example 249: 3-(7-(Difluoromethoxy)-1-methyl-1H-benzo[d][1,2,3]triazol-5-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic Acid and its Trifluoroacetic Acid Salt

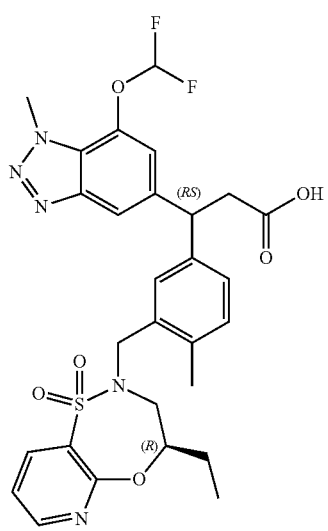

(R)-4-ethyl-3,4-dihydro-2H-pyrido[2,3-b][1,4,5]oxathiazepine 1,1-dioxide (Intermediate 91, 75.3 mg, 0.330 mmol) was dissolved in DMF (0.75 mL). The solution was cooled in an ice bath and NaH (60% dispersion in mineral oil, 39.6 mg, 0.990 mmol) was added. The mixture was stirred in the ice bath for 10 minutes. A solution of methyl 3-(3-(chloromethyl)-4-methylphenyl)-3-(7-(difluoromethoxy)-1-methyl-1H-benzo[d][1,2,3]triazol-5-yl)propanoate in DMF (Example 1, Step C, 1.0 mL, 0.30 M, 0.30 mmol) was added. The reaction mixture was stirred in the ice bath for 40 minutes. An aqueous solution of NaOH (0.60 mL, 1.0 M, 0.60 mmol) was added and the mixture was heated in an oil bath at 60° C. for 30 minutes. The reaction mixture was filtered, the filtrate was concentrated under reduced pressure and purified by preparative HPLC (10-90% $CH_3CN$—$H_2O$, 0.1% TFA) to afford the title compound and its trifluoroacetic acid salt (94.6 mg) as a white powder. MS (ESI): mass calcd. for $C_{28}H_{29}F_2N_5O_6S$, 601.2; m/z found, 602.2 $[M+H]^+$. $^1$H NMR (400 MHz, $CDCl_3$) δ 8.48 (dd, J=4.6, 2.0 Hz, 1H), 8.25 (dd, J=7.8, 1.8 Hz, 1H), 7.74 (d, J=1.0 Hz, 1H), 7.30-7.24 (m, 1H), 7.18-7.09 (m, 3H), 6.99 (s, 1H), 6.69 (t, J=72.8 Hz, 1H), 4.68-4.61 (m, 1H), 4.48-4.37 (m, 5H), 4.05 (dd, J=14.4, 1.3 Hz, 1H), 3.62-3.52 (m, 1H), 3.18-3.06 (m, 3H), 2.31 (s, 3H), 1.75-1.61 (m, 1H), 1.55-1.40 (m, 1H), 0.99 (t, J=7.3 Hz, 3H).

Example 250: (*S)-3-(7-(Difluoromethoxy)-1-methyl-1H-benzo[d][1,2,3]triazol-5-yl)-3-(3-(((R)-4-ethyl-1,1-dioxido-3,4-dihydro-2H-pyrido[2,3-b][1,4,5]oxathiazepin-2-yl)methyl)-4-methylphenyl) propanoic Acid

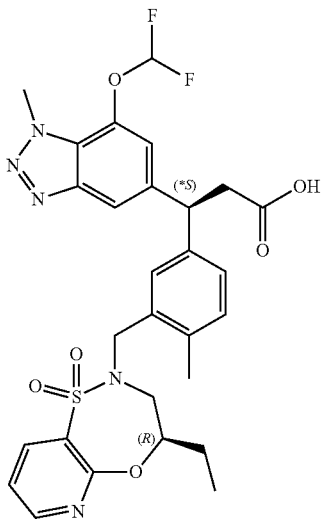

The mixture of 3-(7-(difluoromethoxy)-1-methyl-1H-benzo[d][1,2,3]triazol-5-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic acid and its trifluoroacetic acid salt (Example 249, 92 mg) were separated by chiral SFC (stationary phase: Chiralpak AD-H 5 μm 250×20 mm, mobile phase: 80% $CO_2$, 20% MeOH) to afford two diastereoisomers. The first eluting isomer (36 mg, 44%) was designated (*S): MS (ESI): mass calcd. for $C_{28}H_{29}F_2N_5O_6S$, 601.2; m/z found, 602.2 $[M+H]^+$. $^1$H NMR (400 MHz, MeOH-$d_4$) δ 8.46 (br s, 1H), 8.29 (dd, J=7.8, 1.8 Hz, 1H), 7.71 (s, 1H), 7.41 (dd, J=7.6, 5.1, Hz, 1H), 7.30-7.24 (m, 1H), 7.24-6.86 (m, 4H), 4.64 (t, J=7.6 Hz, 1H), 4.58 (d, J=13.6 Hz, 1H), 4.41 (s, 3H), 4.32-4.22 (m, 1H), 3.94 (d, J=13.6 Hz, 1H), 3.68 (dd, J=15.4, 10.4 Hz, 1H), 3.16-3.06 (m, 2H), 2.98-2.89 (m, 1H), 2.33 (s, 3H), 1.62-1.49 (m, 1H), 1.41-1.24 (m, 1H), 0.90 (t, J=7.3 Hz, 3H).

Example 251: (*R)-3-(7-(Difluoromethoxy)-1-methyl-1H-benzo[d][1,2,3]triazol-5-yl)-3-(3-(((R)-4-ethyl-1,1-dioxido-3,4-dihydro-2H-pyrido[2,3-b][1,4,5]oxathiazepin-2-yl)methyl)-4-methylphenyl) propanoic Acid

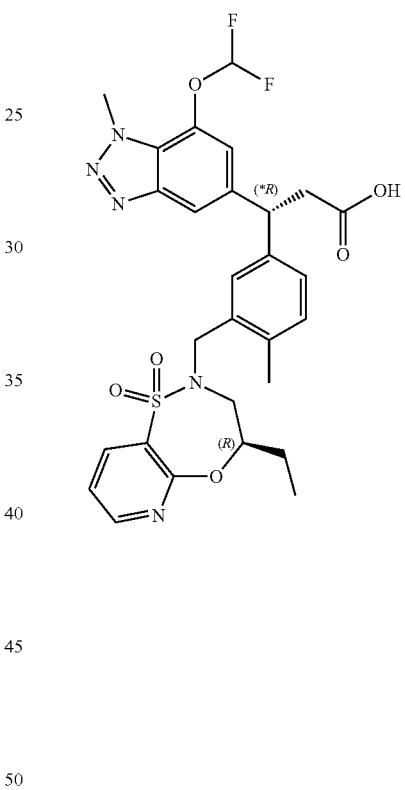

The second eluting isomer (34 mg, 42%) from the mixture that was separated by chiral SFC described in Example 250 was designated (*R): MS (ESI): mass calcd. for $C_{28}H_{29}F_2N_5O_6S$, 601.2; m/z found, 602.3 $[M+H]^+$. $^1$H NMR (400 MHz, MeOH-$d_4$) δ 8.46 (br s, 1H), 8.29 (dd, J=7.6, 2.0 Hz, 1H), 7.74 (s, 1H), 7.41 (dd, J=7.6, 5.1, Hz, 1H), 7.28-7.24 (m, 1H), 7.24-6.85 (m, 4H), 4.64 (br t, J=7.6 Hz, 1H), 4.56 (d, J=14.2 Hz, 1H), 4.42 (s, 3H), 4.28-4.19 (m, 1H), 3.94 (d, J=14.2 Hz, 1H), 3.67 (dd, J=15.4, 10.4 Hz, 1H), 3.20-3.00 (m, 2H), 2.93 (d, J=14.2 Hz, 1H), 2.32 (s, 3H), 1.60-1.48 (m, 1H), 1.36-1.23 (m, 1H), 0.89 (t, J=7.3 Hz, 3H).

Example 252: 3-(3-((1',1'-Dioxidospiro[oxetane-3, 4'-pyrido[2,3-b][1,4,5]oxathiazepin]-2'(3'H)-yl)methyl)-4-methylphenyl)-3-(1-ethyl-4-methyl-1H-benzo[d][1,2,3]triazol-5-yl)propanoic Acid

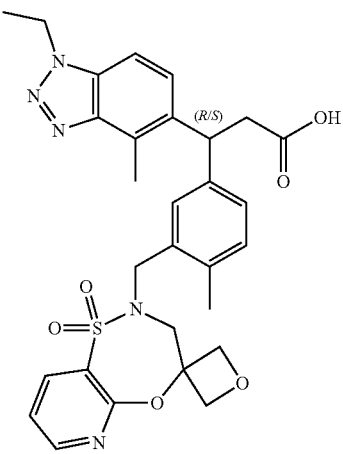 [SMILES: CCn1nnc2c(C)c(C(CC(=O)O)c3ccc(C)c(CN4CC5(COC5)Oc5ncccc5S4(=O)=O)c3)ccc21]

DMF (1.1 mL) was added to mixture of 2',3'-dihydrospiro[oxetane-3,4'-pyrido[2,3-b][1,4,5]oxathiazepine] 1',1'-dioxide (Intermediate 59, 71 mg, 0.29 mmol) and sodium hydride (60% dispersion in mineral oil, 13 mg, 0.33 mmol) which had been cooled to 0° C. After 10 minutes, a solution of ethyl 3-(3-(chloromethyl)-4-methylphenyl)-3-(1-ethyl-4-methyl-1H-benzo[d][1,2,3]triazol-5-yl)propanoate (Intermediate 31, 90 mg, 0.23 mmol) in DMF (0.45 mL) was added and the mixture was allowed to warm to room temperature. After 2 hours, additional sodium hydride (15 mg) was added and the mixture allowed to stir overnight. The mixture was filtered and the filtrate was purified by reverse phase HPLC (acetonitrile-water containing 0.05% NH$_4$OH) to provide the title compound (14 mg, 11%). MS (ESI): mass calcd. for C$_{29}$H$_{31}$N$_5$O$_6$S, 577.2; m/z found, 578.2 [M+H]$^+$. $^1$H NMR (400 MHz, DMSO-d$_6$) δ 8.63-8.58 (m, 1H), 8.22 (dd, J=7.6, 1.9 Hz, 1H), 7.54-7.47 (m, 2H), 7.38 (d, J=8.7 Hz, 1H), 7.17 (d, J=1.8 Hz, 1H), 7.10-7.02 (m, 2H), 4.90-4.80 (m, 1H), 4.70-4.60 (m, 2H), 4.46-4.35 (m, 4H), 4.25 (s, 2H), 3.79 (s, 2H), 2.71 (s, 3H), 2.58-2.54 (m, 2H), 2.17 (s, 3H), 1.49-1.42 (m, 3H).

Example 253: 3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(3-(trifluoromethyl)-[1,2,4]triazolo[4,3-a]pyridin-7-yl)propanoic Acid

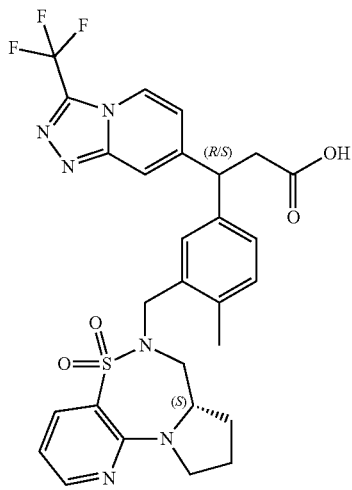

Step A: Ethyl (E)-3-(3-(trifluoromethyl)-[1,2,4]triazolo[4,3-a]pyridin-7-yl)acrylate. A mixture containing 7-bromo-3-(trifluoromethyl)-[1,2,4]triazolo[4,3-a]pyridine (Intermediate 110, 441 mg, 1.66 mmol), sodium acetate (372 mg, 4.54 mmol), Herrmann's catalyst (172 mg, 0.183 mmol), ethyl acrylate (0.8 mL, 7.4 mmol), and DMA (7 mL) was placed in a sealed tube and heated at 150° C. in a microwave reactor. After 1 hour, the mixture was cooled to room temperature. Ethyl acetate was added and the mixture was filtered through diatomaceous earth. Hexanes were added and the organic solution was washed sequentially with water and brine. The organic layer was dried over MgSO$_4$, filtered, and combined with the organic layer from a separate, small-scale reaction starting with 55 mg of 7-bromo-3-(trifluoromethyl)-[1,2,4]triazolo[4,3-a]pyridine. The combined organic layers were absorbed onto diatomaceous earth for purification by flash column chromatography (hexanes-ethyl acetate) to afford the title compound (407 mg, 77%). MS (ESI): mass calcd. for C$_{12}$H$_{10}$F$_3$N$_3$O$_2$, 285.1; m/z found, 286.1 [M+H]$^+$. $^1$H NMR (400 MHz, CDCl$_3$) δ 8.22 (d, J=7.3 Hz, 1H), 7.96 (s, 1H), 7.68 (d, J=16.0 Hz, 1H), 7.26-7.20 (m, 1H), 6.58 (d, J=16.0 Hz, 1H), 4.36-4.28 (m, 2H), 1.41-1.33 (m, 3H).

Step B: Ethyl 3-(3-(acetoxymethyl)-4-methylphenyl)-3-(3-(trifluoromethyl)-[1,2,4]triazolo[4,3-a]pyridin-7-yl)propanoate. Triethylamine (0.35 mL, 2.5 mmol) and [Rh(COD)Cl]$_2$ (55 mg, 0.11 mmol) were added sequentially to a slurry of ethyl (E)-3-(3-(trifluoromethyl)-[1,2,4]triazolo[4,3-a]pyridin-7-yl)acrylate (283 mg, 0.992 mmol) and 2-methyl-5-(4,4,5,5-tetramethyl-1,3,2-dioxaborolan-2-yl)benzyl acetate (Intermediate 20, 583 mg, 2.01 mmol) in 1,4-dioxane (3 mL) and water (1.5 mL). The reaction vessel was heated to 95° C. After 45 minutes, ethyl acetate, hexanes, and half-saturated aqueous sodium chloride solution were added. The biphasic mixture was separated. The organic layer was dried over Na$_2$SO$_4$, filtered, and combined with the organic layer from a separate, small-scale reaction starting with 100 mg of ethyl (E)-3-(3-(trifluoromethyl)-[1,2,4]triazolo[4,3-a]pyridin-7-yl)acrylate. Diatomaceous earth was added and the slurry was concentrated to dryness under reduced pressure. The solids were purified by flash column chromatography (hexanes-ethyl acetate) to afford the title compound (408 mg) which was used without further purification. MS (ESI): mass calcd. for C$_{22}$H$_{22}$F$_3$N$_3$O$_4$, 449.2; m/z found, 450.1 [M+H]$^+$.

Step C: Ethyl 3-(3-(hydroxymethyl)-4-methylphenyl)-3-(3-(trifluoromethyl)-[1,2,4]triazolo[4,3-a]pyridin-7-yl)propanoate. Potassium carbonate (304 mg, 2.2 mmol) was added to a solution of ethyl 3-(3-(acetoxymethyl)-4-methylphenyl)-3-(3-(trifluoromethyl)-[1,2,4]triazolo[4,3-a]pyridin-7-yl)propanoate (390 mg, 0.868 mmol) in ethanol (7 mL) at room temperature. After 18 hours, the mixture was partioned between ethyl acetate, hexanes, and water. The layers were separated and the organic layer was washed with brine, dried over Na$_2$SO$_4$, filtered, and then absorbed onto diatomaceous earth. Purification by flash column chromatography (hexanes-ethyl acetate) provided the title compound (219 mg, 62%) as a yellow foam. MS (ESI): mass calcd. for C$_{20}$H$_{20}$F$_3$N$_3$O$_3$, 407.1; m/z found, 408.1 [M+H]$^+$.

Step D: Ethyl 3-(3-(((S)-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(trifluoromethyl)-[1,2,4]triazolo[4,3-a]pyridin-7-yl)propanoate. Diisopropyl azodicarboxylate (0.0725 mL, 0.363 mmol) was added to a mixture of ethyl 3-(3-(hydroxymethyl)-4-methylphenyl)-3-(3-(trifluoromethyl)-[1,2,4]triazolo[4,3-a]pyridin-7-yl)propanoate (100 mg, 0.245 mmol), (S)-6,7,7a,8,9,10-hexahydropyrido[2,3-f]pyrrolo[2,1-d][1,2,5]thiadiazepine 5,5-dioxide (Intermediate 75, 89 mg, 0.37 mmol), and triphenyl phosphine (123 mg, 0.368 mmol) in THF (1 mL) at room temperature. After 2 hours, additional diisopropyl azodicarboxylate (0.0725 mL) and triphenyl phosphine (100 mg) were added. After 20 minutes, the mixture was filtered through diatomaceous earth and then the filtrate was absorbed onto diatomaceous earth. Purification by flash column chromatography (hexanes-ethyl acetate) provided the title compound (137 mg, 89%). MS (ESI): mass calcd. for $C_{30}H_{31}F_3N_6O_4S$, 628.2; m/z found, 629.2 [M+H]$^+$.

Step E: 3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(3-(trifluoromethyl)-[1,2,4]triazolo[4,3-a]pyridin-7-yl)propanoic acid. A mixture containing ethyl 3-(3-(((S)-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(trifluoromethyl)-[1,2,4]triazolo[4,3-a]pyridin-7-yl)propanoate (137 mg, 0.218 mmol), 1 M aqueous NaOH solution (0.44 mL, 0.44 mmol), and THF (1 mL) was stirred at room temperature overnight. 1 M Aqueous HCl solution was added until the pH of the reaction mixture was 3-4. Ethyl acetate was added and the resulting biphasic mixture was separated. The organic layer was washed with brine, dried over $Na_2SO_4$, filtered, concentrated to dryness under reduced pressure, and purified by reverse phase HPLC (acetonitrile-water containing 0.05% $NH_4OH$). The pure fractions resulting from the preparative basic HPLC were collected, concentrated under reduced pressure, adjusted to pH 3-4 with 1 M aqueous HCl solution, and then extracted with dichloromethane. These extractions resulted in several organic solvent fractions which were combined, dried over $Na_2SO_4$, filtered, and concentrated to dryness under reduced pressure to provide the title compound (47 mg, 36% yield). MS (ESI): mass calcd. for $C_{28}H_{27}F_3N_6O_4S$, 600.2; m/z found, 601.1 [M+H]$^+$. $^1$H NMR (400 MHz, DMSO-d$_6$) δ 12.30 (s, 1H), 8.51 (d, J=7.1 Hz, 1H), 8.38-8.32 (m, 1H), 8.05-7.97 (m, 2H), 7.35-7.24 (m, 2H), 7.19-7.13 (m, 2H), 6.97-6.87 (m, 1H), 4.61-4.52 (m, 1H), 4.37-4.13 (m, 3H), 3.68-3.56 (m, 1H), 3.56-3.45 (m, 1H), 3.27-2.88 (m, 4H), 2.23 (s, 3H), 2.02-1.82 (m, 1H), 1.76-1.55 (m, 2H), 1.42 (s, 1H).

Example 254: (*S)-3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(3-(trifluoromethyl)-[1,2,4]triazolo[4,3-a]pyridin-7-yl)propanoic Acid

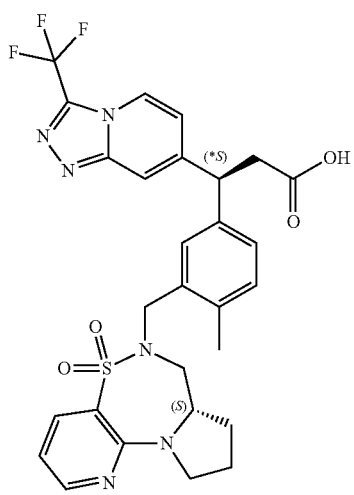

The mixture of 3-(3-(((S)-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(trifluoromethyl)-[1,2,4]triazolo[4,3-a]pyridin-7-yl)propanoic acid isomers (Example 253, 47 mg) was separated by chiral SFC (stationary phase: Chiralpak AD-H 5 μm 250×20 mm, mobile phase: 60% $CO_2$, 40% iPrOH) to afford two diastereoisomers. The first eluting isomer (18 mg) was designated (*S). MS: mass calcd. for $C_{28}H_{27}F_3N_6O_4S$, 600.2; m/z found, 600.2 [M]$^+$. $^1$H NMR (400 MHz, DMSO-d$_6$) δ 8.50 (d, J=7.1 Hz, 1H), 8.37-8.32 (m, 1H), 8.01 (dd, J=7.7, 1.8 Hz, 1H), 7.98 (s, 1H), 7.33-7.25 (m, 2H), 7.18-7.12 (m, 2H), 6.92 (dd, J=7.8, 4.7 Hz, 1H), 4.61-4.53 (m, 1H), 4.35-4.15 (m, 3H), 3.69-3.57 (m, 1H), 3.57-3.47 (m, 1H), 3.21-2.92 (m, 4H), 2.22 (s, 3H), 1.94-1.81 (m, 1H), 1.78-1.66 (m, 2H), 1.41 (s, 1H).

Example 255: (*R)-3-(3-(((S)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(3-(trifluoromethyl)-[1,2,4]triazolo[4,3-a]pyridin-7-yl)propanoic Acid

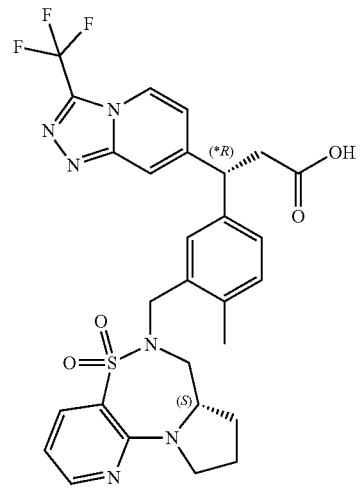

The second eluting isomer (20 mg) from the chiral separation described in Example 254 was designated (*R). MS: mass calcd. for $C_{28}H_{27}F_3N_6O_4S$, 600.2; m/z found, 600.2 [M]$^+$. $^1$H NMR (400 MHz, DMSO-d$_6$) δ 8.50 (d, J=7.2 Hz, 1H), 8.35 (dd, J=4.7, 1.8 Hz, 1H), 8.01 (dd, J=7.8, 1.8 Hz, 1H), 7.98 (s, 1H), 7.33-7.27 (m, 1H), 7.24 (d, J=1.9 Hz, 1H), 7.16-7.12 (m, 2H), 6.92 (dd, J=7.8, 4.7 Hz, 1H), 4.60-4.51 (m, 1H), 4.37-4.22 (m, 2H), 4.20-4.11 (m, 1H), 3.66-3.54 (m, 1H), 3.50 (s, 1H), 3.19-3.07 (m, 2H), 3.04-2.87 (m, 2H), 2.22 (s, 3H), 2.00-1.89 (m, 1H), 1.70-1.55 (m, 2H), 1.47-1.37 (m, 1H).

Example 256: 3-(3-(((R)-4-Ethyl-1,1-dioxido-3,4-dihydro-2H-pyrido[2,3-b][1,4,5]oxathiazepin-2-yl)methyl)-4-methylphenyl)-3-(3-(trifluoromethyl)-[1,2,4]triazolo[4,3-a]pyridin-7-yl)propanoic Acid

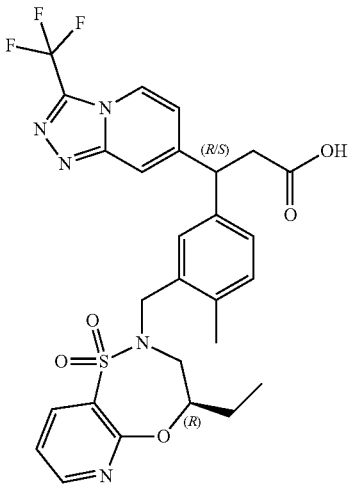

The title compound (118 mg, 77%) was prepared using analogous conditions as described in Example 253 where (R)-4-ethyl-3,4-dihydro-2H-pyrido[2,3-b][1,4,5]oxathiazepine 1,1-dioxide (Intermediate 91) was used instead of (S)-6,7,7a,8,9,10-hexahydropyrido[2,3-f]pyrrolo[2,1-d][1,2,5]thiadiazepine 5,5-dioxide in Step D. MS (ESI): mass calcd. for $C_{27}H_{26}F_3N_5O_5S$, 589.2; m/z found, 590.1 [M+H]$^+$. $^1$H NMR (400 MHz, DMSO-d$_6$) δ 12.29 (s, 1H), 8.58-8.53 (m, 1H), 8.52-8.47 (m, 1H), 8.26-8.21 (m, 1H), 7.99-7.94 (m, 1H), 7.47 (dd, J=7.6, 4.9 Hz, 1H), 7.36-7.28 (m, 2H), 7.20-7.12 (m, 2H), 4.59-4.50 (m, 1H), 4.45 (d, J=13.9 Hz, 1H), 4.39-4.23 (m, 1H), 3.93-3.83 (m, 1H), 3.73-3.61 (m, 1H), 3.25-3.12 (m, 1H), 3.12-2.98 (m, 1H), 2.89-2.73 (m, 1H), 2.26 (s, 3H), 1.60-1.31 (m, 2H), 0.96-0.88 (m, 3H).

Example 257: (*S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(3-(trifluoromethyl)-[1,2,4]triazolo[4,3-a]pyridin-7-yl)propanoic Acid

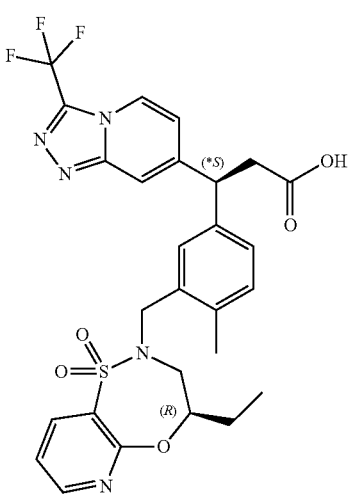

The mixture of 3-(3-(((R)-4-ethyl-1,1-dioxido-3,4-dihydro-2H-pyrido[2,3-b][1,4,5]oxathiazepin-2-yl)methyl)-4-methylphenyl)-3-(3-(trifluoromethyl)-[1,2,4]triazolo[4,3-a]pyridin-7-yl)propanoic acid isomers (Example 256) was separated by chiral SFC (stationary phase: Chiralpak AD-H 5 μm 250×20 mm, mobile phase: 60% CO$_2$, 40% MeOH) to afford two diastereoisomers. The first eluting isomer (47 mg) was designated (*S). MS: mass calcd. for $C_{27}H_{26}F_3N_5O_5S$, 589.2; m/z found, 589.2 [M]$^+$. $^1$H NMR (400 MHz, DMSO-d$_6$) δ 8.56 (dd, J=4.8, 1.9 Hz, 1H), 8.49 (d, J=7.1 Hz, 1H), 8.26-8.21 (m, 1H), 7.94 (s, 1H), 7.46 (dd, J=7.6, 4.8 Hz, 1H), 7.35-7.28 (m, 2H), 7.19-7.11 (m, 2H), 4.59-4.50 (m, 1H), 4.45 (d, J=13.9 Hz, 1H), 4.40-4.29 (m, 1H), 3.89 (d, J=13.9 Hz, 1H), 3.73-3.61 (m, 1H), 3.18-3.05 (m, 1H), 3.05-2.95 (m, 1H), 2.86 (d, J=15.3 Hz, 1H), 2.26 (s, 3H), 1.59-1.47 (m, 1H), 1.43-1.32 (m, 1H), 0.97-0.87 (m, 3H).

Example 258: (*R)-3-(3-(((R)-4-Ethyl-1,1-dioxido-3,4-dihydro-2H-pyrido[2,3-b][1,4,5]oxathiazepin-2-yl)methyl)-4-methylphenyl)-3-(3-(trifluoromethyl)-[1,2,4]triazolo[4,3-a]pyridin-7-yl)propanoic Acid

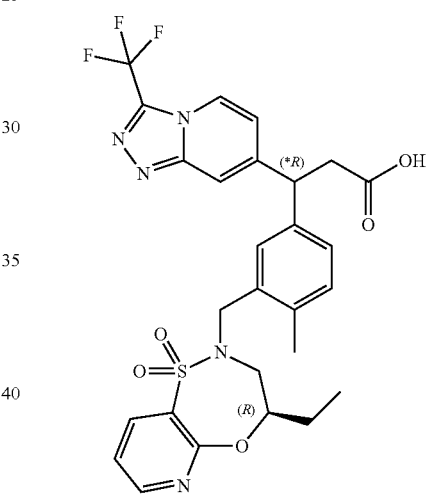

The second eluting isomer (47 mg) from the chiral separation described in Example 257 was designated (*R). MS: mass calcd. for $C_{27}H_{26}F_3N_5O_5S$, 589.2; m/z found, 589.2[M]$^+$. $^1$H NMR (400 MHz, DMSO-d$_6$) δ 8.57-8.53 (m, 1H), 8.48 (d, J=7.1 Hz, 1H), 8.25-8.21 (m, 1H), 7.93 (s, 1H), 7.49-7.43 (m, 1H), 7.34-7.29 (m, 1H), 7.27 (s, 1H), 7.18-7.10 (m, 2H), 4.58-4.49 (m, 1H), 4.45 (d, J=13.9 Hz, 1H), 4.33-4.23 (m, 1H), 3.88 (d, J=13.9 Hz, 1H), 3.72-3.60 (m, 1H), 3.17-3.05 (m, 1H), 2.93 (s, 1H), 2.78 (d, J=15.3 Hz, 1H), 2.26 (s, 3H), 1.49-1.37 (m, 1H), 1.27-1.13 (m, 1H), 0.85-0.76 (m, 3H).

Example 259: 3-(3-((1',1'-Dioxidospiro[oxetane-3, 4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic Acid

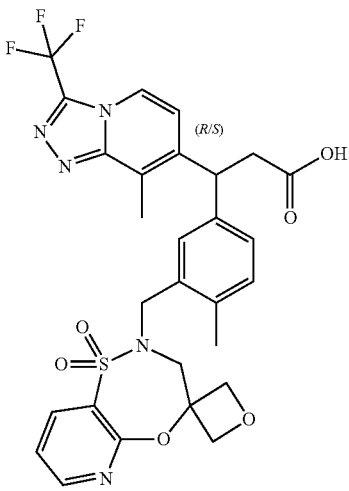 [SMILES: Cc1ccc(C(CC(=O)O)c2ccn3c(C(F)(F)F)nnc3c2C)cc1CN1CC2(COC2)Oc2ncccc2S1(=O)=O]

The title compound (86 mg) was prepared using analogous conditions as described in Example 7 using 2',3'-dihydrospiro[oxetane-3,4'-pyrido[2,3-b][1,4,5]oxathiazepine] 1',1'-dioxide (Intermediate 59) instead of 2',3'-dihydrospiro[cyclopropane-1,4'-pyrido[2,3-b][1,4,5]oxathiazepine] 1',1'-dioxide in Step A. MS (ESI): mass calcd. for $C_{28}H_{26}F_3N_5O_6S$, 617.2; m/z found, 618.1 [M+H]$^+$. $^1$H NMR (400 MHz, DMSO-d$_6$) δ 8.63-8.57 (m, 1H), 8.33 (d, J=7.1 Hz, 1H), 8.24-8.19 (m, 1H), 7.53-7.48 (m, 1H), 7.23-7.16 (m, 2H), 7.14-7.08 (m, 2H), 4.88-4.80 (m, 1H), 4.44-4.20 (m, 6H), 3.84-3.72 (m, 2H), 2.77-2.69 (m, 5H), 2.20 (s, 3H).

Example 260: (*S)-3-(3-((1',1'-Dioxidospiro[oxetane-3,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic Acid

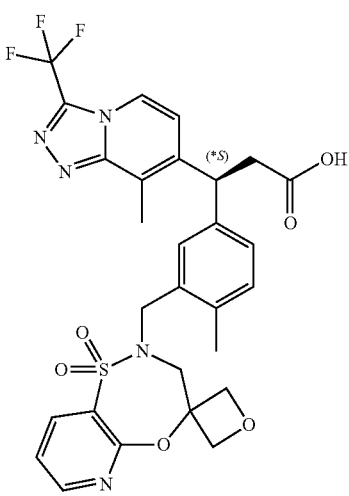 [SMILES: Cc1ccc([C@H](CC(=O)O)c2ccn3c(C(F)(F)F)nnc3c2C)cc1CN1CC2(COC2)Oc2ncccc2S1(=O)=O]

The mixture of 3-(3-((1',1'-dioxidospiro[oxetane-3,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic acid isomers (Example 259, 80 mg) was separated by chiral SFC (stationary phase: Chiralpak AD-H 5 μm 250×20 mm, Mobile phase: 65% CO$_2$, 30% iPrOH) to afford two enantiomers. The first eluting isomer (37 mg) was designated (*S). MS (ESI): mass calcd. for $C_{28}H_{26}F_3N_5O_6S$, 617.2; m/z found, 618.2 [M+H]$^+$. $^1$H NMR (400 MHz, DMSO-d$_6$) δ 8.60 (dd, J=4.9, 1.9 Hz, 1H), 8.36 (d, J=7.2 Hz, 1H), 8.24-8.20 (m, 1H), 7.53-7.48 (m, 1H), 7.28-7.21 (m, 2H), 7.18-7.13 (m, 2H), 4.88-4.79 (m, 1H), 4.45-4.22 (m, 6H), 3.85-3.71 (m, 2H), 3.02 (d, J=7.5 Hz, 2H), 2.72 (s, 3H), 2.20 (s, 3H).

Example 261: (*R)-3-(3-((1',1'-Dioxidospiro[oxetane-3,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic Acid

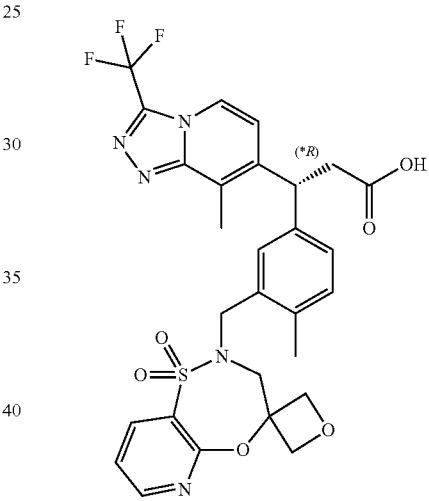

The second eluting isomer (39 mg) from the chiral separation described in Example 260 was designated (*R). MS (ESI): mass calcd. for $C_{28}H_{26}F_3N_5O_6S$, 617.2; m/z found, 618.2 [M+H]$^+$. $^1$H NMR (400 MHz, DMSO-d$_6$) δ 8.62-8.58 (m, 1H), 8.32 (d, J=7.1 Hz, 1H), 8.22 (dd, J=7.7, 1.9 Hz, 1H), 7.50 (dd, J=7.6, 4.8 Hz, 1H), 7.21-7.15 (m, 2H), 7.13-7.08 (m, 2H), 4.86-4.79 (m, 1H), 4.44-4.20 (m, 6H), 3.84-3.72 (m, 2H), 2.72-2.69 (m, 5H), 2.19 (s, 3H).

Example 262: (*S)-3-(3-(((*S)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

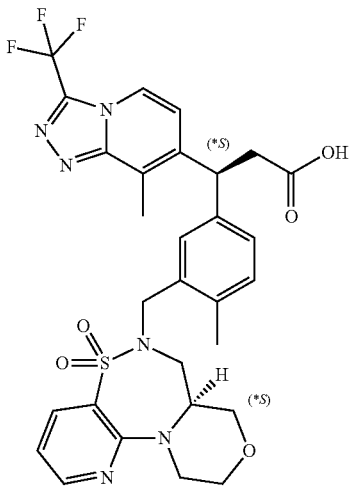 [SMILES: Cc1ccc([C@H](CC(=O)O)c2ccn3c(C(F)(F)F)nnc3c2C)cc1CN1C[C@H]2COCCN2c2ncccc2S1(=O)=O]

The title compound (49 mg) was prepared using analogous conditions as described in Example 7 using (*S)-6,7,7a,8,10,11-hexahydro-[1,4]oxazino[3,4-d]pyrido[2,3-f][1,2,5]thiadiazepine 5,5-dioxide (Intermediate 13) instead of 2',3'-dihydrospiro[cyclopropane-1,4'-pyrido[2,3-b][1,4,5]oxathiazepine] 1',1'-dioxide in Step A and the following chiral SFC separation conditions in Step B: stationary phase: Chiralpak AD-H 5 μm 250×20 mm, Mobile phase: 50% CO$_2$, 50% EtOH. The title compound was the first eluting isomer and designated (*S, *S). MS (ESI): mass calcd. for C$_{29}$H$_{29}$F$_3$N$_6$O$_5$S, 630.2; m/z found, 631.2 [M+H]$^+$. $^1$H NMR (400 MHz, DMSO-d$_6$) δ 8.41-8.33 (m, 2H), 8.05-8.00 (m, 1H), 7.29-7.24 (m, 1H), 7.24-7.11 (m, 3H), 7.01-6.95 (m, 1H), 4.84-4.74 (m, 1H), 4.36-4.21 (m, 3H), 4.21-4.11 (m, 1H), 3.84-3.75 (m, 1H), 3.66-3.55 (m, 2H), 3.53-3.39 (m, 2H), 3.31-3.24 (m, 1H), 3.24-3.13 (m, 1H), 3.09-2.96 (m, 2H), 2.70 (s, 3H), 2.15 (s, 3H).

Example 263: (*R)-3-(3-(((*S)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

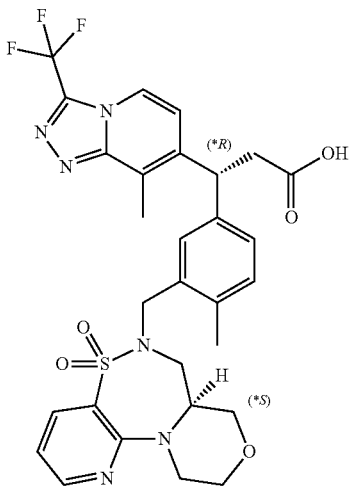 [SMILES: Cc1ccc([C@@H](CC(=O)O)c2ccn3c(C(F)(F)F)nnc3c2C)cc1CN1C[C@H]2COCCN2c2ncccc2S1(=O)=O]

The second eluting isomer (45 mg) from the chiral separation described in Example 262 was designated (*R, *S). MS (ESI): mass calcd. for C$_{29}$H$_{29}$F$_3$N$_6$O$_5$S, 630.2; m/z found, 631.2 [M+H]$^+$. $^1$H NMR (400 MHz, DMSO-d$_6$) δ 8.38-8.32 (m, 2H), 8.05-7.99 (m, 1H), 7.29-7.20 (m, 2H), 7.18-7.07 (m, 2H), 7.00-6.94 (m, 1H), 4.91-4.80 (m, 1H), 4.39-4.28 (m, 2H), 4.25-4.05 (m, 2H), 3.62-3.41 (m, 4H), 3.24-3.08 (m, 3H), 3.01-2.84 (m, 2H), 2.74 (s, 3H), 2.13 (s, 3H).

Example 264: 3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

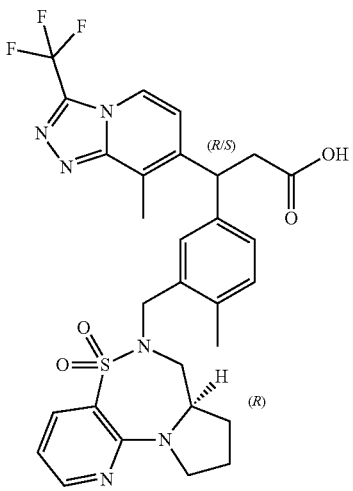

The title compound (92 mg) was prepared using analogous conditions as described in Example 7 using (R)-6,7,7a,8,9,10-hexahydropyrido[2,3-f]pyrrolo[2,1-d][1,2,5]thiadiazepine 5,5-dioxide (Intermediate 4) instead of 2',3'-dihydrospiro[cyclopropane-1,4'-pyrido[2,3-b][1,4,5]oxathiazepine] 1',1'-dioxide in Step A. MS (ESI): mass calcd. for C$_{29}$H$_{29}$F$_3$N$_6$O$_4$S, 614.2; m/z found, 615.1 [M+H]$^+$. $^1$H NMR (400 MHz, DMSO-d$_6$) δ 12.32 (s, 1H), 8.44-8.37 (m, 1H), 8.37-8.31 (m, 1H), 8.04-7.97 (m, 1H), 7.32-7.23 (m, 1H), 7.23-7.12 (m, 3H), 6.95-6.88 (m, 1H), 4.88-4.76 (m, 1H), 4.41-4.12 (m, 3H), 3.67-3.54 (m, 1H), 3.54-3.43 (m, 1H), 3.18-2.86 (m, 4H), 2.78-2.69 (m, 3H), 2.26-2.19 (m, 3H), 1.97-1.79 (m, 1H), 1.75-1.54 (m, 2H), 1.48-1.36 (m, 1H).

Example 265: 3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

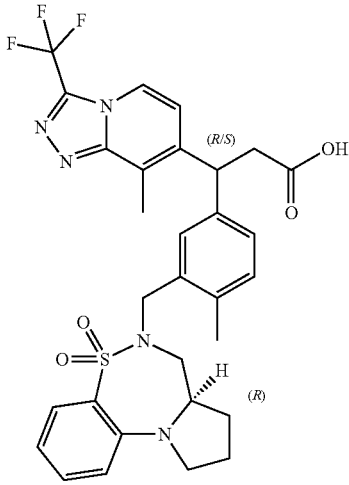

The title compound (109 mg) was prepared using analogous conditions as described in Example 7 using (R)-6,7,7a,8,9,10-hexahydrobenzo[f]pyrrolo[2,1-d][1,2,5]thiadiazepine 5,5-dioxide (Intermediate 83) instead of 2',3'-dihydrospiro[cyclopropane-1,4'-pyrido[2,3-b][1,4,5]oxathiazepine] 1',1'-dioxide in Step A. MS (ESI): mass calcd. for $C_{30}H_{30}F_3N_5O_4S$, 613.2; m/z found, 614.1 [M+H]$^+$. $^1$H NMR (400 MHz, DMSO-d$_6$) δ 12.34 (s, 1H), 8.41 (t, J=6.4 Hz, 1H), 7.77-7.66 (m, 1H), 7.51-7.41 (m, 1H), 7.30-7.24 (m, 1H), 7.22-7.12 (m, 3H), 7.07-6.93 (m, 2H), 4.89-4.76 (m, 1H), 4.27-3.88 (m, 3H), 3.27 (s, 2H), 3.17-3.04 (m, 2H), 3.04-2.80 (m, 2H), 2.78-2.70 (m, 3H), 2.28-2.19 (m, 3H), 1.98-1.52 (m, 3H), 1.36 (s, 1H).

Example 266: (*S)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

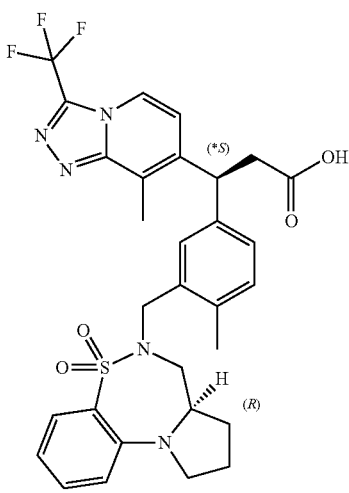

The mixture of 3-(3-(((R)-5,5-dioxido-7a,8,9,10-tetrahydrobenzo[f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid isomers (Example 265, 98 mg) was separated by chiral SFC (stationary phase: Chiralpak AD-H 5 μm 250×20 mm, mobile phase: 60% CO$_2$, 40% iPrOH) to afford two diastereoisomers. The first eluting isomer (39 mg) was designated (*S). MS (ESI): mass calcd. for $C_{30}H_{30}F_3N_5O_4S$, 613.2; m/z found, 614.1 [M+H]$^+$. $^1$H NMR (400 MHz, DMSO-d$_6$) δ 12.35 (s, 1H), 8.40 (d, J=7.1 Hz, 1H), 7.75-7.67 (m, 1H), 7.49-7.40 (m, 1H), 7.29-7.23 (m, 1H), 7.20 (d, J=2.0 Hz, 1H), 7.18-7.11 (m, 2H), 7.05-6.92 (m, 2H), 4.83 (t, J=7.8 Hz, 1H), 4.25-3.99 (m, 3H), 3.30-3.22 (m, 2H), 3.15-3.03 (m, 2H), 3.03-2.93 (m, 1H), 2.85 (s, 1H), 2.75 (s, 3H), 2.23 (s, 3H), 2.01-1.85 (m, 1H), 1.75-1.53 (m, 2H), 1.40-1.32 (m, 1H).

Example 267: (*R)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

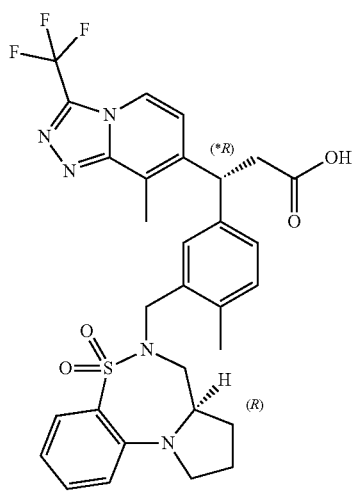

The second eluting isomer (38 mg) from the chiral separation described in Example 266 was designated (*R). MS (ESI): mass calcd. for $C_{30}H_{30}F_3N_5O_4S$, 613.2; m/z found, 614.1 [M+H]$^+$. $^1$H NMR (400 MHz, DMSO-d$_6$) δ 12.33 (s, 1H), 8.41 (d, J=7.2 Hz, 1H), 7.76-7.69 (m, 1H), 7.49-7.42 (m, 1H), 7.30-7.24 (m, 1H), 7.21-7.13 (m, 3H), 7.04 (d, J=8.4 Hz, 1H), 6.97 (t, J=7.6 Hz, 1H), 4.85-4.75 (m, 1H), 4.27-4.15 (m, 1H), 4.15-4.05 (m, 1H), 4.05-3.86 (m, 1H), 3.31-3.23 (m, 2H), 3.13-3.05 (m, 2H), 3.00-2.85 (m, 2H), 2.72 (s, 3H), 2.24 (s, 3H), 1.91-1.63 (m, 3H), 1.40-1.30 (m, 1H).

Example 268: 3-(3-((4,4-Dimethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic Acid

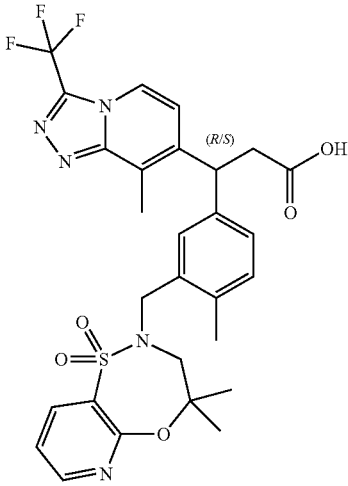 [SMILES: Cc1ccc(C(CC(=O)O)c2ccn3c(C(F)(F)F)nnc3c2C)cc1CN1CC(C)(C)Oc2ncccc2S1(=O)=O]

The title compound (118 mg) was prepared using analogous conditions as described in Example 7 using 4,4-dimethyl-3,4-dihydro-2H-pyrido[2,3-b][1,4,5]oxathiazepine 1,1-dioxide (Intermediate 82) instead of 2',3'-dihydrospiro[cyclopropane-1,4'-pyrido[2,3-b][1,4,5]oxathiazepine] 1',1'-dioxide in Step A. MS (ESI): mass calcd. for $C_{28}H_{28}F_3N_5O_5S$, 603.2; m/z found, 604.2 [M+H]$^+$. $^1$H NMR (400 MHz, DMSO-d$_6$) δ 12.32 (s, 1H), 8.52-8.46 (m, 1H), 8.43 (d, J=7.2 Hz, 1H), 8.16-8.11 (m, 1H), 7.41 (dd, J=7.6, 4.9 Hz, 1H), 7.29-7.17 (m, 3H), 7.13 (d, J=7.7 Hz, 1H), 4.90-4.81 (m, 1H), 4.49-4.34 (m, 2H), 3.68-3.40 (m, 2H), 3.20-3.08 (m, 2H), 2.75 (s, 3H), 2.16 (s, 3H), 1.14-1.05 (m, 6H).

Example 269: (*S)-3-(3-((4,4-Dimethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic Acid

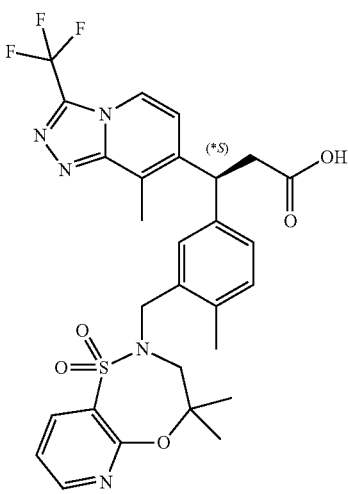 [SMILES: Cc1ccc([C@H](CC(=O)O)c2ccn3c(C(F)(F)F)nnc3c2C)cc1CN1CC(C)(C)Oc2ncccc2S1(=O)=O]

The mixture of 3-(3-((4,4-dimethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid isomers (Example 268, 100 mg) was separated by chiral SFC (stationary phase: Chiralpak AD-H 5 μm 250×20 mm, mobile phase: 60% CO$_2$, 40% EtOH) to afford two diastereoisomers. The first eluting isomer (49 mg) was designated (*S). MS (ESI): mass calcd. for $C_{28}H_{28}F_3N_5O_5S$, 603.2; m/z found, 604.4 [M+H]$^+$. $^1$H NMR (400 MHz, DMSO-d$_6$) δ 12.36 (s, 1H), 8.50-8.47 (m, 1H), 8.43 (d, J=7.2 Hz, 1H), 8.16-8.11 (m, 1H), 7.43-7.38 (m, 1H), 7.27-7.17 (m, 3H), 7.13 (d, J=7.7 Hz, 1H), 4.89-4.81 (m, 1H), 4.49-4.34 (m, 2H), 3.65-3.41 (m, 2H), 3.19-3.06 (m, 2H), 2.74 (s, 3H), 2.15 (s, 3H), 1.18-1.04 (m, 6H).

Example 270: (*R)-3-(3-((4,4-Dimethyl-1,1-dioxido-3,4-dihydro-2H-pyrido[2,3-b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic Acid

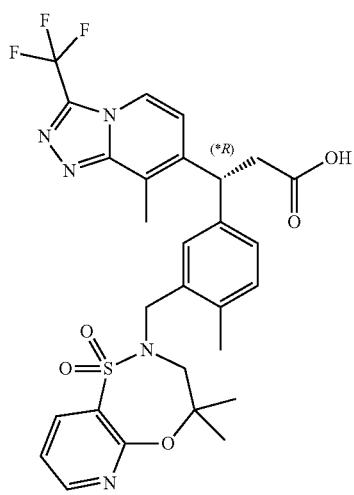 [SMILES: Cc1ccc([C@@H](CC(=O)O)c2ccn3c(C(F)(F)F)nnc3c2C)cc1CN1CC(C)(C)Oc2ncccc2S1(=O)=O]

The second eluting isomer (48 mg) from the chiral separation described in Example 269 was designated (*R). MS (ESI): mass calcd. for $C_{28}H_{28}F_3N_5O_5S$, 603.2; m/z found, 604.4 [M+H]$^+$. $^1$H NMR (400 MHz, DMSO-d$_6$) δ 12.37 (s, 1H), 8.51-8.46 (m, 1H), 8.42 (d, J=7.2 Hz, 1H), 8.15-8.10 (m, 1H), 7.41 (dd, J=7.6, 4.9 Hz, 1H), 7.28-7.17 (m, 3H), 7.13 (d, J=7.7 Hz, 1H), 4.89-4.81 (m, 1H), 4.48-4.34 (m, 2H), 3.65-3.42 (m, 2H), 3.17-3.08 (m, 2H), 2.74 (s, 3H), 2.15 (s, 3H), 1.18-1.03 (m, 6H).

Example 271: 3-(3-(((*R)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

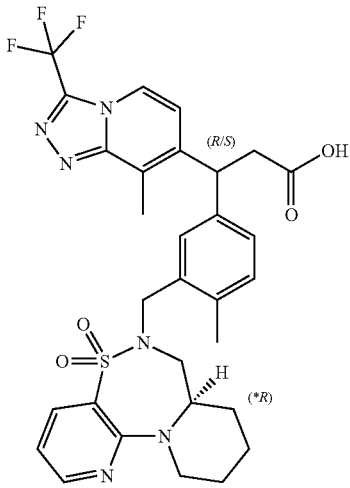

The title compound (139 mg) was prepared using analogous conditions as described in Example 7 using (*R)-7,7a,8,9,10,11-hexahydro-6H-dipyrido[2,1-d:2',3'-f][1,2,5]thiadiazepine 5,5-dioxide (Intermediate 3) instead of 2',3'-dihydrospiro[cyclopropane-1,4'-pyrido[2,3-b][1,4,5]oxathiazepine] 1',1'-dioxide in Step A. MS (ESI): mass calcd. for $C_{30}H_{31}F_3N_6O_4S$, 628.2; m/z found, 629.2 [M+H]$^+$. $^1$H NMR (500 MHz, DMSO-d$_6$) δ 12.28 (s, 1H), 8.45-8.38 (m, 1H), 8.33-8.29 (m, 1H), 8.00-7.96 (m, 1H), 7.33-7.27 (m, 1H), 7.24-7.14 (m, 3H), 6.94-6.89 (m, 1H), 4.88-4.78 (m, 1H), 4.37-4.12 (m, 3H), 4.10-4.00 (m, 1H), 3.29-3.02 (m, 5H), 2.78-2.69 (m, 3H), 2.19-2.12 (m, 3H), 1.61-1.18 (m, 6H).

Example 272: (*S)-3-(3-(((*R)-5,5-Dioxido-7,7a,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

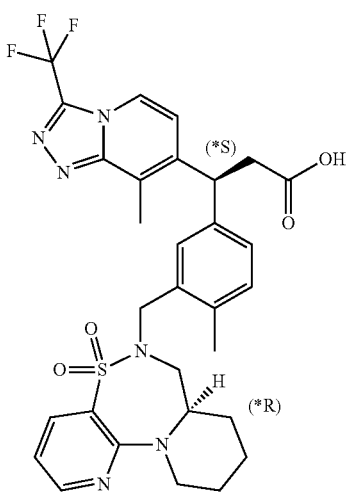 [SMILES: Cc1ccc([C@H](CC(=O)O)c2ccn3c(C(F)(F)F)nnc3c2C)cc1CN1C[C@H]2CCCCN2c2ncccc2S1(=O)=O]

The mixture of 3-(3-(((*R)-5,5-dioxido-7,7a,8,9,10,11-hexahydro-6H-dipyrido[2,1-d:2',3'-][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid isomers (Example 271, 121 mg) was separated by chiral SFC (stationary phase: IA 2×15 cm, mobile phase: 70% CO$_2$, 30% MeOH) to afford two diastereoisomers. The first eluting isomer (56 mg) was designated (*S). MS (ESI): mass calcd. for $C_{30}H_{31}F_3N_6O_4S$, 628.2; m/z found, 629.2 [M+H]$^+$. $^1$H NMR (400 MHz, DMSO-d$_6$) δ 12.40 (s, 1H), 8.41 (d, J=7.5 Hz, 1H), 8.35-8.29 (m, 1H), 8.02-7.95 (m, 1H), 7.34-7.13 (m, 4H), 6.96-6.89 (m, 1H), 4.92-4.80 (m, 1H), 4.40-4.23 (m, 2H), 4.23-4.01 (m, 2H), 3.25-3.00 (m, 5H), 2.76 (s, 3H), 2.17 (s, 3H), 1.58-1.03 (m, 6H).

Example 273: (*R)-3-(3-(((*R)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

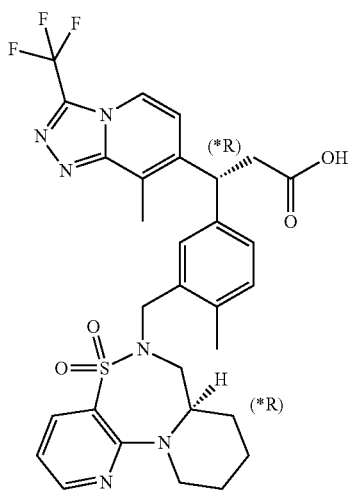 [SMILES: Cc1ccc([C@@H](CC(=O)O)c2ccn3c(C(F)(F)F)nnc3c2C)cc1CN1C[C@H]2CCCCN2c2ncccc2S1(=O)=O]

The second eluting isomer (55 mg) from the chiral separation described in Example 272 was designated (*R). MS (ESI): mass calcd. for $C_{30}H_{31}F_3N_6O_4S$, 628.2; m/z found, 629.2 [M+H]$^+$. $^1$H NMR (400 MHz, DMSO-d$_6$) δ 8.43 (d, J=7.0 Hz, 1H), 8.34-8.28 (m, 1H), 7.98 (dd, J=7.9, 1.8 Hz, 1H), 7.29 (d, J=7.7 Hz, 1H), 7.24-7.17 (m, 2H), 7.15 (d, J=7.7 Hz, 1H), 6.94-6.89 (m, 1H), 4.88-4.76 (m, 1H), 4.31-4.15 (m, 3H), 4.09-3.99 (m, 1H), 3.30-3.19 (m, 1H), 3.14-2.99 (m, 4H), 2.72 (s, 3H), 2.14 (s, 3H), 1.60-1.18 (m, 6H).

Example 274: (*S)-3-(3-(((S)-5,5-Dioxido-7a,8,9,10-tetrahydrobenzo[f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

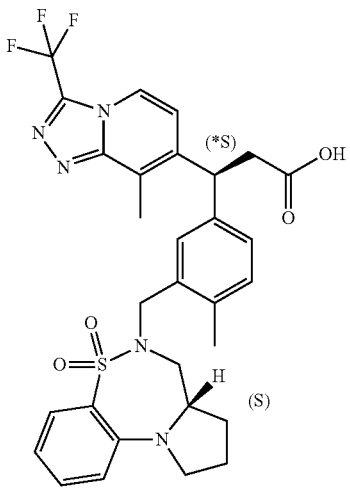

The title compound (63 mg) was prepared using analogous conditions as described in Example 7 using (S)-6,7,7a,8,9,10-hexahydrobenzo[f]pyrrolo[2,1-d][1,2,5]thiadiazepine 5,5-dioxide (Intermediate 84) instead of 2',3'-dihydrospiro[cyclopropane-1,4'-pyrido[2,3-b][1,4,5]oxathiazepine] 1',1'-dioxide in Step A and using an chiral SFC with an isocratic mobile phase of 60% $CO_2$ and 40% MeOH. The first eluting isomer was designated (*S): MS (ESI): mass calcd. for $C_{30}H_{30}F_3N_5O_4S$, 613.2; m/z found, 614.1 [M+H]$^+$. $^1$H NMR (500 MHz, DMSO-d) δ 12.30 (s, 1H), 8.40 (d, J=7.1 Hz, 1H), 7.72 (dd, J=7.9, 1.8 Hz, 1H), 7.49-7.43 (m, 1H), 7.29-7.24 (m, 1H), 7.21-7.13 (m, 3H), 7.03 (d, J=8.4 Hz, 1H), 6.97 (t, J=7.6 Hz, 1H), 4.86-4.76 (m, 1H), 4.26-3.88 (m, 3H), 3.29-3.22 (m, 2H coincident with water), 3.14-3.03 (m, 2H), 3.01-2.87 (m, 2H), 2.72 (s, 3H), 2.24 (s, 3H), 1.90-1.63 (m, 3H), 1.40-1.32 (m, 1H).

Example 275: (*R)-3-(3-(((S)-5,5-Dioxido-7a,8,9,10-tetrahydrobenzo[f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

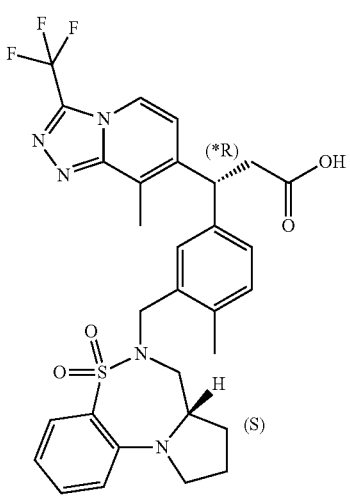

The second eluting isomer (62 mg) from the chiral separation described in Example 274 was designated (*R). MS (ESI): mass calcd. for $C_{30}H_{30}F_3N_5O_4S$, 613.2; m/z found, 614.1 [M+H]$^+$. $^1$H NMR (500 MHz, DMSO-d$_6$) δ 8.39 (d, J=7.1 Hz, 1H), 7.71 (dd, J=7.9, 1.6 Hz, 1H), 7.48-7.42 (m, 1H), 7.28-7.23 (m, 1H), 7.22-7.11 (m, 3H), 7.03-6.93 (m, 2H), 4.87-4.80 (m, 1H), 4.23-3.99 (m, 3H), 3.29-3.24 (m, 2H), 3.13-2.94 (m, 3H), 2.91-2.80 (m, 1H), 2.75 (s, 3H), 2.23 (s, 3H), 1.98-1.87 (m, 1H), 1.73-1.53 (m, 2H), 1.40-1.33 (m, 1H).

Example 276: (*S)-3-(3-(((*R)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

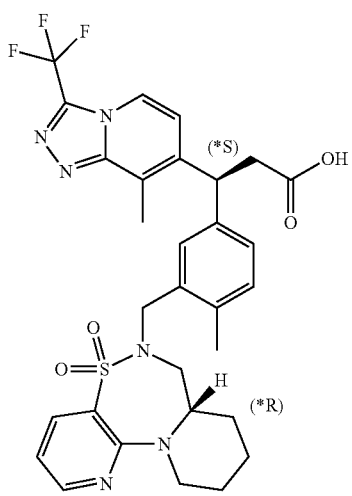

The title compound (42 mg) was prepared using analogous conditions as described in Example 7 using (*R)-6,7,7a,8,10,11-hexahydro-[1,4]oxazino[3,4-d]pyrido[2,3-f][1,2,5]thiadiazepine 5,5-dioxide (Intermediate 14) instead of 2',3'-dihydrospiro[cyclopropane-1,4'-pyrido[2,3-b][1,4,5]oxathiazepine] 1',1'-dioxide in Step A and the following chiral SFC conditions in Step B: stationary phase: Daicel Chiralpak AD-H 5 µm 250×20 mm, mobile phase: 50% $CO_2$, 50% EtOH) to afford two enantiomers. The first eluting isomer was designated (*S): MS(ESI): mass calcd. for $C_{29}H_{29}F_3N_6O_5S$, 630.2; m/z found, 631.2 [M+H]$^+$. $^1$H NMR (400 MHz, DMSO-d$_6$) δ 12.38 (s, 1H), 8.41-8.31 (m, 2H), 8.06-7.99 (m, 1H), 7.33-7.23 (m, 2H), 7.20-7.11 (m, 2H), 7.02-6.94 (m, 1H), 4.90-4.79 (m, 1H), 4.39-4.27 (m, 2H), 4.26-4.17 (m, 1H), 4.15-4.04 (m, 1H), 3.62-3.39 (m, 5H), 3.26-3.06 (m, 4H), 2.76 (s, 3H), 2.14 (s, 3H).

Example 277: (*R)-3-(3-(((*R)-5,5-Dioxido-7a,8,10,11-tetrahydro-[1,4]oxazino[3,4-d]pyrido[2,3-f][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

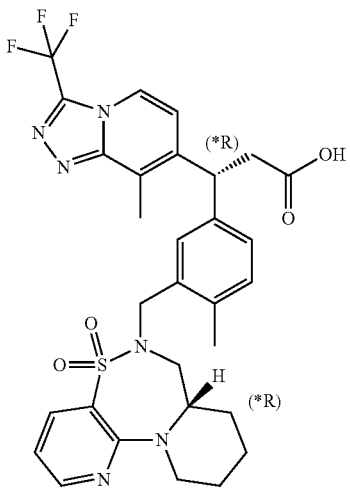 [SMILES: Cc1ccc([C@@H](CC(=O)O)c2ccn3c(C(F)(F)F)nnc3c2C)cc1CN1C[C@@H]2CCCCN2c2ncccc2S1(=O)=O]

The second eluting isomer (62 mg) from the chiral separation described in Example 276 was designated (*R). MS(ESI): mass calcd. for $C_{29}H_{29}F_3N_6O_5S$, 630.2; m/z found, 631.2 [M+H]$^+$. $^1$H NMR (400 MHz, DMSO-d$_6$) δ 12.36 (s, 1H), 8.42-8.32 (m, 2H), 8.05-7.98 (m, 1H), 7.31-7.12 (m, 4H), 7.01-6.94 (m, 1H), 4.83-4.75 (m, 1H), 4.36-4.21 (m, 3H), 4.20-4.10 (m, 1H), 3.84-3.75 (m, 1H), 3.65-3.54 (m, 2H), 3.53-3.38 (m, 2H), 3.29-3.05 (m, 4H), 2.70 (s, 3H), 2.15 (s, 3H).

Example 278: 3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic Acid

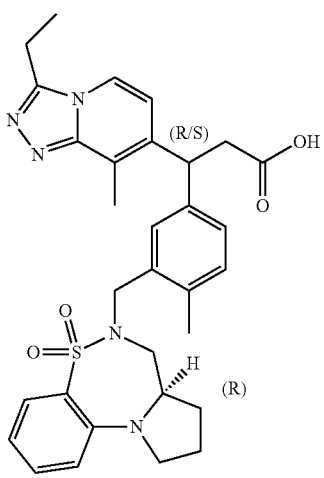

Step A: Ethyl 3-(3-(acetoxymethyl)-4-methylphenyl)-3-(3-ethyl-8-methyl-[1,2,4]triazolo[4,3-a]pyridin-7-yl)propanoate. A mixture of ethyl (E)-3-(3-ethyl-8-methyl-[1,2,4]triazolo[4,3-a]pyridin-7-yl)acrylate (Intermediate 112, 248 mg, 0.956 mmol), 2-methyl-5-(4,4,5,5-tetramethyl-1,3,2-dioxaborolan-2-yl)benzyl acetate (Intermediate 20, 834 mg, 2.87 mmol), 1 M aqueous potassium hydroxide solution (1.2 mL, 1.2 mmol), and [Rh(COD)Cl]$_2$ in dioxane (5.2 mL) was stirred at room temperature. After 5 hours, the mixture was diluted with ethyl acetate and washed with brine. The organic layer was dried over anhydrous sodium sulfate and then absorbed onto diatomaceous earth for purification by flash chromatography. MS(ESI): mass calcd. for $C_{24}H_{29}N_3O_4$, 423.2; m/z found, 424.2 [M+H]$^+$.

Step B: Ethyl 3-(3-ethyl-8-methyl-[1,2,4]triazolo[4,3-a]pyridin-7-yl)-3-(3-(hydroxymethyl)-4-methylphenyl)propanoate. A mixture of ethyl 3-(3-(acetoxymethyl)-4-methylphenyl)-3-(3-ethyl-8-methyl-[1,2,4]triazolo[4,3-a]pyridin-7-yl)propanoate (279 mg, 0.659 mmol) and potassium carbonate (390 mg, 2.82 mmol) in ethanol (5 mL) was stirred at room temperature. After 24 hours, the mixture was partitioned between water and ethyl acetate. The layers were separated. The organic extracts were washed with brine, dried over anhydrous sodium sulfate and then absorbed onto diatomaceous earth for purification by flash column chromatography (dichloromethane-methanol) to provide the title compound (178 mg, 71%) which was taken onto the next step without further characterization. MS(ESI): mass calcd. for $C_{22}H_{27}N_3O_3$, 381.2; m/z found, 382.2 [M+H]$^+$. Alternatively, the title compound can also be prepared using analogous conditions as described in Step A above using (3-(hydroxymethyl)-4-methylphenyl)boronic acid instead of 2-methyl-5-(4,4,5,5-tetramethyl-1,3,2-dioxaborolan-2-yl)benzyl acetate and triethyl amine instead of potassium hydroxide as base.

Step C: Ethyl 3-(3-(((R)-5,5-dioxido-7a,8,9,10-tetrahydrobenzo[f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoate. The title compound (176 mg) was prepared using analogous conditions as described in Example 7, Step A using (R)-6,7,7a,8,9,10-hexahydrobenzo[f]pyrrolo[2,1-d][1,2,5]thiadiazepine 5,5-dioxide (Intermediate 83) instead of 2',3'-dihydrospiro[cyclopropane-1,4'-pyrido[2,3-b][1,4,5]oxathiazepine] 1',1'-dioxide and using ethyl 3-(3-ethyl-8-methyl-[1,2,4]triazolo[4,3-a]pyridin-7-yl)-3-(3-(hydroxymethyl)-4-methylphenyl)propanoate instead of ethyl 3-(3-(hydroxymethyl)-4-methylphenyl)-3-(8-methyl-3-(trifluoromethyl)-[1,2,4]triazolo[4,3-a]pyridin-7-yl)propanoate. MS(ESI): mass calcd. for $C_{33}H_{39}N_5O_4S$, 601.3; m/z found, 602.3 [M+H]$^+$.

Step D: 3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic acid. The title compound (132 mg) was prepared using analogous conditions as described in Example 7, Step B using ethyl 3-(3-(((R)-5,5-dioxido-7a,8,9,10-tetrahydrobenzo[f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoate instead of ethyl 3-(3-((1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoate. MS (ESI): mass calcd. for $C_{31}H_{35}N_5O_4S$, 573.2; m/z found, 574.1 [M+H]$^+$. $^1$H NMR (400 MHz, DMSO-d$_6$) δ 12.23 (s, 1H), 8.15 (t, J=7.4 Hz, 1H), 7.77-7.66 (m, 1H), 7.50-7.39 (m, 1H), 7.28-7.22 (m, 1H), 7.22-7.17 (m, 1H), 7.17-7.11 (m, 1H), 7.07-6.93 (m, 2H), 6.87-6.80 (m, 1H), 4.82-4.68 (m, 1H), 4.27-3.92 (m, 3H), 3.12-2.82 (m, 6H), 2.66-2.56 (m, 3H), 2.23 (s, 3H), 1.97-1.50 (m, 3H), 1.42-1.26 (m, 4H), 3.30-3.23 (m, 2H).

Example 279: (*S)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic Acid

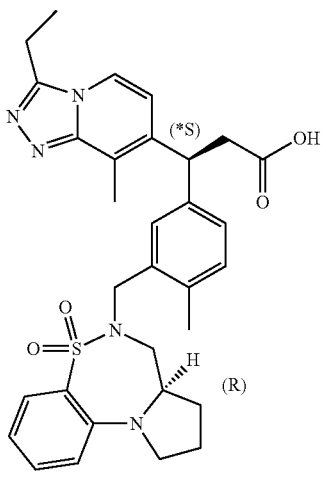

The mixture of 3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic acid isomers (Example 278, 126 mg) were separated by chiral SFC (stationary phase: LUX-CEL-4, 2×25 cm; mobile phase: 40% methanol, 10% acetonitrile, 50% CO$_2$) to afford two diastereoisomers. The first eluting isomer (61 mg) was designated (*S): $^1$H NMR (400 MHz, DMSO-d$_6$) δ 12.36 (s, 1H), 8.13 (d, J=7.2 Hz, 1H), 7.73-7.69 (m, 1H), 7.48-7.42 (m, 1H), 7.26-7.18 (m, 2H), 7.15-7.11 (m, 1H), 7.03-6.93 (m, 2H), 6.81-6.77 (m, 1H), 4.80-4.71 (m, 1H), 4.24-4.00 (m, 3H), 3.29-3.20 (m, 2H), 3.10-2.79 (m, 6H), 2.64 (s, 3H), 2.22 (s, 3H), 1.99-1.85 (m, 1H), 1.72-1.52 (m, 2H), 1.39-1.27 (m, 4H).

Example 280: (*R)-3-(3-(((R)-5,5-Dioxido-7a,8,9,10-tetrahydrobenzo[f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic Acid

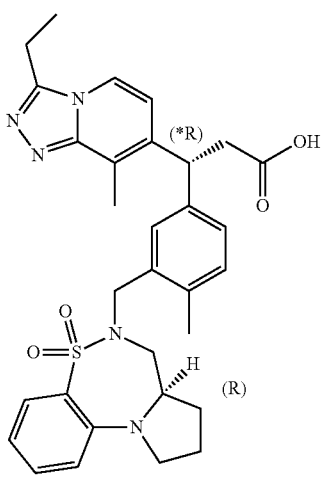

The second eluting isomer (63 mg) from the chiral separation described in Example 279 was designated (*R): $^1$H NMR (400 MHz, DMSO-d$_6$) δ 12.40 (br s, 1H), 8.14 (d, J=7.0 Hz, 1H), 7.75-7.69 (m, 1H), 7.49-7.42 (m, 1H), 7.26-7.09 (m, 3H), 7.05-6.94 (m, 2H), 6.85 (d, J=7.2 Hz, 1H), 4.79-4.67 (m, 1H), 4.23-3.88 (m, 3H), 3.28-3.17 (m, 2H), 3.08-2.86 (m, 6H), 2.60 (s, 3H), 2.23 (s, 3H), 1.93-1.60 (m, 3H), 1.38-1.26 (m, 4H).

Example 281: 3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic Acid

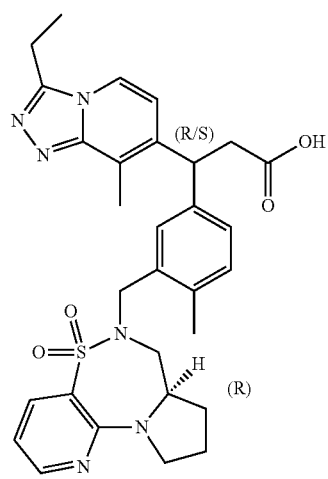

The title compound (50 mg) was prepared using analogous conditions as described in Example 278 using (R)-6,7,7a,8,9,10-hexahydropyrido[2,3-f]pyrrolo[2,1-d][1,2,5]thiadiazepine 5,5-dioxide (Intermediate 4) instead of (R)-6,7,7a,8,9,10-hexahydrobenzo[f]pyrrolo[2,1-d][1,2,5]thiadiazepine 5,5-dioxide in Step C. MS (ESI): mass calcd. for C$_{30}$H$_{34}$N$_6$O$_4$S, 574.2; m/z found, 575.2 [M+H]$^+$. $^1$H NMR (400 MHz, DMSO-d$_6$) δ 12.37-12.13 (s, 1H), 8.37-8.33 (m, 1H), 8.18-8.12 (m, 1H), 8.04-7.99 (m, 1H), 7.28-7.18 (m, 2H), 7.16-7.12 (m, 1H), 6.95-6.90 (m, 1H), 6.90-6.78 (m, 1H), 4.79-4.68 (m, 1H), 4.40-4.12 (m, 3H), 3.68-3.55 (m, 1H), 3.55-3.44 (m, 1H), 3.16-2.88 (m, 6H), 2.65-2.58 (m, 3H), 2.24-2.17 (m, 3H), 2.01-1.82 (m, 1H), 1.77-1.55 (m, 2H), 1.47-1.37 (m, 1H), 1.35-1.27 (m, 3H).

Example 282: (*S)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic Acid

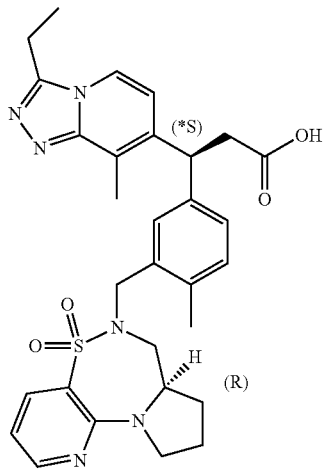

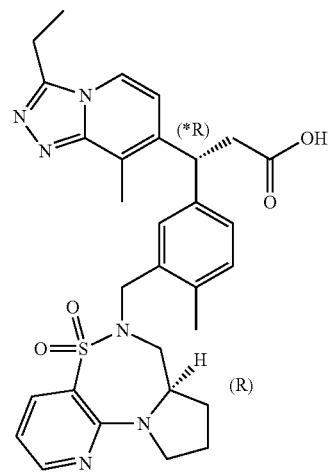

The mixture of 3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic acid isomers (Example 281, 45 mg) were separated by chiral SFC (stationary phase: CHIRALPAK AD-H 5 µm 250×20 mm; mobile phase: 50% methanol, 50% $CO_2$) to afford two diastereoisomers. The first eluting isomer (23 mg) was designated (*S): MS (ESI): mass calcd. for $C_{30}H_{34}N_6O_4S$, 574.2; m/z found, 575.2 [M+H]$^+$. $^1$H NMR (400 MHz, DMSO-d$_6$) δ 8.36-8.32 (m, 1H), 8.13 (d, J=7.2 Hz, 1H), 8.03-7.97 (m, 1H), 7.25-7.17 (m, 2H), 7.12 (d, J=7.7 Hz, 1H), 6.92 (dd, J=7.8, 4.7 Hz, 1H), 6.79 (d, J=7.3 Hz, 1H), 4.78-4.71 (m, 1H), 4.39-4.24 (m, 2H), 4.18-4.11 (m, 1H), 3.64-3.53 (m, 1H), 3.53-3.45 (m, 1H), 3.16-3.07 (m, 1H), 3.07-2.88 (m, 5H), 2.63 (s, 3H), 2.21 (s, 3H), 1.92 (d, J=19.0 Hz, 1H), 1.72-1.52 (m, 2H), 1.41 (d, J=11.5 Hz, 1H), 1.35-1.27 (m, 3H); Example 283: (*R)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-ethyl-8-methyl-[1,2,4]triazolo[4,3-a]pyridin-7-yl)propanoic Acid The second eluting isomer (22 mg) from the chiral separation described in Example 282 was designated (*R): MS (ESI): mass calcd. for $C_{30}H_{34}N_6O_4S$, 574.2; m/z found, 575.2 [M+H]$^+$. $^1$H NMR (400 MHz, DMSO-d$_6$) δ 8.36-8.32 (m, 1H), 8.14 (d, J=7.3 Hz, 1H), 8.01 (dd, J=7.7, 1.8 Hz, 1H), 7.25-7.19 (m, 1H), 7.17 (d, J=2.0 Hz, 1H), 7.12 (d, J=7.8 Hz, 1H), 6.95-6.90 (m, 1H), 6.84 (d, J=7.3 Hz, 1H), 4.78-4.68 (m, 1H), 4.31-4.14 (m, 3H), 3.67-3.56 (m, 1H), 3.51-3.43 (m, 1H), 3.12-2.86 (m, 6H), 2.59 (s, 3H), 2.21 (s, 3H), 1.92-1.81 (m, 1H), 1.69 (s, 2H), 1.40 (s, 1H), 1.35-1.26 (m, 3H).

Example 284: 3-(3-((4,4-Dimethyl-1,1-dioxido-3,4-dihydro-2H-benzo[b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic Acid

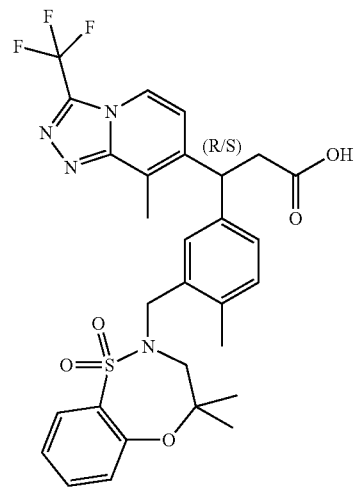 [SMILES: Cc1ccc(C(CC(=O)O)c2ccn3c(C(F)(F)F)nnc3c2C)cc1CN1CC(C)(C)Oc2ccccc2S1(=O)=O]

The title compound (132 mg) was prepared using analogous conditions as described in Example 7 using 4,4-dimethyl-3,4-dihydro-2H-benzo[b][1,4,5]oxathiazepine 1,1-dioxide (Intermediate 81) instead of 2',3'-dihydrospiro[cyclopropane-1,4'-pyrido[2,3-b][1,4,5]oxathiazepine] 1',1'-dioxide in Step A. MS (ESI): mass calcd. for $C_{29}H_{29}F_3N_4O_5S$, 602.2; m/z found, 603.2 [M+H]$^+$. $^1$H NMR (400 MHz, DMSO-$d_6$) δ 12.32 (s, 1H), 8.42 (d, J=7.1 Hz, 1H), 7.72-7.65 (m, 1H), 7.61-7.53 (m, 1H), 7.32-7.10 (m, 6H), 4.88-4.79 (m, 1H), 4.46-4.28 (m, 2H), 3.53-3.32 (m, 2H), 3.20-3.06 (m, 2H), 2.75 (s, 3H), 2.15 (s, 3H), 1.12-0.96 (m, 6H).

Example 285: (*S)-3-(3-((4,4-Dimethyl-1,1-dioxido-3,4-dihydro-2H-benzo[b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic Acid

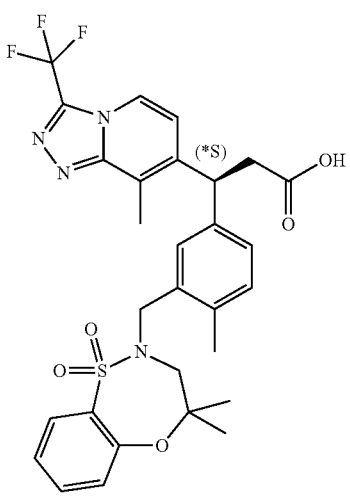 [SMILES: Cc1ccc([C@H](CC(=O)O)c2ccn3c(C(F)(F)F)nnc3c2C)cc1CN1CC(C)(C)Oc2ccccc2S1(=O)=O]

The mixture of 3-(3-((4,4-dimethyl-1,1-dioxido-3,4-dihydro-2H-benzo[b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic acid isomers (Example 284, 98 mg) were separated by chiral SFC (stationary phase: CHIRALPAK AD-H 5 μm 250×20 mm; mobile phase: 45% ethanol, 55% $CO_2$) to afford two enantiomers. The first eluting isomer (39 mg) was designated (*S): MS (ESI): mass calcd. for $C_{29}H_{29}F_3N_4O_5S$, 602.2; m/z found, 603.2 [M+H]$^+$. $^1$H NMR (500 MHz, DMSO-$d_6$) δ 12.35 (s, 1H), 8.41 (d, J=7.2 Hz, 1H), 7.69 (dd, J=7.7, 1.7 Hz, 1H), 7.60-7.53 (m, 1H), 7.32-7.27 (m, 1H), 7.26-7.20 (m, 2H), 7.20-7.10 (m, 3H), 4.88-4.81 (m, 1H), 4.44-4.29 (m, 2H), 3.55-3.33 (m, 2H), 3.17-3.06 (m, 2H), 2.74 (s, 3H), 2.15 (s, 3H), 1.12-0.99 (m, 6H).

Example 286: (*R)-3-(3-((4,4-Dimethyl-1,1-dioxido-3,4-dihydro-2H-benzo[b][1,4,5]oxathiazepin-2-yl)methyl)-4-methylphenyl)-3-(8-methyl-3-(trifluoromethyl)-[1,2,4]triazolo[4,3-a]pyridin-7-yl)propanoic Acid

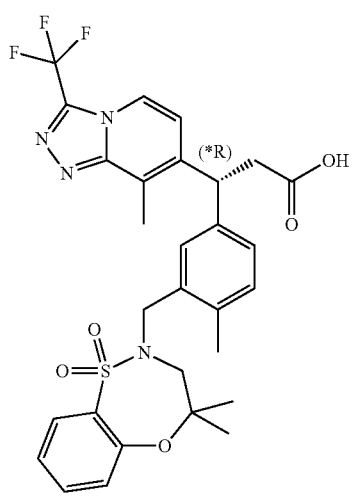 [SMILES: Cc1ccc([C@@H](CC(=O)O)c2ccn3c(C(F)(F)F)nnc3c2C)cc1CN1CC(C)(C)Oc2ccccc2S1(=O)=O]

The second eluting isomer (43 mg) from the chiral separation described in Example 285 was designated (*R): MS (ESI): mass calcd. for $C_{29}H_{29}F_3N_4O_5S$, 602.2; m/z found, 603.2 [M+H]$^+$. $^1$H NMR (500 MHz, DMSO-$d_6$) δ 12.36 (s, 1H), 8.41 (d, J=7.2 Hz, 1H), 7.69 (dd, J=7.7, 1.7 Hz, 1H), 7.59-7.54 (m, 1H), 7.31-7.27 (m, 1H), 7.26-7.10 (m, 5H), 4.87-4.82 (m, 1H), 4.44-4.29 (m, 2H), 3.53-3.33 (m, 2H), 3.16-3.04 (m, 2H), 2.74 (s, 3H), 2.15 (s, 3H), 1.07 (s, 3H), 1.04 (s, 3H).

Example 287: 3-(3-((1,1-Dioxidospiro[benzo[b][1,4,5]oxathiazepine-4,3'-oxetan]-2(3H)-yl)methyl)-4-methylphenyl)-3-(8-methyl-3-(trifluoromethyl)-[1,2,4]triazolo[4,3-a]pyridin-7-yl)propanoic Acid

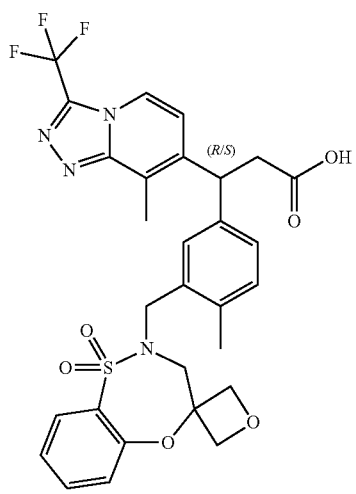 [SMILES: Cc1ccc(C(CC(=O)O)c2ccn3c(C(F)(F)F)nnc3c2C)cc1CN1CC2(COC2)Oc2ccccc2S1(=O)=O]

The title compound (96 mg) was prepared using analogous conditions as described in Example 7 using 2,3-dihydrospiro[benzo[b][1,4,5]oxathiazepine-4,3'-oxetane]

1,1-dioxide (Intermediate 7) instead of 2',3'-dihydrospiro[cyclopropane-1,4'-pyrido[2,3-b][1,4,5]oxathiazepine] 1',1'-dioxide in Step A. MS (ESI): mass calcd. for $C_{29}H_{27}F_3N_4O_6S$, 616.2; m/z found, 617.2 [M+H]$^+$. $^1$H NMR (400 MHz, DMSO-d$_6$) δ 12.32 (s, 1H), 8.36 (d, J=7.2 Hz, 1H), 7.78-7.73 (m, 1H), 7.72-7.66 (m, 1H), 7.48 (dd, J=8.1, 1.1 Hz, 1H), 7.43-7.36 (m, 1H), 7.31-7.25 (m, 1H), 7.23 (d, J=2.0 Hz, 1H), 7.20-7.14 (m, 2H), 4.87-4.80 (m, 1H), 4.42 (d, J=7.5 Hz, 1H), 4.36 (d, J=7.6 Hz, 1H), 4.31 (d, J=7.5 Hz, 1H), 4.27-4.14 (m, 3H), 3.76-3.62 (m, 2H), 3.16-3.07 (m, 2H), 2.73 (s, 3H), 2.2 (s, 3H).

Example 288: (*R)-3-(3-((1,1-dioxidospiro[benzo[b][1,4,5]oxathiazepine-4,3'-oxetan]-2(3H)-yl)methyl)-4-methylphenyl)-3-(8-methyl-3-(trifluoromethyl)-[1,2,4]triazolo[4,3-a]pyridin-7-yl)propanoic Acid

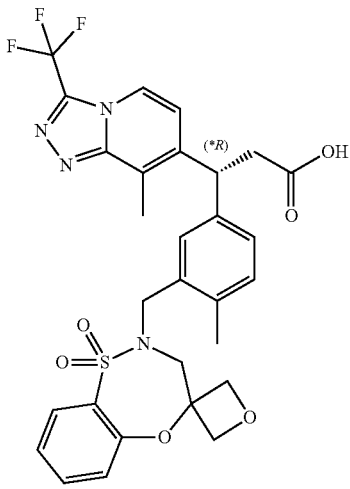 [SMILES: Cc1ccc([C@@H](CC(=O)O)c2ccn3c(C(F)(F)F)nnc3c2C)cc1CN1CC2(COC2)Oc2ccccc2S1(=O)=O]

The mixture of 3-(3-((1,1-dioxidospiro[benzo[b][1,4,5]oxathiazepine-4,3'-oxetan]-2(3H)-yl)methyl)-4-methylphenyl)-3-(8-methyl-3-(trifluoromethyl)-[1,2,4]triazolo[4,3-a]pyridin-7-yl)propanoic acid isomers (Example 287, 89 mg) were separated by chiral SFC (stationary phase: CHIRALPAK AD-H 5 μm 250×20 mm; mobile phase: 45% ethanol, 55% CO$_2$) to afford two enantiomers. The first eluting isomer (43 mg) was Example 26 and designated (*S). The second eluting isomer was designated (*R): MS (ESI): mass calcd. for $C_{29}H_{27}F_3N_4O_6S$, 616.2; m/z found, 617.2 [M+H]$^+$. $^1$H NMR (500 MHz, DMSO-d$_6$) δ 12.34 (s, 1H), 8.36 (d, J=7.1 Hz, 1H), 7.75 (dd, J=7.8, 1.7 Hz, 1H), 7.71-7.66 (m, 1H), 7.50-7.46 (m, 1H), 7.42-7.37 (m, 1H), 7.27 (dd, J=7.8, 2.0 Hz, 1H), 7.22 (d, J=2.0 Hz, 1H), 7.19-7.13 (m, 2H), 4.87-4.79 (m, 1H), 4.42 (d, J=7.5 Hz, 1H), 4.36 (d, J=7.6 Hz, 1H), 4.30 (d, J=7.6 Hz, 1H), 4.27-4.15 (m, 3H), 3.74-3.63 (m, 2H), 3.16-3.05 (m, 2H), 2.73 (s, 3H), 2.21 (s, 3H).

Example 289: 3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

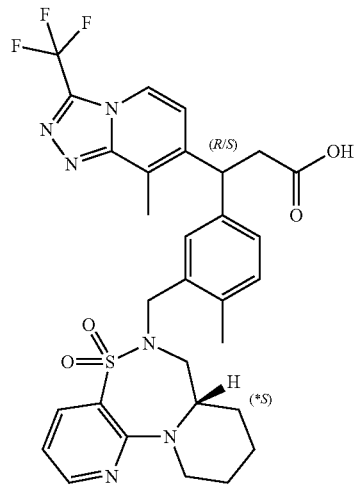

The title compound (171 mg) was prepared using analogous conditions as described in Example 7 using (*S)-7,7a,8,9,10,11-hexahydro-6H-dipyrido[2,1-d:2',3'-f][1,2,5]thiadiazepine 5,5-dioxide (Intermediate 2) instead of 2',3'-dihydrospiro[cyclopropane-1,4'-pyrido[2,3-b][1,4,5]oxathiazepine] 1',1'-dioxide in Step A. MS (ESI): mass calcd. for $C_{30}H_{31}F_3N_6O_4S$, 628.2; m/z found, 629.2 [M+H]$^+$. $^1$H NMR (500 MHz, DMSO-d$_6$) δ 12.30 (s, 1H), 8.44-8.39 (m, 1H), 8.33-8.29 (m, 1H), 8.00-7.95 (m, 1H), 7.33-7.27 (m, 1H), 7.24-7.14 (m, 3H), 6.94-6.89 (m, 1H), 4.89-4.77 (m, 1H), 4.36-4.14 (m, 3H), 4.09-4.01 (m, 1H), 3.29-3.02 (m, 5H), 2.78-2.70 (m, 3H), 2.20-2.12 (m, 3H), 1.62-1.09 (m, 6H).

Example 290: (*S)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

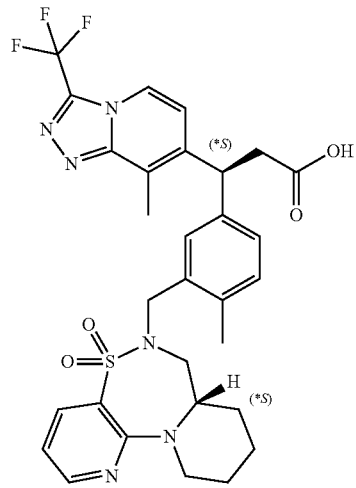

The mixture of 3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid isomers (Example 289, 117 mg) were separated by chiral SFC (stationary phase: CHIRALPAK IA 2×25 cm; mobile phase: 40% methanol, 60% CO$_2$) to afford two diastereoisomers. The first eluting isomer (54 mg) was designated (*S): MS (ESI): mass calcd. for C$_{30}$H$_{31}$F$_3$N$_6$O$_4$S, 628.2; m/z found, 629.2 [M+H]$^+$. $^1$H NMR (400 MHz, DMSO-d$_6$) δ 12.42 (s, 1H), 8.47-8.39 (m, 1H), 8.34-8.27 (m, 1H), 8.01-7.94 (m, 1H), 7.34-7.26 (m, 1H), 7.26-7.11 (m, 3H), 6.95-6.88 (m, 1H), 4.82 (t, J=7.7 Hz, 1H), 4.30-4.14 (m, 3H), 4.10-3.99 (m, 1H), 3.30-3.18 (m, 1H), 3.15-3.00 (m, 4H), 2.72 (s, 3H), 2.14 (s, 3H), 1.64-1.13 (m, 6H).

Example 291: (*R)-3-(3-(((*S)-5,5-Dioxido-7,7a,9,10,11-hexahydro-6H-dipyrido[2,1-d:2',3'-][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

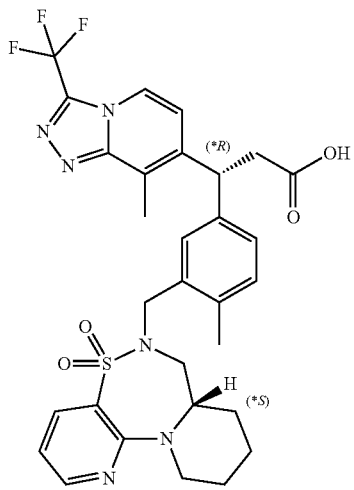

The second eluting isomer (59 mg) from the chiral separation described in Example 290 was designated (*R): MS (ESI): mass calcd. for C$_{30}$H$_{31}$F$_3$N$_6$O$_4$S, 628.2; m/z found, 629.2 [M+H]$^+$. $^1$H NMR (400 MHz, DMSO-d$_6$) δ 12.49 (s, 1H), 8.41 (d, J=7.1 Hz, 1H), 8.33-8.28 (m, 1H), 8.00-7.95 (m, 1H), 7.29 (d, J=7.8 Hz, 1H), 7.22 (s, 1H), 7.19-7.13 (m, 2H), 6.94-6.89 (m, 1H), 4.91-4.77 (m, 1H), 4.38-4.21 (m, 2H), 4.19-4.01 (m, 2H), 3.25-2.99 (m, 5H), 2.76 (s, 3H), 2.17 (s, 3H), 1.58-1.04 (m, 6H).

Example 292: (*S)-3-(3-(((*S)-5,5-Dioxido-7,7a,8,9-tetrahydro-6H-azeto[2,1-d]pyrido[2,3-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

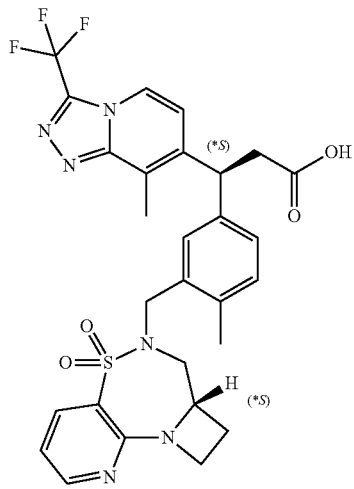

The title compound (93 mg) was prepared using analogous conditions as described in Example 7 using (*S)-7,7a,8,9-tetrahydro-6H-azeto[2,1-d]pyrido[2,3-f][1,2,5]thiadiazepine 5,5-dioxide (Intermediate 113) instead of 2',3'-dihydrospiro[cyclopropane-1,4'-pyrido[2,3-b][1,4,5]oxathiazepine] 1',1'-dioxide in Step A and the following chiral SFC conditions after Step B: stationary phase: Chiracel OD-H 5 μm 250×20 mm, mobile phase: 50% CO$_2$, 50% EtOH) to afford two diastereoisomers. The first eluting isomer was designated (*S): MS(ESI): mass calcd. for C$_{28}$H$_{27}$F$_3$N$_6$O$_4$S, 600.2; m/z found, 601.2 [M+H]$^+$. $^1$H NMR (500 MHz, DMSO-d$_6$) δ 12.58-12.14 (s, 1H), 8.42-8.37 (m, 2H), 8.02-7.98 (dd, J=7.7, 1.7 Hz, 1H), 7.34-7.30 (d, J=2.1 Hz, 1H), 7.27-7.23 (m, 1H), 7.21-7.17 (d, J=7.3 Hz, 1H), 7.17-7.13 (d, J=7.9 Hz, 1H), 7.02-6.98 (dd, J=7.7, 4.9 Hz, 1H), 4.86-4.78 (m, 1H), 4.55-4.46 (m, 1H), 4.46-4.39 (d, J=14.4 Hz, 1H), 4.17-4.09 (m, 1H), 4.09-4.01 (d, J=14.4 Hz, 1H), 3.68-3.61 (m, 1H), 3.60-3.53 (m, 1H), 3.14-3.08 (d, J=7.8 Hz, 2H), 2.95-2.88 (m, 1H), 2.76-2.71 (s, 3H), 2.28-2.23 (s, 3H), 2.21-2.11 (m, 1H), 2.10-2.02 (m, 1H).

Example 293: (*R)-3-(3-(((*S)-5,5-Dioxido-7,7a,8,9-tetrahydro-6H-azeto[2,1-d]pyrido[2,3-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

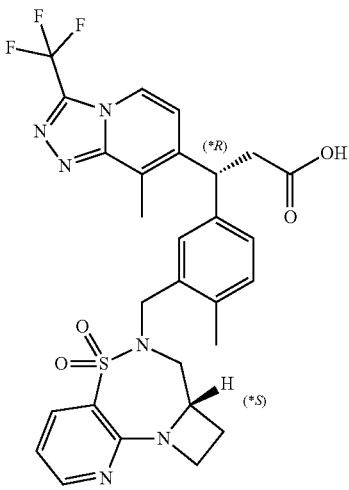

The second eluting isomer (94 mg) from the chiral separation described in Example 292 was designated (*R): MS(ESI): mass calcd. for C$_{28}$H$_{27}$F$_3$N$_6$O$_4$S, 600.2; m/z found, 601.2 [M+H]$^+$. $^1$H NMR (500 MHz, DMSO-d$_6$) δ 12.49-12.17 (s, 1H), 8.41-8.37 (m, 2H), 8.02-7.98 (m, 1H), 7.33-7.29 (d, J=2.0 Hz, 1H), 7.26-7.22 (m, 1H), 7.18-7.13 (m, 2H), 7.02-6.98 (dd, J=7.7, 4.8 Hz, 1H), 4.85-4.77 (m, 1H), 4.50-4.39 (m, 2H), 4.15-4.06 (m, 1H), 4.06-4.01 (d, J=14.2 Hz, 1H), 3.66-3.52 (m, 2H), 3.17-3.02 (m, 2H), 2.91-2.84 (m, 1H), 2.76-2.71 (s, 3H), 2.28-2.23 (s, 3H), 2.18-2.08 (m, 1H), 1.98-1.90 (m, 1H).

Example 294: (*S)-3-(3-(((*R)-5,5-Dioxido-7,7a,8,9-tetrahydro-6H-azeto[2,1-d]pyrido[2,3-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

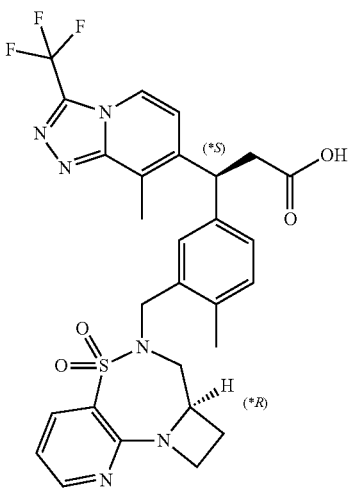

The title compound (101 mg) was prepared using analogous conditions as described in Example 26 using (*R)-7,7a,8,9-tetrahydro-6H-azeto[2,1-d]pyrido[2,3-f][1,2,5]thiadiazepine 5,5-dioxide (Intermediate 114) instead of 2',3'-dihydrospiro[cyclopropane-1,4'-pyrido[2,3-b][1,4,5]oxathiazepine] 1',1'-dioxide in Step A and the chiral SFC conditions as described in Example 292 to afford two diastereoisomers after Step B. The first eluting isomer was designated (*S): MS(ESI): mass calcd. for C$_{28}$H$_{27}$F$_3$N$_6$O$_4$S, 600.2; m/z found, 601.2 [M+H]$^+$. $^1$H NMR (500 MHz, DMSO-d$_6$) δ 12.31 (s, 1H), 8.41-8.37 (m, 2H), 8.02-7.98 (m, 1H), 7.31 (d, J=2.0 Hz, 1H), 7.26-7.21 (m, 1H), 7.17-7.14 (m, 2H), 7.00 (dd, J=7.7, 4.8 Hz, 1H), 4.85-4.78 (m, 1H), 4.50-4.40 (m, 2H), 4.15-4.06 (m, 1H), 4.04 (d, J=14.2 Hz, 1H), 3.66-3.53 (m, 2H), 3.17-3.03 (m, 2H), 2.91-2.83 (m, 1H), 2.74 (s, 3H), 2.26 (s, 3H), 2.18-2.08 (m, 1H), 1.98-1.90 (m, 1H).

Example 295: (*R)-3-(3-(((*R)-5,5-Dioxido-7,7a,8,9-tetrahydro-6H-azeto[2,1-d]pyrido[2,3-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

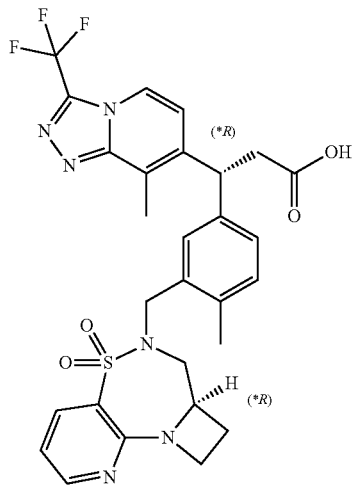 [SMILES: Cc1ccc([C@@H](CC(=O)O)c2ccn3c(C(F)(F)F)nnc3c2C)cc1CN1C[C@H]2CCN2c2ncccc2S1(=O)=O]

The second eluting isomer (103 mg) from the chiral separation described in Example 294 was designated (*R): MS(ESI): mass calcd. for C$_{28}$H$_{27}$F$_3$N$_6$O$_4$S, 600.2; m/z found, 601.2 [M+H]$^+$. $^1$H NMR (500 MHz, DMSO-d$_6$) δ 12.32 (s, 1H), 8.42-8.37 (m, 2H), 8.01-7.98 (m, 1H), 7.32 (d, J=2.0 Hz, 1H), 7.27-7.23 (m, 1H), 7.19 (d, J=7.3 Hz, 1H), 7.15 (d, J=7.9 Hz, 1H), 7.02-6.97 (m, 1H), 4.85-4.78 (m, 1H), 4.53-4.45 (m, 1H), 4.42 (d, J=14.3 Hz, 1H), 4.16-4.09 (m, 1H), 4.05 (d, J=14.4 Hz, 1H), 3.69-3.61 (m, 1H), 3.61-3.52 (m, 1H), 3.10 (d, J=7.8 Hz, 2H), 2.95-2.88 (m, 1H), 2.74 (s, 3H), 2.25 (s, 3H), 2.21-2.10 (m, 1H), 2.08-2.02 (m, 1H).

Example 296: 3-(6-(((R)-5,5-Dioxido-7a,8,9,10-tetrahydropyrido[2,3-f]pyrrolo[2,1-d][1,2,5]thiadiaz-epin-6(7H)-yl)methyl)-5-methylpyridin-2-yl)-3-(1-ethyl-4-methyl-1H-benzo[d][1,2,3]triazol-5-yl)propanoic Acid

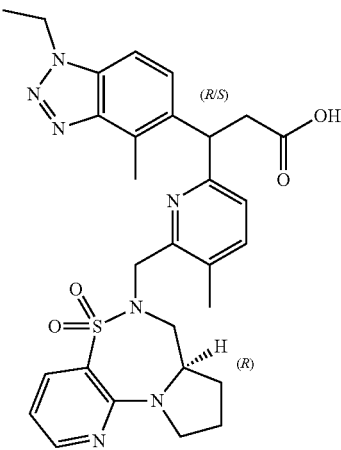

The title compound (92 mg) was prepared using analogous conditions as described in Example 7 using (R)-6,7,7a,8,9,10-hexahydropyrido[2,3-f]pyrrolo[2,1-d][1,2,5]thiadiazepine 5,5-dioxide (Intermediate 4) instead of 2',3'-dihydrospiro[cyclopropane-1,4'-pyrido[2,3-b][1,4,5]oxathiazepine] 1',1'-dioxide, ethyl 3-(1-ethyl-4-methyl-1H-benzo[d][1,2,3]triazol-5-yl)-3-(6-(hydroxymethyl)-5-ethylpyridin-2-yl)propanoate (Intermediate 115) instead of ethyl 3-(3-(hydroxymethyl)-4-methylphenyl)-3-(8-ethyl-3-(trifluoromethyl)-[1,2,4]triazolo[4,3-a]pyridin-7-yl)propanoate, and di-tert-butyl azodicarboxylate instead of diisopropyl azodicarboxylate in Step A. MS(ESI): mass calcd. for $C_{29}H_{33}N_7O_4S$, 575.2; m/z found, 576.2 $[M+H]^+$. $^1H$ NMR (400 MHz, DMSO-$d_6$) δ 12.18-11.99 (s, 1H), 8.35-8.32 (m, 1H), 8.03-7.99 (m, 1H), 7.59-7.54 (d, J=8.7 Hz, 1H), 7.51-7.46 (m, 1H), 7.45-7.40 (m, 1H), 7.22-7.14 (dd, J=17.9, 7.8 Hz, 1H), 6.93-6.87 (m, 1H), 4.99-4.89 (m, 1H), 4.72-4.59 (m, 2H), 4.54-4.39 (m, 2H), 4.36-4.23 (m, 2H), 3.69-3.47 (m, 2H), 3.46-3.35 (m, 1H), 3.33-3.20 (m, 2H), 2.99-2.87 (m, 1H), 2.87-2.80 (m, 3H), 2.27-2.17 (m, 3H), 2.10-1.94 (m, 1H), 1.93-1.84 (m, 1H), 1.84-1.73 (m, 1H), 1.57-1.38 (m, 4H).

Example 297: (*S)-3-(6-(((R)-5,5-Dioxido-7a,8,9,10-tetrahydropyrido[2,3-f]pyrrolo[2,1-d][1,2,5]thiadiazepin-6(7H)-yl)methyl)-5-methylpyridin-2-yl)-3-(1-ethyl-4-methyl-1H-benzo[d][1,2,3]triazol-5-yl)propanoic Acid

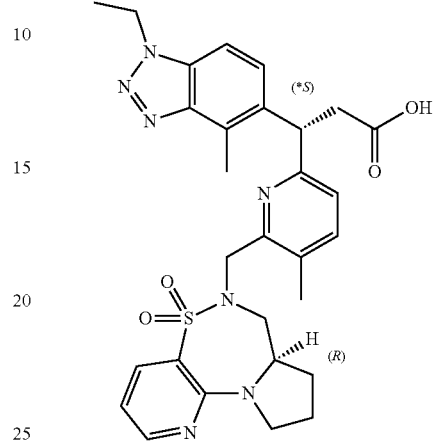

The mixture of 3-(6-(((R)-5,5-dioxido-7a,8,9,10-tetrahydropyrido[2,3-f]pyrrolo[2,1-d][1,2,5]thiadiazepin-6(7H)-yl)methyl)-5-methylpyridin-2-yl)-3-(1-ethyl-4-methyl-1H-benzo[d][1,2,3]triazol-5-yl)propanoic acid isomers (Example 296, 68 mg) were separated by chiral SFC (stationary phase: Chiralpak AD-H 5 μm 2×25 cm; mobile phase: 35% ethanol, 65% $CO_2$) to afford two diastereoisomers. The first eluting isomer (28 mg) was designated (*S): MS(ESI): mass calcd. for $C_{29}H_{33}N_7O_4S$, 575.2; m/z found, 576.2 $[M+H]^+$. $^1H$ NMR (400 MHz, DMSO-$d_6$) δ 12.41-11.82 (m, 1H), 8.35-8.31 (m, 1H), 8.03-7.98 (m, 1H), 7.58-7.54 (m, 1H), 7.51-7.47 (m, 1H), 7.44-7.39 (m, 1H), 7.22-7.17 (m, 1H), 6.92-6.87 (m, 1H), 4.97-4.90 (m, 1H), 4.69-4.61 (m, 2H), 4.51-4.40 (m, 2H), 4.30-4.23 (m, 1H), 3.64-3.47 (m, 2H), 3.29-3.20 (m, 3H), 2.97-2.88 (m, 1H), 2.86-2.79 (m, 3H), 2.25-2.20 (m, 3H), 2.06-1.93 (m, 1H), 1.84-1.71 (m, 2H), 1.49-1.36 (m, 4H).

Example 298: (*R)-3-(6-(((R)-5,5-Dioxido-7a,8,9,10-tetrahydropyrido[2,3-f]pyrrolo[2,1-d][1,2,5]thiadiazepin-6(7H)-yl)methyl)-5-methylpyridin-2-yl)-3-(1-ethyl-4-methyl-1H-benzo[d][1,2,3]triazol-5-yl)propanoic Acid

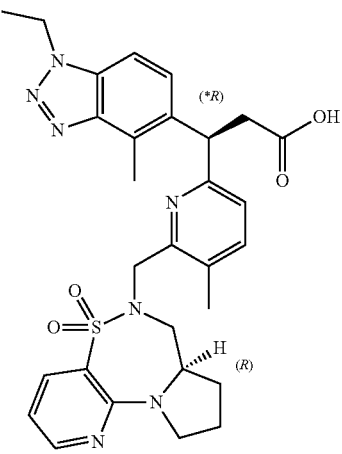

The second eluting isomer (31 mg) from the chiral separation described in Example 297 was designated (*R): MS(ESI): mass calcd. for $C_{29}H_{33}N_7O_4S$, 575.2; m/z found, 576.2 [M+H]$^+$. $^1$H NMR (400 MHz, DMSO-d$_6$) δ 8.36-8.31 (dd, J=4.8, 1.8 Hz, 1H), 8.04-7.99 (dd, J=7.8, 1.8 Hz, 1H), 7.57-7.53 (m, 1H), 7.49-7.41 (m, 2H), 7.18-7.13 (d, J=7.8 Hz, 1H), 6.93-6.88 (m, 1H), 4.98-4.91 (m, 1H), 4.70-4.60 (m, 2H), 4.50-4.38 (m, 2H), 4.36-4.27 (m, 1H), 3.67-3.57 (m, 1H), 3.57-3.47 (m, 1H), 3.44-3.32 (m, 3H), 2.93-2.80 (m, 4H), 2.25-2.17 (s, 3H), 2.10-1.94 (m, 1H), 1.92-1.82 (m, 2H), 1.57-1.41 (m, 4H).

Example 299: (*S)-3-(3-(((*S)-5,5-Dioxido-7,7a,8,9,10,11-hexahydro-6H-benzo[f]pyrido[2,1-d][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

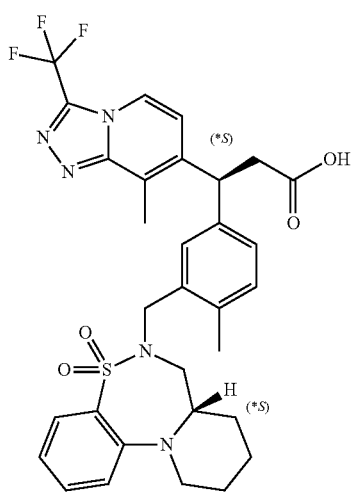 [SMILES: Cc1ccc([C@H](CC(=O)O)c2ccn3c(C(F)(F)F)nnc3c2C)cc1CN1C[C@@H]2CCCCN2c2ccccc2S1(=O)=O]

The title compound (113 mg) was prepared using analogous conditions as described in Example 26 using (*S)-7,7a,8,9,10,11-hexahydro-6H-benzo[f]pyrido[2,1-d][1,2,5]thiadiazepine 5,5-dioxide (Intermediate 76) instead of 2,3-dihydrospiro[benzo[b][1,4,5]oxathiazepine-4,3'-oxetane] 1,1-dioxide in Step A. MS(ESI): mass calcd. for $C_{31}H_{32}F_3N_5O_4S$, 627.2; m/z found, 628.2 [M+H]$^+$. $^1$H NMR (400 MHz, DMSO-d$_6$) δ 12.51-12.16 (s, 1H), 8.42-8.37 (d, J=7.1 Hz, 1H), 7.71-7.66 (m, 1H), 7.52-7.45 (m, 1H), 7.33-7.27 (m, 1H), 7.27-7.08 (m, 5H), 4.85-4.77 (m, 1H), 4.42-4.31 (d, J=14.0 Hz, 1H), 4.05-3.95 (m, 1H), 3.71-3.58 (m, 1H), 3.48-3.38 (m, 1H), 3.27-3.02 (m, 4H), 2.77-2.71 (s, 3H), 2.65-2.52 (m, 1H), 2.27-2.20 (s, 3H), 1.72-1.36 (m, 3H), 1.36-0.97 (m, 3H).

Example 300: (*S)-3-(3-(((*R)-5,5-Dioxido-7,7a,8,9,10,11-hexahydro-6H-benzo[f]pyrido[2,1-d][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

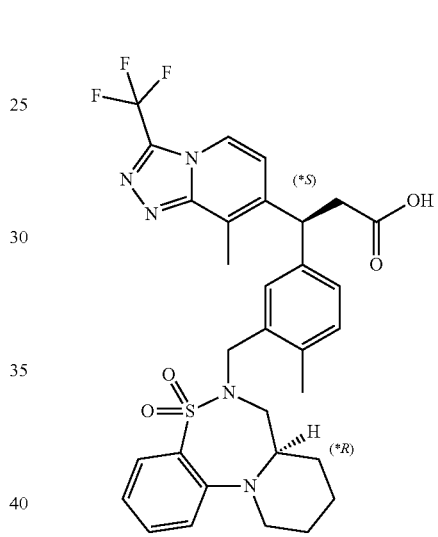

The title compound (107 mg) was prepared using analogous conditions as described in Example 26 using (*R)-7,7a,8,9,10,11-hexahydro-6H-benzo[f]pyrido[2,1-d][1,2,5]thiadiazepine 5,5-dioxide (Intermediate 116) instead of 2,3-dihydrospiro[benzo[b][1,4,5]oxathiazepine-4,3'-oxetane] 1,1-dioxide in Step A. MS(ESI): mass calcd. for $C_{31}H_{32}F_3N_5O_4S$, 627.2; m/z found, 628.2 [M+H]$^+$. $^1$H NMR (400 MHz, DMSO-d$_6$) δ 12.36-12.27 (s, 1H), 8.43-8.37 (d, J=7.1 Hz, 1H), 7.70-7.64 (dd, J=7.9, 1.6 Hz, 1H), 7.50-7.44 (m, 1H), 7.32-7.27 (m, 1H), 7.26-7.14 (m, 4H), 7.12-7.05 (m, 1H), 4.87-4.76 (m, 1H), 4.34-4.24 (d, J=14.1 Hz, 1H), 4.17-4.03 (d, J=14.1 Hz, 1H), 3.84-3.67 (s, 1H), 3.41-3.24 (m, 1H), 3.24-3.05 (m, 3H), 2.76-2.71 (s, 4H), 2.27-2.20 (s, 3H), 1.66-1.42 (m, 1H), 1.34-1.10 (m, 6H).

Example 301: 3-(6-(((*S)-5,5-Dioxido-7,7a,8,9,10, 11-hexahydro-6H-dipyrido[2,1-d:2',3'-][1,2,5]thiadiazepin-6-yl)methyl)-5-methylpyridin-2-yl)-3-(1-ethyl-4-methyl-1H-benzo[d][1,2,3]triazol-5-yl)propanoic Acid

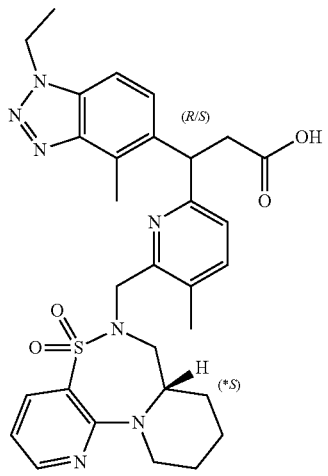 [SMILES: CCn1nnc2c(C)c(C(CC(=O)O)c3ccc(C)c(CN4C[C@@H]5CCCCN5c5ncccc5S4(=O)=O)n3)ccc21]

The title compound (108 mg) was prepared using analogous conditions as described in Example 296 using (*S)-7,7a,8,9,10,11-hexahydro-6H-dipyrido[2,1-d:2',3'-f][1,2,5]thiadiazepine 5,5-dioxide (Intermediate 2) instead of (R)-6,7,7a,8,9,10-hexahydropyrido[2,3-f]pyrrolo[2,1-d][1,2,5]thiadiazepine 5,5-dioxide in Step A. MS (ESI): mass calcd. for $C_{30}H_{35}N_7O_4S$, 589.2; m/z found, 590.3 [M+H]+. 1H NMR (400 MHz, CDCl3) δ 8.35-8.29 (m, 1H), 8.09-8.03 (m, 1H), 7.45-7.37 (dd, J=12.1, 7.8 Hz, 1H), 7.32-7.25 (m, 1H), 7.24-7.17 (m, 1H), 6.95-6.81 (m, 2H), 5.11-4.99 (m, 1H), 4.79-4.53 (m, 4H), 4.44-4.27 (m, 2H), 3.71-3.29 (m, 4H), 3.11-2.93 (m, 1H), 2.93-2.88 (m, 3H), 2.39-2.31 (m, 3H), 1.87-1.48 (m, 9H).

Example 302: (*S)-3-(6-(((*S)-5,5-Dioxido-7,7a,8,9,10,11-hexahydro-6H-dipyrido[2,1-d:2',3'-][1,2,5]thiadiazepin-6-yl)methyl)-5-methylpyridin-2-yl)-3-(1-ethyl-4-methyl-1H-benzo[d][1,2,3]triazol-5-yl)propanoic Acid

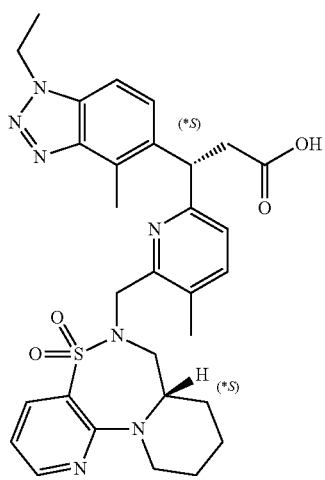 [SMILES: CCn1nnc2c(C)c([C@H](CC(=O)O)c3ccc(C)c(CN4C[C@@H]5CCCCN5c5ncccc5S4(=O)=O)n3)ccc21]

The mixture of 3-(6-(((*S)-5,5-dioxido-7,7a,8,9,10,11-hexahydro-6H-dipyrido[2,1-d:2',3'-][1,2,5]thiadiazepin-6-yl)methyl)-5-methylpyridin-2-yl)-3-(1-ethyl-4-methyl-1H-benzo[d][1,2,3]triazol-5-yl)propanoic acid isomers (Example 301, 99 mg) were separated by chiral SFC (stationary phase: Chiralpak AD-H 5 μm 3×25 cm; mobile phase: 45% methanol, 55% $CO_2$) to afford two diastereoisomers. The first eluting isomer (44 mg) was designated (*S): MS (ESI): mass calcd. for $C_{30}H_{35}N_7O_4S$, 589.2; m/z found, 590.2 [M+H]+. 1H NMR (500 MHz, DMSO-d6) δ 12.09 (s, 1H), 8.33-8.29 (m, 1H), 8.00-7.96 (m, 1H), 7.57 (d, J=8.6 Hz, 1H), 7.48 (d, J=7.9 Hz, 1H), 7.42 (d, J=8.7 Hz, 1H), 7.19 (d, J=7.9 Hz, 1H), 6.93-6.90 (m, 1H), 5.02-4.92 (m, 1H), 4.70-4.62 (m, 2H), 4.53 (d, J=14.2 Hz, 1H), 4.47-4.39 (m, 1H), 4.29 (d, J=14.2 Hz, 1H), 4.24-4.15 (m, 1H), 3.73-3.63 (m, 1H), 3.44-3.25 (m, 3H, coincident with water), 2.93 (dd, J=16.3, 7.1 Hz, 1H), 2.85 (s, 3H), 2.17 (s, 3H), 1.76-1.55 (m, 3H), 1.51-1.41 (m, 6H).

Example 303: (*R)-3-(6-(((*S)-5,5-Dioxido-7,7a,8,9,10,11-hexahydro-6H-dipyrido[2,1-d:2',3'-][1,2,5]thiadiazepin-6-yl)methyl)-5-methylpyridin-2-yl)-3-(1-ethyl-4-methyl-1H-benzo[d][1,2,3]triazol-5-yl)propanoic Acid

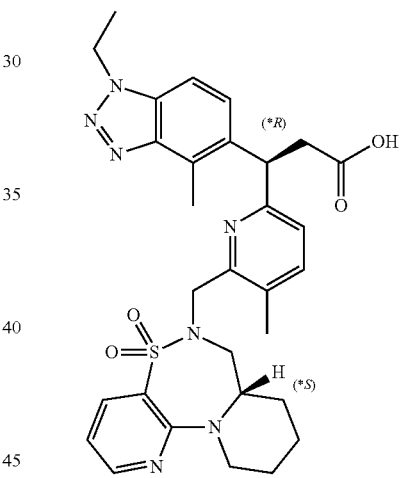

The second eluting isomer (44 mg) from the chiral separation described in Example 302 was designated (*R): MS (ESI): mass calcd. for $C_{30}H_{35}N_7O_4S$, 589.2; m/z found, 590.2 [M+H]+. 1H NMR (500 MHz, DMSO-d6) δ 12.12 (s, 1H), 8.32-8.29 (m, 1H), 8.00-7.95 (m, 1H), 7.58 (d, J=8.7 Hz, 1H), 7.52 (d, J=7.9 Hz, 1H), 7.47 (d, J=8.7 Hz, 1H), 7.26 (d, J=7.8 Hz, 1H), 6.93-6.89 (m, 1H), 5.01-4.91 (m, 1H), 4.70-4.61 (m, 2H), 4.53 (d, J=13.7 Hz, 1H), 4.43-4.35 (m, 1H), 4.25-4.15 (m, 2H), 3.56-3.47 (m, 1H), 3.38-3.21 (m, 2H), 3.17-3.11 (m, 1H), 3.03-2.94 (m, 1H), 2.84 (s, 3H), 2.19 (s, 3H), 1.68-1.51 (m, 3H), 1.48-1.41 (m, 3H), 1.34-1.16 (m, 3H).

Example 304: 3-(6-(((*R)-5,5-Dioxido-7,7a,8,9,10,11-hexahydro-6H-dipyrido[2,1-d:2',3'-][1,2,5]thiadiazepin-6-yl)methyl)-5-methylpyridin-2-yl)-3-(1-ethyl-4-methyl-1H-benzo[d][1,2,3]triazol-5-yl)propanoic Acid

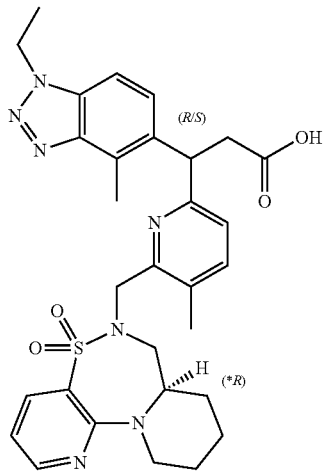 [SMILES: CCn1nnc2c(C)c(C(CC(=O)O)c3ccc(C)c(CN4C[C@H]5CCCCN5c5ncccc5S4(=O)=O)n3)ccc21]

The title compound (96 mg) was prepared using analogous conditions as described in Example 301 using (*R)-7,7a,8,9,10,11-hexahydro-6H-dipyrido[2,1-d:2',3'-f][1,2,5]thiadiazepine 5,5-dioxide (Intermediate 3) instead of (*S)-7,7a,8,9,10,11-hexahydro-6H-dipyrido[2,1-d:2',3'-f][1,2,5]thiadiazepine 5,5-dioxide in Step A. MS (ESI): mass calcd. for $C_{30}H_{35}N_7O_4S$, 589.2; m/z found, 590.2 [M+H]$^+$. $^1$H NMR (400 MHz, CDCl$_3$) δ 8.35-8.29 (m, 1H), 8.08-8.04 (m, 1H), 7.45-7.37 (m, 1H), 7.32-7.24 (m, 1H), 7.24-7.17 (m, 1H), 6.95-6.81 (m, 2H), 5.10-4.99 (m, 1H), 4.76-4.53 (m, 4H), 4.42-4.27 (m, 2H), 3.72-3.29 (m, 4H), 3.10-2.95 (m, 1H), 2.93-2.87 (m, 3H), 2.40-2.31 (m, 3H), 1.87-1.45 (m, 9H).

Example 305: (*S)-3-(6-(((*R)-5,5-Dioxido-7,7a,8,9,10,11-hexahydro-6H-dipyrido[2,1-d:2',3'-][1,2,5]thiadiazepin-6-yl)methyl)-5-methylpyridin-2-yl)-3-(1-ethyl-4-methyl-1H-benzo[d][1,2,3]triazol-5-yl)propanoic Acid

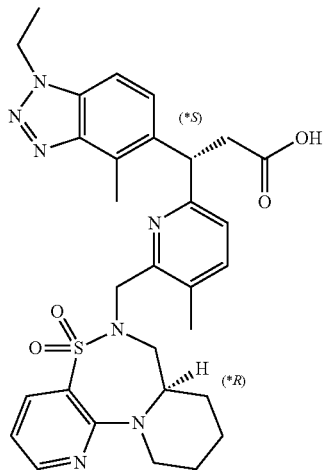

The mixture of 3-(6-(((*R)-5,5-dioxido-7,7a,8,9,10,11-hexahydro-6H-dipyrido[2,1-d:2',3'-][1,2,5]thiadiazepin-6-yl)methyl)-5-methylpyridin-2-yl)-3-(1-ethyl-4-methyl-1H-benzo[d][1,2,3]triazol-5-yl)propanoic acid isomers (Example 304, 89 mg) were separated by chiral SFC (stationary phase: Chiralpak AD-H 5 μm 3×25 cm; mobile phase: 45% ethanol, 55% CO$_2$) to afford two diastereoisomers. The first eluting isomer (40 mg) was designated (*S): MS (ESI): mass calcd. for $C_{30}H_{35}N_7O_4S$, 589.2; m/z found, 590.2 [M+H]$^+$. $^1$H NMR (500 MHz, DMSO-d$_6$) δ 12.12 (s, 1H), 8.32-8.29 (m, 1H), 7.98 (dd, J=7.8, 1.8 Hz, 1H), 7.58 (d, J=8.7 Hz, 1H), 7.53-7.50 (m, 1H), 7.47 (d, J=8.7 Hz, 1H), 7.26 (d, J=7.8 Hz, 1H), 6.93-6.89 (m, 1H), 4.96 (t, J=7.7 Hz, 1H), 4.68-4.61 (m, 2H), 4.53 (d, J=13.7 Hz, 1H), 4.44-4.36 (m, 1H), 4.25-4.14 (m, 2H), 3.55-3.46 (m, 1H), 3.29-3.20 (m, 2H), 3.18-3.11 (m, 1H), 3.04-2.95 (m, 1H), 2.84 (s, 3H), 2.19 (s, 3H), 1.68-1.50 (m, 3H), 1.47-1.42 (m, 3H), 1.33-1.16 (m, 3H).

Example 306: (*R)-3-(6-(((*R)-5,5-Dioxido-7,7a,8,9,10,11-hexahydro-6H-dipyrido[2,1-d:2',3'-f][1,2,5]thiadiazepin-6-yl)methyl)-5-methylpyridin-2-yl)-3-(1-ethyl-4-methyl-1H-benzo[d][1,2,3]triazol-5-yl)propanoic Acid

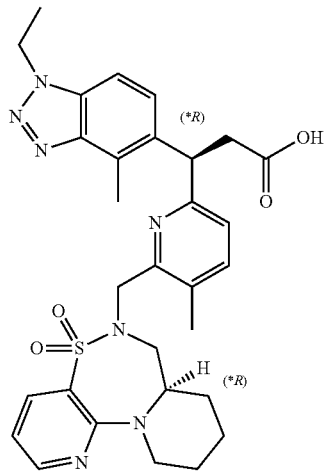 [SMILES: CCn1nnc2c(C)c([C@@H](CC(=O)O)c3ccc(C)c(CN4C[C@H]5CCCCN5c5ncccc5S4(=O)=O)n3)ccc21]

The second eluting isomer (42 mg) from the chiral separation described in Example 305 was designated (*R): MS (ESI): mass calcd. for $C_{30}H_{35}N_7O_4S$, 589.2; m/z found, 590.2 [M+H]$^+$. $^1$H NMR (500 MHz, DMSO-d$_6$) δ 12.06 (s, 1H), 8.34-8.29 (m, 1H), 7.99 (dd, J=7.8, 1.8 Hz, 1H), 7.57 (d, J=8.7 Hz, 1H), 7.49 (d, J=7.9 Hz, 1H), 7.42 (d, J=8.7 Hz, 1H), 7.19 (d, J=7.8 Hz, 1H), 6.92 (dd, J=7.8, 4.6 Hz, 1H), 5.01-4.95 (m, 1H), 4.69-4.63 (m, 2H), 4.53 (d, J=14.3 Hz, 1H), 4.47-4.40 (m, 1H), 4.29 (d, J=14.3 Hz, 1H), 4.23-4.17 (m, 1H), 3.73-3.63 (m, 1H), 3.44-3.34 (m, 3H), 2.97-2.90 (m, 1H), 2.85 (s, 3H), 2.17 (s, 3H), 1.76-1.56 (m, 3H), 1.52-1.39 (m, 6H).

Example 307: (*S)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoic Acid

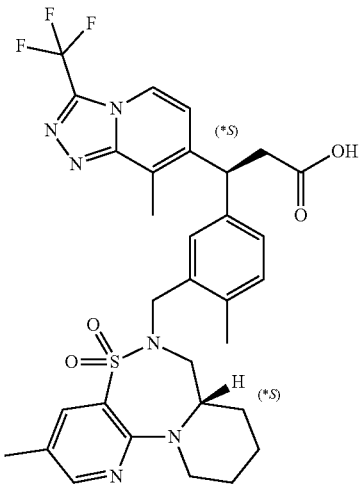 [SMILES: Cc1cnc2c(c1)S(=O)(=O)N(Cc1cc([C@H](CC(=O)O)c3ccn4c(C(F)(F)F)nnc4c3C)ccc1C)C[C@@H]1CCCCN21]

The title compound (82 mg) was prepared using analogous conditions as described in Example 26 using (*S)-3-methyl-7,7a,8,9,10,11-hexahydro-6H-dipyrido[2,1-d:2',3'-f][1,2,5]thiadiazepine 5,5-dioxide (Intermediate 77) instead of 2,3-dihydrospiro[benzo[b][1,4,5]oxathiazepine-4,3'-oxetane] 1,1-dioxide in Step A. MS (ESI): mass calcd. for $C_{31}H_{33}F_3N_6O_4S$, 642.2; m/z found, 643.1 [M+H]$^+$. $^1$H NMR (400 MHz, CDCl$_3$) δ 8.17-8.11 (m, 1H), 8.03-7.98 (d, J=7.2 Hz, 1H), 7.89-7.85 (m, 1H), 7.21-7.17 (d, J=2.0 Hz, 1H), 7.16-7.11 (m, 1H), 7.08-7.03 (m, 1H), 6.91-6.88 (d, J=7.2 Hz, 1H), 4.97-4.90 (m, 1H), 4.51-4.37 (m, 2H), 4.30-4.22 (m, 1H), 4.22-4.11 (m, 1H), 3.31-3.23 (m, 2H), 3.23-3.12 (m, 2H), 3.10-2.99 (m, 1H), 2.87-2.78 (s, 3H), 2.28-2.26 (s, 3H), 2.26-2.24 (s, 3H), 1.79-0.78 (m, 6H).

Example 308: (*S)-3-(4-methyl-3-(((*R)-3-methyl-5,5-dioxido-7,7a,8,9,10,11-hexahydro-6H-dipyrido[2,1-d:2',3'-][1,2,5]thiadiazepin-6-yl)methyl)phenyl)-3-(8-methyl-3-(trifluoromethyl)-[1,2,4]triazolo[4,3-a]pyridin-7-yl)propanoic Acid

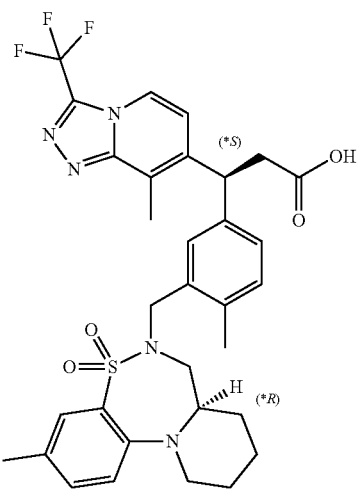 [SMILES: Cc1ccc2c(c1)S(=O)(=O)N(Cc1cc([C@H](CC(=O)O)c3ccn4c(C(F)(F)F)nnc4c3C)ccc1C)C[C@H]1CCCCN21]

The title compound (142 mg) was prepared using analogous conditions as described in Example 26 using (*R)-3-methyl-7,7a,8,9,10,11-hexahydro-6H-dipyrido[2,1-d:2',3'-f][1,2,5]thiadiazepine 5,5-dioxide (Intermediate 117) instead of 2,3-dihydrospiro[benzo[b][1,4,5]oxathiazepine-4,3'-oxetane] 1,1-dioxide in Step A and ethanol as a co-solvent in Step B. MS (ESI): mass calcd. for $C_{31}H_{33}F_3N_6O_4S$, 642.2; m/z found, 643.1 [M+H]$^+$. $^1$H NMR (400 MHz, CDCl$_3$) δ 8.16-8.10 (m, 1H), 8.00 (d, J=7.2 Hz, 1H), 7.90-7.84 (m, 1H), 7.19-7.11 (m, 2H), 7.10-7.04 (m, 1H), 6.87 (d, J=7.3 Hz, 1H), 4.99-4.92 (m, 1H), 4.48-4.39 (m, 2H), 4.21 (d, J=14.7 Hz, 1H), 4.18-4.10 (m, 1H), 3.23-3.11 (m, 4H), 3.08-2.98 (m, 1H), 2.85 (s, 3H), 2.27 (s, 6H), 1.71-1.23 (m, 6H).

Example 309: (*S)-3-(3-(((*S)-3-fluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

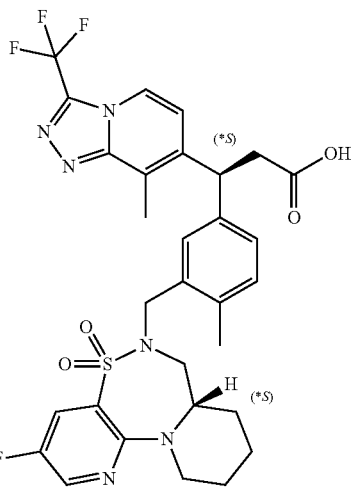

The title compound (181 mg) was prepared using analogous conditions as described in Example 26 using (*S)-3-fluoro-7,7a,8,9,10,11-hexahydro-6H-dipyrido[2,1-d:2',3'-f][1,2,5]thiadiazepine 5,5-dioxide (Intermediate 78) instead of 2,3-dihydrospiro[benzo[b][1,4,5]oxathiazepine-4,3'-oxetane] 1,1-dioxide in Step A. MS (ESI): mass calcd. for $C_{30}H_{30}F_4N_6O_4S$, 646.2; m/z found, 647.1 [M+H]$^+$. $^1$H NMR (500 MHz, CDCl$_3$) δ 8.19 (d, J=2.9 Hz, 1H), 8.01 (d, J=7.2 Hz, 1H), 7.82-7.78 (m, 1H), 7.19 (d, J=1.9 Hz, 1H), 7.16-7.12 (m, 1H), 7.09-7.05 (m, 1H), 6.91 (d, J=7.3 Hz, 1H), 4.98-4.90 (m, 1H), 4.52-4.38 (m, 2H), 4.25 (d, J=15.1 Hz, 1H), 4.21-4.11 (m, 1H), 3.32-3.24 (m, 2H), 3.24-3.13 (m, 2H), 3.10-3.01 (m, 1H), 2.82 (s, 3H), 2.25 (s, 3H), 1.82-1.36 (m, 6H).

Example 310: (*S)-3-(3-(((*R)-3-fluoro-5,5-di-oxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

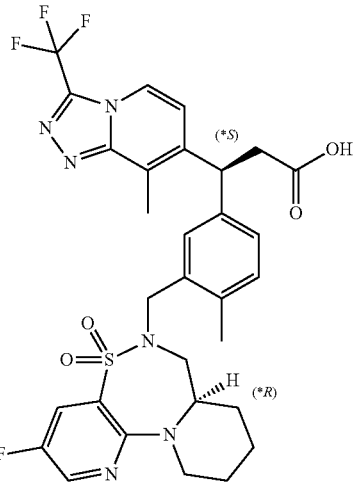

The title compound (250 mg) was prepared using analogous conditions as described in Example 26 using (*R)-3-fluoro-7,7a,8,9,10,11-hexahydro-6H-dipyrido[2,1-d:2',3'-f][1,2,5]thiadiazepine 5,5-dioxide (Intermediate 79) instead of 2,3-dihydrospiro[benzo[b][1,4,5]oxathiazepine-4,3'-oxetane] 1,1-dioxide in Step A. MS (ESI): mass calcd. for C$_{30}$H$_{30}$F$_4$N$_6$O$_4$S, 646.2; m/z found, 647.2 [M+H]$^+$. $^1$H NMR (500 MHz, CDCl$_3$) δ 8.18 (d, J=3.0 Hz, 1H), 8.01 (d, J=7.3 Hz, 1H), 7.83-7.78 (m, 1H), 7.18-7.13 (m, 2H), 7.12-7.07 (m, 1H), 6.88 (d, J=7.2 Hz, 1H), 4.98-4.92 (m, 1H), 4.50-4.38 (m, 2H), 4.21 (d, J=14.7 Hz, 1H), 4.18-4.10 (m, 1H), 3.27-3.13 (m, 4H), 3.09-3.01 (m, 1H), 2.84 (s, 3H), 2.27 (s, 3H), 1.76-1.25 (m, 6H).

Example 311: (*S)-3-(3-((8'-Fluoro-1',1'-dioxidospiro[cyclopropane-1,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic Acid

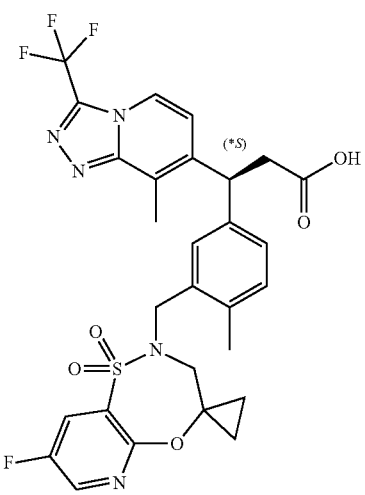 [SMILES: Cc1ccc([C@H](CC(=O)O)c2ccn3c(C(F)(F)F)nnc3c2C)cc1CN1CC2(CC2)Oc2ncc(F)cc2S1(=O)=O]

The title compound (68 mg) was prepared using analogous conditions as described in Example 26 using 8'-fluoro-2',3'-dihydrospiro[cyclopropane-1,4'-pyrido[2,3-b][1,4,5]oxathiazepine] 1',1'-dioxide (Intermediate 80) instead of 2,3-dihydrospiro[benzo[b][1,4,5]oxathiazepine-4,3'-oxetane] 1,1-dioxide in Step A. MS (ESI): mass calcd. for C$_{28}$H$_{25}$F$_4$N$_5$O$_5$S, 619.2; m/z found, 620.1 [M+H]$^+$. $^1$H NMR (400 MHz, CDCl$_3$) δ 8.28 (d, J=3.0 Hz, 1H), 8.03-7.98 (m, 2H), 7.17-7.10 (m, 2H), 7.07-7.02 (m, 1H), 6.86 (d, J=7.2 Hz, 1H), 4.97-4.89 (m, 1H), 4.40-4.28 (m, 2H), 3.55 (s, 2H), 3.21-3.11 (m, 1H), 3.06-2.97 (m, 1H), 2.81 (s, 3H), 2.28 (s, 3H), 1.23-1.10 (m, 2H), 0.62-0.48 (m, 2H).

Example 312: (*S)-3-(3-((3-Cyano-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

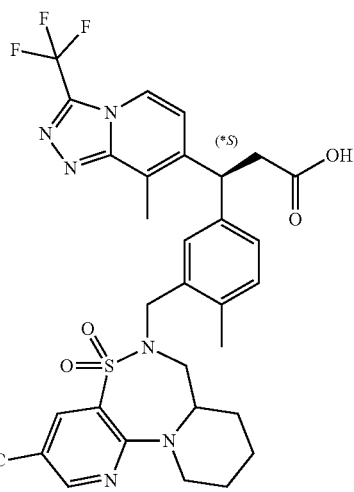

The title compound (934 mg) was prepared using analogous conditions as described in Example 26 using 7,7a,8,9,10,11-hexahydro-6H-dipyrido[2,1-d:2',3'-f][1,2,5]thiadiazepine-3-carbonitrile 5,5-dioxide (Intermediate 9) instead of 2,3-dihydrospiro[benzo[b][1,4,5]oxathiazepine-4,3'-oxetane] 1,1-dioxide in Step A. MS (ESI): mass calcd. for C$_{31}$H$_{30}$F$_3$N$_7$O$_4$S, 653.2; m/z found, 654.0 [M+H]$^+$. $^1$H NMR (400 MHz, DMSO-d$_6$) δ 12.32 (s, 1H), 8.67 (d, J=2.2 Hz, 1H), 8.47-8.39 (m, 2H), 7.34-7.13 (m, 4H), 4.88-4.76 (m, 1H), 4.53-4.07 (m, 4H), 3.38-3.08 (m, 5H), 2.79-2.71 (m, 3H), 2.16-2.10 (m, 3H), 1.69-1.12 (m, 6H).

575

Example 313: 2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

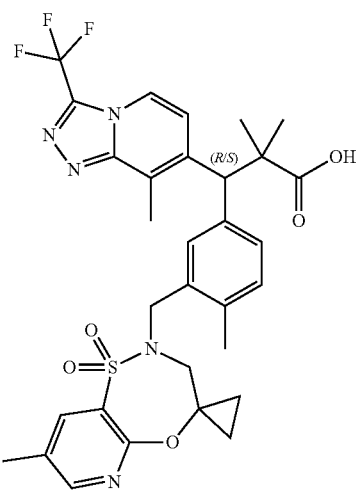 [SMILES: Cc1cnc2c(c1)S(=O)(=O)N(Cc1cc(C(c3ccn4c(C(F)(F)F)nnc4c3C)C(C)(C)C(=O)O)ccc1C)CC1(CC1)O2]

Step A: Methyl 2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate. Di-tert-butyl azodicarboxylate (204 mg, 0.865 mmol) was added to a mixture of 3-(3-(hydroxymethyl)-4-methylphenyl)-2,2-dimethyl-3-(8-methyl-3-(trifluomethyl)-[,2,4]triazolo[4,3-a]pyridine-7-yl)propanoate (Intermediate 48, 222 mg, 0.51 mmol), 8'-methyl-2',3'-dihydrospiro[cyclopropane-1,4'-pyrido[2,3-b][1,4,5]oxathiazepine] 1',1'-dioxide (Intermediate 6, 162 mg, 0.672 mmol), and triphenylphosphine (204 mg, 0.768 mmol) in THF (6.7 mL). After stirring overnight, the mixture was directly loaded onto silica gel for purification by flash column chromatography (ethyl acetate-hexanes) to afford the title compound (352 mg) which was used in the next step without further purification. MS (ESI): mass calcd. for $C_{32}H_{34}F_3N_5O_5S$, 657.2; m/z found, 658.2 [M+H]$^+$.

Step B: 2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid. Methyl 2,2-dimethyl-3-[4-methyl-3-[(8'-methyl-1,1-dioxospiro[3H-pyrido[2,3-b][1,4,5]oxathiazepine-4,1'-cyclopropane]-2-yl)methyl]phenyl]-3-[8-methyl-3-(trifluoromethyl)-[1,2,4]triazolo[4,3-a]pyridin-7-yl]propanoate (352 mg, 0.535 mmol) was dissolved in pyridine (15 mL) and the mixture was flushed with argon. Lithium iodide (291 mg, 2.17 mmol) was added and the mixture was heated in a microwave reactor at 150° C. for 2 hours. The mixture was concentrated and purified by basic reverse phase HPLC ($C_{18}$, acetonitrile-water, 20 nM NH$_4$OH). MS (ESI): mass calcd. for $C_{31}H_{32}F_3N_5O_5S$, 643.2; m/z found, 644.2

576

[M+H]$^+$. $^1$H NMR (400 MHz, DMSO-d$_6$) δ 12.54 (s, 1H), 8.38 (d, J=7.1 Hz, 1H), 8.33 (d, J=2.2 Hz, 1H), 8.08 (d, J=2.3 Hz, 1H), 7.27 (d, J=7.3 Hz, 1H), 7.23-7.15 (m, 1H), 7.15-7.05 (m, 2H), 4.76 (s, 1H), 4.25-4.10 (m, 2H), 3.61-3.17 (m, 2H), 2.61 (s, 3H), 2.37 (s, 3H), 2.24 (s, 3H), 1.32-1.14 (m, 6H), 0.97-0.81 (m, 2H), 0.64-0.44 (m, 2H).

Example 314: (*S)-2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

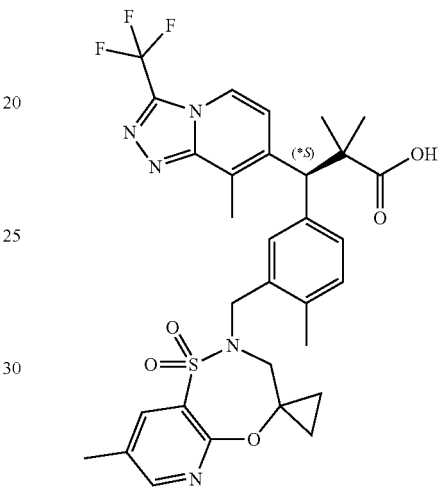

The mixture of 2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid isomers (Example 313, 215 mg) were separated by chiral SFC (stationary phase: Chiralpak IG 5 μm 2×25 cm; mobile phase: 30% ethanol-DCM (4:1), 70% CO$_2$) to afford two enantiomers. The first eluting isomer (67 mg) was designated (*S): MS (ESI): mass calcd. for $C_{31}H_{32}F_3N_5O_5S$, 643.2; m/z found, 644.3 [M+H]$^+$. $^1$H NMR (400 MHz, DMSO-d$_6$) δ 12.49 (s, 1H), 8.39 (d, J=7.3 Hz, 1H), 8.33 (dd, J=2.2, 0.9 Hz, 1H), 8.08 (dd, J=2.2, 0.9 Hz, 1H), 7.25 (d, J=7.4 Hz, 1H), 7.23-7.17 (m, 1H), 7.17-7.07 (m, 2H), 4.77 (s, 1H), 4.26-4.11 (m, 2H), 3.65-3.36 (m, 2H), 2.62 (s, 3H), 2.37 (s, 3H), 2.24 (s, 3H), 1.28 (s, 3H), 1.22 (s, 3H), 0.97-0.81 (m, 2H), 0.63-0.45 (m, 2H).

Example 315: (*R)-2,2-Dimethyl-3-(4-methyl-3-((8'-methyl-1',1'-dioxidospiro[cyclopropane-1,4'-pyrido[2,3-b][1,4,5]oxathiazepine]-2'(3'H)-yl)methyl)phenyl)-3-(8-methyl-3-(trifluoromethyl)-[1,2,4]triazolo[4,3-a]pyridin-7-yl)propanoic Acid

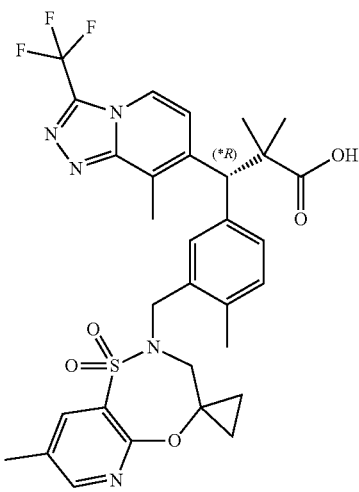 [SMILES: Cc1cnc2c(c1)S(=O)(=O)N(Cc1cc([C@H](c3ccn4c(C(F)(F)F)nnc4c3C)C(C)(C)C(=O)O)ccc1C)CC1(CC1)O2]

The second eluting isomer (70 mg) from the chiral separation described in Example 314 was designated (*R): MS (ESI): mass calcd. for $C_{31}H_{32}F_3N_5O_5S$, 643.2; m/z found, 644.4 [M+H]$^+$. $^1$H NMR (400 MHz, DMSO-d$_6$) δ 12.53 (s, 1H), 8.39 (d, J=7.3 Hz, 1H), 8.34-8.29 (m, 1H), 8.08 (d, J=2.3 Hz, 1H), 7.26 (d, J=7.3 Hz, 1H), 7.21-7.16 (m, 1H), 7.16-7.07 (m, 2H), 4.77 (s, 1H), 4.25-4.09 (m, 2H), 3.59-3.39 (m, 2H), 2.62 (s, 3H), 2.37 (s, 3H), 2.24 (s, 3H), 1.27 (s, 3H), 1.21 (s, 3H), 0.96-0.83 (m, 2H), 0.62-0.44 (m, 2H).

Example 316: 3-(3-((1',1'-Dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

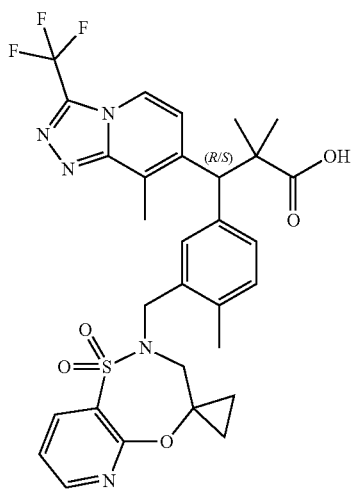

The title compound (157 mg) was prepared using analogous conditions as described in Example 61 using 2',3'-dihydrospiro[cyclopropane-1,4'-pyrido[2,3-b][1,4,5]oxathiazepine] 1',1'-dioxide (Intermediate 5) instead of 8'-methyl-2',3'-dihydrospiro[cyclopropane-1,4'-pyrido[2,3-b][1,4,5]oxathiazepine] 1',1'-dioxide in Step A. $^1$H NMR (400 MHz, DMSO-d$_6$) δ 8.54-8.50 (m, 1H), 8.39 (d, J=7.3 Hz, 1H), 8.26 (dd, J=7.6, 1.9 Hz, 1H), 7.53-7.48 (m, 1H), 7.28 (d, J=7.3 Hz, 1H), 7.21-7.15 (m, 1H), 7.14-7.08 (m, 2H), 4.76 (s, 1H), 4.26-4.11 (m, 2H), 3.62-3.39 (m, 2H), 2.61 (s, 3H), 2.24 (s, 3H), 1.26 (s, 3H), 1.19 (s, 3H), 0.98-0.84 (m, 2H), 0.66-0.49 (m, 2H).

Example 317: (*S)-3-(3-((1',1'-Dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

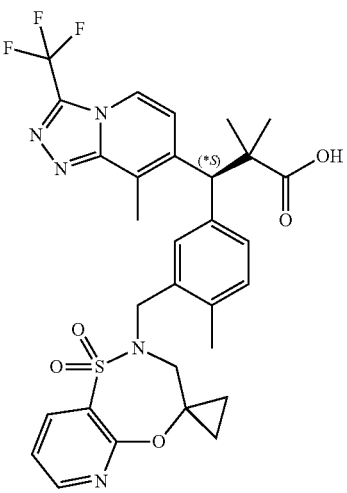 [SMILES: Cc1ccc([C@@H](c2ccn3c(C(F)(F)F)nnc3c2C)C(C)(C)C(=O)O)cc1CN1CC2(CC2)Oc2ncccc2S1(=O)=O]

The mixture of 3-(3-((1',1'-Dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid isomers (Example 316, 150 mg) were separated by chiral SFC (stationary phase: Chiralpak IG 5 μm 2×25 cm; mobile phase: 30% ethanol-DCM (4:1), 70% CO$_2$) to afford two enantiomers. The first eluting isomer (22 mg) was designated (*S): MS (ESI): mass calcd. for $C_{30}H_{30}F_3N_5O_5S$, 629.2; m/z found, 630.3 [M+H]$^+$. $^1$H NMR (400 MHz, DMSO-d$_6$) δ 12.48 (s, 1H), 8.54-8.50 (m, 1H), 8.40 (d, J=7.2 Hz, 1H), 8.26 (dd, J=7.6, 1.9 Hz, 1H), 7.54-7.48 (m, 1H), 7.26 (d, J=7.3 Hz, 1H), 7.22-7.17 (m, 1H), 7.15-7.09 (m, 2H), 4.77 (s, 1H), 4.28-4.14 (m, 2H), 3.61-3.38 (m, 2H), 2.62 (s, 3H), 2.24 (s, 3H), 1.28 (s, 3H), 1.22 (s, 3H), 0.98-0.84 (m, 2H), 0.66-0.50 (m, 2H).

Example 318: (*R)-3-(3-((1',1'-Dioxidospiro[cyclo-propane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

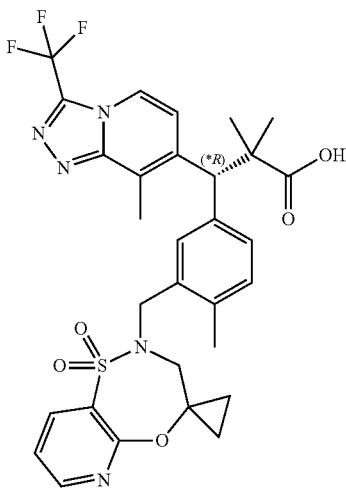 [SMILES: Cc1ccc([C@H](c2ccn3c(C(F)(F)F)nnc3c2C)C(C)(C)C(=O)O)cc1CN1CC2(CC2)Oc2ncccc2S1(=O)=O]

The second eluting isomer (22 mg) from the chiral separation described in Example 317 was designated (*R): MS (ESI): mass calcd. for $C_{30}H_{30}F_3N_5O_5S$, 629.2; m/z found, 630.3 [M+H]⁺. ¹H NMR (400 MHz, DMSO-d₆) δ 8.54-8.48 (m, 1H), 8.39 (d, J=7.2 Hz, 1H), 8.26 (dd, J=7.6, 1.9 Hz, 1H), 7.53-7.47 (m, 1H), 7.29 (d, J=7.2 Hz, 1H), 7.21-7.15 (m, 1H), 7.15-7.06 (m, 2H), 4.76 (s, 1H), 4.26-4.12 (m, 2H), 3.63-3.39 (m, 2H), 2.61 (s, 3H), 2.24 (s, 3H), 1.26 (s, 3H), 1.19 (s, 3H), 0.97-0.81 (m, 2H), 0.67-0.49 (m, 2H).

Example 319: 3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(3-(trifluoromethyl)-[1,2,4]triazolo[4,3-a]pyridin-7-yl)propanoic Acid

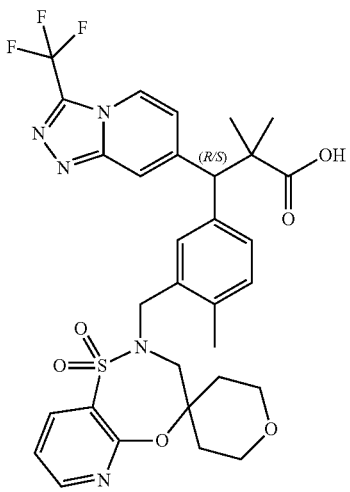 [SMILES: Cc1ccc(C(c2ccn3c(C(F)(F)F)nnc3c2)C(C)(C)C(=O)O)cc1CN1CC2(CCOCC2)Oc2ncccc2S1(=O)=O]

Step A: Methyl 3-(3-(hydroxymethyl)-4-methylphenyl)-2,2-dimethyl-3-(3-(trifluoromethyl)-[1,2,4]triazolo[4,3-a]pyridin-7-yl)propanoate. A 25% solution of sodium methoxide in methanol (1 mL) was added to a solution of methyl 2,2-dimethyl-3-(4-methyl-3-((pivaloyloxy)methyl)phenyl)-3-(3-(trifluoromethyl)-[1,2,4]triazolo[4,3-a]pyridin-7-yl)propanoate (Intermediate 122, 438 mg, 0.866 mmol) in methanol (2 mL). After 2 hours, the mixture was partitioned between saturated aqueous ammonium chloride solution and ethyl acetate. The layers were separated, and the organic extracts were dried over anhydrous Na₂SO₄, filtered, and concentrated to dryness under reduced pressure to afford the title compound as an amber oil. MS (ESI): mass calcd. for $C_{21}H_{22}F_3N_3O_3$, 421.2; m/z found, 422.1 [M+H]⁺.

Step B: 3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(3-(trifluoromethyl)-[1,2,4]triazolo[4,3-a]pyridin-7-yl)propanoic acid. The title compound (150 mg) was prepared using analogous conditions as described in Example 26 using methyl 3-(3-(hydroxymethyl)-4-methylphenyl)-2,2-dimethyl-3-(3-(trifluoromethyl)-[1,2,4]triazolo[4,3-a]pyridin-7-yl)propanoate instead of (*S)-3-(3-(hydroxymethyl)-4-methylphenyl)-3-(8-methyl-3-(trifluoromethyl)-[1,2,4]triazolo[4,3-a]pyridin-7-yl)propanoate and 2,2',3,3',5,6-hexahydrospiro[pyran-4,4'-pyrido[2,3-b][1,4,5]oxathiazepine] 1',1'-dioxide (Intermediate 36) was used instead of 2,3-dihydrospiro[benzo[b][1,4,5]oxathiazepine-4,3'-oxetane] 1,1-dioxide in Step A. MS (ESI): mass calcd. for $C_{31}H_{32}F_3N_5O_6S$, 659.2; m/z found, 660.2 [M+H]⁺. ¹H NMR (500 MHz, DMSO-d₆) δ 12.55 (s, 1H), 8.54 (dd, J=4.9, 1.9 Hz, 1H), 8.48 (d, J=7.2 Hz, 1H), 8.17 (dd, J=7.6, 1.9 Hz, 1H), 7.98-7.94 (m, 1H), 7.45-7.41 (m, 1H), 7.30 (d, J=1.9 Hz, 1H), 7.27-7.22 (m, 1H), 7.19-7.14 (m, 1H), 7.04-7.00 (m, 1H), 4.59 (s, 1H), 4.45 (s, 2H), 3.82-3.71 (m, 2H), 3.63-3.33 (m, 4H), 2.20 (s, 3H), 1.56-1.42 (m, 4H), 1.30-1.22 (m, 6H).

Example 320: (*S)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(3-(trifluoromethyl)-[1,2,4]triazolo[4,3-a]pyridin-7-yl)propanoic Acid

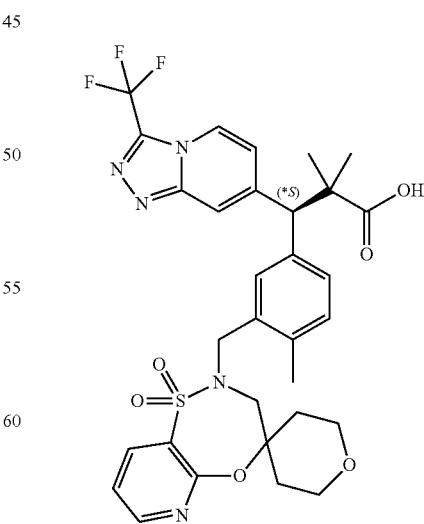

The mixture of 3-(3-((1',1'-dioxido-2,3,5,6-tetrahydrospiro[pyran-4,4'-pyrido[2,3-b][1,4,5]oxathiazepin]-2'

(3'H)-yl)methyl)-4-methylphenyl)-2,2-dimethyl-3-(3-(trifluoromethyl)-[1,2,4]triazolo[4,3-a]pyridin-7-yl)propanoic acid isomers (Example 319, 146 mg) were separated by chiral SFC (stationary phase: Chiralpak AD-H 5 μm 2×25 cm; mobile phase: 45% ethanol, 55% $CO_2$) to afford two enantiomers. The first eluting isomer (63 mg) was designated (*S): MS (ESI): mass calcd. for $C_{31}H_{32}F_3N_5O_6S$, 659.2; m/z found, 660.3 [M+H]$^+$. $^1$H NMR (400 MHz, DMSO-$d_6$) δ 12.53 (s, 1H), 8.56-8.51 (m, 1H), 8.48 (d, J=7.1 Hz, 1H), 8.19-8.13 (m, 1H), 7.96 (s, 1H), 7.45-7.40 (m, 1H), 7.30 (d, J=2.0 Hz, 1H), 7.27-7.22 (m, 1H), 7.17-7.13 (m, 1H), 7.02 (dd, J=7.2, 1.7 Hz, 1H), 4.59 (s, 1H), 4.48-4.41 (m, 2H), 3.84-3.69 (m, 2H), 3.64-3.38 (m, 4H), 2.20 (s, 3H), 1.55-1.42 (m, 4H), 1.27 (s, 3H), 1.25 (s, 3H).

Example 321: (*R)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(3-(trifluoromethyl)-[1,2,4]triazolo[4,3-a]pyridin-7-yl)propanoic Acid

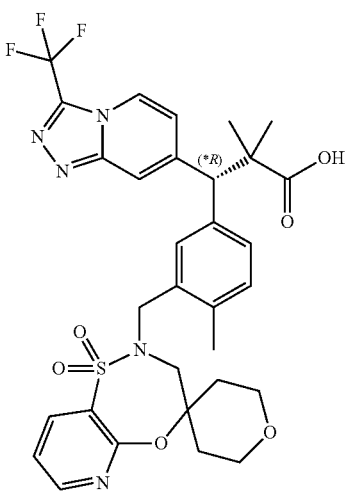 [SMILES: Cc1ccc([C@H](c2ccn3c(C(F)(F)F)nnc3c2)C(C)(C)C(=O)O)cc1CN1CC2(CCOCC2)Oc2ncccc2S1(=O)=O]

The second eluting isomer (61 mg) from the chiral separation described in Example 320 was designated (*R): MS (ESI): mass calcd. for $C_{31}H_{32}F_3N_5O_6S$, 659.2; m/z found, 660.3 [M+H]$^+$. $^1$H NMR (400 MHz, DMSO-$d_6$) δ 12.53 (s, 1H), 8.53 (dd, J=4.8, 2.0 Hz, 1H), 8.47 (d, J=7.2 Hz, 1H), 8.17 (dd, J=7.6, 1.9 Hz, 1H), 7.96 (s, 1H), 7.46-7.39 (m, 1H), 7.30 (d, J=2.0 Hz, 1H), 7.27-7.22 (m, 1H), 7.17-7.13 (m, 1H), 7.02 (dd, J=7.2, 1.7 Hz, 1H), 4.59 (s, 1H), 4.48-4.42 (m, 2H), 3.84-3.70 (m, 2H), 3.66-3.33 (m, 4H), 2.20 (s, 3H), 1.55-1.41 (m, 4H), 1.26 (s, 3H), 1.24 (s, 3H).

Example 322: 2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(3-(trifluoromethyl)-[1,2,4]triazolo[4,3-a]pyridin-7-yl)propanoic Acid

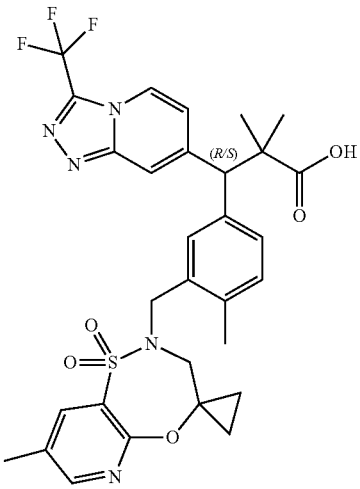 [SMILES: Cc1cnc2c(c1)S(=O)(=O)N(Cc1cc(C(c3ccn4c(C(F)(F)F)nnc4c3)C(C)(C)C(=O)O)ccc1C)CC1(CC1)O2]

The title compound (186 mg) was prepared using analogous conditions as described in Example 26 using methyl 3-(3-(hydroxymethyl)-4-methylphenyl)-2,2-dimethyl-3-(3-(trifluoromethyl)-[1,2,4]triazolo[4,3-a]pyridin-7-yl)propanoate (Example 319, Step A) instead of (*S)-3-(3-(hydroxymethyl)-4-methylphenyl)-3-(8-methyl-3-(trifluoromethyl)-[1,2,4]triazolo[4,3-a]pyridin-7-yl)propanoate and 8'-methyl-2',3'-dihydrospiro[cyclopropane-1,4'-pyrido[2,3-b][1,4,5]oxathiazepine] 1',1'-dioxide (Intermediate 6) instead of 2,3-dihydrospiro[benzo[b][1,4,5]oxathiazepine-4,3'-oxetane] 1,1-dioxide in Step A. MS (ESI): mass calcd. for $C_{30}H_{30}F_3N_5O_5S$, 629.2; m/z found, 630.3 [M+H]$^+$. $^1$H NMR (400 MHz, DMSO-$d_6$) δ 12.50 (s, 1H), 8.46 (d, J=7.1 Hz, 1H), 8.35-8.30 (m, 1H), 8.08 (dd, J=2.2, 0.9 Hz, 1H), 7.95 (s, 1H), 7.26-7.13 (m, 3H), 7.03-6.97 (m, 1H), 4.55 (s, 1H), 4.28-4.17 (m, 2H), 3.66-3.39 (m, 2H), 2.37 (s, 3H), 2.25 (s, 3H), 1.28-1.17 (m, 6H), 0.99-0.87 (m, 2H), 0.69-0.54 (m, 2H).

Example 323: (*S)-2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(3-(trifluoromethyl)-[1,2,4]triazolo[4,3-a]pyridin-7-yl)propanoic Acid

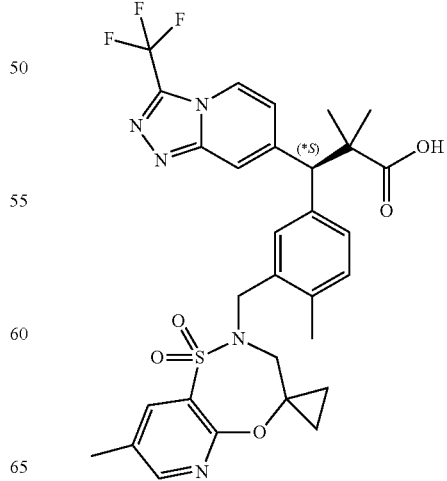

The mixture of 2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(3-(trifluoromethyl)-[1,2,4]triazolo[4,3-a]pyridin-7-yl)propanoic acid isomers (Example 322, 75 mg) were separated by chiral SFC (stationary phase: Chiralpak AD-H 5 μm 2×25 cm; mobile phase: 40% ethanol, 60% CO$_2$) to afford two enantiomers. The first eluting isomer (35 mg) was designated (*S): MS (ESI): mass calcd. for C$_{30}$H$_{30}$F$_3$N$_5$O$_5$S, 629.2; m/z found, 630.3 [M+H]$^+$. $^1$H NMR (400 MHz, DMSO-d$_6$) δ 12.50 (s, 1H), 8.46 (d, J=7.1 Hz, 1H), 8.35-8.30 (m, 1H), 8.08 (d, J=2.3 Hz, 1H), 7.95 (s, 1H), 7.25-7.14 (m, 3H), 7.01-6.97 (m, 1H), 4.55 (s, 1H), 4.29-4.16 (m, 2H), 3.64-3.51 (m, 2H), 2.37 (s, 3H), 2.25 (s, 3H), 1.27-1.20 (m, 6H), 0.99-0.86 (m, 2H), 0.68-0.54 (m, 2H).

Example 324: (*R)-2,2-Dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(3-(trifluoromethyl)-[1,2,4]triazolo[4,3-a]pyridin-7-yl)propanoic Acid

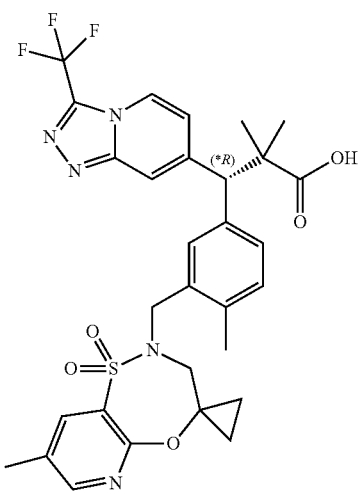 [SMILES: Cc1cnc2c(c1)S(=O)(=O)N(Cc1cc([C@H](c3ccn4c(C(F)(F)F)nnc4c3)C(C)(C)C(=O)O)ccc1C)CC1(CC1)O2]

The second eluting isomer (31 mg) from the chiral separation described in Example 323 was designated (*R): MS (ESI): mass calcd. for C$_{30}$H$_{30}$F$_3$N$_5$O$_5$S, 629.2; m/z found, 630.3 [M+H]$^+$. $^1$H NMR (400 MHz, DMSO-d$_6$) δ 8.44 (d, J=7.1 Hz, 1H), 8.34-8.29 (m, 1H), 8.11-8.06 (m, 1H), 7.95 (s, 1H), 7.23-7.11 (m, 3H), 6.99 (dd, J=7.3, 1.7 Hz, 1H), 4.54 (s, 1H), 4.27-4.13 (m, 2H), 3.66-3.38 (m, 2H), 2.37 (s, 3H), 2.25 (s, 3H), 1.21-1.14 (m, 6H), 0.98-0.84 (m, 2H), 0.69-0.53 (m, 2H).

Example 325: (*S)-2,2-Dimethyl-3-(8-methyl-3-(trifluoromethyl)-[1,2,4]triazolo[4,3-a]pyridin-7-yl)-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic Acid

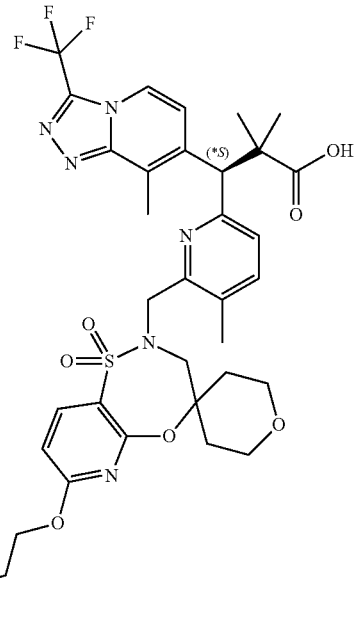

Step A: 2,2-Dimethyl-3-(8-methyl-3-(trifluoromethyl)-[1,2,4]triazolo[4,3-a]pyridin-7-yl)-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid. The title compound (90 mg) was prepared using analogous conditions as described in Example 38 using 7'-(2-morpholinoethoxy)-2,2',3,3',5,6-hexahydrospiro[pyran-4,4'-pyrido[2,3-b][1,4,5]oxathiazepine] 1',1'-dioxide (Intermediate 146) instead of 2,2',3,3',5,6-hexahydrospiro[pyran-4,4'-pyrido[2,3-b][1,4,5]oxathiazepine] 1',1'-dioxide in Step D.

Step B: (*S)-2,2-Dimethyl-3-(8-methyl-3-(trifluoromethyl)-[1,2,4]triazolo[4,3-a]pyridin-7-yl)-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid. The mixture of 2,2-Dimethyl-3-(8-methyl-3-(trifluoromethyl)-[1,2,4]triazolo[4,3-a]pyridin-7-yl)-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid isomers (85 mg) were separated by chiral SFC (stationary phase: Chiralpak AD-H 2×25 cm; mobile phase: 20% ethanol with 0.1% ammonium hydroxide, 80% CO$_2$) to afford two enantiomers. The first eluting isomer (39 mg) was designated (*S): MS (ESI): mass calcd. for C$_{37}$H$_{44}$F$_3$N$_7$O$_8$S, 803.3; m/z found, 804.3 [M+H]$^+$. $^1$H NMR (400 MHz, CDCl$_3$) δ 8.06 (d, J=8.5 Hz, 1H), 7.96 (d, J=7.4 Hz, 1H), 7.51 (d, J=8.2 Hz, 1H), 7.29-7.26 (m, 1H coincident with chloroform), 7.07 (d, J=7.9 Hz, 1H), 6.68 (d, J=8.5 Hz, 1H), 4.79 (s, 1H), 4.72-4.66 (m, 1H), 4.57-4.47 (m, 3H), 4.12-4.03 (m, 2H), 3.85-3.72 (m, 8H), 2.94 (s, 3H), 2.80 (t, J=5.8 Hz, 2H), 2.61-2.55 (m, 4H), 2.37 (s, 3H), 1.86-1.72 (m, 4H coincident with water), 1.42 (s, 3H), 1.41 (s, 3H).

Example 326: (*R)-2,2-Dimethyl-3-(8-methyl-3-(trifluoromethyl)-[1,2,4]triazolo[4,3-a]pyridin-7-yl)-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic Acid

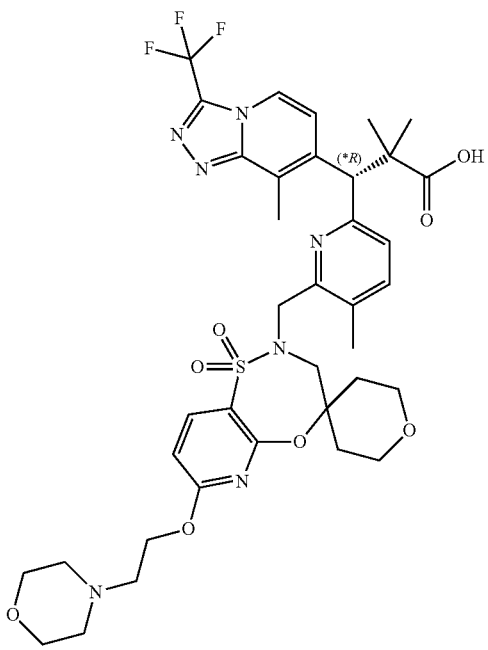 [SMILES: Cc1ccc([C@H](c2ccn3c(C(F)(F)F)nnc3c2C)C(C)(C)C(=O)O)nc1CN1CC2(CCOCC2)Oc2nc(OCCN3CCOCC3)ccc2S1(=O)=O]

The second eluting isomer (40 mg) from the chiral separation described in Example 325 was designated (*R): MS (ESI): mass calcd. for $C_{37}H_{44}F_3N_7O_8S$, 803.3; m/z found, 804.3 [M+H]$^+$. $^1$H NMR (400 MHz, CDCl$_3$) δ 8.06 (d, J=8.5 Hz, 1H), 7.95 (d, J=7.4 Hz, 1H), 7.51 (d, J=7.9 Hz, 1H), 7.25-7.23 (m, 1H), 7.07 (d, J=7.8 Hz, 1H), 6.68 (d, J=8.5 Hz, 1H), 4.79 (s, 1H), 4.72-4.66 (m, 1H), 4.57-4.47 (m, 3H), 4.12-4.03 (m, 2H), 3.86-3.72 (m, 8H), 2.94 (s, 3H), 2.80 (t, J=5.8 Hz, 2H), 2.60-2.56 (m, 4H), 2.37 (s, 3H), 1.88-1.73 (m, 4H), 1.43 (s, 3H), 1.41 (s, 3H).

Example 327: 3-(1-(Cyclopropylmethyl)-4-methyl-1H-benzo[d][1,2,3]triazol-5-yl)-2,2-dimethyl-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic Acid

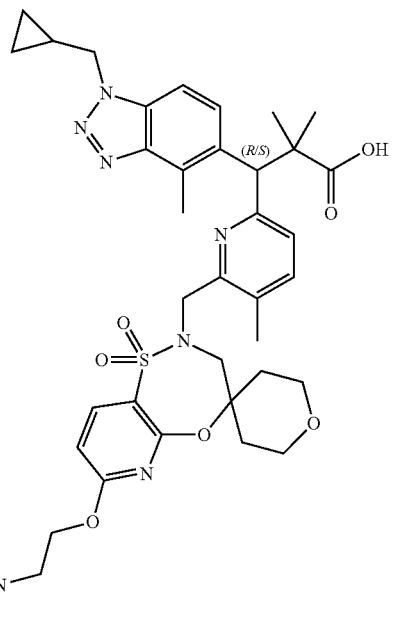

Step A: (6-(((tert-Butyldimethylsilyl)oxy)methyl)-5-methylpyridin-2-yl)(1-(cyclopropylmethyl)-4-methyl-1H-benzo[d][1,2,3]triazol-5-yl)methanol. A 1.6 M solution of n-butyllithium in hexanes (6 mL, 9.6 mmol) was added dropwise to a solution of 6-bromo-2-(((tert-butyldimethylsilyl)oxy)methyl)-3-methylpyridine (Intermediate 120, 3 g, 9.5 mmol) in THF (20 mL) which had been cooled to −78° C. After 30 seconds, a solution of 1-(cyclopropylmethyl)-4-methyl-1H-benzo[d][1,2,3]triazole-5-carbaldehyde (1.5 g, 6.7 mmol) in THF (14 mL) was added. After 2 minutes, saturated aqueous ammonium chloride solution (5 mL) was added and the flask was removed from the cooling bath. After reaching room temperature, the mixture was partitioned between ethyl acetate and water and the layers were separated. The organic extracts were dried over anhydrous sodium sulfate, filtered, and concentrated under reduced pressure. The residue was purified by reverse phase column chromatography (RediSep Gold C$_{18}$ column, eluting with water-acetonitrile with 0.05% v/v TFA) to afford the title compound (608 mg, 20%). MS (ESI): mass calcd. for $C_{25}H_{36}N_4O_2Si$, 452.3; m/z found, 453.3 [M+H]$^+$.

Step B: tert-Butyl 3-(6-(((tert-butyldimethylsilyl)oxy)methyl)-5-methylpyridin-2-yl)-3-(1-(cyclopropylmethyl)-4-methyl-1H-benzo[d][1,2,3]triazol-5-yl)-2,2-dimethylpropanoate. DBU (0.05 mL, 0.3 mmol) was added to a mixture of trichloroacetonitrile (0.3 mL, 3 mmol) and (6-(((tert-butyldimethylsilyl)oxy)methyl)-5-methylpyridin-2-yl)(1-(cyclopropylmethyl)-4-methyl-1H-benzo[d][1,2,3]triazol-5-yl)methanol (608 mg, 1.34 mmol) in acetonitrile (10 mL). After 1 hour, ((1-(tert-butoxy)-2-methylprop-1-en-1-yl)oxy)trimethylsilane (Intermediate 20, 1.5 g, 6.6 mmol) and then a solution of trifluoromethansulfonimide (275 mg, 1 mmol)

in acetonitrile (1 mL) were added in sequence. After 1 hour, saturated aqueous sodium bicarbonate solution was added and the mixture was partitioned between brine and ethyl acetate. The layers were separated. The organic extracts were dried over anhydrous sodium sulfate, filtered, and absorbed onto diatomaceous earth for purification by flash column chromatography (hexanes-ethyl acetate) to afford the title compound (368 mg, 47%). MS (ESI): mass calcd. for $C_{33}H_{50}N_4O_3Si$, 578.4; m/z found, 579.3 $[M+H]^+$.

Step C: tert-Butyl 3-(1-(cyclopropylmethyl)-4-methyl-1H-benzo[d][1,2,3]triazol-5-yl)-3-(6-(hydroxymethyl)-5-methylpyridin-2-yl)-2,2-dimethylpropanoate. A 1 M solution of TBAF in THF (1 mL, 1 mmol) was added to a solution of tert-butyl 3-(6-(((tert-butyldimethylsilyl)oxy)methyl)-5-methylpyridin-2-yl)-3-(1-(cyclopropylmethyl)-4-methyl-1H-benzo[d][1,2,3]triazol-5-yl)-2,2-dimethylpropanoate (368 mg, 0.636 mmol) in THF (4 ml). After 2 hours, the mixture was partitioned between saturated aqueous ammonium chloride solution and ethyl acetate. The layers were separated. The organic extracts were dried over anhydrous sodium sulfate, filtered, and absorbed onto diatomaceous earth purification by flash column chromatography (hexanes-ethyl acetate) to afford the title compound (266 mg, 90%). MS (ESI): mass calcd. for $C_{27}H_{36}N_4O_3$, 464.3; m/z found, 465.3 $[M+H]^+$. $^1$H NMR (400 MHz, DMSO-$d_6$) δ 7.59 (d, J=8.7 Hz, 1H), 7.43-7.35 (m, 1H), 7.28 (d, J=8.8 Hz, 1H), 6.81 (d, J=7.8 Hz, 1H), 5.07 (s, 1H), 4.71-4.64 (m, 1H), 4.64-4.59 (m, 1H), 4.59-4.56 (m, 1H), 4.56-4.50 (m, 2H), 2.85 (s, 3H), 2.19 (s, 3H), 1.39-1.28 (m, 3H), 1.20 (s, 9H), 1.10 (s, 3H), 0.57-0.40 (m, 4H).

Step D: tert-Butyl 3-(1-(cyclopropylmethyl)-4-methyl-1H-benzo[d][1,2,3]triazol-5-yl)-2,2-dimethyl-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoate. The title compound (372 mg) was prepared using analogous conditions as described in Example 38, Step D using tert-Butyl 3-(1-(cyclopropylmethyl)-4-methyl-1H-benzo[d][1,2,3]triazol-5-yl)-3-(6-(hydroxymethyl)-5-methylpyridin-2-yl)-2,2-dimethylpropanoate instead of methyl 3-(6-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate and 7'-(2-morpholinoethoxy)-2,2',3,3',5,6-hexahydrospiro[pyran-4,4'-pyrido[2,3-b][1,4,5]oxathiazepine] 1',1'-dioxide (Intermediate 146) instead of 2,2',3,3',5,6-hexahydrospiro[pyran-4,4'-pyrido[2,3-b][1,4,5]oxathiazepine] 1',1'-dioxide. MS (ESI): mass calcd. for $C_{44}H_{59}N_7O_8S$, 845.4; m/z found, 846.4 $[M+H]^+$. $^1$H NMR (400 MHz, CDCl$_3$) δ 8.07 (d, J=8.4 Hz, 1H), 7.62 (d, J=8.8 Hz, 1H), 7.34-7.29 (m, 2H), 6.91 (d, J=7.9 Hz, 1H), 6.64 (d, J=8.4 Hz, 1H), 5.07 (s, 1H), 4.79 (d, J=13.8 Hz, 1H), 4.53-4.38 (m, 5H), 4.10-4.02 (m, 2H), 3.81-3.59 (m, 8H), 1.52-1.44 (m, 3H), 2.95 (s, 3H), 2.83-2.74 (m, 2H), 2.63-2.53 (m, 4H), 2.36 (s, 3H), 1.95-1.85 (m, 1H), 1.77-1.57 (m, 4H), 1.42-1.32 (m, 1H), 1.21 (s, 11H), 0.66-0.59 (m, 2H), 0.50-0.43 (m, 2H).

Step E: 3-(1-(Cyclopropylmethyl)-4-methyl-1H-benzo[d][1,2,3]triazol-5-yl)-2,2-dimethyl-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid. TFA (1 mL) was added to a solution of tert-butyl 3-(1-(cyclopropylmethyl)-4-methyl-1H-benzo[d][1,2,3]triazol-5-yl)-2,2-dimethyl-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoate (344 mg, 0.407 mmol) in DCM (4 mL). The solution was heated at 50° C. After 3 hours, additional TFA (1 mL) was added and the mixture was stirred overnight. The mixture was allowed to cool to room temperature and then concentrated under reduced pressure. The residue was dissolved in water and the pH was adjusted to 4-5 by addition of 1 M aqueous HCl solution. The aqueous portion was extracted with ethyl acetate which resulted in multiple organic extracts which were combined, dried over anhydrous sodium sulfate, filtered, and concentrated under reduced pressure. The residue was purified by reverse phase column chromatography (XBridge OBD $C_{18}$ column, 50×250 mm, eluent: 20 mM aqueous ammonia-acetonitrile) to afford the title compound (221 mg, 69%). MS (ESI): mass calcd. for $C_{40}H_{51}N_7O_8S$, 789.6; m/z found, 790.4 $[M+H]^+$. $^1$H NMR (400 MHz, CDCl$_3$) δ 8.09 (d, J=8.5 Hz, 1H), 7.53-7.45 (m, 2H), 7.31 (d, J=8.8 Hz, 1H), 7.10 (d, J=7.9 Hz, 1H), 6.70 (d, J=8.4 Hz, 1H), 4.78 (s, 1H), 4.69-4.62 (m, 2H), 4.50 (s, 1H), 4.41 (d, J=7.0 Hz, 2H), 4.18-3.62 (m, 12H), 3.01 (s, 3H), 2.89-2.49 (m, 5H), 2.38 (s, 3H), 1.84-1.69 (m, 4H), 1.44 (s, 3H), 1.36-1.20 (m, 4H), 0.65-0.55 (m, 2H), 0.48-0.41 (m, 2H).

Example 328: (*S)-3-(1-(Cyclopropylmethyl)-4-methyl-1H-benzo[d][1,2,3]triazol-5-yl)-2,2-dimethyl-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic Acid

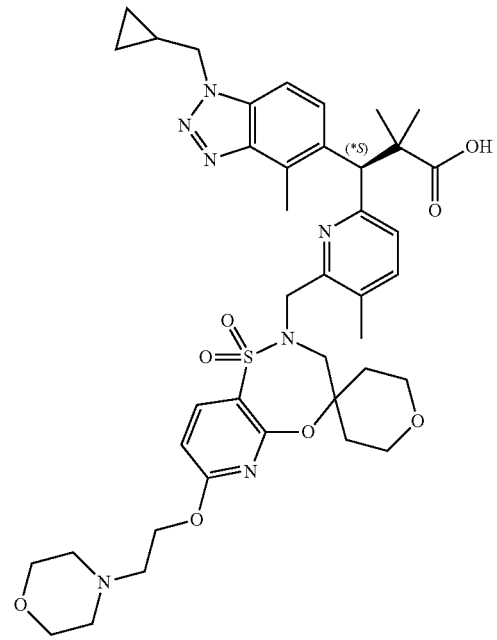 [SMILES: Cc1ccc([C@@H](c2ccc3c(nnn3CC3CC3)c2C)C(C)(C)C(=O)O)nc1CN1CC2(CCOCC2)Oc2nc(OCCN3CCOCC3)ccc2S1(=O)=O]

The mixture of 3-(1-(Cyclopropylmethyl)-4-methyl-1H-benzo[d][1,2,3]triazol-5-yl)-2,2-dimethyl-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid isomers (Example 327, 197 mg) were separated by chiral SFC (stationary phase: Chiralpak AD-H 2×25 cm; mobile phase: 40% ethanol with 0.1% ammonia-methanol, 60% $CO_2$) to afford two enantiomers. The first eluting isomer (94 mg) was designated (*S): MS (ESI): mass calcd. for $C_{40}H_{51}N_7O_8S$, 789.6; m/z found, 790.3 $[M+H]^+$. $^1$H NMR (400 MHz, CDCl₃) δ 8.07 (d, J=8.5 Hz, 1H), 7.53-7.47 (m, 2H), 7.31 (d, J=8.8 Hz, 1H), 7.10 (d, J=7.9 Hz, 1H), 6.69 (d, J=8.5 Hz, 1H), 4.78 (s, 1H), 4.69-4.61 (m, 2H), 4.49 (t, J=5.8 Hz, 2H), 4.41 (d, J=7.1 Hz, 2H), 4.15-4.03 (m, 2H), 3.88-3.81 (m, 1H), 3.81-3.68 (m, 7H), 3.01 (s, 3H), 2.80 (t, J=5.8 Hz, 2H), 2.61-2.55 (m, 4H), 2.38 (s, 3H), 1.85-1.69 (m, 4H), 1.44 (s, 3H), 1.36-1.31 (m, 4H), 0.65-0.57 (m, 2H), 0.49-0.40 (m, 2H).

Example 329: (*R)-3-(1-(Cyclopropylmethyl)-4-methyl-1H-benzo[d][1,2,3]triazol-5-yl)-2,2-dimethyl-3-(5-methyl-6-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic Acid

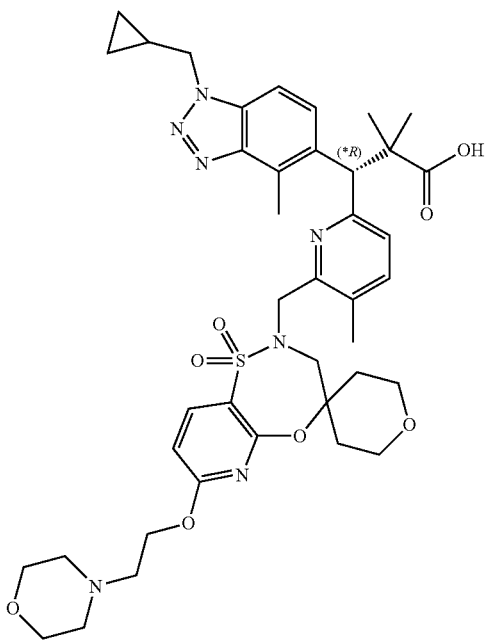 [SMILES: Cc1ccc([C@H](c2ccc3c(nnn3CC3CC3)c2C)C(C)(C)C(=O)O)nc1CN1CC2(CCOCC2)Oc2nc(OCCN3CCOCC3)ccc2S1(=O)=O]

The second eluting isomer (97 mg) from the chiral separation described in Example 328 was designated (*R): MS (ESI): mass calcd. for C₄₀H₅₁N₇O₈S, 789.6; m/z found, 790.3 [M+H]⁺. ¹H NMR (400 MHz, CDCl₃) δ 8.07 (d, J=8.4 Hz, 1H), 7.53-7.48 (m, 2H), 7.31 (d, J=8.8 Hz, 1H), 7.10 (d, J=7.9 Hz, 1H), 6.69 (d, J=8.5 Hz, 1H), 4.78 (s, 1H), 4.71-4.61 (m, 2H), 4.52-4.46 (m, 2H), 4.41 (d, J=7.1 Hz, 2H), 4.14-4.03 (m, 2H), 3.88-3.81 (m, 1H), 3.81-3.70 (m, 7H), 3.01 (s, 3H), 2.80 (t, J=5.8 Hz, 2H), 2.61-2.55 (m, 4H), 2.38 (s, 3H), 1.84-1.69 (m, 4H), 1.44 (s, 3H), 1.37-1.29 (m, 4H), 0.65-0.58 (m, 2H), 0.47-0.41 (m, 2H).

Example 330: (*S)-3-(3,7-Dimethyl-7H-pyrrolo[2,3-c]pyridazin-6-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic Acid

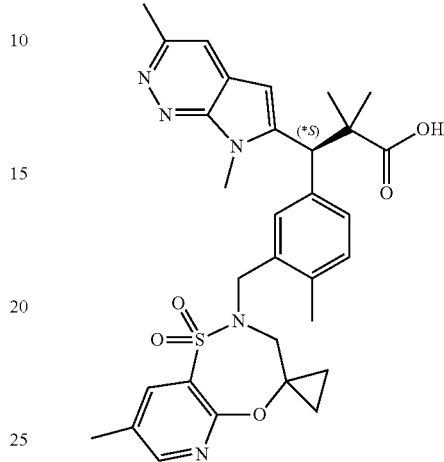

Step A: (3-(((tert-Butyldimethylsilyl)oxy)methyl)-4-methylphenyl)(3,7-dimethyl-7H-pyrrolo[2,3-c]pyridazin-6-yl)methanol. 3,7-Dimethyl-7H-pyrrolo[2,3-c]pyridazine-6-carbaldehyde (Intermediate 149, 1.0 g, 5.7 mmol), tert-butyldimethyl((2-methyl-5-(4,4,5,5-tetramethyl-1,3,2-dioxaborolan-2-yl)benzyl)oxy)silane (Intermediate 43, 3.1 g, 8.6 mmol), P(1-nap)₃ (942 mg, 2.28 mmol), K₂CO₃ (3.94 g, 28.5 mmol), and 1,4-dioxane (30 mL) were added to a 100 mL round-bottomed flask. The mixture was sparged with N₂ for 5 minutes and then treated with PdCl₂ (202 mg, 1.14 mmol). The mixture was sparged with N₂ for another 5 minutes and then heated at 110° C. for 16 hours before it was allowed to cool to room temperature, poured into water (50 mL), and extracted with dichloromethane (50 mL×3). The aqueous portion was separated and extracted with ethyl acetate (3×200 mL). The extractions resulted in several organic solvent fractions which were combined, dried over anhydrous Na₂SO₄, filtered, and concentrated to dryness under reduced pressure. The material was purified by FCC (petroleum ether/ethyl acetate=20:1 to 2:1, gradient elution) to afford the title compound (1.41 g, 50% yield). MS (ESI): mass calcd. for C₂₃H₃₃N₃O₂Si, 411.23; m/z found, 412.2 [M+H]⁺.

Step B: Methyl 3-(3-(((tert-butyldimethylsilyl)oxy)methyl)-4-methylphenyl)-3-(3,7-dimethyl-7H-pyrrolo[2,3-c]pyridazin-6-yl)-2,2-dimethylpropanoate. 2,2,2-Trichloroacetonitrile (0.37 mL, 3.7 mmol) was added to a solution of (3-(((tert-butyldimethylsilyl)oxy)methyl)-4-methylphenyl)(3,7-dimethyl-7H-pyrrolo[2,3-c]pyridazin-6-yl)methanol (1.0 g, 2.4 mmol), DBU (36 µL, 0.24 mmol), and DCE (20 mL) under N₂. The resulting mixture was stirred at room temperature for 1 hour before treating with ((1-methoxy-2-methylprop-1-en-1-yl)oxy)trimethylsilane (1.69 g, 9.70 mmol) and TiCl₄ (1M in dichloromethane, 3.64 mL, 3.64 mmol). The mixture was stirred at room temperature for 1.5 hours before it was quenched with saturated aqueous NaHCO₃(60 mL) and extracted with dichloromethane (60 mL×3). These extractions resulted in several organic solvent fractions which were combined, dried over anhydrous Na₂SO₄, filtered, and concentrated to dryness under reduced pressure. The material was purified by FCC (eluent:petroleum ether/ethyl acetate=1:1 to 0:1, gradient elution) to afford the title compound (550 mg, 41% yield). MS (ESI): mass calcd. for $C_{28}H_{41}N_3O_3Si$, 495.29; m/z found, 496.3 $[M+H]^+$.

Step C: Methyl 3-(3,7-dimethyl-7H-pyrrolo[2,3-c]pyridazin-6-yl)-3-(3-(hydroxymethyl)-4-methylphenyl)-2,2-dimethylpropanoate. TBAF (1 M in THF, 2.2 mL, 2.2 mmol) was added to a solution of methyl 3-(3-(((tert-butyldimethylsilyl)oxy)methyl)-4-methylphenyl)-3-(3,7-dimethyl-7H-pyrrolo[2,3-c]pyridazin-6-yl)-2,2-dimethylpropanoate (550 mg, 1.11 mmol) and THF (10 mL). The resulting mixture was stirred at room temperature for 2 hours before it was quenched with $H_2O$ (50 mL) and extracted with ethyl acetate (50 mL×3). These extractions resulted in several organic solvent fractions which were combined, washed with brine (30 mL×3), dried over anhydrous $Na_2SO_4$, filtered, and concentrated to dryness under reduced pressure. The material was purified by FCC (eluent: petroleum ether/ethyl acetate=5:1 to 0:1, gradient elution, then dichloromethane:methanol=10:1) to afford the title compound (380 mg, 71% yield). MS (ESI): mass calcd. for $C_{22}H_{27}N_3O_3$ 381.21; m/z found, 382.2 $[M+H]^+$.

Step D: Methyl 3-(3-(chloromethyl)-4-methylphenyl)-3-(3,7-dimethyl-7H-pyrrolo[2,3-c]pyridazin-6-yl)-2,2-dimethylpropanoate. $SOCl_2$ (0.57 mL, 7.8 mmol) was added to a solution of methyl 3-(3,7-dimethyl-7H-pyrrolo[2,3-c]pyridazin-6-yl)-3-(3-(hydroxymethyl)-4-methylphenyl)-2,2-dimethylpropanoate (300 mg, 0.786 mmol) and dichloromethane (10 mL). The resulting mixture was stirred at room temperature for 1 hour, then was concentrated to dryness under reduced pressure to afford the title compound (320 mg), which was used in the next step without further purification. MS (ESI): mass calcd. for $C_{22}H_{26}ClN_3O_2$ 399.17; m/z found, 400.2 $[M+H]^+$.

Step E: Methyl 3-(3,7-dimethyl-7H-pyrrolo[2,3-c]pyridazin-6-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoate. Methyl 3-(3-(chloromethyl)-4-methylphenyl)-3-(3,7-dimethyl-7H-pyrrolo[2,3-c]pyridazin-6-yl)-2,2-dimethylpropanoate (320 mg, 0.8 mmol), 8'-methyl-2',3'-dihydrospiro[cyclopropane-1,4'-pyrido[2,3-b][1,4,5]oxathiazepine] 1',1'-dioxide (Intermediate 6, 192 mg, 0.799 mmol), $K_2CO_3$ (332 mg, 2.40 mmol), and $CH_3CN$ (10 mL) were added to a 100 mL round-bottomed flask. The resulting mixture was heated at 80° C. for 16 hours before it was allowed to cool to room temperature, quenched with $H_2O$ (40 mL) and extracted with ethyl acetate (30 mL×3). These extractions resulted in several organic solvent fractions which were combined, dried over anhydrous $Na_2SO_4$, filtered, and concentrated to dryness under reduced pressure. The material was purified by FCC (eluent:petroleum ether/ethyl acetate=1:1 to 0:1, gradient elution, then dichloromethane:methanol=10:1) to afford the title compound (390 mg, 68%) which was used without further purification. MS (ESI): mass calcd. for $C_{32}H_{37}N_5O_5S$, 603.25; m/z found, 604.3 $[M+H]^+$.

Step F: 3-(3,7-Dimethyl-7H-pyrrolo[2,3-c]pyridazin-6-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid. LiOH*$H_2O$ (271 mg, 6.46 mmol) was added to a solution of methyl 3-(3,7-dimethyl-7H-pyrrolo[2,3-c]pyridazin-6-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoate (390 mg, 0.646 mmol), 1,4-dioxane (5 mL), and $H_2O$ (5 mL). The resulting mixture was heated at 75° C. for 2 hours before being allowed to cool to room temperature, diluted with $H_2O$ (30 mL), and extracted with ethyl acetate (30 mL×3). The pH of aqueous phase was adjusted to pH=6-7 with 1N HCl and the resulting mixture extracted with ethyl acetate (50 mL×3). These extractions resulted in several organic solvent fractions which were combined, dried over anhydrous $Na_2SO_4$, filtered, and concentrated to dryness under reduced pressure to give the title compound (300 mg, 73% yield). MS (ESI): mass calcd. for $C_{31}H_{35}N_5O_5S$, 589.24; m/z found, 590.3 $[M+H]^+$. $^1H$ NMR (400 MHz, DMSO-$d_6$) δ 12.31 (br s, 1H), 8.32 (d, J=1.8 Hz, 1H), 8.03 (d, J=2.0 Hz, 1H), 7.62 (s, 1H), 7.16 (s, 2H), 7.09 (s, 1H), 6.62 (s, 1H), 4.73 (s, 1H), 3.58-3.53 (m, 7H), 2.65 (s, 3H), 2.36 (s, 3H), 2.25 (s, 3H), 1.23 (d, J=3.5 Hz, 6H), 0.88 (s, 2H), 0.50 (s, 2H).

Step G: (*S)-3-(3,7-Dimethyl-7H-pyrrolo[2,3-c]pyridazin-6-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid. The mixture of 3-(3,7-dimethyl-7H-pyrrolo[2,3-c]pyridazin-6-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid isomers was separated by chiral SFC (DAICEL CHIRALCEL OD-H 250 mm×30 mm, 5 m, mobile phase: 35% to 35% (v/v) supercritical $CO_2$ in i-PrOH and $H_2O$ with 0.1% $NH_3$) to afford two enantiomers. The first eluting isomer (89.6 mg) was designated (*S): MS (ESI): mass calcd. for $C_{31}H_{35}N_5O_5S$, 589.24; m/z found, 590.3 $[M+H]^+$. $^1H$ NMR (400 MHz, DMSO-$d_6$) δ 8.32 (d, J=1.7 Hz, 1H), 8.03 (d, J=2.0 Hz, 1H), 7.61 (s, 1H), 7.16 (s, 2H), 7.09 (s, 1H), 6.62 (s, 1H), 4.72 (s, 1H), 4.28-4.21 (m, 1H), 4.16-4.07 (m, 1H), 3.72-3.59 (m, 1H), 3.55 (s, 3H), 3.28-3.18 (m, 1H), 2.64 (s, 3H), 2.36 (s, 3H), 2.25 (s, 3H), 1.22 (s, 6H), 0.92-0.84 (m, 2H), 0.55-0.47 (m, 2H).

Example 331: (*R)-3-(3,7-Dimethyl-7H-pyrrolo[2,3-c]pyridazin-6-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic Acid

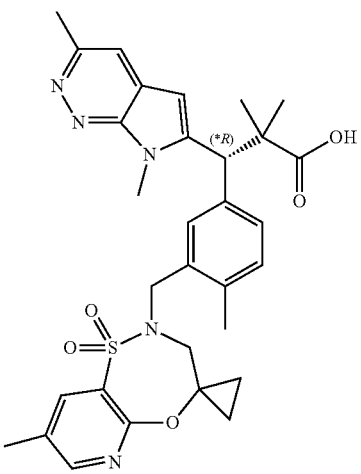 [SMILES: Cc1cnc2c(c1)S(=O)(=O)N(Cc1cc([C@H](c3cc4cc(C)nnc4n3C)C(C)(C)C(=O)O)ccc1C)CC1(CC1)O2]

The second eluting isomer from the chiral separation described in Example 330 was further purified by preparative acidic HPLC (Boston Uni C18 150 mm×40 mm×5 μm column, mobile phase: 26% to 56% (v/v) $CH_3CN$ and $H_2O$ with 0.225% HCOOH) to give the title compound (35.7 mg) and was designated (*R): MS (ESI): mass calcd. for $C_{31}H_{35}N_5O_5S$, 589.24; m/z found, 590.3 [M+H]$^+$. $^1$H NMR (400 MHz, DMSO-d$_6$) δ 8.32 (d, J=1.8 Hz, 1H), 8.03 (d, J=2.0 Hz, 1H), 7.61 (s, 1H), 7.16 (s, 2H), 7.09 (s, 1H), 6.62 (s, 1H), 4.73 (s, 1H), 4.28-4.21 (m, 1H), 4.16-4.07 (m, 1H), 3.71-3.58 (m, 1H), 3.55 (s, 3H), 3.29-3.23 (m, 1H), 2.64 (s, 3H), 2.36 (s, 3H), 2.25 (s, 3H), 1.27-1.19 (m, 6H), 0.93-0.84 (m, 2H), 0.55-0.45 (m, 2H).

Example 332: (*S)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic Acid

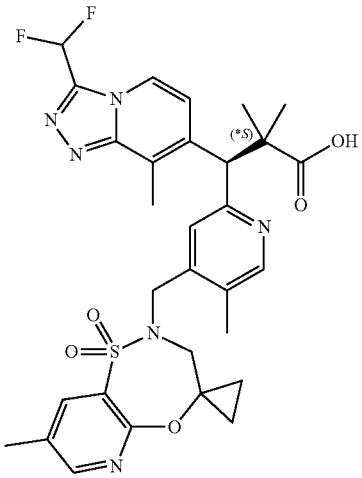 [SMILES: Cc1cnc2c(c1)S(=O)(=O)N(Cc1cc([C@@H](c3ccn4c(C(F)F)nnc4c3C)C(C)(C)C(=O)O)ncc1C)CC1(CC1)O2]

Step A: (4-(((tert-Butyldimethylsilyl)oxy)methyl)-5-methylpyridin-2-yl)(3-(difluoromethyl)-8-methyl-[1,2,4]triazolo[4,3-a]pyridin-7-yl)methanol. i-PrMgCl.LiCl (1.3 M in THF, 30 mL, 39 mmol) was added dropwise to a 250 mL three-necked round-bottomed flask containing a solution of 3-(difluoromethyl)-7-iodo-8-methyl-[1,2,4]triazolo[4,3-a]pyridine (Intermediate 148, 10.0 g, 32.4 mmol) and THF (120 mL) that had been cooled to −10° C. This mixture was stirred at −10° C. for 1 hour before adding a solution of 4-(((tert-butyldimethylsilyl)oxy)methyl)-5-methylpicolinaldehyde (Intermediate 147, 9.5 g, 36 mmol) and THF (30 mL) dropwise. The resulting mixture was stirred for 16 hours, gradually warming to room temperature, then was poured into saturated aqueous NH$_4$Cl (70 mL) and extracted with ethyl acetate (80 mL×3). These extractions resulted in several organic solvent fractions which were combined, washed with brine (50 mL), dried over anhydrous Na$_2$SO$_4$, filtered, and concentrated to dryness under reduced pressure. The material was purified by FCC (petroleum ether/ethyl acetate=1:0 to 0:1, gradient elution) to give the title compound (7.5 g, 45% yield). MS (ESI): mass calcd. for $C_{22}H_{30}F_2N_4O_2Si$; 448.21 m/z found, 449.5 [M+H]$^+$.

Step B: 7-((4-(((tert-Butyldimethylsilyl)oxy)methyl)-5-methylpyridin-2-yl)chloromethyl)-3-(difluoromethyl)-8-methyl-[1,2,4]triazolo[4,3-a]pyridine. SOCl$_2$ (1.1 mL, 15 mmol) was added dropwise to a 100 mL three-necked round-bottomed flask containing a solution of (4-(((tert-butyldimethylsilyl)oxy)methyl)-5-methylpyridin-2-yl)(3-(difluoromethyl)-8-methyl-[1,2,4]triazolo[4,3-a]pyridin-7-yl)methanol (6.0 g, 12 mmol), 2,6-di-tert-butylpyridine (6.8 mL, 29 mmol), and dichloromethane (80 mL) that had been cooled to 0° C. The resulting mixture was stirred at 0° C. for 40 minutes, basified with saturated aqueous NaHCO$_3$ to pH=8, poured into water (50 mL), and extracted with dichloromethane (50 mL×3). These extractions resulted in several organic solvent fractions which were combined, washed with brine (50 mL), dried over anhydrous Na$_2$SO$_4$, filtered, and concentrated to dryness under reduced pressure. The material was purified by FCC (petroleum ether/ethyl acetate=1:0 to 1:1) to give the title compound (5 g, 86% yield). MS (ESI): mass calcd. for $C_{22}H_{29}ClF_2N_4OSi$; 466.18 m/z found, 467.4 [M+H]$^+$.

Step C: tert-Butyl 3-(4-(((tert-butyldimethylsilyl)oxy)methyl)-5-methylpyridin-2-yl)-3-(3-(difluoromethyl)-8-methyl-[1,2,4]triazolo[4,3-a]pyridin-7-yl)-2,2-dimethylpropanoate. InBr$_3$ (1.9 g, 5.4 mmol) was added to a 250 mL round-bottomed flask containing a solution of 7-((4-(((tert-butyldimethyl silyl)oxy)methyl)-5-methylpyridin-2-yl)chloromethyl)-3-(difluoromethyl)-8-methyl-[1,2,4]triazolo[4,3-a]pyridine (5.0 g, 11 mmol), ((1-(tert-butoxy)-2-methylprop-1-en-1-yl)oxy)trimethylsilane (Intermediate 271, 23.0 g, 106 mmol), and dichloromethane (80 mL) under N$_2$. The resulting mixture was stirred at room temperature for 50 hours. The mixture was further treated with ((1-(tert-Butoxy)-2-methylprop-1-en-1-yl)oxy)trimethylsilane (15 g, 69 mmol) and InBr$_3$ (1.0 g, 2.8 mmol). The resulting mixture was stirred at room temperature for 30 hours, then was poured into H$_2$O (50 mL) and extracted with dichloromethane (100 mL×3). These extractions resulted in several organic solvent fractions which were combined, dried over anhydrous Na$_2$SO$_4$, filtered, and concentrated to dryness under reduced pressure. The material was purified by FCC (petroleum ether/ethyl acetate=100:1 to 2:1) to afford the title compound (900 mg, 12% yield). MS (ESI): mass calcd. for $C_{30}H_{44}F_2N_4O_3Si$, 574.32; m/z found, 575.2 [M+H]$^+$.

Step D: tert-Butyl 3-(3-(difluoromethyl)-8-methyl-[1,2,4]triazolo[4,3-a]pyridin-7-yl)-3-(4-(hydroxymethyl)-5-methylpyridin-2-yl)-2,2-dimethylpropanoate. TBAF (1 M in THF, 2.7 mL, 2.7 mmol) was added to a 30 mL round-bottomed flask containing a solution of tert-butyl 3-(4-(((tert-butyldimethylsilyl)oxy)methyl)-5-methylpyridin-2-yl)-3-(3-(difluoromethyl)-8-methyl-[1,2,4]triazolo[4,3-a]pyridin-7-yl)-2,2-dimethylpropanoate (900 mg, 1.33 mmol) and THF (15 mL). The resulting mixture was stirred for 4 hours at room temperature, then was poured into water (30 mL) and extracted with ethyl acetate (30 mL×3). These extractions resulted in several organic solvent fractions which were combined, washed with brine (20 mL), dried over anhydrous Na$_2$SO$_4$, filtered, and concentrated to dryness under reduced pressure. The material was purified by FCC (ethyl acetate) to give the title compound (450 mg, 71% yield). MS (ESI): mass calcd. for $C_{24}H_{30}F_2N_4O_3$ 460.23; m/z found, 461.1 [M+H]$^+$. An alternative procedure to prepare the title compound, tert-Butyl 3-(3-(difluoromethyl)-8-methyl-[1,2,4]triazolo[4,3-a]pyridin-7-yl)-3-(4-(hydroxymethyl)-5-methylpyridin-2-yl)-2,2-dimethylpropanoate, is described in the preparation of Intermediate 191.

Step E: tert-Butyl 3-(4-(chloromethyl)-5-methylpyridin-2-yl)-3-(3-(difluoromethyl)-8-methyl-[1,2,4]triazolo[4,3-a]pyridin-7-yl)-2,2-dimethylpropanoate. SOCl$_2$ (0.4 mL, 6 mmol) was added to a solution of tert-butyl 3-(3-(difluoromethyl)-8-methyl-[1,2,4]triazolo[4,3-a]pyridin-7-yl)-3-(4-(hydroxymethyl)-5-methylpyridin-2-yl)-2,2-dimethylpropanoate (450 mg, 0.977 mmol) and dichloromethane (8 mL) under N$_2$. The resulting mixture was stirred at room temperature for 1 hour, then was concentrated to dryness under reduced pressure to give the title compound (480 mg), which was used in the next step without further purification. MS (ESI): mass calcd. for $C_{24}H_{29}ClF_2N_4O_2$ 478.19; m/z found, 479.1 [M+H]$^+$. An alternative procedure to prepare the title compound, tert-Butyl 3-(4-(chloromethyl)-5-methylpyridin-2-yl)-3-(3-(difluoromethyl)-8-methyl-[1,2,4]triazolo[4,3-a]pyridin-7-yl)-2,2-dimethylpropanoate, is described in the preparation of Intermediate 192.

Step F: tert-Butyl 3-(3-(difluoromethyl)-8-methyl-[1,2,4]triazolo[4,3-a]pyridin-7-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoate. tert-Butyl 3-(4-(chloromethyl)-5-methylpyridin-2-yl)-3-(3-(difluoromethyl)-8-methyl-[1,2,4]triazolo[4,3-a]pyridin-7-yl)-2,2-dimethylpropanoate (200 mg, 0.42 mmol), 8'-methyl-2',3'-dihydrospiro[cyclopropane-1,4'-pyrido[2,3-b][1,4,5]oxathiazepine] 1',1'-dioxide (Intermediate 6, 90 mg, 0.38 mmol), $K_2CO_3$ (290 mg, 2.10 mmol), and $CH_3CN$ (8 mL) were added to a 30 mL round-bottomed flask. The resulting mixture was stirred at 80° C. for 16 hours, then was allowed to cool to room temperature, poured into water (20 mL), and extracted with ethyl acetate (20 mL×3). These extractions resulted in several organic solvent fractions which were combined, washed with brine (20 mL), dried over anhydrous $Na_2SO_4$, filtered, and concentrated to dryness under reduced pressure to give the title compound (260 mg, 84% yield), which was used in the next step without further purification. MS (ESI): mass calcd. for $C_{34}H_{40}F_2N_6O_5S$, 682.27; m/z found, 683.1 [M+H]$^+$.

Step G: Methyl 3-(3-(difluoromethyl)-8-methyl-[1,2,4]triazolo[4,3-a]pyridin-7-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoate. 4 N HCl in 1,4-dioxane (5 mL) was added to a solution of tert-butyl 3-(3-(difluoromethyl)-8-methyl-[1,2,4]triazolo[4,3-a]pyridin-7-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoate (260 mg, 0.38 mmol), 1,4-dioxane (5 mL), and 3 drops of MeOH. The resulting mixture was stirred at room temperature for 16 hours, then an additional 4 N HCl in 1,4-dioxane (5 mL) was added. The mixture was stirred at room temperature for another 16 hours before concentrating to dryness under reduced pressure to give the title compound (300 mg), which was used in the next step without further purification. MS (ESI): mass calcd. for $C_{31}H_{34}F_2N_6O_5S$, 640.23; m/z found, 641.2 [M+H]$^+$.

Step H: 3-(3-(Difluoromethyl)-8-methyl-[1,2,4]triazolo[4,3-a]pyridin-7-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid. LiOH*$H_2O$ (120 mg, 2.86 mmol) was added to a solution of methyl 3-(3-(difluoromethyl)-8-methyl-[1,2,4]triazolo[4,3-a]pyridin-7-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoate (300 mg, 0.468 mmol) and 1,4-dioxane: $H_2O$ (1:1, 8 mL). The resulting mixture was stirred at 60° C. for 4 hours, then the pH was adjusted to pH=6 using 1 N HCl. The mixture was concentrated to dryness under reduced pressure and then purified by preparative acidic HPLC (Xtimate C18, 150×40 mm×10 m column, mobile phase: 35% to 65% (v/v) $CH_3CN$ and $H_2O$ with 0.2% HCOOH) to give the title compound (170 mg, 54% yield). MS (ESI): mass calcd. for $C_{30}H_{32}F_2N_6O_5S$, 626.21; m/z found, 627.1 [M+H]$^+$.

Step I: (*S)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid. The mixture of 3-(3-(difluoromethyl)-8-methyl-[1,2,4]triazolo[4,3-a]pyridin-7-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid isomers was separated by chiral SFC (DAICEL CHIRALPAK AS-H 250 mm×30 mm, 5 am, mobile phase: 30% to 30% (v/v) supercritical $CO_2$ in EtOH and $H_2O$ with 0.1% $NH_3$) to afford two enantiomers. The first eluting isomer (47.5 mg) was designated (*S): MS (ESI): mass calcd. for $C_{30}H_{32}F_2N_6O_5S$, 626.21; m/z found, 627.3 [M+H]$^+$. $^1$H NMR (400 MHz, DMSO-d$_6$) δ 12.47 (s, 1H), 8.36-8.33 (m, 2H), 8.32-8.30 (m, 1H), 8.04-8.02 (m, 1H), 7.85-7.56 (m, 1H), 7.30 (d, J=7.3 Hz, 1H), 7.16 (s, 1H), 4.95 (s, 1H), 4.27-4.14 (m, 2H), 3.85-3.52 (m, 2H), 2.74 (s, 3H), 2.34 (s, 3H), 2.19 (s, 3H), 1.29 (s, 3H), 1.25 (s, 3H), 0.98-0.84 (m, 2H), 0.76-0.57 (m, 2H).

Example 333: (*R)-3-(3-(difluoromethyl)-8-methyl-[1,2,4]triazolo[4,3-a]pyridin-7-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic Acid

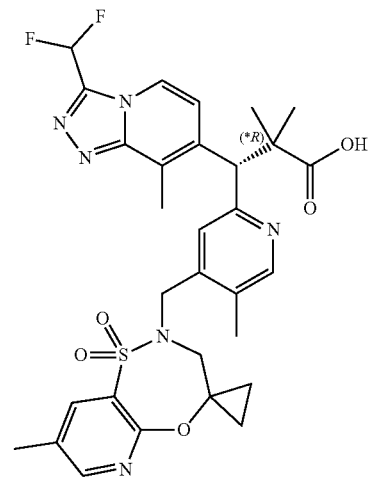 [SMILES: Cc1cnc2c(c1)S(=O)(=O)N(Cc1cc([C@H](c3ccn4c(C(F)F)nnc4c3C)C(C)(C)C(=O)O)ncc1C)CC1(CC1)O2]

The second eluting isomer (45.5 mg) from the chiral separation described in Example 332 was designated (*R): MS (ESI): mass calcd. for $C_{30}H_{32}F_2N_6O_5S$, 626.21; m/z found, 627.3 [M+H]$^+$. $^1$H NMR (400 MHz, DMSO-d$_6$) δ 12.52 (s, 1H), 8.36-8.33 (m, 2H), 8.33-8.30 (m, 1H), 8.04-8.01 (m, 1H), 7.84-7.57 (m, 1H), 7.29 (d, J=7.5 Hz, 1H), 7.15 (s, 1H), 4.95 (s, 1H), 4.26-4.14 (m, 2H), 3.80-3.45 (m, 2H), 2.74 (s, 3H), 2.34 (s, 3H), 2.19 (s, 3H), 1.30 (s, 3H), 1.25 (s, 3H), 0.98-0.84 (m, 2H), 0.76-0.57 (m, 2H).

Example 334: (*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[cyclopropane-1,4'-pyrido[2,3-b][1,4,5]oxathiazepin]-2'(3'H)-yl)methyl)pyridin-2-yl)propanoic Acid

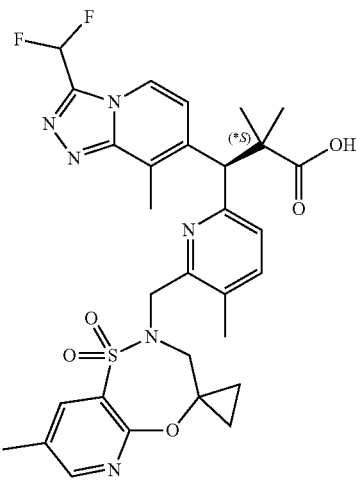 [SMILES: Cc1cnc2c(c1)S(=O)(=O)N(Cc1nc([C@@H](c3ccn4c(C(F)F)nnc4c3C)C(C)(C)C(=O)O)ccc1C)CC1(CC1)O2]

Step A: (6-(((tert-Butyldimethylsilyl)oxy)methyl)-5-methylpyridin-2-yl)(3-(difluoromethyl)-8-methyl-[1,2,4]triazolo[4,3-a]pyridin-7-yl)methanol. i-PrMgCl.LiCl (1.3 M in THF, 25.4 mL, 33.0 mmol) was added dropwise to a 500 mL three-necked round-bottomed flask containing a 0° C. solution of 3-(difluoromethyl)-7-iodo-8-methyl-[1,2,4]triazolo[4,3-a]pyridine (Intermediate 148, 6.8 g, 22 mmol) and THF (80 mL). The resulting mixture was stirred at 0° C. for 1 hour, then a solution of 6-(((tert-butyldimethylsilyl)oxy)methyl)-5-methylpicolinaldehyde (Intermediate 57, 6.1 g, 23 mmol) and THF (20 mL) was added dropwise at 0° C. The resulting mixture was stirred for 16 hours with gradual warming to room temperature, then was poured into saturated aqueous NH$_4$Cl (50 mL) and extracted with ethyl acetate (60 mL×3). These extractions resulted in several organic solvent fractions which were combined, washed with brine (50 mL), dried over anhydrous Na$_2$SO$_4$, filtered, and concentrated to dryness under reduced pressure. The material was triturated with petroleum ether/ethyl acetate (10:1, 20 mL) and the solid was isolated via filtration. The filter cake was washed with petroleum ether/ethyl acetate (10:1, 5 mL×3) and dried under reduced pressure to give the title compound (4.3 g, 42% yield). The filtrate was concentrated to dryness under reduced pressure and the material was purified by FCC (petroleum ether/ethyl acetate=1:0 to 2:3) to give a second batch of the title compound (1.9 g, 5% yield). MS (ESI): mass calcd. for C$_{22}$H$_{30}$F$_2$N$_4$O$_2$Si, 448.2; m/z found, 449.2 [M+H]$^+$.

Step B: 7-((6-(((tert-Butyldimethylsilyl)oxy)methyl)-5-methylpyridin-2-yl)chloromethyl)-3-(difluoromethyl)-8-methyl-[1,2,4]triazolo[4,3-a]pyridine. SOCl$_2$ (0.57 mL, 7.8 mmol) was added dropwise to a 100 mL round-bottomed flask containing a 0° C. solution of (6-(((tert-butyldimethylsilyl)oxy)methyl)-5-methylpyridin-2-yl)(3-(difluoromethyl)-8-methyl-[1,2,4]triazolo[4,3-a]pyridin-7-yl)methanol (2.7 g, 6.0 mmol), 2,6-di-tert-butylpyridine (3.4 mL, 15 mmol), and dichloromethane (30 mL). The resulting mixture was stirred at 0° C. for 40 minutes, then the pH of the solution was adjusted to pH=8-9 with saturated aqueous NaHCO$_3$, it was then poured into water (40 mL) and extracted with dichloromethane (50 mL×3). These extractions resulted in several organic solvent fractions which were combined, washed with brine (30 mL), dried over anhydrous Na$_2$SO$_4$, filtered, and concentrated to dryness under reduced pressure. The material was purified by FCC (petroleum ether/ethyl acetate=1:0 to 1:1) to give the title compound (2.2 g, 73% yield). MS (ESI): mass calcd. for C$_{22}$H$_{29}$ClF$_2$N$_4$OS, 466.2; m/z found, 467.2 [M+H].

Step C: Methyl 3-(6-(((tert-butyldimethylsilyl)oxy)methyl)-5-methylpyridin-2-yl)-3-(3-(difluoromethyl)-8-methyl-[1,2,4]triazolo[4,3-a]pyridin-7-yl)-2,2-dimethylpropanoate. InBr$_3$ (228 mg, 0.643 mmol) was added to a 100 mL round-bottomed flask containing a solution of 7-((6-(((tert-butyldimethylsilyl)oxy)methyl)-5-methylpyridin-2-yl)chloromethyl)-3-(difluoromethyl)-8-methyl-[1,2,4]triazolo[4,3-a]pyridine (1.0 g, 2.1 mmol), ((1-methoxy-2-methylprop-1-en-1-yl)oxy)trimethylsilane (1.87 g, 10.7 mmol) and dichloromethane (30 mL) under N$_2$. The resulting mixture was stirred at room temperature for 48 hours, then was poured into water (30 mL) and extracted with dichloromethane (30 mL×3). These extractions resulted in several organic solvent fractions which were combined, washed with brine (30 mL), dried over anhydrous Na$_2$SO$_4$, filtered, and concentrated to dryness under reduced pressure. The material was purified by FCC (petroleum ether/ethyl acetate=1:0 to 3:1) to give the title compound (460 mg, 37% yield). MS (ESI): mass calcd. for C$_{27}$H$_{38}$F$_2$N$_4$O$_3$Si, 532.3; m/z found, 533.3 [M+H]$^+$.

Step D: Methyl 3-(3-(difluoromethyl)-8-methyl-[1,2,4]triazolo[4,3-a]pyridin-7-yl)-3-(6-(hydroxymethyl)-5-methylpyridin-2-yl)-2,2-dimethylpropanoate. TBAF (1 M in THF, 1.74 mL, 1.74 mmol) was added to a 100 mL round-bottomed flask containing a solution of methyl 3-(6-(((tert-butyldimethylsilyl)oxy)methyl)-5-methylpyridin-2-yl)-3-(3-(difluoromethyl)-8-methyl-[1,2,4]triazolo[4,3-a]pyridin-7-yl)-2,2-dimethylpropanoate (460 mg, 0.86 mmol) and THF (10 mL). The resulting mixture was stirred for 2 hours at room temperature, then was poured into water (30 mL) and extracted with ethyl acetate (30 mL×3). These extractions resulted in several organic solvent fractions which were combined, washed with brine (30 mL), dried over anhydrous Na$_2$SO$_4$, filtered, and concentrated to dryness under reduced pressure. The material was purified by FCC (petroleum ether/ethyl acetate=1:0 to 1:1) to give the title compound (330 mg, 81% yield). MS (ESI): mass calcd. for C$_{21}$H$_{24}$F$_2$N$_4$O$_3$ 418.2; m/z found, 419.2 [M+H]$^+$. An alternative procedure to prepare the title compound, methyl 3-(3-(difluoromethyl)-8-methyl-[1,2,4]triazolo[4,3-a]pyridin-7-yl)-3-(6-(hydroxymethyl)-5-methylpyridin-2-yl)-2,2-dimethylpropanoate, is described in the preparation of Intermediate 195.

Step E: Methyl 3-(6-(chloromethyl)-5-methylpyridin-2-yl)-3-(3-(difluoromethyl)-8-methyl-[1,2,4]triazolo[4,3-a]pyridin-7-yl)-2,2-dimethylpropanoate. SOCl$_2$ (0.17 mL, 2.3 mmol) was added to a 100 mL round-bottomed flask containing a solution of benzyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate (330 mg, 0.79 mmol), and dichloromethane (5 mL). The resulting mixture was stirred for 0.5 hours at room temperature, then was concentrated to dryness under reduced pressure to give the title compound (350 mg), which was used in the next step without further purification. MS (ESI): mass calcd. for C$_{21}$H$_{23}$ClF$_2$N$_4$O$_2$ 436.2; m/z found, 437.2 [M+H]$^+$. An alternative procedure to prepare the title compound, methyl 3-(6-(chloromethyl)-5-methylpyridin-2-yl)-3-(3-(difluoromethyl)-8-methyl-[1,2,4]triazolo[4,3-a]pyridin-7-yl)-2,2-dimethylpropanoate, is described in the preparation of Intermediate 196.

Step F: Methyl 3-(3-(difluoromethyl)-8-methyl-[1,2,4]triazolo[4,3-a]pyridin-7-yl)-2,2-dimethyl-3-(5-methyl-6-((8'-methyl-1',1'-dioxidospiro[cyclopropane-1,4'-pyrido[2,3-b][1,4,5]oxathiazepin]-2'(3'H)-yl)methyl)pyridin-2-yl)propanoate. Methyl 3-(6-(chloromethyl)-5-methylpyridin-2-yl)-3-(3-(difluoromethyl)-8-methyl-[1,2,4]triazolo[4,3-a]pyridin-7-yl)-2,2-dimethylpropanoate (300 mg, 0.69 mmol), 8'-methyl-2',3'-dihydrospiro[cyclopropane-1,4'-pyrido[2,3-b][1,4,5]oxathiazepine] 1',1'-dioxide (Intermediate 6, 168 mg, 0.699 mmol), K$_2$CO$_3$ (384 mg, 2.78 mmol), and CH$_3$CN (10 mL) were added to a 50 mL round-bottomed flask. The resulting mixture was stirred at 80° C. for 4 hours, then was allowed to cool to room temperature, poured into water (30 mL), and extracted with ethyl acetate (30 mL×3). These extractions resulted in several organic solvent fractions which were combined, washed with brine (30 mL), dried over anhydrous Na$_2$SO$_4$, filtered, and concentrated to dryness under reduced pressure to give the title compound (500 mg), which was used in the next step without further purification. MS (ESI): mass calcd. for C$_{31}$H$_{34}$F$_2$N$_6$O$_5$S, 640.2; m/z found, 642.4 [M+H]$^+$.

Step G: 3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid. (Methyl 3-(3-(difluoromethyl)-8-methyl-[1,2,4]triazolo[4,3-a]pyridin-7-yl)-2,2-dimethyl-3-(5-methyl-6-((8'-methyl-1',1'-dioxidospiro[cyclopropane-1,4'-pyrido[2,3-b][1,4,5]oxathiazepin]-2'(3'H)-yl)methyl)pyridin-2-yl)propanoate) (480 mg, 0.65 mmol), NaOH (130 mg, 3.25 mmol), 1,4-dioxane (3 mL), and H$_2$O (3 mL) were added to a 100 mL round-bottomed flask. The resulting mixture was stirred at 65° C. for 16 hours, then was allowed to cool to room temperature, poured into water (10 mL), acidified with 1N HCl to pH=5-6, and extracted with ethyl acetate (30 mL×3). These extractions resulted in several organic solvent fractions which were combined, washed with brine (20 mL), dried over anhydrous Na$_2$SO$_4$, filtered, and concentrated to dryness under reduced pressure. The material was purified by preparative acidic HPLC (DuraShell 150 mm×25 mm×5 μm column, mobile phase: 32% to 62% (v/v) CH$_3$CN and H$_2$O with 0.2% HCOOH) to give the title compound (160 mg, 39% yield). MS (ESI): mass calcd. for C$_{30}$H$_{32}$F$_2$N$_6$O$_5$S, 626.2; m/z found, 627.3 [M+H]$^+$. $^1$H NMR (400 MHz, DMSO-d$_6$) δ 12.39 (br s, 1H), 8.36 (d, J=1.8 Hz, 1H), 8.29 (d, J=7.3 Hz, 1H), 8.14 (d, J=2.2 Hz, 1H), 7.85-7.56 (m, 1H), 7.54 (d, J=7.9 Hz, 1H), 7.29 (d, J=7.3 Hz, 1H), 7.21 (d, J=7.9 Hz, 1H), 4.92 (s, 1H), 4.43-4.25 (m, 2H), 3.83-3.57 (m, 2H), 2.72 (s, 3H), 2.39 (s, 3H), 2.32 (s, 3H), 1.30 (s, 3H), 1.23 (s, 3H), 1.07-0.93 (m, 2H), 0.86 (br s, 2H).

Step F: (*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid. The mixture of 3-(3-(difluoromethyl)-8-methyl-[1,2,4]triazolo[4,3-a]pyridin-7-yl)-2,2-dimethyl-3-(5-methyl-6-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid isomers was separated by chiral SFC (DAICEL CHIRALCEL OJ-H 250 mm×30 mm×5 m, mobile phase: 40% to 40% (v/v) supercritical CO$_2$ in EtOH and H$_2$O with 0.1% NH$_3$) to afford two enantiomers. The first eluting isomer (76.4 mg) was designated (*S): MS (ESI): mass calcd. for C$_{30}$H$_{32}$F$_2$N$_6$O$_5$S, 626.2; m/z found, 627.3 [M+H]$^+$. $^1$H NMR (400 MHz, DMSO-d$_6$) δ 12.35 (s, 1H), 8.37-8.35 (m, 1H), 8.29 (d, J=7.2 Hz, 1H), 8.15-8.13 (m, 1H), 7.84-7.57 (m, 1H), 7.54 (d, J=8.0 Hz, 1H), 7.29 (d, J=7.2 Hz, 1H), 7.22 (d, J=8.0 Hz, 1H), 4.93 (s, 1H), 4.41-4.30 (m, 2H), 3.70 (s, 2H), 2.72 (s, 1H), 2.72 (s, 2H), 2.39 (s, 3H), 2.33 (s, 3H), 1.30 (s, 3H), 1.22 (s, 3H), 1.04-0.95 (m, 2H), 0.89-0.80 (m, 2H).

Example 335: (*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[cyclopropane-1,4'-pyrido[2,3-b][1,4,5]oxathiazepin]-2'(3'H)-yl)methyl)pyridin-2-yl)propanoic Acid

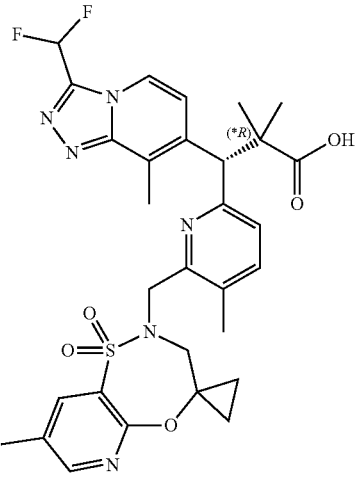 [SMILES: Cc1cnc2c(c1)S(=O)(=O)N(Cc1nc([C@H](c3ccn4c(C(F)F)nnc4c3C)C(C)(C)C(=O)O)ccc1C)CC1(CC1)O2]

The second eluting isomer (71.9 mg) from the chiral separation described in Example 334 was designated (*R): MS (ESI): mass calcd. for C$_{30}$H$_{32}$F$_2$N$_6$O$_5$S, 626.2; m/z found, 627.3 [M+H]$^+$. $^1$H NMR (400 MHz, DMSO-d$_6$) δ 12.18 (s, 1H), 8.36-8.34 (m, 1H), 8.28 (d, J=7.2 Hz, 1H), 8.14-8.12 (m, 1H), 7.84-7.56 (m, 1H), 7.53 (d, J=8.0 Hz, 1H), 7.29 (d, J=7.2 Hz, 1H), 7.22 (d, J=8.0 Hz, 1H), 4.93 (s, 1H), 4.41-4.30 (m, 2H), 3.82-3.56 (m, 2H), 2.72 (s, 3H), 2.39 (s, 3H), 2.32 (s, 3H), 1.29 (s, 3H), 1.22 (s, 3H), 1.03-0.95 (m, 2H), 0.89-0.80 (m, 2H).

Example 336: (*S)-3-(3-((1',1'-Dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

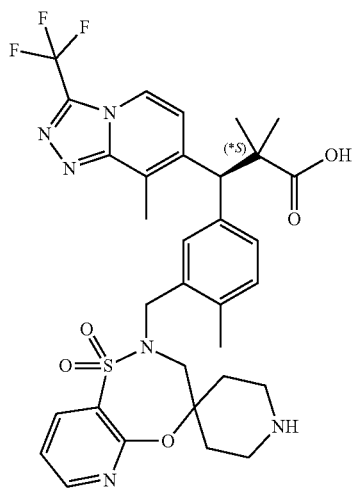 [SMILES: Cc1ccc([C@@H](c2ccn3c(C(F)(F)F)nnc3c2C)C(C)(C)C(=O)O)cc1CN1CC2(CCNCC2)Oc2ncccc2S1(=O)=O]

Step A: Benzyl 3-(3-(chloromethyl)-4-methylphenyl)-2,2-dimethyl-3-(8-methyl-3-(trifluoromethyl)-[1,2,4]triazolo[4,3-a]pyridin-7-yl)propanoate. SOCl$_2$ (1.85 mL, 25.5 mmol) was added to benzyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate (Intermediate 71, 4.3 g, 8.4 mmol) and dichloromethane (40 mL). The resulting mixture was stirred for 1 hour at room temperature. The mixture was combined with another batch of the same compound and concentrated to dryness under reduced pressure to give the title compound (5.2 g). MS (ESI): mass calcd. for C$_{28}$H$_{27}$ClF$_3$N$_3$O$_2$ 529.2; m/z found, 530.2 [M+H]$^+$. $^1$H NMR (400 MHz, DMSO-d$_6$) δ 8.25 (d, J=7.3 Hz, 1H), 7.31 (d, J=1.8 Hz, 1H), 7.25 (d, J=7.3 Hz, 1H), 7.22-7.18 (m, 1H), 7.14-7.02 (m, 6H), 5.06 (d, J=12.3 Hz, 1H), 4.89 (d, J=12.3 Hz, 1H), 4.73 (s, 1H), 4.70 (s, 2H), 2.56 (s, 3H), 2.31 (s, 3H), 1.35 (s, 3H), 1.29 (s, 3H).

Step B: tert-Butyl 2'-(5-(3-(benzyloxy)-2,2-dimethyl-1-(8-methyl-3-(trifluoromethyl)-[1,2,4]triazolo[4,3-a]pyridin-7-yl)-3-oxopropyl)-2-methylbenzyl)-2',3'-dihydrospiro[piperidine-4,4'-pyrido[2,3-b][1,4,5]oxathiazepine]-1-carboxylate 1',1'-dioxide. Benzyl 3-(3-(chloromethyl)-4-methylphenyl)-2,2-dimethyl-3-(8-methyl-3-(trifluoromethyl)-[1,2,4]triazolo[4,3-a]pyridin-7-yl)propanoate (600 mg, 1.13 mmol), tert-butyl 2',3'-dihydrospiro[piperidine-4,4'-pyrido[2,3-b][1,4,5]oxathiazepine]-1-carboxylate 1',1'-dioxide (Intermediate 150, 418 mg, 1.13 mmol), K$_2$CO$_3$ (630 mg, 4.56 mmol), and CH$_3$CN (10 mL) were added to a 30 mL tube. The resulting mixture was stirred at 80° C. for 6 hours, then was allowed to cool to room temperature, poured into water (30 mL), and extracted with ethyl acetate (30 mL×3). These extractions resulted in several organic solvent fractions which were combined, washed with brine (30 mL), dried over anhydrous Na$_2$SO$_4$, filtered, and concentrated to dryness under reduced pressure to give the title compound (950 mg, 92% yield). MS (ESI): mass calcd. for C$_{44}$H$_{49}$F$_3$N$_6$O$_7$S, 862.31; m/z found, 863.4 [M+H]$^+$. $^1$H NMR (400 MHz, DMSO-d$_6$): 8.54 (dd, J=2.0, 5.0 Hz, 1H), 8.26 (d, J=7.3 Hz, 1H), 8.15 (dd, J=1.9, 7.7 Hz, 1H), 7.44 (dd, J=4.9, 7.7 Hz, 1H), 7.24 (d, J=7.3 Hz, 2H), 7.08 (s, 2H), 7.05-7.00 (m, 5H), 5.07 (d, J=12.0 Hz, 1H), 4.88 (d, J=12.3 Hz, 1H), 4.73 (s, 1H), 4.47-4.32 (m, 2H), 3.66 (d, J=11.8 Hz, 4H), 3.21 (d, J=9.5 Hz, 2H), 2.51 (s, 3H), 2.14 (s, 3H), 1.67-1.55 (m, 2H), 1.53-1.43 (m, 2H), 1.36 (s, 9H), 1.36 (br s, 3H), 1.30 (s, 3H).

Step C: 3-(3-((1-(tert-Butoxycarbonyl)-1',1'-dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. (tert-Butyl 2'-(5-(3-(benzyloxy)-2,2-dimethyl-1-(8-methyl-3-(trifluoromethyl)-[1,2,4]triazolo[4,3-a]pyridin-7-yl)-3-oxopropyl)-2-methylbenzyl)-2',3'-dihydrospiro[piperidine-4,4'-pyrido[2,3-b][1,4,5]oxathiazepine]-1-carboxylate 1',1'-dioxide) (950 mg, 1.10 mmol), MeOH (20 mL), and wet Pd/C (100 mg, 5 wt. %) were added to a 100 mL round-bottomed flask. The resulting mixture was stirred under an atmosphere of H$_2$ (15 psi, balloon) at room temperature for 16 hours. The suspension was filtered through a pad diatomaceous earth, such as of Celite® and the pad washed with ethyl acetate (10 mL×2). The filtrate was concentrated to dryness under reduced pressure to give the title compound (850 mg, 92% yield). MS (ESI): mass calcd. for C$_{37}$H$_{43}$F$_3$N$_6$O$_7$S, 772.29; m/z found, 773.2 [M+H]$^+$.

Step D: (*S)-3-(3-((1-(tert-Butoxycarbonyl)-1',1'-dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. The mixture of 3-(3-((1-(tert-Butoxycarbonyl)-1',1'-dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid isomers was separated by chiral SFC (DAICEL CHIRALPAK IC 250 mm×30 mm, 5 µm, mobile phase: 45% to 45% (v/v) supercritical CO$_2$ in EtOH and H$_2$O with 0.1% NH$_3$) to afford two enantiomers. The first eluting isomer (330 mg) was designated (*S): MS (ESI): mass calcd. for C$_{37}$H$_{43}$F$_3$N$_6$O$_7$S, 772.29; m/z found, 773.4 [M+H]$^+$.

Step E: (*S)-3-(3-((1',1'-Dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. ((*S)-3-(3-((1-(tert-Butoxycarbonyl)-1',1'-dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid) (310 mg, 0.401 mmol), 4 N HCl in 1,4-dioxane (10 mL, 40 mmol), and 1,4-dioxane (5 mL) were added to a 100 mL round-bottomed flask. The resulting mixture was stirred for 16 hours at room temperature before concentrating to dryness under reduced pressure. The material was purified by chiral SFC (DAICEL CHIRALCEL OD-H 250 mm×30 mm×5 µm column, mobile phase: 30% to 30% (v/v) EtOH and H$_2$O with 0.1% NH$_3$) to give the title compound (50.3 mg, 18% yield). MS (ESI): mass calcd. for C$_{37}$H$_{43}$F$_3$N$_6$O$_7$S, 672.23; m/z found, 673.2 [M+H]$^+$. $^1$H NMR (400 MHz, CD$_3$OD): 8.52-8.49 (m, 1H), 8.33-8.29 (m, 1H), 8.26 (d, J=7.2 Hz, 1H), 7.47-7.44 (m, 1H), 7.43-7.38 (m, 1H), 7.35 (s, 1H), 7.28-7.23 (m, 1H), 7.09 (d, J=8.0 Hz, 1H), 5.14 (s, 1H), 4.63-4.50 (m, 2H), 3.66-3.52 (m, 2H), 3.44-3.34 (m, 2H), 3.30-2.97 (m, 2H), 2.83 (s, 3H), 2.19 (s, 3H), 2.05-1.50 (m, 4H), 1.42 (s, 3H), 1.23 (s, 3H).

Example 337: (*R)-3-(3-((1',1'-Dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

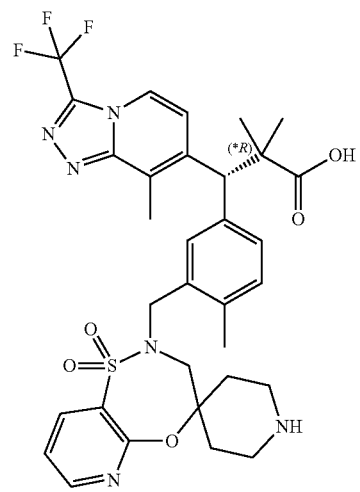 [SMILES: Cc1ccc([C@H](c2ccn3c(C(F)(F)F)nnc3c2C)C(C)(C)C(=O)O)cc1CN1CC2(CCNCC2)Oc2ncccc2S1(=O)=O]

Step A: (*R)-3-(3-((1-(tert-butoxycarbonyl)-1',1'-dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. The second eluting isomer (290 mg) from the chiral separation described in Example 336, Step D was designated (*R): MS (ESI): mass calcd. for $C_{37}H_{43}F_3N_6O_7S$, 772.29; m/z found, 773.4 [M+H]$^+$.

Step B: (*R)-3-(3-((1',1'-Dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. (*R)-3-(3-((1-(tert-Butoxycarbonyl)-1',1'-dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid (290 mg, 0.375 mmol), 4 N HCl in 1,4-dioxane (10 mL, 40 mmol), and 1,4-dioxane (5 mL) were added to a 100 mL round-bottomed flask. The resulting mixture was stirred for 16 hours at room temperature, then was concentrated to dryness under reduced pressure. The material was purified by preparative acidic HPLC (DuraShell 150 mm×25 mm×5 µm column, mobile phase: 15% to 45% (v/v) $CH_3CN$ and $H_2O$ with 0.2% HCOOH) to give the title compound (117.1 mg, 45% yield). MS (ESI): mass calcd. for $C_{37}H_{43}F_3N_6O_7S$, 672.23; m/z found, 673.3 [M+H]$^+$. $^1$H NMR (400 MHz, $CD_3OD$) δ 8.52-8.49 (m, 1H), 8.34-8.23 (m, 3H), 7.47-7.39 (m, 2H), 7.35 (s, 1H), 7.25 (d, J=8.0 Hz, 1H), 7.09 (d, J=8.0 Hz, 1H), 5.12 (s, 1H), 4.63-4.50 (m, 2H), 3.69-3.51 (m, 2H), 3.45-3.35 (m, 2H), 3.26-3.07 (m, 2H), 2.82 (s, 3H), 2.19 (s, 3H), 2.00-1.62 (m, 4H), 1.42 (s, 3H), 1.24 (s, 3H).

Example 338: (*S)-3-(3-((1',1'-Dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

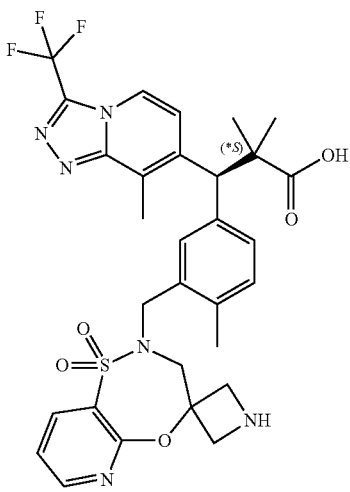 [SMILES: Cc1ccc([C@@H](c2ccn3c(C(F)(F)F)nnc3c2C)C(C)(C)C(=O)O)cc1CN1CC2(CNC2)Oc2ncccc2S1(=O)=O]

Step A: 3-(3-((1-(tert-Butoxycarbonyl)-1',1'-dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. The title compound (700 mg, 93% yield) was prepared using analogous conditions as described in Example 336 where tert-Butyl 2',3'-dihydrospiro[azetidine-3,4'-pyrido[2,3-b][1,4,5]oxathiazepine]-1-carboxylate 1',1'-dioxide (Intermediate 151) was used instead of tert-Butyl 2',3'-dihydrospiro[piperidine-4,4'-pyrido[2,3-b][1,4,5]oxathiazepine]-1-carboxylate 1',1'-dioxide. MS (ESI): mass calcd. for $C_{35}H_{39}F_3N_6O_7S$, 744.26; m/z found, 745.2 [M+H]$^+$.

Step B: (*S)-3-(3-((1-(tert-Butoxycarbonyl)-1',1'-dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. The mixture of 3-(3-((1-(tert-Butoxycarbonyl)-1',1'-dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid isomers was separated by chiral SFC (DAICEL CHIRALPAK IG 250 mm×30 mm, 10 m, mobile phase: 40% to 40% (v/v) supercritical $CO_2$ in IPA and $H_2O$ with 0.1% $NH_3$). The first eluting isomer was designated (*S) and was further purified by preparative acidic HPLC (DuraShell, 150 mm×25 mm×5 µm column, mobile phase: 40% to 70% (v/v) $CH_3CN$ and $H_2O$ with 0.2% HCOOH) to give the title compound (300 mg, 43%). MS (ESI): mass calcd. for $C_{35}H_{39}F_3N_6O_7S$, 744.26; m/z found, 745.2 [M+H]$^+$.

Step C: (*S)-3-(3-((1',1'-Dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. (*S)-3-(3-((1-(tert-Butoxycarbonyl)-1',1'-dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)) propanoic acid (300 mg, 0.403 mmol) and formic acid (10 mL) were added to a 100 mL round-bottomed flask. The resulting mixture was stirred for 16 hours at room temperature, then was concentrated to dryness under reduced pressure. The material was purified by preparative acidic HPLC (DuraShell 150 mm×25 mm×5 µm column mobile phase: 20% to 50% (v/v) $CH_3CN$ and $H_2O$ with 0.2% HCOOH) to give the title compound (137 mg, 47% yield). MS (ESI): mass calcd. for $C_{35}H_{39}F_3N_6O_7S$, 644.20; m/z found, 645.3 [M+H]$^+$. $^1$H NMR (400 MHz, $CDCl_3$) δ 8.55-8.50 (m, 1H), 8.30-8.26 (m, 1H), 8.23 (br s, 1H), 8.00 (d, J=7.2 Hz, 1H), 7.41-7.34 (m, 3H), 7.13-7.08 (m, 2H), 4.85-4.73 (m, 2H), 4.16-4.07 (m, 2H), 3.98 (s, 2H), 3.96-3.86 (m, 2H), 3.14-3.05 (m, 1H), 2.85 (s, 3H), 2.21 (s, 3H), 1.40 (s, 3H), 1.33 (s, 3H).

Example 339: (*R)-3-(3-((1',1'-Dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid Example 340: (*S)-2,2-Dimethyl-3-(4-methyl-3-((8'-methyl-1',1'-dioxidospiro[piperidine-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

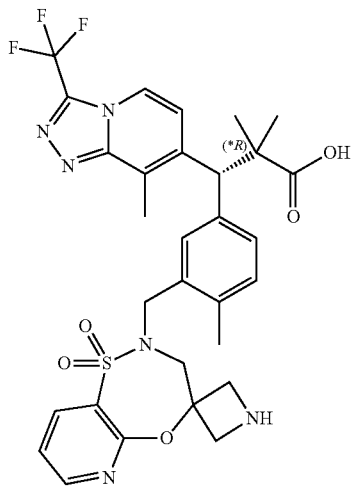 [SMILES: Cc1ccc([C@H](c2ccn3c(C(F)(F)F)nnc3c2C)C(C)(C)C(=O)O)cc1CN1CC2(CNC2)Oc2ncccc2S1(=O)=O]

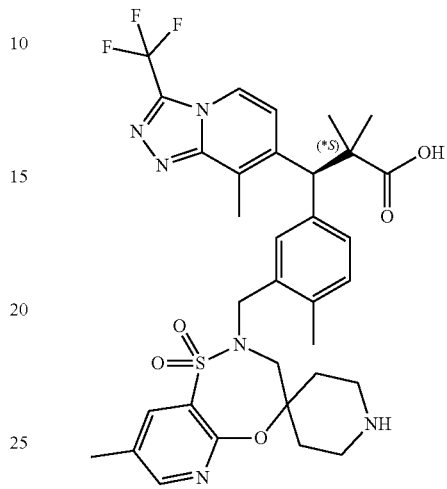

Step A: (*R)-3-(3-((1-(tert-butoxycarbonyl)-1',1'-dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. The second eluting isomer (390 mg) from the chiral separation described in Example 338, Step B was designated (*R): MS (ESI): mass calcd. for $C_{35}H_{39}F_3N_6O_7S$, 744.26; m/z found, 745.2 [M+H]$^+$.

Step B: (*R)-3-(3-((1',1'-Dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. (*R)-3-(3-((1-(tert-Butoxycarbonyl)-1',1'-dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid (370 mg, 0.497 mmol) and formic acid (10 mL) were added to a 100 mL round-bottomed flask. The resulting mixture was stirred for 16 hours at room temperature, then was concentrated to dryness under reduced pressure to give the title compound (244.8 mg, 68% yield). MS (ESI): mass calcd. for $C_{35}H_{39}F_3N_6O_7S$, 644.20; m/z found, 645.3 [M+H]$^+$. $^1$H NMR (400 MHz, CD$_3$OD) δ 8.61-8.57 (m, 1H), 8.34-8.30 (m, 1H), 8.27 (d, J=7.2 Hz, 1H), 8.16 (br s, 1H), 7.59-7.51 (m, 2H), 7.46 (s, 1H), 7.20-7.16 (m, 1H), 7.13-7.09 (m, 1H), 4.94 (s, 1H), 4.64 (d, J=14.0 Hz, 1H), 4.28 (d, J=13.6 Hz, 1H), 4.13 (s, 2H), 4.03 (d, J=11.6 Hz, 1H), 3.95 (d, J=6.8 Hz, 2H), 3.61 (d, J=11.6 Hz, 1H), 2.78 (s, 3H), 2.20 (s, 3H), 1.40 (s, 3H), 1.28 (s, 3H).

Step A: 3-(3-((1-(tert-Butoxycarbonyl)-8'-methyl-1',1'-dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. The title compound (600 mg, 38% yield) was prepared using analogous conditions as described in Example 336 where tert-butyl 8'-methyl-2',3'-dihydrospiro[piperidine-4,4'-pyrido[2,3-b][1,4,5]oxathiazepine]-1-carboxylate 1',1'-dioxide (Intermediate 152) was used instead of tert-butyl 2',3'-dihydrospiro[piperidine-4,4'-pyrido[2,3-b][1,4,5]oxathiazepine]-1-carboxylate 1',1'-dioxide. MS (ESI): mass calcd. for $C_{38}H_{45}F_3N_6O_7S$, 786.30; m/z found, 787.3 [M+H]$^+$.

Step B: (*S)-3-(3-((1-(tert-Butoxycarbonyl)-8'-methyl-1',1'-dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. The mixture of 3-(3-((1-(tert-butoxycarbonyl)-8'-methyl-1',1'-dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid isomers was separated by chiral SFC (DAICEL CHIRALPAK IC 250 mm×50 mm, 5 am, mobile phase: 45% to 45% (v/v) supercritical CO$_2$ in MeOH and H$_2$O with 0.1% NH$_3$). The first eluting isomer (220 mg) was designated (*S): MS (ESI): mass calcd. for $C_{38}H_{45}F_3N_6O_7S$, 786.30; m/z found, 787.3 [M+H]$^+$.

Step C: (*S)-2,2-Dimethyl-3-(4-methyl-3-((8'-methyl-1',1'-dioxidospiro[piperidine-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid. 4N HCl in 1,4-dioxane (5 mL) was added to a solution of (*S)-3-(3-((1-(tert-butoxycarbonyl)-8'-methyl-1',1'-dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid (220 mg, 0.280 mmol) and 1,4-dioxane (5 mL). The resulting mixture was stirred at room temperature for 1.5 hours, then was concentrated to dryness under reduced pressure. The material was purified by preparative acidic HPLC (Agela ASB 150 mm×25 mm×5 am column, mobile phase: 33% to 63% (v/v) CH$_3$CN and H$_2$O with 0.05% HCl) to give the title compound (100.6 mg, 48% yield). MS (ESI): mass calcd. for C$_{33}$H$_{37}$F$_3$N$_6$O$_5$S, 686.25; m/z found, 687.3 [M+H]$^+$. $^1$H NMR (400 MHz, DMSO-d$_6$) δ 9.36-9.25 (m, 1H), 9.15-9.01 (m, 1H), 8.47 (d, J=7.0 Hz, 1H), 8.40 (d, J=1.8 Hz, 1H), 8.01 (d, J=2.3 Hz, 1H), 7.33 (d, J=7.3 Hz, 1H), 7.29-7.25 (m, 1H), 7.19-7.14 (m, 1H), 7.13-7.09 (m, 1H), 4.81 (s, 1H), 4.50-4.34 (m, 2H), 3.56-3.38 (m, 2H), 3.31-3.20 (m, 2H), 3.19-3.09 (m, 2H), 2.66 (s, 3H), 2.37 (s, 3H), 2.16 (s, 3H), 1.93-1.79 (m, 4H), 1.32 (s, 3H), 1.27 (s, 3H).

Example 341: (*R)-2,2-Dimethyl-3-(4-methyl-3-((8'-methyl-1',1'-dioxidospiro[piperidine-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

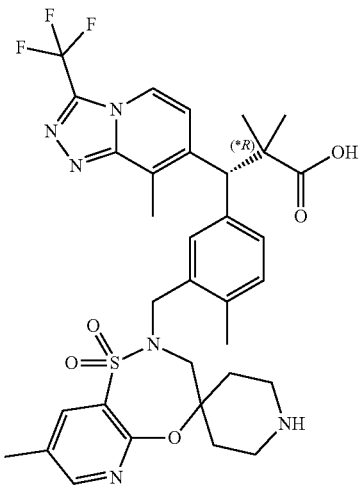 [SMILES: Cc1cnc2c(c1)S(=O)(=O)N(Cc1cc([C@H](c3ccn4c(C(F)(F)F)nnc4c3C)C(C)(C)C(=O)O)ccc1C)CC1(CCNCC1)O2]

Step A: (*R)-3-(3-((1-(tert-butoxycarbonyl)-8'-methyl-1',1'-dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. The second eluting isomer (220 mg) from the chiral separation described in Example 340, Step B was designated (*R): MS (ESI): RT=0.904 min, mass calcd. For C$_{38}$H$_{45}$F$_3$N$_6$O$_7$S, 786.30 m/z found 787.3 [M+H]$^+$.

Step B: (*R)-2,2-Dimethyl-3-(4-methyl-3-((8'-methyl-1',1'-dioxidospiro[piperidine-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid. 4N HCl in 1,4-dioxane (5 mL) was added to a solution of (*R)-3-(3-((1-(tert-butoxycarbonyl)-8'-methyl-1',1'-dioxidospiro[piperidine-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid (220 mg, 0.280 mmol) and 1,4-dioxane (5 mL). The resulting mixture was stirred at room temperature for 1.5 hours, then was concentrated to dryness under reduced pressure. The material was purified by preparative acidic HPLC (Venusil ASB Phenyl, 250 mm×50 mm×10 m column, mobile phase: 30% to 60% (v/v) CH$_3$CN and H$_2$O with 0.05% HCl) to give the title compound (110 mg, 53% yield). MS (ESI): mass calcd. for C$_{33}$H$_{37}$F$_3$N$_6$O$_5$S, 686.25; m/z found, 687.1 [M+H]$^+$. $^1$H NMR (400 MHz, DMSO-d$_6$) δ 9.43-9.33 (m, 1H), 9.22-9.09 (m, 1H), 8.47 (d, J=7.0 Hz, 1H), 8.40 (d, J=1.8 Hz, 1H), 8.01 (d, J=2.0 Hz, 1H), 7.32 (d, J=7.5 Hz, 1H), 7.28-7.25 (m, 1H), 7.18-7.14 (m, 1H), 7.13-7.09 (m, 1H), 4.81 (s, 1H), 4.48-4.41 (m, 2H), 3.77-3.60 (m, 2H), 3.32-3.20 (m, 2H), 3.18-3.09 (m, 2H), 2.66 (s, 3H), 2.37 (s, 3H), 2.16 (s, 3H), 1.92-1.82 (m, 4H), 1.32 (s, 3H), 1.27 (s, 3H).

Example 342: (*S)-2,2-Dimethyl-3-(4-methyl-3-((8'-methyl-1',1'-dioxidospiro[azetidine-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

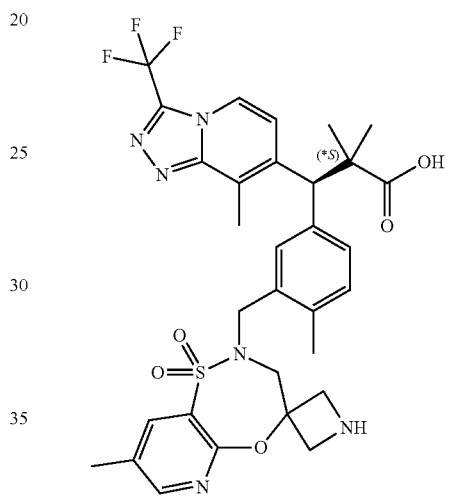

Step A: tert-Butyl 2'-(5-(3-(benzyloxy)-2,2-dimethyl-1-(8-methyl-3-(trifluoromethyl)-[1,2,4]triazolo[4,3-a]pyridin-7-yl)-3-oxopropyl)-2-methylbenzyl)-8'-methyl-2',3'-dihydrospiro[azetidine-3,4'-pyrido[2,3-b][1,4,5]oxathiazepine]-1-carboxylate 1',1'-dioxide.

Benzyl 3-(3-(chloromethyl)-4-methylphenyl)-2,2-dimethyl-3-(8-methyl-3-(trifluoromethyl)-[1,2,4]triazolo[4,3-a]pyridin-7-yl)propanoate (Example 336, Step A, 1.0 g, 1.9 mmol), K$_2$CO$_3$ (1.0 g, 7.2 mmol), and MeCN (20 mL) were added to a 50 mL round-bottomed flask. The resulting mixture was stirred for 10 mins at room temperature and then treated with tert-butyl 8'-methyl-2',3'-dihydrospiro[azetidine-3,4'-pyrido[2,3-b][1,4,5]oxathiazepine]-1-carboxylate 1',1'-dioxide (Intermediate 153, 671 mg, 1.89 mmol). The resulting mixture was stirred for 16 hours at 80° C., then was poured into water (20 mL) and extracted with ethyl acetate (30 mL×3). These extractions resulted in several organic solvent fractions which were combined, washed with brine (50 mL), dried over anhydrous Na$_2$SO$_4$, filtered, and concentrated to dryness under reduced pressure. The material was combined with another batch of the same compound and purified by FCC (petroleum ether/ethyl acetate=1:0 to 3:7) to give the title compound (1.5 g). MS (ESI): mass calcd. for C$_{43}$H$_{47}$F$_3$N$_6$O$_7$S, 848.93; m/z found, 849.4 [M+H]$^+$. $^1$H NMR (400 MHz, DMSO-d$_6$) δ 8.43 (d, J=1.8 Hz, 1H), 8.22 (d, J=7.1 Hz, 1H), 8.04 (d, J=2.0 Hz, 1H), 7.22 (d, J=7.3 Hz, 2H), 7.13-7.08 (m, 2H), 7.06-6.95 (m, 5H), 5.07 (d, J=12.1 Hz, 1H), 4.88 (d, J=12.1 Hz, 1H), 4.71 (s, 1H), 4.37-4.28 (m, 1H), 4.22 (d, J=16.3 Hz, 1H), 3.86-3.69 (m, 6H), 2.51 (s, 3H), 2.38 (s, 3H), 2.19 (s, 3H), 1.36 (s, 9H), 1.35 (s, 3H), 1.30 (s, 3H).

Step B: 3-(3-((1-(tert-Butoxycarbonyl)-8'-methyl-1',1'-dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. tert-Butyl 2'-(5-(3-(benzyloxy)-2,2-dimethyl-1-(8-methyl-3-(trifluoromethyl)-[1,2,4]triazolo[4,3-a]pyridin-7-yl)-3-oxopropyl)-2-methylbenzyl)-8'-methyl-2',3'-dihydrospiro[azetidine-3,4'-pyrido[2,3-b][1,4,5]oxathiazepine]-1-carboxylate 1',1'-dioxide (1.3 g, 1.5 mmol), MeOH (10 mL), and wet Pd/C (100 mg, 10 wt. %) were added to a 50 mL hydrogenation bottle. The resulting mixture was stirred under $H_2$ (50 psi) at room temperature for 1.5 hours. The suspension was filtered through a pad diatomaceous earth, such as of Celite® and the pad washed with MeOH (10 mL×3). The filtrate was concentrated to dryness under reduced pressure. The material was combined with another batch of the same compound to give the title product (1.1 g). MS (ESI): mass calcd. for $C_{36}H_{41}F_3N_6O_7S$, 758.27; m/z found, 759.1 [M+H]$^+$.

Step C: (*S)-3-(3-((1-(tert-Butoxycarbonyl)-8'-methyl-1',1'-dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. The mixture of 3-(3-((1-(tert-butoxycarbonyl)-8'-methyl-1',1'-dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid isomers was separated by chiral SFC (DAICEL CHIRALPAK IC 250 mm×30 mm, 10 m, mobile phase: 30% to 30% (v/v) supercritical $CO_2$ in MeOH and $H_2O$ with 0.1% $NH_3$). The first eluting isomer (500 mg) was designated (*S): MS (ESI): mass calcd. for $C_{36}H_{41}F_3N_6O_7S$, 758.27; m/z found, 759.3 [M+H]$^+$.

Step D: (*S)-2,2-Dimethyl-3-(4-methyl-3-((8'-methyl-1',1'-dioxidospiro[azetidine-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid. HCOOH (6 mL) and (*R)-3-(3-((1-(tert-butoxycarbonyl)-8'-methyl-1',1'-dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid (500 mg, 0.659 mmol) were added to a 100 mL round-bottomed flask. The resulting mixture was stirred at room temperature for 16 hours, then was concentrated to dryness under reduced pressure. The material was purified by preparative acidic HPLC (DuraShell, 150 mm×25 mm×5 μm column, mobile phase: 20% to 50% (v/v) $CH_3CN$ and $H_2O$ with 0.225% HCOOH) to give the title compound (350 mg, 80% yield). MS (ESI): mass calcd. for $C_{36}H_{41}F_3N_6O_7S$, 658.27; m/z found, 659.3 [M+H]$^+$. $^1$H NMR (400 MHz, DMSO-$d_6$) δ 8.44 (s, 1H), 8.34 (d, J=7.1 Hz, 1H), 8.16 (s, 1H), 8.07 (s, 1H), 7.87 (s, 1H), 7.35 (s, 1H), 7.17-7.14 (m, 1H), 7.11-7.08 (m, 1H), 4.65 (s, 1H), 4.53 (d, J=13.5 Hz, 1H), 4.12 (d, J=13.7 Hz, 1H), 4.01-3.96 (m, 2H), 3.80 (s, 4H), 2.65 (s, 3H), 2.38 (s, 3H), 2.18 (s, 3H), 1.22 (s, 3H), 1.12 (s, 3H).

Example 343: (*R)-2,2-Dimethyl-3-(4-methyl-3-((8'-methyl-1',1'-dioxidospiro[azetidine-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

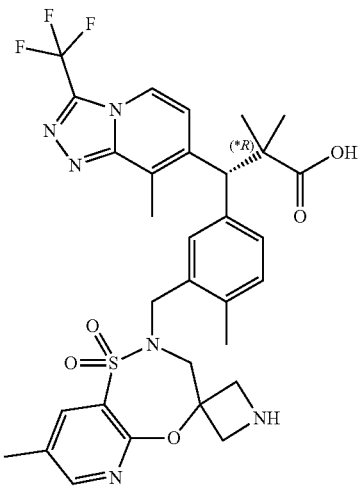 [SMILES: Cc1cnc2c(c1)S(=O)(=O)N(Cc1cc([C@H](c3ccn4c(C(F)(F)F)nnc4c3C)C(C)(C)C(=O)O)ccc1C)CC1(CNC1)O2]

Step A: (*R)-3-(3-((1-(tert-butoxycarbonyl)-8'-methyl-1',1'-dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. The second eluting isomer (550 mg) from the chiral separation described in Example 342, Step C was designated (*R): MS (ESI): mass calcd. for $C_{36}H_{41}F_3N_6O_7S$, 758.27; m/z found, 759.3 [M+H]$^+$.

Step B: (*R)-2,2-Dimethyl-3-(4-methyl-3-((8'-methyl-1',1'-dioxidospiro[azetidine-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid. HCOOH (6 mL) and (*R)-3-(3-((1-(tert-butoxycarbonyl)-8'-methyl-1',1'-dioxidospiro[azetidine-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid (530 mg, 0.698 mmol) were added to a 100 mL round-bottomed flask. The resulting mixture was stirred at room temperature for 16 hours, then was concentrated to dryness under reduced pressure. The material was purified by preparative acidic HPLC (DuraShell, 150 mm×25 mm×5 μm column, mobile phase: 20% to 50% (v/v) $CH_3CN$ and $H_2O$ with 0.2% HCOOH), and then further purified by preparative HPLC (Xtimate C18, 150 mm×40 mm×10 μm column, mobile phase: 23% to 53% (v/v) $CH_3CN$ and $H_2O$ with 0.2% HCOOH) to give the title compound (180 mg, 36% yield). MS (ESI): mass calcd. for $C_{36}H_{41}F_3N_6O_7S$, 658.27; m/z found, 659.1 [M+H]$^+$. $^1$H NMR (400 MHz, DMSO-$d_6$) δ 8.45 (d, J=1.8 Hz, 1H), 8.35 (d, J=7.3 Hz, 1H), 8.08 (d, J=1.8 Hz, 1H), 7.93 (s, 1H), 7.35 (s, 1H), 7.17 (d, J=7.7 Hz, 1H), 7.11 (d, J=1.0 Hz, 1H), 4.63 (s, 1H), 4.55 (d, J=13.2 Hz, 1H), 4.13-4.08 (m, 1H), 3.95 (s, 3H), 3.80 (s, 3H), 2.66 (s, 3H), 2.39 (s, 3H), 2.33 (s, 1H), 2.19 (s, 3H), 1.22 (s, 3H), 1.14 (s, 3H).

Example 344: (*R)-3-(3-((7'-(3-((2-(2-Aminoethoxy)ethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

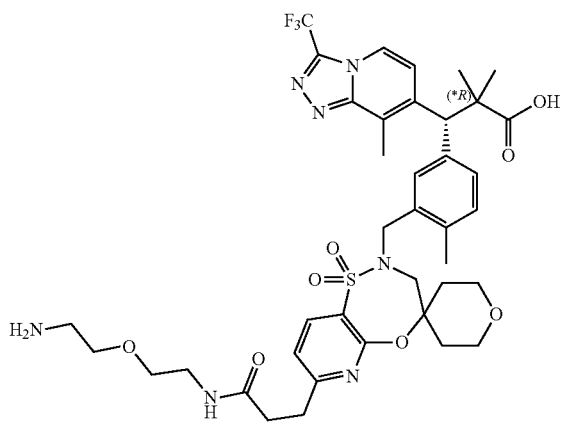 [SMILES: Cc1ccc([C@H](c2ccn3c(C(F)(F)F)nnc3c2C)C(C)(C)C(=O)O)cc1CN1CC2(CCOCC2)Oc2nc(CCC(=O)NCCOCCN)ccc2S1(=O)=O]

Step A: (E)-tert-Butyl 3-(1',1'-dioxido-2,2',3,3',5,6-hexahydrospiro[pyran-4,4'-pyrido[2,3-b][1,4,5]oxathiazepin]-7'-yl)acrylate. tert-Butyl acrylate (477 mg, 3.72 mmol), Pd(OAc)$_2$ (32.1 mg, 0.143 mmol), 2-(di-tert-butylphosphino)biphenyl (85.5 mg, 0.287 mmol), and Et$_3$N (580 mg, 5.73 mmol) were added to a solution of 7'-bromo-2,2',3,3',5,6-hexahydrospiro[pyran-4,4'-pyrido[2,3-b][1,4,5]oxathiazepine] 1',1'-dioxide (1.00 g, 2.86 mmol, Intermediate 124) and DMF (18 mL). The resulting mixture was sparged with N$_2$ for 5 minutes and then stirred while heating at 120° C. for 3 hours before cooling to room-temperature and concentrating to dryness under reduced pressure. The residue was diluted with sat. NH$_4$Cl (7 mL) and the resultant mixture was extracted with ethyl acetate (2×). These extractions resulted in several fractions which were combined, dried over sodium sulfate and concentrated to dryness under reduced pressure. The residue was purified by flash column chromatography (eluent:petroleum ether/ethyl acetate; 10:1 to 1:5, gradient) to afford the title compound (805 mg, 71%) as a yellow solid. MS (ESI): mass calcd. for C$_{18}$H$_{24}$N$_2$O$_6$S, 396.1 m/z found 396.9 [M+H]$^+$.

Step B: tert-Butyl 3-(1',1'-dioxido-2,2',3,3',5,6-hexahydrospiro[pyran-4,4'-pyrido[2,3-b][1,4,5]oxathiazepin]-7'-yl)propanoate. (E)-tert-Butyl 3-(1',1'-dioxido-2,2',3,3',5,6-hexahydrospiro[pyran-4,4'-pyrido[2,3-b][1,4,5]oxathiazepin]-7'-yl)acrylate (805 mg, 2.03 mmol), MeOH (10 mL), and dry Pd/C (200 mg, 10 wt. %, 0.189 mmol) were added to 75 mL hydrogenation vessel. The resultant mixture was stirred at room temperature for 16 hours under H$_2$ (50 psi). The suspension was filtered through a pad diatomaceous earth, such as of Celite® and the pad was washed with MeOH (20 mL). The filtrate was concentrated to dryness under reduced pressure to give the product. This was combined with an additional batch of tert-Butyl 3-(1',1'-dioxido-2,2',3,3',5,6-hexahydrospiro[pyran-4,4'-pyrido[2,3-b][1,4,5]oxathiazepin]-7'-yl)propanoate and purified by flash column chromatography (eluent:petroleum ether/ethyl acetate; 10:1 to 1:5, gradient) to afford the title compound (781 mg). MS (ESI): mass calcd. for C$_{18}$H$_{26}$N$_2$O$_6$S, 398.2 m/z found 399.2 [M+H]$^+$. $^1$H NMR (400 MHz, DMSO-d$_6$) δ 8.60-8.10 (m, 1H), 8.02 (d, J=7.8 Hz, 1H), 7.24 (d, J=7.8 Hz, 1H), 3.81 (t, J=9.8 Hz, 2H), 3.57 (d, J=10.8 Hz, 2H), 3.47 (s, 2H), 2.97 (t, J=7.0 Hz, 2H), 2.64 (t, J=7.0 Hz, 2H), 1.72-1.46 (m, 4H), 1.34 (s, 9H).

Step C: (*R)-Methyl 3-(3-((7'-(3-(tert-butoxy)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate. DIAD (2.33 g, 11.5 mmol) was added to a solution of (*R)-methyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate (2.5 g, 5.7 mmol, Intermediate 141), tert-butyl 3-(1',1'-dioxido-2,2',3,3',5,6-hexahydrospiro[pyran-4,4'-pyrido[2,3-b][1,4,5]oxathiazepin]-7'-yl)propanoate (2.8 g, 6.9 mmol), PPh$_3$ (3.02 g, 11.5 mmol), and THF (30 mL). The resultant mixture was stirred at room temperature for 3 hours before concentrating to dryness under reduced pressure to give the product, which was purified by flash chromatography (eluent: petroleum ether/ethyl acetate; 10:1 to 1:3, gradient) to afford the title compound (2.06 g, 37%). MS (ESI): mass calcd. for C$_{40}$H$_{48}$F$_3$N$_5$O$_8$S, 815.3 m/z found 816.3 [M+H]$^+$. $^1$H NMR (400 MHz, DMSO-d$_6$) δ 8.41 (d, J=7.1 Hz, 1H), 8.05 (d, J=7.8 Hz, 1H), 7.29 (d, J=7.8 Hz, 1H), 7.25-7.16 (m, 3H), 7.16-7.09 (m, 1H), 4.80 (s, 1H), 4.54-4.24 (m, 2H), 3.76 (d, J=9.1 Hz, 2H), 3.55-3.40 (m, 6H), 2.99 (t, J=6.9 Hz, 2H), 2.76-2.59 (m, 5H), 2.15 (s, 3H), 2.07 (s, 1H), 1.52-1.40 (m, 4H), 1.36 (s, 12H), 1.29 (s, 3H).

Step D: (*R)-3-(2'-(5-(3-Methoxy-2,2-dimethyl-1-(8-methyl-3-(trifluoromethyl)-[1,2,4]triazolo[4,3-a]pyridin-7-yl)-3-oxopropyl)-2-methylbenzyl)-1',1'-dioxido-2,2',3,3',5,6-hexahydrospiro[pyran-4,4'-pyrido[2,3-b][1,4,5]oxathiazepin]-7'-yl)propanoic acid. 4 N HCl in 1,4-dioxane (10 mL) was added to a solution of (*R)-methyl 3-(3-((7'-(3-(tert-butoxy)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate (1.20 g, 1.47 mmol) and 1,4-dioxane (5 mL) at room-temperature. The mixture was stirred at room-temperature for 1 hour before concentrating to dryness under reduced pressure to afford the title compound (1.10 g, 98%), which was used in the next step without further purification. MS (ESI): mass calcd. for C$_{36}$H$_{40}$F$_3$N$_5$O$_8$S, 759.3 m/z found 760.2 [M+H]$^+$.

Step E: (*R)-Methyl 3-(3-((7'-(2,2-dimethyl-4,12-dioxo-3,8-dioxa-5,11-diazatetradecan-14-yl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate. HATU (286 mg, 0.752 mmol) was added to a solution of (*R)-3-(2'-(5-(3-methoxy-2,2-dimethyl-1-(8-methyl-3-(trifluoromethyl)-[1,2,4]triazolo[4,3-a]pyridin-7-yl)-3-oxopropyl)-2-methylbenzyl)-1',1'-dioxido-2,2',3,3',5,6-hexahydrospiro[pyran-4,4'-pyrido[2,3-b][1,4,5]oxathiazepin]-7'-yl)propanoic acid (1.1 g, 0.58 mmol), tert-butyl (2-(2-aminoethoxy)ethyl)carbamate (130 mg, 0.636 mmol), DIPEA (374 mg, 2.89 mmol), and DMF (15 mL) at 0° C. The resultant mixture was stirred at room-temperature for 16 hours. This was combined with an additional batch of (*R)-Methyl 3-(3-((7'-(2,2-dimethyl-4,12-dioxo-3,8-dioxa-5,11-diazatetradecan-14-yl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate, diluted with H$_2$O (15 mL) and extracted with ethyl acetate (2×). These extractions resulted in several fractions which were combined, dried over sodium sulfate and concentrated to dryness under reduced pressure. The residue was purified by flash column chromatography (eluent:petroleum ether/ethyl acetate; 10:1 to 0:10, gradient) to afford the title compound (1.2 g). MS (ESI): mass calcd. for $C_{45}H_{58}F_3N_7O_{10}S$, 945.4 m/z found 946.4 [M+H]+.

Step F: (*R)-3-(3-((7'-(2,2-Dimethyl-4,12-dioxo-3,8-dioxa-5,11-diazatetradecan-14-yl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. (*R)-Methyl 3-(3-((7'-(2,2-dimethyl-4,12-dioxo-3,8-dioxa-5,11-diazatetradecan-14-yl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate (500 mg, 0.529 mmol) was added to a solution of LiOH*H$_2$O (127 mg, 5.30 mmol), THF (3 mL), MeOH (3 mL), and H$_2$O (3 mL). The resultant mixture was stirred at 65° C. for 16 hours before cooling to room-temperature, adjusting the pH to 6-7 with 1 N HCl, and extracting with ethyl acetate (2×). These extractions resulted in several fractions which were combined and concentrated to dryness under reduced pressure to afford the product (467 mg, 95%). MS (ESI): mass calcd. for $C_{44}H_{56}F_3N_7O_{10}S$, 931.4 m/z found 932.7 [M+H]+.

Step G: (*R)-3-(3-((7'-(3-((2-(2-Aminoethoxy)ethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. 4 N HCl in 1,4-dioxane (3 mL) was added to a solution of (*R)-3-(3-((7'-(2,2-dimethyl-4,12-dioxo-3,8-dioxa-5,11-diazatetradecan-14-yl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid (250 mg, 0.268 mmol) and 1,4-dioxane (3 mL) at room-temperature. The resultant mixture was stirred at room-temperature for 1 hour. This was combined with an additional batch of (*R)-3-(3-((7'-(3-((2-(2-Aminoethoxy)ethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid and concentrated to dryness under reduced pressure to give the product, which was further purified by reverse phase preparative HPLC (stationary phase: Phenomenex Synergi C18 150×30 mm, 4 μm column; eluent: 17% to 37% (v/v) CH$_3$CN and aqueous HCl (0.006 N)) to afford pure product. The product was suspended in water (10 mL), extracted with ethyl acetate (3×). These extractions resulted in several fractions that were dried over anhydrous Na$_2$SO$_4$, filtered, and concentrated to dryness under reduced pressure to afford the title compound (8.7 mg, 4%). MS (ESI): mass calcd. for $C_{39}H_{48}F_3N_7O_8S$, 831.3 m/z found 832.4 [M+H]+. $^1$H NMR (400 MHz, DMSO-d$_6$) δ 12.40 (s, 1H), 8.42 (d, J=7.1 Hz, 1H), 8.29 (s, 1H), 8.09 (s, 1H), 7.92 (d, J=7.3 Hz, 1H), 7.42-7.32 (m, 1H), 7.29 (s, 1H), 7.18 (d, J=7.6 Hz, 1H), 7.06 (d, J=7.8 Hz, 1H), 6.17 (d, J=7.3 Hz, 1H), 5.26 (s, 1H), 4.74 (s, 1H), 4.41-4.31 (m, 2H), 3.64-3.43 (m, 8H), 3.42 (d, J=4.9 Hz, 3H), 3.25 (d, J=4.9 Hz, 2H), 3.07-2.93 (m, 4H), 2.79 (t, J=6.9 Hz, 2H), 2.66 (s, 2H), 2.56-2.52 (m, 2H), 2.18 (s, 3H), 1.53 (s, 2H), 1.26 (d, J=15.4 Hz, 6H).

Example 345: (*S)-3-(3-((7'-(3-((2-(2-aminoethoxy)ethyl)amino)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

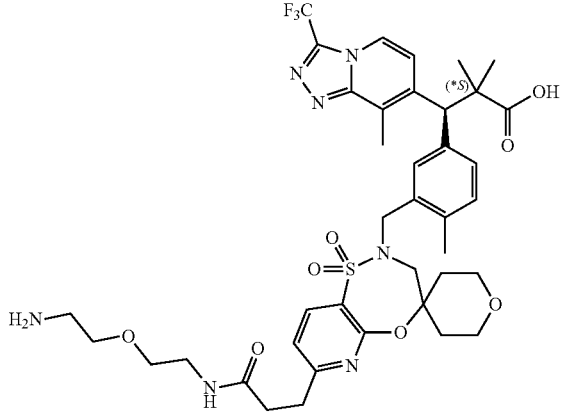 [SMILES: Cc1ccc([C@@H](c2ccn3c(C(F)(F)F)nnc3c2C)C(C)(C)C(=O)O)cc1CN1CC2(CCOCC2)Oc2nc(CCC(=O)NCCOCCN)ccc2S1(=O)=O]

The title compound (2.04 g) was prepared using analogous conditions as described in Example 344 where (*S)-methyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate (Intermediate 143) was used instead of (*R)-methyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate (Intermediate 141) in step C. MS (ESI): mass calcd. for $C_{40}H_{48}F_3N_5O_8S$, 815.3 m/z found 816.1 [M+H]+. $^1$H NMR (400 MHz, DMSO-d$_6$) δ 8.41 (d, J=7.3 Hz, 1H), 8.05 (d, J=7.6 Hz, 1H), 7.29 (d, J=7.8 Hz, 1H), 7.25-7.17 (m, 3H), 7.15-7.09 (m, 1H), 4.85-4.72 (m, 1H), 4.52-4.21 (m, 2H), 3.84-3.69 (m, 2H), 3.60-3.34 (m, 6H), 2.99 (t, J=7.0 Hz, 2H), 2.72-2.59 (m, 5H), 2.16 (s, 3H), 2.07 (s, 1H), 1.54-1.39 (m, 4H), 1.36 (s, 12H), 1.29 (s, 3H).

Example 346: (*S)-3-(3,7-Dimethyl-7H-pyrrolo[2,3-c]pyridazin-6-yl)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoic Acid

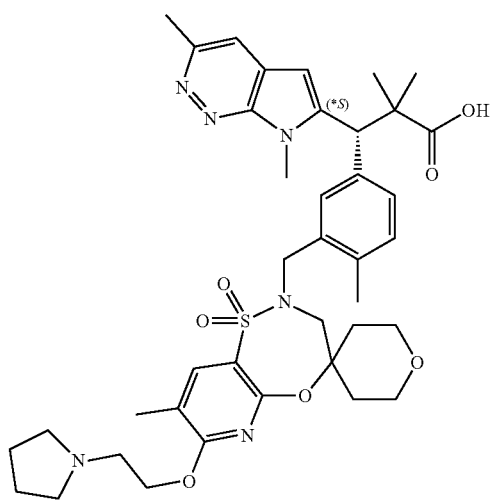 [SMILES: Cc1cc2cc([C@@H](c3ccc(C)c(CN4CC5(CCOCC5)Oc5nc(OCCN6CCCC6)c(C)cc5S4(=O)=O)c3)C(C)(C)C(=O)O)n(C)c2nn1]

Step A: (3-(((tert-Butyldimethylsilyl)oxy)methyl)-4-methylphenyl)(3,7-dimethyl-7H-pyrrolo[2,3-c]pyridazin-6-yl)methanol. A mixture of 3,7-Dimethyl-7H-pyrrolo[2,3-c]pyridazine-6-carbaldehyde (Intermediate 149, 1.0 g, 5.7 mmol), tert-butyldimethyl((2-methyl-5-(4,4,5,5-tetramethyl-1,3,2-dioxaborolan-2-yl)benzyl)oxy)silane (3.1 g, 8.6 mmol), P(1-nap)$_3$ (942 mg, 2.28 mmol), K$_2$CO$_3$ (3.94 g, 28.5 mmol), and 1,4-dioxane (30 mL) was sparged with N$_2$ for 5 minutes and then treated with PdCl$_2$ (202 mg, 1.14 mmol). The mixture was sparged with N$_2$ for another 5 minutes and then stirred and heated at 110° C. for 16 hours before cooling to room-temperature, pouring it into water (50 mL), and extracting with dichloromethane (3×). These extractions resulted in several fractions that were dried over Na$_2$SO$_4$, filtered, and concentrated to dryness under reduced pressure. The residue was purified by flash chromatography (eluent: petroleum ether/ethyl acetate; 20:1 to 2:1, gradient) to afford the title compound (1.41 g, 50%). MS (ESI): mass calcd. for C$_{23}$H$_{33}$N$_3$O$_2$Si, 411.2, m/z found 412.2 [M+H]$^+$.

Step B: tert-Butyl 3-(3-(((tert-butyldimethylsilyl)oxy)methyl)-4-methylphenyl)-3-(3,7-dimethyl-7H-pyrrolo[2,3-c]pyridazin-6-yl)-2,2-dimethylpropanoate. 2,2,2-Trichloroacetonitrile (682 µL, 6.80 mmol) was added to a solution of (3-(((tert-butyldimethylsilyl)oxy)methyl)-4-methylphenyl)(3,7-dimethyl-7H-pyrrolo[2,3-c]pyridazin-6-yl)methanol (1.4 g, 3.4 mmol), DBU (101 µL, 0.676 mmol), and DCE (30 mL) under N$_2$. The resultant mixture was stirred at room-temperature for 1 hour before treating with ((1-(tert-butoxy)-2-methylprop-1-en-1-yl)oxy)trimethylsilane (8.1 g, 37 mmol) and BF$_3$.OEt$_2$ (558 µL, 4.42 mmol). The mixture was then stirred at room-temperature for another 1.5 hours before quenching with water (60 mL) and extracting with dichloromethane (3×). These extractions resulted in several fractions that were dried over anhydrous Na$_2$SO$_4$, filtered, and concentrated to dryness under reduced pressure. The residue was purified by flash chromatography (eluent:petroleum ether/ethyl acetate; 20:1 to 1:1, gradient) to afford the title compound (600 mg, 27%). MS (ESI): mass calcd. for C$_{31}$H$_{47}$N$_3$O$_3$Si, 537.3, m/z found 538.3 [M+H]$^+$.

Step C: tert-Butyl 3-(3,7-dimethyl-7H-pyrrolo[2,3-c]pyridazin-6-yl)-3-(3-(hydroxymethyl)-4-methylphenyl)-2,2-dimethylpropanoate. TBAF (2.23 mL, 1 M in THF, 2.23 mmol) was added to a solution of tert-butyl 3-(3-(((tert-butyldimethylsilyl)oxy)methyl)-4-methylphenyl)-3-(3,7-dimethyl-7H-pyrrolo[2,3-c]pyridazin-6-yl)-2,2-dimethylpropanoate (600 mg, 1.12 mmol) and THF (10 mL). The resultant mixture was stirred at room-temperature for 2 hours before quenching with H$_2$O (50 mL) and extracting with ethyl acetate (3×). These extractions resulted in several fractions that were washed with brine (3×), dried over anhydrous Na$_2$SO$_4$, filtered, and concentrated to dryness under reduced pressure. The residue was purified by flash chromatography (eluent:petroleum ether/ethyl acetate; 10:1 to 1:1, gradient) to afford the title compound (222 mg, 45%). MS (ESI): mass calcd. for C$_{25}$H$_{33}$N$_3$O$_3$ 423.3, m/z found 424.3 [M+H]$^+$. $^1$H NMR (400 MHz, DMSO-d$_6$) δ 7.59 (s, 1H), 7.25 (s, 1H), 7.08-7.02 (m, 2H), 6.58 (s, 1H), 5.05-4.97 (m, 1H), 4.59 (s, 1H), 4.42-4.36 (m, 2H), 3.59 (s, 3H), 2.61 (s, 3H), 2.16 (s, 3H), 1.21 (s, 3H), 1.18 (s, 3H), 1.07 (s, 9H).

Step D: tert-Butyl 3-(3-(chloromethyl)-4-methylphenyl)-3-(3,7-dimethyl-7H-pyrrolo[2,3-c]pyridazin-6-yl)-2,2-dimethylpropanoate. SOCl$_2$ (0.16 mL, 2.2 mmol) was added to a solution consisting of tert-butyl 3-(3,7-dimethyl-7H-pyrrolo[2,3-c]pyridazin-6-yl)-3-(3-(hydroxymethyl)-4-methylphenyl)-2,2-dimethylpropanoate (190 mg, 0.449 mmol) and dichloromethane (5 mL). The resultant mixture was stirred at room-temperature for 1 hour before concentrating to dryness under reduced pressure to afford the title compound (200 mg), which was used in the next step without further purification. MS (ESI): mass calcd. for C$_{25}$H$_{32}$ClN$_3$O$_2$ 411.2, m/z found 442.2 [M+H]$^+$.

Step E: tert-Butyl 3-(3,7-dimethyl-7H-pyrrolo[2,3-c]pyridazin-6-yl)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoate. A mixture of tert-Butyl 3-(3-(chloromethyl)-4-methylphenyl)-3-(3,7-dimethyl-7H-pyrrolo[2,3-c]pyridazin-6-yl)-2,2-dimethylpropanoate (200 mg), 8'-methyl-7'-(2-(pyrrolidin-1-yl)ethoxy)-2,2',3,3',5,6-hexahydrospiro[pyran-4,4'-pyrido[2,3-b][1,4,5]oxathiazepine] 1',1'-dioxide (180 mg, 0.453 mmol, Intermediate 145), K$_2$CO$_3$ (188 mg, 1.36 mmol), and CH$_3$CN (10 mL) was stirred at 90° C. for 16 hours before cooling to room-temperature, pouring it into H$_2$O (50 mL) and extracting with ethyl acetate (3×). These extractions resulted in several fractions that were dried over anhydrous Na$_2$SO$_4$, filtered, and concentrated to dryness under reduced pressure to afford the title compound (360 mg, 100%), which was used in the next step without further purification. MS mass calcd. for C$_{43}$H$_{58}$N$_6$O$_7$S, 802.4, m/z found 803.5 [M+H]$^+$.

Step F: 3-(3,7-Dimethyl-7H-pyrrolo[2,3-c]pyridazin-6-yl)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoic acid. 4 N HCl in 1,4-dioxane (10 mL) was added drop-wise to tert-butyl 3-(3,7-dimethyl-7H-pyrrolo[2,3-c]pyridazin-6-yl)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoate (360 mg), and 1,4-dioxane (3 mL). The resultant mixture was stirred at room-temperature for 16 hours before concentrating to dryness under reduced pressure to give the product, which was purified by reverse phase preparative HPLC (stationary phase: Waters Xbridge Prep OBD C18 150 mm×30 mm×10 m column; eluent: 20% to 50% (v/v) CH$_3$CN and H$_2$O with 10 mM NH$_4$HCO$_3$) to afford the title compound (150 mg, 45%). MS (ESI): mass calcd. for C$_{39}$H$_{50}$N$_6$O$_7$S, 746.4, m/z found 747.3 [M+H]$^+$.

Step G: (*S)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(pyrrolidine-1-yl)-ethoxy)2,3,5,6-tetrahydrospiro[pyran-4,4'-pyrido[2,3-b][1,4,5]oxathiazepin]-2',(3'H)-yl)methyl)phenyl)propanoic acid. The mixture of 3-(3,7-Dimethyl-7H-pyrrolo[2,3-c]pyridazin-6-yl)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoic acid isomers were separated by chiral SFC (stationary phase: DAICEL CHIRALPAK IG 250 mm×30 mm, 10 m, mobile phase: 50% to 50% (v/v) supercritical CO$_2$ in i-PrOH and H$_2$O with 0.1% NH$_3$). The first eluting isomer (36 mg, 24%) was designated (*S). MS (ESI): mass calcd. for C$_{39}$H$_{50}$N$_6$O$_7$S, 746.4, m/z found 747.4 [M+H]$^+$. $^1$H NMR (400 MHz, DMSO-d$_6$) δ 7.81 (s, 1H), 7.59 (s, 1H), 7.23 (s, 1H), 7.13 (s, 2H), 6.63 (s, 1H), 4.73 (s, 1H), 4.47-4.34 (m, 4H), 3.84-3.73 (m, 2H), 3.58 (s, 3H), 3.55-3.50 (m, 6H), 2.84-2.78 (m, 2H), 2.63 (s, 3H), 2.55-2.53 (m, 2H), 2.19 (s, 3H), 2.14 (s, 3H), 1.71-1.63 (m, 4H), 1.56-1.42 (m, 4H), 1.23 (d, J=6.4 Hz, 6H).

Example 347: (*R)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(pyrrolidine-1-yl)-ethoxy)2,3,5,6-tetrahydrospiro[pyran-4,4'-pyrido[2,3-b][1,4,5]oxathiazepin]-2',(3'H)-yl)methyl)phenyl)propanoic Acid Example 348: (*S)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)2,3,5,6-tetrahydrospiro[pyran-4,4'-pyrido[2,3-b][1,4,5]oxathiazepin]-2',(3'H)-yl)methyl)phenyl)propanoic Acid

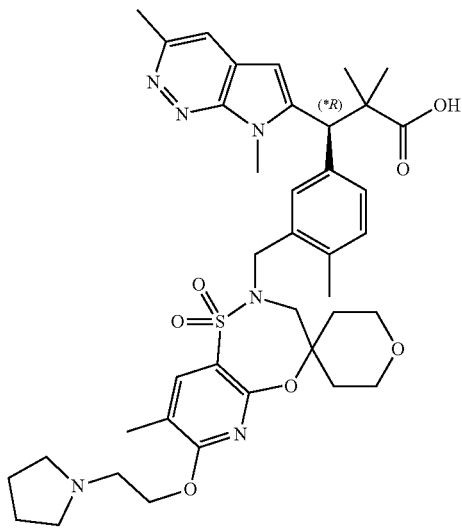 [SMILES: Cc1cc2cc([C@H](c3ccc(C)c(CN4CC5(CCOCC5)Oc5nc(OCCN6CCCC6)c(C)cc5S4(=O)=O)c3)C(C)(C)C(=O)O)n(C)c2nn1]

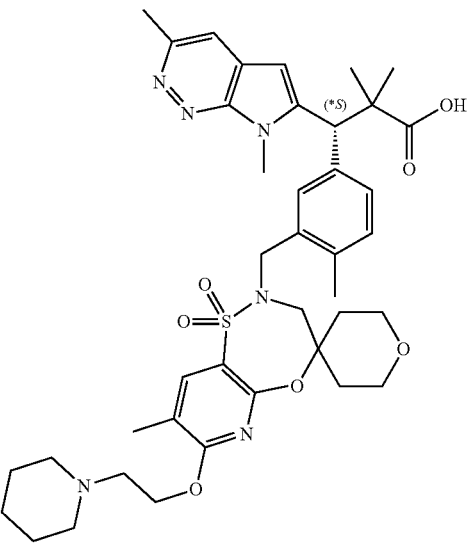 [SMILES: Cc1cc2cc([C@@H](c3ccc(C)c(CN4CC5(CCOCC5)Oc5nc(OCCN6CCCCC6)c(C)cc5S4(=O)=O)c3)C(C)(C)C(=O)O)n(C)c2nn1]

The mixture of 3-(3,7-dimethyl-7H-pyrrolo[2,3-c]pyridazin-6-yl)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoic acid isomers (Example 346) were separated by chiral SFC (stationary phase: DAICEL CHIRALPAK IG 250 mm×30 mm, 10 μm, mobile phase: 50% to 50% (v/v) supercritical $CO_2$ in i-PrOH and $H_2O$ with 0.1% $NH_3$). The second eluting isomer (38 mg, 25%) was designated (*R). MS (ESI): mass calcd. for $C_{39}H_{50}N_6O_7S$, 746.4, m/z found 747.5 $[M+H]^+$. $^1H$ NMR (400 MHz, DMSO-$d_6$) δ 7.82 (s, 1H), 7.59 (s, 1H), 7.23 (s, 1H), 7.13 (s, 2H), 6.64 (s, 1H), 4.74 (s, 1H), 4.45-4.35 (m, 4H), 3.85-3.74 (m, 2H), 3.59 (s, 3H), 3.56-3.53 (m, 6H), 2.85-2.79 (m, 2H), 2.63 (s, 3H), 2.56-2.54 (m, 2H), 2.19 (s, 3H), 2.14 (s, 3H), 1.70-1.64 (m, 4H), 1.57-1.43 (m, 4H), 1.23 (d, J=6.1 Hz, 6H).

Step A: tert-Butyl 3-(3,7-dimethyl-7H-pyrrolo[2,3-c]pyridazin-6-yl)-2,2-dimethyl-3-(4-methyl-3-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoate. tert-Butyl 3-(3-(chloromethyl)-4-methylphenyl)-3-(3,7-dimethyl-7H-pyrrolo[2,3-c]pyridazin-6-yl)-2,2-dimethylpropanoate (200 mg, Example 346, step D), 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide (182 mg, 0.442 mmol, Intermediate 72), $K_2CO_3$ (188 mg, 1.36 mmol), and $CH_3CN$ (10 mL) were mixed and stirred at 80° C. for 16 hours before cooling to room-temperature, quenching with water (80 mL) and extracting with ethyl acetate (3×). These extractions resulted in several fractions that were dried over anhydrous $Na_2SO_4$, filtered, and concentrated to dryness under reduced pressure to afford the compound (290 mg), which was used in the next step without further purification. MS (ESI): mass calcd. for $C_{44}H_{60}N_6O_7S$, 816.4, m/z found 817.5 $[M+H]^+$.

Step B: 3-(3,7-Dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)2,3,5,6-tetrahydrospiro[pyran-4,4'-pyrido[2,3-b][1,4,5]oxathiazepin]-2',(3'H)-yl)methyl)phenyl)propanoic acid. 4 N HCl in 1,4-dioxane (6 mL) was added drop-wise to tert-butyl 3-(3,7-dimethyl-7H-pyrrolo[2,3-c]pyridazin-6-yl)-2,2-dimethyl-3-(4-methyl-3-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoate (280 mg, 0.34 mmol) and 1,4-dioxane (5 mL). The resultant mixture was stirred at room-temperature for 16 hours before concentrating to dryness under reduced pressure to give the product, which was purified by preparative HPLC (stationary phase: Waters Xbridge Prep OBD C18 150×30 mm×5 μm column; eluent: 20% to 40% (v/v) $CH_3CN$ and $H_2O$ with 10 mM NH₄HCO₃) to afford the title compound (120 mg, 46%). MS (ESI): mass calcd. for C₄₀H₅₂N₆O₇S, 760.4, m/z found 761.3 [M+H]⁺.

Step C: (*S)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)2,3,5,6-tetrahydrospiro[pyran-4,4'-pyrido[2,3-b][1,4,5]oxathiazepin]-2',(3'H)-yl)methyl)phenyl)propanoic acid. The mixture of 3-(3,7-dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)2,3,5,6-tetrahydrospiro[pyran-4,4'-pyrido[2,3-b][1,4,5]oxathiazepin]-2',(3'H)-yl)methyl)phenyl)propanoic acid isomers were separated by chiral SFC (stationary phase: DAICEL CHIRALPAK IG 250 mm×30 mm, 10 am, mobile phase: 50% to 50% (v/v) supercritical CO₂ in i-PrOH and H₂O with 0.1% NH₃). The first eluting isomer (29 mg, 23%) was designated (*S). MS (ESI): mass calcd. for C₄₀H₅₂N₆O₇S, 760.4, m/z found 761.3 [M+H]⁺. ¹H NMR (400 MHz, DMSO-d₆) δ 7.82 (s, 1H), 7.61 (s, 1H), 7.25 (s, 1H), 7.14 (s, 2H), 6.64 (s, 1H), 4.74 (s, 1H), 4.47-4.34 (m, 4H), 3.86-3.74 (m, 2H), 3.60 (s, 3H), 3.58-3.38 (m, 6H), 3.31-3.25 (m, 2H), 2.78-2.69 (m, 2H), 2.64 (s, 3H), 2.20 (s, 3H), 2.14 (s, 3H), 1.58-1.33 (m, 10H), 1.26 (s, 6H).

Example 349: (*R)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)2,3,5,6-tetrahydrospiro[pyran-4,4'-pyrido[2,3-b][1,4,5]oxathiazepin]-2',(3'H)-yl)methyl)phenyl)propanoic Acid

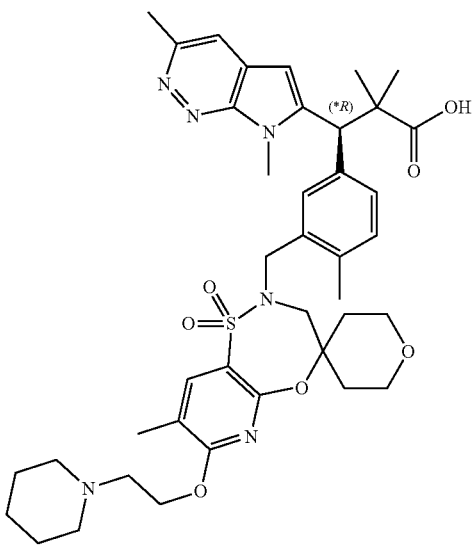 [SMILES: Cc1cc2cc([C@H](c3ccc(C)c(CN4CC5(CCOCC5)Oc5nc(OCCN6CCCCC6)c(C)cc5S4(=O)=O)c3)C(C)(C)C(=O)O)n(C)c2nn1]

The mixture of 3-(3,7-dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)2,3,5,6-tetrahydrospiro[pyran-4,4'-pyrido[2,3-b][1,4,5]oxathiazepin]-2',(3'H)-yl)methyl)phenyl)propanoic acid isomers (Example 348) were separated by chiral SFC (stationary phase: DAICEL CHIRALPAK IG 250 mm×30 mm, 10 m, mobile phase: 50% to 50% (v/v) supercritical CO₂ in i-PrOH and H₂O with 0.1% NH₃). The second eluting isomer (33 mg, 27%) was designated (*R). MS (ESI): mass calcd. for C₄₀H₅₂N₆O₇S, 760.4, m/z found 761.3 [M+H]⁺. ¹H NMR (400 MHz, DMSO-d₆) δ 7.80 (s, 1H), 7.58 (s, 1H), 7.21 (s, 1H), 7.11 (s, 2H), 6.61 (s, 1H), 4.71 (s, 1H), 4.46-4.32 (m, 4H), 3.82-3.70 (m, 2H), 3.57 (s, 3H), 3.55-3.45 (m, 6H), 3.15-3.02 (m, 2H), 2.83-2.70 (m, 2H), 2.61 (s, 3H), 2.17 (s, 3H), 2.11 (s, 3H), 1.55-1.35 (m, 10H), 1.23 (s, 6H).

Example 350: (*S)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)spiro[cyclopropane-1,4'-pyrido[2,3-b][1,4,5]oxathiazepin]-2',(3'H)-yl)methyl)phenyl)propanoic Acid

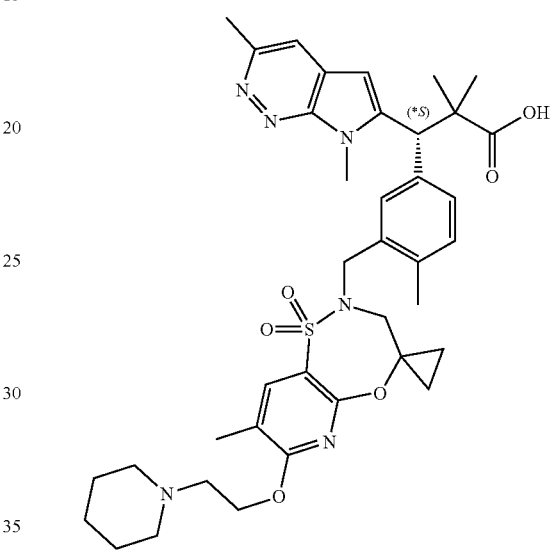

Step A: tert-Butyl 3-(3,7-dimethyl-7H-pyrrolo[2,3-c]pyridazin-6-yl)-2,2-dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl)propanoate. A mixture of tert-Butyl 3-(3-(chloromethyl)-4-methylphenyl)-3-(3,7-dimethyl-7H-pyrrolo[2,3-c]pyridazin-6-yl)-2,2-dimethylpropanoate (210 mg, Example 346, step D), 8'-methyl-7'-(2-(piperidin-1-yl)ethoxy)-2',3'-dihydrospiro[cyclopropane-1,4'-pyrido[2,3-b][1,4,5]oxathiazepine] 1',1'-dioxide (175 mg, 0.476 mmol, Intermediate 136), K₂CO₃ (197 mg, 1.43 mmol), and CH₃CN (10 mL) was stirred at 90° C. for 16 hours before cooling to room-temperature. The suspension was filtered through a pad diatomaceous earth, such as of Celite® and the pad washed with ethyl acetate (50 mL). The filtrate was concentrated to dryness under reduced pressure to afford the title product (360 mg, 0.47 mmol), which was used next step without further purification. MS (ESI): mass calcd. for C₄₂H₅₆N₆O₆S, 772.4, m/z found 773.5 [M+H]⁺.

Step B: 3-(3,7-Dimethyl-7H-pyrrolo[2,3-c]pyridazin-6-yl)-2,2-dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl)propanoic acid. 4 N HCl in 1,4-dioxane (6 mL) was added drop-wise to a solution of tert-butyl 3-(3,7-dimethyl-7H-pyrrolo[2,3-c]pyridazin-6-yl)-2,2-dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl)propanoate (360 mg, 0.47 mmol) and 1,4-dioxane (2 mL). The resultant mixture was stirred at room-temperature for 16 hours before concentrating to dryness under reduced pressure. The residue was purified by preparative HPLC using a Phenomenex Gemini-NX C18 150 mm×30 mm×5 μm column (eluent: 30% to 50% (v/v) CH$_3$CN and H$_2$O with 0.04% NH$_3$H$_2$O and 10 mM NH$_4$HCO$_3$) to afford the title compound (100 mg, 30%). MS (ESI): mass calcd. for C$_{38}$H$_{48}$N$_6$O$_6$S, 716.3, m/z found 717.4 [M+H]$^+$.

Step C: (*S)-3-(3,7-dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)spiro[cyclopropane-1,4'-pyrido[2,3-b][1,4,5]oxathiazepin]-2',(3'H)-yl)methyl)phenyl)propanoic acid. The mixture of 3-(3,7-Dimethyl-7H-pyrrolo[2,3-c]pyridazin-6-yl)-2,2-dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl)propanoic acid isomers were separated by chiral SFC (stationary phase: DAICEL CHIRALPAK IG 250 mm×30 mm, 10 m; mobile phase: 45% to 45% (v/v) supercritical CO$_2$ in i-PrOH and H$_2$O with 0.1% NH$_3$). The first eluting isomer (25 mg, 25%) was designated (*S). MS (ESI): mass calcd. for C$_{38}$H$_{48}$N$_6$O$_6$S, 716.3, m/z found 717.4 [M+H]$^+$. $^1$H NMR (400 MHz, DMSO-d$_6$) δ 7.92 (s, 1H), 7.62 (s, 1H), 7.17 (s, 2H), 7.07 (s, 1H), 6.62 (s, 1H), 4.73 (s, 1H), 4.52-4.39 (m, 2H), 4.27-4.17 (m, 1H), 4.14-4.06 (m, 1H), 3.64-3.59 (m, 1H), 3.55 (s, 3H), 3.30-3.23 (m, 7H), 2.65 (s, 3H), 2.26 (s, 3H), 2.17 (s, 3H), 1.64-1.35 (m, 6H), 1.25-1.22 (m, 6H), 0.97-0.89 (m, 2H), 0.61-0.42 (m, 2H).

Example 351: (*R)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(piperidine-1-yl)-ethoxy)spiro[cyclopropane-1,4'-pyrido[2,3-b][1,4,5]oxathiazepin]-2',(3'H)-yl)methyl)phenyl)propanoic Acid

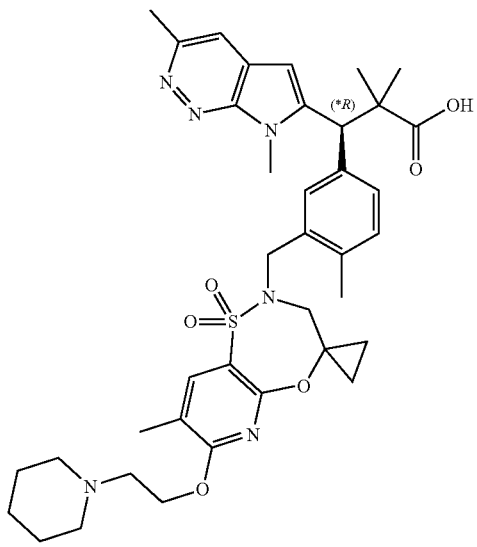 [SMILES: Cc1cc2cc([C@H](c3ccc(C)c(CN4CC5(CC5)Oc5nc(OCCN6CCCCC6)c(C)cc5S4(=O)=O)c3)C(C)(C)C(=O)O)n(C)c2nn1]

The second eluting isomer, (24 mg, 24%), from the chiral separation described in Example 350 was designated (*R). MS (ESI): mass calcd. for C$_{38}$H$_{48}$N$_6$O$_6$S, 716.3, m/z found 717.4 [M+H]$^+$. $^1$H NMR (400 MHz, DMSO-d$_6$) δ 7.88 (s, 1H), 7.58 (s, 1H), 7.14 (s, 2H), 7.04 (s, 1H), 6.59 (s, 1H), 4.69 (s, 1H), 4.47-4.35 (m, 2H), 4.23-4.14 (m, 1H), 4.11- 4.03 (m, 1H), 3.61-3.56 (m, 1H), 3.51 (s, 3H), 3.25-3.17 (m, 7H), 2.61 (s, 3H), 2.23 (s, 3H), 2.13 (s, 3H), 1.59-1.37 (m, 6H), 1.21-1.19 (m, 6H), 0.93-0.88 (m, 2H), 0.54-0.41 (m, 2H).

Example 352: (*S)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(pyrrolidin-1-yl)-ethoxy)spiro[cyclopropane-1,4'-pyrido[2,3-b][1,4,5]oxathiazepin]-2',(3'H)-yl)methyl)phenyl)propanoic Acid

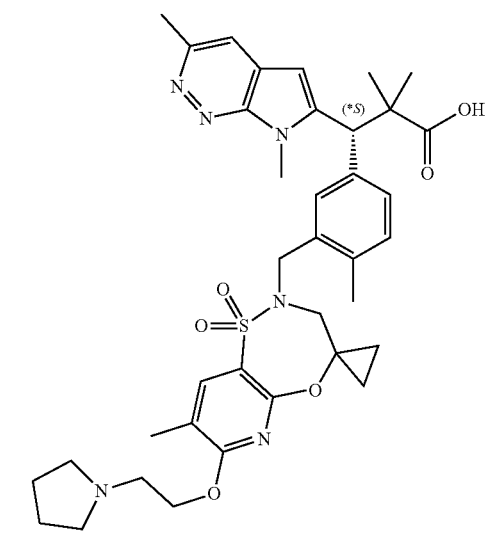 [SMILES: Cc1cc2cc([C@@H](c3ccc(C)c(CN4CC5(CC5)Oc5nc(OCCN6CCCC6)c(C)cc5S4(=O)=O)c3)C(C)(C)C(=O)O)n(C)c2nn1]

Step A: Methyl 3-(3-(((tert-butyldimethylsilyl)oxy)methyl)-4-methylphenyl)-3-(3,7-dimethyl-7H-pyrrolo[2,3-c]pyridazin-6-yl)-2,2-dimethylpropanoate. 2,2,2-trichloroacetonitrile (0.37 mL, 3.7 mmol) was added to a solution of (3-(((tert-butyldimethylsilyl)oxy)methyl)-4-methylphenyl)(3,7-dimethyl-7H-pyrrolo[2,3-c]pyridazin-6-yl)methanol (1.0 g, 2.4 mmol, Example 346, Step A), DBU (36 μL, 0.24 mmol), and DCE (20 mL) under N$_2$. The resultant mixture was stirred at room-temperature for 1 hour before treating with ((1-methoxy-2-methylprop-1-en-1-yl)oxy)trimethylsilane (1.69 g, 9.70 mmol) and TiCl$_4$ (3.64 mL, 1 M in dichloromethane, 3.64 mmol). The mixture was stirred at room-temperature for another 1.5 hours before quenching with sat. NaHCO$_3$(60 mL) and extracting with dichloromethane (3×). These extractions resulted in several fractions that were dried over anhydrous Na$_2$SO$_4$, filtered, and concentrated to dryness under reduced pressure. The residue was purified by flash chromatography (eluent:petroleum ether/ethyl acetate; 1:1 to 0:1, gradient) to afford the title compound (550 mg, 41%). MS (ESI): mass calcd. for C$_{28}$H$_{41}$N$_3$O$_3$Si, 495.3, m/z found 496.3 [M+H]$^+$.

Step B: Methyl 3-(3,7-dimethyl-7H-pyrrolo[2,3-c]pyridazin-6-yl)-3-(3-(hydroxymethyl)-4-methylphenyl)-2,2-dimethylpropanoate. TBAF (2.2 mL, 1 M in THF, 2.2 mmol) was added to a solution consisting of methyl 3-(3-(((tert-butyldimethylsilyl)oxy)methyl)-4-methylphenyl)-3-(3,7-dimethyl-7H-pyrrolo[2,3-c]pyridazin-6-yl)-2,2-dimethylpropanoate (550 mg, 1.11 mmol) and THF (10 mL). The resultant mixture was stirred at room-temperature for 2 hours before quenching with H$_2$O (50 mL) and extracting with ethyl acetate (3×). These extractions resulted in several fractions that were combined, washed with brine (3×), dried over anhydrous $Na_2SO_4$, filtered, and concentrated to dryness under reduced pressure. The residue was purified by flash chromatography (eluent:petroleum ether/ethyl acetate; 5:1 to 0:1 (gradient), then dichloromethane/methanol 10:1, isocratic) to afford the title compound (380 mg, 71%). MS (ESI): mass calcd. for $C_{22}H_{27}N_3O_3$ 381.2, m/z found 382.2 $[M+H]^+$.

Step C: Methyl 3-(3-(chloromethyl)-4-methylphenyl)-3-(3,7-dimethyl-7H-pyrrolo[2,3-c]pyridazin-6-yl)-2,2-dimethylpropanoate. $SOCl_2$ (0.57 mL, 7.8 mmol) was added to a solution consisting of methyl 3-(3,7-dimethyl-7H-pyrrolo[2,3-c]pyridazin-6-yl)-3-(3-(hydroxymethyl)-4-methylphenyl)-2,2-dimethylpropanoate (300 mg, 0.786 mmol) and dichloromethane (10 mL). The resultant mixture was stirred at room-temperature for 1 hour before concentrating to dryness under reduced pressure to afford the title compound (320 mg), which was used next step without further purification. MS (ESI): mass calcd. for $C_{22}H_{26}ClN_3O_2$ 399.2, m/z found 400.2 $[M+H]^+$.

Step D: Methyl 3-(3,7-dimethyl-7H-pyrrolo[2,3-c]pyridazin-6-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoate. Methyl 3-(3-(chloromethyl)-4-methylphenyl)-3-(3,7-dimethyl-7H-pyrrolo[2,3-c]pyridazin-6-yl)-2,2-dimethylpropanoate (160 mg), 8'-methyl-7'-(2-(pyrrolidin-1-yl)ethoxy)-2',3'-dihydrospiro[cyclopropane-1,4'-pyrido[2,3-b][1,4,5]oxathiazepine] 1',1'-dioxide (141 mg, 0.399 mmol, Intermediate 137), $K_2CO_3$ (166 mg, 1.20 mmol), and $CH_3CN$ (10 mL) were mixed and stirred at 80° C. for 16 hours before cooling to room-temperature. The resulting suspension was filtered through a pad diatomaceous earth, such as of Celite® and the pad washed with ethyl acetate (50 mL). The filtrate was concentrated to dryness under reduced pressure to give the product (300 mg), which was used next step without further purification. MS (ESI): mass calcd. for $C_{38}H_{48}N_6O_6S$, 716.3, m/z found 717.3 $[M+H]^+$.

Step E: 3-(3,7-Dimethyl-7H-pyrrolo[2,3-c]pyridazin-6-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoic acid. LiOH*$H_2O$ (176 mg, 4.19 mmol) was added to a solution consisting of methyl 3-(3,7-dimethyl-7H-pyrrolo[2,3-c]pyridazin-6-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoate (300 mg, 0.418 mmol), 1,4-dioxane (5 mL), and $H_2O$ (5 mL). The resulting mixture was then stirred at 75° C. for 1 hour before cooling to room-temperature, diluting with $H_2O$ (30 mL), and washing with ethyl acetate (3×). The aqueous phase was adjusted to pH=6 to 7 with 1 N HCl and concentrated to dryness under reduced pressure. The residue was purified by preparative HPLC (stationary phase: Waters Xbridge C18, 150 mm×50 mm×5 μm column; eluent: 20% to 50% (v/v) $CH_3CN$ and $H_2O$ with 10 mM $NH_4HCO_3$) to afford the title compound (130 mg, 43%). MS (ESI): mass calcd. for $C_{37}H_{46}N_6O_6S$, 702.3, m/z found 703.3 $[M+H]^+$.

Step F: (*S)-3-(3,7-Dimethyl-7H-pyrrolo[2,3-c]pyridazin-6-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoic acid. The mixture of 3-(3,7-dimethyl-7H-pyrrolo[2,3-c]pyridazin-6-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoic acid isomers were separated by chiral SFC (stationary phase: DAICEL CHIRALPAK IG 250 mm×30 mm, 10 μm; mobile phase: 50% to 50% (v/v) supercritical $CO_2$ in i-PrOH and $H_2O$ with 0.1% $NH_3$). The first eluting isomer (42 mg, 30%) was designated (*S). MS (ESI): mass calcd. for $C_{37}H_{46}N_6O_6S$, 702.3, m/z found 703.4 $[M+H]^+$. $^1$H NMR (400 MHz, DMSO-$d_6$) δ 7.86 (s, 1H), 7.57 (s, 1H), 7.13 (s, 2H), 7.03 (s, 1H), 6.58 (s, 1H), 4.68 (s, 1H), 4.39-4.31 (m, 2H), 4.23-4.14 (m, 1H), 4.10-4.02 (m, 1H), 3.58-3.56 (m, 1H), 3.51 (s, 3H), 3.28-3.28 (m, 1H), 2.87-2.80 (m, 2H), 2.61 (s, 3H), 2.59-2.54 (m, 4H), 2.23 (s, 3H), 2.12 (s, 3H), 1.69-1.63 (m, 4H), 1.18 (s, 6H), 0.92-0.87 (m, 2H), 0.54-0.39 (m, 2H).

Example 353: (*R)-3-(3,7-Dimethyl-7H-pyrrolo[2,3-c]pyridazine-6-yl)-2,2-dimethyl-3-(4-methyl-3-((8'-methyl-1',1'-dioxido-7'-(2-(pyrrolidin-1-yl)-ethoxy)spiro[cyclopropane-1,4'-pyrido[2,3-b][1,4,5]oxathiazepin]-2'-(3'H)-yl)methyl)phenyl)propanoic Acid

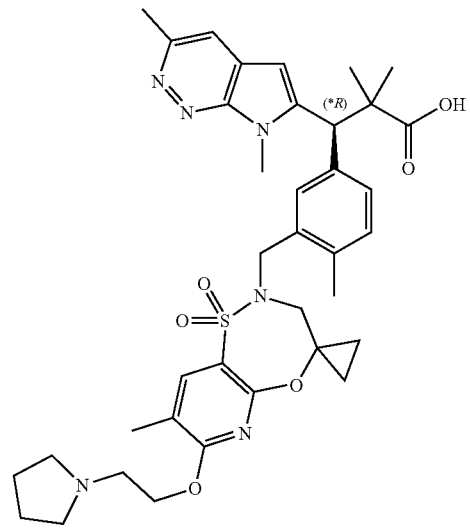

The second eluting isomer (36 mg, 27%) from the chiral separation described in Example 352 was designated (*R). MS (ESI): mass calcd. for $C_{37}H_{46}N_6O_6S$, 702.3, m/z found 703.4 $[M+H]^+$. $^1$H NMR (400 MHz, DMSO-$d_6$) δ 7.90 (s, 1H), 7.61 (s, 1H), 7.16 (s, 2H), 7.07 (s, 1H), 6.62 (s, 1H), 4.72 (s, 1H), 4.43-4.37 (m, 2H), 4.26-4.19 (m, 1H), 4.14-4.06 (m, 1H), 3.70-3.67 (m, 1H), 3.55 (s, 3H), 3.33-3.31 (m, 1H), 2.97-2.88 (m, 2H), 2.71-2.61 (m, 7H), 2.26 (s, 3H), 2.16 (s, 3H), 1.76-1.68 (m, 4H), 1.22 (s, 6H), 0.97-0.88 (m, 2H), 0.56-0.43 (m, 2H).

Example 354: (*S)-3-(3-(Difluoromethyl)-8-methyl-
[1,2,4]triazolo[4,3-a]pyridin-7-yl)-2,2-dimethyl-3-
(5-methyl-6-((8'-methyl-1',1'-dioxido-7'-(2-(piperi-
din-1-yl)ethoxy)-2,3,5,6-tetrahydrospiro[pyran-4,4'-
pyrido[2,3-b][1,4,5]oxathiazepin]-2'(3'H)-yl)methyl)
pyridin-2-yl)propanoic Acid

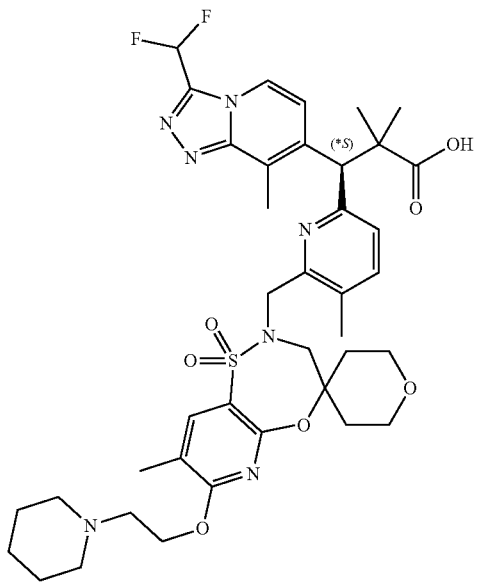 [SMILES: Cc1ccc([C@@H](c2ccn3c(C(F)F)nnc3c2C)C(C)(C)C(=O)O)nc1CN1CC2(CCOCC2)Oc2nc(OCCN3CCCCC3)c(C)cc2S1(=O)=O]

Step A: 6-chloro-3-methylpyridin-2-yl)methanol. Borane tetrahydrofuran complex (219 mL, 1 M in THF, 219 mmol) was added drop-wise to a solution consisting of 6-chloro-3-methylpicolinic acid (25.0 g, 146 mmol) and THF (200 mL) at 0° C. The mixture was stirred at 50° C. for 3 hours before cooling to 0° C. followed by drop-wise addition of MeOH (300 mL) at 0° C. The reaction was stirred for an additional 1 hour with gradual warming to room-temperature. The mixture was concentrated to dryness under reduced pressure to afford the title compound (22.5 g, 98%), which was used in the next step without further purification. $^1$H NMR (400 MHz, DMSO-$d_6$) δ 7.63 (d, J=8.0 Hz, 1H), 7.31 (d, J=8.0 Hz, 1H), 4.50 (s, 2H), 2.30 (s, 3H).

Step B: 2-(((tert-Butyldimethylsilyl)oxy)methyl)-6-chloro-3-methylpyridine. TBSCl (25.9 g, 172 mmol) was added to a solution of (6-chloro-3-methylpyridin-2-yl)methanol (22.5 g, 143 mmol), imidazole (19.5 g, 286 mmol), and dichloromethane (400 mL) 0° C. The mixture was stirred for 2.5 hours with gradual warming to room-temperature. The suspension was isolated via filtration. The filter cake was washed with ethyl acetate (3×), and the filtrate concentrated to dryness under reduced pressure to give the product, which was purified by flash chromatography (eluent:petroleum ether/ethyl acetate; 1:0 to 9:1, gradient) to afford title compound (22.9 g, 59%). $^1$H NMR (400 MHz, DMSO-$d_6$) δ 7.65 (d, J=8.0 Hz, 1H), 7.33 (d, J=8.0 Hz, 1H), 4.70 (s, 2H), 2.32 (s, 3H), 0.85-0.84 (m, 9H), 0.04 (s, 6H).

Step C: 2-(((tert-Butyldimethylsilyl)oxy)methyl)-3-methyl-6-vinylpyridine. Pd(dppf)Cl$_2$ (2.5 g, 3.4 mmol) was added to a solution consisting of 2-(((tert-butyldimethylsilyl)oxy)methyl)-6-chloro-3-methylpyridine (22.9 g, 84.2 mmol), potassium trifluoro(vinyl)borate (22.8 g, 170 mmol), K$_3$PO$_4$ (54.2 g, 255 mmol), 1,4-dioxane (300 mL), and H$_2$O (60 mL) under N$_2$. The mixture was stirred at 100° C. for 16 hours, cooled to room-temperature, poured into water (50 mL), and extracted with ethyl acetate (3×). These extractions resulted in several fractions that were combined, washed with brine (100 mL), dried over anhydrous Na$_2$SO$_4$, filtered, and concentrated to dryness under reduced pressure. The residue was purified by flash chromatography (eluent:petroleum ether/ethyl acetate; 1:0 to 5:1, gradient) to afford the title product (17.3 g, 78%). $^1$H NMR (400 MHz, CDCl$_3$) δ 7.41 (d, J=7.8 Hz, 1H), 7.18 (d, J=7.8 Hz, 1H), 6.79 (dd, J=10.8, 17.6 Hz, 1H), 6.14 (dd, J=1.1, 17.4 Hz, 1H), 5.40 (dd, J=1.1, 10.9 Hz, 1H), 4.84 (s, 2H), 2.40 (s, 3H), 0.90 (s, 9H), 0.08 (s, 6H).

Step D: 6-(((tert-Butyldimethylsilyl)oxy)methyl)-5-methylpicolinaldehyde. K$_2$OsO$_4$.2H$_2$O (1.2 g, 3.3 mmol) was added to a solution consisting of 2-(((tert-butyldimethylsilyl)oxy)methyl)-3-methyl-6-vinylpyridine (17.3 g, 65.7 mmol), 1,4-dioxane (250 mL), and H$_2$O (250 mL). The resultant mixture was treated with NaIO$_4$ (41.9 g, 196 mmol) in portions slowly and then stirred at room-temperature for 6 hours. The resultant suspension was isolated via filtration and the filter cake washed with ethyl acetate (3×). The filtrate was separated and the aqueous layer extracted with ethyl acetate (2×). These extractions resulted in several fractions that were combined, washed with brine (100 mL), dried over anhydrous Na$_2$SO$_4$, filtered, and concentrated to dryness under reduced pressure. The residue was purified by flash chromatography (eluent:petroleum ether/ethyl acetate; 1:0 to 9:1, gradient) to afford the title compound (7.3 g, 31%). MS (ESI): mass calcd. for C$_{14}$H$_{23}$NO$_2$Si, 265.2 m/z found 266.2 [M+H]$^+$. $^1$H NMR (400 MHz, DMSO-$d_6$) δ 9.93 (s, 1H), 7.86-7.77 (m, 2H), 4.86 (s, 2H), 2.46 (s, 3H), 0.86 (s, 9H), 0.06 (s, 6H).

Step E: (6-(((tert-Butyldimethylsilyl)oxy)methyl)-5-methylpyridin-2-yl)(3-(difluoromethyl)-8-methyl-[1,2,4]triazolo[4,3-a]pyridin-7-yl)methanol. i-PrMgCl.LiCl (25.4 mL, 1.3 M in THF, 33.0 mmol) was added drop-wise to a solution of 3-(difluoromethyl)-7-iodo-8-methyl-[1,2,4]triazolo[4,3-a]pyridine (6.8 g, 22 mmol, Intermediate 148) and THF (80 mL) at 0° C. The resultant mixture was stirred at 0° C. for 1 hour and then treated with a solution of 6-(((tert-butyldimethylsilyl)oxy)methyl)-5-methylpicolinaldehyde (6.1 g, 23 mmol) and THF (20 mL) by drop-wise addition at 0° C. The mixture was stirred for 16 hours with gradual warming to room-temperature, poured into sat. NH$_4$Cl (50 mL), and extracted with ethyl acetate (3×). These extractions resulted in several fractions that were combined, washed with brine (50 mL), dried over anhydrous Na$_2$SO$_4$, filtered, and concentrated to dryness under reduced pressure. The residue was triturated with petroleum ether: ethyl acetate (10:1, 20 mL and the suspension isolated via filtration. The filter cake was washed with petroleum ether/ ethyl acetate (10:1, 3×) before drying under reduced pressure to afford the title compound (4.3 g, 44%). The filtrate was concentrated to dryness under reduced pressure to give the product, which was purified by flash chromatography (eluent:petroleum ether/ethyl acetate; 1:0 to 2:3, gradient) to afford the second batch of title compound (1.9 g, 19%). MS (ESI): mass calcd. for C$_{22}$H$_{30}$F$_2$N$_4$O$_2$Si, 448.2 m/z found 449.2 [M+H].

Step F: 7-((6-(((tert-Butyldimethylsilyl)oxy)methyl)-5-methylpyridin-2-yl)chloromethyl)-3-(difluoromethyl)-8-methyl-[1,2,4]triazolo[4,3-a]pyridine. SOCl$_2$(0.57 mL, 7.8 mmol) was added drop-wise to a solution consisting of (6-(((tert-butyldimethylsilyl)oxy)methyl)-5-methylpyridin-2-yl)(3-(difluoromethyl)-8-methyl-[1,2,4]triazolo[4,3-a]pyridin-7-yl)methanol (2.7 g, 6.0 mmol), 2,6-di-tertbutylpyridine (3.4 mL, 15 mmol), and dichloromethane (30 mL) at 0° C. The resulting mixture was stirred at 0° C. for 40 minutes before adjusting the pH with aq. NaHCO₃ to pH=8-9, poured into water (40 mL), and extracted with dichloromethane (3×). These extraction resulted in several fractions that were combined, washed with brine (30 mL), dried over anhydrous Na₂SO₄, filtered, and concentrated to dryness under reduced pressure. The residue was purified by flash chromatography (eluent: petroleum ether/ethyl acetate; 1:0 to 1:1, gradient) to afford the title compound (2.2 g, 73%). MS (ESI): mass calcd. for $C_{22}H_{29}ClF_2N_4OS$, 466.2 m/z found 467.2 [M+H]⁺.

Step G: tert-Butyl 3-(6-(((tert-butyldimethylsilyl)oxy)methyl)-5-methylpyridin-2-yl)-3-(3-(difluoromethyl)-8-methyl-[1,2,4]triazolo[4,3-a]pyridin-7-yl)-2,2-dimethylpropanoate. InBr₃ (501 mg, 1.41 mmol) was added to a solution of 7-((6-(((tert-butyldimethylsilyl)oxy)methyl)-5-methylpyridin-2-yl)chloromethyl)-3-(difluoromethyl)-8-methyl-[1,2,4]triazolo[4,3-a]pyridine (2.2 g, 4.7 mmol), ((1-(tert-butoxy)-2-methylprop-1-en-1-yl)oxy)trimethylsilane (10.2 g, 47.1 mmol), and dichloromethane (40 mL) under N₂. The resultant mixture was stirred at room-temperature for 5 days, poured it into water (30 mL) and extracted with dichloromethane (3×). These extractions resulted in several fractions that were combined, washed with brine (30 mL), dried over anhydrous Na₂SO₄, filtered, and concentrated to dryness under reduced pressure. The residue was purified by flash chromatography (eluent:petroleum ether/ethyl acetate; 1:0 to 3:2, gradient) to afford the title compound (1.3 g, 48%), which was used in the next step without further purification. MS (ESI): mass calcd. for $C_{30}H_{44}F_2N_4O_3S$, 574.3 m/z found 575.3 [M+H]⁺.

Step H: tert-Butyl 3-(3-(difluoromethyl)-8-methyl-[1,2,4]triazolo[4,3-a]pyridin-7-yl)-3-(6-(hydroxymethyl)-5-methylpyridin-2-yl)-2,2-dimethylpropanoate. TBAF (4.4 mL, 1 M in THF, 4.4 mmol) was added to a solution of tert-butyl 3-(6-(((tert-butyldimethylsilyl)oxy)methyl)-5-methylpyridin-2-yl)-3-(3-(difluoromethyl)-8-methyl-[1,2,4]triazolo[4,3-a]pyridin-7-yl)-2,2-dimethylpropanoate (1.3 g) and THF (10 mL). The resultant mixture was stirred for 2 hours at room-temperature, poured into water (30 mL) and extracted with ethyl acetate (3×). These extractions resulted in several fraction that were combined, washed with brine (30 mL), dried over anhydrous Na₂SO₄, filtered, and concentrated to dryness under reduced pressure. The residue was purified by flash chromatography (eluent: petroleum ether/ethyl acetate; 1:0 to 1:1, gradient) to afford the title compound (350 mg, 32%). MS (ESI): mass calcd. for $C_{24}H_{30}F_2N_4O_3$ 460.2 m/z found 461.2 [M+H]⁺. An alternative procedure to prepare the title compound, tert-butyl 3-(3-(difluoromethyl)-8-methyl-[1,2,4]triazolo[4,3-a]pyridin-7-yl)-3-(6-(hydroxymethyl)-5-methylpyridin-2-yl)-2,2-dimethylpropanoate, is described in the preparation of Intermediate 193.

Step I: tert-Butyl 3-(6-(chloromethyl)-5-methylpyridin-2-yl)-3-(3-(difluoromethyl)-8-methyl-[1,2,4]triazolo[4,3-a]pyridin-7-yl)-2,2-dimethylpropanoate. SOCl₂ (0.18 mL, 2.5 mmol) was added to a solution consisting of tert-butyl 3-(3-(difluoromethyl)-8-methyl-[1,2,4]triazolo[4,3-a]pyridin-7-yl)-3-(6-(hydroxymethyl)-5-methylpyridin-2-yl)-2,2-dimethylpropanoate (350 mg, 0.760 mmol) and dichloromethane (4 mL). The resultant mixture was stirred for 0.5 hours at room-temperature before concentrating to dryness under reduced pressure to afford the title compound (320 mg, 88%), which was used in the next step without further purification. MS (ESI): mass calcd. for $C_{24}H_{29}ClF_2N_4O_2$ 478.2 m/z found 479.2 [M+H]⁺. An alternative procedure to prepare the title compound, tert-butyl 3-(6-(chloromethyl)-5-methylpyridin-2-yl)-3-(3-(difluoromethyl)-8-methyl-[1,2,4]triazolo[4,3-a]pyridin-7-yl)-2,2-dimethylpropanoate, is described in the preparation of Intermediate 194.

Step J: tert-Butyl 3-(3-(difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoate. tert-Butyl 3-(6-(chloromethyl)-5-methylpyridin-2-yl)-3-(3-(difluoromethyl)-8-methyl-[1,2,4]triazolo[4,3-a]pyridin-7-yl)-2,2-dimethylpropanoate (230 mg, 0.480 mmol), 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide (200 mg, 0.486 mmol, Intermediate 72), K₂CO₃ (403 mg, 2.92 mmol), and CH₃CN (5 mL) were mixed and stirred at 80° C. for 6 hours. The reaction was cooled to room-temperature, poured into water (20 mL), and extracted with ethyl acetate (3×). These extractions resulted in several organic fractions that were combined, washed with brine (20 mL), dried over anhydrous Na₂SO₄, filtered, and concentrated to dryness under reduced pressure to afford the title compound (320 mg, 78%), which was used in the next step without further purification. MS (ESI): mass calcd. for $C_{43}H_{57}F_2N_7O_7S$, 853.4 m/z found 854.1 [M+H]⁺. ¹H NMR (400 MHz, DMSO-d₆) δ 8.29 (d, J=7.3 Hz, 1H), 7.89 (s, 1H), 7.83-7.65 (m, 1H), 7.63-7.56 (m, 1H), 7.52 (d, J=7.7 Hz, 1H), 7.23 (d, J=7.7 Hz, 1H), 4.90 (s, 1H), 4.63-4.46 (m, 2H), 4.43 (t, J=6.0 Hz, 2H), 3.92-3.81 (m, 2H), 3.66 (d, J=19.8 Hz, 4H), 2.75 (s, 3H), 2.68 (d, J=6.2 Hz, 2H), 2.45 (br s, 6H), 2.25 (s, 3H), 2.16 (s, 3H), 1.62 (d, J=7.5 Hz, 4H), 1.52-1.47 (m, 4H), 1.37 (s, 3H), 1.24 (s, 3H), 1.16 (s, 9H).

Step K: 3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid. (tert-butyl 3-(3-(difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoate) (320 mg, 0.375 mmol), 4 N HCl in 1,4-dioxane (30 mL, 120 mmol), and 1,4-dioxane (5 mL) were mixed and stirred for 24 hours at room-temperature before concentrating to dryness under reduced pressure. The residue was purified by reverse-phase preparative HPLC (stationary phase: Agela ASB 150 mm×25 mm×5 μm column; eluent: 25% to 50% (v/v) CH₃CN and H₂O with 0.05% HCl) to afford the title compound (200 mg, 67%). MS (ESI): mass calcd. for $C_{39}H_{49}F_2N_7O_7S$, 797.3 m/z found 798.4 [M+H]⁺.

Step L: (*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid. The mixture of 3-(3-(difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid isomers were separated by chiral SFC (stationary phase: DAICEL CHIRALPAK AD-H 250 mm×30 mm×5 am; eluent: 25% to 25% (v/v) in EtOH and H₂O with 0.1% NH₃). The first eluting isomer (60 mg, 30%) was designated (*S). MS (ESI): mass calcd. for $C_{39}H_{49}F_2N_7O_7S$, 797.3 m/z found 798.3 [M+H]⁺. ¹H NMR (400 MHz, DMSO-d₆) δ 8.27 (d, J=7.2 Hz, 1H), 7.90 (s, 1H), 7.71 (t, J=52 Hz, 1H), 7.67 (d, J=7.2 Hz, 1H), 7.51 (d, J=8.0 Hz, 1H), 7.24 (d, J=7.6 Hz, 1H), 4.95 (s, 1H), 4.55 (s, 2H), 4.49-4.42 (m, 2H), 3.91-3.80 (m, 2H), 3.77-3.67 (m, 2H), 3.64-3.59 (m, 2H), 3.31-3.00 (m, 6H), 2.75 (s, 3H), 2.24 (s, 3H), 2.16 (s, 3H), 1.76-1.64 (m, 2H), 1.63-1.56 (m, 2H), 1.55-1.46 (m, 4H), 1.42-1.35 (m, 2H), 1.33 (s, 3H), 1.29 (s, 3H).

Example 355: (*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic Acid

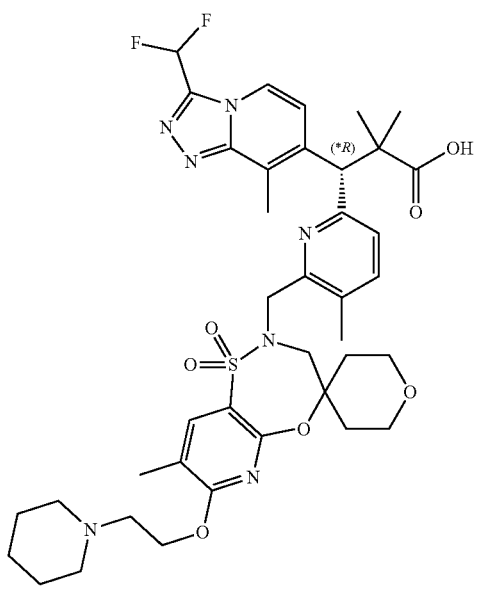 [SMILES: Cc1ccc([C@H](c2ccn3c(C(F)F)nnc3c2C)C(C)(C)C(=O)O)nc1CN1CC2(CCOCC2)Oc2nc(OCCN3CCCCC3)c(C)cc2S1(=O)=O]

The mixture of 3-(3-(difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid isomers that were separated as described in Example 354, Step L also provided the second eluting isomer that was designated (*R) but required further purification by reverse phase HPLC (stationary phase: Xtimate C18 150 mm×25 mm×5 m; eluent: 15% to 45% (v/v) in water and ACN with 0.225% HCOOH) to afford the title compound (29 mg, 14%). MS (ESI): mass calcd. for $C_{39}H_{49}F_2N_7O_7S$, 797.3 m/z found 798.3 [M+H]$^+$. $^1$H NMR (400 MHz, DMSO-d$_6$) δ 8.27 (d, J=7.3 Hz, 1H), 7.89 (s, 1H), 7.71 (t, J=52 Hz, 1H), 7.67 (d, J=7.3 Hz, 1H), 7.51 (d, J=7.9 Hz, 1H), 7.23 (d, J=7.3 Hz, 1H), 4.95 (s, 1H), 4.59-4.50 (m, 2H), 4.44 (t, J=6.0 Hz, 2H), 3.86 (t, J=11.6 Hz, 2H), 3.78-3.68 (m, 2H), 3.67-3.56 (m, 4H), 3.15-2.91 (m, 2H), 2.75 (s, 3H), 2.70 (t, J=6.2 Hz, 2H), 2.24 (s, 3H), 2.16 (s, 3H), 1.78-1.65 (m, 2H), 1.63-1.56 (m, 2H), 1.52-1.47 (m, 4H), 1.40-1.35 (m, 2H), 1.33 (s, 3H), 1.29 (s, 3H).

Example 356: (*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic Acid

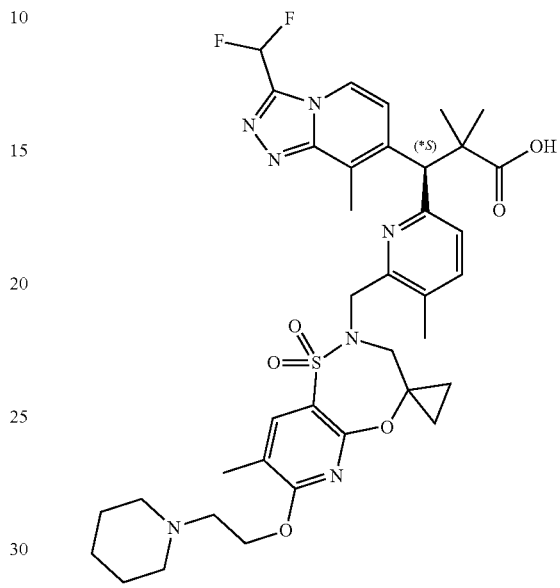

Step A: tert-Butyl 3-(3-(difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoate. tert-Butyl 3-(6-(chloromethyl)-5-methylpyridin-2-yl)-3-(3-(difluoromethyl)-8-methyl-[1,2,4]triazolo[4,3-a]pyridin-7-yl)-2,2-dimethylpropanoate (185 mg, 0.386 mmol), 8'-methyl-7'-(2-(piperidin-1-yl)ethoxy)-2',3'-dihydrospiro[cyclopropane-1,4'-pyrido[2,3-b][1,4,5]oxathiazepine] 1',1'-dioxide (140 mg, 0.381 mmol, Intermediate 136), K$_2$CO$_3$ (320 mg, 2.32 mmol), and CH$_3$CN (5 mL) were mixed and stirred at 80° C. for 6 hours. The reaction was cooled to room-temperature, poured into water (20 mL), and extracted with ethyl acetate (3×). These extractions resulted in the isolation of several fractions that were combined, washed with brine (50 mL), dried over anhydrous Na$_2$SO$_4$, filtered, and concentrated to dryness under reduced pressure to afford the title compound (320 mg), which was used in the next step without further purification. MS (ESI): mass calcd. for $C_{41}H_{53}F_2N_7O_6S$, 809.4 m/z found 810.4 [M+H]$^+$. $^1$H NMR (400 MHz, DMSO-d$_6$) δ 8.30 (d, J=7.3 Hz, 1H), 7.99 (s, 1H), 7.84-7.57 (m, 1H), 7.55 (d, J=7.9 Hz, 1H), 7.19 (t, J=7.6 Hz, 2H), 4.87 (s, 1H), 4.38 (t, J=6.0 Hz, 2H), 4.35-4.25 (m, 2H), 2.72 (s, 3H), 2.66 (t, J=6.0 Hz, 2H), 2.43 (br s, 4H), 2.34 (s, 3H), 2.17 (s, 3H), 1.52-1.34 (m, 8H), 1.31 (s, 3H), 1.17 (s, 3H), 1.12 (s, 9H), 1.08-1.03 (m, 2H), 0.85 (br s, 2H).

Step B: 3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic acid. (tert-Butyl 3-(3-(difluoromethyl)-8-methyl-[1,2,4]triazolo[4,3-a]pyridin-7- yl)-2,2-dimethyl-3-(5-methyl-6-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoate) (300 mg, 0.370 mmol), 4 N HCl in 1,4-dioxane (15 mL, 60 mmol), and 1,4-dioxane (5 mL) were mixed and stirred at room-temperature for 16 hours before concentrating to dryness under reduced pressure to give the product, which was purified by reverse phase preparative HPLC (stationary phase: Xtimate C18 150 mm×40 mm×10 μm column; eluent: 15% to 45% (v/v) $CH_3CN$ and $H_2O$ with 0.2% HCOOH) to afford title compound (200 mg, 72%). MS (ESI): mass calcd. for $C_{37}H_{45}F_2N_7O_6S$, 753.3 m/z found 754.4 [M+H]$^+$.

Step C: (*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic acid. The mixture of 3-(3-(difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl) propanoic acid isomers were separated by chiral SFC (stationary phase: DAICEL CHIRALPAK AD-H 250 mm×30 mm×5 m; eluent: 25% to 25% (v/v) in EtOH and $H_2O$ with 0.1% $NH_3$). The first eluting isomer (78 mg, 38%) was designated (*S). MS (ESI): mass calcd. for $C_{37}H_{45}F_2N_7O_6S$, 753.3 m/z found 754.4 [M+H]$^+$. $^1H$ NMR (400 MHz, DMSO-$d_6$) δ 8.28 (d, J=7.2 Hz, 1H), 7.99 (s, 1H), 7.7 (t, J=52 Hz, 1H), 7.53 (d, J=8.0 Hz, 1H), 7.28-7.19 (m, 2H), 4.92 (s, 1H), 4.41-4.36 (m, 2H), 4.36-4.26 (m, 2H), 3.73-3.62 (m, 2H), 2.72 (s, 3H), 2.70-2.64 (m, 2H), 2.48-2.40 (m, 4H), 2.33 (s, 3H), 2.18 (s, 3H), 1.52-1.44 (m, 4H), 1.41-1.34 (m, 2H), 1.30 (s, 3H), 1.22 (s, 3H), 1.09-0.98 (m, 2H), 0.84 (s, 2H).

Example 357: (*R)-3-(3-(difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic Acid

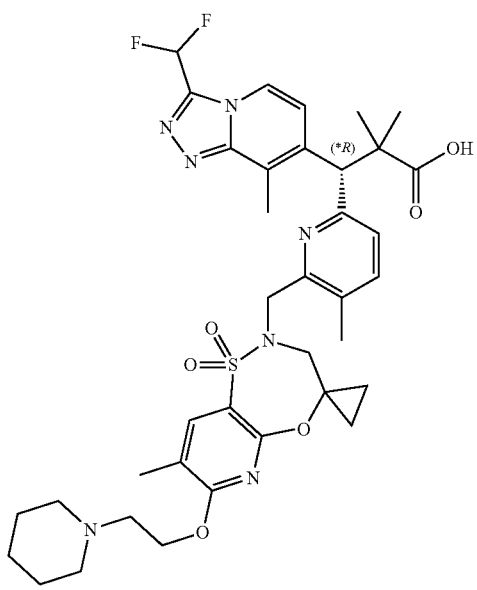 [SMILES: Cc1ccc([C@H](c2ccn3c(C(F)F)nnc3c2C)C(C)(C)C(=O)O)nc1CN1CC2(CC2)Oc2nc(OCCN3CCCCC3)c(C)cc2S1(=O)=O]

The mixture of 3-(3-(difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic acid isomers were that separated by chiral SFC as described in Example 356, Step C also provided a second eluting isomer (74 mg, 35%) that was designated (*R). MS (ESI): mass calcd. for $C_{37}H_{45}F_2N_7O_6S$, 753.3 m/z found 754.3 [M+H]$^+$. $^1H$ NMR (400 MHz, DMSO-$d_6$) δ 8.28 (d, J=7.2 Hz, 1H), 7.99 (s, 1H), 7.7 (t, J=52 Hz, 1H), 7.53 (d, J=8.0 Hz, 1H), 7.28-7.19 (m, 2H), 4.92 (s, 1H), 4.41-4.36 (m, 2H), 4.36-4.26 (m, 2H), 3.73-3.62 (m, 2H), 2.72 (s, 3H), 2.70-2.64 (m, 2H), 2.48-2.40 (m, 4H), 2.33 (s, 3H), 2.18 (s, 3H), 1.52-1.44 (m, 4H), 1.41-1.34 (m, 2H), 1.30 (s, 3H), 1.22 (s, 3H), 1.09-0.98 (m, 2H), 0.84 (s, 2H).

Example 358: (*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic Acid

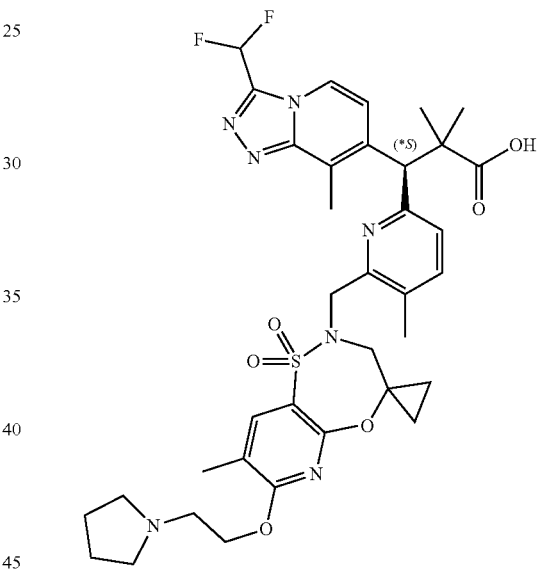

Step A: tert-Butyl 3-(3-(difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoate. tert-Butyl 3-(6-(chloromethyl)-5-methylpyridin-2-yl)-3-(3-(difluoromethyl)-8-methyl-[1,2,4]triazolo[4,3-a]pyridin-7-yl)-2,2-dimethylpropanoate (221 mg, 0.461 mmol), 8'-methyl-7'-(2-(pyrrolidin-1-yl)ethoxy)-2',3'-dihydrospiro[cyclopropane-1,4'-pyrido[2,3-b][1,4,5]oxathiazepine] 1',1'-dioxide (163 mg, 0.461 mmol, Intermediate 137), $K_2CO_3$ (383 mg, 2.77 mmol), and $CH_3CN$ (5 mL) mixed and stirred at 80° C. for 6 hours. The reaction was cooled to room-temperature, poured into water (20 mL), and extracted with ethyl acetate (3×). These extractions resulted in several fractions that were combined, washed with brine (50 mL), dried over anhydrous $Na_2SO_4$, filtered, and concentrated to dryness under reduced pressure to afford the title compound (350 mg, 95%), which was used in the next step without further purification. MS (ESI): mass calcd. for $C_{40}H_{51}F_2N_7O_6S$, 795.4 m/z found 796.4 [M+H]$^+$.

Step B: 3-(3-(Difluoromethyl)-8-methyl-[1,2,4]triazolo[4,3-a]pyridin-7-yl)-2,2-dimethyl-3-(5-methyl-6-((8'- methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid. (tert-Butyl 3-(3-(difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoate) (350 mg, 0.440 mmol), 4 N HCl in 1,4-dioxane (18 mL, 72 mmol), and 1,4-dioxane (5 mL) were mixed and stirred for 16 hours at room-temperature before concentrating to dryness under reduced pressure. The residue was purified by reverse-phase preparative HPLC (stationary phase: Xtimate C18 150 mm×40 mm×10 m column; eluent: 13% to 43% (v/v) $CH_3CN$ and $H_2O$ with 0.2% HCOOH) to afford the title compound (190 mg, 58%). MS (ESI): mass calcd. for $C_{36}H_{43}F_2N_7O_6S$, 739.3 m/z found 740.4 [M+H]$^+$.

Step C: (*S)-3-(3-(Difluoromethyl)-8-methyl-[1,2,4]triazolo[4,3-a]pyridine-7-yl)-2,2-dimethyl-3-(5-methyl-6-((8'-methyl-1',1'-dioxido-7'-(2-(pyrrolidin-1-yl)ethoxy)spiro[cyclopropane-1,4'-pyrido[2,3-b] 1,4,5]oxathiazepin]-2'(3'H)-yl)methyl)-5-methylpyridin-2-yl)-2,2-dimethylpropanoic acid. The mixture of 3-(3-(difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid isomers were separated by chiral SFC (stationary phase: Phenomenex-Amylose-1 250 mm×30 mm×5 μm column; eluent: 30% to 30% (v/v) EtOH with 0.1% % $NH_3/H_2O$). The first eluting isomer (59 mg, 30%) was designated (*S). MS (ESI): mass calcd. for $C_{36}H_{43}F_2N_7O_6S$, 739.3 m/z found 740.4 [M+H]$^+$. $^1$H NMR (400 MHz, DMSO-d$_6$) δ 8.28 (d, J=7.2 Hz, 1H), 7.99 (s, 1H), 7.66 (t, J=51.6 Hz, 1H), 7.53 (d, J=7.6 Hz, 1H), 7.28-7.19 (m, 2H), 4.92 (s, 1H), 4.40 (t, J=5.6 Hz, 2H), 4.37-4.27 (m, 2H), 3.70-3.65 (m, 2H), 2.85 (t, J=5.4 Hz, 2H), 2.71 (s, 3H), 2.61-2.56 (m, 4H), 2.33 (s, 3H), 2.19 (s, 3H), 1.72-1.66 (m, 4H), 1.30 (s, 3H), 1.21 (s, 3H), 1.08-0.98 (m, 2H), 0.83 (s, 2H).

Example 359: (*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(pyrrolidin-1-yl)ethoxy)spiro[cyclopropane-1,4'-pyrido[2,3-b][[,4,5]oxathiazepin]-2'(3'H)-yl)methyl)pyridin-2-yl)propanoic Acid

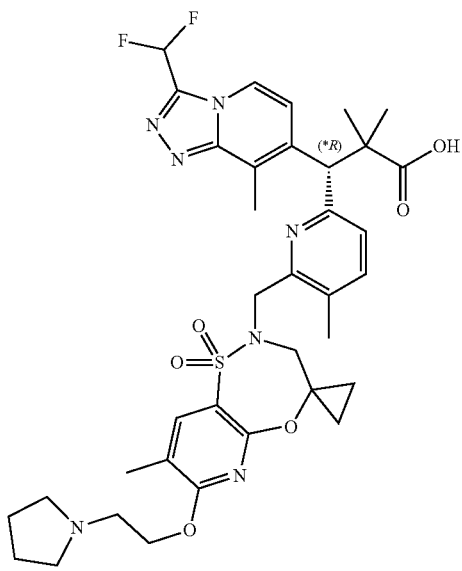 [SMILES: Cc1ccc([C@H](c2ccn3c(C(F)F)nnc3c2C)C(C)(C)C(=O)O)nc1CN1CC2(CC2)Oc2nc(OCCN3CCCC3)c(C)cc2S1(=O)=O]

The mixture of 3-(3-(difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid isomers were separated by chiral SFC as described in Example 358, Step C also provided a second eluting isomer (69 mg, 33%) that was designated (*R). MS (ESI): mass calcd. for $C_{36}H_{43}F_2N_7O_6S$, 739.3 m/z found 740.3 [M+H]$^+$. $^1$H NMR (400 MHz, DMSO-d$_6$) δ 8.28 (d, J=7.3 Hz, 1H), 8.00 (s, 1H), 7.84-7.56 (m, 1H), 7.54 (d, J=7.9 Hz, 1H), 7.28-7.19 (m, 2H), 4.92 (s, 1H), 4.41 (t, J=5.5 Hz, 2H), 4.37-4.28 (m, 2H), 3.70-3.65 (m, 2H), 2.90 (t, J=5.5 Hz, 2H), 2.71 (s, 3H), 2.67-2.62 (m, 4H), 2.33 (s, 3H), 2.19 (s, 3H), 1.75-1.67 (m, 4H), 1.30 (s, 3H), 1.22 (s, 3H), 1.08-0.99 (m, 2H), 0.89-0.79 (m, 2H).

Example 360: (*R)-3-(3-((7'-(2-(4,4-Difluoropiperidin-1-yl)ethoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic Acid

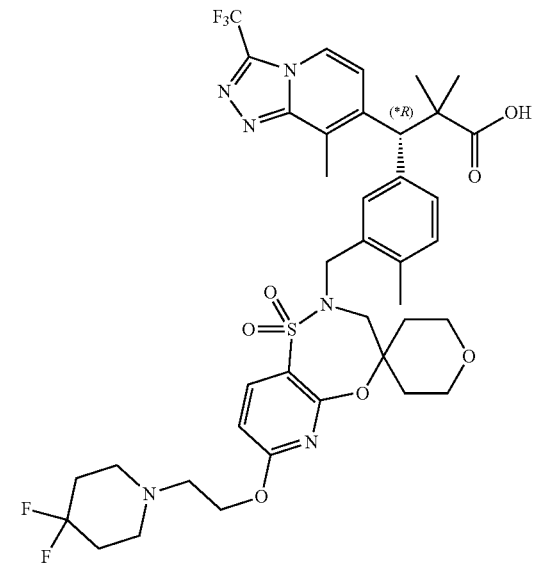 [SMILES: Cc1ccc([C@H](c2ccn3c(C(F)(F)F)nnc3c2C)C(C)(C)C(=O)O)cc1CN1CC2(CCOCC2)Oc2nc(OCCN3CCC(F)(F)CC3)ccc2S1(=O)=O]

The title compound (78 mg, 48%) was prepared using analogous conditions as described in Example 126 where 7'-(2-(4,4-difluoropiperidin-1-yl)ethoxy)-2,2',3,3',5,6-hexahydrospiro[pyran-4,4'-pyrido[2,3-b][1,4,5]oxathiazepine] 1',1'-dioxide (Intermediate 125) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine]1',1'-dioxide (Intermediate 72) and benzyl (*R)-3-(3-(hydroxymethyl)-4-methylphenyl)-2,2-dimethyl-3-(8-methyl-3-(trifluoromethyl)[1,2,4]triazolo[4,3-a]pyridine-7-yl) propanoate (Intermediate 139) instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 17) in step A. MS (ESI): mass calcd. for $C_{39}H_{45}F_5N_6O_7S$, 836.3; m/z found, 837.3 [M+H]$^+$. $^1$H NMR (400 MHz, DMSO-d$_6$) δ 12.51 (s, 1H), 8.42 (d, J=7.2 Hz, 1H), 8.02 (s, 1H), 7.26 (dd, J=7.6, 2.8 Hz, 2H), 7.21 (d, J=1.8 Hz, 1H), 7.15 (d, J=7.9 Hz, 1H), 6.82-6.76 (m, 1H), 4.81 (s, 1H), 4.50-4.29 (m, 4H), 3.79-3.65 (m, 3H), 3.46 (s, 3H), 2.79 (s, 1H), 2.65-2.52 (m, 6H), 2.19 (s, 4H), 1.96 (s, 3H), 1.52 (d, J=15.1 Hz, 2H), 1.30 (d, J=22.7 Hz, 9H).

Example 361: (*R)-3-(3-((7'-(((1R,3R)-3-Hydroxycyclobutyl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

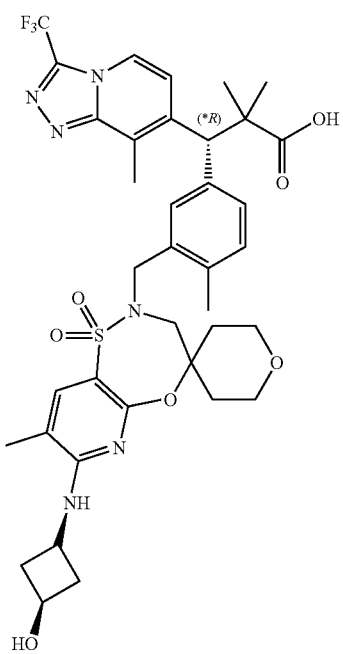

The title compound (97 mg, 55%) was prepared using analogous conditions as described in Example 114 where 3-aminocyclobutan-1-ol was used instead of 3-aminopropan-1-ol in Step A and methyl (*R)-3-(3-((7'-chloro-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate (Intermediate 142) instead of methyl 3-(3-((7'-chloro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(3-(trifluoromethyl)-[1,2,4]triazolo[4,3-a]pyridine-7-yl)propanoate (Intermediate 69). MS (ESI): mass calcd. for $C_{37}H_{43}F_3N_6O_7S$, 772.3; m/z found, 773.3 [M+H]$^+$. $^1$H NMR (400 MHz, DMSO-$d_6$) δ 8.39 (d, J=7.2 Hz, 1H), 7.47 (d, J=1.0 Hz, 1H), 7.29-7.20 (m, 2H), 7.19 (d, J=2.0 Hz, 1H), 7.13 (d, J=8.0 Hz, 1H), 6.78 (d, J=6.2 Hz, 1H), 5.06 (d, J=5.6 Hz, 1H), 4.79 (s, 1H), 4.37 (d, J=15.1 Hz, 1H), 4.24 (d, J=15.1 Hz, 1H), 3.99-3.70 (m, 4H), 3.42 (d, J=10.6 Hz, 1H), 3.35-3.21 (m, 3H), 2.67-2.57 (m, 5H), 2.19 (s, 3H), 2.06 (s, 3H), 1.93-1.75 (m, 2H), 1.50-1.42 (m, 2H), 1.35-1.17 (m, 8H).

Example 362: (*R)-2,2-Dimethyl-3-(4-methyl-3-((8'-methyl-7'-(((R-1-morpholinopropan-2-yl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

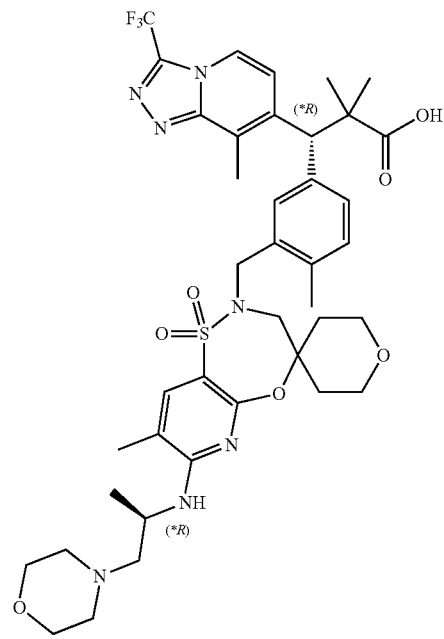 [SMILES: Cc1ccc([C@H](c2ccn3c(C(F)(F)F)nnc3c2C)C(C)(C)C(=O)O)cc1CN1CC2(CCOCC2)Oc2nc(N[C@H](C)CN3CCOCC3)c(C)cc2S1(=O)=O]

The mixture of (*R)-2,2-dimethyl-3-(4-methyl-3-((8'-methyl-7'-(((1-morpholinopropan-2-yl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl) propanoic acid isomers (Example 364) were separated by chiral SFC (Stationary phase: Whelk-O1 (S,S) 5 μm 25*21.2 mm, Mobile phase: 68% CO$_2$, 32% (70% i-PrOH/DCM with 0.3% i-PrNH$_2$). The first eluting isomer (21 mg) was designated *R/*R: MS (ESI): mass calcd. for $C_{40}H_{50}F_3N_7O_7S$, 829.3; m/z found, 830.3 [M+H]$^+$. $^1$H NMR (600 MHz, CDCl$_3$) δ 7.95 (d, J=7.2 Hz, 1H), 7.59 (s, 1H), 7.23-7.17 (m, 2H), 7.04 (dd, J=8.9, 7.0 Hz, 2H), 4.82 (s, 1H), 4.43 (d, J=14.3 Hz, 1H), 4.34 (d, J=14.5 Hz, 1H), 3.98-3.55 (m, 8H), 3.48-3.40 (m, 2H), 2.75-2.50 (m, 6H), 2.19-2.05 (m, 6H), 1.65-1.52 (m, 5H), 1.49-1.15 (m, 13H).

637

Example 363: (*R)-2,2-Dimethyl-3-(4-methyl-3-((8'-methyl-7'-(((S-1-morpholinopropan-2-yl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

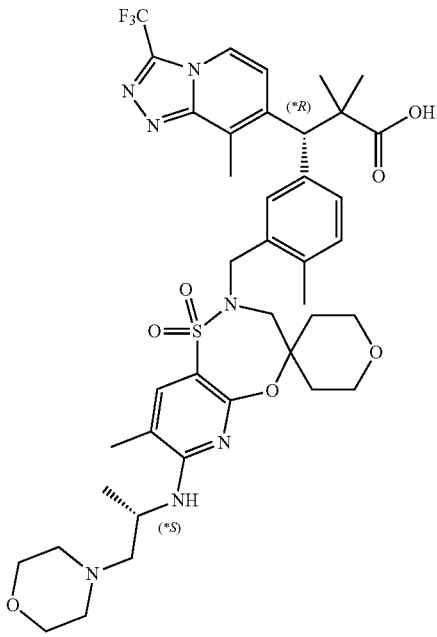 [SMILES: Cc1ccc([C@H](c2ccn3c(C(F)(F)F)nnc3c2C)C(C)(C)C(=O)O)cc1CN1CC2(CCOCC2)Oc2nc(N[C@@H](C)CN3CCOCC3)c(C)cc2S1(=O)=O]

The mixture of (*R)-2,2-dimethyl-3-(4-methyl-3-((8'-methyl-7'-(((1-morpholinopropan-2-yl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl) propanoic acid isomers (Example 364) were separated by chiral SFC as described in Example 362, provided a second eluting isomer (20 mg) that was designated *R/*S: MS (ESI): mass calcd. for $C_{40}H_{50}F_3N_7O_7S$, 829.3; m/z found, 830.3 [M+H]$^+$. $^1$H NMR (600 MHz, CDCl$_3$) δ 7.93 (d, J=7.3 Hz, 1H), 7.60 (s, 1H), 7.18-7.11 (m, 2H), 7.09-7.05 (m, 1H), 7.03 (d, J=7.9 Hz, 1H), 4.81 (s, 1H), 4.46-4.29 (m, 2H), 3.90-3.80 (m, 6H), 3.55 (d, J=11.1 Hz, 2H), 3.49-3.42 (m, 2H), 2.77-2.60 (m, 6H), 2.18 (d, J=18.4 Hz, 6H), 1.66-1.48 (m, 5H), 1.41-1.14 (m, 13H).

638

Example 364: (*R)-2,2-Dimethyl-3-(4-methyl-3-((8'-methyl-7'-(((1-morpholinopropan-2-yl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

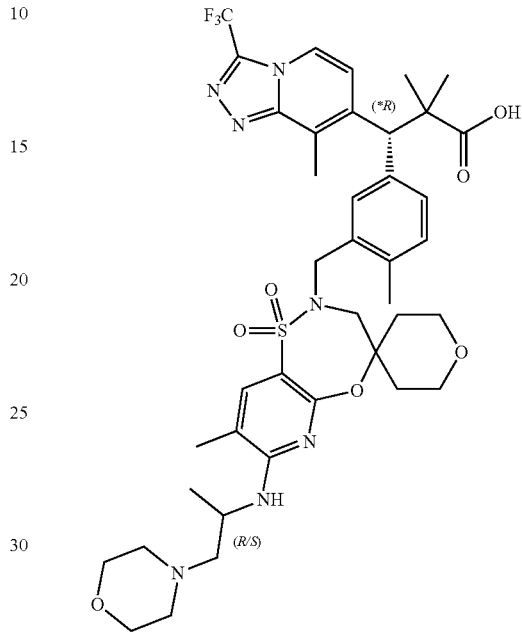

The title compound (65 mg, 57%) was prepared using analogous conditions as described in Example 114 where 1-morpholinopropan-2-amine was used instead of 3-aminopropan-1-ol in Step A and methyl (*R)-3-(3((7'-chloro-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]]pyridine-7-yl) propanoate (Intermediate 142) instead of methyl 3-(3-((7'-chloro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(3-(trifluoromethyl)-[1,2,4]triazolo[4,3-a]pyridine-7-yl) propanoate (Intermediate 69). MS (ESI): mass calcd. for $C_{40}H_{50}F_3N_7O_7S$, 829.3; m/z found, 830.3 [M+H]$^+$.

Example 365: (*R)-2,2-Dimethyl-3-(4-methyl-3-((8'-methyl-7'-((2-morpholinoethyl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

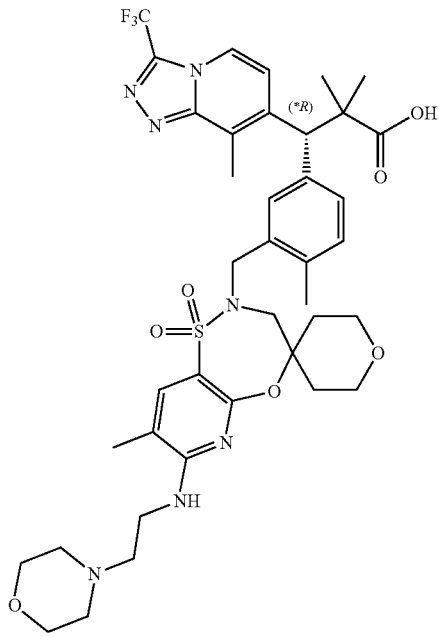 [SMILES: Cc1ccc([C@H](c2ccn3c(C(F)(F)F)nnc3c2C)C(C)(C)C(=O)O)cc1CN1CC2(CCOCC2)Oc2nc(NCCN3CCOCC3)c(C)cc2S1(=O)=O]

The title compound (142 mg, 58%) was prepared using analogous conditions as described in Example 114 where 2-morpholinoethan-1-amine was used instead of 3-aminopropan-1-ol in Step A and methyl (*R)-3-(3((7'-chloro-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl) propanoate (Intermediate 142) instead of methyl 3-(3-((7'-chloro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(3-(trifluoromethyl)-[1,2,4]triazolo[4,3-a]pyridine-7-yl)propanoate (Intermediate 69). MS (ESI): mass calcd. for $C_{39}H_{48}F_3N_7O_7S$, 815.3; m/z found, 816.3 $[M+H]^+$. $^1H$ NMR (400 MHz, DMSO-$d_6$) δ 8.39 (d, J=7.2 Hz, 1H), 7.49-7.45 (m, 1H), 7.29-7.17 (m, 3H), 7.13 (d, J=7.9 Hz, 1H), 6.75 (t, J=5.6 Hz, 1H), 4.79 (s, 1H), 4.37 (d, J=15.2 Hz, 1H), 4.27 (d, J=15.2 Hz, 1H), 3.82-3.72 (m, 2H), 3.60-3.54 (m, 4H), 3.46-3.40 (m, 4H), 3.38-3.20 (m, 1H), 2.64 (s, 3H), 2.50-2.40 (m, 6H), 2.19 (s, 3H), 2.03 (s, 3H), 1.51-1.43 (m, 2H), 1.38-1.20 (m, 9H).

Example 366: (*R)-2,2-Dimethyl-3-(4-methyl-3-((8'-methyl-7'-((2-morpholinoethyl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

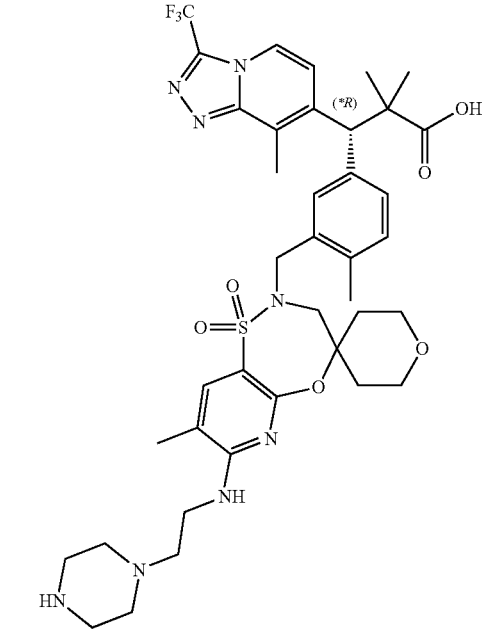 [SMILES: Cc1ccc([C@H](c2ccn3c(C(F)(F)F)nnc3c2C)C(C)(C)C(=O)O)cc1CN1CC2(CCOCC2)Oc2nc(NCCN3CCNCC3)c(C)cc2S1(=O)=O]

Step A: tert-Butyl (*R)-4-(2-((2'-(5-(3-methoxy-2,2-dimethyl-1-(8-methyl-3-(trifluoromethyl)-[1,2,4]triazolo[4,3-a]pyridine-7-yl)-3-oxopropyl)-2-methylbenzyl)-8'-methyl-1',1'-dioxido-2,2',3,3',5,6-hexahydrospiro[pyran-4,4'-pyrido[2,3-b][1,4,5]oxathiazxepin]-7'-yl)amino)ethyl)piperazine-1-carboxylate. The title compound (244 mg, 97%) was prepared using analogous conditions as described in Example 114 where tert-butyl 4-(2-aminoethyl)piperazine-1-carboxylate was used instead of 3-aminopropan-1-ol in Step A and methyl (*R)-3-(3((7'-chloro-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]]pyridine-7-yl)propanoate (Intermediate 142) instead of methyl 3-(3-((7'-chloro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(3-(trifluoromethyl)-[1,2,4]triazolo[4,3-a]pyridine-7-yl)propanoate (Intermediate 69). MS (ESI): mass calcd. for $C_{45}H_{59}F_3N_8O_8S$, 928.4; m/z found, 929.3 $[M+H]^+$.

Step B: Methyl (*R)-2,2-dimethyl-3-(4-methyl-3-((8'-methyl-1',1'-dioxido-7'-((2-(piperazin-1-yl)ethyl)amino-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoate. tert-butyl (*R)-4-(2-((2'-(5-(3-methoxy-2,2-dimethyl-1-(8-methyl-3-(trifluoromethyl)-[1,2,4]triazolo[4,3-a]pyridine-7-yl)-3-oxopropyl)-2-methylbenzyl)-8'-methyl-1',1'-dioxido-2,2',3,3',5,6-hexahydrospiro[pyran-4,4'-pyrido[2,3-b][1,4,5]oxathiazxepin]-7'-yl)amino)ethyl)piperazine-1-carboxylate (244 mg, 0.26 mmol) was dissolved in a 50/50 solution of TFA/DCM (2 mL) and stirred at r.t. for 1 h. The solvent was removed under reduced pressure yielding 275 mg (99%) of the title compound as the bis-TFA-salt which was used in the next step without purification. MS (ESI): mass calcd. for $C_{40}H_{53}F_3N_8O_6S$.2TFA, 828.4; m/z found, 829.3 $[M+H]^+$.

Step C: (*R)-2,2-Dimethyl-3-(4-methyl-3-((8'-methyl-7'-((2-morpholinoethyl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid. The title compound (113 mg, 52%) was prepared using analogous conditions as described in Example 114 where methyl (*R)-2,2-dimethyl-3-(4-methyl-3-((8'-methyl-1',1'-dioxido-7'-((2-(piperazin-1-yl)ethyl)amino-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoate was used instead of methyl (*R)-2,2-dimethyl-3-(4-methyl-3-((8'-methyl-1',1'-dioxido-7'-((2-(piperazin-1-yl)ethyl)amino-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoate in Step B. MS (ESI): mass calcd. for $C_{39}H_{49}F_3N_8O_6S$, 814.3; m/z found, 815.3 $[M+H]^+$. $^1H$ NMR (400 MHz, DMSO-$d_6$) δ 8.37 (d, J=7.2 Hz, 1H), 7.48 (d, J=1.0 Hz, 1H), 7.33 (d, J=7.3 Hz, 1H), 7.25-7.23 (m, 1H), 7.20-7.14 (m, 1H), 7.11 (d, J=7.9 Hz, 1H), 6.72 (t, J=5.7 Hz, 1H), 4.79 (s, 1H), 4.35 (d, J=14.7 Hz, 1H), 4.24 (d, J=14.8 Hz, 1H), 3.82-3.72 (m, 2H), 3.60-3.10 (m, 6H), 2.79-2.70 (m, 4H), 2.62 (s, 3H), 2.45-2.35 (m, 7H), 2.19 (s, 3H), 2.03 (s, 3H), 1.52-1.47 (m, 2H), 1.30-1.17 (m, 8H).

Example 367: (*R)-2,2-Dimethyl-3-(4-methyl-3-((8'-methyl-1',1'-dioxido-7'-(((S)-1-(pyrrolidine-1-yl)propan-2-yl)amino)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

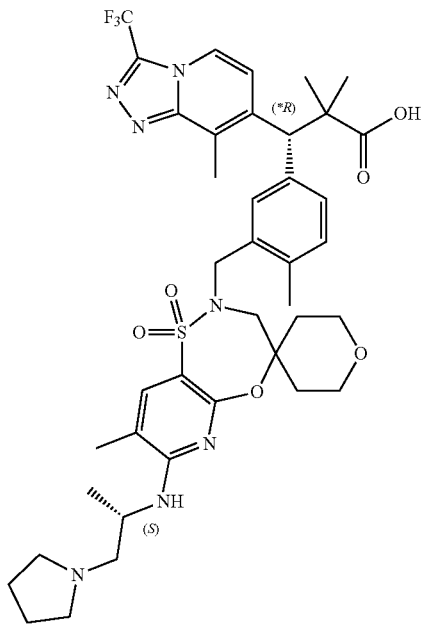

The title compound (93 mg, 79%) was prepared using analogous conditions as described in Example 114 where (S)-1-(pyrrolidine-1-yl)propan-2-amine was used instead of 3-aminopropan-1-ol in Step A and methyl (*R)-3-(3((7'-chloro-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate (Intermediate 142) instead of methyl 3-(3-((7'-chloro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate (Intermediate 69). MS (ESI): mass calcd. for $C_{40}H_{50}F_3N_7O_6S$, 813.3; m/z found, 814.3 $[M+H]^+$. $^1H$ NMR (400 MHz, DMSO-$d_6$) δ 8.38 (d, J=7.2 Hz, 1H), 7.47 (s, 1H), 7.29-7.21 (m, 2H), 7.18 (s, 1H), 7.13 (d, J=7.8 Hz, 1H), 6.36 (d, J=7.7 Hz, 1H), 4.79 (s, 1H), 4.39-4.35 (m, 1H), 4.31-4.19 (m, 2H), 3.83-3.74 (m, 2H), 3.45-3.27 (m, 3H), 2.64 (s, 3H), 2.58-2.37 (m, 6H), 2.19 (s, 3H), 2.04 (s, 3H), 1.69-1.63 (m, 4H), 1.52-1.42 (m, 1H), 1.36-1.11 (m, 12H).

Example 368: (*R)-3-(3-((1',1'-Dioxido-7'-(2-(piperazin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic Acid

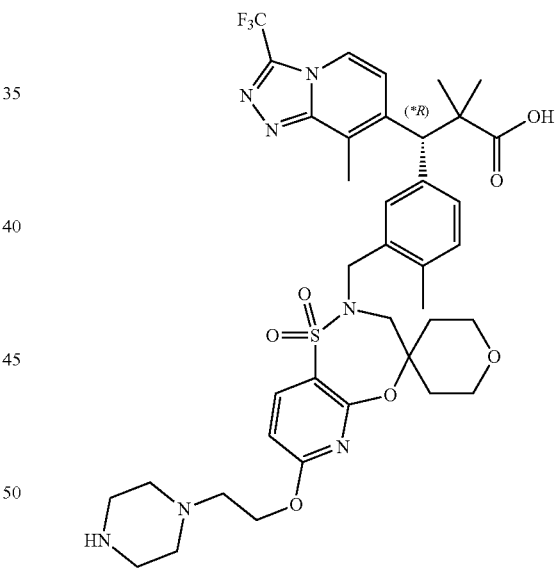

Step A: tert-Butyl (*R)-4-(2-((2'-(5-(3-(benzyloxy)-2,2-dimethyl-1-(8-methyl-3-(trifluoromethyl)-[1,2,4]triazolo[4,3-a]pyridine-7-yl)-3-oxopropyl)-2-methylbenzyl)-1',1'-dioxido-2,2',3,3',5,6-hexahydrospiro[pyran]4,4'-pyrido[2,3-b][1,4,5]oxathiazepin]-7'-yl)oxy)ethyl)piperazine-1-carboxylate. The title compound (417 mg, 108%) was prepared using analogous conditions as described in Example 126 where tert-butyl 4-(2-((1',1'-dioxido-2,2',3,3',5,6-hexahydrospiro[pyran-4,4'-pyrido[2,3-b][1,4,5]oxathiazepin]-7'-yl)oxy)ethyl)piperazine-1-carboxylate (Intermediate 126) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine]1',1'-dioxide (Intermediate 72)

and benzyl (*R)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 139) instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 71) in step A. MS (ESI): mass calcd. for $C_{50}H_{60}F_3N_7O_9S$, 991.4; m/z found, 992.3 $[M+H]^+$.

Step B: (*R)-3-(3-((7'-(2-(4-(tert-Butoxycarbonyl)piperazine-1-yl_ethoxy)-1',1'-dioxido-2,3,5,6-tetrahydrospiro[pyran]4,4'-pyrido[2,3-b][1,4,5]oxathiazepin]-2'(3'H)-yl)methyl)-4-methylphenyl-2,2-dimethyl-3-(8-methyl-3-(trifluoromethyl)-[1,2,4]triazolo[4,3-a]pyridine-7-yl)propanoic acid. The title compound (367 mg, 97%) was prepared using analogous conditions as described in Example 126 where tert-butyl (*R)-4-(2-((2'-(5-(3-(benzyloxy)-2,2-dimethyl-1-(8-methyl-3-(trifluoromethyl)-[1,2,4]triazolo[4,3-a]pyridine-7-yl)-3-oxopropyl)-2-methylbenzyl)-1',1'-dioxido-2,2',3,3',5,6-hexahydrospiro[pyran]4,4'-pyrido[2,3-b][1,4,5]oxathiazepin]-7'-yl)oxy)ethyl)piperazine-1-carboxylate was used instead of benzyl (*S)-2,2-dimethyl-3-(4-methyl-3-((8'-methyl-1',1'-dioxido-7'-(2-(piperidin-1-yl)ethyoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoate in step B. MS (ESI): mass calcd. for $C_{43}H_{54}F_3N_7O_9S$, 901.4; m/z found, 902.3 $[M+H]^+$.

Step C: (*R)-3-(3-((1',1'-Dioxido-7'-(2-(piperazin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic acid. (*R)-3-(3-((7'-(2-(4-(tert-butoxycarbonyl)piperazine-1-yl_ethoxy)-1',1'-dioxido-2,3,5,6-tetrahydrospiro[pyran]4,4'-pyrido[2,3-b][1,4,5]oxathiazepin]-2'(3'H)-yl)methyl)-4-methylphenyl-2,2-dimethyl-3-(8-methyl-3-(trifluoromethyl)-[1,2,4]triazolo[4,3-a]pyridine-7-yl)propanoic acid (367 mg, 0.41 mmol) was dissolved in a 1:1 mixture of TFA/DCM (2.0 mL) and stirred at r.t. for 1 h. The solvent was then removed under reduced pressure and the resulting residue purified by reverse phase HPLC (eluent: MeCN/H$_2$O (with 20 mM NH$_4$OH), 10:90 to 70:30, gradient) to afford the title compound (213 mg, 65%). MS (ESI): mass calcd. for $C_{38}H_{46}F_3N_7O_7S$, 801.3; m/z found, 802.3 $[M+H]^+$. $^1$H NMR (400 MHz, DMSO-d$_6$) δ 8.38 (d, J=7.2 Hz, 1H), 7.99 (d, J=8.4 Hz, 1H), 7.32 (d, J=7.3 Hz, 1H), 7.24 (d, J=7.9 Hz, 1H), 7.19 (s, 1H), 7.12 (d, J=7.8 Hz, 1H), 6.76 (d, J=8.4 Hz, 1H), 4.79 (s, 1H), 4.47-4.27 (m, 4H), 3.74 (q, J=10.5 Hz, 2H), 3.60-3.10 (m, 5H), 2.75-2.60 (m, 9H), 2.47-2.35 (s, 4H), 2.18 (s, 3H), 1.55-1.47 (m, 2H), 1.42-1.30 (m, 2H), 1.25 (s, 3H), 1.22 (s, 3H).

Example 369: (*R)-2,2-Dimethyl-3-(4-methyl-3-(8'-methyl-1',1'-dioxido-7'-(2-(piperidin-4-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic Acid

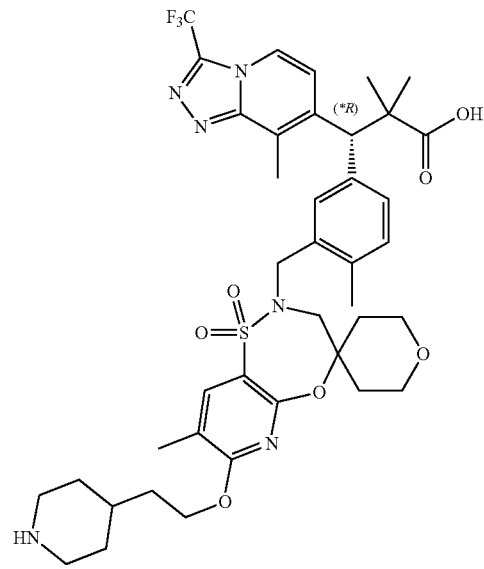 [SMILES: Cc1ccc([C@H](c2ccn3c(C(F)(F)F)nnc3c2C)C(C)(C)C(=O)O)cc1CN1CC2(CCOCC2)Oc2nc(OCCC3CCNCC3)c(C)cc2S1(=O)=O]

The title compound (115 mg, 65%) was prepared using analogous conditions as described in Example 368 where tert-butyl 4-(2-((8'-methyl-1',1'-dioxido-2,2',3',5,6-hexahydrospiro[pyran-4,4'-pyrido[2,3-b][1,4,5]oxathiazepin]-7'-yl)oxy)ethyl)piperidine-1-carboxylate (Intermediate 133) was used instead of tert-butyl 4-(2-((1',1'-dioxido-2,2',3,3',5,6-hexahydrospiro[pyran-4,4'-pyrido[2,3-b][1,4,5]oxathiazepin]-7'-yl)oxy)ethyl)piperazine-1-carboxylate (Intermediate 126) in step A. MS (ESI): mass calcd. for $C_{40}H_{49}F_3N_6O_7S$, 814.3; m/z found, 815.3 $[M+H]^+$. $^1$H NMR (400 MHz, DMSO-d$_6$) δ 8.29 (d, J=7.2 Hz, 1H), 7.79 (s, 1H), 7.29 (d, J=7.4 Hz, 1H), 7.21-7.13 (m, 1H), 7.09-6.99 (m, 2H), 4.69 (s, 1H), 4.39-4.22 (m, 4H), 3.73-3.62 (m, 2H), 3.45-3.32 (m, 2H), 2.96 (d, J=11.4 Hz, 2H), 2.57-2.49 (m, 5H), 2.17-2.00 (m, 6H), 1.68-1.34 (m, 8H), 1.33-1.00 (m, 12H).

Example 370: (*S)-2,2-Dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic Acid

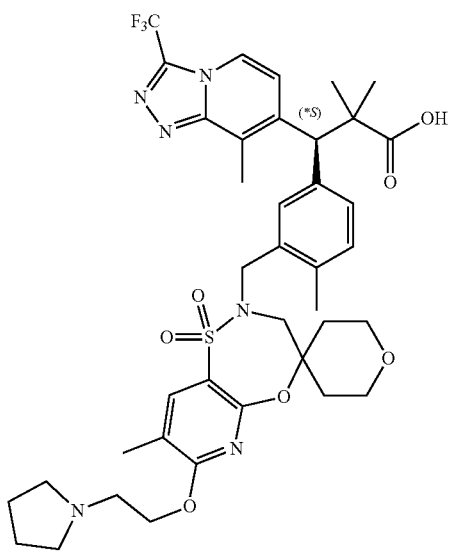 [SMILES: Cc1ccc([C@@H](c2ccn3c(C(F)(F)F)nnc3c2C)C(C)(C)C(=O)O)cc1CN1CC2(CCOCC2)Oc2nc(OCCN3CCCC3)c(C)cc2S1(=O)=O]

Step A: tert-Butyl (*S)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoate. The title compound (645 mg, 44%) was prepared using analogous conditions as described in Example 126 where 8'-methyl-7'-(2-(pyrrolidin-1-yl)ethoxy)-2,2',3,3',5,6-hexahydrospiro[pyran-4,4'-pyrido[2,3-b][1,4,5]oxathiazepine]1',1'-dioxide (Intermediate 134) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide (Intermediate 72) and tert-butyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 128) instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 71) in step A. MS (ESI): mass calcd. for $C_{43}H_{55}F_3N_6O_7S$, 856.4; m/z found, 857.3 [M+H]$^+$.

Step B: (*S)-2,2-Dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic acid. To a 25-mL round bottom flask fitted with a reflux condenser was added tert-butyl (*S)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoate (80 mg 0.09 mmol), DCM (3.0 mL) and TFA (0.75 mL). The mixture was heated to 50° C. for 3 h then cooled, and solvent removed under reduced pressure. The residue was purified by reverse phase HPLC (eluent: MeCN/H$_2$O (with 20 mM NH$_4$OH), 10:90 to 70:30, gradient) to afford the title compound (55 mg, 74%). MS (ESI): mass calcd. for $C_{39}H_{47}F_3N_6O_7S$, 800.3; m/z found, 801.3 [M+H]$^+$. $^1$H NMR (400 MHz, DMSO-d$_6$) δ 8.32 (d, J=7.2 Hz, 1H), 7.86 (s, 1H), 7.40 (d, J=7.4 Hz, 1H), 7.30-7.25 (m, 1H), 7.14-7.04 (m, 2H), 4.81 (s, 1H), 4.47-4.23 (m, 4H), 3.79-3.70 (m, 2H), 3.45-3.20 (m, 4H), 2.81 (t, J=5.9 Hz, 2H), 2.62-2.43 (m, 5H), 2.19 (s, 3H), 2.15 (s, 3H), 1.77-1.61 (m, 4H), 1.47 (d, J=13.8 Hz, 2H), 1.40-1.22 (m, 4H), 1.16 (s, 3H), 1.10 (s, 3H).

Example 371: (*S)-3-(3-1',1'-Dioxido-7'-(2-(piperidin-1-yl)ethoxy)spiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic Acid

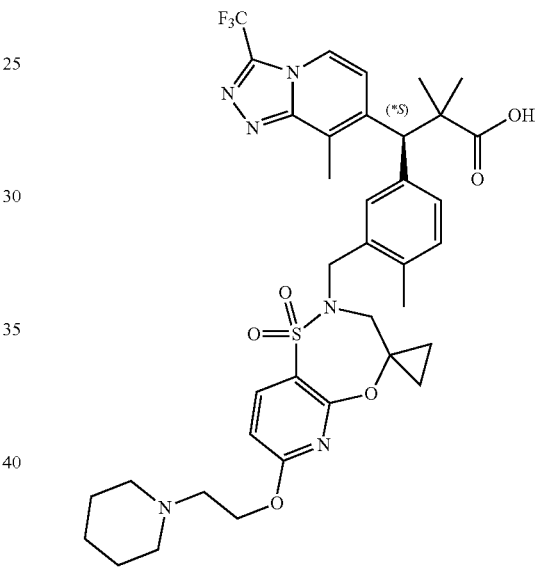

Step A: tert-Butyl (*S)-3-((3-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoate. The title compound (230 mg, 59%) was prepared using analogous conditions as described in Example 126 where 7'-(2-(piperidin-1-yl)ethoxy)-2',3'-dihydrospiro[cyclopropane-1,4'-pyrido[2,3-b][1,4,5]oxathiazepine]1',1'-dioxide (Intermediate 127) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine]1',1'-dioxide (Intermediate 72) and tert-butyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 128) instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 71) in step A. MS (ESI): mass calcd. for $C_{41}H_{51}F_3N_6O_6S$, 812.4; m/z found, 813.3 [M+H]$^+$. $^1$H NMR (400 MHz, CDCl$_3$) δ 8.02 (d, J=8.5 Hz, 1H), 7.95 (d, J=7.3 Hz, 1H), 7.14 (d, J=7.3 Hz, 1H), 7.05-6.97 (m, 3H), 6.61 (d, J=8.4 Hz, 1H), 4.64 (s, 1H), 4.44

(s, 2H), 4.20 (s, 2H), 3.49-3.30 (m, 2H), 2.79 (d, J=16.2 Hz, 2H), 2.67-2.62 (m, 3H), 2.50-2.40 (m, 3H), 2.24 (s, 3H), 1.75-1.53 (m, 4H), 1.42 (s, 2H), 1.29 (s, 4H), 1.20 (s, 4H), 1.15 (s, 8H), 1.13-1.06 (m, 2H), 0.51-0.41 (m, 2H).

Step B: (*S)-3-(3-1',1'-Dioxido-7'-(2-(piperidin-1-yl)ethoxy)spiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoic acid. The title compound (154 mg, 72%) was prepared using analogous conditions as described in Example 370 where tert-butyl (*S)-3-((3-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoate was used instead of tert-butyl (*R)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoate in Step B. MS (ESI): mass calcd. for $C_{37}H_{43}F_3N_6O_6S$, 756; m/z found, 757.3 [M+H]$^+$. $^1$H NMR (400 MHz, DMSO-$d_6$) δ 8.33 (d, J=7.1 Hz, 1H), 7.19 (d, J=7.4 Hz, 1H), 7.13 (d, J=8.0 Hz, 1H), 7.06 (d, J=7.8 Hz, 1H), 7.02 (s, 1H), 6.76 (d, J=8.4 Hz, 1H), 4.70 (s, 1H), 4.27 (t, J=5.9 Hz, 2H), 4.18-4.02 (m, 2H), 3.50-3.10 (m, 3H), 2.62-2.50 (m, 5H), 2.40-2.30 (m, 4H), 2.17 (s, 3H), 1.45-1.35 (m, 4H), 1.34-1.26 (m, 2H), 1.21 (s, 3H), 1.15 (s, 3H), 0.94-0.83 (m, 2H), 0.54-0.42 (m, 2H).

Example 372: (*S)-2,2-Dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

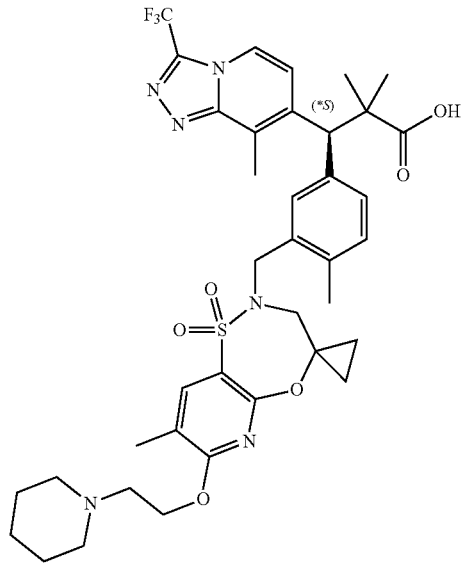 [SMILES: Cc1ccc([C@@H](c2ccn3c(C(F)(F)F)nnc3c2C)C(C)(C)C(=O)O)cc1CN1CC2(CC2)Oc2nc(OCCN3CCCCC3)c(C)cc2S1(=O)=O]

Step A: tert-Butyl (*S)-2,2-dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoate. The title compound (244 mg, 56%) was prepared using analogous conditions as described in Example 126 where 8'-methyl-7'-(2-(piperidin-1-yl)ethoxy)-2',3'-dihydrospiro[cyclopropane-1,4'-pyrido[2,3-b][1,4,5]oxathiazepine] 1',1'-dioxide (Intermediate 136) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide Intermediate 72) and tert-butyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 128) instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 71) in step A. mass calcd. for $C_{42}H_{53}F_3N_6O_6S$, 826.4; m/z found, 827.3 [M+H]$^+$.

Step B: (*S)-2,2-Dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid. The title compound (190 mg, 84%) was prepared using analogous conditions as described in Example 370 where tert-butyl (*S)-2,2-dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoate was used instead of tert-butyl (*R)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoate in Step B. MS (ESI): mass calcd. for $C_{38}H_{45}F_3N_6O_6S$, 770.3; m/z found, 771.3 [M+H]$^+$. $^1$H NMR (400 MHz, DMSO-$d_6$) δ 7.87 (d, J=1.0 Hz, 1H), 7.17 (d, J=7.4 Hz, 1H), 7.13 (dd, J=7.9, 1.9 Hz, 1H), 7.06 (d, J=7.9 Hz, 1H), 7.01 (d, J=2.0 Hz, 1H), 4.70 (s, 1H), 4.30 (t, J=6.0 Hz, 2H), 4.16-4.01 (m, 2H), 3.50-3.10 (m, 3H), 2.63-2.51 (m, 5H), 2.42-2.34 (m, 4H), 2.18 (s, 3H), 2.09 (d, J=0.9 Hz, 3H), 1.46-1.35 (m, 4H), 1.31 (q, J=6.0 Hz, 2H), 1.22 (s, 3H), 1.15 (s, 3H), 0.92-0.83 (m, 2H), 0.51-0.35 (m, 2H).

Example 373: (*S)-2,2-Dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

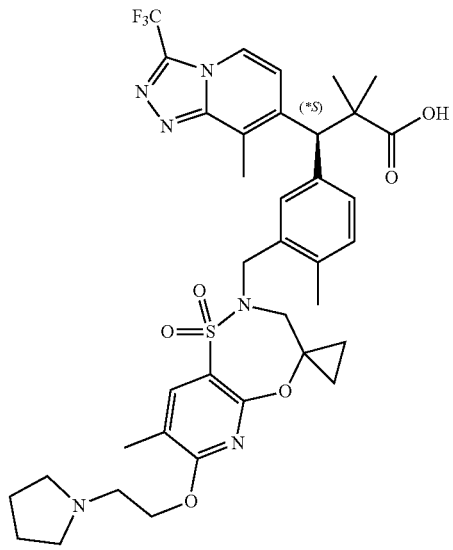 [SMILES: Cc1ccc([C@@H](c2ccn3c(C(F)(F)F)nnc3c2C)C(C)(C)C(=O)O)cc1CN1CC2(CC2)Oc2nc(OCCN3CCCC3)c(C)cc2S1(=O)=O]

Step A: tert-Butyl (*S)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoate. The title compound (133 mg, 32%) was prepared using analogous conditions as described in Example 126 where 8'-methyl-7'-(2-(pyrrolidin-1-yl)ethoxy)-2',3'-dihydrospiro[cyclopropane-1,4'-pyrido[2,3-b][1,4,5]oxathiazepine] 1',1'-dioxide (Intermediate 137) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide (Intermediate 72) and tert-butyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 128) instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 71) in step A. mass calcd. for $C_{41}H_{51}F_3N_6O_6S$, 812.4; m/z found, 813.3 [M+H]$^+$.

Step B: (*S)-2,2-Dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid. The title compound was prepared using analogous conditions as described in Example 370 where tert-butyl (*S)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoate was used instead of tert-butyl (*R)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoate in Step B. MS (ESI): mass calcd. for $C_{37}H_{43}F_3N_6O_6S$, 756.3; m/z found, 757.2 [M+H]$^+$. $^1$H NMR (400 MHz, DMSO-$d_6$) δ 8.40 (d, J=7.2 Hz, 1H), 7.96 (s, 1H), 7.27-7.18 (m, 2H), 7.14 (d, J=7.9 Hz, 1H), 7.09 (d, J=2.0 Hz, 1H), 4.77 (s, 1H), 4.43 (t, J=5.6 Hz, 2H), 4.22-4.13 (m, 2H), 3.60-3.05 (m, 3H), 2.98 (s, 2H), 2.73 (s, 3H), 2.63 (s, 3H), 2.25 (s, 3H), 2.23-2.14 (m, 3H), 1.80-1.70 (m, 4H), 1.29 (s, 3H), 1.23 (s, 3H), 0.94 (s, 2H), 0.60-0.44 (m, 2H).

Example 374: (*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl) propanoic Acid

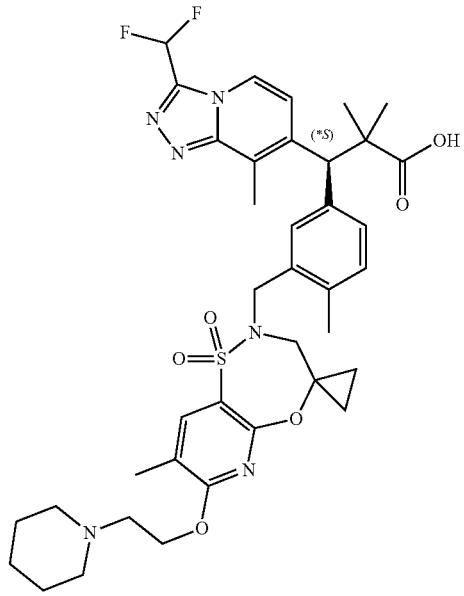 [SMILES: Cc1ccc([C@@H](c2ccn3c(C(F)F)nnc3c2C)C(C)(C)C(=O)O)cc1CN1CC2(CC2)Oc2nc(OCCN3CCCCC3)c(C)cc2S1(=O)=O]

Step A: tert-Butyl (*S)-3-(3-(difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl)propanoate. The title compound (183 mg, 58%) was prepared using analogous conditions as described in Example 126 where 8'-methyl-7'-(2-(piperidin-1-yl)ethoxy)-2',3'-dihydrospiro[cyclopropane-1,4'-pyrido[2,3-b][1,4,5]oxathiazepine] 1',1'-dioxide (Intermediate 136) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide (Intermediate 72) and tert-butyl (*S)-3-(3-(difluoromethyl)-8-methyl-[1,2,4]triazolo[4,3-a]pyridine-7-yl)-3-(3-(hydroxymethyl)-4-methylphenyl)-2,2-dimethylpropanoate (Intermediate 129) instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 71) in step A. mass calcd. for $C_{42}H_{54}F_2N_6O_6S$, 808.4; m/z found, 809.3 [M+H]$^+$.

Step B: (*S)-3-(3-(Difluoromethyl)-8-methy-[1,2,4]triazolo[4,3-a]pyridine-7-yl)-2,2-dimethyl-3-(4-methyl-3-((8'-methyl-1',1'-dioxido-7'-(2-(piperidin-1-yl)ethoxy)spiro[cy clopropane-1,4'-pyrido[2,3-b][1,4,5]oxathiazepin]-2'(3'H)-yl)methyl)phenyl)propanoic acid. The title compound (97 mg, 57%) was prepared using analogous conditions as described in Example 370 where tert-butyl (*S)-3-(3-(difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)phenyl) propanoate was used instead of tert-butyl (*R)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl) propanoate in Step B. MS (ESI): mass calcd. for $C_{38}H_{46}F_2N_6O_6S$, 752.3; m/z found, 753.4 $[M+H]^+$. $^1H$ NMR (400 MHz, DMSO-$d_6$) δ 8.37 (d, J=7.3 Hz, 1H), 7.94 (d, J=1.0 Hz, 1H), 7.76-7.58 (m, 1H), 7.24-7.18 (m, 2H), 7.16-7.07 (m, 2H), 4.75 (s, 1H), 4.37 (t, J=5.9 Hz, 2H), 4.25-4.09 (m, 2H), 3.55-3.25 (m, 2H), 2.66 (t, J=6.0 Hz, 2H), 2.60 (s, 3H), 2.49-2.38 (m, 4H), 2.25 (s, 3H), 2.16 (s, 3H), 1.48 (p, J=5.5 Hz, 4H), 1.38 (q, J=5.8 Hz, 2H), 1.28 (s, 3H), 1.22 (s, 3H), 1.01-0.89 (m, 2H), 0.58-0.44 (m, 2H).

Example 375: (*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl) propanoic Acid

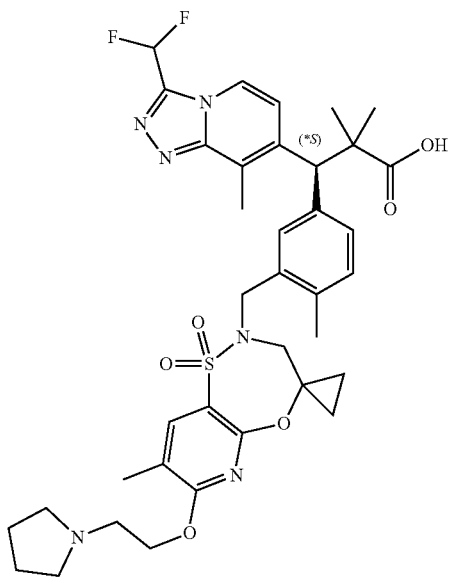 [SMILES: Cc1ccc([C@@H](c2ccn3c(C(F)F)nnc3c2C)C(C)(C)C(=O)O)cc1CN1CC2(CC2)Oc2nc(OCCN3CCCC3)c(C)cc2S1(=O)=O]

Step A: tert-Butyl (*S)-3-(3-(difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoate. The title compound (57 mg, 18%) was prepared using analogous conditions as described in Example 126 where 8'-methyl-7'-(2-(pyrrolidin-1-yl)ethoxy)-2',3'-dihydrospiro[cyclopropane-1,4'-pyrido[2,3-b][1,4,5]oxathiazepine]1',1'-dioxide (Intermediate 137) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide Intermediate 72) and tert-butyl (*S)-3-(3-(difluoromethyl)-8-methyl-[1,2,4]triazolo[4,3-a]pyridine-7-yl)-3-(3-(hydroxymethyl)-4-methylphenyl)-2,2-dimethylpropanoate (Intermediate 129) instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 71) in step A. mass calcd. for $C_{41}H_{52}F_2N_6O_6S$, 794.4; m/z found, 795.3 $[M+H]^+$.

Step B: (*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoic acid. The title compound (29 mg, 55%) was prepared using analogous conditions as described in Example 370 where tert-butyl (*S)-3-(3-(difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl) propanoate was used instead of tert-butyl (*R)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl) propanoate in Step B. MS (ESI): mass calcd. for $C_{37}H_{44}F_2N_6O_6S$, 738.3; m/z found, 739.3 $[M+H]^+$. $^1H$ NMR (400 MHz, DMSO-$d_6$) δ 8.30 (d, J=7.3 Hz, 1H), 7.91 (s, 1H), 7.65 (t, J=51.6 Hz, 1H), 7.18-7.00 (m, 4H), 4.68 (s, 1H), 4.44 (br s, 2H), 4.10 (q, J=14.6 Hz, 2H), 3.50-3.15 (m, 9H), 2.53 (s, 3H), 2.18-2.13 (m, 6H), 1.79 (br s, 3H), 1.22 (s, 3H), 1.16 (s, 3H), 0.92-0.83 (m, 2H), 0.52-0.39 (m, 2H).

Example 376: 3-(*R)-2,2-Dimethyl-3-(4-methyl-3-((8'-methyl-1',1'-dioxido-7'-((1-piperidin-1-yl)propan-2-yl)amino)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

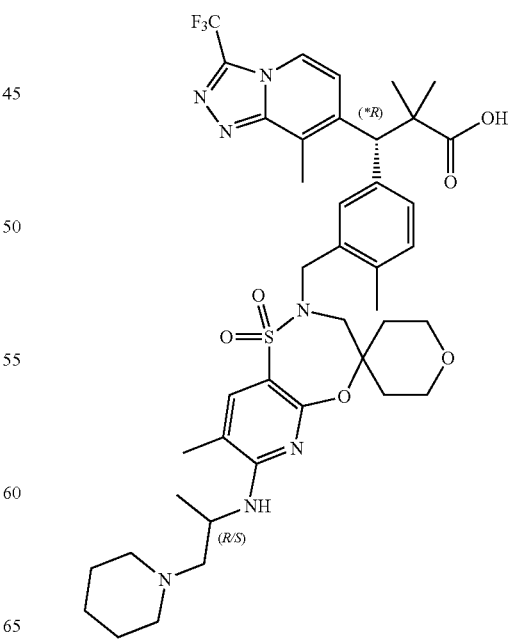

The title compound (65 mg, 57%) was prepared using analogous conditions as described in Example 114 where 1-(piperidin-1-yl)propan-2-amine was used instead of 3-aminopropan-1-ol in Step A and methyl (*R)-3-(3((7'-chloro-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate (Intermediate 142) instead of methyl 3-(3-((7'-chloro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(3-(trifluoromethyl)-[1,2,4]triazolo[4,3-a]pyridine-7-yl)propanoate (Intermediate 69). MS (ESI): mass calcd. for $C_{41}H_{52}F_3N_7O_8S$, 827.4; m/z found, 828.3 [M+H]+. 1H NMR (400 MHz, DMSO-$d_6$) δ 8.32 (d, J=7.2 Hz, 1H), 7.41 (s, 1H), 7.23-7.10 (m, 3H), 7.05 (d, J=8.0 Hz, 1H), 6.25 (d, J=7.3 Hz, 1H), 4.72 (s, 1H), 4.30 (d, J=15.1 Hz, 1H), 4.25-4.09 (m, 2H), 3.78-3.65 (m, 2H), 3.41-3.10 (m, 3H), 2.57 (s, 3H), 2.40-2.32 (m, 3H), 2.30-2.22 (m, 2H), 2.20-2.09 (m, 4H), 1.93 (s, 3H), 1.44-1.35 (m, 6H), 1.35-1.08 (m, 14H).

Example 377: (*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoic Acid

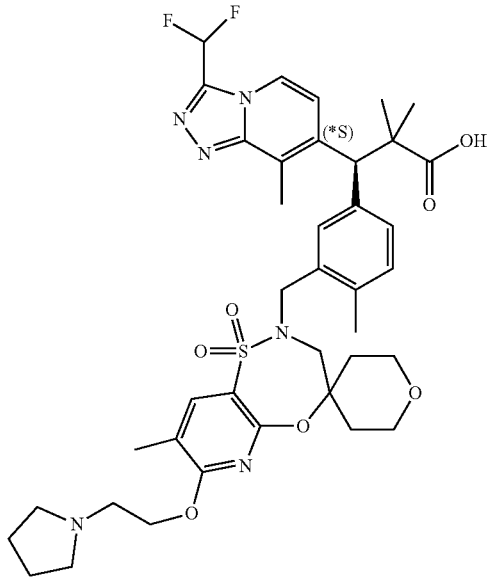 [SMILES: Cc1ccc([C@@H](c2ccn3c(C(F)F)nnc3c2C)C(C)(C)C(=O)O)cc1CN1CC2(CCOCC2)Oc2nc(OCCN3CCCC3)c(C)cc2S1(=O)=O]

Step A: tert-Butyl (*S)-3-(3-(difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoate. The title compound (70 mg, 23%) was prepared using analogous conditions as described in Example 126 where 8'-methyl-7'-(2-(pyrrolidin-1-yl)ethoxy)-2,2',3,3',5,6-hexahydrospiro[pyran-4,4'-pyrido[2,3-b][1,4,5]oxathiazepine] 1',1'-dioxide (Intermediate 134) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide Intermediate 72) and tert-butyl (*S)-3-(3-(difluoromethyl)-8-methyl-[1,2,4]triazolo[4,3-a]pyridine-7-yl)-3-(3-(hydroxymethyl)-4-methylphenyl)-2,2-dimethylpropanoate (Intermediate 129) instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 71) in step A. mass calcd. for $C_{43}H_{56}F_2N_6O_7S$, 838.4; m/z found, 839.3 [M+H]+.

Step B: (*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoic acid. The title compound (35 mg, 54%) was prepared using analogous conditions as described in Example 370 where tert-butyl (*S)-3-(3-(difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoate was used instead of tert-butyl (*R)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoate in Step B. MS (ESI): mass calcd. for $C_{39}H_{48}F_2N_6O_7S$, 782.3; m/z found, 783.3 [M+H]+. 1H NMR (400 MHz, DMSO-$d_6$) δ 8.32 (d, J=7.2 Hz, 1H), 7.80 (s, 1H), 7.62 (t, J=51.7 Hz, 1H), 7.20-7.12 (m, 3H), 7.06 (d, J=8.1 Hz, 1H), 4.71 (s, 1H), 4.43-4.22 (m, 4H), 3.76-3.65 (m, 2H), 3.48-3.15 (s, 5H), 2.87 (br s, 1H), 2.70-2.55 (m, 6H), 2.15-2.06 (m, 6H), 1.66 (br s, 4H), 1.50-1.27 (m, 4H), 1.27-1.15 (m, 7H).

Example 378: (*S)-3-(3-((7'-(2-(4-Methoxypiperidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

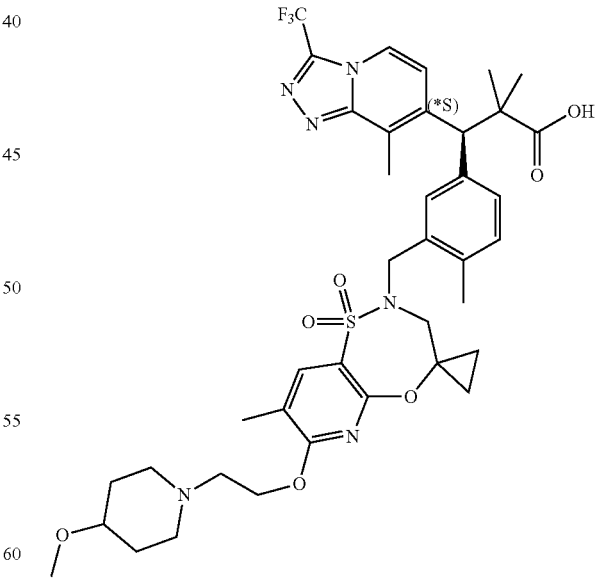

Step A: tert-Butyl (*S)-3-(3-((7'-(2-(4-methoxypiperidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)

propanoate. The title compound (159 mg, 45%) was prepared using analogous conditions as described in Example 126 where 7'-(2-(4-methoxypiperidine-1-yl)ethoxy)-8'-methyl-2',3'-dihydrospiro[cyclopropane-1,4'-pyrido[2,3-b][1,4,5]oxathiazepine] 1',1'-dioxide (Intermediate 138) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide Intermediate 72) and tert-butyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 128) instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 71) in step A. mass calcd. for $C_{43}H_{55}F_3N_6O_7S$, 856.4; m/z found, 857.3 [M+H]$^+$.

Step B: (*S)-3-(3-((7'-(2-(4-Methoxypiperidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid. The title compound (105 mg, 72%) was prepared using analogous conditions as described in Example 370 where tert-butyl (*S)-3-(3-((7'-(2-(4-methoxypiperidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate was used instead of tert-butyl (*R)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoate in Step B. MS (ESI): mass calcd. for $C_{39}H_{47}F_3N_6O_7S$, 800.3; m/z found, 801.3 [M+H]$^+$. $^1$H NMR (400 MHz, DMSO-d$_6$) δ 8.40 (d, J=6.9 Hz, 1H), 7.94 (s, 1H), 7.30-7.03 (m, 4H), 4.77 (s, 1H), 4.40-4.33 (m, 2H), 4.25-4.07 (m, 2H), 3.60-3.12 (m, 4H), 2.83-2.56 (m, 8H), 2.28-2.13 (m, 9H), 1.81 (d, J=12.1 Hz, 2H), 1.45-1.35 (m, 2H), 1.34-1.19 (m, 6H), 1.00-0.88 (m, 2H), 0.59-0.42 (m, 2H).

Example 379: (*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoic Acid

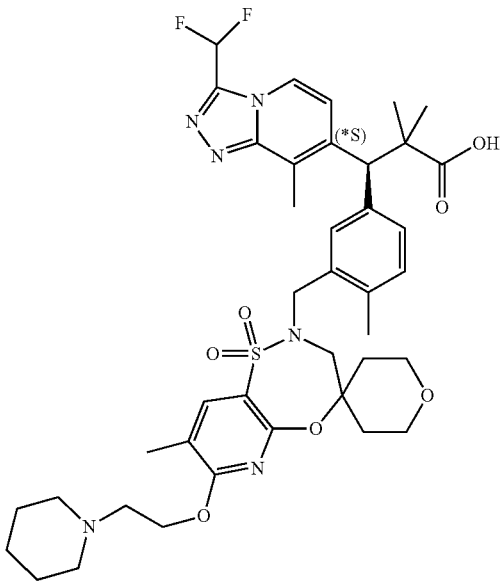 [SMILES: Cc1ccc([C@@H](c2ccn3c(C(F)F)nnc3c2C)C(C)(C)C(=O)O)cc1CN1CC2(CCOCC2)Oc2nc(OCCN3CCCCC3)c(C)cc2S1(=O)=O]

Step A: (*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoate. The title compound (211 mg, 46%) was prepared using analogous conditions as described in Example 126 where tert-butyl (*S)-3-(3-(difluoromethyl)-8-methyl-[1,2,4]triazolo[4,3-a]pyridine-7-yl)-3-(3-(hydroxymethyl)-4-methylphenyl)-2,2-dimethylpropanoate (Intermediate 129) instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 71) in step A. mass calcd. for $C_{44}H_{58}F_2N_6O_7S$, 852.4; m/z found, 853.3 [M+H]$^+$.

Step B: (*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoic acid. The title compound (142 mg, 76%) was prepared using analogous conditions as described in Example 370 where (*S)-3-(3-(difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)phenyl)propanoate was used instead of tert-butyl (*R)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoate in Step B. MS (ESI): mass calcd. for $C_{40}H_{50}F_2N_6O_7S$, 796.3; m/z found, 797.3 [M+H]$^+$. $^1$H NMR (400 MHz, DMSO-d$_6$) δ 8.39 (d, J=7.2 Hz, 1H), 7.86 (d, J=1.0 Hz, 1H), 7.70 (t, J=51.7 Hz, 1H), 7.28-7.20 (m, 3H), 7.14 (d, J=7.7 Hz, 1H), 4.78 (s, 1H), 4.48-4.30 (m, 4H), 3.85-3.70 (m, 2H), 3.55-3.24 (m, 4H), 2.68 (t, J=6.0 Hz, 2H), 2.63 (s, 3H), 2.49-2.43 (m, 4H), 2.19 (s, 3H), 2.15 (s, 3H), 1.57-1.33 (m, 10H), 1.31 (s, 3H), 1.26 (s, 3H).

Example 380: (*R)-2,2-Dimethyl-3-(4-methyl-3-((8'-methyl-1',1'-dioxido-7'-(((S)-1-piperidin-1-yl)propan-2-yl)amino)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

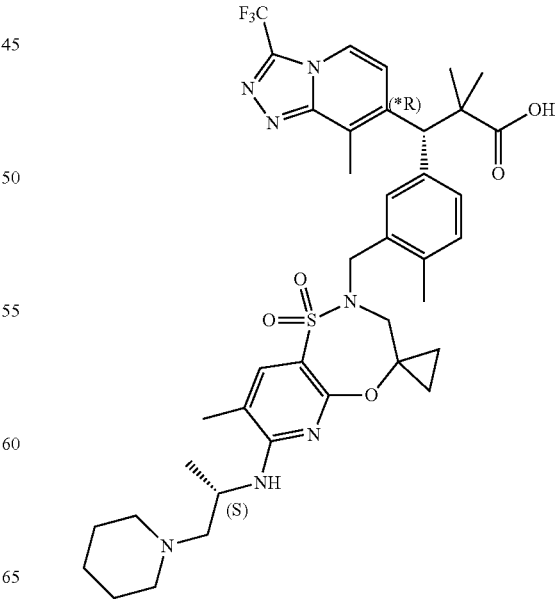

The title compound (125 mg, 55%) was prepared using analogous conditions as described in Example 114 where (S)-1-(piperidin-1-yl)propan-2-amine was used instead of 3-aminopropan-1-ol in Step A and methyl (*R)-3-(3((7'-chloro-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl) propanoate (Intermediate 143) instead of methyl 3-(3-((7'-chloro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl) propanoate (Intermediate 69). MS (ESI): mass calcd. for $C_{39}H_{48}F_3N_7O_5S$, 783.3; m/z found, 784.3 [M+H]$^+$. $^1$H NMR (400 MHz, DMSO-d$_6$) δ 8.39 (d, J=7.2 Hz, 1H), 7.55 (s, 1H), 7.28 (d, J=7.4 Hz, 1H), 7.20 (dd, J=7.8, 1.9 Hz, 1H), 7.13 (d, J=8.0 Hz, 1H), 7.04 (s, 1H), 6.40 (d, J=7.4 Hz, 1H), 4.76 (s, 1H), 4.22-3.98 (m, 3H), 3.50-3.15 (m, 2H), 2.61 (s, 3H), 2.46-2.29 (m, 5H), 2.28-2.22 (m, 4H), 2.06 (s, 3H), 1.51-1.43 (m, 4H), 1.42-1.35 (m, 2H), 1.30-1.12 (m, 9H), 0.95-0.80 (m, 2H), 0.48-0.42 (m, 1H), 0.37-0.30 (m, 1H).

Example 381: (*S)-3-(3-(((*S)-1',1'-Dioxido-4,5-dihydro-2H-spiro[furan-3,4'-pyrido[2,3-b][1,4,5] oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

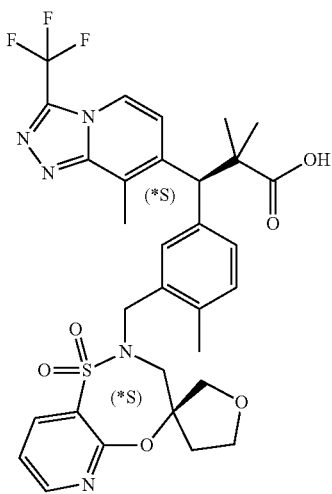 [SMILES: Cc1ccc([C@@H](c2ccn3c(C(F)(F)F)nnc3c2C)C(C)(C)C(=O)O)cc1CN1C[C@]2(CCOC2)Oc2ncccc2S1(=O)=O]

Step A: Methyl (*S)-3-(3-(((*S)-1',1'-dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate. A mixture containing methyl (*S)-3-(3-(chloromethyl)-4-methylphenyl)-2,2-dimethyl-3-(8-methyl-3-(trifluoromethyl)-[1,2,4]triazolo[4,3-a]pyridin-7-yl) propanoate (Intermediate 160, 100 mg, 0.220 mmol), (*S)-2',3',4,5-tetrahydro-2H-spiro[furan-3,4'-pyrido[2,3-b][1,4,5]oxathiazepine] 1',1'-dioxide (Intermediate 154, 63 mg, 0.25 mmol) potassium carbonate (153 mg, 1.11 mmol), and acetonitrile (2 mL) was stirred at 80° C. After 16 hours, the mixture was cooled to room temperature and the resulting suspension was filtered. The filtrate was concentrated under reduced pressure to afford the title compound as a colorless oil (180 mg). This material was used without further purification. MS (ESI): mass calcd. for $C_{32}H_{34}F_3N_5O_6S$, 673.2; m/z found, 674.1 [M+H]$^+$.

Step B: (*S)-3-(3-(((*S)-1',1'-Dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl) propanoic acid. Sodium hydroxide (42 mg, 1.1 mmol) was added to a stirring solution of methyl (*S)-3-(3-(((*S)-1',1'-dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate (140 mg, 0.208) in dioxane-water (1:1, 3 mL). The mixture was warmed to 65° C. After 6 hours, the reaction was cooled to room temperature. 1 M aqueous HCl solution was added until the pH was 5 and then the mixture was extracted with ethyl acetate. This resulted in numerous organic fractions which were combined, dried over anhydrous sodium sulfate, filtered, and then concentrated under reduced pressure. The residue was purified by preparative TLC (dichloromethane-methanol) and then by reverse phase HPLC (Agela Durashell C18, 150×25 mm×5 μm column, eluent: 38% to 68% (v/v) CH$_3$CN in H$_2$O with 0.225% formic acid) to provide the title compound (20 mg, 15%). MS (ESI): mass calcd. for $C_{31}H_{32}F_3N_5O_6S$, 659.2; m/z found, 660.3 [M+H]$^+$. $^1$H NMR (400 MHz, DMSO-d$_6$) δ 12.51 (br s, 1H), 8.55 (dd, J=2.0, 4.9 Hz, 1H), 8.41 (d, J=7.3 Hz, 1H), 8.20 (dd, J=1.8, 7.7 Hz, 1H), 7.48 (dd, J=4.9, 7.6 Hz, 1H), 7.27-7.21 (m, 2H), 7.20-7.18 (m, 1H), 7.14 (d, J=7.8 Hz, 1H), 4.79 (s, 1H), 4.36-4.20 (m, 2H), 3.97-3.89 (m, 1H), 3.83-3.75 (m, 1H), 3.72-3.67 (m, 1H), 3.59-3.49 (m, 2H), 3.38-3.37 (m, 1H), 2.64 (s, 3H), 2.20 (s, 3H), 1.90-1.82 (m, 1H), 1.77-1.68 (m, 1H), 1.30 (s, 3H), 1.24 (s, 3H).

Example 382: (*S)-3-(3-(((*R)-1',1'-Dioxido-4,5-dihydro-2H-spiro[furan-3,4'-pyrido[2,3-b][1,4,5] oxathiazepin]-2'(3'H)-yl)methyl)-4-methylphenyl)-2,2-dimethyl-3-(8-methyl-3-(trifluoromethyl)-[1,2,4] triazolo[4,3-a]pyridin-7-yl)propanoic Acid

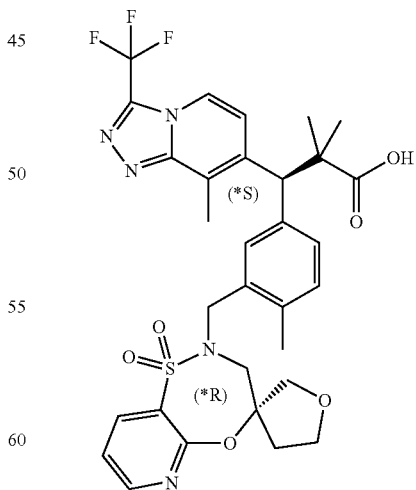

The title compound (67 mg) was prepared using analogous conditions as described in Example 381 using (*R)-2',3',4,5-tetrahydro-2H-spiro[furan-3,4'-pyrido[2,3-b][1,4,5] oxathiazepine] 1',1'-dioxide (Intermediate 155) instead of (*S)-2',3',4,5-tetrahydro-2H-spiro[furan-3,4'-pyrido[2,3-b][1,4,5]oxathiazepine] 1',1'-dioxide in Step A. MS (ESI): mass calcd. for $C_{31}H_{32}F_3N_5O_6S$, 659.2; m/z found, 660.2 [M+H]⁺. ¹H NMR (400 MHz, DMSO-d₆) δ 12.55 (br s, 1H), 8.55 (dd, J=1.9, 4.9 Hz, 1H), 8.42 (d, J=7.3 Hz, 1H), 8.20 (dd, J=2.0, 7.5 Hz, 1H), 7.48 (dd, J=4.8, 7.5 Hz, 1H), 7.28 (d, J=7.3 Hz, 1H), 7.24 (s, 1H), 7.21-7.17 (m, 1H), 7.15-7.11 (m, 1H), 4.79 (s, 1H), 4.37-4.22 (m, 2H), 4.01-3.94 (m, 1H), 3.85-3.79 (m, 1H), 3.76-3.61 (m, 3H), 3.44-3.41 (m, 1H), 2.64 (s, 3H), 2.19 (s, 3H), 1.91-1.78 (m, 2H), 1.31 (s, 3H), 1.25 (s, 3H).

Example 383: (*S)-2,2-Dimethyl-3-(4-methyl-3-(((*S)-8'-methyl-1',1'-dioxido-4,5-dihydro-2H-spiro[furan-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

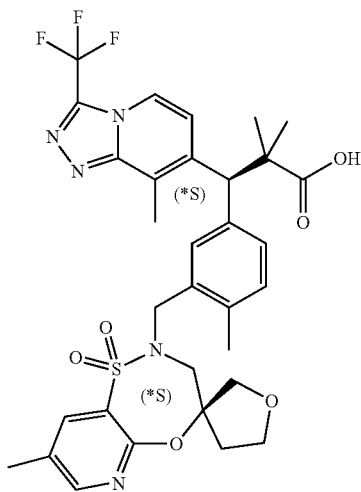 [SMILES: Cc1cnc2c(c1)S(=O)(=O)N(Cc1cc([C@@H](c3ccn4c(C(F)(F)F)nnc4c3C)C(C)(C)C(=O)O)ccc1C)C[C@]1(CCOC1)O2]

The title compound (57 mg) was prepared using analogous conditions as described in Example 381 using (*S)-8'-methyl-2',3',4,5-tetrahydro-2H-spiro[furan-3,4'-pyrido[2,3-b][1,4,5]oxathiazepine] 1',1'-dioxide (Intermediate 156) instead of (*S)-2',3',4,5-tetrahydro-2H-spiro[furan-3,4'-pyrido[2,3-b][1,4,5]oxathiazepine] 1',1'-dioxide in Step A. MS (ESI): mass calcd. for $C_{32}H_{34}F_3N_5O_6S$, 673.2; m/z found, 674.3 [M+H]⁺. ¹H NMR (400 MHz, DMSO-d₆) δ 12.52 (br s, 1H), 8.41 (d, J=7.1 Hz, 1H), 8.37-8.35 (m, 1H), 8.04-7.99 (m, 1H), 7.27-7.21 (m, 2H), 7.19-7.17 (m, 1H), 7.15 (d, J=8.0 Hz, 1H), 4.79 (s, 1H), 4.36-4.19 (m, 2H), 3.96-3.87 (m, 1H), 3.80-3.65 (m, 2H), 3.58-3.45 (m, 2H), 3.36-3.35 (m, 1H), 2.64 (s, 3H), 2.36 (s, 3H), 2.21 (s, 3H), 1.90-1.81 (m, 1H), 1.76-1.65 (m, 1H), 1.31 (s, 3H), 1.25 (s, 3H).

Example 384: (*S)-2,2-Dimethyl-3-(4-methyl-3-(((*R)-8'-methyl-1',1'-dioxido-4,5-dihydro-2H-spiro[furan-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

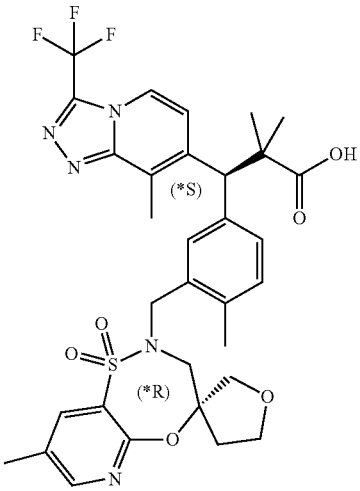 [SMILES: Cc1cnc2c(c1)S(=O)(=O)N(Cc1cc([C@@H](c3ccn4c(C(F)(F)F)nnc4c3C)C(C)(C)C(=O)O)ccc1C)C[C@@]1(CCOC1)O2]

The title compound (97 mg) was prepared using analogous conditions as described in Example 381 using (*R)-8'-methyl-2',3',4,5-tetrahydro-2H-spiro[furan-3,4'-pyrido[2,3-b][1,4,5]oxathiazepine] 1',1'-dioxide (Intermediate 157) instead of (*S)-2',3',4,5-tetrahydro-2H-spiro[furan-3,4'-pyrido[2,3-b][1,4,5]oxathiazepine] 1',1'-dioxide in Step A. MS (ESI): mass calcd. for $C_{32}H_{34}F_3N_5O_6S$, 673.2; m/z found, 674.2 [M+H]⁺. ¹H NMR (400 MHz, CDCl₃) δ 12.54 (br s, 1H), 8.42 (d, J=7.3 Hz, 1H), 8.39-8.35 (m, 1H), 8.04-8.00 (m, 1H), 7.28 (d, J=7.3 Hz, 1H), 7.24 (s, 1H), 7.21-7.17 (m, 1H), 7.15-7.11 (m, 1H), 4.79 (s, 1H), 4.35-4.22 (m, 2H), 4.01-3.93 (m, 1H), 3.83-3.57 (m, 4H), 3.42-3.39 (m, 1H), 2.64 (s, 3H), 2.37 (s, 3H), 2.20 (s, 3H), 1.92-1.77 (m, 2H), 1.31 (s, 3H), 1.25 (s, 3H).

Example 385: (*R)-3-(3-(((*S)-1',1'-Dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

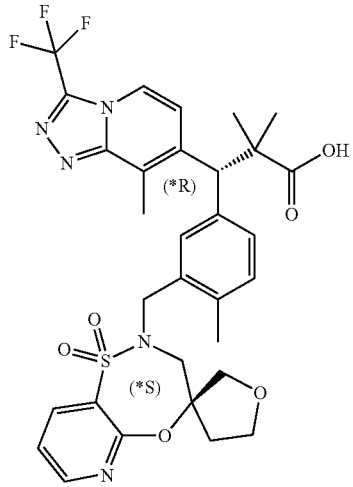 [SMILES: Cc1ccc([C@H](c2ccn3c(C(F)(F)F)nnc3c2C)C(C)(C)C(=O)O)cc1CN1C[C@]2(CCOC2)Oc2ncccc2S1(=O)=O]

The title compound (42 mg) was prepared using analogous conditions as described in Example 381 using methyl (*R)-3-(3-(chloromethyl)-4-methylphenyl)-2,2-dimethyl-3-(8-methyl-3-(trifluoromethyl)-[1,2,4]triazolo[4,3-a]pyridin-7-yl)propanoate (Intermediate 161 instead of methyl (*S)-3-(3-(chloromethyl)-4-methylphenyl)-2,2-dimethyl-3-(8-methyl-3-(trifluoromethyl)-[1,2,4]triazolo[4,3-a]pyridin-7-yl)propanoate in Step A. MS (ESI): mass calcd. for $C_{31}H_{32}F_3N_5O_6S$, 659.2; m/z found, 660.3 [M+H]$^+$. $^1$H NMR (400 MHz, DMSO-d$_6$) δ 12.57 (br s, 1H), 8.56-8.53 (m, 1H), 8.41 (d, J=7.2 Hz, 1H), 8.22-8.18 (m, 1H), 7.50-7.45 (m, 1H), 7.28-7.21 (m, 2H), 7.19 (s, 1H), 7.14 (d, J=7.6 Hz, 1H), 4.79 (s, 1H), 4.37-4.20 (m, 2H), 3.97-3.88 (m, 1H), 3.79 (d, J=15.6 Hz, 1H), 3.69 (d, J=10.0 Hz, 1H), 3.60-3.48 (m, 2H), 3.38 (s, 1H), 2.64 (s, 3H), 2.20 (s, 3H), 1.90-1.82 (m, 1H), 1.79-1.66 (m, 1H), 1.30 (s, 3H), 1.25 (s, 3H).

Example 386: (*R)-3-(3-(((*R)-1',1'-Dioxido-4,5-dihydro-2H-spiro[furan-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

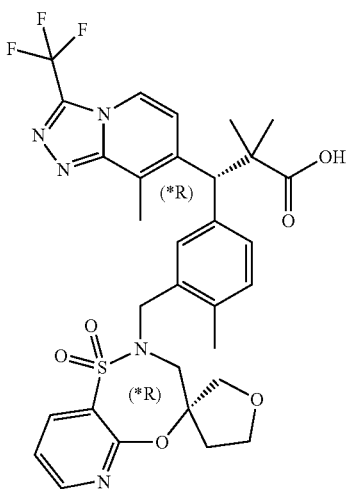 [SMILES: Cc1ccc([C@H](c2ccn3c(C(F)(F)F)nnc3c2C)C(C)(C)C(=O)O)cc1CN1C[C@@]2(CCOC2)Oc2ncccc2S1(=O)=O]

The title compound (41 mg) was prepared using analogous conditions as described in Example 381 using methyl (*R)-3-(3-(chloromethyl)-4-methylphenyl)-2,2-dimethyl-3-(8-methyl-3-(trifluoromethyl)-[1,2,4]triazolo[4,3-a]pyridin-7-yl)propanoate (Intermediate 161) instead of methyl (*S)-3-(3-(chloromethyl)-4-methylphenyl)-2,2-dimethyl-3-(8-methyl-3-(trifluoromethyl)-[1,2,4]triazolo[4,3-a]pyridin-7-yl)propanoate and (*R)-2',3',4,5-tetrahydro-2H-spiro[furan-3,4'-pyrido[2,3-b][1,4,5]oxathiazepine] 1',1'-dioxide (Intermediate 155) instead of (*S)-2',3',4,5-tetrahydro-2H-spiro[furan-3,4'-pyrido[2,3-b][1,4,5]oxathiazepine] 1',1'-dioxide in Step A. MS (ESI): mass calcd. for $C_{31}H_{32}F_3N_5O_6S$, 659.2; m/z found, 660.3 [M+H]$^+$. $^1$H NMR (400 MHz, DMSO-d$_6$) δ 12.57 (br s, 1H), 8.56-8.53 (m, 1H), 8.41 (d, J=7.2 Hz, 1H), 8.22-8.18 (m, 1H), 7.50-7.45 (m, 1H), 7.28-7.21 (m, 2H), 7.19 (s, 1H), 7.14 (d, J=7.6 Hz, 1H), 4.79 (s, 1H), 4.37-4.20 (m, 2H), 3.97-3.88 (m, 1H), 3.79 (d, J=15.6 Hz, 1H), 3.69 (d, J=10.0 Hz, 1H), 3.60-3.48 (m, 2H), 3.38 (s, 1H), 2.64 (s, 3H), 2.20 (s, 3H), 1.90-1.82 (m, 1H), 1.79-1.66 (m, 1H), 1.30 (s, 3H), 1.25 (s, 3H).

Example 387: (*R)-2,2-Dimethyl-3-(4-methyl-3-(((*S)-8'-methyl-1',1'-dioxido-4,5-dihydro-2H-spiro[furan-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

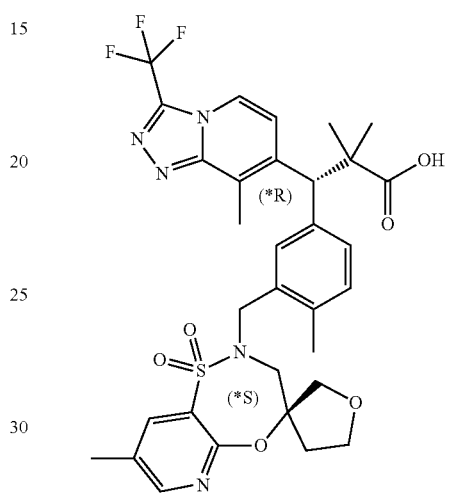

The title compound (76 mg) was prepared using analogous conditions as described in Example 381 using methyl (*R)-3-(3-(chloromethyl)-4-methylphenyl)-2,2-dimethyl-3-(8-methyl-3-(trifluoromethyl)-[1,2,4]triazolo[4,3-a]pyridin-7-yl)propanoate (Intermediate 161) instead of methyl (*S)-3-(3-(chloromethyl)-4-methylphenyl)-2,2-dimethyl-3-(8-methyl-3-(trifluoromethyl)-[1,2,4]triazolo[4,3-a]pyridin-7-yl)propanoate and (*S)-8'-methyl-2',3',4,5-tetrahydro-2H-spiro[furan-3,4'-pyrido[2,3-b][1,4,5]oxathiazepine] 1',1'-dioxide (Intermediate 156) instead of (*S)-2',3',4,5-tetrahydro-2H-spiro[furan-3,4'-pyrido[2,3-b][1,4,5]oxathiazepine]1',1'-dioxide in Step A. MS (ESI): mass calcd. for $C_{32}H_{34}F_3N_5O_6S$, 673.2; m/z found, 674.3 [M+H]$^+$. $^1$H NMR (400 MHz, DMSO-d$_6$) δ 12.53 (br s, 1H), 8.42 (d, J=7.2 Hz, 1H), 8.36 (d, J=2.0 Hz, 1H), 8.01 (d, J=2.0 Hz, 1H), 7.27 (d, J=7.2 Hz, 1H), 7.23 (s, 1H), 7.21-7.17 (m, 1H), 7.15-7.11 (m, 1H), 4.79 (s, 1H), 4.35-4.21 (m, 2H), 4.01-3.93 (m, 1H), 3.79 (d, J=15.4 Hz, 1H), 3.75-3.71 (m, 1H), 3.69 (d, J=10.4 Hz, 1H), 3.61 (br d, J=15.4 Hz, 1H), 3.41 (d, J=10.0 Hz, 1H), 2.64 (s, 3H), 2.36 (s, 3H), 2.19 (s, 3H), 1.92-1.76 (m, 2H), 1.31 (s, 3H), 1.25 (s, 3H).

Example 388: (*R)-2,2-Dimethyl-3-(4-methyl-3-(((*R)-8'-methyl-1',1'-dioxido-4,5-dihydro-2H-spiro[furan-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

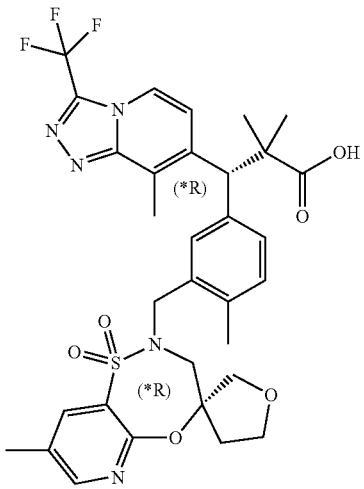 [SMILES: Cc1cnc2c(c1)S(=O)(=O)N(Cc1cc([C@H](c3ccn4c(C(F)(F)F)nnc4c3C)C(C)(C)C(=O)O)ccc1C)C[C@@]1(CCOC1)O2]

The title compound (18 mg) was prepared using analogous conditions as described in Example 381 using methyl (*R)-3-(3-(chloromethyl)-4-methylphenyl)-2,2-dimethyl-3-(8-methyl-3-(trifluoromethyl)-[1,2,4]triazolo[4,3-a]pyridin-7-yl)propanoate (Intermediate 161) instead of methyl (*S)-3-(3-(chloromethyl)-4-methylphenyl)-2,2-dimethyl-3-(8-methyl-3-(trifluoromethyl)-[1,2,4]triazolo[4,3-a]pyridin-7-yl)propanoate and (*R)-8'-methyl-2',3',4,5-tetrahydro-2H-spiro[furan-3,4'-pyrido[2,3-b][1,4,5]oxathiazepine] 1',1'-dioxide (Intermediate 157) instead of (*S)-2',3',4,5-tetrahydro-2H-spiro[furan-3,4'-pyrido[2,3-b][1,4,5]oxathiazepine]1',1'-dioxide in Step A. MS (ESI): mass calcd. for $C_{32}H_{34}F_3N_5O_6S$, 673.2; m/z found, 674.1 $[M+H]^+$. $^1H$ NMR (400 MHz, $CDCl_3$) δ 8.31 (d, J=1.6 Hz, 1H), 8.05 (d, J=2.0 Hz, 1H), 8.02 (d, J=7.2 Hz, 1H), 7.34 (d, J=7.2 Hz, 1H), 7.19-7.11 (m, 3H), 4.80 (s, 1H), 4.49-4.36 (m, 2H), 4.14-4.03 (m, 2H), 3.87 (d, J=10.4 Hz, 1H), 3.77-3.61 (m, 2H), 3.55 (d, J=10.4 Hz, 1H), 2.83 (s, 3H), 2.42 (s, 3H), 2.28 (s, 3H), 2.10-2.06 (m, 1H), 1.84-1.75 (m, 1H), 1.41 (s, 3H), 1.35 (s, 3H).

Example 389: (*S)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

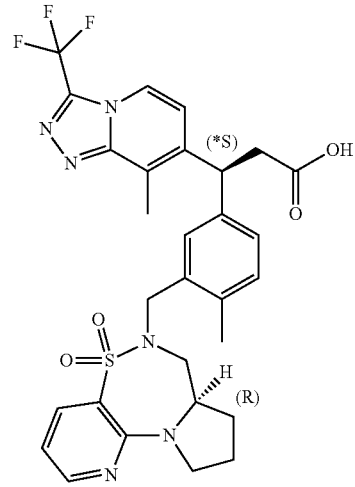

The mixture of 3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic acid isomers (Example 264, 86 mg) was separated by chiral SFC (stationary phase: Chiralpak AD-H 5 μm 250×30 mm, Mobile phase: 60% $CO_2$, 40% iPrOH) to afford two isomers. The first eluting isomer (41 mg) was designated (*S). MS (ESI): mass calcd. for $C_{29}H_{29}F_3N_6O_4S$, 614.2; m/z found, 615.5 $[M+H]^+$. $^1H$ NMR (400 MHz, DMSO-$d_6$) δ 8.37 (d, J=7.2 Hz, 1H), 8.35-8.31 (m, 1H), 8.02-7.97 (m, 1H), 7.26-7.20 (m, 1H), 7.20-7.16 (m, 1H), 7.16-7.08 (m, 2H), 6.93-6.88 (m, 1H), 4.86-4.79 (m, 1H), 4.40-4.23 (m, 2H), 4.16-4.10 (m, 1H), 3.62-3.45 (m, 2H), 3.15-3.07 (m, 1H), 2.97-2.86 (m, 3H), 2.74 (s, 3H), 2.21 (s, 3H), 2.00-1.87 (m, 1H), 1.71-1.51 (m, 2H), 1.46-1.35 (m, 1H).

Example 390: (*R)-3-(3-(((R)-5,5-Dioxido-7a,8,9,10-tetrahydropyrido[2,3-f]pyrrolo[2,1-d][1,2,5]thiadiazepin-6(7H)-yl)methyl)-4-methylphenyl)-3-(8-methyl-3-(trifluoromethyl)-[1,2,4]triazolo[4,3-a]pyridin-7-yl)propanoic Acid

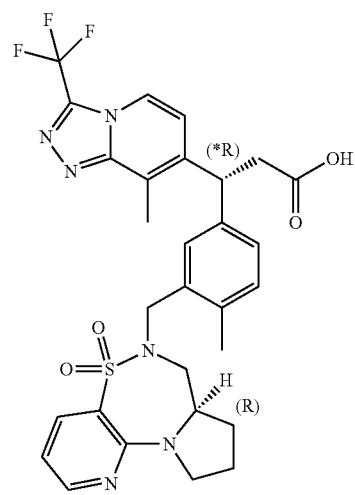

The second eluting isomer (38 mg) from the chiral separation described in Example 389 was designated (*R). MS (ESI): mass calcd. for $C_{29}H_{29}F_3N_6O_4S$, 614.2; m/z found, 615.5 [M+H]$^+$. $^1$H NMR (400 MHz, DMSO-d$_6$) δ 8.39 (d, J=7.3 Hz, 1H), 8.36-8.31 (m, 1H), 8.03-7.98 (m, 1H), 7.26-7.21 (m, 1H), 7.18-7.10 (m, 3H), 6.95-6.89 (m, 1H), 4.80 (t, J=7.7 Hz, 1H), 4.30-4.15 (m, 3H), 3.68-3.57 (m, 1H), 3.51-3.42 (m, 1H), 3.08-2.90 (m, 4H), 2.70 (s, 3H), 2.22 (s, 3H), 1.92-1.78 (m, 1H), 1.75-1.57 (m, 2H), 1.45-1.35 (m, 1H).

Example 391: (R/S)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic Acid

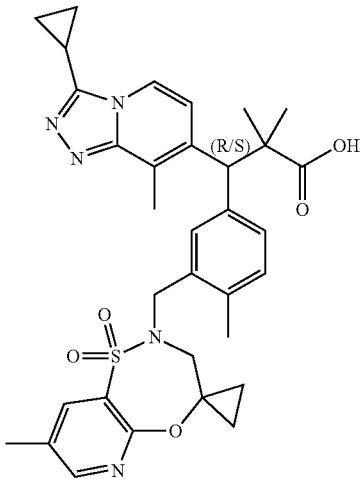 [SMILES: Cc1cnc2c(c1)S(=O)(=O)N(Cc1cc(C(c3ccn4c(C5CC5)nnc4c3C)C(C)(C)C(=O)O)ccc1C)CC1(CC1)O2]

Step A: (R/S)-Methyl 3-(3-cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoate. A solution of methyl 3-(3-cyclopropyl-8-methyl-[1,2,4]triazolo[4,3-a]pyridin-7-yl)-3-(3-(hydroxymethyl)-4-methylphenyl)-2,2-dimethylpropanoate (Intermediate 55, 201.7 mg, 0.495 mmol), 8'-methyl-2',3'-dihydrospiro[cyclopropane-1,4'-pyrido[2,3-b][1,4,5]oxathiazepine] 1',1'-dioxide (Intermediate 6, 131.8 mg, 0.549 mmol), and triphenylphosphine (210 mg, 0.801 mmol) in THF (7.5 mL) was stirred at room temperature for 1 minute. DBAD (183 mg, 0.795 mmol) was added and the solution was stirred at room temperature for 5 hours. The reaction was then concentrated and purified by flash column chromatography (10% EtOAc/hexanes –10% MeOH/DCM) to afford the title compound (212.9 mg, 68% yield). MS (ESI): mass calcd. for $C_{34}H_{39}N_5O_5S$, 629.3; m/z found, 630.3 [M+H]$^+$.

Step B: (R/S)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid. Aqueous lithium hydroxide (2M, 5 mL, 10 mmol) was added to a solution of (R/S)-methyl 3-(3-cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoate (300 mg, 0.105 mmol) in MeOH (10 mL). The reaction was stirred at 70° C. overnight, then allowed to cool to room temperature. The reaction was acidified to pH 3-4 using 1M HCl and then extracted with DCM. These extractions resulted in several organic solvent fractions which were combined, dried over anhydrous MgSO$_4$, filtered, and concentrated to dryness under reduced pressure. The material was purified by FCC (0-50% MeOH/EtOAc) and repurified by preparative acidic HPLC (XBridge C$_{18}$, acetonitrile-water containing 0.05% TFA). The pure fractions resulting from the preparative acidic HPLC were collected and lyophilized to dryness to provide the title compound (125.1 mg, 43% yield). MS (ESI): mass calcd. for $C_{33}H_{37}N_5O_5S$, 615.2; m/z found, 616.3 [M+H]$^+$.

Example 392: (*S)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic Acid

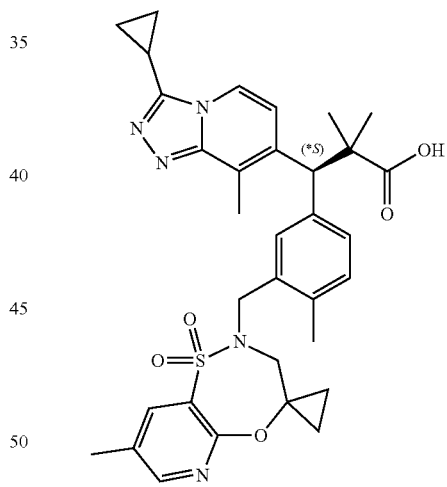

The mixture of (R/S)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid isomers (Example 391) was separated by chiral SFC (Chiralpak AS-H, mobile phase: 80% CO$_2$, 20% MeOH) to afford two enantiomers. The first eluting isomer (59 mg) was designated (*S): MS (ESI): mass calcd. for $C_{33}H_{37}N_5O_5S$, 615.2; m/z found, 616.3 [M+H]$^+$. $^1$H NMR (400 MHz, CDCl$_3$) δ 8.28-8.21 (m, 1H), 8.08 (s, 1H), 7.99-7.89 (m, 1H), 7.19-7.06 (m, 4H), 4.76 (s, 1H), 4.34-4.20 (m, 2H), 3.55-3.40 (m, 2H), 2.63 (s, 3H), 2.41 (s, 3H), 2.30 (s, 3H), 1.99 (s, 1H), 1.45-1.30 (m, 6H), 1.22-0.92 (m, 6H), 0.57-0.39 (m, 2H).

Example 393: (*R)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic Acid

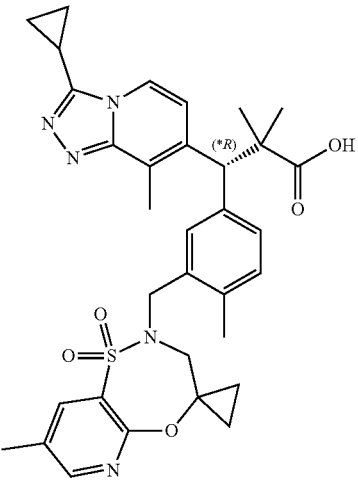 [SMILES: Cc1cnc2c(c1)S(=O)(=O)N(Cc1cc([C@H](c3ccn4c(C5CC5)nnc4c3C)C(C)(C)C(=O)O)ccc1C)CC1(CC1)O2]

The second eluting isomer (45 mg) from the chiral separation described in Example 392 was designated (*R): MS (ESI): mass calcd. for $C_{33}H_{37}N_5O_5S$, 615.2; m/z found, 616.3 [M+H]$^+$. $^1$H NMR (500 MHz, CDCl$_3$) δ 8.24 (s, 1H), 8.10-8.05 (m, 1H), 7.94-7.88 (m, 1H), 7.18-7.06 (m, 4H), 4.76 (s, 1H), 4.37-4.21 (m, 2H), 3.48 (s, 2H), 2.61 (s, 3H), 2.41 (s, 3H), 2.31 (s, 3H), 1.98 (s, 1H), 1.47-1.29 (m, 6H), 1.22-0.92 (m, 6H), 0.55-0.37 (m, 2H).

Example 394: (R/S)-3-(1-Cyclopropyl-4-methyl-1H-benzo[d][1,2,3]triazol-5-yl)-2,2-dimethyl-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic Acid

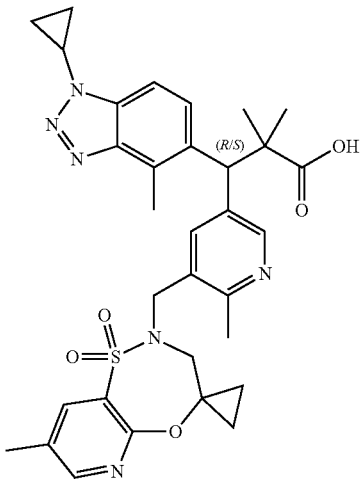 [SMILES: Cc1cnc2c(c1)S(=O)(=O)N(Cc1cc(C(c3ccc4c(nnn4C4CC4)c3C)C(C)(C)C(=O)O)cnc1C)CC1(CC1)O2]

The title compound (200 mg, 55% yield) was prepared using analogous conditions as described in Example 391 where methyl 3-(1-cyclopropyl-4-methyl-1H-benzo[d][1,2,3]triazol-5-yl)-3-(5-(hydroxymethyl)-6-methylpyridin-3-yl)-2,2-dimethylpropanoate (Intermediate 56) was used instead of methyl 3-(3-cyclopropyl-8-methyl-[1,2,4]triazolo[4,3-a]pyridin-7-yl)-3-(3-(hydroxymethyl)-4-methylphenyl)-2,2-dimethylpropanoate. MS (ESI): mass calcd. for $C_{32}H_{36}N_6O_5S$, 616.2; m/z found, 617.3 [M+H]$^+$.

Example 395: (*S)-3-(1-Cyclopropyl-4-methyl-1H-benzo[d][1,2,3]triazol-5-yl)-2,2-dimethyl-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic Acid

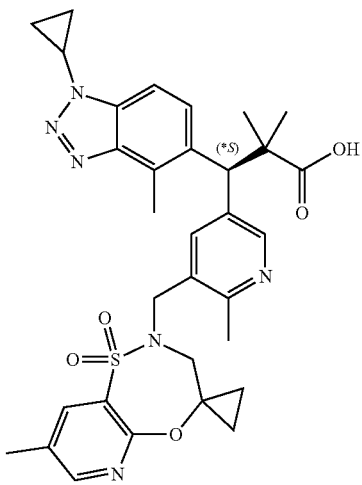 [SMILES: Cc1cnc2c(c1)S(=O)(=O)N(Cc1cc([C@@H](c3ccc4c(nnn4C4CC4)c3C)C(C)(C)C(=O)O)cnc1C)CC1(CC1)O2]

The mixture of (R S)-3-(1-Cyclopropyl-4-methyl-1H-benzo[d][1,2,3]triazol-5-yl)-2,2-dimethyl-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic acid isomers (Example 394) was separated by chiral SFC (Chiralpak AS-H, mobile phase: 80% CO$_2$, 20% MeOH) to afford two enantiomers. The first eluting isomer (75 mg) was designated (*S): MS (ESI): mass calcd. for $C_{32}H_{36}N_6O_5S$, 616.2; m/z found, 617.3 [M+H]$^+$. $^1$H NMR (500 MHz, CDCl$_3$) δ 8.59-8.54 (m, 1H), 8.25-8.21 (m, 1H), 8.05-8.01 (m, 1H), 7.61-7.56 (m, 1H), 7.52 (s, 1H), 7.51-7.47 (m, 1H), 5.05 (s, 1H), 4.36-4.13 (m, 2H), 3.79-3.71 (m, 1H), 3.57-3.29 (m, 2H), 2.86 (s, 3H), 2.54 (s, 3H), 2.39 (s, 3H), 1.46-1.07 (m, 12H), 0.49-0.32 (m, 2H).

Example 396: (*R)-3-(1-Cyclopropyl-4-methyl-1H-benzo[d][1,2,3]triazol-5-yl)-2,2-dimethyl-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic Acid

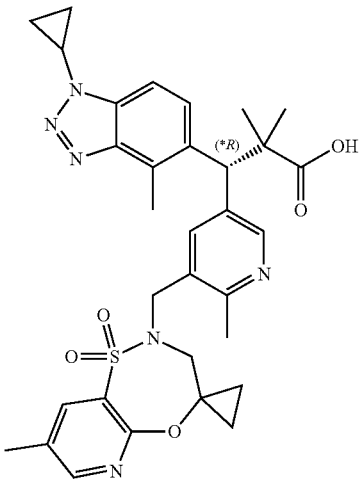 [SMILES: Cc1cnc2c(c1)S(=O)(=O)N(Cc1cc([C@H](c3ccc4c(nnn4C4CC4)c3C)C(C)(C)C(=O)O)cnc1C)CC1(CC1)O2]

The second eluting isomer (61 mg) from the chiral separation described in Example 395 was designated (*R): MS (ESI): mass calcd. for $C_{32}H_{36}N_6O_5S$, 616.2; m/z found, 617.3 [M+H]⁺. ¹H NMR (500 MHz, CDCl₃) δ 8.56-8.54 (m, 1H), 8.25-8.22 (m, 1H), 8.04-8.01 (m, 1H), 7.60-7.57 (m, 1H), 7.51-7.44 (m, 2H), 5.06 (s, 1H), 4.37-4.11 (m, 2H), 3.79-3.72 (m, 1H), 3.58-3.27 (m, 2H), 2.87 (s, 3H), 2.53 (s, 3H), 2.43-2.35 (m, 3H), 1.50-1.23 (m, 12H), 0.48-0.28 (m, 2H).

Example 397: (R/S)-3-(1-Cyclopropyl-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

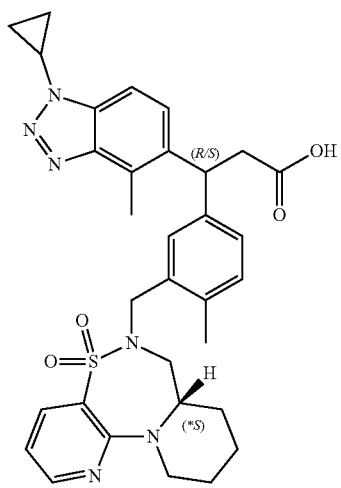 [SMILES: Cc1ccc(C(CC(=O)O)c2ccc3c(nnn3C3CC3)c2C)cc1CN1C[C@@H]2CCCCN2c2ncccc2S1(=O)=O]

The title compound (480 mg, 93% yield) was prepared using analogous conditions as described in Example 391 where ethyl 3-(1-cyclopropyl-4-methyl-1H-benzo[d][1,2,3]triazol-5-yl)-3-(3-(hydroxymethyl)-4-methylphenyl)propanoate (Intermediate 32 Step B) was used instead of methyl 3-(3-cyclopropyl-8-methyl-[1,2,4]triazolo[4,3-a]pyridin-7-yl)-3-(3-(hydroxymethyl)-4-methylphenyl)-2,2-dimethylpropanoate and (*S)-7,7a,8,9,10,11-hexahydro-6H-dipyrido[2,1-d:2',3'-f][1,2,5]thiadiazepine 5,5-dioxide (Intermediate 2) was used instead of 8'-methyl-2',3'-dihydrospiro[cyclopropane-1,4'-pyrido[2,3-b][1,4,5]oxathiazepine] 1',1'-dioxide. MS (ESI): mass calcd. for $C_{32}H_{36}N_6O_4S$, 616.2; m/z found, 601.3 [M+H]⁺.

Example 398: (*S)-3-(1-Cyclopropyl-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

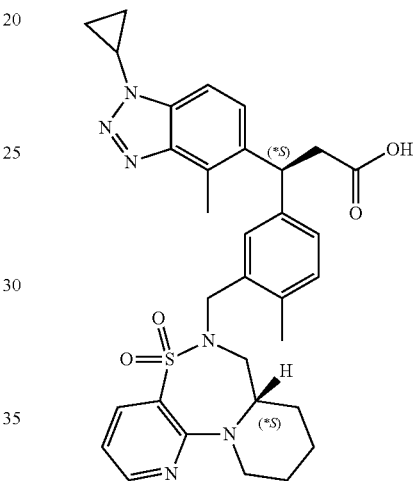

The mixture of (R/5)-3-(1-cyclopropyl-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid isomers (Example 397) was separated by chiral SFC (1ˢᵗ separation: Chiralpak IA, mobile phase: 50% CO₂, 50% EtOH, 2ⁿᵈ separation: Chiralpak OD-H, mobile phase: 70% CO₂, 30% MeOH) to afford two diastereomers. The first eluting isomer (188 mg) was designated (*S): MS (ESI): mass calcd. for $C_{32}H_{36}N_6O_4S$, 600.2; m/z found, 601.3 [M+H]⁺. ¹H NMR (500 MHz, CDCl₃) δ 8.30-8.25 (m, 1H), 8.03 (dd, J=7.8, 1.9 Hz, 1H), 7.46-7.42 (m, 1H), 7.37-7.32 (m, 1H), 7.11-7.04 (m, 3H), 6.81 (dd, J=7.8, 4.7 Hz, 1H), 4.98-4.91 (m, 1H), 4.50-4.45 (m, 1H), 4.42 (d, J=14.3 Hz, 1H), 4.22-4.09 (m, 2H), 3.75-3.68 (m, 1H), 3.21-3.01 (m, 5H), 2.80 (s, 3H), 2.24 (s, 3H), 1.64-1.55 (m, 1H), 1.51-1.21 (m, 9H).

Example 399: (*R)-3-(1-Cyclopropyl-4-methyl-1H-benzo[d][1,2,3]triazol-5-yl)-3-(3-(((*S)-5,5-dioxido-7,7a,8,9,10,11-hexahydro-6H-dipyrido[2,1-d:2',3'-][1,2,5]thiadiazepin-6-yl)methyl)-4-methylphenyl)propanoic Acid

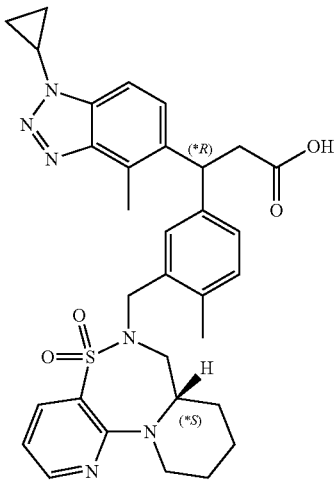 [SMILES: Cc1ccc(C(CC(=O)O)c2ccc3c(nnn3C3CC3)c2C)cc1CN1C[C@@H]2CCCCN2c2ncccc2S1(=O)=O]

The second eluting isomer (191 mg) from the chiral separation described in Example 398 was designated (*R): MS (ESI): mass calcd. for $C_{32}H_{36}N_6O_4S$, 600.2; m/z found, 601.3 $[M+H]^+$. $^1H$ NMR (500 MHz, $CDCl_3$) δ 8.29-8.25 (m, 1H), 8.04 (dd, J=7.8, 1.9 Hz, 1H), 7.43 (d, J=8.6 Hz, 1H), 7.32 (d, J=8.6 Hz, 1H), 7.13-7.09 (m, 2H), 7.07 (s, 1H), 6.81 (dd, J=7.8, 4.7 Hz, 1H), 4.99-4.91 (m, 1H), 4.50-4.40 (m, 2H), 4.22-4.14 (m, 1H), 4.14-4.08 (m, 1H), 3.74-3.68 (m, 1H), 3.18-3.00 (m, 5H), 2.83 (s, 3H), 2.25 (s, 3H), 1.69-1.46 (m, 3H), 1.40-1.14 (m, 7H).

Example 400: 3-(1-(cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid and its Trifluoroacetate Salt

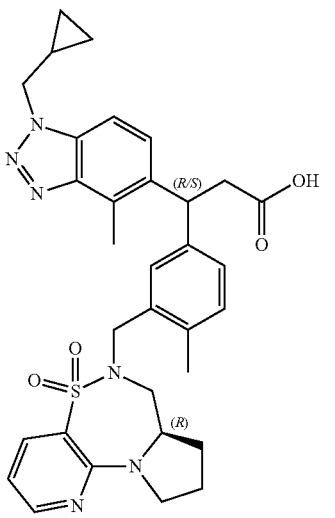

Step A: Ethyl 3-(3-(chloromethyl)-4-methylphenyl)-3-(1-(cyclopropylmethyl)-4-methyl-1H-benzo[d][1,2,3]triazol-5-yl)propanoate. A solution of ethyl 3-(1-(cyclopropylmethyl)-4-methyl-1H-benzo[d][1,2,3]triazol-5-yl)-3-(3-(hydroxymethyl)-4-methylphenyl)propanoate (Example 11, Step A, 218 mg, 0.535 mmol) in DCM (2.1 mL) was treated with thionyl chloride (0.16 mL, 2.2 mmol) in one portion under air at room temperature, and the vial was sealed and stirred for a few minutes. The reaction was then treated with DMF (30 µL, 0.39 mmol) and stirred at room temperature under air (sealed) for 55 minutes. The solution was then treated with 6 mL 1 M $NaHCO_3$ and 4 mL DCM and stirred for 10 minutes. The aqueous layer was extracted with DCM (4 mL), the organic layers combined, dried ($Na_2SO_4$), filtered, and concentrated to provide the title compound as a clear yellow oil (211 mg, 92%) which was used in the next step without further purification. MS (ESI): mass calcd. for $C_{24}H_{28}ClN_3O_2$, 425.2; m/z found, 426.1 $[M+H]^+$.

Step B: Ethyl 3-(1-(cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoate. A vial was charged with 3 Å molecular sieves (1 bead; freshly activated under vacuum with heat gun for 2 min), (R)-6,7,7a,8,9,10-hexahydropyrido[2,3-f]pyrrolo[2,1-d][1,2,5]thiadiazepine 5,5-dioxide (Intermediate 4, 63.9 mg, 0.267 mmol), and DMF (0.6 mL). The solution was stirred under positive argon pressure (capped) for 10 minutes, and was then treated with sodium hydride (60.8% dispersion in mineral oil) (13.8 mg, 0.35 mmol) in one portion at room temperature under air. The reaction was immediately sealed and stirred on an ice bath under positive argon pressure for 10 minutes, and was then treated with a solution of ethyl 3-(3-(chloromethyl)-4-methylphenyl)-3-(1-(cyclopropylmethyl)-4-methyl-1H-benzo[d][1,2,3]triazol-5-yl)propanoate in DMF (0.53 mL, 0.46 M, 0.244 mmol) dropwise over 2 minutes. The reaction mixture was stirred on an ice bath for 1.5 hours, then removed from the ice bath and stirred at room-temperature for 40 minutes. The reaction was quenched with 3 mL 1 M $NaH_2PO_4$ and extracted with EtOAc (2×3 mL). The combined organic layers were dried ($Na_2SO_4$), filtered, and concentrated to give the title compound as a clear yellow oil (146 mg) that was used in the next step without further purification. MS (ESI): mass calcd. for $C_{34}H_{40}N_6O_4S$, 628.3; m/z found, 629.4 $[M+H]^+$.

Step C: 3-(1-(Cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid trifluoroacetate. A vial containing ethyl 3-(1-(cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoate (146 mg, 0.233 mmol) was charged with THF (1 mL), MeOH (1 mL), and NaOH (3M in $H_2O$) (0.25 mL, 0.75 mmol), and the resulting mixture was stirred at room temperature under air (capped) for 30 minutes, then for 30 minutes at 60° C. The reaction was concentrated and the residue partitioned with 0.75 mL 1 M HCl, 1 mL 1 M $NaH_2PO_4$, and 5 mL EtOAc. The aqueous layer was extracted with EtOAc (1×2 mL), and the combined organic layers were dried ($Na_2SO_4$), filtered, and concentrated to provide 3-(1-(cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid. The compound was purified by $C_{18}$ reverse phase HPLC (10-90% $CH_3CN$—$H_2O$, 0.1% TFA) to provide 3-(1-

(cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid as its trifluoroacetate salt (145 mg). MS (ESI): mass calcd. for $C_{32}H_{36}N_6O_4S$, 600.3; m/z found, 601.3 $[M+H]^+$. $^1H$ NMR (400 MHz, $CD_3OD$) δ 8.25-8.17 (m, 2H), 7.62-7.56 (m, 1H), 7.52-7.40 (m, 1H), 7.22 (d, J=8.1 Hz, 1H), 7.17-7.13 (m, 1H), 7.09-7.04 (m, 1H), 6.97-6.92 (m, 1H), 5.00-4.94 (m, 1H), 4.61-4.52 (m, 3H), 4.45-4.37 (m, 1H), 4.18-4.11 (m, 1H), 3.60-3.42 (m, 2H), 3.20-3.01 (m, 3H), 2.94-2.76 (m, 4H), 2.25 (s, 3H), 1.98-1.86 (m, 1H), 1.78-1.67 (m, 1H), 1.63-1.50 (m, 1H), 1.48-1.31 (m, 2H), 0.65-0.47 (m, 4H).

Example 401: (*R)-3-(1-(Cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid

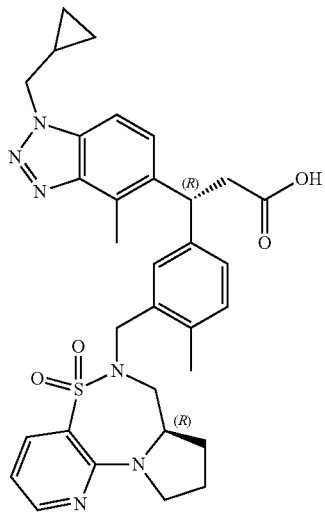

The isomeric mixture of 3-(1-(cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid as the trifluoroacetate salts (Example 400, 140 mg) were separated by chiral SFC (stationary phase: Chiralpak IA, 250×20 mm, mobile phase: 65% $CO_2$, 35% EtOH) to afford two diastereoisomers. The first eluting isomer (44 mg, 31%) was designated (*R): MS (ESI): mass calcd. for $C_{32}H_{36}N_6O_4S$, 600.3; m/z found, 601.3 $[M+H]^+$. $^1H$ NMR (400 MHz, $CDCl_3$) δ (dd, J=1.8, 4.8 Hz, 1H), 8.08 (dd, J=1.8, 7.8 Hz, 1H), 7.36-7.29 (m, 2H), 7.09 (d, J=1.5 Hz, 3H), 6.83-6.79 (m, 1H), 4.96 (t, J=7.8 Hz, 1H), 4.59-4.51 (m, 1H), 4.49-4.39 (m, 3H), 4.12 (d, J=13.6 Hz, 1H), 3.73 (q, J=6.7 Hz, 1H), 3.64-3.57 (m, 2H), 3.22-3.03 (m, 3H), 2.85 (s, 3H), 2.82-2.76 (m, 1H), 2.27 (s, 3H), 1.97-1.86 (m, 1H), 1.85-1.70 (m, 1H), 1.46-1.34 (m, 2H), 0.63 (td, J=5.6, 8.1 Hz, 2H), 0.50-0.45 (m, 2H).

Example 402: (*S)-3-(1-(Cyclopropylmethyl)-4-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

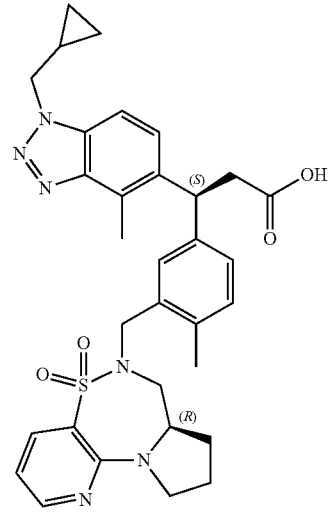

The second eluting isomer (41 mg, 29%) from the chiral separation described in Example 401 was designated (*S): MS (ESI): mass calcd. for $C_{32}H_{36}N_6O_4S$, 600.3; m/z found, 601.3 $[M+H]^+$. $^1H$ NMR (400 MHz, $CD_3OD$) δ (dd, J=1.8, 4.8 Hz, 1H), 8.04 (dd, J=2.0, 7.6 Hz, 1H), 7.61 (d, J=8.6 Hz, 1H), 7.50 (d, J=8.6 Hz, 1H), 7.23 (dd, J=1.5, 7.6 Hz, 1H), 7.17-7.12 (m, 1H), 7.02 (s, 1H), 6.88-6.84 (m, 1H), 4.99-4.93 (m, 1H), 4.55 (d, J=7.1 Hz, 2H), 4.43-4.29 (m, 2H), 4.14 (d, J=13.6 Hz, 1H), 3.56 (dt, J=5.8, 10.7 Hz, 1H), 3.40-3.33 (m, 1H), 3.16-3.01 (m, 3H), 2.93-2.80 (m, 1H), 2.76 (s, 3H), 2.26 (s, 3H), 1.94-1.82 (m, 1H), 1.72-1.57 (m, 2H), 1.51-1.33 (m, 2H), 0.67-0.47 (m, 4H)

Example 403: 3-(7-Cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid and its Trifluoroacetate Salt

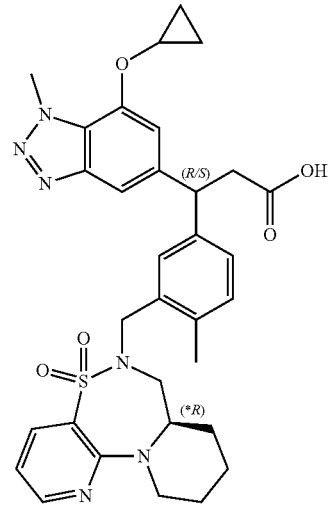

Step A: Methyl 3-(7-cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoate. A vial was charged with (*R)-7,7a,8,9,10,11-hexahydro-6H-dipyrido[2,1-d:2',3'-f][1,2,5]thiadiazepine 5,5-dioxide (Intermediate 4, 57.5 mg, 0.227 mmol) and DMF (0.52 mL). The solution was then treated with sodium hydride (60.8% dispersion in mineral oil) (11.1 mg, 0.281 mmol) in one portion at room temperature under air. The reaction was immediately sealed and stirred on an ice bath under positive argon pressure for 10 minutes, and was then treated with a solution of methyl 3-(3-(chloromethyl)-4-methylphenyl)-3-(7-cyclopropoxy-1-methyl-1H-benzo[d][1,2,3]triazol-5-yl)propanoate in DMF (0.448 mL, 0.46 M, 0.206 mmol) dropwise over 2 minutes. The reaction mixture was stirred on an ice bath for 20 minutes. The reaction was quenched with 3 mL 1 M NaH$_2$PO$_4$ and extracted with EtOAc (2×3 mL). The combined organic layers were dried (Na$_2$SO$_4$), filtered, and concentrated to give the title compound as a clear yellow oil (142 mg) that was used in the next step without further purification. MS (ESI): mass calcd. for C$_{33}$H$_{38}$N$_6$O$_5$S, 630.3; m/z found, 631.3 [M+H]$^+$.

Step B: 3-(7-Cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid trifluoroacetate. Methyl 3-(7-cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoate (130 mg, 0.206 mmol) was treated with LiOH (1M in H$_2$O) (0.62 mL, 0.62 mmol), MeOH (0.82 mL), and THF (0.82 mL). The resulting mixture was stirred under air (capped) at 60° C. for 40 min, and was then cooled to room temperature and brought to pH ~2 with 4.3 eq TFA (68 uL), brought to 3 mL volume with MeOH, and filtered through a 0.45 um syringe filter to afford 3-(7-cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid. This compound was purified by C$_{18}$ reverse phase HPLC (10-90% CH$_3$CN—H$_2$O, 0.1% TFA) to provide 3-(7-cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid as its trifluoroacetate salt (84 mg, 56%). MS (ESI): mass calcd. for C$_{32}$H$_{36}$N$_6$O$_5$S, 616.2; m/z found, 617.3 [M+H]$^+$. $^1$H NMR (400 MHz, CD$_3$OD) δ 8.25 (d, J=4.8 Hz, 1H), 8.15-8.11 (m, 1H), 7.43 (d, J=10.1 Hz, 1H), 7.29 (dt, J=1.5, 8.1 Hz, 1H), 7.21-7.12 (m, 3H), 6.96 (ddd, J=1.5, 4.9, 7.7 Hz, 1H), 4.66-4.59 (m, 1H), 4.45-4.38 (m, 2H), 4.37-4.35 (m, 3H), 4.31-4.19 (m, 1H), 4.01-3.92 (m, 2H), 3.28-3.21 (m, 1H), 3.15-2.98 (m, 4H), 2.22 (d, J=4.0 Hz, 3H), 1.68-1.49 (m, 2H), 1.44-1.28 (m, 3H), 1.28-1.11 (m, 1H), 0.92-0.73 (m, 4H).

Example 404: (*R)-3-(7-Cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

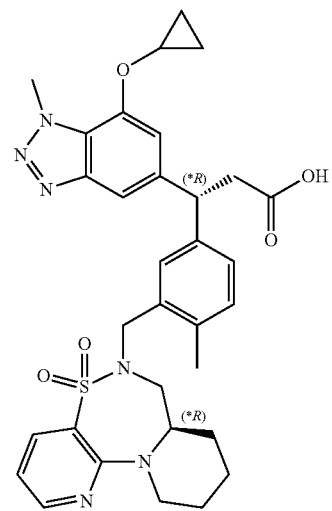

The mixture of 3-(7-cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid trifluoroacetate isomers (Example 403, 79 mg) were separated by chiral SFC (stationary phase: Chiralpak AD-H, 250×30 mm, mobile phase: 70% CO$_2$, 30% EtOH) to afford two diastereoisomers. The first eluting isomer (28 mg, 35%) was designated (*R): MS (ESI): mass calcd. for C$_{32}$H$_{36}$N$_6$O$_5$S, 616.2; m/z found, 617.6 [M+H]$^+$. $^1$H NMR (400 MHz, CD$_3$OD) δ 8.25 (dd, J=1.8, 4.8 Hz, 1H), 8.00 (dd, J=1.8, 7.8 Hz, 1H), 7.45 (s, 1H), 7.30 (dd, J=1.8, 7.8 Hz, 1H), 7.19-7.13 (m, 3H), 6.87 (dd, J=4.8, 7.8 Hz, 1H), 4.64 (t, J=8.1 Hz, 1H), 4.42-4.30 (m, 5H), 4.29-4.18 (m, 1H), 4.06 (td, J=4.7, 13.3 Hz, 1H), 3.96 (tt, J=3.0, 6.1 Hz, 1H), 3.25-3.05 (m, 4H), 2.96 (ddd, J=3.5, 10.2, 13.5 Hz, 1H), 2.22 (s, 3H), 1.65-1.50 (m, 2H), 1.40-1.28 (m, 3H), 1.20-1.07 (m, 1H), 0.93-0.72 (m, 4H).

Example 405: (*S)-3-(7-Cyclopropoxy-1-methyl-1H-benzo[d][1,2,3]triazol-5-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

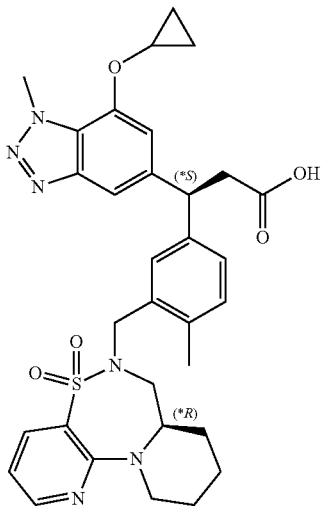

The second eluting isomer (31 mg, 39%) from the chiral separation described in Example 404 was designated (*S): MS (ESI): mass calcd. for $C_{32}H_{36}N_6O_5S$, 616.2; m/z found, 617.5 [M+H]$^+$. $^1$H NMR (400 MHz, CD$_3$OD) δ 8.25 (dd, J=1.8, 4.8 Hz, 1H), 8.01 (dd, J=1.8, 7.8 Hz, 1H), 7.42 (s, 1H), 7.27 (dd, J=1.8, 7.8 Hz, 1H), 7.22-7.13 (m, 3H), 6.87 (dd, J=4.5, 7.6 Hz, 1H), 4.63 (br t, J=7.8 Hz, 1H), 4.43-4.27 (m, 5H), 4.27-4.20 (m, 1H), 4.10-3.93 (m, 2H), 3.24 (dd, J=12.4, 13.4 Hz, 1H), 3.16-2.99 (m, 4H), 2.22 (s, 3H), 1.66-1.40 (m, 3H), 1.32-1.25 (m, 3H), 0.93-0.73 (m, 4H).

Example 406: 2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

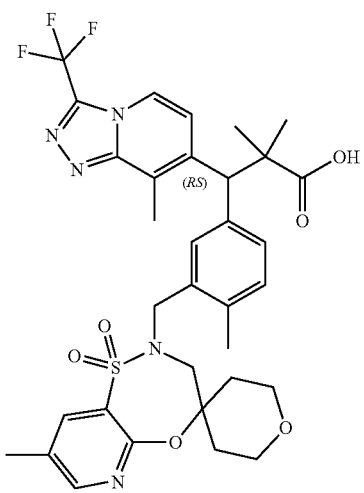 [SMILES: Cc1cnc2c(c1)S(=O)(=O)N(Cc1cc(C(c3ccn4c(C(F)(F)F)nnc4c3C)C(C)(C)C(=O)O)ccc1C)CC1(CCOCC1)O2]

Step A: (3-(((tert-Butyldimethylsilyl)oxy)methyl)-4-methylphenyl)(8-methyl-3-(trifluoromethyl)-[1,2,4]triazolo[4,3-a]pyridin-7-yl)methanol. A solution of nBuLi (2.95 mL, 2.5 M in Hexanes, 7.38 mmol) was added dropwise at −78° C. to ((5-bromo-2-methylbenzyl)oxy)(tert-butyl)dimethylsilane (Intermediate 19, 1.78 g, 5.67 mmol) in THF (80 mL). The resulting mixture was stirred for 1 hour. 8-Methyl-3-(trifluoromethyl)-[1,2,4]triazolo[4,3-a]pyridine-7-carbaldehyde (Intermediate 28, 1.30 g, 5.67 mmol) in THF (5 mL) was then added dropwise. The resulting solution was warmed to room temperature over a period of 4 hours and quenched with a saturated aqueous NH$_4$Cl solution (40 mL). The aqueous layer was extracted with EtOAc. These extractions resulted in several organic solvent fractions which were combined and concentrated to dryness under reduced pressure. The residue was purified by flash column chromatography (10% EtOAc/Hexanes) to provide the title compound (1.60 g, 60.6%). MS (ESI): mass calcd. for $C_{23}H_{30}F_3N_3O_2Si$, 465.21; m/z found, 466.2 [M+H]$^+$. $^1$H NMR (500 MHz, CDCl$_3$) δ 8.04 (d, J=7.2 Hz, 1H), 7.45 (d, J=7.2 Hz, 1H), 7.36-7.31 (m, 1H), 7.18 (dd, J=7.7, 2.0 Hz, 1H), 7.09 (d, J=7.8 Hz, 1H), 6.13 (d, J=3.2 Hz, 1H), 4.61 (s, 2H), 2.65-2.61 (m, 4H), 2.18 (s, 3H), 0.82 (s, 9H), 0.01 (d, J=8.5 Hz, 6H).

Step B: Methyl 3-(3-(((tert-Butyldimethylsilyl)oxy)methyl)-4-methylphenyl)-2,2-dimethyl-3-(8-methyl-3-(trifluoromethyl)-[1,2,4]triazolo[4,3-a]pyridin-7-yl)propanoate. 2,2,2-Trichloroacetonitrile (1.29 g, 8.94 mmol) and DBU (80.0 mg, 0.525 mmol) were added to (3-(((tert-butyldimethylsilyl)oxy)methyl)-4-methylphenyl)(8-methyl-3-(trifluoromethyl)-[1,2,4]triazolo[4,3-a]pyridin-7-yl)methanol (1.60 g, 3.44 mmol) in acetonitrile (5 mL) at room temperature, and the mixture was stirred for 45 minutes. ((1-Methoxy-2-methylprop-1-en-1-yl)oxy)trimethylsilane (1.38 g, 7.90 mmol) and bis(trifluoromethanesulfonyl)imide (96.6 mg, 0.344 mmol) were then added sequentially, and the mixture was stirred at room temperature for 16 hours. Another portion of ((1-methoxy-2-methylprop-1-en-1-yl)oxy)trimethyl silane (1.38 g, 7.90 mmol) and bis(trifluoromethanesulfonyl)imide (96.6 mg, 0.344 mmol) were then added sequentially, and the mixture was stirred at 50° C. for 16 hours. The reaction was quenched with aqueous saturated NaHCO$_3$ solution (20 mL) and extracted with EtOAc. These extractions resulted in several organic solvent fractions which were combined and concentrated to dryness under reduced pressure. The residue was purified by flash column chromatography (10% EtOAc/Hexanes) to provide the title compound (1.20 g, 63%). MS (ESI): mass calcd. for $C_{28}H_{38}F_3N_3O_3Si$, 549.26; m/z found, 550.3 [M+H]$^+$. $^1$H NMR (500 MHz, CDCl$_3$) δ 7.96 (d, J=7.3 Hz, 1H), 7.27-7.14 (m, 2H), 7.01 (d, J=1.3 Hz, 2H), 4.79 (s, 1H), 4.60 (s, 2H), 3.55 (s, 3H), 2.73 (s, 3H), 2.16 (s, 3H), 1.39 (s, 3H), 1.32 (s, 3H), 0.83 (s, 9H), 0.00 (d, J=3.6 Hz, 6H).

Step C: Methyl 3-(3-(chloromethyl)-4-methylphenyl)-2,2-dimethyl-3-(8-methyl-3-(trifluoromethyl)-[1,2,4]triazolo[4,3-a]pyridin-7-yl)propanoate. Methyl 3-(3-(((tert-butyldimethylsilyl)oxy)methyl)-4-methylphenyl)-2,2-dimethyl-3-(8-methyl-3-(trifluoromethyl)-[1,2,4]triazolo[4,3-a]pyridin-7-yl)propanoate (550 mg, 1.00 mmol) was dissolved in DCM (10 mL), and SOCl$_2$ (0.31 mL, 4.33 mmol) was added. The mixture was stirred at room temperature for 2 hours. The mixture was concentrated and purified with flash column chromatography (10% EtOAc/Hexanes) to provide the title compound (400 mg, 88%). MS (ESI): mass calcd. for $C_{22}H_{23}ClF_3N_3O_2$, 453.14; m/z found, 454.3 [M+H]$^+$. $^1$H NMR (500 MHz, CDCl$_3$) δ 7.95 (d, J=7.3 Hz, 1H), 7.20-

7.02 (m, 4H), 4.79 (s, 1H), 4.62-4.47 (m, 2H), 3.55 (s, 3H), 2.79 (s, 3H), 2.39 (s, 3H), 1.43 (s, 3H), 1.35 (s, 3H).

Step D: 2,2-Dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid. DMF (0.5 mL) was added to a stirring mixture of 8'-methyl-2,2',3,3',5,6-Hexahydrospiro[pyran-4,4'-pyrido[2,3-b][1,4,5]oxathiazepine] 1',1'-dioxide (Intermediate 37, 200 mg, 0.703 mmol) and KOtBu (118 mg, 1.05 mmol). After 10 minutes, a solution of methyl 3-(3-(chloromethyl)-4-methylphenyl)-3-(1-ethyl-4-methyl-1H-benzo[d][1,2,3]triazol-5-yl)-2,2-dimethylpropanoate (319 mg, 0.703 mmol) in DMF (0.5 mL) was added and the mixture was stirred at room temperature for 1 hour. Water (20 mL) was added and the aqueous layer was extracted with EtOAc (15 mL×3). These extractions resulted in several organic solvent fractions which were combined and concentrated under reduced pressure. LiOH (3M, 1 mL) was added to the residue in THF (1 mL) and MeOH (1 mL), The mixture was heated at 50° C. for 24 hours. Water (5 mL) was added, and the pH of the mixture was adjusted to ~3-4 by adding 1 M aqueous HCl solution. The aqueous layer was extracted with EtOAc (15 mL×3). These extractions resulted in several organic solvent fractions which were combined and concentrated. The residue was purified by flash column chromatography (10% methanol/$CH_2Cl_2$) to provide the title compound (150 mg, 31%). MS (ESI): mass calcd. for $C_{33}H_{36}F_3N_5O_6S$, 687.23; m/z found, 688.3 $[M+H]^+$. $^1$H NMR (600 MHz, $CD_3OD$) δ 8.17-8.20 (m, 2H), 7.93 (d, J=2.3 Hz, 1H), 7.40 (d, J=7.3 Hz, 1H), 7.24 (d, J=7.9 Hz, 1H), 7.06 (d, J=7.4 Hz, 1H), 6.96 (s, 1H), 4.83 (s, 1H), 4.50-4.22 (m, 2H), 3.77-3.64 (m, 2H), 3.33-3.24 (m, 2H), 3.20-3.02 (m, 2H), 2.55 (s, 3H), 2.28 (s, 3H), 2.15 (s, 3H), 1.44-1.33 (m, 2H), 1.26 (s, 3H), 1.16 (s, 3H), 1.12-1.02 (m, 2H).

Example 407: (*S)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

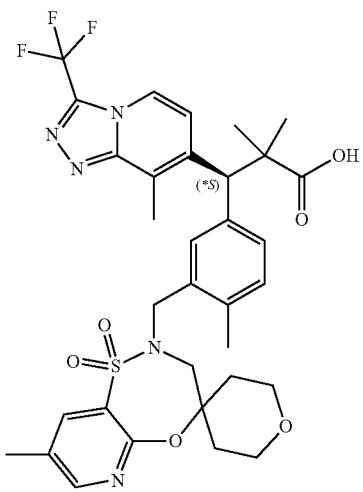 [SMILES: Cc1cnc2c(c1)S(=O)(=O)N(Cc1cc([C@@H](c3ccn4c(C(F)(F)F)nnc4c3C)C(C)(C)C(=O)O)ccc1C)CC1(CCOCC1)O2]

The mixture of isomers of 2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid (Example 406, 150 mg) were separated by chiral SFC (stationary phase: OZ-H 2×25 cm, mobile phase: 60% $CO_2$, 40% MeOH) to afford two enantiomers. The first eluting enantiomer (68 mg) was designated 9*S): MS (ESI): mass calcd. for $C_{33}H_{36}F_3N_5O_6S$, 687.23; m/z found, 688.3 $[M+H]^+$.

Example 408: (*R)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

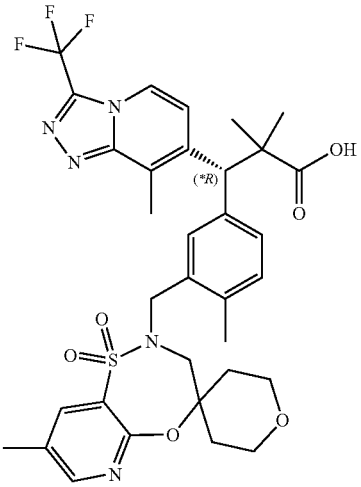 [SMILES: Cc1cnc2c(c1)S(=O)(=O)N(Cc1cc([C@H](c3ccn4c(C(F)(F)F)nnc4c3C)C(C)(C)C(=O)O)ccc1C)CC1(CCOCC1)O2]

The second eluting enantiomer (53 mg) from the chiral separation described in Example 407 was designated (*R): MS (ESI): mass calcd. for $C_{33}H_{36}F_3N_5O_6S$, 687.23; m/z found, 688.3 $[M+H]^+$.

Example 409: (*S)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

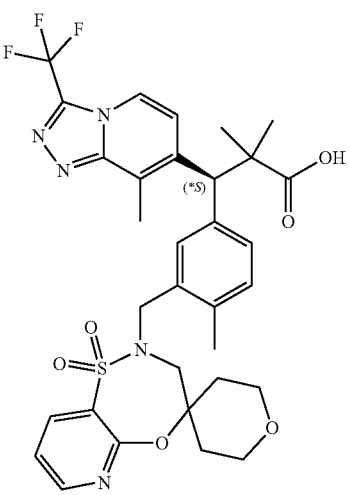 [SMILES: Cc1ccc([C@@H](c2ccn3c(C(F)(F)F)nnc3c2C)C(C)(C)C(=O)O)cc1CN1CC2(CCOCC2)Oc2ncccc2S1(=O)=O]

3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid (111 mg, 23.4% yield) was prepared using analogous conditions as described in Example 406 where 2,2',3,3',5,6-hexahydrospiro[pyran-4,4'-pyrido[2,3-b][1,4,5]oxathiazepine] 1',1'-dioxide (Intermediate 36) was used instead of 8'-methyl-2,2',3,3',5,6-Hexahydrospiro[pyran-4,4'-pyrido[2,3-b][1,4,5]oxathiazepine] 1',1'-dioxide in Step D. MS (ESI): mass calcd. for $C_{33}H_{34}F_3N_5O_6S$, 673.22; m/z found, 674.3 [M+H]$^+$. The mixture of isomers of 3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid (106 mg) was separated by chiral SFC (stationary phase: IC 2×25 cm, mobile phase: 60% $CO_2$, 40% EtOH) to afford two enantiomers. The first eluting enantiomer (44 mg) was designated (*S): MS (ESI): mass calcd. for $C_{33}H_{34}F_3N_5O_6S$, 673.22; m/z found, 674.3 [M+H]$^+$. $^1$H NMR (500 MHz, CDCl$_3$) δ 8.49 (dd, J=4.9, 1.9 Hz, 1H), 8.20 (dd, J=7.6, 1.9 Hz, 1H), 8.01 (d, J=7.1 Hz, 1H), 7.33-7.20 (m, 3H), 7.17-7.01 (m, 2H), 4.87 (s, 1H), 4.59-4.37 (m, 2H), 4.09-3.93 (m, 2H), 3.74-3.31 (m, 4H), 2.77 (s, 3H), 2.23 (s, 3H), 1.66-1.45 (m, 4H), 1.40-1.10 (m, 6H).

Example 410: (*R)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

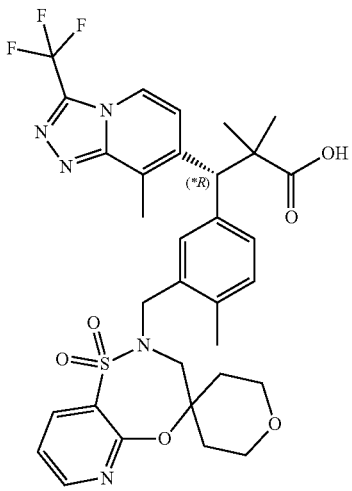 [SMILES: Cc1ccc([C@H](c2ccn3c(C(F)(F)F)nnc3c2C)C(C)(C)C(=O)O)cc1CN1CC2(CCOCC2)Oc2ncccc2S1(=O)=O]

The second eluting enantiomer (42 mg) from the chiral separation described in Example 409 was designated (*R): mass calcd. for $C_{33}H_{34}F_3N_5O_6S$, 673.22; m/z found, 674.3 [M+H]$^+$. $^1$H NMR (500 MHz, CDCl$_3$) D 8.48 (dd, J=5.0, 1.9 Hz, 1H), 8.18 (dd, J=7.5, 1.9 Hz, 1H), 7.98 (d, J=6.8 Hz, 1H), 7.37-7.15 (m, 3H), 7.04 (br s, 2H), 4.95-4.78 (m, 1H), 4.62-4.34 (m, 2H), 4.05-3.88 (m, 2H), 3.69-3.40 (m, 4H), 2.75 (s, 3H), 2.21 (s, 3H)

Example 414: (*S)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic Acid

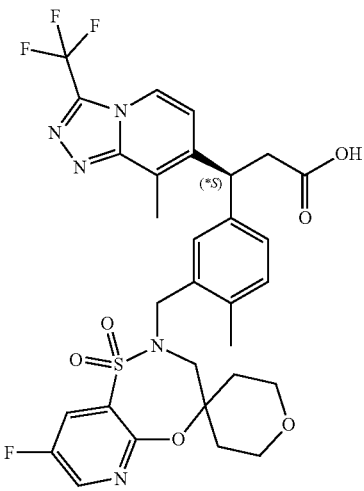 [SMILES: Cc1ccc([C@H](CC(=O)O)c2ccn3c(C(F)(F)F)nnc3c2C)cc1CN1CC2(CCOCC2)Oc2ncc(F)cc2S1(=O)=O]

Thionyl chloride (200 mg, 1.69 mmol) was added to ethyl (*S)-3-(3-(hydroxymethyl)-4-methylphenyl)-3-(8-methyl-3-(trifluoromethyl)-[1,2,4]triazolo[4,3-a]pyridin-7-yl)propanoate (Intermediate 26, 146 mg, 0.347 mmol) in CH$_2$Cl$_2$ (4 mL). The mixture was stirred at room temperature for 0.5 h. The mixture was concentrated under reduced pressure. iPr$_2$NEt (0.5 mL) was added to a mixture of 8'-fluoro-2,2',3,3',5,6-hexahydrospiro[pyran-4,4'-pyrido[2,3-b][1,4,5]oxathiazepine] 1',1'-dioxide (Intermediate 166, 100 mg, 0.347 mmol), ethyl (*S)-3-(3-(chloromethyl)-4-methylphenyl)-3-(8-methyl-3-(trifluoromethyl)-[1,2,4]triazolo[4,3-a]pyridin-7-yl)propanoate (152 mg, 0.347 mmol) in CH$_3$CN. The mixture was stirred at 150° C. for 16 hours. The mixture was concentrated under reduced pressure. NaOH (1M, 2 mL) was added to the residue in THF (2 mL). The mixture was stirred at RT for 24 hours. Water (5 mL) was added, and the pH of the mixture was adjusted to ~3-4 by adding 1 M aqueous HCl solution. The aqueous layer was extracted with EtOAc (15 mL×3). These extractions resulted in several organic solvent fractions which were combined and concentrated. The residue was purified by flash column chromatography (10% methanol/CH$_2$Cl$_2$) to provide the title compound (35 mg, 15%). MS (ESI): mass calcd. for $C_{30}H_{29}F_4N_5O_6S$, 663.18; m/z found, 664.2 [M+H]$^+$. $^1$H NMR (500 MHz, CD$_3$OD) δ 8.26 (d, J=3.1 Hz, 1H), 8.17 (d, J=7.1 Hz, 1H), 7.90 (dd, J=6.7, 3.1 Hz, 1H), 7.27-7.18 (m, 1H), 7.13-7.06 (m, 2H), 7.00 (d, J=2.0 Hz, 1H), 4.98-4.85 (m, 1H), 4.52-4.30 (m, 2H), 3.77-3.57 (m, 2H), 3.36-3.26 (m, 2H), 3.21-3.10 (m, 2H), 3.00-2.77 (m, 2H), 2.66 (s, 3H), 2.13 (s, 3H), 1.49-1.34 (m, 2H), 1.23-1.01 (m, 2H).

Example 415: (*S)-3-(3-((8-fluoro-1,1-dioxido-2',3', 5',6'-tetrahydrospiro[benzo[b][1,4,5]oxathiazepine-4, 4'-pyran]-2(3H)-yl)methyl)-4-methylphenyl)-3-(8-methyl-3-(trifluoromethyl)-[1,2,4]triazolo[4,3-a]pyridin-7-yl)propanoic Acid

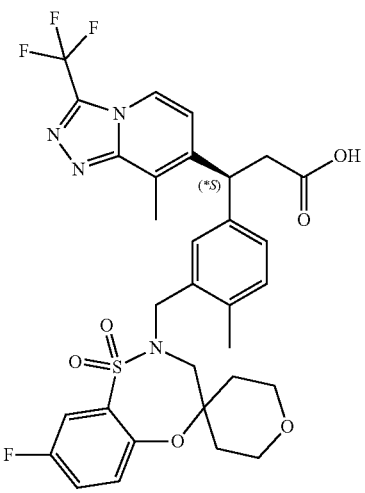 [SMILES: Cc1ccc([C@H](CC(=O)O)c2ccn3c(C(F)(F)F)nnc3c2C)cc1CN1CC2(CCOCC2)Oc2ccc(F)cc2S1(=O)=O]

Step A: Ethyl (*S)-3-(3-((8-fluoro-1,1-dioxido-2',3',6'-tetrahydrospiro[benzo[b][1,4,5]oxathiazepine-4,4'-pyran]-2(3H)-yl)methyl)-4-methylphenyl)-3-(8-methyl-3-(trifluoromethyl)-[1,2,4]triazolo[4,3-a]pyridin-7-yl)propanoate. Thionyl chloride (200 mg, 1.69 mmol) was added to ethyl (*S)-3-(3-(hydroxymethyl)-4-methylphenyl)-3-(8-methyl-3-(trifluoromethyl)-[1,2,4]triazolo[4,3-a]pyridin-7-yl)propanoate (Intermediate 26, 519 mg, 1.23 mmol) in $CH_2Cl_2$ (4 mL). The mixture was stirred at room temperature for 0.5 h. The mixture was concentrated under reduced pressure. $iPr_2NEt$ (0.5 mL) was added to a mixture of 8-fluoro-2,2', 3,3',5',6'-hexahydrospiro[benzo[b][1,4,5]oxathiazepine-4, 4'-pyran] 1,1-dioxide (Intermediate 164, 352 mg, 1.23 mmol) and ethyl (*S)-3-(3-(chloromethyl)-4-methylphenyl)-3-(8-methyl-3-(trifluoromethyl)-[1,2,4]triazolo[4,3-a]pyridin-7-yl)propanoate (540 mg, 1.23 mmol) in $CH_3CN$ (3 mL). The mixture was stirred at 150° C. for 16 hours. The mixture was concentrated under reduced pressure providing the title compound (650 mg, 94.1%). MS (ESI): mass calcd. for $C_{33}H_{34}F_4N_4O_6S$, 690.21; m/z found, 690.8 [M+H]$^+$.

Step B: (**S)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)-3-(8-methyl-3-(trifluoromethyl)-[1,2,4]triazolo[4,3-a]pyridin-7-yl)propanoic acid. NaOH (1M, 2 mL) was added to ethyl (*S)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)-3-(8-methyl-3-(trifluoromethyl)-[1,2,4]triazolo[4,3-a]pyridin-7-yl)propanoate (100 mg) in THF (2 mL). The mixture was stirred at RT for 24 hours. Water (5 mL) was added, and the pH of the mixture was adjusted to ~3-4 by adding 1 M aqueous HCl solution. The aqueous layer was extracted with EtOAc (15 mL×3). These extractions resulted in several organic solvent fractions which were combined and concentrated. The residue was purified by flash column chromatography (10% methanol/$CH_2Cl_2$) to provide the title compound (63 mg, 66%). MS (ESI): mass calcd. for $C_{31}H_{30}F_4N_4O_6S$, 662.18; m/z found, 662.8 [M+H]$^+$. $^1$H NMR (500 MHz, $CD_3OD$) δ 8.18 (d, J=7.2 Hz, 1H), 7.43-7.32 (m, 1H), 7.29-7.14 (m, 3H), 7.12-7.06 (m, 2H), 7.00 (d, J=2.2 Hz, 1H), 4.97-4.86 (m, 1H), 4.51-4.25 (m, 2H), 3.55-3.37 (m, 2H), 3.23-3.04 (m, 4H), 2.93-2.78 (m, 2H), 2.67 (s, 3H), 2.13 (s, 3H), 1.45-1.34 (m, 2H), 1.17-1.02 (m, 2H).

Example 416: (3S*)-3-(3-((8-fluoro-1,1-dioxido-2', 3',5',6'-tetrahydrospiro[benzo[b][1,4,5]oxathiazepine-4,4'-pyran]-2(3H)-yl)methyl)-4-methylphenyl)-2-methyl-3-(8-methyl-3-(trifluoromethyl)-[1,2,4]triazolo[4,3-a]pyridin-7-yl)propanoic Acid

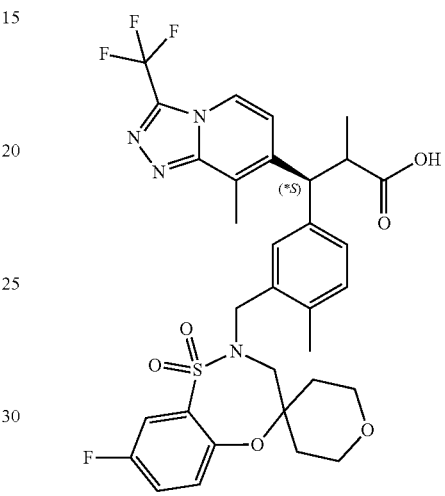

LDA (0.796 mL, 1.0 M in THF, 0.796 mmol) was added dropwise at −78° C. to ethyl (*S)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)-3-(8-methyl-3-(trifluoromethyl)-[1,2,4]triazolo[4,3-a]pyridin-7-yl)propanoate (Example 415, Step A; 250 mg, 0.362 mmol) in THF (2 mL). The resulting mixture was stirred for 0.5 hour. Methyl iodide (0.0563 mL, 0.905 mmol) in THF (1 mL) was added. The resulting solution was warmed to room temperature over a period of 2 hours. $NH_4Cl$ saturated solution (5 mL) was added. The aqueous layer was extracted with $CH_2Cl_2$ (15 mL×3). These extractions resulted in several organic solvent fractions which were combined and concentrated to dryness under reduced pressure. NaOH (1M, 2 mL) was added to the residue in THF (2 mL). The mixture was stirred at RT for 24 hours. Water (5 mL) was added, and the pH of the mixture was adjusted to ~3-4 by adding 1 M aqueous HCl solution. The aqueous layer was extracted with EtOAc (15 mL×3). These extractions resulted in several organic solvent fractions which were combined and concentrated. The residue was purified by flash column chromatography (10% ethanol/$CH_2Cl_2$) to provide the title compound (51 mg, 21% yield). MS (ESI): mass calcd. for $C_{32}H_{32}F_4N_4O_6S$, 676.20; m/z found, 677.3 [M+H]$^+$. $^1$H NMR (500 MHz, $CD_3OD$) δ 8.18 (d, J=7.2 Hz, 1H), 7.47-7.36 (m, 2H), 7.29-7.14 (m, 4H), 7.07 (d, J=7.7 Hz, 1H), 4.55-4.31 (m, 3H), 3.51-3.27 (m, 3H), 3.17-2.99 (m, 4H), 2.65 (s, 3H), 2.10 (s, 3H), 1.44-1.28 (m, 2H), 1.10-0.92 (m, 5H).

Example 417: 3-(1-Ethyl-4-methyl-1H-benzo[d][1,2,3]triazol-5-yl)-3-(6-((8-fluoro-1,1-dioxido-2',3',5',6'-tetrahydrospiro[benzo[b][1,4,5]oxathiazepine-4,4'-pyran]-2(3H)-yl)methyl)-5-methylpyridin-2-yl)propanoic acid

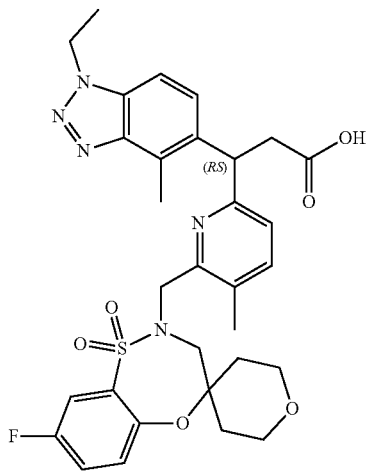 [SMILES: CCn1nnc2c(C)c(C(CC(=O)O)c3ccc(C)c(CN4CC5(CCOCC5)Oc5ccc(F)cc5S4(=O)=O)n3)ccc21]

Thionyl chloride (200 mg, 1.69 mmol) was added to ethyl 3-(1-ethyl-4-methyl-1H-benzo[d][1,2,3]triazol-5-yl)-3-(6-(hydroxymethyl)-5-methylpyridin-2-yl)propanoate (Intermediate 115, 382 mg, 1.50 mmol) in CH$_2$Cl$_2$ (4 mL). The mixture was stirred at room temperature for 0.5 h. The mixture was concentrated under reduced pressure. iPr$_2$NEt (0.5 mL) was added to a mixture of the residue and 8-fluoro-2,2',3,3',5',6'-hexahydrospiro[benzo[b][1,4,5]oxathiazepine-4,4'-pyran] 1,1-dioxide (Intermediate 164, 431 mg, 1.50 mmol) in CH$_3$CN (3 mL). The mixture was stirred at 150° C. for 16 hours. The mixture was concentrated under reduced pressure. NaOH (1M, 2 mL) was added to the residue in THF (2 mL). The mixture was stirred at room temperature for 24 hours. Water (5 mL) was added, and the pH of the mixture was adjusted to ~3-4 by adding 1 M aqueous HCl solution. The aqueous layer was extracted with EtOAc (15 mL×3). These extractions resulted in several organic solvent fractions which were combined and concentrated. The residue was purified by flash column chromatography (10% methanol/CH$_2$Cl$_2$) to provide the title compound (44 mg, 4.3%). MS (ESI): mass calcd. for C$_{31}$H$_{34}$FN$_5$O$_6$S, 623.22; m/z found, 624.3 [M+H]$^+$. $^1$H NMR (500 MHz, CD$_3$OD) δ 7.61 (d, J=8.7 Hz, 1H), 7.54-7.45 (m, 3H), 7.35 (dd, J=8.7, 4.4 Hz, 1H), 7.30-7.19 (m, 2H), 5.20-5.10 (m, 1H), 4.72-4.50 (m, 4H), 3.74-3.57 (m, 2H), 3.56-3.37 (m, 4H), 3.33-3.25 (m, 1H), 3.02-2.90 (m, 1H), 2.95 (s, 3H), 2.28 (s, 3H), 1.61-1.52 (m, 3H), 1.52-1.42 (m, 2H), 1.35-1.18 (m, 2H).

Example 418: (*S)-3-(1-ethyl-4-methyl-1H-benzo[d][1,2,3]triazol-5-yl)-3-(6-((8-fluoro-1,1-dioxido-2',3',5',6'-tetrahydrospiro[benzo[b][1,4,5]oxathiazepine-4,4'-pyran]-2(3H)-yl)methyl)-5-methylpyridin-2-yl)propanoic Acid

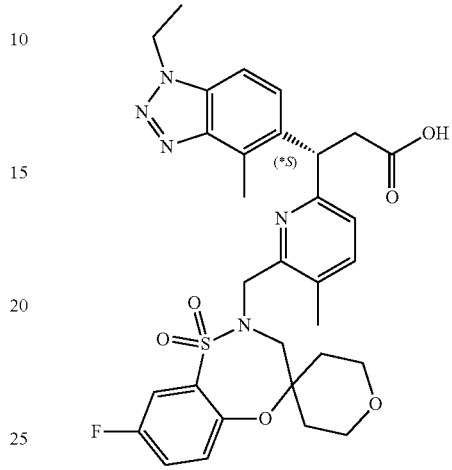

The mixture of 3-(1-Ethyl-4-methyl-1H-benzo[d][1,2,3]triazol-5-yl)-3-(6-((8-fluoro-1,1-dioxido-2',3',5',6'-tetrahydrospiro[benzo[b][1,4,5]oxathiazepine-4,4'-pyran]-2(3H)-yl)methyl)-5-methylpyridin-2-yl)propanoic acid (44 mg, Example 417) were separated by chiral SFC (Stationary phase: CHIRALPAK AD-H 5 μm 250*30 mm, Mobile phase: 60% CO$_2$, 40% MeOH) to afford two enantiomers. The first eluting enantiomer (19 mg) was designated (*S): MS (ESI): mass calcd. for C$_{31}$H$_{34}$FN$_5$O$_6$S, 623.22; m/z found, 624.3 [M+H]$^+$.

Example 419: (*R)-3-(1-ethyl-4-methyl-1H-benzo[d][1,2,3]triazol-5-yl)-3-(6-((8-fluoro-1,1-dioxido-2',3',5',6'-tetrahydrospiro[benzo[b][1,4,5]oxathiazepine-4,4'-pyran]-2(3H)-yl)methyl)-5-methylpyridin-2-yl)propanoic Acid

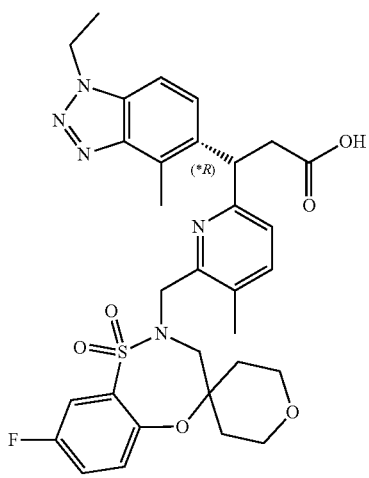

The second eluting enantiomer (21 mg) from the chiral separation described in Example 418 was designated (*R): MS (ESI): mass calcd. for $C_{31}H_{34}FN_5O_6S$, 623.22; m/z found, 624.3 [M+H]+.

Example 420: (*S)-3-(1-ethyl-4-methyl-1H-benzo[d][1,2,3]triazol-5-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoic Acid

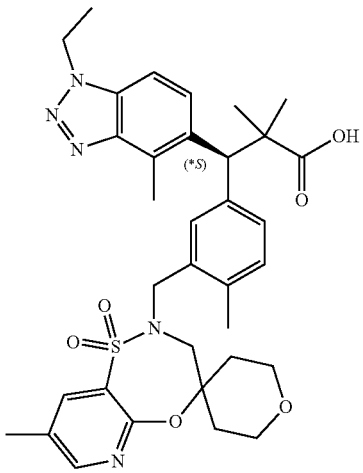 [SMILES: CCn1nnc2c(C)c([C@H](c3ccc(C)c(CN4CC5(CCOCC5)Oc5ncc(C)cc5S4(=O)=O)c3)C(C)(C)C(=O)O)ccc21]

3-(1-ethyl-4-methyl-1H-benzo[d][1,2,3]triazol-5-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoic acid (23 mg, 10% yield) was prepared using analogous conditions as described in Example 14 where 8'-methyl-2,2',3,3',5,6-hexahydrospiro[pyran-4,4'-pyrido[2,3-b][1,4,5]oxathiazepine] 1',1'-dioxide (Intermediate 37) was used in Step C. MS (ESI): mass calcd. for $C_{34}H_{41}N_5O_6S$, 647.28; m/z found, 648.3 [M+H]+. 1H NMR (500 MHz, CD3OD) δ 8.15 (d, J=2.3 Hz, 1H), 7.94 (d, J=2.3 Hz, 1H), 7.65 (d, J=8.8 Hz, 1H), 7.38 (d, J=8.7 Hz, 1H), 7.26-7.20 (m, 1H), 7.00 (d, J=7.8 Hz, 1H), 6.82 (d, J=2.1 Hz, 1H), 4.95 (s, 1H), 4.61-4.55 (m, 2H), 4.40-4.36 (m, 1H), 4.25-4.21 (m, 1H), 3.75-3.64 (m, 2H), 3.30-3.23 (m, 2H), 3.14-3.08 (m, 2H), 2.57 (s, 3H), 2.28 (s, 3H), 2.16 (s, 3H), 1.52-1.45 (m, 3H), 1.36-1.22 (m, 5H), 1.12-1.08 (s, 3H), 1.02-0.93 (m, 1H), 0.85-0.75 (m, 1H). The mixture of isomers of 3-(1-ethyl-4-methyl-1H-benzo[d][1,2,3]triazol-5-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoic acid (23 mg) were separated by chiral SFC (Stationary phase: CHIRALPAK AD-H 5 μm 250*30 mm, Mobile phase: 60% CO2, 40% iPrOH) to afford two enantiomers. The first eluting enantiomer (5 mg) was designated (*S): MS (ESI): mass calcd. for $C_{34}H_{41}N_5O_6S$, 647.28; m/z found, 648.3 [M+H]+.

Example 421: (*R)-3-(1-ethyl-4-methyl-1H-benzo[d][1,2,3]triazol-5-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoic Acid

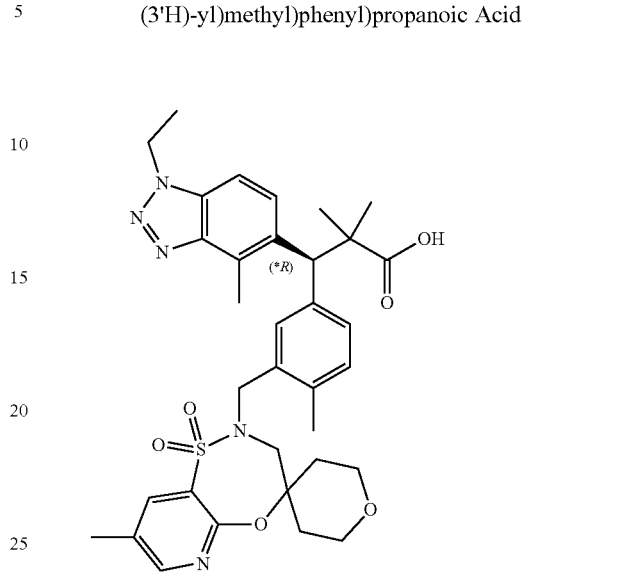

The second eluting enantiomer (5 mg) from the chiral separation described in Example 420 was designated (*R): MS (ESI): mass calcd. for $C_{34}H_{41}N_5O_6S$, 647.28; m/z found, 648.3 [M+H]+.

Example 422: (*S)-3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-2,2-dimethyl-3-(8-methyl-3-(trifluoromethyl)-[1,2,4]triazolo[4,3-a]pyridin-7-yl)propanoic Acid

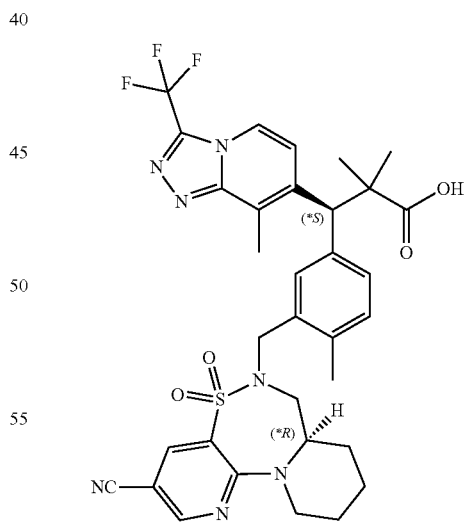

Thionyl chloride (200 mg, 1.69 mmol) was added to methyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate (Intermediate 48, 218 mg, 0.5 mmol) in CH2Cl2 (4 mL). The mixture was stirred at room temperature for 0.5 h. The mixture was concentrated under reduced pressure providing methyl 3-(3-(chloromethyl)-4- methylphenyl)-3-(1-ethyl-4-methyl-1H-benzo[d][1,2,3]triazol-5-yl)-2,2-dimethylpropanoate. A mixture of (*R)-7,7a,8,9,10,11-hexahydro-6H-dipyrido[2,1-d:2',3'-f][1,2,5]thiadiazepine-3-carbonitrile 5,5-dioxide (Intermediate 10, 142 mg, 0.500 mmol), methyl 3-(3-(chloromethyl)-4-methylphenyl)-3-(1-ethyl-4-methyl-1H-benzo[d][1,2,3]triazol-5-yl)-2,2-dimethylpropanoate (229 mg, 0.500 mmol) and iPr$_2$NEt (0.5 mL) was stirred and heated at 150° C. for 16 hours. The mixture was concentrated. The residue was re-dissolved into pyridine (2 mL). Lithium iodide (30 mg, 0.224 mmol) was added. The mixture was heated at 150° C. for 5 hours. The mixture was concentrated. Water (20 mL) was added, and the pH of the mixture was adjusted to ~3-4 by adding 1 M aqueous HCl solution. The aqueous layer was extracted with EtOAc (30 mL×3). These extractions resulted in several organic solvent fractions which were combined and concentrated. The residue was purified by flash column chromatography (20% methanol/CH$_2$Cl$_2$) to provide 3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-2,2-dimethyl-3-(8-methyl-3-(trifluoromethyl)-[1,2,4]triazolo[4,3-a]pyridin-7-yl)propanoic acid (94 mg, 27%). MS (ESI): mass calcd. for C$_{33}$H$_{34}$F$_3$N$_7$O$_4$S, 681.23; m/z found, 682.2 [M+H]$^+$. The mixture of isomers of 3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-2,2-dimethyl-3-(8-methyl-3-(trifluoromethyl)-[1,2,4]triazolo[4,3-a]pyridin-7-yl)propanoic acid (94 mg) were separated by chiral SFC (stationary phase: IG 2×25 cm, mobile phase: 70% CO$_2$, 30% EtOH) to afford two diastereomers. The first eluting diastereomer (41 mg) was designated (*S): MS (ESI): mass calcd. for C$_{33}$H$_{34}$F$_3$N$_7$O$_4$S, 681.23; m/z found, 682.2 [M+H]$^+$. $^1$H NMR (500 MHz, CD$_3$OD) δ 8.51 (d, J=2.1 Hz, 1H), 8.34 (d, J=7.0 Hz, 1H), 8.25 (d, J=2.1 Hz, 1H), 7.48 (d, J=7.0 Hz, 1H), 7.32 (d, J=7.6 Hz, 1H), 7.21 (s, 1H), 7.16 (d, J=7.6 Hz, 1H), 4.57-4.39 (m, 2H), 4.33-4.13 (m, 2H), 3.34 (s, 1H), 3.30-3.10 (m, 3H), 2.72 (s, 3H), 2.20 (s, 3H), 1.75-1.53 (m, 3H), 1.47-1.29 (m, 9H).

Example 423: (*R)-3-(3-(((*R)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-2,2-dimethyl-3-(8-methyl-3-(trifluoromethyl)-[1,2,4]triazolo[4,3-a]pyridin-7-yl)propanoic Acid

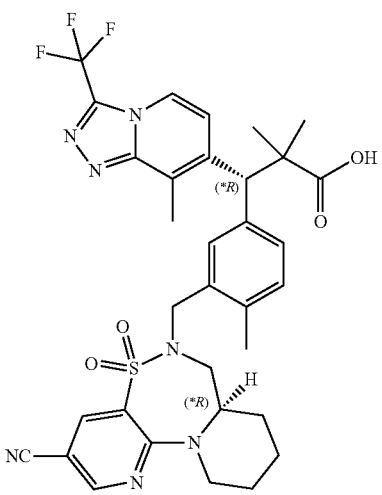 [SMILES: Cc1ccc([C@H](c2ccn3c(C(F)(F)F)nnc3c2C)C(C)(C)C(=O)O)cc1CN1C[C@H]2CCCCN2c2ncc(C#N)cc2S1(=O)=O]

The second eluting diastereomer (35 mg) from the chiral separation described in Example 422 was designated (*R): MS (ESI): for C$_{33}$H$_{34}$F$_3$N$_7$O$_4$S, 681.23; m/z found, 682.2 [M+H]$^+$. $^1$H NMR (500 MHz, CD$_3$OD) δ 8.51 (d, J=2.1 Hz, 1H), 8.36 (d, J=7.0 Hz, 1H), 8.26 (d, J=2.1 Hz, 1H), 7.49 (d, J=7.0 Hz, 1H), 7.31-7.22 (m, 2H), 7.16 (d, J=7.6 Hz, 1H), 4.60-4.52 (m, 1H), 4.43 (d, J=14.6 Hz, 1H), 4.31-4.22 (m, 2H), 3.34 (s, 1H), 3.32-3.18 (m, 3H), 2.71 (s, 3H), 2.20 (s, 3H), 1.79-1.61 (m, 2H), 1.59-1.21 (m, 10H).

Example 424: (*S)-3-(3-(((*S)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-2,2-dimethyl-3-(8-methyl-3-(trifluoromethyl)-[1,2,4]triazolo[4,3-a]pyridin-7-yl)propanoic Acid

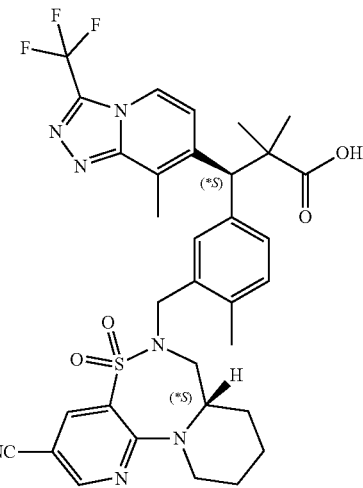

Thionyl chloride (200 mg, 1.69 mmol) was added to methyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate (Intermediate 48, 218 mg, 0.5 mmol) in CH$_2$Cl$_2$ (4 mL). The mixture was stirred at room temperature for 0.5 h. The mixture was concentrated under reduced pressure providing methyl 3-(3-(chloromethyl)-4-methylphenyl)-3-(1-ethyl-4-methyl-1H-benzo[d][1,2,3]triazol-5-yl)-2,2-dimethylpropanoate. A mixture of (*S)-7,7a,8,9,10,11-hexahydro-6H-dipyrido[2,1-d:2',3'-f][1,2,5]thiadiazepine-3-carbonitrile 5,5-dioxide (Intermediate 11, 142 mg, 0.500 mmol), methyl 3-(3-(chloromethyl)-4-methylphenyl)-3-(1-ethyl-4-methyl-1H-benzo[d][1,2,3]triazol-5-yl)-2,2-dimethylpropanoate (229 mg, 0.500 mmol) and iPr$_2$NEt (0.5 mL) in CH$_3$CN (3 mL) was heated at 150° C. for 16 hours and then the mixture was concentrated. The residue was re-dissolved into pyridine (2 mL) and lithium iodide (30 mg, 0.224 mmol) was added. The mixture was heated at 150° C. for 5 hours. The mixture was concentrated. Water (20 mL) was added, and the pH of the mixture was adjusted to ~3-4 by adding 1 M aqueous HCl solution. The aqueous layer was extracted with EtOAc (30 mL×3). These extractions resulted in several organic solvent fractions which were combined and concentrated. The residue was purified by flash column chromatography (20% methanol/CH$_2$Cl$_2$) to provide 3-(3-(((*S)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-2,2-dimethyl-3-(8-methyl-3-(trifluoromethyl)-[1,2,4]triazolo[4,3-a]pyridin-7- yl)propanoic acid (100 mg, 29%). MS (ESI): mass calcd. for $C_{33}H_{34}F_3N_7O_4S$, 681.23; m/z found, 682.2 [M+H]⁺. The mixture of 3-(3-(((*S)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-2,2-dimethyl-3-(8-methyl-3-(trifluoromethyl)-[1,2,4]triazolo[4,3-a]pyridin-7-yl) propanoic acid (100 mg) were separated by chiral SFC (stationary phase: AD-H 2×25 cm, mobile phase: 15-24% isopropanol (0.1% diethylamine)/CO₂) to afford two diastereomers. The first eluting diastereomer (55 mg) was designated (*S): MS (ESI): mass calcd. for $C_{33}H_{34}F_3N_7O_4S$, 681.23; m/z found, 682.2 [M+H]⁺. ¹H NMR (500 MHz, CDCl₃) δ 8.46 (d, J=2.1 Hz, 1H), 8.22 (d, J=2.1 Hz, 1H), 8.03 (d, J=6.7 Hz, 1H), 7.34-7.27 (m, 2H), 7.17-7.07 (m, 2H), 4.80 (s, 1H), 4.71-4.62 (m, 1H), 4.49 (d, J=15.0 Hz, 1H), 4.42-4.34 (m, 1H), 4.14 (d, J=15.0 Hz, 1H), 3.50-3.18 (m, 4H), 2.71 (s, 3H), 2.21 (s, 3H), 1.86-1.62 (m, 3H), 1.58-1.46 (m, 3H), 1.43-1.30 (m, 6H).

Example 425: (*R)-3-(3-(((*S)-3-cyano-5,5-dioxido-7,7a,8,9,10,11-hexahydro-6H-dipyrido[2,1-d:2',3'-f][1,2,5]thiadiazepin-6-yl)methyl)-4-methylphenyl)-2,2-dimethyl-3-(8-methyl-3-(trifluoromethyl)-[1,2,4]triazolo[4,3-a]pyridin-7-yl)propanoic Acid

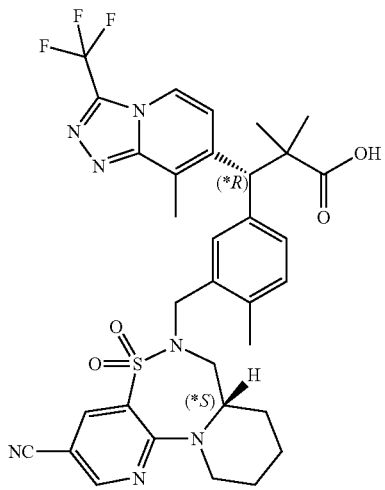 [SMILES: Cc1ccc([C@H](c2ccn3c(C(F)(F)F)nnc3c2C)C(C)(C)C(=O)O)cc1CN1C[C@@H]2CCCCN2c2ncc(C#N)cc2S1(=O)=O]

The second eluting diastereomer (35 mg) from the chiral separation described in Example 424 was designated (*R): mass calcd. for $C_{33}H_{34}F_3N_7O_4S$, 681.23; m/z found, 682.2 [M+H]⁺. ¹H NMR (500 MHz, CDCl₃) δ 8.45 (d, J=2.1 Hz, 1H), 8.22 (d, J=2.1 Hz, 1H), 8.04 (d, J=7.2 Hz, 1H), 7.33 (d, J=7.4 Hz, 1H), 7.22 (d, J=1.7 Hz, 1H), 7.17-7.07 (m, 2H), 4.82 (s, 1H), 4.69-4.60 (m, 1H), 4.52 (d, J=14.8 Hz, 1H), 4.40-4.26 (m, 1H), 4.09 (d, J=14.8 Hz, 1H), 3.48 (s, 1H), 3.38-3.12 (m, 3H), 2.71 (s, 3H), 2.23 (s, 3H), 1.83-1.58 (m, 3H), 1.56-1.32 (m, 9H).3.50-3.18 (m, 4H), 2.71 (s, 3H), 2.21 (s, 3H), 1.86-1.62 (m, 3H), 1.58-1.46 (m, 3H), 1.43-1.30 (m, 6H).

Example 426: (S)-3-(7-(difluoromethoxy)-1-methyl-1H-benzo[d][1,2,3]triazol-5-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic Acid

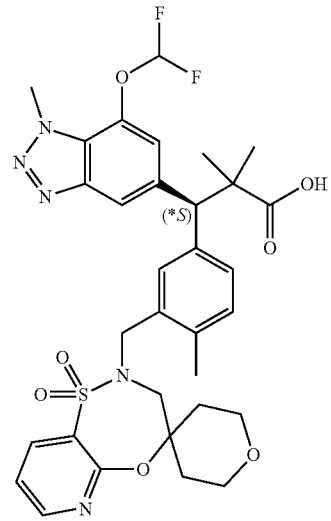 [SMILES: Cc1ccc([C@@H](c2cc(OC(F)F)c3c(c2)nnn3C)C(C)(C)C(=O)O)cc1CN1CC2(CCOCC2)Oc2ncccc2S1(=O)=O]

Step A: (3-(((tert-butyldimethylsilyl)oxy)methyl)-4-methylphenyl)(7-(difluoromethoxy)-1-methyl-1H-benzo[d][1,2,3]triazol-5-yl)methanol. A solution of nBuLi (0.700 mL, 2.5 M in hexanes, 1.75 mmol) was added dropwise at −78° C. to ((5-bromo-2-methylbenzyl)oxy)(tert-butyl)dimethylsilane (Intermediate 19, 312 mg, 0.99 mmol) in THF (40 mL). The resulting mixture was stirred for 1 hour. 7-(difluoromethoxy)-1-methyl-1H-benzo[d][1,2,3]triazole-5-carbaldehyde (Intermediate 164, 227 mg, 0.99 mmol) in THF (5 mL) was added dropwise and the resulting solution was warmed to room temperature over a period of 4 hours. The mixture was quenched with aqueous saturated NH₄Cl solution (20 mL) and the aqueous layer was extracted with EtOAc (30 mL×2). These extractions resulted in several organic solvent fractions which were combined and concentrated to dryness under reduced pressure to provide the title compound (329 mg, 71.6%). MS (ESI): mass calcd. for $C_{23}H_{31}F_2N_3O_3Si$, 463.6; m/z found, 464.2 [M+H]⁺.

Step B: Methyl (S)-3-(3-(chloromethyl)-4-methylphenyl)-3-(7-(difluoromethoxy)-1-methyl-1H-benzo[d][1,2,3]triazol-5-yl)-2,2-dimethylpropanoate. 2,2,2-Trichloroacetonitrile (266 mg, 1.85 mmol) and DBU (5 uL, 0.0330 mmol) were added to (3-(((tert-butyldimethylsilyl)oxy)methyl)-4-methylphenyl)(7-(difluoromethoxy)-1-methyl-1H-benzo[d][1,2,3]triazol-5-yl)methanol (329 mg, 0.710 mmol) in acetonitrile (5 mL) at room temperature, and the mixture was stirred for 45 minutes. ((1-Methoxy-2-methylprop-1-en-1-yl)oxy)trimethylsilane (294 mg, 1.68 mmol) and bis(trifluoromethanesulfonyl)imide (21.0 mg, 0.070 mmol) were then added sequentially, and the mixture was stirred at room temperature for 16 hours. The reaction was quenched with aqueous saturated NaHCO₃ solution (20 mL), and extracted with DCM (50 mL×3). These extractions resulted in several organic solvent fractions which were combined and concentrated to dryness under reduced pressure. The residue was dissolved in DCM (10 mL) and SOCl₂ (0.257 mL, 3.54 mmol) was added and stirred at room temperature for 2 hours. The mixture was concentrated, and the residue was purified by flash column chromatography (10% EtOAc/Hexanes) to provide the title compound (250 mg, 57%). MS (ESI): mass calcd. for $C_{22}H_{24}ClF_2N_3O_3$, 451.9; m/z found, 452.1 [M+H]$^+$.

Step C: (*S)-3-(7-(difluoromethoxy)-1,4-dimethyl-1H-benzo[d][1,2,3]triazol-5-yl)-3-(3-(((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid. A mixture of 2,2',3,3',5,6-hexahydrospiro[pyran-4,4'-pyrido[2,3-b][1,4,5]oxathiazepine] 1',1'-dioxide (Intermediate 36, 89 mg, 0.33 mmol), methyl (S)-3-(3-(chloromethyl)-4-methylphenyl)-3-(7-(difluoromethoxy)-1-methyl-1H-benzo[d][1,2,3]triazol-5-yl)-2,2-dimethylpropanoate (148 mg, 0.33 mmol) and iPr$_2$NEt (0.5 mL) was stirred and heated at 150° C. for 16 hours. The mixture was concentrated. LiOH (3M, 1 mL) was added to the residue in THF (1 mL) and MeOH (1 mL), The mixture was heated at 70° C. for 8 hours. Water (5 mL) was added, and the pH of the mixture was adjusted to ~3-4 by adding 1 M aqueous HCl solution. The aqueous layer was extracted with EtOAc (15 mL×3). These extractions resulted in several organic solvent fractions which were combined and concentrated. The residue was purified by flash column chromatography (10% methanol/CH$_2$Cl$_2$) to provide 3-(7-(difluoromethoxy)-1,4-dimethyl-1H-benzo[d][1,2,3]triazol-5-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid (46 mg, 21%). MS (ESI): mass calcd. for $C_{32}H_{35}F_2N_5O_7S$, 671.22; m/z found, 672.2 [M+H]$^+$. The mixture of 3-(7-(difluoromethoxy)-1,4-dimethyl-1H-benzo[d][1,2,3]triazol-5-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid (46 mg) were separated by chiral SFC (stationary phase: IG 2×25 cm, mobile phase: 20% Methanol (0.1% NPA)/CO$_2$) to afford two enantiomers. The first eluting enantiomer (12 mg) was designated (*S): MS (ESI): mass calcd. for $C_{32}H_{35}F_2N_5O_7S$, 671.22; m/z found, 672.2 [M+H]$^+$. $^1$H NMR (400 MHz, CDCl$_3$) δ 8.61-8.40 (m, 1H), 8.26-8.12 (m, 1H), 7.84 (s, 1H), 7.23-6.91 (m, 5H), 6.49-6.85 (m, 1H), 4.66-4.30 (m, 6H), 4.01-3.88 (m, 2H), 3.55-3.39 (m, 4H), 2.23 (s, 3H), 1.61-0.74 (m, 10H).

Example 427: (R*)-3-(7-(difluoromethoxy)-1-methyl-1H-benzo[d][1,2,3]triazol-5-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic Acid

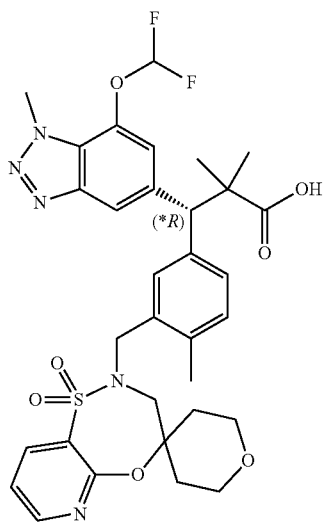 [SMILES: Cc1ccc([C@H](c2cc(OC(F)F)c3c(c2)nnn3C)C(C)(C)C(=O)O)cc1CN1CC2(CCOCC2)Oc2ncccc2S1(=O)=O]

The second eluting enantiomer (12 mg) from the chiral separation described in Example 426 was designated (*R): MS (ESI): mass calcd. for $C_{32}H_{35}F_2N_5O_7S$, 671.22; m/z found, 672.2 [M+H]$^+$. $^1$H NMR (400 MHz, CDCl$_3$) δ 8.61-8.40 (m, 1H), 8.25-8.08 (m, 1H), 7.87 (s, 1H), 7.25-7.01 (m, 5H), 6.49-6.85 (m, 1H), 4.62-4.35 (m, 6H), 3.98-3.84 (m, 2H), 3.58-3.33 (m, 4H), 2.24 (s, 3H), 1.60-0.74 (m, 10H).

Example 428: (S*)-3-(1-(cyclopropylmethyl)-4-methyl-1H-benzo[d][1,2,3]triazol-5-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic Acid

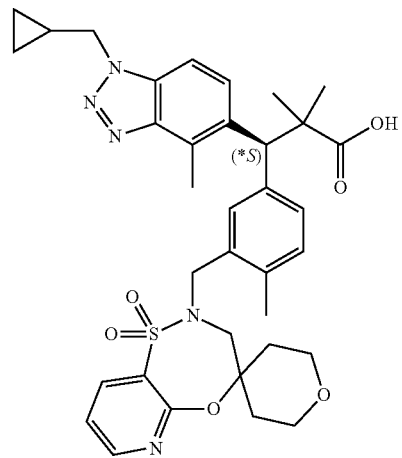 [SMILES: Cc1ccc([C@@H](c2ccc3c(nnn3CC3CC3)c2C)C(C)(C)C(=O)O)cc1CN1CC2(CCOCC2)Oc2ncccc2S1(=O)=O]

Step A: (5-(((tert-butyldimethylsilyl)oxy)methyl)-6-methylpyridin-3-yl)(1-(cyclopropylmethyl)-4-methyl-1H-benzo[d][1,2,3]triazol-5-yl)methanol. A solution of n-BuLi (4.8 mL, 2.5 M in Hexanes, 12 mmol) was added dropwise at −78° C. to ((5-bromo-2-methylbenzyl)oxy)(tert-butyl)dimethylsilane (Intermediate 19, 2.93 g, 9.29 mmol) in THF (120 mL). The resulting mixture was stirred for 1 hour. 1-(cyclopropylmethyl)-4-methyl-1H-benzo[d][1,2,3]triazole-5-carbaldehyde (Intermediate 119, 2.00 g, 9.29 mmol) in THF (10 mL) was added dropwise and the resulting solution was warmed to room temperature over a period of 4 hours. The mixture was quenched with aqueous saturated NH$_4$Cl solution (100 mL) and the aqueous layer was extracted with EtOAc (100 mL×2). These extractions resulted in several organic solvent fractions which were combined and concentrated to dryness under reduced pressure. The residue was purified by flash column chromatography (10% EtOAc/Hexanes) providing the title compound (2.60 g, 61.8%). MS (ESI): mass calcd. for $C_{25}H_{36}N_4O_2Si$, 452.26; m/z found, 453.3 [M+H]$^+$. $^1$H NMR (500 MHz, CDCl$_3$) δ 8.37 (d, J=2.2 Hz, 1H), 7.70 (d, J=8.7 Hz, 1H), 7.59 (d, J=2.2 Hz, 1H), 7.37 (d, J=8.6 Hz, 1H), 6.35-6.17 (m, 1H), 4.74 (s, 1H), 4.61 (s, 2H), 4.53-4.39 (m, 2H), 2.70 (s, 3H), 2.38 (s, 3H), 1.46-1.32 (m, 1H), 0.81 (s, 9H), 0.69-0.58 (m, 2H), 0.53-0.43 (m, 2H), 0.00 (s, 6H).

Step B: methyl 3-(5-(chloromethyl)-6-methylpyridin-3-yl)-3-(1-(cyclopropylmethyl)-4-methyl-1H-benzo[d][1,2,3]triazol-5-yl)-2,2-dimethylpropanoate. 2,2,2-Trichloroacetonitrile (1.08 g, 7.48 mmol) and DBU (20.3 □L, 0.136 mmol) were added to (5-(((tert-butyldimethylsilyl)oxy)methyl)-6-methylpyridin-3-yl)(1-(cyclopropylmethyl)-4- methyl-1H-benzo[d][1,2,3]triazol-5-yl)methanol (1.08 g, 2.87 mmol) in acetonitrile (30 mL) at room temperature, and the mixture was stirred for 45 minutes. ((1-Methoxy-2-methylprop-1-en-1-yl)oxy)trimethylsilane (1.19 g, 6.83 mmol) and bis(trifluoromethanesulfonyl)imide (87.0 mg, 0.31 mmol) were then added sequentially, and the mixture was stirred at room temperature for 16 hours. The reaction was quenched with aqueous saturated NaHCO$_3$ solution (20 mL), and extracted with DCM (50 mL×3). These extractions resulted in several organic solvent fractions which were combined and concentrated to dryness under reduced pressure. The residue was dissolved in DCM (20 mL) and SOCl$_2$ (1.04 mL, 14.3 mmol) was added and stirred at room temperature for 2 hours. The mixture was concentrated and the residue was purified by flash column chromatography (10% EtOAc/Hexanes) to provide the title compound (394 mg, 31.1%). MS (ESI): mass calcd. for $C_{24}H_{29}ClN_4O_2$, 440.2; m/z found, 441.2 [M+H]$^+$.

Step C: (*S)-3-(1-(cyclopropylmethyl)-4,7-dimethyl-1H-benzo[d][1,2,3]triazol-5-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid A mixture of 2,2',3,3',5,6-hexahydrospiro[pyran-4,4'-pyrido[2,3-b][1,4,5]oxathiazepine] 1',1'-dioxide (Intermediate 36, 92 mg, 0.34 mmol), methyl 3-(5-(chloromethyl)-6-methylpyridin-3-yl)-3-(1-(cyclopropylmethyl)-4-methyl-1H-benzo[d][1,2,3]triazol-5-yl)-2,2-dimethylpropanoate (394 mg, 0.894 mmol) and iPr$_2$NEt (0.5 mL) was stirred and heated at 150° C. for 16 hours. The mixture was concentrated. LiOH (3M, 1 mL) was added to the residue in THF (1 mL) and MeOH (1 mL), The mixture was heated at 70° C. for 8 hours. Water (5 mL) was added, and the pH of the mixture was adjusted to ~3-4 by adding 1 M aqueous HCl solution. The aqueous layer was extracted with EtOAc (15 mL×3). These extractions resulted in several organic solvent fractions which were combined and concentrated. The residue was purified by flash column chromatography (10% methanol/CH$_2$Cl$_2$) to provide 3-(1-(cyclopropylmethyl)-4,7-dimethyl-1H-benzo[d][1,2,3]triazol-5-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid (40 mg, 18%). MS (ESI): mass calcd. for $C_{32}H_{35}F_2N_5O_7S$, 671.22; m/z found, 672.2 [M+H]$^+$. The mixture of 3-(7-(difluoromethoxy)-1,4-dimethyl-1H-benzo[d][1,2,3]triazol-5-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid (40 mg) were separated by chiral SFC (stationary phase: AD-H 2×25 cm, mobile phase: 30% Methanol (0.2% NPA)/CO$_2$) to afford two enantiomers. The first eluting enantiomer (12 mg) was designated (*S): MS (ESI): mass calcd. for $C_{34}H_{40}N_6O_6S$, 660.27; m/z found, 661.3 [M+H]$^+$. $^1$H NMR (500 MHz, CD$_3$OD) δ 8.47 (dd, J=4.9, 1.9 Hz, 1H), 8.36 (s, 1H), 8.21 (dd, J=7.6, 1.9 Hz, 1H), 7.78 (s, 1H), 7.64 (s, 1H), 7.57 (d, J=7.9 Hz, 1H), 7.38 (dd, J=7.6, 4.9 Hz, 1H), 5.03 (s, 1H), 4.63-4.40 (m, 3H), 3.97-3.88 (m, 1H), 3.54-3.33 (m, 3H), 2.73 (s, 3H), 2.43 (s, 3H), 1.54-1.22 (m, 13H), 0.67-0.58 (m, 2H), 0.55-0.46 (m, 2H).

Example 429: (R*)-3-(1-(cyclopropylmethyl)-4-methyl-1H-benzo[d][1,2,3]triazol-5-yl)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic Acid

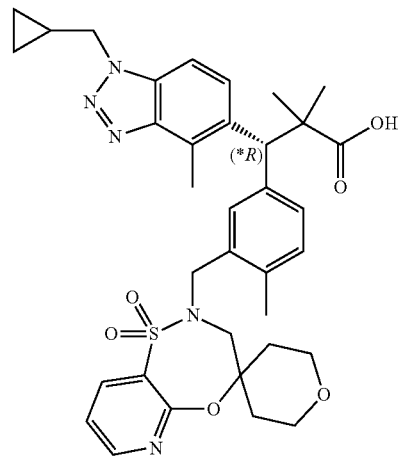 [SMILES: Cc1ccc([C@H](c2ccc3c(nnn3CC3CC3)c2C)C(C)(C)C(=O)O)cc1CN1CC2(CCOCC2)Oc2ncccc2S1(=O)=O]

The second eluting enantiomer (13 mg) from the chiral separation described in Example 428 was designated (*R): MS (ESI): mass calcd. for $C_{34}H_{40}N_6O_6S$, 660.27; m/z found, 661.2 [M+H]$^+$. $^1$H NMR (500 MHz, CD$_3$OD) δ 8.47 (dd, J=4.9, 1.9 Hz, 1H), 8.36 (s, 1H), 8.21 (dd, J=7.6, 2.0 Hz, 1H), 7.78 (d, J=8.7 Hz, 1H), 7.64 (s, 1H), 7.57 (d, J=8.5 Hz, 1H), 7.38 (dd, J=7.7, 4.9 Hz, 1H), 5.07-4.94 (m, 1H), 4.59-4.42 (m, 3H), 3.97-3.85 (m, 1H), 3.55-3.33 (m, 3H), 2.73 (s, 3H), 2.43 (s, 3H), 1.54-1.25 (m, 13H), 0.68-0.56 (m, 2H), 0.55-0.44 (m, 2H).

Example 430: (*S)-3-(3-((4,4-dimethyl-1,1-dioxido-3,4-dihydro-2H-pyrido[2,3-b][1,4,5]oxathiazepin-2-yl)methyl)-4-methylphenyl)-2,2-dimethyl-3-(8-methyl-3-(trifluoromethyl)-[1,2,4]triazolo[4,3-a]pyridin-7-yl)propanoic Acid

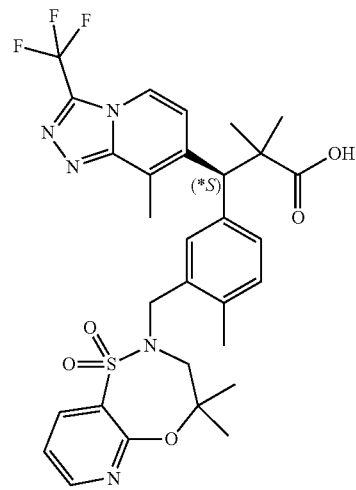 [SMILES: Cc1ccc([C@@H](c2ccn3c(C(F)(F)F)nnc3c2C)C(C)(C)C(=O)O)cc1CN1CC(C)(C)Oc2ncccc2S1(=O)=O]

Thionyl chloride (200 mg, 1.69 mmol) was added to methyl 3-(3-(hydroxymethyl)-4-methylphenyl)-2,2-dimethyl-3-(8-methyl-3-(trifluoromethyl)-[1,2,4]triazolo[4,3-a]pyridin-7-yl)propanoate (Intermediate 48, 218 mg, 0.5 mmol) in CH$_2$Cl$_2$ (4 mL). The mixture was stirred at room temperature for 0.5 h. The mixture was concentrated under reduced pressure providing methyl 3-(3-(chloromethyl)-4-methylphenyl)-3-(1-ethyl-4-methyl-1H-benzo[d][1,2,3]triazol-5-yl)-2,2-dimethylpropanoate. A mixture of 4,4-dimethyl-3,4-dihydro-2H-pyrido[2,3-b][1,4,5]oxathiazepine 1,1-dioxide (Intermediate 82, 784 mg, 0.34 mmol), methyl 3-(3-(chloromethyl)-4-methylphenyl)-3-(1-ethyl-4-methyl-1H-benzo[d][1,2,3]triazol-5-yl)-2,2-dimethylpropanoate (226 mg, 0.500 mmol) and iPr$_2$NEt (0.5 mL) in CH$_3$CN (3 mL) was stirred and heated at 150° C. for 16 hours. The mixture was concentrated. LiOH (3M, 1 mL) was added to the residue in THF (1 mL) and MeOH (1 mL), The mixture was heated at 70° C. for 8 hours. Water (5 mL) was added, and the pH of the mixture was adjusted to ~3-4 by adding 1 M aqueous HCl solution. The aqueous layer was extracted with EtOAc (15 mL×3). These extractions resulted in several organic solvent fractions which were combined and concentrated. The residue was purified by flash column chromatography (10% methanol/CH$_2$Cl$_2$) to provide 3-(3-((4,4-dimethyl-1,1-dioxido-3,4-dihydro-2H-pyrido[2,3-b][1,4,5]oxathiazepin-2-yl)methyl)-4-methylphenyl)-2,2-dimethyl-3-(8-methyl-3-(trifluoromethyl)-[1,2,4]triazolo[4,3-a]pyridin-7-yl)propanoic acid (380 mg) MS (ESI): mass calcd. for C$_{30}$H$_{32}$F$_3$N$_5$O$_5$S, 631.21; m/z found, 632.2 [M+H]$^+$. The mixture of (3-((4,4-dimethyl-1,1-dioxido-3,4-dihydro-2H-pyrido[2,3-b][1,4,5]oxathiazepin-2-yl)methyl)-4-methylphenyl)-2,2-dimethyl-3-(8-methyl-3-(trifluoromethyl)-[1,2,4]triazolo[4,3-a]pyridin-7-yl)propanoic acid (380 mg) were separated by chiral SFC (stationary phase: Chiralpak IG 5 μm 250×20 mm, Mobile phase: 50% CO$_2$, 50% EtOH) to afford two enantiomers. The first eluting enantiomer (61 mg) was designated (*S): MS (ESI): mass calcd. for C$_{30}$H$_{32}$F$_3$N$_5$O$_5$S, 631.21; m/z found, 632.2 [M+H]$^+$. $^1$H NMR (600 MHz, CDCl$_3$) δ 8.52-8.38 (m, 1H), 8.20-8.10 (m, 1H), 7.98 (d, J=7.1 Hz, 1H), 7.41-7.19 (m, 3H), 7.07-6.94 (m, 2H), 6.46-6.26 (m, 1H), 4.84 (s, 1H), 4.57-4.29 (m, 2H), 3.66-3.46 (m, 2H), 2.70 (s, 3H), 2.17 (s, 3H), 1.33-1.16 (m, 12H).

Example 431: (*R)-3-(3-((4,4-dimethyl-1,1-dioxido-3,4-dihydro-2H-pyrido[2,3-b][1,4,5]oxathiazepin-2-yl)methyl)-4-methylphenyl)-2,2-dimethyl-3-(8-methyl-3-(trifluoromethyl)-[1,2,4]triazolo[4,3-a]pyridin-7-yl)propanoic Acid

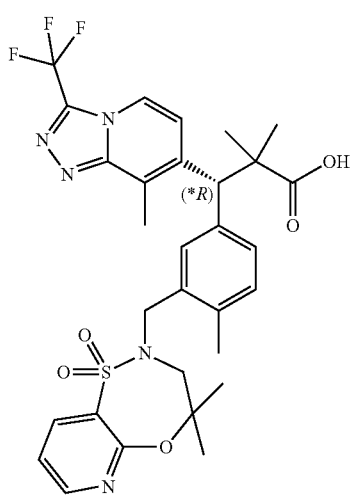 [SMILES: Cc1ccc([C@H](c2ccn3c(C(F)(F)F)nnc3c2C)C(C)(C)C(=O)O)cc1CN1CC(C)(C)Oc2ncccc2S1(=O)=O]

The second eluting enantiomer (56 mg) from the chiral separation described in Example 430 was designated (*R): mass calcd. for C$_{30}$H$_{32}$F$_3$N$_5$O$_5$S, 631.21; m/z found, 632.2 [M+H]$^+$. $^1$H NMR (600 MHz, CDCl$_3$) δ 8.55-8.33 (m, 1H), 8.19-8.12 (m, 1H), 8.00 (d, J=7.0 Hz, 1H), 7.38-7.22 (m, 3H), 7.07-6.94 (m, 2H), 6.78-6.57 (m, 1H), 4.84 (s, 1H), 4.56-4.29 (m, 2H), 3.66-3.46 (m, 2H), 2.71 (s, 3H), 2.19 (s, 3H), 1.41-1.15 (m, 12H).

Example 432: (*S)-3-(3-((1',1'-dioxido-2,3,5,6-tetrahydrospiro[pyran-4,4'-pyrido[2,3-b][1,4,5]oxathiazepin]-2'(3'H)-yl)methyl)-4-methylphenyl)-3-(8-methyl-3-(trifluoromethyl)-[1,2,4]triazolo[4,3-a]pyridin-7-yl)propanoic Acid

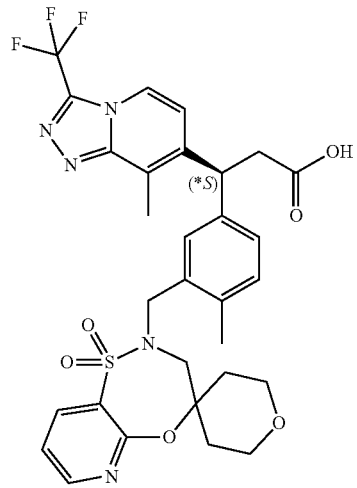 [SMILES: Cc1ccc([C@H](CC(=O)O)c2ccn3c(C(F)(F)F)nnc3c2C)cc1CN1CC2(CCOCC2)Oc2ncccc2S1(=O)=O]

Thionyl chloride (50 mg, 0.42 mmol) was added to ethyl (*S)-3-(3-(hydroxymethyl)-4-methylphenyl)-3-(8-methyl-3-(trifluoromethyl)-[1,2,4]triazolo[4,3-a]pyridin-7-yl)propanoate (Intermediate 26, 120 mg, 0.285 mmol) in CH$_2$Cl$_2$ (4 mL). The mixture was stirred at room temperature for 0.5 h. The mixture was concentrated under reduced pressure. iPr$_2$NEt (0.5 mL) was added to a mixture of 2,2',3,3',5,6-hexahydrospiro[pyran-4,4'-pyrido[2,3-b][1,4,5]oxathiazepine] 1',1'-dioxide (Intermediate 36, 95 mg, 0.35 mmol) and ethyl (*S)-3-(3-(chloromethyl)-4-methylphenyl)-3-(8-methyl-3-(trifluoromethyl)-[1,2,4]triazolo[4,3-a]pyridin-7-yl)propanoate in CH$_3$CN (3 mL). The mixture was stirred at 150° C. for 16 hours. The mixture was concentrated under reduced pressure. NaOH (1M, 2 mL) was added to the residue in THF (2 mL) and the mixture was stirred at RT for 24 hours. Water (5 mL) was added, and the pH of the mixture was adjusted to ~3-4 by adding 1 M aqueous HCl solution. The aqueous layer was extracted with EtOAc (15 mL×3). These extractions resulted in several organic solvent fractions which were combined and concentrated. The residue was purified by flash column chromatography (10% methanol/CH$_2$Cl$_2$) to provide the title compound (72 mg, 39%). MS (ESI): mass calcd. for C$_{30}$H$_{30}$F$_3$N$_5$O$_6$S, 645.19; m/z found, 645.9 [M+H]$^+$. $^1$H NMR (500 MHz, CD$_3$OD) δ 8.49 (dd, J=4.9, 1.9 Hz, 1H), 8.33 (d, J=7.2 Hz, 1H), 8.27-8.15 (m, 1H), 7.46-7.29 (m, 2H), 7.26-7.18 (m, 2H), 7.11 (d, J=2.2 Hz, 1H), 5.09-4.97 (m, 1H), 4.60-4.39 (m, 2H), 3.91-3.71 (m, 2H), 3.49-3.34 (m, 3H), 3.28-3.18 (m, 1H), 3.06-2.88 (m, 2H), 2.85-2.75 (s, 3H), 2.31-2.21 (s, 3H), 1.57-1.44 (m, 2H), 1.33-1.15 (m, 2H).

Example 433: (*S)-2,2-difluoro-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)-3-(8-methyl-3-(trifluoromethyl)-[1,2,4]triazolo[4,3-a]pyridin-7-yl)propanoic Acid

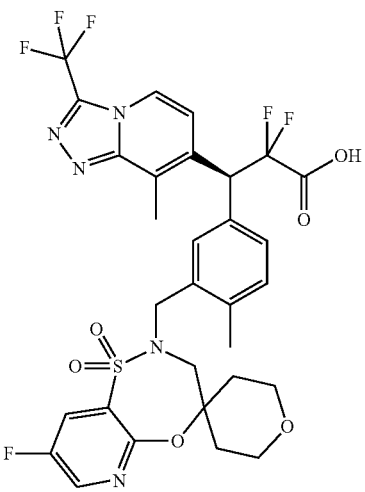 [SMILES: Cc1ccc([C@@H](c2ccn3c(C(F)(F)F)nnc3c2C)C(F)(F)C(=O)O)cc1CN1CC2(CCOCC2)Oc2ncc(F)cc2S1(=O)=O]

Step A: Ethyl (*S)-3-(3-((8-fluoro-1,1-dioxido-2',3',56'-tetrahydrospiro[benzo[b][1,4,5]oxathiazepine-4,4'-pyran]-2(3H)-yl)methyl)-4-methylphenyl)-3-(8-methyl-3-(trifluoromethyl)-[1,2,4]triazolo[4,3-a]pyridin-7-yl)propanoate. Thionyl chloride (200 mg, 1.69 mmol) was added to ethyl (*S)-3-(3-(hydroxymethyl)-4-methylphenyl)-3-(8-methyl-3-(trifluoromethyl)-[1,2,4]triazolo[4,3-a]pyridin-7-yl)propanoate (Intermediate 26, 519 mg, 1.23 mmol) in $CH_2Cl_2$ (4 mL). The mixture was stirred at room temperature for 0.5 h. The mixture was concentrated under reduced pressure. $iPr_2NEt$ (0.5 mL) was added to a mixture of 8-fluoro-2,2',3,3',5',6'-hexahydrospiro[benzo[b][1,4,5]oxathiazepine-4,4'-pyran] 1,1-dioxide (Intermediate 165, 352 mg, 1.23 mmol) and ethyl (*S)-3-(3-(chloromethyl)-4-methylphenyl)-3-(8-methyl-3-(trifluoromethyl)-[1,2,4]triazolo[4,3-a]pyridin-7-yl)propanoate (540 mg, 1.23 mmol) in $CH_3CN$ (3 mL). The mixture was stirred at 150° C. for 16 hours. The mixture was concentrated under reduced pressure providing the title compound (650 mg, 94.1%). MS (ESI): mass calcd. for $C_{33}H_{34}F_4N_4O_6S$, 690.21; m/z found, 690.8 $[M+H]^+$.

Step B: (*S)-2,2-difluoro-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)-3-(8-methyl-3-(trifluoromethyl)-[1,2,4]triazolo[4,3-a]pyridin-7-yl)propanoic acid. The mixture of ethyl (*S)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)-3-(8-methyl-3-(trifluoromethyl)-[1,2,4]triazolo[4,3-a]pyridin-7-yl)propanoate (300 mg, 0.434 mmoL) in THF (2 mL) was cooled to −78° C. Then LDA (1.17 mL, 1.17 mmol, 1 M in hexane/THF) was added. The reaction was then stirred at −78° C. for 30 min and followed by addition of N-fluoro-N-(phenylsulfonyl)benzenesulfonamide (301 mg, 0.956 mmol). The reaction was then stirred for 15 min at −78° C. and then removed from acetone/dry ice bath and allowed to warm to room temperature. The mixture was then stirred at this temperature for 2 hours. The reaction was quenched with saturated $NH_4Cl$ (5 mL), and the aqueous layer was extracted with EtOAc (15 mL×3). These extractions resulted in several organic solvent fractions which were combined and concentrated. The residue was purified by preparative TLC (10% methanol/$CH_2Cl_2$) to provide the title compound (35 mg, 12%). MS (ESI): mass calcd. for $C_{31}H_{28}F_6N_4O_6S$, 698.64; m/z found, 699.2 $[M+H]^+$. $^1$H NMR (500 MHz, $CD_3OD$) D 8.25 (d, J=7.3 Hz, 1H), 7.46-7.15 (m, 6H), 7.07 (d, J=7.8 Hz, 1H), 5.37-5.21 (m, 1H), 4.49-4.34 (m, 2H), 3.60-3.44 (m, 2H), 3.23-3.14 (m, 4H), 2.65 (s, 3H), 2.15 (s, 3H), 1.53-1.35 (m, 2H), 1.25-1.04 (m, 2H).

Example 434: 3-(3,7-Dimethyl-7H-pyrrolo[2,3-c]pyridazin-6-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

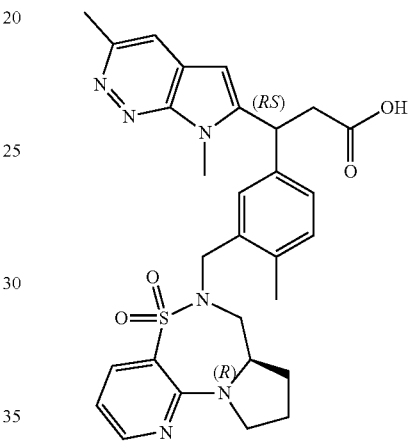

Step A: Ethyl 3-(3,7-dimethyl-7H-pyrrolo[2,3-c]pyridazin-6-yl)-3-(3-(hydroxymethyl)-4-methylphenyl)propanoate. To a solution of ethyl (E)-3-(3,7-dimethyl-7H-pyrrolo[2,3-c]pyridazin-6-yl)acrylate (Intermediate 174 2.00 g, 8.15 mmol) in a mixture of 1,4-dioxane (56 mL) and water (deionized, 27 mL) was added sequentially (3-(hydroxymethyl)-4-methylphenyl)boronic acid (2.05 g, 12.3 mmol), $Et_3N$ (1.72 mL, 12.3 mmol), and chloro(1,5-cyclooctadiene)rhodium(I) dimer (207 mg, 12.3 mmol). The reaction vessel was evacuated and back-filled with Ar. The mixture was heated in an oil bath at 95° C. for 50 minutes. The reaction mixture was partitioned between EtOAc and water (25 mL each). The aqueous phase was extracted with EtOAc (2×25 mL). These extractions resulted in several organic solvent fractions which were combined, dried over $Na_2SO_4$, filtered, and concentrated to dryness under reduced pressure. The residue was purified by flash column chromatography (eluent: 0-100% ethyl acetate/hexanes) to provide the title compound (2.70 g, 90%) as a light tan foam. MS (ESI): mass calcd. for $C_{21}H_{25}N_3O_3$, 367.2; m/z found, 368.2 $[M+H]^+$. $^1$H NMR (400 MHz, $CDCl_3$) δ 7.37 (s, 1H), 7.30 (d, J=2.1 Hz, 1H), 7.06 (d, J=7.8 Hz, 1H), 6.97 (dd, J=7.7, 2.1 Hz, 1H), 6.35 (s, 1H), 4.74-4.60 (m, 3H), 4.12-4.05 (m, 2H), 3.65 (s, 1H), 3.63 (s, 3H), 3.15 (dd, J=16.0, 8.9 Hz, 1H), 2.96 (dd, J=16.0, 6.7 Hz, 1H), 2.70 (s, 3H), 2.25 (s, 3H), 1.16 (t, J=7.1 Hz, 3H).

Step B: Ethyl 3-(3,7-dimethyl-7H-pyrrolo[2,3-c]pyridazin-6-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoate. A solution of ethyl 3-(3,7-dimethyl-7H-pyrrolo[2,3-c]pyridazin-6-yl)-3-(3-(hydroxymethyl)-4-methylphenyl)propanoate (450 mg, 1.23 mmol), (R)-6,7,7a,8,9,10-hexahydropyrido[2,3-f]pyrrolo[2,1-d][1,2,5]thiadiazepine 5,5-dioxide (Intermediate 4, 293 mg, 1.23 mmol), and triphenylphosphine (482 mg, 1.84 mmol) in THF (8 mL) was stirred at room temperature for 1 minute. DBAD (423 mg, 1.84 mmol) was added and the solution was stirred at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (650 mg, 90%) as a white foam. MS (ESI): mass calcd. for $C_{31}H_{36}N_6O_4S$, 588.3; m/z found, 589.3 $[M+H]^+$. $^1$H NMR (400 MHz, $CDCl_3$) δ 8.31-8.27 (m, 1H), 8.06 (dt, J=7.7, 2.1 Hz, 1H), 7.43 (d, J=5.2 Hz, 1H), 7.17-7.01 (m, 3H), 6.86-6.78 (m, 1H), 6.36 (dd, J=6.8, 0.8 Hz, 1H), 5.30 (s, 1H), 4.72 (td, J=7.8, 2.4 Hz, 1H), 4.49-4.31 (m, 2H), 4.22-4.01 (m, 3H), 3.80-3.42 (m, 4H), 3.29-3.10 (m, 2H), 2.99-2.90 (m, 1H), 2.77 (d, J=3.0 Hz, 4H), 2.28 (d, J=17.6 Hz, 3H), 2.03-1.73 (m, 2H), 1.50-1.32 (m, 2H), 1.31-1.13 (m, 3H).

Step C: 3-(3,7-Dimethyl-7H-pyrrolo[2,3-c]pyridazin-6-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid. A mixture containing ethyl 3-(3,7-dimethyl-7H-pyrrolo[2,3-c]pyridazin-6-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoate (650 mg, 1.10 mmol), 1 M aqueous NaOH solution (10.0 mL, 10.0 mmol), THF (10 mL) and ethanol (0.65 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered, and concentrated to dryness under reduced pressure. The residue was purified by flash column chromatography (eluent: 0-10% MeOH/DCM) to provide the title compound (598 mg, 97%) as a white foam. MS (ESI): mass calcd. for $C_{29}H_{32}N_6O_4S$, 560.2; m/z found, 561.2 $[M+H]^+$. $^1$H NMR (500 MHz, $CDCl_3$) δ 11.31 (s, 2H), 8.28 (dt, J=4.4, 2.0 Hz, 1H), 8.06-7.99 (m, 1H), 7.65 (d, J=2.4 Hz, 1H), 7.22-7.14 (m, 1H), 7.12-6.99 (m, 2H), 6.80 (dd, J=7.7, 4.8 Hz, 1H), 6.69 (d, J=3.4 Hz, 1H), 4.87-4.77 (m, 1H), 4.55 (s, 1H), 4.37 (dd, J=14.7, 3.5 Hz, 1H), 4.20-4.09 (m, 1H), 3.73 (d, J=6.7 Hz, 3H), 3.68-3.53 (m, 2H), 3.45 (s, 1H), 3.36-3.24 (m, 2H), 3.08-3.00 (m, 1H), 2.92-2.78 (m, 4H), 2.24 (d, J=12.9 Hz, 3H), 1.99-1.91 (m, 1H), 1.88-1.74 (m, 1H).

Example 435: (*S)-3-(3,7-Dimethyl-7H-pyrrolo[2,3-c]pyridazin-6-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

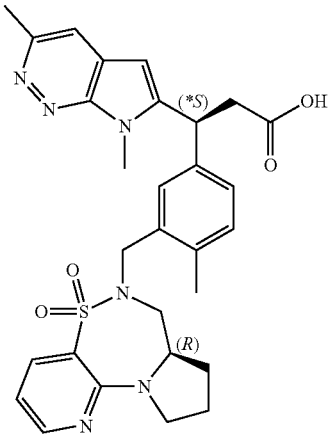

The mixture of 3-(3,7-dimethyl-7H-pyrrolo[2,3-c]pyridazin-6-yl)-3-(3-(((R)-5,5-dioxido-7a, 8,9,10-tetrahydropyrido[2,3-f]pyrrolo[2,1-d][1,2,5]thiadiazepin-6(7H)-yl)methyl)-4-methylphenyl)propanoic acid isomers (Example 434, 598 mg) was separated by chiral SFC (stationary phase: Daicel Chiralpak AD-H 5 μm 250×20 mm, isocratic mobile phase: 70% $CO_2$, 30% MeOH (0.3% $iPrNH_2$)) to afford two diastereomers. The first eluting isomer (276 mg) was designated (*S). MS (ESI): mass calcd. for $C_{29}H_{32}N_6O_4S$, 560.2; m/z found, 561.2 $[M+H]^+$. $^1$H NMR (500 MHz, $CDCl_3$) δ 11.31 (s, 2H), 8.28 (dt, J=4.4, 2.0 Hz, 1H), 8.06-7.99 (m, 1H), 7.65 (d, J=2.4 Hz, 1H), 7.22-7.14 (m, 1H), 7.12-6.99 (m, 2H), 6.80 (dd, J=7.7, 4.8 Hz, 1H), 6.69 (d, J=3.4 Hz, 1H), 4.82 (td, J=8.5, 5.8 Hz, 1H), 4.55 (s, 1H), 4.37 (dd, J=14.7, 3.5 Hz, 1H), 4.15 (dd, J=19.4, 14.8 Hz, 1H), 3.73 (d, J=6.7 Hz, 3H), 3.66-3.47 (m, 2H), 3.45 (s, 1H), 3.36-3.24 (m, 2H), 3.09-3.00 (m, 1H), 2.92-2.78 (m, 4H), 2.24 (d, J=12.9 Hz, 3H), 1.99-1.90 (m, 1H), 1.88-1.74 (m, 1H).

Example 436: (*R)-3-(3,7-Dimethyl-7H-pyrrolo[2,3-c]pyridazin-6-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

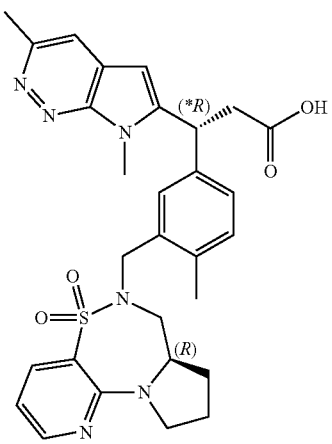

The second eluting isomer (300 mg) from the chiral separation described in Example 435 was designated (*R). MS (ESI): mass calcd. for $C_{29}H_{32}N_6O_4S$, 560.2; m/z found, 561.2 [M+H]$^+$. $^1$H NMR (500 MHz, CDCl$_3$) δ 11.31 (s, 2H), 8.28 (dt, J=4.4, 2.0 Hz, 1H), 8.06-7.99 (m, 1H), 7.65 (d, J=2.4 Hz, 1H), 7.22-7.14 (m, 1H), 7.12-6.99 (m, 2H), 6.80 (dd, J=7.7, 4.8 Hz, 1H), 6.69 (d, J=3.4 Hz, 1H), 4.82 (td, J=8.5, 5.8 Hz, 1H), 4.55 (s, 1H), 4.37 (dd, J=14.7, 3.5 Hz, 1H), 4.15 (dd, J=19.4, 14.8 Hz, 1H), 3.73 (d, J=6.7 Hz, 3H), 3.69-3.59 (m, 2H), 3.45 (s, 1H), 3.36-3.24 (m, 2H), 3.14-3.04 (m, 1H), 2.92-2.78 (m, 4H), 2.24 (d, J=12.9 Hz, 3H), 1.97-1.77 (m, 1H), 1.88-1.74 (m, 1H).

Example 437: 3-(3,7-Dimethyl-7H-pyrrolo[2,3-c]pyridazin-6-yl)-3-(3-(((S)-5,5-dioxido-7a, 8,9,10-tetrahydropyrido[2,3-f]pyrrolo[2,1-d][1,2,5]thiadiazepin-6(7H)-yl)methyl)-4-methylphenyl)propanoic Acid

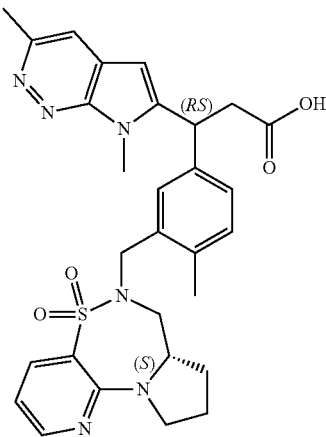

Step A: Ethyl 3-(3,7-dimethyl-7H-pyrrolo[2,3-c]pyridazin-6-yl)-3-(3-(((S)-5,5-dioxido-7a, 8,9,10-tetrahydropyrido[2,3-f]pyrrolo[2,1-d][1,2,5]thiadiazepin-6(7H)-yl)methyl)-4-methylphenyl)propanoate. A solution of ethyl 3-(3,7-dimethyl-7H-pyrrolo[2,3-c]pyridazin-6-yl)-3-(3-(hydroxymethyl)-4-methylphenyl)propanoate (Example 434, Step A, 450 mg, 1.23 mmol), (S)-6,7,7a,8,9,10-hexahydropyrido[2,3-f]pyrrolo[2,1-d][1,2,5]thiadiazepine 5,5-dioxide (Intermediate 75, 293 mg, 1.23 mmol), and triphenylphosphine (482 mg, 1.84 mmol) in THF (8 mL) was stirred at room temperature for 1 minute. DBAD (423 mg, 1.84 mmol) was added and the solution was stirred at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (650 mg, 90%) as a white foam. MS (ESI): mass calcd. for $C_{31}H_{36}N_6O_4S$, 588.3; m/z found, 589.3 [M+H]$^+$. $^1$H NMR (400 MHz, CDCl$_3$) δ 8.29-8.20 (m, 1H), 8.06 (dt, J=7.7, 2.1 Hz, 1H), 7.43 (d, J=5.2 Hz, 1H), 7.17-7.01 (m, 3H), 6.88-6.82 (m, 1H), 6.36 (dd, J=6.8, 0.8 Hz, 1H), 5.30 (s, 1H), 4.72 (td, J=7.8, 2.4 Hz, 1H), 4.45-4.35 (m, 2H), 4.22-4.01 (m, 3H), 3.80-3.42 (m, 4H), 3.29-3.10 (m, 2H), 2.99-2.89 (m, 1H), 2.77 (d, J=3.0 Hz, 4H), 2.28 (d, J=17.6 Hz, 3H), 2.03-1.73 (m, 2H), 1.50-1.32 (m, 2H), 1.31-1.13 (m, 3H).

Step B: 3-(3,7-Dimethyl-7H-pyrrolo[2,3-c]pyridazin-6-yl)-3-(3-(((S)-5,5-dioxido-7a, 8,9,10-tetrahydropyrido[2,3-f]pyrrolo[2,1-d][1,2,5]thiadiazepin-6(7H)-yl)methyl)-4-methylphenyl)propanoic acid. A mixture containing ethyl 3-(3,7-dimethyl-7H-pyrrolo[2,3-c]pyridazin-6-yl)-3-(3-(((S)-5,5-dioxido-7a,8,9,10-tetrahydropyrido[2,3-f]pyrrolo[2,1-d][1,2,5]thiadiazepin-6(7H)-yl)methyl)-4-methylphenyl)propanoate (650 mg, 1.10 mmol), 1 M aqueous NaOH solution (10.0 mL, 10.0 mmol), THF (10 mL) and ethanol (0.65 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over Na$_2$SO$_4$, filtered, and concentrated to dryness under reduced pressure. The residue was purified by flash column chromatography (eluent: 0-10% MeOH/DCM) to provide the title compound (600 mg, 97%) as a white foam. MS (ESI): mass calcd. for $C_{29}H_{32}N_6O_4S$, 560.2; m/z found, 561.2 [M+H]$^+$. $^1$H NMR (400 MHz, CDCl$_3$) δ 8.28 (dt, J=4.8, 1.8 Hz, 1H), 8.04 (dt, J=7.7, 1.5 Hz, 1H), 7.45 (d, J=3.7 Hz, 1H), 7.17-6.97 (m, 3H), 6.79 (dd, J=7.7, 4.8 Hz, 1H), 6.53 (d, J=3.0 Hz, 1H), 4.78 (dt, J=8.3, 5.4 Hz, 1H), 4.52 (d, J=11.5 Hz, 1H), 4.37 (dd, J=14.5, 12.3 Hz, 1H), 4.19-4.03 (m, 1H), 3.74-3.44 (m, 6H), 3.30-3.17 (m, 2H), 3.01 (dd, J=16.2, 6.1 Hz, 1H), 2.90-2.72 (m, 1H), 2.68 (d, J=4.0 Hz, 3H), 2.25 (d, J=13.8 Hz, 3H), 1.98-1.90 (m, 2H), 1.84-1.62 (m, 1H), 1.57-1.34 (m, 1H).

Example 438: (*S)-3-(3,7-Dimethyl-7H-pyrrolo[2,3-c]pyridazin-6-yl)-3-(3-(((S)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

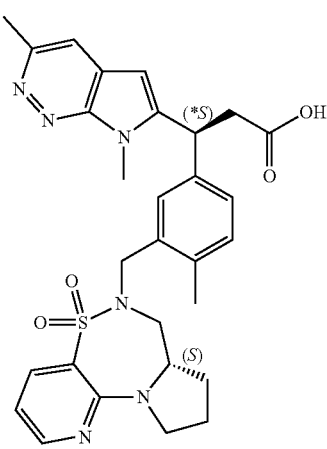

The mixture of 3-(3,7-dimethyl-7H-pyrrolo[2,3-c]pyridazin-6-yl)-3-(3-(((S)-5,5-dioxido-7a, 8,9,10-tetrahydropyrido[2,3-f]pyrrolo[2,1-d][1,2,5]thiadiazepin-6(7H)-yl)methyl)-4-methylphenyl)propanoic acid isomers (Example 437, 600 mg) was separated by chiral SFC (stationary phase: Daicel Chiralpak AD-H 5 μm 250×30 mm, isocratic mobile phase: 60% CO$_2$, 40% MeOH (0.3% iPrNH$_2$)) to afford two diastereomers. The first eluting isomer (276 mg) was designated (*S). MS (ESI): mass calcd. for $C_{29}H_{32}N_6O_4S$, 560.2; m/z found, 561.2 [M+H]$^+$. $^1$H NMR (400 MHz, CDCl$_3$) δ 8.29 (dd, J=4.8, 1.8 Hz, 1H), 8.03 (dd, J=7.8, 1.9 Hz, 1H), 7.35 (s, 1H), 7.12 (d, J=1.7 Hz, 1H), 7.08-6.96 (m, 2H), 6.80 (dd, J=7.7, 4.7 Hz, 1H), 6.38 (s, 1H), 4.70 (t, J=7.5 Hz, 1H), 4.45 (s, 1H), 4.34 (d, J=14.8 Hz, 1H), 4.13 (d, J=14.9 Hz, 1H), 3.74-3.61 (m, 5H), 3.68-3.60 (m, 1H), 3.17 (dd, J=13.4, 3.5 Hz, 1H), 3.01 (dd, J=16.0, 8.8 Hz, 2H), 2.88-2.72 (m, 1H), 2.68 (s, 3H), 2.21 (s, 3H), 1.96-1.72 (m, 3H), 1.44-1.39 (m, 1H).

Example 439: (*R)-3-(3,7-Dimethyl-7H-pyrrolo[2,3-c]pyridazin-6-yl)-3-(3-(((S)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

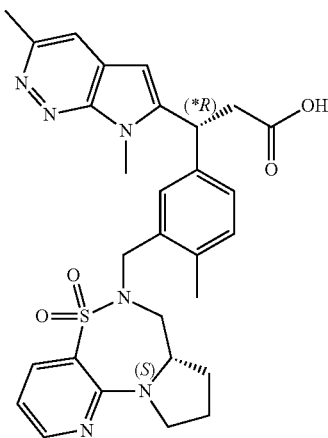

The second eluting isomer (293 mg) from the chiral separation described in Example 438 was designated (*R). MS (ESI): mass calcd. for $C_{29}H_{32}N_6O_4S$, 560.2; m/z found, 561.2 [M+H]$^+$. $^1$H NMR (500 MHz, CDCl$_3$) δ 8.28 (dd, J=4.8, 1.9 Hz, 1H), 8.04 (dd, J=7.8, 1.8 Hz, 1H), 7.40 (s, 1H), 7.06 (d, J=6.2 Hz, 3H), 6.80 (dd, J=7.8, 4.8 Hz, 1H), 6.67 (s, 3H), 6.39 (s, 1H), 4.70 (t, J=7.4 Hz, 1H), 4.56 (t, J=10.7 Hz, 1H), 4.40 (d, J=14.3 Hz, 1H), 4.03 (d, J=14.4 Hz, 1H), 3.75-3.65 (m, 4H), 3.56 (td, J=10.7, 5.7 Hz, 1H), 3.47 (dd, J=11.5, 6.1 Hz, 1H), 3.27 (dd, J=13.4, 3.8 Hz, 1H), 3.08 (s, 1H), 2.99 (s, 1H), 2.72 (s, 3H), 2.25 (s, 3H), 2.02-1.87 (m, 1H), 1.63 (p, J=6.0 Hz, 1H).

Example 440: 3-(3,7-Dimethyl-7H-pyrrolo[2,3-c]pyridazin-6-yl)-3-(3-(((S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

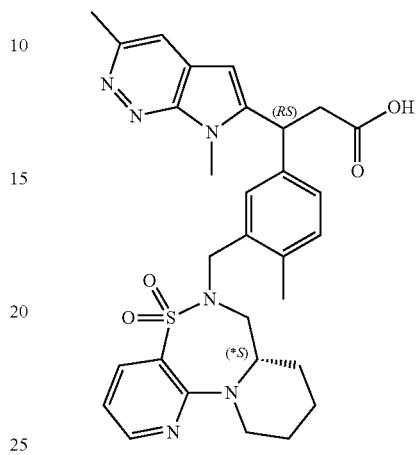

Step A: Ethyl 3-(3,7-dimethyl-7H-pyrrolo[2,3-c]pyridazin-6-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoate. A solution of ethyl 3-(3,7-dimethyl-7H-pyrrolo[2,3-c]pyridazin-6-yl)-3-(3-(hydroxymethyl)-4-methylphenyl)propanoate (Example 434, Step A, 400 mg, 1.09 mmol), (*S)-7,7a,8,9,10,11-hexahydro-6H-dipyrido[2,1-d:2',3'-f][1,2,5]thiadiazepine 5,5-dioxide (Intermediate 2, 260 mg, 1.03 mmol), and triphenylphosphine (482 mg, 1.84 mmol) in THF (8 mL) was stirred at room temperature for 1 minute. DBAD (428 mg, 1.63 mmol) was added and the solution was stirred at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (650 mg, 99%) as a white foam. MS (ESI): mass calcd. for $C_{32}H_{38}N_6O_4S$, 602.2; m/z found, 603.2 [M+H]$^+$. $^1$H NMR (600 MHz, CDCl$_3$) δ 8.29-8.20 (m, 1H), 8.09-8.00 (m, 1H), 7.44 (d, J=6.4 Hz, 2H), 7.23-6.99 (m, 3H), 6.80 (td, J=7.4, 4.6 Hz, 1H), 6.40 (d, J=11.9 Hz, 1H), 4.75 (t, J=7.7 Hz, 1H), 4.52-4.47 (m, 2H), 4.26-4.00 (m, 5H), 3.76 (d, J=2.8 Hz, 3H), 3.30-2.91 (m, 5H), 2.76 (d, J=6.1 Hz, 3H), 2.31-2.21 (m, 3H), 1.71-1.54 (m, 2H), 1.45-1.30 (m, 2H), 1.20-1.15 (m, 3H).

Step B: 3-(3,7-Dimethyl-7H-pyrrolo[2,3-c]pyridazin-6-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid. A mixture of ethyl 3-(3,7-dimethyl-7H-pyrrolo[2,3-c]pyridazin-6-yl)-3-(3-(((S)-5,5-dioxido-7,7a,8,9,10,11-hexahydro-6H-dipyrido[2,1-d:2',3'-f][1,2,5]thiadiazepin-6-yl)methyl)-4-methylphenyl)propanoate (650 mg, 1.08 mmol), 1 M aqueous NaOH solution (10.0 mL, 10.0 mmol), THF (10 mL) and ethanol (0.65 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered, and concentrated to dryness under reduced pressure. The residue was purified by flash column chromatography (eluent: 0-10% MeOH/DCM) to provide the title compound (612 mg, 98%) as a white foam. MS (ESI): mass calcd. for $C_{30}H_{34}N_6O_4S$, 574.2; m/z found, 575.2 [M+H]$^+$. $^1$H NMR (400 MHz, CDCl$_3$) δ 8.85 (s, 3H), 8.28 (td, J=4.4, 1.8 Hz, 1H), 8.00 (dt, J=7.7, 1.5 Hz, 1H), 7.64 (s, 1H), 7.18-6.99 (m, 3H), 6.89-6.80 (m, 1H), 6.69 (s, 1H), 4.88-4.80 (m, 1H), 4.55-4.36 (m, 2H), 4.28-4.10 (m, 2H), 3.74 (d, J=3.4 Hz, 3H), 3.36-2.99 (m, 5H), 2.81 (d, J=3.2 Hz, 3H), 2.23 (d, J=11.5 Hz, 3H), 1.81-1.58 (m, 2H), 1.50-1.30 (m, 2H).

Example 441: (*S)-3-(3,7-Dimethyl-7H-pyrrolo[2,3-c]pyridazin-6-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

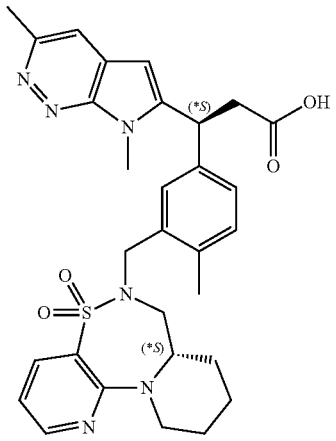 [SMILES: Cc1cc2cc([C@@H](CC(=O)O)c3ccc(C)c(CN4C[C@@H]5CCCCN5c5ncccc5S4(=O)=O)c3)n(C)c2nn1]

The mixture of 3-(3,7-dimethyl-7H-pyrrolo[2,3-c]pyridazin-6-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid (Example 440, 612 mg) was separated by chiral SFC (stationary phase: Daicel Chiralpak AD-H 5 μm 250×20 mm, isocratic mobile phase: 70% $CO_2$, 30% MeOH (0.3% iPrNH$_2$)) to afford two diastereomers. The first eluting isomer (291 mg) was designated (*S). MS (ESI): mass calcd. for $C_{30}H_{34}N_6O_4S$, 574.2; m/z found, 575.2 [M+H]$^+$. $^1$H NMR (500 MHz, CDCl$_3$) δ 8.28 (dd, J=4.6, 1.9 Hz, 1H), 8.00 (dd, J=7.8, 1.9 Hz, 1H), 7.35 (s, 1H), 7.11 (d, J=1.7 Hz, 1H), 7.09-7.00 (m, 2H), 6.81 (dd, J=7.8, 4.7 Hz, 1H), 6.63 (s, 1H), 6.38 (s, 1H), 5.30 (s, 1H), 4.69 (dd, J=8.9, 6.2 Hz, 1H), 4.38 (dd, J=15.5, 8.1 Hz, 2H), 4.20 (dt, J=13.3, 4.9 Hz, 1H), 4.14 (d, J=15.0 Hz, 1H), 3.71 (s, 3H), 3.29-3.20 (m, 1H), 3.12 (dd, J=13.5, 11.8 Hz, 1H), 3.06 (dd, J=13.5, 3.9 Hz, 1H), 3.03-2.89 (m, 2H), 2.75 (dd, J=15.7, 6.2 Hz, 1H), 2.69 (s, 3H), 2.20 (s, 3H), 1.65 (dt, J=13.0, 5.4 Hz, 1H), 1.58-1.42 (m, 2H), 1.34-1.26 (m, 1H).

Example 442: (*R)-3-(3,7-Dimethyl-7H-pyrrolo[2,3-c]pyridazin-6-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

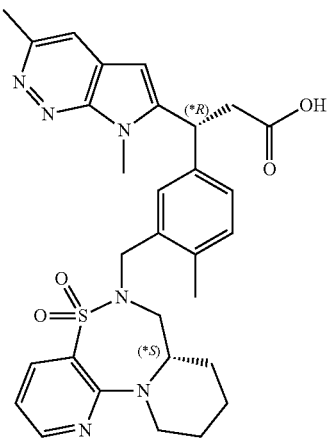 [SMILES: Cc1cc2cc([C@H](CC(=O)O)c3ccc(C)c(CN4C[C@@H]5CCCCN5c5ncccc5S4(=O)=O)c3)n(C)c2nn1]

The second eluting isomer (299 mg) from the chiral separation described in Example 441 was designated (*R). MS (ESI): mass calcd. for $C_{30}H_{34}N_6O_4S$, 574.7; m/z found, 575.2 [M+H]$^+$. $^1$H NMR (500 MHz, CDCl$_3$) δ 8.27 (dd, J=4.6, 1.8 Hz, 1H), 8.00 (dd, J=7.8, 1.9 Hz, 1H), 7.36 (s, 1H), 7.07 (d, J=3.8 Hz, 3H), 6.94 (s, 1H), 6.85 (s, 1H), 6.80 (dd, J=7.8, 4.6 Hz, 1H), 6.38 (s, 1H), 5.31 (s, 1H), 4.71 (t, J=7.5 Hz, 1H), 4.48 (dd, J=19.8, 13.2 Hz, 2H), 4.17 (dt, J=13.2, 4.8 Hz, 1H), 4.01 (d, J=14.4 Hz, 1H), 3.73 (s, 3H), 3.19 (dd, J=13.5, 3.7 Hz, 1H), 3.10-2.92 (m, 4H), 2.78-2.71 (m, 1H), 2.72 (s, 3H), 2.25 (s, 3H), 1.65-1.53 (m, 2H), 1.32-1.17 (m, 1H).

Example 443: 3-(3,7-Dimethyl-7H-pyrrolo[2,3-c]pyridazin-6-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

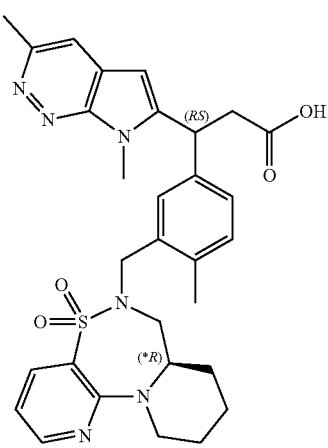 [SMILES: Cc1cc2cc(C(CC(=O)O)c3ccc(C)c(CN4C[C@H]5CCCCN5c5ncccc5S4(=O)=O)c3)n(C)c2nn1]

Step A: Ethyl 3-(3,7-dimethyl-7H-pyrrolo[2,3-c]pyridazin-6-yl)-3-(3-(((*R)-5,5-dioxido-7,7a,8,9,10,11- hexahydro-6H-dipyrido[2,1-d:2',3'-f][1,2,5]thiadiazepin-6-yl)methyl)-4-methylphenyl)propanoate. A solution of ethyl 3-(3,7-dimethyl-7H-pyrrolo[2,3-c]pyridazin-6-yl)-3-(3-(hydroxymethyl)-4-methylphenyl)propanoate (Example 434, Step A, 400 mg, 1.09 mmol), (*R)-7,7a,8,9,10,11-hexahydro-6H-dipyrido[2,1-d:2',3'-f][1,2,5]thiadiazepine 5,5-dioxide (Intermediate 3, 260 mg, 1.03 mmol), and triphenylphosphine (482 mg, 1.84 mmol) in THF (8 mL) was stirred at room temperature for 1 minute. DBAD (428 mg, 1.63 mmol) was added and the solution was stirred at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (600 mg, 91%) as a white foam. MS (ESI): mass calcd. for $C_{32}H_{38}N_6O_4S$, 602.3; m/z found, 603.3 $[M+H]^+$. $^1H$ NMR (400 MHz, $CDCl_3$) δ 8.29-8.20 (m, 1H), 8.08-7.97 (m, 1H), 7.73-7.63 (m, 1H), 7.59-7.38 (m, 1H), 7.20-7.01 (m, 3H), 6.80 (dt, J=7.8, 4.8 Hz, 1H), 6.39 (d, J=6.9 Hz, 1H), 4.74 (t, J=7.7 Hz, 1H), 4.56-4.36 (m, 2H), 4.26-4.00 (m, 4H), 3.76 (d, J=1.5 Hz, 3H), 3.29-2.91 (m, 5H), 2.76 (d, J=4.0 Hz, 3H), 2.33-2.22 (m, 3H), 1.80-1.12 (m, 8H).

Step B: 3-(3,7-Dimethyl-7H-pyrrolo[2,3-c]pyridazin-6-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid. A mixture of ethyl 3-(3,7-dimethyl-7H-pyrrolo[2,3-c]pyridazin-6-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoate (600 mg, 1.08 mmol), 1 M aqueous NaOH solution (9.2 mL, 9.2 mmol), THF (9.2 mL) and ethanol (0.58 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered, and concentrated to dryness under reduced pressure. The residue was purified by flash column chromatography (eluent: 0-10% MeOH/DCM) to provide the title compound (560 mg, 98%) as a white foam. MS (ESI): mass calcd. for $C_{30}H_{34}N_6O_4S$, 574.2; m/z found, 575.3 $[M+H]^+$. $^1H$ NMR (400 MHz, $CDCl_3$) δ 9.55 (s, 2H), 8.29-8.00 (m, 1H), 8.01 (dt, J=7.8, 1.6 Hz, 1H), 7.44 (d, J=4.3 Hz, 1H), 7.18-7.00 (m, 3H), 6.86-6.79 (m, 1H), 6.53 (s, 1H), 5.30 (s, 1H), 4.80 (dt, J=10.1, 5.4 Hz, 1H), 4.53-4.35 (m, 2H), 4.24-4.03 (m, 2H), 3.72 (d, J=4.4 Hz, 3H), 3.30-2.96 (m, 4H), 2.68 (d, J=7.4 Hz, 3H), 2.24 (d, J=17.4 Hz, 3H), 1.77-1.43 (m, 2H), 1.41 (s, 1H), 1.38 (s, 2H).

Example 444: (*S)-3-(3,7-Dimethyl-7H-pyrrolo[2,3-c]pyridazin-6-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

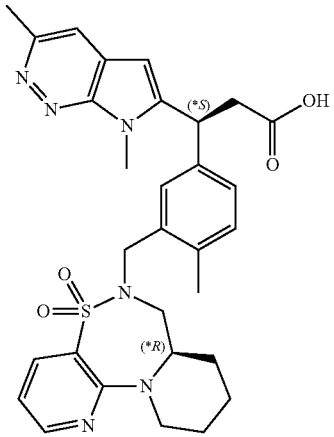 [SMILES: Cc1cc2cc([C@@H](CC(=O)O)c3ccc(C)c(CN4C[C@H]5CCCCN5c5ncccc5S4(=O)=O)c3)n(C)c2nn1]

The mixture of 3-(3,7-dimethyl-7H-pyrrolo[2,3-c]pyridazin-6-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid (Example 443, 516 mg) was separated by chiral SFC (stationary phase: Daicel Chiralpak AD-H 5 μm 250×20 mm, isocratic mobile phase: 70% $CO_2$, 30% MeOH (0.3% $iPrNH_2$)) to afford two diastereomers. The first eluting isomer (269 mg) was designated (*S). MS (ESI): mass calcd. for $C_{30}H_{34}N_6O_4S$, 574.2; m/z found, 575.2 $[M+H]^+$. $^1H$ NMR (500 MHz, $CDCl_3$) δ 8.26 (dd, J=4.6, 1.9 Hz, 1H), 7.99 (dd, J=7.8, 1.9 Hz, 1H), 7.35 (s, 1H), 7.10-7.03 (m, 3H), 6.81 (s, 1H), 6.79 (dd, J=7.8, 4.6 Hz, 1H), 6.38 (s, 1H), 5.30 (s, 1H), 4.70 (dd, J=8.6, 6.4 Hz, 1H), 4.53-4.41 (m, 2H), 4.16 (dt, J=13.2, 4.7 Hz, 1H), 4.00 (d, J=14.4 Hz, 1H), 3.72 (s, 3H), 3.17 (dd, J=13.5, 3.8 Hz, 1H), 3.04 (t, J=12.9 Hz, 1H), 3.01-2.91 (m, 3H), 2.76-2.68 (m, 1H), 2.71 (s, 3H), 2.24 (s, 3H), 1.63-1.52 (m, 1H), 1.42-1.30 (m, 1H), 1.35 (s, 1H), 1.33-1.23 (m, 1H).

Example 445: (*R)-3-(3,7-Dimethyl-7H-pyrrolo[2,3-c]pyridazin-6-yl)-3-(3-(((*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

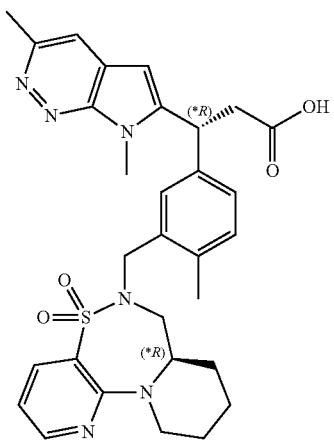 [SMILES: Cc1cc2cc([C@H](CC(=O)O)c3ccc(C)c(CN4C[C@H]5CCCCN5c5ncccc5S4(=O)=O)c3)n(C)c2nn1]

The second eluting isomer (266 mg) from the chiral separation described in Example 444 was designated (*R). MS (ESI): mass calcd. for $C_{30}H_{34}N_6O_4S$, 574.2; m/z found, 575.2 [M+H]$^+$. $^1$H NMR (500 MHz, CDCl$_3$) δ 8.27 (dd, J=4.6, 1.8 Hz, 1H), 8.00 (dd, J=7.8, 1.9 Hz, 1H), 7.36 (s, 1H), 7.07 (d, J=3.8 Hz, 3H), 6.94 (s, 1H), 6.85 (s, 1H), 6.80 (dd, J=7.8, 4.6 Hz, 1H), 6.38 (s, 1H), 5.31 (s, 1H), 4.71 (t, J=7.5 Hz, 1H), 4.42-4.34 (m, 2H), 4.17 (dt, J=13.2, 4.8 Hz, 1H), 4.01 (d, J=14.4 Hz, 1H), 3.73 (s, 3H), 3.19 (dd, J=13.5, 3.7 Hz, 1H), 3.10-2.92 (m, 4H), 2.78-2.71 (m, 1H), 2.72 (s, 3H), 2.25 (s, 3H), 1.63-1.57 (m, 2H), 1.32-1.17 (m, 1H).

Example 446: 3-(3-(Difluoromethyl)-8-methyl-[1,2,4]triazolo[4,3-a]pyridin-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

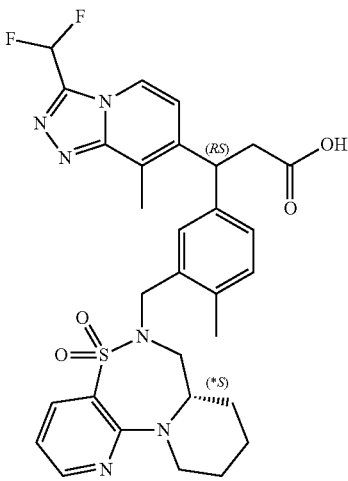 [SMILES: Cc1ccc(C(CC(=O)O)c2ccn3c(C(F)F)nnc3c2C)cc1CN1C[C@@H]2CCCCN2c2ncccc2S1(=O)=O]

Step A: Ethyl 3-(3-(difluoromethyl)-8-methyl-[1,2,4]triazolo[4,3-a]pyridin-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoate. Diisopropyl azodicarboxylate (0.32 mL, 1.63 mmol) was added to ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 400 mg, 0.99 mmol), (*S)-7,7a,8,9,10,11-hexahydro-6H-dipyrido[2,1-d:2',3'-f][1,2,5]thiadiazepine 5,5-dioxide (Intermediate 2, 357 mg, 1.41 mmol), and triphenylphosphine (386 mg, 1.47 mmol) in THF (11 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (630 mg, 99%) as a white foam. MS (ESI): mass calcd. for $C_{32}H_{36}F_2N_6O_4S$, 638.3 m/z found, 639.3 [M+H]$^+$. $^1$H NMR (400 MHz, CDCl$_3$) δ 8.29 (dd, J=4.7, 1.9 Hz, 1H), 8.16 (d, J=7.2 Hz, 1H), 8.04 (dd, J=7.8, 1.9 Hz, 1H), 7.24-7.06 (m, 3H), 6.91-6.78 (m, 2H), 4.95 (dt, J=8.9, 6.4 Hz, 1H), 4.61-4.40 (m, 2H), 4.32-4.03 (m, 5H), 3.33-2.96 (m, 5H), 2.83 (d, J=9.5 Hz, 3H), 2.27 (d, J=10.1 Hz, 3H), 2.04 (s, 2H), 1.83-1.33 (m, 4H), 1.34-1.11 (m, 3H).

Step B: 3-(3-(Difluoromethyl)-8-methyl-[1,2,4]triazolo[4,3-a]pyridin-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid. A mixture containing ethyl 3-(3-(difluoromethyl)-8-methyl-[1,2,4]triazolo[4,3-a]pyridin-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoate (630 mg, 0.99 mmol), 1 M aqueous NaOH solution (9.0 mL, 9.0 mmol), THF (9.0 mL) and ethanol (0.06 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over Na$_2$SO$_4$, filtered, and concentrated to dryness under reduced pressure. The residue was purified by flash column chromatography (eluent: 0-10% MeOH/DCM) to provide the title compound (595 mg, 99%) as a white foam. MS (ESI): mass calcd. for $C_{30}H_{32}F_2N_6O_4S$, 610.2 m/z found, 611.2 [M+H]$^+$. $^1$H NMR (400 MHz, CDCl$_3$) δ 9.25 (s, 1H), 8.29 (dd, J=4.7, 1.9 Hz, 1H), 8.15 (d, J=7.1 Hz, 1H), 8.04 (dd, J=7.8, 1.9 Hz, 1H), 7.25-7.09 (m, 3H), 7.13-7.06 (m, 1H), 6.89 (dd, J=10.6, 7.3 Hz, 1H), 6.88-6.80 (m, 1H), 5.00-4.90 (m, 1H), 4.56-4.38 (m, 2H), 4.28-4.07 (m, 4H), 3.32-3.20 (m, 1H), 3.24-3.11 (m, 3H), 3.10-3.00 (m, 1H), 2.77 (d, J=8.3 Hz, 3H), 2.25 (d, J=9.5 Hz, 3H), 2.04 (s, 1H), 1.72-1.52 (m, 2H), 1.45-1.35 (m, 1H).

Example 447: (*S)-3-(3-(Difluoromethyl)-8-methyl-[1,2,4]triazolo[4,3-a]pyridin-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

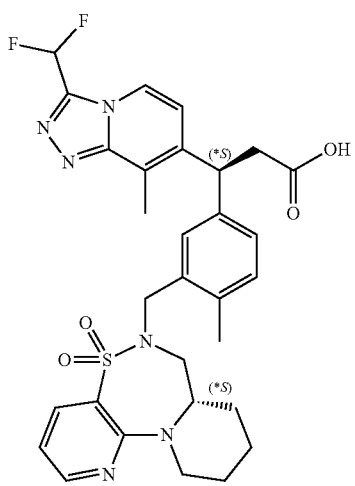 [SMILES: Cc1ccc([C@H](CC(=O)O)c2ccn3c(C(F)F)nnc3c2C)cc1CN1C[C@@H]2CCCCN2c2ncccc2S1(=O)=O]

The mixture of 3-(3-(difluoromethyl)-8-methyl-[1,2,4]triazolo[4,3-a]pyridin-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid isomers (Example 446, 595 mg) was separated by chiral SFC (stationary phase: Daicel Chiralpak IC 5 μm 250×30 mm, isocratic mobile phase: 62% CO$_2$, 38% MeOH (0.3% iPrNH₂)) to afford two diastereomers. The first eluting isomer (297 mg) was designated (*S). MS (ESI): mass calcd. for $C_{30}H_{32}F_2N_6O_4S$, 610.2; m/z found, 611.2 [M+H]⁺. ¹H NMR (400 MHz, CDCl₃) δ 9.16 (s, 1H), 8.29 (dd, J=4.7, 1.9 Hz, 1H), 8.15 (d, J=7.1 Hz, 1H), 8.04 (dd, J=7.8, 1.9 Hz, 1H), 7.24-7.05 (m, 4H), 6.89 (dd, J=10.8, 7.2 Hz, 1H), 6.88-6.80 (m, 1H), 4.95 (q, J=8.0 Hz, 1H), 4.57-4.38 (m, 2H), 4.28-4.07 (m, 3H), 3.31-3.18 (m, 1H), 3.17 (dd, J=10.9, 6.7 Hz, 3H), 3.10-3.00 (m, 1H), 2.77 (d, J=9.2 Hz, 3H), 2.25 (d, J=9.7 Hz, 3H), 2.06 (d, J=11.5 Hz, 1H), 1.65 (s, 1H), 1.72-1.58 (m, 1H), 1.53 (s, 1H), 1.44-1.32 (m, 1H).

Example 448: (*R)-3-(3-(Difluoromethyl)-8-methyl-[1,2,4]triazolo[4,3-a]pyridin-7-yl)-3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

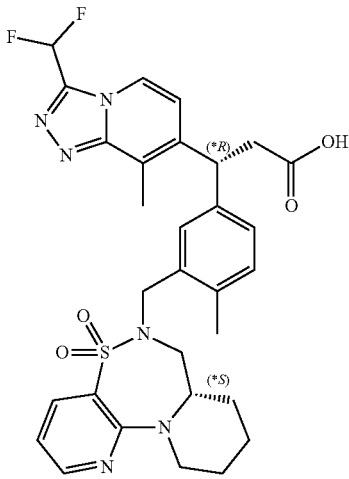 [SMILES: Cc1ccc([C@@H](CC(=O)O)c2ccn3c(C(F)F)nnc3c2C)cc1CN1C[C@@H]2CCCCN2c2ncccc2S1(=O)=O]

The second eluting isomer (298 mg) from the chiral separation described in Example 446 was designated (*R). MS (ESI): mass calcd. for $C_{30}H_{32}F_2N_6O_4S$, 610.2; m/z found, 611.2 [M+H]⁺. ¹H NMR (400 MHz, CDCl₃) δ 8.21 (dd, J=4.7, 1.8 Hz, 1H), 8.03 (d, J=7.1 Hz, 1H), 7.94 (dd, J=7.8, 1.8 Hz, 1H), 7.11 (d, J=2.9 Hz, 1H), 7.01 (s, 2H), 6.84-6.70 (m, 2H), 5.23 (s, 1H), 5.17-5.12 (m, 5H), 4.84 (s, 1H), 4.48-4.34 (m, 2H), 4.17 (dt, J=13.3, 5.0 Hz, 1H), 4.04 (d, J=14.7 Hz, 1H), 3.22-3.10 (m, 2H), 3.14-3.04 (m, 1H), 2.72 (s, 3H), 2.16 (s, 3H), 1.60 (dd, J=11.0, 5.9 Hz, 1H), 1.59-1.43 (m, 1H), 1.35-1.28 (m, 2H).

Example 449: 3-(3-(Difluoromethyl)-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

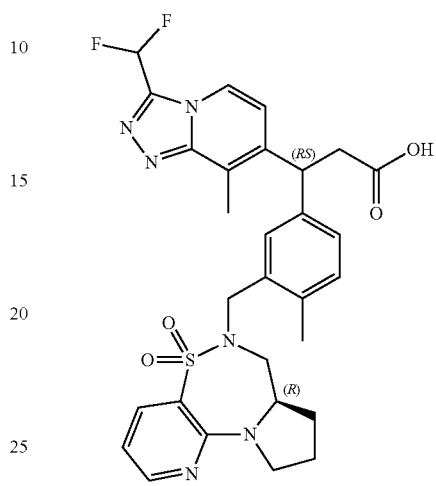

Step A: Ethyl 3-(3-(difluoromethyl)-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoate. Diisopropyl azodicarboxylate (0.45 mL, 2.28 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 550 mg, 1.36 mmol), (R)-6,7,7a,8,9,10-hexahydropyrido[2,3-f]pyrrolo[2,1-d][1,2,5]thiadiazepine 5,5-dioxide (Intermediate 4, 457 mg, 1.91 mmol), and triphenylphosphine (529 mg, 2.02 mmol) in THF (10 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over Na₂SO₄, filtered and concentrated under reduced pressure. The residue was purified by flash column chromatography (eluent: 0-100% ethyl acetate/hexanes) to provide the title compound (820 mg, 96%) as a white foam. MS (ESI): mass calcd. for $C_{31}H_{34}F_2N_6O_4S$, 624.3; m/z found, 625.3 [M+H]⁺. ¹H NMR (400 MHz, CDCl₃) δ 8.30 (dt, J=4.7, 1.7 Hz, 1H), 8.20-8.12 (m, 1H), 8.08 (dd, J=7.7, 1.8 Hz, 1H), 7.18-7.05 (m, 3H), 6.89-6.77 (m, 2H), 4.99-4.90 (m, 1H), 4.66-4.58 (m, 1H), 4.42 (dd, J=14.6, 6.2 Hz, 1H), 4.25-4.00 (m, 3H), 3.75-3.58 (m, 2H), 3.38-3.30 (m, 1H), 3.13 (dd, J=15.8, 6.9 Hz, 1H), 3.08-2.98 (m, 1H), 2.93-2.78 (m, 4H), 2.28 (d, J=4.0 Hz, 3H), 2.11-1.63 (m, 4H), 1.58-1.43 (m, 1H), 1.30-1.13 (m, 3H).

Step B: 3-(3-(Difluoromethyl)-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid. A mixture containing ethyl 3-(3-(difluoromethyl)-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoate (820 mg, 1.31 mmol), 1 M aqueous NaOH solution (12.0 mL, 12.0 mmol), and THF (12.0 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered, and concentrated to dryness under reduced pressure. The residue was purified by flash column chromatography (eluent: 0-10% MeOH/DCM) to provide the title compound (778 mg, 99%) as a white foam. MS (ESI): mass calcd. for $C_{29}H_{30}F_2N_6O_4S$, 596.2; m/z found, 597.2 $[M+H]^+$. $^1H$ NMR (400 MHz, $CDCl_3$) δ 8.29 (dt, J=4.8, 1.8 Hz, 2H), 8.14 (t, J=6.5 Hz, 1H), 8.07 (dt, J=7.7, 1.8 Hz, 1H), 7.24-7.04 (m, 4H), 6.88 (dd, J=14.0, 7.3 Hz, 1H), 6.85-6.75 (m, 1H), 4.94 (dt, J=9.1, 6.2 Hz, 1H), 4.61 (s, 1H), 4.41 (dd, J=14.6, 6.2 Hz, 1H), 4.23-4.09 (m, 1H), 3.70-3.55 (m, 2H), 3.38-3.30 (m, 1H), 3.19-3.08 (m, 1H), 3.05-2.98 (m, 1H), 2.86 (td, J=12.3, 3.2 Hz, 1H), 2.76 (d, J=6.5 Hz, 3H), 2.26 (d, J=5.0 Hz, 3H), 2.07-1.93 (m, 1H), 1.93-1.77 (m, 1H), 1.79-1.60 (m, 1H), 1.55-1.40 (m, 1H).

Example 450: (\*S)-3-(3-(Difluoromethyl)-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

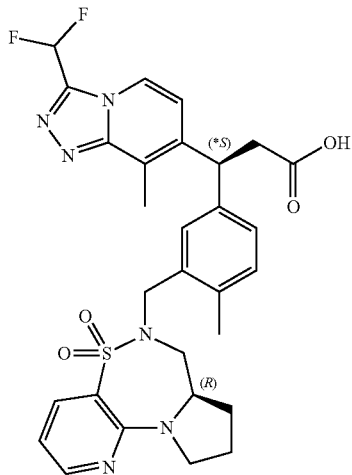

The mixture of 3-(3-(difluoromethyl)-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid isomers (Example 449, 778 mg) was separated by chiral SFC (stationary phase: Daicel Chiralpak AD-H 5 μm 250×30 mm, isocratic mobile phase: 55% $CO_2$, 45% MeOH) to afford two diastereomers. The first eluting isomer (374 mg) was designated (\*S). MS (ESI): mass calcd. for $C_{29}H_{30}F_2N_6O_4S$, 596.2; m/z found, 597.2 $[M+H]^+$. $^1H$ NMR (500 MHz, $CDCl_3$) δ 8.28 (dd, J=4.8, 1.8 Hz, 1H), 8.13 (d, J=7.2 Hz, 1H), 8.06 (dd, J=7.7, 1.7 Hz, 1H), 7.20 (s, 1H), 7.17-7.05 (m, 4H), 6.88 (d, J=7.2 Hz, 1H), 6.80 (dd, J=7.8, 4.8 Hz, 1H), 4.95 (dd, J=8.9, 6.7 Hz, 1H), 4.60 (d, J=11.2 Hz, 1H), 4.41 (d, J=14.5 Hz, 1H), 4.17 (d, J=14.5 Hz, 1H), 3.70 (q, J=7.0 Hz, 1H), 3.61 (dd, J=10.5, 4.7 Hz, 2H), 3.29 (dd, J=13.3, 3.7 Hz, 1H), 3.15 (dd, J=16.0, 6.6 Hz, 1H), 3.04 (dd, J=16.0, 9.0 Hz, 1H), 2.85 (t, J=12.6 Hz, 1H), 2.77 (s, 3H), 2.26 (s, 3H), 1.99-1.90 (m, 1H), 1.85-1.77 (m, 1H), 1.49-1.38 (m, 1H).

Example 451: (\*R)-3-(3-(Difluoromethyl)-8-methyl-[1,2,4]triazolo[4,3-a]pyridin-7-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic Acid

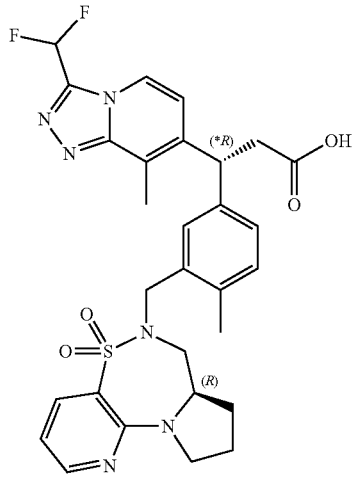

The second eluting isomer (389 mg) from the chiral separation described in Example 450 was designated (\*R). MS (ESI): mass calcd. for $C_{29}H_{30}F_2N_6O_4S$, 596.2; m/z found, 597.2 $[M+H]^+$. $^1H$ NMR (500 MHz, $CDCl_3$) δ 8.28 (dd, J=4.8, 1.8 Hz, 1H), 8.15 (d, J=7.2 Hz, 1H), 8.06 (dd, J=7.8, 1.8 Hz, 1H), 7.20 (s, 1H), 7.16 (d, J=1.9 Hz, 1H), 7.15-7.05 (m, 2H), 6.91 (d, J=7.2 Hz, 1H), 6.80 (dd, J=7.7, 4.8 Hz, 1H), 4.97-4.90 (m, 1H), 4.61 (s, 1H), 4.40 (d, J=14.7 Hz, 1H), 4.19 (d, J=14.7 Hz, 1H), 3.75-3.56 (m, 2H), 3.46 (s, 1H), 3.36 (dd, J=13.3, 3.7 Hz, 1H), 3.16 (dd, J=16.0, 6.6 Hz, 1H), 3.05 (dd, J=16.0, 9.0 Hz, 1H), 2.87 (t, J=12.5 Hz, 1H), 2.76 (s, 3H), 2.25 (s, 3H), 2.06-1.94 (m, 1H), 1.92-1.83 (m, 1H), 1.74 (qt, J=11.9, 7.0 Hz, 1H), 1.50 (dd, J=13.5, 5.9 Hz, 1H).

Example 452: 3-(3-((10,10-Difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

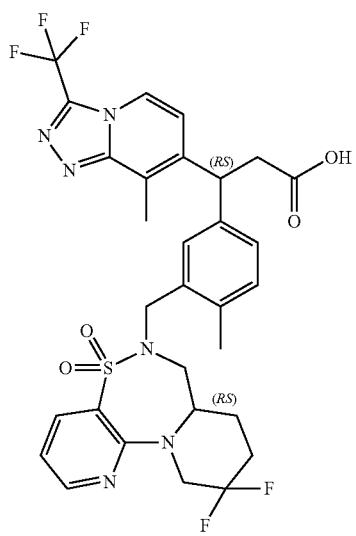 [SMILES: Cc1ccc(C(CC(=O)O)c2ccn3c(C(F)(F)F)nnc3c2C)cc1CN1CC2CCC(F)(F)CN2c2ncccc2S1(=O)=O]

Step A: tert-Butyl 2-(((2-chloropyridine)-3-sulfonamido)methyl)-5,5-difluoropiperidine-1-carboxylate. Potassium carbonate (145 mg, 1.05 mmol) was added to a mixture of tert-butyl 2-(aminomethyl)-5,5-difluoropiperidine-1-carboxylate (250 mg, 0.99 mmol), in THF (3.37 mL) and H$_2$O (0.67 mL). 2-Chloropyridine-3-sulfonyl chloride (212 mg, 0.99 mmol) was then added and the mixture was stirred at room temperature for 6.5 hours. The mixture was concentrated to dryness under reduced pressure and partitioned between ethyl acetate and water. The aqueous layer was extracted with ethyl acetate. These extractions resulted in several organic solvent fractions which were combined, dried over anhydrous MgSO$_4$, filtered, and concentrated to dryness under reduced pressure. The residue was purified by flash column chromatography (eluent: 0-100% ethyl acetate/hexanes) to afford the title compound (400 mg, 94%) as a white solid. MS (ESI): mass calcd. for $C_{16}H_{22}ClF_2N_3O_4S$, 425.1; m/z found, 426.0 [M+H]$^+$. $^1$H NMR (400 MHz, CDCl$_3$) D 8.57 (dd, J=4.7, 1.9 Hz, 1H), 8.39 (dd, J=7.8, 1.9 Hz, 1H), 7.45 (dd, J=7.8, 4.8 Hz, 1H), 6.17 (s, 1H), 4.40-4.30 (m, 1H), 3.34-3.25 (m, 1H), 3.05 (dt, J=13.4, 5.7 Hz, 2H), 2.10-1.80 (m, 4H), 1.79-1.70 (m, 1H), 1.47 (s, 9H).

Step B: 10,10-Difluoro-7,7a,8,9,10,11-hexahydro-6H-dipyrido[2,1-d:2',3'-f][1,2,5]thiadiazepine 5,5-dioxide. A solution of 20% TFA in DCM (3.27 mL, 42.8 mol) was added to tert-butyl 2-(((2-chloropyridine)-3-sulfonamido)methyl)-5,5-difluoropiperidine-1-carboxylate (400 mg, 0.94 mmol). The resulting mixture was stirred for 2.5 hours at room temperature, then concentrated to dryness under reduced pressure. The residue was purified by flash column chromatography (eluent: 0-100% ethyl acetate/hexanes) to afford the title compound (250 mg, 92%). MS (ESI): mass calcd. for $C_{11}H_{13}F_2N_3O_2S$, 289.0 m/z found, 290.0 [M+H]$^+$. $^1$H NMR (400 MHz, CDCl$_3$) D 8.24 (dd, J=4.5, 1.8 Hz, 1H), 7.87 (dt, J=7.8, 1.3 Hz, 1H), 6.82 (dd, J=7.9, 4.6 Hz, 1H), 5.83-5.75 (m, 1H), 4.68-4.60 (m, 1H), 4.33 (dq, J=10.6, 5.2 Hz, 1H), 3.65-3.32 (m, 3H), 2.27-1.96 (m, 3H), 1.77-1.63 (m, 1H).

Step C: Ethyl 3-(3-((10,10-difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoate. Diisopropyl azodicarboxylate (0.28 mL, 1.42 mmol) was added to a stirring mixture of ethyl 3-(3-(hydroxymethyl)-4-methylphenyl)-3-(8-methyl-3-(trifluoromethyl)-[1,2,4]triazolo[4,3-a]pyridin-7-yl)propanoate (Intermediate 25, 364 mg, 0.84 mmol), 10,10-difluoro-7,7a,8,9,10,11-hexahydro-6H-dipyrido[2,1-d:2',3'-f][1,2,5]thiadiazepine 5,5-dioxide (250 mg, 0.86 mmol), and triphenylphosphine (336 mg, 1.28 mmol) in THF (9.8 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (500 mg, 84%) as a white foam. MS (ESI): mass calcd. for $C_{32}H_{33}F_5N_6O_4S$, 692.2 m/z found, 693.2 [M+H]$^+$. $^1$H NMR (400 MHz, CDCl$_3$) δ 8.34 (dd, J=4.6, 1.8 Hz, 1H), 8.09-8.00 (m, 2H), 7.20-7.08 (m, 3H), 7.01-6.90 (m, 2H), 4.98-4.89 (m, 1H), 4.68-4.61 (m, 1H), 4.50 (d, J=14.6 Hz, 1H), 4.37-4.02 (m, 4H), 3.69-3.58 (m, 1H), 3.36-2.96 (m, 4H), 2.83 (d, J=2.3 Hz, 3H), 2.27 (d, J=6.6 Hz, 1H), 2.14-1.93 (m, 5H), 1.69-1.55 (m, 1H), 1.30-1.13 (m, 3H).

Step D: 3-(3-((10,10-Difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid. A mixture containing ethyl 3-(3-((10,10-difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoate (500 mg, 0.72 mmol), 1 M aqueous NaOH solution (6.7 mL, 9.0 mmol), and THF (6.7 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over Na$_2$SO$_4$, filtered, and concentrated to dryness under reduced pressure. The residue was purified by flash column chromatography (eluent: 0-10% MeOH/DCM) to provide the title compound (458 mg, 95%) as a white foam. MS (ESI): mass calcd. for $C_{30}H_{29}F_5N_6O_4S$, 664.2; m/z found, 665.2 [M+H]$^+$. $^1$H NMR (400 MHz, CDCl$_3$) δ 8.33 (dd, J=4.7, 1.8 Hz, 1H), 8.09 (dt, J=7.8, 1.7 Hz, 1H), 8.03 (d, J=7.2 Hz, 1H), 7.18-7.04 (m, 3H), 7.01-6.89 (m, 2H), 4.97-4.88 (m, 1H), 4.60 (td, J=12.5, 5.8 Hz, 1H), 4.48 (d, J=14.8 Hz, 1H), 4.32-4.07 (m, 2H), 3.69-3.58 (m, 1H), 3.29-3.25 (m, 1H), 3.24-3.09 (m, 2H), 3.05 (dt, J=16.3, 8.5 Hz, 1H), 2.77 (s, 3H), 2.26 (d, J=6.4 Hz, 3H), 2.04 (s, 3H), 1.65-1.55 (m, 1H), 1.26 (t, J=7.1 Hz, 1H).

Example 453: (*S)-3-(3-(((*S)-10,10-Difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

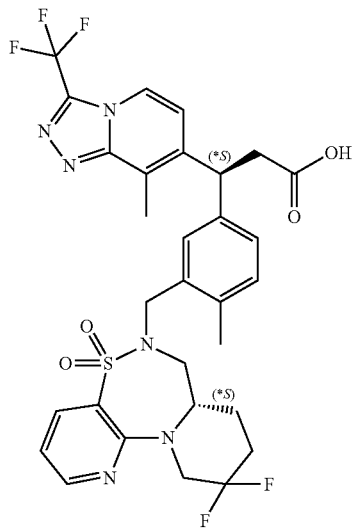 [SMILES: Cc1ccc([C@H](CC(=O)O)c2ccn3c(C(F)(F)F)nnc3c2C)cc1CN1C[C@@H]2CCC(F)(F)CN2c2ncccc2S1(=O)=O]

The mixture of 4 diastereomers of 3-(3-((10,10-difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid (Example 452, 458 mg) was separated using two chiral separation methods. The mixture of 4 diastereomers was initially subjected to Chiral Separation Method V: chiral SFC (stationary phase: Chiralpak AD-H m 250×30 mm, isocratic mobile phase: 60% CO$_2$, 40% iPrOH) to provide Example 455 and Example 456 and a mixture of the two remaining diastereomers (Example 453 and Example 454). The mixture of Example 453 and Example 454 was subsequently separated using Chiral Separation Method VI: chiral SFC (stationary phase: Lux Cellulose-4 5 µm 250×21.2 mm, Mobile phase: 70% $CO_2$, 30% EtOH) to afford Example 453 and Example 454. The chiral separation method, order of elution and designated stereochemistry is tabulated below in Table 5. When the stereochemical configuration is written as, for example (*S, *R), with the first configuration, (*S), corresponds to the configuration at the 3-propanoic carbon and the second configuration, (*R), corresponds to the stereochemistry at the sultam. The characterization for (*S)-3-(3-(((*S)-10,10-difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid (Example 453, 78 mg) is as follows: MS (ESI): mass calcd. for $C_{30}H_{29}F_5N_6O_4S$, 664.2; m/z found, 665.2 [M+H]$^+$. $^1$H NMR (500 MHz, CDCl$_3$) δ 8.27 (dd, J=4.7, 1.8 Hz, 1H), 8.03 (dd, J=7.8, 1.8 Hz, 1H), 7.95 (d, J=7.2 Hz, 1H), 7.14-6.98 (m, 3H), 6.90-6.82 (m, 2H), 4.96 (s, 1H), 4.85 (dd, J=8.9, 6.8 Hz, 1H), 4.56 (d, J=12.5 Hz, 1H), 4.42 (d, J=14.8 Hz, 1H), 4.19-4.13 (m, 1H), 4.10 (d, J=14.8 Hz, 1H), 3.69-3.55 (m, 1H), 3.25 (dd, J=13.4, 3.7 Hz, 1H), 3.13-3.01 (m, 2H), 2.98 (dd, J=16.1, 9.0 Hz, 1H), 2.72 (s, 2H), 2.19 (s, 3H), 1.97-1.84 (m, 3H), 1.20-1.07 (m, 2H).

TABLE 5

Chiral separation method, order of elution and esignated stereochemistry for Examples 453-456

| Example # | Chiral Separation method/order of elution | Configuration |
|---|---|---|
| 453 | Method VI, first eluting | (*S, *S) |
| 454 | Method VI, second eluting | (*S, *R) |
| 455 | Method V, second eluting | (*R, *S) |
| 456 | Method V, third eluting | (*R, *R) |

Example 454: (*S)-3-(3-(((*R)-10,10-difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

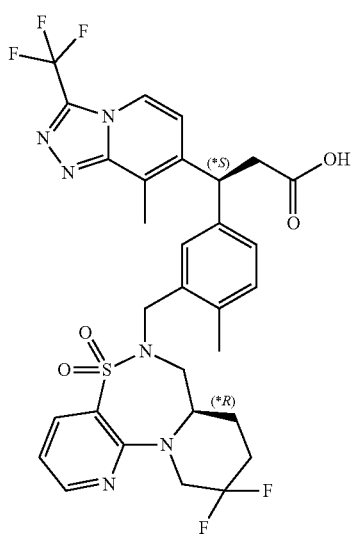 [SMILES: Cc1ccc([C@H](CC(=O)O)c2ccn3c(C(F)(F)F)nnc3c2C)cc1CN1C[C@H]2CCC(F)(F)CN2c2ncccc2S1(=O)=O]

The title compound (84 mg) was obtained as described in Example 453 and Table 5. MS (ESI): mass calcd. for $C_{30}H_{29}F_5N_6O_4S$, 664.2; m/z found, 665.2 [M+H]$^+$. $^1$H NMR (500 MHz, CDCl$_3$) δ 8.35 (dd, J=4.7, 1.8 Hz, 1H), 8.11 (dd, J=7.8, 1.8 Hz, 1H), 8.03 (d, J=7.2 Hz, 1H), 7.23-7.11 (m, 2H), 7.11 (dd, J=7.8, 2.0 Hz, 1H), 7.00-6.88 (m, 2H), 4.94 (dd, J=8.9, 6.8 Hz, 1H), 4.66-4.57 (m, 1H), 4.50 (d, J=14.6 Hz, 1H), 4.28-4.22 m, 1H), 4.19 (d, J=14.6 Hz, 1H), 3.78-3.63 (m, 1H), 3.29 (dd, J=13.4, 3.7 Hz, 1H), 3.24-3.10 (m, 2H), 3.05 (dd, J=16.1, 9.0 Hz, 1H), 2.80 (s, 3H), 2.28 (s, 3H), 2.08-2.00 (m, 3H), 1.62 (dt, J=9.9, 5.4 Hz, 1H), 1.29-1.19 (m, 1H).

Example 455: (*R)-3-(3-(((*S)-10,10-Difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

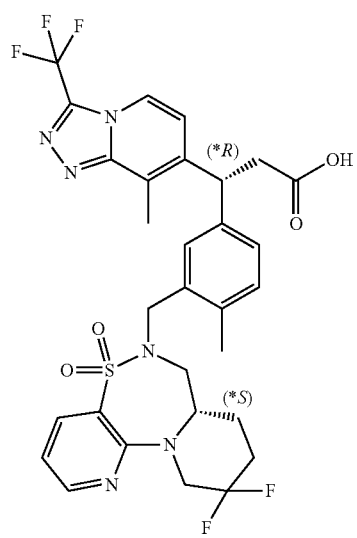 [SMILES: Cc1ccc([C@@H](CC(=O)O)c2ccn3c(C(F)(F)F)nnc3c2C)cc1CN1C[C@@H]2CCC(F)(F)CN2c2ncccc2S1(=O)=O]

The title compound (84 mg) was obtained as described in Example 453 and Table 5. MS (ESI): mass calcd. for $C_{30}H_{29}F_5N_6O_4S$, 664.2; m/z found, 665.2 [M+H]$^+$. $^1$H NMR (500 MHz, CDCl$_3$) δ 8.26 (dd, J=4.7, 1.8 Hz, 1H), 8.02 (dd, J=7.8, 1.8 Hz, 1H), 7.93 (d, J=7.1 Hz, 1H), 7.18-6.93 (m, 3H), 6.86 (dd, J=7.7, 4.7 Hz, 2H), 4.84 (t, J=7.8 Hz, 1H), 4.52 (dd, J=12.2, 4.5 Hz, 1H), 4.41 (d, J=14.7 Hz, 1H), 4.19-4.13 (m, 1H), 4.10 (d, J=14.7 Hz, 1H), 3.67-3.54 (m, 1H), 3.22 (dd, J=13.4, 3.7 Hz, 1H), 3.11 (t, J=12.8 Hz, 1H), 3.04 (dd, J=15.9, 6.7 Hz, 1H), 2.92 (dd, J=15.9, 8.9 Hz, 1H), 2.71 (s, 3H), 2.19 (s, 3H), 1.99-1.92 (m, 3H), 1.53 (dd, J=12.3, 7.6 Hz, 1H), 1.22-1.13 (m, 1H).

Example 456: (*R)-3-(3-(((*R)-10,10-Difluoro-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic Acid

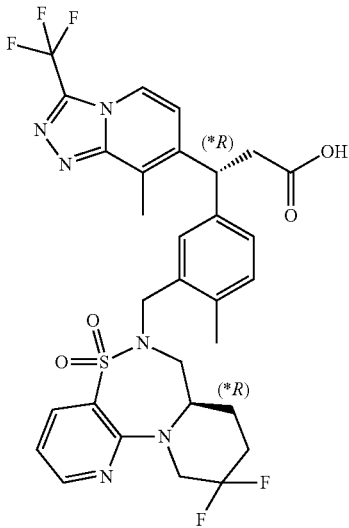 [SMILES: Cc1ccc([C@@H](CC(=O)O)c2ccn3c(C(F)(F)F)nnc3c2C)cc1CN1C[C@H]2CCC(F)(F)CN2c2ncccc2S1(=O)=O]

The title compound (97 mg) was obtained as described in Example 453 and Table 5. MS (ESI): mass calcd. for $C_{30}H_{29}F_5N_6O_4S$, 664.2; m/z found, 665.2 [M+H]⁺. ¹H NMR (500 MHz, CDCl₃) δ 8.35 (dd, J=4.7, 1.8 Hz, 1H), 8.09 (dd, J=7.8, 1.8 Hz, 1H), 8.01 (d, J=7.1 Hz, 1H), 7.21-7.16 (m, 1H), 7.16-7.06 (m, 2H), 6.99-6.90 (m, 2H), 4.91 (t, J=7.7 Hz, 1H), 4.63 (d, J=11.7 Hz, 1H), 4.48 (d, J=14.9 Hz, 1H), 4.29-4.22 (m, 1H), 4.18 (d, J=14.9 Hz, 1H), 3.76-3.63 (m, 1H), 3.35 (dd, J=13.4, 3.7 Hz, 1H), 3.17 (t, J=12.9 Hz, 1H), 3.07 (dd, J=16.0, 6.5 Hz, 1H), 2.97 (dd, J=15.9, 8.6 Hz, 1H), 2.79 (s, 3H), 2.25 (s, 3H), 2.03 (d, J=9.1 Hz, 3H), 1.61 (d, J=10.2 Hz, 1H), 1.29-1.02 (m, 1H).

Example 457: 3-(3-(Difluoromethyl)-8-methyl-[1,2,4]triazolo[4,3-a]pyridin-7-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic Acid

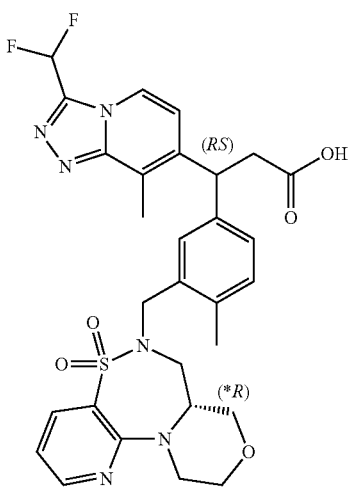 [SMILES: Cc1ccc(C(CC(=O)O)c2ccn3c(C(F)F)nnc3c2C)cc1CN1C[C@@H]2COCCN2c2ncccc2S1(=O)=O]

Step A: Ethyl 3-(3-(difluoromethyl)-8-methyl-[1,2,4]triazolo[4,3-a]pyridin-7-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoate.

Diisopropyl azodicarboxylate (0.45 mL, 2.28 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 550 mg, 1.36 mmol), (*R)-6,7,7a,8,10,11-hexahydro-[1,4]oxazino[3,4-d]pyrido[2,3-f][1,2,5]thiadiazepine 5,5-dioxide (Intermediate 14, 488 mg, 1.91 mmol), and triphenylphosphine (529 mg, 2.02 mmol) in THF (10 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine. The organic fractions were dried over Na₂SO₄, filtered and concentrated under reduced pressure. The residue was purified by flash column chromatography (eluent: 0-100% ethyl acetate/hexanes) to provide the title compound (850 mg, 97%) as a white foam. MS (ESI): mass calcd. for $C_{31}H_{34}F_2N_6O_5S$, 640.2; m/z found, 641.2 [M+H]⁺. ¹H NMR (500 MHz, CDCl₃) δ 8.29-8.25 (m, 1H), 8.13 (t, J=6.8 Hz, 1H), 8.05 (dt, J=7.9, 2.0 Hz, 1H), 7.76-7.42 (m, 2H), 7.33-7.03 (m, 4H), 6.94-6.71 (m, 2H), 4.97-4.91 (m, 1H), 4.59-4.53 (m, 1H), 4.49-4.35 (m, 1H), 4.27 (dd, J=14.7, 2.9 Hz, 2H), 4.16-4.01 (m, 3H), 3.79-3.67 (m, 2H), 3.67-3.50 (m, 2H), 3.17-3.10 (m, 1H), 3.03-2.93 (m, 1H), 2.81 (d, J=10.0 Hz, 3H), 2.20 (d, J=7.3 Hz, 3H), 1.15 (td, J=7.1, 0.9 Hz, 3H).

Step B: 3-(3-(Difluoromethyl)-8-methyl-[1,2,4]triazolo[4,3-a]pyridin-7-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid. A mixture containing ethyl 3-(3-(difluoromethyl)-8-methyl-[1,2,4]triazolo[4,3-a]pyridin-7-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoate (850 mg, 1.33 mmol), 1 M aqueous NaOH solution (12 mL, 12 mmol), and THF (12 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over Na₂SO₄, filtered, and concentrated to dryness under reduced pressure. The residue was purified by flash column chromatography (eluent: 0-10% MeOH/DCM) to provide the title compound (800 mg, 98%) as a white foam. MS (ESI): mass calcd. for $C_{29}H_{30}F_2N_6O_5S$, 612.2; m/z found, 613.2 [M+H]⁺. ¹H NMR (500 MHz, CDCl₃) δ 10.26 (s, 1H), 8.33-8.27 (m, 1H), 8.20 (d, J=7.2 Hz, 1H), 8.10-8.06 (m, 1H), 7.29-7.19 (m, 1H), 7.18-7.06 (m, 2H), 7.01-6.83 (m, 3H), 4.99-4.88 (m, 1H), 4.57-4.39 (m, 2H), 4.40-4.25 (m, 2H), 4.17-4.07 (m, 1H), 3.80-3.53 (m, 4H), 3.33-3.04 (m, 3H), 3.05-2.98 (m, 1H), 2.78 (s, 1H), 2.71 (s, 2H), 2.19 (d, J=2.7 Hz, 3H).

Example 458: (*S)-3-(3-(Difluoromethyl)-8-methyl-[1,2,4]triazolo[4,3-a]pyridin-7-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic Acid

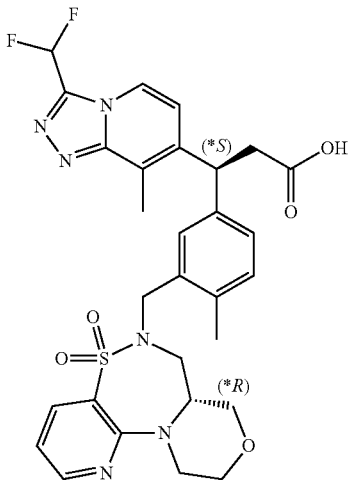 [SMILES: Cc1ccc([C@H](CC(=O)O)c2ccn3c(C(F)F)nnc3c2C)cc1CN1C[C@@H]2COCCN2c2ncccc2S1(=O)=O]

The mixture of 3-(3-(difluoromethyl)-8-methyl-[1,2,4]triazolo[4,3-a]pyridin-7-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid isomers (Example 457, 800 mg) was separated by chiral SFC (stationary phase: Chiralpak AD-H 5 μm 250×30 mm, isocratic mobile phase: 60% $CO_2$, 40% iPrOH) to afford two diastereomers. The first eluting isomer (331 mg) was designated (*S). MS (ESI): mass calcd. for $C_{29}H_{30}F_2N_6O_5S$, 612.2; m/z found, 613.2 [M+H]$^+$. $^1$H NMR (400 MHz, CDCl$_3$) δ 8.33 (dd, J=4.7, 1.8 Hz, 1H), 8.21-8.07 (m, 2H), 7.28-7.07 (m, 4H), 6.96-6.83 (m, 2H), 4.98 (t, J=7.9 Hz, 1H), 4.58 (d, J=12.6 Hz, 1H), 4.50-4.30 (m, 3H), 3.83 (d, J=10.0 Hz, 1H), 3.76 (q, J=7.1 Hz, 1H), 3.74-3.58 (m, 4H), 3.30 (dd, J=13.0, 3.9 Hz, 1H), 3.24-3.07 (m, 2H), 3.02 (dd, J=15.7, 7.9 Hz, 1H), 2.82 (s, 3H), 2.22 (s, 3H).

Example 459: (*R)-3-(3-(Difluoromethyl)-8-methyl-[1,2,4]triazolo[4,3-a]pyridin-7-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic Acid

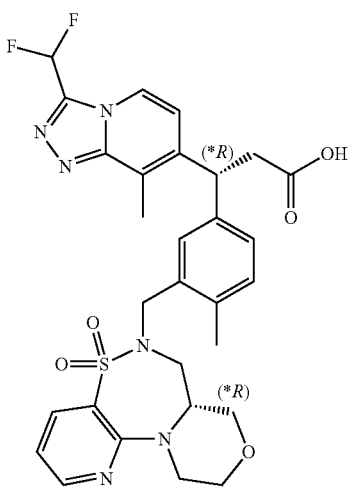 [SMILES: Cc1ccc([C@@H](CC(=O)O)c2ccn3c(C(F)F)nnc3c2C)cc1CN1C[C@@H]2COCCN2c2ncccc2S1(=O)=O]

The second eluting isomer (372 mg) from the chiral separation described in Example 458 was designated (*R). MS (ESI): mass calcd. for $C_{29}H_{30}F_2N_6O_5S$, 612.2; m/z found, 613.2 [M+H]$^+$. $^1$H NMR (400 MHz, CDCl$_3$) δ 8.22 (dd, J=4.6, 1.9 Hz, 1H), 8.09-7.96 (m, 2H), 7.15-6.96 (m, 4H), 6.85-6.72 (m, 2H), 4.87 (t, J=7.9 Hz, 1H), 4.65 (s, 1H), 4.49-4.43 (m, 1H), 4.33 (d, J=14.4 Hz, 1H), 4.30-4.18 (m, 2H), 3.76-3.63 (m, 1H), 3.66-3.52 (m, 2H), 3.50 (d, J=12.5 Hz, 2H), 3.20 (dd, J=13.1, 4.0 Hz, 1H), 3.05 (qd, J=9.3, 8.8, 4.6 Hz, 2H), 2.90 (dd, J=15.6, 8.0 Hz, 1H), 2.71 (s, 3H), 2.11 (s, 3H).

Example 460: 3-(3-(Difluoromethyl)-8-methyl-[1,2,4]triazolo[4,3-a]pyridin-7-yl)-3-(3-(((*S)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic Acid

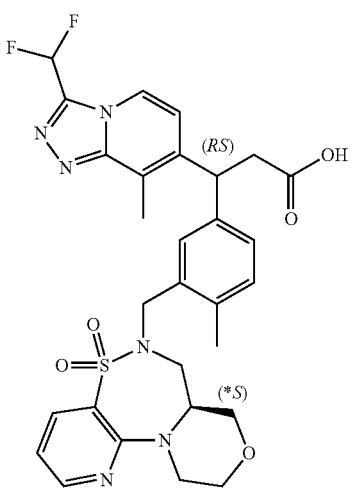 [SMILES: Cc1ccc(C(CC(=O)O)c2ccn3c(C(F)F)nnc3c2C)cc1CN1C[C@H]2COCCN2c2ncccc2S1(=O)=O]

Step A: Ethyl 3-(3-(difluoromethyl)-8-methyl-[1,2,4]triazolo[4,3-a]pyridin-7-yl)-3-(3-(((*R)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoate.

Diisopropyl azodicarboxylate (0.45 mL, 2.28 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 500 mg, 1.24 mmol), (*S)-6,7,7a,8,10,11-hexahydro-[1,4]oxazino[3,4-d]pyrido[2,3-f][1,2,5]thiadiazepine 5,5-dioxide (Intermediate 13, 444 mg, 1.74 mmol), and triphenylphosphine (481 mg, 1.83 mmol) in THF (8.7 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (780 mg, 98%) as a white foam. MS (ESI): mass calcd. for $C_{31}H_{34}F_2N_6O_5S$, 640.2; m/z found, 641.2 [M+H]$^+$. $^1$H NMR (500 MHz, CDCl$_3$) δ 8.25-8.21 (m, 1H), 8.10 (t, J=6.8 Hz, 1H), 8.00 (dt, J=7.8, 2.1 Hz, 1H), 7.66-7.58 (m, 1H), 7.43-7.38 (m, 1H), 7.17-7.02 (m, 3H), 6.85-6.73 (m, 2H), 4.94-4.85 (m, 1H), 4.55-4.50 (m, 1H), 4.43-4.31 (m, 1H), 4.27-4.23 (m, 1H), 4.09-3.98 (m, 3H), 3.73-3.44 (m, 4H), 3.34-3.19 (m, 1H), 3.14-3.04 (m, 1H), 2.99-2.93 (m, 1H), 2.77 (d, J=11.0 Hz, 2H), 2.16 (d, J=8.1 Hz, 2H), 1.98 (s, 3H), 1.19 (t, J=7.1 Hz, 3H).

Step B: 3-(3-(Difluoromethyl)-8-methyl-[1,2,4]triazolo[4,3-a]pyridin-7-yl)-3-(3-(((*S)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid. A mixture containing ethyl 3-(3-(difluoromethyl)-8-methyl-[1,2,4]triazolo[4,3-a]pyridin-7-yl)-3-(3-(((*S)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoate (780 mg, 1.22 mmol), 1 M aqueous NaOH solution (11 mL, 11 mmol), and THF (11 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered, and concentrated to dryness under reduced pressure. The residue was purified by flash column chromatography (eluent: 0-10% MeOH/DCM) to provide the title compound (720 mg, 97%) as a white foam. MS (ESI): mass calcd. for $C_{29}H_{30}F_2N_6O_5S$, 612.2; m/z found, 613.2 [M+H]$^+$. $^1$H NMR (500 MHz, CDCl$_3$) δ 10.61 (s, 1H), 8.33-8.30 (m, 1H), 8.20 (d, J=7.2 Hz, 1H), 8.08-8.04 (m, 1H), 7.28-7.19 (m, 1H), 7.18-7.06 (m, 2H), 6.96-6.83 (m, 2H), 4.99-4.88 (m, 1H), 4.63 (dt, J=12.6, 3.6 Hz, 1H), 4.56-4.24 (m, 4H), 4.10 (dt, J=11.2, 3.5 Hz, 1H), 3.79-3.52 (m, 4H), 3.28-3.20 (m, 1H), 3.26-3.17 (m, 1H), 3.19-3.12 (m, 1H), 2.78 (s, 1H), 2.71 (s, 3H), 2.19 (d, J=2.7 Hz, 3H).

Example 461: (*S)-3-(3-(Difluoromethyl)-8-methyl-[1,2,4]triazolo[4,3-a]pyridin-7-yl)-3-(3-(((*S)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic Acid

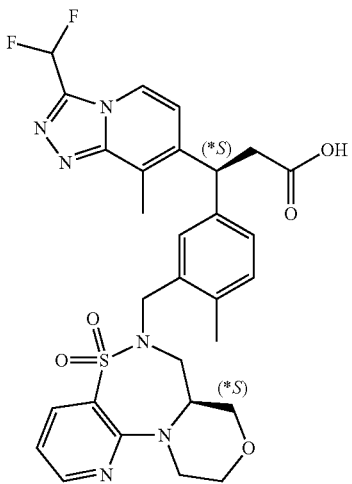 [SMILES: Cc1ccc([C@H](CC(=O)O)c2ccn3c(C(F)F)nnc3c2C)cc1CN1C[C@H]2COCCN2c2ncccc2S1(=O)=O]

The mixture of 3-(3-(Difluoromethyl)-8-methyl-[1,2,4]triazolo[4,3-a]pyridin-7-yl)-3-(3-(((*S)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic acid isomers (Example 460, 720 mg) was separated by chiral SFC (stationary phase: Chiralpak AD-H 5 μm 250×30 mm, isocratic mobile phase: 60% $CO_2$, 40% iPrOH) to afford two diastereomers. The first eluting isomer (331 mg) was designated (*S). MS (ESI): mass calcd. for $C_{29}H_{30}F_2N_6O_5S$, 612.2; m/z found, 613.2 [M+H]$^+$. $^1$H NMR (400 MHz, CDCl$_3$) δ 8.34 (dd, J=4.6, 1.8 Hz, 1H), 8.23 (d, J=7.2 Hz, 1H), 8.11 (dd, J=7.8, 1.9 Hz, 1H), 7.31 (d, J=2.0 Hz, 1H), 7.17-7.09 (m, 1H), 7.03-6.89 (m, 3H), 4.94 (dd, J=9.8, 6.0 Hz, 1H), 4.73-4.63 (m, 1H), 4.59 (s, 2H), 4.56-4.46 (m, 2H), 4.33 (d, J=13.9 Hz, 1H), 4.18 (dt, J=11.4, 3.3 Hz, 1H), 3.84-3.66 (m, 4H), 3.32 (dd, J=13.4, 4.0 Hz, 1H), 3.27-3.21 (m, 1H), 3.13 (dd, J=14.6, 9.8 Hz, 1H), 2.98 (dd, J=14.6, 6.1 Hz, 1H), 2.75 (s, 3H), 2.22 (s, 3H).

Example 462: (*R)-3-(3-(Difluoromethyl)-8-methyl-[1,2,4]triazolo[4,3-a]pyridin-7-yl)-3-(3-(((*S)-5,5-dioxido-7a,8,10,11-tetrahydro-[1,4]oxazino[3,4-d]pyrido[2,3-f][1,2,5]thiadiazepin-6(7H)-yl)methyl)-4-methylphenyl)propanoic Acid

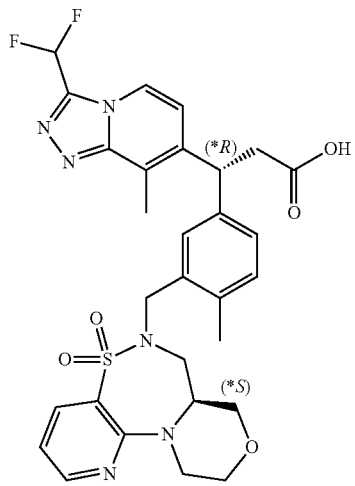 [SMILES: Cc1ccc([C@@H](CC(=O)O)c2ccn3c(C(F)F)nnc3c2C)cc1CN1C[C@H]2COCCN2c2ncccc2S1(=O)=O]

The second eluting isomer (386 mg) from the chiral separation described in Example 461 was designated (*R). MS (ESI): mass calcd. for $C_{29}H_{30}F_2N_6O_5S$, 612.2; m/z found, 613.2 [M+H]$^+$. $^1$H NMR (400 MHz, CDCl$_3$) δ 8.23 (dd, J=4.6, 1.9 Hz, 1H), 8.12 (d, J=7.1 Hz, 1H), 8.00 (dd, J=7.8, 1.8 Hz, 1H), 7.22-7.12 (m, 2H), 7.07-6.99 (m, 1H), 6.90 (dd, J=7.8, 2.0 Hz, 1H), 6.87-6.78 (m, 2H), 4.98 (s, 1H), 4.84 (dd, J=9.5, 6.3 Hz, 1H), 4.61-4.51 (m, 1H), 4.39-4.35 (m, 2H), 4.22 (d, J=14.0 Hz, 1H), 4.09-3.90 (m, 1H), 3.72-3.55 (m, 4H), 3.21 (dd, J=13.3, 4.0 Hz, 1H), 3.16-3.11 (m, 1H), 3.04 (dd, J=14.8, 9.6 Hz, 1H), 2.89 (dd, J=14.8, 6.3 Hz, 1H), 2.64 (s, 3H), 2.11 (s, 3H).

Example 463: 3-(3-(Difluoromethyl)-8-methyl-[1,2,4]triazolo[4,3-a]pyridin-7-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic Acid

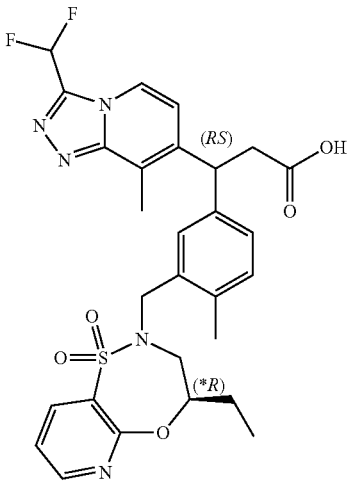 [SMILES: CC[C@@H]1CN(Cc2cc(C(CC(=O)O)c3ccn4c(C(F)F)nnc4c3C)ccc2C)S(=O)(=O)c2cccnc2O1]

Step A: Ethyl 3-(3-(difluoromethyl)-8-methyl-[1,2,4]triazolo[4,3-a]pyridin-7-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoate. Diisopropyl azodicarboxylate (0.41 mL, 2.07 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 500 mg, 1.24 mmol), (R)-4-ethyl-3,4-dihydro-2H-pyrido[2,3-b][1,4,5]oxathiazepine 1,1-dioxide (Intermediate 91, 397 mg, 1.74 mmol), and triphenylphosphine (529 mg, 2.02 mmol) in THF (8.7 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (730 mg, 96%) as a white foam. MS (ESI): mass calcd. for $C_{30}H_{33}F_2N_5O_5S$, 613.2; m/z found, 614.2 [M+H]$^+$. $^1$H NMR (500 MHz, CDCl$_3$) δ 8.46 (dt, J=4.6, 2.2 Hz, 1H), 8.25-8.20 (m, 1H), 8.14 (dd, J=7.3, 3.0 Hz, 1H), 7.58-7.37 (m, 1H), 7.31-7.22 (m, 1H), 6.83 (dd, J=7.3, 1.0 Hz, 1H), 4.96-4.91 (m, 1H), 4.43 (dt, J=14.3, 9.2 Hz, 2H), 4.15-4.01 (m, 3H), 3.58-3.52 (m, 1H), 3.16-3.10 (m, 2H), 3.00-2.95 (m, 1H), 2.80 (d, J=2.0 Hz, 3H), 2.39 (d, J=10.8 Hz, 1H), 2.29 (d, J=1.4 Hz, 3H), 2.02 (s, 1H), 1.80-1.64 (m, 1H), 1.56-1.51 (m, 1H), 1.24 (t, J=7.2 Hz, 1H), 1.15 (td, J=7.1, 2.2 Hz, 3H), 1.00 (dt, J=26.7, 7.4 Hz, 3H).

Step B: 3-(3-(Difluoromethyl)-8-methyl-[1,2,4]triazolo[4,3-a]pyridin-7-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic acid. A mixture containing ethyl 3-(3-(difluoromethyl)-8-methyl-[1,2,4]triazolo[4,3-a]pyridin-7-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoate (750 mg, 1.22 mmol), 1 M aqueous NaOH solution (11 mL, 11 mmol), and THF (11 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered, and concentrated to dryness under reduced pressure. The residue was purified by flash column chromatography (eluent: 0-10% MeOH/DCM) to provide the title compound (650 mg, 91%) as a white foam. MS (ESI): mass calcd. for $C_{28}H_{29}F_2N_5O_5S$, 585.6; m/z found, 586.2 [M+H]$^+$. $^1$H NMR (500 MHz, CDCl$_3$) δ 9.99 (s, 1H), 8.47 (dt, J=4.9, 1.9 Hz, 1H), 8.27-8.21 (m, 1H), 8.15 (dd, J=7.1, 5.0 Hz, 1H), 7.33-7.24 (m, 1H), 7.24-7.10 (m, 3H), 7.13-7.06 (m, 1H), 6.91 (dd, J=7.3, 2.6 Hz, 1H), 4.95 (dt, J=8.8, 6.3 Hz, 1H), 4.43 (t, J=14.4 Hz, 2H), 4.07 (dd, J=14.4, 9.6 Hz, 1H), 3.59-3.51 (m, 1H), 3.23-3.14 (m, 1H), 3.17-3.10 (m, 1H), 3.09-3.02 (m, 1H), 2.75 (d, J=4.8 Hz, 3H), 2.29 (s, 3H), 1.73-1.58 (m, 1H), 1.49-1.41 (m, 1H), 1.00-0.91 (m, 2H), 0.91 (d, J=7.4 Hz, 1H).

Example 464: (*S)-3-(3-(Difluoromethyl)-8-methyl-[1,2,4]triazolo[4,3-a]pyridin-7-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic Acid

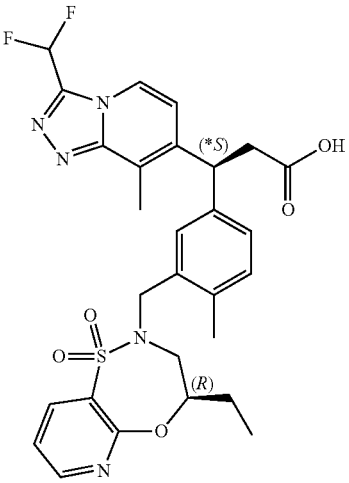

The mixture of 3-(3-(difluoromethyl)-8-methyl-[1,2,4]triazolo[4,3-a]pyridin-7-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic acid isomers (Example 463, 650 mg) was separated by chiral SFC (stationary phase: Chiralpak AD-H 5 μm 250×30 mm, isocratic mobile phase: 55% CO$_2$, 45% EtOH) to afford two diastereomers. The first eluting isomer (313 mg) was designated (*S). MS (ESI): mass calcd. for $C_{28}H_{29}F_2N_5O_5S$, 585.6; m/z found, 586.2 [M+H]$^+$. $^1$H NMR (500 MHz, CDCl$_3$) δ 8.48 (s, 1H), 8.25 (dd, J=7.7, 2.0 Hz, 1H), 8.14 (d, J=7.2 Hz, 1H), 7.29 (q, J=7.1 Hz, 2H), 7.22-7.07 (m, 3H), 6.88 (d, J=7.2 Hz, 1H), 4.95 (t, J=7.7 Hz, 1H), 4.47-4.38 (m, 2H), 4.12 (d, J=14.4 Hz, 1H), 3.73 (q, J=7.0 Hz, 1H), 3.58 (dd, J=14.9, 10.9 Hz, 1H), 3.21-3.13 (m, 2H), 3.04 (dd, J=15.8, 8.7 Hz, 1H), 2.77

(s, 3H), 2.30 (s, 3H), 1.69 (dt, J=14.7, 7.5 Hz, 1H), 1.55-1.51 (m, 1H), 0.99 (t, J=7.3 Hz, 3H).

Example 465: (*R)-3-(3-(Difluoromethyl)-8-methyl-[1,2,4]triazolo[4,3-a]pyridin-7-yl)-3-(3-(((R)-4-ethyl-1,1-dioxido-3,4-dihydro-2H-pyrido[2,3-b][1,4,5]oxathiazepin-2-yl)methyl)-4-methylphenyl)propanoic Acid

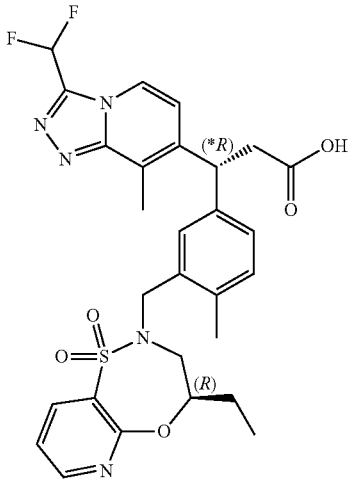

The second eluting isomer (297 mg) from the chiral separation described in Example 464 was designated (*R). MS (ESI): mass calcd. for C$_{28}$H$_{29}$F$_2$N$_5$O$_5$S, 585.6; m/z found, 586.2 [M+H]$^+$. $^1$H NMR (500 MHz, CDCl$_3$) δ 9.99 (s, 1H), 8.47 (dt, J=4.9, 1.9 Hz, 1H), 8.27-8.21 (m, 1H), 8.15 (dd, J=7.1, 5.0 Hz, 1H), 7.33-7.24 (m, 1H), 7.24-7.10 (m, 3H), 7.13-7.06 (m, 1H), 6.91 (dd, J=7.3, 2.6 Hz, 1H), 4.95 (dt, J=8.8, 6.3 Hz, 1H), 4.43 (t, J=14.4 Hz, 2H), 4.07 (dd, J=14.4, 9.6 Hz, 1H), 3.59-3.52 (m, 1H), 3.23-3.14 (m, 1H), 3.17-3.10 (m, 1H), 3.09-3.02 (m, 1H), 2.75 (d, J=4.8 Hz, 3H), 2.29 (s, 3H), 1.73-1.58 (m, 1H), 1.49-1.43 (m, 1H), 1.00-0.91 (m, 2H), 0.91 (d, J=7.4 Hz, 1H).

Example 466: 3-(3-(Difluoromethyl)-8-methyl-[1,2,4]triazolo[4,3-a]pyridin-7-yl)-3-(3-((1,1-dioxidospiro[benzo[b][1,4,5]oxathiazepine-4,3'-oxetan]-2(3H)-yl)methyl)-4-methylphenyl)propanoic Acid

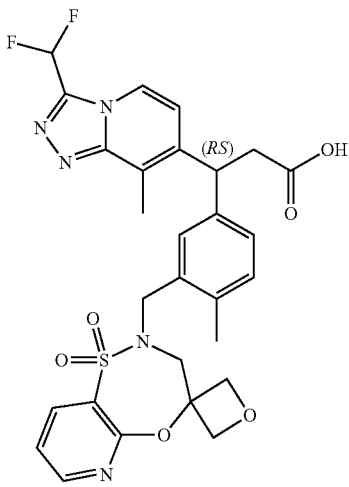 [SMILES: Cc1ccc(C(CC(=O)O)c2ccn3c(C(F)F)nnc3c2C)cc1CN1CC2(COC2)Oc2ncccc2S1(=O)=O]

Step A: Ethyl 3-(3-(difluoromethyl)-8-methyl-[1,2,4]triazolo[4,3-a]pyridin-7-yl)-3-(3-((1,1-dioxidospiro[benzo[b][1,4,5]oxathiazepine-4,3'-oxetan]-2(3H)-yl)methyl)-4-methylphenyl)propanoate. Diisopropyl azodicarboxylate (0.33 mL, 1.66 mmol) was added to ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 400 mg, 0.99 mmol), 2,3-dihydrospiro[benzo[b][1,4,5]oxathiazepine-4,3'-oxetane] 1,1-dioxide (Intermediate 7, 335 mg, 1.39 mmol), and triphenylphosphine (385 mg, 1.47 mmol) in THF (7.0 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (550 mg, 89%) as a white foam. MS (ESI): mass calcd. for C$_{31}$H$_{32}$F$_2$N$_4$O$_6$S, 626.2; m/z found, 627.2 [M+H]$^+$. $^1$H NMR (500 MHz, CDCl$_3$) δ 8.12 (d, J=7.2 Hz, 1H), 7.82 (dt, J=7.8, 1.9 Hz, 1H), 7.54 (td, J=7.7, 1.7 Hz, 1H), 7.40-7.23 (m, 3H), 7.19-7.05 (m, 4H), 6.82 (d, J=7.2 Hz, 1H), 4.93 (t, J=7.9 Hz, 1H), 4.57 (dd, J=10.6, 7.6 Hz, 2H), 4.30-4.21 (m, 3H), 4.13-3.99 (m, 2H), 3.76-3.63 (m, 2H), 3.12 (dd, J=15.8, 7.1 Hz, 1H), 3.00 (dd, J=15.8, 8.6 Hz, 1H), 2.79 (s, 3H), 2.24 (s, 3H), 1.14 (td, J=7.1, 1.7 Hz, 3H).

Step B: 3-(3-(Difluoromethyl)-8-methyl-[1,2,4]triazolo[4,3-a]pyridin-7-yl)-3-(3-((1,1-dioxidospiro[benzo[b][1,4,5]oxathiazepine-4,3'-oxetan]-2(3H)-yl)methyl)-4-methylphenyl)propanoic acid. A mixture containing ethyl 3-(3-(difluoromethyl)-8-methyl-[1,2,4]triazolo[4,3-a]pyridin-7-yl)-3-(3-((1,1-dioxidospiro[benzo[b][1,4,5]oxathiazepine-4,3'-oxetan]-2(3H)-yl)methyl)-4-methylphenyl)propanoate (550 mg, 0.88 mmol), 1 M aqueous NaOH solution (8.1 mL, 8.1 mmol), and THF (8.1 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over Na$_2$SO$_4$, filtered, and concentrated to dryness under reduced pressure. The residue was purified by flash column chromatography (eluent: 0-10% MeOH/DCM) to provide the title compound (500 mg, 95%) as a white foam. MS (ESI): mass calcd. for C$_{29}$H$_{28}$F$_2$N$_4$O$_6$S, 598.2; m/z found, 599.2 [M+H]$^+$. $^1$H NMR (500 MHz, CDCl$_3$) δ 8.51 (s, 1H), 8.07 (d, J=7.2 Hz, 1H), 7.77 (dd, J=7.8, 1.7 Hz, 1H), 7.59-7.42 (m, 3H), 7.35 (td, J=7.6, 3.0 Hz, 1H), 7.25-7.18 (m, 1H), 7.15-6.98 (m, 1H), 6.83 (d, J=7.3 Hz, 1H), 4.83 (t, J=7.9 Hz, 1H), 4.54 (dd, J=9.5, 7.6 Hz, 2H), 4.33 (d, J=14.4 Hz, 1H), 4.24-4.14 (m, 3H), 4.04 (q, J=7.1 Hz, 1H), 3.70 (d, J=15.2 Hz, 1H), 3.61 (d, J=15.2 Hz, 1H), 3.05 (dd, J=15.3, 8.4 Hz, 1H), 2.93 (dd, J=15.2, 7.4 Hz, 1H), 2.63 (s, 3H), 2.18 (s, 3H).

Example 467: (\*S)-3-(3-(Difluoromethyl)-8-methyl-[1,2,4]triazolo[4,3-a]pyridin-7-yl)-3-(3-((1,1-dioxidospiro[benzo[b][1,4,5]oxathiazepine-4,3'-oxetan]-2(3H)-yl)methyl)-4-methylphenyl)propanoic Acid

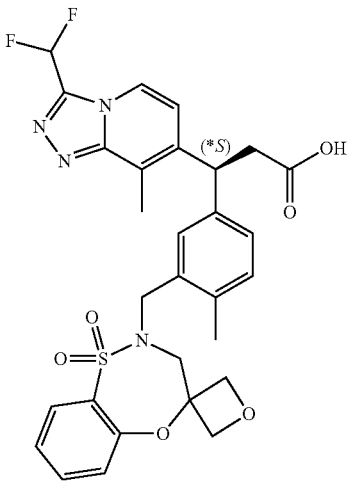 [SMILES: Cc1ccc([C@H](CC(=O)O)c2ccn3c(C(F)F)nnc3c2C)cc1CN1CC2(COC2)Oc2ccccc2S1(=O)=O]

The mixture of 3-(3-(difluoromethyl)-8-methyl-[1,2,4]triazolo[4,3-a]pyridin-7-yl)-3-(3-((1,1-dioxidospiro[benzo[b][1,4,5]oxathiazepine-4,3'-oxetan]-2(3H)-yl)methyl)-4-methylphenyl)propanoic acid isomers (Example 466, 500 mg) was separated by chiral SFC (stationary phase: Chiralpak AD-H 5 μm 250×30 mm, isocratic mobile phase: 55% $CO_2$, 45% EtOH) to afford two enantiomers. The first eluting isomer (199 mg) was further purified by preparative LC (Stationary phase: irregular bare silica 24 g, Mobile phase: Gradient from 90% DCM, 10% MeOH to 85% DCM, 15% MeOH) to afford the isomer (172 mg) which was designated (\*S). MS (ESI): mass calcd. for $C_{29}H_{28}F_2N_4O_6S$, 598.2; m/z found, 599.2 [M+H]$^+$. $^1$H NMR (500 MHz, CDCl$_3$) δ 8.14 (d, J=7.2 Hz, 1H), 7.86 (d, J=7.8 Hz, 1H), 7.57 (t, J=7.8 Hz, 1H), 7.39-7.26 (m, 3H), 7.21 (d, J=9.1 Hz, 1H), 7.11 (d, J=8.8 Hz, 1H), 7.02 (d, J=7.8 Hz, 1H), 6.88 (d, J=7.1 Hz, 1H), 4.86 (d, J=8.4 Hz, 1H), 4.64 (s, 2H), 4.42 (d, J=14.6 Hz, 1H), 4.27 (d, J=13.4 Hz, 3H), 3.80 (d, J=15.4 Hz, 1H), 3.76-3.68 (m, 1H), 3.06 (s, 1H), 2.93 (s, 1H), 2.69 (s, 3H), 2.25 (s, 3H).

Example 468: (\*R)-3-(3-(Difluoromethyl)-8-methyl-[1,2,4]triazolo[4,3-a]pyridin-7-yl)-3-(3-((1,1-dioxidospiro[benzo[b][1,4,5]oxathiazepine-4,3'-oxetan]-2(3H)-yl)methyl)-4-methylphenyl)propanoic Acid

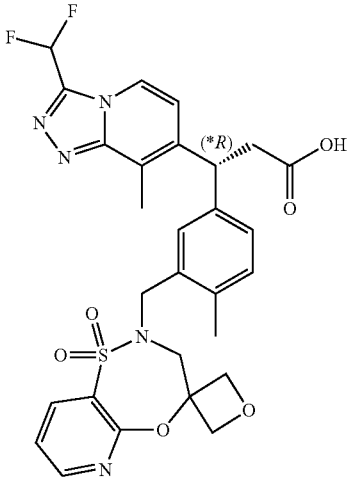 [SMILES: Cc1ccc([C@@H](CC(=O)O)c2ccn3c(C(F)F)nnc3c2C)cc1CN1CC2(COC2)Oc2ncccc2S1(=O)=O]

The second eluting isomer (209 mg) from the chiral separation described in Example 467 was designated (\*R). MS (ESI): mass calcd. for $C_{29}H_{28}F_2N_4O_6S$, 598.6; m/z found, 599.2 [M+H]$^+$. $^1$H NMR (500 MHz, CDCl$_3$) δ 8.18 (d, J=7.2 Hz, 1H), 7.88 (dd, J=7.8, 1.7 Hz, 1H), 7.58 (td, J=7.8, 1.7 Hz, 1H), 7.38 (dd, J=8.1, 1.1 Hz, 1H), 7.33 (dd, J=7.6, 1.2 Hz, 1H), 7.33-7.07 (m, 3H), 7.04 (dd, J=7.9, 1.9 Hz, 1H), 6.93 (d, J=7.3 Hz, 1H), 4.90 (t, J=8.0 Hz, 1H), 4.67 (t, J=8.0 Hz, 2H), 4.48 (d, J=14.3 Hz, 1H), 4.34-4.23 (m, 3H), 3.82 (d, J=15.3 Hz, 1H), 3.76-3.69 (m, 1H), 3.12 (dd, J=14.9, 9.1 Hz, 1H), 3.01 (dd, J=14.9, 6.8 Hz, 1H), 2.72 (s, 3H), 2.28 (s, 3H).

Example 469: 3-(3-(Difluoromethyl)-8-methyl-[1,2,4]triazolo[4,3-a]pyridin-7-yl)-3-(3-((1',1'-dioxidospiro[oxetane-3,4'-pyrido[2,3-b][1,4,5]oxathiazepin]-2'(3'H)-yl)methyl)-4-methylphenyl)propanoic Acid

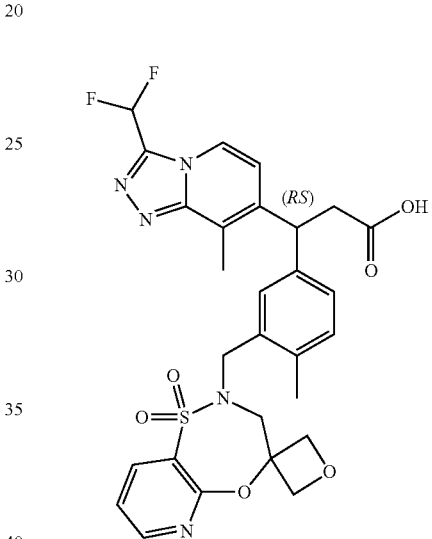

Step A: Ethyl 3-(3-(difluoromethyl)-8-methyl-[1,2,4]triazolo[4,3-a]pyridin-7-yl)-3-(3-((1',1'-dioxidospiro[oxetane-3,4'-pyrido[2,3-b][1,4,5]oxathiazepin]-2'(3'H)-yl)methyl)-4-methylphenyl)propanoate. Diisopropyl azodicarboxylate (0.33 mL, 1.66 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 400 mg, 0.99 mmol), 2',3'-dihydrospiro[oxetane-3,4'-pyrido[2,3-b][1,4,5]oxathiazepine] 1',1'-dioxide (Intermediate 59, 337 mg, 1.39 mmol), and triphenylphosphine (385 mg, 1.47 mmol) in THF (7.0 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (540 mg, 87%) as a white foam. MS (ESI): mass calcd. for $C_{30}H_{31}F_2N_5O_6S$, 627.2; m/z found, 628.2 [M+H]$^+$. $^1$H NMR (500 MHz, CDCl$_3$) δ 8.47 (dd, J=4.8, 1.9 Hz, 1H), 8.14 (dd, J=7.6, 1.9 Hz, 1H), 8.07 (d, J=7.2 Hz, 1H), 7.63-7.53 (m, 2H), 7.50-7.32 (m, 3H), 7.30-7.18 (m, 1H), 7.14-6.98 (m, 4H), 6.76 (d, J=7.2 Hz, 1H), 4.87 (t, J=7.9 Hz, 1H), 4.64 (dd, J=7.6, 6.2 Hz, 2H), 4.37-4.23 (m, 2H), 3.77-3.63 (m, 1H), 3.06 (dd, J=15.8, 7.2 Hz, 1H), 2.94 (dd, J=15.8, 8.6 Hz, 1H), 2.74 (s, 3H), 2.18 (s, 3H), 1.09 (t, J=7.1 Hz, 3H).

Step B: 3-(3-(Difluoromethyl)-8-methyl-[1,2,4]triazolo[4,3-a]pyridin-7-yl)-3-(3-((1',1'-dioxidospiro[oxetane-3,4'-pyrido[2,3-b][1,4,5]oxathiazepin]-2'(3'H)-yl)methyl)-4-methylphenyl)propanoic acid. A mixture containing ethyl 3-(3-(difluoromethyl)-8-methyl-[1,2,4]triazolo[4,3-a]pyridin-7-yl)-3-(3-((1',1'-dioxidospiro[oxetane-3,4'-pyrido[2,3-b][1,4,5]oxathiazepin]-2'(3'H)-yl)methyl)-4-methylphenyl)propanoate (540 mg, 0.86 mmol), 1 M aqueous NaOH solution (8 mL, 8 mmol), and THF (8 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered, and concentrated to dryness under reduced pressure. The residue was purified by flash column chromatography (eluent: 0-10% MeOH/DCM) to provide the title compound (480 mg, 93%) as a white foam. MS (ESI): mass calcd. for $C_{28}H_{27}F_2N_5O_6S$, 599.2; m/z found, 600.2 [M+H]$^+$. $^1$H NMR (500 MHz, CDCl$_3$) δ 10.58 (s, 1H), 8.52 (dd, J=4.9, 1.9 Hz, 1H), 8.21 (dd, J=7.7, 1.9 Hz, 1H), 8.15 (d, J=7.2 Hz, 1H), 7.36-7.29 (m, 1H), 7.22-7.02 (m, 4H), 6.92 (d, J=7.3 Hz, 1H), 4.93 (t, J=7.9 Hz, 1H), 4.67 (t, J=7.7 Hz, 2H), 4.43 (d, J=14.5 Hz, 1H), 4.36-4.25 (m, 3H), 3.84 (d, J=15.1 Hz, 1H), 3.75 (d, J=15.1 Hz, 1H), 3.15 (dd, J=15.5, 8.1 Hz, 1H), 3.03 (dd, J=15.5, 7.7 Hz, 1H), 2.71 (s, 3H), 2.24 (s, 3H).

Example 470: (*S)-3-(3-(Difluoromethyl)-8-methyl-[1,2,4]triazolo[4,3-a]pyridin-7-yl)-3-(3-((1',1'-dioxidospiro[oxetane-3,4'-pyrido[2,3-b][1,4,5]oxathiazepin]-2'(3'H)-yl)methyl)-4-methylphenyl)propanoic Acid

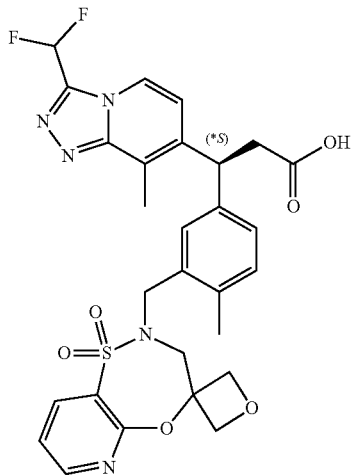 [SMILES: Cc1ccc([C@H](CC(=O)O)c2ccn3c(C(F)F)nnc3c2C)cc1CN1CC2(COC2)Oc2ncccc2S1(=O)=O]

The mixture of 3-(3-(difluoromethyl)-8-methyl-[1,2,4]triazolo[4,3-a]pyridin-7-yl)-3-(3-((1',1'-dioxidospiro[oxetane-3,4'-pyrido[2,3-b][1,4,5]oxathiazepin]-2'(3'H)-yl)methyl)-4-methylphenyl)propanoic acid isomers (Example 469, 480 mg) was separated by chiral SFC (stationary phase: Chiralpak AD-H 5 μm 250×30 mm, isocratic mobile phase: 55% $CO_2$, 45% EtOH) to afford two enantiomers. The first eluting isomer (223 mg) was further purified by preparative LC (Stationary phase: irregular bare silica 24 g, Mobile phase: Gradient from 90% DCM, 10% MeOH to 85% DCM, 15% MeOH) to afford the isomer (213 mg) which was designated (*S). MS (ESI): mass calcd. for $C_{28}H_{27}F_2N_5O_6S$, 599.2; m/z found, 600.2 [M+H]$^+$. $^1$H NMR (500 MHz, CDCl$_3$) δ 8.45 (dd, J=5.1, 1.9 Hz, 1H), 8.14 (dd, J=7.7, 2.0 Hz, 1H), 8.06 (d, J=7.1 Hz, 1H), 7.29-7.16 (m, 1H), 7.13 (d, J=10.7 Hz, 1H), 7.03 (t, J=8.3 Hz, 1H), 6.97 (d, J=7.9 Hz, 1H), 6.81 (d, J=7.2 Hz, 1H), 5.22 (s, 1H), 4.82 (t, J=8.0 Hz, 1H), 4.61 (t, J=6.8 Hz, 2H), 4.35 (d, J=14.6 Hz, 1H), 4.30-4.23 (m, 3H), 3.77 (d, J=15.3 Hz, 1H), 3.70 (d, J=15.2 Hz, 1H), 3.00 (s, 1H), 2.88 (s, 1H), 2.62 (s, 3H), 2.16 (s, 3H).

Example 471: (*R)-3-(3-(Difluoromethyl)-8-methyl-[1,2,4]triazolo[4,3-a]pyridin-7-yl)-3-(3-((1',1'-dioxidospiro[oxetane-3,4'-pyrido[2,3-b][1,4,5]oxathiazepin]-2'(3'H)-yl)methyl)-4-methylphenyl)propanoic Acid

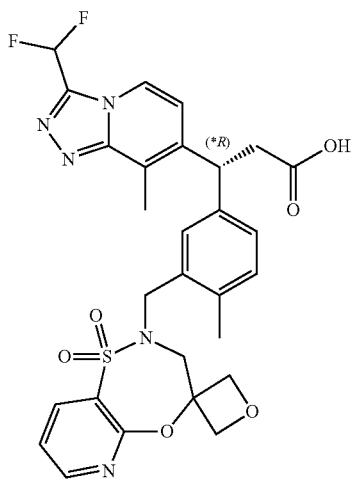 [SMILES: Cc1ccc([C@@H](CC(=O)O)c2ccn3c(C(F)F)nnc3c2C)cc1CN1CC2(COC2)Oc2ncccc2S1(=O)=O]

The second eluting isomer (202 mg) from the chiral separation described in Example 470 was designated (*R). MS (ESI): mass calcd. for $C_{28}H_{27}F_2N_5O_6S$, 599.2; m/z found, 600.2 [M+H]$^+$. $^1$H NMR (500 MHz, CDCl$_3$) δ 8.56 (dd, J=5.0, 1.9 Hz, 1H), 8.25 (dd, J=7.7, 1.9 Hz, 1H), 8.19 (d, J=7.2 Hz, 1H), 7.39-7.31 (m, 1H), 7.23 (s, 1H), 7.21-7.10 (m, 1H), 7.05 (dd, J=7.8, 1.9 Hz, 1H), 6.93 (d, J=7.3 Hz, 1H), 4.95-4.87 (m, 1H), 4.76 (dd, J=10.3, 7.7 Hz, 2H), 4.52 (d, J=14.2 Hz, 1H), 4.41-4.31 (m, 3H), 3.89 (d, J=15.3 Hz, 1H), 3.83-3.68 (m, 2H), 3.13 (dd, J=15.0, 9.2 Hz, 1H), 3.01 (dd, J=15.0, 6.7 Hz, 1H), 2.73 (s, 3H), 2.27 (s, 3H).

Example 472: 3-(3-(Difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)propanoic Acid

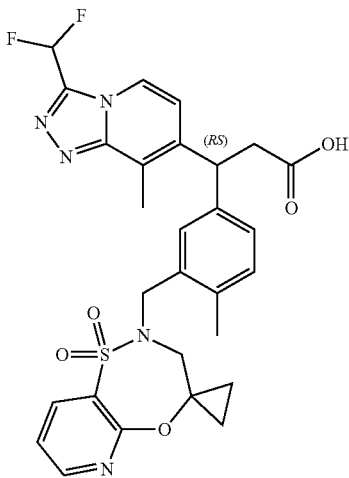 [SMILES: Cc1ccc(C(CC(=O)O)c2ccn3c(C(F)F)nnc3c2C)cc1CN1CC2(CC2)Oc2ncccc2S1(=O)=O]

Step A: Ethyl 3-(3-(difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)propanoate. Diisopropyl azodicarboxylate (0.33 mL, 1.66 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 400 mg, 0.99 mmol), 2',3'-dihydrospiro[cyclopropane-1,4'-pyrido[2,3-b][1,4,5]oxathiazepine] 1',1'-dioxide (Intermediate 5, 224 mg, 0.99 mmol), and triphenylphosphine (414 mg, 1.58 mmol) in THF (13 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (550 mg, 91%) as a white foam. MS (ESI): mass calcd. for $C_{30}H_{31}F_2N_5O_5S$, 611.2; m/z found, 612.2 [M+H]$^+$. $^1$H NMR (400 MHz, CDCl$_3$) δ 8.43 (dd, J=4.8, 2.0 Hz, 1H), 8.26 (dd, J=7.7, 2.0 Hz, 1H), 8.15 (d, J=7.2 Hz, 1H), 7.71-7.60 (m, 1H), 7.58-7.40 (m, 1H), 7.36-7.27 (m, 1H), 7.16-7.04 (m, 3H), 6.83 (d, J=7.2 Hz, 1H), 4.91 (t, J=7.8 Hz, 1H), 4.30 (s, 1H), 4.07 (dq, J=16.2, 7.1 Hz, 2H), 3.52 (s, 2H), 3.12 (dd, J=15.9, 7.3 Hz, 1H), 3.00 (dd, J=15.9, 8.5 Hz, 1H), 2.78 (s, 3H), 2.28 (s, 3H), 1.23-1.17 (m, 5H), 0.60-0.48 (m, 2H).

Step B: 3-(3-(Difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)propanoic acid. A mixture containing ethyl 3-(3-(difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)propanoate (550 mg, 0.90 mmol), 1 M aqueous NaOH solution (8.3 mL, 8.3 mmol), THF (8.3 mL) and ethanol (0.05 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered, and concentrated to dryness under reduced pressure. The residue was purified by flash column chromatography (eluent: 0-10% MeOH/DCM) to provide the title compound (520 mg, 99%) as a white foam. MS (ESI): mass calcd. for $C_{28}H_{27}F_2N_5O_5S$, 583.3; m/z found, 584.3 [M+H]$^+$. $^1$H NMR (500 MHz, CDCl$_3$) δ 9.18 (s, 1H), 8.44 (dd, J=4.9, 1.9 Hz, 1H), 8.30 (dd, J=7.6, 1.9 Hz, 1H), 8.16 (d, J=7.2 Hz, 1H), 7.37-7.30 (m, 1H), 7.16-7.08 (m, 2H), 7.07 (dd, J=8.0, 2.0 Hz, 1H), 6.88 (d, J=7.3 Hz, 1H), 5.30 (s, 1H), 4.95 (t, J=7.8 Hz, 1H), 4.37-4.26 (m, 2H), 3.49 (d, J=18.5 Hz, 2H), 3.17 (dd, J=15.9, 7.1 Hz, 1H), 3.04 (dd, J=15.9, 8.5 Hz, 1H), 2.76 (s, 3H), 2.29 (s, 3H), 1.06 (s, 2H), 0.53-0.43 (m, 2H).

Example 473: (*S)-3-(3-(Difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)propanoic Acid

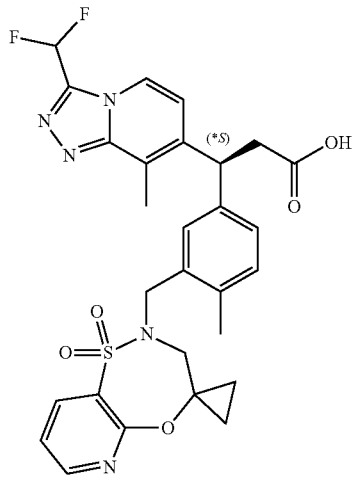 [SMILES: Cc1ccc([C@H](CC(=O)O)c2ccn3c(C(F)F)nnc3c2C)cc1CN1CC2(CC2)Oc2ncccc2S1(=O)=O]

The mixture of 3-(3-(difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)propanoic acid isomers (Example 472, 520 mg) was separated by chiral SFC (stationary phase: Chiralpak AD-H 5 μm 250×30 mm, isocratic mobile phase: 55% CO$_2$, 45% EtOH) to afford two enantiomers. The first eluting isomer (254 mg) was further purified by preparative LC (Stationary phase: irregular bare silica 40 g, Mobile phase: Gradient from 90% DCM, 10% MeOH to 80% DCM, 20% MeOH) to afford the isomer (235 mg) which was designated (*S). MS (ESI): mass calcd. for $C_{28}H_{27}F_2N_5O_5S$, 583.3; m/z found, 584.3 [M+H]$^+$. $^1$H NMR (500 MHz, CDCl$_3$) δ 8.45 (dd, J=5.1, 1.9 Hz, 1H), 8.14 (dd, J=7.7, 2.0 Hz, 1H), 8.06 (d, J=7.1 Hz, 1H), 7.29-7.16 (m, 1H), 7.13 (d, J=10.7 Hz, 1H), 7.03 (t, J=8.3 Hz, 1H), 6.97 (d, J=7.9 Hz, 1H), 6.81 (d, J=7.2 Hz, 1H), 5.22 (s, 1H), 4.82 (t, J=8.0 Hz, 1H), 4.61 (t, J=6.8 Hz, 2H), 4.35 (d, J=14.6 Hz, 1H), 4.30-4.23 (m, 3H), 3.77 (d, J=15.3 Hz, 1H), 3.70 (d, J=15.2 Hz, 1H), 3.00 (s, 1H), 2.88 (s, 1H), 2.62 (s, 3H), 2.16 (s, 3H).

Example 474: (*R)-3-(3-(Difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)propanoic Acid

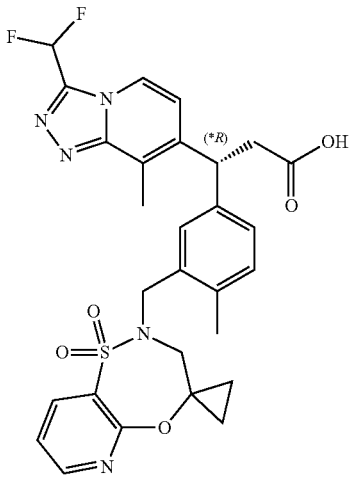 [SMILES: Cc1ccc([C@@H](CC(=O)O)c2ccn3c(C(F)F)nnc3c2C)cc1CN1CC2(CC2)Oc2ncccc2S1(=O)=O]

The second eluting isomer (202 mg) from the chiral separation described in Example 473 was designated (*R). MS (ESI): mass calcd. for $C_{28}H_{27}F_2N_5O_5S$, 583.3; m/z found, 584.3 [M+H]⁺. ¹H NMR (500 MHz, CDCl₃) δ 8.45 (dd, J=4.9, 1.9 Hz, 1H), 8.30 (dd, J=7.6, 1.9 Hz, 1H), 8.14 (d, J=7.2 Hz, 1H), 7.37-7.30 (m, 1H), 7.12 (d, J=8.0 Hz, 2H), 7.06 (d, J=7.5 Hz, 1H), 6.84 (d, J=7.3 Hz, 1H), 5.31 (s, 1H), 4.94 (t, J=7.8 Hz, 1H), 4.36 (d, J=14.5 Hz, 1H), 4.28 (d, J=14.6 Hz, 1H), 3.59 (d, J=15.5 Hz, 1H), 3.47 (d, J=12.3 Hz, 1H), 3.13 (dd, J=15.9, 7.0 Hz, 1H), 2.99 (dd, J=15.8, 8.5 Hz, 1H), 2.77 (s, 3H), 2.29 (s, 3H), 1.24 (t, J=7.0 Hz, 1H), 1.09-1.02 (m, 2H), 0.57-0.50 (m, 2H).

Example 475: 3-(3-(Difluoromethyl)-8-methyl-[1,2,4]triazolo[4,3-a]pyridin-7-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

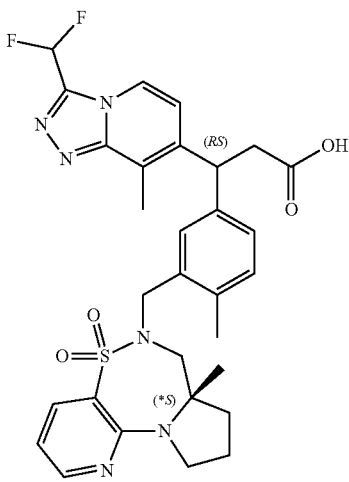 [SMILES: Cc1ccc(C(CC(=O)O)c2ccn3c(C(F)F)nnc3c2C)cc1CN1C[C@]2(C)CCCN2c2ncccc2S1(=O)=O]

Step A: Ethyl 3-(3-(difluoromethyl)-8-methyl-[1,2,4]triazolo[4,3-a]pyridin-7-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoate. DBAD (347 mg, 1.51 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 400 mg, 0.99 mmol), (*S)-7a-methyl-6,7,7a,8,9,10-hexahydropyrido[2,3-f]pyrrolo[2,1-d][1,2,5]thiadiazepine 5,5-dioxide (Intermediate 39, 326 mg, 1.29 mmol), and triphenylphosphine (403 mg, 1.54 mmol) in THF (12 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over Na₂SO₄, filtered and concentrated under reduced pressure. The residue was purified by flash column chromatography (eluent: 0-100% ethyl acetate/hexanes) to provide the title compound (500 mg, 79%) as a white foam. MS (ESI): mass calcd. for $C_{32}H_{36}F_2N_6O_4S$, 638.9; m/z found, 638.9 [M]⁺. ¹H NMR (500 MHz, CDCl₃) δ 8.41-8.32 (m, 1H), 8.12 (dd, J=7.7, 1.9 Hz, 1H), 7.44 (d, J=3.0 Hz, 1H), 7.31-7.27 (m, 1H), 7.23 (d, J=1.8 Hz, 1H), 7.15-7.03 (m, 2H), 6.95-6.85 (m, 3H), 4.26 (dd, J=21.6, 15.5 Hz, 1H), 4.16-4.02 (m, 4H), 3.06 (d, J=8.9 Hz, 1H), 2.90-2.77 (m, 4H), 2.24 (d, J=10.2 Hz, 4H), 2.02 (s, 3H), 1.23 (t, J=7.1 Hz, 3H), 1.14 (td, J=7.1, 2.5 Hz, 3H), 0.84 (d, J=6.0 Hz, 3H).

Step B: 3-(3-(Difluoromethyl)-8-methyl-[1,2,4]triazolo[4,3-a]pyridin-7-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid. A mixture containing ethyl 3-(3-(difluoromethyl)-8-methyl-[1,2,4]triazolo[4,3-a]pyridin-7-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoate (500 mg, 0.78 mmol), 1 M aqueous NaOH solution (7.2 mL, 7.2 mmol), THF (7.2 mL) and ethanol (0.05 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over Na₂SO₄, filtered, and concentrated to dryness under reduced pressure. The residue was purified by flash column chromatography (eluent: 0-10% MeOH/DCM) to provide the title compound (440 mg, 92%) as a white foam. MS (ESI): mass calcd. for $C_{30}H_{32}F_2N_6O_4S$, 610.2; m/z found, 611.3 [M+H]⁺. ¹H NMR (500 MHz, CDCl₃) δ 8.38 (s, 1H), 8.16 (dd, J=13.6, 7.4 Hz, 2H), 7.29 (d, J=14.8 Hz, 2H), 7.15-7.02 (m, 3H), 6.92 (dt, J=13.4, 7.2 Hz, 2H), 5.85 (s, 1H), 4.96 (d, J=8.2 Hz, 1H), 4.78 (t, J=15.8 Hz, 1H), 4.30-4.22 (m, 1H), 3.93 (d, J=10.1 Hz, 1H), 3.57 (s, 1H), 3.21-3.10 (m, 1H), 3.04 (s, 1H), 2.84-2.80 (m, 3H), 2.26 (d, J=11.6 Hz, 3H), 1.88 (d, J=19.7 Hz, 3H), 1.79 (d, J=6.3 Hz, 1H), 0.86 (d, J=6.9 Hz, 3H).

739

Example 476: (*S)-3-(3-(Difluoromethyl)-8-methyl-[1,2,4]triazolo[4,3-a]pyridin-7-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

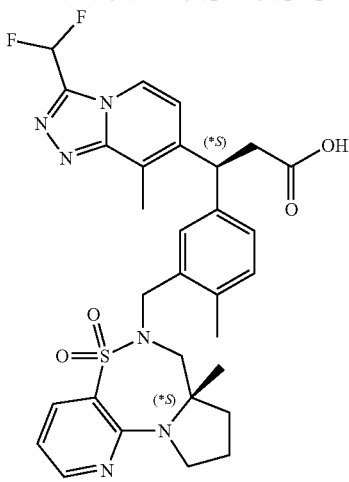 [SMILES: Cc1ccc([C@H](CC(=O)O)c2ccn3c(C(F)F)nnc3c2C)cc1CN1C[C@]2(C)CCCN2c2ncccc2S1(=O)=O]

The mixture of 3-(3-(difluoromethyl)-8-methyl-[1,2,4]triazolo[4,3-a]pyridin-7-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic acid isomers (Example 475, 440 mg) was separated by chiral SFC (stationary phase: Chiralpak IA 5 µm 250×20 mm, isocratic mobile phase: 60% $CO_2$, 40% EtOH) to afford two diastereomers. The first eluting isomer (195 mg) was designated (*S). MS (ESI): mass calcd. for $C_{30}H_{32}F_2N_6O_4S$, 610.2; m/z found, 611.3 [M+H]+. $^1$H NMR (500 MHz, CDCl$_3$) δ 8.31 (dd, J=4.8, 1.8 Hz, 1H), 8.11-7.99 (m, 2H), 7.31-7.17 (m, 2H), 7.18-7.02 (m, 1H), 7.05-6.91 (m, 2H), 6.90-6.76 (m, 2H), 5.85 (s, 1H), 4.90 (dd, J=8.9, 6.8 Hz, 1H), 4.68 (d, J=15.8 Hz, 1H), 4.21 (d, J=15.8 Hz, 1H), 3.89-3.82 (m, 1H), 3.71 (d, J=14.7 Hz, 1H), 3.49-3.45 (m, 1H), 3.14 (dd, J=16.0, 6.8 Hz, 1H), 3.00 (dd, J=16.0, 8.9 Hz, 1H), 2.72 (s, 3H), 2.18 (s, 3H), 1.84-1.68 (m, 4H), 0.78 (s, 3H).

Example 477: (*R)-3-(3-(Difluoromethyl)-8-methyl-[1,2,4]triazolo[4,3-a]pyridin-7-yl)-3-(4-methyl-3-(((*S)-7a-methyl-5,5-dioxido-7a,8,9,10-tetrahydropyrido[2,3-f]pyrrolo[2,1-d][1,2,5]thiadiazepin-6(7H)-yl)methyl)phenyl)propanoic Acid

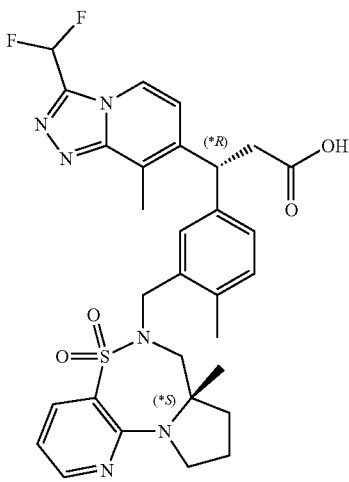 [SMILES: Cc1ccc([C@@H](CC(=O)O)c2ccn3c(C(F)F)nnc3c2C)cc1CN1C[C@]2(C)CCCN2c2ncccc2S1(=O)=O]

740

The second eluting isomer (202 mg) from the chiral separation described in Example 476 was designated (*R). MS (ESI): mass calcd. for $C_{30}H_{32}F_2N_6O_4S$, 610.2; m/z found, 611.3 [M+H]+. $^1$H NMR (500 MHz, CDCl$_3$) δ 8.38 (dd, J=4.8, 1.9 Hz, 1H), 8.23-8.11 (m, 2H), 7.26 (d, J=1.9 Hz, 1H), 7.20-7.06 (m, 3H), 7.00-6.86 (m, 2H), 6.48 (s, 1H), 5.31 (s, 1H), 5.01-4.94 (m, 1H), 4.80 (d, J=15.3 Hz, 1H), 4.27 (d, J=15.3 Hz, 1H), 3.95-3.85 (m, 1H), 3.66 (d, J=14.7 Hz, 1H), 3.57-3.48 (m, 1H), 3.20 (dd, J=16.1, 6.8 Hz, 1H), 3.09 (dd, J=16.1, 8.9 Hz, 1H), 2.79 (s, 3H), 2.28 (s, 3H), 1.80 (dt, J=8.0, 5.1 Hz, 2H), 1.80-1.69 (m, 1H), 1.69-1.63 (m, 1H), 0.83 (s, 3H).

Example 478: 3-(6-(((*S)-5,5-Dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

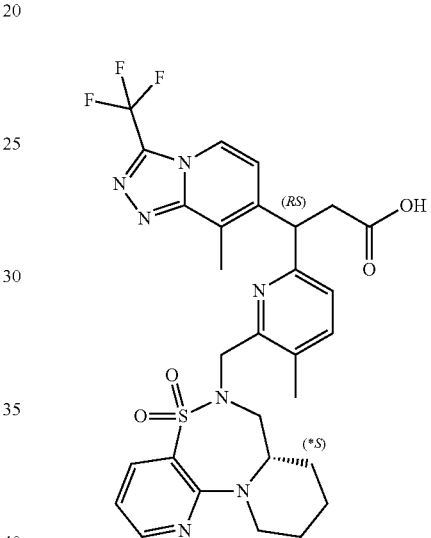

Step A: Ethyl 3-(6-(((*S)-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoate. Diisopropyl azodicarboxylate (0.15 mL, 0.78 mmol) was added to a stirring mixture of ethyl 3-(6-(hydroxymethyl)-5-methylpyridin-2-yl)-3-(8-methyl-3-(trifluoromethyl)-[1,2,4]triazolo[4,3-a]pyridin-7-yl)propanoate (Example 33, Step B, 200 mg, 0.47 mmol), (*S)-7,7a,8,9,10,11-hexahydro-6H-dipyrido[2,1-d:2',3'-f][1,2,5]thiadiazepine 5,5-dioxide (Intermediate 2, 170 mg, 0.67 mmol), and triphenylphosphine (184 mg, 0.70 mmol) in THF (5 mL) at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (311 mg, 99%) as a white foam. MS (ESI): mass calcd. for $C_{31}H_{34}F_3N_7O_4S$, 657.8; m/z found, 657.8 [M]+. $^1$H NMR (500 MHz, CDCl$_3$) δ 8.25 (dd, J=4.7, 1.8 Hz, 1H), 8.03-7.93 (m, 2H), 7.39-7.33 (m, 1H), 7.30-7.22 (m, 1H), 6.78 (dd, J=7.8, 4.7 Hz, 1H), 5.00 (q, J=7.7 Hz, 1H), 4.71-4.56 (m, 2H), 4.38-4.22 (m, 2H), 4.11-3.95 (m, 2H), 3.59-3.31 (m, 4H), 3.07-3.00 (m, 1H), 2.88-2.84 (m, 3H), 2.29-2.21 (m, 1H), 1.99 (s, 2H), 1.81-1.60 (m, 4H), 1.57-1.50 (m, 2H), 1.39 (tt, J=10.5, 4.7 Hz, 1H), 1.12 (t, J=7.1 Hz, 3H).

Step B: 3-(6-(((*S)-5,5-Dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid. A mixture containing ethyl 3-(6-(((*S)-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoate (311 mg, 0.47 mmol), 1 M aqueous NaOH solution (4.4 mL, 4.4 mmol), THF (4.4 mL) and ethanol (0.03 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered, concentrated to dryness under reduced pressure. The residue was purified by flash column chromatography (eluent: 0-10% MeOH/DCM) to provide the title compound (296 mg, 99%) as a white foam. This foam was further purified via preparative LC (Stationary phase: irregular bare silica 40 g, Mobile phase: 94% DCM, 6% MeOH) to provide the title compound as a white foam (286 mg). MS (ESI): mass calcd. for $C_{29}H_{30}F_3N_7O_4S$, 629.2; m/z found, 629.9 [M]+. $^1$H NMR (500 MHz, $CDCl_3$) δ 8.33-8.30 (m, 1H), 8.09-8.03 (m, 1H), 7.99 (dd, J=14.1, 7.2 Hz, 1H), 7.47-7.38 (m, 1H), 7.28 (d, J=2.2 Hz, 1H), 7.10-7.00 (m, 1H), 6.86-6.82 (m, 1H), 5.08-4.99 (m, 1H), 4.73 (dd, J=14.6, 2.7 Hz, 1H), 4.66 (tt, J=11.4, 5.8 Hz, 1H), 4.39-4.26 (m, 2H), 3.64-3.35 (m, 5H), 3.09-3.05 (m, 1H), 2.87 (d, J=3.7 Hz, 3H), 2.34 (s, 1H), 2.28 (s, 2H), 1.78 (s, 2H), 1.83-1.68 (m, 1H), 1.21 (t, J=7.0 Hz, 3H).

Example 479: (*S)-3-(6-(((*S)-5,5-Dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

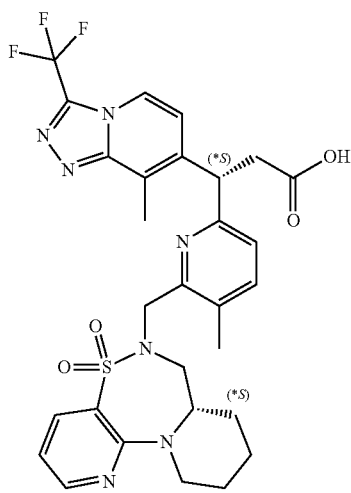 [SMILES: Cc1ccc([C@@H](CC(=O)O)c2ccn3c(C(F)(F)F)nnc3c2C)nc1CN1C[C@@H]2CCCCN2c2ncccc2S1(=O)=O]

The mixture of 3-(6-(((S)-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid isomers (Example 478, 286 mg) was separated by chiral SFC (Chiralpak AD-H 5 µm 250×20 mm, Mobile phase: 50% $CO_2$, 50% EtOH) to afford two diastereomers. The first eluting diastereomer (124 mg) was further purified using preparative LC (Stationary phase: irregular bare silica 40 g, Mobile phase: 97% DCM, 3% MeOH) to provide the diastereomer (117 mg) which was designated (*S). MS (ESI): mass calcd. for $C_{29}H_{30}F_3N_7O_4S$, 629.2; m/z found, 629.9 [M]+. $^1$H NMR (500 MHz, $CDCl_3$) δ 8.32 (dd, J=4.6, 1.9 Hz, 1H), 8.06 (dd, J=7.8, 1.9 Hz, 1H), 8.00 (d, J=7.2 Hz, 1H), 7.43-7.38 (m, 1H), 7.23 (d, J=7.3 Hz, 1H), 7.03 (d, J=7.8 Hz, 1H), 6.84 (dd, J=7.8, 4.6 Hz, 1H), 5.04 (t, J=7.4 Hz, 1H), 4.73 (d, J=15.2 Hz, 1H), 4.64 (dt, J=10.3, 5.1 Hz, 1H), 4.35 (dd, J=14.3, 4.2 Hz, 2H), 3.73 (q, J=7.0 Hz, 1H), 3.63-3.48 (m, 3H), 3.45-3.35 (m, 1H), 3.01 (dd, J=16.4, 6.7 Hz, 1H), 2.88 (s, 3H), 2.29 (s, 3H), 1.83-1.72 (m, 1H), 1.63 (dd, J=13.7, 6.5 Hz, 1H), 1.59-1.53 (m, 1H), 1.33-1.21 (m, 3H).

Example 480: (*R)-3-(6-(((*S)-5,5-Dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

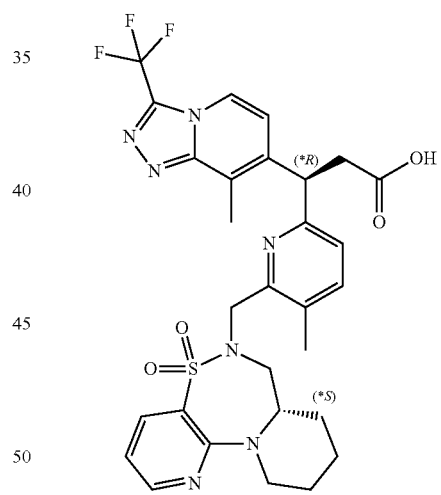

The second eluting diastereomer (130 mg) from the chiral separation described in Example 479 was designated (*R). MS (ESI): mass calcd. for $C_{29}H_{30}F_3N_7O_4S$, 629.2; m/z found, 629.9 [M]+. $^1$H NMR (500 MHz, $CDCl_3$) δ 8.32 (dd, J=4.7, 1.8 Hz, 1H), 8.06 (dd, J=7.8, 1.8 Hz, 1H), 7.98 (d, J=7.2 Hz, 1H), 7.47-7.38 (m, 1H), 7.20 (d, J=7.3 Hz, 1H), 7.09 (d, J=7.8 Hz, 1H), 6.85 (dd, J=7.8, 4.7 Hz, 1H), 5.02 (t, J=7.3 Hz, 1H), 4.73 (d, J=14.1 Hz, 1H), 4.63 (dq, J=14.3, 4.5 Hz, 1H), 4.39-4.23 (m, 2H), 3.74 (q, J=7.1 Hz, 1H), 3.54 (t, J=12.9 Hz, 1H), 3.53-3.40 (m, 2H), 3.29 (dd, J=13.4, 3.7 Hz, 1H), 3.10 (dd, J=16.4, 7.2 Hz, 1H), 2.88 (s, 3H), 2.35 (s, 3H), 1.79 (d, J=5.8 Hz, 1H), 1.77-1.67 (m, 1H), 1.62-1.40 (m, 3H), 1.25 (t, J=7.0 Hz, 1H).

Example 481: (R/S)-3-(6-((1',1'-Dioxidospiro[cyclo-propane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic Acid

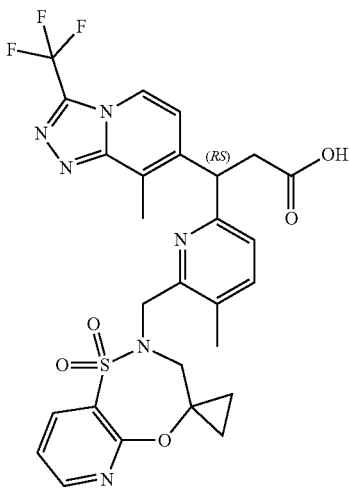 [SMILES: Cc1ccc(C(CC(=O)O)c2ccn3c(C(F)(F)F)nnc3c2C)nc1CN1CC2(CC2)Oc2ncccc2S1(=O)=O]

Step A: Ethyl 3-(6-((1',1'-dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoate. DBAD (149 mg, 0.65 mmol) was added to a stirring mixture of ethyl 3-(6-(hydroxymethyl)-5-methylpyridin-2-yl)-3-(8-methyl-3-(trifluoromethyl)-[1,2,4]triazolo[4,3-a]pyridin-7-yl)propanoate (Example 33, Step B, 180 mg, 0.43 mmol), 2',3'-dihydrospiro[cyclopropane-1,4'-pyrido[2,3-b][1,4,5]oxathiazepine]1',1'-dioxide (Intermediate 5, 96.4 mg, 0.43 mmol), and triphenylphosphine (177 mg, 0.68 mmol) in THF (5.8 mL) at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (250 mg, 93%) as a white foam. MS (ESI): mass calcd. for $C_{29}H_{29}F_3N_6O_5S$, 630.2; m/z found, 630.8 [M+H]$^+$. $^1$H NMR (500 MHz, CDCl$_3$) δ 8.42 (dd, J=4.9, 1.9 Hz, 1H), 8.25 (dd, J=7.6, 1.9 Hz, 1H), 7.93 (d, J=7.2 Hz, 1H), 7.41 (d, J=7.9 Hz, 1H), 7.31 (dd, J=7.6, 4.9 Hz, 1H), 7.10-7.00 (m, 2H), 4.92 (t, J=7.6 Hz, 1H), 4.47 (d, J=13.4 Hz, 1H), 4.35 (d, J=13.4 Hz, 1H), 4.09-3.92 (m, 2H), 3.71 (d, J=15.1 Hz, 1H), 3.43 (d, J=15.4 Hz, 1H), 3.27 (dd, J=16.1, 8.2 Hz, 1H), 2.91-2.73 (m, 4H), 2.36 (s, 3H), 1.18-1.10 (m, 5H), 0.94-0.86 (m, 1H), 0.80-0.70 (m, 1H).

Step B: 3-(6-((1',1'-Dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid. A mixture containing ethyl 3-(6-((1',1'-dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoate (250 mg, 0.40 mmol), 1 M aqueous NaOH solution (3.7 mL, 3.7 mmol), THF (3.7 mL) and ethanol (0.02 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered, concentrated to dryness under reduced pressure. The residue was purified by flash column chromatography (eluent: 0-10% MeOH/DCM) to provide the title compound (230 mg, 96%) as a white foam.

This foam was further purified via preparative LC (Stationary phase: irregular bare silica 40 g, Mobile phase: 95% DCM, 5% MeOH) to provide the title compound as a white foam (220 mg, 92%). MS (ESI): mass calcd. for $C_{27}H_{25}F_3N_6O_5S$, 602.2; m/z found, 602.8 [M]-. $^1$H NMR (500 MHz, CDCl$_3$) δ 8.45 (dd, J=4.9, 2.0 Hz, 1H), 8.31 (dd, J=7.6, 1.9 Hz, 1H), 7.96 (d, J=7.2 Hz, 1H), 7.44 (d, J=7.9 Hz, 1H), 7.35 (dd, J=7.6, 4.9 Hz, 1H), 7.08 (dd, J=7.6, 4.7 Hz, 2H), 4.98 (t, J=7.5 Hz, 1H), 4.54 (d, J=13.5 Hz, 1H), 4.38 (d, J=13.5 Hz, 1H), 4.10 (q, J=7.1 Hz, 2H), 3.80 (d, J=14.9 Hz, 1H), 3.38 (dd, J=16.4, 8.0 Hz, 1H), 2.95 (dd, J=16.4, 7.0 Hz, 1H), 2.81 (s, 3H), 2.39 (s, 3H), 1.18 (dt, J=11.8, 6.1 Hz, 1H), 1.09 (dt, J=11.4, 6.1 Hz, 1H), 0.75 (dt, J=10.4, 6.5 Hz, 2H).

Example 482: (*S)-3-(6-((1',1'-Dioxidospiro[cyclo-propane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic Acid

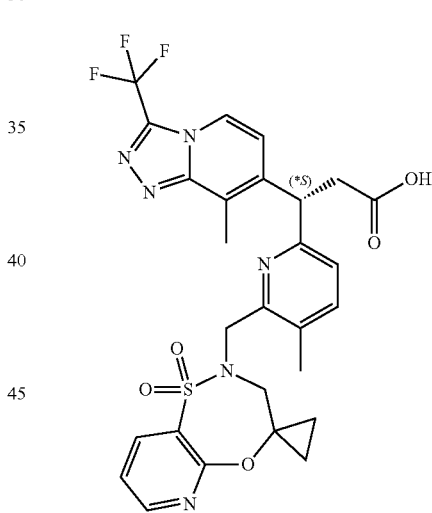

The mixture of 3-(6-((1',1'-dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid isomers (Example 481, 220 mg) was separated by chiral SFC (Chiralpak AD-H 5 μm 250×30 mm, Mobile phase: 65% CO$_2$, 35% MeOH) to afford two enantiomers. The first eluting enantiomer (100 mg) was designated (*S). MS (ESI): mass calcd. for $C_{27}H_{25}F_3N_6O_5S$, 602.2; m/z found, 602.8 [M]$^+$. $^1$H NMR (500 MHz, CDCl$_3$) δ 8.38 (dd, J=4.9, 1.9 Hz, 1H), 8.23 (dd, J=7.6, 2.0 Hz, 1H), 7.86 (d, J=7.2 Hz, 1H), 7.35 (d, J=7.8 Hz, 1H), 7.26 (dd, J=7.6, 4.9 Hz, 1H), 7.19 (s, 1H), 7.00 (dd, J=11.9, 7.5 Hz, 2H), 4.87 (t, J=7.5 Hz, 1H), 4.46 (d, J=13.6 Hz, 1H), 4.30 (d, J=13.6 Hz, 1H), 3.72 (d, J=15.7 Hz, 1H), 3.43 (d, J=15.6 Hz, 1H), 3.15 (dd, J=16.0, 7.6 Hz, 1H), 2.82-2.73 (m, 1H), 2.73 (s, 3H), 2.31 (s, 3H), 0.94-0.83 (m, 2H), 0.84 (d, J=6.7 Hz, 1H), 0.72-0.63 (m, 1H).

Example 483: (*R)-3-(6-((1',1'-Dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic Acid

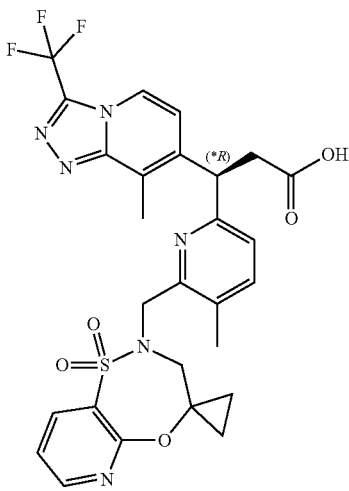 [SMILES: Cc1ccc([C@H](CC(=O)O)c2ccn3c(C(F)(F)F)nnc3c2C)nc1CN1CC2(CC2)Oc2ncccc2S1(=O)=O]

The second eluting enantiomer (100 mg) from the chiral separation described in Example 482 was designated (*R). MS (ESI): mass calcd. for $C_{27}H_{25}F_3N_6O_5S$, 602.2; m/z found, 602.8 [M]$^+$. $^1$H NMR (500 MHz, CDCl$_3$) δ 8.38 (dd, J=4.9, 1.9 Hz, 1H), 8.23 (dd, J=7.6, 2.0 Hz, 1H), 7.86 (d, J=7.2 Hz, 1H), 7.37-7.27 (m, 1H), 7.25 (dd, J=7.6, 4.9 Hz, 1H), 7.19 (s, 1H), 7.01 (t, J=8.1 Hz, 2H), 4.87 (t, J=7.6 Hz, 1H), 4.44 (d, J=13.6 Hz, 1H), 4.29 (d, J=13.6 Hz, 1H), 3.71 (d, J=15.7 Hz, 1H), 3.43 (d, J=15.7 Hz, 1H), 3.10 (dd, J=15.9, 7.5 Hz, 1H), 2.79-2.72 (m, 1H), 2.73 (s, 3H), 2.31 (s, 3H), 0.97-0.79 (m, 3H), 0.72-0.64 (m, 1H).

Example 484: 3-(6-((1,1-Dioxidospiro[benzo[b][1,4,5]oxathiazepine-4,3'-oxetan]-2(3H)-yl)methyl)-5-methylpyridin-2-yl)-3-(8-methyl-3-(trifluoromethyl)-[1,2,4]triazolo[4,3-a]pyridin-7-yl)propanoic Acid

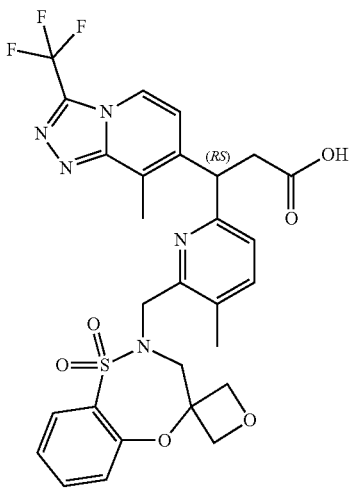 [SMILES: Cc1ccc(C(CC(=O)O)c2ccn3c(C(F)(F)F)nnc3c2C)nc1CN1CC2(COC2)Oc2ccccc2S1(=O)=O]

Step A: Ethyl 3-(6-((1',1'-dioxidospiro[oxetane-3,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoate. Diisopropyl azodicarboxylate (0.17 mL, 0.88 mmol) was added to a stirring mixture of ethyl 3-(6-(hydroxymethyl)-5-methylpyridin-2-yl)-3-(8-methyl-3-(trifluoromethyl)-[1,2,4]triazolo[4,3-a]pyridin-7-yl)propanoate (Example 33, Step B, 220 mg, 0.52 mmol), 2,3-dihydrospiro[benzo[b][1,4,5]oxathiazepine-4,3'-oxetane] 1,1-dioxide (Intermediate 7, 0.74 mmol), and triphenylphosphine (203 mg, 0.77 mmol) in THF (6 mL) at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (310 mg, 92%) as a white foam. MS (ESI): mass calcd. for $C_{30}H_{30}F_3N_5O_6S$, 645.2; m/z found, 645.8 [M]$^+$. $^1$H NMR (500 MHz, CDCl$_3$) δ 7.96 (d, J=7.2 Hz, 1H), 7.83 (dt, J=7.9, 1.8 Hz, 1H), 7.64-7.37 (m, 4H), 7.33-7.21 (m, 1H), 7.22-7.10 (m, 2H), 4.99 (t, J=7.6 Hz, 1H), 4.69 (dd, J=7.2, 2.8 Hz, 2H), 4.65-4.55 (m, 1H), 4.52 (d, J=7.4 Hz, 1H), 4.42-4.34 (m, 1H), 4.26 (d, J=14.0 Hz, 1H), 4.11-3.88 (m, 3H), 3.72 (d, J=15.3 Hz, 1H), 3.41 (dd, J=16.2, 8.0 Hz, 1H), 2.97 (dd, J=16.2, 7.2 Hz, 1H), 2.84 (s, 2H), 2.35 (s, 3H), 1.10 (td, J=7.1, 1.4 Hz, 3H).

Step B: 3-(6-((1,1-Dioxidospiro[benzo[b][1,4,5]oxathiazepine-4,3'-oxetan]-2(3H)-yl)methyl)-5-methylpyridin-2-yl)-3-(8-methyl-3-(trifluoromethyl)-[1,2,4]triazolo[4,3-a]pyridin-7-yl)propanoic acid. A mixture containing ethyl 3-(6-((1,1-dioxidospiro[benzo[b][1,4,5]oxathiazepine-4,3'-oxetan]-2(3H)-yl)methyl)-5-methylpyridin-2-yl)-3-(8-methyl-3-(trifluoromethyl)-[1,2,4]triazolo[4,3-a]pyridin-7-yl)propanoate (310 mg, 0.48 mmol), 1 M aqueous NaOH solution (4.4 mL, 4.4 mmol), THF (4.4 mL) and ethanol (0.03 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered, concentrated to dryness under reduced pressure. The residue was purified by flash column chromatography (eluent: 0-10% MeOH/DCM) to provide the title compound (292 mg, 98%) as a white foam. This foam was further purified by preparative LC (Stationary phase: irregular bare silica 40 g, Mobile phase: 97% DCM, 3% MeOH) to provide the title compound (284 mg, 96%). MS (ESI): mass calcd. for $C_{28}H_{26}F_3N_5O_6S$, 617.2; m/z found, 617.8 [M]$^+$. $^1$H NMR (400 MHz, CDCl$_3$) δ 9.29 (s, 1H), 8.00 (d, J=7.1 Hz, 1H), 7.86 (dd, J=7.8, 1.7 Hz, 1H), 7.60 (td, J=7.7, 1.7 Hz, 1H), 7.50-7.39 (m, 2H), 7.16 (d, J=7.3 Hz, 1H), 7.09 (d, J=7.8 Hz, 1H), 5.30 (s, 1H), 5.04 (dd, J=8.8, 6.3 Hz, 1H), 4.72 (dd, J=7.5, 4.2 Hz, 2H), 4.63 (t, J=7.7 Hz, 2H), 4.46 (d, J=13.9 Hz, 1H), 4.35 (d, J=14.0 Hz, 1H), 3.98 (d, J=15.2 Hz, 1H), 3.79 (d, J=15.4 Hz, 1H), 3.52-3.41 (m, 1H), 2.98 (dd, J=16.3, 6.3 Hz, 1H), 2.81 (s, 3H), 2.39 (s, 3H).

Example 485: (*S)-3-(6-((1,1-dioxidospiro[benzo[b][1,4,5]oxathiazepine-4,3'-oxetan]-2(3H)-yl)methyl)-5-methylpyridin-2-yl)-3-(8-methyl-3-(trifluoromethyl)-[1,2,4]triazolo[4,3-a]pyridin-7-yl)propanoic Acid

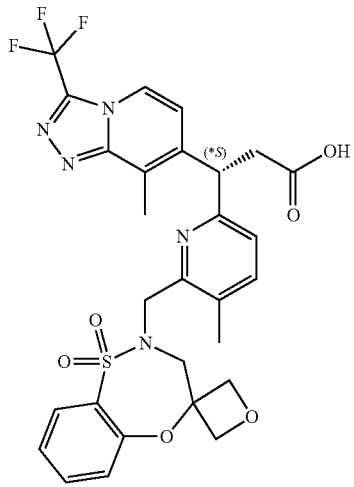

The mixture of 3-(6-((1,1-Dioxidospiro[benzo[b][1,4,5]oxathiazepine-4,3'-oxetan]-2(3H)-yl)methyl)-5-methylpyridin-2-yl)-3-(8-methyl-3-(trifluoromethyl)-[1,2,4]triazolo[4,3-a]pyridin-7-yl)propanoic acid isomers (Example 484, 292 mg) was separated by chiral SFC (Chiralpak AD-H 5 μm 250×30 mm, Mobile phase: 65% $CO_2$, 35% MeOH) to afford two enantiomers. The first eluting enantiomer (100 mg) was designated (*S). MS (ESI): mass calcd. for $C_{28}H_{26}F_3N_5O_6S$, 617.2; m/z found, 617.8 [M]+. $^1$H NMR (500 MHz, $CDCl_3$) δ 7.88 (d, J=7.1 Hz, 1H), 7.81 (dd, J=7.8, 1.7 Hz, 1H), 7.52 (td, J=7.8, 1.7 Hz, 1H), 7.43-7.27 (m, 2H), 6.94 (dd, J=9.1, 7.6 Hz, 2H), 5.23 (s, 1H), 4.94 (dd, J=9.2, 5.9 Hz, 1H), 4.64 (dd, J=7.5, 2.1 Hz, 2H), 4.63-4.41 (m, 3H), 4.21 (d, J=13.9 Hz, 1H), 3.87 (d, J=15.4 Hz, 1H), 3.74 (d, J=15.4 Hz, 1H), 3.25 (dd, J=16.0, 9.3 Hz, 1H), 2.84-2.74 (m, 1H), 2.74 (s, 3H), 2.32 (s, 3H).

Example 486: (*R)-3-(6-((1,1-dioxidospiro[benzo[b][1,4,5]oxathiazepine-4,3'-oxetan]-2(3H)-yl)methyl)-5-methylpyridin-2-yl)-3-(8-methyl-3-(trifluoromethyl)-[1,2,4]triazolo[4,3-a]pyridin-7-yl)propanoic Acid

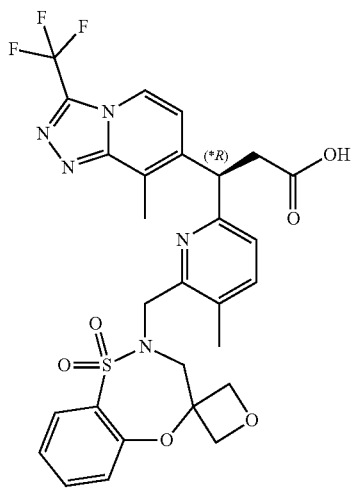 [SMILES: Cc1ccc([C@H](CC(=O)O)c2ccn3c(C(F)(F)F)nnc3c2C)nc1CN1CC2(COC2)Oc2ccccc2S1(=O)=O]

The second eluting enantiomer (100 mg) from the chiral separation described in Example 485 was designated (*R). MS (ESI): mass calcd. for $C_{28}H_{26}F_3N_5O_6S$, 617.2; m/z found, 617.8 [M]+. $^1$H NMR (500 MHz, $CDCl_3$) δ 7.88 (d, J=7.1 Hz, 1H), 7.80 (dd, J=7.8, 1.7 Hz, 1H), 7.52 (td, J=7.8, 1.7 Hz, 1H), 7.35 (t, J=7.4 Hz, 2H), 7.03-6.88 (m, 2H), 5.23 (s, 1H), 4.94 (dd, J=9.0, 6.0 Hz, 1H), 4.63 (d, J=7.5 Hz, 2H), 4.56 (d, J=7.5 Hz, 1H), 4.52-4.39 (m, 2H), 4.21 (d, J=13.9 Hz, 1H), 3.87 (d, J=15.4 Hz, 1H), 3.73 (d, J=15.4 Hz, 1H), 3.24 (dd, J=15.9, 9.0 Hz, 1H), 2.82-2.75 (m, 1H), 2.74 (s, 3H), 2.32 (s, 3H).

Example 487: 3-(8-Methyl-3-(trifluoromethyl)-[1,2,4]triazolo[4,3-a]pyridin-7-yl)-3-(5-methyl-6-(((*S)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic Acid

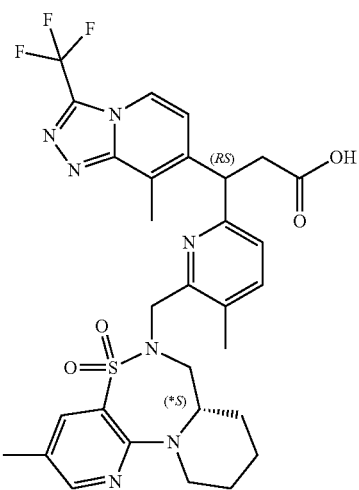 [SMILES: Cc1cnc2c(c1)S(=O)(=O)N(Cc1nc(C(CC(=O)O)c3ccn4c(C(F)(F)F)nnc4c3C)ccc1C)C[C@@H]1CCCCN21]

Step A: Ethyl 3-(8-methyl-3-(trifluoromethyl)-[1,2,4]triazolo[4,3-a]pyridin-7-yl)-3-(5-methyl-6-(((*S)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoate. Diisopropyl azodicarboxylate (0.08 mL, 0.39 mmol) was added to a stirring mixture of ethyl 3-(6-(hydroxymethyl)-5-methylpyridin-2-yl)-3-(8-methyl-3-(trifluoromethyl)-[1,2,4]triazolo[4,3-a]pyridin-7-yl)propanoate (Example 33, Step B, 100 mg, 0.24 mmol), (*S)-3-methyl-7,7a,8,9,10,11-hexahydro-6H-dipyrido[2,1-d:2',3'-f][1,2,5]thiadiazepine 5,5-dioxide (Intermediate 77, 90 mg, 0.34 mmol), and triphenylphosphine (92 mg, 0.35 mmol) in THF (3 mL) at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (150 mg, 94%) as a white foam. MS (ESI): mass calcd. for $C_{32}H_{36}F_3N_7O_4S$, 671.9; m/z found, 671.9 [M]+. $^1$H NMR (500 MHz, $CDCl_3$) δ 8.15 (dd, J=2.2, 1.0 Hz, 1H), 7.99 (dd, J=11.2, 7.2 Hz, 1H), 7.89-7.85 (m, 1H), 7.42 (dd, J=12.8, 7.8 Hz, 1H), 7.27 (dd, J=10.5, 7.3 Hz, 1H), 7.13-7.07 (m, 1H), 5.04 (td, J=7.5, 5.7 Hz, 1H), 4.75-4.54 (m, 2H), 4.39-4.26 (m, 2H), 4.18-3.98 (m, 1H), 3.63-3.35 (m, 4H), 3.14-2.88 (m, 4H), 2.35 (s, 1H), 2.29 (d, J=3.1 Hz, 2H), 2.05 (s, 1H), 1.87-1.36 (m, 7H), 1.35-1.23 (m, 2H), 1.17 (t, J=7.1 Hz, 3H).

Step B: 3-(8-Methyl-3-(trifluoromethyl)-[1,2,4]triazolo[4,3-a]pyridin-7-yl)-3-(5-methyl-6-(((*S)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic acid. A mixture containing ethyl 3-(8-methyl-3-(trifluoromethyl)-[1,2,4]triazolo[4,3-a]pyridin-7-yl)-3-(5-methyl-6-(((*S)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoate (150 mg, 0.22 mmol), 1 M aqueous NaOH solution (2 mL, 2 mmol), THF (2 mL) and ethanol (0.01 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered, concentrated to dryness under reduced pressure. The residue was purified by flash column chromatography (eluent: 0-10% MeOH/DCM) to provide the title compound (136 mg, 95%) as a white foam. This foam was further purified via preparative LC (Stationary phase: irregular bare silica 40 g, Mobile phase: 97% DCM, 3% MeOH) to provide the title compound as a white foam (126 mg, 88%). MS (ESI): mass calcd. for $C_{30}H_{32}F_3N_7O_4S$, 643.2; m/z found, 643.8 [M+H]$^+$. $^1$H NMR (500 MHz, CDCl$_3$) δ 8.21-8.09 (m, 1H), 7.98 (dd, J=16.1, 7.2 Hz, 1H), 7.89-7.84 (m, 1H), 7.66-7.60 (m, 1H), 7.48-7.37 (m, 1H), 7.07 (dd, J=25.8, 7.8 Hz, 1H), 5.03 (q, J=7.1 Hz, 1H), 4.73-4.66 (m, 1H), 4.56 (dt, J=12.4, 7.1 Hz, 1H), 4.36 (d, J=15.1 Hz, 1H), 4.33-4.19 (m, 1H), 3.60-3.49 (m, 1H), 3.51-3.42 (m, 2H), 3.46-3.33 (m, 1H), 3.09-3.04 (m, 1H), 2.87 (d, J=2.3 Hz, 3H), 2.35 (s, 3H), 2.34-2.21 (m, 3H), 1.78-1.70 (m, 3H), 1.66 (d, J=13.9 Hz, 1H), 1.20 (t, J=7.0 Hz, 2H).

Example 488: (*S)-3-(8-Methyl-3-(trifluoromethyl)-[1,2,4]triazolo[4,3-a]pyridin-7-yl)-3-(5-methyl-6-(((*S)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic Acid

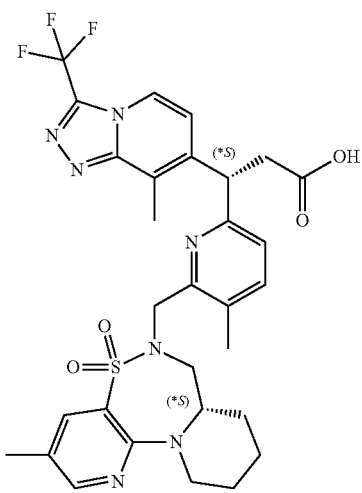 [SMILES: Cc1cnc2c(c1)S(=O)(=O)N(Cc1nc([C@@H](CC(=O)O)c3ccn4c(C(F)(F)F)nnc4c3C)ccc1C)C[C@@H]1CCCCN21]

The mixture of 3-(8-methyl-3-(trifluoromethyl)-[1,2,4]triazolo[4,3-a]pyridin-7-yl)-3-(5-methyl-6-(((*S)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic acid isomers (Example 487, 126 mg) was separated by chiral SFC (Chiralpak AD-H 5 μm 250×30 mm, Mobile phase: 30% $CO_2$, 70% MeOH) to afford two diastereomers. The first eluting diastereomer (44 mg) was designated (*S). MS (ESI): mass calcd. for $C_{30}H_{32}F_3N_7O_4S$, 643.2; m/z found, 643.8 [M+H]$^+$. $^1$H NMR (500 MHz, CDCl$_3$) δ 8.17 (d, J=2.3 Hz, 1H), 8.01 (d, J=7.2 Hz, 1H), 7.89 (d, J=2.2 Hz, 1H), 7.48-7.35 (m, 1H), 7.27-7.14 (m, 1H), 7.03 (d, J=7.8 Hz, 1H), 5.05 (t, J=7.4 Hz, 1H), 4.71 (d, J=15.1 Hz, 1H), 4.63-4.51 (m, 1H), 4.37 (d, J=15.1 Hz, 1H), 4.26 (dt, J=13.2, 4.7 Hz, 1H), 3.68-3.55 (m, 2H), 3.51 (dd, J=13.2, 3.9 Hz, 1H), 3.44-3.38 (m, 1H), 3.07-2.92 (m, 1H), 2.90 (s, 3H), 2.37-2.23 (m, 6H), 1.79-1.72 (m, 3H), 1.67-1.59 (m, 1H), 1.33-1.21 (m, 2H).

Example 489: (*R)-3-(8-Methyl-3-(trifluoromethyl)-[1,2,4]triazolo[4,3-a]pyridin-7-yl)-3-(5-methyl-6-(((*S)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic Acid

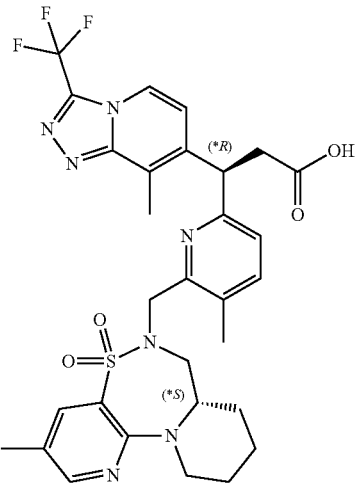 [SMILES: Cc1cnc2c(c1)S(=O)(=O)N(Cc1nc([C@H](CC(=O)O)c3ccn4c(C(F)(F)F)nnc4c3C)ccc1C)C[C@@H]1CCCCN21]

The second eluting diastereomer (47 mg) from the chiral separation described in Example 488 was designated (*R). MS (ESI): mass calcd. for $C_{30}H_{32}F_3N_7O_4S$, 643.2; m/z found, 643.8 [M+H]$^+$. $^1$H NMR (500 MHz, CDCl$_3$) δ 8.16 (d, J=2.3 Hz, 1H), 7.97 (d, J=7.2 Hz, 1H), 7.88 (dd, J=2.3, 0.8 Hz, 1H), 7.45 (d, J=7.7 Hz, 1H), 7.28 (s, 1H), 7.18 (d, J=7.3 Hz, 1H), 7.08 (d, J=7.8 Hz, 1H), 5.03 (t, J=7.3 Hz, 1H), 4.71 (d, J=14.0 Hz, 1H), 4.56 (dd, J=12.3, 4.8 Hz, 1H), 4.32 (d, J=14.0 Hz, 1H), 4.26 (dt, J=13.2, 4.8 Hz, 1H), 3.59-3.50 (m, 1H), 3.49-3.43 (m, 2H), 3.26 (dd, J=13.4, 3.7 Hz, 1H), 3.10 (dd, J=16.5, 7.2 Hz, 1H), 2.89 (s, 3H), 2.36 (s, 3H), 2.29 (s, 3H), 1.79-1.65 (m, 3H), 1.54 (q, J=6.7 Hz, 1H), 1.33-1.21 (m, 2H).

Example 490: 3-(8-Methyl-3-(trifluoromethyl)-[1,2,4]triazolo[4,3-a]pyridin-7-yl)-3-(5-methyl-6-(((*R)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic Acid

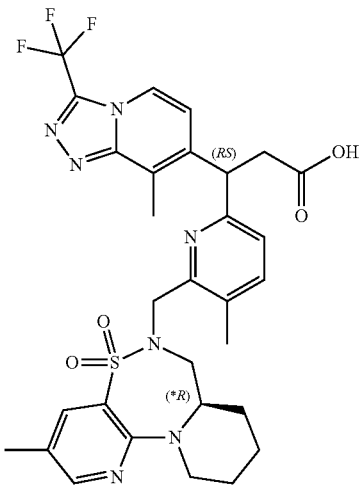 [SMILES: Cc1cnc2c(c1)S(=O)(=O)N(Cc1nc(C(CC(=O)O)c3ccn4c(C(F)(F)F)nnc4c3C)ccc1C)C[C@H]1CCCCN21]

Step A: Ethyl 3-(8-methyl-3-(trifluoromethyl)-[1,2,4]triazolo[4,3-a]pyridin-7-yl)-3-(5-methyl-6-(((*R)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoate. Diisopropyl azodicarboxylate (0.09 mL, 0.47 mmol) was added to a stirring mixture of ethyl 3-(6-(hydroxymethyl)-5-methylpyridin-2-yl)-3-(8-methyl-3-(trifluoromethyl)-[1,2,4]triazolo[4,3-a]pyridin-7-yl)propanoate (Example 33, Step B, 120 mg, 0.28 mmol), (*R)-3-methyl-7,7a,8,9,10,11-hexahydro-6H-dipyrido[2,1-d:2',3'-f][1,2,5]thiadiazepine 5,5-dioxide (Intermediate 117 108 mg, 0.40 mmol), and triphenylphosphine (111 mg, 0.42 mmol) in THF (3 mL) at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (180 mg, 94%) as a white foam. MS (ESI): mass calcd. for $C_{32}H_{36}F_3N_7O_4S$, 671.7; m/z found, 671.9 [M]+. $^1$H NMR (400 MHz, $CDCl_3$) δ 8.14 (dt, J=2.0, 0.9 Hz, 1H), 7.99 (dd, J=11.0, 7.2 Hz, 1H), 7.90-7.84 (m, 1H), 7.42 (dd, J=12.8, 7.8 Hz, 1H), 7.27 (dd, J=10.9, 7.3 Hz, 1H), 7.11-7.07 (m, 1H), 5.03 (td, J=7.5, 5.7 Hz, 1H), 4.75-4.53 (m, 1H), 4.38-4.25 (m, 2H), 4.17-3.97 (m, 2H), 3.62-3.34 (m, 4H), 3.22 (dd, J=13.5, 3.8 Hz, 1H), 3.14-2.88 (m, 4H), 2.34 (s, 3H), 2.28 (d, J=3.1 Hz, 3H), 1.88-1.36 (m, 6H), 1.36-1.12 (m, 3H).

Step B: 3-(8-Methyl-3-(trifluoromethyl)-[1,2,4]triazolo[4,3-a]pyridin-7-yl)-3-(5-methyl-6-(((*R)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic acid. A mixture containing ethyl 3-(8-methyl-3-(trifluoromethyl)-[1,2,4]triazolo[4,3-a]pyridin-7-yl)-3-(5-methyl-6-(((*R)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoate (180 mg, 0.27 mmol), 1 M aqueous NaOH solution (2.5 mL, 2.5 mmol), THF (2.5 mL) and ethanol (0.02 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated to dryness under reduced pressure. The residue was purified by flash column chromatography (eluent: 0-10% MeOH/DCM) to provide the title compound (162 mg, 94%) as a white foam. This foam was further purified by preparative LC (Stationary phase: irregular bare silica 40 g, Mobile phase: 97% DCM, 3% MeOH) to provide the title compound as a white foam (152 mg, 88%). MS (ESI): mass calcd. for $C_{30}H_{32}F_3N_7O_4S$, 643.2; m/z found, 643.9 [M+H]+. $^1$H NMR (500 MHz, $CDCl_3$) δ 8.15 (t, J=2.7 Hz, 1H), 7.99 (dd, J=15.1, 7.2 Hz, 1H), 7.88 (dd, J=6.3, 2.2 Hz, 1H), 7.62 (s, 1H), 7.42 (dd, J=18.2, 7.8 Hz, 1H), 7.29 (d, J=6.4 Hz, 1H), 7.04 (d, J=7.8 Hz, 1H), 5.03 (q, J=7.2 Hz, 1H), 4.73-4.66 (m, 1H), 4.57 (s, 1H), 4.26-4.22 (m, 1H), 3.60-3.49 (m, 2H), 3.49 (s, 1H), 3.51-3.40 (m, 2H), 3.08-3.04 (m, 1H), 2.87 (d, J=2.2 Hz, 3H), 2.34 (s, 1H), 2.34-2.22 (m, 4H), 1.43 (s, 2H), 1.20 (t, J=7.0 Hz, 4H).

Example 491: (*S)-3-(8-Methyl-3-(trifluoromethyl)-[1,2,4]triazolo[4,3-a]pyridin-7-yl)-3-(5-methyl-6-(((*R)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic Acid

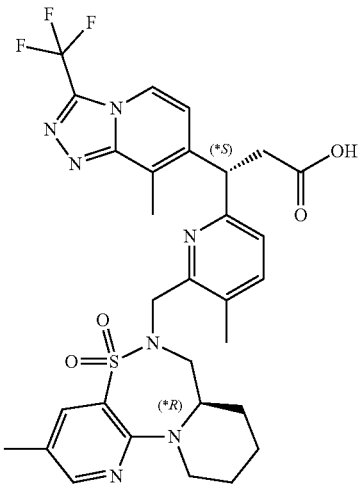 [SMILES: Cc1cnc2c(c1)S(=O)(=O)N(Cc1nc([C@@H](CC(=O)O)c3ccn4c(C(F)(F)F)nnc4c3C)ccc1C)C[C@H]1CCCCN21]

The mixture of 3-(8-methyl-3-(trifluoromethyl)-[1,2,4]triazolo[4,3-a]pyridin-7-yl)-3-(5-methyl-6-(((*R)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic acid isomers (Example 490, 152 mg) was separated by chiral SFC (Chiralpak AD-H 5 μm 250×30 mm, Mobile phase: 30% $CO_2$, 70% MeOH) to afford two diastereomers. The first eluting diastereomer (55 mg) was designated (*S). MS (ESI): mass calcd. for $C_{30}H_{32}F_3N_7O_4S$, 643.2; m/z found, 643.9 [M+H]+. $^1$H NMR (500 MHz, $CDCl_3$) δ 8.16 (d, J=2.2 Hz, 1H), 7.97 (d, J=7.2 Hz, 1H), 7.88 (d, J=2.2 Hz, 1H), 7.45 (d, J=7.8 Hz, 1H), 7.28 (s, 1H), 7.08 (d, J=7.8 Hz, 1H), 5.31 (s, 1H), 5.03 (t, J=7.4 Hz, 1H), 4.71 (d, J=14.0 Hz, 1H), 4.60-4.52 (m, 1H), 4.32 (d, J=13.9 Hz, 1H), 4.25 (dd, J=13.3, 4.8 Hz, 1H), 3.60-3.46 (m, 2H), 3.49-3.42 (m, 1H), 3.26 (dd, J=13.5, 3.7 Hz, 1H), 3.10 (dd, J=16.4, 7.2 Hz, 1H), 2.88 (s, 3H), 2.42-2.23 (m, 5H), 1.80-1.66 (m, 1H), 1.55 (dt, J=12.7, 6.9 Hz, 1H), 1.45 (s, 2H), 1.26 (d, J=9.0 Hz, 2H).

Example 492: (*R)-3-(8-Methyl-3-(trifluoromethyl)-[1,2,4]triazolo[4,3-a]pyridin-7-yl)-3-(5-methyl-6-((((*R)-3-methyl-5,5-dioxido-7,7a,8,9,10,11-hexahydro-6H-dipyrido[2,1-d:2',3'-f][1,2,5]thiadiazepin-6-yl)methyl)pyridin-2-yl)propanoic Acid

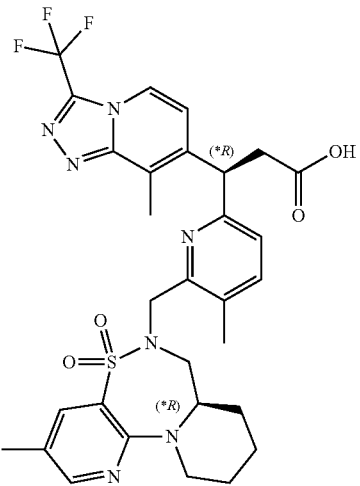 [SMILES: Cc1cnc2c(c1)S(=O)(=O)N(Cc1nc([C@H](CC(=O)O)c3ccn4c(C(F)(F)F)nnc4c3C)ccc1C)C[C@H]1CCCCN21]

The second eluting diastereomer (58 mg) from the chiral separation described in Example 491 was designated (*R). MS (ESI): mass calcd. for $C_{30}H_{32}F_3N_7O_4S$, 643.2; m/z found, 643.9 [M+H]+. $^1$H NMR (500 MHz, CDCl$_3$) δ 8.08 (d, J=2.2 Hz, 1H), 7.91 (d, J=7.2 Hz, 1H), 7.80 (d, J=2.2 Hz, 1H), 7.32 (d, J=7.8 Hz, 1H), 7.09 (d, J=7.3 Hz, 1H), 6.93 (d, J=7.8 Hz, 1H), 5.23 (s, 1H), 4.95 (t, J=7.2 Hz, 1H), 4.62 (d, J=14.9 Hz, 1H), 4.48 (dd, J=12.2, 5.0 Hz, 1H), 4.28 (d, J=15.0 Hz, 1H), 4.18 (dt, J=13.3, 4.9 Hz, 1H), 3.52-3.38 (m, 3H), 3.32 (dt, J=13.6, 6.9 Hz, 1H), 2.91 (dd, J=16.8, 6.2 Hz, 1H), 2.80 (s, 3H), 2.28-2.14 (m, 5H), 1.74-1.61 (m, 3H), 1.45 (s, 1H), 1.24-1.11 (m, 2H).

Example 493: 3-(6-((1',1'-Dioxidospiro[oxetane-3,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic Acid

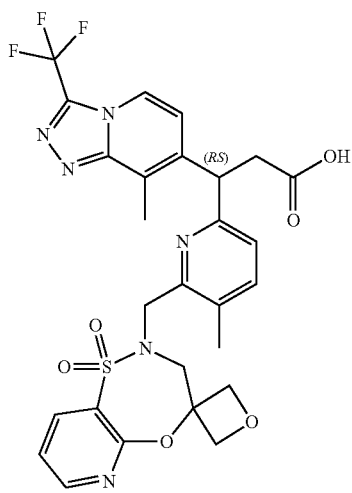

Step A: Ethyl 3-(6-((1',1'-dioxidospiro[oxetane-3,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoate. Diisopropyl azodicarboxylate (0.08 mL, 0.39 mmol) was added to a stirring mixture of ethyl 3-(6-(hydroxymethyl)-5-methylpyridin-2-yl)-3-(8-methyl-3-(trifluoromethyl)-[1,2,4]triazolo[4,3-a]pyridin-7-yl)propanoate (Example 33, Step B, 100 mg, 0.24 mmol), 2',3'-dihydrospiro[oxetane-3,4'-pyrido[2,3-b][1,4,5]oxathiazepine] 1',1'-dioxide (Intermediate 59, 81 mg, 0.34 mmol), and triphenylphosphine (92.1 mg, 0.35 mmol) in THF (3 mL) at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (70 mg, 46%) as a white foam. MS (ESI): mass calcd. for $C_{29}H_{29}F_3N_6O_6S$, 646.6; m/z found, 646.9 [M]+.

Step B: 3-(6-((1',1'-Dioxidospiro[oxetane-3,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid. A mixture containing ethyl 3-(6-((1',1'-dioxidospiro[oxetane-3,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoate (70 mg, 0.11 mmol), 1 M aqueous NaOH solution (1 mL, 1 mmol), THF (1 mL) and ethanol (0.01 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated to dryness under reduced pressure. The residue was purified by flash column chromatography (eluent: 0-10% MeOH/DCM) to provide the title compound (53 mg, 79%) as a white foam. This foam was further purified via preparative LC (Stationary phase: irregular bare silica 40 g, Mobile phase: 97% DCM, 3% MeOH) to provide the title compound as a white foam (43 mg, 64%). MS (ESI): mass calcd. for $C_{27}H_{25}F_3N_6O_6S$, 618.2; m/z found, 618.2 [M]+. $^1$H NMR (500 MHz, CDCl$_3$) δ 8.57 (dd, J=4.9, 1.9 Hz, 1H), 8.26 (dd, J=7.6, 1.9 Hz, 1H), 7.98 (d, J=7.2 Hz, 1H), 7.46 (d, J=7.9 Hz, 1H), 7.37 (dd, J=7.6, 4.9 Hz, 1H), 7.04 (t, J=7.2 Hz, 2H), 5.31 (s, 1H), 5.06 (dd, J=9.8, 5.4 Hz, 1H), 4.85 (d, J=7.5 Hz, 2H), 4.72-4.58 (m, 2H), 4.44 (d, J=14.1 Hz, 1H), 4.17-4.07 (m, 2H), 3.91 (d, J=15.4 Hz, 1H), 3.47 (dd, J=16.2, 9.8 Hz, 1H), 2.96-2.86 (m, 1H), 2.84 (s, 3H), 2.39 (s, 3H).

Example 494: (*S)-3-(6-((1',1'-Dioxidospiro[oxet-
ane-3,4'-pyrido[2,3-b][1,4,5]oxathiazepin]-2'(3'H)-
yl)methyl)-5-methylpyridin-2-yl)-3-(8-methyl-3-
(trifluoromethyl)-[1,2,4]triazolo[4,3-a]pyridin-7-yl)
propanoic Acid

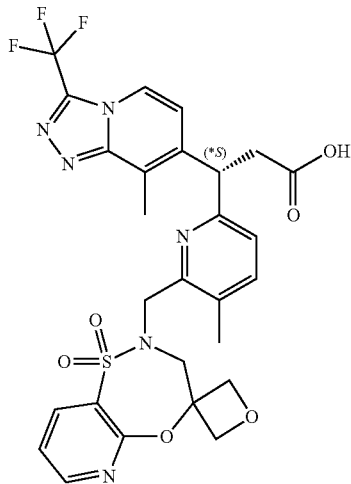

The mixture of 3-(6-((1',1'-dioxidospiro[oxetane-3,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid isomers (Example 493, 43 mg) was separated by chiral SFC (Chiralpak AD-H 5 μm 250×30 mm, Mobile phase: 30% $CO_2$, 70% MeOH) to afford two enantiomers. The first eluting enantiomer (21 mg) was designated (*S). MS (ESI): mass calcd. for $C_{27}H_{25}F_3N_6O_6S$, 618.2; m/z found, 618.2 [M]$^+$. $^1$H NMR (500 MHz, CDCl$_3$) δ 8.57 (dd, J=4.9, 1.9 Hz, 1H), 8.26 (dd, J=7.6, 1.9 Hz, 1H), 7.98 (d, J=7.2 Hz, 1H), 7.46 (d, J=7.9 Hz, 1H), 7.37 (dd, J=7.6, 4.9 Hz, 1H), 7.04 (t, J=7.2 Hz, 2H), 5.31 (s, 1H), 5.06 (dd, J=9.8, 5.4 Hz, 1H), 4.85 (d, J=7.5 Hz, 2H), 4.72-4.58 (m, 2H), 4.44 (d, J=14.1 Hz, 1H), 4.17-4.07 (m, 2H), 3.91 (d, J=15.4 Hz, 1H), 3.47 (dd, J=16.2, 9.8 Hz, 1H), 2.96-2.86 (m, 1H), 2.84 (s, 3H), 2.39 (s, 3H).

Example 495: (*R)-3-(6-((1',1'-Dioxidospiro[oxet-
ane-3,4'-pyrido[2,3-b][1,4,5]oxathiazepin]-2'(3'H)-
yl)methyl)-5-methylpyridin-2-yl)-3-(8-methyl-3-
(trifluoromethyl)-[1,2,4]triazolo[4,3-a]pyridin-7-yl)
propanoic Acid

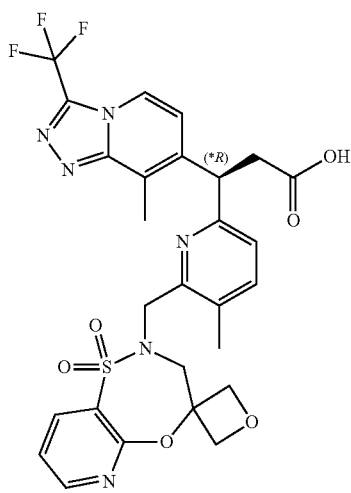 [SMILES: Cc1ccc([C@H](CC(=O)O)c2ccn3c(C(F)(F)F)nnc3c2C)nc1CN1CC2(COC2)Oc2ncccc2S1(=O)=O]

The second eluting enantiomer (22 mg) from the chiral separation described in Example 494 was designated (*R). MS (ESI): mass calcd. for $C_{27}H_{25}F_3N_6O_6S$, 618.2; m/z found, 618.2 [M]$^+$. $^1$H NMR (500 MHz, CDCl$_3$) δ 8.50 (dd, J=4.8, 2.0 Hz, 1H), 8.18 (dd, J=7.7, 1.9 Hz, 1H), 7.90 (d, J=7.2 Hz, 1H), 7.38 (d, J=7.9 Hz, 1H), 7.29 (dd, J=7.6, 4.9 Hz, 1H), 6.89 (dd, J=21.1, 7.5 Hz, 2H), 5.23 (s, 1H), 5.03-4.94 (m, 1H), 4.80 (dd, J=12.2, 7.4 Hz, 2H), 4.70-4.61 (m, 2H), 4.53 (d, J=7.3 Hz, 1H), 4.31 (d, J=14.0 Hz, 1H), 4.03 (d, J=15.3 Hz, 1H), 3.85 (d, J=15.4 Hz, 1H), 3.65 (q, J=7.1 Hz, 0H), 3.34 (dd, J=16.0, 10.4 Hz, 1H), 2.85-2.76 (m, 1H), 2.76 (s, 3H), 2.33 (s, 3H).

Example 496: 3-(6-(((*S)-3-Fluoro-5,5-dioxido-7,
7a,8,9,10,11-hexahydro-6H-dipyrido[2,1-d:2',3'-f][1,
2,5]thiadiazepin-6-yl)methyl)-5-methylpyridin-2-yl)-
3-(8-methyl-3-(trifluoromethyl)-[1,2,4]triazolo[4,3-
a]pyridin-7-yl)propanoic Acid

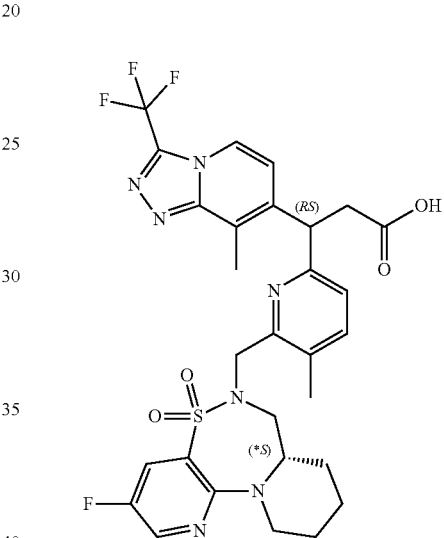

Step A: Ethyl 3-(6-(((*S)-3-fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoate. Diisopropyl azodicarboxylate (0.12 mL, 0.59 mmol) was added to a stirring mixture of ethyl 3-(6-(hydroxymethyl)-5-methylpyridin-2-yl)-3-(8-methyl-3-(trifluoromethyl)-[1,2,4]triazolo[4,3-a]pyridin-7-yl)propanoate (Example 33, Step B, 150 mg, 0.34 mmol), (*S)-3-fluoro-7,7a,8,9,10,11-hexahydro-6H-dipyrido[2,1-d:2',3'-f][1,2,5]thiadiazepine 5,5-dioxide (Intermediate 78, 137 mg, 0.50 mmol), and triphenylphosphine (138 mg, 0.53 mmol) in THF (4 mL) at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (200 mg, 83%) as a white foam. MS (ESI): mass calcd. for $C_{31}H_{33}F_4N_7O_4S$, 675.7; m/z found, 675.8 [M]$^+$. $^1$H NMR (500 MHz, CDCl$_3$) δ 8.06 (s, 1H), 8.00 (d, J=7.2 Hz, 1H), 7.74 (d, J=7.3 Hz, 1H), 7.43 (dd, J=7.7, 1.0 Hz, 1H), 7.14 (d, J=7.7 Hz, 1H), 4.89 (d, J=15.4 Hz, 1H), 4.64-4.40 (m, 3H), 4.35 (d, J=15.4 Hz, 1H), 3.73 (dq, J=10.4, 6.7 Hz, 1H), 3.62 (dd, J=13.1, 4.5 Hz, 1H), 3.54-3.42 (m, 2H), 3.29-3.22 (m, 1H), 2.83 (s, 3H), 2.59 (d, J=2.3 Hz, 3H), 2.29 (s, 3H), 1.86-1.71 (m, 3H), 1.69-1.62 (m, 1H), 1.57-1.42 (m, 1H), 1.21 (dd, J=7.4, 6.3 Hz, 4H).

Step B: 3-(6-(((*S)-3-Fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid. A mixture containing ethyl 3-(6-(((*S)-3-fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoate (200 mg, 0.30 mmol), 1 M aqueous NaOH solution (1.5 mL, 1.5 mmol) and THF (1.5 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered, concentrated to dryness under reduced pressure. The residue was purified by flash column chromatography (eluent: 0-10% MeOH/DCM) to provide the title compound (180 mg, 94%) as a white foam. MS (ESI): mass calcd. for $C_{29}H_{29}F_4N_7O_4S$, 647.2; m/z found, 647.8 [M+H]$^+$. $^1$H NMR (500 MHz, CDCl$_3$) δ 8.19 (d, J=2.9 Hz, 1H), 7.99 (dd, J=12.0, 7.2 Hz, 1H), 7.80 (td, J=7.7, 2.9 Hz, 1H), 7.47-7.38 (m, 1H), 7.32-7.21 (m, 1H), 7.09-7.05 (m, 1H), 6.44 (s, 1H), 4.72 (dd, J=14.7, 7.0 Hz, 1H), 4.59-4.52 (m, 1H), 4.38-4.32 (m, 1H), 4.31-4.21 (m, 1H), 3.65-3.39 (m, 4H), 3.42-3.22 (m, 1H), 3.09-3.04 (m, 1H), 2.86 (d, J=3.3 Hz, 3H), 2.33-2.27 (m, 3H), 1.82-1.65 (m, 3H), 1.67-1.48 (m, 1H), 1.47-1.38 (m, 1H), 1.22 (s, 1H).

Example 497: (*S)-3-(6-(((*S)-3-Fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

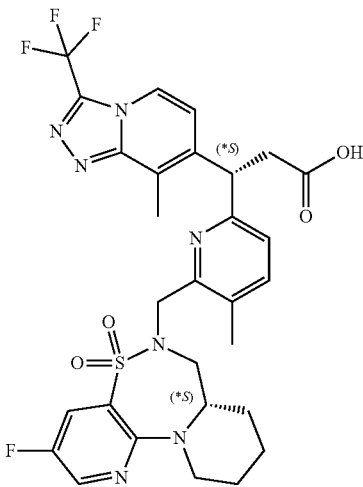 [SMILES: Cc1ccc([C@@H](CC(=O)O)c2ccn3c(C(F)(F)F)nnc3c2C)nc1CN1C[C@@H]2CCCCN2c2ncc(F)cc2S1(=O)=O]

The mixture of 3-(6-(((*S)-3-fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl) propanoic acid isomers (Example 496, 180 mg) was separated by chiral SFC (Chiralpak AD-H 5 μm 250×30 mm, Mobile phase: 70% $CO_2$, 30% iPrOH) to afford two diastereomers. The first eluting diastereomer (78 mg) was designated (*S). MS (ESI): mass calcd. for $C_{29}H_{29}F_4N_7O_4S$, 647.2; m/z found, 647.8 [M+H]$^+$. $^1$H NMR (500 MHz, CDCl$_3$) δ 8.11 (d, J=2.9 Hz, 1H), 7.90 (d, J=7.2 Hz, 1H), 7.73 (dd, J=7.4, 3.0 Hz, 1H), 7.32 (d, J=7.8 Hz, 1H), 7.17 (d, J=7.3 Hz, 1H), 6.97 (d, J=7.8 Hz, 1H), 4.94 (t, J=7.4 Hz, 1H), 4.63 (d, J=15.2 Hz, 1H), 4.49 (dq, J=10.4, 4.9 Hz, 1H), 4.28 (d, J=15.2 Hz, 1H), 4.17 (dt, J=13.3, 4.8 Hz, 1H), 3.53-3.42 (m, 2H), 3.38 (dd, J=16.2, 7.5 Hz, 1H), 3.29-3.23 (m, 1H), 2.93 (dd, J=16.3, 7.3 Hz, 1H), 2.79 (s, 3H), 2.20 (s, 3H), 1.73-1.63 (m, 2H), 1.54 (dd, J=13.7, 6.5 Hz, 1H), 1.45 (dq, J=10.7, 5.2, 4.7 Hz, 2H), 1.21-1.11 (m, 1H).

Example 498: (*R)-3-(6-(((*S)-3-Fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

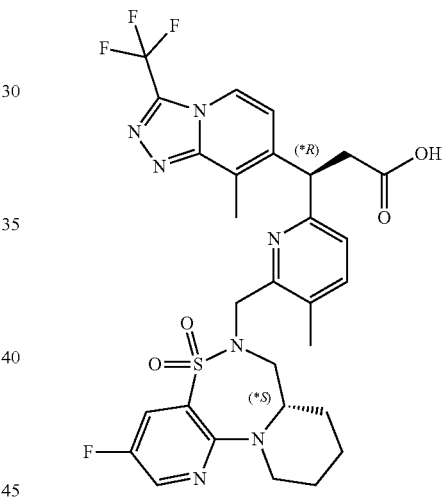

The second eluting diastereomer (80 mg) from the chiral separation described in Example 497 was designated (*R). MS (ESI): mass calcd. for $C_{29}H_{29}F_4N_7O_4S$, 647.2; m/z found, 647.8 [M+H]$^+$. $^1$H NMR (500 MHz, CDCl$_3$) δ 8.11 (d, J=3.0 Hz, 1H), 7.88 (d, J=7.2 Hz, 1H), 7.71 (dd, J=7.4, 2.9 Hz, 1H), 7.38-7.32 (m, 1H), 7.18-7.08 (m, 1H), 7.01 (d, J=7.8 Hz, 1H), 4.92 (t, J=7.4 Hz, 1H), 4.63 (d, J=14.3 Hz, 1H), 4.47 (dd, J=12.6, 5.0 Hz, 1H), 4.26-4.14 (m, 2H), 3.95 (dq, J=12.3, 6.1 Hz, 0H), 3.47 (t, J=13.0 Hz, 1H), 3.35-3.30 (m, 2H), 3.24 (dd, J=13.4, 3.7 Hz, 1H), 2.95 (dd, J=16.2, 7.4 Hz, 1H), 2.79 (s, 3H), 2.24 (s, 3H), 1.68-1.58 (m, 1H), 1.47 (dq, J=12.4, 6.2 Hz, 1H), 1.37-1.33 (m, 2H), 1.21-1.07 (m, 2H).

Example 499: 3-(3-(Difluoromethyl)-8-methyl-[1,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic Acid

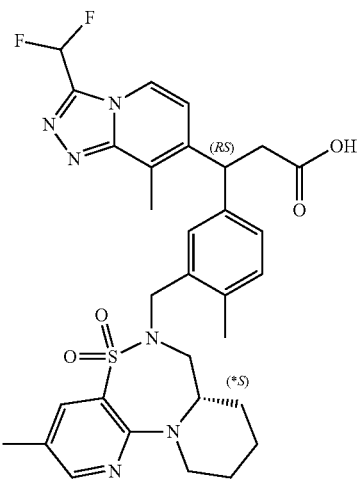 [SMILES: Cc1cnc2c(c1)S(=O)(=O)N(Cc1cc(C(CC(=O)O)c3ccn4c(C(F)F)nnc4c3C)ccc1C)C[C@@H]1CCCCN21]

Step A: Ethyl 3-(3-(difluoromethyl)-8-methyl-[1,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoate. Diisopropyl azodicarboxylate (0.20 mL, 1.02 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 250 mg, 0.62 mmol), (*S)-3-methyl-7,7a,8,9,10,11-hexahydro-6H-dipyrido[2,1-d:2',3'-f][1,2,5]thiadiazepine 5,5-dioxide (Intermediate 77, 235 mg, 0.88 mmol), and triphenylphosphine (241 mg, 0.92 mmol) in THF (7 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (380 mg, 94%) as a white foam. MS (ESI): mass calcd. for $C_{33}H_{38}F_2N_6O_4S$, 652.3; m/z found, 652.9 [M]$^+$. $^1$H NMR (400 MHz, CDCl$_3$) δ 8.16-8.06 (m, 2H), 7.82 (dt, J=2.1, 1.1 Hz, 1H), 7.19-7.03 (m, 4H), 6.83 (dd, J=16.5, 7.2 Hz, 1H), 4.91 (q, J=8.2 Hz, 1H), 4.45-4.40 (m, 2H), 4.24-3.98 (m, 3H), 3.23-3.05 (m, 4H), 2.99-2.92 (m, 1H), 2.79 (d, J=12.0 Hz, 3H), 2.32-2.16 (m, 4H), 1.99 (s, 2H), 1.66-1.60 (m, 4H), 1.50-1.27 (m, 3H), 1.13 (td, J=7.1, 2.3 Hz, 3H).

Step B: 3-(3-(Difluoromethyl)-8-methyl-[1,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic acid. A mixture containing ethyl 3-(3-(difluoromethyl)-8-methyl-[1,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoate (380 mg, 0.58 mmol), 1 M aqueous NaOH solution (5.4 mL, 5.4 mmol), THF (5.4 mL) and ethanol (0.03 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered, and concentrated to dryness under reduced pressure. The residue was purified by flash column chromatography (eluent: 0-10% MeOH/DCM) to provide the title compound (348 mg, 96%) as a white foam which was further purified by preparative LC (Stationary phase: irregular bare silica 40 g, Mobile phase: 97% DCM, 3% MeOH) to provide the title compound as a white foam (338 mg, 93%). MS (ESI): mass calcd. for $C_{31}H_{34}F_2N_6O_4S$, 624.2; m/z found, 624.2 [M]-. $^1$H NMR (500 MHz, CDCl$_3$) δ 8.20-8.08 (m, 2H), 7.88 (d, J=2.2 Hz, 1H), 7.24-7.16 (m, 1H), 7.18-7.02 (m, 3H), 6.89 (dd, J=14.2, 7.3 Hz, 1H), 5.31 (s, 1H), 4.95 (q, J=9.2 Hz, 1H), 4.43 (dd, J=17.4, 14.5 Hz, 1H), 4.25-4.20 (m, 1H), 4.15-4.07 (m, 1H), 3.49 (q, J=7.0 Hz, 1H), 3.30-3.19 (m, 1H), 3.21-3.12 (m, 2H), 3.09-3.00 (m, 1H), 2.78 (d, J=10.2 Hz, 3H), 2.33-2.19 (m, 6H), 1.61 (dt, J=12.5, 5.4 Hz, 1H), 1.49 (dt, J=18.8, 7.2 Hz, 2H), 1.44-1.31 (m, 1H), 1.26 (s, 1H), 1.21 (t, J=7.0 Hz, 1H).

Example 500: (*S)-3-(3-(Difluoromethyl)-8-methyl-[1,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic Acid

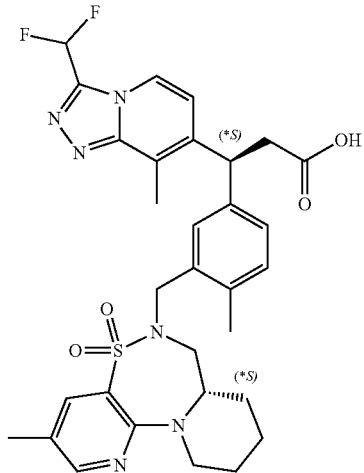 [SMILES: Cc1cnc2c(c1)S(=O)(=O)N(Cc1cc([C@H](CC(=O)O)c3ccn4c(C(F)F)nnc4c3C)ccc1C)C[C@@H]1CCCCN21]

The mixture of 3-(3-(difluoromethyl)-8-methyl-[1,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic acid isomers (Example 499, 338 mg) was separated by chiral SFC (stationary phase: Chiralpak AD-H 5 μm 250×30 mm, isocratic mobile phase: 45% CO$_2$, 55% MeOH) to afford two diastereomers. The first eluting isomer (157 mg) was designated (*S). MS (ESI): mass calcd. for $C_{31}H_{34}F_2N_6O_4S$, 624.2; m/z found, 624.2 [M]$^+$. $^1$H NMR (400 MHz, CDCl$_3$) δ 8.09-8.02 (m, 2H), 7.79 (d, J=2.2 Hz, 1H), 7.12 (d, J=2.3 Hz, 2H), 7.08-6.95 (m, 2H), 6.79 (d, J=7.2 Hz, 1H), 5.22 (s, 1H), 4.86 (t, J=7.8 Hz, 1H), 4.33 (dd, J=14.8, 5.5 Hz, 2H), 4.17 (d, J=14.9 Hz, 1H), 4.05 (dt, J=13.3, 4.8 Hz, 1H), 3.17

(d, J=2.0 Hz, 1H), 3.15 (s, 1H), 3.16-3.01 (m, 2H), 2.94 (dd, J=15.9, 8.8 Hz, 1H), 2.69 (s, 3H), 2.18 (d, J=6.6 Hz, 6H), 1.61-1.49 (m, 1H), 1.45-1.27 (m, 4H), 1.21-1.12 (m, 1H).

Example 501: (*R)-3-(3-(Difluoromethyl)-8-methyl-[1,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic Acid

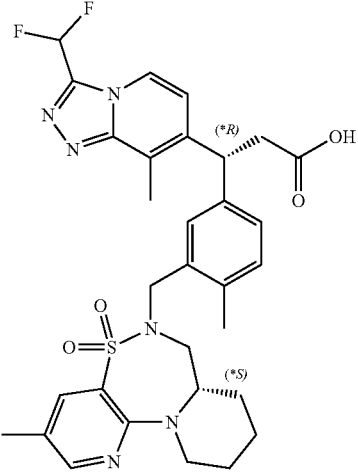 [SMILES: Cc1cnc2c(c1)S(=O)(=O)N(Cc1cc([C@@H](CC(=O)O)c3ccn4c(C(F)F)nnc4c3C)ccc1C)C[C@@H]1CCCCN21]

The second eluting isomer (145 mg) from the chiral separation described in Example 500 was designated (*R). MS (ESI): mass calcd. for $C_{31}H_{34}F_2N_6O_4S$, 624.2; m/z found, 624.2 [M]+. $^1$H NMR (400 MHz, CDCl$_3$) δ 8.08-8.03 (m, 2H), 7.79 (d, J=2.2 Hz, 1H), 7.19 (s, 1H), 7.15-6.98 (m, 3H), 6.76 (d, J=7.2 Hz, 1H), 5.84 (s, 1H), 4.88 (s, 1H), 4.38-4.32 (m, 2H), 4.11 (d, J=14.7 Hz, 1H), 4.04 (dt, J=13.3, 4.9 Hz, 1H), 3.11-3.07 (m, 3H), 2.94 (s, 1H), 2.72 (s, 3H), 2.19 (s, 6H), 1.56 (dd, J=9.9, 5.4 Hz, 2H), 1.43 (s, 1H), 1.36-1.22 (m, 1H), 1.18 (s, 1H), 1.16 (d, J=6.8 Hz, 1H).

Example 502: 3-(3-(Difluoromethyl)-8-methyl-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic Acid

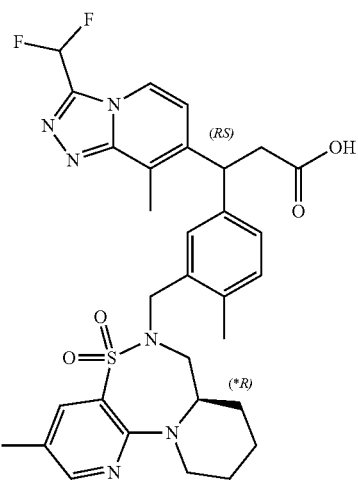 [SMILES: Cc1cnc2c(c1)S(=O)(=O)N(Cc1cc(C(CC(=O)O)c3ccn4c(C(F)F)nnc4c3C)ccc1C)C[C@H]1CCCCN21]

Step A: Ethyl 3-(3-(difluoromethyl)-8-methyl-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoate. Diisopropyl azodicarboxylate (0.22 mL, 1.14 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 280 mg, 0.69 mmol), (*R)-3-methyl-7,7a,8,9,10,11-hexahydro-6H-dipyrido[2,1-d:2',3'-f][1,2,5]thiadiazepine 5,5-dioxide (Intermediate 117, 264 mg, 0.99 mmol), and triphenylphosphine (270 mg, 1.03 mmol) in THF (8 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (450 mg, 99%) as a white foam. MS (ESI): mass calcd. for $C_{33}H_{38}F_2N_6O_4S$, 652.8; m/z found, 652.9 [M]+. $^1$H NMR (400 MHz, CDCl$_3$) δ 8.14-8.04 (m, 2H), 7.85-7.80 (m, 1H), 7.18-7.02 (m, 4H), 6.83 (dd, J=17.5, 7.2 Hz, 1H), 4.89 (td, J=9.0, 6.9 Hz, 1H), 4.46-4.32 (m, 2H), 4.23-3.96 (m, 4H), 3.26-3.03 (m, 4H), 2.99-2.96 (m, 1H), 2.77 (d, J=12.7 Hz, 3H), 2.28-2.14 (m, 3H), 1.97 (s, 3H), 1.70-1.26 (m, 3H), 1.26-1.03 (m, 6H).

Step B: 3-(3-(Difluoromethyl)-8-methyl-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic acid. A mixture containing ethyl 3-(3-(difluoromethyl)-8-methyl-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoate (450 mg, 0.69 mmol), 1 M aqueous NaOH solution (6.4 mL, 6.4 mmol), THF (6.4 mL) and ethanol (0.04 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over Na$_2$SO$_4$, filtered, and concentrated to dryness under reduced pressure. The residue was purified by flash column chromatography (eluent: 0-10% MeOH/DCM) to provide the title compound (428 mg, 99%) as a white foam which was further purified by preparative LC (Stationary phase: irregular bare silica 40 g, Mobile phase: 97% DCM, 3% MeOH) to provide the title compound (418 mg, 97%) as a white foam. MS (ESI): mass calcd. for $C_{31}H_{34}F_2N_6O_4S$, 624.2; m/z found, 624.9 [M]+. $^1$H NMR (500 MHz, CDCl$_3$) δ 8.20-8.08 (m, 2H), 7.88 (d, J=2.3 Hz, 1H), 7.24-7.16 (m, 1H), 7.18-7.02 (m, 3H), 6.89 (dd, J=14.6, 7.3 Hz, 1H), 6.72 (s, 1H), 4.96 (td, J=9.7, 6.6 Hz, 1H), 4.48-4.37 (m, 2H), 4.24-4.20 (m, 1H), 4.14-4.07 (m, 1H), 3.30-3.12 (m, 4H), 3.09-3.02 (m, 1H), 2.78 (d, J=10.8 Hz, 3H), 2.33-2.19 (m, 6H), 1.63-1.59 (m, 1H), 1.53-1.47 (m, 2H), 1.39-1.36 (m, 2H), 1.21 (t, J=7.0 Hz, 1H).

Example 503: (*S)-3-(3-(Difluoromethyl)-8-methyl-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic Acid

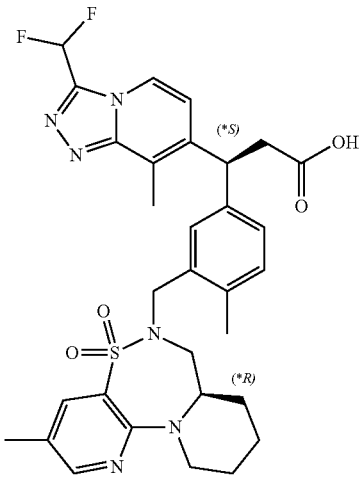 [SMILES: Cc1cnc2c(c1)S(=O)(=O)N(Cc1cc([C@H](CC(=O)O)c3ccn4c(C(F)F)nnc4c3C)ccc1C)C[C@H]1CCCCN21]

The mixture of 3-(3-(difluoromethyl)-8-methyl-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic acid isomers (Example 502, 418 mg) was purified by chiral SFC (stationary phase: Chiralpak AD-H 5 μm 250×30 mm, isocratic mobile phase: 50% $CO_2$, 50% EtOH) to afford two diastereomers. The first eluting isomer (174 mg) was designated (*S). MS (ESI): mass calcd. for $C_{31}H_{34}F_2N_6O_4S$, 624.2; m/z found, 624.9 [M]$^+$. $^1$H NMR (400 MHz, CDCl$_3$) δ 8.20-8.13 (m, 2H), 7.90 (d, J=2.3 Hz, 1H), 7.26-7.08 (m, 4H), 6.88 (d, J=7.2 Hz, 1H), 6.48 (s, 1H), 4.99 (t, J=7.8 Hz, 1H), 4.52-4.39 (m, 2H), 4.23 (d, J=14.6 Hz, 1H), 4.13 (dt, J=13.2, 4.8 Hz, 1H), 3.19-3.12 (m, 4H), 3.05 (dd, J=15.9, 9.0 Hz, 1H), 2.83 (s, 3H), 2.30 (s, 6H), 1.67-1.63 (m, 2H), 1.45-1.40 (m, 3H), 1.27 (dd, J=9.2, 6.1 Hz, 1H).

Example 504: (*R)-3-(3-(Difluoromethyl)-8-methyl-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic Acid

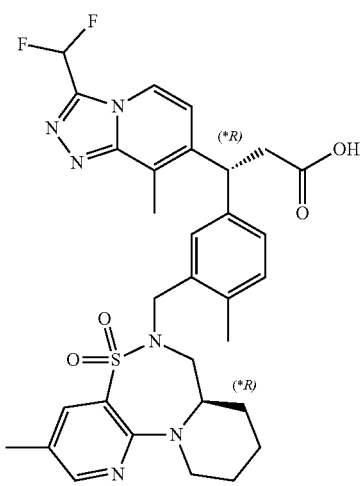 [SMILES: Cc1cnc2c(c1)S(=O)(=O)N(Cc1cc([C@@H](CC(=O)O)c3ccn4c(C(F)F)nnc4c3C)ccc1C)C[C@H]1CCCCN21]

The second eluting isomer (174 mg) from the chiral separation described in Example 503 was designated (*R). MS (ESI): mass calcd. for $C_{31}H_{34}F_2N_6O_4S$, 624.2; m/z found, 624.9 [M]$^+$. $^1$H NMR (400 MHz, CDCl$_3$) δ 8.10-8.03 (m, 2H), 7.80 (d, J=2.3 Hz, 1H), 7.15-6.96 (m, 4H), 6.79 (d, J=7.2 Hz, 1H), 6.47 (s, 1H), 4.86 (t, J=7.8 Hz, 1H), 4.40-4.28 (m, 2H), 4.17 (d, J=14.9 Hz, 1H), 4.04 (dt, J=13.2, 4.9 Hz, 1H), 3.23-3.13 (m, 2H), 3.09-3.02 (m, 2H), 2.96 (t, J=12.5 Hz, 1H), 2.70 (s, 3H), 2.18 (d, J=6.1 Hz, 6H), 1.59-1.53 (m, 2H), 1.38-1.33 (m, 1H), 1.30 (s, 2H), 1.26 (s, 1H).

Example 505: 3-(6-(((*S)-3-Fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-2-methyl-3-(8-methyl-3-(trifluoromethyl)-[1,2,4]triazolo[4,3-a]pyridin-7-yl)propanoic Acid

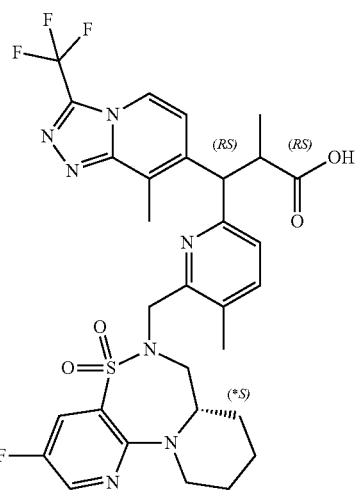

Step A: Ethyl 3-(6-(((*S)-3-fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-2-methyl-3-(8-methyl-3-(trifluoromethyl)-[1,2,4]triazolo[4,3-a]pyridin-7-yl)propanoate. A solution of LDA (1.07 mL, 2 M in THF/heptane/ethylbenzene, 2.13 mmol) was added dropwise at −78° C. to ethyl 3-(6-(((*S)-3-fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoate (Example 496, Step A, 1.20 g, 1.78 mmol) in THF (23 mL) and the resulting mixture was stirred for 0.5 hour. Iodomethane (0.44 mL, 7.10 mmol) was added dropwise and the resulting solution was warmed to room temperature over a period of 2 hours. The mixture was quenched with aqueous saturated NaHCO$_3$ solution (10 mL) and the aqueous layer was extracted with EtOAc (15 mL×3). These extractions resulted in several organic solvent fractions which were combined and concentrated to dryness under reduced pressure. The residue was purified by flash column chromatography (eluent: 30% DCM/EtOAc) to provide the title compound (450 mg, 37%) as a white foam. MS (ESI): mass calcd. for $C_{32}H_{35}F_4N_7O_4S$, 689.2; m/z found, 689.9 [M+H]$^+$.

Step B: 3-(6-(((*S)-3-Fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-2-methyl-3-(8-methyl-3-

(trifluoromethyl)-[1,2,4]triazolo[4,3-a]pyridin-7-yl)propanoic acid. A mixture containing ethyl 3-(6-(((*S)-3-fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-2-methyl-3-(8-methyl-3-(trifluoromethyl)-[1,2,4]triazolo[4,3-a]pyridin-7-yl)propanoate (110 mg, 0.16 mmol), 1 M aqueous NaOH solution (1.5 mL, 1.5 mmol), THF (1.5 mL) and ethanol (0.05 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated to dryness under reduced pressure. The residue was purified by flash column chromatography (eluent: 0-10% DCM/MeOH) to provide the title compound (100 mg, 95%) as a white foam. This foam was further purified by preparative LC (Stationary phase: irregular bare silica 40 g, Mobile phase: 97% DCM, 3% MeOH) to provide the title compound (100 mg, 95%) as a white foam. MS (ESI): mass calcd. for $C_{30}H_{31}F_4N_7O_4S$, 661.2; m/z found, 661.9 [M]+. $^1$H NMR (500 MHz, $CDCl_3$) δ 8.22 (dd, J=3.0, 2.2 Hz, 1H), 8.01 (dd, J=15.1, 7.3 Hz, 1H), 7.88-7.76 (m, 2H), 7.49-7.44 (m, 1H), 7.15 (dd, J=15.1, 7.7 Hz, 1H), 5.31 (s, 1H), 4.75 (d, J=15.1 Hz, 1H), 4.66-4.55 (m, 2H), 4.44-4.24 (m, 2H), 3.86-3.69 (m, 1H), 3.59-3.47 (m, 2H), 3.49-3.34 (m, 1H), 2.78 (d, J=10.0 Hz, 3H), 2.29 (s, 3H), 1.81 (dt, J=13.9, 7.0 Hz, 2H), 1.73-1.49 (m, 3H), 1.31-1.12 (m, 4H).

Example 506: (3*S)-3-(6-(((S)-3-fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-2-methyl-3-(8-methyl-3-(trifluoromethyl)-[1,2,4]triazolo[4,3-a]pyridin-7-yl) propanoic Acid

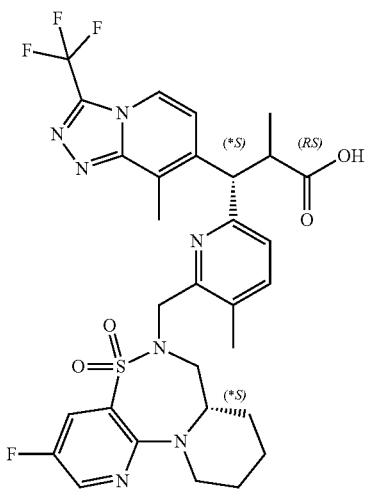 [SMILES: Cc1ccc([C@H](c2ccn3c(C(F)(F)F)nnc3c2C)C(C)C(=O)O)nc1CN1C[C@@H]2CCCCN2c2ncc(F)cc2S1(=O)=O]

The mixture of 3-(6-(((*S)-3-fluoro-5,5-dioxido-7,7a,8,9,10,11-hexahydro-6H-dipyrido[2,1-d:2',3'-f][1,2,5]thiadiaz-epin-6-yl)methyl)-5-methylpyridin-2-yl)-2-methyl-3-(8-methyl-3-(trifluoromethyl)-[1,2,4]triazolo[4,3-a]pyridin-7-yl)propanoic acid isomers (Example 505, 100 mg) were separated by chiral SFC (Chiralpak AD-H 5 μm 250×30 mm, Mobile phase: 30% $CO_2$, 70% MeOH) to afford two diastereomers. The first eluting diastereomer (40 mg) was designated (*S). MS (ESI): mass calcd. for $C_{30}H_{31}F_4N_7O_4S$, 661.2; m/z found, 661.9 [M]+. $^1$H NMR (500 MHz, $CDCl_3$) δ 8.21 (d, J=3.0 Hz, 1H), 8.00 (d, J=7.2 Hz, 1H), 7.83 (dd, J=7.4, 2.9 Hz, 1H), 7.73 (d, J=7.4 Hz, 1H), 7.47-7.41 (m, 1H), 7.14 (d, J=7.7 Hz, 1H), 5.31 (s, 1H), 4.73 (d, J=15.3 Hz, 1H), 4.64-4.52 (m, 2H), 4.40 (d, J=15.3 Hz, 1H), 4.28 (dt, J=13.4, 4.8 Hz, 1H), 3.79-3.69 (m, 1H), 3.58 (t, J=4.5 Hz, 1H), 3.55-3.43 (m, 1H), 3.39-3.32 (m, 1H), 2.78 (s, 3H), 2.29 (s, 3H), 1.87-1.71 (m, 2H), 1.65 (dq, J=12.2, 6.1 Hz, 2H), 1.57-1.51 (m, 2H), 1.29-1.12 (m, 3H).

Example 507: (3*R)-3-(6-(((*S)-3-Fluoro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-2-methyl-3-(8-methyl-3-(trifluoromethyl)-[1,2,4]triazolo[4,3-a]pyridin-7-yl) propanoic Acid

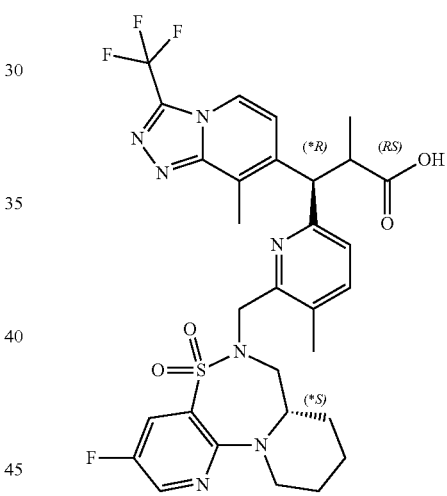

The second eluting isomer (50 mg) from the chiral separation described in Example 506 was designated (*R). MS (ESI): mass calcd. for $C_{30}H_{31}F_4N_7O_4S$, 661.2; m/z found, 661.9 [M]+. $^1$H NMR (400 MHz, $CDCl_3$) δ 8.20 (d, J=2.9 Hz, 1H), 7.98 (d, J=7.2 Hz, 1H), 7.82 (dd, J=7.4, 3.0 Hz, 1H), 7.69 (d, J=7.3 Hz, 1H), 7.43 (d, J=7.8 Hz, 1H), 7.12 (d, J=7.8 Hz, 1H), 5.68 (s, 1H), 4.72 (d, J=15.2 Hz, 1H), 4.57 (t, J=9.8 Hz, 2H), 4.38 (d, J=15.3 Hz, 1H), 4.27 (dt, J=13.3, 4.7 Hz, 1H), 3.74 (dq, J=10.4, 6.7 Hz, 1H), 3.61-3.58 (m, 1H), 3.54-3.41 (m, 1H), 3.39-3.35 (m, 1H), 2.79 (s, 3H), 2.28 (s, 3H), 1.84-1.76 (m, 2H), 1.79-1.70 (m, 1H), 1.74-1.56 (m, 1H), 1.58-1.46 (m, 2H), 1.18 (d, J=6.8 Hz, 3H).

Example 508: 3-(6-((8'-Fluoro-1',1'-dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic Acid

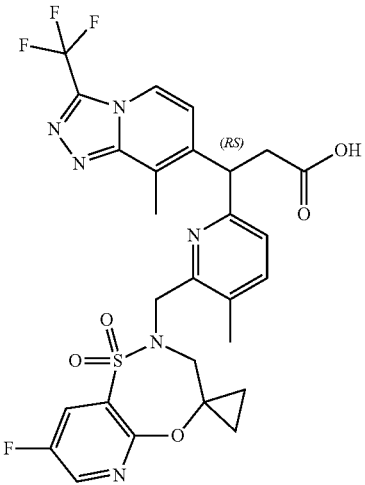 [SMILES: Cc1ccc(C(CC(=O)O)c2ccn3c(C(F)(F)F)nnc3c2C)nc1CN1CC2(CC2)Oc2ncc(F)cc2S1(=O)=O]

Step A: Ethyl 3-(6-((8'-fluoro-1',1'-dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoate. Diisopropyl azodicarboxylate (0.38 mL, 1.95 mmol) was added to a stirring mixture of ethyl 3-(6-(hydroxymethyl)-5-methylpyridin-2-yl)-3-(8-methyl-3-(trifluoromethyl)-[1,2,4]triazolo[4,3-a]pyridin-7-yl)propanoate (Example 33, Step B, 500 mg, 1.18 mmol), 8'-fluoro-2',3'-dihydrospiro[cyclopropane-1,4'-pyrido[2,3-b][1,4,5]oxathiazepine] 1',1'-dioxide (Intermediate 80, 411 mg, 1.68 mmol), and triphenylphosphine (460 mg, 1.76 mmol) in THF (13 mL) at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (700 mg, 91%) as a white foam. MS (ESI): mass calcd. for $C_{29}H_{28}F_4N_6O_5S$, 648.2; m/z found, 649.2 [M+H]$^+$. $^1$H NMR (500 MHz, CDCl$_3$) δ 8.26 (d, J=3.0 Hz, 1H), 8.02-7.85 (m, 2H), 7.44 (dd, J=7.8, 0.9 Hz, 1H), 7.09-7.05 (m, 2H), 4.95 (dd, J=8.1, 7.0 Hz, 1H), 4.55-4.33 (m, 2H), 4.13-3.95 (m, 3H), 3.29 (dd, J=16.1, 8.2 Hz, 1H), 2.93-2.74 (m, 3H), 2.37 (s, 3H), 2.00 (s, 2H), 1.28-1.04 (m, 3H), 0.91-0.88 (m, 2H), 0.82-0.69 (m, 2H).

Step B: 3-(6-((8'-Fluoro-1',1'-dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid. A mixture containing ethyl 3-(6-((8'-fluoro-1',1'-dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoate (700 mg, 1.08 mmol), 1 M aqueous NaOH solution (10 mL, 10 mmol) and THF (10 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered, concentrated to dryness under reduced pressure. The residue was purified by flash column chromatography (eluent: 0-10% MeOH/DCM) to provide the title compound (657 mg, 98%) as a white foam. This foam was further purified by preparative LC (Stationary phase: irregular 15-40 µm 50 g Merck, Mobile phase: 0.4% $H_2O$, 95% DCM, 5% MeOH) to provide the title compound (537 mg, 80%) as a white foam. MS (ESI): mass calcd. for $C_{27}H_{24}F_4N_6O_5S$, 620.6; m/z found, 621.1 [M+H]$^+$. $^1$H NMR (500 MHz, CDCl$_3$) δ 8.73 (s, 1H), 8.30 (d, J=3.1 Hz, 1H), 8.04 (dd, J=6.4, 3.1 Hz, 1H), 7.97 (d, J=7.2 Hz, 1H), 7.49-7.42 (m, 1H), 7.08 (dd, J=15.3, 7.6 Hz, 2H), 4.99 (t, J=7.5 Hz, 1H), 4.56 (d, J=13.6 Hz, 1H), 4.43 (d, J=13.7 Hz, 1H), 3.80 (d, J=15.9 Hz, 1H), 3.49 (q, J=7.0 Hz, 1H), 3.40 (dd, J=16.4, 8.1 Hz, 1H), 2.95 (dd, J=16.4, 6.9 Hz, 1H), 2.82 (s, 3H), 2.40 (s, 3H), 1.28-1.16 (m, 1H), 1.18-1.10 (m, 1H), 0.99-0.90 (m, 1H), 0.76 (dt, J=10.7, 6.3 Hz, 1H).

Example 509: (*S)-3-(6-((8'-Fluoro-1',1'-dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic Acid

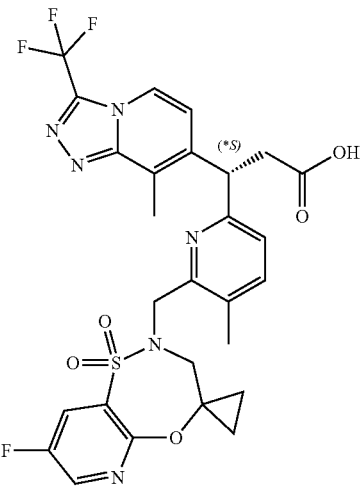 [SMILES: Cc1ccc([C@@H](CC(=O)O)c2ccn3c(C(F)(F)F)nnc3c2C)nc1CN1CC2(CC2)Oc2ncc(F)cc2S1(=O)=O]

The mixture of 3-(6-((8'-fluoro-1',1'-dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic acid isomers (Example 508, 537 mg) was separated by chiral SFC (Chiralpak AD-H 5 µm 250×30 mm, Mobile phase: 60% $CO_2$, 40% EtOH) to afford two enantiomers. The first eluting enantiomer (233 mg) was designated (*S). MS (ESI): mass calcd. for $C_{27}H_{24}F_4N_6O_5S$, 620.6; m/z found, 621.1 [M+H]$^+$. $^1$H NMR (500 MHz, CDCl$_3$) δ 8.31 (d, J=3.1 Hz, 1H), 8.05 (dd, J=6.4, 3.0 Hz, 1H), 7.97 (d, J=7.2 Hz, 1H), 7.49-7.44 (m, 1H), 7.09-7.05 (m, 2H), 5.99 (s, 2H), 4.99 (t, J=7.5 Hz, 1H), 4.58 (d, J=13.7 Hz, 1H), 4.43 (d, J=13.7 Hz, 1H), 3.83 (s, 1H), 3.40 (dd, J=16.4, 8.0 Hz, 1H), 2.95 (dd, J=16.4, 7.0 Hz, 1H), 2.83 (s, 3H), 2.41 (s, 3H), 1.26-1.22 (m, 1H), 1.11 (dt, J=11.4, 6.4 Hz, 1H), 0.96 (t, J=6.7 Hz, 1H), 0.73 (dt, J=10.7, 6.6 Hz, 1H).

Example 510: (*R)-3-(6-((8'-Fluoro-1',1'-dioxidospiro[cyclopropane-1,4'-pyrido[2,3-b][1,4,5]oxathiazepin]-2'(3'H)-yl)methyl)-5-methylpyridin-2-yl)-3-(8-methyl-3-(trifluoromethyl)-[1,2,4]triazolo[4,3-a]pyridin-7-yl)propanoic Acid

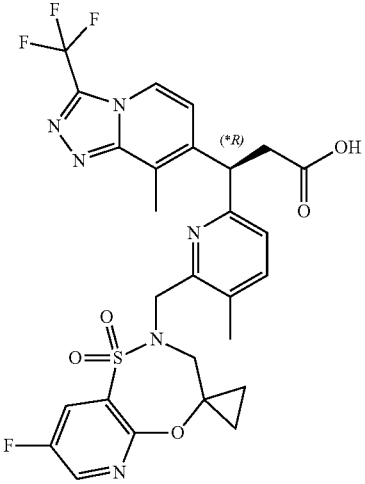 [SMILES: Cc1ccc([C@H](CC(=O)O)c2ccn3c(C(F)(F)F)nnc3c2C)nc1CN1CC2(CC2)Oc2ncc(F)cc2S1(=O)=O]

The second eluting enantiomer (225 mg) from the chiral separation described in Example 509 was designated (*R). MS (ESI): mass calcd. for $C_{27}H_{24}F_4N_6O_5S$, 620.6; m/z found, 621.1 [M+H]$^+$. $^1$H NMR (500 MHz, CDCl$_3$) δ 8.31 (d, J=3.1 Hz, 1H), 8.06 (dd, J=6.4, 3.1 Hz, 1H), 7.97 (d, J=7.2 Hz, 1H), 7.47 (d, J=7.8 Hz, 1H), 7.09 (d, J=7.8 Hz, 1H), 7.04 (d, J=7.3 Hz, 1H), 5.31 (s, 2H), 4.99 (t, J=7.5 Hz, 1H), 4.59 (d, J=13.7 Hz, 1H), 4.43 (d, J=13.6 Hz, 1H), 3.83 (s, 1H), 3.40 (dd, J=16.4, 8.0 Hz, 1H), 2.95 (dd, J=16.4, 6.9 Hz, 1H), 2.84 (s, 3H), 2.41 (s, 3H), 1.29-1.20 (m, 1H), 1.12 (dt, J=11.5, 6.5 Hz, 1H), 0.96 (s, 1H), 0.73 (dt, J=10.7, 6.6 Hz, 1H).

Example 511: (*S)-3-(3-(Difluoromethyl)-8-methyl-[1,2,4]triazolo[4,3-a]pyridin-7-yl)-3-(3-(((*S)-3-fluoro-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

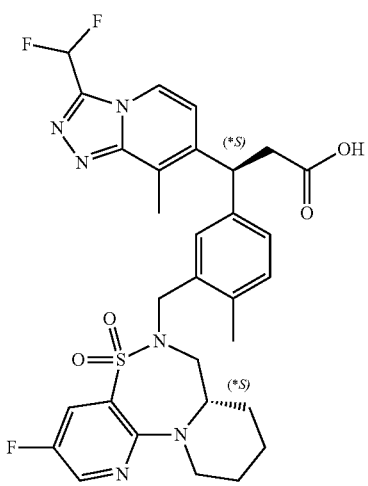 [SMILES: Cc1ccc([C@H](CC(=O)O)c2ccn3c(C(F)F)nnc3c2C)cc1CN1C[C@@H]2CCCCN2c2ncc(F)cc2S1(=O)=O]

Step A: Ethyl (*S)-3-(3-(difluoromethyl)-8-methyl-[1,2,4]triazolo[4,3-a]pyridin-7-yl)-3-(3-(((*S)-3-fluoro-5,5-dioxido-7,7a,8,9,10,11-hexahydro-6H-dipyrido[2,1-d:2',3'-f][1,2,5]thiadiazepin-6-yl)methyl)-4-methylphenyl)propanoate. Diisopropyl azodicarboxylate (0.40 mL, 2.04 mmol) was added to a stirring mixture of ethyl (*S)-3-(3-(difluoromethyl)-8-methyl-[1,2,4]triazolo[4,3-a]pyridin-7-yl)-3-(3-(hydroxymethyl)-4-methylphenyl)propanoate (Intermediate 167, 500 mg, 1.24 mmol), (*S)-3-fluoro-7,7a,8,9,10,11-hexahydro-6H-dipyrido[2,1-d:2',3'-f][1,2,5]thiadiazepine 5,5-dioxide (Intermediate 78, 478 mg, 1.76 mmol), and triphenylphosphine (482 mg, 1.84 mmol) in THF (14 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (750 mg, 92%) as a white foam. MS (ESI): mass calcd. for $C_{32}H_{35}F_6N_6O_4S$, 656.7; m/z found, 656.9 [M]$^+$. $^1$H NMR (500 MHz, CDCl$_3$) δ 8.19-8.12 (m, 2H), 7.79 (dd, J=7.4, 3.0 Hz, 1H), 7.17-7.07 (m, 3H), 6.86 (d, J=7.2 Hz, 1H), 4.93 (dd, J=8.8, 6.9 Hz, 1H), 4.49-4.39 (m, 2H), 4.24 (d, J=14.8 Hz, 1H), 4.18-4.03 (m, 4H), 3.30-3.08 (m, 4H), 3.01 (dd, J=15.9, 8.8 Hz, 1H), 2.81 (s, 3H), 2.24 (s, 3H), 1.79-1.56 (m, 3H), 1.58-1.32 (m, 3H), 1.16 (t, J=7.1 Hz, 3H).

Step B: (*S)-3-(3-(Difluoromethyl)-8-methyl-[1,2,4]triazolo[4,3-a]pyridin-7-yl)-3-(3-(((*S)-3-fluoro-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid. A mixture containing ethyl (*S)-3-(3-(difluoromethyl)-8-methyl-[1,2,4]triazolo[4,3-a]pyridin-7-yl)-3-(3-(((*S)-3-fluoro-5,5-dioxido-7,7a,8,9,10,11-hexahydro-6H-dipyrido[2,1-d:2',3'-f][1,2,5]thiadiazepin-6-yl)methyl)-4-methylphenyl)propanoate (550 mg, 0.84 mmol), 1 M aqueous NaOH solution (7.7 mL, 7.7 mmol) and THF (7.7 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over Na$_2$SO$_4$, filtered, and concentrated to dryness under reduced pressure. The residue was purified by flash column chromatography (eluent: 0-10% MeOH/DCM) to provide the title compound (504 mg, 95%) as a white foam. MS (ESI): mass calcd. for $C_{30}H_{31}F_3N_6O_4S$, 628.7; m/z found, 629.2 [M+H]$^+$. $^1$H NMR (500 MHz, CDCl$_3$) δ 9.60 (s, 1H), 8.22-8.12 (m, 2H), 7.80 (dd, J=7.4, 3.0 Hz, 1H), 7.23-7.06 (m, 4H), 6.92 (d, J=7.3 Hz, 1H), 5.30 (s, 1H), 4.96 (dd, J=9.1, 6.6 Hz, 1H), 4.47-4.34 (m, 2H), 4.26 (d, J=14.9 Hz, 1H), 4.11 (dt, J=13.4, 5.0 Hz, 1H), 3.33-3.03 (m, 5H), 2.77 (s, 3H), 2.25 (s, 3H), 1.77-1.56 (m, 2H), 1.55-1.31 (m, 3H).

Example 512: (*S)-3-(3-(Difluoromethyl)-8-methyl-[1,2,4]triazolo[4,3-a]pyridin-7-yl)-3-(3-(((*R)-3-fluoro-5,5-dioxido-7,7a,8,9,10,11-hexahydro-6H-dipyrido[2,1-d:2',3'-f][1,2,5]thiadiazepin-6-yl)methyl)-4-methylphenyl)propanoic Acid

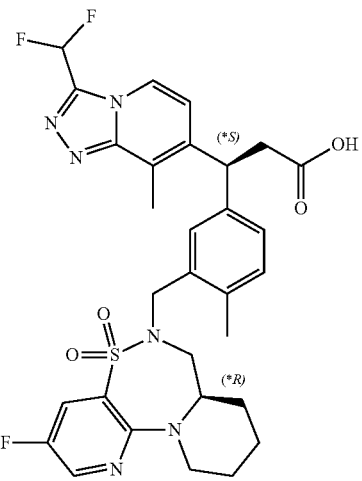 [SMILES: Cc1ccc([C@H](CC(=O)O)c2ccn3c(C(F)F)nnc3c2C)cc1CN1C[C@H]2CCCCN2c2ncc(F)cc2S1(=O)=O]

Step A: Ethyl (*S)-3-(3-(difluoromethyl)-8-methyl-[1,2,4]triazolo[4,3-a]pyridin-7-yl)-3-(3-(((*R)-3-fluoro-5,5-dioxido-7,7a,8,9,10,11-hexahydro-6H-dipyrido[2,1-d:2',3'-f][1,2,5]thiadiazepin-6-yl)methyl)-4-methylphenyl)propanoate. Diisopropyl azodicarboxylate (0.40 mL, 2.04 mmol) was added to a stirring mixture of ethyl (*S)-3-(3-(difluoromethyl)-8-methyl-[1,2,4]triazolo[4,3-a]pyridin-7-yl)-3-(3-(hydroxymethyl)-4-methylphenyl)propanoate (Intermediate 167, 500 mg, 1.24 mmol), (*S)-3-fluoro-7,7a,8,9,10,11-hexahydro-6H-dipyrido[2,1-d:2',3'-f][1,2,5]thiadiazepine 5,5-dioxide (Intermediate 79, 478 mg, 1.76 mmol), and triphenylphosphine (482 mg, 1.84 mmol) in THF (14 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (600 mg, 74%) as a white foam. MS (ESI): mass calcd. for $C_{32}H_{35}F_6N_6O_4S$, 656.7; m/z found, 657.3 [M+H]$^+$. $^1$H NMR (500 MHz, CDCl$_3$) δ 8.16-8.10 (m, 2H), 7.75 (dd, J=7.4, 2.9 Hz, 1H), 7.19-7.05 (m, 4H), 6.83 (d, J=7.2 Hz, 1H), 4.92 (dd, J=8.8, 6.9 Hz, 1H), 4.48-4.32 (m, 2H), 4.22-3.96 (m, 5H), 3.24-3.05 (m, 4H), 2.99 (dd, J=15.8, 8.9 Hz, 1H), 2.80 (s, 3H), 2.24 (s, 3H), 1.72-1.48 (m, 2H), 1.46-1.05 (m, 6H).

Step B: (*S)-3-(3-(Difluoromethyl)-8-methy-[1,2,4]triazolo[4,3-a]pyridin-7-yl)-3-(3-(((*R)-3-fluoro-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid. A mixture containing ethyl (*S)-3-(3-(difluoromethyl)-8-methyl-[1,2,4]triazolo[4,3-a]pyridin-7-yl)-3-(3-(((*R)-3-fluoro-5,5-dioxido-7,7a,8,9,10,11-hexahydro-6H-dipyrido[2,1-d:2',3'-f][1,2,5]thiadiazepin-6-yl)methyl)-4-methylphenyl)propanoate (600 mg, 0.91 mmol), 1 M aqueous NaOH solution (8.4 mL, 8.4 mmol) and THF (8.4 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered and concentrated to dryness under reduced pressure. The residue was purified by flash column chromatography (eluent: 0-10% MeOH/DCM) to provide the title compound (550 mg, 96%) as a white foam. MS (ESI): mass calcd. for $C_{30}H_{31}F_3N_6O_4S$, 628.7; m/z found, 629.2 [M+H]$^+$. $^1$H NMR (500 MHz, CDCl$_3$) δ 10.44 (s, 1H), 8.19-8.11 (m, 2H), 7.79 (dd, J=7.4, 3.0 Hz, 1H), 7.25-7.08 (m, 4H), 6.91 (d, J=7.3 Hz, 1H), 5.29 (s, 1H), 4.97 (dd, J=9.1, 6.5 Hz, 1H), 4.50-4.34 (m, 2H), 4.25-4.03 (m, 2H), 3.32-3.02 (m, 5H), 2.78 (s, 3H), 2.26 (s, 3H), 1.72-1.53 (m, 2H), 1.48-1.20 (m, 3H).

Example 513: (3*S)-3-(8-Ethyl-3-(trifluoromethyl)-[1,2,4]triazolo[4,3-a]pyridin-7-yl)-2-methyl-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic Acid

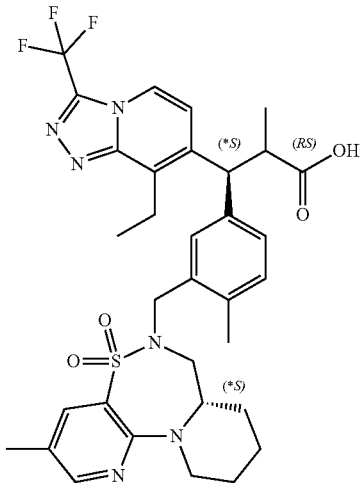 [SMILES: CCc1c([C@H](c2ccc(C)c(CN3C[C@@H]4CCCCN4c4ncc(C)cc4S3(=O)=O)c2)C(C)C(=O)O)ccn2c(C(F)(F)F)nnc12]

Step A: Ethyl (*S)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoate. Diisopropyl azodicarboxylate (0.77 mL, 3.91 mmol) was added to a stirring mixture of ethyl (*S)-3-(3-(hydroxymethyl)-4-methylphenyl)-3-(8-methyl-3-(trifluoromethyl)-[1,2,4]triazolo[4,3-a]pyridin-7-yl)propanoate (Intermediate 26, 1.00 g, 2.37 mmol), (*S)-3-methyl-7,7a,8,9,10,11-hexahydro-6H-dipyrido[2,1-d:2',3'-f][1,2,5]thiadiazepine 5,5-dioxide (Intermediate 77, 901 mg, 3.37 mmol), and triphenylphosphine (923 mg, 3.52 mmol) in THF (27 mL) at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (1.3 g, 82%) as a white foam. MS (ESI): mass calcd. for $C_{33}H_{37}F_3N_6O_4S$, 670.8; m/z found, 671.2 [M+H]$^+$. $^1$H NMR (500 MHz, CDCl$_3$) δ 8.13 (dd, J=2.3, 0.8 Hz, 1H), 8.02 (d, J=7.2 Hz, 1H), 7.86 (dd, J=2.3, 0.9 Hz, 1H), 7.21-7.09 (m, 2H), 7.07 (dd, J=7.9, 2.0 Hz, 1H), 6.92 (d, J=7.3 Hz, 1H), 4.94 (dd, J=9.0, 6.8 Hz, 1H), 4.53-4.35 (m, 2H), 4.29-3.99 (m, 4H), 3.32-2.96 (m, 5H), 2.84 (d, J=0.7 Hz, 3H), 2.26 (d, J=8.5 Hz, 6H), 1.81-1.60 (m, 3H), 1.59-1.37 (m, 3H), 1.23-1.18 (m, 3H).

Step B: Ethyl (3*S)-3-(8-ethyl-3-(trifluoromethyl)-[1,2,4]triazolo[4,3-a]pyridin-7-yl)-2-methyl-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoate. A solution of LDA (2.91 mL, 1 M in hexane/THF, 2.91 mmol) was added dropwise at −78° C. to ethyl (*S)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoate (1.30 g, 1.94 mmol) in THF (25 mL) and the resulting mixture was stirred for 0.5 hour. Iodomethane (0.24 mL, 3.88 mmol) was added dropwise and the resulting solution was warmed to room temperature over a period of 2 hours. The mixture was quenched with aqueous saturated NaHCO$_3$ solution (10 mL) and the aqueous layer was extracted with EtOAc (15 mL×3). These extractions resulted in several organic solvent fractions which were combined and concentrated to dryness under reduced pressure. The residue was purified by flash column chromatography (eluent: 30% DCM/EtOAc) to provide the title compound (150 mg, 11%) as a white foam. MS (ESI): mass calcd. for $C_{35}H_{41}F_3N_6O_4S$, 698.8; m/z found, 699.3 [M+H]$^+$.

Step C: (3*S)-3-(8-Ethyl-3-(trifluoromethyl)-[1,2,4]triazolo[4,3-a]pyridin-7-yl)-2-methyl-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic acid. A mixture containing ethyl (3*S)-3-(8-ethyl-3-(trifluoromethyl)-[1,2,4]triazolo[4,3-a]pyridin-7-yl)-2-methyl-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoate (150 mg, 0.21 mmol), 1 M aqueous NaOH solution (2 mL, 2 mmol) and THF (2 mL) was stirred at 50° C. overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated to dryness under reduced pressure. The residue was purified by flash column chromatography (eluent: 0-10% MeOH/DCM) to provide the title compound (113 mg, 79%) as a white foam. MS (ESI): mass calcd. for $C_{33}H_{37}F_3N_6O_4S$, 670.8; m/z found, 671.2 [M+H]$^+$. $^1$H NMR (600 MHz, CDCl$_3$) δ 8.14 (d, J=2.3 Hz, 1H), 8.05 (d, J=7.2 Hz, 1H), 7.88 (dd, J=2.2, 0.9 Hz, 1H), 7.31-7.25 (m, 2H), 7.20-7.12 (m, 2H), 4.51-4.40 (m, 3H), 4.24 (d, J=15.0 Hz, 1H), 4.20-4.09 (m, 1H), 3.38-3.17 (m, 6H), 2.26 (d, J=18.9 Hz, 6H), 2.05 (d, J=6.0 Hz, 1H), 1.77-1.60 (m, 3H), 1.56-1.46 (m, 1H), 1.46-1.29 (m, 2H), 1.30-1.23 (m, 6H).

Example 514: (3*S)-2-Methyl-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoic Acid

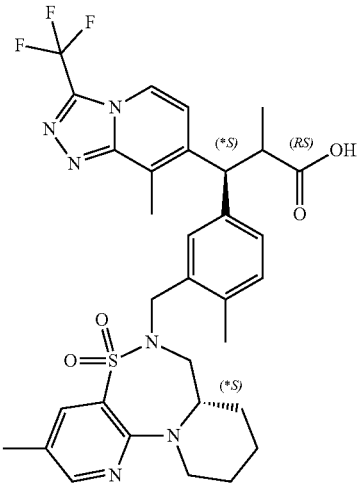 [SMILES: Cc1cnc2c(c1)S(=O)(=O)N(Cc1cc([C@@H](c3ccn4c(C(F)(F)F)nnc4c3C)C(C)C(=O)O)ccc1C)C[C@@H]1CCCCN21]

Step A: Ethyl (3*S)-2-methyl-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoate. A solution of LDA (2.91 mL, 1 M in hexane/THF, 2.91 mmol) was added dropwise at −78° C. to ethyl (*S)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoate (Example 513, Step A, 1.30 g, 1.94 mmol) in THF (25 mL) and the resulting mixture was stirred for 0.5 hour. Iodomethane (0.24 mL, 3.88 mmol) was added dropwise and the resulting solution was warmed to room temperature over a period of 2 hours. The mixture was quenched with aqueous saturated NaHCO$_3$ solution (10 mL) and the aqueous layer was extracted with EtOAc (15 mL×3). These extractions resulted in several organic solvent fractions which were combined and concentrated to dryness under reduced pressure. The residue was purified by flash column chromatography (eluent: 30% DCM/EtOAc) to provide the title compound (200 mg, 15%) as a white foam. MS (ESI): mass calcd. for $C_{34}H_{39}F_3N_6O_4S$, 684.8; m/z found, 685.3 [M+H]$^+$.

Step B: (3*S)-2-Methyl-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoic acid. A mixture containing ethyl (3*S)-2-methyl-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoate (200 mg, 0.29 mmol), 1 M aqueous NaOH solution (2.7 mL, 2.7 mmol) and THF (2.7 mL) was stirred at 50° C. overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated to dryness under reduced pressure. The residue was purified by flash column chromatography (eluent: 0-10% MeOH/DCM) to provide the title compound (113 mg, 79%) as a white foam. MS (ESI): mass calcd. for C$_{32}$H$_{35}$F$_3$N$_6$O$_4$S, 656.2; m/z found, 656.2 [M]$^+$. $^1$H NMR (600 MHz, CDCl$_3$) δ 8.17-8.12 (m, 1H), 8.06-7.99 (m, 1H), 7.91-7.86 (m, 1H), 7.28-7.18 (m, 2H), 7.15 (d, J=1.4 Hz, 2H), 4.52-4.47 (m, 1H), 4.49-4.43 (m, 1H), 4.45-4.38 (m, 1H), 4.26 (d, J=15.0 Hz, 1H), 4.19 (dt, J=13.3, 4.9 Hz, 1H), 3.49 (q, J=7.0 Hz, 2H), 3.37 (dq, J=11.2, 6.7 Hz, 1H), 3.32-3.19 (m, 3H), 2.76 (s, 3H), 2.31-2.20 (m, 4H), 1.81-1.63 (m, 1H), 1.58-1.52 (m, 1H), 1.49-1.31 (m, 2H), 1.27 (d, J=6.9 Hz, 3H), 1.21 (t, J=7.0 Hz, 3H).

Example 515: (3*S)-3-(8-Ethyl-3-(trifluoromethyl)-[1,2,4]triazolo[4,3-a]pyridin-7-yl)-2-methyl-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic Acid

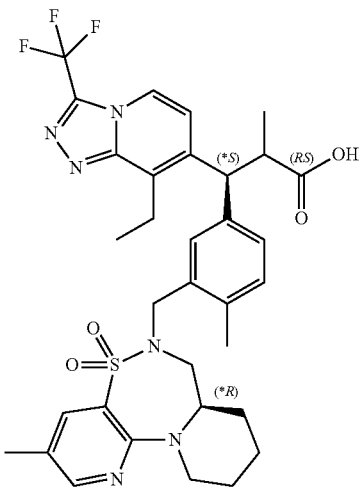 [SMILES: CCc1c([C@H](c2ccc(C)c(CN3C[C@H]4CCCCN4c4ncc(C)cc4S3(=O)=O)c2)C(C)C(=O)O)ccn2c(C(F)(F)F)nnc12]

Step A: Ethyl (*S)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoate. Diisopropyl azodicarboxylate (0.77 mL, 3.91 mmol) was added to a stirring mixture of ethyl (*S)-3-(3-(hydroxymethyl)-4-methylphenyl)-3-(8-methyl-3-(trifluoromethyl)-[1,2,4]triazolo[4,3-a]pyridin-7-yl)propanoate (Intermediate 26, 1.00 g, 2.37 mmol), (*R)-3-methyl-7,7a,8,9,10,11-hexahydro-6H-dipyrido[2,1-d:2',3'-f][1,2,5]thiadiazepine 5,5-dioxide (Intermediate 117 901 mg, 3.37 mmol), and triphenylphosphine (923 mg, 3.52 mmol) in THF (27 mL) at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (1.4 g, 88%) as a white foam. MS (ESI): mass calcd. for C$_{33}$H$_{37}$F$_3$N$_6$O$_4$S, 670.8; m/z found, 671.2 [M+H]$^+$. $^1$H NMR (500 MHz, CDCl$_3$) δ 8.12 (dd, J=2.3, 0.9 Hz, 1H), 8.02 (d, J=7.2 Hz, 1H), 7.85 (dd, J=2.3, 0.9 Hz, 1H), 7.18-7.04 (m, 3H), 6.90 (d, J=7.3 Hz, 1H), 4.95 (dd, J=9.0, 6.8 Hz, 1H), 4.48-4.35 (m, 2H), 4.25-3.99 (m, 4H), 3.25-3.06 (m, 4H), 3.00 (dd, J=15.8, 9.1 Hz, 1H), 2.85 (s, 3H), 2.27 (d, J=2.9 Hz, 6H), 1.78-1.55 (m, 3H), 1.54-1.09 (m, 6H).

Step B: Ethyl (3*S)-3-(8-ethyl-3-(trifluoromethyl)-[1,2,4]triazolo[4,3-a]pyridin-7-yl)-2-methyl-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoate. A solution of LDA (3.13 mL, 1 M in hexane/THF, 3.13 mmol) was added dropwise at −78° C. to ethyl (*S)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoate (1.40 g, 2.09 mmol) in THF (25 mL) and the resulting mixture was stirred for 0.5 hour. Iodomethane (0.26 mL, 4.17 mmol) was added dropwise and the resulting solution was warmed to room temperature over a period of 2 hours. The mixture was quenched with aqueous saturated NaHCO$_3$ solution (10 mL) and the aqueous layer was extracted with EtOAc (15 mL×3). These extractions resulted in several organic solvent fractions which were combined and concentrated to dryness under reduced pressure. The residue was purified by preparative acidic HPLC (0.05% TFA in water, 0.05% TFA in acetonitrile) to provide the title compound (300 mg, 21%) as a white foam. MS (ESI): mass calcd. for C$_{35}$H$_{41}$F$_3$N$_6$O$_4$S, 698.3; m/z found, 699.3 [M+H]$^+$.

Step C: (3*S)-3-(8-Ethyl-3-(trifluoromethyl)-[1,2,4]triazolo[4,3-a]pyridin-7-yl)-2-methyl-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic acid. A mixture containing ethyl (3*S)-3-(8-ethyl-3-(trifluoromethyl)-[1,2,4]triazolo[4,3-a]pyridin-7-yl)-2-methyl-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoate (250 mg, 0.36 mmol), 1 M aqueous NaOH solution (3.3 mL, 3.3 mmol) and THF (3.3 mL) was stirred at 50° C. overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated to dryness under reduced pressure. The residue was purified by flash column chromatography (eluent: 0-10% MeOH/DCM) to provide the title compound (133 mg, 48%) as a white foam. MS (ESI): mass calcd. for C$_{33}$H$_{37}$F$_3$N$_6$O$_4$S, 670.8; m/z found, 671.2 [M+H]$^+$. $^1$H NMR (600 MHz, CDCl$_3$) δ 9.33 (s, 2H), 8.13 (d, J=2.3 Hz, 1H), 8.06-7.98 (m, 1H), 7.90-7.84 (m, 1H), 7.30 (d, J=7.4 Hz, 1H), 7.26 (d, J=1.9 Hz, 1H), 7.19-7.07 (m, 2H), 4.47 (d, J=11.4 Hz, 1H), 4.45-4.35 (m, 2H), 4.34 (d, J=11.3 Hz, 1H), 4.25 (d, J=14.9 Hz, 1H), 4.22-4.10 (m, 1H), 3.39-3.13 (m, 5H), 2.25 (d, J=17.6 Hz, 6H), 1.75-1.63 (m, 1H), 1.64-1.61 (m, 1H), 1.54-1.45 (m, 1H), 1.39-1.36 (m, 2H), 1.29-1.20 (m, 5H), 1.17 (d, J=6.9 Hz, 1H).

Example 516: (*S)-3-(8-Ethyl-3-(trifluoromethyl)-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic Acid

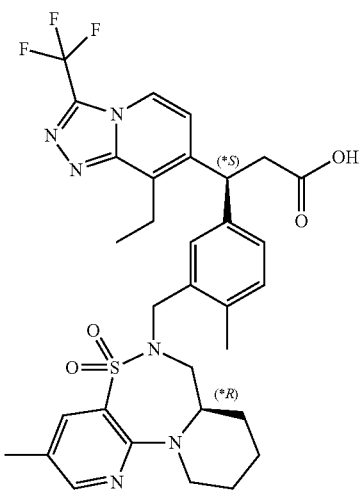 [SMILES: CCc1c([C@@H](CC(=O)O)c2ccc(C)c(CN3C[C@H]4CCCCN4c4ncc(C)cc4S3(=O)=O)c2)ccn2c(C(F)(F)F)nnc12]

Step A: Ethyl (*S)-3-(8-ethyl-3-(trifluoromethyl)-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoate. A solution of LDA (3.13 mL, 1 M in hexane/THF, 3.13 mmol) was added dropwise at −78° C. to ethyl (*S)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoate (Example 515, Step A, 1.40 g, 2.09 mmol) in THF (25 mL) and the resulting mixture was stirred for 0.5 hour. Iodomethane (0.26 mL, 4.17 mmol) was added dropwise and the resulting solution was warmed to room temperature over a period of 2 hours. The mixture was quenched with aqueous saturated NaHCO$_3$ solution (10 mL) and the aqueous layer was extracted with EtOAc (15 mL×3). These extractions resulted in several organic solvent fractions which were combined and concentrated to dryness under reduced pressure. The residue was purified by preparative acidic HPLC (0.05% TFA in water, 0.05% TFA in acetonitrile) to provide the title compound (70 mg, 5%) as a white foam. MS (ESI): mass calcd. for $C_{34}H_{39}F_3N_6O_4S$, 684.8; m/z found, 685.3 [M+H]$^+$.

Step B: (*S)-3-(8-Ethyl-3-(trifluoromethyl)-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic acid. A mixture containing ethyl (*S)-3-(8-ethyl-3-(trifluoromethyl)-[1,2,4]triazolo[4,3-a]pyridin-7-yl)-3-(4-methyl-3-(((*R)-3-methyl-5,5-dioxido-7,7a,8,9,10,11-hexahydro-6H-dipyrido[2,1-d:2',3'-f][1,2,5]thiadiazepin-6-yl)methyl)phenyl)propanoate (70 mg, 0.1 mmol), 1 M aqueous NaOH solution (0.9 mL, 0.9 mmol) and THF (0.9 mL) was stirred at 50° C. overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated to dryness under reduced pressure. The residue was purified by flash column chromatography (eluent: 0-10% MeOH/DCM) to provide the title compound (33 mg, 49%) as a white foam. MS (ESI): mass calcd. for $C_{32}H_{35}F_3N_6O_4S$, 656.7; m/z found, 657.3 [M+H]$^+$. $^1$H NMR (600 MHz, CDCl$_3$) δ 8.12 (d, J=2.2 Hz, 1H), 8.01 (d, J=7.2 Hz, 1H), 7.86 (t, J=2.7 Hz, 1H), 7.19 (d, J=1.9 Hz, 1H), 7.18-7.06 (m, 2H), 6.91 (d, J=7.3 Hz, 1H), 5.00-4.89 (m, 1H), 4.51-4.35 (m, 2H), 4.20 (dd, J=14.9, 4.7 Hz, 1H), 4.09 (dt, J=13.3, 4.9 Hz, 1H), 3.39-3.19 (m, 2H), 3.22-3.10 (m, 3H), 3.06-2.94 (m, 1H), 2.78 (s, 1H), 2.69 (s, 1H), 2.27 (s, 1H), 2.26 (s, 6H), 2.05 (s, 1H), 1.69-1.58 (m, 2H), 1.55-1.40 (m, 1H), 1.42-1.23 (m, 4H).

Example 517: (*S)-3-(8-Ethyl-3-(trifluoromethyl)-[1,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic Acid

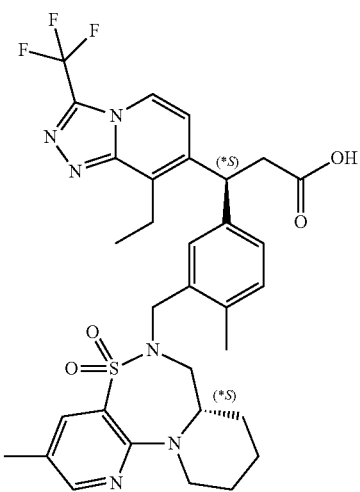 [SMILES: CCc1c([C@@H](CC(=O)O)c2ccc(C)c(CN3C[C@@H]4CCCCN4c4ncc(C)cc4S3(=O)=O)c2)ccn2c(C(F)(F)F)nnc12]

Step A: Ethyl (*S)-3-(8-ethyl-3-(trifluoromethyl)-[1,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoate. A solution of LDA (2.91 mL, 1 M in hexane/THF, 2.91 mmol) was added dropwise at −78° C. to ethyl (*S)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)-3-(8-methyl-3-(trifluoromethyl)-[1,2,4]triazolo[4,3-a]pyridin-7-yl)propanoate (Example 513, Step A, 1.30 g, 1.94 mmol) in THF (25 mL) and the resulting mixture was stirred for 0.5 hour. Iodomethane (0.24 mL, 3.88 mmol) was added dropwise and the resulting solution was warmed to room temperature over a period of 2 hours. The mixture was quenched with aqueous saturated NaHCO$_3$ solution (10 mL) and the aqueous layer was extracted with EtOAc (15 mL×3). These extractions resulted in several organic solvent fractions which were combined and concentrated to dryness under reduced pressure. The residue was purified by preparative acidic HPLC (0.05% TFA in water, 0.05% TFA in acetonitrile) to provide the title compound (80 mg, 6%) as a white foam. MS (ESI): mass calcd. for $C_{34}H_{39}F_3N_6O_4S$, 684.8; m/z found, 685.3 [M+H]$^+$.

Step B: (*S)-3-(8-Ethyl-3-(trifluoromethyl)-[1,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoic acid. A mixture containing ethyl (*S)-3-(8-ethyl-3-(trifluoromethyl)-[,2,4]triazolo[4,3-a]pyridin-7-yl)-3-(4-methyl-3-(((*S)-3-methyl-5,5-dioxido-7,7a,8,9,10,11-hexahydro-6H-dipyrido[2,1-d:2',3'-f][1,2,5]thiadiazepin-6-yl)methyl)phenyl)propanoate (80 mg, 0.12 mmol), 1 M aqueous NaOH solution (2.7 mL, 2.7 mmol) and THF (2.7 mL) was stirred at 50° C. overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated to dryness under reduced pressure. The residue was purified by flash column chromatography (eluent: 0-10% MeOH/DCM) to provide the title compound (39 mg, 45%) as a white foam. MS (ESI): mass calcd. for $C_{32}H_{35}F_3N_6O_4S$, 656.2; m/z found, 657.3 [M+H]$^+$. $^1$H NMR (600 MHz, $CDCl_3$) δ 8.17-8.12 (m, 1H), 8.06-7.99 (m, 1H), 7.91-7.86 (m, 1H), 7.28-7.18 (m, 2H), 7.15 (d, J=1.4 Hz, 2H), 4.52-4.47 (m, 1H), 4.49-4.43 (m, 1H), 4.45-4.38 (m, 1H), 4.26 (d, J=15.0 Hz, 1H), 4.19 (dt, J=13.3, 4.9 Hz, 1H), 3.49 (q, J=7.0 Hz, 2H), 3.37 (dq, J=11.2, 6.7 Hz, 1H), 3.32-3.19 (m, 3H), 2.76 (s, 3H), 2.31-2.20 (m, 6H), 1.81-1.63 (m, 1H), 1.56-1.54 (m, 1H), 1.49-1.31 (m, 2H), 1.27 (d, J=6.9 Hz, 1H), 1.21 (t, J=7.0 Hz, 3H).

Example 518: 3-(6-((3-Chloro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

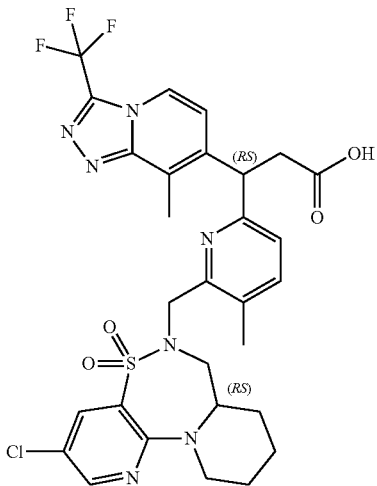 [SMILES: Cc1ccc(C(CC(=O)O)c2ccn3c(C(F)(F)F)nnc3c2C)nc1CN1CC2CCCCN2c2ncc(Cl)cc2S1(=O)=O]

Step A: Ethyl 3-(6-((3-chloro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoate. DBAD (303 mg, 1.32 mmol) was added to a stirring mixture of ethyl 3-(6-(hydroxymethyl)-5-methylpyridin-2-yl)-3-(8-methyl-3-(trifluoromethyl)-[1,2,4]triazolo[4,3-a]pyridin-7-yl)propanoate (Example 33, Step B, 367 mg, 0.87 mmol), 3-chloro-7,7a,8,9,10,11-hexahydro-6H-dipyrido[2,1-d:2',3'-f][1,2,5]thiadiazepine 5,5-dioxide (Intermediate 152 300 mg, 1.04 mmol), and triphenylphosphine (343 mg, 1.31 mmol) in THF (11 mL) at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (550 mg, 91%) as a white foam. MS (ESI): mass calcd. for $C_{31}H_{33}ClF_3N_7O_4S$, 692.2; m/z found, 692.2 [M]+. $^1$H NMR (400 MHz, $CDCl_3$) δ 8.22 (d, J=2.5 Hz, 1H), 8.06-7.97 (m, 2H), 7.44 (dd, J=13.8, 7.8 Hz, 1H), 7.35-7.18 (m, 1H), 7.12 (dd, J=21.0, 7.8 Hz, 1H), 5.05 (q, J=7.2 Hz, 1H), 4.79-4.57 (m, 2H), 4.40-4.24 (m, 2H), 4.20-3.99 (m, 3H), 3.64-3.50 (m, 2H), 3.49-3.30 (m, 2H), 3.09-3.03 (m, 1H), 2.92 (d, J=2.2 Hz, 3H), 2.34 (s, 1H), 2.28 (s, 2H), 1.87-1.68 (m, 3H), 1.72-1.51 (m, 2H), 1.18 (t, J=7.1 Hz, 3H).

Step B: 3-(6-((3-Chloro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid. A mixture containing ethyl 3-(6-((3-chloro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoate (550 mg, 0.80 mmol), 1 M aqueous NaOH solution (2.4 mL, 2.4 mmol) and THF (20 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated to dryness under reduced pressure. The residue was purified by flash column chromatography (eluent: 0-10% MeOH/DCM) to provide the title compound (487 mg, 92%) as a white foam. MS (ESI): mass calcd. for $C_{29}H_{29}ClF_3N_7O_4S$, 663.2; m/z found, 664.2 [M+H]$^+$. $^1$H NMR (400 MHz, $CDCl_3$) δ 9.87 (s, 1H), 8.21 (dd, J=2.3, 1.3 Hz, 1H), 8.05-7.95 (m, 2H), 7.48-7.31 (m, 1H), 7.25 (d, J=7.3 Hz, 1H), 7.08 (dd, J=21.3, 7.8 Hz, 1H), 5.03 (t, J=7.4 Hz, 1H), 4.73 (dd, J=14.8, 9.9 Hz, 1H), 4.66-4.60 (m, 1H), 4.39-4.24 (m, 2H), 3.67-3.22 (m, 4H), 3.09-3.02 (m, 1H), 2.86 (d, J=3.0 Hz, 3H), 2.33 (s, 2H), 2.26 (s, 1H), 1.84-1.65 (m, 2H), 1.55-1.50 (m, 2H), 1.19 (t, J=7.0 Hz, 2H).

Example 519: (*S)-3-(6-(((*S)-3-Chloro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

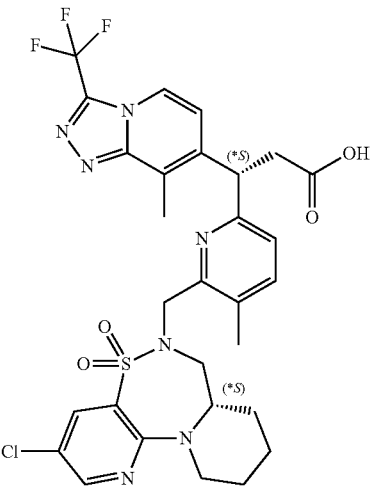 [SMILES: Cc1ccc([C@@H](CC(=O)O)c2ccn3c(C(F)(F)F)nnc3c2C)nc1CN1C[C@@H]2CCCCN2c2ncc(Cl)cc2S1(=O)=O]

The mixture of 4 diastereomers of 3-(6-((3-chloro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid (Example 518, 487 mg) was separated using two chiral separation methods. The mixture of 4 diastereomers was initially subjected to Chiral Separation Method VII: chiral SFC (stationary phase: Daicel Chiralpak AD-H 5 μm 250×30 mm, Mobile phase: 45% $CO_2$, 55% EtOH) to provide Example 519 and Example 520 and a mixture of the two remaining diastereomers (Example 521 and Example 522). The mixture of Example 521 and Example 522 was subsequently separated using Chiral Separation Method VIII: chiral SFC (stationary phase: Daicel Chiralpak IG 5 μm 250×20 mm, Mobile phase: 60% $CO_2$, 40% EtOH) to afford Example 521 and Example 522. The chiral separation method, order of elution and designated stereochemistry is tabulated below in Table 6. When the stereochemical configuration is written as, for example (*S, *R), with the first configuration, (*S), corresponds to the configuration at the 3-propanoic carbon and the second configuration, (*R), corresponds to the stereochemistry at the sultam. The characterization for (*S)-3-(6-(((*S)-3-chloro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic acid (Example 519, 92 mg) is as follows: MS (ESI): mass calcd. for $C_{29}H_{29}ClF_3N_7O_4S$, 663.2; m/z found, 664.2 [M+H]$^+$. $^1$H NMR (500 MHz, CDCl$_3$) δ 8.21 (d, J=2.5 Hz, 1H), 8.03-7.97 (m, 2H), 7.43-7.37 (m, 1H), 7.24 (d, J=7.3 Hz, 1H), 7.03 (d, J=7.8 Hz, 1H), 5.03 (t, J=7.4 Hz, 1H), 4.75 (d, J=15.6 Hz, 1H), 4.64 (dt, J=9.7, 5.2 Hz, 1H), 4.36-4.28 (m, 2H), 3.64-3.47 (m, 3H), 3.35 (dt, J=13.8, 7.1 Hz, 1H), 3.02 (dd, J=16.5, 6.6 Hz, 1H), 2.88 (s, 3H), 2.27 (s, 3H), 1.77 (dt, J=9.9, 6.0 Hz, 3H), 1.66-1.53 (m, 1H), 1.49 (d, J=17.6 Hz, 1H), 1.27-1.21 (m, 1H).

TABLE 6

Chiral separation method, Order of elution and Designated stereochemistry for Examples 519-522

| Example # | Chiral Separation method/order of elution | Configuration |
| --- | --- | --- |
| 519 | Method VII, second eluting | (*S, *S) |
| 520 | Method VII, third eluting | (*S, *R) |
| 521 | Method VIII, first eluting | (*R, *S) |
| 522 | Method VIII, second eluting | (*R, *R) |

Example 520: (*S)-3-(6-(((*R)-3-Chloro-5,5-dioxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

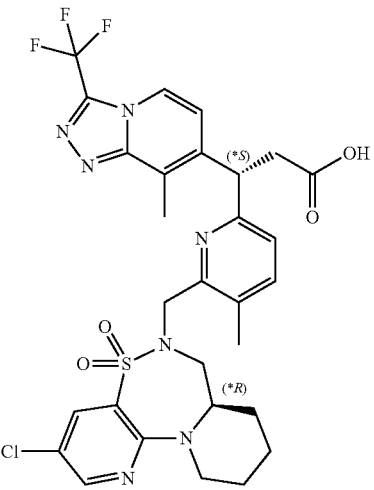 [SMILES: Cc1ccc([C@@H](CC(=O)O)c2ccn3c(C(F)(F)F)nnc3c2C)nc1CN1C[C@H]2CCCCN2c2ncc(Cl)cc2S1(=O)=O]

The title compound (124 mg) was obtained as described in Example 519 and Table 6. MS (ESI): mass calcd. for $C_{29}H_{29}ClF_3N_7O_4S$, 663.2; m/z found, 664.2 [M+H]$^+$. $^1$H NMR (500 MHz, CDCl$_3$) δ 8.21 (d, J=2.5 Hz, 1H), 8.01-7.94 (m, 2H), 7.44 (d, J=7.8 Hz, 1H), 7.18 (d, J=7.3 Hz, 1H), 7.08 (d, J=7.7 Hz, 1H), 5.01 (t, J=7.4 Hz, 1H), 4.72 (d, J=14.2 Hz, 1H), 4.61 (dq, J=13.9, 4.5 Hz, 1H), 4.35-4.24 (m, 2H), 3.58-3.37 (m, 3H), 3.29 (dd, J=13.4, 3.7 Hz, 1H), 3.08 (dd, J=16.5, 7.3 Hz, 1H), 2.86 (s, 3H), 2.33 (s, 3H), 1.76 (td, J=10.4, 4.7 Hz, 2H), 1.54 (h, J=7.7, 6.9 Hz, 1H), 1.45 (tt, J=10.8, 5.9 Hz, 2H), 1.27-1.20 (m, 1H).

Example 521: (*R)-3-(6-(((*S)-3-Chloro-5,5-di-oxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

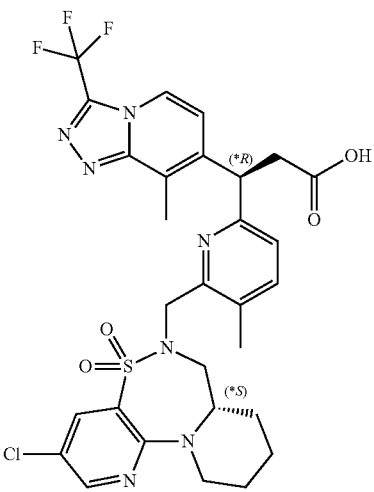 [SMILES: Cc1ccc([C@H](CC(=O)O)c2ccn3c(C(F)(F)F)nnc3c2C)nc1CN1C[C@@H]2CCCCN2c2ncc(Cl)cc2S1(=O)=O]

The title compound (75 mg) was obtained as described in Example 519 and Table 6. MS (ESI): mass calcd. for $C_{29}H_{29}ClF_3N_7O_4S$, 663.2; m/z found, 664.2 [M+H]$^+$. $^1$H NMR (500 MHz, CDCl$_3$) δ 8.21 (d, J=2.5 Hz, 1H), 8.02-7.94 (m, 2H), 7.42-7.37 (m, 1H), 7.29-7.20 (m, 1H), 7.04 (d, J=7.8 Hz, 1H), 5.01 (t, J=7.4 Hz, 1H), 4.72 (d, J=15.4 Hz, 1H), 4.61 (dd, J=11.4, 5.4 Hz, 1H), 4.31 (dd, J=14.4, 3.3 Hz, 2H), 3.60-3.50 (m, 2H), 3.52-3.40 (m, 1H), 3.33 (dt, J=13.8, 7.0 Hz, 1H), 3.00 (dd, J=16.2, 7.4 Hz, 1H), 2.86 (s, 3H), 2.26 (s, 3H), 1.80-1.69 (m, 2H), 1.61 (dd, J=13.8, 6.7 Hz, 1H), 1.54 (dd, J=9.0, 4.8 Hz, 1H), 1.25 (s, 1H), 0.99 (d, J=5.9 Hz, 1H).

Example 522: (*R)-3-(6-(((*R)-3-Chloro-5,5-di-oxido-7,7a,8,9,10,11-hexahydro-6H-dipyrido[2,1-d:2',3'-f][1,2,5]thiadiazepin-6-yl)methyl)-5-methylpyridin-2-yl)-3-(8-methyl-3-(trifluoromethyl)-[1,2,4]triazolo[4,3-a]pyridin-7-yl)propanoic Acid

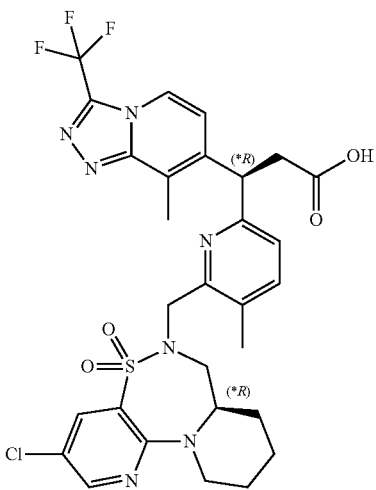 [SMILES: Cc1ccc([C@H](CC(=O)O)c2ccn3c(C(F)(F)F)nnc3c2C)nc1CN1C[C@H]2CCCCN2c2ncc(Cl)cc2S1(=O)=O]

The title compound (141 mg) was obtained as described in Example 519 and Table 6. MS (ESI): mass calcd. for $C_{29}H_{29}ClF_3N_7O_4S$, 663.2; m/z found, 664.2 [M+H]$^+$. $^1$H NMR (500 MHz, CDCl$_3$) δ 8.20 (d, J=2.5 Hz, 1H), 8.02-7.93 (m, 2H), 7.42 (d, J=7.7 Hz, 1H), 7.22 (d, J=7.3 Hz, 1H), 7.10 (d, J=7.8 Hz, 1H), 4.99 (t, J=7.4 Hz, 1H), 4.76 (s, 1H), 4.71 (d, J=14.3 Hz, 1H), 4.63-4.56 (m, 1H), 4.30 (dt, J=13.2, 4.7 Hz, 1H), 4.24 (d, J=14.3 Hz, 1H), 3.52 (t, J=13.0 Hz, 1H), 3.42-3.28 (m, 2H), 3.01 (dd, J=16.2, 7.8 Hz, 1H), 2.85 (s, 3H), 2.30 (s, 3H), 1.69 (td, J=10.8, 6.4 Hz, 1H), 1.51 (dd, J=13.1, 6.4 Hz, 1H), 1.41 (dd, J=9.0, 4.8 Hz, 1H), 1.25 (s, 1H), 0.96 (d, J=5.6 Hz, 2H).

Example 523: 3-(3-(Difluoromethyl)-8-methyl-[1,2,4]triazolo[4,3-a]pyridin-7-yl)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)propanoic Acid

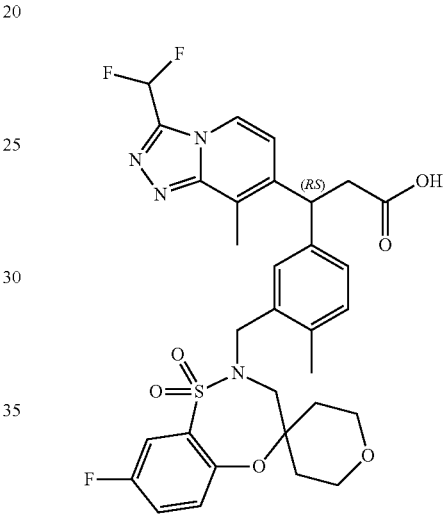

Step A: Ethyl 3-(3-(difluoromethyl)-8-methyl-[1,2,4]triazolo[4,3-a]pyridin-7-yl)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)propanoate.

Di-tert-butyl azodicarboxylate (DBAD, 368 mg, 1.56 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 421 mg, 1.04 mmol), 8-fluoro-2,2',3,3',5',6'-hexahydrospiro[benzo[b][1,4,5]oxathiazepine-4,4'-pyran] 1,1-dioxide (Intermediate 165, 300 mg, 1.04 mmol), and triphenylphosphine (411 mg, 1.57 mmol) in THF (10 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (680 mg, 97%) as a white foam. MS (ESI): mass calcd. for $C_{33}H_{35}F_3N_4O_6S$, 672.7; m/z found, 673.2 [M+H]$^+$. $^1$H NMR (500 MHz, CDCl$_3$) δ 8.15 (d, J=7.2 Hz, 1H), 7.53 (dd, J=7.4, 3.1 Hz, 1H), 7.25-7.13 (m, 3H), 7.16-7.07 (m, 2H), 6.85 (d, J=7.3 Hz, 1H), 4.94 (dd, J=8.7, 7.1 Hz, 1H), 4.50 (d, J=15.2 Hz, 1H), 4.44 (d, J=15.1 Hz, 1H), 4.13-4.01 (m, 3H), 3.66 (t, J=11.3 Hz, 2H), 3.52-3.43 (m, 2H), 3.34 (s, 2H), 3.14 (dd, J=15.9, 7.1 Hz, 1H), 3.03 (dd, J=15.9, 8.7 Hz, 1H), 2.80 (s, 3H), 2.22 (s, 3H), 1.67-1.61 (m, 2H), 1.42-1.32 (m, 2H), 1.14 (t, J=7.1 Hz, 3H).

Step B: 3-(3-(Difluoromethyl)-8-methyl-[1,2,4]triazolo[4,3-a]pyridin-7-yl)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)propanoic acid. A mixture containing ethyl 3-(3-(difluoromethyl)-8-methyl-[1,2,4]triazolo[4,3-a]pyridin-7-yl)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)propanoate (680 mg, 1.01 mmol), 1 M aqueous NaOH solution (3 mL, 3 mmol) and THF (5 mL) was stirred at room temperature overnight 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over Na$_2$SO$_4$, filtered, and concentrated to dryness under reduced pressure. The residue was purified by flash column chromatography (eluent: 0-10% MeOH/DCM) to provide the title compound (624 mg, 96%) as a white foam. MS (ESI): mass calcd. for C$_{31}$H$_{31}$F$_3$N$_4$O$_6$S, 644.2; m/z found, 645.3 [M+H]$^+$. $^1$H NMR (500 MHz, CDCl$_3$) δ 10.87 (s, 1H), 8.16 (d, J=7.1 Hz, 1H), 7.66-7.58 (m, 2H), 7.53 (td, J=7.2, 2.2 Hz, 2H), 7.25-7.09 (m, 6H), 6.96 (d, J=7.3 Hz, 1H), 4.97 (t, J=7.8 Hz, 1H), 4.49 (s, 2H), 3.64 (q, J=10.3 Hz, 2H), 3.50 (d, J=10.7 Hz, 1H), 3.44 (s, 2H), 3.20 (dd, J=16.0, 7.1 Hz, 1H), 3.08 (dd, J=16.0, 8.4 Hz, 1H), 2.75 (s, 3H), 2.23 (s, 3H), 1.61 (t, J=11.8 Hz, 2H).

Example 524: (*S)-3-(3-(Difluoromethyl)-8-methyl-[1,2,4]triazolo[4,3-a]pyridin-7-yl)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)propanoic Acid

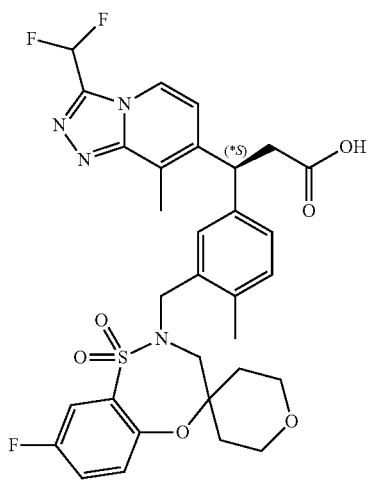 [SMILES: Cc1ccc([C@H](CC(=O)O)c2ccn3c(C(F)F)nnc3c2C)cc1CN1CC2(CCOCC2)Oc2ccc(F)cc2S1(=O)=O]

The mixture of 3-(3-(difluoromethyl)-8-methyl-[1,2,4]triazolo[4,3-a]pyridin-7-yl)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)propanoic acid isomers (Example 523, 624 mg) was separated by chiral SFC (stationary phase: ethylpyridine 5 μm 150×30 mm, Mobile phase: 60% CO$_2$, 40% MeOH), followed by chiral SFC (stationary phase: Chiralpak AD-H 5 μm 250×30 mm, Mobile phase: 50% CO$_2$, 50% MeOH) to afford two enantiomers. The first eluting isomer (261 mg) was designated (*S). MS (ESI): mass calcd. for C$_{31}$H$_{31}$F$_3$N$_4$O$_6$S, 644.2; m/z found, 645.3 [M+H]$^+$. $^1$H NMR (400 MHz, CDCl$_3$) δ 8.15 (d, J=7.1 Hz, 1H), 7.57 (dd, J=7.4, 3.0 Hz, 1H), 7.26-7.16 (m, 3H), 7.19-7.05 (m, 3H), 6.88 (d, J=7.2 Hz, 1H), 4.93 (t, J=7.8 Hz, 1H), 4.53 (d, J=14.9 Hz, 1H), 4.47 (d, J=14.8 Hz, 1H), 3.75-3.59 (m, 3H), 3.51 (s, 1H), 3.47 (s, 1H), 3.40 (s, 2H), 3.14 (dd, J=15.8, 8.3 Hz, 2H), 2.98 (dd, J=15.7, 7.4 Hz, 1H), 2.75 (s, 3H), 2.23 (s, 3H), 1.64 (d, J=14.1 Hz, 1H), 1.58 (d, J=14.3 Hz, 1H).

Example 525: (*R)-3-(3-(Difluoromethyl)-8-methyl-[1,2,4]triazolo[4,3-a]pyridin-7-yl)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)propanoic Acid

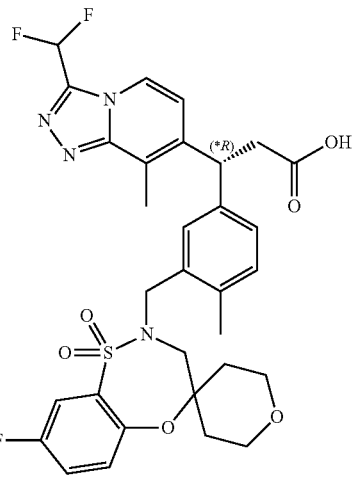

The second eluting isomer (258 mg) from the chiral separation described in Example 524 was designated (*R). MS (ESI): mass calcd. for C$_{31}$H$_{31}$F$_3$N$_4$O$_6$S, 644.2; m/z found, 645.3 [M+H]$^+$. $^1$H NMR (400 MHz, CDCl$_3$) δ 8.16 (d, J=7.2 Hz, 1H), 7.58 (dd, J=7.4, 3.0 Hz, 1H), 7.27-7.14 (m, 4H), 7.16-7.06 (m, 3H), 6.89 (d, J=7.2 Hz, 1H), 4.93 (t, J=7.8 Hz, 1H), 4.56 (d, J=14.7 Hz, 1H), 4.46 (d, J=14.7 Hz, 1H), 3.70 (dd, J=15.9, 9.2 Hz, 3H), 3.52 (s, 1H), 3.48 (s, 1H), 3.40 (s, 2H), 3.16 (dd, J=15.7, 8.4 Hz, 1H), 3.00 (dd, J=15.4, 7.0 Hz, 1H), 2.76 (s, 3H), 2.24 (s, 3H), 1.65 (d, J=14.1 Hz, 1H), 1.57 (d, J=14.4 Hz, 1H).

Example 526: 3-(3-(Difluoromethyl)-8-methyl-[1,2,4]triazolo[4,3-a]pyridin-7-yl)-3-(3-((8'-fluoro-1',1'-dioxidospiro[cyclopropane-1,4'-pyrido[2,3-b][1,4,5]oxathiazepin]-2'(3'H)-yl)methyl)-4-methylphenyl)propanoic Acid

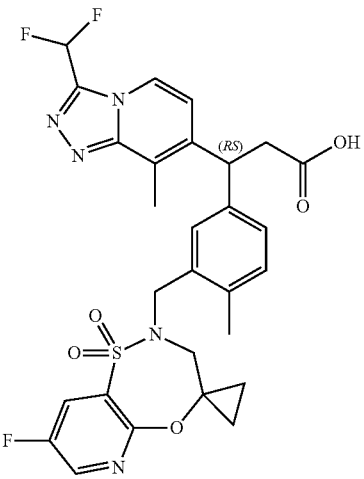 [SMILES: Cc1ccc(C(CC(=O)O)c2ccn3c(C(F)F)nnc3c2C)cc1CN1CC2(CC2)Oc2ncc(F)cc2S1(=O)=O]

Step A: Ethyl 3-(3-(difluoromethyl)-8-methyl-[1,2,4]triazolo[4,3-a]pyridin-7-yl)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)propanoate.
Di-tert-butyl azodicarboxylate (437 mg, 1.86 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 500 mg, 1.23 mmol), 8'-fluoro-2',3'-dihydrospiro[cyclopropane-1,4'-pyrido[2,3-b][1,4,5]oxathiazepine] 1',1'-dioxide (Intermediate 80, 303 mg, 1.24 mmol), and triphenylphosphine (488 mg, 1.86 mmol) in THF (10 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (780 mg, 99%) as a white foam. MS (ESI): mass calcd. for C$_{30}$H$_{30}$F$_3$N$_5$O$_5$S, 629.7; m/z found, 630.3 [M+H]$^+$. $^1$H NMR (400 MHz, CDCl$_3$) δ 8.25 (d, J=3.0 Hz, 1H), 8.15 (d, J=7.2 Hz, 1H), 7.97 (dd, J=6.5, 3.1 Hz, 1H), 7.21-7.08 (m, 2H), 7.12-7.02 (m, 2H), 6.83 (d, J=7.2 Hz, 1H), 4.90 (t, J=7.9 Hz, 1H), 4.30 (s, 2H), 4.07 (dq, J=14.2, 7.1 Hz, 2H), 3.52 (s, 2H), 3.11 (dd, J=15.8, 7.3 Hz, 1H), 2.99 (dd, J=15.9, 8.4 Hz, 1H), 2.76 (s, 3H), 2.27 (s, 3H), 1.22-1.08 (m, 5H), 0.57-0.45 (m, 2H).
Step B: 3-(3-(Difluoromethyl)-8-methyl-[1,2,4]triazolo[4,3-a]pyridin-7-yl)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)propanoic acid. A mixture containing ethyl 3-(3-(difluoromethyl)-8-methyl-[1,2,4]triazolo[4,3-a]pyridin-7-yl)-3-(3-((8-fluoro-1,1-dioxido-2',3',5',6'-tetrahydrospiro[benzo[b][1,4,5]oxathiazepine-4,4'-pyran]-2(3H)-yl)methyl)-4-methylphenyl)propanoate (780 mg, 1.24 mmol), 1 M aqueous NaOH solution (12.4 mL, 12.4 mmol) and THF (12.4 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over Na$_2$SO$_4$, filtered, and concentrated to dryness under reduced pressure. The residue was purified by flash column chromatography (eluent: 0-10% MeOH/DCM) to provide the title compound (737 mg, 98%) as a white foam. MS (ESI): mass calcd. for C$_{28}$H$_{26}$F$_3$N$_5$O$_5$S, 601.2; m/z found, 602.0 [M+H]$^+$. $^1$H NMR (500 MHz, CDCl$_3$) δ 8.26 (d, J=3.0 Hz, 1H), 8.12 (d, J=7.1 Hz, 1H), 7.99 (dd, J=6.4, 3.1 Hz, 1H), 7.18 (s, 1H), 7.14-7.06 (m, 2H), 7.04 (dd, J=7.9, 1.9 Hz, 1H), 6.86 (d, J=7.3 Hz, 1H), 4.89 (t, J=7.8 Hz, 1H), 4.31 (s, 2H), 3.55 (s, 2H), 3.43 (s, 1H), 3.08 (dd, J=15.9, 7.0 Hz, 1H), 2.96 (dd, J=15.9, 8.4 Hz, 1H), 2.67 (s, 3H), 2.25 (s, 3H), 1.25 (d, J=6.8 Hz, 1H), 1.12 (s, 1H), 0.51 (s, 2H).

Example 527: (*S)-3-(3-(Difluoromethyl)-8-methyl-[1,2,4]triazolo[4,3-a]pyridin-7-yl)-3-(3-((8'-fluoro-1',1'-dioxidospiro[cyclopropane-1,4'-pyrido[2,3-b][1,4,5]oxathiazepin]-2'(3'H)-yl)methyl)-4-methylphenyl)propanoic Acid

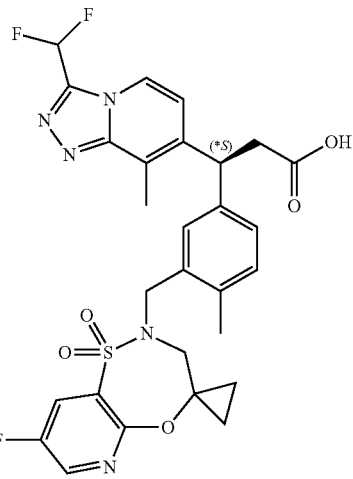

The mixture of 3-(3-(Difluoromethyl)-8-methyl-[1,2,4]triazolo[4,3-a]pyridin-7-yl)-3-(3-((8'-fluoro-1',1'-dioxidospiro[cyclopropane-1,4'-pyrido[2,3-b][1,4,5]oxathiazepin]-2'(3'H)-yl)methyl)-4-methylphenyl)propanoic acid isomers (Example 526, 737 mg) was separated by chiral SFC (stationary phase: ethylpyridine 5 μm 150×30 mm, Mobile phase: 60% CO$_2$, 40% MeOH), followed by chiral SFC (stationary phase: Chiralpak AD-H 5 μm 250×30 mm, Mobile phase: 55% CO$_2$, 45% MeOH) to afford two enantiomers. The first eluting isomer (309 mg) was designated (*S). MS (ESI): mass calcd. for C$_{28}$H$_{26}$F$_3$N$_5$O$_5$S, 601.2; m/z found, 602.0 [M+H]$^+$. $^1$H NMR (400 MHz, CDCl$_3$) δ 8.28 (d, J=3.0 Hz, 1H), 8.14 (d, J=7.1 Hz, 1H), 8.02 (dd, J=6.3, 3.0 Hz, 1H), 7.18 (d, J=30.3 Hz, 1H), 7.15-7.04 (m, 3H), 6.82 (d, J=7.2 Hz, 1H), 4.95 (t, J=7.8 Hz, 1H), 4.37 (d, J=14.6 Hz, 1H), 4.29 (d, J=14.5 Hz, 1H), 3.56 (s, 2H), 3.16 (dd, J=15.9, 7.1 Hz, 1H), 3.02 (dd, J=16.0, 8.5 Hz, 1H), 2.77 (s, 3H), 2.29 (s, 3H), 1.13 (dt, J=9.6, 5.1 Hz, 1H), 1.10-1.02 (m, 1H), 0.49-0.44 (m, 2H).

Example 528: (*R)-3-(3-(Difluoromethyl)-8-methyl-[1,2,4]triazolo[4,3-a]pyridin-7-yl)-3-(3-((8'-fluoro-1',1'-dioxidospiro[cyclopropane-1,4'-pyrido[2,3-b][1,4,5]oxathiazepin]-2'(3'H)-yl)methyl)-4-methylphenyl)propanoic Acid

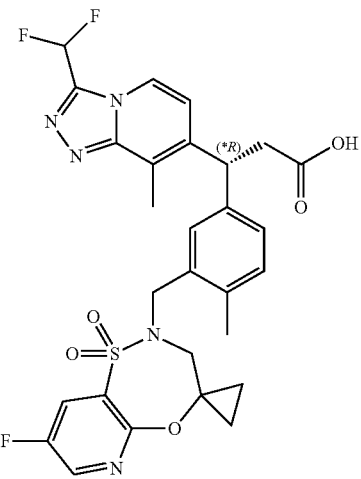 [SMILES: Cc1ccc([C@@H](CC(=O)O)c2ccn3c(C(F)F)nnc3c2C)cc1CN1CC2(CC2)Oc2ncc(F)cc2S1(=O)=O]

The second eluting isomer (307 mg) from the chiral separation described in Example 527 was designated (*R). MS (ESI): mass calcd. for $C_{28}H_{26}F_3N_5O_5S$, 601.2; m/z found, 602.0 [M+H]$^+$. $^1$H NMR (400 MHz, CDCl$_3$) δ 8.28 (d, J=3.1 Hz, 1H), 8.14 (d, J=7.2 Hz, 1H), 8.01 (dd, J=6.3, 3.0 Hz, 1H), 7.20-7.16 (m, 1H), 7.15-7.04 (m, 3H), 6.83 (d, J=7.3 Hz, 1H), 4.95 (t, J=7.8 Hz, 1H), 4.36 (d, J=14.6 Hz, 1H), 4.29 (d, J=14.6 Hz, 1H), 3.56 (s, 2H), 3.16 (dd, J=16.0, 7.1 Hz, 1H), 3.02 (dd, J=15.9, 8.5 Hz, 1H), 2.76 (s, 3H), 2.29 (s, 3H), 1.16-1.10 (m, 2H), 0.55-0.43 (m, 2H).

Example 529: 3-(3-((8'-Chloro-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic Acid

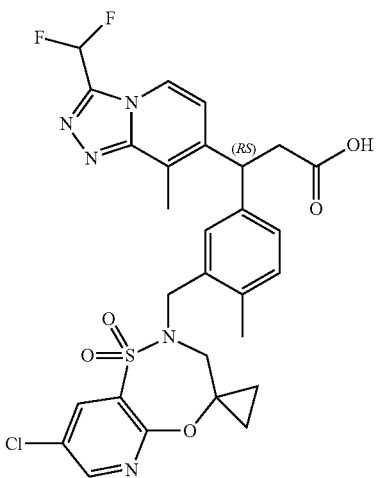 [SMILES: Cc1ccc(C(CC(=O)O)c2ccn3c(C(F)F)nnc3c2C)cc1CN1CC2(CC2)Oc2ncc(Cl)cc2S1(=O)=O]

Step A: Ethyl 3-(3-((8'-chloro-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoate. Di-tert-butyl azodicarboxylate (1.12 g, 4.87 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 1.21 g, 3.00 mmol), 8'-chloro-2',3'-dihydrospiro[cyclopropane-1,4'-pyrido[2,3-b][1,4,5]oxathiazepine]1',1'-dioxide (Intermediate 96, 900 mg, 3.45 mmol), and triphenylphosphine (1.28 g, 4.89 mmol) in THF (45 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (1.80 g, 93%) as a white foam. MS (ESI): mass calcd. for $C_{30}H_{30}ClF_2N_5O_5S$, 646.1; m/z found, 646.2 [M]$^+$. $^1$H NMR (500 MHz, CDCl$_3$) δ 8.38 (d, J=2.5 Hz, 1H), 8.24 (d, J=2.5 Hz, 1H), 8.18 (d, J=7.2 Hz, 1H), 7.18-7.06 (m, 3H), 6.85 (d, J=7.2 Hz, 1H), 4.93 (t, J=7.9 Hz, 1H), 4.34 (s, 2H), 4.16-4.07 (m, 2H), 4.07 (d, J=7.1 Hz, 1H), 3.54 (s, 2H), 3.14 (dd, J=15.9, 7.3 Hz, 1H), 3.02 (dd, J=15.9, 8.5 Hz, 1H), 2.80 (s, 3H), 2.30 (s, 2H), 2.04 (s, 1H), 1.26 (t, J=7.1 Hz, 1H), 1.25-1.14 (m, 4H), 0.62-0.52 (m, 2H).

Step B: 3-(3-((8'-Chloro-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic acid. A mixture containing ethyl 3-(3-((8'-chloro-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoate (500 mg, 0.77 mmol), 1 M aqueous NaOH solution (3 mL, 3 mmol) and THF (4 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over Na$_2$SO$_4$, filtered, and concentrated to dryness under reduced pressure. The residue was purified by flash column chromatography (eluent: 0-10% MeOH/DCM) to provide the title compound (300 mg, 63%) as an oil. MS (ESI): mass calcd. for $C_{28}H_{26}ClF_2N_5O_5S$, 618.1; m/z found, 618.1 [M]$^+$. $^1$H NMR (500 MHz, CDCl$_3$) δ 10.21 (s, 1H), 8.37 (d, J=2.6 Hz, 1H), 8.23 (d, J=2.6 Hz, 1H), 8.17 (d, J=7.1 Hz, 1H), 7.17-7.06 (m, 3H), 6.91 (d, J=7.3 Hz, 1H), 5.30 (s, 1H), 4.95 (t, J=7.8 Hz, 1H), 4.33 (s, 2H), 3.53 (s, 2H), 3.18 (dd, J=16.0, 7.1 Hz, 1H), 3.06 (dd, J=16.0, 8.5 Hz, 1H), 2.74 (s, 3H), 2.29 (s, 3H), 1.15-1.05 (m, 2H), 0.58-0.48 (m, 2H).

Example 530: (*S)-3-(3-((8'-Chloro-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic Acid

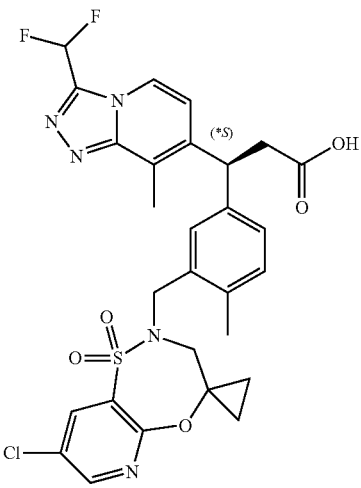 [SMILES: Cc1ccc([C@H](CC(=O)O)c2ccn3c(C(F)F)nnc3c2C)cc1CN1CC2(CC2)Oc2ncc(Cl)cc2S1(=O)=O]

The mixture of 3-(3-((8'-chloro-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic acid isomers (Example 529, 300 mg) was separated by chiral SFC (stationary phase: Chiralpak AD-H 5 μm 250×30 mm, Mobile phase: 55% $CO_2$, 45% EtOH) to afford two enantiomers. The first eluting isomer (150 mg) was designated (*S). MS (ESI): mass calcd. for $C_{28}H_{26}ClF_2N_5O_5S$, 618.1; m/z found, 618.1 [M]+. $^1$H NMR (400 MHz, $CDCl_3$) δ 8.37 (d, J=2.6 Hz, 1H), 8.24 (d, J=2.6 Hz, 1H), 8.14 (d, J=7.2 Hz, 1H), 7.17-7.00 (m, 4H), 6.82 (d, J=7.2 Hz, 1H), 5.30 (s, 1H), 4.95 (t, J=7.8 Hz, 1H), 4.37 (d, J=14.6 Hz, 1H), 4.30 (d, J=14.5 Hz, 1H), 3.56 (d, J=15.5 Hz, 1H), 3.47 (d, J=16.1 Hz, 1H), 3.16 (dd, J=16.0, 7.1 Hz, 1H), 3.02 (dd, J=16.0, 8.6 Hz, 1H), 2.77 (s, 3H), 2.29 (s, 3H), 1.17-1.02 (m, 2H), 0.58-0.45 (m, 2H).

Example 531: (*R)-3-(3-((8'-Chloro-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic Acid

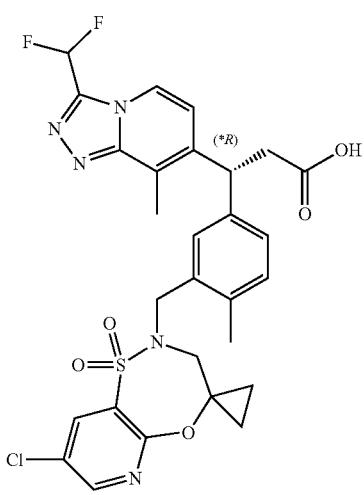 [SMILES: Cc1ccc([C@@H](CC(=O)O)c2ccn3c(C(F)F)nnc3c2C)cc1CN1CC2(CC2)Oc2ncc(Cl)cc2S1(=O)=O]

The second eluting isomer (150 mg) from the chiral separation described in Example 530 was designated (*R). MS (ESI): mass calcd. for $C_{28}H_{26}ClF_2N_5O_5S$, 618.1; m/z found, 618.1 [M]+. $^1$H NMR (400 MHz, $CDCl_3$) δ 8.37 (d, J=2.6 Hz, 1H), 8.24 (d, J=2.6 Hz, 1H), 8.14 (d, J=7.2 Hz, 1H), 7.17-7.03 (m, 4H), 6.81 (d, J=7.3 Hz, 1H), 5.30 (s, 1H), 4.95 (t, J=7.8 Hz, 1H), 4.37 (d, J=14.6 Hz, 1H), 4.30 (d, J=14.6 Hz, 1H), 3.57 (d, J=15.4 Hz, 1H), 3.47 (d, J=15.2 Hz, 1H), 3.16 (dd, J=15.9, 7.1 Hz, 1H), 3.02 (dd, J=15.9, 8.5 Hz, 1H), 2.78 (s, 3H), 2.29 (s, 3H), 1.13 (dt, J=10.3, 5.4 Hz, 1H), 1.07 (dt, J=12.0, 5.3 Hz, 1H), 0.55-0.50 (m, 2H).

Example 532: 3-(3-(Difluoromethyl)-8-methyl-[1,2,4]triazolo[4,3-a]pyridin-7-yl)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)propanoic Acid

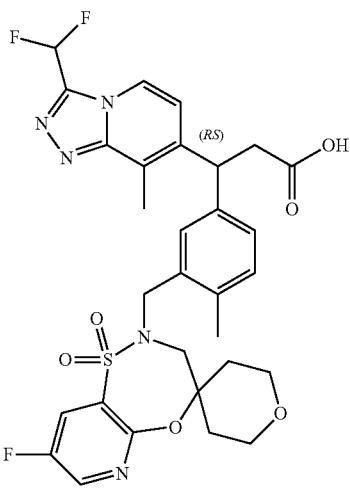 [SMILES: Cc1ccc(C(CC(=O)O)c2ccn3c(C(F)F)nnc3c2C)cc1CN1CC2(CCOCC2)Oc2ncc(F)cc2S1(=O)=O]

Step A: Ethyl 3-(3-(difluoromethyl)-8-methyl-[1,2,4]triazolo[4,3-a]pyridin-7-yl)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)propanoate.

Di-tert-butyl azodicarboxylate (206 mg, 1.30 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 350 mg, 0.87 mmol), 8'-fluoro-2,2',3,3',5,6-hexahydrospiro[pyran-4,4'-pyrido[2,3-b][1,4,5]oxathiazepine] 1',1'-dioxide (Intermediate 166, 300 mg, 1.04 mmol), and triphenylphosphine (341 mg, 1.30 mmol) in THF (10 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (550 mg, 94%) as a white foam. MS (ESI): mass calcd. for $C_{32}H_{34}F_3N_5O_6S$, 673.7; m/z found, 674.2 [M+H]+.

Step B: 3-(3-(Difluoromethyl)-8-methyl-[1,2,4]triazolo[4,3-a]pyridin-7-yl)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)propanoic acid. A mixture containing ethyl 3-(3-(difluoromethyl)-8-methyl-[1,2,4]triazolo[4,3-a]pyridin-7-yl)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)propanoate (600 mg, 0.89 mmol), 1 M aqueous NaOH solution (3.6 mL, 3.6 mmol), THF (4.4 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered, and concentrated to dryness under reduced pressure. The residue was purified by flash column chromatography (eluent: 0-10% MeOH/DCM) to provide the title compound (550 mg, 96%) as a white foam. MS (ESI): mass calcd. for $C_{30}H_{30}F_3N_5O_6S$, 645.2; m/z found, 646.2 [M+H]$^+$. $^1$H NMR (500 MHz, CDCl$_3$) δ 8.31 (d, J=3.1 Hz, 1H), 8.17 (d, J=7.1 Hz, 1H), 7.93 (dd, J=6.3, 3.1 Hz, 1H), 7.23-7.07 (m, 4H), 6.90 (d, J=7.3 Hz, 1H), 4.94 (t, J=7.8 Hz, 1H), 4.53 (d, J=14.9 Hz, 1H), 4.47 (d, J=14.8 Hz, 1H), 3.94 (qd, J=11.9, 6.0 Hz, 2H), 3.66-3.59 (m, 1H), 3.50 (d, J=44.8 Hz, 4H), 3.17 (dd, J=15.9, 8.1 Hz, 1H), 3.02 (dd, J=15.9, 7.5 Hz, 1H), 2.74 (s, 3H), 2.23 (s, 3H), 1.61 (d, J=13.9 Hz, 1H), 1.58-1.45 (m, 1H), 1.38-1.32 (m, 1H).

Example 533: (*S)-3-(3-(Difluoromethyl)-8-methyl-[1,2,4]triazolo[4,3-a]pyridin-7-yl)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)propanoic Acid

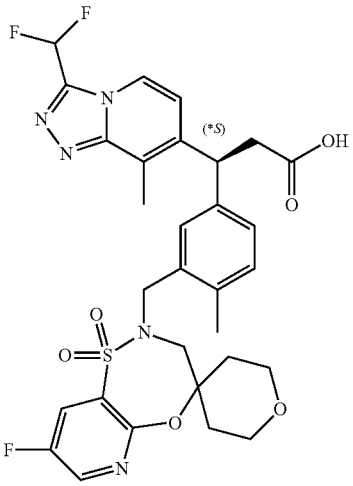 [SMILES: Cc1ccc([C@H](CC(=O)O)c2ccn3c(C(F)F)nnc3c2C)cc1CN1CC2(CCOCC2)Oc2ncc(F)cc2S1(=O)=O]

The mixture of 3-(3-(difluoromethyl)-8-methyl-[1,2,4]triazolo[4,3-a]pyridin-7-yl)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)propanoic acid isomers (Example 532, 550 mg) was separated by chiral SFC (stationary phase: Chiralpak AD-H 5 μm 250×30 mm, Mobile phase: 50% CO$_2$, 50% EtOH) to afford two enantiomers. The first eluting isomer (233 mg) was designated (*S). MS (ESI): mass calcd. for $C_{30}H_{30}F_3N_5O_6S$, 645.2; m/z found, 646.2 [M+H]$^+$. $^1$H NMR (500 MHz, CDCl$_3$) δ 8.23 (d, J=3.0 Hz, 1H), 8.08 (d, J=7.2 Hz, 1H), 7.87 (dd, J=6.4, 3.1 Hz, 1H), 7.15-6.96 (m, 4H), 6.77 (d, J=7.3 Hz, 1H), 4.84 (dd, J=9.4, 6.2 Hz, 1H), 4.50 (d, J=14.6 Hz, 1H), 4.40 (d, J=14.7 Hz, 1H), 3.89-3.85 (m, 2H), 3.60 (d, J=11.5 Hz, 1H), 3.46 (s, 5H), 3.04 (dd, J=15.6, 9.7 Hz, 1H), 2.85 (dd, J=15.8, 6.0 Hz, 1H), 2.67 (s, 3H), 2.16 (s, 3H), 1.39 (s, 1H), 1.20-1.11 (m, 1H).

Example 534: (*R)-3-(3-(Difluoromethyl)-8-methyl-[1,2,4]triazolo[4,3-a]pyridin-7-yl)-3-(3-((8'-fluoro-1',1'-dioxido-2,3,5,6-tetrahydrospiro[pyran-4,4'-pyrido[2,3-b][1,4,5]oxathiazepin]-2'(3'H)-yl)methyl)-4-methylphenyl)propanoic Acid

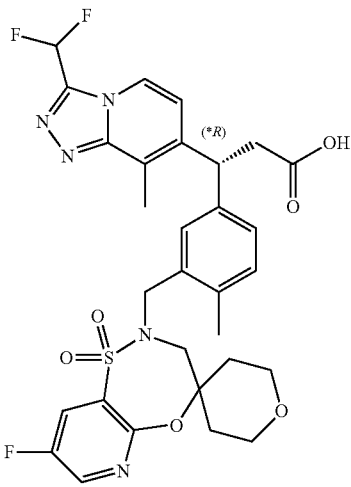 [SMILES: Cc1ccc([C@@H](CC(=O)O)c2ccn3c(C(F)F)nnc3c2C)cc1CN1CC2(CCOCC2)Oc2ncc(F)cc2S1(=O)=O]

The second eluting isomer (228 mg) from the chiral separation described in Example 533 was designated (*R). MS (ESI): mass calcd. for $C_{30}H_{30}F_3N_5O_6S$, 645.2; m/z found, 646.2 [M+H]$^+$. $^1$H NMR (500 MHz, CDCl$_3$) δ 8.32 (d, J=3.0 Hz, 1H), 8.17 (d, J=7.2 Hz, 1H), 7.95 (dd, J=6.4, 3.1 Hz, 1H), 7.32 (d, J=2.3 Hz, 1H), 7.26-7.02 (m, 4H), 6.88 (d, J=7.2 Hz, 1H), 4.94 (dd, J=8.9, 6.7 Hz, 1H), 4.58 (d, J=14.7 Hz, 1H), 4.47 (d, J=14.6 Hz, 1H), 4.02-3.89 (m, 2H), 3.72-3.68 (m, 1H), 3.58-3.52 (m, 3H), 3.16 (dd, J=15.8, 9.0 Hz, 1H), 2.98 (dd, J=15.8, 6.7 Hz, 1H), 2.76 (s, 3H), 2.24 (s, 3H), 1.50 (d, J=14.6 Hz, 1H), 1.31 (s, 1H), 1.31-1.19 (m, J=6.4 Hz, 1H).

Example 535: 3-(3-(Difluoromethyl)-8-methyl-[1,2,4]triazolo[4,3-a]pyridin-7-yl)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic Acid

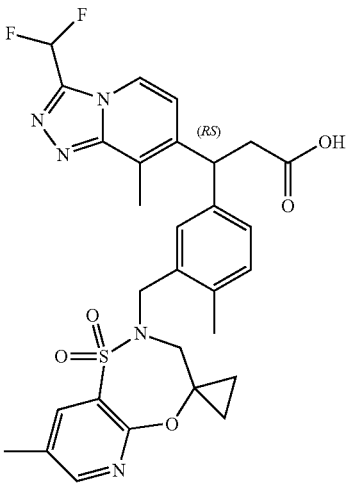 [SMILES: Cc1cnc2c(c1)S(=O)(=O)N(Cc1cc(C(CC(=O)O)c3ccn4c(C(F)F)nnc4c3C)ccc1C)CC1(CC1)O2]

Step A: Ethyl 3-(3-(difluoromethyl)-8-methyl-[1,2,4]triazolo[4,3-a]pyridin-7-yl)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoate. Diisopropyl azodicarboxylate (0.40 mL, 2.04 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 500 mg, 1.24 mmol), 8'-methyl-2',3'-dihydrospiro[cyclopropane-1,4'-pyrido[2,3-b][1,4,5]oxathiazepine] 1',1'-dioxide (Intermediate 6, 423 mg, 1.76 mmol), and triphenylphosphine (482 mg, 1.84 mmol) in THF (14 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (770 mg, 99%) as a white foam. MS (ESI): mass calcd. for $C_{31}H_{33}F_2N_5O_5S$, 625.7; m/z found, 626.3 $[M+H]^+$. $^1H$ NMR (500 MHz, $CDCl_3$) δ 8.20 (d, J=2.3 Hz, 1H), 8.11 (d, J=7.1 Hz, 1H), 8.03 (d, J=2.3 Hz, 1H), 7.13-7.01 (m, 3H), 6.82 (d, J=7.2 Hz, 1H), 4.89 (t, J=7.8 Hz, 1H), 4.27 (s, 2H), 4.12-3.97 (m, 2H), 3.49 (s, 2H), 3.10 (dd, J=15.9, 7.3 Hz, 1H), 2.98 (dd, J=15.8, 8.5 Hz, 1H), 2.76 (s, 3H), 2.70 (d, J=4.0 Hz, 1H), 2.34 (s, 3H), 2.25 (s, 3H), 1.98 (d, J=1.2 Hz, 2H), 1.19-1.13 (m, 3H), 0.53-0.42 (m, 2H).

Step B: 3-(3-(Difluoromethyl)-8-methyl-[1,2,4]triazolo[4,3-a]pyridin-7-yl)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid. A mixture containing ethyl 3-(3-(difluoromethyl)-8-methyl-[1,2,4]triazolo[4,3-a]pyridin-7-yl)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoate (770 mg, 1.23 mmol), 1 M aqueous NaOH solution (11.3 mL, 11.3 mmol) and THF (11.3 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered, and concentrated to dryness under reduced pressure. The residue was purified by flash column chromatography (eluent: 0-10% MeOH/DCM) to provide the title compound (720 mg, 98%) as a white foam. MS (ESI): mass calcd. for $C_{29}H_{29}F_2N_5O_5S$, 597.2; m/z found, 598.2 $[M+H]^+$. $^1H$ NMR (400 MHz, $CDCl_3$) δ 8.25 (d, J=2.4 Hz, 1H), 8.18 (d, J=7.1 Hz, 1H), 8.10 (d, J=2.3 Hz, 1H), 7.17-7.05 (m, 3H), 6.91 (d, J=7.3 Hz, 1H), 5.31 (s, 1H), 4.96 (t, J=7.8 Hz, 1H), 4.31 (d, J=2.6 Hz, 2H), 3.51 (s, 2H), 3.43 (d, J=15.1 Hz, 1H), 3.18 (dd, J=15.9, 7.0 Hz, 1H), 3.06 (dd, J=15.9, 8.5 Hz, 1H), 2.77 (s, 3H), 2.41 (s, 3H), 2.30 (s, 3H), 1.12-0.99 (m, 1H), 1.05 (s, 1H), 0.46 (s, 2H).

Example 536: (*S)-3-(3-(Difluoromethyl)-8-methyl-[1,2,4]triazolo[4,3-a]pyridin-7-yl)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic Acid

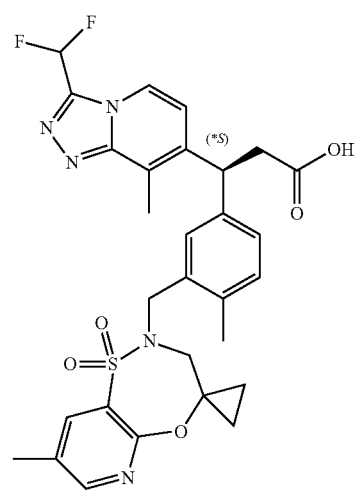 [SMILES: Cc1cnc2c(c1)S(=O)(=O)N(Cc1cc([C@H](CC(=O)O)c3ccn4c(C(F)F)nnc4c3C)ccc1C)CC1(CC1)O2]

The mixture of 3-(3-(difluoromethyl)-8-methyl-[1,2,4]triazolo[4,3-a]pyridin-7-yl)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid isomers (Example 535, 720 mg) was separated by chiral SFC (stationary phase: Chiralpak AD-H 5 μm 250×30 mm, Mobile phase: 65% $CO_2$, 35% EtOH) to afford two enantiomers. The first eluting isomer (349 mg) was designated (*S). MS (ESI): mass calcd. for $C_{29}H_{29}F_2N_5O_5S$, 597.2; m/z found, 598.2 $[M+H]^+$. $^1H$ NMR (500 MHz, $CDCl_3$) δ 8.25 (dd, J=2.4, 0.9 Hz, 1H), 8.21-8.04 (m, 2H), 7.28 (s, 1H), 7.18 (d, J=39.6 Hz, 1H), 7.14-7.05 (m, 2H), 7.05 (dd, J=7.9, 2.0 Hz, 1H), 6.82 (d, J=7.2 Hz, 1H), 5.13 (s, 2H), 4.96 (t, J=7.8 Hz, 1H), 4.37 (d, J=14.5 Hz, 1H), 4.26 (d, J=14.5 Hz, 1H), 3.59 (d, J=15.8 Hz, 1H), 3.43 (d, J=15.1 Hz, 1H), 3.14 (dd, J=15.8, 7.2 Hz, 1H), 2.99 (dd, J=15.8, 8.5 Hz, 1H), 2.79 (s, 3H), 2.42 (s, 3H), 1.16-0.96 (m, 3H), 0.50 (dt, J=10.4, 6.1 Hz, 1H), 0.43 (dt, J=10.6, 6.1 Hz, 1H).

Example 537: (*R)-3-(3-(Difluoromethyl)-8-methyl-[1,2,4]triazolo[4,3-a]pyridin-7-yl)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic Acid

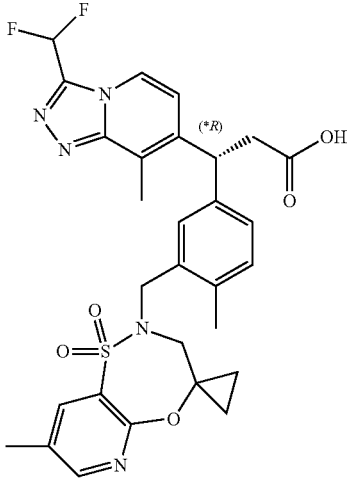 [SMILES: Cc1cnc2c(c1)S(=O)(=O)N(Cc1cc([C@@H](CC(=O)O)c3ccn4c(C(F)F)nnc4c3C)ccc1C)CC1(CC1)O2]

The second eluting isomer (339 mg) from the chiral separation described in Example 536 was designated (*R). MS (ESI): mass calcd. for $C_{29}H_{29}F_2N_5O_5S$, 597.2; m/z found, 598.2 [M+H]$^+$. $^1$H NMR (500 MHz, CDCl$_3$) δ 8.25 (dd, J=2.4, 0.9 Hz, 1H), 8.21-8.03 (m, 2H), 7.28-7.12 (m, 1H), 7.12 (d, J=2.4 Hz, 2H), 7.05 (dd, J=7.8, 2.0 Hz, 1H), 6.82 (d, J=7.2 Hz, 1H), 4.96 (t, J=7.8 Hz, 1H), 4.79 (s, 2H), 4.37 (d, J=14.6 Hz, 1H), 3.59 (d, J=15.7 Hz, 1H), 3.43 (s, 1H), 3.13 (dd, J=15.8, 7.2 Hz, 1H), 2.99 (dd, J=15.8, 8.4 Hz, 1H), 2.79 (s, 3H), 2.42 (s, 3H), 2.30 (s, 3H), 1.08-0.97 (m, 2H), 0.54-0.39 (m, 2H).

Example 538: (*S)-3-(4-Methyl-3-((7'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

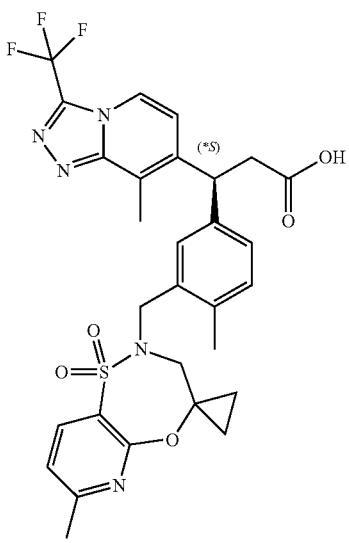 [SMILES: Cc1ccc2c(n1)OC1(CC1)CN(Cc1cc([C@H](CC(=O)O)c3ccn4c(C(F)(F)F)nnc4c3C)ccc1C)S2(=O)=O]

Step A: Ethyl (*S)-3-(4-methyl-3-((7'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate. DBAD (304 mg, 1.32 mmol) was added to a stirring mixture of ethyl (*S)-3-(3-(hydroxymethyl)-4-methylphenyl)-3-(8-methyl-3-(trifluoromethyl)-[1,2,4]triazolo[4,3-a]pyridin-7-yl)propanoate (Intermediate 26, 350 mg, 0.83 mmol), 8'-methyl-2',3'-dihydrospiro[cyclopropane-1,4'-pyrido[2,3-b][1,4,5]oxathiazepine] 1',1'-dioxide (Intermediate 6, 423 mg, 1.76 mmol), and triphenylphosphine (349 mg, 1.33 mmol) in THF (12 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (530 mg, 99%) as a white foam. MS (ESI): mass calcd. for $C_{31}H_{32}F_3N_5O_5S$, 643.2; m/z found, 644.2 [M+H]$^+$. $^1$H NMR (500 MHz, CDCl$_3$) δ 8.12 (d, J=7.7 Hz, 1H), 8.01 (d, J=7.2 Hz, 1H), 7.18-6.99 (m, 4H), 6.90 (d, J=7.3 Hz, 1H), 4.91 (dd, J=8.6, 7.2 Hz, 1H), 4.29 (s, 2H), 4.07 (dq, J=21.5, 7.1 Hz, 3H), 3.51 (q, J=15.1, 14.6 Hz, 2H), 3.12 (dd, J=15.9, 7.1 Hz, 1H), 2.99 (dd, J=15.9, 8.6 Hz, 1H), 2.80 (s, 3H), 2.27 (s, 3H), 2.02 (s, 1H), 1.27-1.08 (m, 6H), 0.64-0.49 (m, 2H).

Step B: 3-(3-(Difluoromethyl)-8-methyl-[1,2,4]triazolo[4,3-a]pyridin-7-yl)-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid. A mixture containing ethyl (*S)-3-(4-methyl-3-((7'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate (530 mg, 0.82 mmol), 1 M aqueous NaOH solution (7.6 mL, 7.6 mmol) and THF (7.6 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over Na$_2$SO$_4$, filtered and concentrated to dryness under reduced pressure. The residue was purified by flash column chromatography (eluent: 0-10% MeOH/DCM) to provide the title compound (483 mg, 95%) as a white foam. MS (ESI): mass calcd. for $C_{29}H_{28}F_3N_5O_5S$, 615.6; m/z found, 616.2 [M+H]$^+$. $^1$H NMR (400 MHz, CDCl$_3$) δ 8.15 (d, J=7.8 Hz, 1H), 8.02 (d, J=7.1 Hz, 1H), 7.19-7.10 (m, 3H), 7.06 (dd, J=8.0, 1.9 Hz, 1H), 6.93 (d, J=7.3 Hz, 1H), 5.30 (s, 1H), 4.97 (t, J=7.8 Hz, 1H), 4.35 (d, J=14.6 Hz, 1H), 4.26 (d, J=14.6 Hz, 1H), 3.57 (d, J=15.3 Hz, 1H), 3.49-3.39 (m, 1H), 3.18 (dd, J=16.1, 7.0 Hz, 1H), 3.04 (dd, J=16.1, 8.6 Hz, 1H), 2.81 (s, 3H), 2.55 (s, 3H), 2.29 (s, 3H), 1.15 (dt, J=12.2, 6.3 Hz, 1H), 1.02 (dt, J=11.7, 6.2 Hz, 1H), 0.56-0.50 (m, 1H), 0.48-0.40 (m, 1H).

Example 539: 3-(3-(((*R)-3-Cyano-5,5-dioxido-7a, 8,9,10-tetrahydropyrido[2,3-f]pyrrolo[2,1-d][1,2,5] thiadiazepin-6(7H)-yl)methyl)-4-methylphenyl)-3-(3-(difluoromethyl)-8-methyl-[1,2,4]triazolo[4,3-a]pyridin-7-yl)propanoic Acid

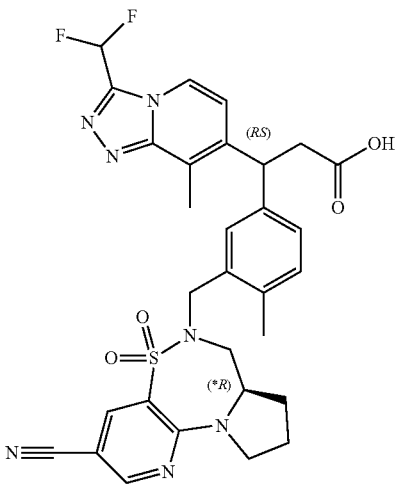

Step A: Ethyl 3-(3-(((*R)-3-cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoate. DBAD (453 mg, 1.97 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 500 mg, 1.24 mmol), (*R)-6,7,7a,8,9,10-hexahydropyrido[2,3-f]pyrrolo[2,1-d][1,2,5]thiadiazepine-3-carbonitrile 5,5-dioxide (Intermediate 87, 4022 mg, 1.52 mmol), and triphenylphosphine (521 mg, 1.99 mmol) in THF (18 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (750 mg, 93%) as a white foam. MS (ESI): mass calcd. for $C_{32}H_{33}F_2N_7O_4S$, 649.7; m/z found, 649.6 [M]+. $^1$H NMR (500 MHz, $CDCl_3$) δ 8.48 (d, J=2.2 Hz, 1H), 8.23 (t, J=2.0 Hz, 1H), 8.16 (d, J=7.2 Hz, 1H), 7.20-7.09 (m, 2H), 7.12-7.04 (m, 2H), 6.83 (dd, J=7.3, 6.2 Hz, 1H), 4.96-4.83 (m, 2H), 4.52 (dd, J=14.7, 6.0 Hz, 1H), 4.09 (dq, J=19.7, 7.2 Hz, 4H), 3.74-3.70 (m, 2H), 3.11 (dt, J=15.8, 6.9 Hz, 1H), 3.05-3.00 (m, 1H), 2.91-2.81 (m, 1H), 2.81 (d, J=2.1 Hz, 3H), 2.26 (d, J=6.0 Hz, 3H), 2.04 (s, 1H), 1.57-1.52 (m, 1H), 1.33-1.14 (m, 5H).

Step B: 3-(3-(((*R)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoic acid. A mixture containing ethyl 3-(3-(((*R)-3-cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoate (750 mg, 1.15 mmol), 1 M aqueous NaOH solution (10.6 mL, 10.6 mmol) and THF (10.6 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered and concentrated to dryness under reduced pressure. The residue was purified by flash column chromatography (eluent: 0-10% MeOH/DCM) to provide the title compound (692 mg, 92%) as a white foam. MS (ESI): mass calcd. for $C_{30}H_{29}F_2N_7O_4S$, 621.2; m/z found, 621.6 [M]+. $^1$H NMR (400 MHz, $CDCl_3$) δ 8.49 (d, J=2.1 Hz, 1H), 8.26-8.15 (m, 1H), 7.23 (s, 1H), 7.20-7.08 (m, 3H), 6.93 (t, J=6.9 Hz, 1H), 5.32 (s, 2H), 5.00-4.82 (m, 2H), 4.53 (dd, J=14.8, 2.8 Hz, 1H), 4.12 (dd, J=14.8, 4.4 Hz, 1H), 3.72 (dt, J=8.8, 4.6 Hz, 2H), 3.51-3.33 (m, 1H), 3.19 (dt, J=15.9, 7.0 Hz, 1H), 3.10-3.04 (m, 1H), 2.96-2.83 (m, 1H), 2.76 (d, J=1.5 Hz, 3H), 2.27 (d, J=4.3 Hz, 3H), 2.12-2.06 (m, 1H), 1.98-1.90 (m, 1H), 1.88-1.68 (m, 1H), 1.59-1.51 (m, 1H).

Example 540: (*S)-3-(3-(((*R)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoic Acid

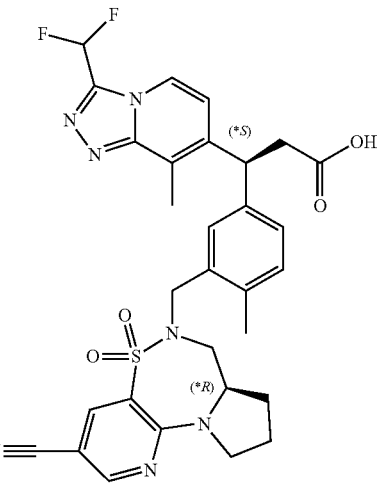

The mixture of 3-(3-(((*R)-3-cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl) propanoic acid isomers (Example 539, 692 mg) was separated by chiral SFC (stationary phase: Chiralpak AD-H 5 μm 250×30 mm, Mobile phase: 50% $CO_2$, 50% EtOH) to provide two diastereomers. The first eluting diastereomer (330 mg) was designated (*S). MS (ESI): mass calcd. for $C_{30}H_{29}F_2N_7O_4S$, 621.2; m/z found, 621.6 [M]+. $^1$H NMR (500 MHz, $CDCl_3$) δ 8.49 (d, J=2.1 Hz, 1H), 8.24 (d, J=2.2 Hz, 1H), 8.16 (d, J=7.2 Hz, 1H), 7.15 (d, J=7.7 Hz, 1H), 7.13-7.07 (m, 2H), 6.86 (d, J=7.3 Hz, 1H), 4.94 (dd, J=8.9, 6.7 Hz, 1H), 4.92-4.84 (m, 1H), 4.53 (d, J=14.7 Hz, 1H), 4.32 (s, 2H), 4.10 (d, J=14.7 Hz, 1H), 3.71 (dd, J=8.5, 4.8 Hz, 2H), 3.36 (dd, J=13.1, 3.6 Hz, 1H), 3.15 (d, J=15.9, 6.7 Hz, 1H), 3.04 (dd, J=15.9, 9.0 Hz, 1H), 2.87 (q, J=13.0, 12.4 Hz, 1H), 2.78 (s, 3H), 2.27 (s, 3H), 2.14-2.02 (m, 1H), 1.92-1.88 (m, 1H), 1.79-1.69 (m, 1H), 1.58-1.50 (m, 1H).

Example 541: (*R)-3-(3-(((*R)-3-Cyano-5,5-di-oxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoic Acid

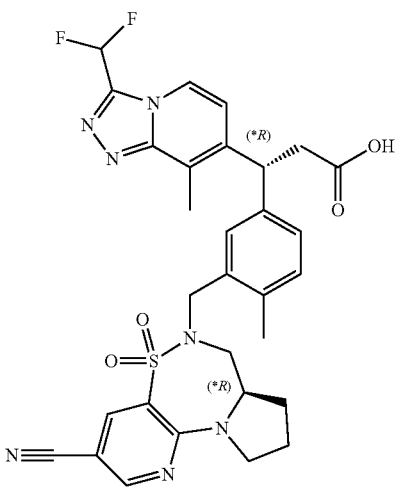 [SMILES: Cc1ccc([C@@H](CC(=O)O)c2ccn3c(C(F)F)nnc3c2C)cc1CN1C[C@H]2CCCN2c2ncc(C#N)cc2S1(=O)=O]

The second eluting diastereomer (330 mg) from the chiral separation described in Example 540 was designated (*R). MS (ESI): mass calcd. for $C_{30}H_{29}F_2N_7O_4S$, 621.2; m/z found, 621.6 [M]+. $^1$H NMR (500 MHz, CDCl$_3$) δ 8.50 (d, J=2.2 Hz, 1H), 8.24 (d, J=2.1 Hz, 1H), 8.15 (d, J=7.2 Hz, 1H), 7.18-7.13 (m, 2H), 7.13-7.07 (m, 1H), 6.88 (d, J=7.2 Hz, 1H), 4.98-4.86 (m, 2H), 4.52 (d, J=14.9 Hz, 1H), 4.34 (s, 3H), 4.11 (d, J=14.9 Hz, 1H), 3.78-3.69 (m, 2H), 3.45 (dd, J=13.1, 3.6 Hz, 1H), 3.17 (dd, J=16.0, 6.6 Hz, 1H), 3.05 (dd, J=15.9, 9.0 Hz, 1H), 2.88 (t, J=12.5 Hz, 1H), 2.78 (s, 3H), 2.26 (s, 3H), 2.14-2.03 (m, 1H), 1.86-1.76 (m, 1H), 1.60-1.53 (m, 1H).

Example 542: 3-(3-(((S)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoic Acid

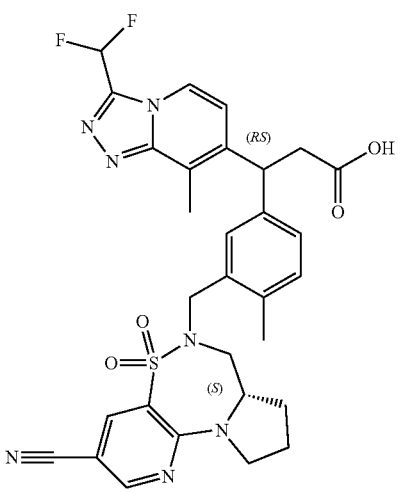

Step A: Ethyl 3-(3-(((*S)-3-cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoate.

DBAD (453 mg, 1.97 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, Step C, 500 mg, 1.24 mmol), (*S)-6,7,7a,8,9,10-hexahydropyrido[2,3-f]pyrrolo[2,1-d][1,2,5]thiadiazepine-3-carbonitrile 5,5-dioxide (Intermediate 88, 402 mg, 1.52 mmol), and triphenylphosphine (521 mg, 1.99 mmol) in THF (18 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (790 mg, 98%) as a white foam. MS (ESI): mass calcd. for $C_{32}H_{33}F_2N_7O_4S$, 649.7; m/z found, 650.3 [M+H]+. $^1$H NMR (500 MHz, CDCl$_3$) δ 8.46 (d, J=2.2 Hz, 1H), 8.22 (t, J=1.9 Hz, 1H), 8.15 (d, J=7.2 Hz, 1H), 7.17-7.02 (m, 3H), 6.83 (t, J=7.3 Hz, 1H), 4.95-4.81 (m, 2H), 4.51 (dd, J=14.6, 5.7 Hz, 1H), 4.16-3.98 (m, 4H), 3.77-2.98 (m, 2H), 3.11 (dt, J=15.8, 6.8 Hz, 1H), 3.03-2.97 (m, 1H), 2.86-2.74 (m, 4H), 2.25 (d, J=5.7 Hz, 3H), 2.14-2.00 (m, 1H), 2.03 (s, 1H), 1.58-1.50 (m, 1H), 1.24 (t, J=7.1 Hz, 2H), 1.16 (td, J=7.1, 2.2 Hz, 3H).

Step B: 3-(3-(((*S)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoic acid. A mixture containing ethyl 3-(3-(((*S)-3-cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoate (790 mg, 1.22 mmol), 1 M aqueous NaOH solution (11 mL, 11 mmol) and THF (11 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over Na$_2$SO$_4$, filtered and concentrated to dryness under reduced pressure. The residue was purified by flash column chromatography (eluent: 0-10% MeOH/DCM) to provide the title compound (750 mg, 99%) as a white foam. MS (ESI): mass calcd. for $C_{30}H_{29}F_2N_7O_4S$, 621.2; m/z found, 621.6 [M]+. $^1$H NMR (500 MHz, CDCl$_3$) δ 8.47 (d, J=2.2 Hz, 2H), 8.21 (d, J=2.1 Hz, 2H), 8.16 (d, J=7.2 Hz, 1H), 7.19-7.03 (m, 3H), 6.90 (t, J=7.7 Hz, 2H), 4.97-4.81 (m, 2H), 4.51 (dd, J=14.8, 3.4 Hz, 1H), 4.10 (dd, J=14.8, 5.2 Hz, 1H), 3.72-3.68 (m, 1H), 3.49-3.39 (m, 1H), 3.19-3.15 (m, 1H), 3.09-3.03 (m, 1H), 2.87 (q, J=12.3 Hz, 1H), 2.74 (d, J=1.9 Hz, 3H), 2.25 (d, J=5.6 Hz, 3H), 2.09-2.03 (m, 1H), 1.95-1.90 (m, 1H), 1.86-1.67 (m, 1H), 1.58-1.53 (m, 1H).

Example 543: (*S)-3-(3-(((S)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoic Acid

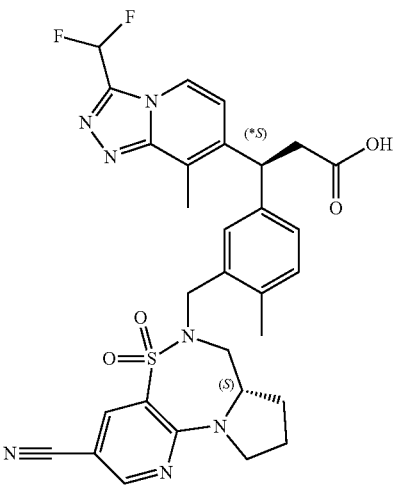

The mixture of 3-(3-(((*S)-3-cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoic acid (Example 542, 730 mg) was separated by chiral SFC (stationary phase: Chiralpak IA 5 μm 250×20 mm, Mobile phase: 40% CO$_2$, 60% MeOH (0.6% formic acid)) to provide two diastereomers. The first eluting diastereomer (367 mg) was designated (*S). MS (ESI): mass calcd. for C$_{30}$H$_{29}$F$_2$N$_7$O$_4$S, 621.2; m/z found, 622.3 [M+H]$^+$. $^1$H NMR (500 MHz, CDCl$_3$) δ 8.49 (d, J=2.2 Hz, 1H), 8.24 (d, J=2.1 Hz, 1H), 8.16 (d, J=7.2 Hz, 1H), 7.18-7.12 (m, 3H), 7.13-7.07 (m, 1H), 6.89 (d, J=7.2 Hz, 1H), 4.98-4.86 (m, 2H), 4.52 (d, J=14.9 Hz, 1H), 4.11 (d, J=14.9 Hz, 1H), 3.79-3.69 (m, 2H), 3.52-3.41 (m, 1H), 3.18 (dd, J=16.0, 6.5 Hz, 1H), 3.06 (dd, J=16.0, 9.0 Hz, 1H), 2.88 (t, J=12.5 Hz, 1H), 2.78 (s, 3H), 2.26 (s, 3H), 2.09 (dt, J=11.3, 5.8 Hz, 1H), 2.00-1.93 (m, 1H), 1.62-1.57 (m, 1H), 1.29-1.21 (m, 1H).

Example 544: (*R)-3-(3-(((S)-3-Cyano-5,5-dioxido-7a,8,9,10-tetrahydropyrido[2,3-f]pyrrolo[2,1-d][1,2,5]thiadiazepin-6(7H)-yl)methyl)-4-methylphenyl)-3-(3-(difluoromethyl)-8-methyl-[1,2,4]triazolo[4,3-a]pyridin-7-yl)propanoic Acid

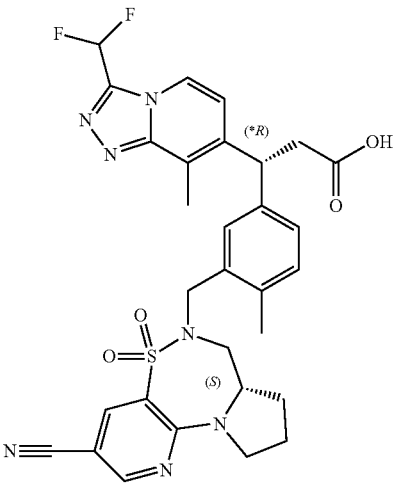

The second eluting diastereomer (365 mg) from the chiral separation described in Example 543 was designated (*R). MS (ESI): mass calcd. for C$_{30}$H$_{29}$F$_2$N$_7$O$_4$S, 621.2; m/z found, 622.3 [M+H]$^+$. $^1$H NMR (500 MHz, CDCl$_3$) δ 8.49 (s, 1H), 8.24 (s, 1H), 8.16 (d, J=6.9 Hz, 1H), 7.28 (s, 1H), 7.18-7.07 (m, 3H), 6.99 (s, 1H), 6.87 (d, J=7.2 Hz, 1H), 4.94 (s, 1H), 4.88 (s, 1H), 4.52 (d, J=14.8 Hz, 1H), 4.10 (d, J=14.8 Hz, 1H), 3.71 (s, 1H), 3.37 (d, J=13.0 Hz, 1H), 3.17-3.11 (m, 1H), 3.03 (d, J=16.9 Hz, 1H), 2.87 (d, J=12.6 Hz, 1H), 2.78 (s, 3H), 2.27 (s, 3H), 2.08 (s, 1H), 1.91 (s, 1H), 1.75 (s, 1H), 1.21 (s, 1H).

Example 545: (2*S,3*R)-2-Methyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

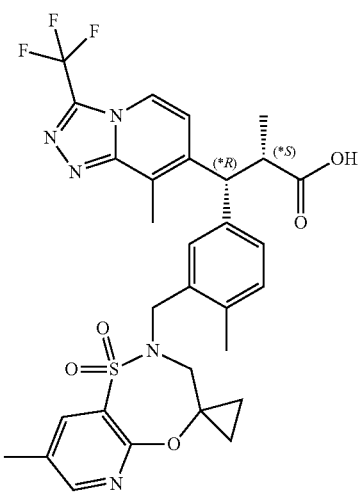 [SMILES: Cc1cnc2c(c1)S(=O)(=O)N(Cc1cc([C@H](c3ccn4c(C(F)(F)F)nnc4c3C)[C@H](C)C(=O)O)ccc1C)CC1(CC1)O2]

Step A: Ethyl (2*S,3*R)-2-methyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate. Diisopropyl azodicarboxylate (0.06 mL, 0.31 mmol) was added to a stirring mixture of methyl (2*S,3*R)-3-(3-(hydroxymethyl)-4-methylphenyl)-2-methyl-3-(8-methyl-3-(trifluoromethyl)-[1,2,4]triazolo[4,3-a]pyridin-7-yl)propanoate (Intermediate 175, 80 mg, 0.19 mmol), 8'-methyl-2',3'-dihydrospiro[cyclopropane-1,4'-pyrido[2,3-b][1,4,5]oxathiazepine] 1',1'-dioxide (Intermediate 6, 65 mg, 0.27 mmol) and triphenylphosphine (74 mg, 0.28 mmol) in THF (2.2 mL) at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (100 mg, 82%) as a white foam. MS (ESI): mass calcd. for C$_{31}$H$_{32}$F$_3$N$_5$O$_5$S, 643.7; m/z found, 644.3 [M+H]$^+$.

Step B: (2*S,3*R)-2-Methyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid. A mixture containing ethyl (2*S,3*R)-2-methyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate (100 mg, 0.16 mmol), 1 M aqueous NaOH solution (1.4 mL, 1.4 mmol), THF (1.4 mL) and ethanol (0.1 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered, and concentrated to dryness under reduced pressure. The residue was purified by flash column chromatography (eluent: 0-10% MeOH/DCM) to provide the title compound (97 mg, 99%) as a white foam. MS (ESI): mass calcd. for $C_{30}H_{30}F_3N_5O_5S$, 629.7; m/z found, 630.1 $[M+H]^+$. $^1$H NMR (600 MHz, $CDCl_3$) δ 8.24 (dd, J=2.4, 0.8 Hz, 1H), 8.10-8.02 (m, 2H), 7.24 (d, J=7.3 Hz, 1H), 7.18 (d, J=1.7 Hz, 1H), 7.17-7.10 (m, 2H), 6.51 (s, 1H), 4.46 (d, J=11.4 Hz, 1H), 4.32 (s, 2H), 3.54 (d, J=15.1 Hz, 1H), 3.47 (d, J=15.4 Hz, 1H), 3.35 (dq, J=11.3, 6.8 Hz, 1H), 2.73 (s, 3H), 2.41 (s, 3H), 2.27 (s, 3H), 1.23 (d, J=6.8 Hz, 3H), 1.20-1.11 (m, 2H), 0.52 (s, 2H).

Example 546: (2*R,3*R)-2-Methyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

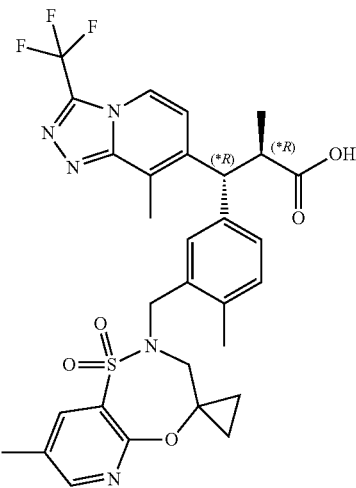 [SMILES: Cc1cnc2c(c1)S(=O)(=O)N(Cc1cc([C@H](c3ccn4c(C(F)(F)F)nnc4c3C)[C@@H](C)C(=O)O)ccc1C)CC1(CC1)O2]

Step A: Ethyl (2*R,3*R)-2-methyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate. Diisopropyl azodicarboxylate (0.06 mL, 0.31 mmol) was added to a stirring mixture of methyl (2*R,3*R)-3-(3-(hydroxymethyl)-4-methylphenyl)-2-methyl-3-(8-methyl-3-(trifluoromethyl)-[1,2,4]triazolo[4,3-a]pyridin-7-yl)propanoate (Intermediate 176, 50 mg, 0.12 mmol), 8'-methyl-2',3'-dihydrospiro[cyclopropane-1,4'-pyrido[2,3-b][1,4,5]oxathiazepine] 1',1'-dioxide (Intermediate 6, 40 mg, 0.17 mmol) and triphenylphosphine (46 mg, 0.18 mmol) in THF (2 mL) at room temperature. After 1 hour, ethyl acetate and water were added. The biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (70 mg, 92%) as a white foam. MS (ESI): mass calcd. for $C_{31}H_{32}F_3N_5O_5S$, 643.7; m/z found, 644.2 $[M+H]^+$.

Step B: (2*R,3*R)-2-Methyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid. A mixture containing ethyl (2*R,3*R)-2-methyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate (70 mg, 0.11 mmol), 1 M aqueous NaOH solution (1.0 mL, 1.4 mmol) and THF (1.0 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered and concentrated to dryness under reduced pressure. The residue was purified by flash column chromatography (eluent: 0-10% MeOH/DCM) to provide the title compound (47 mg, 69%) as a white foam. MS (ESI): mass calcd. for $C_{30}H_{30}F_3N_5O_5S$, 629.7; m/z found, 630.1 $[M+H]^+$. $^1$H NMR (600 MHz, $CDCl_3$) δ 11.13 (s, 1H), 8.24 (dd, J=2.4, 0.9 Hz, 1H), 8.07 (dd, J=2.4, 0.8 Hz, 1H), 8.00 (d, J=7.2 Hz, 1H), 7.29 (d, J=1.8 Hz, 1H), 7.12-7.02 (m, 2H), 6.93 (d, J=7.3 Hz, 1H), 4.63 (d, J=11.5 Hz, 1H), 4.35-4.24 (m, 2H), 3.61 (d, J=15.5 Hz, 1H), 3.47 (d, J=15.2 Hz, 1H), 3.35 (dq, J=13.6, 6.9 Hz, 1H), 2.85 (s, 3H), 2.41 (s, 3H), 2.22 (s, 3H), 1.19-1.13 (m, 5H), 0.65-0.56 (m, 2H).

Example 547: 3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanamide

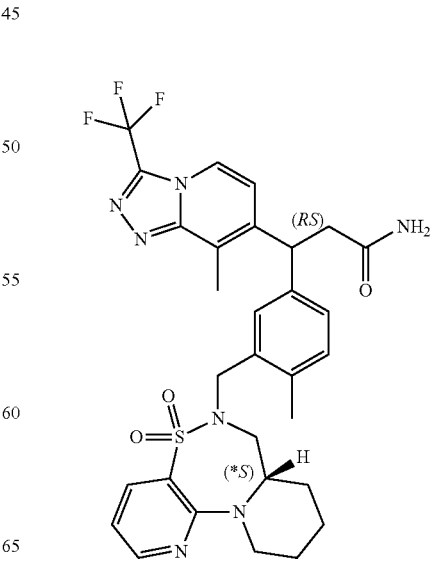

To a solution of 3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanoic acid (Example 289, 100 mg, 0.16 mmol) in DCM (3 mL) was added sequentially ammonium hydroxide (17 mg, 0.48 mmol), N-(3-dimethylaminopropyl)-N¹-ethylcarbodiimide hydrochloride (93 mg, 0.48 mmol). The reaction mixture was stirred at room temperature overnight and partitioned between EtOAc and water (25 mL each). The aqueous phase was extracted with EtOAc (2×25 mL). These extractions resulted in several organic solvent fractions which were combined, dried over $Na_2SO_4$, filtered, and concentrated to dryness under reduced pressure. The residue was purified by flash column chromatography (eluent: 0-10% MeOH/DCM) to provide the title compound (90 mg, 90%) as a white foam. MS (ESI): mass calcd. for $C_{20}H_{32}F_3N_7O_3S$, 627.2; m/z found, 628.3 [M+H]⁺. ¹H NMR (500 MHz, $CDCl_3$) δ 8.23 (dd, J=4.6, 1.8 Hz, 1H), 8.00-7.89 (m, 2H), 7.24 (d, J=2.0 Hz, 1H), 7.03 (d, J=7.9 Hz, 1H), 6.95 (dd, J=7.9, 2.0 Hz, 1H), 6.83-6.73 (m, 2H), 5.65 (s, 1H), 5.31 (s, 1H), 5.23 (s, 1H), 4.96 (t, J=7.6 Hz, 1H), 4.50 (dq, J=14.0, 4.7 Hz, 1H), 4.41 (d, J=15.3 Hz, 1H), 4.25 (dt, J=13.4, 4.9 Hz, 1H), 4.16 (d, J=15.3 Hz, 1H), 3.29 (dd, J=13.2, 3.8 Hz, 1H), 3.24-3.15 (m, 2H), 2.99 (dd, J=15.0, 7.7 Hz, 1H), 2.83-2.75 (m, 4H), 2.17 (s, 3H), 1.77-1.61 (m, 2H), 1.56-1.38 (m, 3H).

Example 548: (*S)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanamide

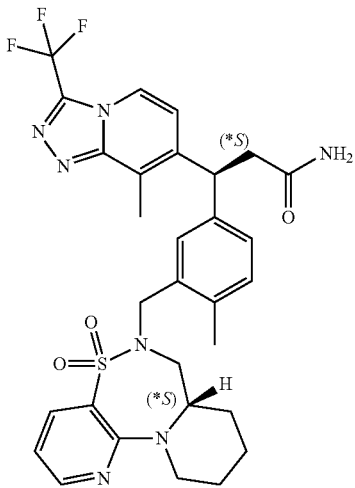 [SMILES: Cc1ccc([C@H](CC(N)=O)c2ccn3c(C(F)(F)F)nnc3c2C)cc1CN1C[C@@H]2CCCCN2c2ncccc2S1(=O)=O]

The mixture of 3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanamide (Example 547, 85 mg) was separated by chiral SFC (stationary phase: Chiralpak AD-H 5 μm 250*30 mm, Mobile phase: 50% $CO_2$, 50% iPOH(0.3% $iPrNH_2$)) to provide two diastereomers. The first eluting diastereomer (32 mg, 32%) was designated (*S). MS (ESI): mass calcd. for $C_{20}H_{32}F_3N_7O_3S$, 627.2; m/z found, 628.3 [M+H]⁺. ¹H NMR (500 MHz, $CDCl_3$) δ ¹H NMR (500 MHz, Chloroform-d) δ 8.23 (dd, J=4.7, 1.8 Hz, 1H), 8.00-7.89 (m, 2H), 7.24 (d, J=2.0 Hz, 1H), 7.03 (d, J=7.8 Hz, 1H), 6.95 (dd, J=7.8, 2.0 Hz, 1H), 6.83-6.73 (m, 2H), 5.65 (s, 1H), 5.31 (s, 1H), 5.23 (s, 1H), 4.96 (t, J=7.6 Hz, 1H), 4.55-4.46 (m, 1H), 4.41 (d, J=15.3 Hz, 1H), 4.25 (dt, J=13.3, 4.9 Hz, 1H), 4.16 (d, J=15.3 Hz, 1H), 3.29 (dd, J=13.3, 3.8 Hz, 1H), 3.24-3.15 (m, 2H), 2.99 (dd, J=15.0, 7.7 Hz, 1H), 2.87 (s, 3H), 2.17 (s, 3H), 1.75-1.55 (m, 2H), 1.56-1.43 (m, 1H), 1.46-1.39 (m, 1H), 0.84-0.78 (m, 2H).

Example 549: (*R)-3-(3-(((*S)-5,5-Dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanamide

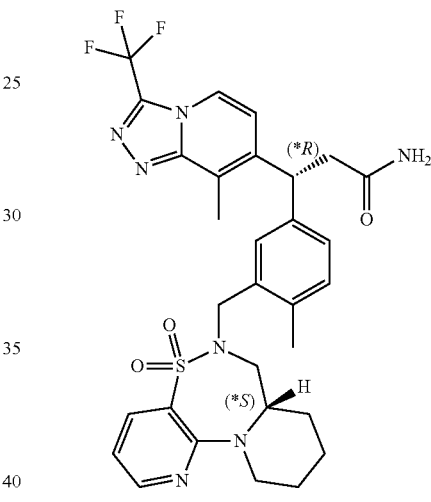

The mixture of 3-(3-(((*S)-5,5-dioxido-7,7a,8,9,10,11-hexahydro-6H-dipyrido[2,1-d:2',3'-f][1,2,5]thiadiazepin-6-yl)methyl)-4-methylphenyl)-3-(8-methyl-3-(trifluoromethyl)-[1,2,4]triazolo[4,3-a]pyridin-7-yl)propanamide (Example 547, 85 mg) was separated by chiral SFC (stationary phase: Chiralpak AD-H 5 μm 250*30 mm, Mobile phase: 50% $CO_2$, 50% iPOH(0.3% $iPrNH_2$)) to provide two diastereomers. The second eluting diastereomer (36 mg, 36%) was designated (*R). MS (ESI): mass calcd. for $C_{20}H_{32}F_3N_7O_3S$, 627.2; m/z found, 628.3 [M+H]⁺. ¹H NMR (500 MHz, $CDCl_3$) δ ¹H NMR (500 MHz, Chloroform-d) δ ¹H NMR (500 MHz, Chloroform-d) δ 8.32 (dd, J=4.6, 1.9 Hz, 1H), 8.09-7.99 (m, 2H), 7.27 (d, J=1.9 Hz, 1H), 7.16-7.06 (m, 2H), 6.93-6.82 (m, 2H), 5.75 (s, 1H), 5.44 (s, 1H), 5.03 (t, J=7.6 Hz, 1H), 4.51-4.58 (m, 1H), 4.48 (d, J=15.2 Hz, 1H), 4.35-4.22 (m, 2H), 3.33-3.20 (m, 3H), 3.05 (dd, J=15.0, 7.3 Hz, 1H), 2.93-2.81 (m, 1H), 2.87 (s, 3H), 2.27 (s, 3H), 1.78-1.63 (m, 1H), 1.59-1.37 (m, 2H), 0.90 (t, J=6.9 Hz, 3H).

Example 551: 3-(3-((8'-Carbamoyl-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic Acid

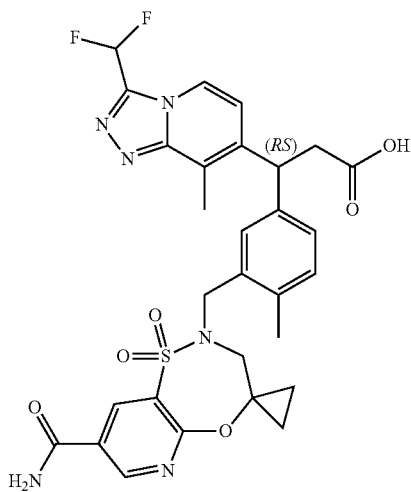 [SMILES: Cc1ccc(C(CC(=O)O)c2ccn3c(C(F)F)nnc3c2C)cc1CN1CC2(CC2)Oc2ncc(C(N)=O)cc2S1(=O)=O]

Step A: Ethyl 3-(3-((8'-chloro-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoate. Di-tert-butyl azodicarboxylate (1.12 g, 4.87 mmol) was added to a stirring mixture of ethyl 3-(3-(difluoromethyl)-8-methyl-[1,2,4]triazolo[4,3-a]pyridin-7-yl)-3-(3-(hydroxymethyl)-4-methylphenyl)propanoate (Example 28, step C, 1.21 g, 3.00 mmol), 8'-chloro-2',3'-dihydrospiro[cyclopropane-1,4'-pyrido[2,3-b][1,4,5]oxathiazepine] 1',1'-dioxide (Intermediate 96, 900 mg, 3.45 mmol), and triphenylphosphine (1.28 g, 4.89 mmol) in THF (45 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over $Na_2SO_4$, filtered and concentrated under reduced pressure. The residue was purified by flash column chromatography (eluent: 0-100% ethyl acetate/hexanes) to provide the title compound (1.80 g, 93%) as a white foam. MS (ESI): mass calcd. for $C_{30}H_{30}ClF_2N_5O_5S$, 645.2; m/z found, 646.2 $[M+H]^+$. $^1H$ NMR (500 MHz, $CDCl_3$) δ 8.38 (d, J=2.5 Hz, 1H), 8.24 (d, J=2.5 Hz, 1H), 8.18 (d, J=7.2 Hz, 1H), 7.18-7.06 (m, 3H), 6.85 (d, J=7.2 Hz, 1H), 4.93 (t, J=7.9 Hz, 1H), 4.34 (s, 2H), 4.16-4.07 (m, 2H), 4.07 (d, J=7.1 Hz, 1H), 3.54 (s, 2H), 3.14 (dd, J=15.9, 7.3 Hz, 1H), 3.02 (dd, J=15.9, 8.5 Hz, 1H), 2.80 (s, 3H), 2.30 (s, 2H), 2.04 (s, 1H), 1.26 (t, J=7.1 Hz, 1H), 1.25-1.14 (m, 4H), 0.62-0.52 (m, 2H).

Step B: Ethyl 3-(3-((8'-cyano-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoate. A mixture containing ethyl 3-(3-((8'-chloro-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoate (1.0 g, 1.55 mmol), zinc cyanide (482 mg, 4.11 mmol), zinc powder (677 mg, 10.1 mmol), tris(dibenzylideneacetone)dipalladium(0) (318 mg, 0.35 mmol), dicyclohexyl[2',4',6'-tris(1-methylethyl)[1,1'-biphenyl]-2-yl]-phosphine (421 mg, 0.88 mmol) and DMA (51.3 mL) was degassed by bubbling nitrogen through the reaction mixture for 15 minutes. The reaction mixture was then heated at 120° C. overnight. Cooled and filtered the reaction mixture, rinsed with ethyl acetate. The filtrate was washed with aqueous sodium bicarbonate and brine solution, dried over $Na_2SO_4$, filtered and concentrated to dryness under reduced pressure. The residue was purified by flash column chromatography (eluent: 0-100% ethyl acetate/hexanes) to provide the title compound (600 mg, 61%) as a white foam. MS (ESI): mass calcd. for $C_{30}H_{31}F_2N_6O_5S$, 636.2; m/z found, 637.2 $[M]^+$. $^1H$ NMR (500 MHz, $CDCl_3$) δ 8.71 (d, J=2.3 Hz, 1H), 8.55 (d, J=2.3 Hz, 1H), 8.17 (d, J=7.2 Hz, 1H), 7.16 (d, J=7.9 Hz, 1H), 7.14-7.06 (m, 2H), 6.83 (d, J=7.3 Hz, 1H), 4.93 (t, J=7.9 Hz, 1H), 4.37 (s, 2H), 4.16-4.03 (m, 2H), 3.54 (s, 2H), 3.13 (dd, J=15.8, 7.4 Hz, 1H), 3.05-2.96 (m, 1H), 2.82-2.78 (m, 3H), 2.30 (s, 3H), 2.07 (d, J=19.1 Hz, 2H), 1.33-1.03 (m, 4H), 0.73-0.64 (m, 2H).

Step C: 3-(3-((8'-Carbamoyl-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic acid. A mixture containing ethyl 3-(3-((8'-cyano-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoate (600 mg, 0.94 mmol), 1 M aqueous NaOH solution (2.6 mL, 2.6 mmol), THF (5.3 mL) and ethanol (0.2 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over $Na_2SO_4$, filtered, and concentrated to dryness under reduced pressure. The residue was purified by flash column chromatography (eluent: 0-10% MeOH/DCM) to provide the title compound (355 mg, 60%) as a white foam. MS (ESI): mass calcd. for $C_{29}H_{26}F_2N_6O_5S$, 626.2; m/z found, 627.2 $[M+H]^+$. $^1H$ NMR (400 MHz, $CDCl_3$) δ $^1H$ NMR (500 MHz, Chloroform-d) δ 7.91 (t, J=5.7 Hz, 1H), 7.85-7.76 (m, 2H), 7.09-7.04 (m, 1H), 6.80-6.68 (m, 3H), 4.70-4.62 (m, 1H), 4.49-4.36 (m, 2H), 4.17 (s, 4H), 3.22 (d, J=3.7 Hz, 2H), 3.20-3.09 (m, 1H), 2.93-2.84 (m, 1H), 2.79-2.71 (m, 1H), 2.51 (d, J=5.1 Hz, 2H), 1.96 (d, J=4.6 Hz, 2H), 0.41-0.31 (m, 2H), 0.00 (d, J=3.7 Hz, 2H).

Example 552: (*S)-3-(3-((8'-Carbamoyl-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic Acid

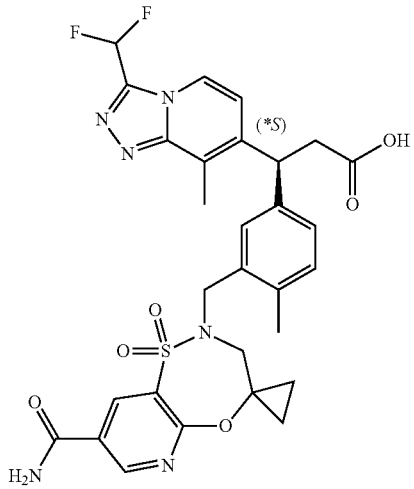

The mixture of 3-(3-((8'-carbamoyl-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic acid (Example 551, 344 mg) was separated by chiral SFC (stationary phase: CHIRALPAK AD-H 5 μm 250*30 mm, Mobile phase: 45% CO$_2$, 55% EtOH) to provide two diastereomers. The first eluting diastereomer (156 mg, 26%) was designated (*S). MS (ESI): mass calcd. for C$_{29}$H$_{26}$F$_2$N$_6$O$_5$S, 626.2; m/z found, 627.2 [M+H]$^+$. $^1$H NMR (400 MHz, CDCl$_3$) δ $^1$H NMR (500 MHz, Chloroform-d) δ 8.18 (d, J=6.5 Hz, 1H), 8.11 (q, J=2.5 Hz, 1H), 7.99 (q, J=2.8 Hz, 1H), 7.37-7.30 (m, 3H), 7.22-7.17 (m, 1H), 7.12-6.93 (m, 4H), 4.75-4.62 (m, 1H), 3.49 (d, J=3.9 Hz, 2H), 3.44-3.31 (m, 2H), 3.14-3.07 (m, 1H), 2.99 (s, 1H), 2.81-2.73 (m, 3H), 2.30-2.17 (m, 3H), 0.63 (t, J=4.0 Hz, 2H), 0.28 (d, J=4.1 Hz, 2H).

Example 553: (*R)-3-(3-((8'-Carbamoyl-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic Acid

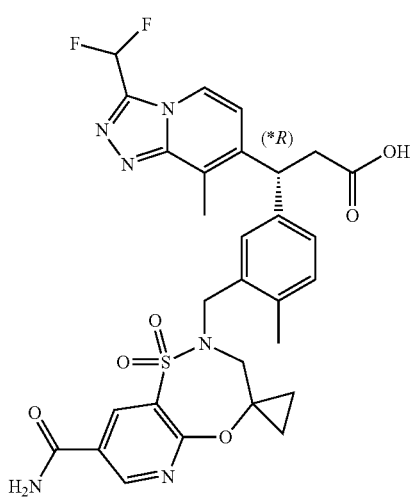 [SMILES: Cc1ccc([C@@H](CC(=O)O)c2ccn3c(C(F)F)nnc3c2C)cc1CN1CC2(CC2)Oc2ncc(C(N)=O)cc2S1(=O)=O]

The mixture of 3-(3-((8'-carbamoyl-1',1'-dioxidospiro[cyclopropane-1,4'-pyrido[2,3-b][1,4,5]oxathiazepin]-2'(3'H)-yl)methyl)-4-methylphenyl)-3-(3-(difluoromethyl)-8-methyl-[1,2,4]triazolo[4,3-a]pyridin-7-yl)propanoic acid (Example 551, 344 mg) was separated by chiral SFC (stationary phase: CHIRALPAK AD-H 5 μm 250*30 mm, Mobile phase: 45% CO$_2$, 55% EtOH) to provide two diastereomers. The second eluting diastereomer (158 mg, 27%) was designated (*R). MS (ESI): mass calcd. for C$_{29}$H$_{26}$F$_2$N$_6$O$_5$S, 626.2; m/z found, 627.2 [M+H]$^+$. $^1$H NMR (400 MHz, CDCl$_3$) δ $^1$H NMR (500 MHz, Chloroform-d) δ 8.19 (d, J=7.0 Hz, 1H), 8.10 (q, J=3.3, 2.9 Hz, 1H), 8.01 (q, J=3.8, 3.3 Hz, 1H), 7.39-7.29 (m, 3H), 7.07-6.95 (m, 3H), 4.76-4.63 (m, 2H), 3.49 (d, J=4.3 Hz, 2H), 3.42-3.30 (m, 3H), 3.12 (dd, J=15.7, 6.9 Hz, 1H), 2.99 (dd, J=15.6, 8.4 Hz, 1H), 2.81-2.72 (m, 3H), 2.26-2.18 (m, 3H), 1.28-1.17 (m, 2H), 0.63 (s, 2H), 0.28 (d, J=5.3 Hz, 2H).

Example 554: (2S,3*R)-3-(3-(Trifluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)-2-methylpropanoic Acid

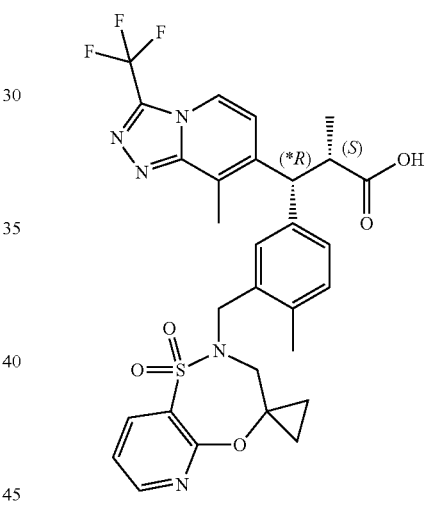

Step A: Methyl (2S,3*R))-3-(3-((1',1'-dioxidospiro[cyclopropane-1,4'-pyrido[2,3-b][1,4,5]oxathiazepin]-2'(3'H)-yl)methyl)-4-methylphenyl)-2-methyl-3-(8-methyl-3-(trifluoromethyl)-[1,2,4]triazolo[4,3-a]pyridin-7-yl)propanoate. Diisopropyl azodicarboxylate (0.13 mL, 0.66 mmol) was added to a stirring mixture of methyl (2*S, 3*R)-3-(3-(hydroxymethyl)-4-methylphenyl)-2-methyl-3-(8-methyl-3-(trifluoromethyl)-[1,2,4]triazolo[4,3-a]pyridin-7-yl)propanoate (Intermediate 175, 168 mg, 0.40 mmol), 2',3'-dihydrospiro[cyclopropane-1,4'-pyrido[2,3-b][1,4,5]oxathiazepine] 1',1'-dioxide (Intermediate 6, 136 mg, 0.60 mmol), and triphenylphosphine (155 mg, 0.60 mmol) in THF (5 mL) at room temperature. After 1 hour, ethyl acetate and water were added and the biphasic mixture was separated. The aqueous layer was extracted with ethyl acetate. These extractions resulted in several organic solvent fractions which were combined and washed sequentially with water and brine solution. The organic fractions were dried over Na$_2$SO$_4$, filtered and concentrated under reduced pressure. The residue was purified by flash column chromatography (eluent: 0-100% ethyl acetate/hexanes) to provide the title compound (240 mg, 96%) as a white foam. MS (ESI): mass calcd. for $C_{30}H_{30}F_3N_5O_5S$, 629.2; m/z found, 630.1 [M+H]$^+$. $^1$H NMR (500 MHz, CDCl$_3$) δ 8.46 (dd, J=4.8, 1.9 Hz, 1H), 8.29 (dd, J=7.7, 1.9 Hz, 1H), 8.04 (d, J=7.2 Hz, 1H), 7.33 (dd, J=7.6, 4.9 Hz, 1H), 7.27-7.09 (m, 4H), 4.47 (d, J=11.5 Hz, 1H), 4.38-4.27 (m, 2H), 3.59 (d, J=15.3 Hz, 1H), 3.52 (s, 3H), 3.50-3.43 (m, 1H), 3.35 (dq, J=11.4, 6.8 Hz, 1H), 2.78 (s, 2H), 2.26 (s, 3H), 1.28-1.15 (m, 6H), 0.62-0.55 (m, 2H).

Step B: (2S,3*R)-3-(3-(Trifluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)-2-methylpropanoic acid. A mixture containing methyl (2S,3*R)-3-(3-((1',1'-dioxidospiro[cyclopropane-1,4'-pyrido[2,3-b][1,4,5]oxathiazepin]-2'(3'H)-yl)methyl)-4-methylphenyl)-2-methyl-3-(8-methyl-3-(trifluoromethyl)-[1,2,4]triazolo[4,3-a]pyridin-7-yl)propanoate (240 mg, 0.38 mmol), 1 M aqueous NaOH solution (3.5 mL, 3.5 mmol), ethanol (0.10 mL) and THF (3.5 mL) was stirred at room temperature overnight. 1 M Aqueous HCl solution was added until the pH was 3-4. Ethyl acetate was added and the resulting biphasic mixture was separated. The aqueous layer was extracted with ethyl acetate. These extractions resulted in several organic solvent fractions which were combined, washed sequentially with water and brine solution, dried over Na$_2$SO$_4$, filtered and concentrated to dryness under reduced pressure. The residue was purified by flash column chromatography (eluent: 0-10% MeOH/DCM) to provide the title compound (225 mg, 96%) as a white foam. MS (ESI): mass calcd. for $C_{29}H_{28}F_3N_5O_5S$, 615.2; m/z found, 616.2 [M+H]$^+$. $^1$H NMR (500 MHz, CDCl$_3$) δ 9.21 (s, 2H), 8.45 (dd, J=4.9, 2.0 Hz, 1H), 8.30 (dd, J=7.6, 2.0 Hz, 1H), 8.05 (d, J=7.2 Hz, 1H), 7.34 (dd, J=7.6, 4.9 Hz, 1H), 7.28 (d, J=7.4 Hz, 1H), 7.20-7.09 (m, 3H), 4.46 (d, J=11.4 Hz, 1H), 4.38-4.26 (m, 1H), 3.57 (d, J=15.2 Hz, 1H), 3.48 (d, J=15.0 Hz, 1H), 3.36 (dq, J=11.3, 6.8 Hz, 1H), 2.70 (s, 3H), 2.27 (s, 3H), 1.17 (q, J=5.7, 4.4 Hz, 3H), 0.58-0.52 (m, 2H), 0.00 (s, 2H).

Example 555: (*S)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)-2,2-dimethylpropanoic Acid

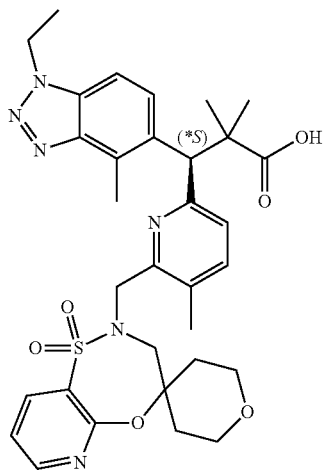 [SMILES: CCn1nnc2c(C)c([C@H](c3ccc(C)c(CN4CC5(CCOCC5)Oc5ncccc5S4(=O)=O)n3)C(C)(C)C(=O)O)ccc21]

Step A: Methyl (R/S)-3-(6-((1',1'-dioxido-2,3,5,6-tetrahydrospiro[pyran-4,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)-2,2-dimethylpropanoate. A solution of methyl 3-(1-ethyl-4-methyl-1H-benzo[d][1,2,3]triazol-5-yl)-3-(6-(hydroxymethyl)-5-methylpyridin-2-yl)-2,2-dimethylpropanoate (Intermediate 168, 150 mg, 0.38 mmol), 2,2',3,3',5,6-hexahydrospiro[pyran-4,4'-pyrido[2,3-b][1,4,5]oxathiazepine] 1',1'-dioxide (Intermediate 36, 126 mg, 0.47 mmol), and triphenylphosphine (158 mg, 0.60 mmol) in THF (4 mL) and DMF (4 ml) was stirred at room temperature for 5 minutes. DBAD (139 mg, 0.61 mmol) was added and the solution was stirred at room temperature for 30 minutes. The reaction was then concentrated under a stream of nitrogen and purified by flash column chromatography (eluent: 0-100% ethyl acetate/hexanes) to afford the title compound (150 mg, 61%) as a white foam. MS (ESI): mass calcd. for $C_{33}H_{40}N_6O_6S$, 648.3; m/z found, 649.2 [M+H]$^+$.

Step B: (R/S)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)-2,2-dimethylpropanoic acid. Lithium hydroxide (111 mg, 4.62 mmol) was added to a solution of methyl 3-(1-ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoate (150 mg, 0.23 mmol) in MeOH (3 mL), THF (3 mL) and water (3 mL). The reaction was stirred at 75° C. overnight then allowed to cool to room temperature. 1 M aqueous HCl solution was added until the pH was approximately 6. DCM was added and the resulting biphasic mixture was separated. The aqueous layer was extracted with DCM. These extractions resulted in several organic solvent fractions which were combined, dried over MgSO$_4$, filtered, and concentrated to dryness under reduced pressure. The material was purified by flash column chromatography (eluent: 0-10% MeOH/DCM) to afford the title compound (80 mg, 55%) as a white foam. MS (ESI): mass calcd. for $C_{32}H_{38}N_6O_6S$, 634.3; m/z found, 635.2 [M+H]$^+$. $^1$H NMR (500 MHz, CDCl$_3$) δ d 11.52 (s, 1H), 8.59 (dd, J=4.9, 2.0 Hz, 1H), 8.25 (dd, J=7.7, 1.9 Hz, 1H), 7.68 (d, J=8.0 Hz, 1H), 7.57 (d, J=8.8 Hz, 1H), 7.41-7.33 (m, 2H), 7.23 (d, J=8.0 Hz, 1H), 4.89 (s, 1H), 4.73 (d, J=2.6 Hz, 2H), 4.64 (q, J=7.3 Hz, 2H), 4.07 (t, J=11.6 Hz, 2H), 4.00-3.90 (m, 2H), 3.78 (td, J=11.9, 4.3 Hz, 2H), 2.98 (s, 3H), 2.39 (s, 3H), 1.88-1.75 (m, 2H), 1.70 (t, J=11.1 Hz, 2H), 1.46 (s, 3H), 1.35 (s, 6H).

Step C: (*S)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)-2,2-dimethylpropanoic acid. The mixture of (R/S)-3-(6-((1',1'-dioxido-2,3,5,6-tetrahydrospiro[pyran-4,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)-2,2-dimethylpropanoic acid (80 mg) was separated by chiral SFC (Stationary phase: CHIRALPAK AD-H 5 μm 250*30 mm, Mobile phase: 70% CO$_2$, 30% EtOH) to afford two diastereomers. The first eluting isomer (25 mg, 17%) was designated (*S): MS: mass calcd. for $C_{32}H_{38}N_6O_6S$, 634.3; m/z found, 635.2 [M+H]$^+$. 1 H NMR (600 MHz, CDCl$_3$) δ 8.45 (dd, J=4.8, 2.0 Hz, 1H), 8.17 (dd, J=7.6, 2.0 Hz, 1H), 7.43 (d, J=8.9 Hz, 1H), 7.37 (d, J=8.0 Hz, 1H), 7.25-7.17 (m, 2H), 6.97 (d, J=7.9 Hz, 1H), 5.22 (s, 1H), 4.83 (s, 1H), 4.60

(s, 2H), 4.60 (t, J=16.4 Hz, 0H), 4.58-4.48 (m, 2H), 4.11-3.95 (m, 2H), 3.73-3.62 (m, 4H), 2.92 (s, 3H), 2.29 (s, 3H), 1.68 (s, 2H), 1.68-1.60 (m, 2H), 1.50 (t, J=7.3 Hz, 3H), 1.30 (d, J=7.7 Hz, 6H).

Example 556: (*R)-3-(6-((1',1'-Dioxido-2,3,5,6-tetrahydrospiro[pyran-4,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)-2,2-dimethylpropanoic Acid

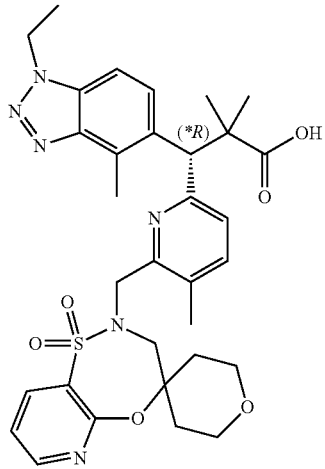 [SMILES: CCn1nnc2c(C)c([C@@H](c3ccc(C)c(CN4CC5(CCOCC5)Oc5ncccc5S4(=O)=O)n3)C(C)(C)C(=O)O)ccc21]

The second eluting isomer (28 mg, 19%) from the chiral separation described in Example 555 was designated (*R): MS: mass calcd. for $C_{32}H_{38}N_6O_6S$, 634.3; m/z found, 635.2 [M+H]$^+$. 1 H NMR (600 MHz, CDCl$_3$) δ 8.46 (dd, J=4.9, 2.0 Hz, 1H), 8.17 (dd, J=7.6, 2.0 Hz, 1H), 7.43 (d, J=8.8 Hz, 1H), 7.37 (d, J=7.9 Hz, 1H), 7.26-7.18 (m, 2H), 6.97 (d, J=7.9 Hz, 1H), 5.22 (s, 1H), 4.83 (s, 1H), 4.60 (s, 2H), 4.58-4.49 (m, 2H), 4.11-3.95 (m, 2H), 3.71 (s, 3H), 3.69-3.63 (m, 1H), 2.92 (s, 3H), 2.29 (s, 3H), 1.75-1.57 (m, 4H), 1.50 (t, J=7.3 Hz, 3H), 1.30 (d, J=13.7 Hz, 6H).

Example 557: (*S)-3-(1-Ethyl-4-methyl-1H-benzo[d][1,2,3]triazol-5-yl)-2,2-dimethyl-3-(5-methyl-6-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic Acid

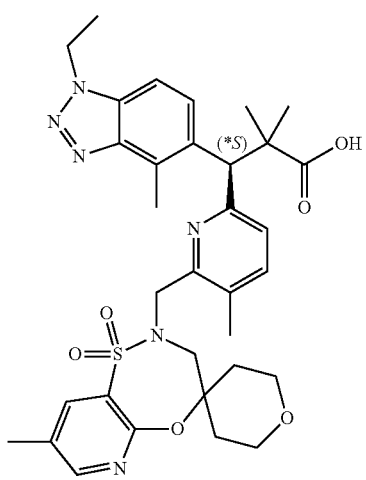 [SMILES: CCn1nnc2c(C)c([C@H](c3ccc(C)c(CN4CC5(CCOCC5)Oc5ncc(C)cc5S4(=O)=O)n3)C(C)(C)C(=O)O)ccc21]

Step A: Methyl (R/S)-3-(1-ethyl-4-methyl-1H-benzo[d][1,2,3]triazol-5-yl)-2,2-dimethyl-3-(5-methyl-6-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoate. A solution of methyl 3-(1-ethyl-4-methyl-1H-benzo[d][1,2,3]triazol-5-yl)-3-(6-(hydroxymethyl)-5-methylpyridin-2-yl)-2,2-dimethylpropanoate (Intermediate 168, 170 mg, 0.43 mmol), 8'-methyl-2,2',3,3',5,6-hexahydrospiro[pyran-4,4'-pyrido[2,3-b][1,4,5]oxathiazepine] 1',1'-dioxide (Intermediate 37, 150 mg, 0.53 mmol), and triphenylphosphine (179 mg, 0.68 mmol) in THF (5 mL) and DMF (5 ml) was stirred at room temperature for 5 minutes. DBAD (158 mg, 0.69 mmol) was added and the solution was stirred at room temperature for 30 minutes. The reaction was then concentrated under a stream of nitrogen and purified by flash column chromatography (eluent: 0-100% ethyl acetate/hexanes) to afford the title compound (250 mg, 88%) as a white foam. MS (ESI): mass calcd. for $C_{34}H_{42}N_6O_6S$, 662.3; m/z found, 663.2 [M+H]$^+$.

Step B: (R/S)-3-(1-Ethyl-4-methyl-1H-benzo[d][1,2,3]triazol-5-yl)-2,2-dimethyl-3-(5-methyl-6-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid. Lithium hydroxide (181 mg, 7.54 mmol) was added to a solution of methyl (R/S)-3-(1-ethyl-4-methyl-1H-benzo[d][1,2,3]triazol-5-yl)-2,2-dimethyl-3-(5-methyl-6-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoate (250 mg, 0.38 mmol) in MeOH (5 mL), THF (5 mL) and water (5 mL). The reaction was stirred at 75° C. overnight then allowed to cool to room temperature. 1 M aqueous HCl solution was added until the pH was approximately 6. DCM was added and the resulting biphasic mixture was separated. The aqueous layer was extracted with DCM. These extractions resulted in several organic solvent fractions which were combined, dried over MgSO$_4$, filtered, and concentrated to dryness under reduced pressure. The material was purified by flash column chromatography (eluent: 0-10% MeOH/DCM) to afford the title compound (220 mg, 90%) as a white foam. MS (ESI): mass calcd. for $C_{33}H_{40}N_6O_6S$, 648.3; m/z found, 649.3 [M+H]$^+$.

Step C: (*S)-3-(1-Ethyl-4-methyl-1H-benzo[d][1,2,3]triazol-5-yl)-2,2-dimethyl-3-(5-methyl-6-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid. The mixture of (R/S)-3-(1-ethyl-4-methyl-1H-benzo[d][1,2,3]triazol-5-yl)-2,2-dimethyl-3-(5-methyl-6-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid (220 mg) was separated by chiral SFC ((Stationary phase: CHIRALPAK AD-H 5 µm 250*30 mm, Mobile phase: 70% CO$_2$, 30% EtOH) to afford two diastereomers. The first eluting isomer (54 mg, 22%) was designated (*S), which was further purified by reverse phase (Stationary phase: YMC-actus Triart C18 10 µm 30*150 mm, Mobile phase: Gradient from 65% HCOONH$_4$ 0.6 g/L pH=3.5, 35% ACN to 25% HCOONH$_4$ 0.6 g/L pH=3.5, 75% ACN) followed by another reverse phase (Stationary phase: YMC-actus Triart C18 10 µm 30*150 mm, Mobile phase: Gradient from 75% NH$_4$HCO$_3$ 0.2%, 25% ACN to 35% NH$_4$HCO$_3$ 0.2%, 65% ACN) to afford the title compound (22 mg, 9%): MS: mass calcd. for $C_{33}H_{40}N_6O_6S$, 648.3; m/z found, 649.3 [M+H]$^+$. $^1$H NMR (600 MHz, CDCl$_3$) δ 8.33 (dd, J=2.4, 0.9 Hz, 1H), 8.06-8.02 (m, 1H), 7.49 (dd, J=15.0, 8.4 Hz, 2H), 7.28 (d, J=9.1 Hz, 1H), 7.07 (d, J=7.9 Hz, 1H), 4.87 (s, 1H), 4.68 (s, 2H), 4.66-4.56 (m, 2H), 4.11-4.04 (m, 2H), 3.79-3.68 (m, 4H), 3.01 (s, 3H), 2.41 (d, J=29.1 Hz, 6H), 1.82-1.73 (m, 2H), 1.76-1.69 (m, 2H), 1.58 (t, J=7.3 Hz, 3H), 1.41 (s, 3H), 1.36 (s, 3H).

Example 558: (*R)-3-(1-Ethyl-4-methyl-1H-benzo[d][1,2,3]triazol-5-yl)-2,2-dimethyl-3-(5-methyl-6-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic Acid

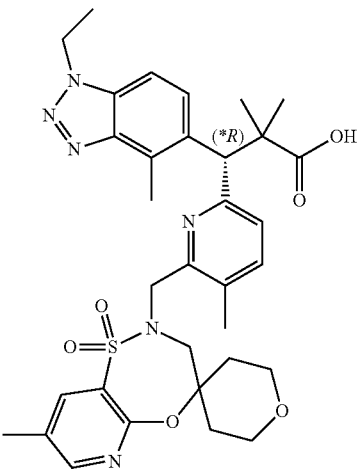 [SMILES: CCn1nnc2c(C)c([C@@H](c3ccc(C)c(CN4CC5(CCOCC5)Oc5ncc(C)cc5S4(=O)=O)n3)C(C)(C)C(=O)O)ccc21]

The second eluting isomer (54 mg, 22%) from the chiral separation described in Example 557 was designated (*R) which was further purified by reverse phase (Stationary phase: YMC-actus Triart C18 10 μm 30*150 mm, Mobile phase: Gradient from 65% HCOONH$_4$ 0.6 g/L pH=3.5, 35% ACN to 25% HCOONH$_4$ 0.6 g/L pH=3.5, 75% ACN) to afford the title compound (43 mg, 18%): MS: mass calcd. for C$_{33}$H$_{40}$N$_6$O$_6$S, 648.3; m/z found, 649.3 [M+H]$^+$. 1H NMR (600 MHz, CDCl$_3$) δ 8.32 (dd, J=2.4, 0.9 Hz, 1H), 8.06-8.02 (m, 1H), 7.48 (dd, J=22.4, 8.4 Hz, 2H), 7.28 (d, J=8.8 Hz, 1H), 7.05 (d, J=7.9 Hz, 1H), 4.89 (s, 1H), 4.67 (s, 2H), 4.61 (q, J=7.3 Hz, 2H), 4.13-4.04 (m, 2H), 3.80-3.68 (m, 4H), 3.00 (s, 3H), 2.43 (s, 3H), 2.38 (s, 3H), 1.80-1.64 (m, 4H), 1.57 (d, J=14.7 Hz, 3H), 1.40 (s, 3H), 1.36 (s, 3H).

Example 559: (R/S)-3-(3-(Difluoromethyl)-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic Acid Step A: Methyl 3-(3-(difluoromethyl)-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoate. A solution of methyl 3-(3-(difluoromethyl)-8-methyl-[1,2,4]triazolo[4,3-a]pyridin-7-yl)-3-(3-(hydroxymethyl)-4-methylphenyl)-2,2-dimethylpropanoate (Intermediate 49, 2.0 g, 4.8 mmol), 8'-methyl-2',3'-dihydrospiro[cyclopropane-1,4'-pyrido[2,3-b][1,4,5]oxathiazepine] 1',1'-dioxide (Intermediate 6, 1.5 g, 6.0 mmol), and triphenylphosphine (1.8 g, 7.1 mmol) in THF (133 mL) and DMF (13 ml) was stirred at room temperature for 5 minutes. DBAD (1.9 g, 7.9 mmol) was added and the solution was stirred at room temperature for 30 minutes. The reaction was then concentrated under a stream of nitrogen and purified by flash column chromatography (eluent: 0-100% ethyl acetate/hexanes) to afford the title compound (2.9 g, 95% yield). MS (ESI): mass calcd. for C$_{32}$H$_{35}$F$_2$N$_5$O$_5$S, 639.2; m/z found, 640.3 [M+H]$^+$.

Step B: (R/S)-3-(3-(Difluoromethyl)-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid. Lithium hydroxide (0.83 g, 19.7 mmol) was added to a solution of methyl 3-(3-(difluoromethyl)-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoate (2.9 g, 3.9 mmol) in MeOH (25 mL) and water (17 mL). The reaction was stirred at 70° C. overnight then allowed to cool to room temperature. 1 M aqueous HCl solution was added until the pH was 3-4. EtOAc was added and the resulting biphasic mixture was separated. The aqueous layer was extracted with EtOAc. These extractions resulted in several organic solvent fractions which were combined, dried over MgSO$_4$, filtered, and concentrated to dryness under reduced pressure. The material was purified by flash column chromatography (eluent: 0-10% MeOH/DCM) to provide the title compound (2.5 g, 99% yield). MS (ESI): mass calcd. for C$_{31}$H$_{33}$F$_2$N$_5$O$_5$S, 625.2; m/z found, 626.2 [M+H]$^+$.

Example 560: (*S)-3-(3-(Difluoromethyl)-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic Acid

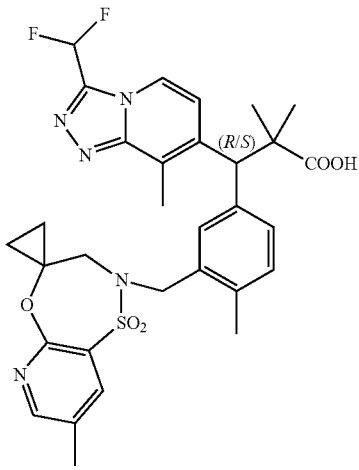 [SMILES: Cc1cnc2c(c1)S(=O)(=O)N(Cc1cc(C(c3ccn4c(C(F)F)nnc4c3C)C(C)(C)C(=O)O)ccc1C)CC1(CC1)O2]

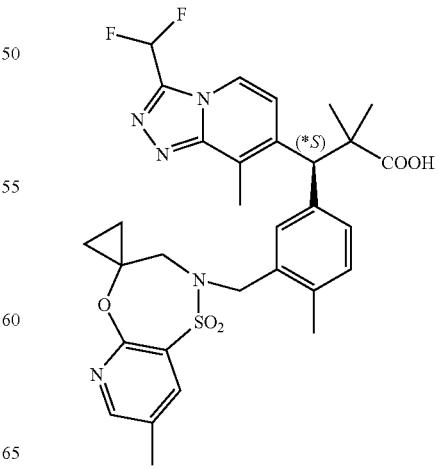

The mixture of (R/S)-3-(3-(difluoromethyl)-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic acid (Example 559, 2.5 g) was separated by chiral SFC (stationary phase: Chiralpak IC, 5 µm, 2×25 cm, Mobile phase: 20% MeOH (0.1% DEA), 80% $CO_2$) to afford two enantiomers. The first eluting isomer (1.17 g, 47%) was designated (*S): MS: mass calcd. for $C_{31}H_{33}F_2N_5O_5S$, 625.2; m/z found, 626.2 $[M+H]^+$. $^1H$ NMR (500 MHz, Chloroform-d) δ 8.26-8.22 (m, 1H), 8.11-8.04 (m, 2H), 7.26-7.23 (m, 1H), 7.32-7.09 (m, 1H), 7.16-7.12 (m, 1H), 7.09-7.05 (m, 1H), 7.04-6.99 (m, 1H), 4.76 (s, 1H), 4.32-4.20 (m, 2H), 3.57-3.40 (m, 2H), 2.63 (s, 3H), 2.40 (s, 3H), 2.30 (s, 3H), 1.27 (s, 3H), 1.21 (s, 3H), 1.18-1.09 (m, 2H), 0.49-0.37 (m, 2H).

Example 561: (*R)-3-(3-(Difluoromethyl)-8-methyl-[1,2,4]triazolo[4,3-a]pyridin-7-yl)-2,2-dimethyl-3-(4-methyl-3-((8'-methyl-1',1'-dioxidospiro[cyclopropane-1,4'-pyrido[2,3-b][1,4,5]oxathiazepin]-2'(3'H)-yl)methyl)phenyl)propanoic Acid

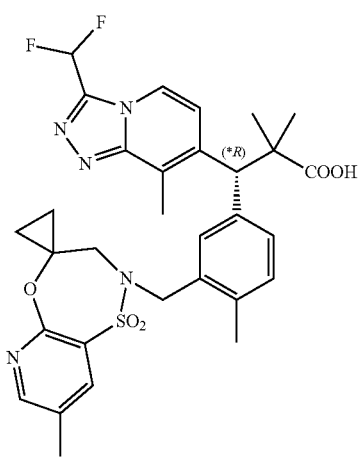 [SMILES: Cc1cnc2c(c1)S(=O)(=O)N(Cc1cc([C@H](c3ccn4c(C(F)F)nnc4c3C)C(C)(C)C(=O)O)ccc1C)CC1(CC1)O2]

The second eluting isomer (1.19 g, 48%) from the chiral separation described in Example 560 was designated (*R): MS: mass calcd. for $C_{31}H_{33}F_2N_5O_5S$, 625.2; m/z found, 626.2 $[M+H]^+$. $^1H$ NMR (500 MHz, Chloroform-d) δ 8.28-8.22 (m, 1H), 8.13-8.05 (m, 2H), 7.28-7.24 (m, 1H), 7.34-7.10 (m, 1H), 7.19-7.13 (m, 1H), 7.10-7.06 (m, 1H), 7.03-6.99 (m, 1H), 4.78 (s, 1H), 4.36-4.19 (m, 2H), 3.54-3.43 (m, 2H), 2.64 (s, 3H), 2.41 (s, 3H), 2.31 (s, 3H), 1.28 (s, 3H), 1.22 (s, 3H), 1.18-1.11 (m, 2H), 0.50-0.37 (m, 2H).

Example 562: (*S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(8-methyl-3-(trifluoromethyl)-[1,2,4]triazolo[4,3-a]pyridin-7-yl)propanoic Acid

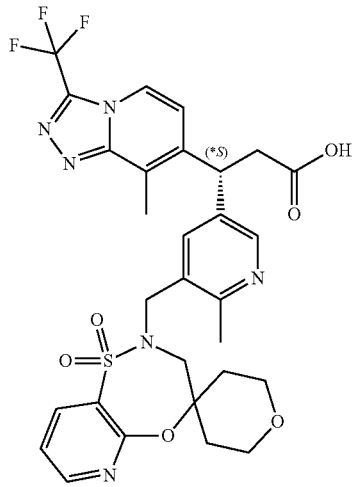 [SMILES: Cc1ncc([C@@H](CC(=O)O)c2ccn3c(C(F)(F)F)nnc3c2C)cc1CN1CC2(CCOCC2)Oc2ncccc2S1(=O)=O]

Step A: Ethyl (*S)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(8-methyl-3-(trifluoromethyl)-[1,2,4]triazolo[4,3-a]pyridin-7-yl)propanoate. A solution of ethyl (*S)-3-(5-(hydroxymethyl)-6-methylpyridin-3-yl)-3-(8-methyl-3-(trifluoromethyl)-[1,2,4]triazolo[4,3-a]pyridin-7-yl)propanoate (Intermediate 173, 200 mg, 0.47 mmol), 2,2',3,3',5,6-hexahydrospiro[pyran-4,4'-pyrido[2,3-b][1,4,5]oxathiazepine] 1',1'-dioxide (Intermediate 36, 158 mg, 0.58 mmol), and triphenylphosphine (198 mg, 0.75 mmol) in THF (5 mL) was stirred at room temperature for 5 minutes. DBAD (175 mg, 0.75 mmol) was added and the solution was stirred at room temperature for 30 minutes. The reaction was then concentrated under a stream of nitrogen and purified by flash column chromatography (eluent: 0-100% ethyl acetate/hexanes) to afford the title compound (300 mg, 94% yield). MS (ESI): mass calcd. for $C_{31}H_{33}F_3N_6O_6S$, 674.2; m/z found, 675.1 $[M+H]^+$. $^1H$ NMR (500 MHz, $CDCl_3$) δ 8.50 (dd, J=4.9, 2.0 Hz, 1H), 8.35 (d, J=2.2 Hz, 1H), 8.16 (dd, J=7.6, 2.0 Hz, 1H), 8.06 (d, J=7.2 Hz, 1H), 7.60 (d, J=2.2 Hz, 1H), 7.29-7.23 (m, 1H), 6.94 (d, J=7.3 Hz, 1H), 4.99 (t, J=7.8 Hz, 1H), 4.47 (s, 2H), 4.13-3.99 (m, 4H), 3.64 (dt, J=21.3, 10.6 Hz, 3H), 3.44 (s, 2H), 3.17 (dd, J=16.0, 7.3 Hz, 1H), 3.08 (dd, J=16.1, 8.5 Hz, 1H), 2.84 (d, J=0.7 Hz, 3H), 2.43 (s, 3H), 1.75-1.64 (m, 1H), 1.66-1.48 (m, 2H), 1.17 (t, J=7.1 Hz, 3H).

Step B: (*S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(8-methyl-3-(trifluoromethyl)-[1,2,4]triazolo[4,3-a]pyridin-7-yl)propanoic acid. Sodium hydroxide solution (1 M, 4.1 mL, 4.1 mmol) was added to a solution of ethyl (*S)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(8-methyl-3-(trifluoromethyl)-[1,2,4]triazolo[4,3-a]pyridin-7-yl)propanoate (300 mg, 0.45 mmol) in THF (5 mL). The reaction was stirred at room temperature overnight. 1 M aqueous HCl solution was added until the pH was 4. DCM was added and the resulting biphasic mixture was separated.

The aqueous layer was extracted with DCM. These extractions resulted in several organic solvent fractions which were combined, dried over MgSO$_4$, filtered, and concentrated to dryness under reduced pressure. The material was purified by flash column chromatography (eluent: 0-10% MeOH/DCM) to provide the title compound to provide the title compound (280 mg, 97% yield). MS (ESI): mass calcd. for $C_{29}H_{29}F_3N_6O_6S$, 646.2; m/z found, 647.1 [M+H]$^+$. $^1$H NMR (500 MHz, CDCl$_3$) δ 8.49 (dd, J=4.9, 2.0 Hz, 1H), 8.40 (d, J=2.1 Hz, 1H), 8.13 (dd, J=7.6, 2.0 Hz, 1H), 8.07 (d, J=7.0 Hz, 1H), 7.88 (s, 2H), 7.68 (d, J=2.2 Hz, 1H), 7.26 (dd, J=7.6, 4.9 Hz, 1H), 6.99 (d, J=7.3 Hz, 1H), 5.01 (t, J=7.7 Hz, 1H), 4.48 (s, 2H), 3.99 (tt, J=9.2, 3.4 Hz, 2H), 3.60 (s, 2H), 3.64-3.56 (m, 1H), 3.52 (s, 1H), 3.44 (s, 1H), 3.19 (dd, J=16.0, 7.8 Hz, 1H), 3.08 (dd, J=16.0, 7.6 Hz, 1H), 2.78 (s, 3H), 2.41 (s, 3H), 1.55-1.50 (m, 2H).

Example 563: (*S)-3-(8-Methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic Acid

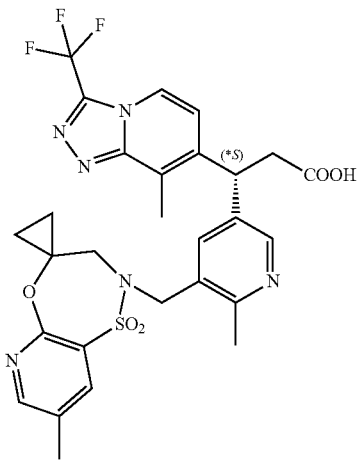 [SMILES: Cc1cnc2c(c1)S(=O)(=O)N(Cc1cc([C@@H](CC(=O)O)c3ccn4c(C(F)(F)F)nnc4c3C)cnc1C)CC1(CC1)O2]

Step A: Ethyl (*S)-3-(8-methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoate. A solution of A solution of ethyl (*S)-3-(5-(hydroxymethyl)-6-methylpyridin-3-yl)-3-(8-methyl-3-(trifluoromethyl)-[1,2,4]triazolo[4,3-a]pyridin-7-yl)propanoate (Intermediate 173, 250 mg, 0.59 mmol), 8'-methyl-2',3'-dihydrospiro[cyclopropane-1,4'-pyrido[2,3-b][1,4,5]oxathiazepine] 1',1'-dioxide (Intermediate 6, 175 mg, 0.73 mmol), and triphenylphosphine (247 mg, 0.94 mmol) in THF (6 mL) was stirred at room temperature for 5 minutes. DBAD (218 mg, 0.95 mmol) was added and the solution was stirred at room temperature for 30 minutes. The reaction was then concentrated under a stream of nitrogen and purified by flash column chromatography (eluent: 0-100% ethyl acetate/hexanes) to afford the title compound (380 mg, 99% yield). MS (ESI): mass calcd. for $C_{30}H_{31}F_3N_6O_5S$, 644.2; m/z found, 645.1 [M+H]$^+$. $^1$H NMR (500 MHz, CDCl$_3$) δ 8.29 (d, J=2.3 Hz, 1H), 8.22 (dd, J=2.4, 0.9 Hz, 1H), 8.06-7.99 (m, 2H), 7.52 (d, J=2.3 Hz, 1H), 6.91 (d, J=7.3 Hz, 1H), 4.93 (t, J=7.8 Hz, 1H), 4.29 (s, 2H), 4.09-4.01 (m, 2H), 3.51 (d, J=15.4 Hz, 1H), 3.41 (s, 1H), 3.13 (dd, J=16.1, 7.4 Hz, 1H), 3.03 (dd, J=16.1, 8.3 Hz, 1H), 2.79 (s, 3H), 2.42 (s, 3H), 2.37 (s, 3H), 1.25-1.10 (m, 5H), 0.65-0.56 (m, 2H).

Step B: (*S)-3-(8-Methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic acid. Sodium hydroxide solution (1 M, 5.4 mL, 5.4 mmol) was added to a solution of ethyl (*S)-3-(8-methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoate (380 mg, 0.59 mmol) in THF (5 mL). The reaction was stirred at room temperature overnight. 1 M aqueous HCl solution was added until the pH was 4. DCM was added and the resulting biphasic mixture was separated. The aqueous layer was extracted with DCM. These extractions resulted in several organic solvent fractions which were combined, dried over MgSO$_4$, filtered, and concentrated to dryness under reduced pressure. The material was purified by flash column chromatography (eluent: 0-10% MeOH/DCM) to provide the title compound to provide the title compound (359 mg, 99% yield). MS (ESI): mass calcd. for $C_{28}H_{27}F_3N_6O_5S$, 616.2; m/z found, 617.2 [M+H]$^+$. $^1$H NMR (500 MHz, CDCl$_3$) δ 8.37 (d, J=2.2 Hz, 1H), 8.24 (dd, J=2.4, 0.9 Hz, 2H), 8.10-8.01 (m, 2H), 7.64 (d, J=2.2 Hz, 1H), 6.96 (d, J=7.3 Hz, 1H), 5.00 (t, J=7.7 Hz, 1H), 4.31 (s, 2H), 3.56-3.48 (m, 1H), 3.46 (s, 1H), 3.17 (dd, J=16.1, 7.8 Hz, 1H), 3.06 (dd, J=16.0, 7.7 Hz, 1H), 2.79 (s, 3H), 2.42 (d, J=19.1 Hz, 6H), 1.14 (s, 2H), 0.58 (q, J=5.7, 4.6 Hz, 2H).

Example 564: (*R)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(8-methyl-3-(trifluoromethyl)-[1,2,4]triazolo[4,3-a]pyridin-7-yl)propanoic Acid

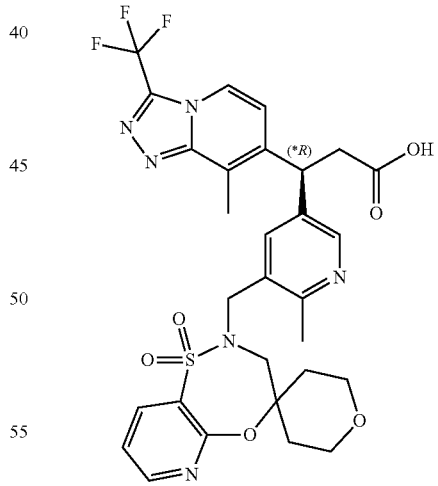

Step A: Ethyl (*R)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(8-methyl-3-(trifluoromethyl)-[1,2,4]triazolo[4,3-a]pyridin-7-yl)propanoate. A solution of ethyl (*R)-3-(5-(hydroxymethyl)-6-methylpyridin-3-yl)-3-(8-methyl-3-(trifluoromethyl)-[1,2,4]triazolo[4,3-a]pyridin-7-yl)propanoate (Intermediate 172, 205 mg, 0.49 mmol), 2,2',3,3',5,6-hexahydrospiro[pyran-4,4'-pyrido[2,3-b][1,4,5]oxathiazepine] 1',1'-dioxide (Intermediate 36, 162 mg, 0.60 mmol), and triphenylphosphine (203 mg, 0.77 mmol) in THF (5 mL) was stirred at room temperature for 5 minutes. DBAD (179 mg, 0.78 mmol) was added and the solution was stirred at room temperature for 30 minutes. The reaction was then concentrated under a stream of nitrogen and purified by flash column chromatography (eluent: 0-100% ethyl acetate/hexanes) to afford the title compound (320 mg, 98% yield). MS (ESI): mass calcd. for $C_{31}H_{33}F_3N_6O_6S$, 674.2; m/z found, 675.1 [M+H]$^+$. $^1$H NMR (500 MHz, CDCl$_3$) δ 8.46 (dd, J=4.9, 2.0 Hz, 1H), 8.32 (d, J=2.2 Hz, 1H), 8.12 (dd, J=7.6, 1.9 Hz, 1H), 8.04 (d, J=7.2 Hz, 1H), 7.57 (d, J=2.2 Hz, 1H), 7.23 (dd, J=7.6, 4.9 Hz, 1H), 6.93 (d, J=7.3 Hz, 1H), 4.96 (t, J=7.8 Hz, 1H), 4.45 (s, 1H), 4.09-3.94 (m, 2H), 3.63-3.56 (m, 3H), 3.47 (s, 1H), 3.15 (dd, J=16.1, 7.3 Hz, 1H), 3.06 (dd, J=16.1, 8.5 Hz, 1H), 2.80 (s, 3H), 2.45 (s, 1H), 2.39 (s, 3H), 1.98 (s, 1H), 1.70-1.60 (m, 2H), 1.58-1.50 (m, 2H), 1.19 (t, J=7.2 Hz, 1H), 1.13 (t, J=7.1 Hz, 3H).

Step B: (*R)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(8-methyl-3-(trifluoromethyl)-[1,2,4]triazolo[4,3-a]pyridin-7-yl)propanoic acid. Sodium hydroxide solution (1 M, 4.4 mL, 4.4 mmol) was added to a solution of ethyl (*R)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-3-(8-methyl-3-(trifluoromethyl)-[1,2,4]triazolo[4,3-a]pyridin-7-yl)propanoate (320 mg, 0.47 mmol) in THF (5 mL). The reaction was stirred at room temperature overnight. 1 M aqueous HCl solution was added until the pH was 4. DCM was added and the resulting biphasic mixture was separated. The aqueous layer was extracted with DCM. These extractions resulted in several organic solvent fractions which were combined, dried over MgSO$_4$, filtered, and concentrated to dryness under reduced pressure. The material was purified by flash column chromatography (eluent: 0-10% MeOH/DCM) to provide the title compound to provide the title compound (300 mg, 98% yield). MS (ESI): mass calcd. for $C_{29}H_{29}F_3N_6O_6S$, 646.2; m/z found, 647.1 [M+H]$^+$. $^1$H NMR (500 MHz, CDCl$_3$) δ 8.51 (dt, J=3.5, 1.8 Hz, 1H), 8.42 (d, J=2.3 Hz, 1H), 8.16 (dt, J=7.7, 2.1 Hz, 1H), 8.09 (d, J=7.1 Hz, 1H), 7.67 (d, J=2.3 Hz, 1H), 7.31-7.24 (m, 1H), 6.99 (d, J=7.3 Hz, 1H), 6.50 (s, 2H), 4.49 (s, 1H), 4.02 (dt, J=16.6, 7.7 Hz, 2H), 3.68-3.59 (m, 3H), 3.56-3.44 (m, 2H), 3.20 (dd, J=16.0, 8.2 Hz, 1H), 3.08 (dd, J=16.0, 7.4 Hz, 1H), 2.80 (d, J=4.5 Hz, 3H), 2.45-2.37 (m, 3H), 1.65-1.46 (m, 4H).

Example 565: (*R)-3-(8-Methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic Acid

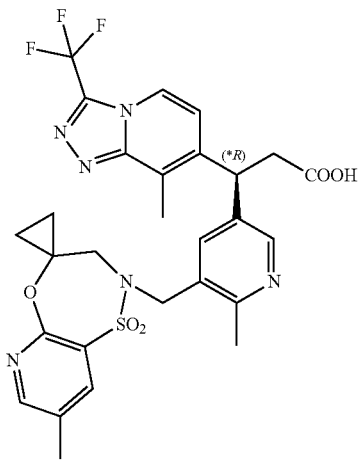 [SMILES: Cc1cnc2c(c1)S(=O)(=O)N(Cc1cc([C@H](CC(=O)O)c3ccn4c(C(F)(F)F)nnc4c3C)cnc1C)CC1(CC1)O2]

Step A: Ethyl (*R)-3-(8-methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoate. A solution of A solution of ethyl (*R)-3-(5-(hydroxymethyl)-6-methylpyridin-3-yl)-3-(8-methyl-3-(trifluoromethyl)-[1,2,4]triazolo[4,3-a]pyridin-7-yl)propanoate (Intermediate 172, 200 mg, 0.47 mmol), 8'-methyl-2',3'-dihydrospiro[cyclopropane-1,4'-pyrido[2,3-b][1,4,5]oxathiazepine] 1',1'-dioxide (Intermediate 6, 140 mg, 0.58 mmol), and triphenylphosphine (198 mg, 0.75 mmol) in THF (5 mL) was stirred at room temperature for 5 minutes. DBAD (174 mg, 0.76 mmol) was added and the solution was stirred at room temperature for 30 minutes. The reaction was then concentrated under a stream of nitrogen and purified by flash column chromatography (eluent: 0-100% ethyl acetate/hexanes) to afford the title compound (300 mg, 98% yield). MS (ESI): mass calcd. for $C_{30}H_{31}F_3N_6O_5S$, 644.2; m/z found, 645.1 [M+H]$^+$. $^1$H NMR (500 MHz, CDCl$_3$) δ 8.31 (d, J=2.3 Hz, 1H), 8.23 (dd, J=2.4, 0.9 Hz, 1H), 8.07-8.01 (m, 2H), 7.53 (d, J=2.3 Hz, 1H), 6.91 (d, J=7.3 Hz, 1H), 4.95 (t, J=7.8 Hz, 1H), 4.31 (s, 1H), 4.07 (dq, J=11.4, 7.2 Hz, 2H), 3.52 (d, J=15.3 Hz, 1H), 3.13 (dd, J=16.1, 7.4 Hz, 1H), 3.04 (dd, J=16.1, 8.3 Hz, 1H), 2.81 (s, 3H), 2.44 (s, 3H), 2.39 (s, 3H), 2.22 (t, J=3.9 Hz, 1H), 2.01 (s, 1H), 1.26-1.18 (m, 3H), 1.16 (t, J=7.1 Hz, 2H), 0.67-0.58 (m, 2H).

Step B: (*R)-3-(8-Methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic acid. Sodium hydroxide solution (1 M, 4.3 mL, 4.3 mmol) was added to a solution of ethyl (*R)-3-(8-methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoate (300 mg, 0.47 mmol) in THF (5 mL). The reaction was stirred at room temperature overnight. 1 M aqueous HCl solution was added until the pH was 4. DCM was added and the resulting biphasic mixture was separated. The aqueous layer was extracted with DCM. These extractions resulted in several organic solvent fractions which were combined, dried over MgSO$_4$, filtered, and concentrated to dryness under reduced pressure. The material was purified by flash column chromatography (eluent: 0-10% MeOH/DCM) to provide the title compound to provide the title compound (280 mg, 98% yield). MS (ESI): mass calcd. for $C_{28}H_{27}F_3N_6O_5S$, 616.2; m/z found, 617.2 [M+H]$^+$. $^1$H NMR (500 MHz, CDCl$_3$) δ 8.37 (d, J=2.2 Hz, 1H), 8.24 (d, J=2.3 Hz, 1H), 8.11-8.01 (m, 2H), 7.64 (d, J=2.2 Hz, 1H), 7.41 (s, 3H), 6.96 (d, J=7.3 Hz, 1H), 4.31 (s, 1H), 3.46 (d, J=0.8 Hz, 2H), 3.17 (dd, J=16.0, 7.8 Hz, 1H), 3.06 (dd, J=16.0, 7.7 Hz, 1H), 2.79 (s, 3H), 2.42 (d, J=19.7 Hz, 6H), 1.15 (s, 2H), 0.58 (s, 2H).

Example 566: (R/S)-3-(3-(Difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)-2,2-dimethylpropanoic Acid

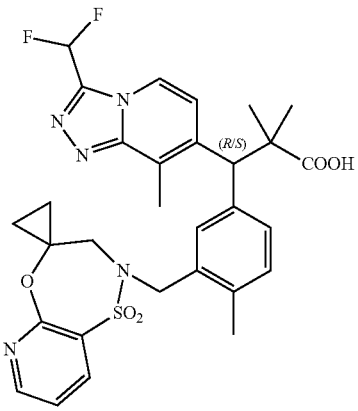

Step A: (R/S)-Methyl 3-(3-(difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)-2,2-dimethylpropanoate. A solution of methyl 3-(3-(difluoromethyl)-8-methyl-[1,2,4]triazolo[4,3-a]pyridin-7-yl)-3-(3-(hydroxymethyl)-4-methylphenyl)-2,2-dimethylpropanoate (Intermediate 49, 300 mg, 0.72 mmol), 2',3'-dihydrospiro[cyclopropane-1,4'-pyrido[2,3-b][1,4,5]oxathiazepine] 1',1'-dioxide (Intermediate 5, 231 mg, 1.02 mmol), and triphenylphosphine (280 mg, 1.07 mmol) in THF (8 mL) was stirred at room temperature for 5 minutes. Diisopropyl azodicarboxylate (0.23 mL, 1.18 mmol) was added and the solution was stirred at room temperature for 30 minutes. The reaction was then concentrated under a stream of nitrogen and purified by flash column chromatography (eluent: 0-100% ethyl acetate/hexanes) to afford the title compound (400 mg, 89% yield). MS (ESI): mass calcd. for $C_{31}H_{33}F_2N_5O_5S$, 625.2; m/z found, 626.2 [M+H]$^+$. $^1$H NMR (500 MHz, CDCl$_3$) δ 8.42 (dd, J=4.8, 1.9 Hz, 1H), 8.25 (dd, J=7.6, 2.0 Hz, 1H), 8.13 (d, J=7.3 Hz, 1H), 7.68-7.58 (m, 1H), 7.48-7.40 (m, 1H), 7.33-7.26 (m, 1H), 7.19 (s, 1H), 7.11-7.01 (m, 2H), 4.74 (s, 1H), 4.34-4.22 (m, 2H), 4.09 (q, J=7.1 Hz, 2H), 3.55-3.44 (m, 2H), 2.69 (s, 3H), 2.28 (s, 3H), 2.01 (s, 1H), 1.33 (d, J=34.9 Hz, 6H), 1.28-1.11 (m, 2H), 0.57-0.47 (m, 2H).

Step B: (R/S)-3-(3-(Difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)-2,2-dimethylpropanoic acid. Lithium iodide (342 mg, 2.56 mmol) was added to a solution of (R/S)-methyl 3-(3-(difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)-2,2-dimethylpropanoate (400 mg, 0.64 mmol) in pyridine (14 mL). The reaction mixture was heated at 150° C. for 6 hours. Concentrated to dryness under reduced pressure. The material was purified by flash column chromatography (eluent: 0-10% MeOH/DCM) to provide the title compound (342 mg, 83% yield). MS (ESI): mass calcd. for $C_{30}H_{31}F_2N_5O_5S$, 611.2; m/z found, 612.2 [M+H]$^+$. $^1$H NMR (500 MHz, CDCl$_3$) δ 9.58 (s, 1H), 8.41 (dd, J=4.9, 1.9 Hz, 1H), 8.25 (dd, J=7.7, 1.9 Hz, 1H), 8.14 (d, J=7.2 Hz, 1H), 7.38-7.22 (m, 2H), 7.22 (d, J=10.0 Hz, 1H), 7.15-7.05 (m, 2H), 4.78 (s, 1H), 4.29 (d, J=14.4 Hz, 1H), 4.24 (d, J=14.3 Hz, 1H), 4.09 (q, J=7.1 Hz, 2H), 3.50-3.41 (m, 1H), 2.62 (s, 3H), 2.28 (s, 3H), 1.39 (s, 3H), 1.32 (s, 3H), 1.05 (s, 2H), 0.45 (s, 2H).

Example 567: (*S)-3-(3-(Difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)-2,2-dimethylpropanoic Acid

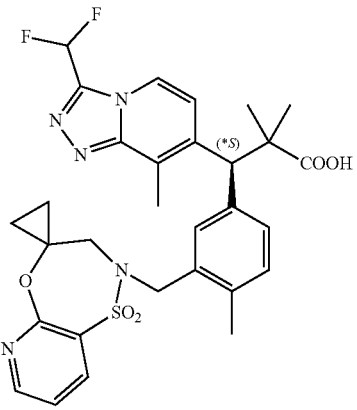 [SMILES: Cc1ccc([C@@H](c2ccn3c(C(F)F)nnc3c2C)C(C)(C)C(=O)O)cc1CN1CC2(CC2)Oc2ncccc2S1(=O)=O]

The mixture of (R/S)-3-(3-(Difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)-2,2-dimethylpropanoic acid isomers (Example 566, 317 mg) was separated by chiral SFC (stationary phase: CHIRALPAK AD-H 5 μm 250*30 mm, Mobile phase: 65% CO$_2$, 35% iPrOH) to afford two diastereomers. The first eluting isomer (129 mg, 33%) was designated (*S): MS: mass calcd. for $C_{30}H_{31}F_2N_5O_5S$, 611.2; m/z found, 612.2 [M+H]$^+$. $^1$H NMR (600 MHz, CDCl$_3$) δ 8.46 (dd, J=4.9, 1.9 Hz, 1H), 8.30 (dd, J=7.6, 2.0 Hz, 1H), 8.17 (d, J=7.3 Hz, 1H), 7.33 (dd, J=7.7, 4.8 Hz, 1H), 7.26-7.22 (m, 1H), 7.16 (s, 1H), 7.12 (d, J=1.2 Hz, 2H), 4.81 (s, 1H), 4.36-4.27 (m, 2H), 3.55 (d, J=15.5 Hz, 1H), 3.46 (d, J=15.6 Hz, 1H), 2.70 (s, 3H), 2.31 (s, 3H), 1.42 (s, 3H), 1.37 (s, 3H), 1.22 (d, J=6.1 Hz, 1H), 1.12 (dt, J=10.0, 5.4 Hz, 1H), 1.05 (dt, J=12.2, 5.4 Hz, 1H), 1.03-0.94 (m, 1H), 0.55-0.48 (m, 2H).

Example 568: (*R)-3-(3-(Difluoromethyl)-8-methyl-[1,2,4]triazolo[4,3-a]pyridin-7-yl)-3-(3-((1',1'-dioxidospiro[cyclopropane-1,4'-pyrido[2,3-b][1,4,5]oxathiazepin]-2'(3'H)-yl)methyl)-4-methylphenyl)-2,2-dimethylpropanoic Acid

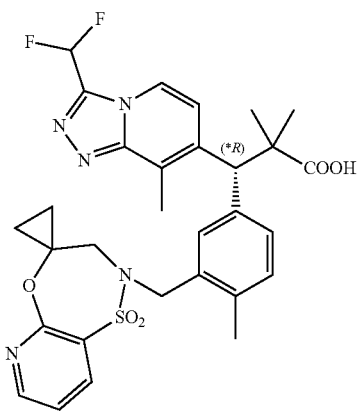 [SMILES: Cc1ccc([C@H](c2ccn3c(C(F)F)nnc3c2C)C(C)(C)C(=O)O)cc1CN1CC2(CC2)Oc2ncccc2S1(=O)=O]

The second eluting isomer (128 mg, 33%) from the chiral separation described in Example 567 was designated (*R): MS: mass calcd. for $C_{30}H_{31}F_2N_5O_5S$, 611.2; m/z found, 612.2 [M+H]+. $^1$H NMR (600 MHz, CDCl$_3$) δ 8.38 (dd, J=4.9, 2.0 Hz, 1H), 8.22 (dd, J=7.6, 2.0 Hz, 1H), 8.09 (d, J=7.3 Hz, 1H), 7.24 (dd, J=7.6, 4.9 Hz, 1H), 7.19-7.13 (m, 2H), 7.07 (d, J=3.1 Hz, 1H), 7.03 (d, J=1.3 Hz, 1H), 4.72 (s, 1H), 4.28-4.18 (m, 2H), 3.47 (d, J=15.3 Hz, 1H), 2.61 (s, 3H), 2.23 (s, 3H), 1.33-1.29 (m, 6H), 1.13 (d, J=6.1 Hz, 3H), 1.04 (dt, J=8.9, 4.9 Hz, 1H), 1.03-0.94 (m, 1H), 0.48-0.38 (m, 2H).

Example 569: (R/S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethyl-3-(8-methyl-3-(trifluoromethyl)-[1,2,4]triazolo[4,3-a]pyridin-7-yl)propanoic Acid

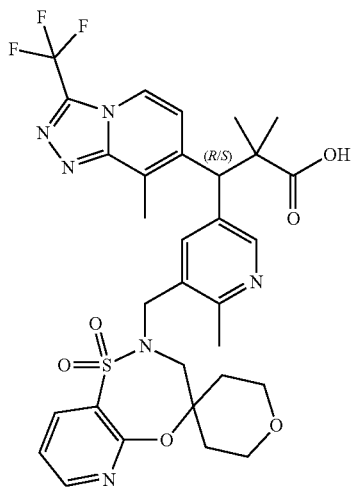 [SMILES: Cc1ncc(C(c2ccn3c(C(F)(F)F)nnc3c2C)C(C)(C)C(=O)O)cc1CN1CC2(CCOCC2)Oc2ncccc2S1(=O)=O]

Step A: (R/S)-Methyl 3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethyl-3-(8-methyl-3-(trifluoromethyl)-[1,2,4]triazolo[4,3-a]pyridin-7-yl)propanoate. Methyl 3-(5-(hydroxymethyl)-6-methylpyridin-3-yl)-2,2-dimethyl-3-(8-methyl-3-(trifluoromethyl)-[1,2,4]triazolo[4,3-a]pyridin-7-yl) propanoate (Intermediate 169, 200 mg, 0.46 mmol), 2,2',3,3',5,6-hexahydrospiro[pyran-4,4'-pyrido[2,3-b][1,4,5]oxathiazepine] 1',1'-dioxide (Intermediate 36, 153 mg, 0.57 mmol), and triphenylphosphine (192 mg, 0.73 mmol) in THF (8 mL) was stirred at room temperature for 5 minutes. DBAD (169 mg, 0.73 mmol) was added and the solution was stirred at room temperature for 30 minutes. The reaction was then concentrated under a stream of nitrogen and purified by flash column chromatography (eluent: 0-100% ethyl acetate/hexanes) to afford the title compound (250 mg, 79% yield). MS (ESI): mass calcd. for $C_{32}H_{35}F_3N_6O_6S$, 688.2; m/z found, 689.2 [M+H]+. $^1$H NMR (400 MHz, CDCl$_3$) δ 8.55-8.51 (m, 1H), 8.36 (dd, J=12.6, 2.2 Hz, 1H), 8.25-8.16 (m, 1H), 8.08 (d, J=7.3 Hz, 1H), 7.74 (d, J=2.2 Hz, 1H), 7.36-7.18 (m, 2H), 4.79 (s, 1H), 4.64-4.48 (m, 1H), 4.45 (d, J=16.3 Hz, 1H), 4.18-4.00 (m, 2H), 3.77-3.64 (m, 3H), 3.65 (s, 3H), 3.49 (d, J=15.3 Hz, 1H), 2.80 (s, 3H), 2.45 (s, 3H), 1.84-1.51 (m, 4H), 1.41 (d, J=18.7 Hz, 6H).

Step B: (R/S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethyl-3-(8-methyl-3-(trifluoromethyl)-[1,2,4]triazolo[4,3-a]pyridin-7-yl)propanoic acid. Lithium hydroxide (59 mg, 2.4 mmol) was added to a solution of (R/S)-methyl 3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethyl-3-(8-methyl-3-(trifluoromethyl)-[1,2,4]triazolo[4,3-a]pyridin-7-yl)propanoate (250 mg, 0.36 mmol) in MeOH (13 mL) and water (12 mL). The reaction was stirred at 75° C. overnight then allowed to cool to room temperature. 1 M aqueous HCl solution was added until the pH was 4. DCM was added and the resulting biphasic mixture was separated. The aqueous layer was extracted with DCM. These extractions resulted in several organic solvent fractions which were combined, dried over MgSO$_4$, filtered, and concentrated to dryness under reduced pressure. The material was purified by flash column chromatography (eluent: 0-10% MeOH/DCM) to provide the title compound to provide the title compound (190 mg, 78% yield). MS (ESI): mass calcd. for $C_{31}H_{33}F_3N_6O_6S$, 674.2; m/z found, 675.1 [M+H]+. $^1$H NMR (400 MHz, CDCl$_3$) δ 8.48-8.39 (m, 2H), 8.12-7.97 (m, 2H), 7.74 (d, J=2.2 Hz, 1H), 7.33 (d, J=7.4 Hz, 1H), 7.24-7.16 (m, 1H), 4.90 (s, 1H), 4.45 (d, J=16.3 Hz, 1H), 4.36 (d, J=16.3 Hz, 1H), 4.06-3.90 (m, 2H), 3.63-3.54 (m, 2H), 3.40 (s, 3H), 2.76 (s, 3H), 2.37 (s, 3H), 1.65-1.51 (m, 2H), 1.58-1.40 (m, 2H), 1.38 (s, 3H), 1.31 (s, 3H).

Example 570: (*S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethyl-3-(8-methyl-3-(trifluoromethyl)-[1,2,4]triazolo[4,3-a]pyridin-7-yl)propanoic Acid

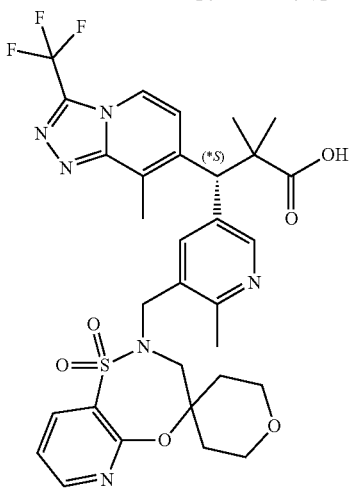 [SMILES: Cc1ncc([C@H](c2ccn3c(C(F)(F)F)nnc3c2C)C(C)(C)C(=O)O)cc1CN1CC2(CCOCC2)Oc2ncccc2S1(=O)=O]

The mixture of (R/S)-3-(5-((1',1'-Dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethyl-3-(8-methyl-3-(trifluoromethyl)-[1,2,4]triazolo[4,3-a]pyridin-7-yl)propanoic acid isomers (184 mg) was separated by chiral SFC (stationary phase: Chiralpak IC 5 μm 250*21.2 mm, Mobile phase: 70% $CO_2$, 30% MeOH(0.3% iPrNH$_2$)) to afford two diastereomers. The first eluting isomer (77 mg, 29%) was designated (*S): MS: mass calcd. for $C_{31}H_{33}F_3N_6O_6S$, 674.2; m/z found, 675.1 [M+H]$^+$. $^1$H NMR (600 MHz, CDCl$_3$) δ 8.52 (dd, J=4.9, 2.0 Hz, 1H), 8.32 (d, J=2.2 Hz, 1H), 8.17 (dd, J=7.6, 2.0 Hz, 1H), 8.01 (d, J=7.2 Hz, 1H), 7.73 (d, J=2.3 Hz, 1H), 7.31-7.23 (m, 2H), 4.94 (s, 1H), 4.57 (d, J=15.8 Hz, 1H), 4.35 (d, J=15.8 Hz, 1H), 4.17-4.00 (m, 2H), 3.73-3.65 (m, 2H), 3.57 (s, 2H), 3.46 (s, 2H), 3.23-3.17 (m, 1H), 2.80 (s, 3H), 2.42 (s, 3H), 1.67 (s, 2H), 1.64-1.52 (m, 1H), 1.29-1.25 (m, 5H).

Example 571 (*R)-3-(5-((1',1'-dioxido-2,3,5,6-tetrahydrospiro[pyran-4,4'-pyrido[2,3-b][1,4,5]oxathiazepin]-2'(3'H)-yl)methyl)-6-methylpyridin-3-yl)-2,2-dimethyl-3-(8-methyl-3-(trifluoromethyl)-[1,2,4]triazolo[4,3-a]pyridin-7-yl)propanoic Acid

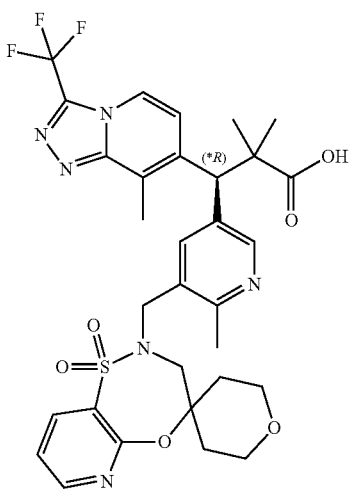 [SMILES: Cc1ncc([C@@H](c2ccn3c(C(F)(F)F)nnc3c2C)C(C)(C)C(=O)O)cc1CN1CC2(CCOCC2)Oc2ncccc2S1(=O)=O]

The second eluting isomer (90 mg, 34%) from the chiral separation described in Example 570 was designated (*R): MS: mass calcd. for $C_{31}H_{33}F_3N_6O_6S$, 674.2; m/z found, 675.1 [M+H]$^+$. $^1$H NMR (600 MHz, CDCl$_3$) δ 8.52 (dd, J=4.9, 2.0 Hz, 1H), 8.32 (d, J=2.2 Hz, 1H), 8.17 (dd, J=7.6, 2.0 Hz, 1H), 8.01 (d, J=7.2 Hz, 1H), 7.74 (d, J=2.2 Hz, 1H), 7.31-7.25 (m, 2H), 4.94 (s, 1H), 4.57 (d, J=15.9 Hz, 1H), 4.35 (d, J=15.9 Hz, 1H), 4.17-4.00 (m, 2H), 3.73-3.65 (m, 2H), 3.57 (s, 1H), 3.50 (s, 1H), 2.79 (s, 3H), 2.42 (s, 3H), 1.71-1.60 (m, 3H), 1.66-1.50 (m, 1H), 1.30 (s, 3H), 1.27-1.20 (m, 4H).

Example 572: (R/S)-2,2-Dimethyl-3-(8-methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-ethylethyl)pyridin-3-yl)propanoic Acid

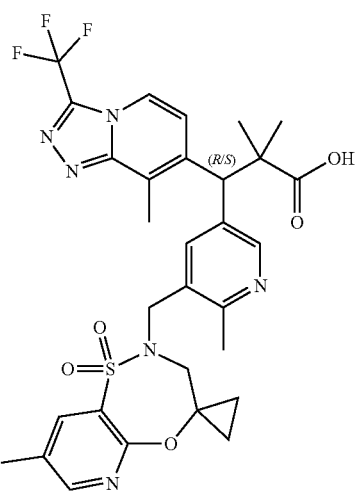 [SMILES: Cc1cnc2c(c1)S(=O)(=O)N(Cc1cc(C(c3ccn4c(C(F)(F)F)nnc4c3C)C(C)(C)C(=O)O)cnc1C)CC1(CC1)O2]

Step A: (R/S)-Methyl 2,2-dimethyl-3-(8-methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoate. Methyl 3-(5-(hydroxymethyl)-6-methylpyridin-3-yl)-2,2-dimethyl-3-(8-methyl-3-(trifluoromethyl)-[1,2,4]triazolo[4,3-a]pyridin-7-yl)propanoate (Intermediate 169, 200 mg, 0.46 mmol), 8'-methyl-2',3'-dihydrospiro[cyclopropane-1,4'-pyrido[2,3-b][1,4,5]oxathiazepine] 1',1'-dioxide (Intermediate 6, 136 mg, 0.57 mmol), and triphenylphosphine (192 mg, 0.73 mmol) in THF (8 mL) was stirred at room temperature for 5 minutes. DBAD (169 mg, 0.73 mmol) was added and the solution was stirred at room temperature for 30 minutes. The reaction was then concentrated under a stream of nitrogen and purified by flash column chromatography (eluent: 0-100% ethyl acetate/hexanes) to afford the title compound (200 mg, 66% yield). MS (ESI): mass calcd. for $C_{31}H_{33}F_3N_6O_5S$, 658.2; m/z found, 659.2 [M+H]$^+$. $^1$H NMR (400 MHz, CDCl$_3$) δ 8.31-8.22 (m, 1H), 8.23-8.16 (m, 1H), 8.03-7.91 (m, 2H), 7.54 (d, J=2.4 Hz, 1H), 7.10 (d, J=7.4 Hz, 1H), 4.68 (s, 1H), 4.34-4.24 (m, 1H), 4.21 (d, J=15.5 Hz, 1H), 3.57 (s, 2H), 3.57 (d, J=18.9 Hz, 1H), 3.50 (d, J=11.5 Hz, 1H), 2.88 (s, 1H), 2.82-2.77 (m, 1H), 2.70 (s, 2H), 2.42 (d, J=17.0 Hz, 3H), 2.34 (d, J=0.9 Hz, 3H), 1.38 (s, 1H), 1.30 (d, J=19.0 Hz, 5H), 1.26-1.10 (m, 2H), 0.63-0.56 (m, 2H).

Step B: (R/S)-2,2-Dimethyl-3-(8-methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic acid. Lithium hydroxide (49 mg, 2.0 mmol) was added to a solution of (R/S)-methyl 2,2-dimethyl-3-(8-methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoate (200 mg, 0.30 mmol) in MeOH (20 mL) and water (10 mL). The reaction was stirred at 75° C. overnight then allowed to cool to room temperature. 1 M aqueous HCl solution was added until the pH was 4. DCM was added and the resulting biphasic mixture was separated. The aqueous layer was extracted with DCM. These extractions resulted in several organic solvent fractions which were combined, dried over MgSO₄, filtered, and concentrated to dryness under reduced pressure. The material was purified by flash column chromatography (eluent: 0-10% MeOH/DCM) to provide the title compound to provide the title compound (150 mg, 77% yield). MS (ESI): mass calcd. for $C_{30}H_{31}F_3N_6O_5S$, 644.2; m/z found, 645.1 $[M+H]^+$. $^1$H NMR (400 MHz, CDCl₃) δ 8.51 (d, J=2.2 Hz, 1H), 8.27 (dd, J=2.5, 0.9 Hz, 1H), 8.13 (d, J=7.3 Hz, 1H), 8.06 (dd, J=2.5, 0.8 Hz, 1H), 7.73 (d, J=2.2 Hz, 1H), 7.38 (d, J=7.3 Hz, 1H), 4.94 (s, 1H), 4.38 (d, J=15.7 Hz, 1H), 4.29 (d, J=15.6 Hz, 1H), 3.56 (s, 2H), 2.84 (s, 3H), 2.51 (s, 3H), 2.42 (s, 3H), 1.44-1.38 (m, 6H), 1.26 (d, J=12.6 Hz, 1H), 1.20 (s, 2H), 0.68-0.60 (m, 2H).

Example 573: (*S)-2,2-Dimethyl-3-(8-methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic Acid

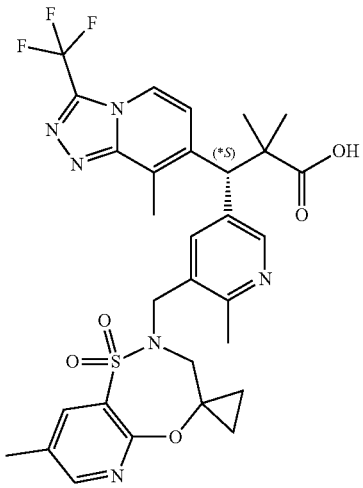 [SMILES: Cc1cnc2c(c1)S(=O)(=O)N(Cc1cc([C@H](c3ccn4c(C(F)(F)F)nnc4c3C)C(C)(C)C(=O)O)cnc1C)CC1(CC1)O2]

The mixture of (R/S)-2,2-Dimethyl-3-(8-methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic acid isomers (Example 572, 144 mg) was separated by chiral SFC (stationary phase: Chiralpak IC 5 μm 250*21.2 mm, Mobile phase: 60% CO₂, 40% MeOH) to afford two enantiomers. The first eluting isomer (41 mg, 21%) was designated (*S): MS: mass calcd. for $C_{30}H_{31}F_3N_6O_5S$, 644.2; m/z found, 645.1 $[M+H]^+$. $^1$H NMR (600 MHz, CDCl₃) δ 8.49-8.45 (m, 1H), 8.26 (d, J=2.4 Hz, 1H), 8.10 (d, J=7.2 Hz, 1H), 8.04 (d, J=2.4 Hz, 1H), 7.71 (d, J=2.1 Hz, 1H), 7.33 (d, J=7.4 Hz, 1H), 4.93 (s, 1H), 4.35 (d, J=15.7 Hz, 1H), 4.28 (d, J=15.7 Hz, 1H), 3.55 (s, 2H), 2.83 (s, 3H), 2.48 (s, 3H), 2.41 (s, 3H), 1.41 (s, 3H), 1.35 (s, 3H), 1.29-1.22 (m, 1H), 1.23-1.16 (m, 2H), 0.61 (q, J=3.2, 2.7 Hz, 2H).

Example 574: (*R)-2,2-Dimethyl-3-(8-methyl-3-(trifluoromethyl)-[1,2,4]triazolo[4,3-a]pyridin-7-yl)-3-(6-methyl-5-((8'-methyl-1',1'-dioxidospiro[cyclopropane-1,4'-pyrido[2,3-b][1,4,5]oxathiazepin]-2'(3'H)-yl)methyl)pyridin-3-yl)propanoic Acid

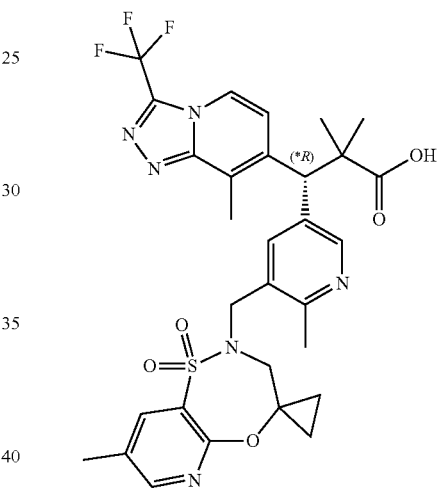

The second eluting isomer (40 mg, 20%) from the chiral separation described in Example 573 was designated (*R): MS: mass calcd. for $C_{30}H_{31}F_3N_6O_5S$, 644.2; m/z found, 645.1 $[M+H]^+$. $^1$H NMR (600 MHz, CDCl₃) δ 8.47 (s, 1H), 8.26 (d, J=2.4 Hz, 1H), 8.10 (d, J=7.2 Hz, 1H), 8.04 (d, J=2.3 Hz, 1H), 7.71 (s, 1H), 7.32 (d, J=7.4 Hz, 1H), 4.93 (s, 1H), 4.35 (d, J=15.6 Hz, 1H), 4.28 (d, J=15.7 Hz, 1H), 3.55 (s, 2H), 2.83 (s, 3H), 2.48 (s, 3H), 2.41 (s, 3H), 1.41 (s, 3H), 1.34 (s, 3H), 1.26 (d, J=6.8 Hz, 1H), 1.27-1.16 (m, 2H), 0.66-0.60 (m, 2H).

Example 575: (R/S)-3-(3-(Difluoromethyl)-8-methyl-[1,2,4]triazolo[4,3-a]pyridin-7-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoic Acid

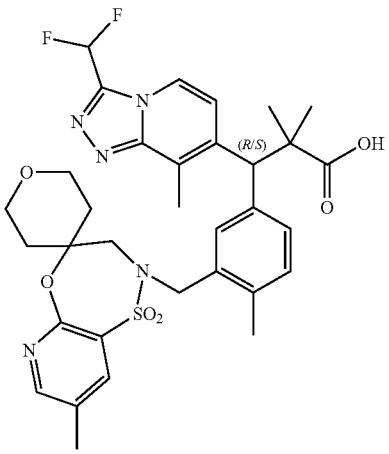 [SMILES: Cc1cnc2c(c1)S(=O)(=O)N(Cc1cc(C(c3ccn4c(C(F)F)nnc4c3C)C(C)(C)C(=O)O)ccc1C)CC1(CCOCC1)O2]

Step A: (R/S)-Methyl 3-(3-(difluoromethyl)-8-methyl-[1,2,4]triazolo[4,3-a]pyridin-7-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoate. A solution of methyl 3-(3-(difluoromethyl)-8-methyl-[1,2,4]triazolo[4,3-a]pyridin-7-yl)-3-(3-(hydroxymethyl)-4-methylphenyl)-2,2-dimethylpropanoate (Intermediate 49, 500 mg, 1.20 mmol), 8'-methyl-2,2',3,3',5,6-hexahydrospiro[pyran-4,4'-pyrido[2,3-b][1,4,5]oxathiazepine] 1',1'-dioxide (Intermediate 37, 430 mg, 1.51 mmol), and triphenylphosphine (466 mg, 1.78 mmol) in THF (33 mL) and DMF (3 ml) was stirred at room temperature for 5 minutes. DBAD (454 mg, 2.0 mmol) was added and the solution was stirred at room temperature for 30 minutes. The reaction was then concentrated under a stream of nitrogen and purified by flash column chromatography (eluent: 0-100% ethyl acetate/hexanes) to afford the title compound (800 mg, 98% yield). MS (ESI): mass calcd. for $C_{34}H_{39}F_2N_5O_6S$, 683.3; m/z found, 684.3 [M+H]$^+$. $^1$H NMR (500 MHz, CDCl$_3$) 8.28 (dd, J=2.4, 0.9 Hz, 1H), 8.17 (d, J=7.3 Hz, 1H), 8.03-7.97 (m, 1H), 7.72-7.63 (m, 2H), 7.59-7.51 (m, 1H), 7.50-7.42 (m, 2H), 7.27-7.19 (m, 1H), 7.18-7.07 (m, 1H), 4.81 (s, 1H), 4.51 (d, J=15.2 Hz, 1H), 4.44 (d, J=15.3 Hz, 1H), 4.03 (td, J=11.6, 2.2 Hz, 1H), 3.61 (s, 3H), 3.50 (s, 2H), 3.47-3.42 (m, 1H), 2.95 (s, 3H), 2.88 (s, 3H), 2.77 (s, 2H), 2.39 (s, 3H), 1.72-1.62 (m, 1H), 1.53-1.43 (m, 1H), 1.43 (s, 3H), 1.37 (s, 3H).

Step B: (R/S)-3-(3-(Difluoromethyl)-8-methyl-[1,2,4]triazolo[4,3-a]pyridin-7-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoic acid. Lithium hydroxide (170 mg, 4.06 mmol) was added to a solution of methyl (R/S)-methyl 3-(3-(difluoromethyl)-8-methyl-[1,2,4]triazolo[4,3-a]pyridin-7-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoate (800 mg, 1.02 mmol) in MeOH (7 mL) and water (4 mL). The reaction was stirred at 75° C. overnight then allowed to cool to room temperature. 1 M aqueous HCl solution was added until the pH was 4. DCM was added and the resulting biphasic mixture was separated. The aqueous layer was extracted with DCM. These extractions resulted in several organic solvent fractions which were combined, dried over MgSO$_4$, filtered, and concentrated to dryness under reduced pressure. The material was purified by flash column chromatography (eluent: 0-10% MeOH/DCM) to provide the title compound to provide the title compound (680 mg, 99% yield). MS (ESI): mass calcd. for $C_{33}H_{37}F_2N_5O_6S$, 669.2; m/z found, 670.3 [M+H]$^+$. $^1$H NMR (400 MHz, CDCl$_3$) δ 8.28 (t, J=1.5 Hz, 1H), 8.15 (d, J=7.2 Hz, 1H), 8.00 (d, J=2.4 Hz, 1H), 7.30-7.19 (m, 2H), 7.17 (dd, J=7.9, 1.9 Hz, 1H), 7.13-7.06 (m, 2H), 4.86 (s, 1H), 4.54-4.41 (m, 2H), 4.01-3.86 (m, 2H), 3.66-3.51 (m, 2H), 3.46 (s, 2H), 2.73 (s, 3H), 2.39 (s, 3H), 2.23 (s, 3H), 2.04 (s, 2H), 1.64-1.50 (m, 2H), 1.44 (s, 3H), 1.36 (s, 3H).

Example 576: (*S)-3-(3-(Difluoromethyl)-8-methyl-[1,2,4]triazolo[4,3-a]pyridin-7-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoic Acid

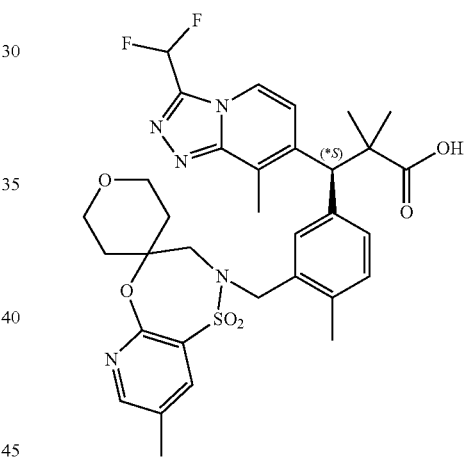

The mixture of (R/S)-3-(3-(difluoromethyl)-8-methyl-[1,2,4]triazolo[4,3-a]pyridin-7-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoic acid isomers (Example 575, 675 mg) was separated by chiral SFC (stationary phase: Chiralpak IC, 5 μm, 150×30 mm, Mobile phase: 35% ethanol, 65% CO$_2$) to afford two diastereomers. The first eluting isomer (275 mg, 40%) was designated (*S): MS: mass calcd. for $C_{33}H_{37}F_2N_5O_6S$, 669.2; m/z found, 670.3 [M+H]$^+$. $^1$H NMR (600 MHz, CDCl$_3$) δ 8.30-8.26 (m, 1H), 8.14 (d, J=7.4 Hz, 1H), 8.01 (d, J=2.4 Hz, 1H), 7.25-7.22 (m, 1H), 7.22-7.07 (m, 4H), 4.87 (s, 1H), 4.53 (d, J=14.5 Hz, 1H), 4.44 (d, J=14.5 Hz, 1H), 4.04-3.93 (m, 2H), 3.72 (q, J=7.0 Hz, 2H), 3.69-3.64 (m, 1H), 3.64-3.58 (m, 1H), 3.48 (s, 2H), 2.76 (s, 3H), 2.39 (s, 3H), 2.24 (s, 3H), 1.63-1.50 (m, 2H), 1.44 (s, 3H), 1.35 (s, 3H).

Example 577: (*R)-3-(3-(Difluoromethyl)-8-methyl-[1,2,4]triazolo[4,3-a]pyridin-7-yl)-2,2-dimethyl-3-(4-methyl-3-((8'-methyl-1',1'-dioxido-2,3,5,6-tetrahydrospiro[pyran-4,4'-pyrido[2,3-b][1,4,5]oxathiazepin]-2'(3'H)-yl)methyl)phenyl)propanoic Acid

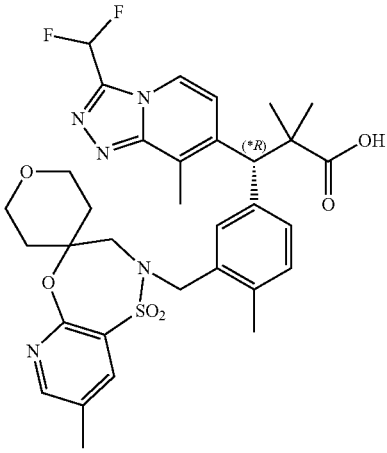 [SMILES: Cc1cnc2c(c1)S(=O)(=O)N(Cc1cc([C@H](c3ccn4c(C(F)F)nnc4c3C)C(C)(C)C(=O)O)ccc1C)CC1(CCOCC1)O2]

The second eluting isomer (260 mg, 38%) from the chiral separation described in Example 576 was designated (*R): MS: mass calcd. for $C_{33}H_{37}F_2N_5O_6S$, 669.2; m/z found, 670.3 [M+H]$^+$. $^1$H NMR (600 MHz, CDCl$_3$) δ 8.28 (d, J=2.6 Hz, 1H), 8.14 (d, J=7.2 Hz, 1H), 8.01 (d, J=2.4 Hz, 1H), 7.23 (s, 1H), 7.22-7.10 (m, 3H), 7.09 (d, J=7.9 Hz, 1H), 4.87 (s, 1H), 4.52 (d, J=14.4 Hz, 1H), 4.45 (d, J=14.5 Hz, 1H), 3.98 (dt, J=21.4, 11.7 Hz, 2H), 3.76-3.59 (m, 4H), 3.48 (s, 2H), 2.76 (s, 3H), 2.39 (s, 3H), 2.24 (s, 3H), 1.60 (d, J=13.9 Hz, 2H), 1.44 (s, 3H), 1.35 (s, 3H).

Example 578: 3-(3-(Difluoromethyl)-8-methyl-[1,2,4]triazolo[4,3-a]pyridin-7-yl)-2,2-dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)propanoic Acid

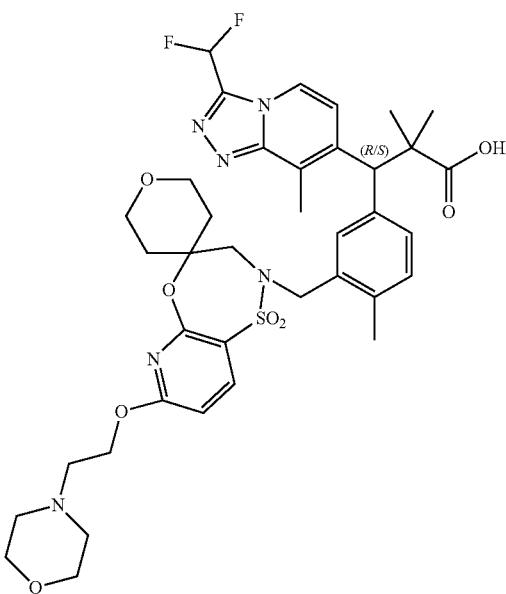 [SMILES: Cc1ccc(C(c2ccn3c(C(F)F)nnc3c2C)C(C)(C)C(=O)O)cc1CN1CC2(CCOCC2)Oc2nc(OCCN3CCOCC3)ccc2S1(=O)=O]

Step A: Methyl (S)-3-(3-(difluoromethyl)-8-methyl-[1,2,4]triazolo[4,3-a]pyridin-7-yl)-2,2-dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)propanoate. A solution of methyl 3-(3-(difluoromethyl)-8-methyl-[1,2,4]triazolo[4,3-a]pyridin-7-yl)-3-(3-(hydroxymethyl)-4-methylphenyl)-2,2-dimethylpropanoate (Intermediate 49, 600 mg, 1.44 mmol), 7'-(2-morpholinoethoxy)-2,2',3,3',5,6-hexahydrospiro[pyran-4,4'-pyrido[2,3-b][1,4,5]oxathiazepine] 1',1'-dioxide (Intermediate 146, 810 mg, 2.02 mmol), and triphenylphosphine (641 mg, 2.40 mmol) in THF (16 mL) and DMF (1 ml) was stirred at room temperature for 5 minutes. DBAD (553 mg, 2.40 mmol) was added and the solution was stirred at room temperature for 30 minutes. The reaction was then concentrated under a stream of nitrogen and purified by flash column chromatography (eluent: 0-100% ethyl acetate/hexanes) to afford the title compound (1.1 g, 96% yield). MS (ESI): mass calcd. for $C_{39}H_{48}F_2N_6O_8S$, 798.3; m/z found, 799.3 [M+H]$^+$. $^1$H NMR (500 MHz, CDCl$_3$) δ 8.17 (d, J=7.3 Hz, 1H), 8.04 (d, J=8.4 Hz, 1H), 7.23-7.19 (m, 1H), 7.17-7.08 (m, 3H), 6.64 (d, J=8.4 Hz, 1H), 5.30 (s, 1H), 4.81 (s, 1H), 4.47 (t, J=5.7 Hz, 3H), 4.40 (d, J=15.0 Hz, 1H), 4.05-3.95 (m, 2H), 3.77-3.71 (m, 4H), 3.62 (td, J=13.0, 4.6 Hz, 2H), 3.61 (s, 3H), 3.45 (s, 1H), 3.40 (s, 1H), 2.82-2.74 (m, 5H), 2.60-2.54 (m, 4H), 2.25 (s, 3H), 1.74-1.63 (m, 2H), 1.49-1.38 (m, 1H), 1.43 (s, 3H), 1.36 (s, 3H).

Step B: 3-(3-(Difluoromethyl)-8-methyl-[1,2,4]triazolo[4,3-a]pyridin-7-yl)-2,2-dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)propanoic acid. Lithium hydroxide (289 mg, 6.88 mmol) was added to a solution of methyl (R/S)-methyl 3-(3-(Difluoromethyl)-8-methyl-[1,2,4]triazolo[4,3-a]pyridin-7-yl)-2,2-dimethyl-3-(4-methyl-3-((8'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)propanoate (1100 mg, 1.38 mmol) in MeOH (9 mL) and water (6 mL). The reaction was stirred at 75° C. overnight then allowed to cool to room temperature. 1 M aqueous HCl solution was added until the pH was 4. DCM was added and the resulting biphasic mixture was separated. The aqueous layer was extracted with DCM. These extractions resulted in several organic solvent fractions which were combined, dried over MgSO$_4$, filtered, and concentrated to dryness under reduced pressure. The material was purified by flash column chromatography (eluent: 0-10% MeOH/DCM) to provide the title compound to provide the title compound (600 mg, 56% yield). MS (ESI): mass calcd. for $C_{38}H_{46}F_2N_6O_8S$, 784.3; m/z found, 785.3 [M+H]$^+$. $^1$H NMR (500 MHz, CDCl$_3$) δ 8.14 (d, J=7.2 Hz, 1H), 8.07 (d, J=8.4 Hz, 1H), 7.24-7.19 (m, 1H), 7.18-7.06 (m, 3H), 6.64 (d, J=8.4 Hz, 1H), 4.84 (s, 1H), 4.75-4.69 (m, 2H), 4.51 (d, J=14.5 Hz, 1H), 4.37 (d, J=14.6 Hz, 1H), 3.97 (t, J=4.8 Hz, 4H), 3.95-3.86 (m, 2H), 3.70-3.59 (m, 2H), 3.46 (s, 10H), 3.40 (s, 2H), 2.74 (s, 3H), 2.24 (s, 3H), 1.62 (d, J=14.0 Hz, 2H), 1.42 (s, 3H), 1.33 (s, 3H).

Example 579: (*S)-3-(3-(Difluoromethyl)-8-methyl-[1,2,4]triazolo[4,3-a]pyridin-7-yl)-2,2-dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)propanoic Acid Example 580: (*R)-3-(3-(Difluoromethyl)-8-methyl-[1,2,4]triazolo[4,3-a]pyridin-7-yl)-2,2-dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)propanoic Acid

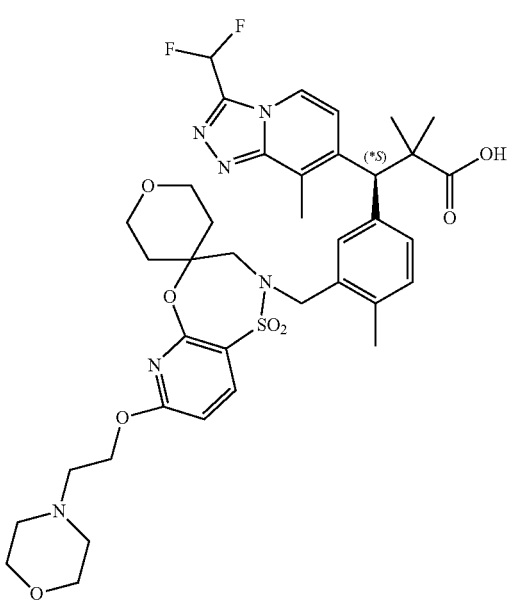 [SMILES: Cc1ccc([C@@H](c2ccn3c(C(F)F)nnc3c2C)C(C)(C)C(=O)O)cc1CN1CC2(CCOCC2)Oc2nc(OCCN3CCOCC3)ccc2S1(=O)=O]

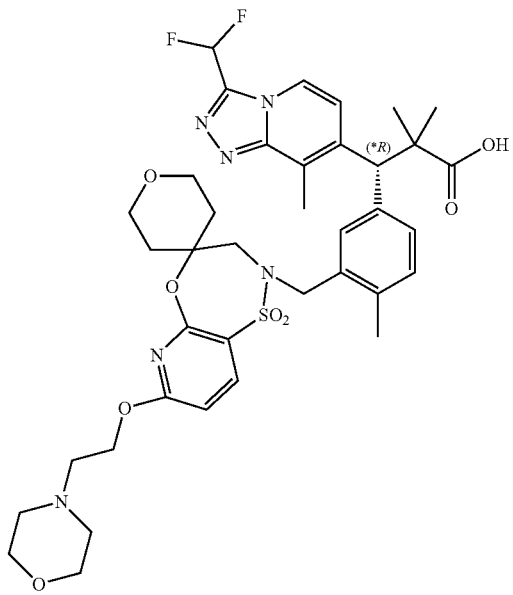 [SMILES: Cc1ccc([C@H](c2ccn3c(C(F)F)nnc3c2C)C(C)(C)C(=O)O)cc1CN1CC2(CCOCC2)Oc2nc(OCCN3CCOCC3)ccc2S1(=O)=O]

The second eluting isomer (260 mg, 24%) from the chiral separation described in Example 579 was designated (*R): MS: mass calcd. for $C_{38}H_{46}F_2N_6O_8S$, 784.3; m/z found, 785.3 [M+H]$^+$. $^1$H NMR (600 MHz, CDCl$_3$) δ 8.14 (d, J=7.3 Hz, 1H), 8.03 (d, J=8.4 Hz, 1H), 7.29 (s, 1H), 7.25-7.13 (m, 3H), 7.13-7.06 (m, 1H), 6.60 (d, J=8.4 Hz, 1H), 4.86 (s, 1H), 4.45 (td, J=5.7, 3.3 Hz, 4H), 4.00-3.90 (m, 2H), 3.71-3.66 (m, 5H), 3.62 (d, J=10.7 Hz, 1H), 3.44 (s, 2H), 2.82-2.75 (m, 5H), 2.58 (t, J=4.7 Hz, 4H), 2.23 (s, 3H), 2.00 (s, 3H), 1.63 (d, J=14.0 Hz, 1H), 1.55-1.48 (m, 1H), 1.42 (s, 3H), 1.32 (s, 3H).

Example 581: 3-(3-(difluoromethyl)-8-methyl-[1,2,4]triazolo[4,3-a]pyridin-7-yl)-3-(3-((7'-methoxy-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic Acid

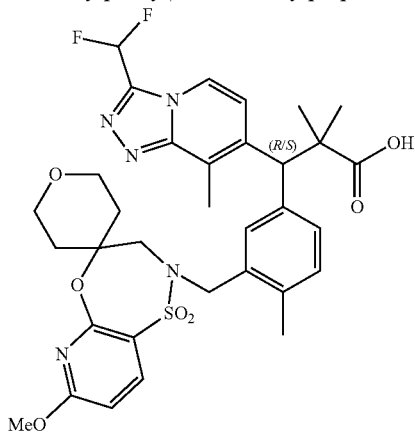

The mixture of 3-(3-(difluoromethyl)-8-methyl-[1,2,4]triazolo[4,3-a]pyridin-7-yl)-2,2-dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)propanoic acid isomers (Example 578, 675 mg) was separated by chiral SFC (stationary phase: IG (2×25 cm). Mobile phase: 30% ethanol, 70% CO$_2$) to afford two enantiomers. The first eluting isomer (277 mg, 26%) was designated (*S): MS: mass calcd. for $C_{38}H_{46}F_2N_6O_8S$, 784.3; m/z found, 785.3 [M+H]$^+$. $^1$H NMR (600 MHz, CDCl$_3$) δ 8.15 (d, J=7.2 Hz, 1H), 8.03 (d, J=8.4 Hz, 1H), 7.26 (s, 1H), 7.23-7.15 (m, 3H), 7.10 (t, J=8.0 Hz, 1H), 6.60 (d, J=8.4 Hz, 1H), 4.86 (s, 1H), 4.51-4.40 (m, 4H), 4.00-3.90 (m, 2H), 3.68 (t, J=4.7 Hz, 5H), 3.61 (d, J=11.1 Hz, 1H), 3.44 (s, 2H), 2.82-2.75 (m, 5H), 2.59 (t, J=4.7 Hz, 4H), 2.24 (s, 3H), 2.00 (s, 3H), 1.63 (d, J=14.0 Hz, 1H), 1.51 (d, J=12.1 Hz, 1H), 1.44 (s, 3H), 1.34 (s, 3H).

Step A: Methyl (S)-3-(3-(difluoromethyl)-8-methyl-[1,2,4]triazolo[4,3-a]pyridin-7-yl)-2,2-dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)propanoate. A solution of methyl 3-(3-(difluoromethyl)-8-methyl-[1,2,4]triazolo[4,3-a]pyridin-7-yl)-3-(3-(hydroxymethyl)-4-methylphenyl)-2,2-dimethylpropanoate (Intermediate 49, 600 mg, 1.44 mmol), 7'-(2-morpholinoethoxy)-2,2',3,3',5,6-hexahydrospiro[pyran-4,4'-pyrido[2,3-b][1,4,5]oxathiazepine] 1',1'-dioxide (Intermediate 146, 810 mg, 2.02 mmol), and triphenylphosphine (641 mg, 2.40 mmol) in THF (16 mL) and DMF (1 ml) was stirred at room temperature for 5 minutes. DBAD (553 mg, 2.40 mmol) was added and the solution was stirred at room temperature for 30 minutes. The reaction was then concentrated under a stream of nitrogen and purified by flash column chromatography (eluent: 0-100% ethyl acetate/hexanes) to afford the title compound (1.1 g, 96% yield). MS (ESI): mass calcd. for $C_{39}H_{48}F_2N_6O_8S$, 798.3; m/z found, 799.3 [M+H]$^+$. $^1$H NMR (500 MHz, CDCl$_3$) δ 8.17 (d, J=7.3 Hz, 1H), 8.04 (d, J=8.4 Hz, 1H), 7.23-7.19 (m, 1H), 7.17-7.08 (m, 3H), 6.64 (d, J=8.4 Hz, 1H), 5.30 (s, 1H), 4.81 (s, 1H), 4.47 (t, J=5.7 Hz, 3H), 4.40 (d, J=15.0 Hz, 1H), 4.05-3.95 (m, 2H), 3.77-3.71 (m, 4H), 3.62 (td, J=13.0, 4.6 Hz, 2H), 3.61 (s, 3H), 3.45 (s, 1H), 3.40 (s, 1H), 2.82-2.74 (m, 5H), 2.60-2.54 (m, 4H), 2.25 (s, 3H), 1.74-1.63 (m, 2H), 1.49-1.38 (m, 1H), 1.43 (s, 3H), 1.36 (s, 3H).

Step B: (R/S)-3-(3-(Difluoromethyl)-8-methyl-[1,2,4]triazolo[4,3-a]pyridin-7-yl)-2,2-dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)propanoic acid. Lithium hydroxide (289 mg, 6.88 mmol) was added to a solution of methyl (R/S)-methyl 3-(3-(difluoromethyl)-8-methyl-[1,2,4]triazolo[4,3-a]pyridin-7-yl)-2,2-dimethyl-3-(4-methyl-3-((7'-(2-morpholinoethoxy)-1',1'-dioxido-2,3,5,6-tetrahydrospiro[pyran-4,4'-pyrido[2,3-b][1,4,5]oxathiazepin]-2'(3'H)-yl)methyl)phenyl)propanoate (1100 mg, 1.38 mmol) in MeOH (9 mL) and water (6 mL). The reaction was stirred at 75° C. overnight then allowed to cool to room temperature. 1 M aqueous HCl solution was added until the pH was 4. DCM was added and the resulting biphasic mixture was separated. The aqueous layer was extracted with DCM. These extractions resulted in several organic solvent fractions which were combined, dried over MgSO$_4$, filtered, and concentrated to dryness under reduced pressure. The material was purified by flash column chromatography (eluent: 0-10% MeOH/DCM) to provide the title compound to provide the title compound (420 mg, 44% yield). MS (ESI): mass calcd. for $C_{33}H_{37}F_2N_5O_7S$, 685.2.3; m/z found, 686.3 [M+H]$^+$. $^1$H NMR (500 MHz, CDCl$_3$) δ 9.71 (s, 1H), 8.16 (d, J=7.2 Hz, 1H), 8.00 (d, J=8.4 Hz, 1H), 7.28-7.19 (m, 2H), 7.15 (dd, J=8.0, 1.9 Hz, 1H), 7.09 (t, J=7.0 Hz, 1H), 6.59 (d, J=8.4 Hz, 1H), 5.28 (s, 1H), 4.84 (s, 1H), 4.50 (d, J=14.5 Hz, 1H), 4.49-4.38 (m, 2H), 4.04-3.92 (m, 5H), 3.65-3.53 (m, 2H), 3.43 (s, 2H), 2.66 (s, 3H), 2.23 (s, 3H), 1.65-1.56 (m, 2H), 1.45 (s, 1H), 1.43 (s, 3H), 1.35 (s, 3H).

Example 582: (*S)-3-(3-(Difluoromethyl)-8-methyl-[1,2,4]triazolo[4,3-a]pyridin-7-yl)-3-(3-((7'-methoxy-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic Acid

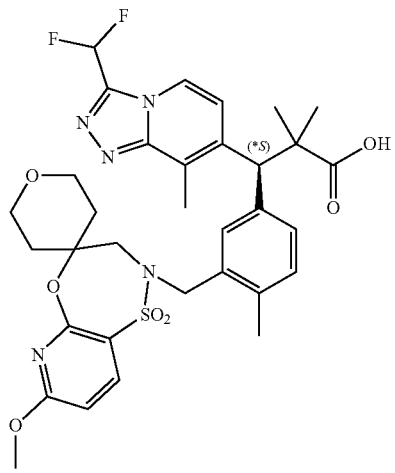 [SMILES: COc1ccc2c(n1)OC1(CCOCC1)CN(Cc1cc([C@@H](c3ccn4c(C(F)F)nnc4c3C)C(C)(C)C(=O)O)ccc1C)S2(=O)=O]

The mixture of: 3-(3-(difluoromethyl)-8-methyl-[1,2,4]triazolo[4,3-a]pyridin-7-yl)-3-(3-((7'-methoxy-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic acid isomers (420 mg) was separated by chiral SFC (stationary phase: IG (2×25 cm). Mobile phase: 30% ethanol, 70% CO$_2$) to afford two enantiomers. The first eluting isomer (199 mg, 21%) was designated (*S): MS: mass calcd. for $C_{33}H_{37}F_2N_5O_7S$, 685.2.3; m/z found, 686.3 [M+H]$^+$. $^1$H NMR (600 MHz, CDCl$_3$) δ 8.15 (d, J=7.3 Hz, 1H), 8.05 (d, J=8.5 Hz, 1H), 7.26-7.11 (m, 4H), 7.10 (d, J=7.9 Hz, 1H), 6.62 (d, J=8.5 Hz, 1H), 4.88 (s, 1H), 4.50 (d, J=14.5 Hz, 1H), 4.45 (d, J=14.5 Hz, 1H), 4.12-4.00 (m, 2H), 3.97 (s, 3H), 3.73 (q, J=7.0 Hz, 2H), 3.69-3.64 (m, 2H), 2.77 (s, 3H), 2.25 (s, 3H), 1.65 (d, J=14.1 Hz, 1H), 1.60 (d, J=14.3 Hz, 1H), 1.52 (s, 1H), 1.46 (s, 3H), 1.43 (d, J=11.3 Hz, 1H), 1.36 (s, 3H).

Example 583: (*R)-3-(3-(Difluoromethyl)-8-methyl-[1,2,4]triazolo[4,3-a]pyridin-7-yl)-3-(3-((7'-methoxy-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethylpropanoic Acid

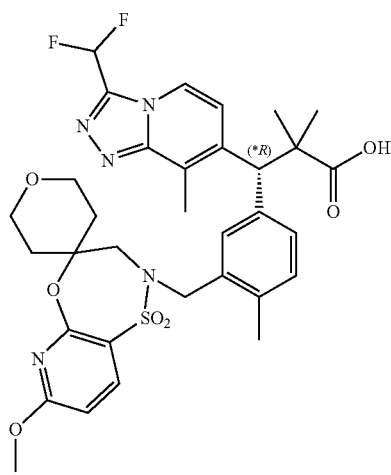 [SMILES: COc1ccc2c(n1)OC1(CCOCC1)CN(Cc1cc([C@H](c3ccn4c(C(F)F)nnc4c3C)C(C)(C)C(=O)O)ccc1C)S2(=O)=O]

The second eluting isomer (203 mg, 22%) from the chiral separation described in Example 582 was designated (*R): MS: mass calcd. for $C_{33}H_{37}F_2N_5O_7S$, 685.2.3; m/z found, 686.3 [M+H]+. 1H NMR (600 MHz, CDCl3) δ 8.16 (d, J=7.2 Hz, 1H), 8.04 (d, J=8.4 Hz, 1H), 7.24 (dd, J=7.8, 4.7 Hz, 2H), 7.16 (dd, J=7.9, 1.9 Hz, 1H), 7.10 (d, J=7.9 Hz, 1H), 6.62 (d, J=8.4 Hz, 1H), 5.31 (s, 1H), 4.88 (s, 1H), 4.52-4.42 (m, 2H), 4.07-3.99 (m, 2H), 3.97 (s, 3H), 3.72 (dd, J=15.1, 8.4 Hz, 1H), 3.65 (d, J=10.8 Hz, 1H), 3.47 (s, 2H), 2.76 (s, 3H), 2.25 (s, 3H), 1.65 (d, J=12.7 Hz, 2H), 1.60 (d, J=14.2 Hz, 2H), 1.46 (s, 3H), 1.37 (s, 3H).

Example 584: (R/S)-2,2-Dimethyl-3-(8-methyl-3-(trifluoromethyl)-[1,2,4]triazolo[4,3-a]pyridin-7-yl)-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic Acid

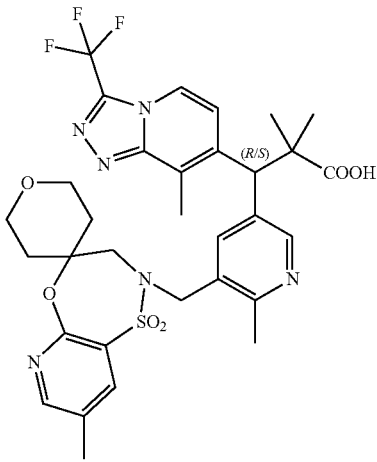 [SMILES: Cc1cnc2c(c1)S(=O)(=O)N(Cc1cc(C(c3ccn4c(C(F)(F)F)nnc4c3C)C(C)(C)C(=O)O)cnc1C)CC1(CCOCC1)O2]

Step A: Methyl 2,2-dimethyl-3-(8-methyl-3-(trifluoromethyl)-[1,2,4]triazolo[4,3-a]pyridin-7-yl)-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoate. A solution of methyl 3-(5-(hydroxymethyl)-6-methylpyridin-3-yl)-2,2-dimethyl-3-(8-methyl-3-(trifluoromethyl)-[1,2,4]triazolo[4,3-a]pyridin-7-yl)propanoate (Intermediate 169, 300 mg, 0.69 mmol), 8'-methyl-2,2',3,3',5,6-hexahydrospiro[pyran-4,4'-pyrido[2,3-b][1,4,5]oxathiazepine]1',1'-dioxide (Intermediate 37, 241 mg, 0.85 mmol), and triphenylphosphine (287 mg, 1.1 mmol) in THF (8 mL) and DMF (1.5 ml) was stirred at room temperature for 5 minutes. DBAD (253 mg, 1.1 mmol) was added and the solution was stirred at room temperature for 30 minutes. The reaction was then concentrated under a stream of nitrogen and purified by flash column chromatography (eluent: 0-100% ethyl acetate/hexanes) to afford the title compound 480 mg, 99% yield). MS (ESI): mass calcd. for $C_{33}H_{37}F_3N_6O_6S$, 702.2; m/z found, 703.3 [M+H]+. 1 H NMR (500 MHz, CDCl3) δ 8.33-8.25 (m, 2H), 8.05 (d, J=7.3 Hz, 1H), 7.93 (d, J=2.5 Hz, 1H), 7.71 (d, J=2.3 Hz, 1H), 7.21 (d, J=7.4 Hz, 1H), 5.26 (s, 1H), 4.75 (s, 1H), 4.48 (d, J=16.2 Hz, 1H), 4.41 (d, J=16.3 Hz, 1H), 4.07-3.98 (m, 2H), 3.61 (s, 5H), 3.49-3.43 (m, 1H), 2.75 (s, 3H), 2.38 (d, J=19.2 Hz, 6H), 1.73 (d, J=2.8 Hz, 1H), 1.68-1.48 (m, 3H), 1.39 (s, 3H), 1.34 (s, 3H).

Step B: (R/S)-2,2-Dimethyl-3-(8-methyl-3-(trifluoromethyl)-[1,2,4]triazolo[4,3-a]pyridin-7-yl)-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid. Lithium hydroxide (110 mg, 4.60 mmol) was added to a solution of methyl 2,2-dimethyl-3-(8-methyl-3-(trifluoromethyl)-[1,2,4]triazolo[4,3-a]pyridin-7-yl)-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoate (480 mg, 0.68 mmol) in MeOH (23 mL) and water (22 mL). The reaction was stirred at 75° C. overnight then allowed to cool to room temperature. 1 M aqueous HCl solution was added until the pH was 4. DCM was added and the resulting biphasic mixture was separated. The aqueous layer was extracted with DCM. These extractions resulted in several organic solvent fractions which were combined, dried over MgSO4, filtered, and concentrated to dryness under reduced pressure. The material was purified by flash column chromatography (eluent: 0-10% MeOH/DCM) to provide the title compound to provide the title compound (456 mg, 97% yield). MS (ESI): mass calcd. for $C_{32}H_{35}F_3N_6O_6S$, 688.2; m/z found, 689.4 [M+H]+. 1H NMR (500 MHz, CDCl3) δ 8.46 (d, J=2.0 Hz, 1H), 8.34 (d, J=2.1 Hz, 1H), 8.28 (d, J=2.4 Hz, 1H), 8.06 (d, J=7.1 Hz, 1H), 7.92 (d, J=2.4 Hz, 1H), 7.77 (d, J=2.1 Hz, 1H), 7.30 (d, J=7.4 Hz, 1H), 5.31 (s, 1H), 4.88 (s, 1H), 4.50 (d, J=16.1 Hz, 1H), 4.37 (d, J=16.1 Hz, 1H), 4.00 (t, J=11.1 Hz, 5H), 3.65-3.58 (m, 2H), 3.46 (q, J=7.1 Hz, 2H), 3.40 (s, 1H), 2.74 (s, 3H), 2.46 (s, 3H), 2.37 (s, 3H), 1.34 (S, 3H), 1.33 (s, 3H).

Example 585: (*S)-2,2-Dimethyl-3-(8-methyl-3-(trifluoromethyl)-[1,2,4]triazolo[4,3-a]pyridin-7-yl)-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic Acid

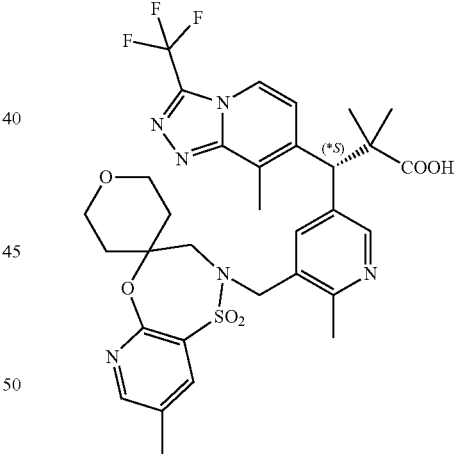

The mixture of (R/S)-2,2-dimethyl-3-(8-methyl-3-(trifluoromethyl)-[1,2,4]triazolo[4,3-a]pyridin-7-yl)-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid isomers (Example 584, 456 mg) was separated by chiral SFC (stationary phase: Chiralpak IC, 2×25 cm, Mobile phase: 35% methanol, 65% CO2, 0.2% NPA) to afford two enantiomers. The first eluting isomer (210 mg) was designated (*S): MS: mass calcd. for $C_{32}H_{35}F_3N_6O_6S$, 688.2; m/z found, 689.4 [M+H]+. 1H NMR (600 MHz, CDCl3) δ 8.46 (d, J=2.0 Hz, 1H), 8.32 (dd, J=2.5, 0.9 Hz, 1H), 8.10 (d, J=7.2 Hz, 1H), 7.98 (d, J=2.4 Hz, 1H), 7.80 (s, 1H), 7.37 (d, J=7.4 Hz, 1H), 5.31 (s, 1H), 4.95 (s, 1H), 4.55 (d, J=15.9 Hz, 1H), 4.42 (d, J=16.0 Hz, 1H), 4.06 (td, J=11.6, 2.3 Hz, 2H), 3.92 (s, 5H), 3.69 (d, J=10.6 Hz, 2H), 3.54 (s, 2H), 2.86 (s, 3H), 2.46 (s, 3H), 2.42 (s, 3H), 1.44 (s, 3H), 1.36 (s, 3H).

Example 586: (*R)-2,2-Dimethyl-3-(8-methyl-3-(trifluoromethyl)-[1,2,4]triazolo[4,3-a]pyridin-7-yl)-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl) propanoic Acid

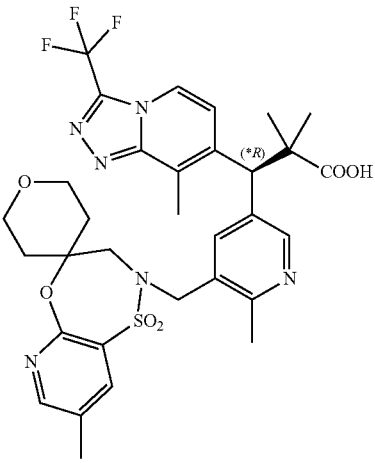 [SMILES: Cc1cnc2c(c1)S(=O)(=O)N(Cc1cc([C@@H](c3ccn4c(C(F)(F)F)nnc4c3C)C(C)(C)C(=O)O)cnc1C)CC1(CCOCC1)O2]

The second eluting isomer (215 mg) from the chiral separation described in Example 585 was designated (*R): MS: mass calcd. for $C_{32}H_{35}F_3N_6O_6S$, 688.2; m/z found, 689.4 [M+H]$^+$. $^1$H NMR (600 MHz, CDCl$_3$) δ 8.47 (d, J=2.4 Hz, 1H), 8.32 (dd, J=2.4, 0.9 Hz, 1H), 8.11 (d, J=7.2 Hz, 1H), 7.99-7.95 (m, 1H), 7.82-7.78 (m, 1H), 7.38 (d, J=7.4 Hz, 1H), 5.31 (s, 1H), 4.95 (s, 1H), 4.55 (d, J=16.0 Hz, 1H), 4.42 (d, J=16.0 Hz, 1H), 4.18 (s, 5H), 4.09-4.02 (m, 2H), 3.68 (d, J=11.6 Hz, 2H), 3.53 (s, 2H), 2.85 (s, 3H), 2.46 (s, 3H), 2.41 (s, 3H), 1.44 (s, 3H), 1.37 (s, 3H).

Example 587: (R/S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic Acid

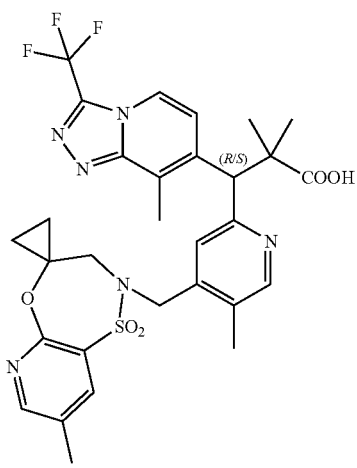 [SMILES: Cc1cnc2c(c1)S(=O)(=O)N(Cc1cc(C(c3ccn4c(C(F)(F)F)nnc4c3C)C(C)(C)C(=O)O)ncc1C)CC1(CC1)O2]

Step A: Methyl 2,2-dimethyl-3-(8-methyl-3-(trifluoromethyl)-[1,2,4]triazolo[4,3-a]pyridin-7-yl)-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl) propanoate. A solution of methyl (R/S)-3-(4-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate (Intermediate 170-racemic, 400 mg, 0.92 mmol), 8'-methyl-2',3'-dihydrospiro[cyclopropane-1,4'-pyrido[2,3-b][1,4,5]oxathiazepine] 1',1'-dioxide (Intermediate 6, 330 mg, 1.38 mmol) and triphenylphosphine (361 mg, 1.38 mmol) in THF (20 mL) was stirred at room temperature for 5 minutes. DBAD (317 mg, 1.38 mmol) was added and the solution was stirred at room temperature for 30 minutes. The reaction was then concentrated and purified by flash column chromatography (eluent: 0-100% ethyl acetate/hexanes) to afford the title compound (530 mg, 88% yield). MS (ESI): mass calcd. for $C_{31}H_{33}F_3N_6O_5S$, 658.2; m/z found, 659.3 [M+H]$^+$. $^1$H NMR (400 MHz, CDCl$_3$) δ 8.28 (s, 1H), 8.17 (dd, J=2.4, 0.9 Hz, 1H), 7.96 (dd, J=2.4, 0.8 Hz, 1H), 7.88 (d, J=7.3 Hz, 1H), 7.52 (d, J=7.4 Hz, 1H), 6.98 (s, 1H), 4.90 (s, 1H), 4.24 (d, J=15.7 Hz, 1H), 4.16 (d, J=15.7 Hz, 1H), 3.55 (s, 4H), 3.45 (d, J=15.2 Hz, 1H), 2.81 (s, 3H), 2.32 (s, 3H), 2.16 (s, 3H), 1.32 (s, 3H), 1.31-1.10 (m, 5H), 0.62-0.48 (m, 2H).

Step B: (R/S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl) propanoic acid. TFA (0.2 mL) was added to a solution of (R/S)-methyl 2,2-dimethyl-3-(8-methyl-3-(trifluoromethyl)-[1,2,4]triazolo[4,3-a]pyridin-7-yl)-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl) propanoate (530 mg, 0.81 mmol) in CH$_3$CN (23 mL) and water (23 mL). The reaction was stirred at 50° C. overnight then allowed to cool to room temperature. 1 M aqueous HCl solution was added until the pH was 4. DCM was added and the resulting biphasic mixture was separated. The aqueous layer was extracted with DCM. These extractions resulted in several organic solvent fractions which were combined, dried over MgSO$_4$, filtered, and concentrated to dryness under reduced pressure. The material was purified by flash column chromatography (eluent: 0-10% MeOH/DCM) to provide the title compound to provide the title compound (489 mg, 94% yield). MS (ESI): mass calcd. for $C_{30}H_{31}F_3N_6O_5S$, 644.2; m/z found, 645.2 [M+H]$^+$. $^1$H NMR (500 MHz, CDCl$_3$) δ 8.37 (s, 1H), 8.23 (d, J=2.3 Hz, 1H), 7.99 (d, J=2.4 Hz, 1H), 7.92 (d, J=7.3 Hz, 1H), 7.34 (t, J=3.7 Hz, 2H), 4.77 (s, 1H), 4.43-4.19 (m, 2H), 3.75-3.48 (m, 2H), 2.91 (s, 3H), 2.38 (s, 3H), 2.25 (s, 3H), 1.39 (s, 3H), 1.31 (s, 3H), 1.18 (d, J=6.0 Hz, 2H), 0.68-0.55 (m, 2H).

Example 588: (*S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic Acid

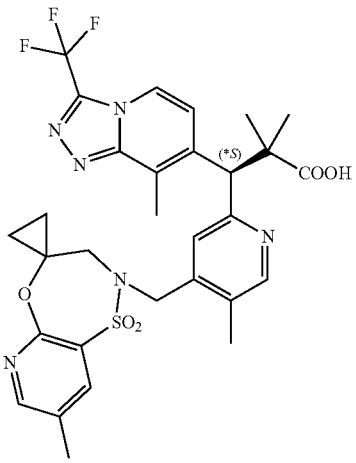 [SMILES: Cc1cnc2c(c1)S(=O)(=O)N(Cc1cc([C@@H](c3ccn4c(C(F)(F)F)nnc4c3C)C(C)(C)C(=O)O)ncc1C)CC1(CC1)O2]

The mixture of (R/S)-2,2-dimethyl-3-(8-methyl-3-(trifluoromethyl)-[1,2,4]triazolo[4,3-a]pyridin-7-yl)-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid isomers (Example 587, 489 mg) was separated by chiral SFC (stationary phase: CHIRALPAK IG 250*20 mm, Mobile phase: 70% $CO_2$, 30% MeOH) to afford two diastereomers. The first eluting isomer (242 mg) was designated (*S): MS (ESI): mass calcd. for $C_{30}H_{31}F_3N_6O_5S$, 644.2; m/z found, 645.2 [M+H]$^+$. $^1$H NMR (600 MHz, CDCl$_3$) δ 8.29 (s, 1H), 8.19 (d, J=2.4 Hz, 1H), 7.96 (d, J=2.5 Hz, 1H), 7.85 (d, J=7.3 Hz, 1H), 7.39 (d, J=7.4 Hz, 1H), 7.25 (s, 1H), 4.78 (s, 1H), 4.28 (d, J=16.4 Hz, 1H), 4.18 (d, J=16.4 Hz, 1H), 3.60 (d, J=15.1 Hz, 1H), 3.47 (d, J=14.9 Hz, 1H), 2.86 (s, 3H), 2.33 (s, 3H), 2.17 (s, 3H), 1.29 (s, 3H), 1.25 (s, 3H), 1.19-1.14 (m, 2H), 0.59 (dd, J=6.8, 3.2 Hz, 2H).

Example 589: (*R)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic Acid

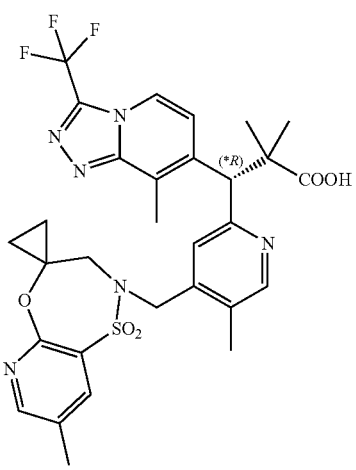 [SMILES: Cc1cnc2c(c1)S(=O)(=O)N(Cc1cc([C@H](c3ccn4c(C(F)(F)F)nnc4c3C)C(C)(C)C(=O)O)ncc1C)CC1(CC1)O2]

The second eluting isomer (241 mg) from the chiral separation described in Example 588 was designated (*R): MS: mass calcd. for $C_{32}H_{35}F_3N_6O_6S$, 674.2; m/z found, 675.3 [M+H]$^+$. $^1$H NMR (600 MHz, CDCl$_3$) δ 8.35 (s, 1H), 8.27 (d, J=2.4 Hz, 1H), 8.05 (d, J=2.2 Hz, 1H), 7.93 (d, J=7.0 Hz, 1H), 7.62 (d, J=7.3 Hz, 1H), 7.29 (s, 1H), 4.73 (s, 1H), 4.35 (d, J=16.1 Hz, 1H), 4.26 (d, J=16.1 Hz, 1H), 3.68 (d, J=15.0 Hz, 1H), 3.54 (d, J=15.2 Hz, 1H), 2.90 (s, 3H), 2.42 (s, 3H), 2.24 (s, 3H), 1.32 (d, J=17.6 Hz, 6H), 1.08 (t, J=7.1 Hz, 2H), 0.66 (d, J=4.2 Hz, 2H).

Example 590: (*S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic Acid

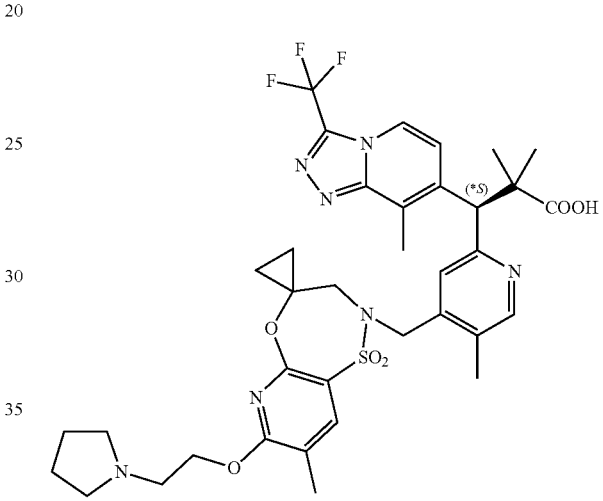

Step A: Methyl (*S)-2,2-dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoate. A solution of methyl (*S)-3-(4-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate (Intermediate 170, 160 mg, 0.37 mmol), 8'-methyl-7'-(2-(pyrrolidin-1-yl)ethoxy)-2',3'-dihydrospiro[cyclopropane-1,4'-pyrido[2,3-b][1,4,5]oxathiazepine] 1',1'-dioxide (Intermediate 137, 182 mg, 0.51 mmol) and triphenylphosphine (142 mg, 0.54 mmol) in THF (10 mL) and DMF (3 mL) was stirred at room temperature for 5 minutes. DBAD (140 mg, 0.61 mmol) was added and the solution was stirred at room temperature for 30 minutes. The reaction was then concentrated and purified by flash column chromatography (eluent: 0-10% MeOH/DCM) to afford the title compound (218 mg, 77% yield). MS (ESI): mass calcd. for $C_{37}H_{44}F_3N_7O_6S$, 771.3; m/z found, 772.3 [M+H]$^+$. $^1$H NMR (400 MHz, CDCl$_3$) δ 8.35 (s, 1H), 7.96 (d, J=7.3 Hz, 1H), 7.86 (d, J=1.0 Hz, 1H), 7.60 (d, J=7.4 Hz, 1H), 7.06 (s, 1H), 4.97 (s, 1H), 4.48 (t, J=5.9 Hz, 2H), 4.28 (d, J=15.6 Hz, 1H), 4.21 (d, J=15.7 Hz, 1H), 3.62 (s, 3H), 3.60-3.44 (m, 2H), 2.90 (d, J=8.3 Hz, 5H), 2.69-2.65 (m, 4H), 2.63-2.60 (m, 1H), 2.27-2.16 (m, 6H), 1.82 (p, J=3.2 Hz, 3H), 1.40 (s, 3H), 1.32 (s, 3H), 1.28-1.20 (m, 2H), 0.67-0.54 (m, 2H).

Step B: (*S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid. TFA (0.4 mL) was added to a solution of methyl (*S)-2,2-dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoate (218 mg, 0.81 mmol) in CH$_3$CN (8 mL) and water (8 mL). The reaction was stirred at 50° C. overnight then allowed to cool to room temperature. 1 M aqueous HCl solution was added until the pH was 4. DCM was added and the resulting biphasic mixture was separated. The aqueous layer was extracted with DCM. These extractions resulted in several organic solvent fractions which were combined, dried over MgSO$_4$, filtered, and concentrated to dryness under reduced pressure. The material was purified by flash column chromatography (eluent: 0-10% MeOH/DCM) to provide the title compound (180 mg, 84% yield). MS (ESI): mass calcd. for C$_{36}$H$_{42}$F$_3$N$_7$O$_6$S, 757.3; m/z found, 758.2 [M+H]$^+$. $^1$H NMR (500 MHz, CDCl$_3$) δ 8.38 (s, 1H), 7.93 (d, J=7.2 Hz, 1H), 7.85 (s, 1H), 7.36 (s, 1H), 7.26 (d, J=7.4 Hz, 1H), 4.75-4.69 (m, 3H), 4.31 (d, J=16.9 Hz, 1H), 4.25 (d, J=16.8 Hz, 1H), 3.97 (s, 2H), 3.64-3.53 (m, 4H), 2.99 (s, 2H), 2.94 (s, 3H), 2.28 (s, 3H), 2.17 (d, J=28.3 Hz, 8H), 1.43 (s, 3H), 1.33 (s, 3H), 1.28-1.17 (m, 1H), 1.21-1.13 (m, 1H), 0.63-0.51 (m, 2H).

Example 591: (*S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic Acid

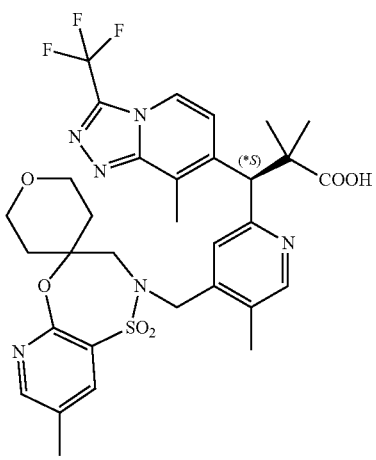 [SMILES: Cc1cnc2c(c1)S(=O)(=O)N(Cc1cc([C@@H](c3ccn4c(C(F)(F)F)nnc4c3C)C(C)(C)C(=O)O)ncc1C)CC1(CCOCC1)O2]

Step A: Methyl (*S)-2,2-dimethyl-3-(8-methyl-3-(trifluoromethyl)-[1,2,4]triazolo[4,3-a]pyridin-7-yl)-3-(5-methyl-4-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoate. A solution of methyl (*S)-3-(4-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate (Intermediate 170, 250 mg, 0.57 mmol), 8'-methyl-2,2',3,3',5,6-hexahydrospiro[pyran-4,4'-pyrido[2,3-b][1,4,5]oxathiazepine]1',1'-dioxide (Intermediate 37, 201 mg, 0.71 mmol) and triphenylphosphine (239 mg, 0.91 mmol) in THF (12 mL) and DMF (1 mL) was stirred at room temperature for 5 minutes. DBAD (211 mg, 0.92 mmol) was added and the solution was stirred at room temperature for 30 minutes. The reaction was then concentrated and purified by flash column chromatography (eluent: 0-100% ethyl acetate/hexanes) to afford the title compound (380 mg, 94% yield). MS (ESI): mass calcd. for C$_{33}$H$_{37}$F$_3$N$_6$O$_6$S, 702.2; m/z found, 703.2 [M+H]$^+$.

Step B: (*S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoic acid. TFA (0.8 mL) was added to a solution of methyl (*S)-2,2-dimethyl-3-(8-methyl-3-(trifluoromethyl)-[1,2,4]triazolo[4,3-a]pyridin-7-yl)-3-(5-methyl-4-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-2-yl)propanoate (380 mg, 0.54 mmol) in CH$_3$CN (15 mL) and water (15 mL). The reaction was stirred at 50° C. overnight then allowed to cool to room temperature. 1 M aqueous HCl solution was added until the pH was 4. DCM was added and the resulting biphasic mixture was separated. The aqueous layer was extracted with DCM. These extractions resulted in several organic solvent fractions which were combined, dried over MgSO$_4$, filtered, and concentrated to dryness under reduced pressure. The material was purified by flash column chromatography (eluent: 0-10% MeOH/DCM) to provide the title compound to provide the title compound (280 mg, 75% yield). MS (ESI): mass calcd. for C$_{32}$H$_{35}$F$_3$N$_6$O$_6$S, 688.2; m/z found, 689.2 [M+H]$^+$. $^1$H NMR (500 MHz, CDCl$_3$) δ 8.38 (s, 1H), 8.29 (dd, J=2.4, 0.9 Hz, 1H), 7.96-7.88 (m, 2H), 7.38-7.32 (m, 2H), 5.29 (s, 1H), 4.81 (s, 1H), 4.52 (d, J=17.1 Hz, 1H), 4.37 (d, J=17.0 Hz, 1H), 4.05-3.97 (m, 2H), 3.68-3.56 (m, 4H), 3.46 (q, J=7.0 Hz, 1H), 2.93 (s, 3H), 2.24 (s, 3H), 1.68 (d, J=15.2 Hz, 2H), 1.64-1.58 (m, 2H), 1.49-1.43 (m, 1H), 1.41 (s, 3H), 1.34 (s, 3H).

Example 592: (*S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic Acid

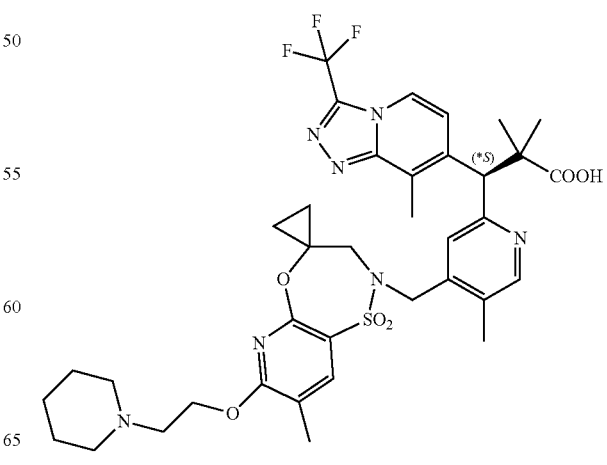

Step A: Methyl (*S)-2,2-dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(piperidin-1-yl)ethoxy) spiro[cyclopropane-1,4'-pyrido[2,3-b][1,4,5]oxathiazepin]-2'(3'H)-yl)methyl)pyridin-2-yl)propanoate. A solution of methyl (*S)-3-(4-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate (Intermediate 170, 160 mg, 0.37 mmol), 8'-methyl-7'-(2-(piperidin-1-yl)ethoxy)-2',3'-dihydrospiro[cyclopropane-1,4'-pyrido[2,3-b][1,4,5]oxathiazepine] 1',1'-dioxide (Intermediate 136, 189 mg, 0.51 mmol) and triphenylphosphine (142 mg, 0.54 mmol) in THF (7 mL) and DMF (3 mL) was stirred at room temperature for 5 minutes. DBAD (140 mg, 0.61 mmol) was added and the solution was stirred at room temperature for 30 minutes. The reaction was then concentrated and purified by flash column chromatography (dryness under reduced pressure. The material was purified by flash column chromatography (eluent: 0-10% MeOH/DCM) to afford the title compound (218 mg, 76% yield). MS (ESI): mass calcd. for $C_{38}H_{46}F_3N_7O_6S$, 785.3; m/z found, 786.3 [M+H]$^+$. $^1$H NMR (500 MHz, CDCl$_3$) δ 8.35 (s, 1H), 7.96 (d, J=7.3 Hz, 1H), 7.86 (d, J=1.0 Hz, 1H), 7.60 (d, J=7.4 Hz, 1H), 7.06 (s, 1H), 4.98 (s, 1H), 4.46 (t, J=6.0 Hz, 2H), 4.28 (d, J=15.6 Hz, 1H), 4.21 (d, J=15.6 Hz, 1H), 3.62 (s, 3H), 3.50 (d, J=17.3 Hz, 2H), 2.90 (s, 3H), 2.77 (t, J=6.0 Hz, 2H), 2.56-2.50 (m, 4H), 2.24 (s, 3H), 2.19 (d, J=0.8 Hz, 3H), 1.61 (t, J=5.7 Hz, 4H), 1.49-1.38 (m, 5H), 1.32 (s, 3H), 1.20 (p, J=6.1 Hz, 2H), 0.67-0.55 (m, 2H).

Step B: (*S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic acid. TFA (0.4 mL) was added to a solution of methyl (*S)-2,2-dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoate (218 mg, 0.28 mmol) in CH$_3$CN (8 mL) and water (8 mL). The reaction was stirred at 50° C. overnight then allowed to cool to room temperature. 1 M aqueous HCl solution was added until the pH was 4. DCM was added and the resulting biphasic mixture was separated. The aqueous layer was extracted with DCM. These extractions resulted in several organic solvent fractions which were combined, dried over MgSO$_4$, filtered, and concentrated to dryness under reduced pressure. The material was purified by flash column chromatography (eluent: 0-10% MeOH/DCM) to provide the title compound to provide the title compound (155 mg, 72% yield). MS (ESI): mass calcd. for $C_{37}H_{44}F_3N_7O_6S$, 771.3; m/z found, 772.3 [M+H]$^+$. $^1$H NMR (500 MHz, CDCl$_3$) δ 8.38 (s, 1H), 8.29 (dd, J=2.4, 0.9 Hz, 1H), 7.96-7.88 (m, 2H), 7.38-7.32 (m, 2H), 5.29 (s, 1H), 4.81 (s, 1H), 4.52 (d, J=17.1 Hz, 1H), 4.37 (d, J=17.0 Hz, 1H), 4.05-3.97 (m, 2H), 3.68-3.56 (m, 4H), 3.46 (q, J=7.0 Hz, 2H), 2.93 (s, 3H), 2.24 (s, 3H), 1.68 (d, J=15.2 Hz, 2H), 1.60 (tq, J=13.7, 5.0, 4.1 Hz, 2H), 1.49-1.43 (m, 1H), 1.41 (s, 3H), 1.34 (s, 3H).

Example 593: (*S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic Acid

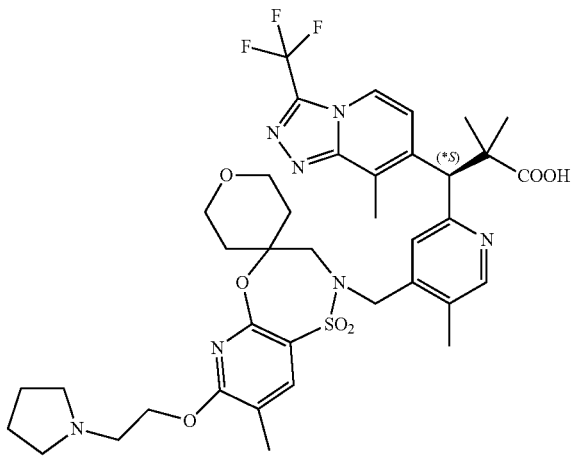 [SMILES: Cc1cnc([C@@H](c2ccn3c(C(F)(F)F)nnc3c2C)C(C)(C)C(=O)O)cc1CN1CC2(CCOCC2)Oc2nc(OCCN3CCCC3)c(C)cc2S1(=O)=O]

Step A: Methyl (*S)-2,2-dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoate. A solution of methyl (*S)-3-(4-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate (Intermediate 170, 160 mg, 0.37 mmol), 8'-methyl-7'-(2-(pyrrolidin-1-yl)ethoxy)-2,2',3,3',5,6-hexahydrospiro[pyran-4,4'-pyrido[2,3-b][1,4,5]oxathiazepine] 1',1'-dioxide (Intermediate 144, 204 mg, 0.51 mmol) and triphenylphosphine (142 mg, 0.54 mmol) in THF (7 mL) and DMF (3 mL) was stirred at room temperature for 5 minutes. DBAD (140 mg, 0.61 mmol) was added and the solution was stirred at room temperature for 30 minutes. The reaction was then concentrated and purified by flash column chromatography (dryness under reduced pressure. The material was purified by flash column chromatography (eluent: 0-10% MeOH/DCM) to afford the title compound (280 mg, 94% yield). MS (ESI): mass calcd. for $C_{39}H_{48}F_3N_7O_7S$, 815.3; m/z found, 816.2 [M+H]$^+$. $^1$H NMR (500 MHz, CDCl$_3$) δ 8.35 (s, 1H), 7.98 (d, J=7.3 Hz, 1H), 7.79 (d, J=1.0 Hz, 1H), 7.57 (d, J=7.4 Hz, 1H), 7.09 (s, 1H), 5.03 (s, 1H), 4.51 (t, J=6.0 Hz, 2H), 4.41 (d, J=16.4 Hz, 1H), 4.35 (d, J=16.3 Hz, 1H), 4.12-3.99 (m, 2H), 3.64 (s, 5H), 3.49 (s, 3H), 2.92 (d, J=7.0 Hz, 5H), 2.71-2.64 (m, 4H), 2.24-2.18 (m, 6H), 1.88-1.78 (m, 4H), 1.76-1.68 (m, 1H), 1.59-1.46 (m, 2H), 1.43 (s, 3H), 1.34 (s, 3H).

Step B: (*S)-2,2-Dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid. Lithium hydroxide (65 mg, 2.7 mmol) was added to a solution of methyl (*S)-2,2-dimethyl-3-(8-methyl-3-(trifluoromethyl)-[1,2,4]triazolo[4,3-a]pyridin-7-yl)-3-(5-methyl-4-((8'-methyl-1',1'-dioxido-7'-(2-(pyrrolidin-1-yl)ethoxy)-2,3,5,6-tetrahydrospiro[pyran-4,4'-pyrido[2,3-b][1, 4,5]oxathiazepin]-2'(3'H)-yl)methyl)pyridin-2-yl) propanoate (220 mg, 0.27 mmol) in THF (11 mL) and water (5 mL). The reaction was stirred at 75° C. overnight then allowed to cool to room temperature. 1 M aqueous HCl solution was added until the pH was 4. DCM was added and the resulting biphasic mixture was separated. The aqueous layer was extracted with DCM. These extractions resulted in several organic solvent fractions which were combined, dried over $MgSO_4$, filtered, and concentrated to dryness under reduced pressure. The material was purified by flash column chromatography (eluent: 0-10% MeOH/DCM) to provide the title compound to provide the title compound (206 mg, 95% yield). MS (ESI): mass calcd. for $C_{38}H_{46}F_3N_7O_7S$, 801.3; m/z found, 802.3 [M+H]+. 1H NMR (400 MHz, $CDCl_3$) δ 13.42 (s, 1H), 8.39 (s, 1H), 7.94 (d, J=7.3 Hz, 1H), 7.80 (d, J=1.0 Hz, 1H), 7.36 (s, 1H), 7.29 (d, J=7.5 Hz, 1H), 4.76 (s, 2H), 4.76 (d, J=10.7 Hz, 1H), 4.46 (d, J=17.2 Hz, 1H), 4.32 (d, J=17.2 Hz, 1H), 4.03-3.89 (m, 4H), 3.76-3.67 (m, 1H), 3.65-3.56 (m, 1H), 3.59 (s, 5H), 2.97 (s, 3H), 2.27 (s, 3H), 2.24-2.12 (m, 7H), 1.82-1.66 (m, 3H), 1.66-1.50 (m, 2H), 1.40 (d, J=37.2 Hz, 6H).

Example 594: (*S)-3-(1-Ethyl-4-methyl-1H-benzo [d][1,2,3]triazol-5-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl) pyridin-2-yl)propanoic Acid

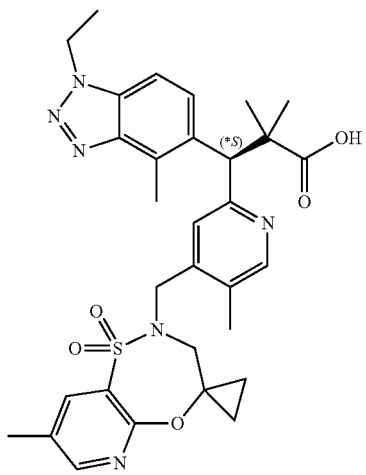 [SMILES: CCn1nnc2c(C)c([C@H](c3cc(CN4CC5(CC5)Oc5ncc(C)cc5S4(=O)=O)c(C)cn3)C(C)(C)C(=O)O)ccc21]

Step A: Methyl (*S)-3-(1-ethyl-4-methyl-1H-benzo[d][1,2,3]triazol-5-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoate. A solution of methyl (*S)-3-(1-ethyl-4-methyl-1H-benzo[d][1,2,3]triazol-5-yl)-3-(4-(hydroxymethyl)-5-methylpyridin-2-yl)-2,2-dimethylpropanoate (Intermediate 171, 150 mg, 0.38 mmol), 8'-methyl-2',3'-dihydrospiro[cyclopropane-1,4'-pyrido[2,3-b][1,4,5]oxathiazepine] 1',1'-dioxide (Intermediate 6, 127 mg, 0.53 mmol), and triphenylphosphine (146 mg, 0.56 mmol) in THF (19 mL) was stirred at room temperature for 5 minutes. DBAD (144 mg, 0.63 mmol) was added and the solution was stirred at room temperature for 30 minutes. The reaction was then concentrated and purified by flash column chromatography (eluent: 0-100% ethyl acetate/hexanes) to afford the title compound (220 mg, 94% yield). MS (ESI): mass calcd. for $C_{32}H_{38}N_6O_5S$, 618.3; m/z found, 619.3 [M+H]+.

Step B: (*S)-3-(1-Ethyl-4-methyl-1H-benzo[d][1,2,3]triazol-5-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic acid. Lithium hydroxide (85 mg, 3.6 mmol) was added to a solution of methyl (*S)-3-(1-ethyl-4-methyl-1H-benzo[d][1,2,3]triazol-5-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoate (220 mg, 0.36 mmol) in THF (16 mL) and water (6 mL). The reaction was stirred at 75° C. overnight then allowed to cool to room temperature. 1 M aqueous HCl solution was added until the pH was approximately 6. DCM was added and the resulting biphasic mixture was separated. The aqueous layer was extracted with DCM. These extractions resulted in several organic solvent fractions which were combined, dried over $MgSO_4$, filtered, and concentrated to dryness under reduced pressure. The material was purified by flash column chromatography (eluent: 0-10% MeOH/DCM) to provide the title compound (180 mg, 84% yield). MS (ESI): mass calcd. for $C_{31}H_{36}N_6O_5S$, 604.3; m/z found, 605.3 [M+H]+. 1H NMR (400 MHz, Chloroform-d) δ 8.35 (s, 1H), 8.23 (d, J=2.4 Hz, 1H), 7.99 (dd, J=2.4, 0.8 Hz, 1H), 7.50 (d, J=8.8 Hz, 1H), 7.27-7.17 (m, 2H), 4.72 (s, 1H), 4.64-4.50 (m, 2H), 4.30 (d, J=16.4 Hz, 1H), 4.23 (d, J=16.4 Hz, 1H), 4.10 (q, J=7.1 Hz, 1H), 3.51 (s, 2H), 3.00 (s, 3H), 2.37 (s, 3H), 2.26 (s, 3H), 2.02 (s, 1H), 1.53 (t, J=7.3 Hz, 3H), 1.25 (s, 3H), 1.23 (d, J=7.1 Hz, 1H), 1.16 (s, 2H), 0.59-0.45 (m, 2H).

Example 595: (*S)-3-(1-Ethyl-4-methyl-1H-benzo [d][1,2,3]triazol-5-yl)-2,2-dimethyl-3-(5-methyl-4-((8'-methyl-1',1'-dioxidospiro[azetidine-3,4'-pyrido [2,3-b][1,4,5]oxathiazepin]-2'(3'H)-yl)methyl) pyridin-2-yl)propanoic Acid

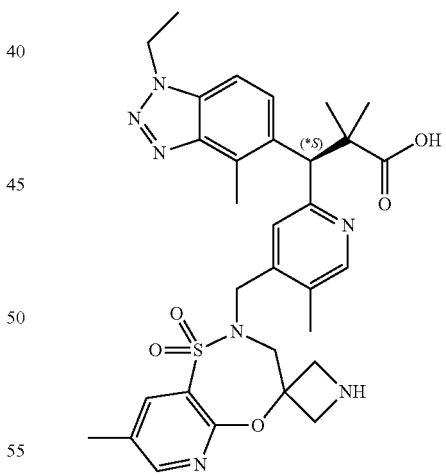

Step A: 3-(1-Ethyl-4-methyl-1H-benzo[d][1,2,3]triazol-5-yl)-3-(4-(hydroxymethyl)-5-methylpyridin-2-yl)-2,2-dimethylpropanoic acid. Tetrabutylammonium fluoride (1 M in THF, 5.1 ml, 5.1 mmol) was added to a solution of methyl 3-(4-(((tert-butyldimethylsilyl)oxy)methyl)-5-methylpyridin-2-yl)-3-(1-ethyl-4-methyl-1H-benzo[d][1,2,3]triazol-5-yl)-2,2-dimethylpropanoate (Intermediate 171, step B, 1.3 g, 2.5 mmol) in THF (28 ml) and 3 drops of DMF. The reaction was stirred at room temperature for 1.5 hours. The reaction was quenched with saturated aqueous $NaHCO_3$, then extracted with EtOAc. These extractions resulted in several organic solvent fractions which were combined, dried over MgSO₄, filtered, and concentrated to an oil under reduced pressure. The material was purified by flash column chromatography (eluent: 0-10% MeOH/DCM) to provide the title compound (400 mg, 41% yield). MS (ESI): mass calcd. for $C_{21}H_{26}N_4O_3$, 382.2; m/z found, 383.2 [M+H]⁺. ¹H NMR (600 MHz, CDCl₃) δ d 8.16 (s, 1H), 7.46 (d, J=8.9 Hz, 1H), 7.11 (d, J=8.8 Hz, 1H), 6.98 (s, 1H), 5.06 (s, 1H), 4.57-4.43 (m, 4H), 3.48 (s, 3H), 2.80 (s, 3H), 2.08 (s, 3H), 1.47 (t, J=7.3 Hz, 3H), 1.32 (d, J=3.9 Hz, 3H), 1.13 (d, J=5.7 Hz, 3H).

Step B: Benzyl 3-(1-ethyl-4-methyl-1H-benzo[d][1,2,3]triazol-5-yl)-3-(4-(hydroxymethyl)-5-methylpyridin-2-yl)-2,2-dimethylpropanoate. (Bromomethyl)benzene (0.15 mL, 1.26 mmol) was added to a solution of 3-(1-ethyl-4-methyl-1H-benzo[d][1,2,3]triazol-5-yl)-3-(4-(hydroxymethyl)-5-methylpyridin-2-yl)-2,2-dimethylpropanoic acid (400 mg, 1.05 mmol), potassium carbonate (361 mg, 2.62 mmol) in ACN (20 mL). The resultant mixture was stirred at room-temperature for 16 hours. Quenched with water (10 mL) and extracting with ethyl acetate (20 mL×3). The combined organic extracts were dried over anhydrous Na₂SO₄, filtered, and concentrated to dryness under reduced pressure to afford the compound, which was purified by FCC (eluent: 0-100% ethyl acetate/hexanes) to afford the title compound. MS (ESI): mass calcd. for $C_{28}H_{32}N_4O_3$, 472.2; m/z found, 473.3 [M+H]⁺. ¹H NMR (500 MHz, CDCl₃) δ 8.14 (s, 1H), 7.51 (d, J=8.8 Hz, 1H), 7.28-7.20 (m, 3H), 7.19-7.12 (m, 3H), 7.03 (s, 1H), 5.16 (s, 1H), 5.07-4.97 (m, 2H), 4.56 (q, J=7.3 Hz, 4H), 3.12 (s, 1H), 2.84 (s, 3H), 2.14 (s, 3H), 1.56 (t, J=7.3 Hz, 3H), 1.47 (s, 3H), 1.26 (s, 3H).

Step C: The mixture of (R/S)-benzyl 3-(1-ethyl-4-methyl-1H-benzo[d][1,2,3]triazol-5-yl)-3-(4-(hydroxymethyl)-5-methylpyridin-2-yl)-2,2-dimethylpropanoate (470 mg) was purified and separated by chiral SFC (stationary phase: AD-H 2*25 cm, Mobile phase: 75% CO₂, 25% EtOH) to afford two enantiomers. The first eluting isomer (226 mg) was designated (*S): MS (ESI): mass calcd. for $C_{28}H_{32}N_4O_3$, 472.2; m/z found, 473.3 [M+H]⁺. The second eluting isomer was designated as (*R), however this Intermediate was not used further.

Step D: tert-Butyl (*S)-2'-((2-(3-(benzyloxy)-1-(1-ethyl-4-methyl-1H-benzo[d][1,2,3]triazol-5-yl)-2,2-dimethyl-3-oxopropyl)-5-methylpyridin-4-yl)methyl)-8'-methyl-2',3'-dihydrospiro[azetidine-3,4'-pyrido[2,3-b][1,4,5]oxathiazepine]-1-carboxylate 1',1'-dioxide. A solution of (*S)-benzyl 3-(1-ethyl-4-methyl-1H-benzo[d][1,2,3]triazol-5-yl)-3-(4-(hydroxymethyl)-5-methylpyridin-2-yl)-2,2-dimethylpropanoate (200 mg, 0.42 mmol), tert-butyl 8'-methyl-2',3'-dihydrospiro[azetidine-3,4'-pyrido[2,3-b][1,4,5]oxathiazepine]-1-carboxylate 1',1'-dioxide (Intermediate 153, 211 mg, 0.59 mmol), and triphenylphosphine (164 mg, 0.62 mmol) in THF (21 mL) was stirred at room temperature for 5 minutes. DBAD (161 mg, 0.70 mmol) was added and the solution was stirred at room temperature for 30 minutes. The reaction was then concentrated and purified by flash column chromatography (eluent: 0-100% ethyl acetate/hexanes) to afford the title compound (250 mg, 73% yield). MS (ESI): mass calcd. for $C_{43}H_{51}N_7O_7S$, 809.4; m/z found, 810.3 [M+H]⁺.

Step E: (*S)-3-(4-((1-(tert-Butoxycarbonyl)-8'-methyl-1',1'-dioxidospiro[azetidine-3,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)-2,2-dimethylpropanoic acid. A solution of tert-Butyl (*S)-2'-((2-(3-(benzyloxy)-1-(1-ethyl-4-methyl-1H-benzo[d][1,2,3]triazol-5-yl)-2,2-dimethyl-3-oxopropyl)-5-methylpyridin-4-yl)methyl)-8'-methyl-2',3'-dihydrospiro[azetidine-3,4'-pyrido[2,3-b][1,4,5]oxathiazepine]-1-carboxylate 1',1'-dioxide (250 mg, 0.31 mmol) in methanol (31 mL) was subjected to hydrogenation reduction conditions on a continuous flow hydrogenation apparatus, such as the H-Cube® system, at 50° C. (20% Pd(OH)₂/carbon cartridge, flow rate=1 mL/min). Material was circulated through system for roughly 40 min at which time all starting material had been consumed. Solvent was removed and the residue (200 mg, 90%) was carried to next step without further purification. MS (ESI): mass calcd. for $C_{36}H_{45}N_7O_7S$, 719.3; m/z found, 720.3 [M+H]⁺.

Step F: (*S)-3-(1-Ethyl-4-methyl-1H-benzo[d][1,2,3]triazol-5-yl)-2,2-dimethyl-3-(5-methyl-4-((8'-methyl-1',1'-dioxidospiro[azetidine-3,4'-pyrido[2,3-b][1,4,5]oxathiazepin]-2'(3'H)-yl)methyl)pyridin-2-yl)propanoic acid. TFA (7 mL) was added to a solution of (*S)-3-(4-((1-(tert-butoxycarbonyl)-8'-methyl-1',1'-dioxidospiro[azetidine-3,4'-pyrido[2,3-b][1,4,5]oxathiazepin]-2'(3'H)-yl)methyl)-5-methylpyridin-2-yl)-3-(1-ethyl-4-methyl-1H-benzo[d][1,2,3]triazol-5-yl)-2,2-dimethylpropanoic acid (200 mg, 0.28 mmol) in DCM (14 mL). The reaction was stirred at room temperature for one hour. And then concentrated to dryness under reduced pressure. The material was purified by flash column chromatography (eluent: 0-10% MeOH/DCM) to provide the title compound (120 mg, 70% yield). MS (ESI): mass calcd. for $C_{31}H_{37}N_7O_5S$, 619.3; m/z found, 620.3 [M+H]⁺. ¹H NMR (500 MHz, CDCl₃) δ 10.16 (s, 1H), 8.40 (d, J=7.2 Hz, 1H), 8.31 (s, 1H), 8.00-7.96 (m, 1H), 7.71 (d, J=8.9 Hz, 1H), 7.31 (d, J=8.8 Hz, 1H), 4.58 (q, J=7.4 Hz, 3H), 4.42 (d, J=16.8 Hz, 1H), 4.25 (d, J=11.7 Hz, 1H), 4.13 (dd, J=25.9, 13.8 Hz, 3H), 4.06 (s, 1H), 3.94 (d, J=15.4 Hz, 1H), 3.29 (s, 3H), 2.78 (s, 3H), 2.39 (s, 3H), 2.28 (s, 3H), 1.53 (d, J=14.8 Hz, 3H), 1.40-1.31 (m, 6H).

Example 596: (*S)-3-(3-((7'-(2-(3-fluoroazetidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

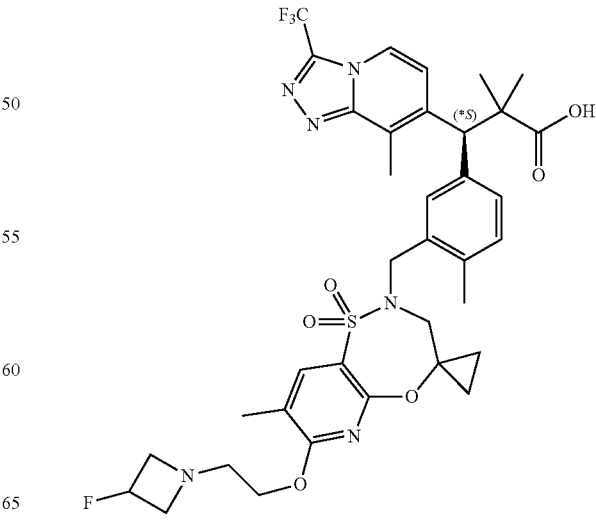

The title compound (36 mg, 63%) was prepared using analogous conditions as described in Example 370 where 7'-(2-(3-fluoroazetidin-1-yl)ethoxy)-8'-methyl-2',3'-dihydrospiro[cyclopropane-1,4'-pyrido[2,3-b][1,4,5]oxathiazepine] 1',1'-dioxide (Intermediate 177) was used instead of 8'-methyl-7'-(2-(pyrrolidin-1-yl)ethoxy)-2,2',3,3',5,6-hexahydrospiro[pyran-4,4'-pyrido[2,3-b][1,4,5]oxathiazepine]1',1'-dioxide (Intermediate 134) in step A. MS (ESI): mass calcd. for $C_{36}H_{40}F_4N_6O_6S$, 760.3; m/z found, 761.1 [M+H]$^+$. $^1$H NMR (400 MHz, DMSO-d$_6$) δ 8.39 (d, J=7.2 Hz, 1H), 7.94 (s, 1H), 7.24 (d, J=7.3 Hz, 1H), 7.19 (dd, J=7.9, 2.0 Hz, 1H), 7.13 (d, J=7.9 Hz, 1H), 7.09 (s, 1H), 5.23-5.19 (m, 0.5H), 5.11-5.07 (m, 0.5H), 4.77 (s, 1H), 4.28-4.23 (m, 2H), 4.16 (q, J=14.5 Hz, 2H), 3.69-3.57 (m, 2H), 3.53-3.13 (m, 4H), 2.82 (t, J=5.3 Hz, 2H), 2.62 (s, 3H), 2.24 (s, 3H), 2.17 (s, 3H), 1.28 (s, 3H), 1.22 (s, 3H), 0.98-0.89 (m, 2H), 0.59-0.44 (m, 2H).

Example 597: (*S)-2,2-dimethyl-3-(4-methyl-3-((8'-methyl-7'-(2-morpholinoethoxy)-1',1'-dioxidospiro[cyclopropane-1,4'-pyrido[2,3-b][1,4,5]oxathiazepin]-2',(3'H)-yl)methyl)phenyl)-3-(8-methyl-3-(trifluoromethyl)-[1,2,4]triazolo[4,3-a]pyridine-7-yl)propanoic Acid

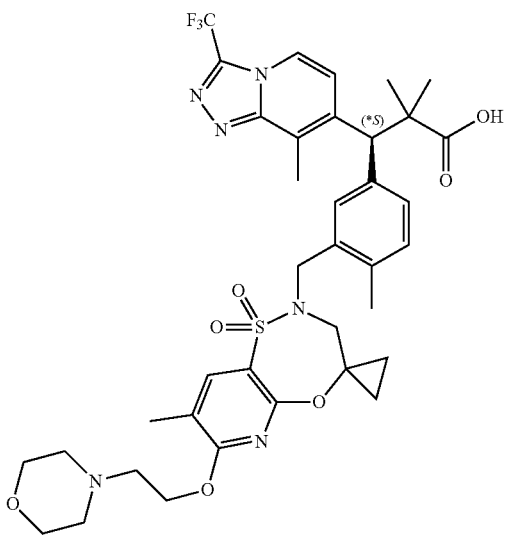 [SMILES: Cc1ccc([C@@H](c2ccn3c(C(F)(F)F)nnc3c2C)C(C)(C)C(=O)O)cc1CN1CC2(CC2)Oc2nc(OCCN3CCOCC3)c(C)cc2S1(=O)=O]

The title compound (250 mg, 55%) was prepared using analogous conditions as described in Example 370 where 8'-methyl-7'-(2-morpholinoethoxy)-2',3'-dihydrospiro[cyclopropane-1,4'-pyrido[2,3-b][1,4,5]oxathiazepine] 1',1'-dioxide (Intermediate 178) was used instead of 8'-methyl-7'-(2-(pyrrolidin-1-yl)ethoxy)-2,2',3,3',5,6-hexahydrospiro[pyran-4,4'-pyrido[2,3-b][1,4,5]oxathiazepine]1',1'-dioxide (Intermediate 134) in step A. MS (ESI): mass calcd. for $C_{37}H_{43}F_3N_6O_7S$, 772.3; m/z found, 773.3 [M+H]$^+$. $^1$H NMR (400 MHz, DMSO-d$_6$) δ 8.39 (d, J=7.2 Hz, 1H), 7.94 (d, J=1.0 Hz, 1H), 7.25 (d, J=7.4 Hz, 1H), 7.19 (dd, J=7.9, 1.9 Hz, 1H), 7.13 (d, J=7.9 Hz, 1H), 7.10-7.07 (m, 1H), 4.77 (s, 1H), 4.38 (t, J=5.8 Hz, 2H), 4.25-4.08 (m, 2H), 3.58-3.54 (m, 4H), 3.51-3.25 (m, 2H), 2.69 (t, J=5.8 Hz, 2H), 2.62 (s, 3H), 2.49-2.42 (m, 4H), 2.25 (s, 3H), 2.16 (s, 3H), 1.28 (s, 3H), 1.21 (s, 3H), 1.01-0.88 (m, 2H), 0.59-0.43 (m, 2H).

Example 598: (*S)-3-(3-((1',1'-dioxido-7'-(2-(pyrrolidine-1-yl)ethoxy)spiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

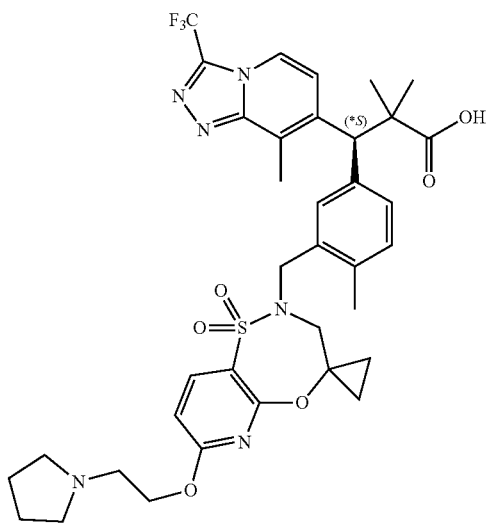 [SMILES: Cc1ccc([C@@H](c2ccn3c(C(F)(F)F)nnc3c2C)C(C)(C)C(=O)O)cc1CN1CC2(CC2)Oc2nc(OCCN3CCCC3)ccc2S1(=O)=O]

The title compound (45 mg, 51%) was prepared using analogous conditions as described in Example 370 where 7'-(2-(pyrrolidin-1-yl)ethoxy)-2',3'-dihydrospiro[cyclopropane-1,4'-pyrido[2,3-b][1,4,5]oxathiazepine] 1',1'-dioxide (Intermediate 179) was used instead of 8'-methyl-7'-(2-(pyrrolidin-1-yl)ethoxy)-2,2',3,3',5,6-hexahydrospiro[pyran-4,4'-pyrido[2,3-b][1,4,5]oxathiazepine]1',1'-dioxide (Intermediate 134) in step A. MS (ESI): mass calcd. for $C_{36}H_{41}F_3N_6O_6S$, 742.3; m/z found, 743.3 [M+H]$^+$. $^1$H NMR (400 MHz, DMSO-d$_6$) δ 8.40 (d, J=7.3 Hz, 1H), 8.07 (d, J=8.4 Hz, 1H), 7.26 (d, J=7.4 Hz, 1H), 7.22-7.16 (m, 1H), 7.16-7.07 (m, 2H), 6.84 (d, J=8.4 Hz, 1H), 4.76 (s, 1H), 4.35 (t, J=5.7 Hz, 2H), 4.27-4.08 (m, 2H), 3.65-3.07 (m, 5H), 2.77 (t, J=5.8 Hz, 2H), 2.62 (s, 3H), 2.24 (s, 3H), 1.71-1.65 (m, 4H), 1.33-1.14 (m, 7H), 0.97-0.93 (s, 2H), 0.61-0.50 (m, 2H).

Example 599: (*S)-3-(3-((7'-(3-amino-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

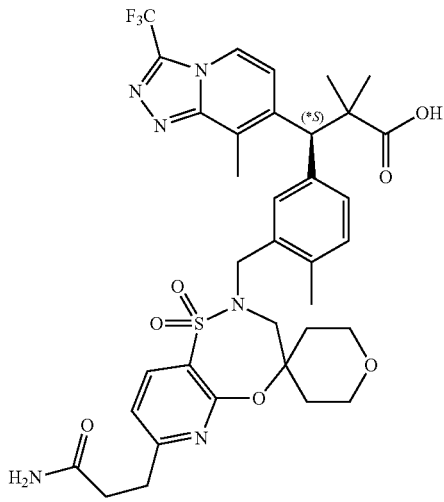 [SMILES: Cc1ccc([C@@H](c2ccn3c(C(F)(F)F)nnc3c2C)C(C)(C)C(=O)O)cc1CN1CC2(CCOCC2)Oc2nc(CCC(N)=O)ccc2S1(=O)=O]

Step A: Benzyl (*S)-3-(3-((7'-(3-(tert-butoxy)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate. To a solution of benzyl (*S)-3-(3-(hydroxymethyl)-4-methylphenyl)-2,2-dimethyl-3-(8-methyl-3-(trifluoromethyl)-[1,2,4]triazolo[4,3-a]pyridine-7-yl)propanoate (860 mg, 1.68 mmol, Intermediate 71), tert-butyl 3-(1',1'-dioxido-2,2',3,3',5,6-hexahydrospiro[pyran-4,4'-pyrido[2,3-b][1,4,5 [oxathiazepin]-7'-yl)propanoate (953 mg, 2.36 mmol, Intermediate 180), PPh₃ (652 mg, 2.49 mmol) in a 1:1 mix of THF (13.5 mL)/DMF (13.5 mL) at room temperature was added DIAD (0.56 mL, 2.84 mmol). The mixture was stirred for 45 min. at room temperature and then poured into saturated bicarbonate and extracted with ethyl acetate (3×). These extractions resulted in several fractions that were combined, dried over sodium sulfate and concentrated to dryness under reduced pressure. The residue was purified by flash chromatography (eluent: ethyl acetate/hexanes, 0:1 to 70:30, gradient) to give the title compound (1225 mg, 82%). MS (ESI): mass calcd. for $C_{46}H_{52}F_3N_5O_8S$, 891.3; m/z found, 892.4 [M+H]⁺. ¹H NMR (600 MHz, DMSO-d₆) δ 8.26 (d, J=7.4 Hz, 1H), 8.05 (d, J=7.7 Hz, 1H), 7.30 (d, J=7.8 Hz, 1H), 7.22 (d, J=7.3 Hz, 1H), 7.21-7.16 (m, 2H), 7.13-7.03 (m, 6H), 5.09 (d, J=12.2 Hz, 1H), 4.92 (d, J=12.2 Hz, 1H), 4.75 (s, 1H), 4.41-4.32 (m, 2H), 3.81-3.69 (m, 2H), 3.35 (d, J=1.8 Hz, 4H), 3.00 (t, J=7.0 Hz, 2H), 2.65 (t, J=7.0 Hz, 2H), 2.54 (s, 3H), 2.16 (s, 3H), 1.49-1.29 (m, 19H).

Step B: (*S)-3-(2'-(5-(3-benzyloxy)-2,2-dimethyl-1-(8-methyl-3-(trifluoromethyl)-[1,2,4]triazolo[4,3-a]pyridine-7-yl)-3-oxopropyl)-2-methylbenzyl)-1',1'-dioxido-2,2',3,3',5,6-hexahydrospiro[pyran-4,4'-pyrido[2,3-b][1,4,5]oxathiazepin]-7'-yl)propanoic acid. Benzyl (*S)-3-(3-((7'-(3-(tert-butoxy)-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate (500 mg, 0.56 mmol) was dissolved in a 1:1 mixture of DCM (2.5 mL) and TFA (2.5 mL) and allowed to stir at room temperature for 1 h. The solvent was then removed under reduced pressure and the resulting residue dissolved in a 1:1 mixture of MeCN/DCM, which was removed under reduced pressure to give the title compound (561 mg, 105%). This material was used in the next step without purification. ¹H NMR (600 MHz, DMSO-d₆) δ 8.17 (d, J=7.3 Hz, 1H), 7.96 (d, J=7.8 Hz, 1H), 7.21 (d, J=7.8 Hz, 1H), 7.16-7.06 (m, 3H), 7.05-6.91 (m, 6H), 5.66 (s, 2H), 5.00 (d, J=12.2 Hz, 1H), 4.83 (d, J=12.2 Hz, 1H), 4.66 (s, 1H), 4.28 (s, 2H), 3.72-3.50 (m, 2H), 3.40-3.25 (m, 3H), 2.92 (t, J=7.1 Hz, 2H), 2.60 (t, J=7.1 Hz, 2H), 2.45 (s, 3H), 2.08 (s, 3H), 1.42-1.20 (m, 9H).

Step C: Benzyl (*S)-3-(3-((7'-(3-amino-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate. TEA (0.14 mL, 1.0 mmol) was added to a solution of (*S)-3-(2'-(5-(3-benzyloxy)-2,2-dimethyl-1-(8-methyl-3-(trifluoromethyl)-[1,2,4]triazolo[4,3-a]pyridine-7-yl)-3-oxopropyl)-2-methylbenzyl)-1',1'-dioxido-2,2',3,3',5,6-hexahydrospiro[pyran-4,4'-pyrido[2,3-b][1,4,5]oxathiazepin]-7'-yl)propanoic acid (167 mg, 0.20 mmol), ammonium chloride (107 mg, 2.0 mmol), and HATU (228 mg, 0.60 mmol) in DCM (5.0 mL). After stirring at room temperature for 24 h the reaction mixture was poured into saturated, aqueous sodium chloride and extracted with ethyl acetate (3×). These extractions resulted in several fractions that were combined, dried over sodium sulfate and concentrated to dryness under reduced pressure. The residue was purified by flash chromatography (eluent: MeOH/DCM, 0:1 to 15:85, gradient) to give the title compound (46 mg, 28%). MS (ESI): mass calcd. for $C_{42}H_{45}F_3N_6O_7S$, 834.3; m/z found, 835.2 [M+H]⁺.

Step D: (*S)-3-(3-((7'-(3-amino-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid. The title compound (39 mg, 95%) was prepared using analogous conditions as described in Example 126, where benzyl (*S)-3-(3-((7'-(3-amino-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate was used instead of benzyl (*S)-2,2-dimethyl-3-(4-methyl-3-((8'-methyl-1',1'-dioxido-7'-(2-(piperidin-1-yl)ethyoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoate in step B. MS (ESI): mass calcd. for $C_{35}H_{39}F_3N_6O_7S$, 744.3; m/z found, 745.2 [M+H]⁺. ¹H NMR (400 MHz, DMSO-d₆) δ 8.42 (d, J=7.2 Hz, 1H), 8.04 (d, J=7.8 Hz, 1H), 7.36 (s, 1H), 7.31-7.21 (m, 4H), 7.14 (d, J=7.8 Hz, 1H), 6.76 (s, 1H), 4.81 (s, 1H), 4.50-4.30 (m, 2H), 3.81-3.72 (m, 2H), 3.51-3.37 (m, 3H), 3.35-3.26 (m, 3H), 2.96 (t, J=7.5 Hz, 2H), 2.66 (s, 3H), 2.18 (s, 3H), 1.47-1.34 (m, 4H), 1.32 (s, 3H), 1.27 (s, 3H).

Example 600: (*S)-2,2-Dimethyl-3-(4-methyl-3-((8'-methyl-1',1'-dioxido-7'-((1-(piperidin-1-yl)propan-2-yl)oxy)-2,3,5,6-tetrahydrospiro[pyran-4,4'-pyrido[2,3-b][1,4,5]oxathiazepin]-2',(3'H)-yl)methyl)phenyl)-3-(8-methyl-3-(trifluoromethyl)-[1,2,4]triazolo[4,3-a]pyridine-7-yl)propanoic Acid

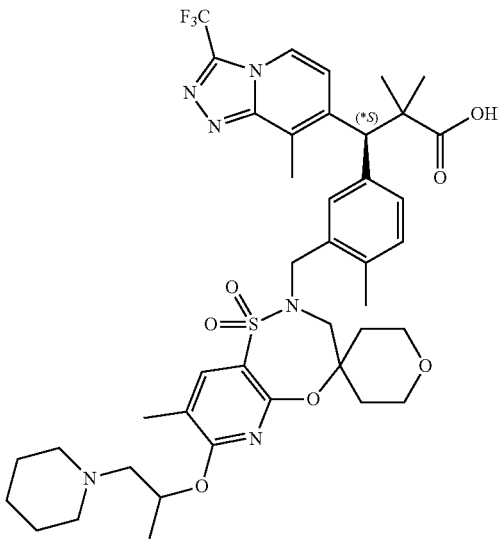 [SMILES: Cc1ccc([C@@H](c2ccn3c(C(F)(F)F)nnc3c2C)C(C)(C)C(=O)O)cc1CN1CC2(CCOCC2)Oc2nc(OC(C)CN3CCCCC3)c(C)cc2S1(=O)=O]

Step A: (*S) tert-butyl 2,2-dimethyl-3-(4-methyl-3-((8-methyl-1',1'-dioxido-7'-((1-(piperidin-1-yl)propane-2-yl)oxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoate. The title compound (214 mg, 68%) was prepared using analogous conditions as described in Example 126) where 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide (Intermediate 181) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide (Intermediate 72) and tert-butyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 128) instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 71) in step A. MS (ESI): mass calcd. for $C_{45}H_{59}F_3N_6O_7S$, 884.4; m/z found, 885.3 [M+H]⁺.

Step B: (*S)-2,2-Dimethyl-3-(4-methyl-3-((8'-methyl-1',1'-dioxido-7'-((1-(piperidin-1-yl)propan-2-yl)oxy)-2,3,5,6-tetrahydrospiro[pyran-4,4'-pyrido[2,3-b][1,4,5]oxathiazepin]-2',(3'H)-yl)methyl)phenyl)-3-(8-methyl-3-(trifluoromethyl)-[1,2,4]triazolo[4,3-a]pyridine-7-yl)propanoic acid. The title compound (115 mg, 57%) was prepared using analogous conditions as described in Example 370) where tert-butyl 2,2-dimethyl-3-(4-methyl-3-((8-methyl-1',1'-dioxido-7'-((1-(piperidin-1-yl)propane-2-yl)oxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoate was used instead of tert-butyl (*R)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a][pyridine-7-yl)propanoate in Step B. MS (ESI): mass calcd. for $C_{41}H_{51}F_3N_6O_7S$, 828.3; m/z found, 829.2 [M+H]⁺. ¹H NMR (400 MHz, DMSO-d₆) δ 8.41 (d, J=7.2 Hz, 1H), 7.84 (s, 1H), 7.31-7.19 (m, 3H), 7.15 (dd, J=8.0, 2.7 Hz, 1H), 5.32-5.26 (m, 1H), 4.81 (s, 1H), 4.50-4.27 (m, 2H), 3.82-3.69 (m, 2H), 3.51-3.25 (m, 3H), 2.66 (d, J=2.0 Hz, 3H), 2.60 (ddd, J=13.0, 6.3, 2.0 Hz, 1H), 2.47-2.36 (m, 5H), 2.19 (d, J=1.9 Hz, 3H), 2.12 (s, 3H), 1.57-1.21 (m, 20H).

Example 601: (*S)-2,2-Dimethyl-3-(4-methyl-3-((8'-methyl-1',1'-dioxido-7'-(((*R)-1-(piperidin-1-yl)propan-2-yl)oxy)-2,3,5,6-tetrahydrospiro[pyran-4,4'-pyrido[2,3-b][1,4,5]oxathiazepin]-2',(3'H)-yl)methyl)phenyl)-3-(8-methyl-3-(trifluoromethyl)-[1,2,4]triazolo[4,3-a]pyridine-7-yl)propanoic Acid

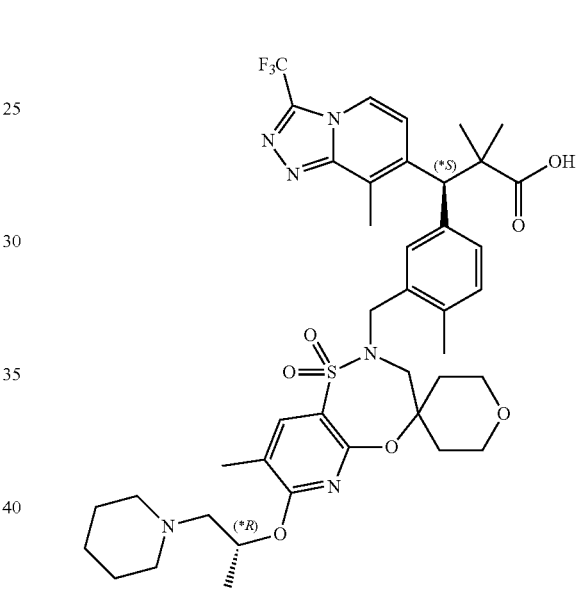

The mixture of (*S)-2,2-dimethyl-3-(4-methyl-3-((8'-methyl-1',1'-dioxido-7'-((1-(piperidin-1-yl)propan-2-yl)oxy)-2,3,5,6-tetrahydrospiro[pyran-4,4'-pyrido[2,3-b][1,4,5]oxathiazepin]-2',(3'H)-yl)methyl)phenyl)-3-(8-methyl-3-(trifluoromethyl)-[1,2,4]triazolo[4,3-a]pyridine-7-yl) propanoic acid isomers (Example 600) were separated by chiral SFC (Stationary phase: Chiracel OJ-H 5 µm 250*30 mm, Mobile phase: 90% $CO_2$, 10% EtOH (w/0.3% i-PrNH₂)) to afford two diastereomers. The first eluting isomer (45 mg) was designated (*R): MS (ESI): mass calcd. for $C_{41}H_{51}F_3N_6O_7S$, 828.3; m/z found, 829.2 [M+H]⁺. ¹H NMR (400 MHz, DMSO-d₆) δ 8.37 (d, J=7.2 Hz, 1H), 7.84 (d, J=0.9 Hz, 1H), 7.32 (d, J=7.3 Hz, 1H), 7.27 (dd, J=7.9, 1.9 Hz, 1H), 7.16 (d, J=2.0 Hz, 1H), 7.12 (d, J=7.9 Hz, 1H), 4.80 (s, 1H), 4.42 (d, J=15.2 Hz, 1H), 4.30 (d, J=15.1 Hz, 1H), 3.74 (q, J=10.6 Hz, 2H), 3.52-3.08 (m, 4H), 2.65-2.54 (m, 4H), 2.45-2.37 (m, 5H), 2.19 (s, 3H), 2.12 (s, 3H), 1.56-1.40 (m, 6H), 1.39-1.13 (m, 14H).

861

Example 602: (*S)-2,2-Dimethyl-3-(4-methyl-3-((8'-methyl-1',1'-dioxido-7'-(((*S)-1-(piperidin-1-yl)propan-2-yl)oxy)-2,3,5,6-tetrahydrospiro[pyran-4,4'-pyrido[2,3-b][1,4,5]oxathiazepin]-2',(3'H)-yl)methyl)phenyl)-3-(8-methyl-3-(trifluoromethyl)-[1,2,4]triazolo[4,3-a]pyridine-7-yl)propanoic Acid

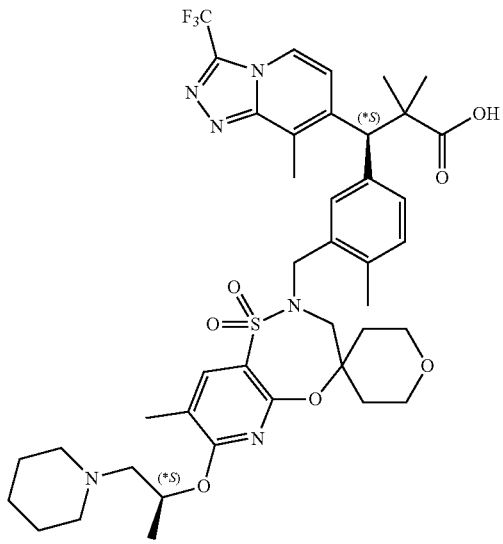 [SMILES: Cc1ccc([C@@H](c2ccn3c(C(F)(F)F)nnc3c2C)C(C)(C)C(=O)O)cc1CN1CC2(CCOCC2)Oc2nc(O[C@@H](C)CN3CCCCC3)c(C)cc2S1(=O)=O]

The mixture of (*S)-2,2-dimethyl-3-(4-methyl-3-((8'-methyl-1',1'-dioxido-7'-((1-(piperidin-1-yl)propan-2-yl)oxy)-2,3,5,6-tetrahydrospiro[pyran-4,4'-pyrido[2,3-b][1,4,5]oxathiazepin]-2',(3'H)-yl)methyl)phenyl)-3-(8-methyl-3-(trifluoromethyl)-[1,2,4]triazolo[4,3-a]pyridine-7-yl)propanoic acid isomers (Example 600) were separated by chiral SFC (Stationary phase: Chiracel OJ-H 5 μm 250*30 mm, Mobile phase: 90% $CO_2$, 10% EtOH (w/0.3% i-$PrNH_2$)) to afford two diastereomers. The second eluting isomer (43 mg) was designated (*S): MS (ESI): mass calcd. for $C_{41}H_{51}F_3N_6O_7S$, 828.3; m/z found, 829.2 [M+H]$^+$. $^1$H NMR (400 MHz, DMSO-$d_6$) δ 8.37 (d, J=7.2 Hz, 1H), 7.84 (d, J=1.0 Hz, 1H), 7.34 (d, J=7.3 Hz, 1H), 7.26 (dd, J=7.9, 1.9 Hz, 1H), 7.17 (d, J=1.9 Hz, 1H), 7.11 (d, J=7.9 Hz, 1H), 4.80 (s, 1H), 4.42-4.31 (m, 2H), 3.74 (dd, J=11.6, 8.9 Hz, 2H), 3.55-3.07 (m, 4H), 2.65-2.55 (m, 4H), 2.44-2.38 (m, 5H), 2.19 (s, 3H), 2.12 (s, 3H), 1.54-1.40 (m, 6H), 1.39-1.15 (m, 14H).

862

Example 603: (*R)-2,2-Dimethyl-3-(4-methyl-3-((8'-methyl-1',1'-dioxido-7'-(((*R)-1-(piperidin-1-yl)propan-2-yl)amino)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

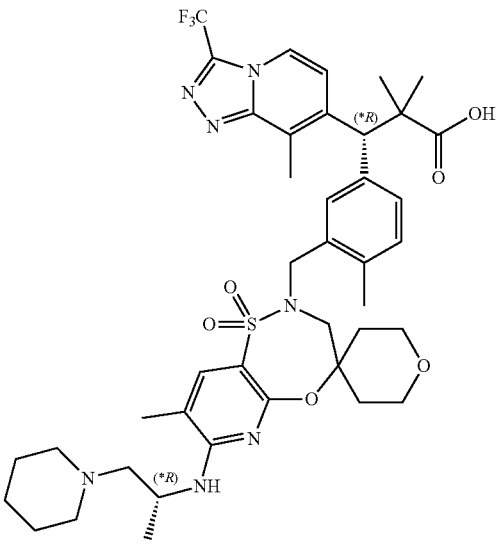 [SMILES: Cc1ccc([C@H](c2ccn3c(C(F)(F)F)nnc3c2C)C(C)(C)C(=O)O)cc1CN1CC2(CCOCC2)Oc2nc(N[C@H](C)CN3CCCCC3)c(C)cc2S1(=O)=O]

The mixture of (*R)-2,2-dimethyl-3-(4-methyl-3-((8'-methyl-1',1'-dioxido-7'-((1-piperidin-1-yl)propan-2-yl)amino)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl) propanoic acid (Example 376) isomers were separated by chiral SFC (Stationary phase: Chiralpak IG 5 μm 250*30 mm, Mobile phase: 55% $CO_2$, 45% MeOH (w/0.3% i-$PrNH_2$)) to afford two diastereomers. The second eluting isomer, designated as (*S), was not isolated. The first eluting isomer (40 mg) was designated (*R): $^1$H NMR (400 MHz, DMSO-$d_6$) δ 8.34 (d, J=7.2 Hz, 1H), 7.48 (d, J=0.9 Hz, 1H), 7.34 (d, J=7.3 Hz, 1H), 7.25 (dd, J=7.8, 1.9 Hz, 1H), 7.14 (d, J=2.0 Hz, 1H), 7.10 (d, J=7.9 Hz, 1H), 6.32 (d, J=7.3 Hz, 1H), 4.79 (s, 1H), 4.40-4.16 (m, 3H), 3.83-3.73 (m, 2H), 3.50-3.08 (m, 3H), 2.60 (s, 3H), 2.47-2.38 (m, 3H), 2.37-2.28 (m, 2H), 2.28-2.16 (m, 4H), 2.05 (s, 3H), 1.51-1.42 (m, 6H), 1.41-1.11 (m, 14H).

Example 604: (*S)-3-(3-((7'-(2-(Azetidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

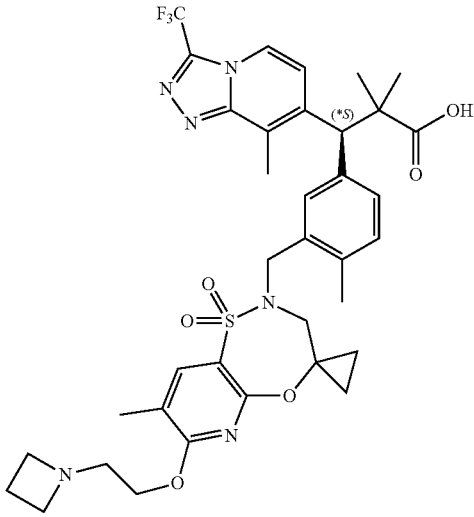 [SMILES: Cc1ccc([C@@H](c2ccn3c(C(F)(F)F)nnc3c2C)C(C)(C)C(=O)O)cc1CN1CC2(CC2)Oc2nc(OCCN3CCC3)c(C)cc2S1(=O)=O]

The title compound (44 mg, 59%) was prepared using analogous conditions as described in Example 370) where 7'-(2-azetidin-1-yl)ethoxy)-8'-methyl-2',3'-dihydrospiro[cyclopropane-1,4'-pyrido[2,3-b][1,4,5]oxathiazepine] 1',1'-dioxide (Intermediate 182) was used instead of 8'-methyl-7'-(2-(pyrrolidin-1-yl)ethoxy)-2,2',3,3',5,6-hexahydrospiro[pyran-4,4'-pyrido[2,3-b][1,4,5]oxathiazepine]1',1'-dioxide (Intermediate 134) in step A. MS (ESI): mass calcd. for $C_{36}H_{41}F_3N_6O_6S$, 742.3; m/z found, 743.3 [M+H]$^+$. $^1$H NMR (400 MHz, DMSO-d$_6$) δ 8.39 (d, J=7.2 Hz, 1H), 7.93 (d, J=0.9 Hz, 1H), 7.25 (d, J=7.3 Hz, 1H), 7.22-7.16 (m, 1H), 7.15-7.04 (m, 2H), 4.76 (s, 1H), 4.26-4.09 (m, 4H), 3.50-3.14 (m, 6H), 2.75-2.65 (m, 2H), 2.61 (s, 3H), 2.24 (s, 3H), 2.15 (s, 3H), 1.97 (p, J=6.9 Hz, 2H), 1.33-1.11 (m, 6H), 0.93 (s, 2H), 0.59-0.42 (m, 2H).

Example 605: (*S)-3-(3-((7'-(3-Cyclobutylamino-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

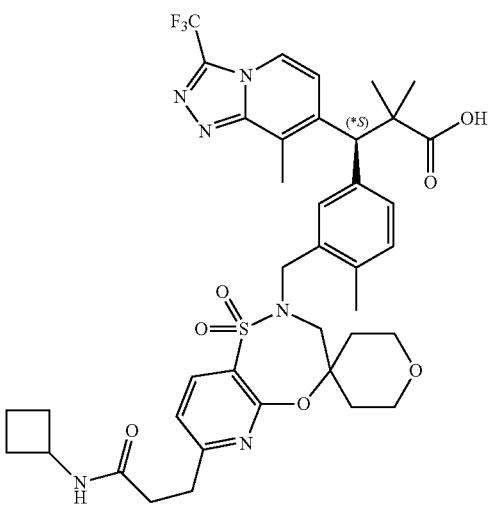 [SMILES: Cc1ccc([C@@H](c2ccn3c(C(F)(F)F)nnc3c2C)C(C)(C)C(=O)O)cc1CN1CC2(CCOCC2)Oc2nc(CCC(=O)NC3CCC3)ccc2S1(=O)=O]

Step A: Benzyl (*S)-3-(3-((7'-(3-cyclobutylamino-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate. To a solution of (*S)-3-(2'-(5-(3-benzyloxy)-2,2-dimethyl-1-(8-methyl-3-(trifluoromethyl)-[1,2,4]triazolo[4,3-a]pyridine-7-yl)-3-oxopropyl)-2-methylbenzyl)-1',1'-dioxido-2,2',3,3',5,6-hexahydrospiro[pyran-4,4'-pyrido[2,3-b][1,4,5]oxathiazepin]-7'-yl)propanoic acid (400 mg, 0.45 mmol, Example 599, Step B), and HATU (364 mg, 0.98 mmol) in DMF (8.0 mL) was added cyclobutyl amine (102 mg, 1.4 mmol) followed by TEA (0.21 mL, 1.5 mmol). After stirring at room temperature for 18 h. the reaction was poured into water and extracted with ethyl acetate (3×). These extractions resulted in several fractions that were combined, dried over sodium sulfate and concentrated to dryness under reduced pressure. The residue was purified by flash chromatography (eluent: ethyl acetate/hexanes, 0:1 to 1:0, gradient) to give the title compound (204 mg, 48%). MS (ESI): mass calcd. for $C_{46}H_{51}F_3N_6O_7S$, 888.3; m/z found, 889.2 [M+H]$^+$.

Step B: (*S)-3-(3-((7'-(3-cyclobutylamino-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid. The title compound (90 mg, 49%) was prepared using analogous conditions as described in Example 126 where benzyl (*S)-3-(3-((7'-(3-cyclobutylamino-3-oxopropyl)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate was used instead of benzyl (*S)-2,2-dimethyl-3-(4-methyl-3-((8'-methyl-1',1'-dioxido-7'-(2-(piperidin-1-yl)ethyoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl]propanoate in Step B. MS (ESI): mass calcd. for $C_{39}H_{51}F_3N_6O_7S$, 798.3; m/z found, 799.2 [M+H]$^+$. $^1$H NMR (400 MHz, DMSO-d$_6$) δ 8.41 (d, J=7.2 Hz, 1H), 8.13 (d, J=7.7 Hz, 1H), 8.03 (d, J=7.8 Hz, 1H), 7.33-7.20 (m, 4H), 7.14 (d, J=7.9 Hz, 1H), 4.81 (s, 1H), 4.45 (d, J=15.5 Hz, 1H), 4.34 (d, J=15.5 Hz, 1H), 4.23-4.10 (m, 1H), 3.74 (q, J=10.3 Hz, 2H), 3.52-3.24 (m, 4H), 2.99-2.93 (m, 2H), 2.65 (s, 3H), 2.51-2.44 (m, 2H), 2.21-2.08 (m, 5H), 1.91-1.77 (m, 2H), 1.66-1.54 (m, 2H), 1.46-1.28 (m, 7H), 1.25 (s, 3H).

Example 606: (*S)-3-(3-((7'-(2-Hydroxyethoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

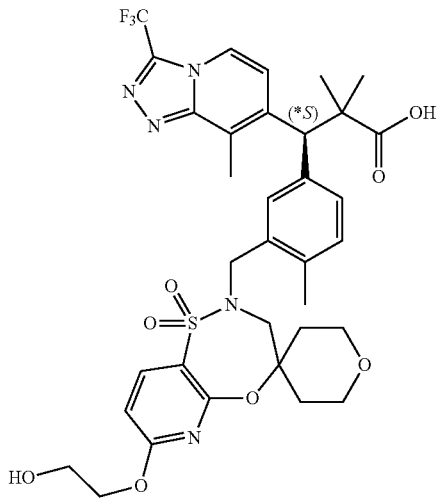 [SMILES: Cc1ccc([C@@H](c2ccn3c(C(F)(F)F)nnc3c2C)C(C)(C)C(=O)O)cc1CN1CC2(CCOCC2)Oc2nc(OCCO)ccc2S1(=O)=O]

Step A: Methyl (*S)-3-(3-((7'-(2-hydroxyethoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate. DIAD (0.08 mL, 0.41 mmol) was added to a solution of methyl (*S)-3-(3-hydroxymethyl)-4-methylphenyl)-2,2-dimethyl-3-(8-methyl-3-(trifluoromethyl)-[1,2,4]triazolo[4,3-a]pyridine-7-yl)propanoate (100 mg, 0.23 mmol, Intermediate 145), 7'-(2-hydroxyethoxy)-2,2',3,3',5,6-hexahydrospiro[pyran-4,4'-pyrido[2,3-b][1,4,5]oxathiazepine]1',1'-dioxide (106 mg, 0.31 mmol Intermediate 183) and PPh$_3$ (89 mg, 0.34 mmol) in a mixture of THF (3.0 mL) and DMF (1.0 mL) at room temperature After stirring for 45 minutes the reaction was poured into saturated bicarbonate and extracted with ethyl acetate (3×). These extractions resulted in several fractions that were combine, dried over sodium sulfate and concentrated to dryness under reduced pressure. The residue was purified by flash chromatography (eluent: ethyl acetate/hexanes, 0:1 to 1:0, gradient) to give the title compound (114 mg, 66%). MS (ESI): mass calcd. for C$_{35}$H$_{40}$F$_3$N$_5$O$_8$S, 747.2; m/z found, 748.2 [M+H]$^+$. $^1$H NMR (400 MHz, DMSO-d$_6$) δ 8.41 (d, J=7.2 Hz, 1H), 8.01 (dd, J=8.5, 1.4 Hz, 1H), 7.24-7.17 (m, 3H), 7.14 (d, J=7.7 Hz, 1H), 6.78 (dd, J=8.3, 1.3 Hz, 1H), 5.76 (d, J=1.3 Hz, 1H), 4.89 (t, J=5.6 Hz, 1H), 4.80 (s, 1H), 4.50-4.26 (m, 4H), 3.55 (s, 3H), 3.53-3.34 (m, 4H), 3.32 (d, J=1.3 Hz, 5H), 2.68 (s, 3H), 2.18 (s, 3H), 1.59-1.37 (m, 4H), 1.36 (s, 3H), 1.30 (s, 3H).

Step B: (*S)-3-(3-((7'-(2-hydroxyethoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid. methyl (*S)-3-(3-((7'-(2-hydroxyethoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoate (106 mg, 0.14 mmol) was dissolved in MeOH (1.2 mL), THF (1.2 mL) and 2M aqueous LiOH (0.5 mL) and heated to 60° C. for 18 h. The reaction was cooled, pH adjusted to ~5.0 with 1N HCl and extracted with ethyl acetate (4×). These extractions resulted in several fractions that were combined, dried over sodium sulfate and concentrated to dryness under reduced pressure. The residue was purified by reverse phase HPLC (eluent: MeCN/H$_2$O w/20 mM NH$_4$OH, 0:1 to 70:30, gradient) to give the title compound (30 mg, 29%). MS (ESI): mass calcd. for C$_{34}$H$_{38}$F$_3$N$_5$O$_8$S, 733.2; m/z found, 734.2 [M+H]$^+$. $^1$H NMR (400 MHz, DMSO-d$_6$) δ 8.34 (d, J=7.2 Hz, 1H), 7.93 (d, J=8.4 Hz, 1H), 7.23-7.16 (m, 2H), 7.13 (d, J=2.0 Hz, 1H), 7.07 (d, J=8.1 Hz, 1H), 6.70 (d, J=8.4 Hz, 1H), 4.80 (s, 1H), 4.73 (s, 1H), 4.37 (d, J=15.4 Hz, 1H), 4.29-4.20 (m, 3H), 3.65 (q, J=7.4, 5.7 Hz, 4H), 3.37 (t, J=13.8 Hz, 3H), 2.58 (s, 3H), 2.11 (s, 3H), 1.41 (s, 2H), 1.24 (s, 5H), 1.18 (s, 4H).

Example 607: (*S)-3-(3-((7'-(3-(3-Hydroxypropoxy)propoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

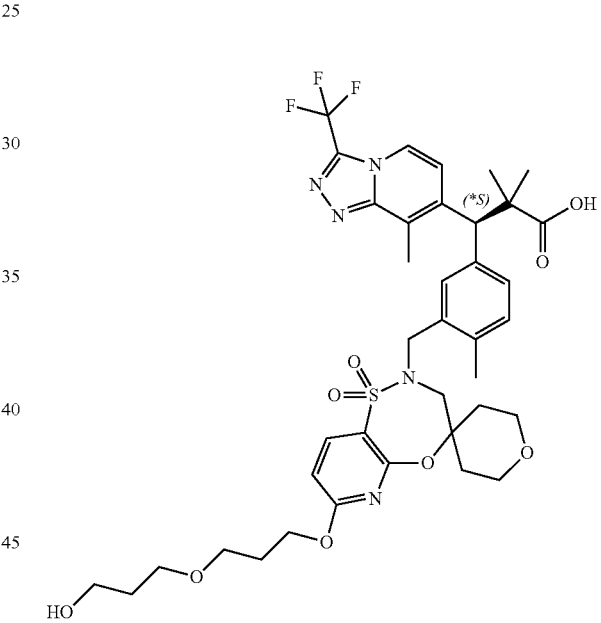

Step A: (*S)-Methyl 3-(3-((7'-(3-(3-hydroxypropoxy)propoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate. A solution consisting of (*S)-methyl 3-(3-(chloromethyl)-4-methylphenyl)-2,2-dimethyl-3-(8-methyl-3-(trifluoromethyl)-[1,2,4]triazolo[4,3-a]pyridin-7-yl)propanoate (Intermediate 160, 250 mg) and CH$_3$CN (5 mL) was added dropwise to a 0° C. (ice/water) mixture consisting of 7'-(3-(3-hydroxypropoxy)propoxy)-2,2',3,3',5,6-hexahydrospiro[pyran-4,4'-pyrido[2,3-b][1,4,5]oxathiazepine]1',1'-dioxide (Intermediate 187, 200 mg, 0.55 mmol), K$_2$CO$_3$ (200 mg, 1.45 mmol), and CH$_3$CN (5 mL). The resultant mixture was stirred at 90° C. for 2 hours, then was poured into water (20 mL) and extracted with ethyl acetate (30 mL×3). These organic solvent fractions were combined, dried over anhydrous Na$_2$SO$_4$, filtered, and concentrated to dryness under reduced pressure to afford the product, which was purified by FCC (eluent:petroleum ether/ethyl acetate=50:1 to 5:1) to afford the title compound (200 mg, 47.6%) as a gray solid. MS (ESI): mass calcd. for $C_{39}H_{48}F_3N_5O_9S$, 819.31; m/z found, 820.2 [M+H]$^+$.

Step B: (*S)-3-(3-((7'-(3-(3-Hydroxypropoxy)propoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. LiOH*H$_2$O (100 mg, 2.38 mmol) was added into to a mixture consisting of (*S)-methyl 3-(3-((7'-(3-(3-hydroxypropoxy)propoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate (200 mg, 0.244 mmol), MeOH (2 mL), THF (2 mL), and H$_2$O (2 mL). The resultant mixture was stirred at 65° C. for 12 hours, then was concentrated to dryness under reduced pressure and adjusted to pH=3-4 with 1 N HCl (2 mL). The mixture was concentrated to dryness under reduced pressure, then purified by preparative acidic HPLC (Xtimate C18, 150 mm×25 mm×5 μm column (eluent: 50% to 64% (v/v) CH$_3$CN and H$_2$O with 0.225% HCOOH)) to give the title compound (81.1 mg, 67.6%) as a white solid. MS (ESI): mass calcd. for $C_{38}H_{46}F_3N_5O_9S$, 805.30; m/z found, 806.3 [M+H]$^+$. $^1$H NMR (400 MHz, DMSO-d$_6$) δ 12.53 (br. s, 1H), 8.42 (d, J=7.2 Hz, 1H), 8.00 (d, J=8.8 Hz, 1H), 7.29-7.24 (m, 2H), 7.22 (s, 1H), 7.15 (d, J=8.0 Hz, 1H), 6.76 (d, J=8.8 Hz, 1H), 4.81 (s, 1H), 4.48-4.41 (m, 1H), 4.37-4.28 (m, 3H), 3.88-3.65 (m, 2H), 3.56-3.39 (m, 9H), 2.66 (s, 3H), 2.19 (s, 3H), 2.03-1.88 (m, 2H), 1.72-1.57 (m, 2H), 1.56-1.46 (m, 2H), 1.45-1.33 (m, 2H), 1.32 (s, 3H), 1.26 (s, 3H).

Example 608: (*R)-3-(3-((7'-(3-(3-Hydroxypropoxy)propoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic Acid

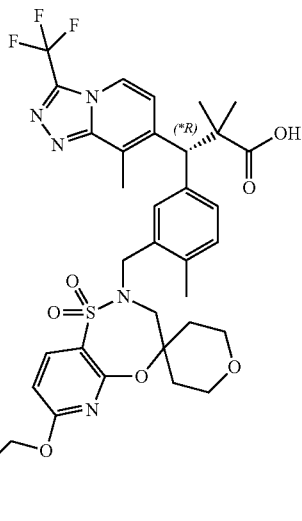

Step A: (*R)-Methyl 3-(3-((7'-(3-(3-hydroxypropoxy)propoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate. 7'-(3-(3-Hydroxypropoxy)propoxy)-2,2',3,3',5,6-hexahydrospiro[pyran-4,4'-pyrido[2,3-b][1,4,5]oxathiazepine] 1',1'-dioxide (Intermediate 187, 185 mg, 0.460 mmol), (*R)-methyl 3-(3-(chloromethyl)-4-methylphenyl)-2,2-dimethyl-3-(8-methyl-3-(trifluoromethyl)-[1,2,4]triazolo[4,3-a]pyridin-7-yl)propanoate (Intermediate 161210 mg, 0.463 mmol), K$_2$CO$_3$ (250 mg, 1.81 mmol), and CH$_3$CN (6 mL) were combined. The resultant mixture was stirred at 50° C. for 5 hours, then was concentrated to dryness under reduced pressure and purified by FCC (eluent: petroleum ether/ethyl acetate=1:0 to 3:1) to afford the title compound (265 mg, 70%) as a yellow solid, which was used in the next step without further purification. MS (ESI): mass calcd. for $C_{39}H_{48}F_3N_5O_9S$, 819.31; m/z found, 820.3 [M+H]$^+$.

Step B: (*R)-3-(3-((7'-(3-(3-Hydroxypropoxy)propoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoic acid. (*R)-Methyl 3-(3-((7'-(3-(3-hydroxypropoxy)propoxy)-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate (265 mg, 0.323 mmol) was added to a solution consisting of LiOH*H$_2$O (80 mg, 2.0 mmol), THF (3 mL), MeOH (3 mL), and H$_2$O (3 mL). The resultant mixture was stirred at 70° C. for 10 hours, then adjusted to pH to 6-7 with 1 N HCl, diluted with H$_2$O (2 mL), and extracted with ethyl acetate (5 ml×2). These organic solvent fractions were combined, concentrated to dryness under reduced pressure, and purified by preparative acidic HPLC (Xtimate C18, 150 mm×25 mm×5 μm column (eluent: 50% to 64% (v/v) CH$_3$CN and H$_2$O with 0.225% HCOOH)) to give the title compound (120.2 mg, 46%) as a white solid. MS (ESI): mass calcd. for $C_{38}H_{46}F_3N_5O_9S$, 805.30; m/z found, 806.3 [M+H]$^+$. $^1$H NMR (400 MHz, DMSO-d$_6$) δ 12.59 (br. s, 1H), 8.42 (d, J=7.2 Hz, 1H), 8.00 (d, J=8.8 Hz, 1H), 7.31-7.23 (m, 2H), 7.22 (s, 1H), 7.15 (d, J=8.0 Hz, 1H), 6.76 (d, J=8.4 Hz, 1H), 4.81 (s, 1H), 4.48-4.40 (m, 1H), 4.37-4.29 (m, 3H), 3.82-3.67 (m, 2H), 3.53-3.38 (m, 9H), 2.66 (s, 3H), 2.19 (s, 3H), 2.00-1.89 (m, 2H), 1.70-1.60 (m, 2H), 1.57-1.46 (m, 2H), 1.45-1.33 (m, 2H), 1.32 (s, 3H), 1.26 (s, 3H).

Example 609: (*R)-2,2-Dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

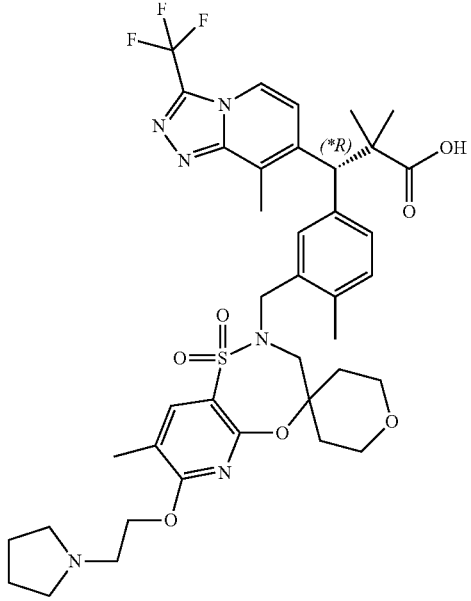 [SMILES: Cc1ccc([C@H](c2ccn3c(C(F)(F)F)nnc3c2C)C(C)(C)C(=O)O)cc1CN1CC2(CCOCC2)Oc2nc(OCCN3CCCC3)c(C)cc2S1(=O)=O]

Step A: tert-Butyl (*R)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate. A solution of tert-butyl (*R)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate (Intermediate 135, 200 mg, 0.419 mmol), 8'-methyl-7'-(2-(pyrrolidin-1-yl)ethoxy)-2,2',3,3',5,6-hexahydrospiro[pyran-4,4'-pyrido[2,3-b][1,4,5]oxathiazepine]1',1'-dioxide (Intermediate 134, 233 mg, 0.59 mmol), and triphenylphosphine (165 mg, 0.628 mmol) in THF (4 mL) was stirred at room temperature for 2 minutes. DBAD (164 mg, 0.712 mmol) was added and the solution was stirred at room temperature for 30 min. The reaction was quenched with water and transferred to a separatory funnel. The aqueous was extracted with EtOAc. These extractions resulted in several organic solvent fractions which were combined, washed with brine dried over $MgSO_4$, filtered, concentrated, and purified by flash column chromatography (0-1$_5$% MeOH/DCM) to provide the title compound (300 mg, 84% yield). MS (ESI): mass calcd. for $C_{43}H_{55}F_3N_6O_7S$, 856.4; m/z found, 429.3 $[M+2H]^{2+}$.

Step B: (*R)-2,2-Dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid. The title compound (200 mg, 34%) was prepared using analogous conditions as described in Example 658 where tert-Butyl (*R)-2,2-dimethyl-3-(4-methyl-3-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate was used instead of tert-Butyl (*R)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate in step B. The mixture was treated with acetonitrile and water and lyophilized to provide the title compound as the TFA salt (320 mg, 99%). MS (ESI): mass calcd. for $C_{39}H_{47}F_3N_6O_7S$, 800.3; m/z found, 401.3 $[M+H]^{2+}$. $^1$H NMR (400 MHz, DMSO-d$_6$) δ 9.74 (s, 1H), 8.42 (d, J=7.2 Hz, 1H), 7.92 (d, J=1.0 Hz, 1H), 7.30-7.22 (m, 2H), 7.20-7.09 (m, 2H), 4.82 (s, 1H), 4.62-4.59 (m, 2H), 4.51-4.29 (m, 2H), 3.79-3.58 (m, 6H), 3.53-3.11 (m, 6H), 2.66 (s, 3H), 2.22 (s, 3H), 2.19 (s, 3H), 2.10-2.01 (m, 2H), 1.92-1.88 (m, 2H), 1.50 (d, J=13.8 Hz, 2H), 1.43-1.24 (m, 8H).

Example 610: (*S)-3-(3-(Difluoromethyl)-8-methyl-[1,2,4]triazolo[4,3-a]pyridin-7-yl)-3-(6-((1',1'-dioxidospiro[oxetane-3,4'-pyrido[2,3-b][1,4,5]oxathiazepin]-2'(3'H)-yl)methyl)-5-methylpyridin-2-yl)-2,2-dimethylpropanoic Acid

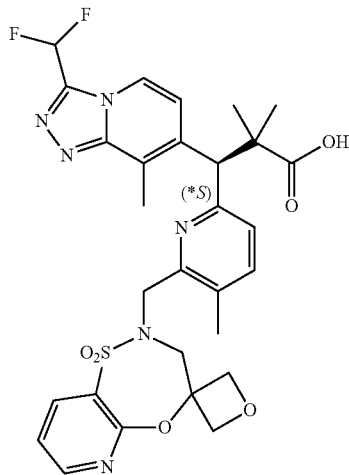 [SMILES: Cc1ccc([C@@H](c2ccn3c(C(F)F)nnc3c2C)C(C)(C)C(=O)O)nc1CN1CC2(COC2)Oc2ncccc2S1(=O)=O]

Step A: Methyl 3-(3-(difluoromethyl)-8-methyl-[1,2,4]triazolo[4,3-a]pyridin-7-yl)-3-(6-((1',1'-dioxidospiro[oxetane-3,4'-pyrido[2,3-b][1,4,5]oxathiazepin]-2'(3'H)-yl)methyl)-5-methylpyridin-2-yl)-2,2-dimethylpropanoate. The title compound (670 mg) was prepared using analogous reaction conditions as described in Example 642, Step A where methyl 3-(6-(chloromethyl)-5-methylpyridin-2-yl)-3-(3-(difluoromethyl)-8-methyl-[1,2,4]triazolo[4,3-a]pyridin-7-yl)-2,2-dimethylpropanoate (Intermediate 196) was used instead of tert-butyl 3-(4-(chloromethyl)-5-methylpyridin-2-yl)-3-(3-(difluoromethyl)-8-methyl-[1,2,4]triazolo[4,3-a]pyridin-7-yl)-2,2-dimethylpropanoate and where 2',3'-dihydrospiro[oxetane-3,4'-pyrido[2,3-b][1,4,5]oxathiazepine]1',1'-dioxide (Intermediate 59) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine]1',1'-dioxide. MS (ESI): mass calcd. for $C_{30}H_{32}F_2N_6O_6S$, 642.2 m/z found, 643.3 $[M+H]^+$. $^1$H NMR (400 MHz, DMSO-d$_6$) δ 8.64 (dd, J=1.9, 4.9 Hz, 1H), 8.30 (d, J=7.3 Hz, 1H), 8.26 (dd, J=1.9, 7.7 Hz, 1H), 7.69 (t, J=51.6 Hz, 1H), 7.54 (dd, J=4.8, 7.8 Hz, 2H), 7.42 (d, J=7.3 Hz, 1H), 7.20 (d, J=7.8 Hz, 1H), 4.96 (s, 1H), 4.66 (d, J=7.8 Hz, 1H), 4.62-4.58 (m, 1H), 4.52 (d, J=7.8 Hz, 2H), 4.48-4.42 (m, 1H), 4.37-4.31 (m, 1H), 4.03 (s, 2H), 3.49 (s, 3H), 2.75 (s, 3H), 2.27 (s, 3H), 1.36 (s, 3H), 1.28 (s, 3H).

Step B: (*S)-3-(3-(Difluoromethyl)-8-methyl-[1,2,4]triazolo[4,3-a]pyridin-7-yl)-3-(6-((1',1'-dioxidospiro[oxetane-3,4'-pyrido[2,3-b][1,4,5]oxathiazepin]-2'(3'H)-yl)methyl)-5-methylpyridin-2-yl)-2,2-dimethylpropanoic acid. A mixture of NaOH (585 mg, 14.6 mmol) and methyl 3-(3-(difluoromethyl)-8-methyl-[1,2,4]triazolo[4,3-a]pyridin-7-yl)-3-(6-((1',1'-dioxidospiro[oxetane-3,4'-pyrido[2,3-b][1,4,5]oxathiazepin]-2'(3'H)-yl)methyl)-5-methylpyridin-2-yl)-2,2-dimethylpropanoate (940 mg, 1.46 mmol) in dioxane-water (1:1, 10 mL) was stirred at 60° C. After 5 hours, the mixture was allowed to cool to room temperature and then the pH was adjusted to 2-3 by adding 3 N aqueous HCl solution. The mixture was poured into water and then extracted with dichloromethane. These extractions resulted in several organic solvent fractions which were combined, dried over $Na_2SO_4$, filtered, and concentrated to dryness under reduced pressure. The residue was purified by preparative HPLC (Xtimate C18, 150×40 mm×10 μm column, eluent: 30% to 80% (v/v) $CH_3CN$ in $H_2O$ with 0.2% HCOOH). The pure fractions were lyophilzed to dryness to provide the title compound as a mixture of enantiomers as a white solid (460 mg, 50%). This mixture was further purified by SFC using a chiral stationary phase (Daicel Chiralcel OJ-H column, 250 mm×30 mm×5 m, eluent: 20% methanol containing 0.1% v/v 25% aqueous ammonia:$CO_2$) to afford two isomers. The first eluting isomer (160.1 mg) was designated (*S): MS (ESI): mass calcd. for $C_{29}H_{30}F_2N_6O_6S$, 628.2 m/z found, 629.3 $[M+H]^+$. $^1H$ NMR (400 MHz, DMSO-$d_6$) δ 12.13 (s, 1H), 8.65-8.62 (m, 1H), 8.30-8.24 (m, 2H), 7.68 (t, J=52.0 Hz, 1H), 7.56-7.51 (m, 3H), 7.26 (d, J=7.8 Hz, 1H), 4.96 (s, 1H), 4.67-4.61 (m, 2H), 4.52 (d, J=7.8 Hz, 2H), 4.39 (s, 2H), 4.10-3.96 (m, 2H), 2.75 (s, 3H), 2.27 (s, 3H), 1.34 (s, 3H), 1.28 (s, 3H).

Example 611: (*R)-3-(3-(Difluoromethyl)-8-methyl-[1,2,4]triazolo[4,3-a]pyridin-7-yl)-3-(6-((1',1'-dioxidospiro[oxetane-3,4'-pyrido[2,3-b][1,4,5]oxathiazepin]-2'(3'H)-yl)methyl)-5-methylpyridin-2-yl)-2,2-dimethylpropanoic Acid

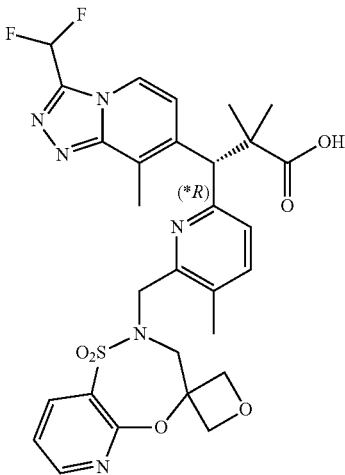 [SMILES: Cc1ccc([C@H](c2ccn3c(C(F)F)nnc3c2C)C(C)(C)C(=O)O)nc1CN1CC2(COC2)Oc2ncccc2S1(=O)=O]

The second eluting isomer (180.5 mg) for the chiral separation described in Example 610 was designated (*R): MS (ESI): mass calcd. for $C_{29}H_{30}F_2N_6O_6S$, 628.2 m/z found, 629.3 $[M+H]^+$. $^1H$ NMR (400 MHz, DMSO-$d_6$) δ 8.65-8.62 (m, 1H), 8.30-8.24 (m, 2H), 7.68 (t, J=51.6 Hz, 1H), 7.56-7.51 (m, 3H), 7.27 (d, J=7.8 Hz, 1H), 4.97 (s, 1H), 4.64 (t, J=8.7 Hz, 2H), 4.52 (d, J=7.8 Hz, 2H), 4.42-4.36 (m, 2H), 4.09-3.97 (m, 2H), 2.75 (s, 3H), 2.27 (s, 3H), 1.34 (s, 3H), 1.27 (s, 3H).

Example 612: (*S)-3-(1-Cyclopropyl-4-methyl-1H-benzo[d][1,2,3]triazol-5-yl)-3-(5-((1',1'-dioxidospiro[oxetane-3,4'-pyrido[2,3-b][1,4,5]oxathiazepin]-2'(3'H)-yl)methyl)-6-methylpyridin-3-yl)-2,2-dimethylpropanoic Acid

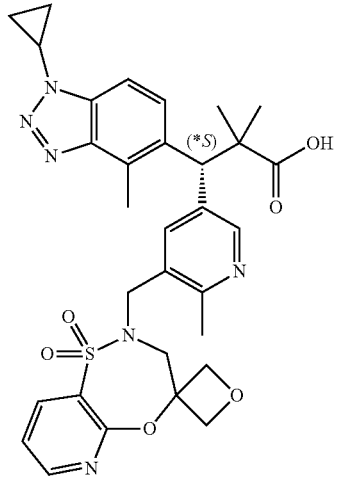 [SMILES: Cc1ncc([C@H](c2ccc3c(nnn3C3CC3)c2C)C(C)(C)C(=O)O)cc1CN1CC2(COC2)Oc2ncccc2S1(=O)=O]

The title compound (89 mg, 15%) was prepared using analogous conditions as described in Example 624 where 2',3'-dihydrospiro[oxetane-3,4'-pyrido[2,3-b][1,4,5]oxathiazepine] 1',1'-15 dioxide (Intermediate 59) was used instead of 8'-methyl-2',3'-dihydrospiro[oxetane-3,4'-pyrido[2,3-b][1,4,5]oxathiazepine] 1',1'-dioxide, in step A. MS (ESI): mass calcd. for $C_{31}H_{34}N_6O_6S$, 618.2 m/z found 619.3 $[M+H]^+$. $^1H$ NMR (400 MHz, DMSO-$d_6$) δ 8.63 (dd, J=1.8, 4.8 Hz, 1H), 8.37-8.35 (m, 1H), 8.20 (dd, J=2.0, 7.8 Hz, 1H), 7.71 (d, J=8.8 Hz, 1H), 7.68-7.65 (m, 1H), 7.60 (d, J=8.5 Hz, 1H), 7.52 (dd, J=4.9, 7.7 Hz, 1H), 4.81 (s, 1H), 4.49-4.40 (m, 4H), 4.38-4.27 (m, 2H), 3.98-3.93 (m, 1H), 3.93-3.83 (m, 2H), 2.70 (s, 3H), 2.37 (s, 3H), 1.28 (s, 3H), 1.24 (s, 3H), 1.24-1.18 (m, 4H).

Example 613: (*R)-3-(1-Cyclopropyl-4-methyl-1H-benzo[d][1,2,3]triazol-5-yl)-3-(5-((1',1'-dioxidospiro[oxetane-3,4'-pyrido[2,3-b][1,4,5]oxathiazepin]-2'(3'H)-yl)methyl)-6-methylpyridin-3-yl)-2,2-dimethylpropanoic Acid

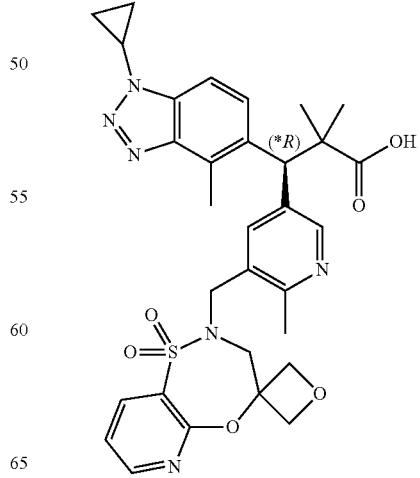

The title compound (127 mg, 22%) was prepared using analogous conditions as described in Example 624 where (*R)-methyl 3-(5-(chloromethyl)-6-methylpyridin-3-yl)-3-(1-cyclopropyl-4-methyl-1H-benzo[d][1,2,3]triazol-5-yl)-2,2-dimethylpropanoate (Intermediate 189) was used instead of (*S)-methyl 3-(5-(chloromethyl)-6-methylpyridin-3-yl)-3-(1-cyclopropyl-4-methyl-1H-benzo[d][1,2,3]triazol-5-yl)-2,2-dimethylpropanoate and 2',3'-dihydrospiro[oxetane-3,4'-pyrido[2,3-b][1,4,5]oxathiazepine] 1',1'-dioxide (Intermediate 59) was used instead of 8'-methyl-2',3'-dihydrospiro[oxetane-3,4'-pyrido[2,3-b][1,4,5]oxathiazepine] 1',1'-dioxide, in step A. MS (ESI): mass calcd. for $C_{31}H_{34}N_6O_6S$, 618.2 m/z found 619.3 [M+H]$^+$. $^1$H NMR (400 MHz, DMSO-d$_6$) δ 8.63 (dd, J=1.9, 4.9 Hz, 1H), 8.37-8.35 (m, 1H), 8.20 (dd, J=1.9, 7.7 Hz, 1H), 7.72-7.69 (m, 1H), 7.68-7.66 (m, 1H), 7.60 (d, J=8.8 Hz, 1H), 7.52 (dd, J=4.9, 7.7 Hz, 1H), 4.81 (s, 1H), 4.49-4.40 (m, 4H), 4.38-4.27 (m, 2H), 3.99-3.93 (m, 1H), 3.93-3.83 (m, 2H), 2.70 (s, 3H), 2.37 (s, 3H), 1.28 (s, 3H), 1.24 (s, 3H), 1.24-1.18 (m, 4H).

Example 614: (*S)-2,2-dimethyl-3-(4-methyl-3-((8'-methyl-1',1'-dioxidospiro[oxetane-3,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic Acid

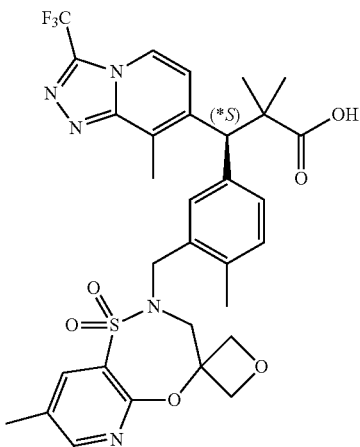 [SMILES: Cc1cnc2c(c1)S(=O)(=O)N(Cc1cc([C@@H](c3ccn4c(C(F)(F)F)nnc4c3C)C(C)(C)C(=O)O)ccc1C)CC1(COC1)O2]

The title compound (276 mg, 60%) was prepared using analogous conditions as described in Example 370 where 8'-methyl-2',3'-dihydrospiro[oxetane-3,4'-pyrido[2,3-b][1,4,5]oxathiazepine] 1',1'-dioxide (Intermediate 190) was used instead of 8'-methyl-7'-(2-(pyrrolidin-1-yl)ethoxy)-2,2',3,3',5,6-hexahydrospiro[pyran-4,4'-pyrido[2,3-b][1,4,5]oxathiazepine] 1',1'-dioxide and tert-butyl (*S)-3-(3-(hydroxymethyl)-4-methylphenyl)-2,2-dimethyl-3-(8-methyl-3-(trifluoromethyl)-[1,2,4]triazolo[4,3-a]pyridine-7-yl)propanoate (Intermediate 128) was used instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate in step A. MS (ESI): mass calcd. for $C_{31}H_{32}F_3N_5O_6S$, 659.2; m/z found, 660.2 [M+H]$^+$. $^1$H NMR (400 MHz, DMSO-d$_6$) δ 8.44-8.42 (m, 1H), 8.38 (d, J=7.2 Hz, 1H), 8.04-8.02 (m, 1H), 7.29 (d, J=7.3 Hz, 1H), 7.27-7.20 (m, 2H), 7.16 (d, J=7.8 Hz, 1H), 4.80 (s, 1H), 4.45-4.32 (m, 3H), 4.32-4.24 (m, 2H), 4.20 (d, J=14.9 Hz, 1H), 3.74 (s, 2H), 2.64 (s, 3H), 2.37 (s, 3H), 2.22 (s, 3H), 1.30 (s, 3H), 1.24 (s, 3H).

Example 615: (*S)-3-(3-((1',1'-dioxidospiro[oxetane-3,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

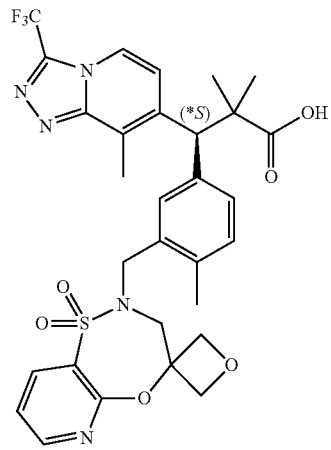 [SMILES: Cc1ccc([C@@H](c2ccn3c(C(F)(F)F)nnc3c2C)C(C)(C)C(=O)O)cc1CN1CC2(COC2)Oc2ncccc2S1(=O)=O]

The title compound (270 mg, 62%) was prepared using analogous conditions as described in Example 370 where 2',3'-dihydrospiro[oxetane-3,4'-pyrido[2,3-b][1,4,5]oxathiazepine] 1',1'-dioxide (Intermediate 59) was used instead of 8'-methyl-7'-(2-(pyrrolidin-1-yl)ethoxy)-2,2',3,3',5,6-hexahydrospiro[pyran-4,4'-pyrido[2,3-b][1,4,5]oxathiazepine] 1',1'-dioxide and tert-butyl (*S)-3-(3-(hydroxymethyl)-4-methylphenyl)-2,2-dimethyl-3-(8-methyl-3-(trifluoromethyl)-[1,2,4]triazolo[4,3-a]pyridine-7-yl)propanoate (Intermediate 128) was used instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate in step A. MS (ESI): mass calcd. for $C_{30}H_{30}F_3N_5O_6S$, 645.2; m/z found, 646.2 [M+H]$^+$. $^1$H NMR (400 MHz, DMSO-d$_6$) δ 8.61 (dd, J=4.9, 1.9 Hz, 1H), 8.38 (d, J=7.3 Hz, 1H), 8.21 (dd, J=7.7, 1.9 Hz, 1H), 7.51 (dd, J=7.7, 4.9 Hz, 1H), 7.29 (d, J=7.4 Hz, 1H), 7.27-7.21 (m, 2H), 7.16 (d, J=7.7 Hz, 1H), 4.80 (s, 1H), 4.44-4.18 (m, 6H), 3.76 (s, 2H), 2.64 (s, 3H), 2.21 (s, 3H), 1.29 (s, 3H), 1.24 (s, 3H).

Example 616: (*S)-3-(3-(difluoromethyl)-8-methyl-[1,2,4]triazolo[4,3-a]pyridine-7-yl)-3-(3-((1',1'-dioxidospiro[oxetane-3,4'-pyrido[2,3-b][1,4,5]oxathiazepin]-2'(3'H)-yl)methyl)-4-methylphenyl)-2,2-dimethylpropanoic Acid

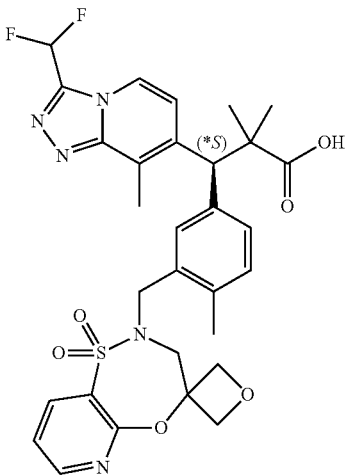 [SMILES: Cc1ccc([C@@H](c2ccn3c(C(F)F)nnc3c2C)C(C)(C)C(=O)O)cc1CN1CC2(COC2)Oc2ncccc2S1(=O)=O]

The title compound (234 mg, 54%) was prepared using analogous conditions as described in Example 370 where 2',3'-dihydrospiro[oxetane-3,4'-pyrido[2,3-b][1,4,5]oxathiazepine] 1',1'-dioxide (Intermediate 59) was used instead of 8'-methyl-7'-(2-(pyrrolidin-1-yl)ethoxy)-2,2',3,3',5,6-hexahydrospiro[pyran-4,4'-pyrido[2,3-b][1,4,5]oxathiazepine] 1',1'-dioxide and tert-butyl (*S)-3-(3-(difluoromethyl)-8-methyl-[1,2,4]triazolo[4,3-a]pyridine-7-yl)-3-(3-(hydroxymethyl)-4-methylphenyl)-2,2-dimethylpropanoate (Intermediate 129) was used instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate in step A. MS (ESI): mass calcd. for $C_{30}H_{31}F_2N_5O_6S$, 627.2; m/z found, 628.2 [M+H]$^+$. $^1$H NMR (400 MHz, DMSO-d$_6$) δ 8.61 (dd, J=4.9, 1.9 Hz, 1H), 8.37 (d, J=7.3 Hz, 1H), 8.21 (dd, J=7.7, 1.9 Hz, 1H), 7.70 (t, J=51.6 Hz, 1H), 7.51 (dd, J=7.7, 4.9 Hz, 1H), 7.29-7.20 (m, 3H), 7.15 (d, J=7.9 Hz, 1H), 4.77 (s, 1H), 4.47-4.18 (m, 6H), 3.80 (s, 2H), 2.61 (s, 3H), 2.21 (s, 3H), 1.29 (s, 3H), 1.24 (s, 3H).

Example 617: (*S)-3-(3-(Difluoromethyl)-8-methyl-[1,2,4]triazolo[4,3-a]pyridin-7-yl)-2,2-dimethyl-3-(4-methyl-3-((8'-methyl-1',1'-dioxidospiro[oxetane-3,4'-pyrido[2,3-b][1,4,5]oxathiazepin]-2'(3'H)-yl)methyl)phenyl)propanoic Acid

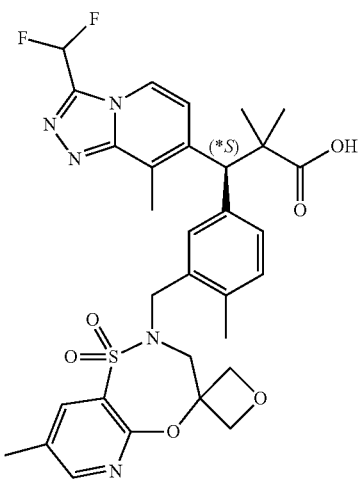 [SMILES: Cc1cnc2c(c1)S(=O)(=O)N(Cc1cc([C@@H](c3ccn4c(C(F)F)nnc4c3C)C(C)(C)C(=O)O)ccc1C)CC1(COC1)O2]

The title compound (220 mg, 46%) was prepared using analogous conditions as described in Example 370 where 8'-methyl-2',3'-dihydrospiro[oxetane-3,4'-pyrido[2,3-b][1,4,5]oxathiazepine] 1',1'-dioxide (Intermediate 190) was used instead of 8'-methyl-7'-(2-(pyrrolidin-1-yl)ethoxy)-2,2',3,3',5,6-hexahydrospiro[pyran-4,4'-pyrido[2,3-b][1,4,5]oxathiazepine] 1',1'-dioxide and tert-butyl (*S)-3-(3-(difluoromethyl)-8-methyl-[1,2,4]triazolo[4,3-a]pyridine-7-yl)-3-(3-(hydroxymethyl)-4-methylphenyl)-2,2-dimethylpropanoate (Intermediate 129) was used instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate in step A. MS (ESI): mass calcd. for $C_{31}H_{33}F_2N_5O_6S$, 641.2; m/z found, 642.2 [M+H]$^+$. $^1$H NMR (400 MHz, DMSO-d$_6$) δ 8.44-8.42 (m, 1H), 8.36 (d, J=7.3 Hz, 1H), 8.05-8.02 (m, 1H), 7.70 (t, J=51.6 Hz, 1H), 7.29-7.20 (m, 3H), 7.15 (d, J=7.9 Hz, 1H), 4.77 (s, 1H), 4.46-4.17 (m, 6H), 3.77 (s, 2H), 2.61 (s, 3H), 2.38 (s, 3H), 2.21 (s, 3H), 1.28 (s, 3H), 1.23 (s, 3H).

Example 618: (R/S)-3-(1-Cyclopropyl-4-methyl-1H-benzo[d][1,2,3]triazol-5-yl)-2,2-dimethyl-3-(4-methyl-3-((8'-methyl-1',1'-dioxido-7'-(((S)-1-(piperidin-1-yl)propan-2-yl)amino)spiro[cyclopropane-1,4'-pyrido[2,3-b][1,4,5]oxathiazepin]-2'(3'H)-yl)methyl)phenyl)propanoic Acid

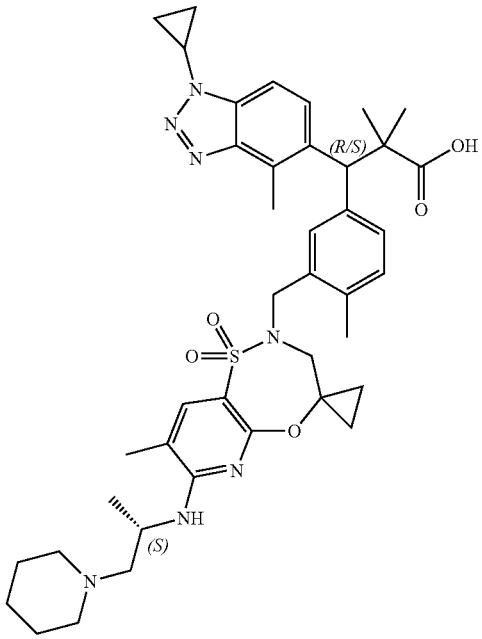

Step A: Methyl 3-(3-((7'-chloro-8'-methyl-1',1'-dioxidospiro[cyclopropane-1,4'-pyrido[2,3-b][1,4,5]oxathiazepin]-2'(3'H)-yl)methyl)-4-methylphenyl)-3-(1-cyclopropyl-4-methyl-1H-benzo[d][1,2,3]triazol-5-yl)-2,2-dimethylpropanoate. Methyl 3-(3-(chloromethyl)-4-methylphenyl)-3-(1-cyclopropyl-4-methyl-1H-benzo[d][1,2,3]triazol-5-yl)-2,2-dimethylpropanoate (Intermediate 186, 600 mg, 1.4 mmol) was dissolved in ACN (7 mL). 7'-Chloro-8'-methyl-2',3'-dihydrospiro[cyclopropane-1,4'-pyrido[2,3-b][1,4,5]oxathiazepine] 1',1'-dioxide (Intermediate 131, 467 mg, 1.7 mmol) and potassium carbonate (317 mg, 2.29 mmol) were added and the reaction was stirred at 80° C. overnight. After this time, the reaction was allowed to cool to room temperature, then was diluted with water and EtOAc and the resulting biphasic mixture was separated. The aqueous layer was extracted with EtOAc. These extractions resulted in several organic solvent fractions which were combined, dried over MgSO$_4$, filtered, and concentrated to dryness under reduced pressure. The material was purified by flash column chromatography (0-1$_{00}$% ethyl acetate/hexanes) to provide the title compound (593.7 mg, 63% yield). MS (ESI): mass calcd. for C$_{34}$H$_{38}$ClN$_5$O$_5$S, 663.2; m/z found, 664.3 [M+H]$^+$.

Step B: Methyl 3-(1-cyclopropyl-4-methyl-1H-benzo[d][1,2,3]triazol-5-yl)-2,2-dimethyl-3-(4-methyl-3-((8'-methyl-1',1'-dioxido-7'-(((S)-1-(piperidin-1-yl)propan-2-yl)amino)spiro[cyclopropane-1,4'-pyrido[2,3-b][1,4,5]oxathiazepin]-2'(3'H)-yl)methyl)phenyl)propanoate. Methyl 3-(3-((7'-chloro-8'-methyl-1',1'-dioxidospiro[cyclopropane-1,4'-pyrido[2,3-b][1,4,5]oxathiazepin]-2'(3'H)-yl)methyl)-4-methylphenyl)-3-(1-cyclopropyl-4-methyl-1H-benzo[d][1,2,3]triazol-5-yl)-2,2-dimethylpropanoate (594 mg, 0.894 mmol), (S)-1-(piperidin-1-yl)propan-2-amine (574.6 mg, 4.04 mmol), and DMSO (4.5 mL) were combined and heated in a microwave reactor at 130° C. for 1 hour. After this time, the reaction was allowed to cool to room temperature, then was diluted with water and EtOAc and the resulting biphasic mixture was separated. The aqueous layer was extracted with EtOAc. These extractions resulted in several organic solvent fractions which were combined, dried over MgSO$_4$, filtered, and concentrated to dryness under reduced pressure. The material was purified by flash column chromatography (0-10% MeOH/DCM) to provide the title compound (610 mg, 89% yield). MS (ESI): mass calcd. for C$_{42}$H$_{55}$N$_7$O$_5$S, 769.4; m/z found, 770.4 [M+H]$^+$.

Step C: (R/S)-3-(1-Cyclopropyl-4-methyl-1H-benzo[d][1,2,3]triazol-5-yl)-2,2-dimethyl-3-(4-methyl-3-((8'-methyl-1',1'-dioxido-7'-(((S)-1-(piperidin-1-yl)propan-2-yl)amino)spiro[cyclopropane-1,4'-pyrido[2,3-b][1,4,5]oxathiazepin]-2'(3'H)-yl)methyl)phenyl)propanoic acid. Methyl 3-(1-cyclopropyl-4-methyl-1H-benzo[d][1,2,3]triazol-5-yl)-2,2-dimethyl-3-(4-methyl-3-((8'-methyl-1',1'-dioxido-7'-(((S)-1-(piperidin-1-yl)propan-2-yl)amino)spiro[cyclopropane-1,4'-pyrido[2,3-b][1,4,5]oxathiazepin]-2'(3'H)-yl)methyl)phenyl)propanoate (610 mg, 0.79 mmol), LiOH (196 mg, 8.2 mmol), 1,4-dioxane (4 mL), and water (4 mL) were combined and heated to 75° C. for 3 hours. After this time, the reaction was allowed to cool to room temperature, and was acidified to pH 4 using 1M HCl. The biphasic mixture was separated and the aqueous layer was extracted with EtOAc. These extractions resulted in several organic solvent fractions which were combined, dried over MgSO$_4$, filtered, and concentrated to dryness under reduced pressure to provide the title compound without further purification (410 mg, 68% yield). MS (ESI): mass calcd. for C$_{41}$H$_{53}$N$_7$O$_5$S, 755.4; m/z found, 756.4 [M+H]$^+$.

Example 619: (*R)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[oxetane-3,4'-pyrido[2,3-b][1,4,5]oxathiazepin]-2'(3'H)-yl)methyl)phenyl)propanoic Acid

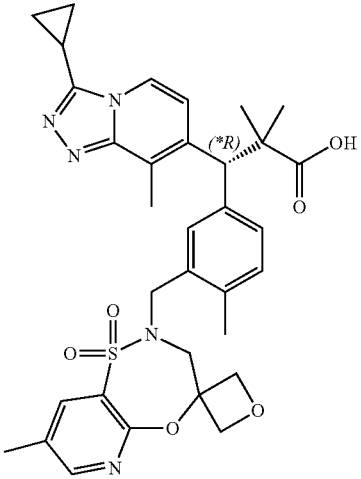 [SMILES: Cc1cnc2c(c1)S(=O)(=O)N(Cc1cc([C@H](c3ccn4c(C5CC5)nnc4c3C)C(C)(C)C(=O)O)ccc1C)CC1(COC1)O2]

Step A: Methyl (*R)-3-(3-cyclopropyl-8-methyl-[1,2,4]triazolo[4,3-a]pyridin-7-yl)-2,2-dimethyl-3-(4-methyl-3-((8'-methyl-1',1'-dioxidospiro[oxetane-3,4'-pyrido[2,3-b][1,4,5]oxathiazepin]-2'(3'H)-yl)methyl)phenyl)propanoate. A solution of methyl (*R)-3-(3-cyclopropyl-8-methyl-[1,2,4]triazolo[4,3-a]pyridin-7-yl)-3-(3-(hydroxymethyl)-4-methylphenyl)-2,2-dimethylpropanoate (Intermediate 186, 209.7 mg, 0.515 mmol), 8'-methyl-2',3'-dihydrospiro[oxetane-3,4'-pyrido[2,3-b][1,4,5]oxathiazepine] 1',1'-dioxide (Intermediate 190, 146.1 mg, 0.57 mmol), and triphenylphosphine (229.6 mg, 0.875 mmol) in THF (2.6 mL) was stirred at room temperature for 1 minute. DBAD (194 mg, 0.843 mmol) was added and the solution was stirred at room temperature for 4 hours. The reaction was concentrated and purified by flash column chromatography (0-1$_0$% MeOH/DCM) to provide the title compound containing residual solvents (380 mg, 114% yield). MS (ESI): mass calcd. for C$_{34}$H$_{39}$N$_5$O$_6$S, 645.3; m/z found, 646.3 [M+H]$^+$.

Step B: (*R)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[oxetane-3,4'-pyrido[2,3-b][1,4,5]oxathiazepin]-2'(3'H)-yl)methyl)phenyl)propanoic acid. Methyl (*R)-3-(3-cyclopropyl-8-methyl-[1,2,4]triazolo[4,3-a]pyridin-7-yl)-2,2-dimethyl-3-(4-methyl-3-((8'-methyl-1',1'-dioxidospiro[oxetane-3,4'-pyrido[2,3-b][1,4,5]oxathiazepin]-2'(3'H)-yl)methyl)phenyl)propanoate (332.3 mg, 0.515 mmol) was dissolved in THF (2 mL). Tetrabutylammonium hydroxide 30-hydrate (2.097 g, 2.62 mmol) and water (2 mL) were added and the resulting mixture was stirred at 70° C. for 3.5 hours. After this time, the reaction was allowed to cool to room temperature, and was acidified to pH 3-4 using 1M HCl. The biphasic mixture was separated and the aqueous layer was extracted with EtOAc. These extractions resulted in several organic solvent fractions which were combined, washed with brine 3 times, dried over MgSO$_4$, filtered, concentrated, and purified by preparative basic HPLC (XBridge C$_{18}$, acetonitrile-water, 20 mM NH$_4$OH) to provide the title compound (173.4 mg, 53% yield). MS (ESI): mass calcd. for C$_{33}$H$_{37}$N$_5$O$_6$S, 631.2; m/z found, 632.3 [M+H]$^+$. $^1$H NMR (400 MHz, CDCl$_3$) δ 8.26-8.22 (m, 1H), 7.96-7.91 (m, 1H), 7.82-7.76 (m, 1H), 7.24-7.20 (m, 1H), 7.06-6.99 (m, 2H), 6.92 (d, J=7.3 Hz, 1H), 4.84-4.79 (m, 1H), 4.74 (s, 1H), 4.67-4.46 (m, 3H), 4.13 (d, J=13.8 Hz, 1H), 3.99-3.90 (m, 1H), 3.85-3.70 (m, 2H), 2.64 (s, 3H), 2.34 (s, 3H), 2.13 (s, 3H), 1.97-1.86 (m, 1H), 1.31 (d, J=34.8 Hz, 6H), 1.13-0.97 (m, 4H).

Example 620: (*R)-3-(3-Cyclopropyl-8-methyl-[1,2,4]triazolo[4,3-a]pyridin-7-yl)-3-(3-((1',1'-dioxidospiro[oxetane-3,4'-pyrido[2,3-b][1,4,5]oxathiazepin]-2'(3'H)-yl)methyl)-4-methylphenyl)-2,2-dimethylpropanoic Acid

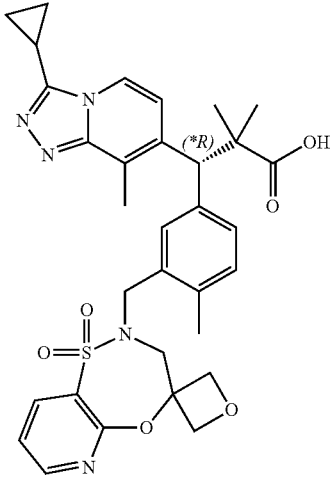 [SMILES: Cc1ccc([C@H](c2ccn3c(C4CC4)nnc3c2C)C(C)(C)C(=O)O)cc1CN1CC2(COC2)Oc2ncccc2S1(=O)=O]

The title compound (97.3 mg, 35.5%) was prepared using analogous conditions as described in Example 619 where 2',3'-dihydrospiro[oxetane-3,4'-pyrido[2,3-b][1,4,5]oxathiazepine] 1',1'-dioxide (Intermediate 59) was used instead of 8'-methyl-2',3'-dihydrospiro[oxetane-3,4'-pyrido[2,3-b][1,4,5]oxathiazepine] 1',1'-dioxide. MS (ESI): mass calcd. for $C_{32}H_{35}N_5O_6S$, 617.2; m/z found, 618.3 [M+H]$^+$. $^1$H NMR (400 MHz, CDCl$_3$) δ 8.57-8.52 (m, 1H), 8.28-8.23 (m, 1H), 7.88 (d, J=7.2 Hz, 1H), 7.39-7.31 (m, 2H), 7.15-7.08 (m, 2H), 6.99 (d, J=7.3 Hz, 1H), 4.94 (d, J=7.2 Hz, 1H), 4.85 (s, 1H), 4.78-4.68 (m, 2H), 4.62 (d, J=7.2 Hz, 1H), 4.23 (d, J=13.8 Hz, 1H), 4.13-4.06 (m, 1H), 3.98-3.90 (m, 1H), 3.80-3.73 (m, 1H), 2.76 (s, 3H), 2.20 (s, 3H), 2.05-1.95 (m, 1H), 1.41 (d, J=35.3 Hz, 6H), 1.24-1.10 (m, 4H).

Example 621: (*S)-3-(3-Cyclopropyl-8-methyl-[1,2,4]triazolo[4,3-a]pyridin-7-yl)-3-(3-((1',1'-dioxidospiro[oxetane-3,4'-pyrido[2,3-b][1,4,5]oxathiazepin]-2'(3'H)-yl)methyl)-4-methylphenyl)-2,2-dimethylpropanoic Acid

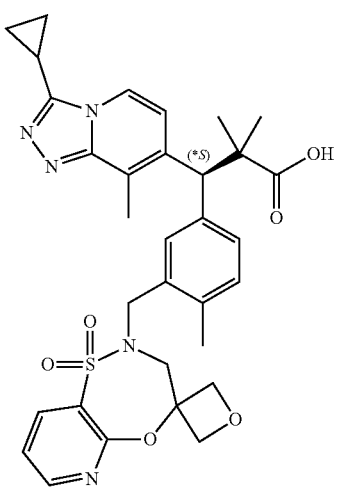 [SMILES: Cc1ccc([C@@H](c2ccn3c(C4CC4)nnc3c2C)C(C)(C)C(=O)O)cc1CN1CC2(COC2)Oc2ncccc2S1(=O)=O]

The title compound (95.8 mg, 30.7%) was prepared using analogous conditions as described in Example 619 where methyl (*S)-3-(3-cyclopropyl-8-methyl-[1,2,4]triazolo[4,3-a]pyridin-7-yl)-3-(3-(hydroxymethyl)-4-methylphenyl)-2,2-dimethylpropanoate (Intermediate 184) was used instead of methyl (*R)-3-(3-cyclopropyl-8-methyl-[1,2,4]triazolo[4,3-a]pyridin-7-yl)-3-(3-(hydroxymethyl)-4-methylphenyl)-2,2-dimethylpropanoate, and 2',3'-dihydrospiro[oxetane-3,4'-pyrido[2,3-b][1,4,5]oxathiazepine] 1',1'-dioxide (Intermediate 59) was used instead of 8'-methyl-2',3'-dihydrospiro[oxetane-3,4'-pyrido[2,3-b][1,4,5]oxathiazepine]1',1'-dioxide. MS (ESI): mass calcd. for $C_{32}H_{35}N_5O_6S$, 617.2; m/z found, 618.3 [M+H]$^+$. $^1$H NMR (400 MHz, CDCl$_3$) δ 8.59-8.51 (m, 1H), 8.29-8.21 (m, 1H), 7.89 (d, J=7.3 Hz, 1H), 7.39-7.31 (m, 2H), 7.17-7.08 (m, 2H), 7.00 (d, J=7.3 Hz, 1H), 4.92 (d, J=7.3 Hz, 1H), 4.85 (s, 1H), 4.79-4.68 (m, 2H), 4.61 (d, J=7.3 Hz, 1H), 4.23 (d, J=13.8 Hz, 1H), 4.13-4.04 (m, 1H), 3.97-3.88 (m, 1H), 3.83-3.75 (m, 1H), 2.75 (s, 3H), 2.21 (s, 3H), 2.06-1.94 (m, 1H), 1.41 (d, J=34.6 Hz, 6H), 1.24-1.07 (m, 4H).

Example 622: (*S)-3-(3-Cyclopropyl-8-methyl-[1,2,4]triazolo[4,3-a]pyridin-7-yl)-2,2-dimethyl-3-(4-methyl-3-((8'-methyl-1',1'-dioxidospiro[oxetane-3,4'-pyrido[2,3-b][1,4,5]oxathiazepin]-2'(3'H)-yl)methyl)phenyl)propanoic Acid

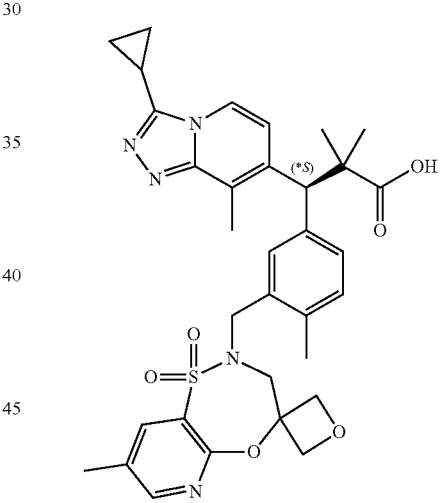

The title compound (97.3 mg, 35.5%) was prepared using analogous conditions as described in Example 619 where methyl (*S)-3-(3-cyclopropyl-8-methyl-[1,2,4]triazolo[4,3-a]pyridin-7-yl)-3-(3-(hydroxymethyl)-4-methylphenyl)-2,2-dimethylpropanoate (Intermediate 184) was used instead of methyl (*R)-3-(3-cyclopropyl-8-methyl-[1,2,4]triazolo[4,3-a]pyridin-7-yl)-3-(3-(hydroxymethyl)-4-methylphenyl)-2,2-dimethylpropanoate. MS (ESI): mass calcd. for $C_{33}H_{37}N_5O_6S$, 631.2; m/z found, 632.3 [M+H]$^+$. $^1$H NMR (400 MHz, CDCl$_3$) δ 8.26-8.21 (m, 1H), 7.95-7.92 (m, 1H), 7.79 (d, J=7.2 Hz, 1H), 7.23-7.20 (m, 1H), 7.06-6.99 (m, 2H), 6.91 (d, J=7.3 Hz, 1H), 4.83 (d, J=7.2 Hz, 1H), 4.74 (s, 1H), 4.67-4.59 (m, 2H), 4.51 (d, J=7.2 Hz, 1H), 4.12 (d, J=13.7 Hz, 1H), 4.00-3.91 (m, 1H), 3.86-3.77 (m, 1H), 3.75-3.66 (m, 1H), 2.66 (s, 3H), 2.34 (s, 3H), 2.12 (s, 3H), 1.95-1.85 (m, 1H), 1.31 (d, J=35.4 Hz, 6H), 1.15-0.98 (m, 4H).

Example 623: (*R)-3-(1-Cyclopropyl-4-methyl-1H-benzo[d][1,2,3]triazol-5-yl)-2,2-dimethyl-3-(6-methyl-5-((8'-methyl-1',1'-dioxidospiro[oxetane-3,4'-pyrido[2,3-b][1,4,5]oxathiazepin]-2'(3'H)-yl)methyl)pyridine-3-yl)propanoic Acid

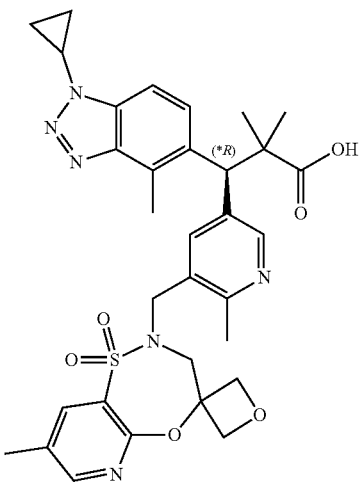 [SMILES: Cc1cnc2c(c1)S(=O)(=O)N(Cc1cc([C@@H](c3ccc4c(nnn4C4CC4)c3C)C(C)(C)C(=O)O)cnc1C)CC1(COC1)O2]

The title compound (277 mg, 42%) was prepared using analogous conditions as described in Example 624 where (*R)-Methyl 3-(5-(chloromethyl)-6-methylpyridin-3-yl)-3-(1-cyclopropyl-4-methyl-1H-benzo[d][1,2,3]triazol-5-yl)-2,2-dimethylpropanoate (Intermediate 189) was used instead (*S)-Methyl 3-(5-(chloromethyl)-6-methylpyridin-3-yl)-3-(1-cyclopropyl-4-methyl-1H-benzo[d][1,2,3]triazol-5-yl)-2,2-dimethylpropanoate in step A. MS (ESI): mass calcd. for $C_{32}H_{36}N_6O_6S$, 632.2 m/z found 633.3 [M+H]$^+$. $^1$H NMR (400 MHz, DMSO-d$_6$) δ 8.47-8.44 (m, 1H), 8.38-8.34 (m, 1H), 8.05-8.00 (m, 1H), 7.72-7.65 (m, 2H), 7.59 (d, J=8.6 Hz, 1H), 4.81 (s, 1H), 4.46-4.40 (m, 4H), 4.36-4.25 (m, 2H), 3.98-3.93 (m, 1H), 3.93-3.81 (m, 2H), 2.70 (s, 3H), 2.38 (s, 3H), 2.37 (s, 3H), 1.28 (s, 3H), 1.24 (s, 3H), 1.24-1.18 (m, 4H).

Example 624: (*S)-3-(1-Cyclopropyl-4-methyl-1H-benzo[d][1,2,3]triazol-5-yl)-2,2-dimethyl-3-(6-methyl-5-((8'-methyl-1',1'-dioxidospiro[oxetane-3,4'-pyrido[2,3-b][1,4,5]oxathiazepin]-2'(3'H)-yl)methyl)pyridine-3-yl)propanoic Acid

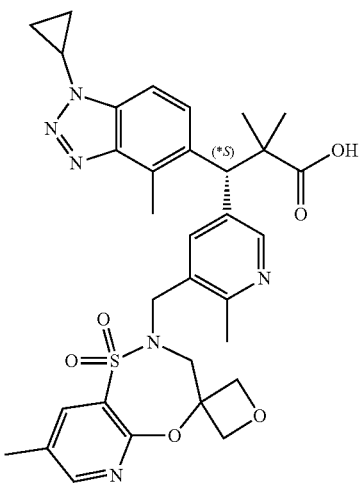 [SMILES: Cc1cnc2c(c1)S(=O)(=O)N(Cc1cc([C@H](c3ccc4c(nnn4C4CC4)c3C)C(C)(C)C(=O)O)cnc1C)CC1(COC1)O2]

Step A: (*S)-Methyl 3-(1-cyclopropyl-4-methyl-1H-benzo[d][1,2,3]triazol-5-yl)-2,2-dimethyl-3-(6-methyl-5-((8'-methyl-1',1'-dioxidospiro[oxetane-3,4'-pyrido[2,3-b][1,4,5]oxathiazepin]-2'(3'H)-yl)methyl)pyridin-3-yl)propanoate. (*S)-Methyl 3-(5-(chloromethyl)-6-methylpyridin-3-yl)-3-(1-cyclopropyl-4-methyl-1H-benzo[d][1,2,3]triazol-5-yl)-2,2-dimethylpropanoate (475 mg, 1.11 mmol, Intermediate 188), 8'-methyl-2',3'-dihydrospiro[oxetane-3,4'-pyrido[2,3-b][1,4,5]oxathiazepine] 1',1'-dioxide (260 mg, 1.02 mmol, Intermediate 190), K$_2$CO$_3$ (770 mg, 5.57 mmol), and CH$_3$CN (10 mL) were added to a 40 mL round-bottomed flask. The resultant mixture was stirred at 80° C. for 8 hours before cooling to room-temperature, pouring into water (20 mL), and extracting with ethyl acetate (3×). These extractions resulted in several fractions that were combined, washed with brine (20 mL), dried over anhydrous Na$_2$SO$_4$, and concentrated to dryness under reduced pressure to give the title compound (670 mg), which was used in the next step without further purification. MS (ESI): mass calcd. for $C_{33}H_{38}N_6O_6S$, 646.3 m/z found 647.2 [M+H]$^+$.

Step B: (*S)-3-(1-Cyclopropyl-4-methyl-1H-benzo[d][1,2,3]triazol-5-yl)-2,2-dimethyl-3-(6-methyl-5-((8'-methyl-1',1'-dioxidospiro[oxetane-3,4'-pyrido[2,3-b][1,4,5]oxathiazepin]-2'(3'H)-yl)methyl)pyridine-3-yl)propanoic acid. LiOH*H$_2$O (425 mg, 10.1 mmol) was added to a solution of (*S)-methyl 3-(1-cyclopropyl-4-methyl-1H-benzo[d][1,2,3]triazol-5-yl)-2,2-dimethyl-3-(6-methyl-5-((8'-methyl-1',1'-dioxidospiro[oxetane-3,4'-pyrido[2,3-b][1,4,5]oxathiazepin]-2'(3'H)-yl)methyl)pyridine-3-yl)propanoate (650 mg, 1.01 mmol) and 1,4-dioxane: H$_2$O (1:1, 10 mL). The resulting mixture was stirred at 60° C. for 4 hours before adjusting the pH to 3 with 1 N HCl and extracting with ethyl acetate (3×). These extractions resulted in several fractions that were combined, dried over anhydrous Na$_2$SO$_4$, filtered, and concentrated to dryness under reduced pressure. The residue was purified by preparative reverse phase HPLC (eluent: MeCN/H$_2$O with 0.225% HCOOH 16% to 46%, gradient) to give the title compound (343 mg, 53%). MS (ESI): mass calcd. for $C_{32}H_{36}N_6O_6S$, 632.2 m/z found 633.3 [M+H]$^+$. $^1$H NMR (400 MHz, DMSO-d$_6$) δ 8.47-8.43 (m, 1H), 8.37-8.34 (m, 1H), 8.04-8.02 (m, 1H), 7.72-7.65 (m, 2H), 7.59 (d, J=8.6 Hz, 1H), 4.81 (s, 1H), 4.46-4.39 (m, 4H), 4.37-4.25 (m, 2H), 3.98-3.93 (m, 1H), 3.93-3.81 (m, 2H), 2.70 (s, 3H), 2.38 (s, 3H), 2.37 (s, 3H), 1.28 (s, 3H), 1.24 (s, 3H), 1.24-1.19 (m, 4H).

Example 625: (*R)-3-(1-Cyclopropyl-4-methyl-1H-benzo[d[1,2,3]triazolo-5-yl)-2,2-dimethyl-3-(6-methyl-5-((8*-methyl-1',1'-dioxido-7'-(2-(pyrrolidine-1-yl)ethoxy)spiro[cyclopropane-1,4'-pyrido[2,3-b][1,4,5]oxathiazepin]-2'(3'H)-yl)methyl)pyridine-3-yl)propanoic Acid

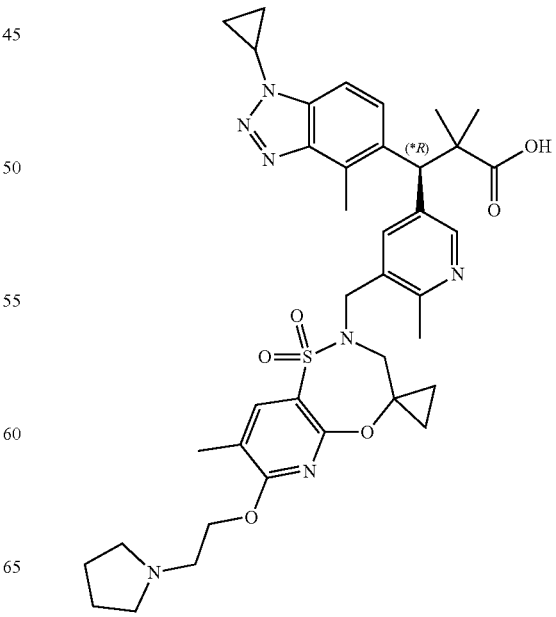

The title compound (150 mg, 23%) was prepared using analogous conditions as described in Example 628 where (*R)-Methyl 3-(5-(chloromethyl)-6-methylpyridin-3-yl)-3-(1-cyclopropyl-4-methyl-1H-benzo[d][1,2,3]triazol-5-yl)-2,2-dimethylpropanoate (Intermediate 189) was used instead of (*S)-Methyl 3-(5-(chloromethyl)-6-methylpyridin-3-yl)-3-(1-cyclopropyl-4-methyl-1H-benzo[d][1,2,3]triazol-5-yl)-2,2-dimethylpropanoate in step A. MS (ESI): mass calcd. for $C_{38}H_{47}N_7O_6S$, 729.3; m/z found 730.4 $[M+H]^+$. $^1$H NMR (400 MHz, DMSO-$d_6$) δ 8.34-8.30 (m, 1H), 7.93 (s, 1H), 7.68-7.64 (m, 1H), 7.61-7.57 (m, 1H), 7.57-7.55 (m, 1H), 4.78 (s, 1H), 4.38 (t, J=5.6 Hz, 2H), 4.24-4.14 (m, 2H), 3.99-3.92 (m, 1H), 2.81 (t, J=5.8 Hz, 2H), 2.68 (s, 3H), 2.57-2.52 (m, 6H), 2.39 (s, 3H), 2.17 (s, 3H), 1.71-1.66 (m, 4H), 1.26 (s, 3H), 1.26-1.22 (m, 4H), 1.21 (s, 3H), 1.02-0.95 (m, 2H), 0.66-0.55 (m, 2H).

Example 626: (*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[oxetane-3,4'-pyrido[2,3-b][1,4,5]oxathiazepin]-2'(3'H)-yl)methyl)pyridin-2-yl)propanoic Acid

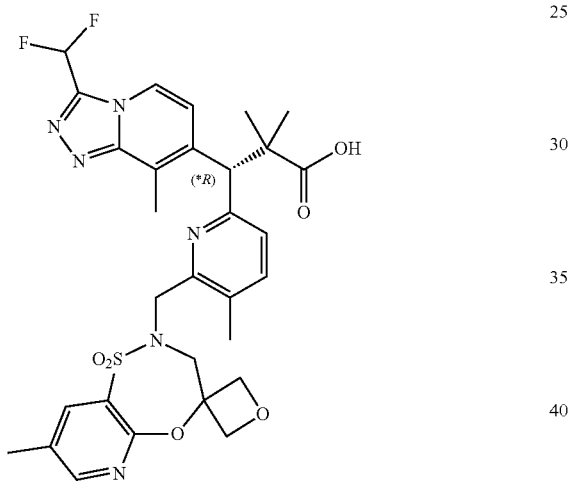

The second eluting isomer (240.8 mg) for the chiral separation described in Example 627 was designated (*R): MS (ESI): mass calcd. for $C_{30}H_{32}F_2N_6O_6S$, 642.2 m/z found, 643.3 $[M+H]^+$. $^1$H NMR (400 MHz, DMSO-$d_6$) δ 12.39 (br s, 1H), 8.46 (d, J=1.8 Hz, 1H), 8.28 (d, J=7.3 Hz, 1H), 8.08 (d, J=1.8 Hz, 1H), 7.68 (t, J=51.6 Hz, 1H), 7.57-7.50 (m, 2H), 7.27 (d, J=7.7 Hz, 1H), 4.96 (s, 1H), 4.67-4.59 (m, 2H), 4.52 (d, J=7.7 Hz, 2H), 4.37 (s, 2H), 4.09-3.94 (m, 2H), 2.75 (s, 3H), 2.39 (s, 3H), 2.28 (s, 3H), 1.34 (s, 3H), 1.28 (s, 3H).

Example 627: (*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[oxetane-3,4'-pyrido[2,3-b][1,4,5]oxathiazepin]-2'(3'H)-yl)methyl)pyridin-2-yl)propanoic Acid

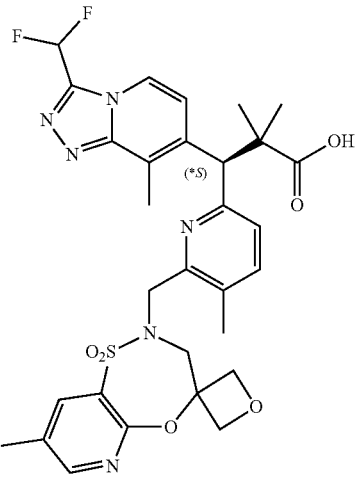 [SMILES: Cc1cnc2c(c1)S(=O)(=O)N(Cc1nc([C@@H](c3ccn4c(C(F)F)nnc4c3C)C(C)(C)C(=O)O)ccc1C)CC1(COC1)O2]

The title compound (50.5 mg) was prepared using analogous reaction conditions as described in Example 610 where 8'-methyl-2',3'-dihydrospiro[oxetane-3,4'-pyrido[2,3-b][1,4,5]oxathiazepine] 1',1'-dioxide (Intermediate 190) was used instead of 2',3'-dihydrospiro[oxetane-3,4'-pyrido[2,3-b][1,4,5]oxathiazepine] 1',1'-dioxide in Step A and the following chiral SFC separation conditions where used in Step B: Daicel Chiralpak IG column, 250 mm×30 mm×10 am, eluent: 40% ethanol containing 0.1% v/v 25% aqueous ammonia:$CO_2$) to afford two isomers. The first eluting isomer (163.9 mg) was designated (*S): MS (ESI): mass calcd. for $C_{30}H_{32}F_2N_6O_6S$, 642.2 m/z found, 643.3 $[M+H]^+$. $^1$H NMR (400 MHz, DMSO-$d_6$) δ 12.33 (br s, 1H), 8.46 (d, J=1.5 Hz, 1H), 8.28 (d, J=7.3 Hz, 1H), 8.08 (d, J=1.8 Hz, 1H), 7.74 (t, J=51.6 Hz, 1H), 7.57-7.50 (m, 2H), 7.27 (d, J=7.9 Hz, 1H), 4.96 (s, 1H), 4.63 (t, J=8.8 Hz, 2H), 4.52 (d, J=7.7 Hz, 2H), 4.37 (s, 2H), 4.09-3.94 (m, 2H), 2.75 (s, 3H), 2.39 (s, 3H), 2.28 (s, 3H), 1.34 (s, 3H), 1.28 (s, 3H).

Example 628: (*S)-3-(1-Cyclopropyl-4-methyl-1H-benzo[d][1,2,3]triazol-5-yl)-2,2-dimethyl-3-(6-methyl-5-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridine-3-yl)propanoic Acid

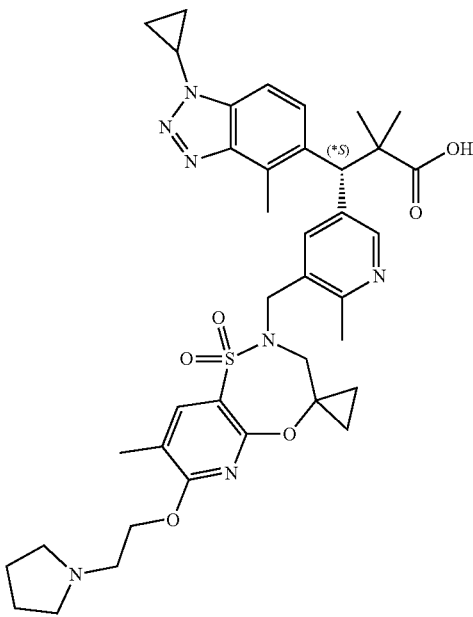 [SMILES: Cc1cc2c(nc1OCCN1CCCC1)OC1(CC1)CN(Cc1cc([C@H](c3ccc4c(nnn4C4CC4)c3C)C(C)(C)C(=O)O)cnc1C)S2(=O)=O]

Step A: (*S)-Methyl 3-(1-cyclopropyl-4-methyl-1H-benzo[d][1,2,3]triazol-5-yl)-2,2-dimethyl-3-(6-methyl-5-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-3-yl)propanoate. (*S)-Methyl 3-(5-(chloromethyl)-6-methylpyridin-3-yl)-3-(1-cyclopropyl-4-methyl-1H-benzo[d][1,2,3]triazol-5-yl)-2,2-dimethylpropanoate (480 mg, 1.12 mmol, Intermediate 188), 8'-methyl-7'-(2-(pyrrolidin-1-yl)ethoxy)-2',3'-dihydrospiro[cyclopropane-1,4'-pyrido[2,3-b][1,4,5]oxathiazepine] 1',1'-dioxide (360 mg, 1.02 mmol, Intermediate 137), $K_2CO_3$ (780 mg, 5.64 mmol), and $CH_3CN$ (15 mL) were added to a 40 mL flask. The resulting suspension was stirred at 80° C. for 6 hours, cooled to room-temperature, poured it into water (30 mL), and extracted with ethyl acetate (3×). These extractions resulted in several fractions that were combined, washed with brine (1×), dried over anhydrous $Na_2SO_4$, filtered, and concentrated to dryness under reduced pressure to give the product (700 mg), which was used in the next step without further purification. MS (ESI): mass calcd. for $C_{39}H_{49}N_7O_6S$, 743.4 m/z found 744.3 [M+H]$^+$.

Step B: (*S)-3-(1-Cyclopropyl-4-methyl-1H-benzo[d][1,2,3]triazol-5-yl)-2,2-dimethyl-3-(6-methyl-5-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-3-yl)propanoic acid. n-Bu$_4$NOH (1.7 g, 16 mmol) was added to a solution of (*S)-methyl 3-(1-cyclopropyl-4-methyl-1H-benzo[d][1,2,3]triazol-5-yl)-2,2-dimethyl-3-(6-methyl-5-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-3-yl)propanoate (400 mg, 0.538 mmol) and t-BuOH:H$_2$O (3:1, 20 mL). The resulting mixture was stirred at 90° C. for 3 hours, poured into aqueous NH$_4$Cl (40 mL), and extracted with ethyl acetate (3×). These extractions resulted in several fractions that were combined, washed with brine (3×), dried over anhydrous Na$_2$SO$_4$, filtered, and concentrated to dryness under reduced pressure. The residue was purified by preparative reverse phase HPLC (eluent: MeCN/H$_2$O with 0.225% HCOOH 12% to 42%, gradient) and the isolated product combined with another batch of (*S)-3-(1-Cyclopropyl-4-methyl-1H-benzo[d][1,2,3]triazol-5-yl)-2,2-dimethyl-3-(6-methyl-5-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-3-yl)propanoic acid to afford the title compound (200 mg). MS (ESI): mass calcd. for $C_{38}H_{47}N_7O_6S$, 729.3; m/z found 730.4 [M+H]$^+$. $^1$H NMR (400 MHz, DMSO-d$_6$) δ 8.34-8.29 (m, 1H), 7.93 (s, 1H), 7.69-7.62 (m, 1H), 7.60-7.53 (m, 2H), 4.78 (s, 1H), 4.42-4.35 (m, 2H), 4.23-4.16 (m, 2H), 4.00-3.92 (m, 1H), 2.81 (t, J=5.8 Hz, 2H), 2.68 (s, 3H), 2.59-2.52 (m, 6H), 2.39 (s, 3H), 2.17 (s, 3H), 1.74-1.63 (m, 4H), 1.25 (s, 3H), 1.25-1.21 (m, 4H), 1.20 (s, 3H), 1.04-0.93 (m, 2H), 0.67-0.53 (m, 2H).

Example 629: (*R)-2,2-Dimethyl-3-(8-methyl-3-(trifluoromethyl)-[1,2,4]triazolo[4,3-a]pyridin-7-yl)-3-(5-methyl-6-((8'-methyl-1',1'-dioxidospiro[azetidine-3,4'-pyrido[2,3-b][1,4,5]oxathiazepin]-2'(3'H)-yl)methyl)pyridin-2-yl)propanoic Acid

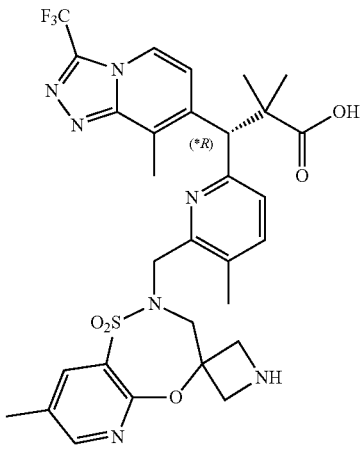 [SMILES: Cc1cnc2c(c1)S(=O)(=O)N(Cc1nc([C@H](c3ccn4c(C(F)(F)F)nnc4c3C)C(C)(C)C(=O)O)ccc1C)CC1(CNC1)O2]

The title compound was prepared (24 mg) was prepared using analogous reaction conditions as described in Example 630, Step B where the second eluting isomer from Example 630, Step A was used instead of the first eluting isomer from Example 630, Step A. MS (ESI): mass calcd. for $C_{30}H_{32}F_3N_7O_5S$, 659.2 m/z found, 660.3 [M+H]$^+$. $^1$H NMR (400 MHz, DMSO-d$_6$) δ 8.50-8.45 (m, 1H), 8.29 (d, J=7.1 Hz, 1H), 8.09 (d, J=1.5 Hz, 1H), 7.79 (s, 1H), 7.54 (d, J=8.1 Hz, 1H), 7.25 (d, J=7.8 Hz, 1H), 4.82 (d, J=13.0 Hz, 1H), 4.69 (s, 1H), 4.26 (d, J=10.8 Hz, 1H), 4.03-3.98 (m, 1H), 3.94-3.89 (m, J=10.0 Hz, 2H), 3.86-3.74 (m, 4H), 2.68 (s, 3H), 2.40 (s, 3H), 2.28 (s, 3H), 1.19 (s, 3H), 1.16 (s, 3H).

Example 630: (*S)-2,2-Dimethyl-3-(8-methyl-3-(trifluoromethyl)-[1,2,4]triazolo[4,3-a]pyridin-7-yl)-3-(5-methyl-6-((8'-methyl-1',1'-dioxidospiro[azetidine-3,4'-pyrido[2,3-b][1,4,5]oxathiazepin]-2'(3'H)-yl)methyl)pyridin-2-yl)propanoic Acid

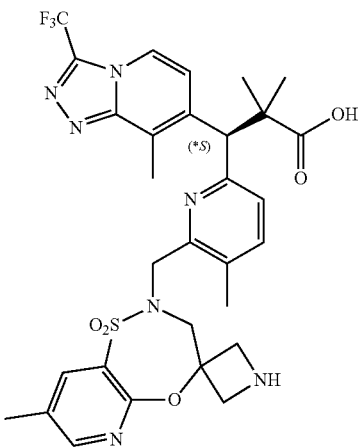 [SMILES: Cc1cnc2c(c1)S(=O)(=O)N(Cc1nc([C@@H](c3ccn4c(C(F)(F)F)nnc4c3C)C(C)(C)C(=O)O)ccc1C)CC1(CNC1)O2]

Step A: tert-Butyl 2'-((6-(3-(tert-butoxy)-2,2-dimethyl-1-(8-methyl-3-(trifluoromethyl)-[1,2,4]triazolo[4,3-a]pyridin-7-yl)-3-oxopropyl)-3-methylpyridin-2-yl)methyl)-8'-methyl-2',3'-dihydrospiro[azetidine-3,4'-pyrido[2,3-b][1,4,5]oxathiazepine]-1-carboxylate 1',1'-dioxide. DIAD (162 mg, 0.801 mmol) was added dropwise to a stirring solution of tert-butyl 3-(6-(hydroxymethyl)-5-methylpyridin-2-yl)-2,2-dimethyl-3-(8-methyl-3-(trifluoromethyl)-[1,2,4]triazolo[4,3-a]pyridin-7-yl)propanoate (Intermediate 197 250 mg, 0.522 mmol), tert-butyl 8'-methyl-2',3'-dihydrospiro[azetidine-3,4'-pyrido[2,3-b][1,4,5]oxathiazepine]-1-carboxylate 1',1'-dioxide (Intermediate 153, 223 mg, 0.627 mmol) and PPh$_3$ (222 mg, 0.846 mmol) in dichloromethane (10 mL) at 0° C. The mixture was allowed to slowly warm to room temperature over the course of 3 hours whereupon the mixture was poured into water and then extracted with dichloromethane. These extractions resulted in several organic solvent fractions which were combined, washed with brine solution, dried over Na$_2$SO$_4$, filtered, and concentrated to dryness under reduced pressure. The residue was purified by preparative HPLC (Phenomenex Gemini-NX column, 150×30 mm×5 m, eluent: 66% to 96% (v/v) CH$_3$CN in H$_2$O with 0.2% HCOOH) to afford the title compound as a mixture of enantiomers. This mixture was purified by SFC using a chiral stationary phase (Regis (S,S) Whelk-O1 column, 250 mm×30 mm, 10 m, eluent: 50% isopropanol containing 0.1% v/v 25% aqueous ammonia:CO$_2$) to afford two isomers. The first eluting isomer (120 mg) was designated (*S): MS (ESI): mass calcd. for C$_{39}$H$_{48}$F$_3$N$_7$O$_7$S, 815.3 m/z found, 816.3 [M+H]$^+$. The second eluting isomer (110 mg) was designated (*R): MS (ESI): mass calcd. for C$_{39}$H$_{48}$F$_3$N$_7$O$_7$S, 815.3 m/z found, 816.3 [M+H]$^+$.

Step B: (*S)-2,2-Dimethyl-3-(8-methyl-3-(trifluoromethyl)-[1,2,4]triazolo[4,3-a]pyridin-7-yl)-3-(5-methyl-6-((8'-methyl-1',1'-dioxidospiro[azetidine-3,4'-pyrido[2,3-b][1,4,5]oxathiazepin]-2'(3'H)-yl)methyl)pyridin-2-yl)propanoic acid. A mixture containing the first eluting isomer from Example DK 518, Step A (160 mg, 0.196 mmol) and 4 M HCl solution in dioxane (10 mL) in dioxane-acetonitrile (3:1, 8 mL) was stirred at room temperature. After 24 hours, the mixture was concentrated to dryness under reduced pressure. The residue was purified by SFC using a chiral stationary phase (Daicel Chiralpak IG column, 250 mm×50 mm×10 μm, eluent: 50% ethanol containing 0.1% v/v 25% aqueous ammonia:CO$_2$) to afford the title compound (43 mg, 33%) as a white solid after concentrating to dryness by lyophilization. MS (ESI): mass calcd. for C$_{30}$H$_{32}$F$_3$N$_7$O$_5$S, 659.2 m/z found, 660.3 [M+H]$^+$. $^1$H NMR (400 MHz, DMSO-d$_6$) δ 8.50-8.45 (m, 1H), 8.29 (d, J=7.2 Hz, 1H), 8.09 (d, J=1.7 Hz, 1H), 7.79 (s, 1H), 7.53 (d, J=7.8 Hz, 1H), 7.25 (d, J=7.8 Hz, 1H), 4.82 (d, J=13.0 Hz, 1H), 4.69 (s, 1H), 4.24 (d, J=10.8 Hz, 1H), 4.00 (d, J=15.6 Hz, 1H), 3.91 (d, J=10.0 Hz, 2H), 3.85-3.75 (m, 4H), 2.68 (s, 3H), 2.40 (s, 3H), 2.28 (s, 3H), 1.19 (s, 3H), 1.16 (s, 3H).

Example 631: (*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[azetidine-3,4'-pyrido[2,3-b][1,4,5]oxathiazepin]-2'(3'H)-yl)methyl)pyridin-2-yl)propanoic Acid

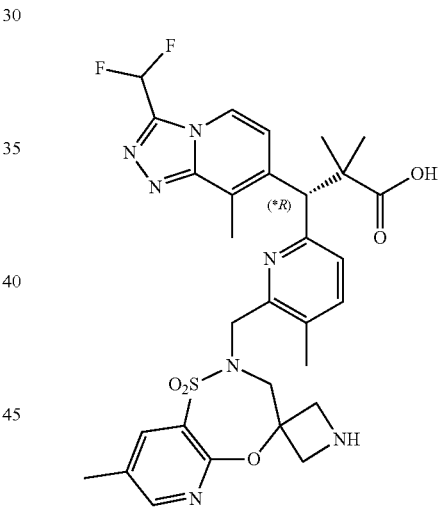

The second eluting isomer (30.4 mg) for the chiral separation described in Example 631 was designated (*R): MS (ESI): mass calcd. for C$_{30}$H$_{33}$F$_2$N$_7$O$_5$S, 641.2 m/z found, 642.2 [M+H]$^+$. $^1$H NMR (400 MHz, DMSO-d$_6$) δ 8.47 (d, J=1.7 Hz, 1H), 8.27 (d, J=7.1 Hz, 1H), 8.09 (d, J=1.7 Hz, 1H), 7.67 (t, J=52 Hz, 1H), 7.67 (s, 1H), 7.53 (d, J=8.1 Hz, 1H), 7.22 (d, J=7.6 Hz, 1H), 4.83 (d, J=13.2 Hz, 1H), 4.69 (s, 1H), 4.25 (d, J=10.8 Hz, 1H), 4.03-3.88 (m, 4H), 3.84-3.78 (m, 2H), 2.66 (s, 3H), 2.40 (s, 3H), 2.27 (s, 3H), 1.21-1.13 (m, 6H).

Example 632: (*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[azetidine-3,4'-pyrido[2,3-b][1,4,5]oxathiazepin]-2'(3'H)-yl)methyl)pyridin-2-yl)propanoic Acid

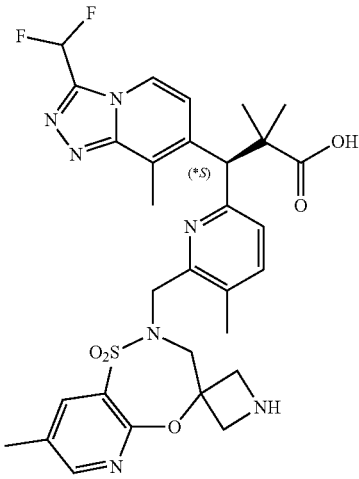 [SMILES: Cc1cnc2c(c1)S(=O)(=O)N(Cc1nc([C@@H](c3ccn4c(C(F)F)nnc4c3C)C(C)(C)C(=O)O)ccc1C)CC1(CNC1)O2]

Step A: tert-Butyl 2'-((6-(1-(3-(difluoromethyl)-8-methyl-[1,2,4]triazolo[4,3-a]pyridin-7-yl)-3-methoxy-2,2-dimethyl-3-oxopropyl)-3-methylpyridin-2-yl)methyl)-8'-methyl-2',3'-dihydrospiro[azetidine-3,4'-pyrido[2,3-b][1,4,5]oxathiazepine]-1-carboxylate 1',1'-dioxide. The title compound (490 mg) was prepared using analogous reaction conditions as described in Example 642, Step A where methyl 3-(6-(chloromethyl)-5-methylpyridin-2-yl)-3-(3-(difluoromethyl)-8-methyl-[1,2,4]triazolo[4,3-a]pyridin-7-yl)-2,2-dimethylpropanoate (Intermediate 196) was used instead of tert-butyl 3-(4-(chloromethyl)-5-methylpyridin-2-yl)-3-(3-(difluoromethyl)-8-methyl-[1,2,4]triazolo[4,3-a]pyridin-7-yl)-2,2-dimethylpropanoate and tert-butyl 8'-methyl-2',3'-dihydrospiro[azetidine-3,4'-pyrido[2,3-b][1,4,5]oxathiazepine]-1-carboxylate 1',1'-dioxide (Intermediate 153) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide. MS (ESI): mass calcd. for $C_{36}H_{43}F_2N_7O_7S$, 755.3 m/z found, 756.3 [M+H]$^+$. $^1$H NMR (400 MHz, Methanol-d$_4$) δ 8.40 (d, J=1.8 Hz, 1H), 8.27 (d, J=7.3 Hz, 1H), 8.17 (d, J=1.8 Hz, 1H), 7.51 (d, J=7.9 Hz, 1H), 7.45 (br d, J=7.3 Hz, 1H), 7.35-7.19 (m, 1H), 7.11 (d, J=7.7 Hz, 1H), 5.10 (s, 1H), 4.57-4.49 (m, 2H), 4.06-3.93 (m, 6H), 3.55 (s, 3H), 2.82 (s, 3H), 2.46 (s, 3H), 2.36 (s, 3H), 1.48 (s, 3H), 1.42 (s, 9H).

Step B: Methyl 3-(3-(difluoromethyl)-8-methyl-[1,2,4]triazolo[4,3-a]pyridin-7-yl)-2,2-dimethyl-3-(5-methyl-6-((8'-methyl-1',1'-dioxidospiro[azetidine-3,4'-pyrido[2,3-b][1,4,5]oxathiazepin]-2'(3'H)-yl)methyl)pyridin-2-yl)propanoate. The title compound (400 mg) was prepared using analogous reaction conditions as described in Example 642, Step B where tert-butyl 2'-((6-(1-(3-(difluoromethyl)-8-methyl-[1,2,4]triazolo[4,3-a]pyridin-7-yl)-3-methoxy-2,2-dimethyl-3-oxopropyl)-3-methylpyridin-2-yl)methyl)-8'-methyl-2',3'-dihydrospiro[azetidine-3,4'-pyrido[2,3-b][1,4,5]oxathiazepine]-1-carboxylate 1',1'-dioxide was used instead of tert-butyl 3-(3-(difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoate. MS (ESI): mass calcd. for $C_{31}H_{35}F_2N_7O_5S$, 655.3 m/z found, 656.3 [M+H]$^+$.

Step C: (*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxidospiro[azetidine-3,4'-pyrido[2,3-b][1,4,5]oxathiazepin]-2'(3'H)-yl)methyl)pyridin-2-yl)propanoic acid. A mixture containing NaOH (68 mg, 1.7 mmol) and methyl 3-(3-(difluoromethyl)-8-methyl-[1,2,4]triazolo[4,3-a]pyridin-7-yl)-2,2-dimethyl-3-(5-methyl-6-((8'-methyl-1',1'-dioxidospiro[azetidine-3,4'-pyrido[2,3-b][1,4,5]oxathiazepin]-2'(3'H)-yl)methyl)pyridin-2-yl)propanoate (340 mg, 0.519 mmol) in THF-water (1:1, 4 mL) was stirred at 75° C. After 6 hours, the mixture was allowed to cool to room temperature and then the pH was adjusted to 6-7 by adding 1 N aqueous HCl solution. The mixture was poured into water and then extracted with ethyl acetate. These extractions resulted in several organic solvent fractions which were combined, washed with brine solution, dried over Na$_2$SO$_4$, filtered, and concentrated to dryness under reduced pressure. The residue was purified by preparative HPLC (Boston Green ODS column, 150×30×5 m column, eluent: 15% to 45% (v/v) CH$_3$CN in H$_2$O with 0.225% HCOOH) to give the title compound (190 mg, 54%) as a mixture of enantiomers. This mixture was purified by SFC using a chiral stationary phase (Daicel Chiralpak IG column, 250 mm×50 mm×10 m, eluent: 50% ethanol containing 0.1% v/v 25% aqueous ammonia:CO$_2$) to afford two isomers both of which were further purified by preparative HPLC (Xtimate C$_{18}$ column, 150 mm×40 mm×10 µm (eluent: 15% to 45% (v/v) CH$_3$CN in water with 0.225% HCOOH). The first eluting isomer (35 mg) was designated (*S): MS (ESI): mass calcd. for $C_{30}H_{33}F_2N_7O_5S$, 641.2 m/z found, 642.2 [M+H]$^+$. $^1$H NMR (400 MHz, DMSO-d$_6$) δ 8.47 (d, J=1.7 Hz, 1H), 8.27 (d, J=7.3 Hz, 1H), 8.08 (d, J=1.7 Hz, 1H), 7.67 (t, J=52 Hz, 1H), 7.67 (s, 1H), 7.52 (d, J=8.1 Hz, 1H), 7.22 (d, J=7.8 Hz, 1H), 4.82 (d, J=13.0 Hz, 1H), 4.69 (s, 1H), 4.24 (d, J=10.5 Hz, 1H), 4.03-3.88 (m, 4H), 3.82-3.77 (m, 2H), 2.65 (s, 3H), 2.39 (s, 3H), 2.27 (s, 3H), 1.18 (s, 6H).

Example 633: (*R)-2,2-Dimethyl-3-(8-methyl-3-(trifluoromethyl)-[1,2,4]triazolo[4,3-a]pyridin-7-yl)-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic Acid

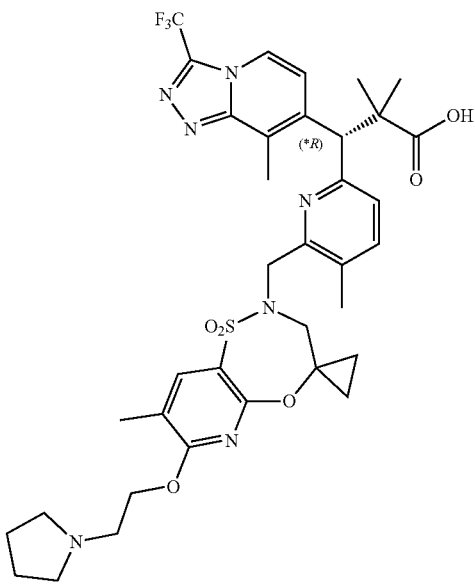 [SMILES: Cc1ccc([C@H](c2ccn3c(C(F)(F)F)nnc3c2C)C(C)(C)C(=O)O)nc1CN1CC2(CC2)Oc2nc(OCCN3CCCC3)c(C)cc2S1(=O)=O]

The second eluting isomer (87.2 mg) for the chiral separation described in Example 634 was designated (*R): MS (ESI): mass calcd. for $C_{36}H_{42}F_3N_7O_6S$, 757.3 m/z found, 758.3 [M+H]$^+$. $^1$H NMR (400 MHz, DMSO-$d_6$) δ 8.30 (d, J=7.1 Hz, 1H), 7.99 (s, 1H), 7.54 (d, J=8.1 Hz, 1H), 7.36 (d, J=7.3 Hz, 1H), 7.23 (d, J=7.8 Hz, 1H), 4.95 (s, 1H), 4.42-4.37 (m, 2H), 4.35-4.23 (m, 2H), 3.73-3.61 (m, 2H), 2.80 (t, J=5.6 Hz, 2H), 2.74 (s, 3H), 2.56-2.52 (m, 4H), 2.33 (s, 3H), 2.18 (s, 3H), 1.72-1.63 (m, 4H), 1.29 (s, 3H), 1.20 (s, 3H), 1.07-0.95 (m, 2H), 0.82 (s, 2H).

Example 634: (*S)-2,2-Dimethyl-3-(8-methyl-3-(trifluoromethyl)-[1,2,4]triazolo[4,3-a]pyridin-7-yl)-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic Acid

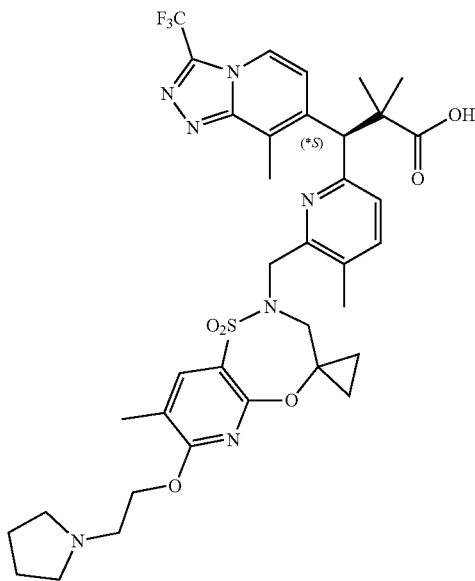 [SMILES: Cc1ccc([C@@H](c2ccn3c(C(F)(F)F)nnc3c2C)C(C)(C)C(=O)O)nc1CN1CC2(CC2)Oc2nc(OCCN3CCCC3)c(C)cc2S1(=O)=O]

Step A: tert-Butyl 2,2-dimethyl-3-(8-methyl-3-(trifluoromethyl)-[1,2,4]triazolo[4,3-a]pyridin-7-yl)-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoate. The title compound (500 mg) was prepared using analogous reaction conditions as described in Example 642, Step A using tert-butyl 3-(6-(chloromethyl)-5-methylpyridin-2-yl)-2,2-dimethyl-3-(8-methyl-3-(trifluoromethyl)-[1,2,4]triazolo[4,3-a]pyridin-7-yl)propanoate (Intermediate 198) instead of tert-butyl 3-(4-(chloromethyl)-5-methylpyridin-2-yl)-3-(3-(difluoromethyl)-8-methyl-[1,2,4]triazolo[4,3-a]pyridin-7-yl)-2,2-dimethylpropanoate and using 8'-methyl-7'-(2-(pyrrolidin-1-yl)ethoxy)-2',3'-dihydrospiro[cyclopropane-1,4'-pyrido[2,3-b][1,4,5]oxathiazepine] 1',1'-dioxide (Intermediate 137) instead of 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide. MS (ESI): mass calcd. for $C_{40}H_{50}F_3N_7O_6S$, 813.2 m/z found, 814.4 [M+H]$^+$.

Step B: (*S)-2,2-Dimethyl-3-(8-methyl-3-(trifluoromethyl)-[1,2,4]triazolo[4,3-a]pyridin-7-yl)-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic acid. A mixture containing tert-butyl 2,2-dimethyl-3-(8-methyl-3-(trifluoromethyl)-[1,2,4]triazolo[4,3-a]pyridin-7-yl)-3-(5-methyl-6-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoate (500 mg, 0.467 mmol) and 4 M HCl solution in dioxane (20 mL) in dioxane-acetonitrile (1:1, 10 mL) was stirred at room temperature. After 16 hours, the mixture was concentrated to dryness under reduced pressure. The residue was purified by preparative HPLC (Xtimate C18 column, 150 mm×40 mm×10 μm (eluent: 25% to 55% (v/v) $CH_3CN$ in water with 0.225% HCOOH) to afford a mixture of enantiomers. This mixture was further purified by SFC using a chiral stationary phase (Daicel Chiralpak IG column, 250 mm×50 mm×10 am, eluent: 50% ethanol containing 0.1% v/v 25% aqueous ammonia:$CO_2$) to afford two isomers. The first eluting isomer (88 mg) was designated (*S): MS (ESI): mass calcd. for $C_{36}H_{42}F_3N_7O_6S$, 757.3 m/z found, 758.3 [M+H]$^+$. $^1$H NMR (400 MHz, DMSO-$d_6$) δ 8.30 (d, J=7.3 Hz, 1H), 7.99 (s, 1H), 7.54 (d, J=7.8 Hz, 1H), 7.36 (d, J=7.3 Hz, 1H), 7.23 (d, J=7.8 Hz, 1H), 4.95 (s, 1H), 4.42-4.37 (m, 2H), 4.36-4.25 (m, 2H), 3.74-3.60 (m, 2H), 2.80 (t, J=5.7 Hz, 2H), 2.74 (s, 3H), 2.56-2.53 (m, 4H), 2.33 (s, 3H), 2.18 (s, 3H), 1.72-1.65 (m, 4H), 1.29 (s, 3H), 1.21 (s, 3H), 1.07-0.96 (m, 2H), 0.87-0.77 (m, 2H).

Example 635: (*R)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic Acid

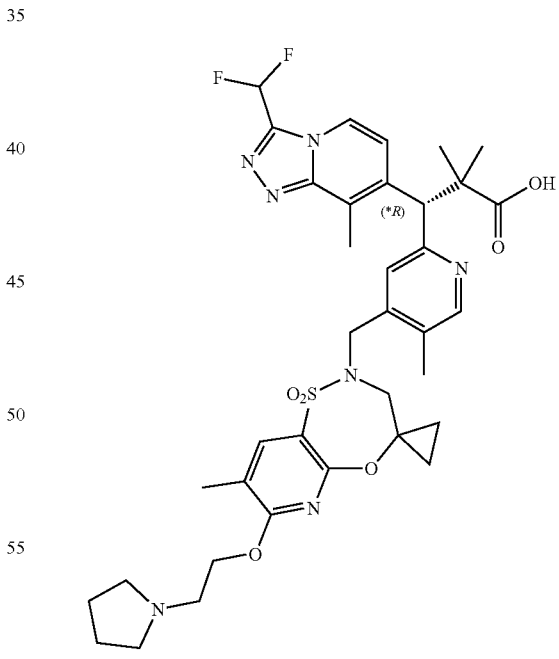

The second eluting isomer (57.6 mg) for the chiral separation described in Example 636 was designated (*R): MS (ESI): mass calcd. for $C_{36}H_{43}F_2N_7O_6S$, 739.3 m/z found, 740.3 [M+H]$^+$. $^1$H NMR (400 MHz, DMSO-$d_6$) δ 8.35-8.30 (m, 2H), 7.90 (s, 1H), 7.84-7.56 (m, 1H), 7.34 (d, J=6.8 Hz, 1H), 7.16 (s, 1H), 4.95 (s, 1H), 4.36 (t, J=5.6 Hz, 2H), 4.22-4.13 (m, 2H), 3.66-3.59 (m, 2H), 3.52-3.46 (m, 4H), 2.78 (t, J=5.6 Hz, 2H), 2.72 (s, 3H), 2.20 (s, 3H), 2.14 (s, 3H), 1.69-1.64 (m, 4H), 1.25 (s, 3H), 1.22 (s, 3H), 1.00-0.91 (m, 2H), 0.75-0.60 (m, 2H).

Example 636: (*S)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)pyridin-2-yl)propanoic Acid

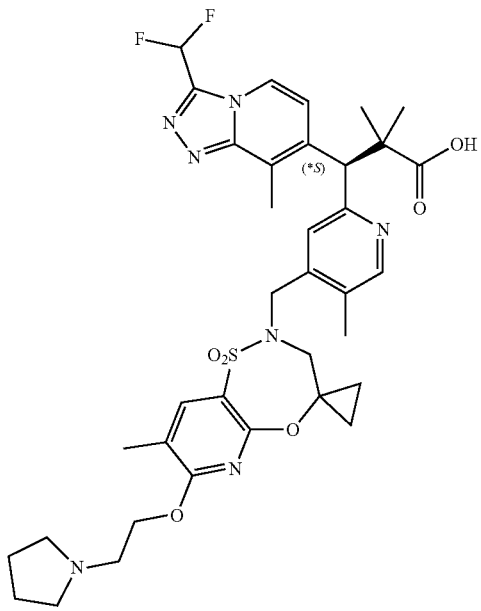 [SMILES: Cc1cnc([C@@H](c2ccn3c(C(F)F)nnc3c2C)C(C)(C)C(=O)O)cc1CN1CC2(CC2)Oc2nc(OCCN3CCCC3)c(C)cc2S1(=O)=O]

(m, 2H), 3.44-3.42 (m, 4H), 2.79 (t, J=5.6 Hz, 2H), 2.73 (s, 3H), 2.20 (s, 3H), 2.14 (s, 3H), 1.70-1.66 (m, 4H), 1.28 (s, 3H), 1.25 (s, 3H), 0.99-0.90 (m, 2H), 0.73-0.56 (m, 2H).

Example 637: (*R)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic Acid

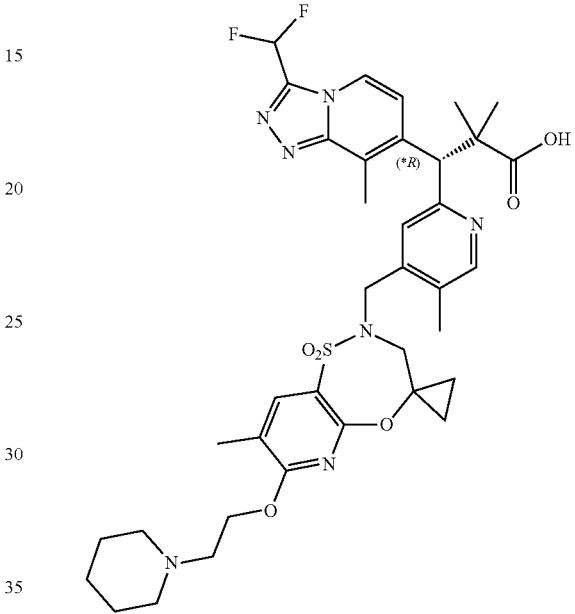

The title compound (58.6 mg) was prepared using analogous reaction conditions as described in Example 640 where 8'-methyl-7'-(2-(pyrrolidin-1-yl)ethoxy)-2',3'-dihydrospiro[cyclopropane-1,4'-pyrido[2,3-b][1,4,5]oxathiazepine] 1',1'-dioxide (Intermediate 137) was used instead of 8'-methyl-7'-(2-(pyrrolidin-1-yl)ethoxy)-2,2',3,3',5,6-hexahydrospiro[pyran-4,4'-pyrido[2,3-b][1,4,5]oxathiazepine] 1',1'-dioxide in Step A and following separation by SFC using a chiral stationary phase (Daicel Chiralpak IG column, 250 mm×50 mm, 10 am, eluent: 50% ethanol containing 0.1% v/v 25% aqueous ammonia:CO₂). The first eluting isomer (58.6 mg) was designated (*S): MS (ESI): mass calcd. for $C_{36}H_{43}F_2N_7O_6S$, 739.3 m/z found, 740.3 [M+H]⁺. ¹H NMR (400 MHz, DMSO-d₆) δ 8.35-8.31 (m, 2H), 7.89 (s, 1H), 7.84-7.56 (m, 1H), 7.30 (d, J=7.1 Hz, 1H), 7.14 (s, 1H), 4.94 (s, 1H), 4.37 (t, J=5.6 Hz, 2H), 4.23-4.12 (m, 2H), 3.86-3.67

The second eluting isomer (51 mg) for the chiral separation described in Example 638 was designated (*R): MS (ESI): mass calcd. for $C_{37}H_{45}F_2N_7O_6S$, 753.3 m/z found, 754.3 [M+H]⁺. ¹H NMR (400 MHz, DMSO-d₆) δ 8.36-8.31 (m, 2H), 7.89 (s, 1H), 7.84-7.57 (m, 1H), 7.28 (d, J=7.3 Hz, 1H), 7.14 (s, 1H), 4.94 (s, 1H), 4.35 (t, J=5.9 Hz, 2H), 4.22-4.12 (m, 2H), 3.67-3.56 (m, 2H), 2.73 (s, 3H), 2.66-2.63 (m, 2H), 2.46-2.40 (m, 4H), 2.20 (s, 3H), 2.13 (s, 3H), 1.49-1.44 (m, 4H), 1.40-1.34 (m, 2H), 1.29 (s, 3H), 1.24 (s, 3H), 1.01-0.87 (m, 2H), 0.76-0.55 (m, 2H).

Example 638: (*S)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(piperidin-1-yl)ethoxy)spiro[cyclopropane-1,4'-pyrido[2,3-b][1,4,5]oxathiazepin]-2'(3'H)-yl)methyl)pyridin-2-yl)propanoic Acid

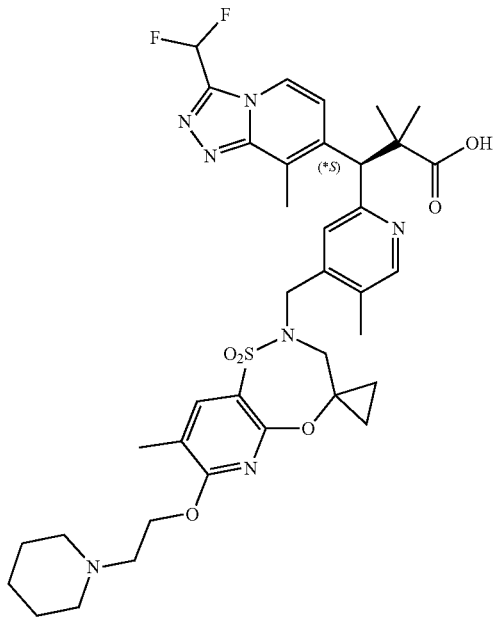 [SMILES: Cc1cnc([C@@H](c2ccn3c(C(F)F)nnc3c2C)C(C)(C)C(=O)O)cc1CN1CC2(CC2)Oc2nc(OCCN3CCCCC3)c(C)cc2S1(=O)=O]

The title compound (50.5 mg) was prepared using analogous reaction and chiral SFC separation conditions as described in Example 640 where 8'-methyl-7'-(2-(piperidin-1-yl)ethoxy)-2',3'-dihydrospiro[cyclopropane-1,4'-pyrido[2,3-b][1,4,5]oxathiazepine] 1',1'-dioxide (Intermediate 136) was used instead of 8'-methyl-7'-(2-(pyrrolidin-1-yl)ethoxy)-2,2',3,3',5,6-hexahydrospiro[pyran-4,4'-pyrido[2,3-b][1,4,5]oxathiazepine] 1',1'-dioxide in Step A. Example 638 was the first eluting isomer and designated (*S): MS (ESI): mass calcd. for $C_{37}H_{45}F_2N_7O_6S$, 753.3 m/z found, 754.3 [M+H]$^+$. $^1$H NMR (400 MHz, DMSO-d$_6$) δ 8.36-8.31 (m, 2H), 7.89 (s, 1H), 7.84-7.56 (m, 1H), 7.30 (d, J=7.3 Hz, 1H), 7.14 (s, 1H), 4.95 (s, 1H), 4.35 (t, J=5.9 Hz, 2H), 4.22-4.13 (m, 2H), 3.70-3.57 (m, 2H), 2.73 (s, 3H), 2.66-2.63 (m, 2H), 2.44-2.39 (m, 4H), 2.20 (s, 3H), 2.13 (s, 3H), 1.51-1.43 (m, 4H), 1.39-1.33 (m, 2H), 1.28 (s, 3H), 1.24 (s, 3H), 1.02-0.87 (m, 2H), 0.77-0.53 (m, 2H).

Example 639: (*R)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic Acid

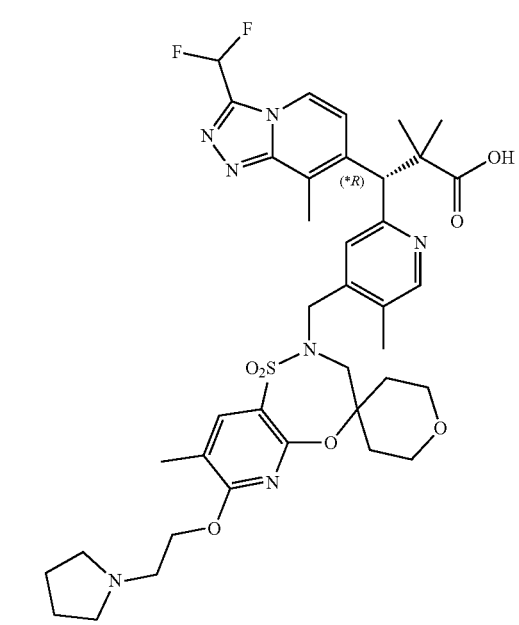 [SMILES: Cc1cnc([C@H](c2ccn3c(C(F)F)nnc3c2C)C(C)(C)C(=O)O)cc1CN1CC2(CCOCC2)Oc2nc(OCCN3CCCC3)c(C)cc2S1(=O)=O]

The second eluting isomer (43.9 mg) for the chiral separation described in Example 640 was designated (*R): MS (ESI): mass calcd. for $C_{38}H_{47}F_2N_7O_7S$, 783.3 m/z found, 784.4 [M+H]$^+$. $^1$H NMR (400 MHz, DMSO-d$_6$) δ 8.37-8.32 (m, 2H), 7.81 (s, 1H), 7.80-7.54 (m, 1H), 7.29 (d, J=7.3 Hz, 1H), 7.17 (s, 1H), 4.97 (s, 1H), 4.44-4.36 (m, 4H), 3.85-3.74 (m, 2H), 3.69-3.53 (m, 4H), 3.50-3.40 (m, 4H), 2.81 (t, J=5.9 Hz, 2H), 2.74 (s, 3H), 2.17 (s, 3H), 2.13 (s, 3H), 1.70-1.65 (m, 4H), 1.61-1.49 (m, 4H), 1.32 (s, 3H), 1.27 (s, 3H).

Example 640: (*S)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic Acid

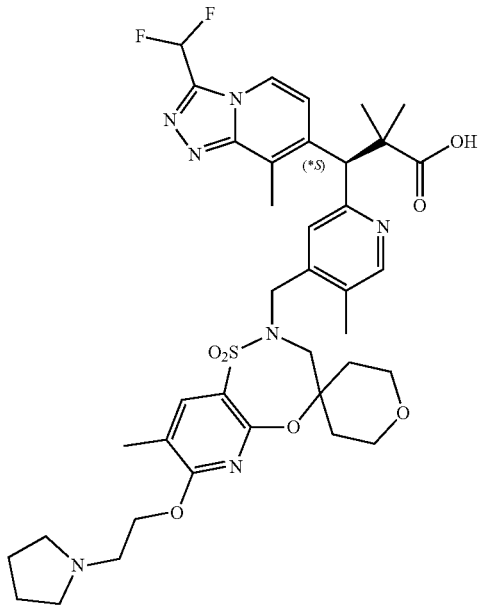 [SMILES: Cc1cnc([C@@H](c2ccn3c(C(F)F)nnc3c2C)C(C)(C)C(=O)O)cc1CN1CC2(CCOCC2)Oc2nc(OCCN3CCCC3)c(C)cc2S1(=O)=O]

Step A: tert-Butyl 3-(3-(difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoate. The title compound (340 mg) was prepared using analogous conditions as described in Example 642, Step A where 8'-methyl-7'-(2-(pyrrolidin-1-yl)ethoxy)-2,2',3,3',5,6-hexahydrospiro[pyran-4,4'-pyrido[2,3-b][1,4,5]oxathiazepine] 1',1'-dioxide (Intermediate 134) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide. MS (ESI): mass calcd. for $C_{42}H_{55}F_2N_7O_7S$, 839.4 m/z found, 840.5 $[M+H]^+$.

Step B: (*S)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid. A 4 N HCl solution in dioxane (15 mL) was added to a stirring solution of tert-butyl 3-(3-(difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoate (340 mg, 0.405 mmol) in dioxane (10 mL). After 20 hours, the mixture was concentrated to dryness under reduced pressure. The residue was dissolved in dioxane (10 mL) and then a 4 N HCl solution in dioxane (15 mL) was added. After 60 hours, the mixture was concentrated to dryness under reduced pressure. The residue was purified by preparative HPLC (Boston Green ODS column, 150 mm×30 mm×5 am, eluent: 15% to 45% (v/v) $CH_3CN$ in $H_2O$ with 0.225% HCOOH). The pure fractions were lyophilized to dryness to afford the title compound as a mixture of enantiomers (140 mg). This mixture was separated by SFC using a chiral stationary phase (Daicel Chiralpak AD-H column, 250 mm×30 mm, 5 am, eluent: 35% isopropanol containing 0.1% v/v 25% aqueous ammonia:$CO_2$) to afford two isomers. The first eluting isomer (42.2 mg) was designated (*S): MS (ESI): mass calcd. for $C_{38}H_{47}F_2N_7O_7S$, 783.3 m/z found, 784.4 $[M+H]^+$. $^1H$ NMR (400 MHz, DMSO-$d_6$) δ 8.37-8.32 (m, 2H), 7.81 (s, 1H), 7.80-7.54 (m, 1H), 7.29 (d, J=7.1 Hz, 1H), 7.18 (s, 1H), 4.97 (s, 1H), 4.45-4.34 (m, 4H), 3.85-3.73 (m, 2H), 3.68-3.49 (m, 4H), 3.48-3.39 (m, 4H), 2.80 (t, J=5.9 Hz, 2H), 2.74 (s, 3H), 2.17 (s, 3H), 2.13 (s, 3H), 1.68 (s, 4H), 1.62-1.48 (m, 4H), 1.31 (s, 3H), 1.27 (s, 3H).

Example 641: (*R)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic Acid

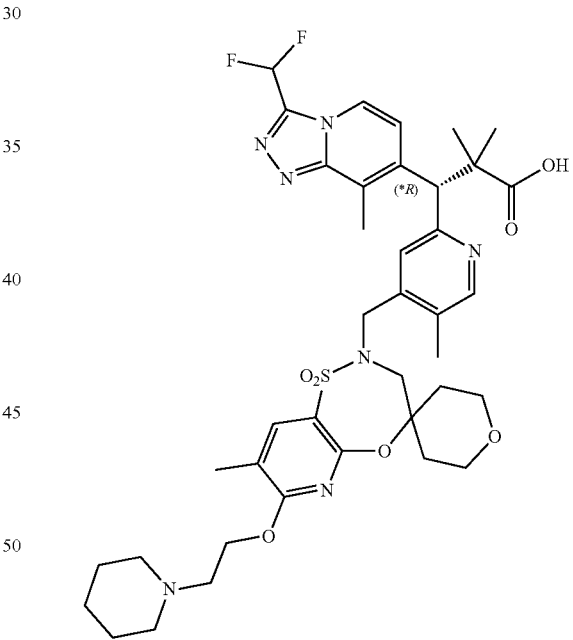

The second eluting isomer (41.7 mg) for the chiral separation described in Example 642 was designated (*R): MS (ESI): mass calcd. for $C_{39}H_{49}F_2N_7O_7S$, 797.3 m/z found, 798.4 $[M+H]^+$. $^1H$ NMR (400 MHz, DMSO-$d_6$) δ 8.35 (d, J=7.1 Hz, 1H), 8.33 (s, 1H), 7.81 (s, 1H), 7.80-7.55 (m, 1H), 7.28 (d, J=7.1 Hz, 1H), 7.17 (s, 1H), 4.97 (s, 1H), 4.43-4.35 (m, 4H), 3.85-3.73 (m, 2H), 3.67-3.60 (m, 2H), 2.73 (s, 3H), 2.72-2.64 (m, 4H), 2.45-2.42 (m, 4H), 2.16 (s, 3H), 2.12 (s, 3H), 1.55-1.45 (m, 8H), 1.39-1.34 (m, 2H), 1.31 (s, 3H), 1.27 (s, 3H).

Example 642: (*S)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic Acid

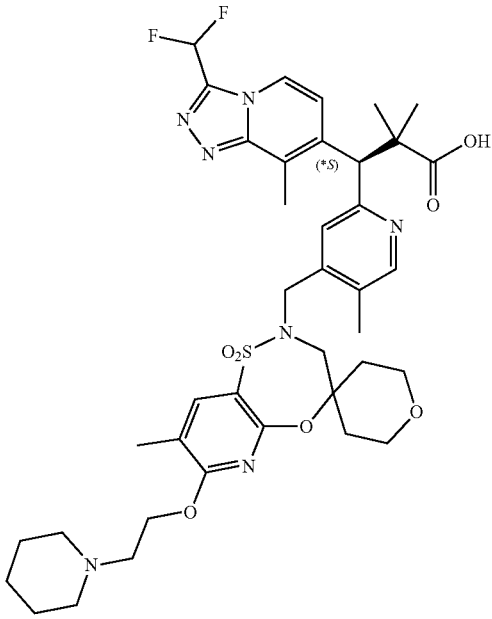 [SMILES: Cc1cnc([C@@H](c2ccn3c(C(F)F)nnc3c2C)C(C)(C)C(=O)O)cc1CN1CC2(CCOCC2)Oc2nc(OCCN3CCCCC3)c(C)cc2S1(=O)=O]

Step A: tert-Butyl 3-(3-(difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoate. A mixture containing tert-butyl 3-(4-(chloromethyl)-5-methylpyridin-2-yl)-3-(3-(difluoromethyl)-8-methyl-[1,2,4]triazolo[4,3-a]pyridin-7-yl)-2,2-dimethylpropanoate (Intermediate 192, 200 mg, 0.418 mmol), 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide (Intermediate 72, 155 mg, 0.377 mmol), and potassium carbonate (290 mg, 2.10 mmol) in acetonitrile (8 mL) was stirred at 80° C. After 16 hours, the mixture was allowed to cool to room temperature, then poured into water, and then extracted with ethyl acetate. These extractions resulted in several organic solvent fractions which were combined, washed with brine solution, dried over $Na_2SO_4$, filtered, and concentrated to dryness under reduced pressure to give the title compound (350 mg, 76%) which was used in the next step without further purification. MS (ESI): mass calcd. for $C_{43}H_{57}F_2N_7O_7S$, 853.4 m/z found, 854.5 [M+H]$^+$.

Step B: Methyl 3-(3-(difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoate. A mixture of tert-butyl 3-(3-(difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoate (350 mg, 0.41 mmol), 4 N HCl in dioxane (8 mL) and 5 drops of methanol was stirred at room temperature. After 16 hours, additional 4 N HCl in dioxane (5 mL) was added. After 16 hours, the mixture was concentrated to dryness under reduced pressure to give the title compound (300 mg) which was used in the next step without further purification. MS (ESI): mass calcd. for $C_{40}H_{51}F_2N_7O_7S$, 811.4 m/z found, 812.4 [M+H]$^+$.

Step C: (*S)-3-(3-(Difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic acid. A mixture containing methyl 3-(3-(difluoromethyl)-8-methyl-[1,2,4]triazolo[4,3-a]pyridin-7-yl)-2,2-dimethyl-3-(5-methyl-4-((8'-methyl-1',1'-dioxido-7'-(2-(piperidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoate (330 mg, 0.406 mmol) and LiOH*$H_2O$ (170 mg, 4.25 mmol) in dioxane:water (1:1, 8 mL) was stirred at 60° C. After 8 hours, the mixture was allowed to cool to room temperature and the pH was adjusted to 6 by adding aqueous 1 M HCl solution. The mixture was concentrated to dryness under reduced pressure and the residue was purified by preparative HPLC (Xtimate C18, 150×40 mm×10 m column, eluent: 20% to 50% (v/v) $CH_3CN$ in $H_2O$ with 0.2% HCOOH). The pure fractions were lyophilzed to dryness to provide the title compound as a mixture of enantiomers as a yellow solid (140 mg). MS (ESI): mass calcd. for $C_{39}H_{49}F_2N_7O_7S$, 797.3 m/z found, 798.3 [M+H]$^+$. This mixture was separated by SFC using a chiral stationary phase (Daicel Chiralpak AD-H column, 250 mm×30 mm, 5 m, eluent: 35% ethanol containing 0.1% v/v 25% aqueous ammonia:$CO_2$) to afford two isomers. The first eluting isomer (45 mg) was designated (*S) which underwent further preparative HPLC purification (Xtimate C18, 150× 40 mm×10 μm column, eluent: 20% to 50% (v/v) $CH_3CN$ in $H_2O$ with 0.2% HCOOH) to afford the title compound (30.1 mg) as a white powder after lyophilization: MS (ESI): mass calcd. for $C_{39}H_{49}F_2N_7O_7S$, 797.3 m/z found, 798.4 [M+H]$^+$. $^1$H NMR (400 MHz, DMSO-d$_6$) δ 8.32 (d, J=7.3 Hz, 1H), 8.30 (s, 1H), 7.78 (s, 1H), 7.77-7.50 (m, 1H), 7.23 (d, J=7.3 Hz, 1H), 7.13 (s, 1H), 4.93 (s, 1H), 4.40-4.32 (m, 4H), 3.81-3.69 (m, 2H), 3.61-3.55 (m, 2H), 2.70 (s, 3H), 2.69-2.61 (m, 4H), 2.43-2.39 (m, 4H), 2.13 (s, 3H), 2.09 (s, 3H), 1.58-1.43 (m, 8H), 1.36-1.31 (m, 2H), 1.28 (s, 3H), 1.24 (s, 3H).

Example 643: (*R)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic Acid

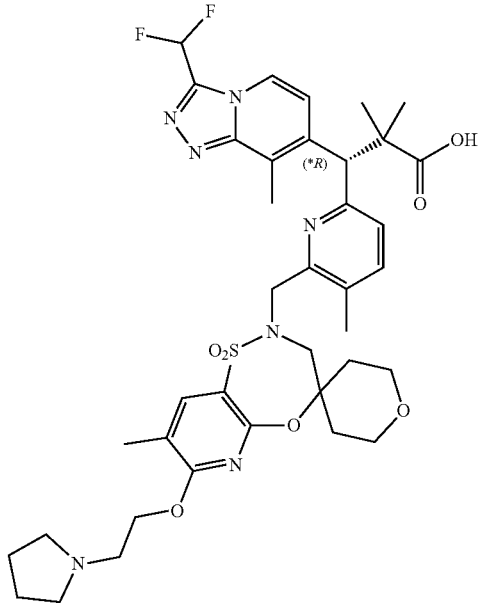 [SMILES: Cc1ccc([C@H](c2ccn3c(C(F)F)nnc3c2C)C(C)(C)C(=O)O)nc1CN1CC2(CCOCC2)Oc2nc(OCCN3CCCC3)c(C)cc2S1(=O)=O]

The second eluting isomer (34.2 mg) for the chiral separation described in Example 644 was designated (*R): MS (ESI): mass calcd. for C$_{38}$H$_{47}$F$_2$N$_7$O$_7$S, 783.3 m/z found, 784.4 [M+H]$^+$. $^1$H NMR (400 MHz, DMSO-d$_6$) δ 8.26 (d, J=7.3 Hz, 1H), 7.89 (s, 1H), 7.70 (t, J=52 Hz, 1H), 7.68 (d, J=7.3 Hz, 1H), 7.51 (d, J=7.9 Hz, 1H), 7.24 (d, J=7.7 Hz, 1H), 4.97 (s, 1H), 4.54 (s, 2H), 4.44 (t, J=5.8 Hz, 2H), 3.86 (t, J=11.1 Hz, 2H), 3.75-3.56 (m, 4H), 2.83 (t, J=6.0 Hz, 2H), 2.75 (s, 3H), 2.59-2.54 (m, 4H), 2.24 (s, 3H), 2.17 (s, 3H), 1.75-1.63 (m, 6H), 1.62-1.55 (m, 2H), 1.31 (s, 3H), 1.28 (s, 3H).

Example 644: (*S)-3-(3-(Difluoromethyl)-8-methyl-[1,2,4]triazolo[4,3-a]pyridin-7-yl)-2,2-dimethyl-3-(5-methyl-6-((8'-methyl-1',1'-dioxido-7'-(2-(pyrrolidin-1-yl)ethoxy)-2,3,5,6-tetrahydrospiro[pyran-4,4'-pyrido[2,3-b][1,4,5]oxathiazepin]-2'(3'H)-yl)methyl)pyridin-2-yl)propanoic Acid

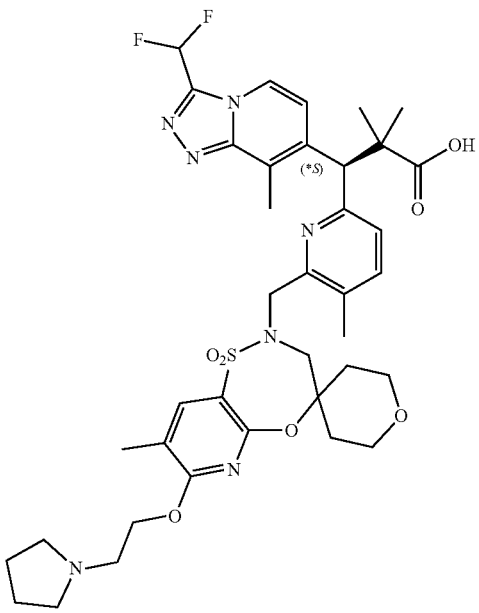 [SMILES: Cc1ccc([C@@H](c2ccn3c(C(F)F)nnc3c2C)C(C)(C)C(=O)O)nc1CN1CC2(CCOCC2)Oc2nc(OCCN3CCCC3)c(C)cc2S1(=O)=O]

The title compound (24.2 mg) was prepared using analogous reaction conditions as described in Example 640 where tert-butyl 3-(6-(chloromethyl)-5-methylpyridin-2-yl)-3-(3-(difluoromethyl)-8-methyl-[1,2,4]triazolo[4,3-a]pyridin-7-yl)-2,2-dimethylpropanoate (Intermediate 194) was used instead of tert-butyl 3-(4-(chloromethyl)-5-methylpyridin-2-yl)-3-(3-(difluoromethyl)-8-methyl-[1,2,4]triazolo[4,3-a]pyridin-7-yl)-2,2-dimethylpropanoate in Step A and following separation by SFC using a chiral stationary phase (Regis (S,) Whelk-O1 column, 250 mm×50 mm, 10 m, eluent: 50% ethanol containing 0.1% v/v 25% aqueous ammonia:CO$_2$) and then further purification by preparative HPLC (Xtimate C$_{18}$ column, 150 mm×25 mm×5 μm (eluent: 20% to 50% (v/v) CH$_3$CN in water with 0.225% HCOOH) in Step B. The first eluting isomer was designated (*S): MS (ESI): mass calcd. for C$_{38}$H$_{47}$F$_2$N$_7$O$_7$S, 783.3 m/z found, 784.3 [M+H]$^+$. $^1$H NMR (400 MHz, DMSO-d$_6$) δ 8.26 (d, J=7.3 Hz, 1H), 7.89 (s, 1H), 7.70 (t, J=52 Hz, 1H), 7.68 (d, J=7.3 Hz, 1H), 7.51 (d, J=7.9 Hz, 1H), 7.40 (t, J=52 Hz, 1H), 7.24 (d, J=7.7 Hz, 1H), 4.97 (s, 1H), 4.54 (s, 2H), 4.44 (t, J=5.8 Hz, 2H), 3.86 (t, J=11.1 Hz, 2H), 3.75-3.56 (m, 4H), 2.83 (t, J=6.0 Hz, 2H), 2.75 (s, 3H), 2.59-2.54 (m, 4H), 2.24 (s, 3H), 2.17 (s, 3H), 1.75-1.63 (m, 6H), 1.62-1.55 (m, 2H), 1.31 (s, 3H), 1.28 (s, 3H).

Example 645: (*R)-3-(1-Cyclopropyl-4-methyl-1H-benzo[d][1,2,3]triazol-5-yl)-2,2-dimethyl-3-(4-methyl-3-((8'-methyl-1',1'-dioxidospiro[azetidine-3,4'-pyrido[2,3-b][1,4,5]oxathiazepin]-2'(3'H)-yl)methyl)phenyl)propanoic Acid

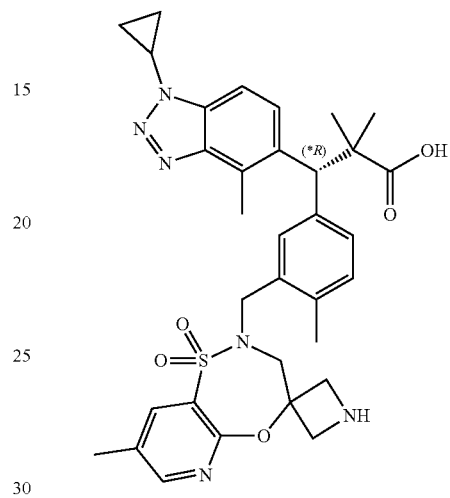

The second eluting isomer (41 mg) from the chiral separation described in Example 646 was designated (*R): MS (ESI): mass calcd. for C$_{33}$H$_{38}$N$_6$O$_5$S, 630.3; m/z found, 631.3 [M+H]$^+$. $^1$H NMR (400 MHz, CDCl$_3$) δ 8.40-8.26 (m, 1H), 8.12-8.01 (m, 1H), 7.67-7.56 (m, 1H), 7.48-7.39 (m, 1H), 7.23-7.00 (m, 3H), 4.72 (s, 1H), 4.65-4.53 (m, 1H), 4.28-4.19 (m, 1H), 4.19-3.64 (m, 7H), 2.81 (s, 3H), 2.43 (s, 3H), 2.22 (s, 3H), 1.42-1.17 (m, 11H).

Example 646: (*S)-3-(1-Cyclopropyl-4-methyl-1H-benzo[d][1,2,3]triazol-5-yl)-2,2-dimethyl-3-(4-methyl-3-((8'-methyl-1',1'-dioxidospiro[azetidine-3,4'-pyrido[2,3-b][1,4,5]oxathiazepin]-2'(3'H)-yl)methyl)phenyl)propanoic Acid

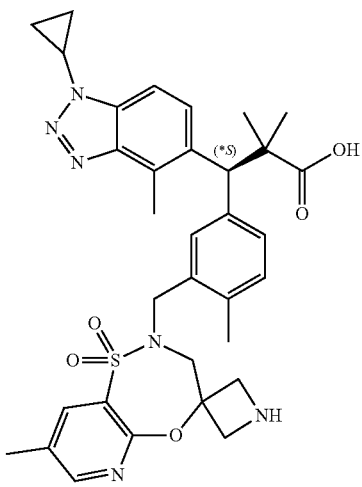 [SMILES: Cc1cnc2c(c1)S(=O)(=O)N(Cc1cc([C@@H](c3ccc4c(nnn4C4CC4)c3C)C(C)(C)C(=O)O)ccc1C)CC1(CNC1)O2]

The mixture of (R/S)-3-(1-cyclopropyl-4-methyl-1H-benzo[d][1,2,3]triazol-5-yl)-2,2-dimethyl-3-((8'-methyl-1',1'-dioxidospiro[azetidine-3,4'-pyrido[2,3-b][1,4,5]oxathiazepin]-2'(3'H)-yl)methyl)phenyl)propanoic acid isomers (Example 651) was separated by chiral SFC (AD-H, mobile phase: 50% $CO_2$, 50% isopropanol with 0.1% DEA) to afford two enantiomers. The first eluting isomer (48 mg) was designated (*S): MS (ESI): mass calcd. for $C_{33}H_{38}N_6O_5S$, 630.3; m/z found, 631.3 $[M+H]^+$. $^1$H NMR (400 MHz, $CDCl_3$) δ 8.26-8.21 (m, 1H), 7.98-7.94 (m, 1H), 7.72-7.65 (m, 1H), 7.37-7.32 (m, 1H), 7.28-7.23 (m, 1H), 7.11-7.01 (m, 2H), 7.01-6.96 (m, 1H), 6.75 (d, J=8.0 Hz, 1H), 4.81 (s, 1H), 4.52 (d, J=13.3 Hz, 1H), 4.31-4.18 (m, 1H), 4.11-3.79 (m, 4H), 3.70-3.59 (m, 2H), 2.81 (s, 3H), 2.35 (s, 3H), 2.16 (s, 3H), 1.37-1.07 (m, 11H).

Example 647: (*R)-3-(1-Cyclopropyl-4-methyl-1H-benzo[d][1,2,3]triazol-5-yl)-3-(3-((1',1'-dioxidospiro[piperidine-4,4'-pyrido[2,3-b][1,4,5]oxathiazepin]-2'(3'H)-yl)methyl)-4-methylphenyl)-2,2-dimethylpropanoic Acid

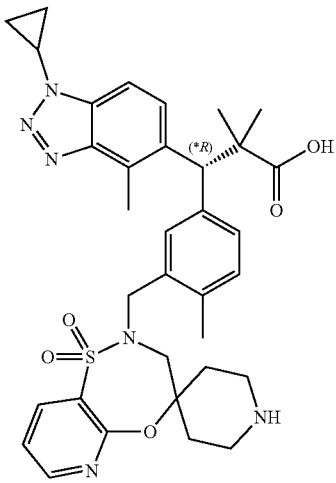 [SMILES: Cc1ccc([C@H](c2ccc3c(nnn3C3CC3)c2C)C(C)(C)C(=O)O)cc1CN1CC2(CCNCC2)Oc2ncccc2S1(=O)=O]

The second eluting isomer (63 mg) from the chiral separation described in Example 648 was designated (*R): MS (ESI): mass calcd. for $C_{34}H_{40}N_6O_5S$, 644.3.2; m/z found, 645.3 $[M+H]^+$. $^1$H NMR (400 MHz, DMSO-$d_6$) δ 8.55-8.51 (m, 1H), 8.24-8.19 (m, 1H), 7.89-7.83 (m, 1H), 7.58-7.52 (m, 1H), 7.49-7.43 (m, 1H), 7.34-7.17 (m, 2H), 7.05-6.97 (m, 1H), 5.17-4.96 (m, 1H), 4.68-4.55 (m, 1H), 4.35-4.23 (m, 1H), 3.97-3.88 (m, 1H), 3.23-2.79 (m, 8H), 2.74 (s, 3H), 2.09 (s, 3H), 1.64-1.46 (m, 1H), 1.30-1.15 (m, 9H), 1.01-0.94 (m, 3H).

Example 648: (*S)-3-(1-Cyclopropyl-4-methyl-1H-benzo[d][1,2,3]triazol-5-yl)-3-(3-((1',1'-dioxidospiro[piperidine-4,4'-pyrido[2,3-b][1,4,5]oxathiazepin]-2'(3'H)-yl)methyl)-4-methylphenyl)-2,2-dimethylpropanoic Acid

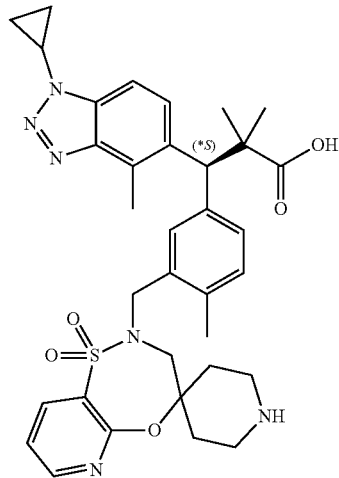 [SMILES: Cc1ccc([C@@H](c2ccc3c(nnn3C3CC3)c2C)C(C)(C)C(=O)O)cc1CN1CC2(CCNCC2)Oc2ncccc2S1(=O)=O]

The mixture of (R/S)-3-(1-cyclopropyl-4-methyl-1H-benzo[d][1,2,3]triazol-5-yl)-3-(3-((1',1'-dioxidospiro[piperidine-4,4'-pyrido[2,3-b][1,4,5]oxathiazepin]-2'(3'H)-yl)methyl)-4-methylphenyl)-2,2-dimethylpropanoic acid isomers (Example 652) was separated by chiral SFC (AD-H, mobile phase: 50% $CO_2$, 50% isopropanol with 0.1% DEA) to afford two enantiomers. The first eluting isomer (63 mg) was designated (*S): MS (ESI): mass calcd. for $C_{34}H_{40}N_6O_5S$, 644.3.2; m/z found, 645.3 [M+H]. $^1$H NMR (400 MHz, DMSO-$d_6$) δ 8.56-8.50 (m, 1H), 8.25-8.19 (m, 1H), 7.90-7.83 (m, 1H), 7.59-7.51 (m, 1H), 7.49-7.42 (m, 1H), 7.36-7.15 (m, 2H), 7.04-6.97 (m, 1H), 5.19-4.97 (m, 1H), 4.65-4.56 (m, 1H), 4.34-4.25 (m, 1H), 3.97-3.89 (m, 1H), 3.27-2.80 (m, 8H), 2.74 (s, 3H), 2.08 (s, 3H), 1.68-1.44 (m, 1H), 1.30-1.13 (m, 9H), 1.04-0.93 (m, 3H).

Example 649: (*R)-3-(1-Cyclopropyl-4-methyl-1H-benzo[d][1,2,3]triazol-5-yl)-2,2-dimethyl-3-(4-methyl-3-((8'-methyl-1',1'-dioxidospiro[piperidine-4,4'-pyrido[2,3-b][1,4,5]oxathiazepin]-2'(3')-yl)methyl)phenyl)propanoic Acid

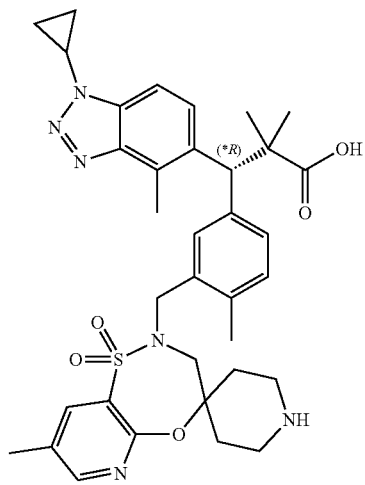 [SMILES: Cc1cnc2c(c1)S(=O)(=O)N(Cc1cc([C@H](c3ccc4c(nnn4C4CC4)c3C)C(C)(C)C(=O)O)ccc1C)CC1(CCNCC1)O2]

The second eluting isomer (58 mg) from the chiral separation described in Example 650 was designated (*R): MS (ESI): mass calcd. for $C_{35}H_{42}N_6O_5S$, 658.3; m/z found, 659.3 [M+H]+. ¹H NMR (400 MHz, DMSO-$d_6$) δ 8.37-8.31 (m, 1H), 8.06-8.02 (m, 1H), 7.91-7.85 (m, 1H), 7.61-7.51 (m, 1H), 7.36-7.12 (m, 2H), 7.05-6.98 (m, 1H), 5.25-4.89 (m, 1H), 4.66-4.53 (m, 1H), 4.35-4.21 (m, 1H), 4.00-3.88 (m, 1H), 3.27-2.81 (m, 8H), 2.73 (s, 3H), 2.37 (s, 3H), 2.10 (s, 3H), 1.69-1.47 (m, 1H), 1.29-1.12 (m, 9H), 1.05-0.92 (m, 3H).

Example 650: (*S)-3-(1-Cyclopropyl-4-methyl-1H-benzo[d][1,2,3]triazol-5-yl)-2,2-dimethyl-3-(4-methyl-3-((8'-methyl-1',1'-dioxidospiro[piperidine-4,4'-pyrido[2,3-b][1,4,5]oxathiazepin]-2'(3'H)-yl)methyl)phenyl)propanoic Acid

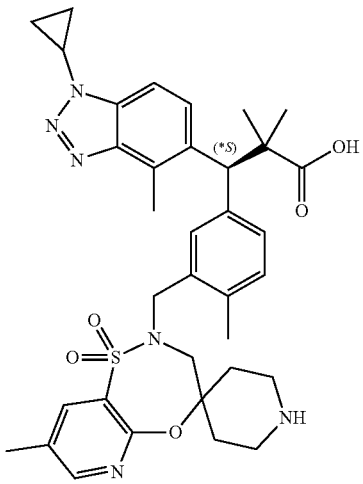 [SMILES: Cc1cnc2c(c1)S(=O)(=O)N(Cc1cc([C@@H](c3ccc4c(nnn4C4CC4)c3C)C(C)(C)C(=O)O)ccc1C)CC1(CCNCC1)O2]

The mixture of (R/S)-3-(1-cyclopropyl-4-methyl-1H-benzo[d][1,2,3]triazol-5-yl)-2,2-dimethyl-3-(4-methyl-3-((8'-methyl-1',1'-dioxidospiro[piperidine-4,4'-pyrido[2,3-b][1,4,5]oxathiazepin]-2'(3'H)-yl)methyl)phenyl)propanoic acid isomers (Example 653) was separated by chiral SFC (OD-H, mobile phase: 70% $CO_2$, 30% MeOH) to afford two enantiomers. The first eluting isomer (62 mg) was designated (*S): MS (ESI): mass calcd. for $C_{35}H_{42}N_6O_5S$, 658.3; m/z found, 659.3 [M+H]+. ¹H NMR (500 MHz, DMSO-$d_6$) δ 8.37-8.32 (m, 1H), 8.06-8.02 (m, 1H), 7.90-7.85 (m, 1H), 7.59-7.52 (m, 1H), 7.37-7.14 (m, 2H), 7.03-6.99 (m, 1H), 5.24-4.91 (m, 1H), 4.66-4.52 (m, 1H), 4.36-4.23 (m, 1H), 3.99-3.88 (m, 1H), 3.13-2.82 (m, 8H), 2.73 (s, 3H), 2.37 (s, 3H), 2.10 (s, 3H), 1.55 (s, 1H), 1.29-1.15 (m, 9H), 1.03-0.93 (m, 3H).

Example 651: (R/S)-3-(1-Cyclopropyl-4-methyl-1H-benzo[d][1,2,3]triazol-5-yl)-2,2-dimethyl-3-(4-methyl-3-((8'-methyl-1',1'-dioxidospiro[azetidine-3,4'-pyrido[2,3-b][1,4,5]oxathiazepin]-2'(3'H)-yl)methyl)phenyl)propanoic Acid

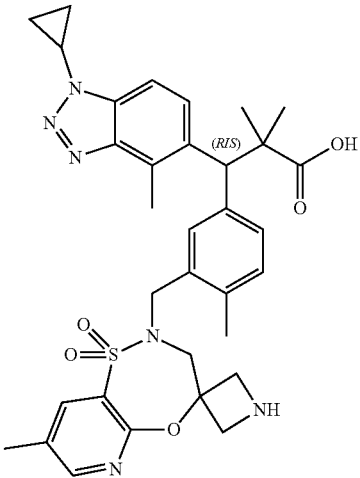 [SMILES: Cc1cnc2c(c1)S(=O)(=O)N(Cc1cc(C(c3ccc4c(nnn4C4CC4)c3C)C(C)(C)C(=O)O)ccc1C)CC1(CNC1)O2]

The title compound (127 mg, 37% yield) was prepared using analogous conditions as described in Example 653 where tert-butyl 8'-methyl-2',3'-dihydrospiro[azetidine-3,4'-pyrido[2,3-b][1,4,5]oxathiazepine]-1-carboxylate 1',1'-dioxide (Intermediate 153) was used instead of tert-butyl 8'-methyl-2',3'-dihydrospiro[piperidine-4,4'-pyrido[2,3-b][1,4,5]oxathiazepine]-1-carboxylate 1',1'-dioxide. MS (ESI): mass calcd. for $C_{33}H_{38}N_6O_5S$, 630.3; m/z found, 631.3 [M+H]+. ¹H NMR (400 MHz, $CDCl_3$) δ 8.25-8.22 (m, 1H), 7.97-7.94 (m, 1H), 7.70-7.64 (m, 1H), 7.37-7.32 (m, 1H), 7.25 (s, 1H), 7.11-7.05 (m, 1H), 7.01-6.96 (m, 1H), 4.81 (s, 1H), 4.56-4.47 (m, 1H), 2.19-2.13 (m, 3H), 4.27-4.18 (m, 1H), 4.05-3.98 (m, 1H), 3.94-3.77 (m, 3H), 3.71-3.59 (m, 2H), 3.05-2.91 (m, 1H), 2.81 (s, 3H), 2.35 (s, 3H), 2.16 (s, 3H), 1.37-1.08 (m, 11H).

Example 652: (R/S)-3-(1-Cyclopropyl-4-methyl-1H-benzo[d][1,2,3]triazol-5-yl)-3-(3-((1',1'-dioxidospiro[piperidine-4,4'-pyrido[2,3-b][1,4,5]oxathiazepin]-2'(3'H)-yl)methyl)-4-methylphenyl)-2,2-dimethylpropanoic Acid

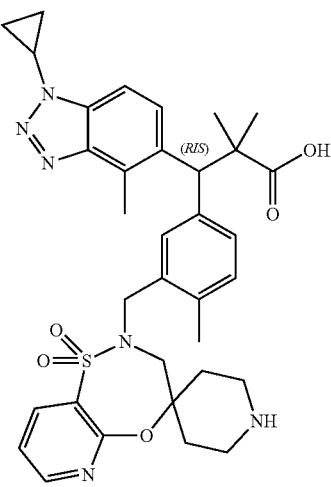 [SMILES: Cc1ccc(C(c2ccc3c(nnn3C3CC3)c2C)C(C)(C)C(=O)O)cc1CN1CC2(CCNCC2)Oc2ncccc2S1(=O)=O]

The title compound (150 mg, 39% yield) was prepared using analogous conditions as described in Example 653 where tert-butyl 2',3'-dihydrospiro[piperidine-4,4'-pyrido[2,3-b][1,4,5]oxathiazepine]-1-carboxylate 1',1'-dioxide (Intermediate 150) was used instead of tert-butyl 8'-methyl-2',3'-dihydrospiro[piperidine-4,4'-pyrido[2,3-b][1,4,5]oxathiazepine]-1-carboxylate 1',1'-dioxide. MS (ESI): mass calcd. for $C_{34}H_{40}N_6O_5S$, 644.3.2; m/z found, 645.3 $[M+H]^+$. $^1$H NMR (400 MHz, CDCl$_3$) δ 9.29 (s, 1H), 8.69-8.37 (m, 2H), 8.31-8.22 (m, 1H), 7.47-7.34 (m, 2H), 7.34-7.28 (m, 1H), 7.24-7.18 (m, 1H), 7.13-7.06 (m, 1H), 7.05-6.97 (m, 1H), 5.00 (s, 1H), 4.87-4.75 (m, 1H), 4.27-4.16 (m, 1H), 3.84-3.40 (m, 5H), 3.28 (d, J=12.2 Hz, 2H), 2.94 (s, 3H), 2.20 (s, 3H), 2.00-1.63 (m, 3H), 1.56-1.16 (m, 11H).

Example 653: (R/S)-3-(1-Cyclopropyl-4-methyl-1H-benzo[d][1,2,3]triazol-5-yl)-2,2-dimethyl-3-(4-methyl-3-((8'-methyl-1',1'-dioxidospiro[piperidine-4,4'-pyrido[2,3-b][1,4,5]oxathiazepin]-2'(3'-yl)methyl)phenyl)propanoic Acid

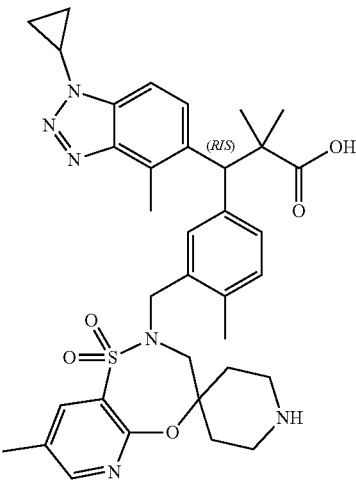 [SMILES: Cc1cnc2c(c1)S(=O)(=O)N(Cc1cc(C(c3ccc4c(nnn4C4CC4)c3C)C(C)(C)C(=O)O)ccc1C)CC1(CCNCC1)O2]

Step A: Tert-butyl 2'-(5-(1-(1-cyclopropyl-4-methyl-1H-benzo[d][1,2,3]triazol-5-yl)-3-methoxy-2,2-dimethyl-3-oxopropyl)-2-methylbenzyl)-8'-methyl-2',3'-dihydrospiro[piperidine-4,4'-pyrido[2,3-b][1,4,5]oxathiazepine]-1-carboxylate 1',1'-dioxide. Methyl 3-(3-(chloromethyl)-4-methylphenyl)-3-(1-cyclopropyl-4-methyl-1H-benzo[d][1,2,3]triazol-5-yl)-2,2-dimethylpropanoate (Intermediate 184, 300 mg, 0.7 mmol) was dissolved in ACN (3.5 mL).

Tert-butyl 8'-methyl-2',3'-dihydrospiro[piperidine-4,4'-pyrido[2,3-b][1,4,5]oxathiazepine]-1-carboxylate 1',1'-dioxide (Intermediate 152, 281.7 mg, 0.735 mmol) and potassium carbonate (393 mg, 2.84 mmol) were added and the reaction was stirred at 80° C. for 2 hours. After this time, the reaction was allowed to cool to room temperature, then was diluted with water and EtOAc and the resulting biphasic mixture was separated. The aqueous layer was extracted with EtOAc. These extractions resulted in several organic solvent fractions which were combined, dried over MgSO$_4$, filtered, and concentrated to dryness under reduced pressure to provide the title compound that was carried forward without further purification (524.1 mg, 92% yield). MS (ESI): mass calcd. for $C_{41}H_{52}N_6O_7S$, 772.4; m/z found, 773.3 $[M+H]^+$.

Step B: 3-(3-((1-(Tert-butoxycarbonyl)-8'-methyl-1',1'-dioxidospiro[piperidine-4,4'-pyrido[2,3-b][1,4,5]oxathiazepin]-2'(3'H)-yl)methyl)-4-methylphenyl)-3-(1-cyclopropyl-4-methyl-1H-benzo[d][1,2,3]triazol-5-yl)-2,2-dimethylpropanoic acid. LiOH solution (2M, 0.35 mL, 0.7 mmol), 1,4-dioxane (2 mL) and water (1.5 mL) were added to tert-butyl 2'-(5-(1-(1-cyclopropyl-4-methyl-1H-benzo[d][1,2,3]triazol-5-yl)-3-methoxy-2,2-dimethyl-3-oxopropyl)-2-methylbenzyl)-8'-methyl-2',3'-dihydrospiro[piperidine-4,4'-pyrido[2,3-b][1,4,5]oxathiazepine]-1-carboxylate 1',1'-dioxide (516 mg, 0.668 mmol), and the resulting mixture was stirred at 75° C. for 8 hours. Additional 2M LiOH solution (1 mL) and 1,4-dioxane (2 mL) were added and the reaction was stirred at 80° C. overnight. Additional 2M LiOH solution (1 mL) and 1,4-dioxane (1 mL) were added and the reaction was stirred at 80° C. for an additional night. After this time, the reaction was allowed to cool to room temperature, and was acidified to pH 4 using 1M HCl. The biphasic mixture was separated and the aqueous layer was extracted with DCM. These extractions resulted in several organic solvent fractions which were combined, dried over MgSO$_4$, filtered, and concentrated to dryness under reduced pressure to provide the title compound that was carried forward without further purification (440 mg, 87% yield). MS (ESI): mass calcd. for $C_{40}H_{50}N_6O_7S$, 758.3; m/z found, 759.3 $[M+H]^+$.

Step C: (R/S)-3-(1-Cyclopropyl-4-methyl-1H-benzo[d][1,2,3]triazol-5-yl)-2,2-dimethyl-3-(4-methyl-3-((8'-methyl-1',1'-dioxidospiro[piperidine-4,4'-pyrido[2,3-b][1,4,5]oxathiazepin]-2'(3'H)-yl)methyl)phenyl)propanoic acid. A solution of 20% TFA in DCM (6 mL) was added to 3-(3-((1-(tert-butoxycarbonyl)-8'-methyl-1',1'-dioxidospiro[piperidine-4,4'-pyrido[2,3-b][1,4,5]oxathiazepin]-2'(3'H)-yl)methyl)-4-methylphenyl)-3-(1-cyclopropyl-4-methyl-1H-benzo[d][1,2,3]triazol-5-yl)-2,2-dimethylpropanoic acid (440 mg, 0.58 mmol) and the resulting solution was stirred at room temperature for 1.25 hours. The reaction was concentrated under reduced pressure, then concentrated under reduced pressure from EtOAc three times. The material was purified by preparative acidic HPLC (XBridge C$_{18}$, acetonitrile-water containing 0.05% TFA) to provide the title compound (164 mg, 43% yield). MS (ESI): mass calcd. for $C_{35}H_{42}N_6O_5S$, 658.3; m/z found, 659.3 $[M+H]^+$. $^1$H NMR (400 MHz, CDCl$_3$) δ 9.26 (s, 1H), 8.54 (s, 1H), 8.26 (s, 1H), 8.10-7.98 (m, 1H), 7.48-7.30 (m, 2H), 7.24-7.16 (m, 1H), 7.14-6.96 (m, 2H), 5.00 (s, 1H), 4.86-4.75 (m, 1H), 4.28-4.16 (m, 1H), 3.80-3.41 (m, 5H), 3.39-3.16 (m, 2H), 2.94 (s, 3H), 2.42 (s, 3H), 2.22 (s, 3H), 1.97-1.63 (m, 3H), 1.48-1.14 (m, 11H).

Example 654: (*R)-3-(5-(((*R)-3-Cyano-5,5-dioxido-7,7a,8,9,10,11-hexahydro-6H-dipyrido[2,1-d:2',3'-f][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoic Acid

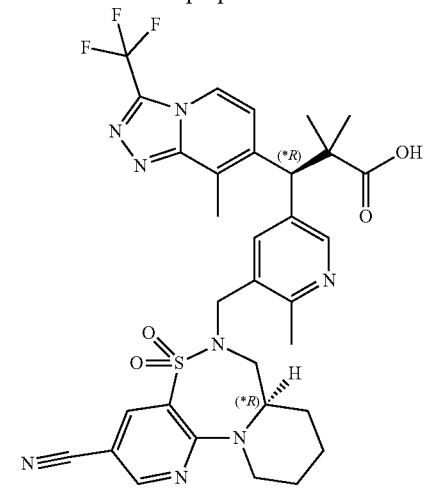

The second eluting isomer (38 mg) in the chiral separation described in Example 655 was designated (*R/*R): MS: mass calcd. for C$_{32}$H$_{33}$F$_3$N$_8$O$_4$S, 682.2; m/z found, 683.3. $^1$H NMR (500 MHz, CDCl$_3$) δ 8.51-8.44 (m, 2H), 8.23-8.19 (m, 1H), 8.12-8.07 (m, 1H), 7.66 (s, 1H), 7.35-7.31 (m, 1H), 4.93 (s, 1H), 4.66-4.52 (m, 2H), 4.41-4.34 (m, 1H), 4.14-4.05 (m, 1H), 3.39-3.24 (m, 2H), 3.17-3.08 (m, 1H), 2.84 (s, 3H), 2.48 (s, 3H), 1.85-1.60 (m, 4H), 1.51-1.45 (m, 1H), 1.45-1.32 (m, 6H), 1.28-1.24 (m, 1H).

Example 655: (*R)-3-(5-(((*S)-3-Cyano-5,5-di-oxido-7,7a,8,9,10,11-hexahydro-6H-dipyrido[2,1-d:2',3'-f][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoic Acid

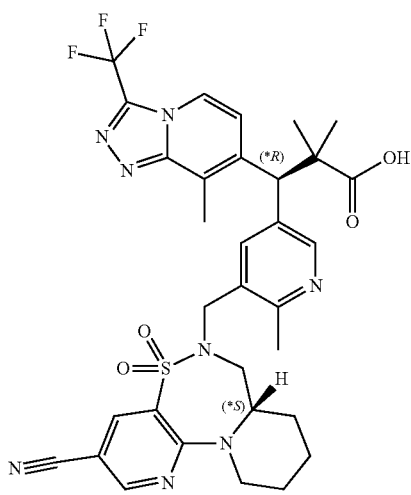 [SMILES: Cc1ncc([C@@H](c2ccn3c(C(F)(F)F)nnc3c2C)C(C)(C)C(=O)O)cc1CN1C[C@@H]2CCCCN2c2ncc(C#N)cc2S1(=O)=O]

The second peak in chiral separation described in Example 657 was further purified by chiral SFC (AS-H, mobile phase: 80% CO$_2$, 20% MeOH) to afford two isomers. The first eluting isomer (42 mg) was designated (*R/*S): MS: mass calcd. for C$_{32}$H$_{33}$F$_3$N$_8$O$_4$S, 682.2; m/z found, 683.2. $^1$H NMR (500 MHz, CDCl$_3$) δ 8.52 (s, 1H), 8.47 (d, J=2.0 Hz, 1H), 8.20 (s, 1H), 8.10 (d, J=7.0 Hz, 1H), 7.64 (s, 1H), 7.33 (d, J=7.4 Hz, 1H), 4.96 (s, 1H), 4.66-4.52 (m, 2H), 4.41-4.33 (m, 1H), 4.12-4.05 (m, 1H), 3.38-3.22 (m, 2H), 3.15-3.06 (m, 1H), 2.85 (s, 3H), 2.48 (s, 3H), 1.84-1.64 (m, 4H), 1.51-1.46 (m, 1H), 1.46-1.34 (m, 6H), 1.26 (s, 1H).

Example 656: (*S)-3-(5-(((*R)-3-Cyano-5,5-di-oxido-7,7a,8,9,10,11-hexahydro-6H-dipyrido[2,1-d:2',3'-f][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoic Acid

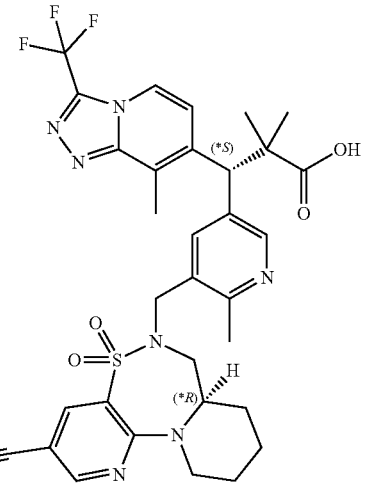

The second eluting isomer from the first peak (37 mg) in the chiral separation described in Example 657 was designated (*S/*R): MS: mass calcd. for C$_{32}$H$_{33}$F$_3$N$_8$O$_4$S, 682.2; m/z found, 683.3. $^1$H NMR (500 MHz, CDCl$_3$) δ 8.48 (d, J=2.1 Hz, 1H), 8.41 (s, 1H), 8.23 (d, J=2.2 Hz, 1H), 8.04 (d, J=7.3 Hz, 1H), 7.76 (s, 1H), 7.32 (d, J=7.3 Hz, 1H), 4.85 (s, 1H), 4.72-4.64 (m, 1H), 4.56-4.47 (m, 1H), 4.42-4.35 (m, 1H), 4.18-4.09 (m, 1H), 3.54-3.44 (m, 1H), 3.39-3.30 (m, 1H), 3.23-3.14 (m, 1H), 2.88-2.78 (m, 4H), 2.45 (s, 3H), 1.85-1.65 (m, 4H), 1.40-1.31 (m, 6H), 1.28-1.23 (m, 1H).

Example 657: (*S)-3-(5-(((*S)-3-Cyano-5,5-di-oxido-7,7a,8,9,10,11-hexahydro-6H-dipyrido[2,1-d:2',3'-f][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoic Acid

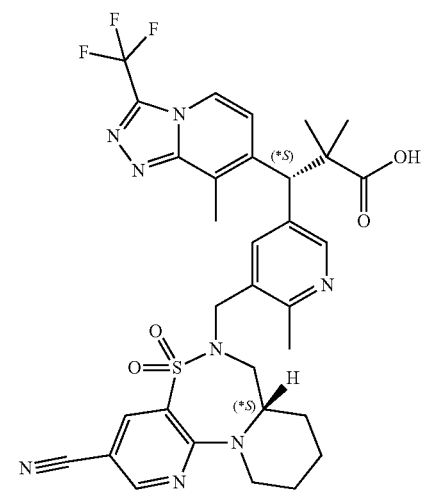 [SMILES: Cc1ncc([C@H](c2ccn3c(C(F)(F)F)nnc3c2C)C(C)(C)C(=O)O)cc1CN1C[C@@H]2CCCCN2c2ncc(C#N)cc2S1(=O)=O]

Step A: Methyl 3-(5-((3-chloro-5,5-dioxido-7,7a,8,9,10,11-hexahydro-6H-dipyrido[2,1-d:2',3'-f][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoate. A solution of methyl 3-(5-(hydroxymethyl)-6-methylpyridin-3-yl)-2,2-dimethyl-3-(8-methyl-3-(trifluoromethyl)-[1,2,4]triazolo[4,3-a]pyridin-7-yl)propanoate (Intermediate 185, 511 mg, 1.17 mmol), 3-chloro-7,7a,8,9,10,11-hexahydro-6H-dipyrido[2,1-d:2',3'-f][1,2,5]thiadiazepine 5,5-dioxide (Intermediate 95, 507 mg, 1.76 mmol), and triphenylphosphine (494 mg, 1.88 mmol) in THF (6 mL) was stirred at room temperature for 1 minute. DBAD (438 mg, 1.90 mmol) was added and the solution was stirred at room temperature for 30 minutes, followed by 50° C. for 30 minutes. Additional 3-chloro-7,7a,8,9,10,11-hexahydro-6H-dipyrido[2,1-d:2',3'-f][1,2,5]thiadiazepine 5,5-dioxide (250 mg), triphenylphosphine (300 mg), DBAD (300 mg) and THF (6 mL) were added, and the reaction was stirred at 50° C. overnight. The reaction was concentrated and purified by flash column chromatography (0-1$_{00}$% EtOAc/hexanes) to provide the title compound which was used without further purification (400 mg, 48% yield). MS (ESI): mass calcd. for $C_{32}H_{35}ClF_3N_7O_4S$, 705.2; m/z found, 706.2 [M+H]$^+$.

Step B: 3-(5-((3-Chloro-5,5-dioxido-7,7a,8,9,10,11-hexahydro-6H-dipyrido[2,1-d:2',3'-f][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoic acid. 2M Aqueous lithium hydroxide (1.5 mL, 3.0 mmol) was added to a solution of methyl 3-(5-((3-chloro-5,5-dioxido-7,7a,8,9,10,11-hexahydro-6H-dipyrido[2,1-d:2',3'-f][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoate (400 mg, 0.57 mmol) in 1,4-dioxane (5 mL). The reaction was stirred at 75° C. overnight then allowed to cool to room temperature. 1 M aqueous HCl solution was added until the pH was 4. EtOAc was added and the resulting biphasic mixture was separated. The aqueous layer was extracted with EtOAc. These extractions resulted in several organic solvent fractions which were combined, dried over MgSO$_4$, filtered, and concentrated to dryness under reduced pressure to provide the title compound which was used without further purification (417 mg, 106% yield). MS (ESI): mass calcd. for $C_{31}H_{33}ClF_3N_7O_4S$, 691.2; m/z found, 692.2 [M+H]$^+$.

Step C: 3-(5-((3-Cyano-5,5-dioxido-7,7a,8,9,10,11-hexahydro-6H-dipyrido[2,1-d:2',3'-f][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoic acid. DMA (3 mL) was added to a mixture of 3-(5-((3-chloro-5,5-dioxido-7,7a,8,9,10,11-hexahydro-6H-dipyrido[2,1-d:2',3'-J][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoic acid (417 mg, 0.602 mmol), zinc cyanide (144.5 mg, 1.23 mmol), XPhos Pd G2 (53.3 mg, 0.068 mmol), and zinc powder (20 mg, 0.3 mmol). Argon was bubbled through the reaction mixture for 1 minute, then the reaction was heated to 120° C. for 2 hours. After this time, the reaction was allowed to cool to room temperature, then was filtered and purified by preparative basic HPLC (XBridge C$_{18}$, acetonitrile-water, 20 mM NH$_4$OH) to provide the title compound (285 mg, 69% yield). MS (ESI): mass calcd. for $C_{32}H_{33}F_3N_8O_4S$, 682.2; m/z found, 683.3 [M+H]$^+$.

Step D: (*S)-3-(5-((((*S)-3-Cyano-5,5-dioxido-7,7a,8,9,10,11-hexahydro-6H-dipyrido[2,1-d:2',3'-f][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoic acid. The mixture of 3-(5-((3-cyano-5,5-dioxido-7,7a,8,9,10,11-hexahydro-6H-dipyrido[2,1-d:2',3'-f][1,2,5]thiadiazepin-6-yl)methyl)-6-methylpyridin-3-yl)-2,2-dimethyl-3-(8-methyl-3-(trifluoromethyl)-[1,2,4]triazolo[4,3-a]pyridin-7-yl)propanoic acid isomers was initially separated by chiral SFC (SFC-B, mobile phase: 70% CO$_2$, 30% MeOH) and then chiral SFC (AS-H, mobile phase: 80% CO$_2$, 20% MeOH) to afford two peaks, a first eluting isomer (*S/*S) and a second eluting isomer, (*S/*R). The first eluting isomer (35 mg): MS: mass calcd. for $C_{32}H_{33}F_3N_8O_4S$, 682.2; m/z found, 683.3. $^1$H NMR (500 MHz, CDCl$_3$) δ 8.50-8.43 (m, 2H), 8.22 (d, J=2.2 Hz, 1H), 8.07 (d, J=7.0 Hz, 1H), 7.75 (s, 1H), 7.32 (d, J=7.4 Hz, 1H), 4.89 (s, 1H), 4.71-4.62 (m, 1H), 4.58-4.48 (m, 1H), 4.46-4.35 (m, 1H), 4.19-4.10 (m, 1H), 3.52-3.44 (m, 1H), 3.40-3.30 (m, 1H), 3.25-3.15 (m, 1H), 2.91-2.79 (m, 4H), 2.47 (s, 3H), 1.87-1.66 (m, 4H), 1.45-1.30 (m, 6H), 1.28-1.24 (m, 1H).

Example 658: (*R)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic Acid

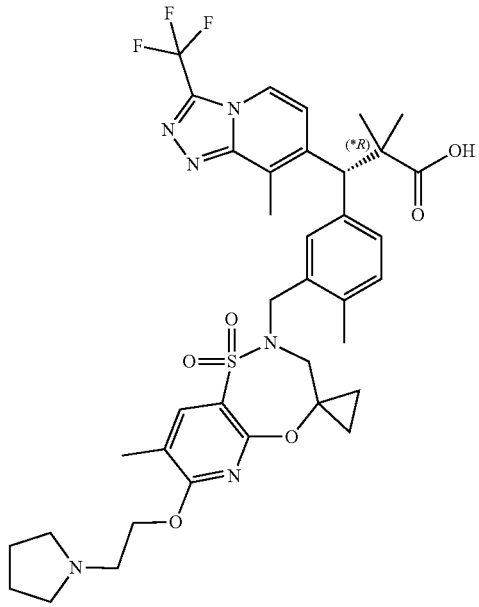 [SMILES: Cc1ccc([C@H](c2ccn3c(C(F)(F)F)nnc3c2C)C(C)(C)C(=O)O)cc1CN1CC2(CC2)Oc2nc(OCCN3CCCC3)c(C)cc2S1(=O)=O]

Step A: tert-Butyl (*R)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate.

The title compound (200 mg, 34%) was prepared using analogous conditions as described in Example 126 where 8'-methyl-7'-(2-(pyrrolidin-1-yl)ethoxy)-2',3'-dihydrospiro[cyclopropane-1,4'-pyrido[2,3-b][1,4,5]oxathiazepine]1',1'-dioxide (Intermediate 137) was used instead of 8'-methyl-7'-(2-(piperidin-1-yl)ethoxy)-2,2',3,3',5,6-hexahydrospiro[pyran-4,4'-pyrido[2,3-b][1,4,5]oxathiazepine] 1',1'-dioxide and tert-butyl (*R)-3-(3-(hydroxymethyl)-4-methylphenyl)-2,2-dimethyl-3-(8-methyl-3-(trifluoromethyl)[1,2,4]triazolo

[4,3-a]pyridine-7-yl)propanoate (Intermediate 135) instead of benzyl (*S)-3-(3-(hydroxymethyl)-4-methylphenyl)-2,2-dimethyl-3-(8-methyl-3-(trifluoromethyl)[1,2,4]triazolo[4,3-a]pyridine-7-yl)propanoate in step A. mass calcd. for $C_{41}H_{51}F_3N_6O_6S$, 812.4; m/z found, 407.3 $[M+2H]^{2+}$.

Step B: (*R)-2,2-Dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid. To a 25-mL round bottom flask fitted with a reflux condenser was added tert-Butyl (*R)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoate (200 mg 0.246 mmol), DCM (4.0 mL) and TFA (1 mL). The mixture was heated to 50° C. for 1.5 h then cooled, and solvent removed under reduced pressure. The mixture was treated with ethyl acetate/hexanes and the precipitated material was dried under vacuum to provide the title compound (180 mg, 84%) as the TFA salt. MS (ESI): mass calcd. for $C_{37}H_{43}F_3N_6O_6S$, 756.3; m/z found, 757.3 $[M+H]^+$. $^1$H NMR (400 MHz, DMSO-$d_6$) δ 12.51 (s, 1H), 9.70 (s, 1H), 8.41 (d, J=7.2 Hz, 1H), 8.01 (d, J=1.0 Hz, 1H), 7.25-7.19 (m, 2H), 7.15 (d, J=8.0 Hz, 1H), 7.08 (d, J=1.9 Hz, 1H), 4.79 (s, 1H), 4.59-4.56 (m, 2H), 4.27-4.08 (m, 2H), 3.63-3.37 (m, 6H), 3.18-3.13 (m, 2H), 2.64 (s, 3H), 2.25 (s, 3H), 2.24 (s, 3H), 2.08-2.01 (m, 2H), 1.91-1.88 (m, 2H), 1.31 (s, 3H), 1.24 (s, 3H), 0.98-0.90 (m, 2H), 0.64-0.45 (m, 2H).

Example 659: (*S)-3-(1-Cyclopropyl-4-methyl-1H-benzo[d][1,2,3]triazol-5-yl)-2,2-dimethyl-3-(4-methyl-3-((8'-methyl-1',1'-dioxido-7'-(((S)-1-(piperidin-1-yl)propan-2-yl)amino)spiro[cyclopropane-1,4'-pyrido[2,3-b][1,4,5]oxathiazepin]-2'(3'H)-yl)methyl)phenyl)propanoic Acid

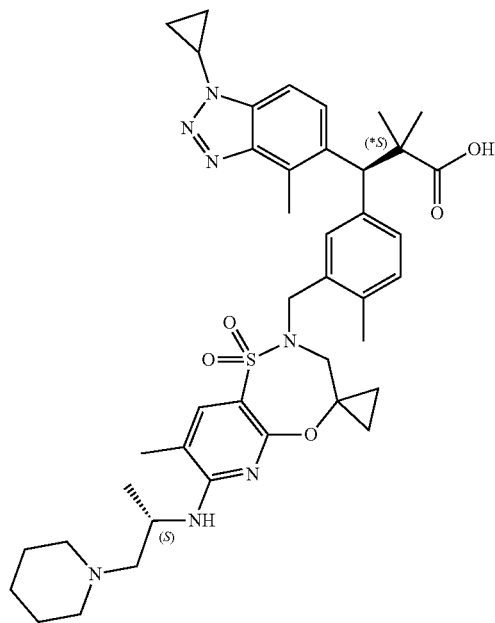

The mixture of (R 5)-3-(1-Cyclopropyl-4-methyl-1H-benzo[d][1,2,3]triazol-5-yl)-2,2-dimethyl-3-(4-methyl-3-((8'-methyl-1',1'-dioxido-7'-(((S)-1-(piperidin-1-yl)propan-2-yl)amino)spiro[cyclopropane-1,4'-pyrido[2,3-b][1,4,5]oxathiazepin]-2'(3'H)-yl)methyl)phenyl)propanoic acid isomers (Example 618) was separated by chiral SFC (IC, mobile phase: 55% $CO_2$, 45% EtOH with 0.3% $iPrNH_2$) to afford two diastereomers. The first eluting isomer (131 mg) was designated (*S): MS (ESI): mass calcd. for $C_{41}H_{53}N_7O_5S$, 755.4; m/z found, 756.3 $[M+H]^+$. $^1$H NMR (400 MHz, DMSO-$d_6$) δ 7.66-7.62 (m, 1H), 7.57-7.52 (m, 2H), 7.17-7.11 (m, 1H), 7.08-7.03 (m, 1H), 7.01-6.97 (m, 1H), 6.39 (d, J=7.5 Hz, 1H), 4.79 (s, 1H), 4.23-3.91 (m, 4H), 2.62 (s, 3H), 2.47-2.30 (m, 6H), 2.29-2.21 (m, 4H), 2.11-2.04 (m, 3H), 1.52-1.42 (m, 4H), 1.42-1.34 (m, 2H), 1.28-1.11 (m, 11H), 1.08-1.01 (m, 3H), 0.97-0.81 (m, 2H), 0.48-0.40 (m, 1H), 0.35-0.27 (m, 1H).

Example 660: (*R)-3-(1-Cyclopropyl-4-methyl-1H-benzo[d][1,2,3]triazol-5-yl)-2,2-dimethyl-3-(4-methyl-3-((8'-methyl-1',1'-dioxido-7'-(((S)-1-(piperidin-1-yl)propan-2-yl)amino)spiro[cyclopropane-1,4'-pyrido[2,3-b][1,4,5]oxathiazepin]-2'(3'H)-yl)methyl)phenyl)propanoic Acid

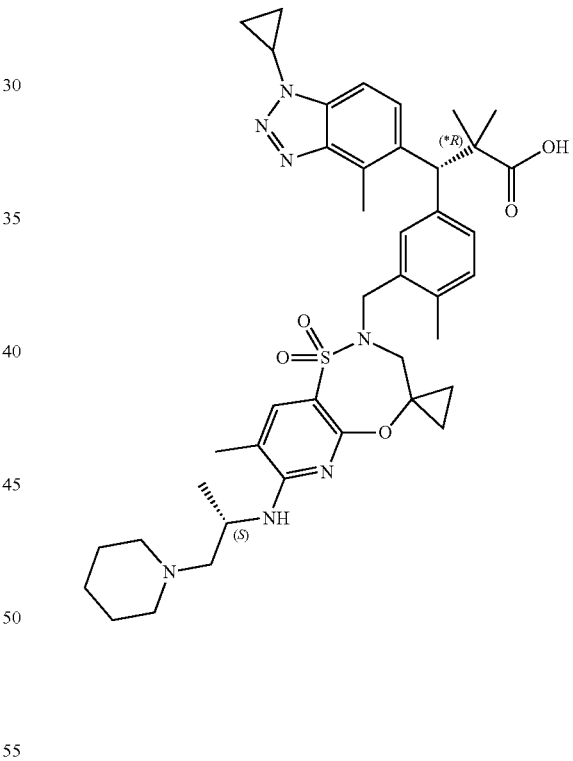

The second eluting isomer (153 mg) from the chiral separation described in Example 659 was designated (*R): MS (ESI): mass calcd. for $C_{41}H_{53}N_7O_5S$, 755.4; m/z found, 756.3 $[M+H]^+$. $^1$H NMR (400 MHz, DMSO-$d_6$) δ 7.63-7.59 (m, 1H), 7.57-7.51 (m, 2H), 7.18-7.14 (m, 1H), 7.09-7.04 (m, 1H), 7.00-6.96 (m, 1H), 6.41-6.37 (m, 1H), 4.80 (s, 1H), 4.22-3.91 (m, 4H), 2.64 (s, 3H), 2.45-2.28 (m, 6H), 2.27-2.21 (m, 4H), 2.10-1.99 (m, 3H), 1.50-1.34 (m, 6H), 1.24-1.10 (m, 14H), 0.90-0.85 (m, 2H), 0.43-0.27 (m, 2H).

Example 661: (*S)-3-(3-((7'-(2-(4-fluoropiperidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

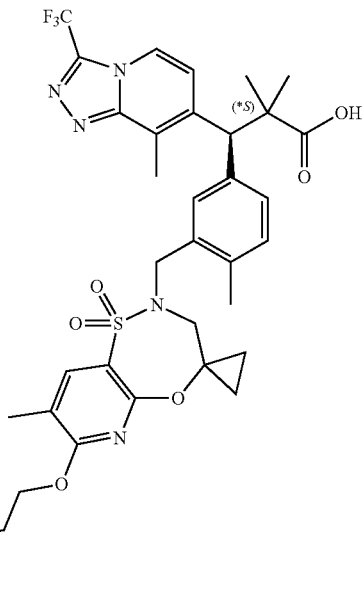

Step A: (*S)-Benzyl 3-(3-((7'-(2-(4-fluoropiperidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate. 7'-(2-(4-Fluoropiperidin-1-yl)ethoxy)-8'-methyl-2',3'-dihydrospiro[cyclopropane-1,4'-pyrido[2,3-b][1,4,5]oxathiazepine] 1',1'-dioxide (430 mg, 1.12 mmol, Intermediate 202) was added to a solution of (*S)-benzyl 3-(3-(chloromethyl)-4-methylphenyl)-2,2-dimethyl-3-(8-methyl-3-(trifluoromethyl)-[1,2,4]triazolo[4,3-a]pyridin-7-yl)propanoate (Intermediate 203, 620 mg, 1.17 mmol), K₂CO₃ (618 mg, 4.47 mmol), and CH₃CN (20 mL). The resulting mixture was stirred at 90° C. for 16 hours before concentrating to dryness under reduced pressure. The residue was diluted with water (10 mL) and the mixture extracted with ethyl acetate (3×). These extractions resulted in several fractions that were combined, dried over anhydrous Na₂SO₄, filtered, and concentrated to dryness under reduced pressure. The residue was purified by flash chromatography (eluent:petroleum ether/ethyl acetate; 10:1 to 0:1, gradient) to afford the title compound (700 mg, 68%). MS (ESI): mass calcd. for C₄₅H₅₀F₄N₆O₆S, 878.3 m/z found 879.5 [M+H]⁺.

Step B: (*S)-3-(3-((7'-(2-(4-fluoropiperidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid. LiOH*H₂O (335 mg, 7.98 mmol) was added to a solution of (*S)-benzyl 3-(3-((7'-(2-(4-fluoropiperidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridin-7-yl)propanoate (700 mg, 0.796 mmol), 1,4-dioxane (10 mL), and H₂O (10 mL). The resulting mixture was stirred while heating at 75° C. for 12 hours before cooling to room-temperature and concentrating to dryness under reduced pressure. The residue was diluted with H₂O (5 mL), pH adjusted to 6-7 with aq. HCl (1 M), and extracted with ethyl acetate (2×). These extractions resulted in several fractions that were combined, dried over anhydrous Na₂SO₄, filtered, and concentrated to dryness under reduced pressure. The residue was purified by reverse-phase preparative HPLC (eluent: CH₃CN/H₂O with 0.225% HCOOH; 28% to 58% (v/v), gradient) to afford the title compound (321 mg, 50%) as a white solid. MS (ESI): mass calcd. for C₃₈H₄₄F₄N₆O₆S, 788.3 m/z found 789.2 [M+H]⁺. ¹H NMR (400 MHz, DMSO-d₆) δ 8.39 (d, J=7.1 Hz, 1H), 7.94 (s, 1H), 7.31-7.18 (m, 2H), 7.15-7.05 (m, 2H), 4.83-4.02 (m, 6H), 2.77-2.56 (m, 9H), 2.46-2.31 (m, 2H), 2.24 (s, 3H), 2.16 (s, 3H), 1.97-1.60 (m, 4H), 1.28 (s, 3H), 1.22 (s, 3H), 1.00-0.86 (m, 2H), 0.59-0.35 (m, 2H).

Example 662: (*S)-3-(3-((7'-(2-(4-fluoropiperidin-1-yl)ethoxy)-8'-methyl-1',1'-dioxidospiro[cyclopropane-1,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic Acid

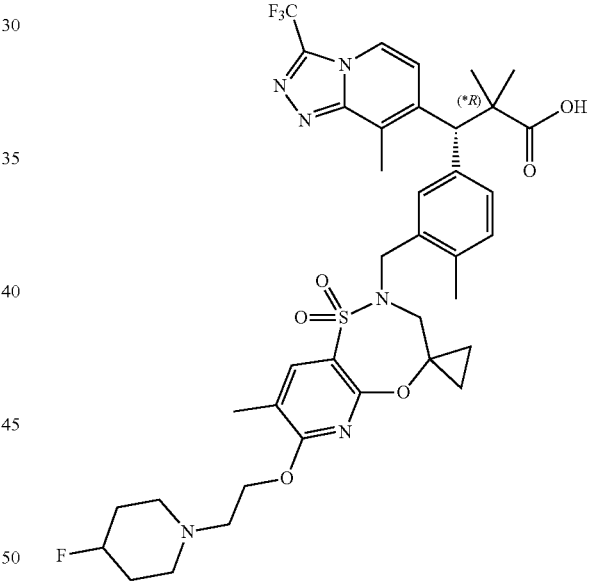

The title compound (350 mg, 62%) was prepared using analogous conditions as described in Example 661 where (*R)-benzyl 3-(3-(chloromethyl)-4-methylphenyl)-2,2-dimethyl-3-(8-methyl-3-(trifluoromethyl)-[1,2,4]triazolo[4,3-a]pyridin-7-yl)propanoate (Intermediate 204) was used instead of (*S)-benzyl 3-(3-(chloromethyl)-4-methylphenyl)-2,2-dimethyl-3-(8-methyl-3-(trifluoromethyl)-[1,2,4]triazolo[4,3-a]pyridin-7-yl)propanoate in step A. MS (ESI): mass calcd. for C₃₈H₄₄F₄N₆O₆S, 788.3 m/z found 789.2 [M+H]⁺. ¹H NMR (400 MHz, DMSO-d₆) δ 8.39 (d, J=7.1 Hz, 1H), 7.94 (s, 1H), 7.28-7.04 (m, 4H), 4.85-4.56 (m, 2H), 4.45-4.30 (m, 2H), 4.24-4.00 (m, 2H), 3.22-2.92 (m, 1H), 2.72-2.58 (m, 8H), 2.45-2.31 (m, 2H), 2.24 (s, 3H), 2.16 (s, 3H), 1.88-1.67 (m, 4H), 1.28 (s, 3H), 1.21 (s, 3H), 0.99-0.84 (m, 2H), 0.60-0.39 (m, 2H).

Example 663: (*S)-3-(3-Cyclopropyl-8-methyl-[1,2,4]triazolo[4,3-a]pyridin-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoic Acid

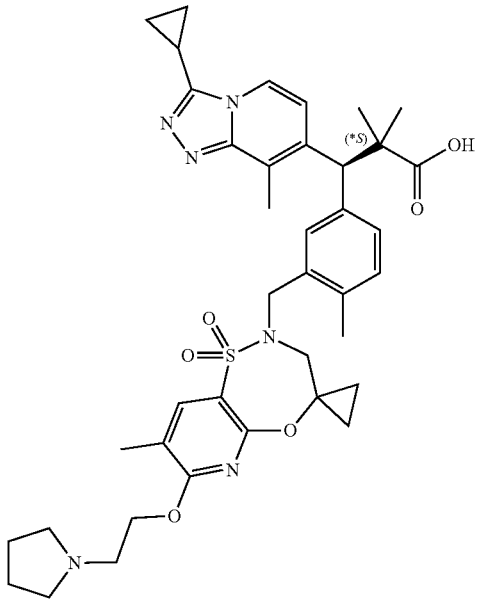 [SMILES: Cc1ccc([C@@H](c2ccn3c(C4CC4)nnc3c2C)C(C)(C)C(=O)O)cc1CN1CC2(CC2)Oc2nc(OCCN3CCCC3)c(C)cc2S1(=O)=O]

Step A: Benzyl (*S)-3-(3-(chloromethyl)-4-methylphenyl)-3-(3-cyclopropyl-8-methyl-[1,2,4]triazolo[4,3-a]pyridin-7-yl)-2,2-dimethylpropanoate. $SOCl_2$ (0.3 mL, 4 mmol) was added to a solution consisting of benzyl (*S)-3-(3-cyclopropyl-8-methyl-[1,2,4]triazolo[4,3-a]pyridin-7-yl)-3-(3-(hydroxymethyl)-4-methylphenyl)-2,2-dimethylpropanoate (Intermediate 199, 400 mg, 0.827 mmol) and dichloromethane (10 mL). The resulting mixture was stirred at room temperature for 1 hour, then concentrated to dryness under reduced pressure to provide the title compound (415 mg), which was used in the next step without further purification. MS (ESI): mass calcd. for $C_{30}H_{32}ClN_3O_2$ 502.05; m/z found, 502.3 [M+H]$^+$. $^1$H NMR (400 MHz, CDCl$_3$) δ 7.99 (s, 1H), 7.42 (s, 1H), 7.11-7.04 (m, 6H), 7.00 (s, 1H), 6.94 (d, J=7.8 Hz, 1H), 5.23 (d, J=11.8 Hz, 1H), 4.79 (d, J=11.8 Hz, 1H), 4.64 (s, 1H), 4.48 (s, 2H), 2.72 (s, 3H), 2.35 (s, 3H), 2.13 (br s, 1H), 1.44 (s, 3H), 1.41-1.38 (m, 1H), 1.36 (s, 3H), 1.34-1.18 (m, 3H).

Step B: Benzyl (*S)-3-(3-cyclopropyl-8-methyl-[1,2,4]triazolo[4,3-a]pyridin-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoate. Benzyl (*S)-3-(3-(chloromethyl)-4-methylphenyl)-3-(3-cyclopropyl-8-methyl-[1,2,4]triazolo[4,3-a]pyridin-7-yl)-2,2-dimethylpropanoate (415 mg, 0.827 mmol), 8'-methyl-7'-(2-(pyrrolidin-1-yl)ethoxy)-2',3'-dihydrospiro[cyclopropane-1,4'-pyrido[2,3-b][1,4,5]oxathiazepine] 1',1'-dioxide (Intermediate 137, 321 mg, 0.908 mmol), $K_2CO_3$ (343 mg, 2.48 mmol) and acetonitrile (20 mL) were combined and the resulting mixture was stirred for 16 hours at 80° C. After this time, the suspension was filtered and the filter cake was washed with acetonitrile (5×3 mL). The filtrate was concentrated to dryness under reduced pressure to provide the title compound (677 mg), which was used in the next step without further purification. MS (ESI): mass calcd. for $C_{46}H_{54}N_6O_6S$, 819.02; m/z found, 819.5 [M+H]$^+$.

Step C: (*S)-3-(3-Cyclopropyl-8-methyl-[1,2,4]triazolo[4,3-a]pyridin-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoic acid. Benzyl (*S)-3-(3-cyclopropyl-8-methyl-[1,2,4]triazolo[4,3-a]pyridin-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoate (677 mg, 0.827 mmol), MeOH (20 mL), and wet Pd/C (100 mg, 10 wt. %) were added combined and the resulting mixture was stirred under $H_2$ (15 psi) at room temperature for 3 hours. After this time, the suspension was filtered, and the filter cake was washed with MeOH (5 mL×3). The filtrate was concentrated to dryness under reduced pressure, combined with another batch of the same compound, and purified by preparative acidic HPLC (Xtimate C18, 150 mm×25 mm×5 μm column, eluent: 25-55% $CH_3CN$ and $H_2O$ with 0.225% HCOOH) to provide the title compound (343.6 mg) as a white solid. MS (ESI): mass calcd. for $C_{39}H_{48}N_6O_6S$, 728.90; m/z found, 729.2 [M+H]$^+$. $^1$H NMR (400 MHz, DMSO-d$_6$) δ 8.24 (d, J=7.3 Hz, 1H), 7.92 (s, 1H), 7.15 (d, J=7.7 Hz, 1H), 7.08 (d, J=7.7 Hz, 2H), 6.91 (d, J=7.3 Hz, 1H), 4.65 (s, 1H), 4.36 (t, J=5.6 Hz, 2H), 4.19-4.14 (m, 1H), 4.11-4.06 (m, 1H), 3.55-3.53 (m, 4H), 2.85 (t, J=5.5 Hz, 2H), 2.60 (s, 3H), 2.32-2.28 (m, 1H), 2.20 (s, 3H), 2.14 (s, 3H), 1.75-1.61 (m, 4H), 1.23 (s, 3H), 1.17 (s, 3H), 1.08-1.01 (m, 2H), 1.01-0.86 (m, 4H), 0.63-0.37 (m, 4H).

Example 664: (*R)-3-(3-Cyclopropyl-8-methyl-[1,2,4]triazolo[4,3-a]pyridin-7-yl)-2,2-dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)propanoic Acid

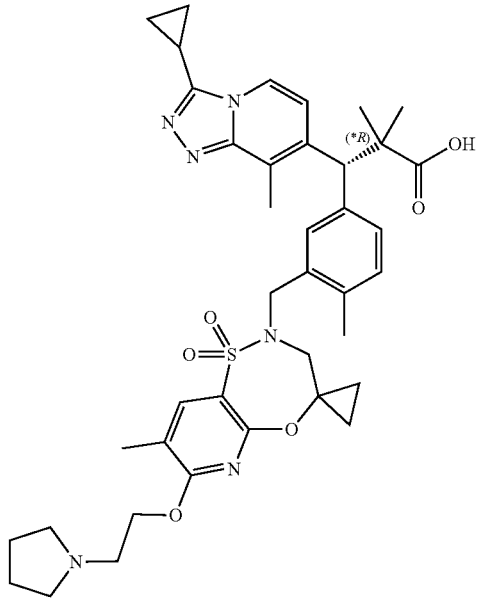 [SMILES: Cc1ccc([C@H](c2ccn3c(C4CC4)nnc3c2C)C(C)(C)C(=O)O)cc1CN1CC2(CC2)Oc2nc(OCCN3CCCC3)c(C)cc2S1(=O)=O]

The title compound (326.1 mg) was prepared using analogous conditions as described in Example 663 where benzyl (*R)-3-(3-cyclopropyl-8-methyl-[1,2,4]triazolo[4,3-a]pyridin-7-yl)-3-(3-(hydroxymethyl)-4-methylphenyl)-2,2-dimethylpropanoate. (Intermediate 200) was used instead of benzyl (*S)-3-(3-cyclopropyl-8-methyl-[1,2,4]triazolo[4,3-a]pyridin-7-yl)-3-(3-(hydroxymethyl)-4-methylphenyl)-2,2-dimethylpropanoate and the final compound was purified by preparative acidic HPLC (Boston Green ODS, 150 mm×30 mm×5 μm column, eluent: 25-55% $CH_3CN$ and $H_2O$ with 0.225% HCOOH). MS (ESI): mass calcd. for $C_{39}H_{48}N_6O_6S$, 728.90; m/z found, 729.4 $[M+H]^+$. $^1H$ NMR (400 MHz, DMSO-$d_6$) δ 8.27 (d, J=7.3 Hz, 1H), 7.95 (d, J=0.7 Hz, 1H), 7.18 (d, J=7.9 Hz, 1H), 7.11 (d, J=7.7 Hz, 2H), 6.95 (d, J=7.5 Hz, 1H), 4.68 (s, 1H), 4.39 (t, J=5.5 Hz, 2H), 4.22-4.18 (m, 1H), 4.12 (d, J=14.8 Hz, 1H), 3.57-3.55 (m, 4H), 2.87 (t, J=5.6 Hz, 2H), 2.62 (s, 3H), 2.33-2.29 (m, 1H), 2.28-2.20 (m, 3H), 2.17 (s, 3H), 1.70 (s, 4H), 1.27 (s, 3H), 1.21 (s, 3H), 1.08 (d, J=2.6 Hz, 2H), 1.03-0.91 (m, 4H), 0.67-0.44 (m, 4H).

Example 665: (*R)-3-(1-Ethyl-4-methyl-1H-benzo[d][1,2,3]triazol-5-yl)-2,2-dimethyl-3-(5-methyl-4-((8'-methyl-1',1'-dioxidospiro[cyclopropane-1,4'-pyrido[2,3-b][1,4,5]oxathiazepin]-2'(3'H)-yl)methyl)pyridin-2-yl)propanoic Acid

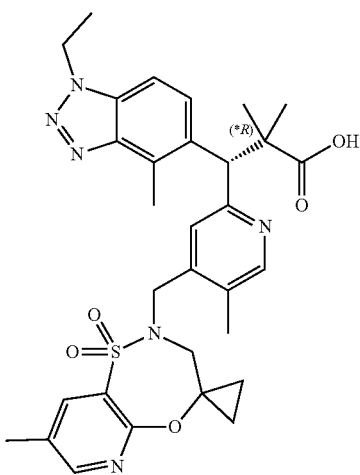 [SMILES: CCn1nnc2c(C)c([C@@H](c3cc(CN4CC5(CC5)Oc5ncc(C)cc5S4(=O)=O)c(C)cn3)C(C)(C)C(=O)O)ccc21]

The title compound was prepared as described in Scheme 1. MS (ESI): mass calcd. for $C_{31}H_{36}N_6O_5S$, 604.2; m/z found, 605.2 $[M+H]^+$. $^1H$ NMR (400 MHz, DMSO-$d_6$) δ12.69 (s, 1H), 8.32 (s, 1H), 8.31-8.29 (m, 1H), 8.01-7.99 (m, 1H), 7.59-7.53 (m, 2H), 7.03 (s, 1H), 5.00 (s, 1H), 4.66 (q, J=7.1 Hz, 2H), 4.23-4.10 (m, 2H), 3.76-3.58 (m, 1H), 3.52-3.40 (m, 1H), 2.82 (s, 3H), 2.33 (s, 3H), 2.17 (s, 3H), 1.47 (t, J=7.3 Hz, 3H), 1.29 (s, 3H), 1.20 (s, 3H), 0.95-0.81 (m, 2H), 0.67-0.51 (m, 2H).

Biological Assay.

Binding potency was assessed using a ThermoFluor® assay and cell based activity in HEK cells was assesses using an ARE assay.

The ARE assay utilizes a luciferase reporter cell line where the signal is proportional to $NrF_2$ activation of the ARE. The cell line is commercially available from Promega and was prepared by stably transfecting HEK293 cells with a vector (pGL4.11) which contains the ARE response element upstream of a minimal promoter. The promoter drives expression of luc2 firefly luciferase gene. Upon disruption of KEAP1-Nrf2 binding by compound, Nrf2 translocates into the nucleus where it binds to the ARE and activates transcription of luciferase.

The materials used in this ARE assay are as follows: Glo-Response ARE-luc2P HEK293 cell line and One-Glo Luciferase Assay System were purchased from Promega (Madison, Wis.). Dulbecco's Modified Eagle medium ((DMEM), low glucose, GlutaMAX, pyruvate), fetal bovine serum (certified, heat inactivated), hygromycin B, Dulbecco's phosphate-buffered saline were purchased from Life Technologies (Grand Island, N.Y.). Penicillin, streptomycin solution (100×) and 0.05% trypsin-EDTA were purchased from Corning (Manassas, Va.). DMSO was purchased from EMD Millipore.

The ARE assay protocol is as follows: cells were maintained in growth medium (DMEM+10% FBS, 200 μg/mL hygromycin B, p-s) between 20-90% confluency by splitting twice per week. One day before the assay, cells were trypsinized, counted to determine viable cell count, and re-suspended in assay medium (DMEM+10% FBS, p-s) at 250,000 cells/mL. Five thousand cells per well were plated in a 384 well, PDL coated, solid white tissue culture plate (Greiner 781201-906) with 100% DMSO. 100% DMSO was used as the low control. A 11-point dose series of the control compound was included on every plate. Compounds were spotted to an intermediate plate (Greiner #781280 V-bottom 384 well plate) using the Echo acoustic dispenser (Labscyte San Jose, Calif.). Spot size was 240 nL.

On the day of the assay, 60 mL per well of assay medium was added to the pre-spotted plate to make 2× compound stocks using the Combi (Thermo Waltham, Mass.). Compound and medium were mixed on the Janus and 20 mL of 2×compound stock was added to the cell plate which already contained 20 mL of assay medium from cell plating. The top dose of compound (final) was typically 20 or 2 mM and the final DMSO concentration was 0.2%. The plates were returned to the tissue culture incubator for 24 hours.

The next day, luciferase activity was measured according to the manufacturer's protocol for One-Glo luciferase reagent. The plates were removed from the incubator and allowed to equilibrate to room temperature for 30 min. Forty microliters of One-Glo reagent (equilibrated to room temperature) was added per well using the Combi. The plates were mixed on an orbital shaker for 3 min. Luminescence was read on the BMG Pherastar multiplate reader (Cary, N.C.) using the luminescence protocol (1 sec interval).

The dose-response data were analyzed in Genedata Screener using 4PL nonlinear regression model. Raw luminescence counts as well as normalized values were used for data analysis.

Results for the compounds tested in the ARE assay are presented in Table 4 as an average of results obtained.

The ThermoFluor® is a fluorescence based assay (Tf) that estimates ligand binding affinities by measuring the effect of a ligand on protein thermal stability (Pantoliano, M. W., et al., J. Biomol. Screen 2001, 6, 429-40.). This approach is applicable to a wide variety of systems, and rigorous in theoretical interpretation through quantitation of equilibrium binding constants (KD).

In a ThermoFluor® experiment where protein stability is monitored as the temperature is steadily increased, an equilibrium binding ligand causes the midpoint of an unfolding transition ($T_m$) to occur at a higher temperature. The shift in the melting point described as a $\Delta T_m$ is proportional to the concentration and affinity of the ligand. The compound potency may be compared as a rank order of either $\Delta T_m$ values at a single compound concentration or in terms of $K_D$ values, estimated from concentration response curves.

The details of the KEAP1 KELCH ThermoFluor® Assay Construct are as follows: Kelch domain of human KEAP1 (321-624 aa) was used in the assay. The protein was expressed in *E. coli* with 6His tag that was cleaved prior to receipt for use.

ThermoFluor® experiments were carried out using instruments owned by Janssen Research and Discovery, L.L.C. through its acquisition of 3-Dimensional Pharmaceuticals, Inc. 1,8-ANS (Invitrogen) was used as a fluorescent dye. Protein (KEAP Kelch) and compound solutions were dispensed into black 384-well polypropylene PCR microplates (Abgene) and overlayed with silicone oil (1 µL, Fluka, type DC 200) to prevent evaporation.

Reference wells contained KEAP Kelch without compounds, and the assay conditions were as follows: 1.1 µM (0.037 mg/mL) KEAP Kelch, 80 µM 1,8-ANS, 25 mM PIPES, pH 7.0, 100 mM NaCl, 0.002% Tween-20.

The binding affinity was estimated as described previously (Matulis, D. et al., Biochemistry 2005, 44, 5258-66) using thermodynamic parameters of protein unfolding listed below.

$\Delta H_{(Tm)}$=50 kcal/mol
$\Delta C_{p(Tm)}$=4 kcal/mol
Reference KEAP Kelch $T_m$: 49.5+/−0.4

ThermoFluor assay data are presented in Table 4 as an average of results obtained.

TABLE 4

ThermoFluor binding and ARE cell-based assay data

| Example # | Tf $K_d$ (nM) | ARE assay (nM) |
|---|---|---|
| 1 | 0.042 | 35 |
| 2 | 0.162 | 180 |
| 3 | 0.041 | 35 |
| 4 | 0.24 | 79 |
| 5 | 0.518 | 110 |
| 6 | 0.089 | 42 |
| 7 | 0.127 | 74 |
| 8 | 0.188 | 660 |
| 9 | <1 | 3.8 |
| 10 | <1 | 5.2 |
| 11 | 0.024 | 4.2 |
| 12 | * | 2.7 |
| 13 | 0.079 | 37.8 |
| 14 | * | 0.7 |
| 15 | * | 0.3 |
| 16 | 838 | 233 |
| 17 | * | 3.6 |
| 18 | * | 1.5 |
| 19 | 1284 | 789 |
| 20 | 0.081 | 6.3 |
| 21 | 0.273 | 28 |
| 22 | 0.081 | 3.9 |
| 23 | 0.278 | 8.3 |
| 24 | 0.264 | 4.1 |
| 25 | 2.123 | 21 |
| 26 | 0.174 | 32 |
| 27 | * | 28.8 |
| 28 | <1 | 23.5 |
| 29 | <1 | 50.9 |
| 30 | <1 | 73.7 |
| 31 | * | 9.9 |
| 32 | * | 13.6 |
| 33 | <1 | 30.6 |
| 34 | <1 | 118.7 |
| 35 | <1 | 65.7 |
| 36 | <1 | 15.2 |
| 37 | <1 | 25.7 |
| 38 | <1 | 7.2 |
| 39 | 4250 | 1260 |
| 40 | NT | NT |
| 41 | <1 | 46 |
| 42 | 7540 | 3460 |
| 43 | NT | NT |
| 44 | <1 | 54.3 |
| 45 | 42600 | 6555 |
| 46 | <1 | 71.9 |
| 47 | <1 | 17.9 |
| 48 | 820 | 6272 |
| 49 | <1 | 71.9 |
| 50 | <1 | 52 |
| 51 | 0.97 | 645.9 |
| 52 | <1 | 8.2 |
| 53 | <1 | 3.9 |
| 54 | 1790 | 955.6 |
| 55 | <1 | 123.7 |
| 56 | <1 | 48 |
| 57 | 5670 | 6658 |
| 58 | 2.4 | 225.7 |
| 59 | 1.2 | 115.8 |
| 60 | 41150 | 12313 |
| 61 | <1 | 41.7 |
| 62 | <1 | 19.2 |
| 63 | 14550 | 3279.9 |
| 64 | <1 | 304.4 |
| 65 | 2.5 | 360 |
| 66 | 1 | 260 |
| 67 | 0.34 | 23 |
| 68 | 1.4 | 250 |
| 69 | 0.16 | 28.5 |
| 70 | 1.9 | 180 |
| 71 | 2.6 | 1160 |
| 72 | 5.4 | 1970 |
| 73 | 3 | 600 |
| 74 | <1 | 24 |
| 75 | <1 | 14 |
| 76 | 4.8 | 136.4 |
| 77 | 0.42 | 15.7 |
| 78 | NT | 8.9 |
| 79 | 5.6 | 153.4 |
| 80 | 8 | 305.9 |
| 81 | 5.5 | 176 |
| 82 | 80 | 3350 |
| 83 | <1 | 232 |
| 84 | <1 | 80.5 |
| 85 | 2.2 | 1508 |
| 86 | 2.4 | 6241 |
| 87 | 1.3 | 2529 |
| 88 | 0.01 | >20,000 |
| 89 | 0.0054 | 6.9 |
| 90 | * | 4.2 |
| 91 | <1 | 14.4 |
| 92 | <1 | 28.6 |
| 93 | <1 | 10 |
| 94 | <1 | 54.2 |
| 95 | 2.5 | 1080 |
| 96 | 1.1 | 491 |
| 97 | 10 | 5288 |
| 98 | * | 16 |
| 99 | <1 | 5.8 |
| 100 | <1 | 13.3 |
| 101 | <1 | 577.2 |
| 102 | <1 | 695.8 |
| 103 | 1.6 | 9132 |
| 104 | NT | NT |
| 105 | 16 | 14,427 |
| 106 | 21 | >20,000 |
| 107 | <1 | 259.1 |
| 108 | <1 | 405.9 |
| 109 | * | 128 |
| 110 | <1 | 485.3 |
| 111 | <1 | 588.2 |
| 112 | <1 | 1312 |
| 113 | NT | 490.3 |
| 114 | * | 145 |

TABLE 4-continued

ThermoFluor binding and ARE cell-based assay data

| Example # | Tf $K_d$ (nM) | ARE assay (nM) |
|---|---|---|
| 115 | <1 | 132.8 |
| 116 | 2680 | 991.1 |
| 117 | <1 | 424.8 |
| 118 | <1 | 324.5 |
| 119 | <1 | 166.1 |
| 120 | 8560 | 19,372 |
| 121 | <1 | 156.6 |
| 122 | 8930 | 12,990 |
| 123 | <1 | 28.9 |
| 124 | <1 | 28.8 |
| 125 | <1 | 140.5 |
| 126 | <1 | 6 |
| 127 | <1 | 11.8 |
| 128 | <1 | 307.6 |
| 129 | <1 | 6.8 |
| 130 | * | 54.8 |
| 131 | * | 1.6 |
| 132 | * | NT |
| 133 | <1 | 2 |
| 134 | <1 | 61.3 |
| 135 | 1.8 | 24 |
| 136 | <1 | 8.3 |
| 137 | 5.8 | 300 |
| 138 | <1 | 14 |
| 139 | <1 | 3.3 |
| 140 | <1 | 19 |
| 141 | <1 | 3.9 |
| 142 | <1 | 1.1 |
| 143 | <1 | 45 |
| 144 | <1 | 3.1 |
| 145 | <1 | 1.1 |
| 146 | <1 | 4.2 |
| 147 | 1.5 | 19 |
| 148 | <1 | 15 |
| 149 | 8.6 | 250 |
| 150 | <1 | 56 |
| 151 | <1 | 10 |
| 152 | 0.12 | 6.5 |
| 153 | <1 | 3 |
| 154 | <1 | 59 |
| 155 | <1 | 6.1 |
| 156 | 2.1 | 3.6 |
| 157 | ~3.2 | 62 |
| 158 | <1 | 6.2 |
| 159 | ~1.2 | 34 |
| 160 | <1 | 19,000 |
| 161 | 2.8 | 15,890 |
| 162 | <1 | 2440 |
| 163 | <1 | 2,750 |
| 164 | 2.3 | 11,170 |
| 165 | <1 | 1,490 |
| 166 | <1 | 7,020 |
| 167 | <1 | 1,140 |
| 168 | <1 | 480 |
| 169 | 1.2 | 5,910 |
| 170 | <1 | 110 |
| 171 | <1 | 88 |
| 172 | <1 | 19 |
| 173 | 4 | 540 |
| 174 | <1 | 15 |
| 175 | <1 | 5.3 |
| 176 | <1 | 31 |
| 177 | 49 | 1,390 |
| 178 | 30 | 440 |
| 179 | 58 | 2,040 |
| 180 | 190 | 2,880 |
| 181 | 110 | 1,110 |
| 182 | 180 | 1,390 |
| 183 | 1.6 | 370 |
| 184 | 1.4 | 130 |
| 185 | 12 | 2,720 |
| 186 | * | 47 |
| 187 | <1 | 550 |
| 188 | <1 | 17 |
| 189 | <1 | 11 |
| 190 | <1 | 57 |
| 191 | * | 1.9 |
| 192 | <1 | 1.4 |
| 193 | * | 1.7 |
| 194 | * | 2 |
| 195 | <1 | 5.7 |
| 196 | <1 | 15 |
| 197 | <1 | 1.8 |
| 198 | * | 5.3 |
| 199 | * | 3.3 |
| 200 | <1 | 61 |
| 201 | 300 | >20,000 |
| 202 | * | 13 |
| 203 | * | 150 |
| 204 | * | 5.9 |
| 205 | <1 | 130 |
| 206 | * | 14 |
| 207 | <1 | 11 |
| 208 | <1 | 19 |
| 209 | <1 | 8.8 |
| 210 | <1 | 7.7 |
| 211 | 1.1 | 42 |
| 212 | <1 | 3.7 |
| 213 | <1 | 8 |
| 214 | <1 | 5.1 |
| 215 | <1 | 3.3 |
| 216 | 2 | 38 |
| 217 | <1 | 11 |
| 218 | <1 | 6.6 |
| 219 | * | 4.5 |
| 220 | <1 | 61 |
| 221 | 19 | 580 |
| 222 | 14 | 350 |
| 223 | 190 | 5,460 |
| 224 | * | 20 |
| 225 | * | 5 |
| 226 | 6 | 160 |
| 227 | <1 | 22 |
| 228 | <1 | 10 |
| 229 | 17,000 | 2,430 |
| 230 | <1 | 480 |
| 231 | <1 | 7 |
| 232 | <1 | 2.6 |
| 233 | <1 | 80 |
| 234 | <1 | 3.3 |
| 235 | <1 | 1.9 |
| 236 | <1 | 6.8 |
| 237 | 1.5 | 19 |
| 238 | <1 | 9.7 |
| 239 | 1.9 | 44 |
| 240 | <1 | 85 |
| 241 | <1 | 28 |
| 242 | 1.8 | 110 |
| 243 | <1 | 35 |
| 244 | <1 | 35 |
| 245 | <1 | 140 |
| 246 | <1 | 87.3 |
| 247 | <1 | 225.2 |
| 248 | <1 | 48.6 |
| 249 | <1 | 28.6 |
| 250 | <1 | 32.8 |
| 251 | <1 | 24.1 |
| 252 | <1 | 21.0 |
| 253 | <1 | 1168.2 |
| 254 | <1 | 3398.6 |
| 255 | <1 | 921.7 |
| 256 | <1 | 378.8 |
| 257 | <1 | 574.1 |
| 258 | <1 | 427.7 |
| 259 | <1 | 200.9 |
| 260 | <1 | 101.0 |
| 261 | <1 | 1389.6 |
| 262 | 1.089 | 14.7 |
| 263 | 14.73 | 1158.2 |
| 264 | <1 | 18.3 |

TABLE 4-continued

ThermoFluor binding and ARE cell-based assay data

| Example # | Tf $K_d$ (nM) | ARE assay (nM) |
|---|---|---|
| 265 | <1 | 31.2 |
| 266 | <1 | 14.6 |
| 267 | <1 | 90.4 |
| 268 | <1 | 516.5 |
| 269 | <1 | 365.1 |
| 270 | 1.28 | 2417.1 |
| 271 | <1 | 22.9 |
| 272 | <1 | 10.9 |
| 273 | <1 | 25.8 |
| 274 | 1.19 | 51.2 |
| 275 | 8.69 | 399.4 |
| 276 | <1 | 112.3 |
| 277 | 1.29 | 101.8 |
| 278 | <1 | 467.2 |
| 279 | <1 | 235.0 |
| 280 | <1 | 4007.7 |
| 281 | <1 | 480.5 |
| 282 | <1 | 293.2 |
| 283 | <1 | 4167.7 |
| 284 | 1.65 | 212.8 |
| 285 | 1.1 | 128.9 |
| 286 | 3.39 | 504.1 |
| 287 | <1 | 28.1 |
| 288 | <1 | 122.6 |
| 289 | <1 | 19.3 |
| 290 | <1 | 8.8 |
| 291 | <1 | 86.8 |
| 292 | <1 | 68.3 |
| 293 | 2.55 | 898.7 |
| 294 | 1.61 | 270.1 |
| 295 | 8.07 | 2090.3 |
| 296 | <1 | 13.6 |
| 297 | <1 | 6.0 |
| 298 | <1 | 21.5 |
| 299 | * | 11.4 |
| 300 | <1 | 5.0 |
| 301 | <1 | 4.7 |
| 302 | <1 | 2.8 |
| 303 | <1 | 27.1 |
| 304 | <1 | 2.9 |
| 305 | <1 | 1.7 |
| 306 | <1 | 9.4 |
| 307 | * | 2.0 |
| 308 | <1 | 1.4 |
| 309 | * | 0.9 |
| 310 | * | 3.0 |
| 311 | <1 | 9.3 |
| 312 | <1 | 13.1 |
| 313 | * | 1.1 |
| 314 | <1 | 1.0 |
| 315 | 287.1 | 147.8 |
| 316 | * | 1.3 |
| 317 | <1 | 1.9 |
| 318 | 1990 | 598.3 |
| 319 | NT | 44.5 |
| 320 | 830.6 | 19422.3 |
| 321 | <1 | 22.0 |
| 322 | * | 22.4 |
| 323 | 297.5 | 16236.8 |
| 324 | <1 | 16.7 |
| 325 | <1 | 17.2 |
| 326 | 3235 | 4602.6 |
| 327 | <1 | 6.9 |
| 328 | <1 | 3.3 |
| 329 | 1878 | 1902.8 |
| 330 | 1592 | 7524.9 |
| 331 | <1 | 17.1 |
| 332 | <1 | 25.6 |
| 333 | 1715 | 3984.7 |
| 334 | <1 | 5.2 |
| 335 | 2436 | 4622.7 |
| 336 | * | 1831.9 |
| 337 | >10,000 | >19.9986 |
| 338 | <1 | 13.1 |
| 339 | 80,186 | 6319.8 |
| 340 | 1.24 | 629.1 |
| 341 | 18758 | >19.9986 |
| 342 | <1 | 5.6 |
| 343 | 32195 | 1573.6 |
| 344 | * | 4928.3 |
| 345 | >10,000 | >19.9986 |
| 346 | * | 49.8 |
| 347 | * | 3576.0 |
| 348 | * | 19.2 |
| 349 | * | 1535.3 |
| 350 | * | 23.4 |
| 351 | * | 836.0 |
| 352 | * | 43.7 |
| 353 | * | 1405.7 |
| 354 | <1 | 20.6 |
| 355 | 3070.4 | 1138.7 |
| 356 | 3547.3 | 11.8 |
| 357 | <1 | 452.0 |
| 358 | 4464.8 | 23.3 |
| 359 | <1 | 1234.0 |
| 360 | <1 | 9.3 |
| 361 | <1 | 60.4 |
| 362 | <1 | 20.5 |
| 363 | <1 | 12.9 |
| 364 | NT | NT |
| 365 | <1 | 23.9 |
| 366 | <1 | 407.2 |
| 367 | <1 | 78.6 |
| 368 | <1 | 255.7 |
| 369 | <1 | 175.7 |
| 370 | <1 | 11.3 |
| 371 | <1 | 6.0 |
| 372 | <1 | 2.9 |
| 373 | <1 | 5.4 |
| 374 | <1 | 4.8 |
| 375 | <1 | 11.5 |
| 376 | <1 | 57.3 |
| 377 | <1 | 44.9 |
| 378 | <1 | 4.0 |
| 379 | <1 | 12.3 |
| 380 | <1 | 14.1 |
| 381 | 2824.9 | 427.2 |
| 382 | <1 | 1.8 |
| 383 | <1 | 1.2 |
| 384 | 246 | 150.2 |
| 385 | <1 | 1.8 |
| 386 | 1063.2 | 343.2 |
| 387 | 1234.8 | 270.2 |
| 388 | <1 | 1.0 |
| 389 | <1 | 12.1 |
| 390 | <1 | 90.9 |
| 391 | <1 | 26.7 |
| 392 | <1 | 11.3 |
| 393 | 2103.8 | 4796.2 |
| 394 | <1 | 40.1 |
| 395 | <1 | 15.7 |
| 396 | 21782 | 4901.2 |
| 397 | <1 | 11.0 |
| 398 | <1 | 1.4 |
| 399 | <1 | 92.9 |
| 400 | <1 | 4.1 |
| 401 | <1 | 2.7 |
| 402 | <1 | 27.9 |
| 403 | <1 | 20.8 |
| 404 | <1 | 19.6 |
| 405 | <1 | 7.4 |
| 406 | * | 3.6 |
| 407 | * | 1.47 |
| 408 | 1283.51 | 789.59 |
| 409 | <1 | 2.64 |
| 410 | 2401.6 | 1220.67 |
| 414 | * | 11.04 |
| 415 | * | 5.10 |
| 416 | * | 2.53 |
| 417 | <1 | 1.77 |

TABLE 4-continued

ThermoFluor binding and ARE cell-based assay data

| Example # | Tf $K_d$ (nM) | ARE assay (nM) |
|---|---|---|
| 418 | <1 | 0.96 |
| 419 | <1 | 4.15 |
| 420 | 268.472 | 57.80 |
| 421 | * | 0.24 |
| 422 | <1 | 1.30 |
| 423 | 586.273 | 409.07 |
| 424 | <1 | 1.65 |
| 425 | <1 | 96.89 |
| 426 |  | 0.90 |
| 427 |  | 293.43 |
| 428 | <1 | 398.84 |
| 429 | * | 17840.20 |
| 430 | 7830.69 | 647.14 |
| 431 | <1 | 2.84 |
| 432 | <1 | 102.66 |
| 433 | * | 237.14 |
| 434 | 1.51496 | 3869.90 |
| 435 | 118.632 | >20,000 |
| 436 | <1 | 2228.44 |
| 437 | 1.83992 | 4375.22 |
| 438 | 233.722 | >20,000 |
| 439 | 1.25603 | 2441.18 |
| 440 | <1 | 713.51 |
| 441 | 60.3393 | >20,000 |
| 442 | <1 | 553.35 |
| 443 | <1 | 1104.84 |
| 444 | 21.2961 | >20,000 |
| 445 | <1 | 715.81 |
| 446 | <1 | 23.83 |
| 447 | * | 2.93 |
| 448 | <1 | 217.52 |
| 449 | <1 | 47.63 |
| 450 | <1 | 25.10 |
| 451 | <1 | 264.97 |
| 452 | <1 | 116.04 |
| 453 | <1 | 162.29 |
| 454 | * | 38.28 |
| 455 | <1 | 797.63 |
| 456 | <1 | 413.52 |
| 457 | 1.02 | 478.85 |
| 458 | <1 | 276.31 |
| 459 | 1.19 | 202.96 |
| 460 | 2.73 | 119.15 |
| 461 | 1.19 | 68.66 |
| 462 | 13.73 | 2931.57 |
| 463 | <1 | 27.65 |
| 464 | * | 24.68 |
| 465 | <1 | 153.85 |
| 466 | <1 | 123.91 |
| 467 | <1 | 79.32 |
| 468 | <1 | 502.34 |
| 469 | <1 | 608.28 |
| 470 | <1 | 472.50 |
| 471 | <1 | 2632.69 |
| 472 | <1 | 244.96 |
| 473 | <1 | 103.66 |
| 474 | <1 | 1577.61 |
| 475 | <1 | 406.35 |
| 476 | <1 | 218.88 |
| 477 | 2.60555 | 1682.29 |
| 478 | <1 | 57.64 |
| 479 | <1 | 48.84 |
| 480 | <1 | 251.59 |
| 481 | <1 | 1290.33 |
| 482 | <1 | 701.13 |
| 483 | <1 | 3450.64 |
| 484 | <1 | 225.74 |
| 485 | <1 | 155.56 |
| 486 | 1.83 | 332.58 |
| 487 | <1 | 18.27 |
| 488 | * | 11.92 |
| 489 | <1 | 29.79 |
| 490 | <1 | 5.85 |
| 491 | <1 | 5.53 |
| 492 | <1 | 12.86 |
| 493 | <1 | 1228.57 |
| 494 | <1 | 577.30 |
| 495 | <1 | 2861.54 |
| 496 | <1 | 7.65 |
| 497 | <1 | 4.47 |
| 498 | <1 | 14.66 |
| 499 | <1 | 12.78 |
| 500 | * | 6.55 |
| 501 | * | 34.54 |
| 502 | * | 3.92 |
| 503 | * | 2.58 |
| 504 | * | 7.22 |
| 505 | NT | NT |
| 506 | * | 7.83 |
| 507 | * | 0.73 |
| 508 | <1 | 92.66 |
| 509 | <1 | 70.37 |
| 510 | <1 | 313.76 |
| 511 | * | 1.52 |
| 512 | * | 3.21 |
| 513 | * | 1.63 |
| 514 | * | 1.70 |
| 515 | * | 1.33 |
| 516 | <1 | 11.08 |
| 517 | * | 10.33 |
| 518 | <1 | 3.48 |
| 519 | <1 | 15.97 |
| 520 | <1 | 15.59 |
| 521 | <1 | 1.97 |
| 522 | * | 5.06 |
| 523 | <1 | 23.88 |
| 524 | * | 19.66 |
| 525 | <1 | 38.83 |
| 526 | <1 | 60.13 |
| 527 | <1 | 22.23 |
| 528 | <1 | 235.51 |
| 529 | <1 | 29.07 |
| 530 | * | 10.25 |
| 531 | <1 | 113.03 |
| 532 | <1 | 41.70 |
| 533 | <1 | 31.34 |
| 534 | <1 | 99.20 |
| 535 | <1 | 146.39 |
| 536 | <1 | 59.66 |
| 537 | <1 | 464.30 |
| 538 | <1 | 58.91 |
| 539 | <1 | 76.02 |
| 540 | <1 | 26.71 |
| 541 | <1 | 223.41 |
| 542 | <1 | 59.65 |
| 543 | <1 | 42.93 |
| 544 | <1 | 278.23 |
| 545 | * | 49.82 |
| 546 | NT | >20,000 |
| 547 | 602.28 | 9642.73 |
| 548 | 260.44 | 2741.58 |
| 549 | 84566.80 | >20,000 |
| 551 | 452.90 | >20,000 |
| 552 | 150.00 | >20,000 |
| 553 | 769.31 | >20,000 |
| 554 | <1 | 181.18 |
| 555 | <1 | 1.42 |
| 556 | 4944.24 | 1751.86 |
| 557 | <1 | 0.56 |
| 558 | 343.48 | 194.98 |
| 559 | * | 4.69 |
| 560 | <1 | 1.90 |
| 561 | 52.53 | 258.29 |
| 562 | 14.80 | 2487.14 |
| 563 | 20.96 | >20,000 |
| 564 | 322.70 | >20,000 |
| 565 | 59.42 | >20,000 |
| 566 | * | 6.81 |
| 567 | * | 2.60 |
| 568 | * | 191.87 |

TABLE 4-continued

ThermoFluor binding and ARE cell-based assay data

| Example # | Tf K$_d$ (nM) | ARE assay (nM) |
|---|---|---|
| 569 | * | 1371.51 |
| 570 | <1 | 1117.12 |
| 571 | 5849.25 | >20,000 |
| 572 | * | 391.74 |
| 573 | <1 | 321.29 |
| 574 | 6746.84 | 14628.50 |
| 575 | <1 | 6.62 |
| 576 | <1 | 2.34 |
| 577 | 717.79 | 768.07 |
| 578 | NT | 0.00 |
| 579 | <1 | 27.77 |
| 580 | 1640.97 | 3238.92 |
| 581 | NT | 0.00 |
| 582 | <1 | 1.43 |
| 583 | 1614.73 | 765.77 |
| 584 | <1 | 477.97 |
| 585 | <1 | 252.81 |
| 586 | 6381.17 | >20,000 |
| 587 | <1 | 17.41 |
| 588 | <1 | 7.64 |
| 589 | 1447.77 | 1965.17 |
| 590 | <1 | 33.17 |
| 591 | <1 | 26.12 |
| 592 | <1 | 17.60 |
| 593 | <1 | 89.74 |
| 594 | <1 | 3.30 |
| 595 | 4.28 | 139.16 |
| 596 | <1 | 3.08 |
| 597 | <1 | 2.79 |
| 598 | <1 | 8.85 |
| 599 | <1 | 246.38 |
| 600 | <1 | 4.58 |
| 601 | <1 | 4.79 |
| 602 | <1 | 2.72 |
| 603 | <1 | 54.97 |
| 604 | <1 | 8.82 |
| 605 | <1 | 109.42 |
| 606 | 1733.01 | >20,000 |
| 607 | 1363.33 | 7617.28 |
| 608 | <1 | 9.12 |
| 609 | 634.02 | >20,000 |
| 610 | <1 | 4.42 |
| 611 | 12844 | 574.12 |
| 612 | 61546 | 19856.40 |
| 613 | <1 | 33.24 |
| 614 | <1 | 0.71 |
| 615 | <1 | 1.09 |
| 616 | <1 | 2.14 |
| 617 | <1 | 1.15 |
| 618 | NT | 0.00 |
| 619 | <1 | 4.48 |
| 620 | <1 | 7.87 |
| 621 | <1 | 5636.38 |
| 622 | 2529.3 | 3227.01 |
| 623 | <1 | 7.50 |
| 624 | 18378.1 | 3662.69 |
| 625 | <1 | 70.62 |
| 626 | 2979.89 | 229.14 |
| 627 | <1 | 1.35 |
| 628 | 15428 | >20,000 |
| 629 | 131432 | >20,000 |
| 630 | 3.81 | 81.85 |
| 631 | 1.08 | 76.75 |
| 632 | 21227.6 | 18071.70 |
| 633 | 2261 | 1751.86 |
| 634 | <1 | 9.53 |
| 635 | 1190.42 | 3594.18 |
| 636 | <1 | 40.23 |
| 637 | * | 615.46 |
| 638 | <1 | 20.10 |
| 639 | 1823.48 | 5170.11 |
| 640 | <1 | 73.88 |
| 641 | * | 2294.03 |
| 642 | <1 | 36.60 |
| 643 | 2418.8 | 9783.63 |
| 644 | <1 | 51.69 |
| 645 | <1 | 1.50 |
| 646 | * | 66.68 |
| 647 | <1 | 11.61 |
| 648 | * | 1352.07 |
| 649 | 1450.11 | 4746.79 |
| 650 | <1 | 4.36 |
| 651 | NT | NT |
| 652 | NT | NT |
| 653 | NT | NT |
| 654 | * | 6884.94 |
| 655 | <1 | 138.01 |
| 656 | * | 3592.53 |
| 657 | <1 | 74.99 |
| 658 | 1213.67 | 6053.41 |
| 659 | <1 | NT |
| 660 | 681.40 | 234.53 |
| 661 | <1 | NT |
| 662 | 568.20 | 308.04 |
| 663 | <1 | 57.5 |
| 664 | 1840 | >20,000 |
| 665 | 180 | 497.00 |

\* atypical dose response curves, binding affinity is not reported,
NT means that the compound was not tested in the assay.

What is claimed is:

1. A compound selected from the group consisting of
(\*R)-3-(7-(Difluoromethoxy)-1-methyl-1H-benzo[d][1,2,3]triazol-5-yl)-3-(3-(((\*R)-5,5-dioxido-7,7a,8,9,10,11-hexahydro-6H-dipyrido[2,1-d:2',3'-f][1,2,5]thiadiazepin-6-yl)methyl)-4-methylphenyl)propanoic acid;
(\*R)-3-(7-Cyclopropoxy-1-methyl-1H-benzo[d][1,2,3]triazol-5-yl)-3-(3-(((R)-5,5-dioxido-7a,8,9,10-tetrahydropyrido[2,3-f]pyrrolo[2,1-d][1,2,5]thiadiazepin-6(7H)-yl)methyl)-4-methylphenyl)propanoic acid;
(\*R)-3-(1-Ethyl-4-methyl-1H-benzo[d][1,2,3]triazol-5-yl)-2,2-dimethyl-3-(6-methyl-5-((8'-methyl-1',1'-dioxido-2,3,5,6-tetrahydrospiro[pyran-4,4'-pyrido[2,3-b][1,4,5]oxathiazepin]-2'(3'H)-yl)methyl)pyridin-3-yl)propanoic acid;
(\*S)-3-(3-((1',1'-Dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(3-(trifluoromethyl)-[1,2,4]triazolo[4,3-a]pyridin-7-yl)propanoic acid;
(\*R)-3-(3-((7'-(((1R,3R)-3-Hydroxycyclobutyl)amino)-8'-methyl-1',1'-dioxido-2,3,5,6-tetrahydrospiro[pyran-4,4'-pyrido[2,3-b][1,4,5]oxathiazepin]-2'(3'H)-yl)methyl)-4-methylphenyl)-2,2-dimethyl-3-(8-methyl-3-(trifluoromethyl)-[1,2,4]triazolo[4,3-a]pyridine-7-yl)propanoic acid;
(\*R)-2,2-Dimethyl-3-(4-methyl-3-((8'-methyl-7'-(((1-morpholinopropan-2-yl)amino)-1',1'-dioxido-2,3,5,6-tetrahydrospiro[pyran-4,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridine-7-yl)propanoic acid;
(\*S)-2,2-Dimethyl-3-(4-methyl-3-((8'-methyl-1',1'-dioxido-7'-(2-(pyrrolidin-1-yl)ethoxy)spiro[cyclopropane-1,4'-pyrido[2,3-b][1,4,5]oxathiazepin]-2'(3'H)-yl)methyl)phenyl)-3-(8-methyl-3-(trifluoromethyl)-[1,2,4]triazolo[4,3-a]pyridin-7-yl)propanoic acid;
(\*S)-3-(3-(Difluoromethyl)-8-methyl-[1,2,4]triazolo[4,3-a]pyridine-7-yl)-2,2-dimethyl-3-(4-methyl-3-((8'-methyl-1',1'-dioxido-7'-(2-(pyrrolidin-1-yl)ethoxy)

spiro[cyclopropane-1,4'-pyrido[2,3-b][1,4,5]
oxathiazepin]-2'(3'H)-yl)methyl)phenyl)propanoic
acid;
(*S)-2,2-Dimethyl-3-(4-methyl-3-(((*S)-8'-methyl-1',1'-
dioxido-4,5-dihydro-2H-spiro[furan-3,4'-pyrido[2,3-b]
[1,4,5]oxathiazepin]-2'(3'H)-yl)methyl)phenyl)-3-(8-
methyl-3-(trifluoromethyl)-[1,2,4]triazolo[4,3-a]
pyridin-7-yl)propanoic acid;
(*R)-3-(3-(((*S)-1',1'-Dioxido-4,5-dihydro-2H-spiro
[furan-3,4'-pyrido[2,3-b][1,4,5]oxathiazepin]-2'(3'H)-
yl)methyl)-4-methylphenyl)-2,2-dimethyl-3-(8-
methyl-3-(trifluoromethyl)-[1,2,4]triazolo[4,3-a]
pyridin-7-yl)propanoic acid;
(*R)-2,2-Dimethyl-3-(4-methyl-3-(((*S)-8'-methyl-1',1'-
dioxido-4,5-dihydro-2H-spiro[furan-3,4'-pyrido[2,3-b]
[1,4,5]oxathiazepin]-2'(3'H)-yl)methyl)phenyl)-3-(8-
methyl-3-(trifluoromethyl)-[1,2,4]triazolo[4,3-a]
pyridin-7-yl)propanoic acid;
(*S)-3-(3-Cyclopropyl-8-methyl-[1,2,4]triazolo[4,3-a]
pyridin-7-yl)-2,2-dimethyl-3-(4-methyl-3-((8'-methyl-
1',1'-dioxidospiro[cyclopropane-1,4'-pyrido[2,3-b][1,
4,5]oxathiazepin]-2'(3'H)-yl)methyl)phenyl)propanoic
acid;
(*R)-3-(1-Cyclopropyl-4-methyl-1H-benzo[d][1,2,3]tri-
azol-5-yl)-2,2-dimethyl-3-(6-methyl-5-((8'-methyl-1',
1'-dioxidospiro[cyclopropane-1,4'-pyrido[2,3-b][1,4,5]
oxathiazepin]-2'(3'H)-yl)methyl)pyridin-3-yl)
propanoic acid;
(*R)-3-(1-ethyl-4-methyl-1H-benzo[d][1,2,3]triazol-5-
yl)-2,2-dimethyl-3-(4-methyl-3-((8'-methyl-1',1'-di-
oxido-2,3,5,6-tetrahydrospiro[pyran-4,4'-pyrido[2,3-b]
[1,4,5]oxathiazepin]-2'(3'H)-yl)methyl)phenyl)
propanoic acid;
(*S)-3-(6-((1',1'-Dioxido-2,3,5,6-tetrahydrospiro[pyran-
4,4'-pyrido[2,3-b][1,4,5]oxathiazepin]-2'(3'H)-yl)
methyl)-5-methylpyridin-2-yl)-3-(1-ethyl-4-methyl-
1H-benzo[d][1,2,3]triazol-5-yl)-2,2-
dimethylpropanoic acid;
(*S)-3-(3-(Difluoromethyl)-8-methyl-[1,2,4]triazolo[4,3-
a]pyridin-7-yl)-2,2-dimethyl-3-(4-methyl-3-((8'-
methyl-',1'-dioxidospiro[cyclopropane-1,4'-pyrido[2,
3-b][1,4,5]oxathiazepin]-2'(3'H)-yl)methyl)phenyl)
propanoic acid;
(*S)-3-(1-Ethyl-4-methyl-1H-benzo[d][1,2,3]triazol-5-
yl)-2,2-dimethyl-3-(5-methyl-4-((8'-methyl-1',1'-dioxi-
dospiro[cyclopropane-1,4'-pyrido[2,3-b][1,4,5]oxathi-
azepin]-2'(3'H)-yl)methyl)pyridin-2-yl)propanoic acid;
(*S)-2,2-dimethyl-3-(4-methyl-3-((8'-methyl-7'-(2-mor-
pholinoethoxy)-1',1'-dioxidospiro[cyclopropane-1,4'-
pyrido[2,3-b][1,4,5]oxathiazepin]-2',(3'H)-yl)methyl)
phenyl)-3-(8-methyl-3-(trifluoromethyl)-[1,2,4]
triazolo[4,3-a]pyridine-7-yl)propanoic acid;
(*S) 2,2-Dimethyl-3-(4-methyl-3-((8'-methyl-1',1'-di-
oxido-7'-(((*R)-1-(piperidin-1-yl)propan-2-yl)oxy)-2,
3,5,6-tetrahydrospiro[pyran-4,4'-pyrido[2,3-b][1,4,5]
oxathiazepin]-2',(3'H)-yl)methyl)phenyl)-3-(8-methyl-
3-(trifluoromethyl)-[1,2,4]triazolo[4,3-a]pyridine-7-yl)
propanoic acid;
(*S)-2,2-Dimethyl-3-(8-methyl-3-(trifluoromethyl)-[1,2,
4]triazolo[4,3-a]pyridin-7-yl)-3-(5-methyl-6-((8'-
methyl-1',1'-dioxido-7'-(2-(pyrrolidin-1-yl)ethoxy)
spiro[cyclopropane-1,4'-pyrido[2,3-b][1,4,5]
oxathiazepin]-2'(3'H)-yl)methyl)pyridin-2-yl)
propanoic acid;
(*S)-3-(3-(Difluoromethyl)-8-methyl-[1,2,4]triazolo[4,3-
a]pyridin-7-yl)-2,2-dimethyl-3-(5-methyl-4-((8'-
methyl-1',1'-dioxido-7'-(2-(piperidin-1-yl)ethoxy)spiro
[cyclopropane-1,4'-pyrido[2,3-b][1,4,5]oxathiazepin]-
2'(3'H)-yl)methyl)pyridin-2-yl)propanoic acid; and
pharmaceutically acceptable salts, and combinations
thereof.

\* \* \* \* \*